(12) United States Patent
Kimura et al.

(10) Patent No.: US 7,122,666 B2
(45) Date of Patent: Oct. 17, 2006

(54) HETEROARYL-SUBSTITUTED PYRROLE DERIVATIVES, THEIR PREPARATION AND THEIR THERAPEUTIC USES

(75) Inventors: Tomio Kimura, Tokyo (JP); Akira Nakao, Tokyo (JP); Nobuyuki Ohkawa, Ohmiya (JP); Takayoshi Nagasaki, Tokyo (JP); Takanori Yamazaki, Kawasaki (JP)

(73) Assignee: Sankyo Company, Limited, Tokyo (JP)

( * ) Notice: Subject to any disclaimer, the term of this patent is extended or adjusted under 35 U.S.C. 154(b) by 327 days.

(21) Appl. No.: 10/354,648

(22) Filed: Jan. 30, 2003

(65) Prior Publication Data
US 2004/0054173 A1    Mar. 18, 2004

Related U.S. Application Data

(60) Continuation-in-part of application No. 10/317,748, filed on Dec. 12, 2002, now abandoned, which is a continuation of application No. 10/099,176, filed on Mar. 14, 2002, now abandoned, and a continuation-in-part of application No. 10/051,630, filed on Jan. 22, 2002, now abandoned, which is a division of application No. 09/619,898, filed on Jul. 19, 2000, now abandoned.

(60) Provisional application No. 60/275,005, filed on Mar. 12, 2001.

(30) Foreign Application Priority Data

Jul. 21, 1999   (JP)   ................... 11-205491
Dec. 27, 1999   (JP)   ................... 11-369678
Jan. 22, 2001   (JP)   ................... 2001-13817

(51) Int. Cl.
*C07D 207/00* (2006.01)
*C07D 209/00* (2006.01)

(52) U.S. Cl. .................. 544/141; 544/295; 544/333; 546/193; 546/269.7; 546/271.4; 546/272.7; 546/276.4

(58) Field of Classification Search ............. 544/60, 544/141, 245, 333; 546/193, 269.7, 271.4, 546/272.7, 276.4; 514/247, 336, 339
See application file for complete search history.

(56) References Cited

U.S. PATENT DOCUMENTS 5,502,051 A   3/1996   Scharfenberg et al.

(Continued)

FOREIGN PATENT DOCUMENTS

EP   0 300 688   1/1989

(Continued)

OTHER PUBLICATIONS

Dzvinchuk, et al., Cyclocondensation of 2-Phenacyl-1H-Benzimidazole with Acylhydrazines: Synthesis and Tautomerism of 2-(Pyrazol-4-Yl)-1H-Benzimidazoles, *Chemistry of Heterocyclic Compounds*, (1999), vol. 35, No. 11, pp. 1319-1324, Kluwer Academic/Plenum Publishers.

(Continued)

*Primary Examiner*—Shaojia A. Jiang
*Assistant Examiner*—Ganapathy Krishnan
(74) *Attorney, Agent, or Firm*—Frishauf, Holtz, Goodman & Chick, P.C.

(57) ABSTRACT

Compounds having activity against production of an inflammatory cytokine of formula (I)':

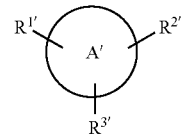

(I)'

A' is pyrrole; $R^{1'}$ is phenyl or naphthyl; $R^{2'}$ is pyridyl or pyrimidinyl; $R^{3'}$ is (IIa)', (IIb)' or (IIc)':

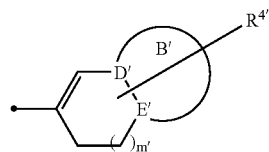

(IIa)'

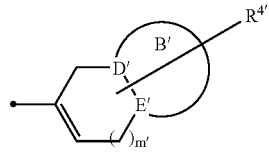

(IIb)'

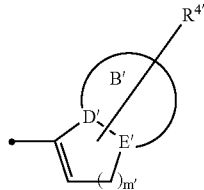

(IIc)' m' is 1; E' is nitrogen; D' is >C($R^{5'}$)—, $R^{5'}$ is hydrogen, Substituent α' or Substituent β'; B' is nitrogen-containing 5-membered heterocyclic; $R^{4'}$ is 1 to 3 substituents from Substituent α', Substituent β' and Substituent γ'; $R^{1'}$ and $R^{3'}$ are bonded to two atoms of the pyrrole adjacent to the pyrrole atom bonded to $R^{2'}$; Substituent α' is hydroxyl, nitro, cyano, halogen, alkoxy, halogeno alkoxy, alkylthio, halogeno alkylthio or —$NR^{a'}R^{b'}$; $R^{a'}$ and $R^{b'}$ are hydrogen, alkyl, alkenyl, alkynyl, aralkyl or alkylsulfonyl, or $R^{a'}$ and $R^{b'}$ with the nitrogen atom form a heterocyclyl; Substituent β' is alkyl, alkenyl, alkynyl, aralkyl or cycloalkyl; Substituent γ' is oxo, hydroxyimino, alkoxyimino, alkylene, alkylenedioxy, alkylsulfinyl, alkylsulfonyl, aryl, aryloxy, alkylidenyl or aralkylidenyl.

118 Claims, No Drawings

U.S. PATENT DOCUMENTS

| | | | |
|---|---|---|---|
| 5,593,991 | A | 1/1997 | Adams et al. |
| 5,658,940 | A | 8/1997 | Muller et al. |
| 5,670,527 | A | 9/1997 | Adams et al. |
| 5,716,955 | A | 2/1998 | Adams et al. |
| 5,739,143 | A | 4/1998 | Adams et al. |
| 5,756,499 | A | 5/1998 | Adams et al. |
| 5,776,954 | A | 7/1998 | de Laszlo et al. |
| 5,792,778 | A * | 8/1998 | de Laszlo et al. .......... 514/318 |
| 5,837,719 | A | 11/1998 | de Laszlo et al. |
| 5,932,576 | A | 8/1999 | Anantanarayan et al. |
| 6,083,949 | A | 7/2000 | Liverton et al. |
| 6,096,739 | A | 8/2000 | Feuerstein |
| 6,214,844 | B1 | 4/2001 | Adams et al. |
| 6,218,537 | B1 | 4/2001 | Adams et al. |
| 6,235,760 | B1 | 5/2001 | Feuerstein |
| 6,274,590 | B1 | 8/2001 | Talley et al. |
| 2004/0147525 | A1 | 7/2004 | Kimura et al. |
| 2005/0159444 | A1 | 7/2005 | Kimura et al. |

FOREIGN PATENT DOCUMENTS

| | | |
|---|---|---|
| EP | 799 823 A1 | 10/1997 |
| EP | 1 031 572 A1 | 8/2000 |
| EP | 1 070 711 A2 | 1/2001 |
| RU | 2060991 C1 | 5/1996 |
| WO | WO 93/14082 | 7/1993 |
| WO | WO 94/15932 | 7/1994 |
| WO | WO 95/02591 | 1/1995 |
| WO | WO 96/21452 | 7/1996 |
| WO | WO 97/05877 | 2/1997 |
| WO | WO 97/05878 | 2/1997 |
| WO | WO 97/12859 | 4/1997 |
| WO | WO 97/12876 | 4/1997 |
| WO | WO 97/16426 | 5/1997 |
| WO | WO 97/16441 | 5/1997 |
| WO | WO 97/16442 | 5/1997 |
| WO | WO 97/23479 | 7/1997 |
| WO | WO 97/36587 | 10/1997 |
| WO | WO 98/24782 | 6/1998 |
| WO | WO 98/52937 | 11/1998 |
| WO | WO 98/52940 | 11/1998 |
| WO | WO 99/01449 | 1/1999 |
| WO | WO 99/18942 | 4/1999 |
| WO | WO 99/58128 | 11/1999 |
| WO | WO 99/58523 | 11/1999 |
| WO | WO 00/01688 | 1/2000 |
| WO | WO 00/31063 | 6/2000 |
| WO | WO 00/31072 | 6/2000 |
| WO | WO 00/39116 | 7/2000 |
| WO | WO 00/64894 | 11/2000 |
| WO | WO 00/66124 | 11/2000 |
| WO | WO 00/69847 | 11/2000 |
| WO | WO 00/75131 A1 | 12/2000 |
| WO | WO 01/01988 A1 | 1/2001 |
| WO | WO 01/10986 A1 | 1/2001 |

OTHER PUBLICATIONS

Liverton et al., "Design and Synthesis of Potent, Selective, and Orally Bioavailable Tetrasubstituted Imidazole Inhibitors of p38 Mitogen-Activated Protein Kinase", *J. Med. Chem.*, (1999) vol. 42, No. 12, pp. 2180-2190, American Chemical Society.

De Laszlo et al., "Potent, Orally Absorbed Glucagon Receptor Antagonists", *Bioorganic & Medicinal Chemistry Letters*, (1999), 9, pp. 641-646, Elsevier Science Ltd.

Wilson et al., "The structural basis for the specificity of pyridinylimidazole inhibitors of p38 MAP kinase", *Chemistry & Biology*, (1997), vol. 4, No. 6, Schreiber & Nicolaou Editors.

Garnes et al., "Synthesis of Two Imidazole Cytokine Inhibitors Labelled with Carbon-14", pp. 356-358, SmithKline Beecham Pharmaceuticals, Isot. Prod. Appl., 21th Century Proc. Int. Conf. Isot. 3rd (2000).

Boehm et al., "1-Substituted 4-Aryl-5-pyridinylimidazoles: A New Class of Cytokine Suppressive Drugs with Low 5-Lipoxygenase and Cyclooxygenase Inhibitory Potency", *J. Med. Chem.*, vol. 39, pp. 3929-3937 (1996).

U.S. Appl. No. 11/301,296, filed Dec. 12, 2005.

* cited by examiner

HETEROARYL-SUBSTITUTED PYRROLE DERIVATIVES, THEIR PREPARATION AND THEIR THERAPEUTIC USES

CROSS REFERENCE TO RELATED APPLICATIONS

This application is a continuation-in-part application of (i) application Ser. No. 10/317,748 filed Dec. 12, 2002 now abandoned, which is a continuation application of application Ser. No. 10/099,176 filed Mar. 14, 2002 now abandoned, which is a divisional application of application Ser. No. 09/619,898 filed Jul. 19, 2000 (abandoned) and (ii) application Ser. No. 10/054,630 filed Jan. 22, 2002 now abandoned, which claims the benefit of Provisional application Ser. No. 60/275,005 filed Mar. 12, 2001, for which priority under 35 USC 119(e) is claimed. The entire contents of application Ser. Nos. 09/619,898 and 10/054,630 are incorporated by reference herein.

BACKGROUND TO THE INVENTION

1. Field of the Invention

The present invention relates to a series of heteroaryl-substituted pyrrole derivatives which have excellent inhibitory activity against the production of inflammatory cytokines such as interleukin (IL)-1, IL-6 and IL-8 and tumor necrosis factor (TNF), particularly IL-1β and TNFα. As a consequence, the compounds of the present invention have valuable anti-pyretic, analgesic, anti-viral and anti-inflammatory activity and are useful in the prophylaxis and treatment of autoimmune diseases such as chronic rheumatism, bone diseases such as osteoporosis and the many other diseases in which the above-described inflammatory cytokines take part. The invention also provides methods and compositions using these novel compounds as well as processes for their preparation.

2. Background Information

Non-steroidal anti-inflammatory drugs (NSAIDs) have been widely used for the treatment and prophylaxis of various inflammatory diseases and in pain relief because they have, as their main pharmacological activity, anti-pyretic, analgesic, and anti-inflammatory activity which is based on their ability to inhibit the biosynthesis of prostaglandin (PG) through the inhibition of cyclooxygenase activity. Another class of compounds commonly used for the tannest of rheumatoid arthritis is tie disease-modifying anti-rheumatic (DMARDs), examples of which include methotrexate and sulphasalazine. This is a wide class of drugs in which the compounds have no common mechanism of action. For the treatment of chronic rheumatism, NSAIDs are used nosotropically and DMARDs are used enotropically. There are a number of problems associated with these classes of drugs. Conventional NSAIDs can induce undesirable side effects including gastointestinal disorders such as gastric ulcers and renal disorders, resulting in difficulties for any patient who has to take such a drug for an extended period of time. DMARDs can also induce undesirable side effects including nausea and diarrhoea and, furthermore, they have not yet been clearly shown to exhibit a stable, long-lasting effect.

A class of active substances generally called cytokines, which are produced in the body by immunocytes, has recently been found. One group of cytokines is known as the inflammatory cytokines and it includes interleukin (IL)-1, IL-6 and IL-8 and tumor necrosis factor (TNF). The inflammatory cytokines have been demonstrated to play a major role in a number of biological processes. These include action as an inflammatory mediator through the stimulation of the arachidonic acid metabolic pathway leading to the production of PG, the migration of leukocytes, the production of acute phase protein, and activation of osteoclasts.

It is believed that the inflammatory cytokines are associated with many diseases including inflammatory diseases and the induction of bone resorption. Due to their mechanism of action, which is different from that of conventional drugs such as those described above, compounds which are able to inhibit the production of inflammatory cytokines are expected to provide an improved new generation of anti-pyretic, analgesic and anti-inflammatory drugs and medicaments for the treatment of autoimmune diseases such as chronic rheumatism, bone diseases such as osteoporosis and the many other diseases in which the above-described inflammatory cytokines are believed to take part.

Compounds which are said to demonstrate inhibitory activity against the production of inflammatory cytokines include various heteroaryl compounds [see, for example, WO 96/21452, WO 97/5877, WO 97/23479 and J. Med. Chem., 39, 3929–3937 (1996)]. Examples of compounds of this type include the following:

SB210313

J. Med. Chem., 39, 3929–3937 (1996)

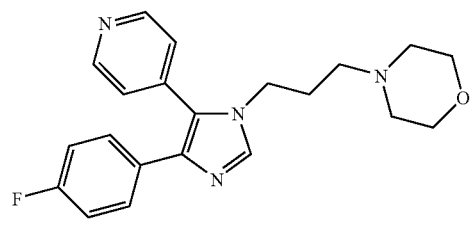

WO 00/31063
C-170

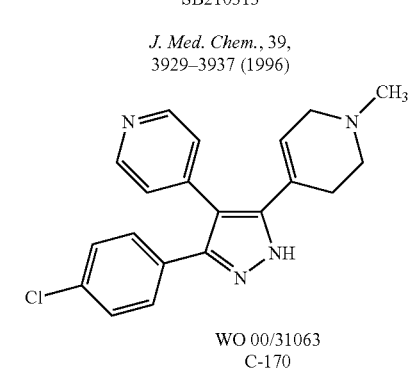

WO97/23479
Compound of
Example 6

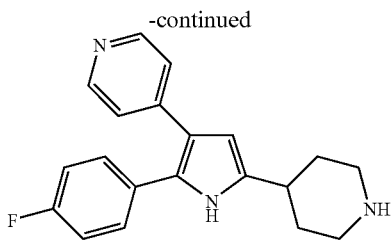

WO97/5877
Compound of
Example 4

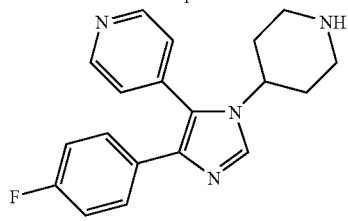

WO96/21452
Compound of
Example 23

There is a need for further compounds having improved activity, pharmacokinetics and safety, and it is this need which is addressed by the present invention. Compounds having the characteristic bicyclic amino group of the compounds of the present invention have been neither disclosed nor suggested in the prior art.

SUMMARY OF THE INVENTION

It is therefore an object of the present invention to provide a series of new compounds which inhibit the production of inflammatory cytokines and consequently show anti-pyretic, analgesic, anti-viral and anti-inflammatory activity and have utility in the prophylaxis and treatment of autoimmune diseases such as chronic rheumatism, bone diseases such as osteoporosis and the many other diseases in which the above-described inflammatory cytokines take part.

It is therefore an object of the present invention to provide a series of new pyrrole derivatives having a novel bicyclic amino substituent which inhibit the production of inflammatory cytokines and consequently show anti-pyretic, analgesic, anti-viral and anti-inflammatory activity and have utility in the prophylaxis and treatment of autoimmune diseases such as chronic rheumatism, bone diseases such as osteoporosis and the many other diseases in which the above-described inflammatory cytokines take part Other objects and advantages of the present invention will become apparent as the description proceeds.

The compounds of the present invention are compounds of the following formula (I), and pharmacologically acceptable salts, esters or other derivatives thereof:

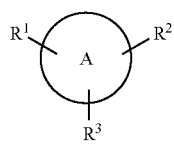

(I)

wherein:
A represents a pyrrole ring;
$R^1$ is selected from the group consisting of
  aryl groups defined below which may optionally be substituted with at least one substituent selected from the group consisting of Substituent group α defined below, Substituent group β defined below, Substituent group γ defined below and Substituent group δ defined below, and
  heteroaryl groups defined below which may optionally be substituted with at least one substituent selected from the group consisting of Substituent group α defined below, Substituent group β defined below, Substituent group γ defined below and Substituent group δ defined below;
$R^2$ represents a heteroaryl group defined below having at least one ring nitrogen atom, said heteroaryl group optionally being substituted with at least one substituent selected from the group consisting of Substituent group α defined below, Substituent group β defined below, Substituent group γ defined below and Substituent group δ defined below;
$R^3$ represents a group of the formula —X—$R^4$, wherein:
  X is selected from the group consisting of single bonds,
    lower alkylene groups, defined below, which may optionally be substituted with at least one substituent selected from Substituent group α defined below,
    lower alkenylene groups, defined below, which may optionally be substituted with at least one substituent selected from Substituent group α defined below, and
    lower alkynylene groups, defined below, which may optionally be substituted with at least one substituent selected from Substituent group α defined below; and
  $R^4$ is selected from the group consisting of
    cycloalkyl groups defined below which are substituted with at least one susbtituent selected from the group consisting of Substituent group β defined below and Substituent group γ defined below and which may optionally be further substituted with at least one substituent selected from the group consisting of Substituent group α defined below and Substituent group δ defined below,
    aryl groups defined below which are substituted with at least one substituent selected from the group consisting of Substituent group β defined below and Substituent group γ defined below and which may optionally be further substituted with at least one substituent selected from the group consisting of Substituent group α defined below and Substituent group δ defined below,
    heterocyclyl groups defined below which may optionally be substituted with at least one substituent selected from the group consisting of Substituent group α defined below and Substituent group δ defined below and which are substituted with at least one substituent selected from the group consisting of Substituent group β defined below and Substituent group γ defined below,
    heterocyclyl groups defined below having at least one nitrogen atom, said heterocyclyl groups optionally being substituted with at least one substituent selected from the group consisting of Substituent group α defined below and Substituent group δ defined below,
    heteroaryl groups defined below which may optionally be substituted with at least one substituent selected from the group consisting of Substituent group α defined below and Substituent group δ defined below and which are substituted with at least one substituent selected from the group consisting of Substituent group β defined below and Substituent group γ defined below, heteroaryl groups defined below having at least one nitrogen atom, said heteroaryl groups optionally being substituted with at least one substituent selected from the group consisting of Substituent group α defined below and Substituent group δ defined below, and groups of formula —NR$^a$R$^b$, wherein R$^a$ and R$^b$ are the same or different from each other and each is independently selected from the group consisting of hydrogen atoms, lower alkyl groups defined below, lower alkenyl groups defined below, lower alkynyl groups defined below, aralkyl groups defined below and lower alkylsulfonyl groups defined below;

PROVIDED THAT said substituents R$^1$ and R$^3$ are bonded to the two atoms of said pyrrole ring which are adjacent to the atom of the pyrrole ring to which said substituent R$^2$ is bonded;

Substituent group α comprises hydroxyl groups, nitro groups, cyano groups, halogen atoms, lower alkoxy groups defined below, halogeno lower alkoxy groups defined below, lower alkylthio groups defined below, and halogeno lower alkylthio groups defined below;

Substituent group β comprises groups of formula —NR$^c$R$^d$, wherein R$^c$ and R$^d$ are the same or different from each other and each is independently selected from the group consisting of hydrogen atoms, lower alkyl groups defined below, lower alkenyl groups defined below, lower alkynyl groups defined below, aralkyl groups defined below and lower alkylsulfonyl groups, or R$^c$ and R$^d$, together with the nitrogen atom to which R$^c$ and R$^d$ are bonded, form a heterocyclyl group defined below;

Substituent group γ comprises lower alkyl groups defined below which are substituted with a group of formula —NR$^c$R$^d$, wherein R$^c$ and R$^d$ are as defined above; and Substituent group δ comprises lower alkyl groups defined below which may optionally be substituted with at least one substituent selected from Substituent group α defined above, lower alkenyl groups defined below which may optionally be substituted with at least one substituent selected from Substituent group α defined above, lower alkynyl groups defined below which may optionally be substituted with at least one substituent selected from Substituent group α defined above, aralkyl groups defined below and cycloalkyl groups defined below.

The present invention also provides a pharmaceutical composition comprising an effective amount of a pharmacologically active compound together with a carrier or diluent therefor, wherein said pharmacologically active compound is a compound of formula (I) or a pharmacologically acceptable salt, ester or other derivative thereof.

The present invention also provides a method for inhibiting the production of inflammatory cytokines in a mammal, which may be human, which comprises administering to said mammal an effective amount of a compound of formula (I) or a pharmacologically acceptable salt, ester or other derivative thereof.

The present invention also provides a method for inhibiting bone resorption in a mammal, which may be human, suffering therefrom which comprises administering to said mammal an effective amount of a compound of formula (I) or a pharmacologically acceptable salt, ester or other derivative thereof.

The present invention also provides a method for the treatment or prophylaxis of inflammatory diseases in a mammal, which may be human, suffering therefrom, which comprises administering to said mammal an effective amount of a compound of formula (I) or a pharmacologically acceptable salt, ester or other derivative thereof.

The present invention also provides a method for the treatment or prophylaxis of viral diseases in a mammal, which may be human, suffering therefrom, which comprises administering to said mammal an effective amount of a compound of formula (I) or a pharmacologically acceptable salt, ester or other derivative thereof.

The present invention also provides a method for relieving pain or pyrexia in a mammal, which may be human, suffering therefrom, which comprises administering to said mammal an effective amount of a compound of formula (I) or a pharmacologically acceptable salt, ester or other derivative thereof.

The present invention also provides a method for the treatment or prophylaxis of chronic rheumatoid arthritis in a mammal, which may be human, suffering therefrom, which comprises administering to said mammal an effective amount of a compound of formula (I) or a pharmacologically acceptable salt, ester or other derivative thereof.

The present invention also provides a method for the treatment or prophylaxis of osteoarthritis in a mammal, which may be human, suffering therefrom, which comprises administering to said mammal an effective amount of a compound of formula (I) or a pharmacologically acceptable salt, ester or other derivative thereof.

The present invention also provides a method for the treatment or prophylaxis of cancer in a mammal, which may be human, suffering therefrom, which comprises administering to said mammal an effective amount of a compound of formula (I) or a pharmacologically acceptable salt, ester or other derivative thereof.

The present invention also provides a method for the treatment or prophylaxis of hepatitis in a mammal, which may be human, suffering therefrom, which comprises administering to said mammal an effective amount of a compound of formula (I) or a pharmacologically acceptable salt, ester or other derivative thereof.

The present invention also provides a method for the treatment or prophylaxis of a disease selected from the group consisting of allergic diseases, septicaemia, psoriasis, osteoporosis, ulcerative colitis, diabetes, nephritis, ischemic heart disease, Alzheimer's disease and arteriosclerosis in a mammal, which may be human, suffering therefrom, which comprises administering to said mammal an effective amount of a compound of formula (I) or a pharmacologically acceptable salt, ester or other derivative thereof.

The compounds of the present invention are compounds of the following formula (I)', and pharmacologically acceptable salts, esters or other derivatives thereof:

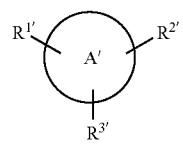

(I)' wherein:
A' represents a pyrrole ring;
R$^{1'}$ is selected from the group consisting of aryl groups defined below which may optionally be substituted with at least one substituent selected from Substituent group α' defined below and Substituent group β' defined below, and heteroaryl groups defined below which may optionally be substituted with at least one substituent selected from Substituent group α' defined below and Substituent group β' defined below;

$R^{2'}$ represents a heteroaryl group defined below which has at least one ring nitrogen atom, said heteroaryl group optionally being substituted with at least one substituent selected from Substituent group α' defined below and Substituent group β' defined below; and $R^{3'}$ represents a group of general formula (IIa)', (IIb)' or (IIc)' shown below:

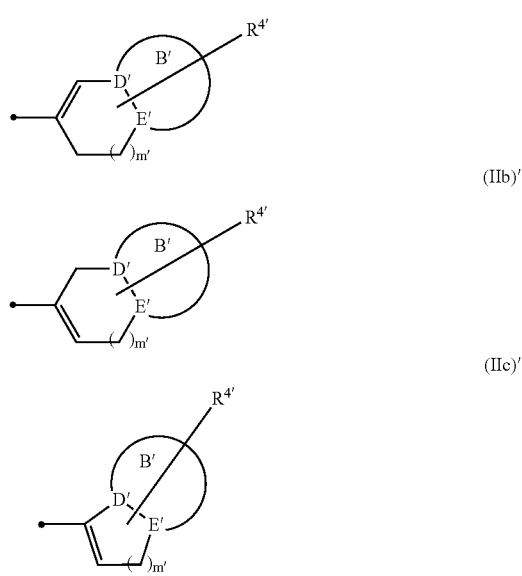

wherein m' represents 1 or 2, one of D' and E' represents a nitrogen atom and the other represents a group of formula >C($R^{5'}$)— (wherein $R^{5'}$ is selected from the group consisting of hydrogen atoms, Substituent group α' defined below and Substituent group β' defined below), B' represents a 4- to 7-membered heterocyclic ring which has at least one ring nitrogen atom (said heterocyclic ring may be saturated or unsaturated, and may optionally be fused with a group selected from aryl groups defined below, heteroaryl groups defined below, cycloalkyl groups defined below and heterocyclyl groups defined below), and $R^{4'}$ represents from 1 to 3 substituents which are independently selected from the group consisting of Substituent group α' defined below, Substituent group β' defined below and Substituent group γ' defined below, or where B' is a heterocyclic ring which is fused to an aryl group, a heteroaryl group, a cycloalkyl group or a heterocyclyl group, $R^{4'}$ may be a hydrogen atom;

PROVIDED THAT said substituents $R^{1'}$ and $R^{3'}$ are bonded to the two atoms of said pyrrole ring which are adjacent to the atom of the pyrrole ring to which said substituent $R^{2'}$ is bonded;

Substituent group α' consists of hydroxyl groups, nitro groups, cyano groups, halogen atoms, lower alkoxy groups defined below, halogeno lower alkoxy groups defined below, lower alkylthio groups defined below, halogeno lower alkylthio groups defined below and groups of formula —$NR^{a'}R^{b'}$ (wherein $R^{a'}$ and $R^{b'}$ are the same or different from each other and each is independently selected from the group consisting of hydrogen atoms, lower alkyl groups defined below, lower alkenyl groups defined below, lower alkynyl groups defined below, aralkyl groups defined below and lower alkylsulfonyl groups defined below, or $R^{a'}$ and $R^{b'}$, taken together with the nitrogen atom to which they are attached, form a heterocyclyl group);

Substituent group β' consists of lower alkyl groups defined below which may optionally be substituted with at least one substituent selected from Substituent group α defined above, lower alkenyl groups defined below which may optionally be substituted with at least one substituent selected from Substituent group α' defined above, lower alkynyl groups defined below which may optionally be substituted with at least one substituent selected from Substituent group α defined above, aralkyl groups defined below and cycloalkyl groups defined below;

Substituents group γ' consists of oxo groups, hydroxyimino groups, lower alkoxyimino groups defined below, lower alkylene groups defined below, lower alkylenedioxy groups defined below, lower alkylsulfinyl groups defined below, lower alkylsulfonyl groups defined below, aryl groups defined below which may optionally be substituted with at least one substituent selected from Substituent group α' defined above and Substituent group β' defined above, aryloxy groups defined below which may optionally be substituted with at least one substituent selected from Substituent group α defined above and Substituent group β' defined above, lower alkylidenyl groups and aralkylidenyl groups.

The present invention also provides a pharmaceutical composition comprising an effective amount of a pharmacologically active compound together with a carrier, such as a diluent, therefor, wherein said pharmacologically active compound is a compound of formula (I)' or a pharmacologically acceptable salt, ester or other derivative thereof.

The present invention also provides a compound of formula (I)' or a pharmacologically acceptable salt, ester or other derivative thereof for use as a medicament.

The present invention also provides the use of at least one compound of formula (I)' or a pharmacologically acceptable salt, ester or other derivative thereof in the manufacture of a medicament for inhibiting the production of inflammatory cytokines in a mammal, which may be human.

The present invention also provides the use of at least one compound of formula (I)' or a pharmacologically acceptable salt, ester or other derivative thereof in the manufacture of a medicament for inhibiting bone resorption in a mammal, which may be human.

The present invention also provides the use of at least one compound of formula (I)' or a pharmacologically acceptable salt, ester or other derivative thereof in the manufacture of a medicament for the treatment or prophylaxis of inflammatory diseases in a mammal, which may be human.

The present invention also provides the use of at least one compound of formula (I)' or a pharmacologically acceptable salt, ester or other derivative thereof in the manufacture of a medicament for the treatment or prophylaxis of viral diseases in a mammal, which may be human.

The present invention also provides the use of at least one compound of formula (I)' or a pharmacologically acceptable salt, ester or other derivative thereof in the manufacture of a medicament for relieving pain or pyrexia in a mammal, which may be human.

The present invention also provides the use of at least one compound of formula (I)' or a pharmacologically acceptable salt, ester or other derivative thereof in the manufacture of a medicament for the treatment or prophylaxis of chronic rheumatoid arthritis in a mammal, which may be human.

The present invention also provides the use of at least one compound of formula (I)' or a pharmacologically acceptable salt, ester or other derivative thereof in the manufacture of a medicament for the treatment or prophylaxis of osteoarthritis in a mammal, which may be human.

The present invention also provides the use of at least one compound of formula (I)' or a pharmacologically acceptable salt, ester or other derivative thereof in the manufacture of a medicament for the treatment or prophylaxis of cancer in a mammal, which may be human.

The present invention also provides the use of at least one compound of formula (I)' or a pharmacologically acceptable salt, ester or other derivative thereof in the manufacture of a medicament for the treatment or prophylaxis of hepatitis in a mammal, which may be human.

The present invention also provides the use of at least one compound of formula (I)' or a pharmacologically acceptable salt, ester or other derivative thereof in the manufacture of a medicament for the treatment or prophylaxis of a disease selected from the group consisting of allergic diseases, septicaemia, psoriasis, asthma, degenerative arthritis, Crohn's disease, systemic lupus erythematosus, osteoporosis, ulcerative colitis, diabetes, nephritis, ischemic heart disease, Alzheimer's disease and arteriosclerosis in a mammal, which may be human.

The present invention also provides a method for inhibiting the production of inflammatory cytokines in a mammal, which may be human, which comprises administering to said mammal an effective amount of a compound of formula (I)' or a pharmacologically acceptable salt, ester or other derivative thereof.

The present invention also provides a method for inhibiting bone resorption in a mammal, which may be human, suffering therefrom which comprises administering to said mammal an effective amount of a compound of formula (I)' or a pharmacologically acceptable salt, ester or other derivative thereof.

The present invention also provides a method for the treatment or prophylaxis of inflammatory diseases in a mammal, which may be human, suffering therefrom, which comprises administering to said mammal an effective amount of a compound of formula (I)' or a pharmacologically acceptable salt, ester or other derivative thereof.

The present invention also provides a method for the treatment or prophylaxis of viral diseases in a mammal, which may be human, suffering therefrom, which comprises administering to said mammal an effective amount of a compound of formula (I)' or a pharmacologically acceptable salt, ester or other derivative thereof.

The present invention also provides a method for relieving pain or pyrexia in a mammal, which may be human, suffering therefrom, which comprises administering to said mammal an effective amount of a compound of formula (I)' or a pharmacologically acceptable salt, ester or other derivative thereof.

The present invention also provides a method for the treatment or prophylaxis of chronic rheumatoid arthritis in a mammal, which may be human, suffering therefrom, which comprises administering to said mammal an effective amount of a compound of formula (I)' or a pharmacologically acceptable salt, ester or other derivative thereof.

The present invention also provides a method for the treatment or prophylaxis of osteoarthritis in a mammal, which may be human, suffering therefrom, which comprises administering to said mammal an effective amount of a compound of formula (I)' or a pharmacologically acceptable salt, ester or other derivative thereof.

The present invention also provides a method for the treatment or prophylaxis of cancer in a mammal, which may be human, suffering therefrom, which comprises administering to said mammal an effective amount of a compound of formula (I)' or a pharmacologically acceptable salt, ester or other derivative thereof.

The present invention also provides a method for the treatment or prophylaxis of hepatitis in a mammal, which may be human, suffering therefrom, which comprises administering to said mammal an effective amount of a compound of formula (I)' or a pharmacologically acceptable salt, ester or other derivative thereof.

The present invention also provides a method for the treatment or prophylaxis of a disease selected from the group consisting of allergic diseases, septicaemia, psoriasis, asthma, degenerative arthritis, Crohn's disease, systemic lupus erythematosus, osteoporosis, ulcerative colitis, diabetes, nephritis, ischemic heart disease, Alzheimer's disease and arteriosclerosis in a mammal, which may be human, suffering therefrom, which comprises administering to said mammal an effective amount of a compound of formula (I)' or a pharmacologically acceptable salt, ester or other derivative thereof.

DETAILED DESCRIPTION OF THE INVENTION

The requirement that the substituents $R^1$ and $R^3$ must be bonded to the two atoms of the pyrrole ring which are adjacent to the atom of the pyrrole ring to which the substituent $R^2$ is bonded in the compounds of the above formula (I) means that the compounds of formula (I) are selected from compounds of the following formulae (I-1) to (I-5):

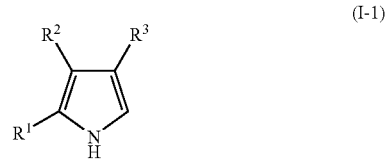
(I-1)

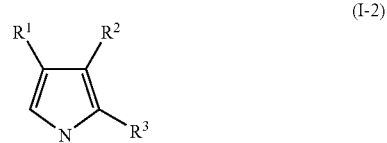
(I-2)

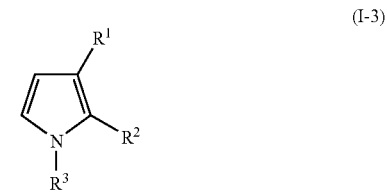
(I-3)

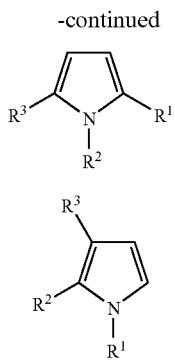

(I-4)

(I-5)

wherein R¹, R² and R³ are as defined above.

Where R¹ represents an aryl group which may optionally be substituted with at least one substituent selected from the group consisting of Substituent group α defined above, Substituent group β defined above, Substituent group γ defined above and Substituent group δ defined above or where R⁴ represents an aryl group which is substituted with at least one substituent selected from the group consisting of Substituent group β defined above and Substituent group γ defined above and which may optionally be further substituted with at least one substituent selected from the group consisting of Substituent group α defined above and Substituent group δ defined above, said aryl groups are aromatic hydrocarbon groups having from 6 to 14 carbon atoms in one or more rings, preferably from 6 to 10 carbon atoms, and examples include phenyl, naphthyl, phenanthryl and anthracenyl groups. Of these, we prefer phenyl and naphthyl groups, most preferably phenyl groups.

The aryl groups defined and exemplified above may be fused with a cycloalkyl group having from 3 to 10 carbon atoms. Examples of such a fused ring group include 5-indanyl groups.

Where R¹ represents an aryl group which is substituted with at least one substituent selected from the group consisting of Substituent group α defined above, Substituent group β defined above, Substituent group γ defined above and Substituent group δ defined above, it is preferably an aryl group substituted with 1 to 4 substituents selected from the group consisting of Substituent group α, Substituent group β, Substituent group γ and Substituent group δ, and more preferably it is an aryl group substituted with 1 to 3 substituents selected from Substituent group α, Substituent group β, Substituent group γ and Substituent group δ. Examples of such substituted aryl groups include 4-fluorophenyl, 3-fluorophenyl, 4-chlorophenyl, 3-chlorophenyl, 3,4-difluorophenyl, 3,4-dichlorophenyl, 3,4,5-trifluorophenyl, 3-chloro-4-fluorophenyl, 3-difluoromethoxyphenyl, 3-trifluoromethoxyphenyl and 3-trifluoromethylphenyl groups.

Where R⁴ represents an aryl group which is substituted with at least one substituent selected from the group consisting of Substituent group β defined above and Substituent group γ defined above and which may optionally be further substituted with at least one substituent selected from the group consisting of Substituent group α defined above and Substituent group δ defined above, it is preferably an aryl group substituted with a group selected from the group consisting of Substituent group β defined above and Substituent group γ defined above and which may optionally be further substituted with one or two groups selected from the group consisting of Substituent group α.

Examples of such substituted aryl groups include 2-aminophenyl, 3-aminophenyl, 4-aminophenyl, 2-aminomethylphenyl, 3-aminomethylphenyl, 4-aminomethylphenyl, 2-(2-aminoethyl)phenyl, 3-(2-aminoethyl)phenyl, 4-(2-aminoethyl)phenyl, 2-methylaminophenyl, 3-methylaminophenyl, 4-methylaminophenyl, 2-(dimethylamino)phenyl, 3-(dimethylamino)phenyl, 4-(dimethylamino)phenyl, 2-methylaminomethylphenyl, 3-methylaminomethylphenyl, 4-methylaminomethylphenyl, 2-(dimethylaminomethyl)phenyl, 3-(dimethylaminomethyl)phenyl, 4-(dimethylaminomethyl)phenyl, 3-amino-4-fluorophenyl, 3-amino-5-fluorophenyl, 2-aminomethyl-4-fluorophenyl, 3-amino-5-chlorophenyl, 2-aminomethyl-3-chlorophenyl, 3-amino-5-difluoromethoxyphenyl and 2-aminomethyl-3-trifluoromethoxyphenyl groups.

Where R¹ represents a heteroaryl group which may optionally be substituted with at least one substituent selected from the group consisting of Substituent group α defined above, Substituent group β defined above, Substituent group γ defined above and Substituent group δ defined above, or where R⁴ represents a heteroaryl group which is substituted with at least one substituent selected from the group consisting of Substituent group β defined above and Substituent group γ defined above and which may optionally be further substituted with at least one substituent selected from the group consisting of Substituent group α defined above and Substituent group δ defined above, said heteroaryl groups are 5- to 7-membered aromatic heterocyclic groups containing from 1 to 3 heteroatoms selected from the group consisting of sulfur atoms, oxygen atoms and nitrogen atoms. Examples of such heteroaryl groups include furyl, thienyl, pyrrolyl, pyrazolyl, imidazolyl, oxazolyl, isoxazolyl, thiazolyl, isothiazolyl, triazolyl, tetrazolyl, thiadiazolyl, pyridyl, pyridazinyl, pyrimidinyl and pyrazinyl groups. We prefer 5- or 6-membered aromatic heterocyclic groups containing one or two heteroatoms selected from the group consisting of sulfur atoms, oxygen atoms and nitrogen atoms, examples of which include furyl, thienyl, pyrrolyl, pyrazolyl, imidazolyl, oxazolyl, isoxazolyl, thiazolyl, isothiazolyl, pyridyl, pyridazinyl, pyrimidinyl and pyrazinyl groups.

Where R¹ represents a heteroaryl group, 5- or 6-membered aromatic heterocyclic groups containing 1 or 2 heteroatoms selected from the group consisting of sulfur atoms, oxygen atoms and nitrogen atoms are more preferred, and furyl, thienyl, pyridyl and pyrimidinyl groups are particularly preferred.

Where R⁴ represents a heteroaryl group, 5- or 6-membered aromatic heterocyclic groups containing one or two nitrogen atoms and optionally containing a further heteroatom selected from the group consisting of sulfur atoms, oxygen atoms and nitrogen atoms are preferred, examples of which include pyrrolyl, pyrazolyl, imidazolyl, oxazolyl, isoxazolyl, thiazolyl, isothiazolyl, pyridyl, pyridazinyl, pyrimidinyl and pyrazinyl groups. Of these, 5- or 6-membered aromatic heterocyclic groups containing one or two nitrogen atoms, such as imidazolyl, pyridyl, pyridazinyl, pyrimidinyl and pyrazinyl groups are preferred, and pyridyl and pyrimidinyl groups are particularly preferred.

The heteroaryl groups defined and exemplified above may be fused with another cyclic group selected from the group consisting of aryl groups defined above and cycloalkyl groups having from 3 to 10 carbon atoms. Examples of such a fused heteroaryl group include indolyl, benzofuranyl, benzothienyl, quinolyl, isoquinolyl, quinazolyl, tetrahydroquinolyl and tetrahydroisoquinolyl groups.

Where $R^1$ represents a heteroaryl group which is substituted with at least one substituent selected from the group consisting of Substituent group α, Substituent group β, Substituent group γ and Substituent group δ, said heteroaryl group is preferably a heteroaryl group substituted with from 1 to 3 substituents selected from the group consisting of Substituent group α, Substituent group β, Substituent group γ and Substituent group δ, and more preferably it is a heteroaryl group substituted with one or two substituents selected from the group consisting of Substituent group α, Substituent group β, Substituent group γ and Substituent group δ. Examples of such substituted heteroaryl groups include 5-fluoro-2-furyl, 4-chloro-2-thienyl, 5-difluoromethoxy-3-furyl, 5-trifluoromethyl-3-thienyl and 5-fluoro-2-oxazolyl groups.

Where $R^4$ represents a heteroaryl group which is substituted with at least one substituent selected from the group consisting of Substituent group β defined above and Substituent group γ defined above and which may optionally be further substituted with at least one substituent selected from the group consisting of Substituent group α defined above and Substituent group δ defined above, it is preferably a heteroaryl group substituted with a substituent selected from the group consisting of Substituent group β defined above and Substituent group γ defined above and which may optionally be further substituted with a substituent selected from Substituent group α.

Examples of such substituted heteroaryl groups include 5-amino-2-furyl, 5-aminomethyl-2-furyl, 5-methylaminomethyl-2-furyl, 5-dimethylaminomethyl-2-furyl, 5-amino-2-thienyl, 5-aminomethyl-2-thienyl, 5-methylaminomethyl-2-thienyl, 5-dimethylaminomethyl-2-thienyl, 5-amino-2-oxazolyl, 5-aminomethyl-2-oxazolyl, 2-amino-4-pyridyl, 2-amino-4-pyrimidinyl, 2-methylamino-4-pyridyl, 2-methylamino-4-pyrimidinyl, 2-benzylamino-4-pyridyl, 2-benzylamino-4-pyrimidinyl, 2-(α-methylbenzylamino)-4-pyridyl, 2-(α-methylbenzylamino)-4-pyrimidinyl, 5-amino-4-fluoro-2-furyl, 5-aminomethyl-4-fluoro-2-furyl, 5-amino-4-fluoro-2-thienyl, 5-aminomethyl-4-fluoro-2-thienyl, 4-amino-5-difluoromethoxy-2-furyl, 4-aminomethyl-5-difluoromethoxy-2-furyl, 4-amino-5-difluoromethoxy-2-thienyl and 4-aminomethyl-5-difluoromethoxy-2-thienyl groups.

Where $R^2$ represents a heteroaryl group having at least one ring nitrogen atom, said heteroaryl group optionally being substituted with at least one substituent selected from the group consisting of Substituent group α defined above, Substituent group β defined above, Substituent group γ defined above and Substituent group δ defined above or $R^4$ represents a heteroaryl group having at least one ring nitrogen atom, said heteroaryl group optionally being substituted with at least one substituent selected from the group consisting of Substituent group α defined above and Substituent group δ defined above, said heteroaryl groups are 5- to 7-membered aromatic heterocyclic groups containing one or two nitrogen atoms and optionally containing one or two further heteroatoms selected from the group consisting of sulfur atoms, oxygen atoms and nitrogen atoms. Examples of such groups include pyrrolyl, pyrazolyl, imidazolyl, oxazolyl, isoxazolyl, thiazolyl, isothiazolyl, triazolyl, tetrazolyl, thiadiazolyl, pyridyl, pyridazinyl, pyrimidinyl and pyrazinyl groups. Of these, we prefer 5- or 6-membered aromatic heterocyclic groups containing one nitrogen atom and optionally containing one further heteroatom selected from the group consisting of sulfur atoms, oxygen atoms and nitrogen atoms, examples of which include pyrrolyl, pyrazolyl, imidazolyl, oxazolyl, isoxazolyl, thiazolyl, isothiazolyl, pyridyl, pyridazinyl, pyrimidinyl and pyrazinyl groups. 5- or 6-membered aromatic heterocyclic groups containing one or two nitrogen atoms, such as imidazolyl, pyridyl, pyridazinyl, pyrimidinyl and pyrazinyl groups are more preferred and pyridyl and pyrimidinyl groups are particularly preferred.

Where $R^2$ represents a heteroaryl group having at least one ring nitrogen atom, 4-pyridyl and 4-pyrimidinyl groups are most preferred.

Where $R^2$ represents a heteroaryl group having at least one ring nitrogen atom, said heteroaryl group optionally being substituted with at least one substituent selected from the group consisting of Substituent group α, Substituent group β, Substituent group γ and Substituent group δ, said heteroaryl group is preferably a group substituted with 1 to 3 substituents selected from the group consisting of Substituent group α, Substituent group β, Substituent group γ and Substituent group δ, more preferably it is a heteroaryl group substituted with one or two substituents selected from the group consisting of Substituent group α, Substituent group β, Substituent group γ and Substituent group δ, still more preferably it is a heteroaryl group substituted with one substituent selected from the group consisting of Substituent group α, Substituent group β, Substituent group γ and Substituent group δ, and particularly preferably it is a 4-pyridyl or 4-pyrimidinyl group which is substituted with one substituent selected from the group consisting of Substituent group α, Substituent group β, Substituent group γ and Substituent group δ at the 2-position of said group. Most preferably, said heteroaryl group is a 4-pyridyl or 4-pyrimidinyl group which is substituted at the 2-position with one substituent selected from the group consisting of Substituent group β and Substituent group γ. Examples of such substituted heteroaryl groups include 2-amino-4-pyridyl, 2-amino-4-pyrimidinyl, 2-methylamino-4-pyridyl, 2-methylamino-4-pyrimidinyl, 2-methoxy-4-pyridyl, 2-methoxy-4-pyrimidinyl, 2-benzylamino-4-pyridyl, 2-benzylamino-4-pyrimidinyl, 2-(α-methylbenzylamino)-4-pyridyl and 2-(α-methylbenzylamino)-4-pyrimidinyl groups.

Where $R^4$ represents a heteroaryl group having at least one nitrogen atom, said heteroaryl group optionally being substituted with at least one substituent selected from the group consisting of Substituent group α defined above and Substituent group δ defined above, it is preferably a heteroaryl group substituted with 1 or 2 substituents selected from the group consisting of Substituent group α and Substituent group δ, and more preferably it is a heteroaryl group substituted with a substituent selected from the group consisting of Substituent group α and Substituent group δ.

Examples of such substituted heteroaryl groups include 2-methyl-4-pyridyl, 2-ethyl-4-pyridyl, 2-benzyl-4-pyridyl, 2-phenethyl-4-pyridyl, 2-fluoro-4-pyridyl, 2,6-difluoro-4-pyridyl and 2,3,5,6-tetrafluoro-4-pyridyl groups.

Where X represents a lower alkylene group which may optionally be substituted with at least one substituent selected from Substituent group α defined above, said lower alkylene group is a straight or branched alkylene group having from 1 to 6 carbon atoms, examples of which include methylene, ethylene, trimethylene, propylene, tetramethylene, 1-methyltrimethylene, 2-methyltrimethylene, 1,1-dimethylethylene, pentamethylene, 1,1-dimethyltrimethylene and hexamethylene groups. Of these, straight or branched alkylene groups having from 1 to 4 carbon atoms are preferred, straight or branched alkylene groups having from 1 to 3 carbon atoms are more preferred, and methylene, ethylene and trimethylene groups are most preferred.

Where X represents a lower alkenylene group which may optionally be substituted with at least one substituent selected from Substituent group α defined above, said lower alkenylene group is a straight or branched alkenylene group having from 2 to 6 carbon atoms, examples of which include vinylene, 1-methylvinylene, propenylene, 1-butenylene, 2-butenylene, 1-pentenylene and 2-pentenylene groups. Of these, straight or branched alkenylene groups having from 2 to 4 carbon atoms are preferred, vinylene, propenylene and butenylene groups are more preferred, and vinylene and propenylene groups are most preferred.

Where X represents a lower alkynylene group which may optionally be substituted with at least one substituent selected from Substituent group α defined above, said lower alkynylene group is a straight or branched alkynylene group having from 2 to 6 carbon atoms. Of these, straight or branched alkynylene groups having from 2 to 4 carbon atoms are preferred, ethynylene, propynylene, 1-butynylene and 2-butynylene groups are more preferred, and ethynylene and propynylene groups are most preferred.

Where $R^4$ represents a cycloalkyl group which is substituted with at least one susbtituent selected from the group consisting of Substituent group β defined above and Substituent group γ defined above and which may optionally be further substituted with at least one substituent selected from the group consisting of Substituent group α defined above and Substituent group δ defined above or where the substituent from Substituent group δ represents a cycloalkyl group, said cycloalkyl group has from 3 to 7 carbon atoms, examples of which include cyclopropyl, cyclobutyl, cyclopentyl, cyclohexyl and cycloheptanyl groups. Of these, cycloalkyl groups having from 3 to 6 carbon atoms are preferred.

Where $R^4$ represents a heterocyclyl group which may optionally be substituted with at least one substituent selected from the group consisting of Substituent group α defined above and Substituent group δ defined above and is substituted with at least one substituent selected from the group consisting of Substituent group β defined above and Substituent group γ defined above, said heterocyclyl group is a non-aromatic heterocyclic group having from 4 to 14 ring atoms in one or more rings, at least one of said ring atoms being a heteroatom selected from the group consisting of sulfur atoms, oxygen atoms and nitrogen atoms. It is preferably a 4- to 12-membered non-aromatic heterocyclic group (and more preferably a 4- to 10-membered non-aromatic heterocyclic group) containing one or two heteroatoms selected from the group consisting of sulfur atoms, oxygen atoms and nitrogen atoms, and more preferably it is a 4- to 12-membered non-aromatic heterocyclic group (preferably a 4- to 10-membered non-aromatic heterocyclic group) containing one nitrogen atom and optionally containing one further heteroatom selected from the group consisting of oxygen atoms, sulfur atoms and nitrogen atoms. Examples of such a group include azetidinyl, pyrrolidinyl, pyrrolinyl, imidazolidinyl, imidazolinyl, pyrazolidinyl, pyrazolinyl, oxazolidinyl, thiazolidinyl, piperidyl, tetrahydropyridyl, dihydropyridyl, piperazinyl, morpholinyl, thiomorpholinyl, homopiperidyl, quinuclidinyl, quinuclidienyl, octahydroindolizinyl, hexahydroindolizinyl, octahydroquinolizinyl, hexahydroquinolizinyl, 8-azabicyclo-[3.2.1]octanyl, 8-azabicyclo[3.2.1]octenyl, 9-azabicyclo[3.3.1]nonanyl and 9-azabicyclo[3.3.1]nonenyl groups, of which piperidyl, tetrahydropyridyl, homopiperidyl, quinuclidinyl, quinuclidienyl, octahydroindolizinyl, hexahydroindolizinyl, octahydroquinolizinyl, hexahydroquinolizinyl, azabicyclo[3.2.1]octanyl, azabicyclo[3.2.1]octenyl, azabicyclo[3.3.1]nonanyl and azabicyclo[3.3.1]nonenyl groups are preferred, tetrahydropyridyl, quinuclidienyl, hexahydroindolizinyl, hexahydroquinolizinyl, azabicyclo[3.2.1]octenyl and azabicyclo[3.3.1]nonenyl groups are more preferred, and tetrahydropyridyl, hexahydroindolizinyl and hexahydroquinolizinyl groups are most preferred.

The heterocyclyl groups defined and exemplified above may be fused with another cyclic group selected from the group consisting of aryl groups defined above and heteroaryl groups defined above. Examples of such a fused heterocyclyl group include tetrahydroquinolinyl, tetrahydroisoquinolinyl, chromanyl, indolinyl and isoindolinyl groups.

Where $R^4$ represents a heterocyclyl group having at least one ring nitrogen atom in which said heterocyclyl group may optionally be substituted with at least one substituent selected from the group consisting of Substituent group α defined above and Substituent group δ defined above, said heterocyclyl group is a 4- to 12-membered non-aromatic heterocyclic group containing one nitrogen atom and optionally containing one further heteroatom selected from the group consisting of oxygen atoms, sulfur atoms and nitrogen atoms. Preferably, it is a 4- to 10-membered non-aromatic heterocyclic group containing one nitrogen atom and optionally containing one further heteroatom selected from the group consisting of oxygen atoms, sulfur atoms and nitrogen atoms. Examples of such a groups include azetidinyl, pyrrolidinyl, pyrrolinyl, imidazolidinyl, imidazolinyl, pyrazolidinyl, pyrazolinyl, oxazolidinyl, thiazolidinyl, piperidyl, tetrahydropyridyl, dihydropyridyl, piperazinyl, morpholinyl, thiomorpholinyl, homopiperidyl, quinuclidinyl, quinuclidienyl, octahydroindolizinyl, hexahydroindolizinyl, octahydroquinolizinyl, hexahydroquinolizinyl, 8-azabicyclo-[3.2.1]octanyl, 8-azabicyclo[3.2.1]octenyl, 9-azabicyclo[3.3.1]nonanyl and 9-azabicyclo[3.3.1]nonenyl groups, of which piperidyl, tetrahydropyridyl, homopiperidyl, quinuclidinyl, quinuclidienyl, octahydroindolizinyl, hexahydroindolizinyl, octahydroquinolizinyl, hexahydroquinolizinyl, azabicyclo[3.2.1]octanyl, azabicyclo[3.2.1]octenyl, azabicyclo[3.3.1]nonanyl and azabicyclo [3.3.1]nonenyl groups are preferred, tetrahydropyridyl, quinuclidienyl, hexahydroindolizinyl, hexahydroquinolizinyl, azabicyclo[3.2.1]octenyl and azabicyclo[3.3.1]nonenyl groups are more preferred, and tetrahydropyridyl, hexahydroindolizinyl and hexahydroquinolizinyl groups are most preferred.

The heterocyclyl groups having at least one ring nitrogen atom defined and exemplified above may be fused with another cyclic group selected from the group consisting of aryl groups defined above and heteroaryl groups defined above. Examples of such fused heterocyclyl groups include tetrahydroquinolinyl, tetrahydroisoquinolinyl, indolinyl and isoindolinyl groups.

The lower alkyl groups in the definition of substituents $R^a$, $R^b$, $R^c$ and $R^d$, the lower alkyl groups which may optionally be substituted with at least one substituent selected from Substituent group α in the definition of Substituent group δ and the lower alkyl moiety of the lower alkyl groups substituted with a group of formula —$NR^cR^d$ in the definition of Substituent group γ are straight or branched alkyl groups having from 1 to 6 carbon atoms. Examples of said lower alkyl groups include methyl, ethyl, propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3- dimethylbutyl, 2,3-dimethylbutyl and 2-ethylbutyl groups. Alkyl groups having from 1 to 4 carbon atoms are preferred, methyl, ethyl and propyl groups are more preferred, and methyl and ethyl groups are most preferred.

The lower alkenyl groups in the definition of substituents $R^a$, $R^b$, $R^c$ and $R^d$ and the lower alkenyl groups which may optionally be substituted with at least one substituent selected from Substituent group α in the definition of Substituent group δ are straight or branched alkenyl groups having from 2 to 6 carbon atoms. Examples of said lower alkenyl groups include vinyl, 2-propenyl, 1-methyl-2-propenyl, 2-methyl-2-propenyl, 2-ethyl-2-propenyl, 2-butenyl, 1-methyl-2-butenyl, 2-methyl-2-butenyl, 1-ethyl-2-butenyl, 3-butenyl, 1-methyl-3-butenyl, 2-methyl-3-butenyl, 1-ethyl-3-butenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 2-hexenyl, 3-hexenyl, 4-hexenyl and 5-hexenyl groups. Alkenyl groups having from 2 to 4 carbon atoms are preferred, and alkenyl groups having 2 or 3 carbon atoms are most preferred.

The lower alkynyl groups in the definition of substituents $R^a$, $R^b$, $R^c$ and $R^d$ and the lower alkynyl groups which may optionally be substituted with at least one substituent selected from Substituent group α in the definition of Substituent group δ are straight or branched alkynyl groups having from 2 to 6 carbon atoms. Examples of said lower alkynyl groups include ethynyl, 2-propynyl, 1-methyl-2-propynyl, 2-butynyl, 1-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl and 5-hexynyl groups. Alkynyl groups having from 2 to 4 carbon atoms are preferred, and alkynyl groups having 2 or 3 carbon atoms are most preferred.

The aralkyl group in the definition of $R^a$, $R^b$, $R^c$, $R^d$ and Substituent group δ is a lower alkyl group as defined above which is substituted with at least one aryl group as defined above. Examples of said aralkyl group include benzyl, phenanthrenylmethyl, anthracenylmethyl, α-naphthylmethyl, β-naphthylmethyl, diphenylmethyl, triphenylmethyl, α-naphthyldiphenylmethyl, 9-anthrylmethyl, piperonyl, 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 1-phenylpentyl, 2-phenylpentyl, 3-phenylpentyl, 4-phenylpentyl, 5-phenylpentyl, 1-naphthylpentyl, 2-naphthylpentyl, 3-naphthylpentyl, 4-naphthylpentyl, 5-naphthylpentyl, 1-phenylhexyl, 2-phenylhexyl, 3-phenylhexyl, 4-phenylhexyl, 5-phenylhexyl, 6-phenylhexyl, 1-naphthylhexyl, 2-naphthylhexyl, 3-naphthylhexyl, 4-naphthylhexyl, 5-naphthylhexyl and 6-naphthylhexyl groups, of which benzyl, phenanthrenylmethyl, anthracenylmethyl, α-naphthylmethyl, β-naphthylmethyl, diphenylmethyl, triphenylmethyl, 9-anthrylmethyl, piperonyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl are preferred.

The aryl moiety of the aralkyl groups defined and exemplified above may be substituted with from 1 to 3 groups selected from the group consisting of Substituent group α defined above, Substituent group β defined above, Substituent group γ defined above and Substituent group δ defined above. Examples of said substituted aralkyl groups include aralkyl groups substituted with at least one halogen atom, examples of which include 2-fluorobenzyl, 3-fluorobenzyl, 4-fluorobenzyl, 2-chlorobenzyl, 3-chlorobenzyl, 4-chlorobenzyl, 2-bromobenzyl, 3-bromobenzyl, 4-bromobenzyl, 3,5-difluorobenzyl, 2,5-difluorophenethyl, 2,6-difluorobenzyl, 2,4-difluorophenethyl, 3,5-dibromobenzyl, 2,5-dibromophenethyl, 2,6-dichlorobenzyl, 2,4-dichlorophenethyl, 2,3,6-trifluorobenzyl, 2,3,4-trifluorophenethyl, 3,4,5-trifluorobenzyl, 2,5,6-trifluorophenethyl, 2,4,6-trifluorobenzyl, 2,3,6-tribromophenethyl, 2,3,4-tribromobenzyl, 3,4,5-tribromophenethyl, 2,5,6-trichlorobenzyl, 2,4,6-trichlorophenethyl, 1-fluoro-2-naphthylmethyl, 2-fluoro-1-naphthylethyl, 3-fluoro-1-naphthylmethyl, 1-chloro-2-naphthylethyl, 2-chloro-1-naphthylmethyl, 3-bromo-1-naphthylethyl, 3,8-difluoro-1-naphthylmethyl, 2,3-difluoro-1-naphthylethyl, 4,8-difluoro-1-naphthylmethyl, 5,6-difluoro-1-naphthylethyl, 3,8-dichloro-1-naphthylmethyl, 2,3-dichloro-1-naphthylethyl, 4,8-dibromo-1-naphthylmethyl, 5,6-dibromo-1-naphthylethyl, 2,3,6-trifluoro-1-naphthylmethyl, 2,3,4-trifluoro-1-naphthylethyl, 3,4,5-trifluoro-1-naphthylmethyl, 4,5,6-trifluoro-1-naphthylethyl, 2,4,8-trifluoro-1-naphthylmethyl, bis(2-fluorophenyl)methyl, 3-fluorophenylphenylmethyl, bis(4-fluorophenyl)methyl, 4-fluorophenylphenylmethyl, bis(2-chlorophenyl)methyl, bis(3-chlorophenyl)methyl, bis(4-chlorophenyl)methyl, 4-chlorophenylphenylmethyl, 2-bromophenylphenylmethyl, 3-bromophenylphenylmethyl, bis(4-bromophenyl)methyl, bis(3,5-difluorophenyl)methyl, bis(2,5-difluorophenyl)methyl, bis(2,6-difluorophenyl)methyl, 2,4-difluorophenylphenylmethyl, bis(3,5-dibromophenyl)methyl, 2,5-dibromophenylphenylmethyl, 2,6-dichlorophenylphenylmethyl, bis(2,4-dichlorophenyl)methyl and bis(2,3,6-trifluorophenyl)methyl groups; aralkyl groups substituted with at least one halogeno lower alkyl group (as defined below), examples of which include 2-trifluoromethylbenzyl, 3-trifluoromethylphenethyl, 4-trifluoromethylbenzyl, 2-trichloromethylphenethyl, 3-dichloromethylbenzyl, 4-trichloromethylphenethyl, 2-tribromomethylbenzyl, 3-dibromomethylphenethyl, 4-dibromomethylbenzyl, 3,5-bistrifluoromethylphenethyl, 2,5-bistrifluoromethylbenzyl, 2,6-bistrifluoromethylphenethyl, 2,4-bistrifluoromethylbenzyl, 3,5-bistribromomethylphenethyl, 2,5-bisdibromomethylbenzyl, 2,6-bisdichloromethylphenethyl, 2,4-bisdichloromethylbenzyl, 2,3,6-tristrifluoromethylphenethyl, 2,3,4-tristrifluoromethylbenzyl, 3,4,5-tristrifluoromethylphenethyl, 2,5,6-tristrifluoromethylbenzyl, 2,4,6-tristrifluoromethylphenethyl, 2,3,6-tristribromomethylbenzyl, 2,3,4-trisdibromomethylphenethyl, 3,4,5-tristribromomethylbenzyl, 2,5,6-trisdichloromethylphenethyl, 2,4,6-trisdichloromethylbenzyl, 1-trifluromethyl-2-naphthylethyl, 2-trifluoromethyl-1-naphthylmethyl, 3-trifluoromethyl-1-naphthylethyl, 1-trichloromethyl-2-naphthylmethyl, 2-dichloromethyl-1-naphthylethyl, 3-tribromomethyl-1-naphthylmethyl, 3,8-bistrifluoromethyl-1-naphthylethyl, 2,3-bistrifluoromethyl-1-naphthylmethyl, 4,8-bistrifluoromethyl-1-naphthylethyl, 5,6-bistrifluoromethyl-1-naphthylmethyl, 3,8-bistrichloromethyl-1-naphthylethyl, 2,3-bisdichloromethyl-1-naphthylmethyl, 4,8-bisdibromomethyl-1-naphthylmethyl, 5,6-bisbromomethyl-1-naphthylmethyl, 2,4,3,6-tristrifluoromethyl-1-naphthylethyl, 2,3,4-tristrifluoromethyl-1-naphthylmethyl, 3,4,5-tristrifluoromethyl-1-naphthylethyl, 4,5,6-tristrifluoromethyl-1-naphthylmethyl, 2,4,8-tristrifluoromethyl-1-naphthylmethyl, bis(4-trifluoromethylphenyl)methyl, 4-trifluoromethylphenylphenylmethyl, bis(2-trichloromethylphenyl)methyl, bis(4-trichloromethylphenyl)methyl, bis(4-trichloromethylphenyl)methyl, 2-tribromomethylphenylphenylmethyl, 3-tribromomethylphenylphenylmethyl, bis(4-tribromomethylphenyl)methyl, bis(3,5-bistrifluoromethylphenyl)methyl, bis(2,5-bistrifluoromethylphenyl)methyl, bis(2,6-bistrifluoromethylphenyl)methyl, 2,4-bistrifluoromethylphenylphenylmethyl, bis(3,5-bistribromomethylphenyl)methyl, 2,5-bistribromomethylphenylphenylmethyl, 2,6-bistrichloromethylphenylphenylmethyl, bis(2,4-bistrichloromethylphenyl)methyl and bis(2,3,6-tristrifluoromethylphenyl)methyl groups; aralkyl groups substituted with at least one lower alkyl group (as defined above), examples of which include 2-methylbenzyl, 3-methylbenzyl, 4-methylbenzyl, 2-methylphenethyl, 4-methylphenethyl, 2-ethylbenzyl, 3-propylphenethyl, 4-ethylbenzyl, 2-butylphenethyl, 3-pentylbenzyl, 4-pentylphenethyl, 3,5-dimethylbenzyl, 2,5-dimethylphenethyl, 2,6-dimethylbenzyl, 2,4-dimethylphenethyl, 3,5-dibutylbenzyl, 2,5-dipentylphenethyl, 2,6-dipropylbenzyl, 2,4-dipropylphenethyl, 2,3,6-trimethylbenzyl, 2,3,4-trimethylphenethyl, 3,4,5-trimethylbenzyl, 2,4,6-trimethylbenzyl, 2,5,6-trimethylphenethyl, 2,3,6-tributylphenethyl, 2,3,4-tripentylbenzyl, 3,4,5-tributylphenethyl, 2,5,6-tripropylbenzyl, 2,4,6-tripropylphenethyl, 1-methyl-2-naphthylmethyl, 2-methyl-1-naphthylethyl, 3-methyl-1-naphthylmethyl, 1-ethyl-2-naphthylethyl, 2-propyl-1-naphthylmethyl, 3-butyl-1-naphthylethyl, 3,8-dimethyl-1-naphthylmethyl, 2,3-dimethyl-1-naphthylethyl, 4,8-dimethyl-1-naphthylmethyl, 5,6-dimethyl-1-naphthylethyl, 3,8-diethyl-1-naphthylmethyl, 2,3-dipropyl-1-naphthylmethyl, 4,8-dipentyl-1-naphthylethyl, 5,6-dibutyl-1-naphthylmethyl, 2,3,6-trimethyl-1-naphthylmethyl, 2,3,4-trimethyl-1-naphthylethyl, 3,4,5-trimethyl-1-naphthylmethyl, 4,5,6-trimethyl-1-naphthylmethyl, 2,4,8-trimethyl-1-naphthylmethyl, bis(2-methylphenyl)methyl, 3-methylphenylphenylmethyl, bis(4-methylphenyl)methyl, 4-methylphenylphenylmethyl, bis(2-ethylphenyl)methyl, bis(3-ethylphenyl)methyl, bis(4-ethylphenyl)methyl, 2-propylphenylphenylmethyl, 3-propylphenylphenylmethyl, bis(4-propylphenyl)methyl, bis(3,5-dimethylphenyl)methyl, bis(2,5-dimethylphenyl)methyl, bis(2,6-dimethylphenyl)methyl, 2,4-dimethylphenylphenylmethyl, bis(3,5-dipropylphenyl)methyl, 2,5-dipropylphenylphenylmethyl, 2,6-diethylphenylphenylmethyl, bis(2,4-diethylphenyl)methyl and bis(2,3,6-trimethylphenyl)methyl groups; aralkyl groups substituted with at least one lower alkoxy group (as defined below), examples of which include 2-methoxybenzyl, 3-methoxybenzyl, 4-methoxybenzyl, 3-methoxyphenethyl, 2-ethoxyphenethyl, 3-propoxybenzyl, 4-ethoxyphenethyl, 2-butoxybenzyl, 3-pentoxyphenethyl, 4-pentoxybenzyl, 3,5-dimethoxyphenethyl, 2,5-dimethoxybenzyl, 2,6-dimethoxyphenethyl, 2,4-dimethoxybenzyl, 3,5-dibutoxyphenethyl, 2,5-dipentoxybenzyl, 2,6-dipropoxyphenethyl, 2,4-dipropoxybenzyl, 2,3,6-trimethoxyphenethyl, 2,3,4-trimethoxybenzyl, 3,4,5-trimethoxyphenethyl, 2,5,6-trimethoxybenzyl, 2,4,6-trimethoxyphenethyl, 2,3,6-tributoxybenzyl, 2,3,4-tripentoxyphenethyl, 3,4,5-tributoxybenzyl, 2,5,6-tripropoxyphenethyl, 2,4,6-tripropoxybenzyl, 1-methoxy-2-naphthylmethyl, 2-methoxy-1-naphthylmethyl, 3-methoxy-1-naphthylmethyl, 1-ethoxy-2-naphthylethyl, 2-propoxy-1-naphthylmethyl, 3-butoxy-1-naphthylethyl, 3,8-dimethoxy-1-naphthylmethyl, 2,3-dimethoxy-1-naphthylethyl, 4,8-dimethoxy-1-naphthylmethyl, 5,6-dimethoxy-1-naphthylmethyl, 3,8-diethoxy-1-naphthylmethyl, 2,3-dipropoxy-1-naphthylethyl, 4,8-dipentoxy-1-naphthylmethyl, 5,6-dibutoxy-1-naphthylmethyl, 2,3,6-trimethoxy-1-naphthylethyl, 2,3,4-trimethoxy-1-naphthylmethyl, 3,4,5-trimethoxy-1-naphthylmethyl, 4,5,6-trimethoxy-1-naphthylethyl, 2,4,8-trimethoxy-1-naphthylmethyl, bis(2-methoxyphenyl)methyl, 3-methoxyphenylphenylmethyl, bis(4-methoxyphenyl)methyl, 4-methoxyphenylphenylmethyl, bis(2-ethoxyphenyl)methyl, bis(3-ethoxyphenyl)methyl, bis(4-ethoxyphenyl)methyl, 2-propoxyphenylphenylmethyl, 3-propoxyphenylphenylmethyl, bis(4-propoxyphenyl)methyl, bis(3,5-dimethoxyphenyl)methyl, bis(2,5-dimethoxyphenyl)methyl, bis(2,6-dimethoxyphenyl)methyl, 2,4-dimethoxyphenylphenylmethyl, bis(3,5-dipropoxyphenyl)methyl, 2,5-dipropoxyphenylphenylmethyl, 2,6-diethoxyphenylphenylmethyl, bis(2,4-diethoxyphenyl)methyl and bis(2,3,6-trimethoxyphenyl)methyl groups; aralkyl groups substituted with at least one amino group, examples of which include 2-aminophenethyl, 3-aminobenzyl, 4-aminophenethyl, 3,5-diaminobenzyl, 2,5-diaminophenethyl, 2,6-diaminobenzyl, 2,4-diaminophenethyl, 2,3,6-triaminobenzyl, 2,3,4-triaminophenethyl, 3,4,5-triaminobenzyl, 2,5,6-triaminophenethyl, 2,4,6-triaminobenzyl, 1-amino-2-naphthylmethyl, 2-amino-1-naphthylethyl, 3-amino-1-naphthylmethyl, 3,8-diamino-1-naphthylmethyl, 2,3-diamino-1-naphthylethyl, 4,8-diamino-1-naphthylmethyl, 5,6-diamino-1-naphthylmethyl, 2,3,6-triamino-1-naphthylethyl, 2,3,4-triamino-1-naphthylmethyl, 3,4,5-triamino-1-naphthylmethyl, 4,5,6-triamino-1-naphthylethyl, 2,4,8-triamino-1-naphthylmethyl, bis(2-aminophenyl)methyl, 3-aminophenylphenylmethyl, bis(4-aminophenyl)methyl, 4-aminophenylphenylmethyl, bis(3,5-diaminophenyl)methyl, bis(2,5-diaminophenyl)methyl, bis(2,6-diaminophenyl)methyl, 2,4-diaminophenylphenylmethyl and bis(2,3,6-triaminophenyl)methyl groups; aralkyl groups substituted with at least one nitro group, examples of which include 2-nitrophenethyl, 3-nitrobenzyl, 4-nitrobenzyl, 4-nitrophenethyl, 3,5-dinitrobenzyl, 2,5-dinitrophenethyl, 2,6-dinitrobenzyl, 2,4-dinitrophenethyl, 2,3,6-trinitrobenzyl, 2,3,4-trinitrophenethyl, 3,4,5-trinitrobenzyl, 2,5,6-trinitrophenethyl, 2,4,6-trinitrobenzyl, 1-nitro-2-naphthylmethyl, 2-nitro-1-naphthylethyl, 3-nitro-1-naphthylmethyl, 3,8-dinitro-1-naphthylmethyl, 2,3-dinitro-1-naphthylethyl, 4,8-dinitro-1-naphthylethyl, 5,6-dinitro-1-naphthylmethyl, 2,3,6-trinitro-1-naphthylethyl, 2,3,4-trinitro-1-naphthylmethyl, 3,4,5-trinitro-1-naphthylmethyl, 4,5,6-trinitro-1-naphthylethyl, 2,4,8-trinitro-1-naphthylmethyl, bis(2-nitrophenyl)methyl, 3-nitrophenylphenylmethyl, bis(4-nitrophenyl)methyl, 4-nitrophenylphenylmethyl, bis(3,5-dinitrophenyl)methyl, bis(2,5-dinitrophenyl)methyl, bis(2,6-dinitrophenyl)methyl, 2,4-dinitrophenylphenylmethyl and bis(2,3,6-trinitrophenyl)methyl groups; and aralkyl groups substituted with at least one cyano group, examples of which include 2-cyanophenethyl, 3-cyanobenzyl, 4-cyanobenzyl, 4-cyanobenzyldiphenylmethyl, 4-cyanophenethyl, 3,5-dicyanobenzyl, 2,5-dicyanophenethyl, 2,6-dicyanobenzyl, 2,4-dicyanophenethyl, 2,3,6-tricyanobenzyl, 2,3,4-tricyanophenethyl, 3,4,5-tricyanobenzyl, 2,5,6-tricyanophenethyl, 2,4,6-tricyanobenzyl, 1-cyano-2-naphthylmethyl, 3-cyano-1-naphthylmethyl, 3,8-dicyano-1-naphthylmethyl, 2,3-dicyano-1-naphthylethyl, 4,8-dicyano-1-naphthylmethyl, 5,6-dicyano-1-naphthylmethyl, 2,3,6-tricyano-1-naphthylmethyl, 2,3,4-tricyano-1-naphthylmethyl, 3,4,5-tricyano-1-naphthylmethyl, 4,5,6-tricyano-1-naphthylmethyl, 2,4,8-tricyano-1-naphthylmethyl, bis(2-cyanophenyl)methyl, 3-cyanophenylphenylmethyl, bis(4-cyanophenyl)methyl, 4-cyanophenylphenylmethyl, bis(3,5-dicyanophenyl)methyl, bis(2,5-dicyanophenyl)methyl, bis (2,6-dicyanophenyl)methyl, 2,4-dicyanophenylphenylmethyl and bis(2,3,6-tricyanophenyl) methyl groups.

Of the above, unsubstituted aralkyl groups and aralkyl groups substituted with at least one substituent selected from the group consisting of halogen atoms, lower alkyl groups and lower alkoxy groups are preferred, unsubstituted aralkyl groups and aralkyl groups substituted with at least one substituent selected from the group consisting of halogen atoms and lower alkyl groups are more preferred, and unsubstituted aralkyl groups are most preferred.

Where substituents $R^a$, $R^b$, $R^c$ or $R^d$ represent a lower alkylsulfonyl group, this is a group in which a lower alkyl group, defined and exemplified above, is bonded to a sulfonyl group (—$SO_2$—). The lower alkylsulfonyl group is preferably a straight or branched alkylsulfonyl group having from 1 to 4 carbon atoms, more preferably a methylsulfonyl, ethylsulfonyl, propylsulfonyl, isopropylsulfonyl or butylsulfonyl group, and most preferably a methylsulfonyl, ethylsulfonyl or propylsulfonyl group.

Where substituents $R^c$ and $R^d$ together with the nitrogen atom to which they are bonded form a heterocyclyl group, said heterocyclyl group is a heterocyclyl group having at least one nitrogen atom as defined above in relation to substituent $R^4$. Examples of said heterocyclyl group include 1-azetidinyl, 1-pyrrolidinyl, 1-pyrrolinyl, 1-imidazolidinyl, 1-imidazolinyl, 1-pyrazolidinyl, 1-pyrazolinyl, 3-oxazolidinyl, 3-thiazolidinyl, 1-piperidyl, tetrahydropyridin-1-yl, dihydropyridin-1-yl, 1-piperazinyl, 4-morpholinyl, 4-thiomorpholinyl, 1-homopiperidyl, 8-azabicyclo-[3.2.1]octan-8-yl, 8-azabicyclo[3.2.1]octen-8-yl, 9-azabicyclo[3.3.1] nonan-9-yl and 9-azabicyclo[3.3.1]nonen-9-yl groups.

Where substituents $R^c$ and $R^d$ together with the nitrogen atom to which they are bonded form a heterocyclyl group as defined and exemplified above, said heterocyclyl groups may be fused with another cyclic group selected from the group consisting of aryl groups defined above and heteroaryl groups defined above. Examples of such fused heterocyclyl groups include tetrahydroquinolin-1-yl and tetrahydroisoquinolin-2-yl.

The halogen atoms in the definition of Substituent group α include fluorine, chlorine, bromine and iodine atoms, of which fluorine and chlorine atoms are preferred.

Where the substituent in the definition of Substituent group α is a lower alkoxy group, this is a group in which an oxygen atom is bonded to a lower alkyl group as defined and exemplified above. The alkoxy groups are preferably straight or branched alkoxy groups having 1 to 4 carbon atoms, more preferably methoxy, ethoxy, propoxy, isopropoxy or butoxy groups, and particularly preferably methoxy, ethoxy or propoxy groups.

Where the substituent in the definition of Substituent group α is a halogeno lower alkoxy group this is a group in which a lower alkoxy group as defined above is substituted with at least one halogen atom as exemplified above. The halogeno lower alkoxy groups preferably have from 1 to 4 carbon atoms, and are more preferably selected from the group consisting of difluoromethoxy, trifluoromethoxy and 2,2,2-trifluoromethoxy groups. Difluoromethoxy groups are most preferred.

Where the substituent in the definition of Substituent group α is a lower alkylthio group this is a group in which a sulfur atom is bonded to a lower alkyl group as defined and exemplified above. The lower alkylthio groups are preferably straight or branched alkylthio groups having 1 to 4 carbon atoms, more preferably methylthio, ethylthio, propylthio, isopropylthio or butylthio groups, and particularly preferably methylthio, ethylthio or propylthio groups.

Where the substituent in the definition of Substituent group α is a halogeno lower alkylthio group this is a group in which a lower alkylthio group as defined above is substituted with at least one halogen atom as exemplified above. The halogeno lower alkylthio groups preferably have from 1 to 4 carbon atoms, and are more preferably selected from the group consisting of difluoromethylthio, trifluoromethylthio and 2,2,2-trifluoroethylthio groups.

A preferred group of substituents of Substituent group α is Substituent group $α^1$ which comprises halogen atoms, lower alkoxy groups as defined above and halogeno lower alkoxy groups as defined above.

A preferred group of substituents of Substituent group β is Substituent group $β^1$ which comprises a group of formula —$NR^cR^d$ wherein one of $R^c$ and $R^d$ is selected from the group consisting of hydrogen atoms and lower alkyl groups as defined above and the other is selected from the group consisting of hydrogen atoms, lower alkyl groups as defined above and aralkyl groups as defined above.

A preferred group of substituents of Substituent group γ is Substituent group $γ^1$ which comprises lower alkyl groups as defined above which are substituted with a substituent selected from the group consisting of amino groups, amino groups substituted with one or two lower alkyl groups as defined above and amino groups substituted with an aralkyl group as defined above. Of these, substituents in which the alkyl moiety which is substituted with a substituent selected from the group consisting of amino groups, amino groups substituted with one or two lower alkyl groups and amino groups substituted with an aralkyl is an alkyl group having from 1 to 4 carbon atoms are preferred. Aminomethyl, 2-aminoethyl, 3-aminopropyl, methylaminomethyl, 2-(methylamino)ethyl, 3-(methylamino)propyl, ethylaminomethyl, 2-(ethylamino)ethyl, 3-(ethylamino)propyl, dimethylaminomethyl, 2-(dimethylamino)ethyl, 3-(dimethylamino) propyl, diethylaminomethyl, 2-(diethylamino)ethyl, 3-(diethylamino)propyl, benzylaminomethyl, 2-(benzylamino)ethyl and 3-(benzylamino)propyl groups are more preferred.

A preferred group of substituents of Substituent group δ is Substituent group $δ^1$ which comprises lower alkyl groups as defined above, halogeno lower alkyl groups, hydroxy lower alkyl groups and nitro lower alkyl groups.

The halogeno lower alkyl groups in the definition of Substituent group $δ^1$ above are lower alkyl groups as defined above which are substituted with at least one halogen atom. Halogeno alkyl groups having from 1 to 4 carbon atoms are preferred, trifluoromethyl, trichloromethyl, difluoromethyl, dichloromethyl, dibromomethyl, fluoromethyl, 2,2,2-trichloroethyl, 2,2,2-trifluoroethyl, 2-bromoethyl, 2-chloroethyl, 2-fluoroethyl and 2,2-dibromoethyl groups are more preferred, trifluoromethyl, trichloromethyl, difluoromethyl and fluoromethyl groups are still more preferred, and trifluoromethyl groups are most preferred.

The hydroxy lower alkyl groups in the definition of Substituent group $δ^1$ above are lower alkyl groups as defined above which are substituted with at least one hydroxy group. Hydroxyalkyl groups having from 1 to 4 carbon atoms are preferred, and hydroxymethyl, 2-hydroxyethyl and 3-hydroxypropyl groups are most preferred.

The nitro lower alkyl groups in the definition of Substituent group $δ^1$ above are lower alkyl groups as defined above which are substituted with at least one nitro group.

Nitroalkyl groups having from 1 to 4 carbon atoms are preferred, and nitromethyl, 2-nitroethyl and 3-nitropropyl are most preferred.

Where $R^3$ is a group of formula —X—$R^4$ wherein X is a single bond and $R^4$ is a heterocyclyl group which may be optionally substituted with at least one group selected from the group consisting of Substituent group α defined above and Substituent group δ defined above and which is substituted with at least one group selected from the group consisting of Substituent group β defined above and Substituent group γ defined above or it is a heterocyclyl group having at least one nitrogen atom which may be optionally substituted with at least one group selected from the group consisting of Substituent group α defined above and Substituent group δ defined above, the group $R^3$ is preferably a group of the following formula (II):

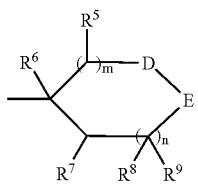

wherein:

m represents 0 or 1;

n represents 1 or 2;

$R^5$, $R^6$, $R^7$, $R^8$ and $R^9$ may be the same or different from one another and each is selected from the group consisting of hydrogen atoms, Substituent group α defined above, Substituent group β defined above, Substituent group γ defined above and Substituent group δ defined above;

one of D and E represents a group of formula >$NR^{10}$ wherein $R^{10}$ is selected from the group consisting of hydrogen atoms, Substituent group γ defined above and Substituent group δ defined above, and the other represents a group of formula >$CR^{11}R^{12}$ wherein $R^{11}$ and $R^{12}$ are the same or different from one another and each is selected from the group consisting of hydrogen atoms, Substituent group α defined above, Substituent group β defined above, Substituent group γ defined above and Substituent group δ defined above, or $R^6$ may form, together with $R^5$ or $R^7$, a single bond, and/or $R^{10}$ and $R^{11}$ together may form a lower alkylene group defined below which is unsubstituted or is substituted with at least one substituent selected from the group consisting of Substituent group α defined above, Substituent group β defined above, Substituent group γ defined above and Substituent group δ defined above.

Preferably, one of $R^5$ and $R^7$ forms a single bond together with $R^6$, and the other is selected from the group consisting of hydrogen atoms, Substituent group α, Substituent group γ and Substituent group δ, more preferably selected from the group consisting of hydrogen atoms, lower alkyl groups as defined above and aralkyl groups as defined above, and most preferably selected from the group consisting of hydrogen atoms, alkyl groups having from 1 to 4 carbon atoms, benzyl groups and phenethyl groups.

Each of $R^8$, $R^9$, $R^{10}$, $R^{11}$ and $R^{12}$ is preferably selected from the group consisting of hydrogen atoms. Substituent group α, Substituent group γ and Substituent group δ, more preferably selected from the group consisting of hydrogen atoms, lower alkyl groups as defined above and aralkyl groups as defined above, and most preferably selected from the group consisting of hydrogen atoms, alkyl groups having from 1 to 4 carbon atoms, benzyl groups and phenethyl groups.

Where $R^{10}$ and $R^{11}$ together form a lower alkylene group, this is a straight or branched alkylene group having from 1 to 6 carbon atoms, examples of which include methylene, ethylene, trimethylene, propylene, tetramethylene, 1-methyltrimethylene, 2-methyltrimethylene, 1,1-dimethylethylene, pentamethylene, 1,1-dimethyltrimethylene, 2,2-dimethyltrimethylene, 1,2-dimethyltrimethylene and hexamethylene groups. Straight or branched alkylene groups having from 3 to 6 carbon atoms are preferred, straight or branched alkylene group having 3 or 4 carbon atoms are more preferred, and straight chain alkylene groups having 3 or 4 carbon atoms are most preferred.

Preferred examples of the above group of formula (II) include:

(a) a group of formula (II) wherein m is 1 and n is 1;

(b) a group of formula (II) wherein one of $R^5$ and $R^7$ together with $R^6$ represents a single bond and the other is a hydrogen atom;

(c) a group of formula (II) wherein $R^7$, $R^8$ and $R^9$ may be the same or different from one another and each is selected from the group consisting of hydrogen atoms, Substituent group α defined above, Substituent group γ defined above and Substituent group δ defined above;

(d) a group of formula (II) wherein $R^{10}$, $R^{11}$ and $R^{12}$ may be the same or different from one another and each is selected from the group consisting of hydrogen atoms, Substituent group α defined above, Substituent group γ defined above and Substituent group δ defined above;

(e) a group of formula (II) wherein $R^{10}$ and $R^{11}$ together form a straight chain alkylene group having 3 or 4 carbon atoms which is unsubstituted or is substituted with at least one substituent selected from the group consisting of Substituent group α defined above, Substituent group β defined above, Substituent group γ defined above and Substituent group δ defined above; and (f) a group of formula (II) wherein each of $R^7$, $R^8$ and $R^9$ is a hydrogen atom, and $R^{10}$ and $R^{11}$ together form a straight chain alkylene group having 3 or 4 carbon atoms which is unsubstituted or is substituted with at least one substituent selected from the group consisting of Substituent group α defined above, Substituent group β defined above, Substituent group γ defined above and Substituent group δ defined above.

Of these, more preferred examples of the above group of formula (II) include:

(g) a group of formula (II) wherein m is 1, n is 1, D represents a group of formula >$CR^{11}R^{12}$ and E represents a group of formula >$NR^{10}$; and (h) a group of formula (II) wherein m is 1, n is 1, D represents a group of formula >$CR^{11}R^{12}$, E represents a group of formula >$NR^{10}$, and at least one of the subsititutents $R^8$, $R^9$, $R^{11}$ and $R^{12}$ is a substituent selected from the group consisting of Substituent group α defined above, Substituent group γ defined above and Substituent group δ defined above.

We also prefer a group of formula —X—$R^4$ wherein X is a lower alkenylene group which may optionally be substituted with at least one substituent selected from Substituent group α defined above and $R^4$ is a heterocyclyl group which may optionally be substituted with at least one group selected from the group consisting of Substituent group α defined above and Substituent group δ defined above and which is substituted with at least one group selected from the group consisting of Substituent group β defined above and Substituent group γ defined above or it is a heterocyclyl group having at least one nitrogen atom which may optionally be substituted with at least one group selected from the group consisting of Substituent group α defined above and Substituent group δ defined above.

In this case, preferred examples of such a heterocyclyl group for $R^4$ include 2-pyrrolidinyl, 1-methyl-2-pyrrolidinyl, 1-ethyl-2-pyrrolidinyl, 1-propyl-2-pyrrolidinyl, 2-piperidinyl, 1-methyl-2-piperidinyl, 1-ethyl-2-piperidinyl and 1-propyl-2-piperidinyl groups.

The present invention encompasses esters and other derivatives of the compounds of formula (I). These esters and other derivatives are compounds of formula (I) in which a functional group (for example, a hydroxyl group, an amino group, an imino group or a sulfonamide group) of said compound of formula (I) is modified by the addition of a protecting group using conventional techniques well-known in the art (see, for example, "Protective Groups in Organic Synthesis, Second Edition, Theodora W. Greene and Peter G. M. Wuts, 1991, John Wiley & Sons, Inc.).

There is no particular restriction on the nature of this protecting group, provided that, where the ester or other derivative is intended for therapeutic purposes, it must be pharmacologically acceptable, i.e. the protecting group must be capable of being removed by a metabolic process (e.g. hydrolysis) on administration of said compound to the body of a live mammal to give a compound of formula (I) or a salt thereof. In other words, the pharmacologically acceptable esters or other derivatives are pro-drugs of the compounds of formula (I) of the present invention. Where, however, the ester or other derivative of the compound of formula (I) of the present invention is intended for non-therapeutic purposes (e.g. as an intermediate in the preparation of other compounds), then the requirement that said ester or other derivative is pharmacologically acceptable does not apply.

Whether an ester or other derivative of a compound of formula (I) of the present invention is pharmacologically acceptable can be easily determined. The compound under investigation is intravenously administered to an experimental animal such as a rat or mouse and the body fluids of the animal are thereafter studied. If a compound of formula (I) or a pharmacologically acceptable salt thereof can be detected in the body fluids, the compound under investigation is judged to be a pharmacologically acceptable ester or other derivative.

The compounds of formula (I) of the present invention can be converted to an ester, examples of which include a compound of formula (I) in which a hydroxyl group present therein is esterified. The ester residue may be a general protecting group where the esterified compound is to be used as an intermediate or a protecting group which is capable of being removed by a metabolic process (e.g. hydrolysis) in vivo where the esterified compound is one which is pharmacologically acceptable.

The general protecting group referred to above is a protecting group which is removable by a chemical process such as hydrolysis, hydrogenolysis, electrolysis or photolysis. Preferred examples of such a general protecting group used to synthesise a compound of formula (I) in which a hydroxyl residue therein is esterified include the following:
(i) aliphatic acyl groups, examples of which include
  alkylcarbonyl groups having from 1 to 25 carbon atoms, examples of which include formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl and heneicosanoyl groups,
  halogenated alkylcarbonyl groups having from 1 to 25 carbons in which the alkyl moiety thereof is substituted by at least one halogen atom, examples of which include chloroacetyl, dichloroacetyl, trichloroacetyl and trifluoroacetyl groups,
  lower alkoxyalkylcarbonyl groups which comprise an alkylcarbonyl group having from 1 to 25 carbon atoms in which the alkyl moiety thereof is substituted with at least one lower alkoxy group as defined above, examples of said lower alkoxyalkylcarbonyl groups including methoxyacetyl groups, and
  unsaturated alkylcarbonyl groups having from 1 to 25 carbon atoms, examples of which include acryloyl, propioloyl, methacryloyl, crotonoyl, isocrotonoyl and (E)-2-methyl-2-butenoyl groups;
  of these, alkylcarbonyl groups having from 1 to 6 carbon atoms are preferred;
(ii) aromatic acyl groups, examples of which include
  arylcarbonyl groups which comprise a carbonyl group which is substituted with an aryl group as defined above, examples of which include benzoyl, α-naphthoyl and β-naphthoyl groups,
  halogenated arylcarbonyl groups which comprise an arylcarbonyl group as defined above which is substituted with at least one halogen atom, examples of which include 2-bromobenzoyl and 4-chlorobenzoyl groups,
  lower alkylated arylcarbonyl groups which comprise an arylcarbonyl group as defined above which is substituted with at least one lower alkyl group as defined above, examples of which include 2,4,6-trimethyl-benzoyl and 4-toluoyl groups,
  lower alkoxylated arylcarbonyl groups which comprise an arylcarbonyl group as defined above which is substituted with at least one lower alkoxy group as defined above, examples of which include 4-anisoyl groups,
  nitrated arylcarbonyl groups which comprise an arylcarbonyl group as defined above which is substituted with at least one nitro group, examples of which include 4-nitrobenzoyl and 2-nitrobenzoyl groups,
  lower alkoxycarbonylated arylcarbonyl groups which comprise an arylcarbonyl group as defined above which is substituted with a carbonyl group which is itself substituted with a lower alkoxy group as defined above, examples of which include 2-(methoxycarbonyl)benzoyl groups, and
  arylated arylcarbonyl groups which comprise an arylcarbonyl group as defined above which is substituted with at least one aryl group as defined above, examples of which include 4-phenylbenzoyl groups;
(iii) alkoxycarbonyl groups, examples of which include
  lower alkoxycarbonyl groups which comprise a carbonyl group substituted with a lower alkoxy group as defined above, examples of which include methoxycarbonyl, ethoxycarbonyl, propoxycarbonyl, butoxycarbonyl, s-butoxycarbonyl, t-butoxycarbonyl and isobutoxycarbonyl groups, and
  lower alkoxycarbonyl groups as defined above which are substituted with at least one substituent selected from the group consisting of halogen atoms and tri(lower alkyl)silyl groups (wherein said lower alkyl groups are as defined above), examples of which include 2,2,2-trichloroethoxycarbonyl and 2-trimethylsilylethoxycarbonyl groups;

(iv) tetrahydropyranyl or tetrahydrothiopyranyl groups which may optionally be substituted with at least one substituent selected from lower alkyl groups as defined above, halogen atoms and lower alkoxy groups as defined above, examples of which include tetrahydropyran-2-yl, 3-bromotetrahydropyran-2-yl, 4-methoxytetrahydropyran-4-yl, tetrahydrothiopyran-2-yl and 4-methoxytetrahydrothiopyran-4-yl groups;

(v) tetrahydrofuranyl or tetrahydrothiofuranyl groups which may optionally be substituted with at least one substituent selected from lower alkyl groups as defined above, halogen atoms and lower alkoxy groups as defined above, examples of which include tetrahydrofuran-2-yl and tetrahydrothiofuran-2-yl groups;

(vi) silyl groups, examples of which include
tri(lower alkyl)silyl groups (wherein said lower alkyl groups are as defined above), examples of which include trimethylsilyl, triethylsilyl, isopropyldimethylsilyl, t-butyldimethylsilyl, methyldiisopropylsilyl, methyl-di-t-butylsilyl and triisopropylsilyl groups, and
tri(lower alkyl)silyl groups in which at least one of said lower alkyl groups is substituted with 1 or 2 aryl groups as defined above, examples of which include diphenylmethylsilyl, diphenylbutylsilyl, diphenylisopropylsilyl and phenyldiisopropylsilyl groups;

(vii) alkoxymethyl groups, examples of which include
lower alkoxymethyl groups which comprise a methyl group which is substituted with a lower alkoxy group as defined above, examples of which include methoxymethyl, 1,1-dimethyl-1-methoxymethyl, ethoxymethyl, propoxymethyl, isopropoxymethyl, butoxymethyl and t-butoxymethyl groups,
lower alkoxylated lower alkoxymethyl groups which comprise a lower alkoxymethyl group as defined above in which the alkoxy moiety thereof is substituted with a lower alkoxy group as defined above, examples of which include 2-methoxyethoxymethyl groups, and
lower halogeno alkoxymethyl groups which comprise a lower alkoxymethyl group as defined above in which the alkoxy moiety thereof is substituted with at least one halogen atom, examples of which include 2,2,2-trichloroethoxymethyl and bis(2-chloroethoxy)methyl groups;

(viii) substituted ethyl groups, examples of which include
lower alkoxylated ethyl groups which comprise an ethyl group which is substituted with a lower alkoxy group as defined above, examples of which include 1-ethoxyethyl and 1-(isopropoxy)ethyl groups, and
halogenated ethyl groups such as 2,2,2-trichloroethyl groups;

(ix) aralkyl groups as define above, examples of which include
lower alkyl groups as defined above which are substituted with from 1 to 3 aryl groups as defined above, examples of which include benzyl, α-naphthylmethyl, β-naphthylmethyl, diphenylmethyl, triphenylmethyl, α-naphthyldiphenylmethyl and 9-anthrylmethyl groups, and
lower alkyl groups as defined above which are substituted with from 1 to 3 aryl groups as defined above in which said aryl moiety is substituted with at least one substituent selected from the group consisting of lower alkyl groups as defined above, lower alkoxy groups as defined above, nitro groups, halogen atoms and cyano groups, examples of which include 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl and 4-cyanobenzyl groups;

(x) "alkenyloxycarbonyl groups" which comprise a carbonyl group which is substituted with an alkenyloxy group having from 2 to 6 carbon atoms, examples of which include vinyloxycarbonyl and allyloxycarbonyl groups; and (xi) aralkyloxycarbonyl groups which comprise a carbonyl group which is substituted with an aralkyloxy group (which is an oxygen atom substituted with an aralkyl group as defined above), in which the aryl moiety thereof may optionally be substituted with one or two substituents selected from lower alkoxy groups as defined above and nitro groups, examples of which include benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups.

The protecting group which is capable of being removed by a metabolic process (e.g. hydrolysis) in vivo is one, which on administration to the body of a live mammal is removable by a metabolic process (e.g. hydrolysis) to give a compound of formula (I) or a salt thereof. Preferred examples of such a protecting group which is used to synthesise a compound of formula (I) in which a hydroxyl residue therein is esterified include the following:

(i) 1-(acyloxy)lower alkyl groups, examples of which include
1-(aliphatic acyloxy)lower alkyl groups which comprise a lower alkyl group as defined above which is substituted with an alkylcarbonyloxy group having from 1 to 6 carbon atoms, examples of which include formyloxymethyl, acetoxymethyl, dimethylaminoacetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl and 1-pivaloyloxyhexyl groups,
1-(cycloalkylcarbonyloxy)lower alkyl groups which comprise a lower alkyl group as defined above which is substituted with a cycloalkylcarbonyloxy group in which a carbonyloxy group is substituted with a cyclohexyl group as defined above, examples of which include cyclopentylcarbonyloxymethyl, cyclohexylcarbonyloxymethyl, 1-cyclopentylcarbonyloxyethyl, 1-cyclohexylcarbonyloxyethyl, 1-cyclopentylcarbonyloxypropyl, 1-cyclohexylcarbonyloxypropyl, 1-cyclopentylcarbonyloxybutyl and 1-cyclohexylcarbonyloxybutyl groups, and
1-(aromatic acyloxy)lower alkyl groups which comprise a lower alkyl group as defined above which is substituted with an aralkyloxycarbonyl group which comprises a carbonyl group which is substituted with an aralkyloxy group (said aralkyloxy group comprising an oxygen atom which is substituted with an aralkyl group as defined above), examples of which include benzoyloxymethyl groups;

(ii) substituted carbonyloxyalkyl groups, examples of which include (lower alkoxycarbonyloxy)alkyl groups which comprise a lower alkyl group as defined above which is substituted with a lower alkoxycarbonyloxy group which comprises a carbonyloxy group substituted with a lower alkoxy group as defined above, examples of which include methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, pentyloxycarbonyloxymethyl, hexyloxycarbonyloxymethyl, cyclohexyloxycarbonyloxymethyl, cyclohexyloxycarbonyloxy(cyclohexyl)methyl, 1-(methoxycarbonyloxy)ethyl, 1-(ethoxycarbonyloxy)ethyl, 1-(propoxycarbonyloxy)ethyl, 1-(isopropoxycarbonyloxy)ethyl, 1-(butoxycarbonyloxy)ethyl, 1-(isobutoxycarbonyloxy)ethyl, 1-(t-butoxycarbonyloxy)ethyl, 1-(pentyloxycarbonyloxy)ethyl, 1-(hexyloxycarbonyloxy)ethyl, 1-(cyclopentyloxycarbonyloxy)ethyl, 1-(cyclopentyloxycarbonyloxy)propyl, 1-(cyclohexyloxycarbonyloxy)propyl, 1-(cyclopentyloxycarbonyloxy)butyl, 1-(cyclohexyloxycarbonyloxy)butyl, 1-(cyclohexyloxycarbonyloxy)ethyl, 1-(ethoxycarbonyloxy)propyl, 1-(methoxycarbonyloxy)propyl, 1-(ethoxycarbonyloxy)propyl, 1-(propoxycarbonyloxy)propyl, 1-(isopropoxycarbonyloxy)propyl, 1-(butoxycarbonyloxy)propyl, 1-(isobutoxycarbonyloxy)propyl, 1-(pentyloxycarbonyloxy)propyl, 1-(hexyloxycarbonyloxy)propyl, 1-(methoxycarbonyloxy)butyl, 1-(ethoxycarbonyloxy)butyl, 1-(propoxycarbonyloxy)butyl, 1-(isopropoxycarbonyloxy)butyl, 1-(butoxycarbonyloxy)butyl, 1-(isobutoxycarbonyloxy)butyl, 1-(methoxycarbonyloxy)pentyl, 1-(ethoxycarbonyloxy)pentyl, 1-(methoxycarbonyloxy)hexyl and 1-(ethoxycarbonyloxy)hexyl groups, and oxodioxolenylmethyl groups, which comprise a methyl group which is substituted with an oxodioxolenyl group which itself may optionally be substituted with a group selected from the group consisting of lower alkyl groups as defined above and aryl groups as defined above which may optionally be substituted with at least one lower alkyl group as defined above, lower alkoxy group as defined above or halogen atom, examples of which include (5-phenyl-2-oxo-1,3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluorophenyl)-2-oxo-1,3-dioxolen-4-yl]methyl, [5-(4-chlorophenyl)-2-oxo-1,3-dioxolen-4-yl]methyl, (2-oxo-1,3-dioxolen-4-yl)-methyl, (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl and (5-butyl-2-oxo-1,3-dioxolen-4-yl) methyl groups;

(iii) phthalidyl groups which comprise a phthalidyl group which may optionally be substituted with a substituent selected from the group consisting of lower alkyl groups as defined above and lower alkoxy groups as defined above, examples of which include phthalidyl, dimethylphthalidyl and dimethoxyphthalidyl groups;

(iv) aliphatic acyl groups as defined and exemplified above in relation to the general protecting group for a hydroxyl group;

(v) aromatic acyl groups as defined and exemplified above in relation to the general protecting group for a hydroxyl group;

(vi) half-ester salt residues of succinic acid;

(vii) phosphate ester salt residues;

(viii) ester-forming residues of an amino acid;

(ix) carbamoyl groups which may optionally be substituted with 1 or 2 lower alkyl groups as defined above; and (x) 1-(acyloxy)alkoxycarbonyl groups which comprise a lower alkoxycarbonyl group as defined above in which the lower alkoxy moiety is substituted with an aliphatic acyloxy group as defined above or an aromatic acyloxy group as defined above, examples of which include pivaloyloxymethyloxycarbonyl groups.

Of the above protecting groups which are capable of being removed by a metabolic process (e.g. hydrolysis) in vivo which are used to synthesise a compound of formula (I) in which a hydroxyl residue therein is esterified, the substituted carbonyloxyalkyl groups are preferred.

In the case where the compound of formula (I) of the present invention has an amino group, an imino group and/or a sulfonamide group, the compound can be converted to a derivative other than the esters described above and the pharmacologically acceptable salts described below. The "other derivatives" of the compounds of formula (I) include such derivatives. Example of such derivatives include an amide derivative in which an aliphatic acyl group defined and exemplified above or an aromatic acyl group defined and exemplified above is bonded to a nitrogen atom of an amino group, imino group and/or sulfonamide group present in said compound of formula (I). Where said derivative is a pharmacologically acceptable derivative of a compound of formula (I) it must be capable of being removed by a metabolic process (e.g. hydrolysis) on administration of said compound to the body of a live mammal to give a compound of formula (I) or a salt thereof.

Where the compound of formula (I) of the present invention or a pharmacologically acceptable ester or other derivative thereof has a basic group, such as an amino group, the compound can be converted to a salt by reacting it with an acid, and in the case where the compound of formula (I) of the present invention or a pharmacologically acceptable ester or other derivative thereof has an acidic group, such as a sulfonamide group, the compound can be converted to a salt by reacting it with a base. The compounds of the present invention encompass such salts. Where said salts are to be used for a therapeutic use, they must be pharmacologically acceptable.

Preferred examples of the salts formed with a basic group present in the compound of formula (I) of the present invention include inorganic acid salts such as hydrohalogenated acid salts (e.g. hydrochlorides, hydrobromides and hydroiodides), nitrates, perchlorates, sulfates and phosphates; organic acid salts such as lower alkanesulfonates in which the lower alkyl moiety thereof is as defined above (e.g. methanesulfonates, trifluoromethanesulfonates and ethanesulfonates), arylsulfonates in which the aryl moiety thereof is as defined above (e.g. benzenesulfonate or p-toluenesulfonate), acetates, malates, fumarates, succinates, citrates, ascorbates, tartrates, oxalates and maleates; and amino acid salts such as glycine salts, lysine salts, arginine salts, ornithine salts, glutamates and aspartates.

Preferred example of the salts formed with an acidic group present in the compound of formula (I) of the present invention include metal salts such as alkali metal salts (e.g. sodium salts, potassium salts and lithium salts), alkali earth metal salts (e.g. calcium salts and magnesium salts), aluminum salts and iron salts; amine salts such as inorganic amine salts (e.g. ammonium salts) and organic amine salts (e.g. t-octylamine salts, dibenzylamine salts, morpholine salts, glucosamine salts, phenylglycinealkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts. N-benzylphenethylamine salts, piperazine salts, tetramethylammonium salts and tris(hydroxymethyl)aminomethane salts; and amino acid salts such as glycine salts, lysine salts, arginine salts, ornithine salts, glutamates and aspartates.

The compound of formula (I) of the present invention can sometimes take up water upon exposure to the atmosphere or when recrystallized to absorb water or to form a hydrate and such hydrates are also included within the scope of the present invention. Additionally, certain other solvents may be taken up by the compounds of the present invention to produce solvates, which also form a part of the present invention.

The compounds of formula (I) of the present invention can sometimes exist in the form of geometrical isomers (cis and trans isomers) and, where said compounds contain one or more asymmetric centres, optical isomers. For the compounds of the present invention, each of said isomers and mixture of said isomers are depicted by a single formula, i.e. the formula (I). Accordingly, the present invention covers both the individual isomers and mixtures thereof in any proportion, including racemic mixtures.

Preferred classes of compounds of the present invention are those compounds of formula (I) and pharmacologically acceptable salts, esters and other derivatives thereof wherein:

(A) $R^1$ is an aryl group defined above which may optionally be substituted with at least one substituent selected from the group consisting of Substituent group α defined above, Substituent group β defined above, Substituent group γ defined above and Substituent group δ defined above;

(B) $R^1$ is a phenyl or naphthyl group which may optionally be substituted with at least one substituent selected from the group consisting of Substituent group α defined above, Substituent group β defined above, Substituent group γ defined above and Substituent group δ defined above;

(C) $R^1$ is a phenyl group which may optionally be substituted with at least one substituent selected from the group consisting of Substituent group $α^1$ defined above, Substituent group $β^1$ defined above, Substituent group $γ^1$ defined above and Substituent group $δ^1$ defined above;

(D) $R^1$ is a phenyl group which may optionally be substituted with at least one substituent selected from the group consisting of halogen atoms, halogeno lower alkyl groups as defined above and a halogeno lower alkoxy groups as defined above;

(E) $R^1$ is a phenyl, 4-fluorophenyl, 3-fluorophenyl, 3-chlorophenyl, 3,4-difluorophenyl, 3,4,5-trifluorophenyl, 3-chloro-4-fluorophenyl, 3-difluoromethoxyphenyl or 3-trifluoromethylphenyl group;

(F) $R^2$ is a 5- or 6-membered aromatic heterocyclic group containing one or two nitrogen atoms, said group optionally being substituted with at least one substituent selected from the group consisting of Substituent group α defined above, Substituent group β defined above, Substituent group γ defined above and Substituent group δ defined above;

(G) $R^2$ is a pyridyl or pyrimidinyl group which may optionally be substituted with at least one substituent selected from the group consisting of Substituent group α defined above, Substituent group β defined above, Substituent group γ defined above and Substituent group δ defined above;

(H) $R^2$ is a 4-pyridyl or 4-pyrimidinyl group which may optionally be substituted with at least one substituent selected from the group consisting of Substituent group α defined above, Substituent group β defined above, Substituent group γ defined above and Substituent group δ defined above;

(I) $R^2$ is a 4-pyridyl or 4-pyrimidinyl group which may optionally be substituted at the 2-position thereof with a substituent selected from the group consisting of Substituent group α defined above, Substituent group β defined above, Substituent group γ defined above and Substituent group δ defined above;

(J) $R^2$ is a 4-pyridyl or 4-pyrimidinyl group which may optionally be substituted at the 2-position thereof with a substituent selected from the group consisting of methoxy, amino, methylamino, benzylamino, and α-methylbenzylamino groups;

(K) $R^4$ is selected from the group consisting of:
cycloalkyl groups having from 3 to 7 carbon atoms, which may be optionally substituted with at least one substituent selected from the group consisting of Substituent group α defined above and Substituent group δ defined above and which are substituted with at least one substituent selected from the group consisting of Substituent group β defined above and Substituent group γ;

phenyl or naphthyl groups which may be optionally substituted with at least one substituent selected from the group consisting of Substituent group α defined above and Substituent group δ defined above and which are substituted with at least one substituent selected from the group consisting of Substituent group β defined above and Substituent group γ;

4- to 12-membered non-aromatic heterocyclic groups containing one or two heteroatoms selected from the group consisting of sulfur atoms, oxygen atoms and nitrogen atoms, which may be optionally substituted with at least one substituent selected from the group consisting of Substituent group α defined above and Substituent group δ defined above and which are substituted with at least one substituent selected from the group consisting of Substituent group β defined above and Substituent group γ defined above;

4- to 12-membered non-aromatic heterocyclic groups containing one nitrogen atom and optionally one further heteroatom selected from the group consisting of oxygen atoms, sulfur atom and nitrogen atoms, which may optionally be substituted with at least one substituent selected from the group consisting of Substituent group α defined above and Substituent group δ defined above;

5- or 6-membered aromatic heterocyclic groups containing one or two heteroatoms selected from the group consisting of sulfur atoms, oxygen atoms and nitrogen atoms, which may be optionally substituted with at least one substituent selected from the group consisting of Substituent group α defined above and Substituent group δ defined above and which are substituted with at least one substituent selected from the group consisting of Substituent group β defined above and Substituent group γ defined above;

5- or 6-membered aromatic heterocyclic groups containing one or two nitrogen atoms, said groups optionally being substituted with at least one substituent selected from the group consisting of Substituent group α and Substituent group δ; and groups of formula —NR$^a$R$^b$ wherein R$^a$ and R$^b$ are as defined above;

(L) X is selected from the group consisting of single bonds, alkylene groups having from 1 to 6 carbon atoms which may optionally be substituted with at least one substituent selected from Substituent group α defined above, alkenylene groups having from 2 to 6 carbon atoms which may optionally be substituted with at least one substituent selected from Substituent group α defined above and alkynylene groups having from 2 to 6 carbon atoms which may optionally be substituted with at least one substituent selected from Substituent group α defined above;

(M) X is selected from the group consisting of single bonds, alkylene groups having from 1 to 4 carbon atoms which may optionally be substituted with at least one substituent selected from Substituent group α defined above, alkenylene groups having from 2 to 4 carbon atoms which may optionally be substituted with at least one substituent selected from Substituent group α defined above and alkynylene groups having from 2 to 4 carbon atoms which may optionally be substituted with at least one substituent selected from Substituent group α defined above;

(N) X is a single bond or an alkenylene group having from 2 to 4 carbon atoms;

(O) R$^3$ is a group of the following formula (II):

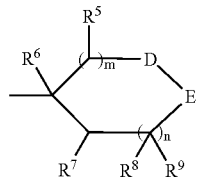

wherein m represents 0 or 1, n represents 1 or 2,

R$^5$, R$^6$, R$^7$, R$^8$ and R$^9$ may be the same or different from one another and each is selected from the group consisting of hydrogen atoms, Substituent group α defined above, Substituent group β defined above, Substituent group γ defined above and Substituent group δ defined above, one of D and E represents a group of formula >NR$^{10}$ wherein R$^{10}$ is selected from the group consisting of hydrogen atoms, Substituent group γ defined above and Substituent group δ defined above, and the other represents a group of formula >CR$^{11}$R$^{12}$ wherein R$^{11}$ and R$^{12}$ are the same or different from one another and each is selected from the group consisting of hydrogen atoms, Substituent group α defined above, Substituent group β defined above, Substituent group γ defined above and Substituent group δ defined above, or R$^6$ may form, together with R$^5$ or R$^7$, a single bond, and/or R$^{10}$ and R$^{11}$ together may form a straight or branched alkylene group having from 1 to 6 carbon atoms which is unsubstituted or is substituted with at least one substituent selected from the group consisting of Substituent group α defined above, Substituent group β defined above, Substituent group γ defined above and Substituent group δ defined above;

(P) R$^3$ is a group of formula (II) as defined above wherein m is 1 and n is 1;

(O) R$^3$ is a group of formula (II) as defined above wherein E represents a group of formula >NR$^{10}$ and D represents a group of formula >CR$^{11}$R$^{12}$;

(R) R$^3$ is a group of formula (II) as defined above wherein one of R$^5$ and R$^7$ together with R$^6$ represents a single bond and the other represents a substituent selected from the group consisting of hydrogen atoms, Substituent group α defined above, Substituent group γ defined above and Substituent group δ defined above, and R$^8$, R$^9$, R$^{10}$, R$^{11}$ and R$^{12}$ may be the same or different from one another and each represents a substituent selected from the group consisting of hydrogen atoms, Substituent group α defined above, Substituent group γ defined above and Substituent group δ defined above, or R$^{10}$ and R$^{11}$ together form an alkylene group having from 1 to 6 carbon atoms which is unsubstituted or is substituted with at least one substituent selected from the group consisting of Substituent group α defined above, Substituent group β defined above, Substituent group γ defined above and Substituent group δ defined above;

(S) R$^3$ is a group of formula (II) as defined above wherein R$^{10}$ and R$^{11}$ together form a straight chain alkylene group having 3 or 4 carbon atoms which is unsubstituted or is substituted with at least one substituent selected from the group consisting of Substituent group α defined above, Substituent group β defined above, Substituent group γ defined above and Substituent group δ defined above;

(T) R$^3$ is a group of formula (II) as defined above wherein each of R$^7$, R$^8$ and R$^9$ is a hydrogen atom, and R$^{10}$ and R$^{11}$ together form a straight chain alkylene group having 3 or 4 carbon atoms which is unsubstituted or is substituted with at least one substituent selected from the group consisting of Substituent group α defined above, Substituent group β defined above, Substituent group γ defined above and Substituent group δ defined above; and (U) said compound of formula (I) is a compound of formula (I-1) or (I-3) below wherein R$^1$, R$^2$ and R$^3$ are as defined above:

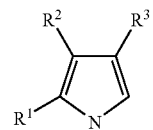

(I-1)

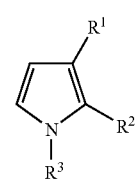

(I-3)

Compounds of formula (I) which comprise an), combination of the factors selected freely from the five groups consisting of (A) to (E) above; (F) to (J) above; (K) above; (L) to (N) above; (O) to (T) above; and (U) above are preferred.

More preferred compounds of the present invention are compounds of formula (I) and pharmacologically acceptable salts, esters and other derivatives thereof, wherein:

(i) R¹ is as defined in (A) above, R² is as defined in (F) above and R³ is a group of formula —X—R⁴ wherein X is as defined in (L) above and R⁴ is as defined in (K) above;
(ii) R¹ is as defined in (A) above, R² is as defined in (F) above and R³ is a group of formula —X—R⁴ wherein X is as defined in (M) above and R⁴ is as defined in (K) above;
(iii) R¹ is as defined in (B) above, R² is as defined in (G) above and R³ is a group of formula —X—R⁴ wherein X is as defined in (N) above and R⁴ is as defined in (K) above;
(iv) R¹ is as defined in (B) above, R² is as defined in (G) above and R³ is as defined in (O) above;
(v) R¹ is as defined in (C) above, R² is as defined in (H) above and R³ is as defined in (P) above;
(vi) R¹ is as defined in (C) above, R² is as defined in (H) above and R³ is as defined in (O) above;
(vii) R¹ is as defined in (D) above, R² is as defined in (I) above and R³ is as defined in (R) above;
(viii) R¹ is as defined in (E) above, R² is as defined in (J) above and R³ is as defined in (S) above;
(ix) R¹ is as defined in (E) above, R² is as defined in (J) above and R³ is as defined in (T) above; and
(x) any of the above compounds (i) to (ix) wherein the compound of formula (I) is a compound of formula (I-1) or (I-3) as defined in (U) above.

Particularly preferred compounds of the present invention are compounds of formula (I) selected from the following group of compounds, and pharmacologically acceptable salts, esters and other derivatives thereof:
4-(3-aminopropyl)-2-(4-fluorophenyl)-3-(pyridin-4-yl)-1H-pyrrole,
4-(3-acetylaminopropyl)-2-(4-fluorophenyl)-3-(pyridin-4-yl)-1H-pyrrole,
2-(4-fluorophenyl)-4-(3-methylaminopropyl)-3-(pyridin-4-yl)-1H-pyrrole,
[5-(4-fluorophenyl)-4-(pyridin-4-yl)-1H-pyrrol-3-yl]-(pyridin-4-yl)methanol,
4-(1-acetyl-1,2,3,6-tetrahydropyridin-4-yl)-2-(4-fluorophenyl)-3-(pyridin-4-yl)-1H-pyrrole,
2-(4-fluorophenyl)-3-(pyridin-4-yl)-4-(1,2,3,6-tetrahydropyridin-4-yl)-1H-pyrrole,
2-(4-fluorophenyl)-4-(piperidin-4-yl)-3-(pyridin-4-yl)-1H-pyrrole,
3-(4-fluorophenyl)-1-(piperidin-4-yl)-2-(pyridin-4-yl)-1H-pyrrole,
1-(1-acetylpiperidin-4-yl)-3-(4-fluorophenyl)-2-(pyridin-4-yl)-1H-pyrrole,
3-(4-fluorophenyl)-1-[1-(2-nitroethyl)piperidin-4-yl]-2-(pyridin-4-yl)-1H-pyrrole,
3-(4-fluorophenyl)-1-[3-(morpholin-1-yl)propyl]-2-(pyridin-4-yl)-1H-pyrrole,
3-(4-fluorophenyl)-1-(piperidin-3-yl)-2-(pyridin-4-yl)-1H-pyrrole,
1-(azetidin-3-yl)-3-(4-fluorophenyl)-2-(pyridin-4-yl)-1H-pyrrole,
4-(3-dimethylaminopropyl)-2-(4-fluorophenyl)-3-(pyridin-4-yl)-1H-pyrrole,
2-(4-fluorophenyl)-4-[3-(piperidin-1-yl)propyl]-3-(pyridin-4-yl)-1H-pyrrole,
2-(4-fluorophenyl)-4-[3-(1-methylpiperazin-4-yl)propyl]-3-(pyridin-4-yl)-1H-pyrrole,
2-(4-fluorophenyl)-4-(1-methyl-1,2,3,6-tetrahydropyridin-4-yl)-3-(pyridin-4-yl)-1H-pyrrole,
2-(4-fluorophenyl)-4-(1-methylpiperidin-4-yl)-3-(pyridin-4-yl)-1H-pyrrole,
3-(4-fluorophenyl)-2-(pyridin-4-yl)-1-(2,2,6,6-tetramethylpiperidin-4-yl)-1H-pyrrole,
2-(4-fluorophenyl)-3-(pyridin-4-yl)-4-(quinuclidin-2-en-3-yl)-1H-pyrrole,
2-(4-fluorophenyl)-3-(pyridin-4-yl)-4-(quinuclidin-3-yl)-1H-pyrrole,
2-(4-fluorophenyl)-4-(4-hydroxypiperidin-4-yl)-3-(pyridin-4-yl)-1H-pyrrole,
3-(4-fluorophenyl)-2-(pyridin-4-yl)-1-(quinuclidin-3-yl)-1H-pyrrole,
1-(4-aminocyclohexyl)-3-(4-fluorophenyl)-2-(pyridin-4-yl)-1H-pyrrole,
3-(4-fluorophenyl)-2-(2-methylaminopyrimidin-4-yl)-1-(piperidin-4-yl)-1H-pyrrole,
2-(4-fluorophenyl)-4-(8-methyl-8-azabicyclo[3.2.1]oct-2-en-3-yl)-3-(pyridin-4-yl)-1H-pyrrole,
2-(4-fluorophenyl)-4-(8-methyl-8-azabicyclo[3.2.1]octan-3-yl)-3-(pyridin-4-yl)-1H-pyrrole,
4-(8-azabicyclo[3.2.1]oct-2-en-3-yl)-2-(4-fluorophenyl)-3-(pyridin-4-yl)-1H-pyrrole,
2-(4-fluorophenyl)-3-(pyridin-4-yl)-4-(1,2,3,6-tetrahydro-2,2,6,6-tetramethylpyridin-4-yl)-1H-pyrrole,
2-(4-fluorophenyl)-3-(pyridin-4-yl)-4-(2,2,6,6-tetramethylpiperidin-4-yl)-1H-pyrrole,
2-(4-fluorophenyl)-4-(2-methyl-1,2,3,6-tetrahydropyridin-4-yl)-3-(pyridin-4-yl)-1H-pyrrole,
2-(4-fluorophenyl)-4-(6-methyl-1,2,3,6-tetrahydropyridin-4-yl)-3-(pyridin-4-yl)-1H-pyrrole,
4-(1-ethyl-1,2,3,6-tetrahydropyridin-4-yl)-2-(4-fluorophenyl)-3-(pyridin-4-yl)-1H-pyrrole,
4-(1-ethylpiperidin-4-yl)-2-(4-fluorophenyl)-3-(pyridin-4-yl)-1H-pyrrole,
2-(4-fluorophenyl)-4-(1-isopropyl-1,2,3,6-tetrahydropyridin-4-yl)-3-(pyridin-4-yl)-1H-pyrrole,
2-(4-fluorophenyl)-4-(1-propyl-1,2,3,6-tetrahydropyridin-4-yl)-3-(pyridin-4-yl)-1H-pyrrole,
2-(4-fluorophenyl)-4-(1-phenethyl-1,2,3,6-tetrahydropyridin-4-yl)-3-(pyridin-4-yl)-1H-pyrrole,
2-(4-fluorophenyl)-4-(1,2,3,5,8,8a-hexahydroindolizin-7-yl)-3-(pyridin-4-yl)-1H-pyrrole,
2-(4-fluorophenyl)-4-(1,2,3,5,6,8a-hexahydroindolizin-7-yl)-3-(pyridin-4-yl)-1H-pyrrole,
4-(1,6-dimethyl-1,2,3,6-tetrahydropyridin-4-yl)-2-(4-fluorophenyl)-3-(pyridin-4-yl)-1H-pyrrole,
4-(1,2-dimethyl-1,2,3,6-tetrahydropyridin-4-yl)-2-(4-fluorophenyl)-3-(pyridin-4-yl)-1H-pyrrole,
2-(4-fluorophenyl)-4-(1,2,2,6,6-pentamethyl-1,2,3,6-tetrahydropyridin-4-yl)-3-(pyridin-4-yl)-1H-pyrrole,
4-(3-dimethylamino-1-propen-1-yl)-2-(4-fluorophenyl)-3-(pyridin-4-yl)-1H-pyrrole,
4-(4-aminobutyl)-2-(4-fluorophenyl)-3-(pyridin-4-yl)-1H-pyrrole,
4-(1-ethyl-6-methyl-1,2,3,6-tetrahydropyridin-4-yl)-2-(4-fluorophenyl)-3-(pyridin-4-yl)-1H-pyrrole,
4-(1-ethyl-2-methyl-1,2,3,6-tetrahydropyridin-4-yl)-2-(4-fluorophenyl)-3-(pyridin-4-yl)-1H-pyrrole,
1-(3-dimethylaminopropyl)-3-(4-fluorophenyl)-2-(pyridin-4-yl)-1H-pyrrole,
2-(4-fluorophenyl)-4-(1,2,3,5,6,7,8,8a-octahydroindolizin-7-yl)-3-(pyridin-4-yl)-1H-pyrrole,
4-(6-allyl-1-methyl-1,2,3,6-tetrahydropyridin-4-yl)-2-(4-fluorophenyl)-3-(pyridin-4-yl)-1H-pyrrole,
4-(2-allyl-1-methyl-1,2,3,6-tetrahydropyridin-4-yl)-2-(4-fluorophenyl)-3-(pyridin-4-yl)-1H-pyrrole,
4-(6-benzyl-1-methyl-1,2,3,6-tetrahydropyridin-4-yl)-2-(4-fluorophenyl)-3-(pyridin-4-yl)-1H-pyrrole, 4-(2-benzyl-1-methyl-1,2,3,6-tetrahydropyridin-4-yl)-2-(4-fluorophenyl)-3-(pyridin-4-yl)-1H-pyrrole,
2-(4-fluorophenyl)-4-(6-methyl-1-propyl-1,2,3,6-tetrahydropyridin-4-yl)-3-(pyridin-4-yl)-1H-pyrrole,
2-(4-fluorophenyl)-4-(2-methyl-1-propyl-1,2,3,6-tetrahydropyridin-4-yl)-3-(pyridin-4-yl)-1H-pyrrole,
2-(4-fluorophenyl)-4-(1,3,4,6,7,9a-hexahydro-2H-quinolizin-8-yl)-3-(pyridin-4-yl)-1H-pyrrole,
2-(4-fluorophenyl)-4-(1,3,4,6,9,9a-hexahydro-2H-quinolizin-8-yl)-3-(pyridin-4-yl)-1H-pyrrole,
2-(4-fluorophenyl)-4-(1,2,3,5,8,8a-hexahydroindolizin-7-yl)-3-(2-methylaminopyrimidin-4-yl)-1H-pyrrole,
2-(4-fluorophenyl)-4-(1,2,3,5,6,8a-hexahydroindolizin-7-yl)-3-(2-methylaminopyrimidin-4-yl)-1H-pyrrole,
2-(3,4-difluorophenyl)-4-(1,2,3,5,8,8a-hexahydroindolizin-7-yl)-3-(pyridin-4-yl)-1H-pyrrole,
2-(3,4-difluorophenyl)-4-(1,2,3,5,6,8a-hexahydroindolizin-7-yl)-3-(pyridin-4-yl)-1H-pyrrole,
4-(1,2,3,5,8,8a-hexahydroindolizin-7-yl)-3-(pyridin-4-yl)-2-(3-trifluoromethylphenyl)-1H-pyrrole,
4-(1,2,3,5,6,8a-hexahydroindolizin-7-yl)-3-(pyridin-4-yl)-2-(3-trifluoromethylphenyl)-1H-pyrrole,
2-(3-fluorophenyl)-4-(1,2,3,5,8,8a-hexahydroindolizin-7-yl)-3-(pyridin-4-yl)-1H-pyrrole,
2-(3-fluorophenyl)-4-(1,2,3,5,6,8a-hexahydroindolizin-7-yl)-3-(pyridin-4-yl)-1H-pyrrole,
2-(3-chlorophenyl)-4-(1,2,3,5,8,8a-hexahydroindolizin-7-yl)-3-(pyridin-4-yl)-1H-pyrrole,
2-(3-chlorophenyl)-4-(1,2,3,5,6,8a-hexahydroindolizin-7-yl)-3-(pyridin-4-yl)-1H-pyrrole,
4-(1,2,3,5,8,8a-hexahydroindolizin-7-yl)-2-phenyl-3-(pyridin-4-yl)-1H-pyrrole, and
4-(1,2,3,5,6,8a-hexahydroindolizin-7-yl)-2-phenyl-3-(pyridin-4-yl)-1H-pyrrole.

The most preferred compounds of the present invention are compounds of formula (I) selected from the following group of compounds, and pharmacologically acceptable salts, esters and other derivatives thereof:
2-(4-fluorophenyl)-3-(pyridin-4-yl)-4-(1,2,3,6-tetrahydropyridin-4-yl)-1H-pyrrole,
3-(4-fluorophenyl)-1-(piperidin-4-yl)-2-(pyridin-4-yl)-1H-pyrrole,
3-(4-fluorophenyl)-1-[3-(morpholin-1-yl)propyl]-2-(pyridin-4-yl)-1H-pyrrole,
4-(8-azabicyclo[3.2.1]oct-2-en-3-yl)-2-(4-fluorophenyl)-3-(pyridin-4-yl)-1H-pyrrole,
2-(4-fluorophenyl)-4-(6-methyl-1,2,3,6-tetrahydropyridin-4-yl)-3-(pyridin-4-yl)-1H-pyrrole,
4-(1-ethyl-1,2,3,6-tetrahydropyridin-4-yl)-2-(4-fluorophenyl)-3-(pyridin-4-yl)-1H-pyrrole,
2-(4-fluorophenyl)-4-(1-isopropyl-1,2,3,6-tetrahydropyridin-4-yl)-3-(pyridin-4-yl)-1H-pyrrole,
2-(4-fluorophenyl)-4-(1-propyl-1,2,3,6-tetrahydropyridin-4-yl)-3-(pyridin-4-yl)-1H-pyrrole,
2-(4-fluorophenyl)-4-(1-phenethyl-1,2,3,6-tetrahydropyridin-4-yl)-3-(pyridin-4-yl)-1H-pyrrole,
2-(4-fluorophenyl)-4-(1,2,3,5,6,8a-hexahydroindolizin-7-yl)-3-(pyridin-4-yl)-1H-pyrrole,
4-(1,6-dimethyl-1,2,3,6-tetrahydropyridin-4-yl)-2-(4-fluorophenyl)-3-(pyridin-4-yl)-1H-pyrrole,
4-(1,2-dimethyl-1,2,3,6-tetrahydropyridin-4-yl)-2-(4-fluorophenyl)-3-(pyridin-4-yl)-1H-pyrrole,
4-(1-ethyl-6-methyl-1,2,3,6-tetrahydropyridin-4-yl)-2-(4-fluorophenyl)-3-(pyridin-4-yl)-1H-pyrrole,
4-(1-ethyl-2-methyl-1,2,3,6-tetrahydropyridin-4-yl)-2-(4-fluorophenyl)-3-(pyridin-4-yl)-1H-pyrrole,
2-(4-fluorophenyl)-4-(6-methyl-1-propyl-1,2,3,6-tetrahydropyridin-4-yl)-3-(pyridin-4-yl)-1H-pyrrole,
2-(4-fluorophenyl)-4-(2-methyl-1-propyl-1,2,3,6-tetrahydropyridin-4-yl)-3-(pyridin-4-yl)-1H-pyrrole,
2-(4-fluorophenyl)-4-(1,3,4,6,7,9a-hexahydro-2H-quinolizin-8-yl)-3-(pyridin-4-yl)-1H-pyrrole,
2-(3,4-difluorophenyl)-4-(1,2,3,5,6,8a-hexahydroindolizin-7-yl)-3-(pyridin-4-yl)-1H-pyrrole, and
4-(1,2,3,5,6,8a-hexahydroindolizin-7-yl)-3-(pyridin-4-yl)-2-(3-trifluoromethylphenyl)-1H-pyrrole.

Specific examples of compounds of formula (I) of the present invention include the following compounds of formula (I-1) (Table 1) and formula (I-3) (Table 2).

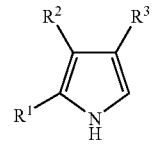
(I-1)

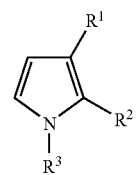
(I-3)

In these Tables, the following abbreviations are used:

| | |
|---|---|
| ABN | 9-azabicyclo[3.3.1]nonanyl |
| deH-ABN | dehydro[9-azabicyclo[3.3.1]nonanyl] (i.e. 9-azabicyclo[3.3.1]nonenyl) |
| ABO | 8-azabicyclo[3.2.1]octanyl |
| deH-ABO | dehydro[8-azabicyclo[3.2.1]octanyl] (i.e. 8-azabicyclo[3.2.1]octenyl) |
| Ac | acetyl |
| Azt | azetidinyl |
| Bn | benzyl |
| Bu | butyl |
| t-Bu | t-butyl |
| Bz | benzoyl |
| Et | ethyl |
| Hp | heptyl |
| Hpip | homopiperidinyl |
| Hx | hexyl |
| cHx | cyclohexyl |
| Ind | indolizinyl |
| Me | methyl |
| Mor | morpholinyl |
| Nn | nonyl |
| Oc | octyl |
| Ph | phenyl |
| Phet | phenethyl |
| Pip | piperidyl |
| deH-Pip | dehydropiperidyl (i.e. tetrahydropyridyl) |
| Piz | piperazinyl |
| Pn | pentyl |
| cPn | cyclopentyl |
| Pr | propyl |
| iPr | isopropyl |
| cPr | cyclopropyl |
| Pym | pyrimidinyl |
| Pyr | pyridyl |
| Pyrd | pyrrolidinyl |
| Qui | quinolizinyl |
| Qun | quinuclidinyl |
| deH-Qun | dehydroquinuclidinyl (i.e. quinuclidienyl) |
| Tmor | thiomorpholinyl. |

TABLE 1

| Compound No. | R¹ | R² | R³ |
|---|---|---|---|
| 1-1 | Ph | 4-Pyr | $H_2N-CH_2$ |
| 1-2 | Ph | 4-Pyr | $H_2N-(CH_2)_2$ |
| 1-3 | Ph | 4-Pyr | $H_2N-(CH_2)_3$ |
| 1-4 | Ph | 4-Pyr | $H_2N-(CH_2)_4$ |
| 1-5 | Ph | 4-Pyr | $MeNH-CH_2$ |
| 1-6 | Ph | 4-Pyr | $MeNH-(CH_2)_2$ |
| 1-7 | Ph | 4-Pyr | $MeNH-(CH_2)_3$ |
| 1-8 | Ph | 4-Pyr | $MeNH-(CH_2)_4$ |
| 1-9 | Ph | 4-Pyr | $EtNH-CH_2$ |
| 1-10 | Ph | 4-Pyr | $EtNH-(CH_2)_2$ |
| 1-11 | Ph | 4-Pyr | $EtNH-(CH_2)_3$ |
| 1-12 | Ph | 4-Pyr | $EtNH-(CH_2)_4$ |
| 1-13 | Ph | 4-Pyr | $Me_2N-CH_2$ |
| 1-14 | Ph | 4-Pyr | $Me_2N-(CH_2)_2$ |
| 1-15 | Ph | 4-Pyr | $Me_2N-(CH_2)_3$ |
| 1-16 | Ph | 4-Pyr | $Me_2N-(CH_2)_4$ |
| 1-17 | Ph | 4-Pyr | $1\text{-Azt-}CH_2$ |
| 1-18 | Ph | 4-Pyr | $1\text{-Azt-}(CH_2)_2$ |
| 1-19 | Ph | 4-Pyr | $1\text{-Azt-}(CH_2)_3$ |
| 1-20 | Ph | 4-Pyr | $1\text{-Azt-}(CH_2)_4$ |
| 1-21 | Ph | 4-Pyr | $1\text{-Pyrd-}CH_2$ |
| 1-22 | Ph | 4-Pyr | $1\text{-Pyrd-}(CH_2)_2$ |
| 1-23 | Ph | 4-Pyr | $1\text{-Pyrd-}(CH_2)_3$ |
| 1-24 | Ph | 4-Pyr | $1\text{-Pyrd-}(CH_2)_4$ |
| 1-25 | Ph | 4-Pyr | $1\text{-Pip-}CH_2$ |
| 1-26 | Ph | 4-Pyr | $1\text{-Pip-}(CH_2)_2$ |
| 1-27 | Ph | 4-Pyr | $1\text{-Pip-}(CH_2)_3$ |
| 1-28 | Ph | 4-Pyr | $1\text{-Pip-}(CH_2)_4$ |
| 1-29 | Ph | 4-Pyr | $1\text{-Mor-}CH_2$ |
| 1-30 | Ph | 4-Pyr | $1\text{-Mor-}(CH_2)_2$ |
| 1-31 | Ph | 4-Pyr | $1\text{-Mor-}(CH_2)_3$ |
| 1-32 | Ph | 4-Pyr | $1\text{-Mor-}(CH_2)_4$ |
| 1-33 | Ph | 4-Pyr | $1\text{-Tmor-}CH_2$ |
| 1-34 | Ph | 4-Pyr | $1\text{-Tmor-}(CH_2)_2$ |
| 1-35 | Ph | 4-Pyr | $1\text{-Tmor-}(CH_2)_3$ |
| 1-36 | Ph | 4-Pyr | $1\text{-Tmor-}(CH_2)_4$ |
| 1-37 | Ph | 4-Pyr | $1\text{-Piz-}CH_2$ |
| 1-38 | Ph | 4-Pyr | $1\text{-Piz-}(CH_2)_2$ |
| 1-39 | Ph | 4-Pyr | $1\text{-Piz-}(CH_2)_3$ |
| 1-40 | Ph | 4-Pyr | $4\text{-Me-1-Piz-}(CH_2)_3$ |
| 1-41 | Ph | 4-Pyr | $1\text{-Piz-}(CH_2)_4$ |
| 1-42 | Ph | 4-Pyr | 3-Azt |
| 1-43 | Ph | 4-Pyr | 1-Me-3-Azt |
| 1-44 | Ph | 4-Pyr | 1-Bn-3-Azt |
| 1-45 | Ph | 4-Pyr | 3-Pyrd |
| 1-46 | Ph | 4-Pyr | 1-Me-3-Pyrd |
| 1-47 | Ph | 4-Pyr | 3-Pip |
| 1-48 | Ph | 4-Pyr | 4-Pip |
| 1-49 | Ph | 4-Pyr | 4-(3,4-deH-Pip) |
| 1-50 | Ph | 4-Pyr | 1-Me-4-Pip |
| 1-51 | Ph | 4-Pyr | 1-Me-4-(3,4-deH-Pip) |
| 1-52 | Ph | 4-Pyr | 1-Et-4-Pip |
| 1-53 | Ph | 4-Pyr | 1-Bn-4-Pip |
| 1-54 | Ph | 4-Pyr | 3-Hpip |
| 1-55 | Ph | 4-Pyr | 1-Me-3-Hpip |
| 1-56 | Ph | 4-Pyr | 4-Hpip |
| 1-57 | Ph | 4-Pyr | 1-Me-4-Hpip |
| 1-58 | Ph | 4-Pyr | 2-Mor |
| 1-59 | Ph | 4-Pyr | 1-Me-2-Mor |
| 1-60 | Ph | 4-Pyr | 2-Tmor |
| 1-61 | Ph | 4-Pyr | 1-Me-2-Tmor |
| 1-62 | Ph | 4-Pyr | 1-Piz |
| 1-63 | Ph | 4-Pyr | 4-Me-1-Piz |
| 1-64 | Ph | 4-Pyr | 2-Piz |
| 1-65 | Ph | 4-Pyr | 4-Pyr |
| 1-66 | Ph | 4-Pyr | 3-Pyr |
| 1-67 | Ph | 4-Pyr | 2-Pyr |
| 1-68 | Ph | 4-Pyr | 4-Pym |
| 1-69 | Ph | 4-Pyr | 5-Pym |
| 1-70 | Ph | 4-Pyr | 2-Pym |
| 1-71 | Ph | 4-Pyr | $3\text{-Azt-}CH_2$ |
| 1-72 | Ph | 4-Pyr | $1\text{-Me-3-Azt-}CH_2$ |
| 1-73 | Ph | 4-Pyr | $3\text{-Pyrd-}CH_2$ |
| 1-74 | Ph | 4-Pyr | $1\text{-Me-3-Pyrd-}CH_2$ |
| 1-75 | Ph | 4-Pyr | $4\text{-Pip-}CH_2$ |
| 1-76 | Ph | 4-Pyr | $1\text{-Me-4-Pip-}CH_2$ |
| 1-77 | Ph | 4-Pyr | $3\text{-Hpip-}CH_2$ |
| 1-78 | Ph | 4-Pyr | $1\text{-Me-3-Hpip-}CH_2$ |
| 1-79 | Ph | 4-Pyr | $4\text{-Hpip-}CH_2$ |
| 1-80 | Ph | 4-Pyr | $1\text{-Me-4-Hpip-}CH_2$ |
| 1-81 | Ph | 4-Pyr | $2\text{-Mor-}CH_2$ |
| 1-82 | Ph | 4-Pyr | $1\text{-Me-2-Mor-}CH_2$ |
| 1-83 | Ph | 4-Pyr | $2\text{-Tmor-}CH_2$ |
| 1-84 | Ph | 4-Pyr | $1\text{-Me-2-Tmor-}CH_2$ |
| 1-85 | Ph | 4-Pyr | $1\text{-Piz-}CH_2$ |
| 1-86 | Ph | 4-Pyr | $4\text{-Me-1-Piz-}CH_2$ |
| 1-87 | Ph | 4-Pyr | $2\text{-Piz-}CH_2$ |
| 1-88 | Ph | 4-Pyr | $4\text{-Pyr-}CH_2$ |
| 1-89 | Ph | 4-Pyr | $3\text{-Pyr-}CH_2$ |
| 1-90 | Ph | 4-Pyr | $2\text{-Pyr-}CH_2$ |
| 1-91 | Ph | 4-Pyr | $4\text{-Pym-}CH_2$ |
| 1-92 | Ph | 4-Pyr | $5\text{-Pym-}CH_2$ |
| 1-93 | Ph | 4-Pyr | $2\text{-Pym-}CH_2$ |
| 1-94 | Ph | 4-Pyr | $H_2N-CH_2CH=CH$ |
| 1-95 | 4-F—Ph | 4-Pyr | $H_2N-CH_2$ |
| 1-96 | 4-F—Ph | 4-Pyr | $H_2N-(CH_2)_2$ |
| 1-97 | 4-F—Ph | 4-Pyr | $H_2N-(CH_2)_3$ |
| 1-98 | 4-F—Ph | 4-Pyr | $H_2N-(CH_2)_4$ |
| 1-99 | 4-F—Ph | 4-Pyr | $MeNH-CH_2$ |
| 1-100 | 4-F—Ph | 4-Pyr | $MeNH-(CH_2)_2$ |
| 1-101 | 4-F—Ph | 4-Pyr | $MeNH-(CH_2)_3$ |
| 1-102 | 4-F—Ph | 4-Pyr | $MeNH-(CH_2)_4$ |
| 1-103 | 4-F—Ph | 4-Pyr | $EtNH-CH_2$ |
| 1-104 | 4-F—Ph | 4-Pyr | $EtNH-(CH_2)_2$ |
| 1-105 | 4-F—Ph | 4-Pyr | $EtNH-(CH_2)_3$ |
| 1-106 | 4-F—Ph | 4-Pyr | $EtNH-(CH_2)_4$ |
| 1-107 | 4-F—Ph | 4-Pyr | $Me_2N-CH_2$ |
| 1-108 | 4-F—Ph | 4-Pyr | $Me_2N-(CH_2)_2$ |
| 1-109 | 4-F—Ph | 4-Pyr | $Me_2N-(CH_2)_3$ |
| 1-110 | 4-F—Ph | 4-Pyr | $Me_2N-(CH_2)_4$ |
| 1-111 | 4-F—Ph | 4-Pyr | $1\text{-Azt-}CH_2$ |
| 1-112 | 4-F—Ph | 4-Pyr | $1\text{-Azt-}(CH_2)_2$ |
| 1-113 | 4-F—Ph | 4-Pyr | $1\text{-Azt-}(CH_2)_3$ |
| 1-114 | 4-F—Ph | 4-Pyr | $1\text{-Azt-}(CH_2)_4$ |
| 1-115 | 4-F—Ph | 4-Pyr | $1\text{-Pyrd-}CH_2$ |
| 1-116 | 4-F—Ph | 4-Pyr | $1\text{-Pyrd-}(CH_2)_2$ |
| 1-117 | 4-F—Ph | 4-Pyr | $1\text{-Pyrd-}(CH_2)_3$ |
| 1-118 | 4-F—Ph | 4-Pyr | $1\text{-Pyrd-}(CH_2)_4$ |
| 1-119 | 4-F—Ph | 4-Pyr | $1\text{-Pip-}CH_2$ |
| 1-120 | 4-F—Ph | 4-Pyr | $1\text{-Pip-}(CH_2)_2$ |
| 1-121 | 4-F—Ph | 4-Pyr | $1\text{-Pip-}(CH_2)_3$ |
| 1-122 | 4-F—Ph | 4-Pyr | $1\text{-Pip-}(CH_2)_4$ |
| 1-123 | 4-F—Ph | 4-Pyr | $1\text{-Mor-}CH_2$ |
| 1-124 | 4-F—Ph | 4-Pyr | $1\text{-Mor-}(CH_2)_2$ |
| 1-125 | 4-F—Ph | 4-Pyr | $1\text{-Mor-}(CH_2)_3$ |
| 1-126 | 4-F—Ph | 4-Pyr | $1\text{-Mor-}(CH_2)_4$ |
| 1-127 | 4-F—Ph | 4-Pyr | $1\text{-Tmor-}CH_2$ |
| 1-128 | 4-F—Ph | 4-Pyr | $1\text{-Tmor-}(CH_2)_2$ |
| 1-129 | 4-F—Ph | 4-Pyr | $1\text{-Tmor-}(CH_2)_3$ |
| 1-130 | 4-F—Ph | 4-Pyr | $1\text{-Tmor-}(CH_2)_4$ |
| 1-131 | 4-F—Ph | 4-Pyr | $1\text{-Piz-}CH_2$ |
| 1-132 | 4-F—Ph | 4-Pyr | $1\text{-Piz-}(CH_2)_2$ |
| 1-133 | 4-F—Ph | 4-Pyr | $1\text{-Piz-}(CH_2)_3$ |
| 1-134 | 4-F—Ph | 4-Pyr | $4\text{-Me-1-Piz-}(CH_2)_3$ |
| 1-135 | 4-F—Ph | 4-Pyr | $4\text{-Bn-1-Piz-}(CH_2)_3$ |
| 1-136 | 4-F—Ph | 4-Pyr | 3-Azt |
| 1-137 | 4-F—Ph | 4-Pyr | 1-Me-3-Azt |
| 1-138 | 4-F—Ph | 4-Pyr | 1-Bn-3-Azt |
| 1-139 | 4-F—Ph | 4-Pyr | 3-Pyrd |
| 1-140 | 4-F—Ph | 4-Pyr | 1-Me-3-Pyrd |
| 1-141 | 4-F—Ph | 4-Pyr | 3-Pip |
| 1-142 | 4-F—Ph | 4-Pyr | 4-Pip |
| 1-143 | 4-F—Ph | 4-Pyr | 4-(3,4-deH-Pip) |
| 1-144 | 4-F—Ph | 4-Pyr | 1-Me-4-Pip |
| 1-145 | 4-F—Ph | 4-Pyr | 1-Me-4-(3,4-deH-Pip) |
| 1-146 | 4-F—Ph | 4-Pyr | 1-Et-4-Pip |
| 1-147 | 4-F—Ph | 4-Pyr | 1-Bn-4-Pip |
| 1-148 | 4-F—Ph | 4-Pyr | 3-Hpip |
| 1-149 | 4-F—Ph | 4-Pyr | 1-Me-3-Hpip |
| 1-150 | 4-F—Ph | 4-Pyr | 4-Hpip |
| 1-151 | 4-F—Ph | 4-Pyr | 1-Me-4-Hpip |
| 1-152 | 4-F—Ph | 4-Pyr | 2-Mor |

TABLE 1-continued

| Compound No. | R¹ | R² | R³ |
|---|---|---|---|
| 1-153 | 4-F—Ph | 4-Pyr | 1-Me-2-Mor |
| 1-154 | 4-F—Ph | 4-Pyr | 2-Tmor |
| 1-155 | 4-F—Ph | 4-Pyr | 1-Me-2-Tmor |
| 1-156 | 4-F—Ph | 4-Pyr | 1-Piz |
| 1-157 | 4-F—Ph | 4-Pyr | 4-Me-1-Piz |
| 1-158 | 4-F—Ph | 4-Pyr | 2-Piz |
| 1-159 | 4-F—Ph | 4-Pyr | 4-Pyr |
| 1-160 | 4-F—Ph | 4-Pyr | 3-Pyr |
| 1-161 | 4-F—Ph | 4-Pyr | 2-Pyr |
| 1-162 | 4-F—Ph | 4-Pyr | 4-Pym |
| 1-163 | 4-F—Ph | 4-Pyr | 5-Pym |
| 1-164 | 4-F—Ph | 4-Pyr | 2-Pym |
| 1-165 | 4-F—Ph | 4-Pyr | 3-Azt-CH$_2$ |
| 1-166 | 4-F—Ph | 4-Pyr | 1-Me-3-Azt-CH$_2$ |
| 1-167 | 4-F—Ph | 4-Pyr | 3-Pyrd-CH$_2$ |
| 1-168 | 4-F—Ph | 4-Pyr | 1-Me-3-Pyrd-CH$_2$ |
| 1-169 | 4-F—Ph | 4-Pyr | 4-Pip-CH$_2$ |
| 1-170 | 4-F—Ph | 4-Pyr | 1-Me-4-Pip-CH$_2$ |
| 1-171 | 4-F—Ph | 4-Pyr | 3-Hpip-CH$_2$ |
| 1-172 | 4-F—Ph | 4-Pyr | 1-Me-3-Hpip-CH$_2$ |
| 1-173 | 4-F—Ph | 4-Pyr | 4-Hpip-CH$_2$ |
| 1-174 | 4-F—Ph | 4-Pyr | 1-Me-4-Hpip-CH$_2$ |
| 1-175 | 4-F—Ph | 4-Pyr | 2-Mor-CH$_2$ |
| 1-176 | 4-F—Ph | 4-Pyr | 1-Me-2-Mor-CH$_2$ |
| 1-177 | 4-F—Ph | 4-Pyr | 2-Tmor-CH$_2$ |
| 1-178 | 4-F—Ph | 4-Pyr | 1-Me-2-Tmor-CH$_2$ |
| 1-179 | 4-F—Ph | 4-Pyr | 1-Piz-CH$_2$ |
| 1-180 | 4-F—Ph | 4-Pyr | 4-Me-1-Piz-CH$_2$ |
| 1-181 | 4-F—Ph | 4-Pyr | 2-Piz-CH$_2$ |
| 1-182 | 4-F—Ph | 4-Pyr | 4-Pyr-CH$_2$ |
| 1-183 | 4-F—Ph | 4-Pyr | 3-Pyr-CH$_2$ |
| 1-184 | 4-F—Ph | 4-Pyr | 2-Pyr-CH$_2$ |
| 1-185 | 4-F—Ph | 4-Pyr | 4-Pym-CH$_2$ |
| 1-186 | 4-F—Ph | 4-Pyr | 5-Pym-CH$_2$ |
| 1-187 | 4-F—Ph | 4-Pyr | 2-Pym-CH$_2$ |
| 1-188 | 3-F—Ph | 4-Pyr | H$_2$N—CH$_2$ |
| 1-189 | 3-F—Ph | 4-Pyr | H$_2$N—(CH$_2$)$_2$ |
| 1-190 | 3-F—Ph | 4-Pyr | H$_2$N—(CH$_2$)$_3$ |
| 1-191 | 3-F—Ph | 4-Pyr | H$_2$N—(CH$_2$)$_4$ |
| 1-192 | 3-F—Ph | 4-Pyr | MeNH—CH$_2$ |
| 1-193 | 3-F—Ph | 4-Pyr | MeNH—(CH$_2$)$_2$ |
| 1-194 | 3-F—Ph | 4-Pyr | MeNH—(CH$_2$)$_3$ |
| 1-195 | 3-F—Ph | 4-Pyr | MeNH—(CH$_2$)$_4$ |
| 1-196 | 3-F—Ph | 4-Pyr | EtNH—CH$_2$ |
| 1-197 | 3-F—Ph | 4-Pyr | EtNH—(CH$_2$)$_2$ |
| 1-198 | 3-F—Ph | 4-Pyr | EtNH—(CH$_2$)$_3$ |
| 1-199 | 3-F—Ph | 4-Pyr | EtNH—(CH$_2$)$_4$ |
| 1-200 | 3-F—Ph | 4-Pyr | Me$_2$N—CH$_2$ |
| 1-201 | 3-F—Ph | 4-Pyr | Me$_2$N—(CH$_2$)$_2$ |
| 1-202 | 3-F—Ph | 4-Pyr | Me$_2$N—(CH$_2$)$_3$ |
| 1-203 | 3-F—Ph | 4-Pyr | Me$_2$N—(CH$_2$)$_4$ |
| 1-204 | 3-F—Ph | 4-Pyr | 1-Azt-CH$_2$ |
| 1-205 | 3-F—Ph | 4-Pyr | 1-Azt-(CH$_2$)$_2$ |
| 1-206 | 3-F—Ph | 4-Pyr | 1-Azt-(CH$_2$)$_3$ |
| 1-207 | 3-F—Ph | 4-Pyr | 1-Azt-(CH$_2$)$_4$ |
| 1-208 | 3-F—Ph | 4-Pyr | 1-Pyrd-CH$_2$ |
| 1-209 | 3-F—Ph | 4-Pyr | 1-Pyrd-(CH$_2$)$_2$ |
| 1-210 | 3-F—Ph | 4-Pyr | 1-Pyrd-(CH$_2$)$_3$ |
| 1-211 | 3-F—Ph | 4-Pyr | 1-Pyrd-(CH$_2$)$_4$ |
| 1-212 | 3-F—Ph | 4-Pyr | 1-Pip-CH$_2$ |
| 1-213 | 3-F—Ph | 4-Pyr | 1-Pip-(CH$_2$)$_2$ |
| 1-214 | 3-F—Ph | 4-Pyr | 1-Pip-(CH$_2$)$_3$ |
| 1-215 | 3-F—Ph | 4-Pyr | 1-Pip-(CH$_2$)$_4$ |
| 1-216 | 3-F—Ph | 4-Pyr | 1-Mor-CH$_2$ |
| 1-217 | 3-F—Ph | 4-Pyr | 1-Mor-(CH$_2$)$_2$ |
| 1-218 | 3-F—Ph | 4-Pyr | 1-Mor-(CH$_2$)$_3$ |
| 1-219 | 3-F—Ph | 4-Pyr | 1-Mor-(CH$_2$)$_4$ |
| 1-220 | 3-F—Ph | 4-Pyr | 1-Tmor-CH$_2$ |
| 1-221 | 3-F—Ph | 4-Pyr | 1-Tmor-(CH$_2$)$_2$ |
| 1-222 | 3-F—Ph | 4-Pyr | 1-Tmor-(CH$_2$)$_3$ |
| 1-223 | 3-F—Ph | 4-Pyr | 1-Tmor-(CH$_2$)$_4$ |
| 1-224 | 3-F—Ph | 4-Pyr | 1-Piz-CH$_2$ |
| 1-225 | 3-F—Ph | 4-Pyr | 1-Piz-(CH$_2$)$_2$ |
| 1-226 | 3-F—Ph | 4-Pyr | 1-Piz-(CH$_2$)$_3$ |
| 1-227 | 3-F—Ph | 4-Pyr | 4-Me-1-Piz-(CH$_2$)$_3$ |
| 1-228 | 3-F—Ph | 4-Pyr | 1-Piz-(CH$_2$)$_4$ |
| 1-229 | 3-F—Ph | 4-Pyr | 3-Azt |
| 1-230 | 3-F—Ph | 4-Pyr | 1-Me-3-Azt |
| 1-231 | 3-F—Ph | 4-Pyr | 1-Bn-3-Azt |
| 1-232 | 3-F—Ph | 4-Pyr | 3-Pyrd |
| 1-233 | 3-F—Ph | 4-Pyr | 1-Me-3-Pyrd |
| 1-234 | 3-F—Ph | 4-Pyr | 3-Pip |
| 1-235 | 3-F—Ph | 4-Pyr | 4-Pip |
| 1-236 | 3-F—Ph | 4-Pyr | 4-(3,4-deH-Pip) |
| 1-237 | 3-F—Ph | 4-Pyr | 1-Me-4-Pip |
| 1-238 | 3-F—Ph | 4-Pyr | 1-Me-4-(3,4-deH-Pip) |
| 1-239 | 3-F—Ph | 4-Pyr | 1-Et-4-Pip |
| 1-240 | 3-F—Ph | 4-Pyr | 1-Bn-4-Pip |
| 1-241 | 3-F—Ph | 4-Pyr | 3-Hpip |
| 1-242 | 3-F—Ph | 4-Pyr | 1-Me-3-Hpip |
| 1-243 | 3-F—Ph | 4-Pyr | 4-Hpip |
| 1-244 | 3-F—Ph | 4-Pyr | 1-Me-4-Hpip |
| 1-245 | 3-F—Ph | 4-Pyr | 2-Mor |
| 1-246 | 3-F—Ph | 4-Pyr | 1-Me-2-Mor |
| 1-247 | 3-F—Ph | 4-Pyr | 2-Tmor |
| 1-248 | 3-F—Ph | 4-Pyr | 1-Me-2-Tmor |
| 1-249 | 3-F—Ph | 4-Pyr | 1-Piz |
| 1-250 | 3-F—Ph | 4-Pyr | 4-Me-1-Piz |
| 1-251 | 3-F—Ph | 4-Pyr | 2-Piz |
| 1-252 | 3-F—Ph | 4-Pyr | 4-Pyr |
| 1-253 | 3-F—Ph | 4-Pyr | 3-Pyr |
| 1-254 | 3-F—Ph | 4-Pyr | 2-Pyr |
| 1-255 | 3-F—Ph | 4-Pyr | 4-Pym |
| 1-256 | 3-F—Ph | 4-Pyr | 5-Pym |
| 1-257 | 3-F—Ph | 4-Pyr | 2-Pym |
| 1-258 | 3-F—Ph | 4-Pyr | 3-Azt-CH$_2$ |
| 1-259 | 3-F—Ph | 4-Pyr | 1-Me-3-Azt-CH$_2$ |
| 1-260 | 3-F—Ph | 4-Pyr | 3-Pyrd-CH$_2$ |
| 1-261 | 3-F—Ph | 4-Pyr | 1-Me-3-Pyrd-CH$_2$ |
| 1-262 | 3-F—Ph | 4-Pyr | 4-Pip-CH$_2$ |
| 1-263 | 3-F—Ph | 4-Pyr | 1-Me-4-Pip-CH$_2$ |
| 1-264 | 3-F—Ph | 4-Pyr | 3-Hpip-CH$_2$ |
| 1-265 | 3-F—Ph | 4-Pyr | 1-Me-3-Hpip-CH$_2$ |
| 1-266 | 3-F—Ph | 4-Pyr | 4-Hpip-CH$_2$ |
| 1-267 | 3-F—Ph | 4-Pyr | 1-Me-4-Hpip-CH$_2$ |
| 1-268 | 3-F—Ph | 4-Pyr | 2-Mor-CH$_2$ |
| 1-269 | 3-F—Ph | 4-Pyr | 1-Me-2-Mor-CH$_2$ |
| 1-270 | 3-F—Ph | 4-Pyr | 2-Tmor-CH$_2$ |
| 1-271 | 3-F—Ph | 4-Pyr | 1-Me-2-Tmor-CH$_2$ |
| 1-272 | 3-F—Ph | 4-Pyr | 1-Piz-CH$_2$ |
| 1-273 | 3-F—Ph | 4-Pyr | 4-Me-1-Piz-CH$_2$ |
| 1-274 | 3-F—Ph | 4-Pyr | 2-Piz-CH$_2$ |
| 1-275 | 3-F—Ph | 4-Pyr | 4-Pyr-CH$_2$ |
| 1-276 | 3-F—Ph | 4-Pyr | 3-Pyr-CH$_2$ |
| 1-277 | 3-F—Ph | 4-Pyr | 2-Pyr-CH$_2$ |
| 1-278 | 3-F—Ph | 4-Pyr | 4-Pym-CH$_2$ |
| 1-279 | 3-F—Ph | 4-Pyr | 5-Pym-CH$_2$ |
| 1-280 | 3-F—Ph | 4-Pyr | 2-Pym-CH$_2$ |
| 1-281 | 3,4-diF-Ph | 4-Pyr | H$_2$N—CH$_2$ |
| 1-282 | 3,4-diF-Ph | 4-Pyr | H$_2$N—(CH$_2$)$_2$ |
| 1-283 | 3,4-diF-Ph | 4-Pyr | H$_2$N—(CH$_2$)$_3$ |
| 1-284 | 3,4-diF-Ph | 4-Pyr | H$_2$N—(CH$_2$)$_4$ |
| 1-285 | 3,4-diF-Ph | 4-Pyr | MeNH—CH$_2$ |
| 1-286 | 3,4-diF-Ph | 4-Pyr | MeNH—(CH$_2$)$_2$ |
| 1-287 | 3,4-diF-Ph | 4-Pyr | MeNH—(CH$_2$)$_3$ |
| 1-288 | 3,4-diF-Ph | 4-Pyr | MeNH—(CH$_2$)$_4$ |
| 1-289 | 3,4-diF-Ph | 4-Pyr | EtNH—CH$_2$ |
| 1-290 | 3,4-diF-Ph | 4-Pyr | EtNH—(CH$_2$)$_2$ |
| 1-291 | 3,4-diF-Ph | 4-Pyr | EtNH—(CH$_2$)$_3$ |
| 1-292 | 3,4-diF-Ph | 4-Pyr | EtNH—(CH$_2$)$_4$ |
| 1-293 | 3,4-diF-Ph | 4-Pyr | Me$_2$N—CH$_2$ |
| 1-294 | 3,4-diF-Ph | 4-Pyr | Me$_2$N—(CH$_2$)$_2$ |
| 1-295 | 3,4-diF-Ph | 4-Pyr | Me$_2$N—(CH$_2$)$_3$ |
| 1-296 | 3,4-diF-Ph | 4-Pyr | Me$_2$N—(CH$_2$)$_4$ |
| 1-297 | 3,4-diF-Ph | 4-Pyr | 1-Azt-CH$_2$ |
| 1-298 | 3,4-diF-Ph | 4-Pyr | 1-Azt-(CH$_2$)$_2$ |
| 1-299 | 3,4-diF-Ph | 4-Pyr | 1-Azt-(CH$_2$)$_3$ |
| 1-300 | 3,4-diF-Ph | 4-Pyr | 1-Azt-(CH$_2$)$_4$ |
| 1-301 | 3,4-diF-Ph | 4-Pyr | 1-Pyrd-CH$_2$ |
| 1-302 | 3,4-diF-Ph | 4-Pyr | 1-Pyrd-(CH$_2$)$_2$ |
| 1-303 | 3,4-diF-Ph | 4-Pyr | 1-Pyrd-(CH$_2$)$_3$ |
| 1-304 | 3,4-diF-Ph | 4-Pyr | 1-Pyrd-(CH$_2$)$_4$ |

TABLE 1-continued

| Compound No. | R¹ | R² | R³ |
|---|---|---|---|
| 1-305 | 3,4-diF-Ph | 4-Pyr | 1-Pip-CH₂ |
| 1-306 | 3,4-diF-Ph | 4-Pyr | 1-Pip-(CH₂)₂ |
| 1-307 | 3,4-diF-Ph | 4-Pyr | 1-Pip-(CH₂)₃ |
| 1-308 | 3,4-diF-Ph | 4-Pyr | 1-Pip-(CH₂)₄ |
| 1-309 | 3,4-diF-Ph | 4-Pyr | 1-Mor-CH₂ |
| 1-310 | 3,4-diF-Ph | 4-Pyr | 1-Mor-(CH₂)₂ |
| 1-311 | 3,4-diF-Ph | 4-Pyr | 1-Mor-(CH₂)₃ |
| 1-312 | 3,4-diF-Ph | 4-Pyr | 1-Mor-(CH₂)₄ |
| 1-313 | 3,4-diF-Ph | 4-Pyr | 1-Tmor-CH₂ |
| 1-314 | 3,4-diF-Ph | 4-Pyr | 1-Tmor-(CH₂)₂ |
| 1-315 | 3,4-diF-Ph | 4-Pyr | 1-Tmor-(CH₂)₃ |
| 1-316 | 3,4-diF-Ph | 4-Pyr | 1-Tmor-(CH₂)₄ |
| 1-317 | 3,4-diF-Ph | 4-Pyr | 1-Piz-CH₂ |
| 1-318 | 3,4-diF-Ph | 4-Pyr | 1-Piz-(CH₂)₂ |
| 1-319 | 3,4-diF-Ph | 4-Pyr | 1-Piz-(CH₂)₃ |
| 1-320 | 3,4-diF-Ph | 4-Pyr | 4-Me-1-Piz-(CH₂)₃ |
| 1-321 | 3,4-diF-Ph | 4-Pyr | 1-Piz-(CH₂)₄ |
| 1-322 | 3,4-diF-Ph | 4-Pyr | 3-Azt |
| 1-323 | 3,4-diF-Ph | 4-Pyr | 1-Me-3-Azt |
| 1-324 | 3,4-diF-Ph | 4-Pyr | 1-Bn-3-Azt |
| 1-325 | 3,4-diF-Ph | 4-Pyr | 3-Pyrd |
| 1-326 | 3,4-diF-Ph | 4-Pyr | 1-Me-3-Pyrd |
| 1-327 | 3,4-diF-Ph | 4-Pyr | 3-Pip |
| 1-328 | 3,4-diF-Ph | 4-Pyr | 4-Pip |
| 1-329 | 3,4-diF-Ph | 4-Pyr | 4-(3,4-deH-Pip) |
| 1-330 | 3,4-diF-Ph | 4-Pyr | 1-Me-4-Pip |
| 1-331 | 3,4-diF-Ph | 4-Pyr | 1-Me-4-(3,4-deH-PiP) |
| 1-332 | 3,4-diF-Ph | 4-Pyr | 1-Et-4-Pip |
| 1-333 | 3,4-diF-Ph | 4-Pyr | 1-Bn-4-Pip |
| 1-334 | 3,4-diF-Ph | 4-Pyr | 3-Hpip |
| 1-335 | 3,4-diF-Ph | 4-Pyr | 1-Me-3-Hpip |
| 1-336 | 3,4-diF-Ph | 4-Pyr | 4-Hpip |
| 1-337 | 3,4-diF-Ph | 4-Pyr | 1-Me-4-Hpip |
| 1-338 | 3,4-diF-Ph | 4-Pyr | 2-Mor |
| 1-339 | 3,4-diF-Ph | 4-Pyr | 1-Me-2-Mor |
| 1-340 | 3,4-diF-Ph | 4-Pyr | 2-Tmor |
| 1-341 | 3,4-diF-Ph | 4-Pyr | 1-Me-2-Tmor |
| 1-342 | 3,4-diF-Ph | 4-Pyr | 1-Piz |
| 1-343 | 3,4-diF-Ph | 4-Pyr | 4-Me-1-Piz |
| 1-344 | 3,4-diF-Ph | 4-Pyr | 2-Piz |
| 1-345 | 3,4-diF-Ph | 4-Pyr | 4-Pyr |
| 1-346 | 3,4-diF-Ph | 4-Pyr | 3-Pyr |
| 1-347 | 3,4-diF-Ph | 4-Pyr | 2-Pyr |
| 1-348 | 3,4-diF-Ph | 4-Pyr | 4-Pym |
| 1-349 | 3,4-diF-Ph | 4-Pyr | 5-Pym |
| 1-350 | 3,4-diF-Ph | 4-Pyr | 2-Pym |
| 1-351 | 3,4-diF-Ph | 4-Pyr | 3-Azt-CH₂ |
| 1-352 | 3,4-diF-Ph | 4-Pyr | 1-Me-3-Azt-CH₂ |
| 1-353 | 3,4-diF-Ph | 4-Pyr | 3-Pyrd-CH₂ |
| 1-354 | 3,4-diF-Ph | 4-Pyr | 1-Me-3-Pyrd-CH₂ |
| 1-355 | 3,4-diF-Ph | 4-Pyr | 4-Pip-CH₂ |
| 1-356 | 3,4-diF-Ph | 4-Pyr | 1-Me-4-Pip-CH₂ |
| 1-357 | 3,4-diF-Ph | 4-Pyr | 3-Hpip-CH₂ |
| 1-358 | 3,4-diF-Ph | 4-Pyr | 1-Me-3-Hpip-CH₂ |
| 1-359 | 3,4-diF-Ph | 4-Pyr | 4-Hpip-CH₂ |
| 1-360 | 3,4-diF-Ph | 4-Pyr | 1-Me-4-Hpip-CH₂ |
| 1-361 | 3,4-diF-Ph | 4-Pyr | 2-Mor-CH₂ |
| 1-362 | 3,4-diF-Ph | 4-Pyr | 1-Me-2-Mor-CH₂ |
| 1-363 | 3,4-diF-Ph | 4-Pyr | 2-Tmor-CH₂ |
| 1-364 | 3,4-diF-Ph | 4-Pyr | 1-Me-2-Tmor-CH₂ |
| 1-365 | 3,4-diF-Ph | 4-Pyr | 1-Piz-CH₂ |
| 1-366 | 3,4-diF-Ph | 4-Pyr | 4-Me-1-Piz-CH₂ |
| 1-367 | 3,4-diF-Ph | 4-Pyr | 2-Piz-CH₂ |
| 1-368 | 3,4-diF-Ph | 4-Pyr | 4-Pyr-CH₂ |
| 1-369 | 3,4-diF-Ph | 4-Pyr | 3-Pyr-CH₂ |
| 1-370 | 3,4-diF-Ph | 4-Pyr | 2-Pyr-CH₂ |
| 1-371 | 3,4-diF-Ph | 4-Pyr | 4-Pym-CH₂ |
| 1-372 | 3,4-diF-Ph | 4-Pyr | 5-Pym-CH₂ |
| 1-373 | 3,4-diF-Ph | 4-Pyr | 2-Pym-CH₂ |
| 1-374 | 3-Cl—Ph | 4-Pyr | H₂N—CH₂ |
| 1-375 | 3-Cl—Ph | 4-Pyr | H₂N—(CH₂)₂ |
| 1-376 | 3-Cl—Ph | 4-Pyr | H₂N—(CH₂)₃ |
| 1-377 | 3-Cl—Ph | 4-Pyr | H₂N—(CH₂)₄ |
| 1-378 | 3-Cl—Ph | 4-Pyr | MeNH—CH₂ |
| 1-379 | 3-Cl—Ph | 4-Pyr | MeNH—(CH₂)₂ |
| 1-380 | 3-Cl—Ph | 4-Pyr | MeNH—(CH₂)₃ |
| 1-381 | 3-Cl—Ph | 4-Pyr | MeNH—(CH₂)₄ |
| 1-382 | 3-Cl—Ph | 4-Pyr | EtNH—CH₂ |
| 1-383 | 3-Cl—Ph | 4-Pyr | EtNH—(CH₂)₂ |
| 1-384 | 3-Cl—Ph | 4-Pyr | EtNH—(CH₂)₃ |
| 1-385 | 3-Cl—Ph | 4-Pyr | EtNH—(CH₂)₄ |
| 1-386 | 3-Cl—Ph | 4-Pyr | Me₂N—CH₂ |
| 1-387 | 3-Cl—Ph | 4-Pyr | Me₂N—(CH₂)₂ |
| 1-388 | 3-Cl—Ph | 4-Pyr | Me₂N—(CH₂)₃ |
| 1-389 | 3-Cl—Ph | 4-Pyr | Me₂N—(CH₂)₄ |
| 1-390 | 3-Cl—Ph | 4-Pyr | 1-Azt-CH₂ |
| 1-391 | 3-Cl—Ph | 4-Pyr | 1-Azt-(CH₂)₂ |
| 1-392 | 3-Cl—Ph | 4-Pyr | 1-Azt-(CH₂)₃ |
| 1-393 | 3-Cl—Ph | 4-Pyr | 1-Azt-(CH₂)₄ |
| 1-394 | 3-Cl—Ph | 4-Pyr | 1-Pyrd-CH₂ |
| 1-395 | 3-Cl—Ph | 4-Pyr | 1-Pyrd-(CH₂)₂ |
| 1-396 | 3-Cl—Ph | 4-Pyr | 1-Pyrd-(CH₂)₃ |
| 1-397 | 3-Cl—Ph | 4-Pyr | 1-Pyrd-(CH₂)₄ |
| 1-398 | 3-Cl—Ph | 4-Pyr | 1-Pip-CH₂ |
| 1-399 | 3-Cl—Ph | 4-Pyr | 1-Pip-(CH₂)₂ |
| 1-400 | 3-Cl—Ph | 4-Pyr | 1-Pip-(CH₂)₃ |
| 1-401 | 3-Cl—Ph | 4-Pyr | 1-Pip-(CH₂)₄ |
| 1-402 | 3-Cl—Ph | 4-Pyr | 1-Mor-CH₂ |
| 1-403 | 3-Cl—Ph | 4-Pyr | 1-Mor-(CH₂)₂ |
| 1-404 | 3-Cl—Ph | 4-Pyr | 1-Mor-(CH₂)₃ |
| 1-405 | 3-Cl—Ph | 4-Pyr | 1-Mor-(CH₂)₄ |
| 1-406 | 3-Cl—Ph | 4-Pyr | 1-Tmor-CH₂ |
| 1-407 | 3-Cl—Ph | 4-Pyr | 1-Tmor-(CH₂)₂ |
| 1-408 | 3-Cl—Ph | 4-Pyr | 1-Tmor-(CH₂)₃ |
| 1-409 | 3-Cl—Ph | 4-Pyr | 1-Tmor-(CH₂)₄ |
| 1-410 | 3-Cl—Ph | 4-Pyr | 1-Piz-CH₂ |
| 1-411 | 3-Cl—Ph | 4-Pyr | 1-Piz-(CH₂)₂ |
| 1-412 | 3-Cl—Ph | 4-Pyr | 1-Piz-(CH₂)₃ |
| 1-413 | 3-Cl—Ph | 4-Pyr | 4-Me-1-Piz-(CH₂)₃ |
| 1-414 | 3-Cl—Ph | 4-Pyr | 1-Piz-(CH₂)₄ |
| 1-415 | 3-Cl—Ph | 4-Pyr | 3-Azt |
| 1-416 | 3-Cl—Ph | 4-Pyr | 1-Me-3-Azt |
| 1-417 | 3-Cl—Ph | 4-Pyr | 1-Bn-3-Azt |
| 1-418 | 3-Cl—Ph | 4-Pyr | 3-Pyrd |
| 1-419 | 3-Cl—Ph | 4-Pyr | 1-Me-3-Pyrd |
| 1-420 | 3-Cl—Ph | 4-Pyr | 3-Pip |
| 1-421 | 3-Cl—Ph | 4-Pyr | 4-Pip |
| 1-422 | 3-Cl—Ph | 4-Pyr | 4-(3,4-deH-Pip) |
| 1-423 | 3-Cl—Ph | 4-Pyr | 1-Me-4-Pip |
| 1-424 | 3-Cl—Ph | 4-Pyr | 1-Me-4-(3,4-deH-Pip) |
| 1-425 | 3-Cl—Ph | 4-Pyr | 1-Et-4-Pip |
| 1-426 | 3-Cl—Ph | 4-Pyr | 1-Bn-4-Pip |
| 1-427 | 3-Cl—Ph | 4-Pyr | 3-Hpip |
| 1-428 | 3-Cl—Ph | 4-Pyr | 1-Me-3-Hpip |
| 1-429 | 3-Cl—Ph | 4-Pyr | 4-Hpip |
| 1-430 | 3-Cl—Ph | 4-Pyr | 1-Me-4-Hpip |
| 1-431 | 3-Cl—Ph | 4-Pyr | 2-Mor |
| 1-432 | 3-Cl—Ph | 4-Pyr | 1-Me-2-Mor |
| 1-433 | 3-Cl—Ph | 4-Pyr | 2-Tmor |
| 1-434 | 3-Cl—Ph | 4-Pyr | 1-Me-2-Tmor |
| 1-435 | 3-Cl—Ph | 4-Pyr | 1-Piz |
| 1-436 | 3-Cl—Ph | 4-Pyr | 4-Me-1-Piz |
| 1-437 | 3-Cl—Ph | 4-Pyr | 2-Piz |
| 1-438 | 3-Cl—Ph | 4-Pyr | 4-Pyr |
| 1-439 | 3-Cl—Ph | 4-Pyr | 3-Pyr |
| 1-440 | 3-Cl—Ph | 4-Pyr | 2-Pyr |
| 1-441 | 3-Cl—Ph | 4-Pyr | 4-Pym |
| 1-442 | 3-Cl—Ph | 4-Pyr | 5-Pym |
| 1-443 | 3-Cl—Ph | 4-Pyr | 2-Pym |
| 1-444 | 3-Cl—Ph | 4-Pyr | 3-Azt-CH₂ |
| 1-445 | 3-Cl—Ph | 4-Pyr | 1-Me-3-Azt-CH₂ |
| 1-446 | 3-Cl—Ph | 4-Pyr | 3-Pyrd-CH₂ |
| 1-447 | 3-Cl—Ph | 4-Pyr | 1-Me-3-Pyrd-CH₂ |
| 1-448 | 3-Cl—Ph | 4-Pyr | 4-Pip-CH₂ |
| 1-449 | 3-Cl—Ph | 4-Pyr | 1-Me-4-Pip-CH₂ |
| 1-450 | 3-Cl—Ph | 4-Pyr | 3-Hpip-CH₂ |
| 1-451 | 3-Cl—Ph | 4-Pyr | 1-Me-3-Hpip-CH₂ |
| 1-452 | 3-Cl—Ph | 4-Pyr | 4-Hpip-CH₂ |
| 1-453 | 3-Cl—Ph | 4-Pyr | 1-Me-4-Hpip-CH₂ |
| 1-454 | 3-Cl—Ph | 4-Pyr | 2-Mor-CH₂ |
| 1-455 | 3-Cl—Ph | 4-Pyr | 1-Me-2-Mor-CH₂ |
| 1-456 | 3-Cl—Ph | 4-Pyr | 2-Tmor-CH₂ |

TABLE 1-continued

| Compound No. | R¹ | R² | R³ |
|---|---|---|---|
| 1-457 | 3-Cl—Ph | 4-Pyr | 1-Me-2-Tmor-CH$_2$ |
| 1-458 | 3-Cl—Ph | 4-Pyr | 1-Piz-CH$_2$ |
| 1-459 | 3-Cl—Ph | 4-Pyr | 4-Me-1-Piz-CH$_2$ |
| 1-460 | 3-Cl—Ph | 4-Pyr | 2-Piz-CH$_2$ |
| 1-461 | 3-Cl—Ph | 4-Pyr | 4-Pyr-CH$_2$ |
| 1-462 | 3-Cl—Ph | 4-Pyr | 3-Pyr-CH$_2$ |
| 1-463 | 3-Cl—Ph | 4-Pyr | 2-Pyr-CH$_2$ |
| 1-464 | 3-Cl—Ph | 4-Pyr | 4-Pym-CH$_2$ |
| 1-465 | 3-Cl—Ph | 4-Pyr | 5-Pym-CH$_2$ |
| 1-466 | 3-Cl—Ph | 4-Pyr | 2-Pym-CH$_2$ |
| 1-467 | Ph | 2-NH$_2$-4-Pym | H$_2$N—CH$_2$ |
| 1-468 | Ph | 2-NH$_2$-4-Pym | H$_2$N—(CH$_2$)$_2$ |
| 1-469 | Ph | 2-NH$_2$-4-Pym | H$_2$N—(CH$_2$)$_3$ |
| 1-470 | Ph | 2-NH$_2$-4-Pym | H$_2$N—(CH$_2$)$_4$ |
| 1-471 | Ph | 2-NH$_2$-4-Pym | MeNH—CH$_2$ |
| 1-472 | Ph | 2-NH$_2$-4-Pym | MeNH—(CH$_2$)$_2$ |
| 1-473 | Ph | 2-NH$_2$-4-Pym | MeNH—(CH$_2$)$_3$ |
| 1-474 | Ph | 2-NH$_2$-4-Pym | MeNH—(CH$_2$)$_4$ |
| 1-475 | Ph | 2-NH$_2$-4-Pym | EtNH—CH$_2$ |
| 1-476 | Ph | 2-NH$_2$-4-Pym | EtNH—(CH$_2$)$_2$ |
| 1-477 | Ph | 2-NH$_2$-4-Pym | EtNH—(CH$_2$)$_3$ |
| 1-478 | Ph | 2-NH$_2$-4-Pym | EtNH—(CH$_2$)$_4$ |
| 1-479 | Ph | 2-NH$_2$-4-Pym | Me$_2$N—CH$_2$ |
| 1-480 | Ph | 2-NH$_2$-4-Pym | Me$_2$N—(CH$_2$)$_2$ |
| 1-481 | Ph | 2-NH$_2$-4-Pym | Me$_2$N—(CH$_2$)$_3$ |
| 1-482 | Ph | 2-NH$_2$-4-Pym | Me$_2$N—(CH$_2$)$_4$ |
| 1-483 | Ph | 2-NH$_2$-4-Pym | 1-Azt-CH$_2$ |
| 1-484 | Ph | 2-NH$_2$-4-Pym | 1-Azt-(CH$_2$)$_2$ |
| 1-485 | Ph | 2-NH$_2$-4-Pym | 1-Azt-(CH$_2$)$_3$ |
| 1-486 | Ph | 2-NH$_2$-4-Pym | 1-Azt-(CH$_2$)$_4$ |
| 1-487 | Ph | 2-NH$_2$-4-Pym | 1-Pyrd-CH$_2$ |
| 1-488 | Ph | 2-NH$_2$-4-Pym | 1-Pyrd-(CH$_2$)$_2$ |
| 1-489 | Ph | 2-NH$_2$-4-Pym | 1-Pyrd-(CH$_2$)$_3$ |
| 1-490 | Ph | 2-NH$_2$-4-Pym | 1-Pyrd-(CH$_2$)$_4$ |
| 1-491 | Ph | 2-NH$_2$-4-Pym | 1-Pip-CH$_2$ |
| 1-492 | Ph | 2-NH$_2$-4-Pym | 1-Pip-(CH$_2$)$_2$ |
| 1-493 | Ph | 2-NH$_2$-4-Pym | 1-Pip-(CH$_2$)$_3$ |
| 1-494 | Ph | 2-NH$_2$-4-Pym | 1-Pip-(CH$_2$)$_4$ |
| 1-495 | Ph | 2-NH$_2$-4-Pym | 1-Mor-CH$_2$ |
| 1-496 | Ph | 2-NH$_2$-4-Pym | 1-Mor-(CH$_2$)$_2$ |
| 1-497 | Ph | 2-NH$_2$-4-Pym | 1-Mor-(CH$_2$)$_3$ |
| 1-498 | Ph | 2-NH$_2$-4-Pym | 1-Mor-(CH$_2$)$_4$ |
| 1-499 | Ph | 2-NH$_2$-4-Pym | 1-Tmor-CH$_2$ |
| 1-500 | Ph | 2-NH$_2$-4-Pym | 1-Tmor-(CH$_2$)$_2$ |
| 1-501 | Ph | 2-NH$_2$-4-Pym | 1-Tmor-(CH$_2$)$_3$ |
| 1-502 | Ph | 2-NH$_2$-4-Pym | 1-Tmor-(CH$_2$)$_4$ |
| 1-503 | Ph | 2-NH$_2$-4-Pym | 1-Piz-CH$_2$ |
| 1-504 | Ph | 2-NH$_2$-4-Pym | 1-Piz-(CH$_2$)$_2$ |
| 1-505 | Ph | 2-NH$_2$-4-Pym | 1-Piz-(CH$_2$)$_3$ |
| 1-506 | Ph | 2-NH$_2$-4-Pym | 4-Me-1-Piz-(CH$_2$)$_3$ |
| 1-507 | Ph | 2-NH$_2$-4-Pym | 1-Piz-(CH$_2$)$_4$ |
| 1-508 | Ph | 2-NH$_2$-4-Pym | 3-Azt |
| 1-509 | Ph | 2-NH$_2$-4-Pym | 1-Me-3-Azt |
| 1-510 | Ph | 2-NH$_2$-4-Pym | 1-Bn-3-Azt |
| 1-511 | Ph | 2-NH$_2$-4-Pym | 3-Pyrd |
| 1-512 | Ph | 2-NH$_2$-4-Pym | 1-Me-3-Pyrd |
| 1-513 | Ph | 2-NH$_2$-4-Pym | 3-Pip |
| 1-514 | Ph | 2-NH$_2$-4-Pym | 4-Pip |
| 1-515 | Ph | 2-NH$_2$-4-Pym | 4-(3,4-deH-Pip) |
| 1-516 | Ph | 2-NH$_2$-4-Pym | 1-Me-4-Pip |
| 1-517 | Ph | 2-NH$_2$-4-Pym | 1-Me-4-(3,4-deH-Pip) |
| 1-518 | Ph | 2-NH$_2$-4-Pym | 1-Et-4-Pip |
| 1-519 | Ph | 2-NH$_2$-4-Pym | 1-Bn-4-Pip |
| 1-520 | Ph | 2-NH$_2$-4-Pym | 3-Hpip |
| 1-521 | Ph | 2-NH$_2$-4-Pym | 1-Me-3-Hpip |
| 1-522 | Ph | 2-NH$_2$-4-Pym | 4-Hpip |
| 1-523 | Ph | 2-NH$_2$-4-Pym | 1-Me-4-Hpip |
| 1-524 | Ph | 2-NH$_2$-4-Pym | 2-Mor |
| 1-525 | Ph | 2-NH$_2$-4-Pym | 1-Me-2-Mor |
| 1-526 | Ph | 2-NH$_2$-4-Pym | 2-Tmor |
| 1-527 | Ph | 2-NH$_2$-4-Pym | 1-Me-2-Tmor |
| 1-528 | Ph | 2-NH$_2$-4-Pym | 1-Piz |
| 1-529 | Ph | 2-NH$_2$-4-Pym | 4-Me-1-Piz |
| 1-530 | Ph | 2-NH$_2$-4-Pym | 2-Piz |
| 1-531 | Ph | 2-NH$_2$-4-Pym | 4-Pyr |
| 1-532 | Ph | 2-NH$_2$-4-Pym | 3-Pyr |
| 1-533 | Ph | 2-NH$_2$-4-Pym | 2-Pyr |
| 1-534 | Ph | 2-NH$_2$-4-Pym | 4-Pym |
| 1-535 | Ph | 2-NH$_2$-4-Pym | 5-Pym |
| 1-536 | Ph | 2-NH$_2$-4-Pym | 2-Pym |
| 1-537 | Ph | 2-NH$_2$-4-Pym | 3-Azt-CH$_2$ |
| 1-538 | Ph | 2-NH$_2$-4-Pym | 1-Me-3-Azt-CH$_2$ |
| 1-539 | Ph | 2-NH$_2$-4-Pym | 3-Pyrd-CH$_2$ |
| 1-540 | Ph | 2-NH$_2$-4-Pym | 1-Me-3-Pyrd-CH$_2$ |
| 1-541 | Ph | 2-NH$_2$-4-Pym | 4-Pip-CH$_2$ |
| 1-542 | Ph | 2-NH$_2$-4-Pym | 1-Me-4-Pip-CH$_2$ |
| 1-543 | Ph | 2-NH$_2$-4-Pym | 3-Hpip-CH$_2$ |
| 1-544 | Ph | 2-NH$_2$-4-Pym | 1-Me-3-Hpip-CH$_2$ |
| 1-545 | Ph | 2-NH$_2$-4-Pym | 4-Hpip-CH$_2$ |
| 1-546 | Ph | 2-NH$_2$-4-Pym | 1-Me-4-Hpip-CH$_2$ |
| 1-547 | Ph | 2-NH$_2$-4-Pym | 2-Mor-CH$_2$ |
| 1-548 | Ph | 2-NH$_2$-4-Pym | 1-Me-2-Mor-CH$_2$ |
| 1-549 | Ph | 2-NH$_2$-4-Pym | 2-Tmor-CH$_2$ |
| 1-550 | Ph | 2-NH$_2$-4-Pym | 1-Me-2-Tmor-CH$_2$ |
| 1-551 | Ph | 2-NH$_2$-4-Pym | 1-Piz-CH$_2$ |
| 1-552 | Ph | 2-NH$_2$-4-Pym | 4-Me-1-Piz-CH$_2$ |
| 1-553 | Ph | 2-NH$_2$-4-Pym | 2-Piz-CH$_2$ |
| 1-554 | Ph | 2-NH$_2$-4-Pym | 4-Pyr-CH$_2$ |
| 1-555 | Ph | 2-NH$_2$-4-Pym | 3-Pyr-CH$_2$ |
| 1-556 | Ph | 2-NH$_2$-4-Pym | 2-Pyr-CH$_2$ |
| 1-557 | Ph | 2-NH$_2$-4-Pym | 4-Pym-CH$_2$ |
| 1-558 | Ph | 2-NH$_2$-4-Pym | 5-Pym-CH$_2$ |
| 1-559 | Ph | 2-NH$_2$-4-Pym | 2-Pym-CH$_2$ |
| 1-560 | 4-F—Ph | 2-NH$_2$-4-Pym | H$_2$N—CH$_2$ |
| 1-561 | 4-F—Ph | 2-NH$_2$-4-Pym | H$_2$N—(CH$_2$)$_2$ |
| 1-562 | 4-F—Ph | 2-NH$_2$-4-Pym | H$_2$N—(CH$_2$)$_3$ |
| 1-563 | 4-F—Ph | 2-NH$_2$-4-Pym | H$_2$N—(CH$_2$)$_4$ |
| 1-564 | 4-F—Ph | 2-NH$_2$-4-Pym | MeNH—CH$_2$ |
| 1-565 | 4-F—Ph | 2-NH$_2$-4-Pym | MeNH—(CH$_2$)$_2$ |
| 1-566 | 4-F—Ph | 2-NH$_2$-4-Pym | MeNH—(CH$_2$)$_3$ |
| 1-567 | 4-F—Ph | 2-NH$_2$-4-Pym | MeNH—(CH$_2$)$_4$ |
| 1-568 | 4-F—Ph | 2-NH$_2$-4-Pym | EtNH—CH$_2$ |
| 1-569 | 4-F—Ph | 2-NH$_2$-4-Pym | EtNH—(CH$_2$)$_2$ |
| 1-570 | 4-F—Ph | 2-NH$_2$-4-Pym | EtNH—(CH$_2$)$_3$ |
| 1-571 | 4-F—Ph | 2-NH$_2$-4-Pym | EtNH—(CH$_2$)$_4$ |
| 1-572 | 4-F—Ph | 2-NH$_2$-4-Pym | Me$_2$N—CH$_2$ |
| 1-573 | 4-F—Ph | 2-NH$_2$-4-Pym | Me$_2$N—(CH$_2$)$_2$ |
| 1-574 | 4-F—Ph | 2-NH$_2$-4-Pym | Me$_2$N—(CH$_2$)$_3$ |
| 1-575 | 4-F—Ph | 2-NH$_2$-4-Pym | Me$_2$N—(CH$_2$)$_4$ |
| 1-576 | 4-F—Ph | 2-NH$_2$-4-Pym | 1-Azt-CH$_2$ |
| 1-577 | 4-F—Ph | 2-NH$_2$-4-Pym | 1-Azt-(CH$_2$)$_2$ |
| 1-578 | 4-F—Ph | 2-NH$_2$-4-Pym | 1-Azt-(CH$_2$)$_3$ |
| 1-579 | 4-F—Ph | 2-NH$_2$-4-Pym | 1-Azt-(CH$_2$)$_4$ |
| 1-580 | 4-F—Ph | 2-NH$_2$-4-Pym | 1-Pyrd-CH$_2$ |
| 1-581 | 4-F—Ph | 2-NH$_2$-4-Pym | 1-Pyrd-(CH$_2$)$_2$ |
| 1-582 | 4-F—Ph | 2-NH$_2$-4-Pym | 1-Pyrd-(CH$_2$)$_3$ |
| 1-583 | 4-F—Ph | 2-NH$_2$-4-Pym | 1-Pyrd-(CH$_2$)$_4$ |
| 1-584 | 4-F—Ph | 2-NH$_2$-4-Pym | 1-Pip-CH$_2$ |
| 1-585 | 4-F—Ph | 2-NH$_2$-4-Pym | 1-Pip-(CH$_2$)$_2$ |
| 1-586 | 4-F—Ph | 2-NH$_2$-4-Pym | 1-Pip-(CH$_2$)$_3$ |
| 1-587 | 4-F—Ph | 2-NH$_2$-4-Pym | 1-Pip-(CH$_2$)$_4$ |
| 1-588 | 4-F—Ph | 2-NH$_2$-4-Pym | 1-Mor-CH$_2$ |
| 1-589 | 4-F—Ph | 2-NH$_2$-4-Pym | 1-Mor-(CH$_2$)$_2$ |
| 1-590 | 4-F—Ph | 2-NH$_2$-4-Pym | 1-Mor-(CH$_2$)$_3$ |
| 1-591 | 4-F—Ph | 2-NH$_2$-4-Pym | 1-Mor-(CH$_2$)$_4$ |
| 1-592 | 4-F—Ph | 2-NH$_2$-4-Pym | 1-Tmor-CH$_2$ |
| 1-593 | 4-F—Ph | 2-NH$_2$-4-Pym | 1-Tmor-(CH$_2$)$_2$ |
| 1-594 | 4-F—Ph | 2-NH$_2$-4-Pym | 1-Tmor-(CH$_2$)$_3$ |
| 1-595 | 4-F—Ph | 2-NH$_2$-4-Pym | 1-Tmor-(CH$_2$)$_4$ |
| 1-596 | 4-F—Ph | 2-NH$_2$-4-Pym | 1-Piz-CH$_2$ |
| 1-597 | 4-F—Ph | 2-NH$_2$-4-Pym | 1-Piz-(CH$_2$)$_2$ |
| 1-598 | 4-F—Ph | 2-NH$_2$-4-Pym | 1-Piz-(CH$_2$)$_3$ |
| 1-599 | 4-F—Ph | 2-NH$_2$-4-Pym | 4-Me-1-Piz-(CH$_2$)$_3$ |
| 1-600 | 4-F—Ph | 2-NH$_2$-4-Pym | 1-Piz-(CH$_2$)$_4$ |
| 1-601 | 4-F—Ph | 2-NH$_2$-4-Pym | 3-Azt |
| 1-602 | 4-F—Ph | 2-NH$_2$-4-Pym | 1-Me-3-Azt |
| 1-603 | 4-F—Ph | 2-NH$_2$-4-Pym | 1-Bn-3-Azt |
| 1-604 | 4-F—Ph | 2-NH$_2$-4-Pym | 3-Pyrd |
| 1-605 | 4-F—Ph | 2-NH$_2$-4-Pym | 1-Me-3-Pyrd |
| 1-606 | 4-F—Ph | 2-NH$_2$-4-Pym | 3-Pip |
| 1-607 | 4-F—Ph | 2-NH$_2$-4-Pym | 4-Pip |
| 1-608 | 4-F—Ph | 2-NH$_2$-4-Pym | 4-(3,4-deH-Pip) |

TABLE 1-continued

| Compound No. | R$^1$ | R$^2$ | R$^3$ |
|---|---|---|---|
| 1-609 | 4-F—Ph | 2-NH$_2$-4-Pym | 1-Me-4-Pip |
| 1-610 | 4-F—Ph | 2-NH$_2$-4-Pym | 1-Me-4-(3,4-deH-Pip) |
| 1-611 | 4-F—Ph | 2-NH$_2$-4-Pym | 1-Et-4-Pip |
| 1-612 | 4-F—Ph | 2-NH$_2$-4-Pym | 1-Bn-4-Pip |
| 1-613 | 4-F—Ph | 2-NH$_2$-4-Pym | 3-Hpip |
| 1-614 | 4-F—Ph | 2-NH$_2$-4-Pym | 1-Me-3-Hpip |
| 1-615 | 4-F—Ph | 2-NH$_2$-4-Pym | 4-Hpip |
| 1-616 | 4-F—Ph | 2-NH$_2$-4-Pym | 1-Me-4-Hpip |
| 1-617 | 4-F—Ph | 2-NH$_2$-4-Pym | 2-Mor |
| 1-618 | 4-F—Ph | 2-NH$_2$-4-Pym | 1-Me-2-Mor |
| 1-619 | 4-F—Ph | 2-NH$_2$-4-Pym | 2-Tmor |
| 1-620 | 4-F—Ph | 2-NH$_2$-4-Pym | 1-Me-2-Tmor |
| 1-621 | 4-F—Ph | 2-NH$_2$-4-Pym | 1-Piz |
| 1-622 | 4-F—Ph | 2-NH$_2$-4-Pym | 4-Me-1-Piz |
| 1-623 | 4-F—Ph | 2-NH$_2$-4-Pym | 2-Piz |
| 1-624 | 4-F—Ph | 2-NH$_2$-4-Pym | 4-Pyr |
| 1-625 | 4-F—Ph | 2-NH$_2$-4-Pym | 3-Pyr |
| 1-626 | 4-F—Ph | 2-NH$_2$-4-Pym | 2-Pyr |
| 1-627 | 4-F—Ph | 2-NH$_2$-4-Pym | 4-Pym |
| 1-628 | 4-F—Ph | 2-NH$_2$-4-Pym | 5-Pym |
| 1-629 | 4-F—Ph | 2-NH$_2$-4-Pym | 2-Pym |
| 1-630 | 4-F—Ph | 2-NH$_2$-4-Pym | 3-Azt-CH$_2$ |
| 1-631 | 4-F—Ph | 2-NH$_2$-4-Pym | 1-Me-3-Azt-CH$_2$ |
| 1-632 | 4-F—Ph | 2-NH$_2$-4-Pym | 3-Pyrd-CH$_2$ |
| 1-633 | 4-F—Ph | 2-NH$_2$-4-Pym | 1-Me-3-Pyrd-CH$_2$ |
| 1-634 | 4-F—Ph | 2-NH$_2$-4-Pym | 4-Pip-CH$_2$ |
| 1-635 | 4-F—Ph | 2-NH$_2$-4-Pym | 1-Me-4-Pip-CH$_2$ |
| 1-636 | 4-F—Ph | 2-NH$_2$-4-Pym | 3-Hpip-CH$_2$ |
| 1-637 | 4-F—Ph | 2-NH$_2$-4-Pym | 1-Me-3-Hpip-CH$_2$ |
| 1-638 | 4-F—Ph | 2-NH$_2$-4-Pym | 4-Hpip-CH$_2$ |
| 1-639 | 4-F—Ph | 2-NH$_2$-4-Pym | 1-Me-4-Hpip-CH$_2$ |
| 1-640 | 4-F—Ph | 2-NH$_2$-4-Pym | 2-Mor-CH$_2$ |
| 1-641 | 4-F—Ph | 2-NH$_2$-4-Pym | 1-Me-2-Mor-CH$_2$ |
| 1-642 | 4-F—Ph | 2-NH$_2$-4-Pym | 2-Tmor-CH$_2$ |
| 1-643 | 4-F—Ph | 2-NH$_2$-4-Pym | 1-Me-2-Tmor-CH$_2$ |
| 1-644 | 4-F—Ph | 2-NH$_2$-4-Pym | 1-Piz-CH$_2$ |
| 1-645 | 4-F—Ph | 2-NH$_2$-4-Pym | 4-Me-1-Piz-CH$_2$ |
| 1-646 | 4-F—Ph | 2-NH$_2$-4-Pym | 2-Piz-CH$_2$ |
| 1-647 | 4-F—Ph | 2-NH$_2$-4-Pym | 4-Pyr-CH$_2$ |
| 1-648 | 4-F—Ph | 2-NH$_2$-4-Pym | 3-Pyr-CH$_2$ |
| 1-649 | 4-F—Ph | 2-NH$_2$-4-Pym | 2-Pyr-CH$_2$ |
| 1-650 | 4-F—Ph | 2-NH$_2$-4-Pym | 4-Pym-CH$_2$ |
| 1-651 | 4-F—Ph | 2-NH$_2$-4-Pym | 5-Pym-CH$_2$ |
| 1-652 | 4-F—Ph | 2-NH$_2$-4-Pym | 2-Pym-CH$_2$ |
| 1-653 | 3-F—Ph | 2-NH$_2$-4-Pym | H$_2$N—CH$_2$ |
| 1-654 | 3-F—Ph | 2-NH$_2$-4-Pym | H$_2$N—(CH$_2$)$_2$ |
| 1-655 | 3-F—Ph | 2-NH$_2$-4-Pym | H$_2$N—(CH$_2$)$_3$ |
| 1-656 | 3-F—Ph | 2-NH$_2$-4-Pym | H$_2$N—(CH$_2$)$_4$ |
| 1-657 | 3-F—Ph | 2-NH$_2$-4-Pym | MeNH—CH$_2$ |
| 1-658 | 3-F—Ph | 2-NH$_2$-4-Pym | MeNH—(CH$_2$)$_2$ |
| 1-659 | 3-F—Ph | 2-NH$_2$-4-Pym | MeNH—(CH$_2$)$_3$ |
| 1-660 | 3-F—Ph | 2-NH$_2$-4-Pym | MeNH—(CH$_2$)$_4$ |
| 1-661 | 3-F—Ph | 2-NH$_2$-4-Pym | EtNH—CH$_2$ |
| 1-662 | 3-F—Ph | 2-NH$_2$-4-Pym | EtNH—(CH$_2$)$_2$ |
| 1-663 | 3-F—Ph | 2-NH$_2$-4-Pym | EtNH—(CH$_2$)$_3$ |
| 1-664 | 3-F—Ph | 2-NH$_2$-4-Pym | EtNH—(CH$_2$)$_4$ |
| 1-665 | 3-F—Ph | 2-NH$_2$-4-Pym | Me$_2$N—CH$_2$ |
| 1-666 | 3-F—Ph | 2-NH$_2$-4-Pym | Me$_2$N—(CH$_2$)$_2$ |
| 1-667 | 3-F—Ph | 2-NH$_2$-4-Pym | Me$_2$N—(CH$_2$)$_3$ |
| 1-668 | 3-F—Ph | 2-NH$_2$-4-Pym | Me$_2$N—(CH$_2$)$_4$ |
| 1-669 | 3-F—Ph | 2-NH$_2$-4-Pym | 1-Azt-CH$_2$ |
| 1-670 | 3-F—Ph | 2-NH$_2$-4-Pym | 1-Azt-(CH$_2$)$_2$ |
| 1-671 | 3-F—Ph | 2-NH$_2$-4-Pym | 1-Azt-(CH$_2$)$_3$ |
| 1-672 | 3-F—Ph | 2-NH$_2$-4-Pym | 1-Azt-(CH$_2$)$_4$ |
| 1-673 | 3-F—Ph | 2-NH$_2$-4-Pym | 1-Pyrd-CH$_2$ |
| 1-674 | 3-F—Ph | 2-NH$_2$-4-Pym | 1-Pyrd-(CH$_2$)$_2$ |
| 1-675 | 3-F—Ph | 2-NH$_2$-4-Pym | 1-Pyrd-(CH$_2$)$_3$ |
| 1-676 | 3-F—Ph | 2-NH$_2$-4-Pym | 1-Pyrd-(CH$_2$)$_4$ |
| 1-677 | 3-F—Ph | 2-NH$_2$-4-Pym | 1-Pip-CH$_2$ |
| 1-678 | 3-F—Ph | 2-NH$_2$-4-Pym | 1-Pip-(CH$_2$)$_2$ |
| 1-679 | 3-F—Ph | 2-NH$_2$-4-Pym | 1-Pip-(CH$_2$)$_3$ |
| 1-680 | 3-F—Ph | 2-NH$_2$-4-Pym | 1-Pip-(CH$_2$)$_4$ |
| 1-681 | 3-F—Ph | 2-NH$_2$-4-Pym | 1-Mor-CH$_2$ |
| 1-682 | 3-F—Ph | 2-NH$_2$-4-Pym | 1-Mor-(CH$_2$)$_2$ |
| 1-683 | 3-F—Ph | 2-NH$_2$-4-Pym | 1-Mor-(CH$_2$)$_3$ |
| 1-684 | 3-F—Ph | 2-NH$_2$-4-Pym | 1-Mor-(CH$_2$)$_4$ |
| 1-685 | 3-F—Ph | 2-NH$_2$-4-Pym | 1-Tmor-CH$_2$ |
| 1-686 | 3-F—Ph | 2-NH$_2$-4-Pym | 1-Tmor-(CH$_2$)$_2$ |
| 1-687 | 3-F—Ph | 2-NH$_2$-4-Pym | 1-Tmor-(CH$_2$)$_3$ |
| 1-688 | 3-F—Ph | 2-NH$_2$-4-Pym | 1-Tmor-(CH$_2$)$_4$ |
| 1-689 | 3-F—Ph | 2-NH$_2$-4-Pym | 1-Piz-CH$_2$ |
| 1-690 | 3-F—Ph | 2-NH$_2$-4-Pym | 1-Piz-(CH$_2$)$_2$ |
| 1-691 | 3-F—Ph | 2-NH$_2$-4-Pym | 1-Piz-(CH$_2$)$_3$ |
| 1-692 | 3-F—Ph | 2-NH$_2$-4-Pym | 4-Me-1-Piz-(CH$_2$)$_3$ |
| 1-693 | 3-F—Ph | 2-NH$_2$-4-Pym | 1-Piz-(CH$_2$)$_4$ |
| 1-694 | 3-F—Ph | 2-NH$_2$-4-Pym | 3-Azt |
| 1-695 | 3-F—Ph | 2-NH$_2$-4-Pym | 1-Me-3-Azt |
| 1-696 | 3-F—Ph | 2-NH$_2$-4-Pym | 1-Bn-3-Azt |
| 1-697 | 3-F—Ph | 2-NH$_2$-4-Pym | 3-Pyrd |
| 1-698 | 3-F—Ph | 2-NH$_2$-4-Pym | 1-Me-3-Pyrd |
| 1-699 | 3-F—Ph | 2-NH$_2$-4-Pym | 3-Pip |
| 1-700 | 3-F—Ph | 2-NH$_2$-4-Pym | 4-Pip |
| 1-701 | 3-F—Ph | 2-NH$_2$-4-Pym | 4-(3,4-deH-Pip) |
| 1-702 | 3-F—Ph | 2-NH$_2$-4-Pym | 1-Me-4-Pip |
| 1-703 | 3-F—Ph | 2-NH$_2$-4-Pym | 1-Me-4-(3,4-deH-Pip) |
| 1-704 | 3-F—Ph | 2-NH$_2$-4-Pym | 1-Et-4-Pip |
| 1-705 | 3-F—Ph | 2-NH$_2$-4-Pym | 1-Bn-4-Pip |
| 1-706 | 3-F—Ph | 2-NH$_2$-4-Pym | 3-Hpip |
| 1-707 | 3-F—Ph | 2-NH$_2$-4-Pym | 1-Me-3-Hpip |
| 1-708 | 3-F—Ph | 2-NH$_2$-4-Pym | 4-Hpip |
| 1-709 | 3-F—Ph | 2-NH$_2$-4-Pym | 1-Me-4-Hpip |
| 1-710 | 3-F—Ph | 2-NH$_2$-4-Pym | 2-Mor |
| 1-711 | 3-F—Ph | 2-NH$_2$-4-Pym | 1-Me-2-Mor |
| 1-712 | 3-F—Ph | 2-NH$_2$-4-Pym | 2-Tmor |
| 1-713 | 3-F—Ph | 2-NH$_2$-4-Pym | 1-Me-2-Tmor |
| 1-714 | 3-F—Ph | 2-NH$_2$-4-Pym | 1-Piz |
| 1-715 | 3-F—Ph | 2-NH$_2$-4-Pym | 4-Me-1-Piz |
| 1-716 | 3-F—Ph | 2-NH$_2$-4-Pym | 2-Piz |
| 1-717 | 3-F—Ph | 2-NH$_2$-4-Pym | 4-Pyr |
| 1-718 | 3-F—Ph | 2-NH$_2$-4-Pym | 3-Pyr |
| 1-719 | 3-F—Ph | 2-NH$_2$-4-Pym | 2-Pyr |
| 1-720 | 3-F—Ph | 2-NH$_2$-4-Pym | 4-Pym |
| 1-721 | 3-F—Ph | 2-NH$_2$-4-Pym | 5-Pym |
| 1-722 | 3-F—Ph | 2-NH$_2$-4-Pym | 2-Pym |
| 1-723 | 3-F—Ph | 2-NH$_2$-4-Pym | 3-Azt-CH$_2$ |
| 1-724 | 3-F—Ph | 2-NH$_2$-4-Pym | 1-Me-3-Azt-CH$_2$ |
| 1-725 | 3-F—Ph | 2-NH$_2$-4-Pym | 3-Pyrd-CH$_2$ |
| 1-726 | 3-F—Ph | 2-NH$_2$-4-Pym | 1-Me-3-Pyrd-CH$_2$ |
| 1-727 | 3-F—Ph | 2-NH$_2$-4-Pym | 4-Pip-CH$_2$ |
| 1-728 | 3-F—Ph | 2-NH$_2$-4-Pym | 1-Me-4-Pip-CH$_2$ |
| 1-729 | 3-F—Ph | 2-NH$_2$-4-Pym | 3-Hpip-CH$_2$ |
| 1-730 | 3-F—Ph | 2-NH$_2$-4-Pym | 1-Me-3-Hpip-CH$_2$ |
| 1-731 | 3-F—Ph | 2-NH$_2$-4-Pym | 4-Hpip-CH$_2$ |
| 1-732 | 3-F—Ph | 2-NH$_2$-4-Pym | 1-Me-4-Hpip-CH$_2$ |
| 1-733 | 3-F—Ph | 2-NH$_2$-4-Pym | 2-Mor-CH$_2$ |
| 1-734 | 3-F—Ph | 2-NH$_2$-4-Pym | 1-Me-2-Mor-CH$_2$ |
| 1-735 | 3-F—Ph | 2-NH$_2$-4-Pym | 2-Tmor-CH$_2$ |
| 1-736 | 3-F—Ph | 2-NH$_2$-4-Pym | 1-Me-2-Tmor-CH$_2$ |
| 1-737 | 3-F—Ph | 2-NH$_2$-4-Pym | 1-Piz-CH$_2$ |
| 1-738 | 3-F—Ph | 2-NH$_2$-4-Pym | 4-Me-1-Piz-CH$_2$ |
| 1-739 | 3-F—Ph | 2-NH$_2$-4-Pym | 2-Piz-CH$_2$ |
| 1-740 | 3-F—Ph | 2-NH$_2$-4-Pym | 4-Pyr-CH$_2$ |
| 1-741 | 3-F—Ph | 2-NH$_2$-4-Pym | 3-Pyr-CH$_2$ |
| 1-742 | 3-F—Ph | 2-NH$_2$-4-Pym | 2-Pyr-CH$_2$ |
| 1-743 | 3-F—Ph | 2-NH$_2$-4-Pym | 4-Pym-CH$_2$ |
| 1-744 | 3-F—Ph | 2-NH$_2$-4-Pym | 5-Pym-CH$_2$ |
| 1-745 | 3-F—Ph | 2-NH$_2$-4-Pym | 2-Pym-CH$_2$ |
| 1-746 | 3,4-diF-Ph | 2-NH$_2$-4-Pym | H$_2$N—CH$_2$ |
| 1-747 | 3,4-diF-Ph | 2-NH$_2$-4-Pym | H$_2$N—(CH$_2$)$_2$ |
| 1-748 | 3,4-diF-Ph | 2-NH$_2$-4-Pym | H$_2$N—(CH$_2$)$_3$ |
| 1-749 | 3,4-diF-Ph | 2-NH$_2$-4-Pym | H$_2$N—(CH$_2$)$_4$ |
| 1-750 | 3,4-diF-Ph | 2-NH$_2$-4-Pym | MeNH—CH$_2$ |
| 1-751 | 3,4-diF-Ph | 2-NH$_2$-4-Pym | MeNH—(CH$_2$)$_2$ |
| 1-752 | 3,4-diF-Ph | 2-NH$_2$-4-Pym | MeNH—(CH$_2$)$_3$ |
| 1-753 | 3,4-diF-Ph | 2-NH$_2$-4-Pym | MeNH—(CH$_2$)$_4$ |
| 1-754 | 3,4-diF-Ph | 2-NH$_2$-4-Pym | EtNH—CH$_2$ |
| 1-755 | 3,4-diF-Ph | 2-NH$_2$-4-Pym | EtNH—(CH$_2$)$_2$ |
| 1-756 | 3,4-diF-Ph | 2-NH$_2$-4-Pym | EtNH—(CH$_2$)$_3$ |
| 1-757 | 3,4-diF-Ph | 2-NH$_2$-4-Pym | EtNH—(CH$_2$)$_4$ |
| 1-758 | 3,4-diF-Ph | 2-NH$_2$-4-Pym | Me$_2$N—CH$_2$ |
| 1-759 | 3,4-diF-Ph | 2-NH$_2$-4-Pym | Me$_2$N—(CH$_2$)$_2$ |
| 1-760 | 3,4-diF-Ph | 2-NH$_2$-4-Pym | Me$_2$N—(CH$_2$)$_3$ |

TABLE 1-continued

| Compound No. | R¹ | R² | R³ |
|---|---|---|---|
| 1-761 | 3,4-diF-Ph | 2-NH$_2$-4-Pym | Me$_2$N—(CH$_2$)$_4$ |
| 1-762 | 3,4-diF-Ph | 2-NH$_2$-4-Pym | 1-Azt-CH$_2$ |
| 1-763 | 3,4-diF-Ph | 2-NH$_2$-4-Pym | 1-Azt-(CH$_2$)$_2$ |
| 1-764 | 3,4-diF-Ph | 2-NH$_2$-4-Pym | 1-Azt-(CH$_2$)$_3$ |
| 1-765 | 3,4-diF-Ph | 2-NH$_2$-4-Pym | 1-Azt-(CH$_2$)$_4$ |
| 1-766 | 3,4-diF-Ph | 2-NH$_2$-4-Pym | 1-Pyrd-CH$_2$ |
| 1-767 | 3,4-diF-Ph | 2-NH$_2$-4-Pym | 1-Pyrd-(CH$_2$)$_2$ |
| 1-768 | 3,4-diF-Ph | 2-NH$_2$-4-Pym | 1-Pyrd-(CH$_2$)$_3$ |
| 1-769 | 3,4-diF-Ph | 2-NH$_2$-4-Pym | 1-Pyrd-(CH$_2$)$_4$ |
| 1-770 | 3,4-diF-Ph | 2-NH$_2$-4-Pym | 1-Pip-CH$_2$ |
| 1-771 | 3,4-diF-Ph | 2-NH$_2$-4-Pym | 1-Pip-(CH$_2$)$_2$ |
| 1-772 | 3,4-diF-Ph | 2-NH$_2$-4-Pym | 1-Pip-(CH$_2$)$_3$ |
| 1-773 | 3,4-diF-Ph | 2-NH$_2$-4-Pym | 1-Pip-(CH$_2$)$_4$ |
| 1-774 | 3,4-diF-Ph | 2-NH$_2$-4-Pym | 1-Mor-CH$_2$ |
| 1-775 | 3,4-diF-Ph | 2-NH$_2$-4-Pym | 1-Mor-(CH$_2$)$_2$ |
| 1-776 | 3,4-diF-Ph | 2-NH$_2$-4-Pym | 1-Mor-(CH$_2$)$_3$ |
| 1-777 | 3,4-diF-Ph | 2-NH$_2$-4-Pym | 1-Mor-(CH$_2$)$_4$ |
| 1-778 | 3,4-diF-Ph | 2-NH$_2$-4-Pym | 1-Tmor-CH$_2$ |
| 1-779 | 3,4-diF-Ph | 2-NH$_2$-4-Pym | 1-Tmor-(CH$_2$)$_2$ |
| 1-780 | 3,4-diF-Ph | 2-NH$_2$-4-Pym | 1-Tmor-(CH$_2$)$_3$ |
| 1-781 | 3,4-diF-Ph | 2-NH$_2$-4-Pym | 1-Tmor-(CH$_2$)$_4$ |
| 1-782 | 3,4-diF-Ph | 2-NH$_2$-4-Pym | 1-Piz-CH$_2$ |
| 1-783 | 3,4-diF-Ph | 2-NH$_2$-4-Pym | 1-Piz-(CH$_2$)$_2$ |
| 1-784 | 3,4-diF-Ph | 2-NH$_2$-4-Pym | 1-Piz-(CH$_2$)$_3$ |
| 1-785 | 3,4-diF-Ph | 2-NH$_2$-4-Pym | 4-Me-1-Piz-(CH$_2$)$_3$ |
| 1-786 | 3,4-diF-Ph | 2-NH$_2$-4-Pym | 1-Piz-(CH$_2$)$_4$ |
| 1-787 | 3,4-diF-Ph | 2-NH$_2$-4-Pym | 3-Azt |
| 1-788 | 3,4-diF-Ph | 2-NH$_2$-4-Pym | 1-Me-3-Azt |
| 1-789 | 3,4-diF-Ph | 2-NH$_2$-4-Pym | 1-Bn-3-Azt |
| 1-790 | 3,4-diF-Ph | 2-NH$_2$-4-Pym | 3-Pyrd |
| 1-791 | 3,4-diF-Ph | 2-NH$_2$-4-Pym | 1-Me-3-Pyrd |
| 1-792 | 3,4-diF-Ph | 2-NH$_2$-4-Pym | 3-Pip |
| 1-793 | 3,4-diF-Ph | 2-NH$_2$-4-Pym | 4-Pip |
| 1-794 | 3,4-diF-Ph | 2-NH$_2$-4-Pym | 4-(3,4-deH-Pip) |
| 1-795 | 3,4-diF-Ph | 2-NH$_2$-4-Pym | 1-Me-4-Pip |
| 1-796 | 3,4-diF-Ph | 2-NH$_2$-4-Pym | 1-Me-4-(3,4-deH-Pip) |
| 1-797 | 3,4-diF-Ph | 2-NH$_2$-4-Pym | 1-Et-4-Pip |
| 1-798 | 3,4-diF-Ph | 2-NH$_2$-4-Pym | 1-Bn-4-Pip |
| 1-799 | 3,4-diF-Ph | 2-NH$_2$-4-Pym | 3-Hpip |
| 1-800 | 3,4-diF-Ph | 2-NH$_2$-4-Pym | 1-Me-3-Hpip |
| 1-801 | 3,4-diF-Ph | 2-NH$_2$-4-Pym | 4-Hpip |
| 1-802 | 3,4-diF-Ph | 2-NH$_2$-4-Pym | 1-Me-4-Hpip |
| 1-803 | 3,4-diF-Ph | 2-NH$_2$-4-Pym | 2-Mor |
| 1-804 | 3,4-diF-Ph | 2-NH$_2$-4-Pym | 1-Me-2-Mor |
| 1-805 | 3,4-diF-Ph | 2-NH$_2$-4-Pym | 2-Tmor |
| 1-806 | 3,4-diF-Ph | 2-NH$_2$-4-Pym | 1-Me-2-Tmor |
| 1-807 | 3,4-diF-Ph | 2-NH$_2$-4-Pym | 1-Piz |
| 1-808 | 3,4-diF-Ph | 2-NH$_2$-4-Pym | 4-Me-1-Piz |
| 1-809 | 3,4-diF-Ph | 2-NH$_2$-4-Pym | 2-Piz |
| 1-810 | 3,4-diF-Ph | 2-NH$_2$-4-Pym | 4-Pyr |
| 1-811 | 3,4-diF-Ph | 2-NH$_2$-4-Pym | 3-Pyr |
| 1-812 | 3,4-diF-Ph | 2-NH$_2$-4-Pym | 2-Pyr |
| 1-813 | 3,4-diF-Ph | 2-NH$_2$-4-Pym | 4-Pym |
| 1-814 | 3,4-diF-Ph | 2-NH$_2$-4-Pym | 5-Pym |
| 1-815 | 3,4-diF-Ph | 2-NH$_2$-4-Pym | 2-Pym |
| 1-816 | 3,4-diF-Ph | 2-NH$_2$-4-Pym | 3-Azt-CH$_2$ |
| 1-817 | 3,4-diF-Ph | 2-NH$_2$-4-Pym | 1-Me-3-Azt-CH$_2$ |
| 1-818 | 3,4-diF-Ph | 2-NH$_2$-4-Pym | 3-Pyrd-CH$_2$ |
| 1-819 | 3,4-diF-Ph | 2-NH$_2$-4-Pym | 1-Me-3-Pyrd-CH$_2$ |
| 1-820 | 3,4-diF-Ph | 2-NH$_2$-4-Pym | 4-Pip-CH$_2$ |
| 1-821 | 3,4-diF-Ph | 2-NH$_2$-4-Pym | 1-Me-4-Pip-CH$_2$ |
| 1-822 | 3,4-diF-Ph | 2-NH$_2$-4-Pym | 3-Hpip-CH$_2$ |
| 1-823 | 3,4-diF-Ph | 2-NH$_2$-4-Pym | 1-Me-3-Hpip-CH$_2$ |
| 1-824 | 3,4-diF-Ph | 2-NH$_2$-4-Pym | 4-Hpip-CH$_2$ |
| 1-825 | 3,4-diF-Ph | 2-NH$_2$-4-Pym | 1-Me-4-Hpip-CH$_2$ |
| 1-826 | 3,4-diF-Ph | 2-NH$_2$-4-Pym | 2-Mor-CH$_2$ |
| 1-827 | 3,4-diF-Ph | 2-NH$_2$-4-Pym | 1-Me-2-Mor-CH$_2$ |
| 1-828 | 3,4-diF-Ph | 2-NH$_2$-4-Pym | 2-Tmor-CH$_2$ |
| 1-829 | 3,4-diF-Ph | 2-NH$_2$-4-Pym | 1-Me-2-Tmor-CH$_2$ |
| 1-830 | 3,4-diF-Ph | 2-NH$_2$-4-Pym | 1-Piz-CH$_2$ |
| 1-831 | 3,4-diF-Ph | 2-NH$_2$-4-Pym | 4-Me-1-Piz-CH$_2$ |
| 1-832 | 3,4-diF-Ph | 2-NH$_2$-4-Pym | 2-Piz-CH$_2$ |
| 1-833 | 3,4-diF-Ph | 2-NH$_2$-4-Pym | 4-Pyr-CH$_2$ |
| 1-834 | 3,4-diF-Ph | 2-NH$_2$-4-Pym | 3-Pyr-CH$_2$ |
| 1-835 | 3,4-diF-Ph | 2-NH$_2$-4-Pym | 2-Pyr-CH$_2$ |
| 1-836 | 3,4-diF-Ph | 2-NH$_2$-4-Pym | 4-Pym-CH$_2$ |
| 1-837 | 3,4-diF-Ph | 2-NH$_2$-4-Pym | 5-Pym-CH$_2$ |
| 1-838 | 3,4-diF-Ph | 2-NH$_2$-4-Pym | 2-Pym-CH$_2$ |
| 1-839 | 3-Cl—Ph | 2-NH$_2$-4-Pym | H$_2$N—CH$_2$ |
| 1-840 | 3-Cl—Ph | 2-NH$_2$-4-Pym | H$_2$N—(CH$_2$)$_2$ |
| 1-841 | 3-Cl—Ph | 2-NH$_2$-4-Pym | H$_2$N—(CH$_2$)$_3$ |
| 1-842 | 3-Cl—Ph | 2-NH$_2$-4-Pym | H$_2$N—(CH$_2$)$_4$ |
| 1-843 | 3-Cl—Ph | 2-NH$_2$-4-Pym | MeNH—CH$_2$ |
| 1-844 | 3-Cl—Ph | 2-NH$_2$-4-Pym | MeNH—(CH$_2$)$_2$ |
| 1-845 | 3-Cl—Ph | 2-NH$_2$-4-Pym | MeNH—(CH$_2$)$_3$ |
| 1-846 | 3-Cl—Ph | 2-NH$_2$-4-Pym | MeNH—(CH$_2$)$_4$ |
| 1-847 | 3-Cl—Ph | 2-NH$_2$-4-Pym | EtNH—CH$_2$ |
| 1-848 | 3-Cl—Ph | 2-NH$_2$-4-Pym | EtNH—(CH$_2$)$_2$ |
| 1-849 | 3-Cl—Ph | 2-NH$_2$-4-Pym | EtNH—(CH$_2$)$_3$ |
| 1-850 | 3-Cl—Ph | 2-NH$_2$-4-Pym | EtNH—(CH$_2$)$_4$ |
| 1-851 | 3-Cl—Ph | 2-NH$_2$-4-Pym | Me$_2$N—CH$_2$ |
| 1-852 | 3-Cl—Ph | 2-NH$_2$-4-Pym | Me$_2$N—(CH$_2$)$_2$ |
| 1-853 | 3-Cl—Ph | 2-NH$_2$-4-Pym | Me$_2$N—(CH$_2$)$_3$ |
| 1-854 | 3-Cl—Ph | 2-NH$_2$-4-Pym | Me$_2$N—(CH$_2$)$_4$ |
| 1-855 | 3-Cl—Ph | 2-NH$_2$-4-Pym | 1-Azt-CH$_2$ |
| 1-856 | 3-Cl—Ph | 2-NH$_2$-4-Pym | 1-Azt-(CH$_2$)$_2$ |
| 1-857 | 3-Cl—Ph | 2-NH$_2$-4-Pym | 1-Azt-(CH$_2$)$_3$ |
| 1-858 | 3-Cl—Ph | 2-NH$_2$-4-Pym | 1-Azt-(CH$_2$)$_4$ |
| 1-859 | 3-Cl—Ph | 2-NH$_2$-4-Pym | 1-Pyrd-CH$_2$ |
| 1-860 | 3-Cl—Ph | 2-NH$_2$-4-Pym | 1-Pyrd-(CH$_2$)$_2$ |
| 1-861 | 3-Cl—Ph | 2-NH$_2$-4-Pym | 1-Pyrd-(CH$_2$)$_3$ |
| 1-862 | 3-Cl—Ph | 2-NH$_2$-4-Pym | 1-Pyrd-(CH$_2$)$_4$ |
| 1-863 | 3-Cl—Ph | 2-NH$_2$-4-Pym | 1-Pip-CH$_2$ |
| 1-864 | 3-Cl—Ph | 2-NH$_2$-4-Pym | 1-Pip-(CH$_2$)$_2$ |
| 1-865 | 3-Cl—Ph | 2-NH$_2$-4-Pym | 1-Pip-(CH$_2$)$_3$ |
| 1-866 | 3-Cl—Ph | 2-NH$_2$-4-Pym | 1-Pip-(CH$_2$)$_4$ |
| 1-867 | 3-Cl—Ph | 2-NH$_2$-4-Pym | 1-Mor-CH$_2$ |
| 1-868 | 3-Cl—Ph | 2-NH$_2$-4-Pym | 1-Mor-(CH$_2$)$_2$ |
| 1-869 | 3-Cl—Ph | 2-NH$_2$-4-Pym | 1-Mor-(CH$_2$)$_3$ |
| 1-870 | 3-Cl—Ph | 2-NH$_2$-4-Pym | 1-Mor-(CH$_2$)$_4$ |
| 1-871 | 3-Cl—Ph | 2-NH$_2$-4-Pym | 1-Tmor-CH$_2$ |
| 1-872 | 3-Cl—Ph | 2-NH$_2$-4-Pym | 1-Tmor-(CH$_2$)$_2$ |
| 1-873 | 3-Cl—Ph | 2-NH$_2$-4-Pym | 1-Tmor-(CH$_2$)$_3$ |
| 1-874 | 3-Cl—Ph | 2-NH$_2$-4-Pym | 1-Tmor-(CH$_2$)$_4$ |
| 1-875 | 3-Cl—Ph | 2-NH$_2$-4-Pym | 1-Piz-CH$_2$ |
| 1-876 | 3-Cl—Ph | 2-NH$_2$-4-Pym | 1-Piz-(CH$_2$)$_2$ |
| 1-877 | 3-Cl—Ph | 2-NH$_2$-4-Pym | 1-Piz-(CH$_2$)$_3$ |
| 1-878 | 3-Cl—Ph | 2-NH$_2$-4-Pym | 4-Me-1-Piz-(CH$_2$)$_3$ |
| 1-879 | 3-Cl—Ph | 2-NH$_2$-4-Pym | 1-Piz-(CH$_2$)$_4$ |
| 1-880 | 3-Cl—Ph | 2-NH$_2$-4-Pym | 3-Azt |
| 1-881 | 3-Cl—Ph | 2-NH$_2$-4-Pym | 1-Me-3-Azt |
| 1-882 | 3-Cl—Ph | 2-NH$_2$-4-Pym | 1-Bn-3-Azt |
| 1-883 | 3-Cl—Ph | 2-NH$_2$-4-Pym | 3-Pyrd |
| 1-884 | 3-Cl—Ph | 2-NH$_2$-4-Pym | 1-Me-3-Pyrd |
| 1-885 | 3-Cl—Ph | 2-NH$_2$-4-Pym | 3-Pip |
| 1-886 | 3-Cl—Ph | 2-NH$_2$-4-Pym | 4-Pip |
| 1-887 | 3-Cl—Ph | 2-NH$_2$-4-Pym | 4-(3,4-deH-Pip) |
| 1-888 | 3-Cl—Ph | 2-NH$_2$-4-Pym | 1-Me-4-Pip |
| 1-889 | 3-Cl—Ph | 2-NH$_2$-4-Pym | 1-Me-4-(3,4-deH-Pip) |
| 1-890 | 3-Cl—Ph | 2-NH$_2$-4-Pym | 1-Et-4-Pip |
| 1-891 | 3-Cl—Ph | 2-NH$_2$-4-Pym | 1-Bn-4-Pip |
| 1-892 | 3-Cl—Ph | 2-NH$_2$-4-Pym | 3-Hpip |
| 1-893 | 3-Cl—Ph | 2-NH$_2$-4-Pym | 1-Me-3-Hpip |
| 1-894 | 3-Cl—Ph | 2-NH$_2$-4-Pym | 4-Hpip |
| 1-895 | 3-Cl—Ph | 2-NH$_2$-4-Pym | 1-Me-4-Hpip |
| 1-896 | 3-Cl—Ph | 2-NH$_2$-4-Pym | 2-Mor |
| 1-897 | 3-Cl—Ph | 2-NH$_2$-4-Pym | 1-Me-2-Mor |
| 1-898 | 3-Cl—Ph | 2-NH$_2$-4-Pym | 2-Tmor |
| 1-899 | 3-Cl—Ph | 2-NH$_2$-4-Pym | 1-Me-2-Tmor |
| 1-900 | 3-Cl—Ph | 2-NH$_2$-4-Pym | 1-Piz |
| 1-901 | 3-Cl—Ph | 2-NH$_2$-4-Pym | 4-Me-1-Piz |
| 1-902 | 3-Cl—Ph | 2-NH$_2$-4-Pym | 2-Piz |
| 1-903 | 3-Cl—Ph | 2-NH$_2$-4-Pym | 4-Pyr |
| 1-904 | 3-Cl—Ph | 2-NH$_2$-4-Pym | 3-Pyr |
| 1-905 | 3-Cl—Ph | 2-NH$_2$-4-Pym | 2-Pyr |
| 1-906 | 3-Cl—Ph | 2-NH$_2$-4-Pym | 4-Pym |
| 1-907 | 3-Cl—Ph | 2-NH$_2$-4-Pym | 5-Pym |
| 1-908 | 3-Cl—Ph | 2-NH$_2$-4-Pym | 2-Pym |
| 1-909 | 3-Cl—Ph | 2-NH$_2$-4-Pym | 3-Azt-CH$_2$ |
| 1-910 | 3-Cl—Ph | 2-NH$_2$-4-Pym | 1-Me-3-Azt-CH$_2$ |
| 1-911 | 3-Cl—Ph | 2-NH$_2$-4-Pym | 3-Pyrd-CH$_2$ |
| 1-912 | 3-Cl—Ph | 2-NH$_2$-4-Pym | 1-Me-3-Pyrd-CH$_2$ |

TABLE 1-continued

| Compound No. | R¹ | R² | R³ |
|---|---|---|---|
| 1-913 | 3-Cl—Ph | 2-NH₂-4-Pym | 4-Pip-CH₂ |
| 1-914 | 3-Cl—Ph | 2-NH₂-4-Pym | 1-Me-4-Pip-CH₂ |
| 1-915 | 3-Cl—Ph | 2-NH₂-4-Pym | 3-Hpip-CH₂ |
| 1-916 | 3-Cl—Ph | 2-NH₂-4-Pym | 1-Me-3-Hpip-CH₂ |
| 1-917 | 3-Cl—Ph | 2-NH₂-4-Pym | 4-Hpip-CH₂ |
| 1-918 | 3-Cl—Ph | 2-NH₂-4-Pym | 1-Me-4-Hpip-CH₂ |
| 1-919 | 3-Cl—Ph | 2-NH₂-4-Pym | 2-Mor-CH₂ |
| 1-920 | 3-Cl—Ph | 2-NH₂-4-Pym | 1-Me-2-Mor-CH₂ |
| 1-921 | 3-Cl—Ph | 2-NH₂-4-Pym | 2-Tmor-CH₂ |
| 1-922 | 3-Cl—Ph | 2-NH₂-4-Pym | 1-Me-2-Tmor-CH₂ |
| 1-923 | 3-Cl—Ph | 2-NH₂-4-Pym | 1-Piz-CH₂ |
| 1-924 | 3-Cl—Ph | 2-NH₂-4-Pym | 4-Me-1-Piz-CH₂ |
| 1-925 | 3-Cl—Ph | 2-NH₂-4-Pym | 2-Piz-CH₂ |
| 1-926 | 3-Cl—Ph | 2-NH₂-4-Pym | 4-Pyr-CH₂ |
| 1-927 | 3-Cl—Ph | 2-NH₂-4-Pym | 3-Pyr-CH₂ |
| 1-928 | 3-Cl—Ph | 2-NH₂-4-Pym | 2-Pyr-CH₂ |
| 1-929 | 3-Cl—Ph | 2-NH₂-4-Pym | 4-Pym-CH₂ |
| 1-930 | 3-Cl—Ph | 2-NH₂-4-Pym | 5-Pym-CH₂ |
| 1-931 | 3-Cl—Ph | 2-NH₂-4-Pym | 2-Pym-CH₂ |
| 1-932 | Ph | 2-MeNH-4-Pym | H₂N—CH₂ |
| 1-933 | Ph | 2-MeNH-4-Pym | H₂N—(CH₂)₂ |
| 1-934 | Ph | 2-MeNH-4-Pym | H₂N—(CH₂)₃ |
| 1-935 | Ph | 2-MeNH-4-Pym | H₂N—(CH₂)₄ |
| 1-936 | Ph | 2-MeNH-4-Pym | MeNH—CH₂ |
| 1-937 | Ph | 2-MeNH-4-Pym | MeNH—(CH₂)₂ |
| 1-938 | Ph | 2-MeNH-4-Pym | MeNH—(CH₂)₃ |
| 1-939 | Ph | 2-MeNH-4-Pym | MeNH—(CH₂)₄ |
| 1-940 | Ph | 2-MeNH-4-Pym | EtNH—CH₂ |
| 1-941 | Ph | 2-MeNH-4-Pym | EtNH—(CH₂)₂ |
| 1-942 | Ph | 2-MeNH-4-Pym | EtNH—(CH₂)₃ |
| 1-943 | Ph | 2-MeNH-4-Pym | EtNH—(CH₂)₄ |
| 1-944 | Ph | 2-MeNH-4-Pym | Me₂N—CH₂ |
| 1-945 | Ph | 2-MeNH-4-Pym | Me₂N—(CH₂)₂ |
| 1-946 | Ph | 2-MeNH-4-Pym | Me₂N—(CH₂)₃ |
| 1-947 | Ph | 2-MeNH-4-Pym | Me₂N—(CH₂)₄ |
| 1-948 | Ph | 2-MeNH-4-Pym | 1-Azt-CH₂ |
| 1-949 | Ph | 2-MeNH-4-Pym | 1-Azt-(CH₂)₂ |
| 1-950 | Ph | 2-MeNH-4-Pym | 1-Azt-(CH₂)₃ |
| 1-951 | Ph | 2-MeNH-4-Pym | 1-Azt-(CH₂)₄ |
| 1-952 | Ph | 2-MeNH-4-Pym | 1-Pyrd-CH₂ |
| 1-953 | Ph | 2-MeNH-4-Pym | 1-Pyrd-(CH₂)₂ |
| 1-954 | Ph | 2-MeNH-4-Pym | 1-Pyrd-(CH₂)₃ |
| 1-955 | Ph | 2-MeNH-4-Pym | 1-Pyrd-(CH₂)₄ |
| 1-956 | Ph | 2-MeNH-4-Pym | 1-Pip-CH₂ |
| 1-957 | Ph | 2-MeNH-4-Pym | 1-Pip-(CH₂)₂ |
| 1-958 | Ph | 2-MeNH-4-Pym | 1-Pip-(CH₂)₃ |
| 1-959 | Ph | 2-MeNH-4-Pym | 1-Pip-(CH₂)₄ |
| 1-960 | Ph | 2-MeNH-4-Pym | 1-Mor-CH₂ |
| 1-961 | Ph | 2-MeNH-4-Pym | 1-Mor-(CH₂)₂ |
| 1-962 | Ph | 2-MeNH-4-Pym | 1-Mor-(CH₂)₃ |
| 1-963 | Ph | 2-MeNH-4-Pym | 1-Mor-(CH₂)₄ |
| 1-964 | Ph | 2-MeNH-4-Pym | 1-Tmor-CH₂ |
| 1-965 | Ph | 2-MeNH-4-Pym | 1-Tmor-(CH₂)₂ |
| 1-966 | Ph | 2-MeNH-4-Pym | 1-Tmor-(CH₂)₃ |
| 1-967 | Ph | 2-MeNH-4-Pym | 1-Tmor-(CH₂)₄ |
| 1-968 | Ph | 2-MeNH-4-Pym | 1-Piz-CH₂ |
| 1-969 | Ph | 2-MeNH-4-Pym | 1-Piz-(CH₂)₂ |
| 1-970 | Ph | 2-MeNH-4-Pym | 1-Piz-(CH₂)₃ |
| 1-971 | Ph | 2-MeNH-4-Pym | 4-Me-1-Piz-(CH₂)₃ |
| 1-972 | Ph | 2-MeNH-4-Pym | 1-Piz-(CH₂)₄ |
| 1-973 | Ph | 2-MeNH-4-Pym | 3-Azt |
| 1-974 | Ph | 2-MeNH-4-Pym | 1-Me-3-Azt |
| 1-975 | Ph | 2-MeNH-4-Pym | 1-Bn-3-Azt |
| 1-976 | Ph | 2-MeNH-4-Pym | 3-Pyrd |
| 1-977 | Ph | 2-MeNH-4-Pym | 1-Me-3-Pyrd |
| 1-978 | Ph | 2-MeNH-4-Pym | 3-Pip |
| 1-979 | Ph | 2-MeNH-4-Pym | 4-Pip |
| 1-980 | Ph | 2-MeNH-4-Pym | 4-(3,4-deH-Pip) |
| 1-981 | Ph | 2-MeNH-4-Pym | 1-Me-4-Pip |
| 1-982 | Ph | 2-MeNH-4-Pym | 1-Me-4-(3,4-deH-Pip) |
| 1-983 | Ph | 2-MeNH-4-Pym | 1-Et-4-Pip |
| 1-984 | Ph | 2-MeNH-4-Pym | 1-Bn-4-Pip |
| 1-985 | Ph | 2-MeNH-4-Pym | 3-Hpip |
| 1-986 | Ph | 2-MeNH-4-Pym | 1-Me-3-Hpip |
| 1-987 | Ph | 2-MeNH-4-Pym | 4-Hpip |
| 1-988 | Ph | 2-MeNH-4-Pym | 1-Me-4-Hpip |
| 1-989 | Ph | 2-MeNH-4-Pym | 2-Mor |
| 1-990 | Ph | 2-MeNH-4-Pym | 1-Me-2-Mor |
| 1-991 | Ph | 2-MeNH-4-Pym | 2-Tmor |
| 1-992 | Ph | 2-MeNH-4-Pym | 1-Me-2-Tmor |
| 1-993 | Ph | 2-MeNH-4-Pym | 1-Piz |
| 1-994 | Ph | 2-MeNH-4-Pym | 4-Me-1-Piz |
| 1-995 | Ph | 2-MeNH-4-Pym | 2-Piz |
| 1-996 | Ph | 2-MeNH-4-Pym | 4-Pyr |
| 1-997 | Ph | 2-MeNH-4-Pym | 3-Pyr |
| 1-998 | Ph | 2-MeNH-4-Pym | 2-Pyr |
| 1-999 | Ph | 2-MeNH-4-Pym | 4-Pym |
| 1-1000 | Ph | 2-MeNH-4-Pym | 5-Pym |
| 1-1001 | Ph | 2-MeNH-4-Pym | 2-Pym |
| 1-1002 | Ph | 2-MeNH-4-Pym | 3-Azt-CH₂ |
| 1-1003 | Ph | 2-MeNH-4-Pym | 1-Me-3-Azt-CH₂ |
| 1-1004 | Ph | 2-MeNH-4-Pym | 3-Pyrd-CH₂ |
| 1-1005 | Ph | 2-MeNH-4-Pym | 1-Me-3-Pyrd-CH₂ |
| 1-1006 | Ph | 2-MeNH-4-Pym | 4-Pip-CH₂ |
| 1-1007 | Ph | 2-MeNH-4-Pym | 1-Me-4-Pip-CH₂ |
| 1-1008 | Ph | 2-MeNH-4-Pym | 3-Hpip-CH₂ |
| 1-1009 | Ph | 2-MeNH-4-Pym | 1-Me-3-Hpip-CH₂ |
| 1-1010 | Ph | 2-MeNH-4-Pym | 4-Hpip-CH₂ |
| 1-1011 | Ph | 2-MeNH-4-Pym | 1-Me-4-Hpip-CH₂ |
| 1-1012 | Ph | 2-MeNH-4-Pym | 2-Mor-CH₂ |
| 1-1013 | Ph | 2-MeNH-4-Pym | 1-Me-2-Mor-CH₂ |
| 1-1014 | Ph | 2-MeNH-4-Pym | 2-Tmor-CH₂ |
| 1-1015 | Ph | 2-MeNH-4-Pym | 1-Me-2-Tmor-CH₂ |
| 1-1016 | Ph | 2-MeNH-4-Pym | 1-Piz-CH₂ |
| 1-1017 | Ph | 2-MeNH-4-Pym | 4-Me-1-Piz-CH₂ |
| 1-1018 | Ph | 2-MeNH-4-Pym | 2-Piz-CH₂ |
| 1-1019 | Ph | 2-MeNH-4-Pym | 4-Pyr-CH₂ |
| 1-1020 | Ph | 2-MeNH-4-Pym | 3-Pyr-CH₂ |
| 1-1021 | Ph | 2-MeNH-4-Pym | 2-Pyr-CH₂ |
| 1-1022 | Ph | 2-MeNH-4-Pym | 4-Pym-CH₂ |
| 1-1023 | Ph | 2-MeNH-4-Pym | 5-Pym-CH₂ |
| 1-1024 | Ph | 2-MeNH-4-Pym | 2-Pym-CH₂ |
| 1-1025 | 4-F—Ph | 2-MeNH-4-Pym | H₂N—CH₂ |
| 1-1026 | 4-F—Ph | 2-MeNH-4-Pym | H₂N—(CH₂)₂ |
| 1-1027 | 4-F—Ph | 2-MeNH-4-Pym | H₂N—(CH₂)₃ |
| 1-1028 | 4-F—Ph | 2-MeNH-4-Pym | H₂N—(CH₂)₄ |
| 1-1029 | 4-F—Ph | 2-MeNH-4-Pym | MeNH—CH₂ |
| 1-1030 | 4-F—Ph | 2-MeNH-4-Pym | MeNH—(CH₂)₂ |
| 1-1031 | 4-F—Ph | 2-MeNH-4-Pym | MeNH—(CH₂)₃ |
| 1-1032 | 4-F—Ph | 2-MeNH-4-Pym | MeNH—(CH₂)₄ |
| 1-1033 | 4-F—Ph | 2-MeNH-4-Pym | EtNH—CH₂ |
| 1-1034 | 4-F—Ph | 2-MeNH-4-Pym | EtNH—(CH₂)₂ |
| 1-1035 | 4-F—Ph | 2-MeNH-4-Pym | EtNH—(CH₂)₃ |
| 1-1036 | 4-F—Ph | 2-MeNH-4-Pym | EtNH—(CH₂)₄ |
| 1-1037 | 4-F—Ph | 2-MeNH-4-Pym | Me₂N—CH₂ |
| 1-1038 | 4-F—Ph | 2-MeNH-4-Pym | Me₂N—(CH₂)₂ |
| 1-1039 | 4-F—Ph | 2-MeNH-4-Pym | Me₂N—(CH₂)₃ |
| 1-1040 | 4-F—Ph | 2-MeNH-4-Pym | Me₂N—(CH₂)₄ |
| 1-1041 | 4-F—Ph | 2-MeNH-4-Pym | 1-Azt-CH₂ |
| 1-1042 | 4-F—Ph | 2-MeNH-4-Pym | 1-Azt-(CH₂)₂ |
| 1-1043 | 4-F—Ph | 2-MeNH-4-Pym | 1-Azt-(CH₂)₃ |
| 1-1044 | 4-F—Ph | 2-MeNH-4-Pym | 1-Azt-(CH₂)₄ |
| 1-1045 | 4-F—Ph | 2-MeNH-4-Pym | 1-Pyrd-CH₂ |
| 1-1046 | 4-F—Ph | 2-MeNH-4-Pym | 1-Pyrd-(CH₂)₂ |
| 1-1047 | 4-F—Ph | 2-MeNH-4-Pym | 1-Pyrd-(CH₂)₃ |
| 1-1048 | 4-F—Ph | 2-MeNH-4-Pym | 1-Pyrd-(CH₂)₄ |
| 1-1049 | 4-F—Ph | 2-MeNH-4-Pym | 1-Pip-CH₂ |
| 1-1050 | 4-F—Ph | 2-MeNH-4-Pym | 1-Pip-(CH₂)₂ |
| 1-1051 | 4-F—Ph | 2-MeNH-4-Pym | 1-Pip-(CH₂)₃ |
| 1-1052 | 4-F—Ph | 2-MeNH-4-Pym | 1-Pip-(CH₂)₄ |
| 1-1053 | 4-F—Ph | 2-MeNH-4-Pym | 1-Mor-CH₂ |
| 1-1054 | 4-F—Ph | 2-MeNH-4-Pym | 1-Mor-(CH₂)₂ |
| 1-1055 | 4-F—Ph | 2-MeNH-4-Pym | 1-Mor-(CH₂)₃ |
| 1-1056 | 4-F—Ph | 2-MeNH-4-Pym | 1-Mor-(CH₂)₄ |
| 1-1057 | 4-F—Ph | 2-MeNH-4-Pym | 1-Tmor-CH₂ |
| 1-1058 | 4-F—Ph | 2-MeNH-4-Pym | 1-Tmor-(CH₂)₂ |
| 1-1059 | 4-F—Ph | 2-MeNH-4-Pym | 1-Tmor-(CH₂)₃ |
| 1-1060 | 4-F—Ph | 2-MeNH-4-Pym | 1-Tmor-(CH₂)₄ |
| 1-1061 | 4-F—Ph | 2-MeNH-4-Pym | 1-Piz-CH₂ |
| 1-1062 | 4-F—Ph | 2-MeNH-4-Pym | 1-Piz-(CH₂)₂ |
| 1-1063 | 4-F—Ph | 2-MeNH-4-Pym | 1-Piz-(CH₂)₃ |
| 1-1064 | 4-F—Ph | 2-MeNH-4-Pym | 4-Me-1-Piz-(CH₂)₃ |

TABLE 1-continued

| Compound No. | R¹ | R² | R³ |
|---|---|---|---|
| 1-1065 | 4-F—Ph | 2-MeNH-4-Pym | 1-Piz-(CH$_2$)$_4$ |
| 1-1066 | 4-F—Ph | 2-MeNH-4-Pym | 3-Azt |
| 1-1067 | 4-F—Ph | 2-MeNH-4-Pym | 1-Me-3-Azt |
| 1-1068 | 4-F—Ph | 2-MeNH-4-Pym | 1-Bn-3-Azt |
| 1-1069 | 4-F—Ph | 2-MeNH-4-Pym | 3-Pyrd |
| 1-1070 | 4-F—Ph | 2-MeNH-4-Pym | 1-Me-3-Pyrd |
| 1-1071 | 4-F—Ph | 2-MeNH-4-Pym | 3-Pip |
| 1-1072 | 4-F—Ph | 2-MeNH-4-Pym | 4-Pip |
| 1-1073 | 4-F—Ph | 2-MeNH-4-Pym | 4-(3,4-deH-Pip) |
| 1-1074 | 4-F—Ph | 2-MeNH-4-Pym | 1-Me-4-Pip |
| 1-1075 | 4-F—Ph | 2-MeNH-4-Pym | 1-Me-4-(3,4-deH-Pip) |
| 1-1076 | 4-F—Ph | 2-MeNH-4-Pym | 1-Et-4-Pip |
| 1-1077 | 4-F—Ph | 2-MeNH-4-Pym | 1-Bn-4-Pip |
| 1-1078 | 4-F—Ph | 2-MeNH-4-Pym | 3-Hpip |
| 1-1079 | 4-F—Ph | 2-MeNH-4-Pym | 1-Me-3-Hpip |
| 1-1080 | 4-F—Ph | 2-MeNH-4-Pym | 4-Hpip |
| 1-1081 | 4-F—Ph | 2-MeNH-4-Pym | 1-Me-4-Hpip |
| 1-1082 | 4-F—Ph | 2-MeNH-4-Pym | 2-Mor |
| 1-1083 | 4-F—Ph | 2-MeNH-4-Pym | 1-Me-2-Mor |
| 1-1084 | 4-F—Ph | 2-MeNH-4-Pym | 2-Tmor |
| 1-1085 | 4-F—Ph | 2-MeNH-4-Pym | 1-Me-2-Tmor |
| 1-1086 | 4-F—Ph | 2-MeNH-4-Pym | 1-Piz |
| 1-1087 | 4-F—Ph | 2-MeNH-4-Pym | 4-Me-1-Piz |
| 1-1088 | 4-F—Ph | 2-MeNH-4-Pym | 2-Piz |
| 1-1089 | 4-F—Ph | 2-MeNH-4-Pym | 4-Pyr |
| 1-1090 | 4-F—Ph | 2-MeNH-4-Pym | 3-Pyr |
| 1-1091 | 4-F—Ph | 2-MeNH-4-Pym | 2-Pyr |
| 1-1092 | 4-F—Ph | 2-MeNH-4-Pym | 4-Pym |
| 1-1093 | 4-F—Ph | 2-MeNH-4-Pym | 5-Pym |
| 1-1094 | 4-F—Ph | 2-MeNH-4-Pym | 2-Pym |
| 1-1095 | 4-F—Ph | 2-MeNH-4-Pym | 3-Azt-CH$_2$ |
| 1-1096 | 4-F—Ph | 2-MeNH-4-Pym | 1-Me-3-Azt-CH$_2$ |
| 1-1097 | 4-F—Ph | 2-MeNH-4-Pym | 3-Pyrd-CH$_2$ |
| 1-1098 | 4-F—Ph | 2-MeNH-4-Pym | 1-Me-3-Pyrd-CH$_2$ |
| 1-1099 | 4-F—Ph | 2-MeNH-4-Pym | 4-Pip-CH$_2$ |
| 1-1100 | 4-F—Ph | 2-MeNH-4-Pym | 1-Me-4-Pip-CH$_2$ |
| 1-1101 | 4-F—Ph | 2-MeNH-4-Pym | 3-Hpip-CH$_2$ |
| 1-1102 | 4-F—Ph | 2-MeNH-4-Pym | 1-Me-3-Hpip-CH$_2$ |
| 1-1103 | 4-F—Ph | 2-MeNH-4-Pym | 4-Hpip-CH$_2$ |
| 1-1104 | 4-F—Ph | 2-MeNH-4-Pym | 1-Me-4-Hpip-CH$_2$ |
| 1-1105 | 4-F—Ph | 2-MeNH-4-Pym | 2-Mor-CH$_2$ |
| 1-1106 | 4-F—Ph | 2-MeNH-4-Pym | 1-Me-2-Mor-CH$_2$ |
| 1-1107 | 4-F—Ph | 2-MeNH-4-Pym | 2-Tmor-CH$_2$ |
| 1-1108 | 4-F—Ph | 2-MeNH-4-Pym | 1-Me-2-Tmor-CH$_2$ |
| 1-1109 | 4-F—Ph | 2-MeNH-4-Pym | 1-Piz-CH$_2$ |
| 1-1110 | 4-F—Ph | 2-MeNH-4-Pym | 4-Me-1-Piz-CH$_2$ |
| 1-1111 | 4-F—Ph | 2-MeNH-4-Pym | 2-Piz-CH$_2$ |
| 1-1112 | 4-F—Ph | 2-MeNH-4-Pym | 4-Pyr-CH$_2$ |
| 1-1113 | 4-F—Ph | 2-MeNH-4-Pym | 3-Pyr-CH$_2$ |
| 1-1114 | 4-F—Ph | 2-MeNH-4-Pym | 2-Pyr-CH$_2$ |
| 1-1115 | 4-F—Ph | 2-MeNH-4-Pym | 4-Pym-CH$_2$ |
| 1-1116 | 4-F—Ph | 2-MeNH-4-Pym | 5-Pym-CH$_2$ |
| 1-1117 | 4-F—Ph | 2-MeNH-4-Pym | 2-Pym-CH$_2$ |
| 1-1118 | 3-F—Ph | 2-MeNH-4-Pym | H$_2$N—CH$_2$ |
| 1-1119 | 3-F—Ph | 2-MeNH-4-Pym | H$_2$N—(CH$_2$)$_2$ |
| 1-1120 | 3-F—Ph | 2-MeNH-4-Pym | H$_2$N—(CH$_2$)$_3$ |
| 1-1121 | 3-F—Ph | 2-MeNH-4-Pym | H$_2$N—(CH$_2$)$_4$ |
| 1-1122 | 3-F—Ph | 2-MeNH-4-Pym | MeNH—CH$_2$ |
| 1-1123 | 3-F—Ph | 2-MeNH-4-Pym | MeNH—(CH$_2$)$_2$ |
| 1-1124 | 3-F—Ph | 2-MeNH-4-Pym | MeNH—(CH$_2$)$_3$ |
| 1-1125 | 3-F—Ph | 2-MeNH-4-Pym | MeNH—(CH$_2$)$_4$ |
| 1-1126 | 3-F—Ph | 2-MeNH-4-Pym | EtNH—CH$_2$ |
| 1-1127 | 3-F—Ph | 2-MeNH-4-Pym | EtNH—(CH$_2$)$_2$ |
| 1-1128 | 3-F—Ph | 2-MeNH-4-Pym | EtNH—(CH$_2$)$_3$ |
| 1-1129 | 3-F—Ph | 2-MeNH-4-Pym | EtNH—(CH$_2$)$_4$ |
| 1-1130 | 3-F—Ph | 2-MeNH-4-Pym | Me$_2$N—CH$_2$ |
| 1-1131 | 3-F—Ph | 2-MeNH-4-Pym | Me$_2$N—(CH$_2$)$_2$ |
| 1-1132 | 3-F—Ph | 2-MeNH-4-Pym | Me$_2$N—(CH$_2$)$_3$ |
| 1-1133 | 3-F—Ph | 2-MeNH-4-Pym | Me$_2$N—(CH$_2$)$_4$ |
| 1-1134 | 3-F—Ph | 2-MeNH-4-Pym | 1-Azt-CH$_2$ |
| 1-1135 | 3-F—Ph | 2-MeNH-4-Pym | 1-Azt-(CH$_2$)$_2$ |
| 1-1136 | 3-F—Ph | 2-MeNH-4-Pym | 1-Azt-(CH$_2$)$_3$ |
| 1-1137 | 3-F—Ph | 2-MeNH-4-Pym | 1-Azt-(CH$_2$)$_4$ |
| 1-1138 | 3-F—Ph | 2-MeNH-4-Pym | 1-Pyrd-CH$_2$ |
| 1-1139 | 3-F—Ph | 2-MeNH-4-Pym | 1-Pyrd-(CH$_2$)$_2$ |
| 1-1140 | 3-F—Ph | 2-MeNH-4-Pym | 1-Pyrd-(CH$_2$)$_3$ |
| 1-1141 | 3-F—Ph | 2-MeNH-4-Pym | 1-Pyrd-(CH$_2$)$_4$ |
| 1-1142 | 3-F—Ph | 2-MeNH-4-Pym | 1-Pip-CH$_2$ |
| 1-1143 | 3-F—Ph | 2-MeNH-4-Pym | 1-Pip-(CH$_2$)$_2$ |
| 1-1144 | 3-F—Ph | 2-MeNH-4-Pym | 1-Pip-(CH$_2$)$_3$ |
| 1-1145 | 3-F—Ph | 2-MeNH-4-Pym | 1-Pip-(CH$_2$)$_4$ |
| 1-1146 | 3-F—Ph | 2-MeNH-4-Pym | 1-Mor-CH$_2$ |
| 1-1147 | 3-F—Ph | 2-MeNH-4-Pym | 1-Mor-(CH$_2$)$_2$ |
| 1-1148 | 3-F—Ph | 2-MeNH-4-Pym | 1-Mor-(CH$_2$)$_3$ |
| 1-1149 | 3-F—Ph | 2-MeNH-4-Pym | 1-Mor-(CH$_2$)$_4$ |
| 1-1150 | 3-F—Ph | 2-MeNH-4-Pym | 1-Tmor-CH$_2$ |
| 1-1151 | 3-F—Ph | 2-MeNH-4-Pym | 1-Tmor-(CH$_2$)$_2$ |
| 1-1152 | 3-F—Ph | 2-MeNH-4-Pym | 1-Tmor-(CH$_2$)$_3$ |
| 1-1153 | 3-F—Ph | 2-MeNH-4-Pym | 1-Tmor-(CH$_2$)$_4$ |
| 1-1154 | 3-F—Ph | 2-MeNH-4-Pym | 1-Piz-CH$_2$ |
| 1-1155 | 3-F—Ph | 2-MeNH-4-Pym | 1-Piz-(CH$_2$)$_2$ |
| 1-1156 | 3-F—Ph | 2-MeNH-4-Pym | 1-Piz-(CH$_2$)$_3$ |
| 1-1157 | 3-F—Ph | 2-MeNH-4-Pym | 4-Me-1-Piz-(CH$_2$)$_3$ |
| 1-1158 | 3-F—Ph | 2-MeNH-4-Pym | 1-Piz-(CH$_2$)$_4$ |
| 1-1159 | 3-F—Ph | 2-MeNH-4-Pym | 3-Azt |
| 1-1160 | 3-F—Ph | 2-MeNH-4-Pym | 1-Me-3-Azt |
| 1-1161 | 3-F—Ph | 2-MeNH-4-Pym | 1-Bn-3-Azt |
| 1-1162 | 3-F—Ph | 2-MeNH-4-Pym | 3-Pyrd |
| 1-1163 | 3-F—Ph | 2-MeNH-4-Pym | 1-Me-3-Pyrd |
| 1-1164 | 3-F—Ph | 2-MeNH-4-Pym | 3-Pip |
| 1-1165 | 3-F—Ph | 2-MeNH-4-Pym | 4-Pip |
| 1-1166 | 3-F—Ph | 2-MeNH-4-Pym | 4-(3,4-deH-Pip) |
| 1-1167 | 3-F—Ph | 2-MeNH-4-Pym | 1-Me-4-Pip |
| 1-1168 | 3-F—Ph | 2-MeNH-4-Pym | 1-Me-4-(3,4-deH-Pip) |
| 1-1169 | 3-F—Ph | 2-MeNH-4-Pym | 1-Et-4-Pip |
| 1-1170 | 3-F—Ph | 2-MeNH-4-Pym | 1-Bn-4-Pip |
| 1-1171 | 3-F—Ph | 2-MeNH-4-Pym | 3-Hpip |
| 1-1172 | 3-F—Ph | 2-MeNH-4-Pym | 1-Me-3-Hpip |
| 1-1173 | 3-F—Ph | 2-MeNH-4-Pym | 4-Hpip |
| 1-1174 | 3-F—Ph | 2-MeNH-4-Pym | 1-Me-4-Hpip |
| 1-1175 | 3-F—Ph | 2-MeNH-4-Pym | 2-Mor |
| 1-1176 | 3-F—Ph | 2-MeNH-4-Pym | 1-Me-2-Mor |
| 1-1177 | 3-F—Ph | 2-MeNH-4-Pym | 2-Tmor |
| 1-1178 | 3-F—Ph | 2-MeNH-4-Pym | 1-Me-2-Tmor |
| 1-1179 | 3-F—Ph | 2-MeNH-4-Pym | 1-Piz |
| 1-1180 | 3-F—Ph | 2-MeNH-4-Pym | 4-Me-1-Piz |
| 1-1181 | 3-F—Ph | 2-MeNH-4-Pym | 2-Piz |
| 1-1182 | 3-F—Ph | 2-MeNH-4-Pym | 4-Pyr |
| 1-1183 | 3-F—Ph | 2-MeNH-4-Pym | 3-Pyr |
| 1-1184 | 3-F—Ph | 2-MeNH-4-Pym | 2-Pyr |
| 1-1185 | 3-F—Ph | 2-MeNH-4-Pym | 4-Pym |
| 1-1186 | 3-F—Ph | 2-MeNH-4-Pym | 5-Pym |
| 1-1187 | 3-F—Ph | 2-MeNH-4-Pym | 2-Pym |
| 1-1188 | 3-F—Ph | 2-MeNH-4-Pym | 3-Azt-CH$_2$ |
| 1-1189 | 3-F—Ph | 2-MeNH-4-Pym | 1-Me-3-Azt-CH$_2$ |
| 1-1190 | 3-F—Ph | 2-MeNH-4-Pym | 3-Pyrd-CH$_2$ |
| 1-1191 | 3-F—Ph | 2-MeNH-4-Pym | 1-Me-3-Pyrd-CH$_2$ |
| 1-1192 | 3-F—Ph | 2-MeNH-4-Pym | 4-Pip-CH$_2$ |
| 1-1193 | 3-F—Ph | 2-MeNH-4-Pym | 1-Me-4-Pip-CH$_2$ |
| 1-1194 | 3-F—Ph | 2-MeNH-4-Pym | 3-Hpip-CH$_2$ |
| 1-1195 | 3-F—Ph | 2-MeNH-4-Pym | 1-Me-3-Hpip-CH$_2$ |
| 1-1196 | 3-F—Ph | 2-MeNH-4-Pym | 4-Hpip-CH$_2$ |
| 1-1197 | 3-F—Ph | 2-MeNH-4-Pym | 1-Me-4-Hpip-CH$_2$ |
| 1-1198 | 3-F—Ph | 2-MeNH-4-Pym | 2-Mor-CH$_2$ |
| 1-1199 | 3-F—Ph | 2-MeNH-4-Pym | 1-Me-2-Mor-CH$_2$ |
| 1-1200 | 3-F—Ph | 2-MeNH-4-Pym | 2-Tmor-CH$_2$ |
| 1-1201 | 3-F—Ph | 2-MeNH-4-Pym | 1-Me-2-Tmor-CH$_2$ |
| 1-1202 | 3-F—Ph | 2-MeNH-4-Pym | 1-Piz-CH$_2$ |
| 1-1203 | 3-F—Ph | 2-MeNH-4-Pym | 4-Me-1-Piz-CH$_2$ |
| 1-1204 | 3-F—Ph | 2-MeNH-4-Pym | 2-Piz-CH$_2$ |
| 1-1205 | 3-F—Ph | 2-MeNH-4-Pym | 4-Pyr-CH$_2$ |
| 1-1206 | 3-F—Ph | 2-MeNH-4-Pym | 3-Pyr-CH$_2$ |
| 1-1207 | 3-F—Ph | 2-MeNH-4-Pym | 2-Pyr-CH$_2$ |
| 1-1208 | 3-F—Ph | 2-MeNH-4-Pym | 4-Pym-CH$_2$ |
| 1-1209 | 3-F—Ph | 2-MeNH-4-Pym | 5-Pym-CH$_2$ |
| 1-1210 | 3-F—Ph | 2-MeNH-4-Pym | 2-Pym-CH$_2$ |
| 1-1211 | 3,4-diF-Ph | 2-MeNH-4-Pym | H$_2$N—CH$_2$ |
| 1-1212 | 3,4-diF-Ph | 2-MeNH-4-Pym | H$_2$N—(CH$_2$)$_2$ |
| 1-1213 | 3,4-diF-Ph | 2-MeNH-4-Pym | H$_2$N—(CH$_2$)$_3$ |
| 1-1214 | 3,4-diF-Ph | 2-MeNH-4-Pym | H$_2$N—(CH$_2$)$_4$ |
| 1-1215 | 3,4-diF-Ph | 2-MeNH-4-Pym | MeNH—CH$_2$ |
| 1-1216 | 3,4-diF-Ph | 2-MeNH-4-Pym | MeNH—(CH$_2$)$_2$ |

TABLE 1-continued

| Compound No. | R¹ | R² | R³ |
|---|---|---|---|
| 1-1217 | 3,4-diF-Ph | 2-MeNH-4-Pym | MeNH—(CH₂)₃ |
| 1-1218 | 3,4-diF-Ph | 2-MeNH-4-Pym | MeNH—(CH₂)₄ |
| 1-1219 | 3,4-diF-Ph | 2-MeNH-4-Pym | EtNH—CH₂ |
| 1-1220 | 3,4-diF-Ph | 2-MeNH-4-Pym | EtNH—(CH₂)₂ |
| 1-1221 | 3,4-diF-Ph | 2-MeNH-4-Pym | EtNH—(CH₂)₃ |
| 1-1222 | 3,4-diF-Ph | 2-MeNH-4-Pym | EtNH—(CH₂)₄ |
| 1-1223 | 3,4-diF-Ph | 2-MeNH-4-Pym | Me₂N—CH₂ |
| 1-1224 | 3,4-diF-Ph | 2-MeNH-4-Pym | Me₂N—(CH₂)₂ |
| 1-1225 | 3,4-diF-Ph | 2-MeNH-4-Pym | Me₂N—(CH₂)₃ |
| 1-1226 | 3,4-diF-Ph | 2-MeNH-4-Pym | Me₂N—(CH₂)₄ |
| 1-1227 | 3,4-diF-Ph | 2-MeNH-4-Pym | 1-Azt-CH₂ |
| 1-1228 | 3,4-diF-Ph | 2-MeNH-4-Pym | 1-Azt-(CH₂)₂ |
| 1-1229 | 3,4-diF-Ph | 2-MeNH-4-Pym | 1-Azt-(CH₂)₃ |
| 1-1230 | 3,4-diF-Ph | 2-MeNH-4-Pym | 1-Azt-(CH₂)₄ |
| 1-1231 | 3,4-diF-Ph | 2-MeNH-4-Pym | 1-Pyrd-CH₂ |
| 1-1232 | 3,4-diF-Ph | 2-MeNH-4-Pym | 1-Pyrd-(CH₂)₂ |
| 1-1233 | 3,4-diF-Ph | 2-MeNH-4-Pym | 1-Pyrd-(CH₂)₃ |
| 1-1234 | 3,4-diF-Ph | 2-MeNH-4-Pym | 1-Pyrd-(CH₂)₄ |
| 1-1235 | 3,4-diF-Ph | 2-MeNH-4-Pym | 1-Pip-CH₂ |
| 1-1236 | 3,4-diF-Ph | 2-MeNH-4-Pym | 1-Pip-(CH₂)₂ |
| 1-1237 | 3,4-diF-Ph | 2-MeNH-4-Pym | 1-Pip-(CH₂)₃ |
| 1-1238 | 3,4-diF-Ph | 2-MeNH-4-Pym | 1-Pip-(CH₂)₄ |
| 1-1239 | 3,4-diF-Ph | 2-MeNH-4-Pym | 1-Mor-CH₂ |
| 1-1240 | 3,4-diF-Ph | 2-MeNH-4-Pym | 1-Mor-(CH₂)₂ |
| 1-1241 | 3,4-diF-Ph | 2-MeNH-4-Pym | 1-Mor-(CH₂)₃ |
| 1-1242 | 3,4-diF-Ph | 2-MeNH-4-Pym | 1-Mor-(CH₂)₄ |
| 1-1243 | 3,4-diF-Ph | 2-MeNH-4-Pym | 1-Tmor-CH₂ |
| 1-1244 | 3,4-diF-Ph | 2-MeNH-4-Pym | 1-Tmor-(CH₂)₂ |
| 1-1245 | 3,4-diF-Ph | 2-MeNH-4-Pym | 1-Tmor-(CH₂)₃ |
| 1-1246 | 3,4-diF-Ph | 2-MeNH-4-Pym | 1-Tmor-(CH₂)₄ |
| 1-1247 | 3,4-diF-Ph | 2-MeNH-4-Pym | 1-Piz-CH₂ |
| 1-1248 | 3,4-diF-Ph | 2-MeNH-4-Pym | 1-Piz-(CH₂)₂ |
| 1-1249 | 3,4-diF-Ph | 2-MeNH-4-Pym | 1-Piz-(CH₂)₃ |
| 1-1250 | 3,4-diF-Ph | 2-MeNH-4-Pym | 4-Me-1-Piz-(CH₂)₃ |
| 1-1251 | 3,4-diF-Ph | 2-MeNH-4-Pym | 1-Piz-(CH₂)₄ |
| 1-1252 | 3,4-diF-Ph | 2-MeNH-4-Pym | 3-Azt |
| 1-1253 | 3,4-diF-Ph | 2-MeNH-4-Pym | 1-Me-3-Azt |
| 1-1254 | 3,4-diF-Ph | 2-MeNH-4-Pym | 1-Bn-3-Azt |
| 1-1255 | 3,4-diF-Ph | 2-MeNH-4-Pym | 3-Pyrd |
| 1-1256 | 3,4-diF-Ph | 2-MeNH-4-Pym | 1-Me-3-Pyrd |
| 1-1257 | 3,4-diF-Ph | 2-MeNH-4-Pym | 3-Pip |
| 1-1258 | 3,4-diF-Ph | 2-MeNH-4-Pym | 4-Pip |
| 1-1259 | 3,4-diF-Ph | 2-MeNH-4-Pym | 4-(3,4-deH-Pip) |
| 1-1260 | 3,4-diF-Ph | 2-MeNH-4-Pym | 1-Me-4-Pip |
| 1-1261 | 3,4-diF-Ph | 2-MeNH-4-Pym | 1-Me-4-(3,4-deH-Pip) |
| 1-1262 | 3,4-diF-Ph | 2-MeNH-4-Pym | 1-Et-4-Pip |
| 1-1263 | 3,4-diF-Ph | 2-MeNH-4-Pym | 1-Bn-4-Pip |
| 1-1264 | 3,4-diF-Ph | 2-MeNH-4-Pym | 3-Hpip |
| 1-1265 | 3,4-diF-Ph | 2-MeNH-4-Pym | 1-Me-3-Hpip |
| 1-1266 | 3,4-diF-Ph | 2-MeNH-4-Pym | 4-Hpip |
| 1-1267 | 3,4-diF-Ph | 2-MeNH-4-Pym | 1-Me-4-Hpip |
| 1-1268 | 3,4-diF-Ph | 2-MeNH-4-Pym | 2-Mor |
| 1-1269 | 3,4-diF-Ph | 2-MeNH-4-Pym | 1-Me-2-Mor |
| 1-1270 | 3,4-diF-Ph | 2-MeNH-4-Pym | 2-Tmor |
| 1-1271 | 3,4-diF-Ph | 2-MeNH-4-Pym | 1-Me-2-Tmor |
| 1-1272 | 3,4-diF-Ph | 2-MeNH-4-Pym | 1-Piz |
| 1-1273 | 3,4-diF-Ph | 2-MeNH-4-Pym | 4-Me-1-Piz |
| 1-1274 | 3,4-diF-Ph | 2-MeNH-4-Pym | 2-Piz |
| 1-1275 | 3,4-diF-Ph | 2-MeNH-4-Pym | 4-Pyr |
| 1-1276 | 3,4-diF-Ph | 2-MeNH-4-Pym | 3-Pyr |
| 1-1277 | 3,4-diF-Ph | 2-MeNH-4-Pym | 2-Pyr |
| 1-1278 | 3,4-diF-Ph | 2-MeNH-4-Pym | 4-Pym |
| 1-1279 | 3,4-diF-Ph | 2-MeNH-4-Pym | 5-Pym |
| 1-1280 | 3,4-diF-Ph | 2-MeNH-4-Pym | 2-Pym |
| 1-1281 | 3,4-diF-Ph | 2-MeNH-4-Pym | 3-Azt-CH₂ |
| 1-1282 | 3,4-diF-Ph | 2-MeNH-4-Pym | 1-Me-3-Azt-CH₂ |
| 1-1283 | 3,4-diF-Ph | 2-MeNH-4-Pym | 3-Pyrd-CH₂ |
| 1-1284 | 3,4-diF-Ph | 2-MeNH-4-Pym | 1-Me-3-Pyrd-CH₂ |
| 1-1285 | 3,4-diF-Ph | 2-MeNH-4-Pym | 4-Pip-CH₂ |
| 1-1286 | 3,4-diF-Ph | 2-MeNH-4-Pym | 1-Me-4-Pip-CH₂ |
| 1-1287 | 3,4-diF-Ph | 2-MeNH-4-Pym | 3-Hpip-CH₂ |
| 1-1288 | 3,4-diF-Ph | 2-MeNH-4-Pym | 1-Me-3-Hpip-CH₂ |
| 1-1289 | 3,4-diF-Ph | 2-MeNH-4-Pym | 4-Hpip-CH₂ |
| 1-1290 | 3,4-diF-Ph | 2-MeNH-4-Pym | 1-Me-4-Hpip-CH₂ |
| 1-1291 | 3,4-diF-Ph | 2-MeNH-4-Pym | 2-Mor-CH₂ |
| 1-1292 | 3,4-diF-Ph | 2-MeNH-4-Pym | 1-Me-2-Mor-CH₂ |
| 1-1293 | 3,4-diF-Ph | 2-MeNH-4-Pym | 2-Tmor-CH₂ |
| 1-1294 | 3,4-diF-Ph | 2-MeNH-4-Pym | 1-Me-2-Tmor-CH₂ |
| 1-1295 | 3,4-diF-Ph | 2-MeNH-4-Pym | 1-Piz-CH₂ |
| 1-1296 | 3,4-diF-Ph | 2-MeNH-4-Pym | 4-Me-1-Piz-CH₂ |
| 1-1297 | 3,4-diF-Ph | 2-MeNH-4-Pym | 2-Piz-CH₂ |
| 1-1298 | 3,4-diF-Ph | 2-MeNH-4-Pym | 4-Pyr-CH₂ |
| 1-1299 | 3,4-diF-Ph | 2-MeNH-4-Pym | 3-Pyr-CH₂ |
| 1-1300 | 3,4-diF-Ph | 2-MeNH-4-Pym | 2-Pyr-CH₂ |
| 1-1301 | 3,4-diF-Ph | 2-MeNH-4-Pym | 4-Pym-CH₂ |
| 1-1302 | 3,4-diF-Ph | 2-MeNH-4-Pym | 5-Pym-CH₂ |
| 1-1303 | 3,4-diF-Ph | 2-MeNH-4-Pym | 2-Pym-CH₂ |
| 1-1304 | 3-Cl—Ph | 2-MeNH-4-Pym | H₂N—CH₂ |
| 1-1305 | 3-Cl—Ph | 2-MeNH-4-Pym | H₂N—(CH₂)₂ |
| 1-1306 | 3-Cl—Ph | 2-MeNH-4-Pym | H₂N—(CH₂)₃ |
| 1-1307 | 3-Cl—Ph | 2-MeNH-4-Pym | H₂N—(CH₂)₄ |
| 1-1308 | 3-Cl—Ph | 2-MeNH-4-Pym | MeNH—CH₂ |
| 1-1309 | 3-Cl—Ph | 2-MeNH-4-Pym | MeNH—(CH₂)₂ |
| 1-1310 | 3-Cl—Ph | 2-MeNH-4-Pym | MeNH—(CH₂)₃ |
| 1-1311 | 3-Cl—Ph | 2-MeNH-4-Pym | MeNH—(CH₂)₄ |
| 1-1312 | 3-Cl—Ph | 2-MeNH-4-Pym | EtNH—CH₂ |
| 1-1313 | 3-Cl—Ph | 2-MeNH-4-Pym | EtNH—(CH₂)₂ |
| 1-1314 | 3-Cl—Ph | 2-MeNH-4-Pym | EtNH—(CH₂)₃ |
| 1-1315 | 3-Cl—Ph | 2-MeNH-4-Pym | EtNH—(CH₂)₄ |
| 1-1316 | 3-Cl—Ph | 2-MeNH-4-Pym | Me₂N—CH₂ |
| 1-1317 | 3-Cl—Ph | 2-MeNH-4-Pym | Me₂N—(CH₂)₂ |
| 1-1318 | 3-Cl—Ph | 2-MeNH-4-Pym | Me₂N—(CH₂)₃ |
| 1-1319 | 3-Cl—Ph | 2-MeNH-4-Pym | Me₂N—(CH₂)₄ |
| 1-1320 | 3-Cl—Ph | 2-MeNH-4-Pym | 1-Azt-CH₂ |
| 1-1321 | 3-Cl—Ph | 2-MeNH-4-Pym | 1-Azt-(CH₂)₂ |
| 1-1322 | 3-Cl—Ph | 2-MeNH-4-Pym | 1-Azt-(CH₂)₃ |
| 1-1323 | 3-Cl—Ph | 2-MeNH-4-Pym | 1-Azt-(CH₂)₄ |
| 1-1324 | 3-Cl—Ph | 2-MeNH-4-Pym | 1-Pyrd-CH₂ |
| 1-1325 | 3-Cl—Ph | 2-MeNH-4-Pym | 1-Pyrd-(CH₂)₂ |
| 1-1326 | 3-Cl—Ph | 2-MeNH-4-Pym | 1-Pyrd-(CH₂)₃ |
| 1-1327 | 3-Cl—Ph | 2-MeNH-4-Pym | 1-Pyrd-(CH₂)₄ |
| 1-1328 | 3-Cl—Ph | 2-MeNH-4-Pym | 1-Pip-CH₂ |
| 1-1329 | 3-Cl—Ph | 2-MeNH-4-Pym | 1-Pip-(CH₂)₂ |
| 1-1330 | 3-Cl—Ph | 2-MeNH-4-Pym | 1-Pip-(CH₂)₃ |
| 1-1331 | 3-Cl—Ph | 2-MeNH-4-Pym | 1-Pip-(CH₂)₄ |
| 1-1332 | 3-Cl—Ph | 2-MeNH-4-Pym | 1-Mor-CH₂ |
| 1-1333 | 3-Cl—Ph | 2-MeNH-4-Pym | 1-Mor-(CH₂)₂ |
| 1-1334 | 3-Cl—Ph | 2-MeNH-4-Pym | 1-Mor-(CH₂)₃ |
| 1-1335 | 3-Cl—Ph | 2-MeNH-4-Pym | 1-Mor-(CH₂)₄ |
| 1-1336 | 3-Cl—Ph | 2-MeNH-4-Pym | 1-Tmor-CH₂ |
| 1-1337 | 3-Cl—Ph | 2-MeNH-4-Pym | 1-Tmor-(CH₂)₂ |
| 1-1338 | 3-Cl—Ph | 2-MeNH-4-Pym | 1-Tmor-(CH₂)₃ |
| 1-1339 | 3-Cl—Ph | 2-MeNH-4-Pym | 1-Tmor-(CH₂)₄ |
| 1-1340 | 3-Cl—Ph | 2-MeNH-4-Pym | 1-Piz-CH₂ |
| 1-1341 | 3-Cl—Ph | 2-MeNH-4-Pym | 1-Piz-(CH₂)₂ |
| 1-1342 | 3-Cl—Ph | 2-MeNH-4-Pym | 1-Piz-(CH₂)₃ |
| 1-1343 | 3-Cl—Ph | 2-MeNH-4-Pym | 4-Me-1-Piz-(CH₂)₃ |
| 1-1344 | 3-Cl—Ph | 2-MeNH-4-Pym | 1-Piz-(CH₂)₄ |
| 1-1345 | 3-Cl—Ph | 2-MeNH-4-Pym | 3-Azt |
| 1-1346 | 3-Cl—Ph | 2-MeNH-4-Pym | 1-Me-3-Azt |
| 1-1347 | 3-Cl—Ph | 2-MeNH-4-Pym | 1-Bn-3-Azt |
| 1-1348 | 3-Cl—Ph | 2-MeNH-4-Pym | 3-Pyrd |
| 1-1349 | 3-Cl—Ph | 2-MeNH-4-Pym | 1-Me-3-Pyrd |
| 1-1350 | 3-Cl—Ph | 2-MeNH-4-Pym | 3-Pip |
| 1-1351 | 3-Cl—Ph | 2-MeNH-4-Pym | 4-Pip |
| 1-1352 | 3-Cl—Ph | 2-MeNH-4-Pym | 4-(3,4-deH-Pip) |
| 1-1353 | 3-Cl—Ph | 2-MeNH-4-Pym | 1-Me-4-Pip |
| 1-1354 | 3-Cl—Ph | 2-MeNH-4-Pym | 1-Me-4-(3,4-deH-Pip) |
| 1-1355 | 3-Cl—Ph | 2-MeNH-4-Pym | 1-Et-4-Pip |
| 1-1356 | 3-Cl—Ph | 2-MeNH-4-Pym | 1-Bn-4-Pip |
| 1-1357 | 3-Cl—Ph | 2-MeNH-4-Pym | 3-Hpip |
| 1-1358 | 3-Cl—Ph | 2-MeNH-4-Pym | 1-Me-3-Hpip |
| 1-1359 | 3-Cl—Ph | 2-MeNH-4-Pym | 4-Hpip |
| 1-1360 | 3-Cl—Ph | 2-MeNH-4-Pym | 1-Me-4-Hpip |
| 1-1361 | 3-Cl—Ph | 2-MeNH-4-Pym | 2-Mor |
| 1-1362 | 3-Cl—Ph | 2-MeNH-4-Pym | 1-Me-2-Mor |
| 1-1363 | 3-Cl—Ph | 2-MeNH-4-Pym | 2-Tmor |
| 1-1364 | 3-Cl—Ph | 2-MeNH-4-Pym | 1-Me-2-Tmor |
| 1-1365 | 3-Cl—Ph | 2-MeNH-4-Pym | 1-Piz |
| 1-1366 | 3-Cl—Ph | 2-MeNH-4-Pym | 4-Me-1-Piz |
| 1-1367 | 3-Cl—Ph | 2-MeNH-4-Pym | 2-Piz |
| 1-1368 | 3-Cl—Ph | 2-MeNH-4-Pym | 4-Pyr |

TABLE 1-continued

| Compound No. | R¹ | R² | R³ |
|---|---|---|---|
| 1-1369 | 3-Cl—Ph | 2-MeNH-4-Pym | 3-Pyr |
| 1-1370 | 3-Cl—Ph | 2-MeNH-4-Pym | 2-Pyr |
| 1-1371 | 3-Cl—Ph | 2-MeNH-4-Pym | 4-Pym |
| 1-1372 | 3-Cl—Ph | 2-MeNH-4-Pym | 5-Pym |
| 1-1373 | 3-Cl—Ph | 2-MeNH-4-Pym | 2-Pym |
| 1-1374 | 3-Cl—Ph | 2-MeNH-4-Pym | 3-Azt-CH₂ |
| 1-1375 | 3-Cl—Ph | 2-MeNH-4-Pym | 1-Me-3-Azt-CH₂ |
| 1-1376 | 3-Cl—Ph | 2-MeNH-4-Pym | 3-Pyrd-CH₂ |
| 1-1377 | 3-Cl—Ph | 2-MeNH-4-Pym | 1-Me-3-Pyrd-CH₂ |
| 1-1378 | 3-Cl—Ph | 2-MeNH-4-Pym | 4-Pip-CH₂ |
| 1-1379 | 3-Cl—Ph | 2-MeNH-4-Pym | 1-Me-4-Pip-CH₂ |
| 1-1380 | 3-Cl—Ph | 2-MeNH-4-Pym | 3-Hpip-CH₂ |
| 1-1381 | 3-Cl—Ph | 2-MeNH-4-Pym | 1-Me-3-Hpip-CH₂ |
| 1-1382 | 3-Cl—Ph | 2-MeNH-4-Pym | 4-Hpip-CH₂ |
| 1-1383 | 3-Cl—Ph | 2-MeNH-4-Pym | 1-Me-4-Hpip-CH₂ |
| 1-1384 | 3-Cl—Ph | 2-MeNH-4-Pym | 2-Mor-CH₂ |
| 1-1385 | 3-Cl—Ph | 2-MeNH-4-Pym | 1-Me-2-Mor-CH₂ |
| 1-1386 | 3-Cl—Ph | 2-MeNH-4-Pym | 2-Tmor-CH₂ |
| 1-1387 | 3-Cl—Ph | 2-MeNH-4-Pym | 1-Me-2-Tmor-CH₂ |
| 1-1388 | 3-Cl—Ph | 2-MeNH-4-Pym | 1-Piz-CH₂ |
| 1-1389 | 3-Cl—Ph | 2-MeNH-4-Pym | 4-Me-1-Piz-CH₂ |
| 1-1390 | 3-Cl—Ph | 2-MeNH-4-Pym | 2-Piz-CH₂ |
| 1-1391 | 3-Cl—Ph | 2-MeNH-4-Pym | 4-Pyr-CH₂ |
| 1-1392 | 3-Cl—Ph | 2-MeNH-4-Pym | 3-Pyr-CH₂ |
| 1-1393 | 3-Cl—Ph | 2-MeNH-4-Pym | 2-Pyr-CH₂ |
| 1-1394 | 3-Cl—Ph | 2-MeNH-4-Pym | 4-Pym-CH₂ |
| 1-1395 | 3-Cl—Ph | 2-MeNH-4-Pym | 5-Pym-CH₂ |
| 1-1396 | 3-Cl—Ph | 2-MeNH-4-Pym | 2-Pym-CH₂ |
| 1-1397 | 3-Cl-4-F—Ph | 4-Pyr | H₂N—(CH₂)₃ |
| 1-1398 | 3-Cl-4-F—Ph | 4-Pyr | MeNH—(CH₂)₃ |
| 1-1399 | 3-Cl-4-F—Ph | 4-Pyr | EtNH—(CH₂)₃ |
| 1-1400 | 3-Cl-4-F—Ph | 4-Pyr | Me₂N—(CH₂)₃ |
| 1-1401 | 3-Cl-4-F—Ph | 4-Pyr | 1-Azt-(CH₂)₃ |
| 1-1402 | 3-Cl-4-F—Ph | 4-Pyr | 1-Pyrd-(CH₂)₃ |
| 1-1403 | 3-Cl-4-F—Ph | 4-Pyr | 1-Pip-(CH₂)₃ |
| 1-1404 | 3-Cl-4-F—Ph | 4-Pyr | 1-Mor-(CH₂)₃ |
| 1-1405 | 3-Cl-4-F—Ph | 4-Pyr | 1-Tmor-(CH₂)₃ |
| 1-1406 | 3-Cl-4-F—Ph | 4-Pyr | 1-Piz-(CH₂)₃ |
| 1-1407 | 3-Cl-4-F—Ph | 4-Pyr | 4-Me-1-Piz-(CH₂)₃ |
| 1-1408 | 3-Cl-4-F—Ph | 4-Pyr | 3-Azt |
| 1-1409 | 3-Cl-4-F—Ph | 4-Pyr | 1-Me-3-Azt |
| 1-1410 | 3-Cl-4-F—Ph | 4-Pyr | 3-Pyrd |
| 1-1411 | 3-Cl-4-F—Ph | 4-Pyr | 1-Me-3-Pyrd |
| 1-1412 | 3-Cl-4-F—Ph | 4-Pyr | 4-Pip |
| 1-1413 | 3-Cl-4-F—Ph | 4-Pyr | 4-(3,4-deH-Pip) |
| 1-1414 | 3-Cl-4-F—Ph | 4-Pyr | 1-Me-4-Pip |
| 1-1415 | 3-Cl-4-F—Ph | 4-Pyr | 1-Me-4-(3,4-deH-Pip) |
| 1-1416 | 3-Cl-4-F—Ph | 4-Pyr | 1-Piz |
| 1-1417 | 3-Cl-4-F—Ph | 4-Pyr | 4-Me-1-Piz |
| 1-1418 | 3-Cl-4-F—Ph | 4-Pyr | 4-Pyr |
| 1-1419 | 3-Cl-4-F—Ph | 4-Pyr | 3-Pyr |
| 1-1420 | 3-Cl-4-F—Ph | 4-Pyr | 4-Pym |
| 1-1421 | 3-Cl-4-F—Ph | 4-Pyr | 5-Pym |
| 1-1422 | 3-Cl-4-F—Ph | 4-Pyr | 3-Pyrd-CH₂ |
| 1-1423 | 3-Cl-4-F—Ph | 4-Pyr | 1-Me-3-Pyrd-CH₂ |
| 1-1424 | 3-Cl-4-F—Ph | 4-Pyr | 4-Pip-CH₂ |
| 1-1425 | 3-Cl-4-F—Ph | 4-Pyr | 1-Me-4-Pip-CH₂ |
| 1-1426 | 3-Cl-4-F—Ph | 4-Pyr | 2-Piz-CH₂ |
| 1-1427 | 3-Cl-4-F—Ph | 4-Pyr | 4-Pyr-CH₂ |
| 1-1428 | 3-Cl-4-F—Ph | 4-Pyr | 3-Pyr-CH₂ |
| 1-1429 | 3-Cl-4-F—Ph | 4-Pyr | 4-Pym-CH₂ |
| 1-1430 | 3-Cl-4-F—Ph | 4-Pyr | 5-Pym-CH₂ |
| 1-1431 | 3-Cl-4-F—Ph | 4-Pyr | 2-Pym-CH₂ |
| 1-1432 | 3,4,5-triF-Ph | 4-Pyr | H₂N—(CH₂)₃ |
| 1-1433 | 3,4,5-triF-Ph | 4-Pyr | MeNH—(CH₂)₃ |
| 1-1434 | 3,4,5-triF-Ph | 4-Pyr | EtNH—(CH₂)₃ |
| 1-1435 | 3,4,5-triF-Ph | 4-Pyr | Me₂N—(CH₂)₃ |
| 1-1436 | 3,4,5-triF-Ph | 4-Pyr | 1-Azt-(CH₂)₃ |
| 1-1437 | 3,4,5-triF-Ph | 4-Pyr | 1-Pyrd-(CH₂)₃ |
| 1-1438 | 3,4,5-triF-Ph | 4-Pyr | 1-Pip-(CH₂)₃ |
| 1-1439 | 3,4,5-triF-Ph | 4-Pyr | 1-Mor-(CH₂)₃ |
| 1-1440 | 3,4,5-triF-Ph | 4-Pyr | 1-Tmor-(CH₂)₃ |
| 1-1441 | 3,4,5-triF-Ph | 4-Pyr | 1-Piz-(CH₂)₃ |
| 1-1442 | 3,4,5-triF-Ph | 4-Pyr | 4-Me-1-Piz-(CH₂)₃ |
| 1-1443 | 3,4,5-triF-Ph | 4-Pyr | 3-Azt |
| 1-1444 | 3,4,5-triF-Ph | 4-Pyr | 1-Me-3-Azt |
| 1-1445 | 3,4,5-triF-Ph | 4-Pyr | 3-Pyrd |
| 1-1446 | 3,4,5-triF-Ph | 4-Pyr | 1-Me-3-Pyrd |
| 1-1447 | 3,4,5-triF-Ph | 4-Pyr | 4-Pip |
| 1-1448 | 3,4,5-triF-Ph | 4-Pyr | 4-(3,4-deH-Pip) |
| 1-1449 | 3,4,5-triF-Ph | 4-Pyr | 1-Me-4-Pip |
| 1-1450 | 3,4,5-triF-Ph | 4-Pyr | 1-Me-4-(3,4-deH-Pip) |
| 1-1451 | 3,4,5-triF-Ph | 4-Pyr | 1-Piz |
| 1-1452 | 3,4,5-triF-Ph | 4-Pyr | 4-Me-1-Piz |
| 1-1453 | 3,4,5-triF-Ph | 4-Pyr | 4-Pyr |
| 1-1454 | 3,4,5-triF-Ph | 4-Pyr | 3-Pyr |
| 1-1455 | 3,4,5-triF-Ph | 4-Pyr | 4-Pym |
| 1-1456 | 3,4,5-triF-Ph | 4-Pyr | 5-Pym |
| 1-1457 | 3,4,5-triF-Ph | 4-Pyr | 3-Pyrd-CH₂ |
| 1-1458 | 3,4,5-triF-Ph | 4-Pyr | 1-Me-3-Pyrd-CH₂ |
| 1-1459 | 3,4,5-triF-Ph | 4-Pyr | 4-Pip-CH₂ |
| 1-1460 | 3,4,5-triF-Ph | 4-Pyr | 1-Me-4-Pip-CH₂ |
| 1-1461 | 3,4,5-triF-Ph | 4-Pyr | 2-Piz-CH₂ |
| 1-1462 | 3,4,5-triF-Ph | 4-Pyr | 4-Pyr-CH₂ |
| 1-1463 | 3,4,5-triF-Ph | 4-Pyr | 3-Pyr-CH₂ |
| 1-1464 | 3,4,5-triF-Ph | 4-Pyr | 4-Pym-CH₂ |
| 1-1465 | 3,4,5-triF-Ph | 4-Pyr | 5-Pym-CH₂ |
| 1-1466 | 3,4,5-triF-Ph | 4-Pyr | 2-Pym-CH₂ |
| 1-1467 | 3-CF₃—Ph | 4-Pyr | H₂N—(CH₂)₃ |
| 1-1468 | 3-CF₃—Ph | 4-Pyr | MeNH—(CH₂)₃ |
| 1-1469 | 3-CF₃—Ph | 4-Pyr | EtNH—(CH₂)₃ |
| 1-1470 | 3-CF₃—Ph | 4-Pyr | Me₂N—(CH₂)₃ |
| 1-1471 | 3-CF₃—Ph | 4-Pyr | 1-Azt-(CH₂)₃ |
| 1-1472 | 3-CF₃—Ph | 4-Pyr | 1-Pyrd-(CH₂)₃ |
| 1-1473 | 3-CF₃—Ph | 4-Pyr | 1-Pip-(CH₂)₃ |
| 1-1474 | 3-CF₃—Ph | 4-Pyr | 1-Mor-(CH₂)₃ |
| 1-1475 | 3-CF₃—Ph | 4-Pyr | 1-Tmor-(CH₂)₃ |
| 1-1476 | 3-CF₃—Ph | 4-Pyr | 1-Piz-(CH₂)₃ |
| 1-1477 | 3-CF₃—Ph | 4-Pyr | 4-Me-1-Piz-(CH₂)₃ |
| 1-1478 | 3-CF₃—Ph | 4-Pyr | 3-Azt |
| 1-1479 | 3-CF₃—Ph | 4-Pyr | 1-Me-3-Azt |
| 1-1480 | 3-CF₃—Ph | 4-Pyr | 3-Pyrd |
| 1-1481 | 3-CF₃—Ph | 4-Pyr | 1-Me-3-Pyrd |
| 1-1482 | 3-CF₃—Ph | 4-Pyr | 4-Pip |
| 1-1483 | 3-CF₃—Ph | 4-Pyr | 4-(3,4-deH-Pip) |
| 1-1484 | 3-CF₃—Ph | 4-Pyr | 1-Me-4-Pip |
| 1-1485 | 3-CF₃—Ph | 4-Pyr | 1-Me-4-(3,4-deH-Pip) |

TABLE 1-continued

| Compound No. | R¹ | R² | R³ |
|---|---|---|---|
| 1-1486 | 3-CF₃—Ph | 4-Pyr | 1-Piz |
| 1-1487 | 3-CF₃—Ph | 4-Pyr | 4-Me-1-Piz |
| 1-1488 | 3-CF₃—Ph | 4-Pyr | 4-Pyr |
| 1-1489 | 3-CF₃—Ph | 4-Pyr | 3-Pyr |
| 1-1490 | 3-CF₃—Ph | 4-Pyr | 4-Pym |
| 1-1491 | 3-CF₃—Ph | 4-Pyr | 5-Pym |
| 1-1492 | 3-CF₃—Ph | 4-Pyr | 3-Pyrd-CH₂ |
| 1-1493 | 3-CF₃—Ph | 4-Pyr | 1-Me-3-Pyrd-CH₂ |
| 1-1494 | 3-CF₃—Ph | 4-Pyr | 4-Pip-CH₂ |
| 1-1495 | 3-CF₃—Ph | 4-Pyr | 1-Me-4-Pip-CH₂ |
| 1-1496 | 3-CF₃—Ph | 4-Pyr | 2-Piz-CH₂ |
| 1-1497 | 3-CF₃—Ph | 4-Pyr | 4-Pyr-CH₂ |
| 1-1498 | 3-CF₃—Ph | 4-Pyr | 3-Pyr-CH₂ |
| 1-1499 | 3-CF₃—Ph | 4-Pyr | 4-Pym-CH₂ |
| 1-1500 | 3-CF₃—Ph | 4-Pyr | 5-Pym-CH₂ |
| 1-1501 | 3-CF₃—Ph | 4-Pyr | 2-Pym-CH₂ |
| 1-1502 | 3-CHF₂O—Ph | 4-Pyr | H₂N—(CH₂)₃ |
| 1-1503 | 3-CHF₂O—Ph | 4-Pyr | MeNH—(CH₂)₃ |
| 1-1504 | 3-CHF₂O—Ph | 4-Pyr | EtNH—(CH₂)₃ |
| 1-1505 | 3-CHF₂O—Ph | 4-Pyr | Me₂N—(CH₂)₃ |
| 1-1506 | 3-CHF₂O—Ph | 4-Pyr | 1-Azt-(CH₂)₃ |
| 1-1507 | 3-CHF₂O—Ph | 4-Pyr | 1-Pyrd-(CH₂)₃ |
| 1-1508 | 3-CHF₂O—Ph | 4-Pyr | 1-Pip-(CH₂)₃ |
| 1-1509 | 3-CHF₂O—Ph | 4-Pyr | 1-Mor-(CH₂)₃ |
| 1-1510 | 3-CHF₂O—Ph | 4-Pyr | 1-Tmor-(CH₂)₃ |
| 1-1511 | 3-CHF₂O—Ph | 4-Pyr | 1-Piz-(CH₂)₃ |
| 1-1512 | 3-CHF₂O—Ph | 4-Pyr | 4-Me-1-Piz-(CH₂)₃ |
| 1-1513 | 3-CHF₂O—Ph | 4-Pyr | 3-Azt |
| 1-1514 | 3-CHF₂O—Ph | 4-Pyr | 1-Me-3-Azt |
| 1-1515 | 3-CHF₂O—Ph | 4-Pyr | 3-Pyrd |
| 1-1516 | 3-CHF₂O—Ph | 4-Pyr | 1-Me-3-Pyrd |
| 1-1517 | 3-CHF₂O—Ph | 4-Pyr | 4-Pip |
| 1-1518 | 3-CHF₂O—Ph | 4-Pyr | 4-(3,4-deH-Pip) |
| 1-1519 | 3-CHF₂O—Ph | 4-Pyr | 1-Me-4-Pip |
| 1-1520 | 3-CHF₂O—Ph | 4-Pyr | 1-Me-4-(3,4-deH-Pip) |
| 1-1521 | 3-CHF₂O—Ph | 4-Pyr | 1-Piz |
| 1-1522 | 3-CHF₂O—Ph | 4-Pyr | 4-Me-1-Piz |
| 1-1523 | 3-CHF₂O—Ph | 4-Pyr | 4-Pyr |
| 1-1524 | 3-CHF₂O—Ph | 4-Pyr | 3-Pyr |
| 1-1525 | 3-CHF₂O—Ph | 4-Pyr | 4-Pym |
| 1-1526 | 3-CHF₂O—Ph | 4-Pyr | 5-Pym |
| 1-1527 | 3-CHF₂O—Ph | 4-Pyr | 3-Pyrd-CH₂ |
| 1-1528 | 3-CHF₂O—Ph | 4-Pyr | 1-Me-3-Pyrd-CH₂ |
| 1-1529 | 3-CHF₂O—Ph | 4-Pyr | 4-Pip-CH₂ |
| 1-1530 | 3-CHF₂O—Ph | 4-Pyr | 1-Me-4-Pip-CH₂ |
| 1-1531 | 3-CHF₂O—Ph | 4-Pyr | 2-Piz-CH₂ |
| 1-1532 | 3-CHF₂O—Ph | 4-Pyr | 4-Pyr-CH₂ |
| 1-1533 | 3-CHF₂O—Ph | 4-Pyr | 3-Pyr-CH₂ |
| 1-1534 | 3-CHF₂O—Ph | 4-Pyr | 4-Pym-CH₂ |
| 1-1535 | 3-CHF₂O—Ph | 4-Pyr | 5-Pym-CH₂ |
| 1-1536 | 3-CHF₂O—Ph | 4-Pyr | 2-Pym-CH₂ |
| 1-1537 | 3-Cl-4-F—Ph | 2-NH₂-4-Pym | H₂N—(CH₂)₃ |
| 1-1538 | 3-Cl-4-F—Ph | 2-NH₂-4-Pym | MeNH—(CH₂)₃ |
| 1-1539 | 3-Cl-4-F—Ph | 2-NH₂-4-Pym | EtNH—(CH₂)₃ |
| 1-1540 | 3-Cl-4-F—Ph | 2-NH₂-4-Pym | Me₂N—(CH₂)₃ |
| 1-1541 | 3-Cl-4-F—Ph | 2-NH₂-4-Pym | 1-Azt-(CH₂)₃ |
| 1-1542 | 3-Cl-4-F—Ph | 2-NH₂-4-Pym | 1-Pyrd-(CH₂)₃ |
| 1-1543 | 3-Cl-4-F—Ph | 2-NH₂-4-Pym | 1-Pip-(CH₂)₃ |
| 1-1544 | 3-Cl-4-F—Ph | 2-NH₂-4-Pym | 1-Mor-(CH₂)₃ |
| 1-1545 | 3-Cl-4-F—Ph | 2-NH₂-4-Pym | 1-Tmor-(CH₂)₃ |
| 1-1546 | 3-Cl-4-F—Ph | 2-NH₂-4-Pym | 1-Piz-(CH₂)₃ |
| 1-1547 | 3-Cl-4-F—Ph | 2-NH₂-4-Pym | 4-Me-1-Piz-(CH₂)₃ |
| 1-1548 | 3-Cl-4-F—Ph | 2-NH₂-4-Pym | 3-Azt |
| 1-1549 | 3-Cl-4-F—Ph | 2-NH₂-4-Pym | 1-Me-3-Azt |
| 1-1550 | 3-Cl-4-F—Ph | 2-NH₂-4-Pym | 3-Pyrd |
| 1-1551 | 3-Cl-4-F—Ph | 2-NH₂-4-Pym | 1-Me-3-Pyrd |
| 1-1552 | 3-Cl-4-F—Ph | 2-NH₂-4-Pym | 4-Pip |
| 1-1553 | 3-Cl-4-F—Ph | 2-NH₂-4-Pym | 4-(3,4-deH-Pip) |
| 1-1554 | 3-Cl-4-F—Ph | 2-NH₂-4-Pym | 1-Me-4-Pip |
| 1-1555 | 3-Cl-4-F—Ph | 2-NH₂-4-Pym | 1-Me-4-(3,4-deH-Pip) |
| 1-1556 | 3-Cl-4-F—Ph | 2-NH₂-4-Pym | 1-Piz |
| 1-1557 | 3-Cl-4-F—Ph | 2-NH₂-4-Pym | 4-Me-1-Piz |
| 1-1558 | 3-Cl-4-F—Ph | 2-NH₂-4-Pym | 4-Pyr |
| 1-1559 | 3-Cl-4-F—Ph | 2-NH₂-4-Pym | 3-Pyr |
| 1-1560 | 3-Cl-4-F—Ph | 2-NH₂-4-Pym | 4-Pym |
| 1-1561 | 3-Cl-4-F—Ph | 2-NH₂-4-Pym | 5-Pym |
| 1-1562 | 3-Cl-4-F—Ph | 2-NH₂-4-Pym | 3-Pyrd-CH₂ |
| 1-1563 | 3-Cl-4-F—Ph | 2-NH₂-4-Pym | 1-Me-3-Pyrd-CH₂ |
| 1-1564 | 3-Cl-4-F—Ph | 2-NH₂-4-Pym | 4-Pip-CH₂ |
| 1-1565 | 3-Cl-4-F—Ph | 2-NH₂-4-Pym | 1-Me-4-Pip-CH₂ |
| 1-1566 | 3-Cl-4-F—Ph | 2-NH₂-4-Pym | 2-Piz-CH₂ |
| 1-1567 | 3-Cl-4-F—Ph | 2-NH₂-4-Pym | 4-Pyr-CH₂ |
| 1-1568 | 3-Cl-4-F—Ph | 2-NH₂-4-Pym | 3-Pyr-CH₂ |
| 1-1569 | 3-Cl-4-F—Ph | 2-NH₂-4-Pym | 4-Pym-CH₂ |

TABLE 1-continued

| Compound No. | R¹ | R² | R³ |
|---|---|---|---|
| 1-1570 | 3-Cl-4-F—Ph | 2-NH₂-4-Pym | 5-Pym-CH₂ |
| 1-1571 | 3-Cl-4-F—Ph | 2-NH₂-4-Pym | 2-Pym-CH₂ |
| 1-1572 | 3,4,5-triF-Ph | 2-NH₂-4-Pym | H₂N—(CH₂)₃ |
| 1-1573 | 3,4,5-triF-Ph | 2-NH₂-4-Pym | MeNH—(CH₂)₃ |
| 1-1574 | 3,4,5-triF-Ph | 2-NH₂-4-Pym | EtNH—(CH₂)₃ |
| 1-1575 | 3,4,5-triF-Ph | 2-NH₂-4-Pym | Me₂N—(CH₂)₃ |
| 1-1576 | 3,4,5-triF-Ph | 2-NH₂-4-Pym | 1-Azt-(CH₂)₃ |
| 1-1577 | 3,4,5-triF-Ph | 2-NH₂-4-Pym | 1-Pyrd-(CH₂)₃ |
| 1-1578 | 3,4,5-triF-Ph | 2-NH₂-4-Pym | 1-Pip-(CH₂)₃ |
| 1-1579 | 3,4,5-triF-Ph | 2-NH₂-4-Pym | 1-Mor-(CH₂)₃ |
| 1-1580 | 3,4,5-triF-Ph | 2-NH₂-4-Pym | 1-Tmor-(CH₂)₃ |
| 1-1581 | 3,4,5-triF-Ph | 2-NH₂-4-Pym | 1-Piz-(CH₂)₃ |
| 1-1582 | 3,4,5-triF-Ph | 2-NH₂-4-Pym | 4-Me-1-Piz-(CH₂)₃ |
| 1-1583 | 3,4,5-triF-Ph | 2-NH₂-4-Pym | 3-Azt |
| 1-1584 | 3,4,5-triF-Ph | 2-NH₂-4-Pym | 1-Me-3-Azt |
| 1-1585 | 3,4,5-triF-Ph | 2-NH₂-4-Pym | 3-Pyrd |
| 1-1586 | 3,4,5-triF-Ph | 2-NH₂-4-Pym | 1-Me-3-Pyrd |
| 1-1587 | 3,4,5-triF-Ph | 2-NH₂-4-Pym | 4-Pip |
| 1-1588 | 3,4,5-triF-Ph | 2-NH₂-4-Pym | 4-(3,4-deH-Pip) |
| 1-1589 | 3,4,5-triF-Ph | 2-NH₂-4-Pym | 1-Me-4-Pip |
| 1-1590 | 3,4,5-triF-Ph | 2-NH₂-4-Pym | 1-Me-4-(3,4-deH-Pip) |
| 1-1591 | 3,4,5-triF-Ph | 2-NH₂-4-Pym | 1-Piz |
| 1-1592 | 3,4,5-triF-Ph | 2-NH₂-4-Pym | 4-Me-1-Piz |
| 1-1593 | 3,4,5-triF-Ph | 2-NH₂-4-Pym | 4-Pyr |
| 1-1594 | 3,4,5-triF-Ph | 2-NH₂-4-Pym | 3-Pyr |
| 1-1595 | 3,4,5-triF-Ph | 2-NH₂-4-Pym | 4-Pym |
| 1-1596 | 3,4,5-triF-Ph | 2-NH₂-4-Pym | 5-Pym |
| 1-1597 | 3,4,5-trif-Ph | 2-NH₂-4-Pym | 3-Pyrd-CH₂ |
| 1-1598 | 3,4,5-triF-Ph | 2-NH₂-4-Pym | 1-Me-3-Pyrd-CH₂ |
| 1-1599 | 3,4,5-triF-Ph | 2-NH₂-4-Pym | 4-Pip-CH₂ |
| 1-1600 | 3,4,5-triF-Ph | 2-NH₂-4-Pym | 1-Me-4-Pip-CH₂ |
| 1-1601 | 3,4,5-triF-Ph | 2-NH₂-4-Pym | 2-Piz-CH₂ |
| 1-1602 | 3,4,5-triF-Ph | 2-NH₂-4-Pym | 4-Pyr-CH₂ |
| 1-1603 | 3,4,5-triF-Ph | 2-NH₂-4-Pym | 3-Pyr-CH₂ |
| 1-1604 | 3,4,5-triF-Ph | 2-NH₂-4-Pym | 4-Pym-CH₂ |
| 1-1605 | 3,4,5-triF-Ph | 2-NH₂-4-Pym | 5-Pym-CH₂ |
| 1-1606 | 3,4,5-triF-Ph | 2-NH₂-4-Pym | 2-Pym-CH₂ |
| 1-1607 | 3-CF₃—Ph | 2-NH₂-4-Pym | H₂N—(CH₂)₃ |
| 1-1608 | 3-CF₃—Ph | 2-NH₂-4-Pym | MeNH—(CH₂)₃ |
| 1-1609 | 3-CF₃—Ph | 2-NH₂-4-Pym | EtNH—(CH₂)₃ |
| 1-1610 | 3-CF₃—Ph | 2-NH₂-4-Pym | Me₂N—(CH₂)₃ |
| 1-1611 | 3-CF₃—Ph | 2-NH₂-4-Pym | 1-Azt-(CH₂)₃ |
| 1-1612 | 3-CF₃—Ph | 2-NH₂-4-Pym | 1-Pyrd-(CH₂)₃ |
| 1-1613 | 3-CF₃—Ph | 2-NH₂-4-Pym | 1-Pip-(CH₂)₃ |
| 1-1614 | 3-CF₃—Ph | 2-NH₂-4-Pym | 1-Mor-(CH₂)₃ |
| 1-1615 | 3-CF₃—Ph | 2-NH₂-4-Pym | 1-Tmor-(CH₂)₃ |
| 1-1616 | 3-CF₃—Ph | 2-NH₂-4-Pym | 1-Piz-(CH₂)₃ |
| 1-1617 | 3-CF₃—Ph | 2-NH₂-4-Pym | 4-Me-1-Piz-(CH₂)₃ |
| 1-1618 | 3-CF₃—Ph | 2-NH₂-4-Pym | 3-Azt |
| 1-1619 | 3-CF₃—Ph | 2-NH₂-4-Pym | 1-Me-3-Azt |
| 1-1620 | 3-CF₃—Ph | 2-NH₂-4-Pym | 3-Pyrd |
| 1-1621 | 3-CF₃—Ph | 2-NH₂-4-Pym | 1-Me-3-Pyrd |
| 1-1622 | 3-CF₃—Ph | 2-NH₂-4-Pym | 4-Pip |
| 1-1623 | 3-CF₃—Ph | 2-NH₂-4-Pym | 4-(3,4-deH-Pip) |
| 1-1624 | 3-CF₃—Ph | 2-NH₂-4-Pym | 1-Me-4-Pip |
| 1-1625 | 3-CF₃—Ph | 2-NH₂-4-Pym | 1-Me-4-(3,4-deH-Pip) |
| 1-1626 | 3-CF₃—Ph | 2-NH₂-4-Pym | 1-Piz |
| 1-1627 | 3-CF₃—Ph | 2-NH₂-4-Pym | 4-Me-1-Piz |
| 1-1628 | 3-CF₃—Ph | 2-NH₂-4-Pym | 4-Pyr |
| 1-1629 | 3-CF₃—Ph | 2-NH₂-4-Pym | 3-Pyr |
| 1-1630 | 3-CF₃—Ph | 2-NH₂-4-Pym | 4-Pym |
| 1-1631 | 3-CF₃—Ph | 2-NH₂-4-Pym | 5-Pym |
| 1-1632 | 3-CF₃—Ph | 2-NH₂-4-Pym | 3-Pyrd-CH₂ |
| 1-1633 | 3-CF₃—Ph | 2-NH₂-4-Pym | 1-Me-3-Pyrd-CH₂ |
| 1-1634 | 3-CF₃—Ph | 2-NH₂-4-Pym | 4-Pip-CH₂ |
| 1-1635 | 3-CF₃—Ph | 2-NH₂-4-Pym | 1-Me-4-Pip-CH₂ |
| 1-1636 | 3-CF₃—Ph | 2-NH₂-4-Pym | 2-Piz-CH₂ |
| 1-1637 | 3-CF₃—Ph | 2-NH₂-4-Pym | 4-Pyr-CH₂ |
| 1-1638 | 3-CF₃—Ph | 2-NH₂-4-Pym | 3-Pyr-CH₂ |
| 1-1639 | 3-CF₃—Ph | 2-NH₂-4-Pym | 4-Pym-CH₂ |
| 1-1640 | 3-CF₃—Ph | 2-NH₂-4-Pym | 5-Pym-CH₂ |
| 1-1641 | 3-CF₃—Ph | 2-NH₂-4-Pym | 2-Pym-CH₂ |
| 1-1642 | 3-CHF₂O—Ph | 2-NH₂-4-Pym | H₂N—(CH₂)₃ |
| 1-1643 | 3-CHF₂O—Ph | 2-NH₂-4-Pym | MeNH—(CH₂)₃ |
| 1-1644 | 3-CHF₂O—Ph | 2-NH₂-4-Pym | EtNH—(CH₂)₃ |
| 1-1645 | 3-CHF₂O—Ph | 2-NH₂-4-Pym | Me₂N—(CH₂)₃ |
| 1-1646 | 3-CHF₂O—Ph | 2-NH₂-4-Pym | 1-Azt-(CH₂)₃ |
| 1-1647 | 3-CHF₂O—Ph | 2-NH₂-4-Pym | 1-Pyrd-(CH₂)₃ |
| 1-1648 | 3-CHF₂O—Ph | 2-NH₂-4-Pym | 1-Pip-(CH₂)₃ |
| 1-1649 | 3-CHF₂O—Ph | 2-NH₂-4-Pym | 1-Mor-(CH₂)₃ |
| 1-1650 | 3-CHF₂O—Ph | 2-NH₂-4-Pym | 1-Tmor-(CH₂)₃ |
| 1-1651 | 3-CHF₂O—Ph | 2-NH₂-4-Pym | 1-Piz-(CH₂)₃ |
| 1-1652 | 3-CHF₂O—Ph | 2-NH₂-4-Pym | 4-Me-1-Piz-(CH₂)₃ |
| 1-1653 | 3-CHF₂O—Ph | 2-NH₂-4-Pym | 3-Azt |
| 1-1654 | 3-CHF₂O—Ph | 2-NH₂-4-Pym | 1-Me-3-Azt |
| 1-1655 | 3-CHF₂O—Ph | 2-NH₂-4-Pym | 3-Pyrd |
| 1-1656 | 3-CHF₂O—Ph | 2-NH₂-4-Pym | 1-Me-3-Pyrd |
| 1-1657 | 3-CHF₂O—Ph | 2-NH₂-4-Pym | 4-Pip |
| 1-1658 | 3-CHF₂O—Ph | 2-NH₂-4-Pym | 4-(3,4-deH-Pip) |
| 1-1659 | 3-CHF₂O—Ph | 2-NH₂-4-Pym | 1-Me-4-Pip |
| 1-1660 | 3-CHF₂O—Ph | 2-NH₂-4-Pym | 1-Me-4-(3,4-deH-Pip) |
| 1-1661 | 3-CHF₂O—Ph | 2-NH₂-4-Pym | 1-Piz |
| 1-1662 | 3-CHF₂O—Ph | 2-NH₂-4-Pym | 4-Me-1-Piz |
| 1-1663 | 3-CHF₂O—Ph | 2-NH₂-4-Pym | 4-Pyr |
| 1-1664 | 3-CHF₂O—Ph | 2-NH₂-4-Pym | 3-Pyr |
| 1-1665 | 3-CHF₂O—Ph | 2-NH₂-4-Pym | 4-Pym |
| 1-1666 | 3-CHF₂O—Ph | 2-NH₂-4-Pym | 5-Pym |
| 1-1667 | 3-CHF₂O—Ph | 2-NH₂-4-Pym | 3-Pyrd-CH₂ |
| 1-1668 | 3-CHF₂O—Ph | 2-NH₂-4-Pym | 1-Me-3-Pyrd-CH₂ |
| 1-1669 | 3-CHF₂O—Ph | 2-NH₂-4-Pym | 4-Pip-CH₂ |
| 1-1670 | 3-CHF₂O—Ph | 2-NH₂-4-Pym | 1-Me-4-Pip-CH₂ |
| 1-1671 | 3-CHF₂O—Ph | 2-NH₂-4-Pym | 2-Piz-CH₂ |
| 1-1672 | 3-CHF₂O—Ph | 2-NH₂-4-Pym | 4-Pyr-CH₂ |
| 1-1673 | 3-CHF₂O—Ph | 2-NH₂-4-Pym | 3-Pyr-CH₂ |
| 1-1674 | 3-CHF₂O—Ph | 2-NH₂-4-Pym | 4-Pym-CH₂ |
| 1-1675 | 3-CHF₂O—Ph | 2-NH₂-4-Pym | 5-Pym-CH₂ |
| 1-1676 | 3-CHF₂O—Ph | 2-NH₂-4-Pym | 2-Pym-CH₂ |
| 1-1677 | 3-Cl-4-F—Ph | 2-MeNH-4-Pym | H₂N—(CH₂)₃ |
| 1-1678 | 3-Cl-4-F—Ph | 2-MeNH-4-Pym | MeNH—(CH₂)₃ |
| 1-1679 | 3-Cl-4-F—Ph | 2-MeNH-4-Pym | EtNH—(CH₂)₃ |
| 1-1680 | 3-Cl-4-F—Ph | 2-MeNH-4-Pym | Me₂N—(CH₂)₃ |

TABLE 1-continued

| Compound No. | R¹ | R² | R³ |
|---|---|---|---|
| 1-1681 | 3-Cl-4-F—Ph | 2-MeNH-4-Pym | 1-Azt-(CH₂)₃ |
| 1-1682 | 3-Cl-4-F—Ph | 2-MeNH-4-Pym | 1-Pyrd-(CH₂)₃ |
| 1-1683 | 3-Cl-4-F—Ph | 2-MeNH-4-Pym | 1-Pip-(CH₂)₃ |
| 1-1684 | 3-Cl-4-F—Ph | 2-MeNH-4-Pym | 1-Mor-(CH₂)₃ |
| 1-1685 | 3-Cl-4-F—Ph | 2-MeNH-4-Pym | 1-Tmor-(CH₂)₃ |
| 1-1686 | 3-Cl-4-F—Ph | 2-MeNH-4-Pym | 1-Piz-(CH₂)₃ |
| 1-1687 | 3-Cl-4-F—Ph | 2-MeNH-4-Pym | 4-Me-1-Piz-(CH₂)₃ |
| 1-1688 | 3-Cl-4-F—Ph | 2-MeNH-4-Pym | 3-Azt |
| 1-1689 | 3-Cl-4-F—Ph | 2-MeNH-4-Pym | 1-Me-3-Azt |
| 1-1690 | 3-Cl-4-F—Ph | 2-MeNH-4-Pym | 3-Pyrd |
| 1-1691 | 3-Cl-4-F—Ph | 2-MeNH-4-Pym | 1-Me-3-Pyrd |
| 1-1692 | 3-Cl-4-F—Ph | 2-MeNH-4-Pym | 4-Pip |
| 1-1693 | 3-Cl-4-F—Ph | 2-MeNH-4-Pym | 4-(3,4-deH-Pip) |
| 1-1694 | 3-Cl-4-F—Ph | 2-MeNH-4-Pym | 1-Me-4-Pip |
| 1-1695 | 3-Cl-4-F—Ph | 2-MeNH-4-Pym | 1-Me-4-(3,4-deH-Pip) |
| 1-1696 | 3-Cl-4-F—Ph | 2-MeNH-4-Pym | 1-Piz |
| 1-1697 | 3-Cl-4-F—Ph | 2-MeNH-4-Pym | 4-Me-1-Piz |
| 1-1698 | 3-Cl-4-F—Ph | 2-MeNH-4-Pym | 4-Pyr |
| 1-1699 | 3-Cl-4-F—Ph | 2-MeNH-4-Pym | 3-Pyr |
| 1-1700 | 3-Cl-4-F—Ph | 2-MeNH-4-Pym | 4-Pym |
| 1-1701 | 3-Cl-4-F—Ph | 2-MeNH-4-Pym | 5-Pym |
| 1-1702 | 3-Cl-4-F—Ph | 2-MeNH-4-Pym | 3-Pyrd-CH₂ |
| 1-1703 | 3-Cl-4-F—Ph | 2-MeNH-4-Pym | 1-Me-3-Pyrd-CH₂ |
| 1-1704 | 3-Cl-4-F—Ph | 2-MeNH-4-Pym | 4-Pip-CH₂ |
| 1-1705 | 3-Cl-4-F—Ph | 2-MeNH-4-Pym | 1-Me-4-Pip-CH₂ |
| 1-1706 | 3-Cl-4-F—Ph | 2-MeNH-4-Pym | 2-Piz-CH₂ |
| 1-1707 | 3-Cl-4-F—Ph | 2-MeNH-4-Pym | 4-Pyr-CH₂ |
| 1-1708 | 3-Cl-4-F—Ph | 2-MeNH-4-Pym | 3-Pyr-CH₂ |
| 1-1709 | 3-Cl-4-F—Ph | 2-MeNH-4-Pym | 4-Pym-CH₂ |
| 1-1710 | 3-Cl-4-F—Ph | 2-MeNH-4-Pym | 5-Pym-CH₂ |
| 1-1711 | 3-Cl-4-F—Ph | 2-MeNH-4-Pym | 2-Pym-CH₂ |
| 1-1712 | 3,4,5-triF-Ph | 2-MeNH-4-Pym | H₂N—(CH₂)₃ |
| 1-1713 | 3,4,5-triF-Ph | 2-MeNH-4-Pym | MeNH—(CH₂)₃ |
| 1-1714 | 3,4,5-triF-Ph | 2-MeNH-4-Pym | EtNH—(CH₂)₃ |
| 1-1715 | 3,4,5-triF-Ph | 2-MeNH-4-Pym | Me₂N—(CH₂)₃ |
| 1-1716 | 3,4,5-triF-Ph | 2-MeNH-4-Pym | 1-Azt-(CH₂)₃ |
| 1-1717 | 3,4,5-triF-Ph | 2-MeNH-4-Pym | 1-Pyrd-(CH₂)₃ |
| 1-1718 | 3,4,5-triF-Ph | 2-MeNH-4-Pym | 1-Pip-(CH₂)₃ |
| 1-1719 | 3,4,5-triF-Ph | 2-MeNH-4-Pym | 1-Mor-(CH₂)₃ |
| 1-1720 | 3,4,5-triF-Ph | 2-MeNH-4-Pym | 1-Tmor-(CH₂)₃ |
| 1-1721 | 3,4,5-triF-Ph | 2-MeNH-4-Pym | 1-Piz-(CH₂)₃ |
| 1-1722 | 3,4,5-triF-Ph | 2-MeNH-4-Pym | 4-Me-1-Piz-(CH₂)₃ |
| 1-1723 | 3,4,5-triF-Ph | 2-MeNH-4-Pym | 3-Azt |
| 1-1724 | 3,4,5-triF-Ph | 2-MeNH-4-Pym | 1-Me-3-Azt |
| 1-1725 | 3,4,5-triF-Ph | 2-MeNH-4-Pym | 3-Pyrd |
| 1-1726 | 3,4,5-triF-Ph | 2-MeNH-4-Pym | 1-Me-3-Pyrd |
| 1-1727 | 3,4,5-triF-Ph | 2-MeNH-4-Pym | 4-Pip |
| 1-1728 | 3,4,5-triF-Ph | 2-MeNH-4-Pym | 4-(3,4-deH-Pip) |
| 1-1729 | 3,4,5-triF-Ph | 2-MeNH-4-Pym | 1-Me-4-Pip |
| 1-1730 | 3,4,5-triF-Ph | 2-MeNH-4-Pym | 1-Me-4-(3,4-deH-Pip) |
| 1-1731 | 3,4,5-triF-Ph | 2-MeNH-4-Pym | 1-Piz |
| 1-1732 | 3,4,5-triF-Ph | 2-MeNH-4-Pym | 4-Me-1-Piz |
| 1-1733 | 3,4,5-triF-Ph | 2-MeNH-4-Pym | 4-Pyr |
| 1-1734 | 3,4,5-triF-Ph | 2-MeNH-4-Pym | 3-Pyr |
| 1-1735 | 3,4,5-triF-Ph | 2-MeNH-4-Pym | 4-Pym |
| 1-1736 | 3,4,5-triF-Ph | 2-MeNH-4-Pym | 5-Pym |
| 1-1737 | 3,4,5-triF-Ph | 2-MeNH-4-Pym | 3-Pyrd-CH₂ |
| 1-1738 | 3,4,5-triF-Ph | 2-MeNH-4-Pym | 1-Me-3-Pyrd-CH₂ |
| 1-1739 | 3,4,5-triF-Ph | 2-MeNH-4-Pym | 4-Pip-CH₂ |
| 1-1740 | 3,4,5-triF-Ph | 2-MeNH-4-Pym | 1-Me-4-Pip-CH₂ |
| 1-1741 | 3,4,5-triF-Ph | 2-MeNH-4-Pym | 2-Piz-CH₂ |
| 1-1742 | 3,4,5-triF-Ph | 2-MeNH-4-Pym | 4-Pyr-CH₂ |
| 1-1743 | 3,4,5-triF-Ph | 2-MeNH-4-Pym | 3-Pyr-CH₂ |
| 1-1744 | 3,4,5-triF-Ph | 2-MeNH-4-Pym | 4-Pym-CH₂ |
| 1-1745 | 3,4,5-triF-Ph | 2-MeNH-4-Pym | 5-Pym-CH₂ |
| 1-1746 | 3,4,5-triF-Ph | 2-MeNH-4-Pym | 2-Pym-CH₂ |
| 1-1747 | 3-CF₃—Ph | 2-MeNH-4-Pym | H₂N—(CH₂)₃ |
| 1-1748 | 3-CF₃—Ph | 2-MeNH-4-Pym | MeNH—(CH₂)₃ |
| 1-1749 | 3-CF₃—Ph | 2-MeNH-4-Pym | EtNH—(CH₂)₃ |
| 1-1750 | 3-CF₃—Ph | 2-MeNH-4-Pym | Me₂N—(CH₂)₃ |
| 1-1751 | 3-CF₃—Ph | 2-MeNH-4-Pym | 1-Azt-(CH₂)₃ |
| 1-1752 | 3-CF₃—Ph | 2-MeNH-4-Pym | 1-Pyrd-(CH₂)₃ |
| 1-1753 | 3-CF₃—Ph | 2-MeNH-4-Pym | 1-Pip-(CH₂)₃ |
| 1-1754 | 3-CF₃—Ph | 2-MeNH-4-Pym | 1-Mor-(CH₂)₃ |
| 1-1755 | 3-CF₃—Ph | 2-MeNH-4-Pym | 1-Tmor-(CH₂)₃ |
| 1-1756 | 3-CF₃—Ph | 2-MeNH-4-Pym | 1-Piz-(CH₂)₃ |
| 1-1757 | 3-CF₃—Ph | 2-MeNH-4-Pym | 4-Me-1-Piz-(CH₂)₃ |
| 1-1758 | 3-CF₃—Ph | 2-MeNH-4-Pym | 3-Azt |
| 1-1759 | 3-CF₃—Ph | 2-MeNH-4-Pym | 1-Me-3-Azt |
| 1-1760 | 3-CF₃—Ph | 2-MeNH-4-Pym | 3-Pyrd |
| 1-1761 | 3-CF₃—Ph | 2-MeNH-4-Pym | 1-Me-3-Pyrd |
| 1-1762 | 3-CF₃—Ph | 2-MeNH-4-Pym | 4-Pip |
| 1-1763 | 3-CF₃—Ph | 2-MeNH-4-Pym | 4-(3,4-deH-Pip) |
| 1-1764 | 3-CF₃—Ph | 2-MeNH-4-Pym | 1-Me-4-Pip |
| 1-1765 | 3-CF₃—Ph | 2-MeNH-4-Pym | 1-Me-4-(3,4-deH-Pip) |
| 1-1766 | 3-CF₃—Ph | 2-MeNH-4-Pym | 1-Piz |
| 1-1767 | 3-CF₃—Ph | 2-MeNH-4-Pym | 4-Me-1-Piz |
| 1-1768 | 3-CF₃—Ph | 2-MeNH-4-Pym | 4-Pyr |
| 1-1769 | 3-CF₃—Ph | 2-MeNH-4-Pym | 3-Pyr |
| 1-1770 | 3-CF₃—Ph | 2-MeNH-4-Pym | 4-Pym |
| 1-1771 | 3-CF₃—Ph | 2-MeNH-4-Pym | 5-Pym |
| 1-1772 | 3-CF₃—Ph | 2-MeNH-4-Pym | 3-Pyrd-CH₂ |
| 1-1773 | 3-CF₃—Ph | 2-MeNH-4-Pym | 1-Me-3-Pyrd-CH₂ |
| 1-1774 | 3-CF₃—Ph | 2-MeNH-4-Pym | 4-Pip-CH₂ |
| 1-1775 | 3-CF₃—Ph | 2-MeNH-4-Pym | 1-Me-4-Pip-CH₂ |
| 1-1776 | 3-CF₃—Ph | 2-MeNH-4-Pym | 2-Piz-CH₂ |
| 1-1777 | 3-CF₃—Ph | 2-MeNH-4-Pym | 4-Pyr-CH₂ |
| 1-1778 | 3-CF₃—Ph | 2-MeNH-4-Pym | 3-Pyr-CH₂ |
| 1-1779 | 3-CF₃—Ph | 2-MeNH-4-Pym | 4-Pym-CH₂ |
| 1-1780 | 3-CF₃—Ph | 2-MeNH-4-Pym | 5-Pym-CH₂ |
| 1-1781 | 3-CF₃—Ph | 2-MeNH-4-Pym | 2-Pym-CH₂ |
| 1-1782 | 3-CHF₂O—Ph | 2-MeNH-4-Pym | H₂N—(CH₂)₃ |
| 1-1783 | 3-CHF₂O—Ph | 2-MeNH-4-Pym | MeNH—(CH₂)₃ |
| 1-1784 | 3-CHF₂O—Ph | 2-MeNH-4-Pym | EtNH—(CH₂)₃ |
| 1-1785 | 3-CHF₂O—Ph | 2-MeNH-4-Pym | Me₂N—(CH₂)₃ |
| 1-1786 | 3-CHF₂O—Ph | 2-MeNH-4-Pym | 1-Azt-(CH₂)₃ |
| 1-1787 | 3-CHF₂O—Ph | 2-MeNH-4-Pym | 1-Pyrd-(CH₂)₃ |
| 1-1788 | 3-CHF₂O—Ph | 2-MeNH-4-Pym | 1-Pip-(CH₂)₃ |
| 1-1789 | 3-CHF₂O—Ph | 2-MeNH-4-Pym | 1-Mor-(CH₂)₃ |
| 1-1790 | 3-CHF₂O—Ph | 2-MeNH-4-Pym | 1-Tmor-(CH₂)₃ |
| 1-1791 | 3-CHF₂O—Ph | 2-MeNH-4-Pym | 1-Piz-(CH₂)₃ |

TABLE 1-continued

| Compound No. | R¹ | R² | R³ |
|---|---|---|---|
| 1-1792 | 3-CHF₂O—Ph | 2-MeNH-4-Pym | 4-Me-1-Piz-(CH₂)₃ |
| 1-1793 | 3-CHF₂O—Ph | 2-MeNH-4-Pym | 3-Azt |
| 1-1794 | 3-CHF₂O—Ph | 2-MeNH-4-Pym | 1-Me-3-Azt |
| 1-1795 | 3-CHF₂O—Ph | 2-MeNH-4-Pym | 3-Pyrd |
| 1-1796 | 3-CHF₂O—Ph | 2-MeNH-4-Pym | 1-Me-3-Pyrd |
| 1-1797 | 3-CHF₂O—Ph | 2-MeNH-4-Pym | 4-Pip |
| 1-1798 | 3-CHF₂O—Ph | 2-MeNH-4-Pym | 4-(3,4-deH-Pip) |
| 1-1799 | 3-CHF₂O—Ph | 2-MeNH-4-Pym | 1-Me-4-Pip |
| 1-1800 | 3-CHF₂O—Ph | 2-MeNH-4-Pym | 1-Me-4-(3,4-deH-Pip) |
| 1-1801 | 3-CHF₂O—Ph | 2-MeNH-4-Pym | 1-Piz |
| 1-1802 | 3-CHF₂O—Ph | 2-MeNH-4-Pym | 4-Me-1-Piz |
| 1-1803 | 3-CHF₂O—Ph | 2-MeNH-4-Pym | 4-Pyr |
| 1-1804 | 3-CHF₂O—Ph | 2-MeNH-4-Pym | 3-Pyr |
| 1-1805 | 3-CHF₂O—Ph | 2-MeNH-4-Pym | 4-Pym |
| 1-1806 | 3-CHF₂O—Ph | 2-MeNH-4-Pym | 5-Pym |
| 1-1807 | 3-CHF₂O—Ph | 2-MeNH-4-Pym | 3-Pyrd-CH₂ |
| 1-1808 | 3-CHF₂O—Ph | 2-MeNH-4-Pym | 1-Me-3-Pyrd-CH₂ |
| 1-1809 | 3-CHF₂O—Ph | 2-MeNH-4-Pym | 4-Pip-CH₂ |
| 1-1810 | 3-CHF₂O—Ph | 2-MeNH-4-Pym | 1-Me-4-Pip-CH₂ |
| 1-1811 | 3-CHF₂O—Ph | 2-MeNH-4-Pym | 2-Piz-CH₂ |
| 1-1812 | 3-CHF₂O—Ph | 2-MeNH-4-Pym | 4-Pyr-CH₂ |
| 1-1813 | 3-CHF₂O—Ph | 2-MeNH-4-Pym | 3-Pyr-CH₂ |
| 1-1814 | 3-CHF₂O—Ph | 2-MeNH-4-Pym | 4-Pym-CH₂ |
| 1-1815 | 3-CHF₂O—Ph | 2-MeNH-4-Pym | 5-Pym-CH₂ |
| 1-1816 | 3-CHF₂O—Ph | 2-MeNH-4-Pym | 2-Pym-CH₂ |
| 1-1817 | Ph | 2-NH₂-4-Pyr | H₂N—(CH₂)₃ |
| 1-1818 | Ph | 2-NH₂-4-Pyr | MeNH—(CH₂)₃ |
| 1-1819 | Ph | 2-NH₂-4-Pyr | EtNH—(CH₂)₃ |
| 1-1820 | Ph | 2-NH₂-4-Pyr | Me₂N—(CH₂)₃ |
| 1-1821 | Ph | 2-NH₂-4-Pyr | 1-Azt-(CH₂)₃ |
| 1-1822 | Ph | 2-NH₂-4-Pyr | 1-Pyrd-(CH₂)₃ |
| 1-1823 | Ph | 2-NH₂-4-Pyr | 1-Pip-(CH₂)₃ |
| 1-1824 | Ph | 2-NH₂-4-Pyr | 1-Mor-(CH₂)₃ |
| 1-1825 | Ph | 2-NH₂-4-Pyr | 1-Tmor-(CH₂)₃ |
| 1-1826 | Ph | 2-NH₂-4-Pyr | 1-Piz-(CH₂)₃ |
| 1-1827 | Ph | 2-NH₂-4-Pyr | 4-Me-1-Piz-(CH₂)₃ |
| 1-1828 | Ph | 2-NH₂-4-Pyr | 3-Azt |
| 1-1829 | Ph | 2-NH₂-4-Pyr | 1-Me-3-Azt |
| 1-1830 | Ph | 2-NH₂-4-Pyr | 3-Pyrd |
| 1-1831 | Ph | 2-NH₂-4-Pyr | 1-Me-3-Pyrd |
| 1-1832 | Ph | 2-NH₂-4-Pyr | 4-Pip |
| 1-1833 | Ph | 2-NH₂-4-Pyr | 4-(3,4-deH-Pip) |
| 1-1834 | Ph | 2-NH₂-4-Pyr | 1-Me-4-Pip |
| 1-1835 | Ph | 2-NH₂-4-Pyr | 1-Me-4-(3,4-deH-Pip) |
| 1-1836 | Ph | 2-NH₂-4-Pyr | 1-Piz |
| 1-1837 | Ph | 2-NH₂-4-Pyr | 4-Me-1-Piz |
| 1-1838 | Ph | 2-NH₂-4-Pyr | 4-Pyr |
| 1-1839 | Ph | 2-NH₂-4-Pyr | 3-Pyr |
| 1-1840 | Ph | 2-NH₂-4-Pyr | 4-Pym |
| 1-1841 | Ph | 2-NH₂-4-Pyr | 5-Pym |
| 1-1842 | Ph | 2-NH₂-4-Pyr | 3-Pyrd-CH₂ |
| 1-1843 | Ph | 2-NH₂-4-Pyr | 1-Me-3-Pyrd-CH₂ |
| 1-1844 | Ph | 2-NH₂-4-Pyr | 4-Pip-CH₂ |
| 1-1845 | Ph | 2-NH₂-4-Pyr | 1-Me-4-Pip-CH₂ |
| 1-1846 | Ph | 2-NH₂-4-Pyr | 2-Piz-CH₂ |
| 1-1847 | Ph | 2-NH₂-4-Pyr | 4-Pyr-CH₂ |
| 1-1848 | Ph | 2-NH₂-4-Pyr | 3-Pyr-CH₂ |
| 1-1849 | Ph | 2-NH₂-4-Pyr | 4-Pym-CH₂ |
| 1-1850 | Ph | 2-NH₂-4-Pyr | 5-Pym-CH₂ |
| 1-1851 | Ph | 2-NH₂-4-Pyr | 2-Pym-CH₂ |
| 1-1852 | 4-F—Ph | 2-NH₂-4-Pyr | H₂N—(CH₂)₃ |
| 1-1853 | 4-F—Ph | 2-NH₂-4-Pyr | MeNH—(CH₂)₃ |
| 1-1854 | 4-F—Ph | 2-NH₂-4-Pyr | EtNH—(CH₂)₃ |
| 1-1855 | 4-F—Ph | 2-NH₂-4-Pyr | Me₂N—(CH₂)₃ |
| 1-1856 | 4-F—Ph | 2-NH₂-4-Pyr | 1-Azt-(CH₂)₃ |
| 1-1857 | 4-F—Ph | 2-NH₂-4-Pyr | 1-Pyrd-(CH₂)₃ |
| 1-1858 | 4-F—Ph | 2-NH₂-4-Pyr | 1-Pip-(CH₂)₃ |
| 1-1859 | 4-F—Ph | 2-NH₂-4-Pyr | 1-Mor-(CH₂)₃ |
| 1-1860 | 4-F—Ph | 2-NH₂-4-Pyr | 1-Tmor-(CH₂)₃ |
| 1-1861 | 4-F—Ph | 2-NH₂-4-Pyr | 1-Piz-(CH₂)₃ |
| 1-1862 | 4-F—Ph | 2-NH₂-4-Pyr | 4-Me-1-Piz-(CH₂)₃ |
| 1-1863 | 4-F—Ph | 2-NH₂-4-Pyr | 3-Azt |
| 1-1864 | 4-F—Ph | 2-NH₂-4-Pyr | 1-Me-3-Azt |
| 1-1865 | 4-F—Ph | 2-NH₂-4-Pyr | 3-Pyrd |
| 1-1866 | 4-F—Ph | 2-NH₂-4-Pyr | 1-Me-3-Pyrd |
| 1-1867 | 4-F—Ph | 2-NH₂-4-Pyr | 4-Pip |
| 1-1868 | 4-F—Ph | 2-NH₂-4-Pyr | 4-(3,4-deH-Pip) |
| 1-1869 | 4-F—Ph | 2-NH₂-4-Pyr | 1-Me-4-Pip |
| 1-1870 | 4-F—Ph | 2-NH₂-4-Pyr | 1-Me-4-(3,4-deH-Pip) |
| 1-1871 | 4-F—Ph | 2-NH₂-4-Pyr | 1-Piz |
| 1-1872 | 4-F—Ph | 2-NH₂-4-Pyr | 4-Me-1-Piz |
| 1-1873 | 4-F—Ph | 2-NH₂-4-Pyr | 4-Pyr |
| 1-1874 | 4-F—Ph | 2-NH₂-4-Pyr | 3-Pyr |
| 1-1875 | 4-F—Ph | 2-NH₂-4-Pyr | 4-Pym |
| 1-1876 | 4-F—Ph | 2-NH₂-4-Pyr | 5-Pym |
| 1-1877 | 4-F—Ph | 2-NH₂-4-Pyr | 3-Pyrd-CH₂ |
| 1-1878 | 4-F—Ph | 2-NH₂-4-Pyr | 1-Me-3-Pyrd-CH₂ |
| 1-1879 | 4-F—Ph | 2-NH₂-4-Pyr | 4-Pip-CH₂ |
| 1-1880 | 4-F—Ph | 2-NH₂-4-Pyr | 1-Me-4-Pip-CH₂ |
| 1-1881 | 4-F—Ph | 2-NH₂-4-Pyr | 2-Piz-CH₂ |
| 1-1882 | 4-F—Ph | 2-NH₂-4-Pyr | 4-Pyr-CH₂ |
| 1-1883 | 4-F—Ph | 2-NH₂-4-Pyr | 3-Pyr-CH₂ |
| 1-1884 | 4-F—Ph | 2-NH₂-4-Pyr | 4-Pym-CH₂ |
| 1-1885 | 4-F—Ph | 2-NH₂-4-Pyr | 5-Pym-CH₂ |
| 1-1886 | 4-F—Ph | 2-NH₂-4-Pyr | 2-Pym-CH₂ |
| 1-1887 | 3-F—Ph | 2-NH₂-4-Pyr | H₂N—(CH₂)₃ |
| 1-1888 | 3-F—Ph | 2-NH₂-4-Pyr | MeNH—(CH₂)₃ |
| 1-1889 | 3-F—Ph | 2-NH₂-4-Pyr | EtNH—(CH₂)₃ |
| 1-1890 | 3-F—Ph | 2-NH₂-4-Pyr | Me₂N—(CH₂)₃ |
| 1-1891 | 3-F—Ph | 2-NH₂-4-Pyr | 1-Azt-(CH₂)₃ |
| 1-1892 | 3-F—Ph | 2-NH₂-4-Pyr | 1-Pyrd-(CH₂)₃ |
| 1-1893 | 3-F—Ph | 2-NH₂-4-Pyr | 1-Pip-(CH₂)₃ |
| 1-1894 | 3-F—Ph | 2-NH₂-4-Pyr | 1-Mor-(CH₂)₃ |
| 1-1895 | 3-F—Ph | 2-NH₂-4-Pyr | 1-Tmor-(CH₂)₃ |
| 1-1896 | 3-F—Ph | 2-NH₂-4-Pyr | 1-Piz-(CH₂)₃ |
| 1-1897 | 3-F—Ph | 2-NH₂-4-Pyr | 4-Me-1-Piz-(CH₂)₃ |
| 1-1898 | 3-F—Ph | 2-NH₂-4-Pyr | 3-Azt |
| 1-1899 | 3-F—Ph | 2-NH₂-4-Pyr | 1-Me-3-Azt |
| 1-1900 | 3-F—Ph | 2-NH₂-4-Pyr | 3-Pyrd |
| 1-1901 | 3-F—Ph | 2-NH₂-4-Pyr | 1-Me-3-Pyrd |
| 1-1902 | 3-F—Ph | 2-NH₂-4-Pyr | 4-Pip |
| 1-1903 | 3-F—Ph | 2-NH₂-4-Pyr | 4-(3,4-deH-Pip) |
| 1-1904 | 3-F—Ph | 2-NH₂-4-Pyr | 1-Me-4-Pip |
| 1-1905 | 3-F—Ph | 2-NH₂-4-Pyr | 1-Me-4-(3,4-deH-Pip) |
| 1-1906 | 3-F—Ph | 2-NH₂-4-Pyr | 1-Piz |
| 1-1907 | 3-F—Ph | 2-NH₂-4-Pyr | 4-Me-1-Piz |
| 1-1908 | 3-F—Ph | 2-NH₂-4-Pyr | 4-Pyr |
| 1-1909 | 3-F—Ph | 2-NH₂-4-Pyr | 3-Pyr |
| 1-1910 | 3-F—Ph | 2-NH₂-4-Pyr | 4-Pym |
| 1-1911 | 3-F—Ph | 2-NH₂-4-Pyr | 5-Pym |
| 1-1912 | 3-F—Ph | 2-NH₂-4-Pyr | 3-Pyrd-CH₂ |
| 1-1913 | 3-F—Ph | 2-NH₂-4-Pyr | 1-Me-3-Pyrd-CH₂ |
| 1-1914 | 3-F—Ph | 2-NH₂-4-Pyr | 4-Pip-CH₂ |
| 1-1915 | 3-F—Ph | 2-NH₂-4-Pyr | 1-Me-4-Pip-CH₂ |
| 1-1916 | 3-F—Ph | 2-NH₂-4-Pyr | 2-Piz-CH₂ |
| 1-1917 | 3-F—Ph | 2-NH₂-4-Pyr | 4-Pyr-CH₂ |
| 1-1918 | 3-F—Ph | 2-NH₂-4-Pyr | 3-Pyr-CH₂ |

TABLE 1-continued

| Compound No. | R¹ | R² | R³ |
|---|---|---|---|
| 1-1919 | 3-F—Ph | 2-NH₂-4-Pyr | 4-Pym-CH₂ |
| 1-1920 | 3-F—Ph | 2-NH₂-4-Pyr | 5-Pym-CH₂ |
| 1-1921 | 3-F—Ph | 2-NH₂-4-Pyr | 2-Pym-CH₂ |
| 1-1922 | 3,4-diF-Ph | 2-NH₂-4-Pyr | H₂N—(CH₂)₃ |
| 1-1923 | 3,4-diF-Ph | 2-NH₂-4-Pyr | MeNH—(CH₂)₃ |
| 1-1924 | 3,4-diF-Ph | 2-NH₂-4-Pyr | EtNH—(CH₂)₃ |
| 1-1925 | 3,4-diF-Ph | 2-NH₂-4-Pyr | Me₂N—(CH₂)₃ |
| 1-1926 | 3,4-diF-Ph | 2-NH₂-4-Pyr | 1-Azt-(CH₂)₃ |
| 1-1927 | 3,4-diF-Ph | 2-NH₂-4-Pyr | 1-Pyrd-(CH₂)₃ |
| 1-1928 | 3,4-diF-Ph | 2-NH₂-4-Pyr | 1-Pip-(CH₂)₃ |
| 1-1929 | 3,4-diF-Ph | 2-NH₂-4-Pyr | 1-Mor-(CH₂)₃ |
| 1-1930 | 3,4-diF-Ph | 2-NH₂-4-Pyr | 1-Tmor-(CH₂)₃ |
| 1-1931 | 3,4-diF-Ph | 2-NH₂-4-Pyr | 1-Piz-(CH₂)₃ |
| 1-1932 | 3,4-diF-Ph | 2-NH₂-4-Pyr | 4-Me-1-Piz-(CH₂)₃ |
| 1-1933 | 3,4-diF-Ph | 2-NH₂-4-Pyr | 3-Azt |
| 1-1934 | 3,4-diF-Ph | 2-NH₂-4-Pyr | 1-Me-3-Azt |
| 1-1935 | 3,4-diF-Ph | 2-NH₂-4-Pyr | 3-Pyrd |
| 1-1936 | 3,4-diF-Ph | 2-NH₂-4-Pyr | 1-Me-3-Pyrd |
| 1-1937 | 3,4-diF-Ph | 2-NH₂-4-Pyr | 4-Pip |
| 1-1938 | 3,4-diF-Ph | 2-NH₂-4-Pyr | 4-(3,4-deH-Pip) |
| 1-1939 | 3,4-diF-Ph | 2-NH₂-4-Pyr | 1-Me-4-Pip |
| 1-1940 | 3,4-diF-Ph | 2-NH₂-4-Pyr | 1-Me-4-(3,4-deH-Pip) |
| 1-1941 | 3,4-diF-Ph | 2-NH₂-4-Pyr | 1-Piz |
| 1-1942 | 3,4-diF-Ph | 2-NH₂-4-Pyr | 4-Me-1-Piz |
| 1-1943 | 3,4-diF-Ph | 2-NH₂-4-Pyr | 4-Pyr |
| 1-1944 | 3,4-diF-Ph | 2-NH₂-4-Pyr | 3-Pyr |
| 1-1945 | 3,4-diF-Ph | 2-NH₂-4-Pyr | 4-Pym |
| 1-1946 | 3,4-diF-Ph | 2-NH₂-4-Pyr | 5-Pym |
| 1-1947 | 3,4-diF-Ph | 2-NH₂-4-Pyr | 3-Pyrd-CH₂ |
| 1-1948 | 3,4-diF-Ph | 2-NH₂-4-Pyr | 1-Me-3-Pyrd-CH₂ |
| 1-1949 | 3,4-diF-Ph | 2-NH₂-4-Pyr | 4-Pip-CH₂ |
| 1-1950 | 3,4-diF-Ph | 2-NH₂-4-Pyr | 1-Me-4-Pip-CH₂ |
| 1-1951 | 3,4-diF-Ph | 2-NH₂-4-Pyr | 2-Piz-CH₂ |
| 1-1952 | 3,4-diF-Ph | 2-NH₂-4-Pyr | 4-Pyr-CH₂ |
| 1-1953 | 3,4-diF-Ph | 2-NH₂-4-Pyr | 3-Pyr-CH₂ |
| 1-1954 | 3,4-diF-Ph | 2-NH₂-4-Pyr | 4-Pym-CH₂ |
| 1-1955 | 3,4-diF-Ph | 2-NH₂-4-Pyr | 5-Pym-CH₂ |
| 1-1956 | 3,4-diF-Ph | 2-NH₂-4-Pyr | 2-Pym-CH₂ |
| 1-1957 | 3-Cl—Ph | 2-NH₂-4-Pyr | H₂N—(CH₂)₃ |
| 1-1958 | 3-Cl—Ph | 2-NH₂-4-Pyr | MeNH—(CH₂)₃ |
| 1-1959 | 3-Cl—Ph | 2-NH₂-4-Pyr | EtNH—(CH₂)₃ |
| 1-1960 | 3-Cl—Ph | 2-NH₂-4-Pyr | Me₂N—(CH₂)₃ |
| 1-1961 | 3-Cl—Ph | 2-NH₂-4-Pyr | 1-Azt-(CH₂)₃ |
| 1-1962 | 3-Cl—Ph | 2-NH₂-4-Pyr | 1-Pyrd-(CH₂)₃ |
| 1-1963 | 3-Cl—Ph | 2-NH₂-4-Pyr | 1-Pip-(CH₂)₃ |
| 1-1964 | 3-Cl—Ph | 2-NH₂-4-Pyr | 1-Mor-(CH₂)₃ |
| 1-1965 | 3-Cl—Ph | 2-NH₂-4-Pyr | 1-Tmor-(CH₂)₃ |
| 1-1966 | 3-Cl—Ph | 2-NH₂-4-Pyr | 1-Piz-(CH₂)₃ |
| 1-1967 | 3-Cl—Ph | 2-NH₂-4-Pyr | 4-Me-1-Piz-(CH₂)₃ |
| 1-1968 | 3-Cl—Ph | 2-NH₂-4-Pyr | 3-Azt |
| 1-1969 | 3-Cl—Ph | 2-NH₂-4-Pyr | 1-Me-3-Azt |
| 1-1970 | 3-Cl—Ph | 2-NH₂-4-Pyr | 3-Pyrd |
| 1-1971 | 3-Cl—Ph | 2-NH₂-4-Pyr | 1-Me-3-Pyrd |
| 1-1972 | 3-Cl—Ph | 2-NH₂-4-Pyr | 4-Pip |
| 1-1973 | 3-Cl—Ph | 2-NH₂-4-Pyr | 4-(3,4-deH-Pip) |
| 1-1974 | 3-Cl—Ph | 2-NH₂-4-Pyr | 1-Me-4-Pip |
| 1-1975 | 3-Cl—Ph | 2-NH₂-4-Pyr | 1-Me-4-(3,4-deH-Pip) |
| 1-1976 | 3-Cl—Ph | 2-NH₂-4-Pyr | 1-Piz |
| 1-1977 | 3-Cl—Ph | 2-NH₂-4-Pyr | 4-Me-1-Piz |
| 1-1978 | 3-Cl—Ph | 2-NH₂-4-Pyr | 4-Pyr |
| 1-1979 | 3-Cl—Ph | 2-NH₂-4-Pyr | 3-Pyr |
| 1-1980 | 3-Cl—Ph | 2-NH₂-4-Pyr | 4-Pym |
| 1-1981 | 3-Cl—Ph | 2-NH₂-4-Pyr | 5-Pym |
| 1-1982 | 3-Cl—Ph | 2-NH₂-4-Pyr | 3-Pyrd-CH₂ |
| 1-1983 | 3-Cl—Ph | 2-NH₂-4-Pyr | 1-Me-3-Pyrd-CH₂ |
| 1-1984 | 3-Cl—Ph | 2-NH₂-4-Pyr | 4-Pip-CH₂ |
| 1-1985 | 3-Cl—Ph | 2-NH₂-4-Pyr | 1-Me-4-Pip-CH₂ |
| 1-1986 | 3-Cl—Ph | 2-NH₂-4-Pyr | 2-Piz-CH₂ |
| 1-1987 | 3-Cl—Ph | 2-NH₂-4-Pyr | 4-Pyr-CH₂ |
| 1-1988 | 3-Cl—Ph | 2-NH₂-4-Pyr | 3-Pyr-CH₂ |
| 1-1989 | 3-Cl—Ph | 2-NH₂-4-Pyr | 4-Pym-CH₂ |
| 1-1990 | 3-Cl—Ph | 2-NH₂-4-Pyr | 5-Pym-CH₂ |
| 1-1991 | 3-Cl—Ph | 2-NH₂-4-Pyr | 2-Pym-CH₂ |
| 1-1992 | Ph | 2-MeNH-4-Pyr | H₂N—(CH₂)₃ |
| 1-1993 | Ph | 2-MeNH-4-Pyr | MeNH—(CH₂)₃ |
| 1-1994 | Ph | 2-MeNH-4-Pyr | EtNH—(CH₂)₃ |
| 1-1995 | Ph | 2-MeNH-4-Pyr | Me₂N—(CH₂)₃ |
| 1-1996 | Ph | 2-MeNH-4-Pyr | 1-Azt-(CH₂)₃ |
| 1-1997 | Ph | 2-MeNH-4-Pyr | 1-Pyrd-(CH₂)₃ |
| 1-1998 | Ph | 2-MeNH-4-Pyr | 1-Pip-(CH₂)₃ |
| 1-1999 | Ph | 2-MeNH-4-Pyr | 1-Mor-(CH₂)₃ |
| 1-2000 | Ph | 2-MeNH-4-Pyr | 1-Tmor-(CH₂)₃ |
| 1-2001 | Ph | 2-MeNH-4-Pyr | 1-Piz-(CH₂)₃ |
| 1-2002 | Ph | 2-MeNH-4-Pyr | 4-Me-1-Piz-(CH₂)₃ |
| 1-2003 | Ph | 2-MeNH-4-Pyr | 3-Azt |
| 1-2004 | Ph | 2-MeNH-4-Pyr | 1-Me-3-Azt |
| 1-2005 | Ph | 2-MeNH-4-Pyr | 3-Pyrd |
| 1-2006 | Ph | 2-MeNH-4-Pyr | 1-Me-3-Pyrd |
| 1-2007 | Ph | 2-MeNH-4-Pyr | 4-Pip |
| 1-2008 | Ph | 2-MeNH-4-Pyr | 4-(3,4-deH-Pip) |
| 1-2009 | Ph | 2-MeNH-4-Pyr | 1-Me-4-Pip |
| 1-2010 | Ph | 2-MeNH-4-Pyr | 1-Me-4-(3,4-deH-Pip) |
| 1-2011 | Ph | 2-MeNH-4-Pyr | 1-Piz |
| 1-2012 | Ph | 2-MeNH-4-Pyr | 4-Me-1-Piz |
| 1-2013 | Ph | 2-MeNH-4-Pyr | 4-Pyr |
| 1-2014 | Ph | 2-MeNH-4-Pyr | 3-Pyr |
| 1-2015 | Ph | 2-MeNH-4-Pyr | 4-Pym |
| 1-2016 | Ph | 2-MeNH-4-Pyr | 5-Pym |
| 1-2017 | Ph | 2-MeNH-4-Pyr | 3-Pyrd-CH₂ |
| 1-2018 | Ph | 2-MeNH-4-Pyr | 1-Me-3-Pyrd-CH₂ |
| 1-2019 | Ph | 2-MeNH-4-Pyr | 4-Pip-CH₂ |
| 1-2020 | Ph | 2-MeNH-4-Pyr | 1-Me-4-Pip-CH₂ |
| 1-2021 | Ph | 2-MeNH-4-Pyr | 2-Piz-CH₂ |
| 1-2022 | Ph | 2-MeNH-4-Pyr | 4-Pyr-CH₂ |
| 1-2023 | Ph | 2-MeNH-4-Pyr | 3-Pyr-CH₂ |
| 1-2024 | Ph | 2-MeNH-4-Pyr | 4-Pym-CH₂ |
| 1-2025 | Ph | 2-MeNH-4-Pyr | 5-Pym-CH₂ |
| 1-2026 | Ph | 2-MeNH-4-Pyr | 2-Pym-CH₂ |
| 1-2027 | 4-F—Ph | 2-MeNH-4-Pyr | H₂N—(CH₂)₃ |
| 1-2028 | 4-F—Ph | 2-MeNH-4-Pyr | MeNH—(CH₂)₃ |
| 1-2029 | 4-F—Ph | 2-MeNH-4-Pyr | EtNH—(CH₂)₃ |
| 1-2030 | 4-F—Ph | 2-MeNH-4-Pyr | Me₂N—(CH₂)₃ |
| 1-2031 | 4-F—Ph | 2-MeNH-4-Pyr | 1-Azt-(CH₂)₃ |
| 1-2032 | 4-F—Ph | 2-MeNH-4-Pyr | 1-Pyrd-(CH₂)₃ |
| 1-2033 | 4-F—Ph | 2-MeNH-4-Pyr | 1-Pip-(CH₂)₃ |
| 1-2034 | 4-F—Ph | 2-MeNH-4-Pyr | 1-Mor-(CH₂)₃ |
| 1-2035 | 4-F—Ph | 2-MeNH-4-Pyr | 1-Tmor-(CH₂)₃ |
| 1-2036 | 4-F—Ph | 2-MeNH-4-Pyr | 1-Piz-(CH₂)₃ |
| 1-2037 | 4-F—Ph | 2-MeNH-4-Pyr | 4-Me-1-Piz-(CH₂)₃ |
| 1-2038 | 4-F—Ph | 2-MeNH-4-Pyr | 3-Azt |
| 1-2039 | 4-F—Ph | 2-MeNH-4-Pyr | 1-Me-3-Azt |
| 1-2040 | 4-F—Ph | 2-MeNH-4-Pyr | 3-Pyrd |
| 1-2041 | 4-F—Ph | 2-MeNH-4-Pyr | 1-Me-3-Pyrd |
| 1-2042 | 4-F—Ph | 2-MeNH-4-Pyr | 4-Pip |
| 1-2043 | 4-F—Ph | 2-MeNH-4-Pyr | 4-(3,4-deH-Pip) |
| 1-2044 | 4-F—Ph | 2-MeNH-4-Pyr | 1-Me-4-Pip |
| 1-2045 | 4-F—Ph | 2-MeNH-4-Pyr | 1-Me-4-(3,4-deH-Pip) |
| 1-2046 | 4-F—Ph | 2-MeNH-4-Pyr | 1-Piz |
| 1-2047 | 4-F—Ph | 2-MeNH-4-Pyr | 4-Me-1-Piz |
| 1-2048 | 4-F—Ph | 2-MeNH-4-Pyr | 4-Pyr |
| 1-2049 | 4-F—Ph | 2-MeNH-4-Pyr | 3-Pyr |
| 1-2050 | 4-F—Ph | 2-MeNH-4-Pyr | 4-Pym |
| 1-2051 | 4-F—Ph | 2-MeNH-4-Pyr | 5-Pym |
| 1-2052 | 4-F—Ph | 2-MeNH-4-Pyr | 3-Pyrd-CH₂ |
| 1-2053 | 4-F—Ph | 2-MeNH-4-Pyr | 1-Me-3-Pyrd-CH₂ |
| 1-2054 | 4-F—Ph | 2-MeNH-4-Pyr | 4-Pip-CH₂ |
| 1-2055 | 4-F—Ph | 2-MeNH-4-Pyr | 1-Me-4-Pip-CH₂ |
| 1-2056 | 4-F—Ph | 2-MeNH-4-Pyr | 2-Piz-CH₂ |
| 1-2057 | 4-F—Ph | 2-MeNH-4-Pyr | 4-Pyr-CH₂ |
| 1-2058 | 4-F—Ph | 2-MeNH-4-Pyr | 3-Pyr-CH₂ |
| 1-2059 | 4-F—Ph | 2-MeNH-4-Pyr | 4-Pym-CH₂ |
| 1-2060 | 4-F—Ph | 2-MeNH-4-Pyr | 5-Pym-CH₂ |
| 1-2061 | 4-F—Ph | 2-MeNH-4-Pyr | 2-Pym-CH₂ |
| 1-2062 | 3-F—Ph | 2-MeNH-4-Pyr | H₂N—(CH₂)₃ |
| 1-2063 | 3-F—Ph | 2-MeNH-4-Pyr | MeNH—(CH₂)₃ |
| 1-2064 | 3-F—Ph | 2-MeNH-4-Pyr | EtNH—(CH₂)₃ |
| 1-2065 | 3-F—Ph | 2-MeNH-4-Pyr | Me₂N—(CH₂)₃ |
| 1-2066 | 3-F—Ph | 2-MeNH-4-Pyr | 1-Azt-(CH₂)₃ |
| 1-2067 | 3-F—Ph | 2-MeNH-4-Pyr | 1-Pyrd-(CH₂)₃ |
| 1-2068 | 3-F—Ph | 2-MeNH-4-Pyr | 1-Pip-(CH₂)₃ |
| 1-2069 | 3-F—Ph | 2-MeNH-4-Pyr | 1-Mor-(CH₂)₃ |
| 1-2070 | 3-F—Ph | 2-MeNH-4-Pyr | 1-Tmor-(CH₂)₃ |

TABLE 1-continued

| Compound No. | R¹ | R² | R³ |
|---|---|---|---|
| 1-2071 | 3-F—Ph | 2-MeNH-4-Pyr | 1-Piz-(CH₂)₃ |
| 1-2072 | 3-F—Ph | 2-MeNH-4-Pyr | 4-Me-1-Piz-(CH₂)₃ |
| 1-2073 | 3-F—Ph | 2-MeNH-4-Pyr | 3-Azt |
| 1-2074 | 3-F—Ph | 2-MeNH-4-Pyr | 1-Me-3-Azt |
| 1-2075 | 3-F—Ph | 2-MeNH-4-Pyr | 3-Pyrd |
| 1-2076 | 3-F—Ph | 2-MeNH-4-Pyr | 1-Me-3-Pyrd |
| 1-2077 | 3-F—Ph | 2-MeNH-4-Pyr | 4-Pip |
| 1-2078 | 3-F—Ph | 2-MeNH-4-Pyr | 4-(3,4-deH-Pip) |
| 1-2079 | 3-F—Ph | 2-MeNH-4-Pyr | 1-Me-4-Pip |
| 1-2080 | 3-F—Ph | 2-MeNH-4-Pyr | 1-Me-4-(3,4-deH-Pip) |
| 1-2081 | 3-F—Ph | 2-MeNH-4-Pyr | 1-Piz |
| 1-2082 | 3-F—Ph | 2-MeNH-4-Pyr | 4-Me-1-Piz |
| 1-2083 | 3-F—Ph | 2-MeNH-4-Pyr | 4-Pyr |
| 1-2084 | 3-F—Ph | 2-MeNH-4-Pyr | 3-Pyr |
| 1-2085 | 3-F—Ph | 2-MeNH-4-Pyr | 4-Pym |
| 1-2086 | 3-F—Ph | 2-MeNH-4-Pyr | 5-Pym |
| 1-2087 | 3-F—Ph | 2-MeNH-4-Pyr | 3-Pyrd-CH₂ |
| 1-2088 | 3-F—Ph | 2-MeNH-4-Pyr | 1-Me-3-Pyrd-CH₂ |
| 1-2089 | 3-F—Ph | 2-MeNH-4-Pyr | 4-Pip-CH₂ |
| 1-2090 | 3-F—Ph | 2-MeNH-4-Pyr | 1-Me-4-Pip-CH₂ |
| 1-2091 | 3-F—Ph | 2-MeNH-4-Pyr | 2-Piz-CH₂ |
| 1-2092 | 3-F—Ph | 2-MeNH-4-Pyr | 4-Pyr-CH₂ |
| 1-2093 | 3-F—Ph | 2-MeNH-4-Pyr | 3-Pyr-CH₂ |
| 1-2094 | 3-F—Ph | 2-MeNH-4-Pyr | 4-Pym-CH₂ |
| 1-2095 | 3-F—Ph | 2-MeNH-4-Pyr | 5-Pym-CH₂ |
| 1-2096 | 3-F—Ph | 2-MeNH-4-Pyr | 2-Pym-CH₂ |
| 1-2097 | 3,4-diF-Ph | 2-MeNH-4-Pyr | H₂N—(CH₂)₃ |
| 1-2098 | 3,4-diF-Ph | 2-MeNH-4-Pyr | MeNH—(CH₂)₃ |
| 1-2099 | 3,4-diF-Ph | 2-MeNH-4-Pyr | EtNH—(CH₂)₃ |
| 1-2100 | 3,4-diF-Ph | 2-MeNH-4-Pyr | Me₂N—(CH₂)₃ |
| 1-2101 | 3,4-diF-Ph | 2-MeNH-4-Pyr | 1-Azt-(CH₂)₃ |
| 1-2102 | 3,4-diF-Ph | 2-MeNH-4-Pyr | 1-Pyrd-(CH₂)₃ |
| 1-2103 | 3,4-diF-Ph | 2-MeNH-4-Pyr | 1-Pip-(CH₂)₃ |
| 1-2104 | 3,4-diF-Ph | 2-MeNH-4-Pyr | 1-Mor-(CH₂)₃ |
| 1-2105 | 3,4-diF-Ph | 2-MeNH-4-Pyr | 1-Tmor-(CH₂)₃ |
| 1-2106 | 3,4-diF-Ph | 2-MeNH-4-Pyr | 1-Piz-(CH₂)₃ |
| 1-2107 | 3,4-diF-Ph | 2-MeNH-4-Pyr | 4-Me-1-Piz-(CH₂)₃ |
| 1-2108 | 3,4-diF-Ph | 2-MeNH-4-Pyr | 3-Azt |
| 1-2109 | 3,4-diF-Ph | 2-MeNH-4-Pyr | 1-Me-3-Azt |
| 1-2110 | 3,4-diF-Ph | 2-MeNH-4-Pyr | 3-Pyrd |
| 1-2111 | 3,4-diF-Ph | 2-MeNH-4-Pyr | 1-Me-3-Pyrd |
| 1-2112 | 3,4-diF-Ph | 2-MeNH-4-Pyr | 4-Pip |
| 1-2113 | 3,4-diF-Ph | 2-MeNH-4-Pyr | 4-(3,4-deH-Pip) |
| 1-2114 | 3,4-diF-Ph | 2-MeNH-4-Pyr | 1-Me-4-Pip |
| 1-2115 | 3,4-diF-Ph | 2-MeNH-4-Pyr | 1-Me-4-(3,4-deH-Pip) |
| 1-2116 | 3,4-diF-Ph | 2-MeNH-4-Pyr | 1-Piz |
| 1-2117 | 3,4-diF-Ph | 2-MeNH-4-Pyr | 4-Me-1-Piz |
| 1-2118 | 3,4-diF-Ph | 2-MeNH-4-Pyr | 4-Pyr |
| 1-2119 | 3,4-diF-Ph | 2-MeNH-4-Pyr | 3-Pyr |
| 1-2120 | 3,4-diF-Ph | 2-MeNH-4-Pyr | 4-Pym |
| 1-2121 | 3,4-diF-Ph | 2-MeNH-4-Pyr | 5-Pym |
| 1-2122 | 3,4-diF-Ph | 2-MeNH-4-Pyr | 3-Pyrd-CH₂ |
| 1-2123 | 3,4-diF-Ph | 2-MeNH-4-Pyr | 1-Me-3-Pyrd-CH₂ |
| 1-2124 | 3,4-diF-Ph | 2-MeNH-4-Pyr | 4-Pip-CH₂ |
| 1-2125 | 3,4-diF-Ph | 2-MeNH-4-Pyr | 1-Me-4-Pip-CH₂ |
| 1-2126 | 3,4-diF-Ph | 2-MeNH-4-Pyr | 2-Piz-CH₂ |
| 1-2127 | 3,4-diF-Ph | 2-MeNH-4-Pyr | 4-Pyr-CH₂ |
| 1-2128 | 3,4-diF-Ph | 2-MeNH-4-Pyr | 3-Pyr-CH₂ |
| 1-2129 | 3,4-diF-Ph | 2-MeNH-4-Pyr | 4-Pym-CH₂ |
| 1-2130 | 3,4-diF-Ph | 2-MeNH-4-Pyr | 5-Pym-CH₂ |
| 1-2131 | 3,4-diF-Ph | 2-MeNH-4-Pyr | 2-Pym-CH₂ |
| 1-2132 | 3-Cl—Ph | 2-MeNH-4-Pyr | H₂N—(CH₂)₃ |
| 1-2133 | 3-Cl—Ph | 2-MeNH-4-Pyr | MeNH—(CH₂)₃ |
| 1-2134 | 3-Cl—Ph | 2-MeNH-4-Pyr | EtNH—(CH₂)₃ |
| 1-2135 | 3-Cl—Ph | 2-MeNH-4-Pyr | Me₂N—(CH₂)₃ |
| 1-2136 | 3-Cl—Ph | 2-MeNH-4-Pyr | 1-Azt-(CH₂)₃ |
| 1-2137 | 3-Cl—Ph | 2-MeNH-4-Pyr | 1-Pyrd-(CH₂)₃ |
| 1-2138 | 3-Cl—Ph | 2-MeNH-4-Pyr | 1-Pip-(CH₂)₃ |
| 1-2139 | 3-Cl—Ph | 2-MeNH-4-Pyr | 1-Mor-(CH₂)₃ |
| 1-2140 | 3-Cl—Ph | 2-MeNH-4-Pyr | 1-Tmor-(CH₂)₃ |
| 1-2141 | 3-Cl—Ph | 2-MeNH-4-Pyr | 1-Piz-(CH₂)₃ |
| 1-2142 | 3-Cl—Ph | 2-MeNH-4-Pyr | 4-Me-1-Piz-(CH₂)₃ |
| 1-2143 | 3-Cl—Ph | 2-MeNH-4-Pyr | 3-Azt |
| 1-2144 | 3-Cl—Ph | 2-MeNH-4-Pyr | 1-Me-3-Azt |
| 1-2145 | 3-Cl—Ph | 2-MeNH-4-Pyr | 3-Pyrd |
| 1-2146 | 3-Cl—Ph | 2-MeNH-4-Pyr | 1-Me-3-Pyrd |
| 1-2147 | 3-Cl—Ph | 2-MeNH-4-Pyr | 4-Pip |
| 1-2148 | 3-Cl—Ph | 2-MeNH-4-Pyr | 4-(3,4-deH-Pip) |
| 1-2149 | 3-Cl—Ph | 2-MeNH-4-Pyr | 1-Me-4-Pip |
| 1-2150 | 3-Cl—Ph | 2-MeNH-4-Pyr | 1-Me-4-(3,4-deH-Pip) |
| 1-2151 | 3-Cl—Ph | 2-MeNH-4-Pyr | 1-Piz |
| 1-2152 | 3-Cl—Ph | 2-MeNH-4-Pyr | 4-Me-1-Piz |
| 1-2153 | 3-Cl—Ph | 2-MeNH-4-Pyr | 4-Pyr |
| 1-2154 | 3-Cl—Ph | 2-MeNH-4-Pyr | 3-Pyr |
| 1-2155 | 3-Cl—Ph | 2-MeNH-4-Pyr | 4-Pym |
| 1-2156 | 3-Cl—Ph | 2-MeNH-4-Pyr | 5-Pym |
| 1-2157 | 3-Cl—Ph | 2-MeNH-4-Pyr | 3-Pyrd-CH₂ |
| 1-2158 | 3-Cl—Ph | 2-MeNH-4-Pyr | 1-Me-3-Pyrd-CH₂ |
| 1-2159 | 3-Cl—Ph | 2-MeNH-4-Pyr | 4-Pip-CH₂ |
| 1-2160 | 3-Cl—Ph | 2-MeNH-4-Pyr | 1-Me-4-Pip-CH₂ |
| 1-2161 | 3-Cl—Ph | 2-MeNH-4-Pyr | 2-Piz-CH₂ |
| 1-2162 | 3-Cl—Ph | 2-MeNH-4-Pyr | 4-Pyr-CH₂ |
| 1-2163 | 3-Cl—Ph | 2-MeNH-4-Pyr | 3-Pyr-CH₂ |
| 1-2164 | 3-Cl—Ph | 2-MeNH-4-Pyr | 4-Pym-CH₂ |
| 1-2165 | 3-Cl—Ph | 2-MeNH-4-Pyr | 5-Pym-CH₂ |
| 1-2166 | 3-Cl—Ph | 2-MeNH-4-Pyr | 2-Pym-CH₂ |
| 1-2167 | Ph | 4-Pym | H₂N—(CH₂)₃ |
| 1-2168 | Ph | 4-Pym | MeNH—(CH₂)₃ |
| 1-2169 | Ph | 4-Pym | EtNH—(CH₂)₃ |
| 1-2170 | Ph | 4-Pym | Me₂N—(CH₂)₃ |
| 1-2171 | Ph | 4-Pym | 1-Azt-(CH₂)₃ |
| 1-2172 | Ph | 4-Pym | 1-Pyrd-(CH₂)₃ |
| 1-2173 | Ph | 4-Pym | 1-Pip-(CH₂)₃ |
| 1-2174 | Ph | 4-Pym | 1-Mor-(CH₂)₃ |
| 1-2175 | Ph | 4-Pym | 1-Tmor-(CH₂)₃ |
| 1-2176 | Ph | 4-Pym | 1-Piz-(CH₂)₃ |
| 1-2177 | Ph | 4-Pym | 4-Me-1-Piz-(CH₂)₃ |
| 1-2178 | Ph | 4-Pym | 3-Azt |
| 1-2179 | Ph | 4-Pym | 1-Me-3-Azt |
| 1-2180 | Ph | 4-Pym | 3-Pyrd |
| 1-2181 | Ph | 4-Pym | 1-Me-3-Pyrd |
| 1-2182 | Ph | 4-Pym | 4-Pip |
| 1-2183 | Ph | 4-Pym | 4-(3,4-deH-Pip) |
| 1-2184 | Ph | 4-Pym | 1-Me-4-Pip |
| 1-2185 | Ph | 4-Pym | 1-Me-4-(3,4-deH-Pip) |
| 1-2186 | Ph | 4-Pym | 1-Piz |
| 1-2187 | Ph | 4-Pym | 4-Me-1-Piz |
| 1-2188 | Ph | 4-Pym | 4-Pyr |
| 1-2189 | Ph | 4-Pym | 3-Pyr |
| 1-2190 | Ph | 4-Pym | 4-Pym |
| 1-2191 | Ph | 4-Pym | 5-Pym |
| 1-2192 | Ph | 4-Pym | 3-Pyrd-CH₂ |
| 1-2193 | Ph | 4-Pym | 1-Me-3-Pyrd-CH₂ |
| 1-2194 | Ph | 4-Pym | 4-Pip-CH₂ |
| 1-2195 | Ph | 4-Pym | 1-Me-4-Pip-CH₂ |
| 1-2196 | Ph | 4-Pym | 2-Piz-CH₂ |
| 1-2197 | Ph | 4-Pym | 4-Pyr-CH₂ |
| 1-2198 | Ph | 4-Pym | 3-Pyr-CH₂ |
| 1-2199 | Ph | 4-Pym | 4-Pym-CH₂ |
| 1-2200 | Ph | 4-Pym | 5-Pym-CH₂ |
| 1-2201 | Ph | 4-Pym | 2-Pym-CH₂ |
| 1-2202 | 4-F—Ph | 4-Pym | H₂N—(CH₂)₃ |
| 1-2203 | 4-F—Ph | 4-Pym | MeNH—(CH₂)₃ |
| 1-2204 | 4-F—Ph | 4-Pym | EtNH—(CH₂)₃ |
| 1-2205 | 4-F—Ph | 4-Pym | Me₂N—(CH₂)₃ |
| 1-2206 | 4-F—Ph | 4-Pym | 1-Azt-(CH₂)₃ |
| 1-2207 | 4-F—Ph | 4-Pym | 1-Pyrd-(CH₂)₃ |
| 1-2208 | 4-F—Ph | 4-Pym | 1-Pip-(CH₂)₃ |
| 1-2209 | 4-F—Ph | 4-Pym | 1-Mor-(CH₂)₃ |
| 1-2210 | 4-F—Ph | 4-Pym | 1-Tmor-(CH₂)₃ |
| 1-2211 | 4-F—Ph | 4-Pym | 1-Piz-(CH₂)₃ |
| 1-2212 | 4-F—Ph | 4-Pym | 4-Me-1-Piz-(CH₂)₃ |
| 1-2213 | 4-F—Ph | 4-Pym | 3-Azt |
| 1-2214 | 4-F—Ph | 4-Pym | 1-Me-3-Azt |
| 1-2215 | 4-F—Ph | 4-Pym | 3-Pyrd |
| 1-2216 | 4-F—Ph | 4-Pym | 1-Me-3-Pyrd |
| 1-2217 | 4-F—Ph | 4-Pym | 4-Pip |
| 1-2218 | 4-F—Ph | 4-Pym | 4-(3,4-deH-Pip) |
| 1-2219 | 4-F—Ph | 4-Pym | 1-Me-4-Pip |
| 1-2220 | 4-F—Ph | 4-Pym | 1-Me-4-(3,4-deH-Pip) |
| 1-2221 | 4-F—Ph | 4-Pym | 1-Piz |
| 1-2222 | 4-F—Ph | 4-Pym | 4-Me-1-Piz |

TABLE 1-continued

| Compound No. | R¹ | R² | R³ |
|---|---|---|---|
| 1-2223 | 4-F—Ph | 4-Pym | 4-Pyr |
| 1-2224 | 4-F—Ph | 4-Pym | 3-Pyr |
| 1-2225 | 4-F—Ph | 4-Pym | 4-Pym |
| 1-2226 | 4-F—Ph | 4-Pym | 5-Pym |
| 1-2227 | 4-F—Ph | 4-Pym | 3-Pyrd-CH₂ |
| 1-2228 | 4-F—Ph | 4-Pym | 1-Me-3-Pyrd-CH₂ |
| 1-2229 | 4-F—Ph | 4-Pym | 4-Pip-CH₂ |
| 1-2230 | 4-F—Ph | 4-Pym | 1-Me-4-Pip-CH₂ |
| 1-2231 | 4-F—Ph | 4-Pym | 2-Piz-CH₂ |
| 1-2232 | 4-F—Ph | 4-Pym | 4-Pyr-CH₂ |
| 1-2233 | 4-F—Ph | 4-Pym | 3-Pyr-CH₂ |
| 1-2234 | 4-F—Ph | 4-Pym | 4-Pym-CH₂ |
| 1-2235 | 4-F—Ph | 4-Pym | 5-Pym-CH₂ |
| 1-2236 | 4-F—Ph | 4-Pym | 2-Pym-CH₂ |
| 1-2237 | 3-F—Ph | 4-Pym | H₂N—(CH₂)₃ |
| 1-2238 | 3-F—Ph | 4-Pym | MeNH—(CH₂)₃ |
| 1-2239 | 3-F—Ph | 4-Pym | EtNH—(CH₂)₃ |
| 1-2240 | 3-F—Ph | 4-Pym | Me₂N—(CH₂)₃ |
| 1-2241 | 3-F—Ph | 4-Pym | 1-Azt-(CH₂)₃ |
| 1-2242 | 3-F—Ph | 4-Pym | 1-Pyrd-(CH₂)₃ |
| 1-2243 | 3-F—Ph | 4-Pym | 1-Pip-(CH₂)₃ |
| 1-2244 | 3-F—Ph | 4-Pym | 1-Mor-(CH₂)₃ |
| 1-2245 | 3-F—Ph | 4-Pym | 1-Tmor-(CH₂)₃ |
| 1-2246 | 3-F—Ph | 4-Pym | 1-Piz-(CH₂)₃ |
| 1-2247 | 3-F—Ph | 4-Pym | 4-Me-1-Piz-(CH₂)₃ |
| 1-2248 | 3-F—Ph | 4-Pym | 3-Azt |
| 1-2249 | 3-F—Ph | 4-Pym | 1-Me-3-Azt |
| 1-2250 | 3-F—Ph | 4-Pym | 3-Pyrd |
| 1-2251 | 3-F—Ph | 4-Pym | 1-Me-3-Pyrd |
| 1-2252 | 3-F—Ph | 4-Pym | 4-Pip |
| 1-2253 | 3-F—Ph | 4-Pym | 4-(3,4-deH-Pip) |
| 1-2254 | 3-F—Ph | 4-Pym | 1-Me-4-Pip |
| 1-2255 | 3-F—Ph | 4-Pym | 1-Me-4-(3,4-deH-Pip) |
| 1-2256 | 3-F—Ph | 4-Pym | 1-Piz |
| 1-2257 | 3-F—Ph | 4-Pym | 4-Me-1-Piz |
| 1-2258 | 3-F—Ph | 4-Pym | 4-Pyr |
| 1-2259 | 3-F—Ph | 4-Pym | 3-Pyr |
| 1-2260 | 3-F—Ph | 4-Pym | 4-Pym |
| 1-2261 | 3-F—Ph | 4-Pym | 5-Pym |
| 1-2262 | 3-F—Ph | 4-Pym | 3-Pyrd-CH₂ |
| 1-2263 | 3-F—Ph | 4-Pym | 1-Me-3-Pyrd-CH₂ |
| 1-2264 | 3-F—Ph | 4-Pym | 4-Pip-CH₂ |
| 1-2265 | 3-F—Ph | 4-Pym | 1-Me-4-Pip-CH₂ |
| 1-2266 | 3-F—Ph | 4-Pym | 2-Piz-CH₂ |
| 1-2267 | 3-F—Ph | 4-Pym | 4-Pyr-CH₂ |
| 1-2268 | 3-F—Ph | 4-Pym | 3-Pyr-CH₂ |
| 1-2269 | 3-F—Ph | 4-Pym | 4-Pym-CH₂ |
| 1-2270 | 3-F—Ph | 4-Pym | 5-Pym-CH₂ |
| 1-2271 | 3-F—Ph | 4-Pym | 2-Pym-CH₂ |
| 1-2272 | 3,4-diF-Ph | 4-Pym | H₂N—(CH₂)₃ |
| 1-2273 | 3,4-diF-Ph | 4-Pym | MeNH—(CH₂)₃ |
| 1-2274 | 3,4-diF-Ph | 4-Pym | EtNH—(CH₂)₃ |
| 1-2275 | 3,4-diF-Ph | 4-Pym | Me₂N—(CH₂)₃ |
| 1-2276 | 3,4-diF-Ph | 4-Pym | 1-Azt-(CH₂)₃ |
| 1-2277 | 3,4-diF-Ph | 4-Pym | 1-Pyrd-(CH₂)₃ |
| 1-2278 | 3,4-diF-Ph | 4-Pym | 1-Pip-(CH₂)₃ |
| 1-2279 | 3,4-diF-Ph | 4-Pym | 1-Mor-(CH₂)₃ |
| 1-2280 | 3,4-diF-Ph | 4-Pym | 1-Tmor-(CH₂)₃ |
| 1-2281 | 3,4-diF-Ph | 4-Pym | 1-Piz-(CH₂)₃ |
| 1-2282 | 3,4-diF-Ph | 4-Pym | 4-Me-1-Piz-(CH₂)₃ |
| 1-2283 | 3,4-diF-Ph | 4-Pym | 3-Azt |
| 1-2284 | 3,4-diF-Ph | 4-Pym | 1-Me-3-Azt |
| 1-2285 | 3,4-diF-Ph | 4-Pym | 3-Pyrd |
| 1-2286 | 3,4-diF-Ph | 4-Pym | 1-Me-3-Pyrd |
| 1-2287 | 3,4-diF-Ph | 4-Pym | 4-Pip |
| 1-2288 | 3,4-diF-Ph | 4-Pym | 4-(3,4-deH-Pip) |
| 1-2289 | 3,4-diF-Ph | 4-Pym | 1-Me-4-Pip |
| 1-2290 | 3,4-diF-Ph | 4-Pym | 1-Me-4-(3,4-deH-Pip) |
| 1-2291 | 3,4-diF-Ph | 4-Pym | 1-Piz |
| 1-2292 | 3,4-diF-Ph | 4-Pym | 4-Me-1-Piz |
| 1-2293 | 3,4-diF-Ph | 4-Pym | 4-Pyr |
| 1-2294 | 3,4-diF-Ph | 4-Pym | 3-Pyr |
| 1-2295 | 3,4-diF-Ph | 4-Pym | 4-Pym |
| 1-2296 | 3,4-diF-Ph | 4-Pym | 5-Pym |
| 1-2297 | 3,4-diF-Ph | 4-Pym | 3-Pyrd-CH₂ |
| 1-2298 | 3,4-diF-Ph | 4-Pym | 1-Me-3-Pyrd-CH₂ |
| 1-2299 | 3,4-diF-Ph | 4-Pym | 4-Pip-CH₂ |
| 1-2300 | 3,4-diF-Ph | 4-Pym | 1-Me-4-Pip-CH₂ |
| 1-2301 | 3,4-diF-Ph | 4-Pym | 2-Piz-CH₂ |
| 1-2302 | 3,4-diF-Ph | 4-Pym | 4-Pyr-CH₂ |
| 1-2303 | 3,4-diF-Ph | 4-Pym | 3-Pyr-CH₂ |
| 1-2304 | 3,4-diF-Ph | 4-Pym | 4-Pym-CH₂ |
| 1-2305 | 3,4-diF-Ph | 4-Pym | 5-Pym-CH₂ |
| 1-2306 | 3,4-diF-Ph | 4-Pym | 2-Pym-CH₂ |
| 1-2307 | 3-Cl—Ph | 4-Pym | H₂N—(CH₂)₃ |
| 1-2308 | 3-Cl—Ph | 4-Pym | MeNH—(CH₂)₃ |
| 1-2309 | 3-Cl—Ph | 4-Pym | EtNH—(CH₂)₃ |
| 1-2310 | 3-Cl—Ph | 4-Pym | Me₂N—(CH₂)₃ |
| 1-2311 | 3-Cl—Ph | 4-Pym | 1-Azt-(CH₂)₃ |
| 1-2312 | 3-Cl—Ph | 4-Pym | 1-Pyrd-(CH₂)₃ |
| 1-2313 | 3-Cl—Ph | 4-Pym | 1-Pip-(CH₂)₃ |
| 1-2314 | 3-Cl—Ph | 4-Pym | 1-Mor-(CH₂)₃ |
| 1-2315 | 3-Cl—Ph | 4-Pym | 1-Tmor-(CH₂)₃ |
| 1-2316 | 3-Cl—Ph | 4-Pym | 1-Piz-(CH₂)₃ |
| 1-2317 | 3-Cl—Ph | 4-Pym | 4-Me-1-Piz-(CH₂)₃ |
| 1-2318 | 3-Cl—Ph | 4-Pym | 3-Azt |
| 1-2319 | 3-Cl—Ph | 4-Pym | 1-Me-3-Azt |
| 1-2320 | 3-Cl—Ph | 4-Pym | 3-Pyrd |
| 1-2321 | 3-Cl—Ph | 4-Pym | 1-Me-3-Pyrd |
| 1-2322 | 3-Cl—Ph | 4-Pym | 4-Pip |
| 1-2323 | 3-Cl—Ph | 4-Pym | 4-(3,4-deH-Pip) |
| 1-2324 | 3-Cl—Ph | 4-Pym | 1-Me-4-Pip |
| 1-2325 | 3-Cl—Ph | 4-Pym | 1-Me-4-(3,4-deH-Pip) |
| 1-2326 | 3-Cl—Ph | 4-Pym | 1-Piz |
| 1-2327 | 3-Cl—Ph | 4-Pym | 4-Me-1-Piz |
| 1-2328 | 3-Cl—Ph | 4-Pym | 4-Pyr |
| 1-2329 | 3-Cl—Ph | 4-Pym | 3-Pyr |
| 1-2330 | 3-Cl—Ph | 4-Pym | 4-Pym |
| 1-2331 | 3-Cl—Ph | 4-Pym | 5-Pym |
| 1-2332 | 3-Cl—Ph | 4-Pym | 3-Pyrd-CH₂ |
| 1-2333 | 3-Cl—Ph | 4-Pym | 1-Me-3-Pyrd-CH₂ |
| 1-2334 | 3-Cl—Ph | 4-Pym | 4-Pip-CH₂ |
| 1-2335 | 3-Cl—Ph | 4-Pym | 1-Me-4-Pip-CH₂ |
| 1-2336 | 3-Cl—Ph | 4-Pym | 2-Piz-CH₂ |
| 1-2337 | 3-Cl—Ph | 4-Pym | 4-Pyr-CH₂ |
| 1-2338 | 3-Cl—Ph | 4-Pym | 3-Pyr-CH₂ |
| 1-2339 | 3-Cl—Ph | 4-Pym | 4-Pym-CH₂ |
| 1-2340 | 3-Cl—Ph | 4-Pym | 5-Pym-CH₂ |
| 1-2341 | 3-Cl—Ph | 4-Pym | 2-Pym-CH₂ |
| 1-2342 | Ph | 2-MeO-4-Pym | H₂N—(CH₂)₃ |
| 1-2343 | Ph | 2-MeO-4-Pym | MeNH—(CH₂)₃ |
| 1-2344 | Ph | 2-MeO-4-Pym | EtNH—(CH₂)₃ |
| 1-2345 | Ph | 2-MeO-4-Pym | Me₂N—(CH₂)₃ |
| 1-2346 | Ph | 2-MeO-4-Pym | 1-Azt-(CH₂)₃ |
| 1-2347 | Ph | 2-MeO-4-Pym | 1-Pyrd-(CH₂)₃ |
| 1-2348 | Ph | 2-MeO-4-Pym | 1-Pip-(CH₂)₃ |
| 1-2349 | Ph | 2-MeO-4-Pym | 1-Mor-(CH₂)₃ |
| 1-2350 | Ph | 2-MeO-4-Pym | 1-Tmor-(CH₂)₃ |
| 1-2351 | Ph | 2-MeO-4-Pym | 1-Piz-(CH₂)₃ |
| 1-2352 | Ph | 2-MeO-4-Pym | 4-Me-1-Piz-(CH₂)₃ |
| 1-2353 | Ph | 2-MeO-4-Pym | 3-Azt |
| 1-2354 | Ph | 2-MeO-4-Pym | 1-Me-3-Azt |
| 1-2355 | Ph | 2-MeO-4-Pym | 3-Pyrd |
| 1-2356 | Ph | 2-MeO-4-Pym | 1-Me-3-Pyrd |
| 1-2357 | Ph | 2-MeO-4-Pym | 4-Pip |
| 1-2358 | Ph | 2-MeO-4-Pym | 4-(3,4-deH-Pip) |
| 1-2359 | Ph | 2-MeO-4-Pym | 1-Me-4-Pip |
| 1-2360 | Ph | 2-MeO-4-Pym | 1-Me-4-(3,4-deH-Pip) |
| 1-2361 | Ph | 2-MeO-4-Pym | 1-Piz |
| 1-2362 | Ph | 2-MeO-4-Pym | 4-Me-1-Piz |
| 1-2363 | Ph | 2-MeO-4-Pym | 4-Pyr |
| 1-2364 | Ph | 2-MeO-4-Pym | 3-Pyr |
| 1-2365 | Ph | 2-MeO-4-Pym | 4-Pym |
| 1-2366 | Ph | 2-MeO-4-Pym | 5-Pym |
| 1-2367 | Ph | 2-MeO-4-Pym | 3-Pyrd-CH₂ |
| 1-2368 | Ph | 2-MeO-4-Pym | 1-Me-3-Pyrd-CH₂ |
| 1-2369 | Ph | 2-MeO-4-Pym | 4-Pip-CH₂ |
| 1-2370 | Ph | 2-MeO-4-Pym | 1-Me-4-Pip-CH₂ |
| 1-2371 | Ph | 2-MeO-4-Pym | 2-Piz-CH₂ |
| 1-2372 | Ph | 2-MeO-4-Pym | 4-Pyr-CH₂ |
| 1-2373 | Ph | 2-MeO-4-Pym | 3-Pyr-CH₂ |
| 1-2374 | Ph | 2-MeO-4-Pym | 4-Pym-CH₂ |

TABLE 1-continued

| Compound No. | R¹ | R² | R³ |
|---|---|---|---|
| 1-2375 | Ph | 2-MeO-4-Pym | 5-Pym-CH₂ |
| 1-2376 | Ph | 2-MeO-4-Pym | 2-Pym-CH₂ |
| 1-2377 | 4-F—Ph | 2-MeO-4-Pym | H₂N—(CH₂)₃ |
| 1-2378 | 4-F—Ph | 2-MeO-4-Pym | MeNH—(CH₂)₃ |
| 1-2379 | 4-F—Ph | 2-MeO-4-Pym | EtNH—(CH₂)₃ |
| 1-2380 | 4-F—Ph | 2-MeO-4-Pym | Me₂N—(CH₂)₃ |
| 1-2381 | 4-F—Ph | 2-MeO-4-Pym | 1-Azt-(CH₂)₃ |
| 1-2382 | 4-F—Ph | 2-MeO-4-Pym | 1-Pyrd-(CH₂)₃ |
| 1-2383 | 4-F—Ph | 2-MeO-4-Pym | 1-Pip-(CH₂)₃ |
| 1-2384 | 4-F—Ph | 2-MeO-4-Pym | 1-Mor-(CH₂)₃ |
| 1-2385 | 4-F—Ph | 2-MeO-4-Pym | 1-Tmor-(CH₂)₃ |
| 1-2386 | 4-F—Ph | 2-MeO-4-Pym | 1-Piz-(CH₂)₃ |
| 1-2387 | 4-F—Ph | 2-MeO-4-Pym | 4-Me-1-Piz-(CH₂)₃ |
| 1-2388 | 4-F—Ph | 2-MeO-4-Pym | 3-Azt |
| 1-2389 | 4-F—Ph | 2-MeO-4-Pym | 1-Me-3-Azt |
| 1-2390 | 4-F—Ph | 2-MeO-4-Pym | 3-Pyrd |
| 1-2391 | 4-F—Ph | 2-MeO-4-Pym | 1-Me-3-Pyrd |
| 1-2392 | 4-F—Ph | 2-MeO-4-Pym | 4-Pip |
| 1-2393 | 4-F—Ph | 2-MeO-4-Pym | 4-(3,4-deH-Pip) |
| 1-2394 | 4-F—Ph | 2-MeO-4-Pym | 1-Me-4-Pip |
| 1-2395 | 4-F—Ph | 2-MeO-4-Pym | 1-Me-4-(3,4-deH-Pip) |
| 1-2396 | 4-F—Ph | 2-MeO-4-Pym | 1-Piz |
| 1-2397 | 4-F—Ph | 2-MeO-4-Pym | 4-Me-1-Piz |
| 1-2398 | 4-F—Ph | 2-MeO-4-Pym | 4-Pyr |
| 1-2399 | 4-F—Ph | 2-MeO-4-Pym | 3-Pyr |
| 1-2400 | 4-F—Ph | 2-MeO-4-Pym | 4-Pym |
| 1-2401 | 4-F—Ph | 2-MeO-4-Pym | 5-Pym |
| 1-2402 | 4-F—Ph | 2-MeO-4-Pym | 3-Pyrd-CH₂ |
| 1-2403 | 4-F—Ph | 2-MeO-4-Pym | 1-Me-3-Pyrd-CH₂ |
| 1-2404 | 4-F—Ph | 2-MeO-4-Pym | 4-Pip-CH₂ |
| 1-2405 | 4-F—Ph | 2-MeO-4-Pym | 1-Me-4-Pip-CH₂ |
| 1-2406 | 4-F—Ph | 2-MeO-4-Pym | 2-Piz-CH₂ |
| 1-2407 | 4-F—Ph | 2-MeO-4-Pym | 4-Pyr-CH₂ |
| 1-2408 | 4-F—Ph | 2-MeO-4-Pym | 3-Pyr-CH₂ |
| 1-2409 | 4-F—Ph | 2-MeO-4-Pym | 4-Pym-CH₂ |
| 1-2410 | 4-F—Ph | 2-MeO-4-Pym | 5-Pym-CH₂ |
| 1-2411 | 4-F—Ph | 2-MeO-4-Pym | 2-Pym-CH₂ |
| 1-2412 | 3-F—Ph | 2-MeO-4-Pym | H₂N—(CH₂)₃ |
| 1-2413 | 3-F—Ph | 2-MeO-4-Pym | MeNH—(CH₂)₃ |
| 1-2414 | 3-F—Ph | 2-MeO-4-Pym | EtNH—(CH₂)₃ |
| 1-2415 | 3-F—Ph | 2-MeO-4-Pym | Me₂N—(CH₂)₃ |
| 1-2416 | 3-F—Ph | 2-MeO-4-Pym | 1-Azt-(CH₂)₃ |
| 1-2417 | 3-F—Ph | 2-MeO-4-Pym | 1-Pyrd-(CH₂)₃ |
| 1-2418 | 3-F—Ph | 2-MeO-4-Pym | 1-Pip-(CH₂)₃ |
| 1-2419 | 3-F—Ph | 2-MeO-4-Pym | 1-Mor-(CH₂)₃ |
| 1-2420 | 3-F—Ph | 2-MeO-4-Pym | 1-Tmor-(CH₂)₃ |
| 1-2421 | 3-F—Ph | 2-MeO-4-Pym | 1-Piz-(CH₂)₃ |
| 1-2422 | 3-F—Ph | 2-MeO-4-Pym | 4-Me-1-Piz-(CH₂)₃ |
| 1-2423 | 3-F—Ph | 2-MeO-4-Pym | 3-Azt |
| 1-2424 | 3-F—Ph | 2-MeO-4-Pym | 1-Me-3-Azt |
| 1-2425 | 3-F—Ph | 2-MeO-4-Pym | 3-Pyrd |
| 1-2426 | 3-F—Ph | 2-MeO-4-Pym | 1-Me-3-Pyrd |
| 1-2427 | 3-F—Ph | 2-MeO-4-Pym | 4-Pip |
| 1-2428 | 3-F—Ph | 2-MeO-4-Pym | 4-(3,4-deH-Pip) |
| 1-2429 | 3-F—Ph | 2-MeO-4-Pym | 1-Me-4-Pip |
| 1-2430 | 3-F—Ph | 2-MeO-4-Pym | 1-Me-4-(3,4-deH-Pip) |
| 1-2431 | 3-F—Ph | 2-MeO-4-Pym | 1-Piz |
| 1-2432 | 3-F—Ph | 2-MeO-4-Pym | 4-Me-1-Piz |
| 1-2433 | 3-F—Ph | 2-MeO-4-Pym | 4-Pyr |
| 1-2434 | 3-F—Ph | 2-MeO-4-Pym | 3-Pyr |
| 1-2435 | 3-F—Ph | 2-MeO-4-Pym | 4-Pym |
| 1-2436 | 3-F—Ph | 2-MeO-4-Pym | 5-Pym |
| 1-2437 | 3-F—Ph | 2-MeO-4-Pym | 3-Pyrd-CH₂ |
| 1-2438 | 3-F—Ph | 2-MeO-4-Pym | 1-Me-3-Pyrd-CH₂ |
| 1-2439 | 3-F—Ph | 2-MeO-4-Pym | 4-Pip-CH₂ |
| 1-2440 | 3-F—Ph | 2-MeO-4-Pym | 1-Me-4-Pip-CH₂ |
| 1-2441 | 3-F—Ph | 2-MeO-4-Pym | 2-Piz-CH₂ |
| 1-2442 | 3-F—Ph | 2-MeO-4-Pym | 4-Pyr-CH₂ |
| 1-2443 | 3-F—Ph | 2-MeO-4-Pym | 3-Pyr-CH₂ |
| 1-2444 | 3-F—Ph | 2-MeO-4-Pym | 4-Pym-CH₂ |
| 1-2445 | 3-F—Ph | 2-MeO-4-Pym | 5-Pym-CH₂ |
| 1-2446 | 3-F—Ph | 2-MeO-4-Pym | 2-Pym-CH₂ |
| 1-2447 | 3,4-diF-Ph | 2-MeO-4-Pym | H₂N—(CH₂)₃ |
| 1-2448 | 3,4-diF-Ph | 2-MeO-4-Pym | MeNH—(CH₂)₃ |
| 1-2449 | 3,4-diF-Ph | 2-MeO-4-Pym | EtNH—(CH₂)₃ |
| 1-2450 | 3,4-diF-Ph | 2-MeO-4-Pym | Me₂N—(CH₂)₃ |
| 1-2451 | 3,4-diF-Ph | 2-MeO-4-Pym | 1-Azt-(CH₂)₃ |
| 1-2452 | 3,4-diF-Ph | 2-MeO-4-Pym | 1-Pyrd-(CH₂)₃ |
| 1-2453 | 3,4-diF-Ph | 2-MeO-4-Pym | 1-Pip-(CH₂)₃ |
| 1-2454 | 3,4-diF-Ph | 2-MeO-4-Pym | 1-Mor-(CH₂)₃ |
| 1-2455 | 3,4-diF-Ph | 2-MeO-4-Pym | 1-Tmor-(CH₂)₃ |
| 1-2456 | 3,4-diF-Ph | 2-MeO-4-Pym | 1-Piz-(CH₂)₃ |
| 1-2457 | 3,4-diF-Ph | 2-MeO-4-Pym | 4-Me-1-Piz-(CH₂)₃ |
| 1-2458 | 3,4-diF-Ph | 2-MeO-4-Pym | 3-Azt |
| 1-2459 | 3,4-diF-Ph | 2-MeO-4-Pym | 1-Me-3-Azt |
| 1-2460 | 3,4-diF-Ph | 2-MeO-4-Pym | 3-Pyrd |
| 1-2461 | 3,4-diF-Ph | 2-MeO-4-Pym | 1-Me-3-Pyrd |
| 1-2462 | 3,4-diF-Ph | 2-MeO-4-Pym | 4-Pip |
| 1-2463 | 3,4-diF-Ph | 2-MeO-4-Pym | 4-(3,4-deH-Pip) |
| 1-2464 | 3,4-diF-Ph | 2-MeO-4-Pym | 1-Me-4-Pip |
| 1-2465 | 3,4-diF-Ph | 2-MeO-4-Pym | 1-Me-4-(3,4-deH-Pip) |
| 1-2466 | 3,4-diF-Ph | 2-MeO-4-Pym | 1-Piz |
| 1-2467 | 3,4-diF-Ph | 2-MeO-4-Pym | 4-Me-1-Piz |
| 1-2468 | 3,4-diF-Ph | 2-MeO-4-Pym | 4-Pyr |
| 1-2469 | 3,4-diF-Ph | 2-MeO-4-Pym | 3-Pyr |
| 1-2470 | 3,4-diF-Ph | 2-MeO-4-Pym | 4-Pym |
| 1-2471 | 3,4-diF-Ph | 2-MeO-4-Pym | 5-Pym |
| 1-2472 | 3,4-diF-Ph | 2-MeO-4-Pym | 3-Pyrd-CH₂ |
| 1-2473 | 3,4-diF-Ph | 2-MeO-4-Pym | 1-Me-3-Pyrd-CH₂ |
| 1-2474 | 3,4-diF-Ph | 2-MeO-4-Pym | 4-Pip-CH₂ |
| 1-2475 | 3,4-diF-Ph | 2-MeO-4-Pym | 1-Me-4-Pip-CH₂ |
| 1-2476 | 3,4-diF-Ph | 2-MeO-4-Pym | 2-Piz-CH₂ |
| 1-2477 | 3,4-diF-Ph | 2-MeO-4-Pym | 4-Pyr-CH₂ |
| 1-2478 | 3,4-diF-Ph | 2-MeO-4-Pym | 3-Pyr-CH₂ |
| 1-2479 | 3,4-diF-Ph | 2-MeO-4-Pym | 4-Pym-CH₂ |
| 1-2480 | 3,4-diF-Ph | 2-MeO-4-Pym | 5-Pym-CH₂ |
| 1-2481 | 3,4-diF-Ph | 2-MeO-4-Pym | 2-Pym-CH₂ |
| 1-2482 | 3-Cl—Ph | 2-MeO-4-Pym | H₂N—(CH₂)₃ |
| 1-2483 | 3-Cl—Ph | 2-MeO-4-Pym | MeNH—(CH₂)₃ |
| 1-2484 | 3-Cl—Ph | 2-MeO-4-Pym | EtNH—(CH₂)₃ |
| 1-2485 | 3-Cl—Ph | 2-MeO-4-Pym | Me₂N—(CH₂)₃ |
| 1-2486 | 3-Cl—Ph | 2-MeO-4-Pym | 1-Azt-(CH₂)₃ |
| 1-2487 | 3-Cl—Ph | 2-MeO-4-Pym | 1-Pyrd-(CH₂)₃ |
| 1-2488 | 3-Cl—Ph | 2-MeO-4-Pym | 1-Pip-(CH₂)₃ |
| 1-2489 | 3-Cl—Ph | 2-MeO-4-Pym | 1-Mor-(CH₂)₃ |
| 1-2490 | 3-Cl—Ph | 2-MeO-4-Pym | 1-Tmor-(CH₂)₃ |
| 1-2491 | 3-Cl—Ph | 2-MeO-4-Pym | 1-Piz-(CH₂)₃ |
| 1-2492 | 3-Cl—Ph | 2-MeO-4-Pym | 4-Me-1-Piz-(CH₂)₃ |
| 1-2493 | 3-Cl—Ph | 2-MeO-4-Pym | 3-Azt |
| 1-2494 | 3-Cl—Ph | 2-MeO-4-Pym | 1-Me-3-Azt |
| 1-2495 | 3-Cl—Ph | 2-MeO-4-Pym | 3-Pyrd |
| 1-2496 | 3-Cl—Ph | 2-MeO-4-Pym | 1-Me-3-Pyrd |
| 1-2497 | 3-Cl—Ph | 2-MeO-4-Pym | 4-Pip |
| 1-2498 | 3-Cl—Ph | 2-MeO-4-Pym | 4-(3,4-deH-Pip) |
| 1-2499 | 3-Cl—Ph | 2-MeO-4-Pym | 1-Me-4-Pip |
| 1-2500 | 3-Cl—Ph | 2-MeO-4-Pym | 1-Me-4-(3,4-deH-Pip) |
| 1-2501 | 3-Cl—Ph | 2-MeO-4-Pym | 1-Piz |
| 1-2502 | 3-Cl—Ph | 2-MeO-4-Pym | 4-Me-1-Piz |
| 1-2503 | 3-Cl—Ph | 2-MeO-4-Pym | 4-Pyr |
| 1-2504 | 3-Cl—Ph | 2-MeO-4-Pym | 3-Pyr |
| 1-2505 | 3-Cl—Ph | 2-MeO-4-Pym | 4-Pym |
| 1-2506 | 3-Cl—Ph | 2-MeO-4-Pym | 5-Pym |
| 1-2507 | 3-Cl—Ph | 2-MeO-4-Pym | 3-Pyrd-CH₂ |
| 1-2508 | 3-Cl—Ph | 2-MeO-4-Pym | 1-Me-3-Pyrd-CH₂ |
| 1-2509 | 3-Cl—Ph | 2-MeO-4-Pym | 4-Pip-CH₂ |
| 1-2510 | 3-Cl—Ph | 2-MeO-4-Pym | 1-Me-4-Pip-CH₂ |
| 1-2511 | 3-Cl—Ph | 2-MeO-4-Pym | 2-Piz-CH₂ |
| 1-2512 | 3-Cl—Ph | 2-MeO-4-Pym | 4-Pyr-CH₂ |
| 1-2513 | 3-Cl—Ph | 2-MeO-4-Pym | 3-Pyr-CH₂ |
| 1-2514 | 3-Cl—Ph | 2-MeO-4-Pym | 4-Pym-CH₂ |
| 1-2515 | 3-Cl—Ph | 2-MeO-4-Pym | 5-Pym-CH₂ |
| 1-2516 | 3-Cl—Ph | 2-MeO-4-Pym | 2-Pym-CH₂ |
| 1-2517 | 4-F—Ph | 4-Pyr | H₂N—CH₂CH=CH |
| 1-2518 | 4-F—Ph | 4-Pyr | MeNH—CH₂CH=CH |
| 1-2519 | 4-F—Ph | 4-Pyr | Me₂N—CH₂CH=CH |
| 1-2520 | 4-F—Ph | 4-Pyr | 3-Pip-CH₂ |
| 1-2521 | 4-F—Ph | 4-Pyr | 1-Me-3-Pip-CH₂ |
| 1-2522 | 4-F—Ph | 4-Pyr | 2-Me-4-Pip |
| 1-2523 | 4-F—Ph | 4-Pyr | 2,2,6,6-tetraMe-4-Pip |
| 1-2524 | 4-F—Ph | 4-Pyr | 1-Ac-4-Pip |
| 1-2525 | 4-F—Ph | 4-Pyr | 1-Ac-4-(3,4-deH-Pip) |
| 1-2526 | 4-F—Ph | 4-Pyr | 4-OH-4-Pip |

TABLE 1-continued

| Compound No. | R¹ | R² | R³ |
|---|---|---|---|
| 1-2527 | 4-F—Ph | 4-Pyr | 4-OH-1-Me-4-Pip |
| 1-2528 | 4-F—Ph | 4-Pyr | AcNH—(CH₂)₃ |
| 1-2529 | 4-F—Ph | 4-Pyr | 4-NH₂-cHx |
| 1-2530 | 4-F—Ph | 4-Pyr | 4-Pyr-CH(OH) |
| 1-2531 | 4-F—Ph | 4-Pyr | 3-Pyr-CH(OH) |
| 1-2532 | 4-F—Ph | 4-Pyr | 2-Pyr-CH(OH) |
| 1-2533 | 4-F—Ph | 4-Pyr | CF₃CONH—(CH₂)₃ |
| 1-2534 | 4-F—Ph | 4-Pyr | BzNH—(CH₂)₃ |
| 1-2535 | 4-F—Ph | 4-Pyr | 2,4,6-triF-BzNH—CH₂ |
| 1-2536 | 4-F—Ph | 4-Pyr | MeSO₂NH—(CH₂)₃ |
| 1-2537 | 4-F—Ph | 4-Pyr | 1-NO₂(CH₂)₂-4-Pip |
| 1-2538 | 4-F—Ph | 4-Pyr | 2,3,5,6-tetraF-4-Pyr |
| 1-2539 | 4-F—Ph | 4-Pyr | 3-Qun |
| 1-2540 | 4-F—Ph | 4-Pyr | 3-(2,3-deH-Qun) |
| 1-2541 | 4-F—Ph | 4-Pyr | 3-ABO |
| 1-2542 | 4-F—Ph | 4-Pyr | 8-Me-3-ABO |
| 1-2543 | 4-F—Ph | 4-Pyr | 3-(2,3-deH-ABO) |
| 1-2544 | 4-F—Ph | 4-Pyr | 8-Me-3-(2,3-deH-ABO) |
| 1-2545 | 4-F—Ph | 4-Pyr | 3-ABN |
| 1-2546 | 4-F—Ph | 4-Pyr | 9-Me-3-ABN |
| 1-2547 | 4-F—Ph | 4-Pyr | 3-(2,3-deH-ABN) |
| 1-2548 | 4-F—Ph | 4-Pyr | 9-Me-3-(2,3-deH-ABN) |
| 1-2549 | 4-F—Ph | 2-NH₂-4-Pym | H₂N—CH₂CH=CH |
| 1-2550 | 4-F—Ph | 2-NH₂-4-Pym | MeNH—CH₂CH=CH |
| 1-2551 | 4-F—Ph | 2-NH₂-4-Pym | Me₂N—CH₂CH=CH |
| 1-2552 | 4-F—Ph | 2-NH₂-4-Pym | 3-Pip-CH₂ |
| 1-2553 | 4-F—Ph | 2-NH₂-4-Pym | 1-Me-3-Pip-CH₂ |
| 1-2554 | 4-F—Ph | 2-NH₂-4-Pym | 2-Me-4-Pip |
| 1-2555 | 4-F—Ph | 2-NH₂-4-Pym | 2,2,6,6-tetraMe-4-Pip |
| 1-2556 | 4-F—Ph | 2-NH₂-4-Pym | 1-Ac-4-Pip |
| 1-2557 | 4-F—Ph | 2-NH₂-4-Pym | 1-Ac-4-(3,4-deH-Pip) |
| 1-2558 | 4-F—Ph | 2-NH₂-4-Pym | 4-OH-4-Pip |
| 1-2559 | 4-F—Ph | 2-NH₂-4-Pym | 4-OH-1-Me-4-Pip |
| 1-2560 | 4-F—Ph | 2-NH₂-4-Pym | AcNH—(CH₂)₃ |
| 1-2561 | 4-F—Ph | 2-NH₂-4-Pym | 4-NH₂-cHx |
| 1-2562 | 4-F—Ph | 2-NH₂-4-Pym | 3-Qun |
| 1-2563 | 4-F—Ph | 2-NH₂-4-Pym | 3-(2,3-deH-Qun) |
| 1-2564 | 4-F—Ph | 2-NH₂-4-Pym | 3-ABO |
| 1-2565 | 4-F—Ph | 2-NH₂-4-Pym | 8-Me-3-ABO |
| 1-2566 | 4-F—Ph | 2-NH₂-4-Pym | 3-(2,3-deH-ABO) |
| 1-2567 | 4-F—Ph | 2-NH₂-4-Pym | 8-Me-3-(2,3-deH-ABO) |
| 1-2568 | 4-F—Ph | 2-NH₂-4-Pym | 3-ABN |
| 1-2569 | 4-F—Ph | 2-NH₂-4-Pym | 9-Me-3-ABN |
| 1-2570 | 4-F—Ph | 2-NH₂-4-Pym | 3-(2,3-deH-ABN) |
| 1-2571 | 4-F—Ph | 2-NH₂-4-Pym | 9-Me-3-(2,3-deH-ABN) |
| 1-2572 | 4-F—Ph | 2-MeNH-4-Pym | H₂N—CH₂CH=CH |
| 1-2573 | 4-F—Ph | 2-MeNH-4-Pym | MeNH—CH₂CH=CH |
| 1-2574 | 4-F—Ph | 2-MeNH-4-Pym | Me₂N—CH₂CH=CH |
| 1-2575 | 4-F—Ph | 2-MeNH-4-Pym | 3-Pip-CH₂ |
| 1-2576 | 4-F—Ph | 2-MeNH-4-Pym | 1-Me-3-Pip-CH₂ |
| 1-2577 | 4-F—Ph | 2-MeNH-4-Pym | 2-Me-4-Pip |
| 1-2578 | 4-F—Ph | 2-MeNH-4-Pym | 2,2,6,6-tetraMe-4-Pip |
| 1-2579 | 4-F—Ph | 2-MeNH-4-Pym | 1-Ac-4-Pip |
| 1-2580 | 4-F—Ph | 2-MeNH-4-Pym | 1-Ac-4-(3,4-deH-Pip) |
| 1-2581 | 4-F—Ph | 2-MeNH-4-Pym | 4-OH-4-Pip |
| 1-2582 | 4-F—Ph | 2-MeNH-4-Pym | 4-OH-1-Me-4-Pip |
| 1-2583 | 4-F—Ph | 2-MeNH-4-Pym | AcNH—(CH₂)₃ |
| 1-2584 | 4-F—Ph | 2-MeNH-4-Pym | 4-NH₂-cHx |
| 1-2585 | 4-F—Ph | 2-MeNH-4-Pym | 3-Qun |
| 1-2586 | 4-F—Ph | 2-MeNH-4-Pym | 3-(2,3-deH-Qun) |
| 1-2587 | 4-F—Ph | 2-MeNH-4-Pym | 3-ABO |
| 1-2588 | 4-F—Ph | 2-MeNH-4-Pym | 8-Me-3-ABO |
| 1-2589 | 4-F—Ph | 2-MeNH-4-Pym | 3-(2,3-deH-ABO) |
| 1-2590 | 4-F—Ph | 2-MeNH-4-Pym | 8-Me-3-(2,3-deH-ABO) |
| 1-2591 | 4-F—Ph | 2-MeNH-4-Pym | 3-ABN |
| 1-2592 | 4-F—Ph | 2-MeNH-4-Pym | 9-Me-3-ABN |
| 1-2593 | 4-F—Ph | 2-MeNH-4-Pym | 3-(2,3-deH-ABN) |
| 1-2594 | 4-F—Ph | 2-MeNH-4-Pym | 9-Me-3-(2,3-deH-ABN) |
| 1-2595 | 4-F—Ph | 2-BnNH-4-Pyr | 4-Pip |
| 1-2596 | 4-F—Ph | 2-BnNH-4-Pyr | 4-(3,4-deH-Pip) |
| 1-2597 | 4-F—Ph | 2-BnNH-4-Pym | 4-Pip |
| 1-2598 | 4-F—Ph | 2-BnNH-4-Pym | 4-(3,4-deH-Pip) |
| 1-2599 | 4-F—Ph | 2-(α-Me—BnNH)-4-Pyr | 4-Pip |
| 1-2600 | 4-F—Ph | 2-(α-Me—BnNH)-4-Pyr | 4-(3,4-deH-Pip) |
| 1-2601 | 4-F—Ph | 2-(α-Me—BnNH)-4-Pym | 4-Pip |
| 1-2602 | 4-F—Ph | 2-(α-Me—BnNH)-4-Pym | 4-(3,4-deH-Pip) |
| 1-2603 | 3-Cl—Ph | 2-BnNH-4-Pyr | 4-Pip |
| 1-2604 | 3-Cl—Ph | 2-BnNH-4-Pyr | 4-(3,4-deH-Pip) |
| 1-2605 | 3-Cl—Ph | 2-BnNH-4-Pym | 4-Pip |
| 1-2606 | 3-Cl—Ph | 2-BnNH-4-Pym | 4-(3,4-deH-Pip) |
| 1-2607 | 3-Cl—Ph | 2-(α-Me—BnNH)-4-Pyr | 4-Pip |
| 1-2608 | 3-Cl—Ph | 2-(α-Me—BnNH)-4-Pyr | 4-(3,4-deH-Pip) |
| 1-2609 | 3-Cl—Ph | 2-(α-Me—BnNH)-4-Pym | 4-Pip |
| 1-2610 | 3-Cl—Ph | 2-(α-Me—BnNH)-4-Pym | 4-(3,4-deH-Pip) |
| 1-2611 | 3-CF₃—Ph | 2-BnNH-4-Pyr | 4-Pip |
| 1-2612 | 3-CF₃—Ph | 2-BnNH-4-Pyr | 4-(3,4-deH-Pip) |
| 1-2613 | 3-CF₃—Ph | 2-BnNH-4-Pym | 4-Pip |
| 1-2614 | 3-CF₃—Ph | 2-BnNH-4-Pym | 4-(3,4-deH-Pip) |
| 1-2615 | 3-CF₃—Ph | 2-(α-Me—BnNH)-4-Pyr | 4-Pip |
| 1-2616 | 3-CF₃—Ph | 2-(α-Me—BnNH)-4-Pyr | 4-(3,4-deH-Pip) |
| 1-2617 | 3-CF₃—Ph | 2-(α-Me—BnNH)-4-Pym | 4-Pip |
| 1-2618 | 3-CF₃—Ph | 2-(α-Me—BnNH)-4-Pym | 4-(3,4-deH-Pip) |
| 1-2619 | 4-F—Ph | 4-Pyr | 2-NH₂-4-Pym |
| 1-2620 | 4-F—Ph | 4-Pyr | 2-MeNH-4-Pym |
| 1-2621 | 4-F—Ph | 4-Pyr | 2-NH₂-4-Pyr |
| 1-2622 | 4-F—Ph | 4-Pyr | 2-MeNH-4-Pyr |
| 1-2623 | 4-F—Ph | 4-Pyr | H₂N—CH₂C(Me)₂CH₂ |
| 1-2624 | 4-F—Ph | 4-Pyr | MeNH—CH₂C(Me)₂CH₂ |
| 1-2625 | 4-F—Ph | 4-Pyr | EtNH—CH₂C(Me)₂CH₂ |
| 1-2626 | 4-F—Ph | 4-Pyr | Me₂N—CH₂C(Me)₂CH₂ |
| 1-2627 | 4-F—Ph | 4-Pyr | 3-(3,4-deH-Pip) |
| 1-2628 | 4-F—Ph | 4-Pyr | 1-Me-3-(3,4-deH-Pip) |
| 1-2629 | 4-F—Ph | 4-Pyr | 1-Et-4-(3,4-deH-Pip) |
| 1-2630 | 4-F—Ph | 4-Pyr | 1-Pr-4-(3,4-deH-Pip) |
| 1-2631 | 4-F—Ph | 4-Pyr | 1-Pr-4-Pip |
| 1-2632 | 4-F—Ph | 4-Pyr | 1-iPr-4-(3,4-deH-Pip) |
| 1-2633 | 4-F—Ph | 4-Pyr | 1-ipr-4-Pip |
| 1-2634 | 4-F—Ph | 4-Pyr | 1-Bu-4-(3,4-deH-Pip) |
| 1-2635 | 4-F—Ph | 4-Pyr | 1-tBu-4-(3,4-deH-Pip) |
| 1-2636 | 4-F—Ph | 4-Pyr | 1-Pn-4-(3,4-deH-Pip) |
| 1-2637 | 4-F—Ph | 4-Pyr | 1-Hx-4-(3,4-deH-Pip) |
| 1-2638 | 4-F—Ph | 4-Pyr | 1-Hp-4-(3,4-deH-Pip) |
| 1-2639 | 4-F—Ph | 4-Pyr | 1-Oc-4-(3,4-deH-Pip) |
| 1-2640 | 4-F—Ph | 4-Pyr | 1-Nn-4-(3,4-deH-Pip) |
| 1-2641 | 4-F—Ph | 4-Pyr | 1-cPr-4-(3,4-deH-Pip) |
| 1-2642 | 4-F—Ph | 4-Pyr | 1-cPn-4-(3,4-deH-Pip) |
| 1-2643 | 4-F—Ph | 4-Pyr | 1-cHx-4-(3,4-deH-Pip) |
| 1-2644 | 4-F—Ph | 4-Pyr | 1-Bn-4-(3,4-deH-Pip) |
| 1-2645 | 4-F—Ph | 4-Pyr | 1-Phet-4-(3,4-deH-Pip) |
| 1-2646 | 4-F—Ph | 4-Pyr | 1-(3-Ph-Pr)-4-(3,4-deH-Pip) |
| 1-2647 | 4-F—Ph | 4-Pyr | 1-(4-Ph-Bu)-4-(3,4-deH-Pip) |
| 1-2648 | 4-F—Ph | 4-Pyr | 1-Allyl-4-(3,4-deH-Pip) |
| 1-2649 | 4-F—Ph | 4-Pyr | 1-Propargyl-4-(3,4-deH-Pip) |
| 1-2650 | 4-F—Ph | 4-Pyr | 2,2,6,6-tetraMe-4-(3,4-deH-Pip) |
| 1-2651 | 4-F—Ph | 4-Pyr | 1,2,2,6,6-pentaMe-4-(3,4-deH-Pip) |
| 1-2652 | 4-F—Ph | 4-Pyr | 1,2,2,6,6-pentaMe-4-Pip |
| 1-2653 | 4-F—Ph | 4-Pyr | 7-(1,2,3,5,6,8a-hexaH-Ind) |
| 1-2654 | 4-F—Ph | 4-Pyr | 7-(1,2,3,5,8,8a-hexaH-Ind) |
| 1-2655 | 4-F—Ph | 4-Pyr | 7-octaH-Ind |
| 1-2656 | 4-F—Ph | 4-Pyr | 8-(1,3,4,6,7,9a-hexaH-2H-Qui) |
| 1-2657 | 4-F—Ph | 4-Pyr | 8-(1,3,4,6,9,9a-hexaH-2H-Qui) |

TABLE 1-continued

| Compound No. | R¹ | R² | R³ |
| --- | --- | --- | --- |
| 1-2658 | 4-F—Ph | 4-Pyr | 8-octaH-Qui |
| 1-2659 | 4-F—Ph | 4-Pyr | 2,2-diMe-4-(3,4-deH-Pip) |
| 1-2660 | 4-F—Ph | 4-Pyr | 1,2,2-triMe-4-(3,4-deH-Pip) |
| 1-2661 | 4-F—Ph | 4-Pyr | 2,2-diMe-4-(4,5-deH-Pip) |
| 1-2662 | 4-F—Ph | 4-Pyr | 1,2,2-triMe-4-(4,5-deH-Pip) |
| 1-2663 | 4-F—Ph | 4-Pyr | 2,6-diMe-4-(3,4-deH-Pip) |
| 1-2664 | 4-F—Ph | 4-Pyr | 1,2,6-triMe-4-(3,4-deH-Pip) |
| 1-2665 | 4-F—Ph | 4-Pyr | 2-Me-4-(3,4-deH-Pip) |
| 1-2666 | 4-F—Ph | 4-Pyr | 1,2-diMe-4-(3,4-deH-Pip) |
| 1-2667 | 4-F—Ph | 4-Pyr | 1-Et-2-Me-4-(3,4-deH-Pip) |
| 1-2668 | 4-F—Ph | 4-Pyr | 1-Pr-2-Me-4-(3,4-deH-Pip) |
| 1-2669 | 4-F—Ph | 4-Pyr | 1-Bu-2-Me-4-(3,4-deH-Pip) |
| 1-2670 | 4-F—Ph | 4-Pyr | 1-Phet-2-Me-4-(3,4-deH-Pip) |
| 1-2671 | 4-F—Ph | 4-Pyr | 2-Et-4-(3,4-deH-Pip) |
| 1-2672 | 4-F—Ph | 4-Pyr | 1-Me-2-Et-4-(3,4-deH-Pip) |
| 1-2673 | 4-F—Ph | 4-Pyr | 1,2-diEt-4-(3,4-deH-Pip) |
| 1-2674 | 4-F—Ph | 4-Pyr | 1-Pr-2-Et-4-(3,4-deH-Pip) |
| 1-2675 | 4-F—Ph | 4-Pyr | 1-Bu-2-Et-4-(3,4-deH-Pip) |
| 1-2676 | 4-F—Ph | 4-Pyr | 1-Phet-2-Et-4-(3,4-deH-Pip) |
| 1-2677 | 4-F—Ph | 4-Pyr | 2-Pr-4-(3,4-deH-Pip) |
| 1-2678 | 4-F—Ph | 4-Pyr | 1-Me-2-Pr-4-(3,4-deH-Pip) |
| 1-2679 | 4-F—Ph | 4-Pyr | 1-Et-2-Pr-4-(3,4-deH-Pip) |
| 1-2680 | 4-F—Ph | 4-Pyr | 1,2-diPr-4-(3,4-deH-Pip) |
| 1-2681 | 4-F—Ph | 4-Pyr | 1-Bu-2-Pr-4-(3,4-deH-Pip) |
| 1-2682 | 4-F—Ph | 4-Pyr | 1-Phet-2-Pr-4-(3,4-deH-Pip) |
| 1-2683 | 4-F—Ph | 4-Pyr | 2-Bu-4-(3,4-deH-Pip) |
| 1-2684 | 4-F—Ph | 4-Pyr | 1-Me-2-Bu-4-(3,4-deH-Pip) |
| 1-2685 | 4-F—Ph | 4-Pyr | 1-Et-2-Bu-4-(3,4-deH-Pip) |
| 1-2686 | 4-F—Ph | 4-Pyr | 1-Pr-2-Bu-4-(3,4-deH-Pip) |
| 1-2687 | 4-F—Ph | 4-Pyr | 1,2-diBu-4-(3,4-deH-Pip) |
| 1-2688 | 4-F—Ph | 4-Pyr | 1-Phet-2-Bu-4-(3,4-deH-Pip) |
| 1-2689 | 4-F—Ph | 4-Pyr | 2-Allyl-4-(3,4-deH-Pip) |
| 1-2690 | 4-F—Ph | 4-Pyr | 1-Me-2-Allyl-4-(3,4-deH-Pip) |
| 1-2691 | 4-F—Ph | 4-Pyr | 1-Et-2-Allyl-4-(3,4-deH-Pip) |
| 1-2692 | 4-F—Ph | 4-Pyr | 1-Pr-2-Allyl-4-(3,4-deH-Pip) |
| 1-2693 | 4-F—Ph | 4-Pyr | 1-Bu-2-Allyl-4-(3,4-deH-Pip) |
| 1-2694 | 4-F—Ph | 4-Pyr | 1-Phet-2-Allyl-4-(3,4-deH-Pip) |
| 1-2695 | 4-F—Ph | 4-Pyr | 2-Bn-4-(3,4-deH-Pip) |
| 1-2696 | 4-F—Ph | 4-Pyr | 1-Me-2-Bn-4-(3,4-deH-Pip) |
| 1-2697 | 4-F—Ph | 4-Pyr | 1-Et-2-Bn-4-(3,4-deH-Pip) |
| 1-2698 | 4-F—Ph | 4-Pyr | 1-Pr-2-Bn-4-(3,4-deH-Pip) |
| 1-2699 | 4-F—Ph | 4-Pyr | 1-Bu-2-Bn-4-(3,4-deH-Pip) |
| 1-2700 | 4-F—Ph | 4-Pyr | 1-Phet-2-Bn-4-(3,4-deH-Pip) |
| 1-2701 | 4-F—Ph | 4-Pyr | 2-Phet-4-(3,4-deH-Pip) |
| 1-2702 | 4-F—Ph | 4-Pyr | 1-Me-2-Phet-4-(3,4-deH-Pip) |
| 1-2703 | 4-F—Ph | 4-Pyr | 1-Et-2-Phet-4-(3,4-deH-Pip) |
| 1-2704 | 4-F—Ph | 4-Pyr | 1-Pr-2-Phet-4-(3,4-deH-Pip) |
| 1-2705 | 4-F—Ph | 4-Pyr | 1-Bu-2-Phet-4-(3,4-deH-Pip) |
| 1-2706 | 4-F—Ph | 4-Pyr | 1,2-diPhet-4-(3,4-deH-Pip) |
| 1-2707 | 4-F—Ph | 4-Pyr | 2-Me-4-(4,5-deH-Pip) |
| 1-2708 | 4-F—Ph | 4-Pyr | 1,2-diMe-4-(4,5-deH-Pip) |
| 1-2709 | 4-F—Ph | 4-Pyr | 1-Et-2-Me-4-(4,5-deH-Pip) |
| 1-2710 | 4-F—Ph | 4-Pyr | 1-Pr-2-Me-4-(4,5-deH-Pip) |
| 1-2711 | 4-F—Ph | 4-Pyr | 1-Bu-2-Me-4-(4,5-deH-Pip) |
| 1-2712 | 4-F—Ph | 4-Pyr | 1-Phet-2-Me-4-(4,5-deH-Pip) |
| 1-2713 | 4-F—Ph | 4-Pyr | 2-Et-4-(4,5-deH-Pip) |
| 1-2714 | 4-F—Ph | 4-Pyr | 1-Me-2-Et-4-(4,5-deH-Pip) |
| 1-2715 | 4-F—Ph | 4-Pyr | 1,2-diEt-4-(4,5-deH-Pip) |
| 1-2716 | 4-F—Ph | 4-Pyr | 1-Pr-2-Et-4-(4,5-deH-Pip) |
| 1-2717 | 4-F—Ph | 4-Pyr | 1-Bu-2-Et-4-(4,5-deH-Pip) |
| 1-2718 | 4-F—Ph | 4-Pyr | 1-Phet-2-Et-4-(4,5-deH-Pip) |
| 1-2719 | 4-F—Ph | 4-Pyr | 2-Pr-4-(4,5-deH-Pip) |
| 1-2720 | 4-F—Ph | 4-Pyr | 1-Me-2-Pr-4-(4,5-deH-Pip) |
| 1-2721 | 4-F—Ph | 4-Pyr | 1-Et-2-Pr-4-(4,5-deH-Pip) |
| 1-2722 | 4-F—Ph | 4-Pyr | 1,2-diPr-4-(4,5-deH-Pip) |
| 1-2723 | 4-F—Ph | 4-Pyr | 1-Bu-2-Pr-4-(4,5-deH-Pip) |
| 1-2724 | 4-F—Ph | 4-Pyr | 1-Phet-2-Pr-4-(4,5-deH-Pip) |
| 1-2725 | 4-F—Ph | 4-Pyr | 2-Bu-4-(4,5-deH-Pip) |
| 1-2726 | 4-F—Ph | 4-Pyr | 1-Me-2-Bu-4-(4,5-deH-Pip) |
| 1-2727 | 4-F—Ph | 4-Pyr | 1-Et-2-Bu-4-(4,5-deH-Pip) |
| 1-2728 | 4-F—Ph | 4-Pyr | 1-Pr-2-Bu-4-(4,5-deH-Pip) |
| 1-2729 | 4-F—Ph | 4-Pyr | 1,2-diBu-4-(4,5-deH-Pip) |
| 1-2730 | 4-F—Ph | 4-Pyr | 1-Phet-2-Bu-4-(4,5-deH-Pip) |
| 1-2731 | 4-F—Ph | 4-Pyr | 2-Allyl-4-(4,5-deH-Pip) |
| 1-2732 | 4-F—Ph | 4-Pyr | 1-Me-2-Allyl-4-(4,5-deH-Pip) |
| 1-2733 | 4-F—Ph | 4-Pyr | 1-Et-2-Allyl-4-(4,5-deH-Pip) |
| 1-2734 | 4-F—Ph | 4-Pyr | 1-Pr-2-Allyl-4-(4,5-deH-Pip) |
| 1-2735 | 4-F—Ph | 4-Pyr | 1-Bu-2-Allyl-4-(4,5-deH-Pip) |
| 1-2736 | 4-F—Ph | 4-Pyr | 1-Phet-2-Allyl-4-(4,5-deH-Pip) |
| 1-2737 | 4-F—Ph | 4-Pyr | 2-Bn-4-(4,5-deH-Pip) |
| 1-2738 | 4-F—Ph | 4-Pyr | 1-Me-2-Bn-4-(4,5-deH-Pip) |
| 1-2739 | 4-F—Ph | 4-Pyr | 1-Et-2-Bn-4-(4,5-deH-Pip) |
| 1-2740 | 4-F—Ph | 4-Pyr | 1-Pr-2-Bn-4-(4,5-deH-Pip) |
| 1-2741 | 4-F—Ph | 4-Pyr | 1-Bu-2-Bn-4-(4,5-deH-Pip) |
| 1-2742 | 4-F—Ph | 4-Pyr | 1-Phet-2-Bn-4-(4,5-deH-Pip) |
| 1-2743 | 4-F—Ph | 4-Pyr | 2-Phet-4-(4,5-deH-Pip) |

TABLE 1-continued

| Compound No. | R¹ | R² | R³ |
|---|---|---|---|
| 1-2744 | 4-F—Ph | 4-Pyr | 1-Me-2-Phet-4-(4,5-deH-Pip) |
| 1-2745 | 4-F—Ph | 4-Pyr | 1-Et-2-Phet-4-(4,5-deH-Pip) |
| 1-2746 | 4-F—Ph | 4-Pyr | 1-Pr-2-Phet-4-(4,5-deH-Pip) |
| 1-2747 | 4-F—Ph | 4-Pyr | 1-Bu-2-Phet-4-(4,5-deH-Pip) |
| 1-2748 | 4-F—Ph | 4-Pyr | 1,2-diPhet-4-(4,5-deH-Pip) |
| 1-2749 | 4-F—Ph | 2-NH₂-4-Pym | H₂N—CH₂C(Me)₂CH₂ |
| 1-2750 | 4-F—Ph | 2-NH₂-4-Pym | MeNH—CH₂C(Me)₂CH₂ |
| 1-2751 | 4-F—Ph | 2-NH₂-4-Pym | EtNH—CH₂C(Me)₂CH₂ |
| 1-2752 | 4-F—Ph | 2-NH₂-4-Pym | Me₂N—CH₂C(Me)₂CH₂ |
| 1-2753 | 4-F—Ph | 2-NH₂-4-Pym | 3-(3,4-deH-Pip) |
| 1-2754 | 4-F—Ph | 2-NH₂-4-Pym | 1-Me-3-(3,4-deH-Pip) |
| 1-2755 | 4-F—Ph | 2-NH₂-4-Pym | 1-Et-4-(3,4-deH-Pip) |
| 1-2756 | 4-F—Ph | 2-NH₂-4-Pym | 1-Pr-4-(3,4-deH-Pip) |
| 1-2757 | 4-F—Ph | 2-NH₂-4-Pym | 1-Pr-4-Pip |
| 1-2758 | 4-F—Ph | 2-NH₂-4-Pym | 1-iPr-4-(3,4-deH-Pip) |
| 1-2759 | 4-F—Ph | 2-NH₂-4-Pym | 1-iPr-4-Pip |
| 1-2760 | 4-F—Ph | 2-NH₂-4-Pym | 1-Bu-4-(3,4-deH-Pip) |
| 1-2761 | 4-F—Ph | 2-NH₂-4-Pym | 1-tBu-4-(3,4-deH-Pip) |
| 1-2762 | 4-F—Ph | 2-NH₂-4-Pym | 1-Pn-4-(3,4-deH-Pip) |
| 1-2763 | 4-F—Ph | 2-NH₂-4-Pym | 1-Hx-4-(3,4-deH-Pip) |
| 1-2764 | 4-F—Ph | 2-NH₂-4-Pym | 1-Hp-4-(3,4-deH-Pip) |
| 1-2765 | 4-F—Ph | 2-NH₂-4-Pym | 1-Oc-4-(3,4-deH-Pip) |
| 1-2766 | 4-F—Ph | 2-NH₂-4-Pym | 1-Nn-4-(3,4-deH-Pip) |
| 1-2767 | 4-F—Ph | 2-NH₂-4-Pym | 1-cPr-4-(3,4-deH-Pip) |
| 1-2768 | 4-F—Ph | 2-NH₂-4-Pym | 1-cPn-4-(3,4-deH-Pip) |
| 1-2769 | 4-F—Ph | 2-NH₂-4-Pym | 1-cHx-4-(3,4-deH-Pip) |
| 1-2770 | 4-F—Ph | 2-NH₂-4-Pym | 1-Bn-4-(3,4-deH-Pip) |
| 1-2771 | 4-F—Ph | 2-NH₂-4-Pym | 1-Phet-4-(3,4-deH-Pip) |
| 1-2772 | 4-F—Ph | 2-NH₂-4-Pym | 1-(3-Ph-Pr)-4-(3,4-deH-Pip) |
| 1-2773 | 4-F—Ph | 2-NH₂-4-Pym | 1-(4-Ph-Bu)-4-(3,4-deH-Pip) |
| 1-2774 | 4-F—Ph | 2-NH₂-4-Pym | 1-Allyl-4-(3,4-deH-Pip) |
| 1-2775 | 4-F—Ph | 2-NH₂-4-Pym | 1-Propargyl-4-(3,4-deH-Pip) |
| 1-2776 | 4-F—Ph | 2-NH₂-4-Pym | 2,2,6,6-tetraMe-4-(3,4-deH-Pip) |
| 1-2777 | 4-F—Ph | 2-NH₂-4-Pym | 1,2,2,6,6-pentaMe-4-(3,4-deH-Pip) |
| 1-2778 | 4-F—Ph | 2-NH₂-4-Pym | 1,2,2,6,6-pentaMe-4-Pip |
| 1-2779 | 4-F—Ph | 2-NH₂-4-Pym | 7-(1,2,3,5,6,8a-hexaH-Ind) |
| 1-2780 | 4-F—Ph | 2-NH₂-4-Pym | 7-(1,2,3,5,8,8a-hexaH-Ind) |
| 1-2781 | 4-F—Ph | 2-NH₂-4-Pym | 7-octaH-Ind |
| 1-2782 | 4-F—Ph | 2-NH₂-4-Pym | 8-(1,3,4,6,7,9a-hexaH-2H-Qui) |
| 1-2783 | 4-F—Ph | 2-NH₂-4-Pym | 8-(1,3,4,6,9,9a-hexaH-2H-Qui) |
| 1-2784 | 4-F—Ph | 2-NH₂-4-Pym | 8-octaH-Qui |
| 1-2785 | 4-F—Ph | 2-NH₂-4-Pym | 2,2-diMe-4-(3,4-deH-Pip) |
| 1-2786 | 4-F—Ph | 2-NH₂-4-Pym | 1,2,2-triMe-4-(3,4-deH-Pip) |
| 1-2787 | 4-F—Ph | 2-NH₂-4-Pym | 2,2-diMe-4-(4,5-deH-Pip) |
| 1-2788 | 4-F—Ph | 2-NH₂-4-Pym | 1,2,2-triMe-4-(4,5-deH-Pip) |
| 1-2789 | 4-F—Ph | 2-NH₂-4-Pym | 2,6-diMe-4-(3,4-deH-Pip) |
| 1-2790 | 4-F—Ph | 2-NH₂-4-Pym | 1,2,6-triMe-4-(3,4-deH-Pip) |
| 1-2791 | 4-F—Ph | 2-NH₂-4-Pym | 2-Me-4-(3,4-deH-Pip) |
| 1-2792 | 4-F—Ph | 2-NH₂-4-Pym | 1,2-diMe-4-(3,4-deH-Pip) |
| 1-2793 | 4-F—Ph | 2-NH₂-4-Pym | 1-Et-2-Me-4-(3,4-deH-Pip) |
| 1-2794 | 4-F—Ph | 2-NH₂-4-Pym | 1-Pr-2-Me-4-(3,4-deH-Pip) |
| 1-2795 | 4-F—Ph | 2-NH₂-4-Pym | 1-Bu-2-Me-4-(3,4-deH-Pip) |
| 1-2796 | 4-F—Ph | 2-NH₂-4-Pym | 1-Phet-2-Me-4-(3,4-deH-Pip) |
| 1-2797 | 4-F—Ph | 2-NH₂-4-Pym | 2-Et-4-(3,4-deH-Pip) |
| 1-2798 | 4-F—Ph | 2-NH₂-4-Pym | 1-Me-2-Et-4-(3,4-deH-Pip) |
| 1-2799 | 4-F—Ph | 2-NH₂-4-Pym | 1,2-diEt-4-(3,4-deH-Pip) |
| 1-2800 | 4-F—Ph | 2-NH₂-4-Pym | 1-Pr-2-Et-4-(3,4-deH-Pip) |
| 1-2801 | 4-F—Ph | 2-NH₂-4-Pym | 1-Bu-2-Et-4-(3,4-deH-Pip) |
| 1-2802 | 4-F—Ph | 2-NH₂-4-Pym | 1-Phet-2-Et-4-(3,4-deH-Pip) |
| 1-2803 | 4-F—Ph | 2-NH₂-4-Pym | 2-Pr-4-(3,4-deH-Pip) |
| 1-2804 | 4-F—Ph | 2-NH₂-4-Pym | 1-Me-2-Pr-4-(3,4-deH-Pip) |
| 1-2805 | 4-F—Ph | 2-NH₂-4-Pym | 1-Et-2-Pr-4-(3,4-deH-Pip) |
| 1-2806 | 4-F—Ph | 2-NH₂-4-Pym | 1,2-diPr-4-(3,4-deH-Pip) |
| 1-2807 | 4-F—Ph | 2-NH₂-4-Pym | 1-Bu-2-Pr-4-(3,4-deH-Pip) |
| 1-2808 | 4-F—Ph | 2-NH₂-4-Pym | 1-Phet-2-Pr-4-(3,4-deH-Pip) |
| 1-2809 | 4-F—Ph | 2-NH₂-4-Pym | 2-Bu-4-(3,4-deH-Pip) |
| 1-2810 | 4-F—Ph | 2-NH₂-4-Pym | 1-Me-2-Bu-4-(3,4-deH-Pip) |
| 1-2811 | 4-F—Ph | 2-NH₂-4-Pym | 1-Et-2-Bu-4-(3,4-deH-Pip) |
| 1-2812 | 4-F—Ph | 2-NH₂-4-Pym | 1-Pr-2-Bu-4-(3,4-deH-Pip) |
| 1-2813 | 4-F—Ph | 2-NH₂-4-Pym | 1,2-diBu-4-(3,4-deH-Pip) |
| 1-2814 | 4-F—Ph | 2-NH₂-4-Pym | 1-Phet-2-Bu-4-(3,4-deH-Pip) |
| 1-2815 | 4-F—Ph | 2-NH₂-4-Pym | 2-Allyl-4-(3,4-deH-Pip) |
| 1-2816 | 4-F—Ph | 2-NH₂-4-Pym | 1-Me-2-Allyl-4-(3,4-deH-Pip) |
| 1-2817 | 4-F—Ph | 2-NH₂-4-Pym | 1-Et-2-Allyl-4-(3,4-deH-Pip) |
| 1-2818 | 4-F—Ph | 2-NH₂-4-Pym | 1-Pr-2-Allyl-4-(3,4-deH-Pip) |
| 1-2819 | 4-F—Ph | 2-NH₂-4-Pym | 1-Bu-2-Allyl-4-(3,4-deH-Pip) |
| 1-2820 | 4-F—Ph | 2-NH₂-4-Pym | 1-Phet-2-Allyl-4-(3,4-deH-Pip) |
| 1-2821 | 4-F—Ph | 2-NH₂-4-Pym | 2-Bn-4-(3,4-deH-Pip) |
| 1-2822 | 4-F—Ph | 2-NH₂-4-Pym | 1-Me-2-Bn-4-(3,4-deH-Pip) |
| 1-2823 | 4-F—Ph | 2-NH₂-4-Pym | 1-Et-2-Bn-4-(3,4-deH-Pip) |
| 1-2824 | 4-F—Ph | 2-NH₂-4-Pym | 1-Pr-2-Bn-4-(3,4-deH-Pip) |
| 1-2825 | 4-F—Ph | 2-NH₂-4-Pym | 1-Bu-2-Bn-4-(3,4-deH-Pip) |
| 1-2826 | 4-F—Ph | 2-NH₂-4-Pym | 1-Phet-2-Bn-4-(3,4-deH-Pip) |
| 1-2827 | 4-F—Ph | 2-NH₂-4-Pym | 2-Phet-4-(3,4-deH-Pip) |
| 1-2828 | 4-F—Ph | 2-NH₂-4-Pym | 1-Me-2-Phet-4-(3,4-deH-Pip) |
| 1-2829 | 4-F—Ph | 2-NH₂-4-Pym | 1-Et-2-Phet-4-(3,4-deH-Pip) |
| 1-2830 | 4-F—Ph | 2-NH₂-4-Pym | 1-Pr-2-Phet-4-(3,4-deH-Pip) |
| 1-2831 | 4-F—Ph | 2-NH₂-4-Pym | 1-Bu-2-Phet-4-(3,4-deH-Pip) |
| 1-2832 | 4-F—Ph | 2-NH₂-4-Pym | 1,2-diPhet-4-(3,4-deH-Pip) |
| 1-2833 | 4-F—Ph | 2-NH₂-4-Pym | 2-Me-4-(4,5-deH-Pip) |
| 1-2834 | 4-F—Ph | 2-NH₂-4-Pym | 1,2-diMe-4-(4,5-deH-Pip) |
| 1-2835 | 4-F—Ph | 2-NH₂-4-Pym | 1-Et-2-Me-4-(4,5-deH-Pip) |
| 1-2836 | 4-F—Ph | 2-NH₂-4-Pym | 1-Pr-2-Me-4-(4,5-deH-Pip) |

TABLE 1-continued

| Compound No. | R¹ | R² | R³ |
|---|---|---|---|
| 1-2837 | 4-F—Ph | 2-NH₂-4-Pym | 1-Bu-2-Me-4-(4,5-deH-Pip) |
| 1-2838 | 4-F—Ph | 2-NH₂-4-Pym | 1-Phet-2-Me-4-(4,5-deH-Pip) |
| 1-2839 | 4-F—Ph | 2-NH₂-4-Pym | 2-Et-4-(4,5-deH-Pip) |
| 1-2840 | 4-F—Ph | 2-NH₂-4-Pym | 1-Me-2-Et-4-(4,5-deH-Pip) |
| 1-2841 | 4-F—Ph | 2-NH₂-4-Pym | 1,2-diEt-4-(4,5-deH-Pip) |
| 1-2842 | 4-F—Ph | 2-NH₂-4-Pym | 1-Pr-2-Et-4-(4,5-deH-Pip) |
| 1-2843 | 4-F—Ph | 2-NH₂-4-Pym | 1-Bu-2-Et-4-(4,5-deH-Pip) |
| 1-2844 | 4-F—Ph | 2-NH₂-4-Pym | 1-Phet-2-Et-4-(4,5-deH-Pip) |
| 1-2845 | 4-F—Ph | 2-NH₂-4-Pym | 2-Pr-4-(4,5-deH-Pip) |
| 1-2846 | 4-F—Ph | 2-NH₂-4-Pym | 1-Me-2-Pr-4-(4,5-deH-Pip) |
| 1-2847 | 4-F—Ph | 2-NH₂-4-Pym | 1-Et-2-Pr-4-(4,5-deH-Pip) |
| 1-2848 | 4-F—Ph | 2-NH₂-4-Pym | 1,2-diPr-4-(4,5-deH-Pip) |
| 1-2849 | 4-F—Ph | 2-NH₂-4-Pym | 1-Bu-2-Pr-4-(4,5-deH-Pip) |
| 1-2850 | 4-F—Ph | 2-NH₂-4-Pym | 1-Phet-2-Pr-4-(4,5-deH-Pip) |
| 1-2851 | 4-F—Ph | 2-NH₂-4-Pym | 2-Bu-4-(4,5-deH-Pip) |
| 1-2852 | 4-F—Ph | 2-NH₂-4-Pym | 1-Me-2-Bu-4-(4,5-deH-Pip) |
| 1-2853 | 4-F—Ph | 2-NH₂-4-Pym | 1-Et-2-Bu-4-(4,5-deH-Pip) |
| 1-2854 | 4-F—Ph | 2-NH₂-4-Pym | 1-Pr-2-Bu-4-(4,5-deH-Pip) |
| 1-2855 | 4-F—Ph | 2-NH₂-4-Pym | 1,2-diBu-4-(4,5-deH-Pip) |
| 1-2856 | 4-F—Ph | 2-NH₂-4-Pym | 1-Phet-2-Bu-4-(4,5-deH-Pip) |
| 1-2857 | 4-F—Ph | 2-NH₂-4-Pym | 2-Allyl-4-(4,5-deH-Pip) |
| 1-2858 | 4-F—Ph | 2-NH₂-4-Pym | 1-Me-2-Allyl-4-(4,5-deH-Pip) |
| 1-2859 | 4-F—Ph | 2-NH₂-4-Pym | 1-Et-2-Allyl-4-(4,5-deH-Pip) |
| 1-2860 | 4-F—Ph | 2-NH₂-4-Pym | 1-Pr-2-Allyl-4-(4,5-deH-Pip) |
| 1-2861 | 4-F—Ph | 2-NH₂-4-Pym | 1-Bu-2-Allyl-4-(4,5-deH-Pip) |
| 1-2862 | 4-F—Ph | 2-NH₂-4-Pym | 1-Phet-2-Allyl-4-(4,5-deH-Pip) |
| 1-2863 | 4-F—Ph | 2-NH₂-4-Pym | 2-Bn-4-(4,5-deH-Pip) |
| 1-2864 | 4-F—Ph | 2-NH₂-4-Pym | 1-Me-2-Bn-4-(4,5-deH-Pip) |
| 1-2865 | 4-F—Ph | 2-NH₂-4-Pym | 1-Et-2-Bn-4-(4,5-deH-Pip) |
| 1-2866 | 4-F—Ph | 2-NH₂-4-Pym | 1-Pr-2-Bn-4-(4,5-deH-Pip) |
| 1-2867 | 4-F—Ph | 2-NH₂-4-Pym | 1-Bu-2-Bn-4-(4,5-deH-Pip) |
| 1-2868 | 4-F—Ph | 2-NH₂-4-Pym | 1-Phet-2-Bn-4-(4,5-deH-Pip) |
| 1-2869 | 4-F—Ph | 2-NH₂-4-Pym | 2-Phet-4-(4,5-deH-Pip) |
| 1-2870 | 4-F—Ph | 2-NH₂-4-Pym | 1-Me-2-Phet-4-(4,5-deH-Pip) |
| 1-2871 | 4-F—Ph | 2-NH₂-4-Pym | 1-Et-2-Phet-4-(4,5-deH-Pip) |
| 1-2872 | 4-F—Ph | 2-NH₂-4-Pym | 1-Pr-2-Phet-4-(4,5-deH-Pip) |
| 1-2873 | 4-F—Ph | 2-NH₂-4-Pym | 1-Bu-2-Phet-4-(4,5-deH-Pip) |
| 1-2874 | 4-F—Ph | 2-NH₂-4-Pym | 1,2-diPhet-4-(4,5-deH-Pip) |
| 1-2875 | 4-F—Ph | 2-MeNH-4-Pym | H₂N—CH₂C(Me)₂CH₂ |
| 1-2876 | 4-F—Ph | 2-MeNH-4-Pym | MeNH—CH₂C(Me)₂CH₂ |
| 1-2877 | 4-F—Ph | 2-MeNH-4-Pym | EtNH—CH₂C(Me)₂CH₂ |
| 1-2878 | 4-F—Ph | 2-MeNH-4-Pym | Me₂N—CH₂C(Me)₂CH₂ |
| 1-2879 | 4-F—Ph | 2-MeNH-4-Pym | 3-(3,4-deH-Pip) |
| 1-2880 | 4-F—Ph | 2-MeNH-4-Pym | 1-Me-3-(3,4-deH-Pip) |
| 1-2881 | 4-F—Ph | 2-MeNH-4-Pym | 1-Et-4-(3,4-deH-Pip) |
| 1-2882 | 4-F—Ph | 2-MeNH-4-Pym | 1-Pr-4-(3,4-deH-Pip) |
| 1-2883 | 4-F—Ph | 2-MeNH-4-Pym | 1-Pr-4-Pip |
| 1-2884 | 4-F—Ph | 2-MeNH-4-Pym | 1-iPr-4-(3,4-deH-Pip) |
| 1-2885 | 4-F—Ph | 2-MeNH-4-Pym | 1-iPr-4-Pip |
| 1-2886 | 4-F—Ph | 2-MeNH-4-Pym | 1-Bu-4-(3,4-deH-Pip) |
| 1-2887 | 4-F—Ph | 2-MeNH-4-Pym | 1-tBu-4-(3,4-deH-Pip) |
| 1-2888 | 4-F—Ph | 2-MeNH-4-Pym | 1-Pn-4-(3,4-deH-Pip) |
| 1-2889 | 4-F—Ph | 2-MeNH-4-Pym | 1-Hx-4-(3,4-deH-Pip) |
| 1-2890 | 4-F—Ph | 2-MeNH-4-Pym | 1-Hp-4-(3,4-deH-Pip) |
| 1-2891 | 4-F—Ph | 2-MeNH-4-Pym | 1-Oc-4-(3,4-deH-Pip) |
| 1-2892 | 4-F—Ph | 2-MeNH-4-Pym | 1-Nn-4-(3,4-deH-Pip) |
| 1-2893 | 4-F—Ph | 2-MeNH-4-Pym | 1-cPr-4-(3,4-deH-Pip) |
| 1-2894 | 4-F—Ph | 2-MeNH-4-Pym | 1-cPn-4-(3,4-deH-Pip) |
| 1-2895 | 4-F—Ph | 2-MeNH-4-Pym | 1-cHx-4-(3,4-deH-Pip) |
| 1-2896 | 4-F—Ph | 2-MeNH-4-Pym | 1-Bn-4-(3,4-deH-Pip) |
| 1-2897 | 4-F—Ph | 2-MeNH-4-Pym | 1-Phet-4-(3,4-deH-Pip) |
| 1-2898 | 4-F—Ph | 2-MeNH-4-Pym | 1-(3-Ph-Pr)-4-(3,4-deH-Pip) |
| 1-2899 | 4-F—Ph | 2-MeNH-4-Pym | 1-(4-Ph-Bu)-4-(3,4-deH-Pip) |
| 1-2900 | 4-F—Ph | 2-MeNH-4-Pym | 1-Allyl-4-(3,4-deH-Pip) |
| 1-2901 | 4-F—Ph | 2-MeNH-4-Pym | 1-Propargyl-4-(3,4-deH-Pip) |
| 1-2902 | 4-F—Ph | 2-MeNH-4-Pym | 2,2,6,6-tetraMe-4-(3,4-deH-Pip) |
| 1-2903 | 4-F—Ph | 2-MeNH-4-Pym | 1,2,2,6,6-pentaMe-4-(3,4-deH-Pip) |
| 1-2904 | 4-F—Ph | 2-MeNH-4-Pym | 1,2,2,6,6-pentaMe-4-Pip |
| 1-2905 | 4-F—Ph | 2-MeNH-4-Pym | 7-(1,2,3,5,6,8a-hexaH-Ind) |
| 1-2906 | 4-F—Ph | 2-MeNH-4-Pym | 7-(1,2,3,5,8,8a-hexaH-Ind) |
| 1-2907 | 4-F—Ph | 2-MeNH-4-Pym | 7-octaH-Ind |
| 1-2908 | 4-F—Ph | 2-MeNH-4-Pym | 8-(1,3,4,6,7,9a-hexaH-2H-Qui) |
| 1-2909 | 4-F—Ph | 2-MeNH-4-Pym | 8-(1,3,4,6,9,9a-hexaH-2H-Qui) |
| 1-2910 | 4-F—Ph | 2-MeNH-4-Pym | 8-octaH-Qui |
| 1-2911 | 4-F—Ph | 2-MeNH-4-Pym | 2,2-diMe-4-(3,4-deH-Pip) |
| 1-2912 | 4-F—Ph | 2-MeNH-4-Pym | 1,2,2-triMe-4-(3,4-deH-Pip) |
| 1-2913 | 4-F—Ph | 2-MeNH-4-Pym | 2,2-diMe-4-(4,5-deH-Pip) |
| 1-2914 | 4-F—Ph | 2-MeNH-4-Pym | 1,2,2-triMe-4-(4,5-deH-Pip) |
| 1-2915 | 4-F—Ph | 2-MeNH-4-Pym | 2,6-diMe-4-(3,4-deH-Pip) |
| 1-2916 | 4-F—Ph | 2-MeNH-4-Pym | 1,2,6-triMe-4-(3,4-deH-Pip) |
| 1-2917 | 4-F—Ph | 2-MeNH-4-Pym | 2-Me-4-(3,4-deH-Pip) |
| 1-2918 | 4-F—Ph | 2-MeNH-4-Pym | 1,2-diMe-4-(3,4-deH-Pip) |
| 1-2919 | 4-F—Ph | 2-MeNH-4-Pym | 1-Et-2-Me-4-(3,4-deH-Pip) |
| 1-2920 | 4-F—Ph | 2-MeNH-4-Pym | 1-Pr-2-Me-4-(3,4-deH-Pip) |
| 1-2921 | 4-F—Ph | 2-MeNH-4-Pym | 1-Bu-2-Me-4-(3,4-deH-Pip) |
| 1-2922 | 4-F—Ph | 2-MeNH-4-Pym | 1-Phet-2-Me-4-(3,4-deH-Pip) |
| 1-2923 | 4-F—Ph | 2-MeNH-4-Pym | 2-Et-4-(3,4-deH-Pip) |
| 1-2924 | 4-F—Ph | 2-MeNH-4-Pym | 1-Me-2-Et-4-(3,4-deH-Pip) |
| 1-2925 | 4-F—Ph | 2-MeNH-4-Pym | 1,2-diEt-4-(3,4-deH-Pip) |
| 1-2926 | 4-F—Ph | 2-MeNH-4-Pym | 1-Pr-2-Et-4-(3,4-deH-Pip) |
| 1-2927 | 4-F—Ph | 2-MeNH-4-Pym | 1-Bu-2-Et-4-(3,4-deH-Pip) |
| 1-2928 | 4-F—Ph | 2-MeNH-4-Pym | 1-Phet-2-Et-4-(3,4-deH-Pip) |
| 1-2929 | 4-F—Ph | 2-MeNH-4-Pym | 2-Pr-4-(3,4-deH-Pip) |
| 1-2930 | 4-F—Ph | 2-MeNH-4-Pym | 1-Me-2-Pr-4-(3,4-deH-Pip) |
| 1-2931 | 4-F—Ph | 2-MeNH-4-Pym | 1-Et-2-Pr-4-(3,4-deH-Pip) |
| 1-2932 | 4-F—Ph | 2-MeNH-4-Pym | 1,2-diPr-4-(3,4-deH-Pip) |

TABLE 1-continued

| Compound No. | R¹ | R² | R³ |
|---|---|---|---|
| 1-2933 | 4-F—Ph | 2-MeNH-4-Pym | 1-Bu-2-Pr-4-(3,4-deH-Pip) |
| 1-2934 | 4-F—Ph | 2-MeNH-4-Pym | 1-Phet-2-Pr-4-(3,4-deH-Pip) |
| 1-2935 | 4-F—Ph | 2-MeNH-4-Pym | 2-Bu-4-(3,4-deH-Pip) |
| 1-2936 | 4-F—Ph | 2-MeNH-4-Pym | 1-Me-2-Bu-4-(3,4-deH-Pip) |
| 1-2937 | 4-F—Ph | 2-MeNH-4-Pym | 1-Et-2-Bu-4-(3,4-deH-Pip) |
| 1-2938 | 4-F—Ph | 2-MeNH-4-Pym | 1-Pr-2-Bu-4-(3,4-deH-Pip) |
| 1-2939 | 4-F—Ph | 2-MeNH-4-Pym | 1,2-diBu-4-(3,4-deH-Pip) |
| 1-2940 | 4-F—Ph | 2-MeNH-4-Pym | 1-Phet-2-Bu-4-(3,4-deH-Pip) |
| 1-2941 | 4-F—Ph | 2-MeNH-4-Pym | 2-Allyl-4-(3,4-deH-Pip) |
| 1-2942 | 4-F—Ph | 2-MeNH-4-Pym | 1-Me-2-Allyl-4-(3,4-deH-Pip) |
| 1-2943 | 4-F—Ph | 2-MeNH-4-Pym | 1-Et-2-Allyl-4-(3,4-deH-Pip) |
| 1-2944 | 4-F—Ph | 2-MeNH-4-Pym | 1-Pr-2-Allyl-4-(3,4-deH-Pip) |
| 1-2945 | 4-F—Ph | 2-MeNH-4-Pym | 1-Bu-2-Allyl-4-(3,4-deH-Pip) |
| 1-2946 | 4-F—Ph | 2-MeNH-4-Pym | 1-Phet-2-Allyl-4-(3,4-deH-Pip) |
| 1-2947 | 4-F—Ph | 2-MeNH-4-Pym | 2-Bn-4-(3,4-deH-Pip) |
| 1-2948 | 4-F—Ph | 2-MeNH-4-Pym | 1-Me-2-Bn-4-(3,4-deH-Pip) |
| 1-2949 | 4-F—Ph | 2-MeNH-4-Pym | 1-Et-2-Bn-4-(3,4-deH-Pip) |
| 1-2950 | 4-F—Ph | 2-MeNH-4-Pym | 1-Pr-2-Bn-4-(3,4-deH-Pip) |
| 1-2951 | 4-F—Ph | 2-MeNH-4-Pym | 1-Bu-2-Bn-4-(3,4-deH-Pip) |
| 1-2952 | 4-F—Ph | 2-MeNH-4-Pym | 1-Phet-2-Bn-4-(3,4-deH-Pip) |
| 1-2953 | 4-F—Ph | 2-MeNH-4-Pym | 2-Phet-4-(3,4-deH-Pip) |
| 1-2954 | 4-F—Ph | 2-MeNH-4-Pym | 1-Me-2-Phet-4-(3,4-deH-Pip) |
| 1-2955 | 4-F—Ph | 2-MeNH-4-Pym | 1-Et-2-Phet-4-(3,4-deH-Pip) |
| 1-2956 | 4-F—Ph | 2-MeNH-4-Pym | 1-Pr-2-Phet-4-(3,4-deH-Pip) |
| 1-2957 | 4-F—Ph | 2-MeNH-4-Pym | 1-Bu-2-Phet-4-(3,4-deH-Pip) |
| 1-2958 | 4-F—Ph | 2-MeNH-4-Pym | 1,2-diPhet-4-(3,4-deH-Pip) |
| 1-2959 | 4-F—Ph | 2-MeNH-4-Pym | 2-Me-4-(4,5-deH-Pip) |
| 1-2960 | 4-F—Ph | 2-MeNH-4-Pym | 1,2-diMe-4-(4,5-deH-Pip) |
| 1-2961 | 4-F—Ph | 2-MeNH-4-Pym | 1-Et-2-Me-4-(4,5-deH-Pip) |
| 1-2962 | 4-F—Ph | 2-MeNH-4-Pym | 1-Pr-2-Me-4-(4,5-deH-Pip) |
| 1-2963 | 4-F—Ph | 2-MeNH-4-Pym | 1-Bu-2-Me-4-(4,5-deH-Pip) |
| 1-2964 | 4-F—Ph | 2-MeNH-4-Pym | 1-Phet-2-Me-4-(4,5-deH-Pip) |
| 1-2965 | 4-F—Ph | 2-MeNH-4-Pym | 2-Et-4-(4,5-deH-Pip) |
| 1-2966 | 4-F—Ph | 2-MeNH-4-Pym | 1-Me-2-Et-4-(4,5-deH-Pip) |
| 1-2967 | 4-F—Ph | 2-MeNH-4-Pym | 1,2-diEt-4-(4,5-deH-Pip) |
| 1-2968 | 4-F—Ph | 2-MeNH-4-Pym | 1-Pr-2-Et-4-(4,5-deH-Pip) |
| 1-2969 | 4-F—Ph | 2-MeNH-4-Pym | 1-Bu-2-Et-4-(4,5-deH-Pip) |
| 1-2970 | 4-F—Ph | 2-MeNH-4-Pym | 1-Phet-2-Et-4-(4,5-deH-Pip) |
| 1-2971 | 4-F—Ph | 2-MeNH-4-Pym | 2-Pr-4-(4,5-deH-Pip) |
| 1-2972 | 4-F—Ph | 2-MeNH-4-Pym | 1-Me-2-Pr-4-(4,5-deH-Pip) |
| 1-2973 | 4-F—Ph | 2-MeNH-4-Pym | 1-Et-2-Pr-4-(4,5-deH-Pip) |
| 1-2974 | 4-F—Ph | 2-MeNH-4-Pym | 1,2-diPr-4-(4,5-deH-Pip) |
| 1-2975 | 4-F—Ph | 2-MeNH-4-Pym | 1-Bu-2-Pr-4-(4,5-deH-Pip) |
| 1-2976 | 4-F—Ph | 2-MeNH-4-Pym | 1-Phet-2-Pr-4-(4,5-deH-Pip) |
| 1-2977 | 4-F—Ph | 2-MeNH-4-Pym | 2-Bu-4-(4,5-deH-Pip) |
| 1-2978 | 4-F—Ph | 2-MeNH-4-Pym | 1-Me-2-Bu-4-(4,5-deH-Pip) |
| 1-2979 | 4-F—Ph | 2-MeNH-4-Pym | 1-Et-2-Bu-4-(4,5-deH-Pip) |
| 1-2980 | 4-F—Ph | 2-MeNH-4-Pym | 1-Pr-2-Bu-4-(4,5-deH-Pip) |
| 1-2981 | 4-F—Ph | 2-MeNH-4-Pym | 1,2-diBu-4-(4,5-deH-Pip) |
| 1-2982 | 4-F—Ph | 2-MeNH-4-Pym | 1-Phet-2-Bu-4-(4,5-deH-Pip) |
| 1-2983 | 4-F—Ph | 2-MeNH-4-Pym | 2-Allyl-4-(4,5-deH-Pip) |
| 1-2984 | 4-F—Ph | 2-MeNH-4-Pym | 1-Me-2-Allyl-4-(4,5-deH-Pip) |
| 1-2985 | 4-F—Ph | 2-MeNH-4-Pym | 1-Et-2-Allyl-4-(4,5-deH-Pip) |
| 1-2986 | 4-F—Ph | 2-MeNH-4-Pym | 1-Pr-2-Allyl-4-(4,5-deH-Pip) |
| 1-2987 | 4-F—Ph | 2-MeNH-4-Pym | 1-Bu-2-Allyl-4-(4,5-deH-Pip) |
| 1-2988 | 4-F—Ph | 2-MeNH-4-Pym | 1-Phet-2-Allyl-4-(4,5-deH-Pip) |
| 1-2989 | 4-F—Ph | 2-MeNH-4-Pym | 2-Bn-4-(4,5-deH-Pip) |
| 1-2990 | 4-F—Ph | 2-MeNH-4-Pym | 1-Me-2-Bn-4-(4,5-deH-Pip) |
| 1-2991 | 4-F—Ph | 2-MeNH-4-Pym | 1-Et-2-Bn-4-(4,5-deH-Pip) |
| 1-2992 | 4-F—Ph | 2-MeNH-4-Pym | 1-Pr-2-Bn-4-(4,5-deH-Pip) |
| 1-2993 | 4-F—Ph | 2-MeNH-4-Pym | 1-Bu-2-Bn-4-(4,5-deH-Pip) |
| 1-2994 | 4-F—Ph | 2-MeNH-4-Pym | 1-Phet-2-Bn-4-(4,5-deH-Pip) |
| 1-2995 | 4-F—Ph | 2-MeNH-4-Pym | 2-Phet-4-(4,5-deH-Pip) |
| 1-2996 | 4-F—Ph | 2-MeNH-4-Pym | 1-Me-2-Phet-4-(4,5-deH-Pip) |
| 1-2997 | 4-F—Ph | 2-MeNH-4-Pym | 1-Et-2-Phet-4-(4,5-deH-Pip) |
| 1-2998 | 4-F—Ph | 2-MeNH-4-Pym | 1-Pr-2-Phet-4-(4,5-deH-Pip) |
| 1-2999 | 4-F—Ph | 2-MeNH-4-Pym | 1-Bu-2-Phet-4-(4,5-deH-Pip) |
| 1-3000 | 4-F—Ph | 2-MeNH-4-Pym | 1,2-diPhet-4-(4,5-deH-Pip) |
| 1-3001 | 4-F—Ph | 2-NH$_2$-4-Pyr | H$_2$N—CH$_2$C(Me)$_2$CH$_2$ |
| 1-3002 | 4-F—Ph | 2-NH$_2$-4-Pyr | MeNH—CH$_2$C(Me)$_2$CH$_2$ |
| 1-3003 | 4-F—Ph | 2-NH$_2$-4-Pyr | EtNH—CH$_2$C(Me)$_2$CH$_2$ |
| 1-3004 | 4-F—Ph | 2-NH$_2$-4-Pyr | Me$_2$N—CH$_2$C(Me)$_2$CH$_2$ |
| 1-3005 | 4-F—Ph | 2-NH$_2$-4-Pyr | 3-(3,4-deH-Pip) |
| 1-3006 | 4-F—Ph | 2-NH$_2$-4-Pyr | 1-Me-3-(3,4-deH-Pip) |
| 1-3007 | 4-F—Ph | 2-NH$_2$-4-Pyr | 1-Et-4-(3,4-deH-Pip) |
| 1-3008 | 4-F—Ph | 2-NH$_2$-4-Pyr | 1-Pr-4-(3,4-deH-Pip) |
| 1-3009 | 4-F—Ph | 2-NH$_2$-4-Pyr | 1-Pr-4-Pip |
| 1-3010 | 4-F—Ph | 2-NH$_2$-4-Pyr | 1-iPr-4-(3,4-deH-Pip) |
| 1-3011 | 4-F—Ph | 2-NH$_2$-4-Pyr | 1-iPr-4-Pip |
| 1-3012 | 4-F—Ph | 2-NH$_2$-4-Pyr | 1-Bu-4-(3,4-deH-Pip) |
| 1-3013 | 4-F—Ph | 2-NH$_2$-4-Pyr | 1-tBu-4-(3,4-deH-Pip) |
| 1-3014 | 4-F—Ph | 2-NH$_2$-4-Pyr | 1-Pn-4-(3,4-deH-Pip) |
| 1-3015 | 4-F—Ph | 2-NH$_2$-4-Pyr | 1-Hx-4-(3,4-deH-Pip) |
| 1-3016 | 4-F—Ph | 2-NH$_2$-4-Pyr | 1-Hp-4-(3,4-deH-Pip) |
| 1-3017 | 4-F—Ph | 2-NH$_2$-4-Pyr | 1-Oc-4-(3,4-deH-Pip) |
| 1-3018 | 4-F—Ph | 2-NH$_2$-4-Pyr | 1-Nn-4-(3,4-deH-Pip) |
| 1-3019 | 4-F—Ph | 2-NH$_2$-4-Pyr | 1-cPr-4-(3,4-deH-Pip) |
| 1-3020 | 4-F—Ph | 2-NH$_2$-4-Pyr | 1-cPn-4-(3,4-deH-Pip) |
| 1-3021 | 4-F—Ph | 2-NH$_2$-4-Pyr | 1-cHx-4-(3,4-deH-Pip) |
| 1-3022 | 4-F—Ph | 2-NH$_2$-4-Pyr | 1-Bn-4-(3,4-deH-Pip) |
| 1-3023 | 4-F—Ph | 2-NH$_2$-4-Pyr | 1-Phet-4-(3,4-deH-Pip) |
| 1-3024 | 4-F—Ph | 2-NH$_2$-4-Pyr | 1-(3-Ph-Pr)-4-(3,4-deH-Pip) |
| 1-3025 | 4-F—Ph | 2-NH$_2$-4-Pyr | 1-(4-Ph-Bu)-4-(3,4-deH-Pip) |
| 1-3026 | 4-F—Ph | 2-NH$_2$-4-Pyr | 1-Allyl-4-(3,4-deH-Pip) |
| 1-3027 | 4-F—Ph | 2-NH$_2$-4-Pyr | 1-Propargyl-4-(3,4-deH-Pip) |

TABLE 1-continued

| Compound No. | R¹ | R² | R³ |
|---|---|---|---|
| 1-3028 | 4-F—Ph | 2-NH₂-4-Pyr | 2,2,6,6-tetraMe-4-(3,4-deH-Pip) |
| 1-3029 | 4-F—Ph | 2-NH₂-4-Pyr | 1,2,2,6,6-pentaMe-4-(3,4-deH-Pip) |
| 1-3030 | 4-F—Ph | 2-NH₂-4-Pyr | 1,2,2,6,6-pentaMe-4-Pip |
| 1-3031 | 4-F—Ph | 2-NH₂-4-Pyr | 7-(1,2,3,5,6,8a-hexaH-Ind) |
| 1-3032 | 4-F—Ph | 2-NH₂-4-Pyr | 7-(1,2,3,5,8,8a-hexaH-Ind) |
| 1-3033 | 4-F—Ph | 2-NH₂-4-Pyr | 7-octaH-Ind |
| 1-3034 | 4-F—Ph | 2-NH₂-4-Pyr | 8-(1,3,4,6,7,9a-hexaH-2H-Qui) |
| 1-3035 | 4-F—Ph | 2-NH₂-4-Pyr | 8-(1,3,4,6,9,9a-hexaH-2H-Qui) |
| 1-3036 | 4-F—Ph | 2-NH₂-4-Pyr | 8-octaH-Qui |
| 1-3037 | 4-F—Ph | 2-NH₂-4-Pyr | 2,2-diMe-4-(3,4-deH-Pip) |
| 1-3038 | 4-F—Ph | 2-NH₂-4-Pyr | 1,2,2-triMe-4-(3,4-deH-Pip) |
| 1-3039 | 4-F—Ph | 2-NH₂-4-Pyr | 2,2-diMe-4-(4,5-deH-Pip) |
| 1-3040 | 4-F—Ph | 2-NH₂-4-Pyr | 1,2,2-triMe-4-(4,5-deH-Pip) |
| 1-3041 | 4-F—Ph | 2-NH₂-4-Pyr | 2,6-diMe-4-(3,4-deH-Pip) |
| 1-3042 | 4-F—Ph | 2-NH₂-4-Pyr | 1,2,6-triMe-4-(3,4-deH-Pip) |
| 1-3043 | 4-F—Ph | 2-NH₂-4-Pyr | 2-Me-4-(3,4-deH-Pip) |
| 1-3044 | 4-F—Ph | 2-NH₂-4-Pyr | 1,2-diMe-4-(3,4-deH-Pip) |
| 1-3045 | 4-F—Ph | 2-NH₂-4-Pyr | 1-Et-2-Me-4-(3,4-deH-Pip) |
| 1-3046 | 4-F—Ph | 2-NH₂-4-Pyr | 1-Pr-2-Me-4-(3,4-deH-Pip) |
| 1-3047 | 4-F—Ph | 2-NH₂-4-Pyr | 1-Bu-2-Me-4-(3,4-deH-Pip) |
| 1-3048 | 4-F—Ph | 2-NH₂-4-Pyr | 1-Phet-2-Me-4-(3,4-deH-Pip) |
| 1-3049 | 4-F—Ph | 2-NH₂-4-Pyr | 2-Et-4-(3,4-deH-Pip) |
| 1-3050 | 4-F—Ph | 2-NH₂-4-Pyr | 1-Me-2-Et-4-(3,4-deH-Pip) |
| 1-3051 | 4-F—Ph | 2-NH₂-4-Pyr | 1,2-diEt-4-(3,4-deH-Pip) |
| 1-3052 | 4-F—Ph | 2-NH₂-4-Pyr | 1-Pr-2-Et-4-(3,4-deH-Pip) |
| 1-3053 | 4-F—Ph | 2-NH₂-4-Pyr | 1-Bu-2-Et-4-(3,4-deH-Pip) |
| 1-3054 | 4-F—Ph | 2-NH₂-4-Pyr | 1-Phet-2-Et-4-(3,4-deH-Pip) |
| 1-3055 | 4-F—Ph | 2-NH₂-4-Pyr | 2-Pr-4-(3,4-deH-Pip) |
| 1-3056 | 4-F—Ph | 2-NH₂-4-Pyr | 1-Me-2-Pr-4-(3,4-deH-Pip) |
| 1-3057 | 4-F—Ph | 2-NH₂-4-Pyr | 1-Et-2-Pr-4-(3,4-deH-Pip) |
| 1-3058 | 4-F—Ph | 2-NH₂-4-Pyr | 1,2-diPr-4-(3,4-deH-Pip) |
| 1-3059 | 4-F—Ph | 2-NH₂-4-Pyr | 1-Bu-2-Pr-4-(3,4-deH-Pip) |
| 1-3060 | 4-F—Ph | 2-NH₂-4-Pyr | 1-Phet-2-Pr-4-(3,4-deH-Pip) |
| 1-3061 | 4-F—Ph | 2-NH₂-4-Pyr | 2-Bu-4-(3,4-deH-Pip) |
| 1-3062 | 4-F—Ph | 2-NH₂-4-Pyr | 1-Me-2-Bu-4-(3,4-deH-Pip) |
| 1-3063 | 4-F—Ph | 2-NH₂-4-Pyr | 1-Et-2-Bu-4-(3,4-deH-Pip) |
| 1-3064 | 4-F—Ph | 2-NH₂-4-Pyr | 1-Pr-2-Bu-4-(3,4-deH-Pip) |
| 1-3065 | 4-F—Ph | 2-NH₂-4-Pyr | 1,2-diBu-4-(3,4-deH-Pip) |
| 1-3066 | 4-F—Ph | 2-NH₂-4-Pyr | 1-Phet-2-Bu-4-(3,4-deH-Pip) |
| 1-3067 | 4-F—Ph | 2-NH₂-4-Pyr | 2-Allyl-4-(3,4-deH-Pip) |
| 1-3068 | 4-F—Ph | 2-NH₂-4-Pyr | 1-Me-2-Allyl-4-(3,4-deH-Pip) |
| 1-3069 | 4-F—Ph | 2-NH₂-4-Pyr | 1-Et-2-Allyl-4-(3,4-deH-Pip) |
| 1-3070 | 4-F—Ph | 2-NH₂-4-Pyr | 1-Pr-2-Allyl-4-(3,4-deH-Pip) |
| 1-3071 | 4-F—Ph | 2-NH₂-4-Pyr | 1-Bu-2-Allyl-4-(3,4-deH-Pip) |
| 1-3072 | 4-F—Ph | 2-NH₂-4-Pyr | 1-Phet-2-Allyl-4-(3,4-deH-Pip) |
| 1-3073 | 4-F—Ph | 2-NH₂-4-Pyr | 2-Bn-4-(3,4-deH-Pip) |
| 1-3074 | 4-F—Ph | 2-NH₂-4-Pyr | 1-Me-2-Bn-4-(3,4-deH-Pip) |
| 1-3075 | 4-F—Ph | 2-NH₂-4-Pyr | 1-Et-2-Bn-4-(3,4-deH-Pip) |
| 1-3076 | 4-F—Ph | 2-NH₂-4-Pyr | 1-Pr-2-Bn-4-(3,4-deH-Pip) |
| 1-3077 | 4-F—Ph | 2-NH₂-4-Pyr | 1-Bu-2-Bn-4-(3,4-deH-Pip) |
| 1-3078 | 4-F—Ph | 2-NH₂-4-Pyr | 1-Phet-2-Bn-4-(3,4-deH-Pip) |
| 1-3079 | 4-F—Ph | 2-NH₂-4-Pyr | 2-Phet-4-(3,4-deH-Pip) |
| 1-3080 | 4-F—Ph | 2-NH₂-4-Pyr | 1-Me-2-Phet-4-(3,4-deH-Pip) |
| 1-3081 | 4-F—Ph | 2-NH₂-4-Pyr | 1-Et-2-Phet-4-(3,4-deH-Pip) |
| 1-3082 | 4-F—Ph | 2-NH₂-4-Pyr | 1-Pr-2-Phet-4-(3,4-deH-Pip) |
| 1-3083 | 4-F—Ph | 2-NH₂-4-Pyr | 1-Bu-2-Phet-4-(3,4-deH-Pip) |
| 1-3084 | 4-F—Ph | 2-NH₂-4-Pyr | 1,2-diPhet-4-(3,4-deH-Pip) |
| 1-3085 | 4-F—Ph | 2-NH₂-4-Pyr | 2-Me-4-(4,5-deH-Pip) |
| 1-3086 | 4-F—Ph | 2-NH₂-4-Pyr | 1,2-diMe-4-(4,5-deH-Pip) |
| 1-3087 | 4-F—Ph | 2-NH₂-4-Pyr | 1-Et-2-Me-4-(4,5-deH-Pip) |
| 1-3088 | 4-F—Ph | 2-NH₂-4-Pyr | 1-Pr-2-Me-4-(4,5-deH-Pip) |
| 1-3089 | 4-F—Ph | 2-NH₂-4-Pyr | 1-Bu-2-Me-4-(4,5-deH-Pip) |
| 1-3090 | 4-F—Ph | 2-NH₂-4-Pyr | 1-Phet-2-Me-4-(4,5-deH-Pip) |
| 1-3091 | 4-F—Ph | 2-NH₂-4-Pyr | 2-Et-4-(4,5-deH-Pip) |
| 1-3092 | 4-F—Ph | 2-NH₂-4-Pyr | 1-Me-2-Et-4-(4,5-deH-Pip) |
| 1-3093 | 4-F—Ph | 2-NH₂-4-Pyr | 1,2-diEt-4-(4,5-deH-Pip) |
| 1-3094 | 4-F—Ph | 2-NH₂-4-Pyr | 1-Pr-2-Et-4-(4,5-deH-Pip) |
| 1-3095 | 4-F—Ph | 2-NH₂-4-Pyr | 1-Bu-2-Et-4-(4,5-deH-Pip) |
| 1-3096 | 4-F—Ph | 2-NH₂-4-Pyr | 1-Phet-2-Et-4-(4,5-deH-Pip) |
| 1-3097 | 4-F—Ph | 2-NH₂-4-Pyr | 2-Pr-4-(4,5-deH-Pip) |
| 1-3098 | 4-F—Ph | 2-NH₂-4-Pyr | 1-Me-2-Pr-4-(4,5-deH-Pip) |
| 1-3099 | 4-F—Ph | 2-NH₂-4-Pyr | 1-Et-2-Pr-4-(4,5-deH-Pip) |
| 1-3100 | 4-F—Ph | 2-NH₂-4-Pyr | 1,2-diPr-4-(4,5-deH-Pip) |
| 1-3101 | 4-F—Ph | 2-NH₂-4-Pyr | 1-Bu-2-Pr-4-(4,5-deH-Pip) |
| 1-3102 | 4-F—Ph | 2-NH₂-4-Pyr | 1-Phet-2-Pr-4-(4,5-deH-Pip) |
| 1-3103 | 4-F—Ph | 2-NH₂-4-Pyr | 2-Bu-4-(4,5-deH-Pip) |
| 1-3104 | 4-F—Ph | 2-NH₂-4-Pyr | 1-Me-2-Bu-4-(4,5-deH-Pip) |
| 1-3105 | 4-F—Ph | 2-NH₂-4-Pyr | 1-Et-2-Bu-4-(4,5-deH-Pip) |
| 1-3106 | 4-F—Ph | 2-NH₂-4-Pyr | 1-Pr-2-Bu-4-(4,5-deH-Pip) |
| 1-3107 | 4-F—Ph | 2-NH₂-4-Pyr | 1,2-diBu-4-(4,5-deH-Pip) |
| 1-3108 | 4-F—Ph | 2-NH₂-4-Pyr | 1-Phet-2-Bu-4-(4,5-deH-Pip) |
| 1-3109 | 4-F—Ph | 2-NH₂-4-Pyr | 2-Allyl-4-(4,5-deH-Pip) |
| 1-3110 | 4-F—Ph | 2-NH₂-4-Pyr | 1-Me-2-Allyl-4-(4,5-deH-Pip) |
| 1-3111 | 4-F—Ph | 2-NH₂-4-Pyr | 1-Et-2-Allyl-4-(4,5-deH-Pip) |
| 1-3112 | 4-F—Ph | 2-NH₂-4-Pyr | 1-Pr-2-Allyl-4-(4,5-deH-Pip) |
| 1-3113 | 4-F—Ph | 2-NH₂-4-Pyr | 1-Bu-2-Allyl-4-(4,5-deH-Pip) |

TABLE 1-continued

| Compound No. | R¹ | R² | R³ |
|---|---|---|---|
| 1-3114 | 4-F—Ph | 2-NH₂-4-Pyr | 1-Phet-2-Allyl-4-(4,5-deH-Pip) |
| 1-3115 | 4-F—Ph | 2-NH₂-4-Pyr | 2-Bn-4-(4,5-deH-Pip) |
| 1-3116 | 4-F—Ph | 2-NH₂-4-Pyr | 1-Me-2-Bn-4-(4,5-deH-Pip) |
| 1-3117 | 4-F—Ph | 2-NH₂-4-Pyr | 1-Et-2-Bn-4-(4,5-deH-Pip) |
| 1-3118 | 4-F—Ph | 2-NH₂-4-Pyr | 1-Pr-2-Bn-4-(4,5-deH-Pip) |
| 1-3119 | 4-F—Ph | 2-NH₂-4-Pyr | 1-Bu-2-Bn-4-(4,5-deH-Pip) |
| 1-3120 | 4-F—Ph | 2-NH₂-4-Pyr | 1-Phet-2-Bn-4-(4,5-deH-Pip) |
| 1-3121 | 4-F—Ph | 2-NH₂-4-Pyr | 2-Phet-4-(4,5-deH-Pip) |
| 1-3122 | 4-F—Ph | 2-NH₂-4-Pyr | 1-Me-2-Phet-4-(4,5-deH-Pip) |
| 1-3123 | 4-F—Ph | 2-NH₂-4-Pyr | 1-Et-2-Phet-4-(4,5-deH-Pip) |
| 1-3124 | 4-F—Ph | 2-NH₂-4-Pyr | 1-Pr-2-Phet-4-(4,5-deH-Pip) |
| 1-3125 | 4-F—Ph | 2-NH₂-4-Pyr | 1-Bu-2-Phet-4-(4,5-deH-Pip) |
| 1-3126 | 4-F—Ph | 2-NH₂-4-Pyr | 1,2-diPhet-4-(4,5-deH-Pip) |
| 1-3127 | 4-F—Ph | 2-MeNH-4-Pyr | H₂N—CH₂C(Me)₂CH₂ |
| 1-3128 | 4-F—Ph | 2-MeNH-4-Pyr | MeNH—CH₂C(Me)₂CH₂ |
| 1-3129 | 4-F—Ph | 2-MeNH-4-Pyr | EtNH—CH₂C(Me)₂CH₂ |
| 1-3130 | 4-F—Ph | 2-MeNH-4-Pyr | Me₂N—CH₂C(Me)₂CH₂ |
| 1-3131 | 4-F—Ph | 2-MeNH-4-Pyr | 3-(3,4-deH-Pip) |
| 1-3132 | 4-F—Ph | 2-MeNH-4-Pyr | 1-Me-3-(3,4-deH-Pip) |
| 1-3133 | 4-F—Ph | 2-MeNH-4-Pyr | 1-Et-4-(3,4-deH-Pip) |
| 1-3134 | 4-F—Ph | 2-MeNH-4-Pyr | 1-Pr-4-(3,4-deH-Pip) |
| 1-3135 | 4-F—Ph | 2-MeNH-4-Pyr | 1-Pr-4-Pip |
| 1-3136 | 4-F—Ph | 2-MeNH-4-Pyr | 1-iPr-4-(3,4-deH-Pip) |
| 1-3137 | 4-F—Ph | 2-MeNH-4-Pyr | 1-iPr-4-Pip |
| 1-3138 | 4-F—Ph | 2-MeNH-4-Pyr | 1-Bu-4-(3,4-deH-Pip) |
| 1-3139 | 4-F—Ph | 2-MeNH-4-Pyr | 1-tBu-4-(3,4-deH-Pip) |
| 1-3140 | 4-F—Ph | 2-MeNH-4-Pyr | 1-Pn-4-(3,4-deH-Pip) |
| 1-3141 | 4-F—Ph | 2-MeNH-4-Pyr | 1-Hx-4-(3,4-deH-Pip) |
| 1-3142 | 4-F—Ph | 2-MeNH-4-Pyr | 1-Hp-4-(3,4-deH-Pip) |
| 1-3143 | 4-F—Ph | 2-MeNH-4-Pyr | 1-Oc-4-(3,4-deH-Pip) |
| 1-3144 | 4-F—Ph | 2-MeNH-4-Pyr | 1-Nn-4-(3,4-deH-Pip) |
| 1-3145 | 4-F—Ph | 2-MeNH-4-Pyr | 1-cPr-4-(3,4-deH-Pip) |
| 1-3146 | 4-F—Ph | 2-MeNH-4-Pyr | 1-cPn-4-(3,4-deH-Pip) |
| 1-3147 | 4-F—Ph | 2-MeNH-4-Pyr | 1-cHx-4-(3,4-deH-Pip) |
| 1-3148 | 4-F—Ph | 2-MeNH-4-Pyr | 1-Bn-4-(3,4-deH-Pip) |
| 1-3149 | 4-F—Ph | 2-MeNH-4-Pyr | 1-Phet-4-(3,4-deH-Pip) |
| 1-3150 | 4-F—Ph | 2-MeNH-4-Pyr | 1-(3-Ph-Pr)-4-(3,4-deH-Pip) |
| 1-3151 | 4-F—Ph | 2-MeNH-4-Pyr | 1-(4-Ph-Bu)-4-(3,4-deH-Pip) |
| 1-3152 | 4-F—Ph | 2-MeNH-4-Pyr | 1-Allyl-4-(3,4-deH-Pip) |
| 1-3153 | 4-F—Ph | 2-MeNH-4-Pyr | 1-Propargyl-4-(3,4-deH-Pip) |
| 1-3154 | 4-F—Ph | 2-MeNH-4-Pyr | 2,2,6,6-tetraMe-4-(3,4-deH-Pip) |
| 1-3155 | 4-F—Ph | 2-MeNH-4-Pyr | 1,2,2,6,6-pentaMe-4-(3,4-deH-Pip) |
| 1-3156 | 4-F—Ph | 2-MeNH-4-Pyr | 1,2,2,6,6-pentaMe-4-Pip |
| 1-3157 | 4-F—Ph | 2-MeNH-4-Pyr | 7-(1,2,3,5,6,8a-hexaH-Ind) |
| 1-3158 | 4-F—Ph | 2-MeNH-4-Pyr | 7-(1,2,3,5,8,8a-hexaH-Ind) |
| 1-3159 | 4-F—Ph | 2-MeNH-4-Pyr | 7-octaH-Ind |
| 1-3160 | 4-F—Ph | 2-MeNH-4-Pyr | 8-(1,3,4,6,7,9a-hexaH-2H-Qui) |
| 1-3161 | 4-F—Ph | 2-MeNH-4-Pyr | 8-(1,3,4,6,9,9a-hexaH-2H-Qui) |
| 1-3162 | 4-F—Ph | 2-MeNH-4-Pyr | 8-octaH-Qui |
| 1-3163 | 4-F—Ph | 2-MeNH-4-Pyr | 2,2-diMe-4-(3,4-deH-Pip) |
| 1-3164 | 4-F—Ph | 2-MeNH-4-Pyr | 1,2,2-triMe-4-(3,4-deH-Pip) |
| 1-3165 | 4-F—Ph | 2-MeNH-4-Pyr | 2,2-diMe-4-(4,5-deH-Pip) |
| 1-3166 | 4-F—Ph | 2-MeNH-4-Pyr | 1,2,2-triMe-4-(4,5-deH-Pip) |
| 1-3167 | 4-F—Ph | 2-MeNH-4-Pyr | 2,6-diMe-4-(3,4-deH-Pip) |
| 1-3168 | 4-F—Ph | 2-MeNH-4-Pyr | 1,2,6-triMe-4-(3,4-deH-Pip) |
| 1-3169 | 4-F—Ph | 2-MeNH-4-Pyr | 2-Me-4-(3,4-deH-Pip) |
| 1-3170 | 4-F—Ph | 2-MeNH-4-Pyr | 1,2-diMe-4-(3,4-deH-Pip) |
| 1-3171 | 4-F—Ph | 2-MeNH-4-Pyr | 1-Et-2-Me-4-(3,4-deH-Pip) |
| 1-3172 | 4-F—Ph | 2-MeNH-4-Pyr | 1-Pr-2-Me-4-(3,4-deH-Pip) |
| 1-3173 | 4-F—Ph | 2-MeNH-4-Pyr | 1-Bu-2-Me-4-(3,4-deH-Pip) |
| 1-3174 | 4-F—Ph | 2-MeNH-4-Pyr | 1-Phet-2-Me-4-(3,4-deH-Pip) |
| 1-3175 | 4-F—Ph | 2-MeNH-4-Pyr | 2-Et-4-(3,4-deH-Pip) |
| 1-3176 | 4-F—Ph | 2-MeNH-4-Pyr | 1-Me-2-Et-4-(3,4-deH-Pip) |
| 1-3177 | 4-F—Ph | 2-MeNH-4-Pyr | 1,2-diEt-4-(3,4-deH-Pip) |
| 1-3178 | 4-F—Ph | 2-MeNH-4-Pyr | 1-Pr-2-Et-4-(3,4-deH-Pip) |
| 1-3179 | 4-F—Ph | 2-MeNH-4-Pyr | 1-Bu-2-Et-4-(3,4-deH-Pip) |
| 1-3180 | 4-F—Ph | 2-MeNH-4-Pyr | 1-Phet-2-Et-4-(3,4-deH-Pip) |
| 1-3181 | 4-F—Ph | 2-MeNH-4-Pyr | 2-Pr-4-(3,4-deH-Pip) |
| 1-3182 | 4-F—Ph | 2-MeNH-4-Pyr | 1-Me-2-Pr-4-(3,4-deH-Pip) |
| 1-3183 | 4-F—Ph | 2-MeNH-4-Pyr | 1-Et-2-Pr-4-(3,4-deH-Pip) |
| 1-3184 | 4-F—Ph | 2-MeNH-4-Pyr | 1,2-diPr-4-(3,4-deH-Pip) |
| 1-3185 | 4-F—Ph | 2-MeNH-4-Pyr | 1-Bu-2-Pr-4-(3,4-deH-Pip) |
| 1-3186 | 4-F—Ph | 2-MeNH-4-Pyr | 1-Phet-2-Pr-4-(3,4-deH-Pip) |
| 1-3187 | 4-F—Ph | 2-MeNH-4-Pyr | 2-Bu-4-(3,4-deH-Pip) |
| 1-3188 | 4-F—Ph | 2-MeNH-4-Pyr | 1-Me-2-Bu-4-(3,4-deH-Pip) |
| 1-3189 | 4-F—Ph | 2-MeNH-4-Pyr | 1-Et-2-Bu-4-(3,4-deH-Pip) |
| 1-3190 | 4-F—Ph | 2-MeNH-4-Pyr | 1-Pr-2-Bu-4-(3,4-deH-Pip) |
| 1-3191 | 4-F—Ph | 2-MeNH-4-Pyr | 1,2-diBu-4-(3,4-deH-Pip) |
| 1-3192 | 4-F—Ph | 2-MeNH-4-Pyr | 1-Phet-2-Bu-4-(3,4-deH-Pip) |
| 1-3193 | 4-F—Ph | 2-MeNH-4-Pyr | 2-Allyl-4-(3,4-deH-Pip) |
| 1-3194 | 4-F—Ph | 2-MeNH-4-Pyr | 1-Me-2-Allyl-4-(3,4-deH-Pip) |
| 1-3195 | 4-F—Ph | 2-MeNH-4-Pyr | 1-Et-2-Allyl-4-(3,4-deH-Pip) |
| 1-3196 | 4-F—Ph | 2-MeNH-4-Pyr | 1-Pr-2-Allyl-4-(3,4-deH-Pip) |
| 1-3197 | 4-F—Ph | 2-MeNH-4-Pyr | 1-Bu-2-Allyl-4-(3,4-deH-Pip) |
| 1-3198 | 4-F—Ph | 2-MeNH-4-Pyr | 1-Phet-2-Allyl-4-(3,4-deH-Pip) |
| 1-3199 | 4-F—Ph | 2-MeNH-4-Pyr | 2-Bn-4-(3,4-deH-Pip) |
| 1-3200 | 4-F—Ph | 2-MeNH-4-Pyr | 1-Me-2-Bn-4-(3,4-deH-Pip) |
| 1-3201 | 4-F—Ph | 2-MeNH-4-Pyr | 1-Et-2-Bn-4-(3,4-deH-Pip) |
| 1-3202 | 4-F—Ph | 2-MeNH-4-Pyr | 1-Pr-2-Bn-4-(3,4-deH-Pip) |
| 1-3203 | 4-F—Ph | 2-MeNH-4-Pyr | 1-Bu-2-Bn-4-(3,4-deH-Pip) |
| 1-3204 | 4-F—Ph | 2-MeNH-4-Pyr | 1-Phet-2-Bn-4-(3,4-deH-Pip) |
| 1-3205 | 4-F—Ph | 2-MeNH-4-Pyr | 2-Phet-4-(3,4-deH-Pip) |
| 1-3206 | 4-F—Ph | 2-MeNH-4-Pyr | 1-Me-2-Phet-4-(3,4-deH-Pip) |
| 1-3207 | 4-F—Ph | 2-MeNH-4-Pyr | 1-Et-2-Phet-4-(3,4-deH-Pip) |
| 1-3208 | 4-F—Ph | 2-MeNH-4-Pyr | 1-Pr-2-Phet-4-(3,4-deH-Pip) |

TABLE 1-continued

| Compound No. | R¹ | R² | R³ |
|---|---|---|---|
| 1-3209 | 4-F—Ph | 2-MeNH-4-Pyr | 1-Bu-2-Phet-4-(3,4-deH-Pip) |
| 1-3210 | 4-F—Ph | 2-MeNH-4-Pyr | 1,2-diPhet-4-(3,4-deH-Pip) |
| 1-3211 | 4-F—Ph | 2-MeNH-4-Pyr | 2-Me-4-(4,5-deH-Pip) |
| 1-3212 | 4-F—Ph | 2-MeNH-4-Pyr | 1,2-diMe-4-(4,5-deH-Pip) |
| 1-3213 | 4-F—Ph | 2-MeNH-4-Pyr | 1-Et-2-Me-4-(4,5-deH-Pip) |
| 1-3214 | 4-F—Ph | 2-MeNH-4-Pyr | 1-Pr-2-Me-4-(4,5-deH-Pip) |
| 1-3215 | 4-F—Ph | 2-MeNH-4-Pyr | 1-Bu-2-Me-4-(4,5-deH-Pip) |
| 1-3216 | 4-F—Ph | 2-MeNH-4-Pyr | 1-Phet-2-Me-4-(4,5-deH-Pip) |
| 1-3217 | 4-F—Ph | 2-MeNH-4-Pyr | 2-Et-4-(4,5-deH-Pip) |
| 1-3218 | 4-F—Ph | 2-MeNH-4-Pyr | 1-Me-2-Et-4-(4,5-deH-Pip) |
| 1-3219 | 4-F—Ph | 2-MeNH-4-Pyr | 1,2-diEt-4-(4,5-deH-Pip) |
| 1-3220 | 4-F—Ph | 2-MeNH-4-Pyr | 1-Pr-2-Et-4-(4,5-deH-Pip) |
| 1-3221 | 4-F—Ph | 2-MeNH-4-Pyr | 1-Bu-2-Et-4-(4,5-deH-Pip) |
| 1-3222 | 4-F—Ph | 2-MeNH-4-Pyr | 1-Phet-2-Et-4-(4,5-deH-Pip) |
| 1-3223 | 4-F—Ph | 2-MeNH-4-Pyr | 2-Pr-4-(4,5-deH-Pip) |
| 1-3224 | 4-F—Ph | 2-MeNH-4-Pyr | 1-Me-2-Pr-4-(4,5-deH-Pip) |
| 1-3225 | 4-F—Ph | 2-MeNH-4-Pyr | 1-Et-2-Pr-4-(4,5-deH-Pip) |
| 1-3226 | 4-F—Ph | 2-MeNH-4-Pyr | 1,2-diPr-4-(4,5-deH-Pip) |
| 1-3227 | 4-F—Ph | 2-MeNH-4-Pyr | 1-Bu-2-Pr-4-(4,5-deH-Pip) |
| 1-3228 | 4-F—Ph | 2-MeNH-4-Pyr | 1-Phet-2-Pr-4-(4,5-deH-Pip) |
| 1-3229 | 4-F—Ph | 2-MeNH-4-Pyr | 2-Bu-4-(4,5-deH-Pip) |
| 1-3230 | 4-F—Ph | 2-MeNH-4-Pyr | 1-Me-2-Bu-4-(4,5-deH-Pip) |
| 1-3231 | 4-F—Ph | 2-MeNH-4-Pyr | 1-Et-2-Bu-4-(4,5-deH-Pip) |
| 1-3232 | 4-F—Ph | 2-MeNH-4-Pyr | 1-Pr-2-Bu-4-(4,5-deH-Pip) |
| 1-3233 | 4-F—Ph | 2-MeNH-4-Pyr | 1,2-diBu-4-(4,5-deH-Pip) |
| 1-3234 | 4-F—Ph | 2-MeNH-4-Pyr | 1-Phet-2-Bu-4-(4,5-deH-Pip) |
| 1-3235 | 4-F—Ph | 2-MeNH-4-Pyr | 2-Allyl-4-(4,5-deH-Pip) |
| 1-3236 | 4-F—Ph | 2-MeNH-4-Pyr | 1-Me-Allyl-4-(4,5-deH-Pip) |
| 1-3237 | 4-F—Ph | 2-MeNH-4-Pyr | 1-Et-2-Allyl-4-(4,5-deH-Pip) |
| 1-3238 | 4-F—Ph | 2-MeNH-4-Pyr | 1-Pr-2-Allyl-4-(4,5-deH-Pip) |
| 1-3239 | 4-F—Ph | 2-MeNH-4-Pyr | 1-Bu-2-Allyl-4-(4,5-deH-Pip) |
| 1-3240 | 4-F—Ph | 2-MeNH-4-Pyr | 1-Phet-2-Allyl-4-(4,5-deH-Pip) |
| 1-3241 | 4-F—Ph | 2-MeNH-4-Pyr | 2-Bn-4-(4,5-deH-Pip) |
| 1-3242 | 4-F—Ph | 2-MeNH-4-Pyr | 1-Me-2-Bn-4-(4,5-deH-Pip) |
| 1-3243 | 4-F—Ph | 2-MeNH-4-Pyr | 1-Et-2-Bn-4-(4,5-deH-Pip) |
| 1-3244 | 4-F—Ph | 2-MeNH-4-Pyr | 1-Pr-2-Bn-4-(4,5-deH-Pip) |
| 1-3245 | 4-F—Ph | 2-MeNH-4-Pyr | 1-Bu-2-Bn-4-(4,5-deH-Pip) |
| 1-3246 | 4-F—Ph | 2-MeNH-4-Pyr | 1-Phet-2-Bn-4-(4,5-deH-Pip) |
| 1-3247 | 4-F—Ph | 2-MeNH-4-Pyr | 2-Phet-4-(4,5-deH-Pip) |
| 1-3248 | 4-F—Ph | 2-MeNH-4-Pyr | 1-Me-2-Phet-4-(4,5-deH-Pip) |
| 1-3249 | 4-F—Ph | 2-MeNH-4-Pyr | 1-Et-2-Phet-4-(4,5-deH-Pip) |
| 1-3250 | 4-F—Ph | 2-MeNH-4-Pyr | 1-Pr-2-Phet-4-(4,5-deH-Pip) |
| 1-3251 | 4-F—Ph | 2-MeNH-4-Pyr | 1-Bu-2-Phet-4-(4,5-deH-Pip) |
| 1-3252 | 4-F—Ph | 2-MeNH-4-Pyr | 1,2-diPhet-4-(4,5-deH-Pip) |
| 1-3253 | Ph | 4-Pyr | 7-(1,2,3,5,6,8a-hexaH-Ind) |
| 1-3254 | Ph | 4-Pyr | 7-(1,2,3,5,8,8a-hexaH-Ind) |
| 1-3255 | 3-F—Ph | 4-Pyr | 7-(1,2,3,5,6,8a-hexaH-Ind) |
| 1-3256 | 3-F—Ph | 4-Pyr | 7-(1,2,3,5,8,8a-hexaH-Ind) |
| 1-3257 | 3-Cl—Ph | 4-Pyr | 7-(1,2,3,5,6,8a-hexaH-Ind) |
| 1-3258 | 3-Cl—Ph | 4-Pyr | 7-(1,2,3,5,8,8a-hexaH-Ind) |
| 1-3259 | 3,4-diF-Ph | 4-Pyr | 7-(1,2,3,5,6,8a-hexaH-Ind) |
| 1-3260 | 3,4-diF-Ph | 4-Pyr | 7-(1,2,3,5,8,8a-hexaH-Ind) |
| 1-3261 | 3-CF₃—Ph | 4-Pyr | 7-(1,2,3,5,6,8a-hexaH-Ind) |
| 1-3262 | 3-CF₃—Ph | 4-Pyr | 7-(1,2,3,5,8,8a-hexaH-Ind) |
| 1-3263 | 4-F—Ph | 4-Pyr | 2-Pyrd-CH=CH— |
| 1-3264 | 4-F—Ph | 4-Pyr | 1-Me-2-Pyrd-CH=CH— |
| 1-3265 | 4-F—Ph | 4-Pyr | 1-Et-2-Pyrd-CH=CH— |
| 1-3266 | 4-F—Ph | 4-Pyr | 1-Pr-2-Pyrd-CH=CH— |
| 1-3267 | 4-F—Ph | 4-Pyr | 2-Pip-CH=CH— |
| 1-3268 | 4-F—Ph | 4-Pyr | 1-Me-2-Pip-CH=CH— |
| 1-3269 | 4-F—Ph | 4-Pyr | 1-Et-2-Pip-CH=CH— |
| 1-3270 | 4-F—Ph | 4-Pyr | 1-Pr-2-Pip-CH=CH— |
| 1-3271 | Ph | 4-Pyr | 2-Pyrd-CH=CH— |
| 1-3272 | Ph | 4-Pyr | 1-Me-2-Pyrd-CH=CH— |
| 1-3273 | Ph | 4-Pyr | 1-Et-2-Pyrd-CH=CH— |
| 1-3274 | Ph | 4-Pyr | 1-Pr-2-Pyrd-CH=CH— |
| 1-3275 | Ph | 4-Pyr | 2-Pip-CH=CH— |
| 1-3276 | Ph | 4-Pyr | 1-Me-2-Pip-CH=CH— |
| 1-3277 | Ph | 4-Pyr | 1-Et-2-Pip-CH=CH— |
| 1-3278 | Ph | 4-Pyr | 1-Pr-2-Pip-CH=CH— |
| 1-3279 | 3-F—Ph | 4-Pyr | 2-Pyrd-CH=CH— |
| 1-3280 | 3-F—Ph | 4-Pyr | 1-Me-2-Pyrd-CH=CH— |
| 1-3281 | 3-F—Ph | 4-Pyr | 1-Et-2-Pyrd-CH=CH— |
| 1-3282 | 3-F—Ph | 4-Pyr | 1-Pr-2-Pyrd-CH=CH— |
| 1-3283 | 3-F—Ph | 4-Pyr | 2-Pip-CH=CH— |
| 1-3284 | 3-F—Ph | 4-Pyr | 1-Me-2-Pip-CH=CH— |
| 1-3285 | 3-F—Ph | 4-Pyr | 1-Et-2-Pip-CH=CH— |
| 1-3286 | 3-F—Ph | 4-Pyr | 1-Pr-2-Pip-CH=CH— |
| 1-3287 | 3-Cl—Ph | 4-Pyr | 2-Pyrd-CH=CH— |
| 1-3288 | 3-Cl—Ph | 4-Pyr | 1-Me-2-Pyrd-CH=CH— |
| 1-3289 | 3-Cl—Ph | 4-Pyr | 1-Et-2-Pyrd-CH=CH— |
| 1-3290 | 3-Cl—Ph | 4-Pyr | 1-Pr-2-Pyrd-CH=CH— |
| 1-3291 | 3-Cl—Ph | 4-Pyr | 2-Pip-CH=CH— |
| 1-3292 | 3-Cl—Ph | 4-Pyr | 1-Me-2-Pip-CH=CH— |
| 1-3293 | 3-Cl—Ph | 4-Pyr | 1-Et-2-Pip-CH=CH— |
| 1-3294 | 3-Cl—Ph | 4-Pyr | 1-Pr-2-Pip-CH=CH— |
| 1-3295 | 3,4-diF-Ph | 4-Pyr | 2-Pyrd-CH=CH— |
| 1-3296 | 3,4-diF-Ph | 4-Pyr | 1-Me-2-Pyrd-CH=CH— |
| 1-3297 | 3,4-diF-Ph | 4-Pyr | 1-Et-2-Pyrd-CH=CH— |
| 1-3298 | 3,4-diF-Ph | 4-Pyr | 1-Pr-2-Pyrd-CH=CH— |
| 1-3299 | 3,4-diF-Ph | 4-Pyr | 2-Pip-CH=CH— |
| 1-3300 | 3,4-diF-Ph | 4-Pyr | 1-Me-2-Pip-CH=CH— |
| 1-3301 | 3,4-diF-Ph | 4-Pyr | 1-Et-2-Pip-CH=CH— |
| 1-3302 | 3,4-diF-Ph | 4-Pyr | 1-Pr-2-Pip-CH=CH— |
| 1-3303 | 3-CF₃—Ph | 4-Pyr | 2-Pyrd-CH=CH— |
| 1-3304 | 3-CF₃—Ph | 4-Pyr | 1-Me-2-Pyrd-CH=CH— |
| 1-3305 | 3-CF₃—Ph | 4-Pyr | 1-Et-2-Pyrd-CH=CH— |
| 1-3306 | 3-CF₃—Ph | 4-Pyr | 1-Pr-2-Pyrd-CH=CH— |
| 1-3307 | 3-CF₃—Ph | 4-Pyr | 2-Pip-CH=CH— |
| 1-3308 | 3-CF₃—Ph | 4-Pyr | 1-Me-2-Pip-CH=CH— |
| 1-3309 | 3-CF₃—Ph | 4-Pyr | 1-Et-2-Pip-CH=CH— |
| 1-3310 | 3-CF₃—Ph | 4-Pyr | 1-Pr-2-Pip-CH=CH— |
| 1-3311 | 4-F—Ph | 4-Pyr | 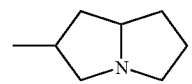 |

TABLE 1-continued

| Compound No. | R¹ | R² | R³ |
|---|---|---|---|
| 1-3312 | 4-F—Ph | 4-Pyr | (structure) |
| 1-3313 | 4-F—Ph | 4-Pyr | (structure) |
| 1-3314 | 4-F—Ph | 4-Pyr | (structure) |
| 1-3315 | 4-F—Ph | 4-Pyr | (structure) |
| 1-3316 | 4-F—Ph | 4-Pyr | (structure) |
| 1-3317 | 4-F—Ph | 4-Pyr | (structure) |
| 1-3318 | 4-F—Ph | 4-Pyr | (structure) |
| 1-3319 | 4-F—Ph | 4-Pyr | (structure) |
| 1-3320 | 4-F—Ph | 4-Pyr | (structure) |
| 1-3321 | 4-F—Ph | 4-Pyr | (structure) |
| 1-3322 | 4-F—Ph | 4-Pyr | (structure) |

TABLE 2

| Compound No. | R¹ | R² | R³ |
|---|---|---|---|
| 2-1 | Ph | 4-Pyr | H$_2$N—CH$_2$ |
| 2-2 | Ph | 4-Pyr | H$_2$N—(CH$_2$)$_2$ |
| 2-3 | Ph | 4-Pyr | H$_2$N—(CH$_2$)$_3$ |
| 2-4 | Ph | 4-Pyr | H$_2$N—(CH$_2$)$_4$ |
| 2-5 | Ph | 4-Pyr | MeNH—CH$_2$ |
| 2-6 | Ph | 4-Pyr | MeNH—(CH$_2$)$_2$ |
| 2-7 | Ph | 4-Pyr | MeNH—(CH$_2$)$_3$ |
| 2-8 | Ph | 4-Pyr | MeNH—(CH$_2$)$_4$ |
| 2-9 | Ph | 4-Pyr | EtNH—CH$_2$ |
| 2-10 | Ph | 4-Pyr | EtNH—(CH$_2$)$_2$ |
| 2-11 | Ph | 4-Pyr | EtNH—(CH$_2$)$_3$ |
| 2-12 | Ph | 4-Pyr | EtNH—(CH$_2$)$_4$ |
| 2-13 | Ph | 4-Pyr | Me$_2$N—CH$_2$ |
| 2-14 | Ph | 4-Pyr | Me$_2$N—(CH$_2$)$_2$ |
| 2-15 | Ph | 4-Pyr | Me$_2$N—(CH$_2$)$_3$ |
| 2-16 | Ph | 4-Pyr | Me$_2$N—(CH$_2$)$_4$ |
| 2-17 | Ph | 4-Pyr | 1-Azt-CH$_2$ |
| 2-18 | Ph | 4-Pyr | 1-Azt-(CH$_2$)$_2$ |
| 2-19 | Ph | 4-Pyr | 1-Azt-(CH$_2$)$_3$ |
| 2-20 | Ph | 4-Pyr | 1-Azt-(CH$_2$)$_4$ |
| 2-21 | Ph | 4-Pyr | 1-Pyrd-CH$_2$ |
| 2-22 | Ph | 4-Pyr | 1-Pyrd-(CH$_2$)$_2$ |
| 2-23 | Ph | 4-Pyr | 1-Pyrd-(CH$_2$)$_3$ |
| 2-24 | Ph | 4-Pyr | 1-Pyrd-(CH$_2$)$_4$ |
| 2-25 | Ph | 4-Pyr | 1-Pip-CH$_2$ |
| 2-26 | Ph | 4-Pyr | 1-Pip-(CH$_2$)$_2$ |
| 2-27 | Ph | 4-Pyr | 1-Pip-(CH$_2$)$_3$ |
| 2-28 | Ph | 4-Pyr | 1-Pip-(CH$_2$)$_4$ |
| 2-29 | Ph | 4-Pyr | 1-Mor-CH$_2$ |
| 2-30 | Ph | 4-Pyr | 1-Mor-(CH$_2$)$_2$ |
| 2-31 | Ph | 4-Pyr | 1-Mor-(CH$_2$)$_3$ |
| 2-32 | Ph | 4-Pyr | 1-Mor-(CH$_2$)$_4$ |
| 2-33 | Ph | 4-Pyr | 1-Tmor-CH$_2$ |
| 2-34 | Ph | 4-Pyr | 1-Tmor-(CH$_2$)$_2$ |
| 2-35 | Ph | 4-Pyr | 1-Tmor-(CH$_2$)$_3$ |
| 2-36 | Ph | 4-Pyr | 1-Tmor-(CH$_2$)$_4$ |
| 2-37 | Ph | 4-Pyr | 1-Piz-CH$_2$ |
| 2-38 | Ph | 4-Pyr | 1-Piz-(CH$_2$)$_2$ |
| 2-39 | Ph | 4-Pyr | 1-Piz-(CH$_2$)$_3$ |
| 2-40 | Ph | 4-Pyr | 4-Me-1-Piz-(CH$_2$)$_3$ |
| 2-41 | Ph | 4-Pyr | 1-Piz-(CH$_2$)$_4$ |
| 2-42 | Ph | 4-Pyr | 3-Azt |
| 2-43 | Ph | 4-Pyr | 1-Me-3-Azt |
| 2-44 | Ph | 4-Pyr | 1-Bn-3-Azt |
| 2-45 | Ph | 4-Pyr | 3-Pyrd |
| 2-46 | Ph | 4-Pyr | 1-Me-3-Pyrd |
| 2-47 | Ph | 4-Pyr | 3-Pip |
| 2-48 | Ph | 4-Pyr | 4-Pip |
| 2-49 | Ph | 4-Pyr | 4-(3,4-deH-Pip) |
| 2-50 | Ph | 4-Pyr | 1-Me-4-Pip |
| 2-51 | Ph | 4-Pyr | 1-Me-4-(3,4-deH-Pip) |
| 2-52 | Ph | 4-Pyr | 1-Et-4-Pip |
| 2-53 | Ph | 4-Pyr | 1-Bn-4-Pip |
| 2-54 | Ph | 4-Pyr | 3-Hpip |
| 2-55 | Ph | 4-Pyr | 1-Me-3-Hpip |
| 2-56 | Ph | 4-Pyr | 4-Hpip |
| 2-57 | Ph | 4-Pyr | 1-Me-4-Hpip |
| 2-58 | Ph | 4-Pyr | 2-Mor |
| 2-59 | Ph | 4-Pyr | 1-Me-2-Mor |
| 2-60 | Ph | 4-Pyr | 2-Tmor |
| 2-61 | Ph | 4-Pyr | 1-Me-2-Tmor |
| 2-62 | Ph | 4-Pyr | 1-Piz |
| 2-63 | Ph | 4-Pyr | 4-Me-1-Piz |
| 2-64 | Ph | 4-Pyr | 2-Piz |
| 2-65 | Ph | 4-Pyr | 4-Pyr |
| 2-66 | Ph | 4-Pyr | 3-Pyr |
| 2-67 | Ph | 4-Pyr | 2-Pyr |
| 2-68 | Ph | 4-Pyr | 4-Pym |
| 2-69 | Ph | 4-Pyr | 5-Pym |
| 2-70 | Ph | 4-Pyr | 2-Pym |
| 2-71 | Ph | 4-Pyr | 3-Azt-CH$_2$ |
| 2-72 | Ph | 4-Pyr | 1-Me-3-Azt-CH$_2$ |
| 2-73 | Ph | 4-Pyr | 3-Pyrd-CH$_2$ |
| 2-74 | Ph | 4-Pyr | 1-Me-3-Pyrd-CH$_2$ |
| 2-75 | Ph | 4-Pyr | 4-Pip-CH$_2$ |

TABLE 2-continued

| Compound No. | R¹ | R² | R³ |
|---|---|---|---|
| 2-76 | Ph | 4-Pyr | 1-Me-4-Pip-CH₂ |
| 2-77 | Ph | 4-Pyr | 3-Hpip-CH₂ |
| 2-78 | Ph | 4-Pyr | 1-Me-3-Hpip-CH₂ |
| 2-79 | Ph | 4-Pyr | 4-Hpip-CH₂ |
| 2-80 | Ph | 4-Pyr | 1-Me-4-Hpip-CH₂ |
| 2-81 | Ph | 4-Pyr | 2-Mor-CH₂ |
| 2-82 | Ph | 4-Pyr | 1-Me-2-Mor-CH₂ |
| 2-83 | Ph | 4-Pyr | 2-Tmor-CH₂ |
| 2-84 | Ph | 4-Pyr | 1-Me-2-Tmor-CH₂ |
| 2-85 | Ph | 4-Pyr | 1-Piz-CH₂ |
| 2-86 | Ph | 4-Pyr | 4-Me-1-Piz-CH₂ |
| 2-87 | Ph | 4-Pyr | 2-Piz-CH₂ |
| 2-88 | Ph | 4-Pyr | 4-Pyr-CH₂ |
| 2-89 | Ph | 4-Pyr | 3-Pyr-CH₂ |
| 2-90 | Ph | 4-Pyr | 2-Pyr-CH₂ |
| 2-91 | Ph | 4-Pyr | 4-Pym-CH₂ |
| 2-92 | Ph | 4-Pyr | 5-Pym-CH₂ |
| 2-93 | Ph | 4-Pyr | 2-Pym-CH₂ |
| 2-94 | Ph | 4-Pyr | H₂N—CH₂CH=CH |
| 2-95 | 4-F—Ph | 4-Pyr | H₂N—CH₂ |
| 2-96 | 4-F—Ph | 4-Pyr | H₂N—(CH₂)₂ |
| 2-97 | 4-F—Ph | 4-Pyr | H₂N—(CH₂)₃ |
| 2-98 | 4-F—Ph | 4-Pyr | H₂N—(CH2)4 |
| 2-99 | 4-F—Ph | 4-Pyr | MeNH—CH₂ |
| 2-100 | 4-F—Ph | 4-Pyr | MeNH—(CH₂)₂ |
| 2-101 | 4-F—Ph | 4-Pyr | MeNH—(CH₂)₃ |
| 2-102 | 4-F—Ph | 4-Pyr | MeNH—(CH₂)₄ |
| 2-103 | 4-F—Ph | 4-Pyr | EtNH—CH₂ |
| 2-104 | 4-F—Ph | 4-Pyr | EtNH—(CH₂)₂ |
| 2-105 | 4-F—Ph | 4-Pyr | EtNH—(CH₂)₃ |
| 2-106 | 4-F—Ph | 4-Pyr | EtNH—(CH₂)₄ |
| 2-107 | 4-F—Ph | 4-Pyr | Me₂N—CH₂ |
| 2-108 | 4-F—Ph | 4-Pyr | Me₂N—(CH₂)₂ |
| 2-109 | 4-F—Ph | 4-Pyr | Me₂N—(CH₂)₃ |
| 2-110 | 4-F—Ph | 4-Pyr | Me₂N—(CH₂)₄ |
| 2-111 | 4-F—Ph | 4-Pyr | 1-Azt-CH₂ |
| 2-112 | 4-F—Ph | 4-Pyr | 1-Azt-(CH₂)₂ |
| 2-113 | 4-F—Ph | 4-Pyr | 1-Azt-(CH₂)₃ |
| 2-114 | 4-F—Ph | 4-Pyr | 1-Azt-(CH₂)₄ |
| 2-115 | 4-F—Ph | 4-Pyr | 1-Pyrd-CH₂ |
| 2-116 | 4-F—Ph | 4-Pyr | 1-Pyrd-(CH₂)₂ |
| 2-117 | 4-F—Ph | 4-Pyr | 1-Pyrd-(CH2)3 |
| 2-118 | 4-F—Ph | 4-Pyr | 1-Pyrd-(CH₂)₄ |
| 2-119 | 4-F—Ph | 4-Pyr | 1-Pip-CH₂ |
| 2-120 | 4-F—Ph | 4-Pyr | 1-Pip-(CH₂)₂ |
| 2-121 | 4-F—Ph | 4-Pyr | 1-Pip-(CH₂)₃ |
| 2-122 | 4-F—Ph | 4-Pyr | 1-Pip-(CH₂)₄ |
| 2-123 | 4-F—Ph | 4-Pyr | 1-Mor-CH₂ |
| 2-124 | 4-F—Ph | 4-Pyr | 1-Mor-(CH₂)₂ |
| 2-125 | 4-F—Ph | 4-Pyr | 1-Mor-(CH₂)₃ |
| 2-126 | 4-F—Ph | 4-Pyr | 1-Mor-(CH₂)₄ |
| 2-127 | 4-F—Ph | 4-Pyr | 1-Tmor-CH₂ |
| 2-128 | 4-F—Ph | 4-Pyr | 1-Tmor-(CH₂)₂ |
| 2-129 | 4-F—Ph | 4-Pyr | 1-Tmor-(CH₂)₃ |
| 2-130 | 4-F—Ph | 4-Pyr | 1-Tmor-(CH₂)₄ |
| 2-131 | 4-F—Ph | 4-Pyr | 1-Piz-CH₂ |
| 2-132 | 4-F—Ph | 4-Pyr | 1-Piz-(CH₂)₂ |
| 2-133 | 4-F—Ph | 4-Pyr | 1-Piz-(CH₂)₃ |
| 2-134 | 4-F—Ph | 4-Pyr | 4-Me-1-Piz-(CH₂)₃ |
| 2-135 | 4-F—Ph | 4-Pyr | 4-Bn-1-Piz-(CH₂)₃ |
| 2-136 | 4-F—Ph | 4-Pyr | 3-Azt |
| 2-137 | 4-F—Ph | 4-Pyr | 1-Me-3-Azt |
| 2-138 | 4-F—Ph | 4-Pyr | 1-Bn-3-Azt |
| 2-139 | 4-F—Ph | 4-Pyr | 3-Pyrd |
| 2-140 | 4-F—Ph | 4-Pyr | 1-Me-3-Pyrd |
| 2-141 | 4-F—Ph | 4-Pyr | 3-Pip |
| 2-142 | 4-F—Ph | 4-Pyr | 4-Pip |
| 2-143 | 4-F—Ph | 4-Pyr | 4-(3,4-deH-Pip) |
| 2-144 | 4-F—Ph | 4-Pyr | 1-Me-4-Pip |
| 2-145 | 4-F—Ph | 4-Pyr | 1-Me-4-(3,4-deH-Pip) |
| 2-146 | 4-F—Ph | 4-Pyr | 1-Et-4-Pip |
| 2-147 | 4-F—Ph | 4-Pyr | 1-Bn-4-Pip |
| 2-148 | 4-F—Ph | 4-Pyr | 3-Hpip |
| 2-149 | 4-F—Ph | 4-Pyr | 1-Me-3-Hpip |
| 2-150 | 4-F—Ph | 4-Pyr | 4-Hpip |
| 2-151 | 4-F—Ph | 4-Pyr | 1-Me-4-Hpip |
| 2-152 | 4-F—Ph | 4-Pyr | 2-Mor |
| 2-153 | 4-F—Ph | 4-Pyr | 1-Me-2-Mor |
| 2-154 | 4-F—Ph | 4-Pyr | 2-Tmor |
| 2-155 | 4-F—Ph | 4-Pyr | 1-Me-2-Tmor |
| 2-156 | 4-F—Ph | 4-Pyr | 1-Piz |
| 2-157 | 4-F—Ph | 4-Pyr | 4-Me-1-Piz |
| 2-158 | 4-F—Ph | 4-Pyr | 2-Piz |
| 2-159 | 4-F—Ph | 4-Pyr | 4-Pyr |
| 2-160 | 4-F—Ph | 4-Pyr | 3-Pyr |
| 2-161 | 4-F—Ph | 4-Pyr | 2-Pyr |
| 2-162 | 4-F—Ph | 4-Pyr | 4-Pym |
| 2-163 | 4-F—Ph | 4-Pyr | 5-Pym |
| 2-164 | 4-F—Ph | 4-Pyr | 2-Pym |
| 2-165 | 4-F—Ph | 4-Pyr | 3-Azt-CH₂ |
| 2-166 | 4-F—Ph | 4-Pyr | 1-Me-3-Azt-CH2 |
| 2-167 | 4-F—Ph | 4-Pyr | 3-Pyrd-CH₂ |
| 2-168 | 4-F—Ph | 4-Pyr | 1-Me-3-Pyrd-CH₂ |
| 2-169 | 4-F—Ph | 4-Pyr | 4-Pip-CH₂ |
| 2-170 | 4-F—Ph | 4-Pyr | 1-Me-4-Pip-CH₂ |
| 2-171 | 4-F—Ph | 4-Pyr | 3-Hpip-CH₂ |
| 2-172 | 4-F—Ph | 4-Pyr | 1-Me-3-Hpip-CH₂ |
| 2-173 | 4-F—Ph | 4-Pyr | 4-Hpip-CH₂ |
| 2-174 | 4-F—Ph | 4-Pyr | 1-Me-4-Hpip-CH₂ |
| 2-175 | 4-F—Ph | 4-Pyr | 2-Mor-CH₂ |
| 2-176 | 4-F—Ph | 4-Pyr | 1-Me-2-Mor-CH₂ |
| 2-177 | 4-F—Ph | 4-Pyr | 2-Tmor-CH₂ |
| 2-178 | 4-F—Ph | 4-Pyr | 1-Me-2-Tmor-CH₂ |
| 2-179 | 4-F—Ph | 4-Pyr | 1-Piz-CH₂ |
| 2-180 | 4-F—Ph | 4-Pyr | 4-Me-1-Piz-CH₂ |
| 2-181 | 4-F—Ph | 4-Pyr | 2-Piz-CH₂ |
| 2-182 | 4-F—Ph | 4-Pyr | 4-Pyr-CH₂ |
| 2-183 | 4-F—Ph | 4-Pyr | 3-Pyr-CH₂ |
| 2-184 | 4-F—Ph | 4-Pyr | 2-Pyr-CH₂ |
| 2-185 | 4-F—Ph | 4-Pyr | 4-Pym-CH₂ |
| 2-186 | 4-F—Ph | 4-Pyr | 5-Pym-CH₂ |
| 2-187 | 4-F—Ph | 4-Pyr | 2-Pym-CH₂ |
| 2-188 | 3-F—Ph | 4-Pyr | H₂N—CH₂ |
| 2-189 | 3-F—Ph | 4-Pyr | H₂N—(CH₂)₂ |
| 2-190 | 3-F—Ph | 4-Pyr | H₂N—(CH₂)₃ |
| 2-191 | 3-F—Ph | 4-Pyr | H₂N—(CH₂)₄ |
| 2-192 | 3-F—Ph | 4-Pyr | MeNH—CH₂ |
| 2-193 | 3-F—Ph | 4-Pyr | MeNH—(CH₂)₂ |
| 2-194 | 3-F—Ph | 4-Pyr | MeNH—(CH₂)₃ |
| 2-195 | 3-F—Ph | 4-Pyr | MeNH—(CH₂)₄ |
| 2-196 | 3-F—Ph | 4-Pyr | EtNH—CH₂ |
| 2-197 | 3-F—Ph | 4-Pyr | EtNH—(CH₂)₂ |
| 2-198 | 3-F—Ph | 4-Pyr | EtNH—(CH₂)₃ |
| 2-199 | 3-F—Ph | 4-Pyr | EtNH—(CH₂)₄ |
| 2-200 | 3-F—Ph | 4-Pyr | Me₂N—CH₂ |
| 2-201 | 3-F—Ph | 4-Pyr | Me₂N—(CH₂)₂ |
| 2-202 | 3-F—Ph | 4-Pyr | Me₂N—(CH₂)₃ |
| 2-203 | 3-F—Ph | 4-Pyr | Me₂N—(CH₂)₄ |
| 2-204 | 3-F—Ph | 4-Pyr | 1-Azt-CH₂ |
| 2-205 | 3-F—Ph | 4-Pyr | 1-Azt-(CH₂)₂ |
| 2-206 | 3-F—Ph | 4-Pyr | 1-Azt-(CH₂)₃ |
| 2-207 | 3-F—Ph | 4-Pyr | 1-Azt-(CH₂)₄ |
| 2-208 | 3-F—Ph | 4-Pyr | 1-Pyrd-CH₂ |
| 2-209 | 3-F—Ph | 4-Pyr | 1-Pyrd-(CH₂)₂ |
| 2-210 | 3-F—Ph | 4-Pyr | 1-Pyrd-(CH₂)₃ |
| 2-211 | 3-F—Ph | 4-Pyr | 1-Pyrd-(CH₂)₄ |
| 2-212 | 3-F—Ph | 4-Pyr | 1-Pip-CH₂ |
| 2-213 | 3-F—Ph | 4-Pyr | 1-Pip-(CH₂)₂ |
| 2-214 | 3-F—Ph | 4-Pyr | 1-Pip-(CH₂)₃ |
| 2-215 | 3-F—Ph | 4-Pyr | 1-Pip-(CH₂)₄ |
| 2-216 | 3-F—Ph | 4-Pyr | 1-Mor-CH₂ |
| 2-217 | 3-F—Ph | 4-Pyr | 1-Mor-(CH₂)₂ |
| 2-218 | 3-F—Ph | 4-Pyr | 1-Mor-(CH₂)₃ |
| 2-219 | 3-F—Ph | 4-Pyr | 1-Mor-(CH₂)₄ |
| 2-220 | 3-F—Ph | 4-Pyr | 1-Tmor-CH₂ |
| 2-221 | 3-F—Ph | 4-Pyr | 1-Tmor-(CH₂)₂ |
| 2-222 | 3-F—Ph | 4-Pyr | 1-Tmor-(CH₂)₃ |
| 2-223 | 3-F—Ph | 4-Pyr | 1-Tmor-(CH₂)₄ |
| 2-224 | 3-F—Ph | 4-Pyr | 1-Piz-CH₂ |
| 2-225 | 3-F—Ph | 4-Pyr | 1-Piz-(CH₂)₂ |

TABLE 2-continued

| Compound No. | R¹ | R² | R³ |
|---|---|---|---|
| 2-226 | 3-F—Ph | 4-Pyr | 1-Piz-(CH₂)₃ |
| 2-227 | 3-F—Ph | 4-Pyr | 4-Me-1-Piz-(CH₂)₃ |
| 2-228 | 3-F—Ph | 4-Pyr | 1-Piz-(CH₂)₄ |
| 2-229 | 3-F—Ph | 4-Pyr | 3-Azt |
| 2-230 | 3-F—Ph | 4-Pyr | 1-Me-3-Azt |
| 2-231 | 3-F—Ph | 4-Pyr | 1-Bn-3-Azt |
| 2-232 | 3-F—Ph | 4-Pyr | 3-Pyrd |
| 2-233 | 3-F—Ph | 4-Pyr | 1-Me-3-Pyrd |
| 2-234 | 3-F—Ph | 4-Pyr | 3-Pip |
| 2-235 | 3-F—Ph | 4-Pyr | 4-Pip |
| 2-236 | 3-F—Ph | 4-Pyr | 4-(3,4-deH-Pip) |
| 2-237 | 3-F—Ph | 4-Pyr | 1-Me-4-Pip |
| 2-238 | 3-F—Ph | 4-Pyr | 1-Me-4-(3,4-deH-Pip) |
| 2-239 | 3-F—Ph | 4-Pyr | 1-Et-4-Pip |
| 2-240 | 3-F—Ph | 4-Pyr | 1-Bn-4-Pip |
| 2-241 | 3-F—Ph | 4-Pyr | 3-Hpip |
| 2-242 | 3-F—Ph | 4-Pyr | 1-Me-3-Hpip |
| 2-243 | 3-F—Ph | 4-Pyr | 4-Hpip |
| 2-244 | 3-F—Ph | 4-Pyr | 1-Me-4-Hpip |
| 2-245 | 3-F—Ph | 4-Pyr | 2-Mor |
| 2-246 | 3-F—Ph | 4-Pyr | 1-Me-2-Mor |
| 2-247 | 3-F—Ph | 4-Pyr | 2-Tmor |
| 2-248 | 3-F—Ph | 4-Pyr | 1-Me-2-Tmor |
| 2-249 | 3-F—Ph | 4-Pyr | 1-Piz |
| 2-250 | 3-F—Ph | 4-Pyr | 4-Me-1-Piz |
| 2-251 | 3-F—Ph | 4-Pyr | 2-Piz |
| 2-252 | 3-F—Ph | 4-Pyr | 4-Pyr |
| 2-253 | 3-F—Ph | 4-Pyr | 3-Pyr |
| 2-254 | 3-F—Ph | 4-Pyr | 2-Pyr |
| 2-255 | 3-F—Ph | 4-Pyr | 4-Pym |
| 2-256 | 3-F—Ph | 4-Pyr | 5-Pym |
| 2-257 | 3-F—Ph | 4-Pyr | 2-Pym |
| 2-258 | 3-F—Ph | 4-Pyr | 3-Azt-CH₂ |
| 2-259 | 3-F—Ph | 4-Pyr | 1-Me-3-Azt-CH₂ |
| 2-260 | 3-F—Ph | 4-Pyr | 3-Pyrd-CH₂ |
| 2-261 | 3-F—Ph | 4-Pyr | 1-Me-3-Pyrd-CH₂ |
| 2-262 | 3-F—Ph | 4-Pyr | 4-Pip-CH₂ |
| 2-263 | 3-F—Ph | 4-Pyr | 1-Me-4-Pip-CH₂ |
| 2-264 | 3-F—Ph | 4-Pyr | 3-Hpip-CH₂ |
| 2-265 | 3-F—Ph | 4-Pyr | 1-Me-3-Hpip-CH₂ |
| 2-266 | 3-F—Ph | 4-Pyr | 4-Hpip-CH₂ |
| 2-267 | 3-F—Ph | 4-Pyr | 1-Me-4-Hpip-CH₂ |
| 2-268 | 3-F—Ph | 4-Pyr | 2-Mor-CH₂ |
| 2-269 | 3-F—Ph | 4-Pyr | 1-Me-2-Mor-CH₂ |
| 2-270 | 3-F—Ph | 4-Pyr | 2-Tmor-CH₂ |
| 2-271 | 3-F—Ph | 4-Pyr | 1-Me-2-Tmor-CH₂ |
| 2-272 | 3-F—Ph | 4-Pyr | 1-Piz-CH₂ |
| 2-273 | 3-F—Ph | 4-Pyr | 4-Me-1-Piz-CH₂ |
| 2-274 | 3-F—Ph | 4-Pyr | 2-Piz-CH₂ |
| 2-275 | 3-F—Ph | 4-Pyr | 4-Pyr-CH₂ |
| 2-276 | 3-F—Ph | 4-Pyr | 3-Pyr-CH₂ |
| 2-277 | 3-F—Ph | 4-Pyr | 2-Pyr-CH₂ |
| 2-278 | 3-F—Ph | 4-Pyr | 4-Pym-CH₂ |
| 2-279 | 3-F—Ph | 4-Pyr | 5-Pym-CH₂ |
| 2-280 | 3-F—Ph | 4-Pyr | 2-Pym-CH₂ |
| 2-281 | 3,4-diF—Ph | 4-Pyr | H₂N—CH₂ |
| 2-282 | 3,4-diF—Ph | 4-Pyr | H₂N—(CH₂)₂ |
| 2-283 | 3,4-diF—Ph | 4-Pyr | H₂N—(CH₂)₃ |
| 2-284 | 3,4-diF—Ph | 4-Pyr | H₂N—(CH₂)₄ |
| 2-285 | 3,4-diF—Ph | 4-Pyr | MeNH—CH₂ |
| 2-286 | 3,4-diF—Ph | 4-Pyr | MeNH—(CH₂)₂ |
| 2-287 | 3,4-diF—Ph | 4-Pyr | MeNH—(CH₂)₃ |
| 2-288 | 3,4-diF—Ph | 4-Pyr | MeNH—(CH₂)₄ |
| 2-289 | 3,4-diF—Ph | 4-Pyr | EtNH—CH₂ |
| 2-290 | 3,4-diF—Ph | 4-Pyr | EtNH—(CH₂)₂ |
| 2-291 | 3,4-diF—Ph | 4-Pyr | EtNH—(CH₂)₃ |
| 2-292 | 3,4-diF—Ph | 4-Pyr | EtNH—(CH₂)₄ |
| 2-293 | 3,4-diF—Ph | 4-Pyr | Me₂N—CH₂ |
| 2-294 | 3,4-diF—Ph | 4-Pyr | Me₂N—(CH₂)₂ |
| 2-295 | 3,4-diF—Ph | 4-Pyr | Me₂N—(CH₂)₃ |
| 2-296 | 3,4-diF—Ph | 4-Pyr | Me₂N—(CH₂)₄ |
| 2-297 | 3,4-diF—Ph | 4-Pyr | 1-Azt-CH₂ |
| 2-298 | 3,4-diF—Ph | 4-Pyr | 1-Azt-(CH₂)₂ |
| 2-299 | 3,4-diF—Ph | 4-Pyr | 1-Azt-(CH₂)₃ |
| 2-300 | 3,4-diF—Ph | 4-Pyr | 1-Azt-(CH₂)₄ |
| 2-301 | 3,4-diF—Ph | 4-Pyr | 1-Pyrd-CH₂ |
| 2-302 | 3,4-diF—Ph | 4-Pyr | 1-Pyrd-(CH₂)₂ |
| 2-303 | 3,4-diF—Ph | 4-Pyr | 1-Pyrd-(CH₂)₃ |
| 2-304 | 3,4-diF—Ph | 4-Pyr | 1-Pyrd-(CH₂)₄ |
| 2-305 | 3,4-diF—Ph | 4-Pyr | 1-Pip-CH₂ |
| 2-306 | 3,4-diF—Ph | 4-Pyr | 1-Pip-(CH₂)₂ |
| 2-307 | 3,4-diF—Ph | 4-Pyr | 1-Pip-(CH₂)₃ |
| 2-308 | 3,4-diF—Ph | 4-Pyr | 1-Pip-(CH₂)₄ |
| 2-309 | 3,4-diF—Ph | 4-Pyr | 1-Mor-CH₂ |
| 2-310 | 3,4-diF—Ph | 4-Pyr | 1-Mor-(CH₂)₂ |
| 2-311 | 3,4-diF—Ph | 4-Pyr | 1-Mor-(CH₂)₃ |
| 2-312 | 3,4-diF—Ph | 4-Pyr | 1-Mor-(CH₂)₄ |
| 2-313 | 3,4-diF—Ph | 4-Pyr | 1-Tmor-CH₂ |
| 2-314 | 3,4-diF—Ph | 4-Pyr | 1-Tmor-(CH₂)₂ |
| 2-315 | 3,4-diF—Ph | 4-Pyr | 1-Tmor-(CH₂)₃ |
| 2-316 | 3,4-diF—Ph | 4-Pyr | 1-Tmor-(CH₂)₄ |
| 2-317 | 3,4-diF—Ph | 4-Pyr | 1-Piz-CH₂ |
| 2-318 | 3,4-diF—Ph | 4-Pyr | 1-Piz-(CH₂)₂ |
| 2-319 | 3,4-diF—Ph | 4-Pyr | 1-Piz-(CH₂)₃ |
| 2-320 | 3,4-diF—Ph | 4-Pyr | 4-Me-1-Piz-(CH₂)₃ |
| 2-321 | 3,4-diF—Ph | 4-Pyr | 1-Piz-(CH₂)₄ |
| 2-322 | 3,4-diF—Ph | 4-Pyr | 3-Azt |
| 2-323 | 3,4-diF—Ph | 4-Pyr | 1-Me-3-Azt |
| 2-324 | 3,4-diF—Ph | 4-Pyr | 1-Bn-3-Azt |
| 2-325 | 3,4-diF—Ph | 4-Pyr | 3-Pyrd |
| 2-326 | 3,4-diF—Ph | 4-Pyr | 1-Me-3-Pyrd |
| 2-327 | 3,4-diF—Ph | 4-Pyr | 3-Pip |
| 2-328 | 3,4-diF—Ph | 4-Pyr | 4-Pip |
| 2-329 | 3,4-diF—Ph | 4-Pyr | 4-(3,4-deH-Pip) |
| 2-330 | 3,4-diF—Ph | 4-Pyr | 1-Me-4-Pip |
| 2-331 | 3,4-diF—Ph | 4-Pyr | 1-Me-4-(3,4-deH-Pip) |
| 2-332 | 3,4-diF—Ph | 4-Pyr | 1-Et-4-Pip |
| 2-333 | 3,4-diF—Ph | 4-Pyr | 1-Bn-4-Pip |
| 2-334 | 3,4-diF—Ph | 4-Pyr | 3-Hpip |
| 2-335 | 3,4-diF—Ph | 4-Pyr | 1-Me-3-Hpip |
| 2-336 | 3,4-diF—Ph | 4-Pyr | 4-Hpip |
| 2-337 | 3,4-diF—Ph | 4-Pyr | 1-Me-4-Hpip |
| 2-338 | 3,4-diF—Ph | 4-Pyr | 2-Mor |
| 2-339 | 3,4-diF—Ph | 4-Pyr | 1-Me-2-Mor |
| 2-340 | 3,4-diF—Ph | 4-Pyr | 2-Tmor |
| 2-341 | 3,4-diF—Ph | 4-Pyr | 1-Me-2-Tmor |
| 2-342 | 3,4-diF—Ph | 4-Pyr | 1-Piz |
| 2-343 | 3,4-diF—Ph | 4-Pyr | 4-Me-1-Piz |
| 2-344 | 3,4-diF—Ph | 4-Pyr | 2-Piz |
| 2-345 | 3,4-diF—Ph | 4-Pyr | 4-Pyr |
| 2-346 | 3,4-diF—Ph | 4-Pyr | 3-Pyr |
| 2-347 | 3,4-diF—Ph | 4-Pyr | 2-Pyr |
| 2-348 | 3,4-diF—Ph | 4-Pyr | 4-Pym |
| 2-349 | 3,4-diF—Ph | 4-Pyr | 5-Pym |
| 2-350 | 3,4-diF—Ph | 4-Pyr | 2-Pym |
| 2-351 | 3,4-diF—Ph | 4-Pyr | 3-Azt-CH₂ |
| 2-352 | 3,4-diF—Ph | 4-Pyr | 1-Me-3-Azt-CH₂ |
| 2-353 | 3,4-diF—Ph | 4-Pyr | 3-Pyrd-CH₂ |
| 2-354 | 3,4-diF—Ph | 4-Pyr | 1-Me-3-Pyrd-CH₂ |
| 2-355 | 3,4-diF—Ph | 4-Pyr | 4-Pip-CH₂ |
| 2-356 | 3,4-diF—Ph | 4-Pyr | 1-Me-4-Pip-CH₂ |
| 2-357 | 3,4-diF—Ph | 4-Pyr | 3-Hpip-CH₂ |
| 2-358 | 3,4-diF—Ph | 4-Pyr | 1-Me-3-Hpip-CH₂ |
| 2-359 | 3,4-diF—Ph | 4-Pyr | 4-Hpip-CH₂ |
| 2-360 | 3,4-diF—Ph | 4-Pyr | 1-Me-4-Hpip-CH₂ |
| 2-361 | 3,4-diF—Ph | 4-Pyr | 2-Mor-CH₂ |
| 2-362 | 3,4-diF—Ph | 4-Pyr | 1-Me-2-Mor-CH₂ |
| 2-363 | 3,4-diF—Ph | 4-Pyr | 2-Tmor-CH₂ |
| 2-364 | 3,4-diF—Ph | 4-Pyr | 1-Me-2-Tmor-CH₂ |
| 2-365 | 3,4-diF—Ph | 4-Pyr | 1-Piz-CH₂ |
| 2-366 | 3,4-diF—Ph | 4-Pyr | 4-Me-1-Piz-CH₂ |
| 2-367 | 3,4-diF—Ph | 4-Pyr | 2-Piz-CH₂ |
| 2-368 | 3,4-diF—Ph | 4-Pyr | 4-Pyr-CH₂ |
| 2-369 | 3,4-diF—Ph | 4-Pyr | 3-Pyr-CH₂ |
| 2-370 | 3,4-diF—Ph | 4-Pyr | 2-Pyr-CH₂ |
| 2-371 | 3,4-diF—Ph | 4-Pyr | 4-Pym-CH₂ |
| 2-372 | 3,4-diF—Ph | 4-Pyr | 5-Pym-CH₂ |
| 2-373 | 3,4-diF—Ph | 4-Pyr | 2-Pym-CH₂ |
| 2-374 | 3-Cl—Ph | 4-Pyr | H₂N—CH₂ |
| 2-375 | 3-Cl—Ph | 4-Pyr | H₂N—(CH₂)₂ |

TABLE 2-continued

| Compound No. | R¹ | R² | R³ |
|---|---|---|---|
| 2-376 | 3-Cl—Ph | 4-Pyr | H$_2$N—(CH$_2$)$_3$ |
| 2-377 | 3-Cl—Ph | 4-Pyr | H$_2$N—(CH$_2$)$_4$ |
| 2-378 | 3-Cl—Ph | 4-Pyr | MeNH—CH$_2$ |
| 2-379 | 3-Cl—Ph | 4-Pyr | MeNH—(CH$_2$)$_2$ |
| 2-380 | 3-Cl—Ph | 4-Pyr | MeNH—(CH$_2$)$_3$ |
| 2-381 | 3-Cl—Ph | 4-Pyr | MeNH—(CH$_2$)$_4$ |
| 2-382 | 3-Cl—Ph | 4-Pyr | EtNH—CH$_2$ |
| 2-383 | 3-Cl—Ph | 4-Pyr | EtNH—(CH$_2$)$_2$ |
| 2-384 | 3-Cl—Ph | 4-Pyr | EtNH—(CH$_2$)$_3$ |
| 2-385 | 3-Cl—Ph | 4-Pyr | EtNH—(CH$_2$)$_4$ |
| 2-386 | 3-Cl—Ph | 4-Pyr | Me$_2$N—CH$_2$ |
| 2-387 | 3-Cl—Ph | 4-Pyr | Me$_2$N—(CH$_2$)$_2$ |
| 2-388 | 3-Cl—Ph | 4-Pyr | Me$_2$N—(CH$_2$)$_3$ |
| 2-389 | 3-Cl—Ph | 4-Pyr | Me$_2$N—(CH$_2$)$_4$ |
| 2-390 | 3-Cl—Ph | 4-Pyr | 1-Azt-CH$_2$ |
| 2-391 | 3-Cl—Ph | 4-Pyr | 1-Azt-(CH$_2$)$_2$ |
| 2-392 | 3-Cl—Ph | 4-Pyr | 1-Azt-(CH$_2$)$_3$ |
| 2-393 | 3-Cl—Ph | 4-Pyr | 1-Azt-(CH$_2$)$_4$ |
| 2-394 | 3-Cl—Ph | 4-Pyr | 1-Pyrd-CH$_2$ |
| 2-395 | 3-Cl—Ph | 4-Pyr | 1-Pyrd-(CH$_2$)$_2$ |
| 2-396 | 3-Cl—Ph | 4-Pyr | 1-Pyrd-(CH$_2$)$_3$ |
| 2-397 | 3-Cl—Ph | 4-Pyr | 1-Pyrd-(CH$_2$)$_4$ |
| 2-398 | 3-Cl—Ph | 4-Pyr | 1-Pip-CH$_2$ |
| 2-399 | 3-Cl—Ph | 4-Pyr | 1-Pip-(CH$_2$)$_2$ |
| 2-400 | 3-Cl—Ph | 4-Pyr | 1-Pip-(CH$_2$)$_3$ |
| 2-401 | 3-Cl—Ph | 4-Pyr | 1-Pip-(CH$_2$)$_4$ |
| 2-402 | 3-Cl—Ph | 4-Pyr | 1-Mor-CH$_2$ |
| 2-403 | 3-Cl—Ph | 4-Pyr | 1-Mor-(CH$_2$)$_2$ |
| 2-404 | 3-Cl—Ph | 4-Pyr | 1-Mor-(CH$_2$)$_3$ |
| 2-405 | 3-Cl—Ph | 4-Pyr | 1-Mor-(CH$_2$)$_4$ |
| 2-406 | 3-Cl—Ph | 4-Pyr | 1-Tmor-(CH$_2$) |
| 2-407 | 3-Cl—Ph | 4-Pyr | 1-Tmor-(CH$_2$)$_2$ |
| 2-408 | 3-Cl—Ph | 4-Pyr | 1-Tmor-(CH$_2$)$_3$ |
| 2-409 | 3-Cl—Ph | 4-Pyr | 1-Tmor-(CH$_2$)$_4$ |
| 2-410 | 3-Cl—Ph | 4-Pyr | 1-Piz-CH$_2$ |
| 2-411 | 3-Cl—Ph | 4-Pyr | 1-Piz-(CH$_2$)$_2$ |
| 2-412 | 3-Cl—Ph | 4-Pyr | 1-Piz-(CH$_2$)$_3$ |
| 2-413 | 3-Cl—Ph | 4-Pyr | 4-Me-1-Piz-(CH$_2$)$_3$ |
| 2-414 | 3-Cl—Ph | 4-Pyr | l-Piz-(CH$_2$)$_4$ |
| 2-415 | 3-Cl—Ph | 4-Pyr | 3-Azt |
| 2-416 | 3-Cl—Ph | 4-Pyr | 1-Me-3-Azt |
| 2-417 | 3-Cl—Ph | 4-Pyr | 1-Bn-3-Azt |
| 2-418 | 3-Cl—Ph | 4-Pyr | 3-Pyrd |
| 2-419 | 3-Cl—Ph | 4-Pyr | 1-Me-3-Pyrd |
| 2-420 | 3-Cl—Ph | 4-Pyr | 3-Pip |
| 2-421 | 3-Cl—Ph | 4-Pyr | 4-Pip |
| 2-422 | 3-Cl—Ph | 4-Pyr | 4-(3,4-deH-Pip) |
| 2-423 | 3-Cl—Ph | 4-Pyr | 1-Me-4-Pip |
| 2-424 | 3-Cl—Ph | 4-Pyr | 1-Me-4-(3,4-deH-Pip) |
| 2-425 | 3-Cl—Ph | 4-Pyr | 1-Et-4-Pip |
| 2-426 | 3-Cl—Ph | 4-Pyr | 1-Bn-4-Pip |
| 2-427 | 3-Cl—Ph | 4-Pyr | 3-Hpip |
| 2-428 | 3-Cl—Ph | 4-Pyr | 1-Me-3-Hpip |
| 2-429 | 3-Cl—Ph | 4-Pyr | 4-Hpip |
| 2-430 | 3-Cl—Ph | 4-Pyr | 1-Me-4-Hpip |
| 2-431 | 3-Cl—Ph | 4-Pyr | 2-Mor |
| 2-432 | 3-Cl—Ph | 4-Pyr | 1-Me-2-Mor |
| 2-433 | 3-Cl—Ph | 4-Pyr | 2-Tmor |
| 2-434 | 3-Cl—Ph | 4-Pyr | 1-Me-2-Tmor |
| 2-435 | 3-Cl—Ph | 4-Pyr | 1-Piz |
| 2-436 | 3-Cl—Ph | 4-Pyr | 4-Me-1-Piz |
| 2-437 | 3-Cl—Ph | 4-Pyr | 2-Piz |
| 2-438 | 3-Cl—Ph | 4-Pyr | 4-Pyr |
| 2-439 | 3-Cl—Ph | 4-Pyr | 3-Pyr |
| 2-440 | 3-Cl—Ph | 4-Pyr | 2-Pyr |
| 2-441 | 3-Cl—Ph | 4-Pyr | 4-Pym |
| 2-442 | 3-Cl—Ph | 4-Pyr | 5-Pym |
| 2-443 | 3-Cl—Ph | 4-Pyr | 2-Pym |
| 2-444 | 3-Cl—Ph | 4-Pyr | 3-Azt-CH$_2$ |
| 2-445 | 3-Cl—Ph | 4-Pyr | 1-Me-3-Azt-CH$_2$ |
| 2-446 | 3-Cl—Ph | 4-Pyr | 3-Pyrd-CH$_2$ |
| 2-447 | 3-Cl—Ph | 4-Pyr | 1-Me-3-Pyrd-CH$_2$ |
| 2-448 | 3-Cl—Ph | 4-Pyr | 4-Pip-CH$_2$ |
| 2-449 | 3-Cl—Ph | 4-Pyr | 1-Me-4-Pip-CH$_2$ |
| 2-450 | 3-Cl—Ph | 4-Pyr | 3-Hpip-CH$_2$ |
| 2-451 | 3-Cl—Ph | 4-Pyr | 1-Me-3-Hpip-CH$_2$ |
| 2-452 | 3-Cl—Ph | 4-Pyr | 4-Hpip-CH$_2$ |
| 2-453 | 3-Cl—Ph | 4-Pyr | 1-Me-4-Hpip-CH$_2$ |
| 2-454 | 3-Cl—Ph | 4-Pyr | 2-Mor-CH$_2$ |
| 2-455 | 3-Cl—Ph | 4-Pyr | 1-Me-2-Mor-CH$_2$ |
| 2-456 | 3-Cl—Ph | 4-Pyr | 2-Tmor-CH$_2$ |
| 2-457 | 3-Cl—Ph | 4-Pyr | 1-Me-2-Tmor-CH$_2$ |
| 2-458 | 3-Cl—Ph | 4-Pyr | 1-Piz-CH$_2$ |
| 2-459 | 3-Cl—Ph | 4-Pyr | 4-Me-1-Piz-CH$_2$ |
| 2-460 | 3-Cl—Ph | 4-Pyr | 2-Piz-CH$_2$ |
| 2-461 | 3-Cl—Ph | 4-Pyr | 4-Pyr-CH$_2$ |
| 2-462 | 3-Cl—Ph | 4-Pyr | 3-Pyr-CH$_2$ |
| 2-463 | 3-Cl—Ph | 4-Pyr | 2-Pyr-CH$_2$ |
| 2-464 | 3-Cl—Ph | 4-Pyr | 4-Pym-CH$_2$ |
| 2-465 | 3-Cl—Ph | 4-Pyr | 5-Pym-CH$_2$ |
| 2-466 | 3-Cl—Ph | 4-Pyr | 2-Pym-CH$_2$ |
| 2-467 | Ph | 2-NH$_2$-4-Pym | H$_2$N—CH$_2$ |
| 2-468 | Ph | 2-NH$_2$-4-Pym | H$_2$N—(CH$_2$)$_2$ |
| 2-469 | Ph | 2-NH$_2$-4-Pym | H$_2$N—(CH$_2$)$_3$ |
| 2-470 | Ph | 2-NH$_2$-4-Pym | H$_2$N—(CH$_2$)$_4$ |
| 2-471 | Ph | 2-NH$_2$-4-Pym | MeNH—CH$_2$ |
| 2-472 | Ph | 2-NH$_2$-4-Pym | MeNH—(CH$_2$)$_2$ |
| 2-473 | Ph | 2-NH$_2$-4-Pym | MeNH—(CH$_2$)$_3$ |
| 2-474 | Ph | 2-NH$_2$-4-Pym | MeNH—(CH$_2$)$_4$ |
| 2-475 | Ph | 2-NH$_2$-4-Pym | EtNH—CH$_2$ |
| 2-476 | Ph | 2-NH$_2$-4-Pym | EtNH—(CH$_2$)$_2$ |
| 2-477 | Ph | 2-NH$_2$-4-Pym | EtNH—(CH$_2$)$_3$ |
| 2-478 | Ph | 2-NH$_2$-4-Pym | EtNH—(CH$_2$)$_4$ |
| 2-479 | Ph | 2-NH$_2$-4-Pym | Me$_2$N—CH$_2$ |
| 2-480 | Ph | 2-NH$_2$-4-Pym | Me$_2$N—(CH$_2$)$_2$ |
| 2-481 | Ph | 2-NH$_2$-4-Pym | Me$_2$N—(CH$_2$)$_3$ |
| 2-482 | Ph | 2-NH$_2$-4-Pym | Me$_2$N—(CH$_2$)$_4$ |
| 2-483 | Ph | 2-NH$_2$-4-Pym | 1-Azt-CH$_2$ |
| 2-484 | Ph | 2-NH$_2$-4-Pym | 1-Azt-(CH$_2$)$_2$ |
| 2-485 | Ph | 2-NH$_2$-4-Pym | 1-Azt-(CH$_2$)$_3$ |
| 2-486 | Ph | 2-NH$_2$-4-Pym | 1-Azt-(CH$_2$)$_4$ |
| 2-487 | Ph | 2-NH$_2$-4-Pym | 1-Pyrd-CH$_2$ |
| 2-488 | Ph | 2-NH$_2$-4-Pym | 1-Pyrd-(CH$_2$)$_2$ |
| 2-489 | Ph | 2-NH$_2$-4-Pym | 1-Pyrd-(CH$_2$)$_3$ |
| 2-490 | Ph | 2-NH$_2$-4-Pym | 1-Pyrd-(CH$_2$)$_4$ |
| 2-491 | Ph | 2-NH$_2$-4-Pym | 1-Pip-CH$_2$ |
| 2-492 | Ph | 2-NH$_2$-4-Pym | 1-Pip-(CH$_2$)$_2$ |
| 2-493 | Ph | 2-NH$_2$-4-Pym | 1-Pip-(CH$_2$)$_3$ |
| 2-494 | Ph | 2-NH$_2$-4-Pym | 1-Pip-(CH$_2$)$_4$ |
| 2-495 | Ph | 2-NH$_2$-4-Pym | 1-Mor-CH$_2$ |
| 2-496 | Ph | 2-NH$_2$-4-Pym | 1-Mor-(CH$_2$)$_2$ |
| 2-497 | Ph | 2-NH$_2$-4-Pym | 1-Mor-(CH$_2$)$_3$ |
| 2-498 | Ph | 2-NH$_2$-4-Pym | 1-Mor-(CH$_2$)$_4$ |
| 2-499 | Ph | 2-NH$_2$-4-Pym | 1-Tmor-CH$_2$ |
| 2-500 | Ph | 2-NH$_2$-4-Pym | 1-Tmor-(CH$_2$)$_2$ |
| 2-501 | Ph | 2-NH$_2$-4-Pym | 1-Tmor-(CH$_2$)$_3$ |
| 2-502 | Ph | 2-NH$_2$-4-Pym | 1-Tmor-(CH$_2$)$_4$ |
| 2-503 | Ph | 2-NH$_2$-4-Pym | 1-Piz-CH$_2$ |
| 2-504 | Ph | 2-NH$_2$-4-Pym | 1-Piz-(CH$_2$)$_2$ |
| 2-505 | Ph | 2-NH$_2$-4-Pym | 1-Piz-(CH$_2$)$_3$ |
| 2-506 | Ph | 2-NH$_2$-4-Pym | 4-Me-1-Piz-(CH$_2$)$_3$ |
| 2-507 | Ph | 2-NH$_2$-4-Pym | 1-Piz-(CH$_2$)$_4$ |
| 2-508 | Ph | 2-NH$_2$-4-Pym | 3-Azt |
| 2-509 | Ph | 2-NH$_2$-4-Pym | 1-Me-3-Azt |
| 2-510 | Ph | 2-NH$_2$-4-Pym | 1-Bn-3-Azt |
| 2-511 | Ph | 2-NH$_2$-4-Pym | 3-Pyrd |
| 2-512 | Ph | 2-NH$_2$-4-Pym | 1-Me-3-Pyrd |
| 2-513 | Ph | 2-NH$_2$-4-Pym | 3-Pip |
| 2-514 | Ph | 2-NH$_2$-4-Pym | 4-Pip |
| 2-515 | Ph | 2-NH$_2$-4-Pym | 4-(3,4-deH-Pip) |
| 2-516 | Ph | 2-NH$_2$-4-Pym | 1-Me-4-Pip |
| 2-517 | Ph | 2-NH$_2$-4-Pym | 1-Me-4-(3,4-deH-Pip) |
| 2-518 | Ph | 2-NH$_2$-4-Pym | 1-Et-4-Pip |
| 2-519 | Ph | 2-NH$_2$-4-Pym | 1-Bn-4-Pip |
| 2-520 | Ph | 2-NH$_2$-4-Pym | 3-Hpip |
| 2-521 | Ph | 2-NH$_2$-4-Pym | 1-Me-3-Hpip |
| 2-522 | Ph | 2-NH$_2$-4-Pym | 4-Hpip |
| 2-523 | Ph | 2-NH$_2$-4-Pym | 1-Me-4-Hpip |
| 2-524 | Ph | 2-NH$_2$-4-Pym | 2-Mor |
| 2-525 | Ph | 2-NH$_2$-4-Pym | 1-Me-2-Mor |

TABLE 2-continued

| Compound No. | R¹ | R² | R³ |
|---|---|---|---|
| 2-526 | Ph | 2-NH$_2$-4-Pym | 2-Tmor |
| 2-527 | Ph | 2-NH$_2$-4-Pym | 1-Me-2-Tmor |
| 2-528 | Ph | 2-NH$_2$-4-Pym | 1-Piz |
| 2-529 | Ph | 2-NH$_2$-4-Pym | 4-Me-1-Piz |
| 2-530 | Ph | 2-NH$_2$-4-Pym | 2-Piz |
| 2-531 | Ph | 2-NH$_2$-4-Pym | 4-Pyr |
| 2-532 | Ph | 2-NH$_2$-4-Pym | 3-Pyr |
| 2-533 | Ph | 2-NH$_2$-4-Pym | 2-Pyr |
| 2-534 | Ph | 2-NH$_2$-4-Pym | 4-Pym |
| 2-535 | Ph | 2-NH$_2$-4-Pym | 5-Pym |
| 2-536 | Ph | 2-NH$_2$-4-Pym | 2-Pym |
| 2-537 | Ph | 2-NH$_2$-4-Pym | 3-Azt-CH$_2$ |
| 2-538 | Ph | 2-NH$_2$-4-Pym | 1-Me-3-Azt-CH$_2$ |
| 2-540 | Ph | 2-NH$_2$-4-Pym | 1-Me-3-Pyrd-CH$_2$ |
| 2-541 | Ph | 2-NH$_2$-4-Pym | 4-Pip-CH$_2$ |
| 2-542 | Ph | 2-NH$_2$-4-Pym | 1-Me-4-Pip-CH$_2$ |
| 2-543 | Ph | 2-NH$_2$-4-Pym | 3-Hpip-CH$_2$ |
| 2-544 | Ph | 2-NH$_2$-4-Pym | 1-Me-3-Hpip-CH$_2$ |
| 2-545 | Ph | 2-NH$_2$-4-Pym | 4-Hpip-CH$_2$ |
| 2-546 | Ph | 2-NH$_2$-4-Pym | 1-Me-4-Hpip-CH$_2$ |
| 2-547 | Ph | 2-NH$_2$-4-Pym | 2-Mor-CH$_2$ |
| 2-548 | Ph | 2-NH$_2$-4-Pym | 1-Me-2-Mor-CH$_2$ |
| 2-549 | Ph | 2-NH$_2$-4-Pym | 2-Tmor-CH$_2$ |
| 2-550 | Ph | 2-NH$_2$-4-Pym | 1-Me-2-Tmor-CH$_2$ |
| 2-551 | Ph | 2-NH$_2$-4-Pym | 1-Piz-CH$_2$ |
| 2-552 | Ph | 2-NH$_2$-4-Pym | 4-Me-1-Piz-CH$_2$ |
| 2-553 | Ph | 2-NH$_2$-4-Pym | 2-Piz-CH$_2$ |
| 2-554 | Ph | 2-NH$_2$-4-Pym | 4-Pyr-CH$_2$ |
| 2-555 | Ph | 2-NH$_2$-4-Pym | 3-Pyr-CH$_2$ |
| 2-556 | Ph | 2-NH$_2$-4-Pym | 2-Pyr-CH$_2$ |
| 2-557 | Ph | 2-NH$_2$-4-Pym | 4-Pym-CH$_2$ |
| 2-558 | Ph | 2-NH$_2$-4-Pym | 5-Pym-CH$_2$ |
| 2-559 | Ph | 2-NH$_2$-4-Pym | 2-Pym-CH$_2$ |
| 2-560 | 4-F—Ph | 2-NH$_2$-4-Pym | H$_2$N—CH$_2$ |
| 2-561 | 4-F—Ph | 2-NH$_2$-4-Pym | H$_2$N—(CH$_2$)$_2$ |
| 2-562 | 4-F—Ph | 2-NH$_2$-4-Pym | H$_2$N—(CH$_2$)$_3$ |
| 2-563 | 4-F—Ph | 2-NH$_2$-4-Pym | H$_2$N—(CH$_2$)$_4$ |
| 2-564 | 4-F—Ph | 2-NH$_2$-4-Pym | MeNH—CH$_2$ |
| 2-565 | 4-F—Ph | 2-NH$_2$-4-Pym | MeNH—(CH$_2$)$_2$ |
| 2-566 | 4-F—Ph | 2-NH$_2$-4-Pym | MeNH—(CH$_2$)$_3$ |
| 2-567 | 4-F—Ph | 2-NH$_2$-4-Pym | MeNH—(CH$_2$)$_4$ |
| 2-568 | 4-F—Ph | 2-NH$_2$-4-Pym | EtNH—CH$_2$ |
| 2-569 | 4-F—Ph | 2-NH$_2$-4-Pym | EtNH—(CH$_2$)$_2$ |
| 2-570 | 4-F—Ph | 2-NH$_2$-4-Pym | EtNH—(CH$_2$)$_3$ |
| 2-571 | 4-F—Ph | 2-NH$_2$-4-Pym | EtNH—(CH$_2$)$_4$ |
| 2-572 | 4-F—Ph | 2-NH$_2$-4-Pym | Me$_2$N—CH$_2$ |
| 2-573 | 4-F—Ph | 2-NH$_2$-4-Pym | Me$_2$N—(CH$_2$)$_2$ |
| 2-574 | 4-F—Ph | 2-NH$_2$-4-Pym | Me$_2$N—(CH$_2$)$_3$ |
| 2-575 | 4-F—Ph | 2-NH$_2$-4-Pym | Me$_2$N—(CH$_2$)$_4$ |
| 2-576 | 4-F—Ph | 2-NH$_2$-4-Pym | 1-Azt-CH$_2$ |
| 2-577 | 4-F—Ph | 2-NH$_2$-4-Pym | 1-Azt-(CH$_2$)$_2$ |
| 2-578 | 4-F—Ph | 2-NH$_2$-4-Pym | 1-Azt-(CH$_2$)$_3$ |
| 2-579 | 4-F—Ph | 2-NH$_2$-4-Pym | 1-Azt-(CH$_2$)$_4$ |
| 2-580 | 4-F—Ph | 2-NH$_2$-4-Pym | 1-Pyrd-CH$_2$ |
| 2-581 | 4-F—Ph | 2-NH$_2$-4-Pym | 1-Pyrd-(CH$_2$)$_2$ |
| 2-582 | 4-F—Ph | 2-NH$_2$-4-Pym | 1-Pyrd-(CH$_2$)$_3$ |
| 2-583 | 4-F—Ph | 2-NH$_2$-4-Pym | 1-Pyrd-(CH$_2$)$_4$ |
| 2-584 | 4-F—Ph | 2-NH$_2$-4-Pym | 1-Pip-CH$_2$ |
| 2-585 | 4-F—Ph | 2-NH$_2$-4-Pym | 1-Pip-(CH$_2$)$_2$ |
| 2-586 | 4-F—Ph | 2-NH$_2$-4-Pym | 1-Pip-(CH$_2$)$_3$ |
| 2-587 | 4-F—Ph | 2-NH$_2$-4-Pym | 1-Pip-(CH$_2$)$_4$ |
| 2-588 | 4-F—Ph | 2-NH$_2$-4-Pym | 1-Mor-CH$_2$ |
| 2-589 | 4-F—Ph | 2-NH$_2$-4-Pym | 1-Mor-(CH$_2$)$_2$ |
| 2-590 | 4-F—Ph | 2-NH$_2$-4-Pym | 1-Mor-(CH$_2$)$_3$ |
| 2-591 | 4-F—Ph | 2-NH$_2$-4-Pym | 1-Mor-(CH$_2$)$_4$ |
| 2-592 | 4-F—Ph | 2-NH$_2$-4-Pym | 1-Tmor-CH$_2$ |
| 2-593 | 4-F—Ph | 2-NH$_2$-4-Pym | 1-Tmor-(CH$_2$)$_2$ |
| 2-594 | 4-F—Ph | 2-NH$_2$-4-Pym | 1-Tmor-(CH$_2$)$_3$ |
| 2-595 | 4-F—Ph | 2-NH$_2$-4-Pym | 1-Tmor-(CH$_2$)$_4$ |
| 2-596 | 4-F—Ph | 2-NH$_2$-4-Pym | 1-Piz-CH$_2$ |
| 2-597 | 4-F—Ph | 2-NH$_2$-4-Pym | 1-Piz-(CH$_2$)$_2$ |
| 2-598 | 4-F—Ph | 2-NH$_2$-4-Pym | 1-Piz-(CH$_2$)$_3$ |
| 2-599 | 4-F—Ph | 2-NH$_2$-4-Pym | 4-Me-1-Piz-(CH$_2$)$_3$ |
| 2-600 | 4-F—Ph | 2-NH$_2$-4-Pym | 1-Piz-(CH$_2$)$_4$ |
| 2-601 | 4-F—Ph | 2-NH$_2$-4-Pym | 3-Azt |
| 2-602 | 4-F—Ph | 2-NH$_2$-4-Pym | 1-Me-3-Azt |
| 2-603 | 4-F—Ph | 2-NH$_2$-4-Pym | 1-Bn-3-Azt |
| 2-604 | 4-F—Ph | 2-NH$_2$-4-Pym | 3-Pyrd |
| 2-605 | 4-F—Ph | 2-NH$_2$-4-Pym | 1-Me-3-Pyrd |
| 2-606 | 4-F—Ph | 2-NH$_2$-4-Pym | 3-Pip |
| 2-607 | 4-F—Ph | 2-NH$_2$-4-Pym | 4-Pip |
| 2-608 | 4-F—Ph | 2-NH$_2$-4-Pym | 4-(3,4-deH-Pip) |
| 2-609 | 4-F—Ph | 2-NH$_2$-4-Pym | 1-Me-4-Pip |
| 2-610 | 4-F—Ph | 2-NH$_2$-4-Pym | 1-Me-4-(3,4-deH-Pip) |
| 2-611 | 4-F—Ph | 2-NH$_2$-4-Pym | 1-Et-4-Pip |
| 2-612 | 4-F—Ph | 2-NH$_2$-4-Pym | 1-Bn-4-Pip |
| 2-613 | 4-F—Ph | 2-NH$_2$-4-Pym | 3-Hpip |
| 2-614 | 4-F—Ph | 2-NH$_2$-4-Pym | 1-Me-3-Hpip |
| 2-615 | 4-F—Ph | 2-NH$_2$-4-Pym | 4-Hpip |
| 2-616 | 4-F—Ph | 2-NH$_2$-4-Pym | 1-Me-4-Hpip |
| 2-617 | 4-F—Ph | 2-NH$_2$-4-Pym | 2-Mor |
| 2-618 | 4-F—Ph | 2-NH$_2$-4-Pym | 1-Me-2-Mor |
| 2-619 | 4-F—Ph | 2-NH$_2$-4-Pym | 2-Tmor |
| 2-620 | 4-F—Ph | 2-NH$_2$-4-Pym | 1-Me-2-Tmor |
| 2-621 | 4-F—Ph | 2-NH$_2$-4-Pym | 1-Piz |
| 2-622 | 4-F—Ph | 2-NH$_2$-4-Pym | 4-Me-1-Piz |
| 2-623 | 4-F—Ph | 2-NH$_2$-4-Pym | 2-Piz |
| 2-624 | 4-F—Ph | 2-NH$_2$-4-Pym | 4-Pyr |
| 2-625 | 4-F—Ph | 2-NH$_2$-4-Pym | 3-Pyr |
| 2-626 | 4-F—Ph | 2-NH$_2$-4-Pym | 2-Pyr |
| 2-627 | 4-F—Ph | 2-NH$_2$-4-Pym | 4-Pym |
| 2-628 | 4-F—Ph | 2-NH$_2$-4-Pym | 5-Pym |
| 2-629 | 4-F—Ph | 2-NH$_2$-4-Pym | 2-Pym |
| 2-630 | 4-F—Ph | 2-NH$_2$-4-Pym | 3-Azt-CH$_2$ |
| 2-631 | 4-F—Ph | 2-NH$_2$-4-Pym | 1-Me-3-Azt-CH$_2$ |
| 2-632 | 4-F—Ph | 2-NH$_2$-4-Pym | 3-Pyrd-CH$_2$ |
| 2-633 | 4-F—Ph | 2-NH$_2$-4-Pym | 1-Me-3-Pyrd-CH$_2$ |
| 2-634 | 4-F—Ph | 2-NH$_2$-4-Pym | 4-Pip-CH$_2$ |
| 2-635 | 4-F—Ph | 2-NH$_2$-4-Pym | 1-Me-4-Pip-CH$_2$ |
| 2-636 | 4-F—Ph | 2-NH$_2$-4-Pym | 3-Hpip-CH$_2$ |
| 2-637 | 4-F—Ph | 2-NH$_2$-4-Pym | 1-Me-3-Hpip-CH$_2$ |
| 2-638 | 4-F—Ph | 2-NH$_2$-4-Pym | 4-Hpip-CH$_2$ |
| 2-639 | 4-F—Ph | 2-NH$_2$-4-Pym | 1-Me-4-Hpip-CH$_2$ |
| 2-640 | 4-F—Ph | 2-NH$_2$-4-Pym | 2-Mor-CH$_2$ |
| 2-641 | 4-F—Ph | 2-NH$_2$-4-Pym | 1-Me-2-Mor-CH$_2$ |
| 2-642 | 4-F—Ph | 2-NH$_2$-4-Pym | 2-Tmor-CH$_2$ |
| 2-643 | 4-F—Ph | 2-NH$_2$-4-Pym | 1-Me-2-Tmor-CH$_2$ |
| 2-644 | 4-F—Ph | 2-NH$_2$-4-Pym | 1-Piz-CH$_2$ |
| 2-645 | 4-F—Ph | 2-NH$_2$-4-Pym | 4-Me-1-Piz-CH$_2$ |
| 2-646 | 4-F—Ph | 2-NH$_2$-4-Pym | 2-Piz-CH$_2$ |
| 2-647 | 4-F—Ph | 2-NH$_2$-4-Pym | 4-Pyr-CH$_2$ |
| 2-648 | 4-F—Ph | 2-NH$_2$-4-Pym | 3-Pyr-CH$_2$ |
| 2-649 | 4-F—Ph | 2-NH$_2$-4-Pym | 2-Pyr-CH$_2$ |
| 2-650 | 4-F—Ph | 2-NH$_2$-4-Pym | 4-Pym-CH$_2$ |
| 2-651 | 4-F—Ph | 2-NH$_2$-4-Pym | 5-Pym-CH$_2$ |
| 2-652 | 4-F—Ph | 2-NH$_2$-4-Pym | 2-Pym-CH$_2$ |
| 2-653 | 3-F—Ph | 2-NH$_2$-4-Pym | H$_2$N—CH$_2$ |
| 2-654 | 3-F—Ph | 2-NH$_2$-4-Pym | H$_2$N—(CH$_2$)$_2$ |
| 2-655 | 3-F—Ph | 2-NH$_2$-4-Pym | H$_2$N—(CH$_2$)$_3$ |
| 2-656 | 3-F—Ph | 2-NH$_2$-4-Pym | H$_2$N—(CH$_2$)$_4$ |
| 2-657 | 3-F—Ph | 2-NH$_2$-4-Pym | MeNH—CH$_2$ |
| 2-658 | 3-F—Ph | 2-NH$_2$-4-Pym | MeNH—(CH$_2$)$_2$ |
| 2-659 | 3-F—Ph | 2-NH$_2$-4-Pym | MeNH—(CH$_2$)$_3$ |
| 2-660 | 3-F—Ph | 2-NH$_2$-4-Pym | MeNH—(CH$_2$)$_4$ |
| 2-661 | 3-F—Ph | 2-NH$_2$-4-Pym | EtNH—CH$_2$ |
| 2-662 | 3-F—Ph | 2-NH$_2$-4-Pym | EtNH—(CH$_2$)$_2$ |
| 2-663 | 3-F—Ph | 2-NH$_2$-4-Pym | EtNH—(CH$_2$)$_3$ |
| 2-664 | 3-F—Ph | 2-NH$_2$-4-Pym | EtNH—(CH$_2$)$_4$ |
| 2-665 | 3-F—Ph | 2-NH$_2$-4-Pym | Me$_2$N—CH$_2$ |
| 2-666 | 3-F—Ph | 2-NH$_2$-4-Pym | Me$_2$N—(CH$_2$)$_2$ |
| 2-667 | 3-F—Ph | 2-NH$_2$-4-Pym | Me$_2$N—(CH$_2$)$_3$ |
| 2-668 | 3-F—Ph | 2-NH$_2$-4-Pym | Me$_2$N—(CH$_2$)$_4$ |
| 2-669 | 3-F—Ph | 2-NH$_2$-4-Pym | 1-Azt-CH$_2$ |
| 2-670 | 3-F—Ph | 2-NH$_2$-4-Pym | 1-Azt-(CH$_2$)$_2$ |
| 2-671 | 3-F—Ph | 2-NH$_2$-4-Pym | 1-Azt-(CH$_2$)$_3$ |
| 2-672 | 3-F—Ph | 2-NH$_2$-4-Pym | 1-Azt-(CH$_2$)$_4$ |
| 2-673 | 3-F—Ph | 2-NH$_2$-4-Pym | 1-Pyrd-CH$_2$ |
| 2-674 | 3-F—Ph | 2-NH$_2$-4-Pym | 1-Pyrd-(CH$_2$)$_2$ |
| 2-675 | 3-F—Ph | 2-NH$_2$-4-Pym | 1-Pyrd-(CH$_2$)$_3$ |
| 2-676 | 3-F—Ph | 2-NH$_2$-4-Pym | 1-Pyrd-(CH$_2$)$_4$ |

TABLE 2-continued

| Compound No. | R¹ | R² | R³ |
|---|---|---|---|
| 2-677 | 3-F—Ph | 2-NH₂-4-Pym | 1-Pip-CH₂ |
| 2-678 | 3-F—Ph | 2-NH₂-4-Pym | 1-Pip-(CH₂)₂ |
| 2-679 | 3-F—Ph | 2-NH₂-4-Pym | 1-Pip-(CH₂)₃ |
| 2-680 | 3-F—Ph | 2-NH₂-4-Pym | 1-Pip-(CH₂)₄ |
| 2-681 | 3-F—Ph | 2-NH₂-4-Pym | 1-Mor-CH₂ |
| 2-682 | 3-F—Ph | 2-NH₂-4-Pym | 1-Mor-(CH₂)₂ |
| 2-683 | 3-F—Ph | 2-NH₂-4-Pym | 1-Mor-(CH₂)₃ |
| 2-684 | 3-F—Ph | 2-NH₂-4-Pym | 1-Mor-(CH₂)₄ |
| 2-685 | 3-F—Ph | 2-NH₂-4-Pym | 1-Tmor-CH₂ |
| 2-686 | 3-F—Ph | 2-NH₂-4-Pym | 1-Tmor-(CH₂)₂ |
| 2-687 | 3-F—Ph | 2-NH₂-4-Pym | 1-Tmor-(CH₂)₃ |
| 2-688 | 3-F—Ph | 2-NH₂-4-Pym | 1-Tmor-(CH₂)₄ |
| 2-689 | 3-F—Ph | 2-NH₂-4-Pym | 1-Piz-CH₂ |
| 2-690 | 3-F—Ph | 2-NH₂-4-Pym | 1-Piz-(CH₂)₂ |
| 2-691 | 3-F—Ph | 2-NH₂-4-Pym | 1-Piz-(CH₂)₃ |
| 2-692 | 3-F—Ph | 2-NH₂-4-Pym | 4-Me-1-Piz-(CH₂)₃ |
| 2-693 | 3-F—Ph | 2-NH₂-4-Pym | 1-Piz-(CH₂)₄ |
| 2-694 | 3-F—Ph | 2-NH₂-4-Pym | 3-Azt |
| 2-695 | 3-F—Ph | 2-NH₂-4-Pym | 1-Me-3-Azt |
| 2-696 | 3-F—Ph | 2-NH₂-4-Pym | 1-Bn-3-Azt |
| 2-697 | 3-F—Ph | 2-NH₂-4-Pym | 3-Pyrd |
| 2-698 | 3-F—Ph | 2-NH₂-4-Pym | 1-Me-3-Pyrd |
| 2-699 | 3-F—Ph | 2-NH₂-4-Pym | 3-Pip |
| 2-700 | 3-F—Ph | 2-NH₂-4-Pym | 4-Pip |
| 2-701 | 3-F—Ph | 2-NH₂-4-Pym | 4-(3,4-deH-Pip) |
| 2-702 | 3-F—Ph | 2-NH₂-4-Pym | 1-Me-4-Pip |
| 2-703 | 3-F—Ph | 2-NH₂-4-Pym | 1-Me-4-(3,4-deH-Pip) |
| 2-704 | 3-F—Ph | 2-NH₂-4-Pym | 1-Et-4-Pip |
| 2-705 | 3-F—Ph | 2-NH₂-4-Pym | 1-Bn-4-Pip |
| 2-706 | 3-F—Ph | 2-NH₂-4-Pym | 3-Hpip |
| 2-707 | 3-F—Ph | 2-NH₂-4-Pym | 1-Me-3-Hpip |
| 2-708 | 3-F—Ph | 2-NH₂-4-Pym | 4-Hpip |
| 2-709 | 3-F—Ph | 2-NH₂-4-Pym | 1-Me-4-Hpip |
| 2-710 | 3-F—Ph | 2-NH₂-4-Pym | 2-Mor |
| 2-711 | 3-F—Ph | 2-NH₂-4-Pym | 1-Me-2-Mor |
| 2-712 | 3-F—Ph | 2-NH₂-4-Pym | 2-Tmor |
| 2-713 | 3-F—Ph | 2-NH₂-4-Pym | 1-Me-2-Tmor |
| 2-714 | 3-F—Ph | 2-NH₂-4-Pym | 1-Piz |
| 2-715 | 3-F—Ph | 2-NH₂-4-Pym | 4-Me-1-Piz |
| 2-716 | 3-F—Ph | 2-NH₂-4-Pym | 2-Piz |
| 2-717 | 3-F—Ph | 2-NH₂-4-Pym | 4-Pyr |
| 2-718 | 3-F—Ph | 2-NH₂-4-Pym | 3-Pyr |
| 2-720 | 3-F—Ph | 2-NH₂-4-Pym | 4-Pym |
| 2-721 | 3-F—Ph | 2-NH₂-4-Pym | 5-Pym |
| 2-722 | 3-F—Ph | 2-NH₂-4-Pym | 2-Pym |
| 2-723 | 3-F—Ph | 2-NH₂-4-Pym | 3-Azt-CH₂ |
| 2-724 | 3-F—Ph | 2-NH₂-4-Pym | 1-Me-3-Azt-CH₂ |
| 2-725 | 3-F—Ph | 2-NH₂-4-Pym | 3-Pyrd-CH₂ |
| 2-726 | 3-F—Ph | 2-NH₂-4-Pym | 1-Me-3-Pyrd-CH₂ |
| 2-727 | 3-F—Ph | 2-NH₂-4-Pym | 4-Pip-CH₂ |
| 2-728 | 3-F—Ph | 2-NH₂-4-Pym | 1-Me-4-Pip-CH₂ |
| 2-729 | 3-F—Ph | 2-NH₂-4-Pym | 3-Hpip-CH₂ |
| 2-730 | 3-F—Ph | 2-NH₂-4-Pym | 1-Me-3-Hpip-CH₂ |
| 2-731 | 3-F—Ph | 2-NH₂-4-Pym | 4-Hpip-CH₂ |
| 2-732 | 3-F—Ph | 2-NH₂-4-Pym | 1-Me-4-Hpip-CH₂ |
| 2-733 | 3-F—Ph | 2-NH₂-4-Pym | 2-Mor-CH₂ |
| 2-734 | 3-F—Ph | 2-NH₂-4-Pym | 1-Me-2-Mor-CH₂ |
| 2-735 | 3-F—Ph | 2-NH₂-4-Pym | 2-Tmor-CH₂ |
| 2-736 | 3-F—Ph | 2-NH₂-4-Pym | 1-Me-2-Tmor-CH₂ |
| 2-737 | 3-F—Ph | 2-NH₂-4-Pym | 1-Piz-CH₂ |
| 2-738 | 3-F—Ph | 2-NH₂-4-Pym | 4-Me-1-Piz-CH₂ |
| 2-739 | 3-F—Ph | 2-NH₂-4-Pym | 2-Piz-CH₂ |
| 2-740 | 3-F—Ph | 2-NH₂-4-Pym | 4-Pyr-CH₂ |
| 2-741 | 3-F—Ph | 2-NH₂-4-Pym | 3-Pyr-CH₂ |
| 2-742 | 3-F—Ph | 2-NH₂-4-Pym | 2-Pyr-CH₂ |
| 2-743 | 3-F—Ph | 2-NH₂-4-Pym | 4-Pym-CH₂ |
| 2-744 | 3-F—Ph | 2-NH₂-4-Pym | 5-Pym-CH₂ |
| 2-745 | 3-F—Ph | 2-NH₂-4-Pym | 2-Pym-CH₂ |
| 2-746 | 3,4-diF—Ph | 2-NH₂-4-Pym | H₂N—CH₂ |
| 2-747 | 3,4-diF—Ph | 2-NH₂-4-Pym | H₂N—(CH₂)₂ |
| 2-748 | 3,4-diF—Ph | 2-NH₂-4-Pym | H₂N—(CH₂)₃ |
| 2-749 | 3,4-diF—Ph | 2-NH₂-4-Pym | H₂N—(CH₂)₄ |
| 2-750 | 3,4-diF—Ph | 2-NH₂-4-Pym | MeNH—CH₂ |
| 2-751 | 3,4-diF—Ph | 2-NH₂-4-Pym | MeNH—(CH₂)₂ |
| 2-752 | 3,4-diF—Ph | 2-NH₂-4-Pym | MeNH—(CH₂)₃ |
| 2-753 | 3,4-diF—Ph | 2-NH₂-4-Pym | MeNH—(CH₂)₄ |
| 2-754 | 3,4-diF—Ph | 2-NH₂-4-Pym | EtNH—CH₂ |
| 2-755 | 3,4-diF—Ph | 2-NH₂-4-Pym | EtNH—(CH₂)₂ |
| 2-756 | 3,4-diF—Ph | 2-NH₂-4-Pym | EtNH—(CH₂)₃ |
| 2-757 | 3,4-diF—P1i | 2-NH₂-4-Pym | EtNH—(CH₂)₄ |
| 2-758 | 3,4-diF—Ph | 2-NH₂-4-Pym | Me₂N—CH₂ |
| 2-759 | 3,4-diF—Ph | 2-NH₂-4-Pym | Me₂N—(CH₂)₂ |
| 2-760 | 3,4-diF—Ph | 2-NH₂-4-Pym | Me₂N—(CH₂)₃ |
| 2-761 | 3,4-diF—Ph | 2-NH₂-4-Pym | Me₂N—(CH₂)₄ |
| 2-762 | 3,4-diF—Ph | 2-NH₂-4-Pym | 1-Azt-CH₂ |
| 2-763 | 3,4-diF—Ph | 2-NH₂-4-Pym | 1-Azt-(CH₂)₂ |
| 2-764 | 3,4-diF—Ph | 2-NH₂-4-Pym | 1-Azt-(CH₂)₃ |
| 2-765 | 3,4-diF—Ph | 2-NH₂-4-Pym | 1-Azt-(CH₂)₄ |
| 2-766 | 3,4-diF—Ph | 2-NH₂-4-Pym | 1-Pyrd-CH₂ |
| 2-767 | 3,4-diF—Ph | 2-NH₂-4-Pym | 1-Pyrd-(CH₂)₂ |
| 2-768 | 3,4-diF—Ph | 2-NH₂-4-Pym | 1-Pyrd-(CH₂)₃ |
| 2-769 | 3,4-diF—Ph | 2-NH₂-4-Pym | 1-Pyrd-(CH₂)₄ |
| 2-770 | 3,4-diF—Ph | 2-NH₂-4-Pym | 1-Pip-CH₂ |
| 2-771 | 3,4-diF—Ph | 2-NH₂-4-Pym | 1-Pip-(CH₂)₂ |
| 2-772 | 3,4-diF—Ph | 2-NH₂-4-Pym | 1-Pip-(CH₂)₃ |
| 2-773 | 3,4-diF—Ph | 2-NH₂-4-Pym | 1-Pip-(CH₂)₄ |
| 2-774 | 3,4-diF—Ph | 2-NH₂-4-Pym | 1-Mor-CH₂ |
| 2-775 | 3,4-diF—Ph | 2-NH₂-4-Pym | 1-Mor-(CH₂)₂ |
| 2-776 | 3,4-diF—Ph | 2-NH₂-4-Pym | 1-Mor-(CH₂)₃ |
| 2-777 | 3,4-diF—Ph | 2-NH₂-4-Pym | 1-Mor-(CH₂)₄ |
| 2-778 | 3,4-diF—Ph | 2-NH₂-4-Pym | 1-Tmor-CH₂ |
| 2-779 | 3,4-diF—Ph | 2-NH₂-4-Pym | 1-Tmor-(CH₂)₂ |
| 2-780 | 3,4-diF—Ph | 2-NH₂-4-Pym | 1-Tmor-(CH₂)₃ |
| 2-781 | 3,4-diF—Ph | 2-NH₂-4-Pym | 1-Tmor-(CH₂)₄ |
| 2-782 | 3,4-diF—Ph | 2-NH₂-4-Pym | 1-Piz-CH₂ |
| 2-783 | 3,4-diF—Ph | 2-NH₂-4-Pym | 1-Piz-(CH₂)₂ |
| 2-784 | 3,4-diF—Ph | 2-NH₂-4-Pym | 1-Piz-(CH₂)₃ |
| 2-785 | 3,4-diF—Ph | 2-NH₂-4-Pym | 4-Me-1-Piz-(CH₂)₃ |
| 2-786 | 3,4-diF—Ph | 2-NH₂-4-Pym | 1-Piz-(CH₂)₄ |
| 2-787 | 3,4-diF—Ph | 2-NH₂-4-Pym | 3-Azt |
| 2-788 | 3,4-diF—Ph | 2-NH₂-4-Pym | 1-Me-3-Azt |
| 2-789 | 3,4-diF—Ph | 2-NH₂-4-Pym | 1-Bn-3-Azt |
| 2-790 | 3,4-diF—Ph | 2-NH₂-4-Pym | 3-Pyrd |
| 2-791 | 3,4-diF—Ph | 2-NH₂-4-Pym | 1-Me-3-Pyrd |
| 2-792 | 3,4-diF—Ph | 2-NH₂-4-Pym | 3-Pip |
| 2-793 | 3,4-diF—Ph | 2-NH₂-4-Pym | 4-Pip |
| 2-794 | 3,4-diF—Ph | 2-NH₂-4-Pym | 4-(3,4-deH-Pip) |
| 2-795 | 3,4-diF—Ph | 2-NH₂-4-Pym | 1-Me-4-Pip |
| 2-796 | 3,4-diF—Ph | 2-NH₂-4-Pym | 1-Me-4-(3,4-deH-Pip) |
| 2-797 | 3,4-diF—Ph | 2-NH₂-4-Pym | 1-Et-4-Pip |
| 2-798 | 3,4-diF—Ph | 2-NH₂-4-Pym | 1-Bn-4-Pip |
| 2-799 | 3,4-diF—Ph | 2-NH₂-4-Pym | 3-Hpip |
| 2-800 | 3,4-diF—Ph | 2-NH₂-4-Pym | 1-Me-3-Hpip |
| 2-801 | 3,4-diF—Ph | 2-NH₂-4-Pym | 4-Hpip |
| 2-802 | 3,4-diF—Ph | 2-NH₂-4-Pym | 1-Me4-Hpip |
| 2-803 | 3,4-diF—Ph | 2-NH₂-4-Pym | 2-Mor |
| 2-804 | 3,4-diF—Ph | 2-NH₂-4-Pym | 1-Me-2-Mor |
| 2-805 | 3,4-diF—Ph | 2-NH₂-4-Pym | 2-Tmor |
| 2-806 | 3,4-diF—Ph | 2-NH₂-4-Pym | 1-Me-2-Tmor |
| 2-807 | 3,4-diF—Ph | 2-NH₂-4-Pym | 1-Piz |
| 2-808 | 3,4-diF—Ph | 2-NH₂-4-Pym | 4-Me-1-Piz |
| 2-809 | 3,4-diF—Ph | 2-NH₂-4-Pym | 2-Piz |
| 2-810 | 3,4-diF—Ph | 2-NH₂-4-Pym | 4-Pyr |
| 2-811 | 3,4-diF—Ph | 2-NH₂-4-Pym | 3-Pyr |
| 2-812 | 3,4-diF—Ph | 2-NH₂-4-Pym | 2-Pyr |
| 2-813 | 3,4-diF—Ph | 2-NH₂-4-Pym | 4-Pym |
| 2-814 | 3,4-diF—Ph | 2-NH₂-4-Pym | 5-Pym |
| 2-815 | 3,4-diP—Ph | 2-NH₂-4-Pym | 2-Pym |
| 2-816 | 3,4-diF—Ph | 2-NH₂-4-Pym | 3-Azt-CH₂ |
| 2-817 | 3,4-diP—Ph | 2-NH₂-4-Pym | 1-Me-3-Azt-CH₂ |
| 2-818 | 3,4-diF—Ph | 2-NH₂-4-Pym | 3-Pyrd-CH₂ |
| 2-819 | 3,4-diF—Ph | 2-NH₂-4-Pym | 1-Me-3-Pyrd-CH₂ |
| 2-820 | 3,4-diF—Ph | 2-NH₂-4-Pym | 4-Pip-CH₂ |
| 2-821 | 3,4-diF—Ph | 2-NH₂-4-Pym | 1-Me-4-Pip-CH₂ |
| 2-822 | 3,4-diF—Ph | 2-NH₂-4-Pym | 3-Hpip-CH₂ |
| 2-823 | 3,4-diF—Ph | 2-NH₂-4-Pym | 1-Me-3-Hpip-CH₂ |
| 2-824 | 3,4-diF—Ph | 2-NH₂-4-Pym | 4-Hpip-CH₂ |
| 2-825 | 3,4-diF—Ph | 2-NH₂-4-Pym | 1-Me-4-Hpip-CH₂ |
| 2-826 | 3,4-diF—Ph | 2-NH₂-4-Pym | 2-Mor-CH₂ |
| 2-827 | 3,4-diF—Ph | 2-NH₂-4-Pym | 1-Me-2-Mor-CH₂ |

TABLE 2-continued

| Compound No. | R¹ | R² | R³ |
|---|---|---|---|
| 2-828 | 3,4-diF—Ph | 2-NH₂-4-Pym | 2-Tmor-CH₂ |
| 2-829 | 3,4-diF—Ph | 2-NH₂-4-Pym | 1-Me-2-Tmor-CH₂ |
| 2-830 | 3,4-diF—Ph | 2-NH₂-4-Pym | 1-Piz-CH₂ |
| 2-831 | 3,4-diF—Ph | 2-NH₂-4-Pym | 4-Me-1-Piz-CH₂ |
| 2-832 | 3,4-diF—Ph | 2-NH₂-4-Pym | 2-Piz-CH₂ |
| 2-833 | 3,4-diF—Ph | 2-NH₂-4-Pym | 4-Pyr-CH₂ |
| 2-834 | 3,4-diF—Ph | 2-NH₂-4-Pym | 3-Pyr-CH₂ |
| 2-835 | 3,4-diF—Ph | 2-NH₂-4-Pym | 2-Pyr-CH₂ |
| 2-836 | 3,4-diF—Ph | 2-NH₂-4-Pym | 4-Pym-CH₂ |
| 2-837 | 3,4-diF—Ph | 2-NH₂-4-Pym | 5-Pym-CH₂ |
| 2-838 | 3,4-diF—Ph | 2-NH₂-4-Pym | 2-Pym-CH₂ |
| 2-839 | 3-Cl—Ph | 2-NH₂-4-Pym | H₂N—CH₂ |
| 2-840 | 3-Cl—Ph | 2-NH₂-4-Pym | H₂N—(CH₂)₂ |
| 2-841 | 3-Cl—Ph | 2-NH₂-4-Pym | H₂N—(CH₂)₃ |
| 2-842 | 3-Cl—Ph | 2-NH₂-4-Pym | H₂N—(CH₂)₄ |
| 2-843 | 3-Cl—Ph | 2—NH₂'—4-Pym | MeNH—CH₂ |
| 2-844 | 3-Cl—Ph | 2-NH₂-4-Pym | MeNH—(CH₂)₂ |
| 2-845 | 3-Cl—Ph | 2-NH₂-4-Pym | MeNH—(CH₂)₃ |
| 2-846 | 3-Cl—Ph | 2-NH₂-4-Pym | MeNH—(CH₂)₄ |
| 2-847 | 3-Cl—Ph | 2-NH₂-4-Pym | EtNH—CH₂ |
| 2-848 | 3-Cl—Ph | 2-NH₂-4-Pym | EtNH—(CH₂)₂ |
| 2-849 | 3-Cl—Ph | 2-NH₂-4-Pym | EtNH—(CH₂)₃ |
| 2-850 | 3-Cl—Ph | 2-NH₂-4-Pym | EtNH—(CH₂)₄ |
| 2-851 | 3-Cl—Ph | 2-NH₂-4-Pym | Me₂N—CH₂ |
| 2-852 | 3-Cl—Ph | 2-NH₂-4-Pym | Me₂N—(CH₂)₂ |
| 2-853 | 3-Cl—Ph | 2-NH₂-4-Pym | Me₂N—(CH₂)₃ |
| 2-854 | 3-Cl—Ph | 2-NH₂-4-Pym | Me₂N—(CH₂)₄ |
| 2-855 | 3-Cl—Ph | 2-NH₂-4-Pym | 1-Azt-CH₂ |
| 2-856 | 3-Cl—Ph | 2-NH₂-4-Pym | 1-Azt-(CH₂)₂ |
| 2-857 | 3-Cl—Ph | 2-NH₂-4-Pym | 1-Azt-(CH₂)₃ |
| 2-858 | 3-Cl—Ph | 2-NH₂-4-Pym | 1-Azt-(CH₂)₄ |
| 2-859 | 3-Cl—Ph | 2-NH₂-4-Pym | 1-Pyrd-CH₂ |
| 2-860 | 3-Cl—Ph | 2-NH₂-4-Pym | 1-Pyrd-(CH₂)₂ |
| 2-861 | 3-Cl—Ph | 2-NH₂-4-Pym | 1-Pyrd-(CH₂)₃ |
| 2-862 | 3-Cl—Ph | 2-NH₂-4-Pym | 1-Pyrd-(CH₂)₄ |
| 2-863 | 3-Cl—Ph | 2-NH₂-4-Pym | 1-Pip-CH₂ |
| 2-864 | 3-Cl—Ph | 2-NH₂-4-Pym | 1-Pip-(CH₂)₂ |
| 2-865 | 3-Cl—Ph | 2-NH₂-4-Pym | 1-Pip-(CH₂)₃ |
| 2-866 | 3-Cl—Ph | 2-NH₂-4-Pym | 1-Pip-(CH₂)₄ |
| 2-867 | 3-Cl—Ph | 2-NH₂-4-Pym | 1-Mor-CH₂ |
| 2-868 | 3-Cl—Ph | 2-NH₂-4-Pym | 1-Mor-(CH₂)₂ |
| 2-869 | 3-Cl—Ph | 2-NH₂-4-Pym | 1-Mor-(CH₂)₃ |
| 2-870 | 3-Cl—Ph | 2-NH₂-4-Pym | 1-Mor-(CH₂)₄ |
| 2-871 | 3-Cl—Ph | 2-NH₂-4-Pym | 1-Tmor-CH₂ |
| 2-872 | 3-Cl—Ph | 2-NH₂-4-Pym | 1-Tmor-(CH₂)₂ |
| 2-873 | 3-Cl—Ph | 2-NH₂-4-Pym | 1-Tmor-(CH₂)₃ |
| 2-874 | 3-Cl—Ph | 2-NH₂-4-Pym | 1-Tmor-(CH₂)₄ |
| 2-875 | 3-Cl—Ph | 2-NH₂-4-Pym | 1-Piz-CH₂ |
| 2-876 | 3-Cl—Ph | 2-NH₂-4-Pym | 1-Piz-(CH₂)₂ |
| 2-877 | 3-Cl—Ph | 2-NH₂-4-Pym | 1-Piz-(CH₂)₃ |
| 2-878 | 3-Cl—Ph | 2-NH₂-4-Pym | 4-Me-1-Piz-(CH₂)₃ |
| 2-879 | 3-Cl—Ph | 2-NH₂-4-Pym | 1-Piz-(CH₂)₄ |
| 2-880 | 3-Cl—Ph | 2-NH₂-4-Pym | 3-Azt |
| 2-881 | 3-Cl—Ph | 2-NH₂-4-Pym | 1-Me-3-Azt |
| 2-882 | 3-Cl—Ph | 2-NH₂-4-Pym | 1-Bn-3-Azt |
| 2-883 | 3-Cl—Ph | 2-NH₂-4-Pym | 3-Pyrd |
| 2-884 | 3-Cl—Ph | 2-NH₂-4-Pym | 1-Me-3-Pyrd |
| 2-885 | 3-Cl—Ph | 2-NH₂-4-Pym | 3-Pip |
| 2-886 | 3-Cl—Ph | 2-NH₂-4-Pym | 4-Pip |
| 2-887 | 3-Cl—Ph | 2-NH₂-4-Pym | 4-(3,4-deH-Pip) |
| 2-888 | 3-Cl—Ph | 2-NH₂-4-Pym | 1-Me-4-Pip |
| 2-889 | 3-Cl—Ph | 2-NH₂-4-Pym | 1-Me-4-(3,4-deH-Pip) |
| 2-890 | 3-Cl—Ph | 2-NH₂-4-Pym | 1-Et-4-Pip |
| 2-891 | 3-Cl—Ph | 2-NH₂-4-Pym | 1-Bn-4-Pip |
| 2-892 | 3-Cl—Ph | 2-NH₂-4-Pym | 3-Hpip |
| 2-893 | 3-Cl—Ph | 2-NH₂-4-Pym | 1-Me-3-Hpip |
| 2-894 | 3-Cl—Ph | 2-NH₂-4-Pym | 4-Hpip |
| 2-895 | 3-Cl—Ph | 2-NH₂-4-Pym | 1-Me-4-Hpip |
| 2-896 | 3-Cl—Ph | 2-NH₂-4-Pym | 2-Mor |
| 2-897 | 3-Cl—Ph | 2-NH₂-4-Pym | 1-Me-2-Mor |
| 2-898 | 3-Cl—Ph | 2-NH₂-4-Pym | 2-Tmor |
| 2-899 | 3-Cl—Ph | 2-NH₂-4-Pym | 1-Me-2-Tmor |
| 2-900 | 3-Cl—Ph | 2-NH₂-4-Pym | 1-Piz |
| 2-901 | 3-Cl—Ph | 2-NH₂-4-Pym | 4-Me-1-Piz |
| 2-902 | 3-Cl—Ph | 2-NH₂-4-Pym | 2-Piz |
| 2-903 | 3-Cl—Ph | 2-NH₂-4-Pym | 4-Pyr |
| 2-904 | 3-Cl—Ph | 2-NH₂-4-Pym | 3-Pyr |
| 2-905 | 3-Cl—Ph | 2-NH₂-4-Pym | 2-Pyr |
| 2-906 | 3-Cl—Ph | 2-NH₂-4-Pym | 4-Pym |
| 2-907 | 3-Cl—Ph | 2-NH₂-4-Pym | 5-Pym |
| 2-908 | 3-Cl—Ph | 2-NH₂-4-Pym | 2-Pym |
| 2-909 | 3-Cl—Ph | 2-NH₂-4-Pym | 3-Azt-CH₂ |
| 2-910 | 3-Cl—Ph | 2-NH₂-4-Pym | 1-Me-3-Azt-CH₂ |
| 2-911 | 3-Cl—Ph | 2-NH₂-4-Pym | 3-Pyrd-CH₂ |
| 2-912 | 3-Cl—Ph | 2-NH₂-4-Pym | 1-Me-3-Pyrd-CH₂ |
| 2-913 | 3-Cl—Ph | 2-NH₂-4-Pym | 4-Pip-CH₂ |
| 2-914 | 3-Cl—Ph | 2-NH₂-4-Pym | 1-Me-4-Pip-CH₂ |
| 2-915 | 3-Cl—Ph | 2—NH₂—4-Pym | 3-Hpip-CH₂ |
| 2-916 | 3-Cl—Ph | 2-NH₂-4-Pym | 1-Me-3-Hpip-CH₂ |
| 2-917 | 3-Cl—Ph | 2-NH₂-4-Pym | 4-Hpip-CH₂ |
| 2-918 | 3-Cl—Ph | 2-NH₂-4-Pym | 1-Me-4-Hpip-CH₂ |
| 2-919 | 3-Cl—Ph | 2-NH₂-4-Pym | 2-Mor-CH₂ |
| 2-920 | 3-Cl—Ph | 2—NH₂—4-Pym | 1-Me-2-Mor-CH₂ |
| 2-921 | 3-Cl—Ph | 2-NH₂-4-Pym | 2-Tmor-CH₂ |
| 2-922 | 3-Cl—Ph | 2-NH₂-4-Pym | 1-Me-2-Tmor-CH₂ |
| 2-923 | 3-Cl—Ph | 2-NH₂-4-Pym | 1-Piz-CH₂ |
| 2-924 | 3-Cl—Ph | 2-NH₂-4-Pym | 4-Me-1-Piz-CH₂ |
| 2-925 | 3-Cl—Ph | 2-NH₂-4-Pym | 2-Piz-CH₂ |
| 2-926 | 3-Cl—Ph | 2-NH₂-4-Pym | 4-Pyr-CH₂ |
| 2-927 | 3-Cl—Ph | 2-NH₂-4-Pym | 3-Pyr-CH₂ |
| 2-928 | 3-Cl—Ph | 2-NH₂-4-Pym | 2-Pyr-CH₂ |
| 2-929 | 3-Cl—Ph | 2-NH₂-4-Pym | 4-Pym-CH₂ |
| 2-930 | 3-Cl—Ph | 2-NH₂-4-Pym | 5-Pym-CH₂ |
| 2-931 | 3-Cl—Ph | 2-NH₂-4-Pym | 2-Pym-CH₂ |
| 2-932 | Ph | 2-MeNH-4-Pym | H₂N—CH₂ |
| 2-933 | Ph | 2-MeNH-4-Pym | H₂N—(CH₂)₂ |
| 2-934 | Ph | 2-MeNH-4-Pym | H₂N—(CH₂)₃ |
| 2-935 | Ph | 2-MeNH-4-Pym | H₂N—(CH₂)₄ |
| 2-936 | Ph | 2-MeNH-4-Pym | MeNH—CH₂ |
| 2-937 | Ph | 2-MeNH-4-Pym | MeNH—(CH₂)₂ |
| 2-938 | Ph | 2-MeNH-4-Pym | MeNH—(CH₂)₃ |
| 2-939 | Ph | 2-MeNH-4-Pym | MeNH—(CH₂)₄ |
| 2-940 | Ph | 2-MeNH-4-Pym | EtNH—CH₂ |
| 2-941 | Ph | 2-MeNH-4-Pym | EtNH—(CH₂)₂ |
| 2-942 | Ph | 2-MeNH-4-Pym | EtNH—(CH₂)₃ |
| 2-943 | Ph | 2-MeNH-4-PyM | EtNH—(CH₂)₄ |
| 2-944 | Ph | 2-MeNH-4-Pym | Me₂N—CH₂ |
| 2-945 | Ph | 2-MeNH-4-Pym | Me₂N—(CH₂)₂ |
| 2-946 | Ph | 2-MeNH-4-Pym | Me₂N—(CH₂)₃ |
| 2-947 | Ph | 2-MeNH-4-Pym | Me₂N—(CH₂)₄ |
| 2-948 | Ph | 2-MeNH-4-Pym | 1-Azt-CH₂ |
| 2-949 | Ph | 2-MeNH-4-Pym | 1-Azt-(CH₂)₂ |
| 2-950 | Ph | 2-MeNH-4-Pym | 1-Azt-(CH₂)₃ |
| 2-951 | Ph | 2-MeNH-4-Pym | 1-Azt-(CH₂)₄ |
| 2-952 | Ph | 2-MeNH-4-Pym | 1-Pyrd-CH₂ |
| 2-953 | Ph | 2-MeNH-4-Pym | 1-Pyrd-(CH₂)₂ |
| 2-954 | Ph | 2-MeNH-4-Pym | 1-Pyrd-(CH₂)₃ |
| 2-955 | Ph | 2-MeNH-4-Pym | 1-Pyrd-(CH₂)₄ |
| 2-956 | Ph | 2-MeNH-4-Pym | 1-Pip-CH₂ |
| 2-957 | Ph | 2-MeNH-4-Pym | 1-Pip-(CH₂)₂ |
| 2-958 | Ph | 2-MeNH-4-Pym | 1-Pip-(CH₂)₃ |
| 2-959 | Ph | 2-MeNH-4-Pym | 1-Pip-(CH₂)₄ |
| 2-960 | Ph | 2-MeNH-4-Pym | 1-Mor-CH₂ |
| 2-961 | Ph | 2-MeNH-4-Pym | 1-Mor-(CH₂)₂ |
| 2-962 | Ph | 2-MeNH-4-Pym | 1-Mor-(CH₂)₃ |
| 2-963 | Ph | 2-MeNH-4-Pym | 1-Mor-(CH₂)₄ |
| 2-964 | Ph | 2-MeNH-4-Pym | 1-Tmor-CH₂ |
| 2-965 | Ph | 2-MeNH-4-Pym | 1-Tmor-(CH₂)₂ |
| 2-966 | Ph | 2-MeNH-4-Pym | 1-Tmor-(CH₂)₃ |
| 2-967 | Ph | 2-MeNH-4-Pym | 1-Tmor-(CH₂)₄ |
| 2-968 | Ph | 2-MeNH-4-Pym | 1-Piz-CH₂ |
| 2-969 | Ph | 2-MeNH-4-Pym | 1-Piz-(CH₂)₂ |
| 2-970 | Ph | 2-MeNH-4-Pym | 1-Piz-(CH₂)₃ |
| 2-971 | Ph | 2-MeNH-4-Pym | 4-Me-1-Piz-(CH₂)₃ |
| 2-972 | Ph | 2-MeNH-4-Pym | 1-Piz-(CH₂)₄ |
| 2-973 | Ph | 2-MeNH-4-Pym | 3-Azt |
| 2-974 | Ph | 2-MeNH-4-Pym | 1-Me-3-Azt |
| 2-975 | Ph | 2-MeNH-4-Pym | 1-Bn-3-Azt |
| 2-976 | Ph | 2-MeNH-4-Pym | 3-Pyrd |
| 2-977 | Ph | 2-MeNH-4-Pym | 1-Me-3-Pyrd |

TABLE 2-continued

| Compound No. | R¹ | R² | R³ |
|---|---|---|---|
| 2-978 | Ph | 2-MeNH-4-Pym | 3-Pip |
| 2-979 | Ph | 2-MeNH-4-Pym | 4-Pip |
| 2-980 | Ph | 2-MeNH-4-Pym | 4-(3,4-deH-Pip) |
| 2-981 | Ph | 2-MeNH-4-Pym | 1-Me-4-Pip |
| 2-982 | Ph | 2-MeNH-4-Pym | 1-Me-4-(3,4-deH-Pip) |
| 2-983 | Ph | 2-MeNH-4-Pym | 1-Et-4-Pip |
| 2-984 | Ph | 2-MeNH-4-Pym | 1-Bn-4-Pip |
| 2-985 | Ph | 2-MeNH-4-Pym | 3-Hpip |
| 2-986 | Ph | 2-MeNH-4-Pym | 1-Me-3-Hpip |
| 2-987 | Ph | 2-MeNH-4-Pym | 4-Hpip |
| 2-988 | Ph | 2-MeNH-4-Pym | 1-Me-4-Hpip |
| 2-989 | Ph | 2-MeNH-4-Pym | 2-Mor |
| 2-990 | Ph | 2-MeNH-4-Pym | 1-Me-2-Mor |
| 2-991 | Ph | 2-MeNH-4-Pym | 2-Tmor |
| 2-992 | Ph | 2-MeNH-4-Pym | 1-Me-2-Tmor |
| 2-993 | Ph | 2-MeNH-4-Pym | 1-Piz |
| 2-994 | Ph | 2-MeNH-4-Pym | 4-Me-1-Piz |
| 2-995 | Ph | 2-MeNH-4-Pym | 2-Piz |
| 2-996 | Ph | 2-MeNH-4-Pym | 4-Pyr |
| 2-997 | Ph | 2-MeNH-4-Pym | 3-Pyr |
| 2-998 | Ph | 2-MeNH-4-Pym | 2-Pyr |
| 2-999 | Ph | 2-MeNH-4-Pym | 4-Pym |
| 2-1000 | Ph | 2-MeNH-4-Pym | 5-Pym |
| 2-1001 | Ph | 2-MeNH-4-Pym | 2-Pym |
| 2-1002 | Ph | 2-MeNH-4-Pym | 3-Azt-CH$_2$ |
| 2-1003 | Ph | 2-MeNH-4-Pym | 1-Me-3-Azt-CH$_2$ |
| 2-1004 | Ph | 2-MeNH-4-Pym | 3-Pyrd-CH$_2$ |
| 2-1005 | Ph | 2-MeNH-4-Pym | 1-Me-3-Pyrd-CH$_2$ |
| 2-1006 | Ph | 2-MeNH-4-Pym | 4-Pip-CH$_2$ |
| 2-1007 | Ph | 2-MeNH-4-Pym | 1-Me-4-Pip-CH$_2$ |
| 2-1008 | Ph | 2-MeNH-4-Pym | 3-Hpip-CH$_2$ |
| 2-1009 | Ph | 2-MeNH-4-Pym | 1-Me-3-Hpip-CH$_2$ |
| 2-1010 | Ph | 2-MeNH-4-Pym | 4-Hpip-CH$_2$ |
| 2-1011 | Ph | 2-MeNH-4-Pym | 1-Me-4-Hpip-CH$_2$ |
| 2-1012 | Ph | 2-MeNH-4-Pym | 2-Mor-CH$_2$ |
| 2-1013 | Ph | 2-MeNH-4-Pym | 1-Me-2-Mor-CH$_2$ |
| 2-1014 | Ph | 2-MeNH-4-Pym | 2-Tmor-CH$_2$ |
| 2-1015 | Ph | 2-MeNH-4-Pym | 1-Me-2-Tmor-CH$_2$ |
| 2-1016 | Ph | 2-MeNH-4-Pym | 1-Piz-CH$_2$ |
| 2-1017 | Ph | 2-MeNH-4-Pym | 4-Me-1-Piz-CH$_2$ |
| 2-1018 | Ph | 2-MeNH-4-Pym | 2-Piz-CH$_2$ |
| 2-1019 | Ph | 2-MeNH-4-Pym | 4-Pyr-CH$_2$ |
| 2-1020 | Ph | 2-MeNH-4-Pym | 3-Pyr-CH$_2$ |
| 2-1021 | Ph | 2-MeNH-4-Pym | 2-Pyr-CH$_2$ |
| 2-1022 | Ph | 2-MeNH-4-Pym | 4-Pym-CH$_2$ |
| 2-1023 | Ph | 2-MeNH-4-Pym | 5-Pym-CH$_2$ |
| 2-1024 | Ph | 2-MeNH-4-Pym | 2-Pym-CH$_2$ |
| 2-1025 | 4-F—Ph | 2-MeNH-4-Pym | H$_2$N—CH$_2$ |
| 2-1026 | 4-F—Ph | 2-MeNH-4-Pym | H$_2$N—(CH$_2$)$_2$ |
| 2-1027 | 4-F—Ph | 2-MeNH-4-Pym | H$_2$N—(CH$_2$)$_3$ |
| 2-1028 | 4-F—Ph | 2-MeNH-4-Pym | H$_2$N—(CH$_2$)$_4$ |
| 2-1029 | 4-F—Ph | 2-MeNH-4-Pym | MeNH—CH$_2$ |
| 2-1030 | 4-F—Ph | 2-MeNH-4-Pym | MeNH—(CH$_2$)$_2$ |
| 2-1031 | 4-F—Ph | 2-MeNH-4-Pym | MeNH—(CH$_2$)$_3$ |
| 2-1032 | 4-F—Ph | 2-MeNH-4-Pym | MeNH—(CH$_2$)$_4$ |
| 2-1033 | 4-F—Ph | 2-MeNH-4-Pym | EtNH—CH$_2$ |
| 2-1034 | 4-F—Ph | 2-MeNH-4-Pym | EtNH—(CH$_2$)$_2$ |
| 2-1035 | 4-F—Ph | 2-MeNH-4-Pym | EtNH—(CH$_2$)$_3$ |
| 2-1036 | 4-F—Ph | 2-MeNH-4-Pym | EtNH—(CH$_2$)$_4$ |
| 2-1037 | 4-F—Ph | 2-MeNH-4-Pym | Me$_2$N—CH$_2$ |
| 2-1038 | 4-F—Ph | 2-MeNH-4-Pym | Me$_2$N—(CH$_2$)$_2$ |
| 2-1039 | 4-F—Ph | 2-MeNH-4-Pym | Me$_2$N—(CH$_2$)$_3$ |
| 2-1040 | 4-F—Ph | 2-MeNH-4—PyM | Me$_2$N—(CH$_2$)$_4$ |
| 2-1041 | 4-F—Ph | 2-MeNH-4-Pym | 1-Azt-CH$_2$ |
| 2-1042 | 4-F—Ph | 2-MeNH-4-Pym | 1-Azt-(CH$_2$)$_2$ |
| 2-1043 | 4-F—Ph | 2-MeNH-4-Pym | 1-Azt-(CH$_2$)$_3$ |
| 2-1044 | 4-F—Ph | 2-MeNH-4-Pym | 1-Azt-(CH$_2$)$_4$ |
| 2-1045 | 4-F—Ph | 2-MeNH-4-Pym | 1-Pyrd-CH$_2$ |
| 2-1046 | 4-F—Ph | 2-MeNH-4-Pym | 1-Pyrd-(CH$_2$)$_2$ |
| 2-1047 | 4-F—Ph | 2-MeNH-4-Pym | 1-Pyrd-(CH$_2$)$_3$ |
| 2-1048 | 4-F—Ph | 2-MeNH-4-Pym | 1-Pyrd-(CH$_2$)$_4$ |
| 2-1049 | 4-F—Ph | 2-MeNH-4-Pym | 1-Pip-CH$_2$ |
| 2-1050 | 4-F—Ph | 2-MeNH-4-Pym | 1-Pip-(CH$_2$)$_2$ |
| 2-1051 | 4-F—Ph | 2-MeNH-4-Pym | 1-Pip-(CH$_2$)$_3$ |
| 2-1052 | 4-F—Ph | 2-MeNH-4-Pym | 1-Pip-(CH$_2$)$_4$ |
| 2-1053 | 4-F—Ph | 2-MeNH-4-Pym | 1-Mor-CH$_2$ |
| 2-1054 | 4-F—Ph | 2-MeNH-4-Pym | 1-Mor-(CH$_2$)$_2$ |
| 2-1055 | 4-F—Ph | 2-MeNH-4-Pym | 1-Mor-(CH$_2$)$_3$ |
| 2-1056 | 4-F—Ph | 2-MeNH-4-Pym | 1-Mor-(CH$_2$)$_4$ |
| 2-1057 | 4-F—Ph | 2-MeNH-4-Pym | 1-Tmor-CH$_2$ |
| 2-1058 | 4-F—Ph | 2-MeNH-4-Pym | 1-Tmor-(CH$_2$)$_2$ |
| 2-1059 | 4-F—Ph | 2-MeNH-4-Pym | 1-Tmor-(CH$_2$)$_3$ |
| 2-1060 | 4-F—Ph | 2-MeNH-4-Pym | 1-Tmor-(CH$_2$)$_4$ |
| 2-1061 | 4-F—Ph | 2-MeNH-4-Pym | 1-Piz-CH$_2$ |
| 2-1062 | 4-F—Ph | 2-MeNH-4-Pym | 1-Piz-(CH$_2$)$_2$ |
| 2-1063 | 4-F—Ph | 2-MeNH-4-Pym | 1-Piz-(CH$_2$)$_3$ |
| 2-1064 | 4-F—Ph | 2-MeNH-4-Pym | 4-Me-1-Piz-(CH$_2$)$_3$ |
| 2-1065 | 4-F—Ph | 2-MeNH-4-Pym | 1-Piz-(CH$_2$)$_4$ |
| 2-1066 | 4-F—Ph | 2-MeNH-4-Pym | 3-Azt |
| 2-1067 | 4-F—Ph | 2-MeNH-4-Pym | 1-Me-3-Azt |
| 2-1068 | 4-F—Ph | 2-MeNH-4-Pym | 1-Bn-3-Azt |
| 2-1069 | 4-F—Ph | 2-MeNH-4-Pym | 3-Pyrd |
| 2-1070 | 4-F—Ph | 2-MeNH-4-Pym | 1-Me-3-Pyrd |
| 2-1071 | 4-F—Ph | 2-MeNH-4-Pym | 3-Pip |
| 2-1072 | 4-F—Ph | 2-MeNH-4-Pym | 4-Pip |
| 2-1073 | 4-F—Ph | 2-MeNH-4-Pym | 4-(3,4-deH-Pip) |
| 2-1074 | 4-F—Ph | 2-MeNH-4-Pym | 1-Me-4-Pip |
| 2-1075 | 4-F—Ph | 2-MeNH-4-Pym | 1-Me-4-(3,4-deH-Pip) |
| 2-1076 | 4-F—Ph | 2-MeNH-4-Pym | 1-Et-4-Pip |
| 2-1077 | 4-F—Ph | 2-MeNH-4-Pym | 1-Bn-4-Pip |
| 2-1078 | 4-F—Ph | 2-MeNH-4-Pym | 3-Hpip |
| 2-1079 | 4-F—Ph | 2-MeNH-4-Pym | 1-Me-3-Hpip |
| 2-1080 | 4-F—Ph | 2-MeNH-4-Pym | 4-Hpip |
| 2-1081 | 4-F—Ph | 2-MeNH-4-Pym | 1-Me-4-Hpip |
| 2-1082 | 4-F—Ph | 2-MeNH-4-Pym | 2-Mor |
| 2-1083 | 4-F—Ph | 2-MeNH-4-Pym | 1-Me-2-Mor |
| 2-1084 | 4-F—Ph | 2-MeNH-4-Pym | 2-Tmor |
| 2-1085 | 4-F—Ph | 2-MeNH-4-Pym | 1-Me-2-Tmor |
| 2-1086 | 4-F—Ph | 2-MeNH-4-Pym | 1-Piz |
| 2-1087 | 4-F—Ph | 2-MeNH-4-Pym | 4-Me-1-Piz |
| 2-1088 | 4-F—Ph | 2-MeNH-4-Pym | 2-Piz |
| 2-1089 | 4-F—Ph | 2-MeNH-4-Pym | 4-Pyr |
| 2-1090 | 4-F—Ph | 2-MeNH-4-Pym | 3-Pyr |
| 2-1091 | 4-F—Ph | 2-MeNH-4-Pym | 2-Pyr |
| 2-1092 | 4-F—Ph | 2-MeNH-4-Pym | 4-Pym |
| 2-1093 | 4-F—Ph | 2-MeNH-4-Pym | 5-Pym |
| 2-1094 | 4-F—Ph | 2-MeNH-4-Pym | 2-Pym |
| 2-1095 | 4-F—Ph | 2-MeNH-4-Pym | 3-Azt-CH$_2$ |
| 2-1096 | 4-F—Ph | 2-MeNH-4-Pym | 1-Me-3-Azt-CH$_2$ |
| 2-1097 | 4-F—Ph | 2-MeNH-4-Pym | 3-Pyrd-CH$_2$ |
| 2-1098 | 4-F—Ph | 2-MeNH-4-Pym | 1-Me-3-Pyrd-CH$_2$ |
| 2-1099 | 4-F—Ph | 2-MeNH-4-Pym | 4-Pip-CH$_2$ |
| 2-1100 | 4-F—Ph | 2-MeNH-4-Pym | 1-Me-4-Pip-CH$_2$ |
| 2-1101 | 4-F—Ph | 2-MeNH-4-Pym | 3-Hpip-CH$_2$ |
| 2-1102 | 4-F—Ph | 2-MeNH-4-Pym | 1-Me-3-Hpip-CH$_2$ |
| 2-1103 | 4-F—Ph | 2-MeNH-4-Pym | 4-Hpip-CH$_2$ |
| 2-1104 | 4-F—Ph | 2-MeNH-4-Pym | 1-Me-4-Hpip-CH$_2$ |
| 2-1105 | 4-F—Ph | 2-MeNH-4-Pym | 2-Mor-CH$_2$ |
| 2-1106 | 4-F—Ph | 2-MeNH-4-Pym | 1-Me-2-Mor-CH$_2$ |
| 2-1107 | 4-F—Ph | 2-MeNH-4-Pym | 2-Tmor-CH$_2$ |
| 2-1108 | 4-F—Ph | 2-MeNH-4-Pym | 1-Me-2-Tmor-CH$_2$ |
| 2-1109 | 4-F—Ph | 2-MeNH-4-Pym | 1-Piz-CH$_2$ |
| 2-1110 | 4-F—Ph | 2-MeNH-4-Pym | 4-Me-1-Piz-CH$_2$ |
| 2-1111 | 4-F—Ph | 2-MeNH-4-Pym | 2-Piz-CH$_2$ |
| 2-1112 | 4-F—Ph | 2-MeNH-4-Pym | 4-Pyr-CH$_2$ |
| 2-1113 | 4-F—Ph | 2-MeNH-4-Pym | 3-Pyr-CH$_2$ |
| 2-1114 | 4-F—Ph | 2-MeNH-4-Pym | 2-Pyr-CH$_2$ |
| 2-1115 | 4-F—Ph | 2-MeNH-4-Pym | 4-Pym-CH$_2$ |
| 2-1116 | 4-F—Ph | 2-MeNH-4-Pym | 5-Pym-CH$_2$ |
| 2-1117 | 4-F—Ph | 2-MeNH-4-Pym | 2-Pym-CH$_2$ |
| 2-1118 | 3-F—Ph | 2-MeNH-4-Pym | H$_2$N—CH$_2$ |
| 2-1119 | 3-F—Ph | 2-MeNH-4-Pym | H$_2$N—(CH$_2$)$_2$ |
| 2-1120 | 3-F—Ph | 2-MeNH-4-Pym | H$_2$N—(CH$_2$)$_3$ |
| 2-1121 | 3-F—Ph | 2-MeNH-4-Pym | H$_2$N—(CH$_2$)$_4$ |
| 2-1122 | 3-F—Ph | 2-MeNH-4-Pym | MeNH—CH$_2$ |
| 2-1123 | 3-F—Ph | 2-MeNH-4-Pym | MeNH—(CH$_2$)$_2$ |
| 2-1124 | 3-F—Ph | 2-MeNH-4-Pym | MeNH—(CH$_2$)$_3$ |
| 2-1125 | 3-F—Ph | 2-MeNH-4-Pym | MeNH—(CH$_2$)$_4$ |
| 2-1126 | 3-F—Ph | 2-MeNH-4-Pym | EtNH—CH$_2$ |
| 2-1127 | 3-F—Ph | 2-MeNH-4-Pym | EtNH—(CH$_2$)$_2$ |

TABLE 2-continued

| Compound No. | R¹ | R² | R³ |
|---|---|---|---|
| 2-1128 | 3-F—Ph | 2-MeNH-4-Pym | EtNH—(CH$_2$)$_3$ |
| 2-1129 | 3-F—Ph | 2-MeNH-4-Pym | EtNH—(CH$_2$)$_4$ |
| 2-1130 | 3-F—Ph | 2-MeNH-4-Pym | Me$_2$N—CH$_2$ |
| 2-1131 | 3-F—Ph | 2-MeNH-4-Pym | Me$_2$N—(CH$_2$)$_2$ |
| 2-1132 | 3-F—Ph | 2-MeNH-4-Pym | Me$_2$N—(CH$_2$)$_3$ |
| 2-1133 | 3-F—Ph | 2-MeNH-4-Pym | Me$_2$N—(CH$_2$)$_4$ |
| 2-1134 | 3-F—Ph | 2-MeNH-4-Pym | 1-Azt-CH$_2$ |
| 2-1135 | 3-F—Ph | 2-MeNH-4-Pym | 1-Azt-(CH$_2$)$_2$ |
| 2-1136 | 3-F—Ph | 2-MeNH-4-Pym | 1-Azt-(CH$_2$)$_3$ |
| 2-1137 | 3-F—Ph | 2-MeNH-4-Pym | 1-Azt-(CH$_2$)$_4$ |
| 2-1138 | 3-F—Ph | 2-MeNH-4-Pym | 1-Pyrd-CH$_2$ |
| 2-1139 | 3-F—Ph | 2-MeNH-4-Pym | 1-Pyrd-(CH$_2$)$_2$ |
| 2-1140 | 3-F—Ph | 2-MeNH-4-Pym | 1-Pyrd-(CH$_2$)$_3$ |
| 2-1141 | 3-F—Ph | 2-MeNH-4-Pym | 1-Pyrd-(CH$_2$)HD 4 |
| 2-1142 | 3-F—Ph | 2-MeNH-4-Pym | 1-Pip-CH$_2$ |
| 2-1143 | 3-F—Ph | 2-MeNH-4-Pym | 1-Pip-(CH$_2$)$_2$ |
| 2-1144 | 3-F—Ph | 2-MeNH-4-Pym | 1-Pip-(CH$_2$)$_3$ |
| 2-1145 | 3-F—Ph | 2-MeNH-4-Pym | 1-Pip-(CH$_2$)$_4$ |
| 2-1146 | 3-F—Ph | 2-MeNH-4-Pym | 1-Mor-CH$_2$ |
| 2-1147 | 3-F—Ph | 2-MeNH-4-Pym | 1-Mor-(CH$_2$)$_2$ |
| 2-1148 | 3-F—Ph | 2-MeNH-4-Pym | 1-Mor-(CH$_2$)$_3$ |
| 2-1149 | 3-F—Ph | 2-MeNH-4-Pym | 1-Mor-(CH$_2$)$_4$ |
| 2-1150 | 3-F—Ph | 2-MeNH-4-Pym | 1-Tmor-CH$_2$ |
| 2-1151 | 3-F—Ph | 2-MeNH-4-Pym | 1-Tmor-(CH$_2$)$_2$ |
| 2-1152 | 3-F—Ph | 2-MeNH-4-Pym | 1-Tmor-(CH$_2$)$_3$ |
| 2-1153 | 3-F—Ph | 2-MeNH-4-Pym | 1-Tmor-(CH$_2$)$_4$ |
| 2-1154 | 3-F—Ph | 2-MeNH-4-Pym | 1-Piz-CH$_2$ |
| 2-1155 | 3-F—Ph | 2-MeNH-4-Pym | 1-Piz-(CH$_2$)$_2$ |
| 2-1156 | 3-F—Ph | 2-MeNH-4-Pym | 1-Piz-(CH$_2$)$_3$ |
| 2-1157 | 3-F—Ph | 2-MeNH-4-Pym | 4-Me-1-Piz-(CH$_2$)$_3$ |
| 2-1158 | 3-F—Ph | 2-MeNH-4-Pym | 1-Piz-(CH$_2$)$_4$ |
| 2-1159 | 3-F—Ph | 2-MeNH-4-Pym | 3-Azt |
| 2-1160 | 3-F—Ph | 2-MeNH-4-Pym | 1-Me-3-Azt |
| 2-1161 | 3-F—Ph | 2-MeNH-4-Pym | 1-Bn-3-Azt |
| 2-1162 | 3-F—Ph | 2-MeNH-4-Pym | 3-Pyrd |
| 2-1163 | 3-F—Ph | 2-MeNH-4-Pym | 1-Me-3-Pyrd |
| 2-1164 | 3-F—Ph | 2-MeNH-4-Pym | 3-Pip |
| 2-1165 | 3-F—Ph | 2-MeNH-4-Pym | 4-Pip |
| 2-1166 | 3-F—Ph | 2-MeNH-4-Pym | 4-(3,4-deH-Pip) |
| 2-1167 | 3-F—Ph | 2-MeNH-4-Pym | 1-Me-4-Pip |
| 2-1168 | 3-F—Ph | 2-MeNH-4-Pym | 1-Me-4-(3,4-deH-Pip) |
| 2-1169 | 3-F—Ph | 2-MeNH-4-Pym | 1-Et-4-Pip |
| 2-1170 | 3-F—Ph | 2-MeNH-4-Pym | 1-Bn-4-Pip |
| 2-1171 | 3-F—Ph | 2-MeNH-4-Pym | 3-Hpip |
| 2-1172 | 3-F—Ph | 2-MeNH-4-Pym | 1-Me-3-Hpip |
| 2-1173 | 3-F—Ph | 2-MeNH-4-Pym | 4-Hpip |
| 2-1174 | 3-F—Ph | 2-MeNH-4-Pym | 1-Me-4-Hpip |
| 2-1175 | 3-F—Ph | 2-MeNH-4-Pym | 2-Mor |
| 2-1176 | 3-F—Ph | 2-MeNH-4-Pym | 1-Me-2-Mor |
| 2-1177 | 3-F—Ph | 2-MeNH-4-Pym | 2-Tmor |
| 2-1178 | 3-F—Ph | 2-MeNH-4-Pym | 1-Me-2-Tmor |
| 2-1179 | 3-F—Ph | 2-MeNH-4-Pym | 1-Piz |
| 2-1180 | 3-F—Ph | 2-MeNH-4-Pym | 4-Me-1-Piz |
| 2-1181 | 3-F—Ph | 2-MeNH-4-Pym | 2-Piz |
| 2-1182 | 3-F—Ph | 2-MeNH-4-Pym | 4-Pyr |
| 2-1183 | 3-F—Ph | 2-MeNH-4-Pym | 3-Pyr |
| 2-1184 | 3-F—Ph | 2-MeNH-4-Pym | 2-Pyr |
| 2-1185 | 3-F—Ph | 2-MeNH-4-Pym | 4-Pym |
| 2-1186 | 3-F—Ph | 2-MeNH-4-Pym | 5-Pym |
| 2-1187 | 3-F—Ph | 2-MeNH-4-Pym | 2-Pym |
| 2-1188 | 3-F—Ph | 2-MeNH-4-Pym | 3-Azt-CH$_2$ |
| 2-1189 | 3-F—Ph | 2-MeNH-4-Pym | 1-Me-3-Azt-CH$_2$ |
| 2-1190 | 3-F—Ph | 2-MeNH-4-Pym | 3-Pyrd-CH$_2$ |
| 2-1191 | 3-F—Ph | 2-MeNH-4-Pym | 1-Me-3-Pyrd-CH$_2$ |
| 2-1192 | 3-F—Ph | 2-MeNH-4-Pym | 4-Pip-CH$_2$ |
| 2-1193 | 3-F—Ph | 2-MeNH-4-Pym | 1-Me-4-Pip-CH$_2$ |
| 2-1194 | 3-F—Ph | 2-MeNH-4-Pym | 3-Hpip-CH$_2$ |
| 2-1195 | 3-F—Ph | 2-MeNH-4-Pym | 1-Me-3-Hpip-CH$_2$ |
| 2-1196 | 3-F—Ph | 2-MeNH-4-Pym | 4-Hpip-CH$_2$ |
| 2-1197 | 3-F—Ph | 2-MeNH-4-Pym | 1-Me-4-Hpip-CH$_2$ |
| 2-1198 | 3-F—Ph | 2-MeNH-4-Pym | 2-Mor-CH$_2$ |
| 2-1199 | 3-F—Ph | 2-MeNH-4-Pym | 1-Me-2-Mor-CH$_2$ |
| 2-1200 | 3-F—Ph | 2-MeNH-4-Pym | 2-Tmor-CH$_2$ |
| 2-1201 | 3-F—Ph | 2-MeNH-4-Pym | 1-Me-2-Tmor-CH$_2$ |
| 2-1202 | 3-F—Ph | 2-MeNH-4-Pym | 1-Piz-CH$_2$ |
| 2-1203 | 3-F—Ph | 2-MeNH-4-Pym | 4-Me-1-Piz-CH$_2$ |
| 2-1204 | 3-F—Ph | 2-MeNH-4-Pym | 2-Piz-CH$_2$ |
| 2-1205 | 3-F—Ph | 2-MeNH-4-Pym | 4-Pyr-CH$_2$ |
| 2-1206 | 3-F—Ph | 2-MeNH-4-Pym | 3-Pyr-CH$_2$ |
| 2-1207 | 3-F—Ph | 2-MeNH-4-Pym | 2-Pyr-CH$_2$ |
| 2-1208 | 3-F—Ph | 2-MeNH-4-Pym | 4-Pym-CH$_2$ |
| 2-1209 | 3-F—Ph | 2-MeNH-4-Pym | 5-Pym-CH$_2$ |
| 2-1210 | 3-F—Ph | 2-MeNH-4-Pym | 2-Pym-CH$_2$ |
| 2-1211 | 3,4-diF—Ph | 2-MeNH-4-Pym | H$_2$N—CH$_2$ |
| 2-1212 | 3,4-diF—Ph | 2-MeNH-4-Pym | H$_2$N—(CH$_2$)$_2$ |
| 2-1213 | 3,4-diF—Ph | 2-MeNH-4-Pym | H$_2$N—(CH$_2$)$_3$ |
| 2-1214 | 3,4-diF—Ph | 2-MeNH-4-Pym | H$_2$N—(CH$_2$)$_4$ |
| 2-1215 | 3,4-diF—Ph | 2-MeNH-4-Pym | MeNH—CH$_2$ |
| 2-1216 | 3,4-diF—Ph | 2-MeNH-4-Pym | MeNH—(CH$_2$)$_2$ |
| 2-1217 | 3,4-diF—Ph | 2-MeNH-4-Pym | MeNH—(CH$_2$)$_3$ |
| 2-1218 | 3,4-diF—Ph | 2-MeNH-4-Pym | MeNH—(CH$_2$)$_4$ |
| 2-1219 | 3,4-diF—Ph | 2-MeNH-4-Pym | EtNH—CH$_2$ |
| 2-1220 | 3,4-diF—Ph | 2-MeNH-4-Pym | EtNH—(CH$_2$)$_2$ |
| 2-1221 | 3,4-diF—Ph | 2-MeNH-4-Pym | EtNH—(CH$_2$)$_3$ |
| 2-1222 | 3,4-diF—Ph | 2-MeNH-4-Pym | EtNH—(CH$_2$)$_4$ |
| 2-1223 | 3,4-diF—Ph | 2-MeNH-4-Pym | Me$_2$N—CH$_2$ |
| 2-1224 | 3,4-diF—Ph | 2-MeNH-4-Pym | Me$_2$N—(CH$_2$)$_2$ |
| 2-1225 | 3,4-diF—Ph | 2-MeNH-4-Pym | Me$_2$N—(CH$_2$)$_3$ |
| 2-1226 | 3,4-diF—Ph | 2-MeNH-4-Pym | Me$_2$N—(CH$_2$)$_4$ |
| 2-1227 | 3,4-diF—Ph | 2-MeNH-4-Pym | 1-Azt-CH$_2$ |
| 2-1228 | 3,4-diF—Ph | 2-MeNH-4-Pym | 1-Azt-(CH$_2$)$_2$ |
| 2-1229 | 3,4-diF—Ph | 2-MeNH-4-Pym | 1-Azt-(CH$_2$)$_3$ |
| 2-1230 | 3,4-diF—Ph | 2-MeNH-4-Pym | 1-Azt-(CH$_2$)$_4$ |
| 2-1231 | 3,4-diF—Ph | 2-MeNH-4-Pym | 1-Pyrd-CH$_2$ |
| 2-1232 | 3,4-diF—Ph | 2-MeNH-4-Pym | 1-Pyrd-(CH$_2$)$_2$ |
| 2-1233 | 3,4-diF—Ph | 2-MeNH-4-Pym | 1-Pyrd-(CH$_2$)$_3$ |
| 2-1234 | 3,4-diF—Ph | 2-MeNH-4-Pym | 1-Pyrd-(CH$_2$)$_4$ |
| 2-1235 | 3,4-diF—Ph | 2-MeNH-4-Pym | 1-Pip-CH$_2$ |
| 2-1236 | 3,4-diF—Ph | 2-MeNH-4-Pym | 1-Pip-(CH$_2$)$_2$ |
| 2-1237 | 3,4-diF—Ph | 2-MeNH-4-Pym | 1-Pip-(CH$_2$)$_3$ |
| 2-1238 | 3,4-diF—Ph | 2-MeNH-4-Pym | 1-Pip-(CH$_2$)$_4$ |
| 2-1239 | 3,4-diF—Ph | 2-MeNH-4-Pym | 1-Mor-CH$_2$ |
| 2-1240 | 3,4-diF—Ph | 2-MeNH-4-Pym | 1-Mor-(CH$_2$)$_2$ |
| 2-1241 | 3,4-diF—Ph | 2-MeNH-4-Pym | 1-Mor-(CH$_2$)$_3$ |
| 2-1242 | 3,4-diF—Ph | 2-MeNH-4-Pym | 1-Mor-(CH$_2$)$_4$ |
| 2-1243 | 3,4-diF—Ph | 2-MeNH-4-Pym | 1-Tmor-CH$_2$ |
| 2-1244 | 3,4-diF—Ph | 2-MeNH-4-Pym | 1-Tmor-(CH$_2$)$_2$ |
| 2-1245 | 3,4-diF—Ph | 2-MeNH-4-Pym | 1-Tmor-(CH$_2$)$_3$ |
| 2-1246 | 3,4-diF—Ph | 2-MeNH-4-Pym | 1-Tmor-(CH$_2$)$_4$ |
| 2-1247 | 3,4-diF—Ph | 2-MeNH-4-Pym | 1-Piz-CH$_2$ |
| 2-1248 | 3,4-diF—Ph | 2-MeNH-4-Pym | 1-Piz-(CH$_2$)$_2$ |
| 2-1249 | 3,4-diF—Ph | 2-MeNH-4-Pym | 1-Piz-(CH$_2$)$_3$ |
| 2-1250 | 3,4-diF—Ph | 2-MeNH-4-Pym | 4-Me-1-Piz-(CH$_2$)$_3$ |
| 2-1251 | 3,4-diF—Ph | 2-MeNH-4-Pym | 1-Piz-(CH$_2$)$_4$ |
| 2-1252 | 3,4-diF—Ph | 2-MeNH-4-Pym | 3-Azt |
| 2-1253 | 3,4-diF—Ph | 2-MeNH-4-Pym | 1-Me-3-Azt |
| 2-1254 | 3,4-diF—Ph | 2-MeNH-4-Pym | 1-Bn-3-Azt |
| 2-1255 | 3,4-diF—Ph | 2-MeNH-4-Pym | 3-Pyrd |
| 2-1256 | 3,4-diF—Ph | 2-MeNH-4-Pym | 1-Me-3-Pyrd |
| 2-1257 | 3,4-diF—Ph | 2-MeNH-4-Pym | 3-Pip |
| 2-1258 | 3,4-diF—Ph | 2-MeNH-4-Pym | 4-Pip |
| 2-1259 | 3,4-diF—Ph | 2-MeNH-4-Pym | 4-(3,4-deH-Pip) |
| 2-1260 | 3,4-diF—Ph | 2-MeNH-4-Pym | 1-Me-4-Pip |
| 2-1261 | 3,4-diF—Ph | 2-MeNH-4-Pym | 1-Me-4-(3,4-deH-Pip) |
| 2-1262 | 3,4-diF—Ph | 2-MeNH-4-Pym | 1-Et-4-Pip |
| 2-1263 | 3,4-diF—Ph | 2-MeNH-4-Pym | 1-Bn-4-Pip |
| 2-1264 | 3,4-diF—Ph | 2-MeNH-4-Pym | 3-Hpip |
| 2-1265 | 3,4-diF—Ph | 2-MeNH-4-Pym | 1-Me-3-Hpip |
| 2-1266 | 3,4-diF—Ph | 2-MeNH-4-Pym | 4-Hpip |
| 2-1267 | 3,4-diF—Ph | 2-MeNH-4-Pym | 1-Me-4-Hpip |
| 2-1268 | 3,4-diF—Ph | 2-MeNH-4-Pym | 2-Mor |
| 2-1269 | 3,4-diF—Ph | 2-MeNH-4-Pym | 1-Me-2-Mor |
| 2-1270 | 3,4-diF—Ph | 2-MeNH-4-Pym | 2-Tmor |
| 2-1271 | 3,4-diF—Ph | 2-MeNH-4-Pym | 1-Me-2-Tmor |
| 2-1272 | 3,4-diF—Ph | 2-MeNH-4-Pym | 1-Piz |
| 2-1273 | 3,4-diF—Ph | 2-MeNH-4-Pym | 4-Me-1-Piz |
| 2-1274 | 3,4-diF—Ph | 2-MeNH-4-Pym | 2-Piz |
| 2-1275 | 3,4-diF—Ph | 2-MeNH-4-Pym | 4-Pyr |
| 2-1276 | 3,4-diF—Ph | 2-MeNH-4-Pym | 3-Pyr |
| 2-1277 | 3,4-diF—Ph | 2-MeNH-4-Pym | 2-Pyr |

TABLE 2-continued

| Compound No. | R¹ | R² | R³ |
|---|---|---|---|
| 2-1278 | 3,4-diF—Ph | 2-MeNH-4-Pym | 4-Pym |
| 2-1279 | 3,4-diF—Ph | 2-MeNH-4-Pym | 5-Pym |
| 2-1280 | 3,4-diF—Ph | 2-MeNH-4-Pym | 2-Pym |
| 2-1281 | 3,4-diF—Ph | 2-MeNH-4-Pym | 3-Azt-CH₂ |
| 2-1282 | 3,4-diF—Ph | 2-MeNH-4-Pym | 1-Me-3-Azt-CH₂ |
| 2-1283 | 3,4-diF—Ph | 2-MeNH-4-Pym | 3-Pyrd-CH₂ |
| 2-1284 | 3,4-diF—Ph | 2-MeNH-4-Pym | 1-Me-3-Pyrd-CH₂ |
| 2-1285 | 3,4-diF—Ph | 2-MeNH-4-Pym | 4-Pip-CH₂ |
| 2-1286 | 3,4-diF—Ph | 2-MeNH-4-Pym | 1-Me-4-Pip-CH₂ |
| 2-1287 | 3,4-diF—Ph | 2-MeNH-4-Pym | 3-Hpip-CH₂ |
| 2-1288 | 3,4-diF—Ph | 2-MeNH-4-Pym | 1-Me-3-Hpip-CH₂ |
| 2-1289 | 3,4-diF—Ph | 2-MeNH-4-Pym | 4-Hpip-CH₂ |
| 2-1290 | 3,4-diF—Ph | 2-MeNH-4-Pym | 1-Me-4-Hpip-CH₂ |
| 2-1291 | 3,4-diF—Ph | 2-MeNH-4-Pym | 2-Mor-CH₂ |
| 2-1292 | 3,4-diF—Ph | 2-MeNH-4-Pym | 1-Me-2-Mor-CH₂ |
| 2-1293 | 3,4-diF—Ph | 2-MeNH-4-Pym | 2-Tmor-CH₂ |
| 2-1294 | 3,4-diF—Ph | 2-MeNH-4-Pym | 1-Me-2-Tmor-CH₂ |
| 2-1295 | 3,4-diF—Ph | 2-MeNH-4-Pym | 1-Piz-CH₂ |
| 2-1296 | 3,4-diF—Ph | 2-MeNH-4-Pym | 4-Me-1-Piz-CH₂ |
| 2-1297 | 3,4-diF—Ph | 2-MeNH-4-Pym | 2-Piz-CH₂ |
| 2-1298 | 3,4-diF—Ph | 2-MeNH-4-Pym | 4-Pyr-CH₂ |
| 2-1299 | 3,4-diF—Ph | 2-MeNH-4-Pym | 3-Pyr-CH₂ |
| 2-1300 | 3,4-diF—Ph | 2-MeNH-4-Pym | 2-Pyr-CH₂ |
| 2-1301 | 3,4-diF—Ph | 2-MeNH-4-Pym | 4-Pym-CH₂ |
| 2-1302 | 3,4-diF—Ph | 2-MeNH-4-Pym | 5-Pym-CH₂ |
| 2-1303 | 3,4-diF—Ph | 2-MeNH-4-Pym | 2-Pym-CH₂ |
| 2-1304 | 3-Cl—Ph | 2-MeNH-4-Pym | H₂N—CH₂ |
| 2-1305 | 3-Cl—Ph | 2-MeNH-4-Pym | H₂N—(CH₂)₂ |
| 2-1306 | 3-Cl—Ph | 2-MeNH-4-Pym | H₂N—(CH₂)₃ |
| 2-1307 | 3-Cl—Ph | 2-MeNH-4-Pym | H₂N—(CH₂)₄ |
| 2-1308 | 3-Cl—Ph | 2-MeNH-4-Pym | MeNH—CH₂ |
| 2-1309 | 3-Cl—Ph | 2-MeNH-4-Pym | MeNH—(CH₂)₂ |
| 2-1310 | 3-Cl—Ph | 2-MeNH-4-Pym | MeNH—(CH₂)₃ |
| 2-1311 | 3-Cl—Ph | 2-MeNH-4-Pym | MeNH—(CH₂)₄ |
| 2-1312 | 3-Cl—Ph | 2-MeNH-4-Pym | EtNH—CH₂ |
| 2-1313 | 3-Cl—Ph | 2-MeNH-4-Pym | EtNH—(CH₂)₂ |
| 2-1314 | 3-Cl—Ph | 2-MeNH-4-Pym | EtNH—(CH₂)₃ |
| 2-1315 | 3-Cl—Ph | 2-MeNH-4-Pym | EtNH—(CH₂)₄ |
| 2-1316 | 3-Cl—Ph | 2-MeNH-4-Pym | Me₂N—CH₂ |
| 2-1317 | 3-Cl—Ph | 2-MeNH-4-Pym | Me₂N—(CH₂)₂ |
| 2-1318 | 3-Cl—Ph | 2-MeNH-4-Pym | Me₂N—(CH₂)₃ |
| 2-1319 | 3-Cl—Ph | 2-MeNH-4-Pym | Me₂N—(CH₂)₄ |
| 2-1320 | 3-Cl—Ph | 2-MeNH-4-Pym | 1-Azt-CH₂ |
| 2-1321 | 3-Cl—Ph | 2-MeNH-4-Pym | 1-Azt-(CH₂)₂ |
| 2-1322 | 3-Cl—Ph | 2-MeNH-4-Pym | 1-Azt-(CH₂)₃ |
| 2-1323 | 3-Cl—Ph | 2-MeNH-4-Pym | 1-Azt-(CH₂)₄ |
| 2-1324 | 3-Cl—Ph | 2-MeNH-4-Pym | 1-Pyrd-CH₂ |
| 2-1325 | 3-Cl—Ph | 2-MeNH-4-Pym | 1-Pyrd-(CH₂)₂ |
| 2-1326 | 3-Cl—Ph | 2-MeNH-4-Pym | 1-Pyrd-(CH₂)₃ |
| 2-1327 | 3-Cl—Ph | 2-MeNH-4-Pym | 1-Pyrd-(CH₂)₄ |
| 2-1328 | 3-Cl—Ph | 2-MeNH-4-Pym | 1-Pip-CH₂ |
| 2-1329 | 3-Cl—Ph | 2-MeNH-4-Pym | 1-Pip-(CH₂)₂ |
| 2-1330 | 3-Cl—Ph | 2-MeNH-4-Pym | 1-Pip-(CH₂)₃ |
| 2-1331 | 3-Cl—Ph | 2-MeNH-4-Pym | 1-Pip-(CH₂)₄ |
| 2-1332 | 3-Cl—Ph | 2-MeNH-4-Pym | 1-Mor-CH₂ |
| 2-1333 | 3-Cl—Ph | 2-MeNH-4-Pym | 1-Mor-(CH₂)₂ |
| 2-1334 | 3-Cl—Ph | 2-MeNH-4-Pym | 1-Mor-(CH₂)₃ |
| 2-1335 | 3-Cl—Ph | 2-MeNH-4-Pym | 1-Mor-(CH₂)₄ |
| 2-1336 | 3-Cl—Ph | 2-MeNH-4-Pym | 1-Tmor-CH₂ |
| 2-1337 | 3-Cl—Ph | 2-MeNH-4-Pym | 1-Tmor-(CH₂)₂ |
| 2-1338 | 3-Cl—Ph | 2-MeNH-4-Pym | 1-Tmor-(CH₂)₃ |
| 2-1339 | 3-Cl—Ph | 2-MeNH-4-Pym | 1-Tmor-(CH₂)₄ |
| 2-1340 | 3-Cl—Ph | 2-MeNH-4-Pym | 1-Piz-CH₂ |
| 2-1341 | 3-Cl—Ph | 2-MeNH-4-Pym | 1-Piz-(CH₂)₂ |
| 2-1342 | 3-Cl—Ph | 2-MeNH-4-Pym | 1-Piz-(CH₂)₃ |
| 2-1343 | 3-Cl—Ph | 2-MeNH-4-Pym | 4-Me-1-Piz-(CH₂)₃ |
| 2-1344 | 3-Cl—Ph | 2-MeNH-4-Pym | 1-Piz-(CH₂)₄ |
| 2-1345 | 3-Cl—Ph | 2-MeNH-4-Pym | 3-Azt |
| 2-1346 | 3-Cl—Ph | 2-MeNH-4-Pym | 1-Me-3-Azt |
| 2-1347 | 3-Cl—Ph | 2-MeNH-4-Pym | 1-Bn-3-Azt |
| 2-1348 | 3-Cl—Ph | 2-MeNH-4-Pym | 3-Pyrd |
| 2-1349 | 3-Cl—Ph | 2-MeNH-4-Pym | 1-Me-3-Pyrd |
| 2-1350 | 3-Cl—Ph | 2-MeNH-4-Pym | 3-Pip |
| 2-1351 | 3-Cl—Ph | 2-MeNH-4-Pym | 4-Pip |
| 2-1352 | 3-Cl—Ph | 2-MeNH-4-Pym | 4-(3,4-deH-Pip) |
| 2-1353 | 3-Cl—Ph | 2-MeNH-4-Pym | 1-Me-4-Pip |
| 2-1354 | 3-Cl—Ph | 2-MeNH-4-Pym | 1-Me-4-(3,4-deH-Pip) |
| 2-1355 | 3-Cl—Ph | 2-MeNH-4-Pym | 1-Et-4-Pip |
| 2-1356 | 3-Cl—Ph | 2-MeNH-4-Pym | 1-Bn-4-Pip |
| 2-1357 | 3-Cl—Ph | 2-MeNH-4-Pym | 3-Hpip |
| 2-1358 | 3-Cl—Ph | 2-MeNH-4-Pym | 1-Me-3-Hpip |
| 2-1359 | 3-Cl—Ph | 2-MeNH-4-Pym | 4-Hpip |
| 2-1360 | 3-Cl—Ph | 2-MeNH-4-Pym | 1-Me-4-Hpip |
| 2-1361 | 3-Cl—Ph | 2-MeNH-4-Pym | 2-Mor |
| 2-1362 | 3-Cl—Ph | 2-MeNH-4-Pym | 1-Me-2-Mor |
| 2-1363 | 3-Cl—Ph | 2-MeNH-4-Pym | 2-Tmor |
| 2-1364 | 3-Cl—Ph | 2-MeNH-4-Pym | 1-Me-2-Tmor |
| 2-1365 | 3-Cl—Ph | 2-MeNH-4-Pym | 1-Piz |
| 2-1366 | 3-Cl—Ph | 2-MeNH-4-Pym | 4-Me-1-Piz |
| 2-1367 | 3-Cl—Ph | 2-MeNH-4-Pym | 2-Piz |
| 2-1368 | 3-Cl—Ph | 2-MeNH-4-Pym | 4-Pyr |
| 2-1369 | 3-Cl—Ph | 2-MeNH-4-Pym | 3-Pyr |
| 2-1370 | 3-Cl—Ph | 2-MeNH-4-Pym | 2-Pyr |
| 2-1371 | 3-Cl—Ph | 2-MeNH-4-Pym | 4-Pym |
| 2-1372 | 3-Cl—Ph | 2-MeNH-4-Pym | 5-Pym |
| 2-1373 | 3-Cl—Ph | 2-MeNH-4-Pym | 2-Pym |
| 2-1374 | 3-Cl—Ph | 2-MeNH-4-Pym | 3-Azt-CH₂ |
| 2-1375 | 3-Cl—Ph | 2-MeNH-4-Pym | 1-Me-3-Azt-CH₂ |
| 2-1376 | 3-Cl—Ph | 2-MeNH-4-Pym | 3-Pyrd-CH₂ |
| 2-1377 | 3-Cl—Ph | 2-MeNH-4-Pym | 1-Me-3-Pyrd-CH₂ |
| 2-1378 | 3-Cl—Ph | 2-MeNH-4-Pym | 4-Pip-CH₂ |
| 2-1379 | 3-Cl—Ph | 2-MeNH-4-Pym | 1-Me-4-Pip-CH₂ |
| 2-1380 | 3-Cl—Ph | 2-MeNH-4-Pym | 3-Hpip-CH₂ |
| 2-1381 | 3-Cl—Ph | 2-MeNH-4-Pym | 1-Me-3-Hpip-CH₂ |
| 2-1382 | 3-Cl—Ph | 2-MeNH-4-Pym | 4-Hpip-CH₂ |
| 2-1383 | 3-Cl—Ph | 2-MeNH-4-Pym | 1-Me-4-Hpip-CH₂ |
| 2-1384 | 3-Cl—Ph | 2-MeNH-4-Pym | 2-Mor-CH₂ |
| 2-1385 | 3-Cl—Ph | 2-MeNH-4-Pym | 1-Me-2-Mor-CH₂ |
| 2-1386 | 3-Cl—Ph | 2-MeNH-4-Pym | 2-Tmor-CH₂ |
| 2-1387 | 3-Cl—Ph | 2-MeNH-4-Pym | 1-Me-2-Tmor-CH₂ |
| 2-1388 | 3-Cl—Ph | 2-MeNH-4-Pym | 1-Piz-CH₂ |
| 2-1389 | 3-Cl—Ph | 2-MeNH-4-Pym | 4-Me-1-Piz-CH₂ |
| 2-1390 | 3-Cl—Ph | 2-MeNH-4-Pym | 2-Piz-CH₂ |
| 2-1391 | 3-Cl—Ph | 2-MeNH-4-Pym | 4-Pyr-CH₂ |
| 2-1392 | 3-Cl—Ph | 2-MeNH-4-Pym | 3-Pyr-CH₂ |
| 2-1393 | 3-Cl—Ph | 2-MeNH-4-Pym | 2-Pyr-CH₂ |
| 2-1394 | 3-Cl—Ph | 2-MeNH-4-Pym | 4-Pym-CH₂ |
| 2-1395 | 3-Cl—Ph | 2-MeNH-4-Pym | 5-Pym-CH₂ |
| 2-1396 | 3-Cl—Ph | 2-MeNH-4-Pym | 2-Pym-CH₂ |
| 2-1397 | 3-Cl-4-F—Ph | 4-Pyr | H₂N—(CH₂)₃ |
| 2-1398 | 3-Cl-4-F—Ph | 4-Pyr | MeNH—(CH₂)₃ |
| 2-1399 | 3-Cl-4-F—Ph | 4-Pyr | EtNH—(CH₂)₃ |
| 2-1400 | 3-Cl-4-F—Ph | 4-Pyr | Me₂N—(CH₂)₃ |
| 2-1401 | 3-Cl-4-F—Ph | 4-Pyr | 1-Azt-(CH₂)₃ |
| 2-1402 | 3-Cl-4-F—Ph | 4-Pyr | 1-Pyrd-(CH₂)₃ |
| 2-1403 | 3-Cl-4-F—Ph | 4-Pyr | 1-Pip-(CH₂)₃ |
| 2-1404 | 3-Cl-4-F—Ph | 4-Pyr | 1-Mor-(CH₂)₃ |
| 2-1405 | 3-Cl-4-F—Ph | 4-Pyr | 1-Tmor-(CH₂)₃ |
| 2-1406 | 3-Cl-4-F—Ph | 4-Pyr | 1-Piz-(CH₂)₃ |
| 2-1407 | 3-Cl-4-F—Ph | 4-Pyr | 4-Me-1-Piz-(CH₂)₃ |
| 2-1408 | 3-Cl-4-F—Ph | 4-Pyr | 3-Azt |
| 2-1409 | 3-Cl-4-F—Ph | 4-Pyr | 1-Me-3-Azt |
| 2-1410 | 3-Cl-4-F—Ph | 4-Pyr | 3-Pyrd |
| 2-1411 | 3-Cl-4-F—Ph | 4-Pyr | 1-Me-3-Pyrd |
| 2-1412 | 3-Cl-4-F—Ph | 4-Pyr | 4-Pip |
| 2-1413 | 3-Cl-4-F—Ph | 4-Pyr | 4-(3,4-deH-Pip) |
| 2-1414 | 3-Cl-4-F—Ph | 4-Pyr | 1-Me-4-Pip |
| 2-1415 | 3-Cl-4-F—Ph | 4-Pyr | 1-Me-4-(3,4-deH-Pip) |
| 2-1416 | 3-Cl-4-F—Ph | 4-Pyr | 1-Piz |
| 2-1417 | 3-Cl-4-F—Ph | 4-Pyr | 4-Me-1-Piz |
| 2-1418 | 3-Cl-4-F—Ph | 4-Pyr | 4-Pyr |
| 2-1419 | 3-Cl-4-F—Ph | 4-Pyr | 3-Pyr |
| 2-1420 | 3-Cl-4-F—Ph | 4-Pyr | 4-Pym |
| 2-1421 | 3-Cl-4-F—Ph | 4-Pyr | 5-Pym |
| 2-1422 | 3-Cl-4-F—Ph | 4-Pyr | 3-Pyrd-CH₂ |
| 2-1423 | 3-Cl-4-F—Ph | 4-Pyr | 1-Me-3-Pyrd-CH₂ |
| 2-1424 | 3-Cl-4-F—Ph | 4-Pyr | 4-Pip-CH₂ |
| 2-1425 | 3-Cl-4-F—Ph | 4-Pyr | 1-Me-4-Pip-CH₂ |
| 2-1426 | 3-Cl-4-F—Ph | 4-Pyr | 2-Piz-CH₂ |
| 2-1427 | 3-Cl-4-F—Ph | 4-Pyr | 4-Pyr-CH₂ |

TABLE 2-continued

| Compound No. | R¹ | R² | R³ |
|---|---|---|---|
| 2-1428 | 3-Cl-4-F—Ph | 4-Pyr | 3-Pyr-CH$_2$ |
| 2-1429 | 3-Cl-4-F—Ph | 4-Pyr | 4-Pym-CH$_2$ |
| 2-1430 | 3-Cl-4-F—Ph | 4-Pyr | 5-Pym-CH$_2$ |
| 2-1431 | 3-Cl-4-F—Ph | 4-Pyr | 2-Pym-CH$_2$ |
| 2-1432 | 3,4,5-triF-Ph | 4-Pyr | H$_2$N—(CH$_2$)$_3$ |
| 2-1433 | 3,4,5-triF-Ph | 4-Pyr | MeNH—(CH$_2$)$_3$ |
| 2-1434 | 3,4,5-triF-Ph | 4-Pyr | EtNH—(CH$_2$)$_3$ |
| 2-1435 | 3,4,5-triF-Ph | 4-Pyr | Me$_2$N—(CH$_2$)$_3$ |
| 2-1436 | 3,4,5-triF-Ph | 4-Pyr | 1-Azt-(CH$_2$)$_3$ |
| 2-1437 | 3,4,5-triF-Ph | 4-Pyr | 1-Pyrd-(CH$_2$)$_3$ |
| 2-1438 | 3,4,5-triF-Ph | 4-Pyr | 1-Pip-(CH$_2$)$_3$ |
| 2-1439 | 3,4,5-triF-Ph | 4-Pyr | 1-Mor-(CH$_2$)$_3$ |
| 2-1440 | 3,4,5-triF-Ph | 4-Pyr | 1-Tmor-(CH$_2$)$_3$ |
| 2-1441 | 3,4,5-triF-Ph | 4-Pyr | 1-Piz-(CH$_2$)$_3$ |
| 2-1442 | 3,4,5-triF-Ph | 4-Pyr | 4-Me-1-Piz-(CH$_2$)$_3$ |
| 2-1443 | 3,4,5-triF-Ph | 4-Pyr | 3-Azt |
| 2-1444 | 3,4,5-triF-Ph | 4-Pyr | 1-Me-3-Azt |
| 2-1445 | 3,4,5-triF-Ph | 4-Pyr | 3-Pyrd |
| 2-1446 | 3,4,5-triF-Ph | 4-Pyr | 1-Me-3-Pyrd |
| 2-1447 | 3,4,5-triF-Ph | 4-Pyr | 4-Pip |
| 2-1448 | 3,4,5-triF-Ph | 4-Pyr | 4-(3,4-deH-Pip) |
| 2-1449 | 3,4,5-triF-Ph | 4-Pyr | 1-Me-4-Pip |
| 2-1450 | 3,4,5-triF-Ph | 4-Pyr | 1-Me-4-(3,4-deH-Pip) |
| 2-1451 | 3,4,5-triF-Ph | 4-Pyr | 1-Piz |
| 2-1452 | 3,4,5-triF-Ph | 4-Pyr | 4-Me-1-Piz |
| 2-1453 | 3,4,5-triF-Ph | 4-Pyr | 4-Pyr |
| 2-1454 | 3,4,5-triF-Ph | 4-Pyr | 3-Pyr |
| 2-1455 | 3,4,5-triF-Ph | 4-Pyr | 4-Pym |
| 2-1456 | 3,4,5-triF-Ph | 4-Pyr | 5-Pym |
| 2-1457 | 3,4,5-triF-Ph | 4-Pyr | 3-Pyrd-CH$_2$ |
| 2-1458 | 3,4,5-triF-Ph | 4-Pyr | 1-Me-3-Pyrd-CH$_2$ |
| 2-1459 | 3,4,5-triF-Ph | 4-Pyr | 4-Pip-CH$_2$ |
| 2-1460 | 3,4,5-triF-Ph | 4-Pyr | 1-Me-4-Pip-CH$_2$ |
| 2-1461 | 3,4,5-triF-Ph | 4-Pyr | 2-Piz-CH$_2$ |
| 2-1462 | 3,4,5-triF-Ph | 4-Pyr | 4-Pyr-CH$_2$ |
| 2-1463 | 3,4,5-triF-Ph | 4-Pyr | 3-Pyr-CH$_2$ |
| 2-1464 | 3,4,5-triF-Ph | 4-Pyr | 4-Pym-CH$_2$ |
| 2-1465 | 3,4,5-triF-Ph | 4-Pyr | 5-Pym-CH$_2$ |
| 2-1466 | 3,4,5-triF-Ph | 4-Pyr | 2-Pym-CH$_2$ |
| 2-1467 | 3-CF$_3$—Ph | 4-Pyr | H$_2$N—(CH$_2$)$_3$ |
| 2-1468 | 3-CF$_3$—Ph | 4-Pyr | MeNH—(CH$_2$)$_3$ |
| 2-1469 | 3-CF$_3$—Ph | 4-Pyr | EtNH—(CH$_2$)$_3$ |
| 2-1470 | 3-CF$_3$—Ph | 4-Pyr | Me$_2$N—(CH$_2$)$_3$ |
| 2-1471 | 3-CF$_3$—Ph | 4-Pyr | 1-Azt-(CH$_2$)$_3$ |
| 2-1472 | 3-CF$_3$—Ph | 4-Pyr | 1-Pyrd-(CH$_2$)$_3$ |
| 2-1473 | 3-CF$_3$—Ph | 4-Pyr | 1-Pip-(CH$_2$)$_3$ |
| 2-1474 | 3-CF$_3$—Ph | 4-Pyr | 1-Mor-(CH$_2$)$_3$ |
| 2-1475 | 3-CF$_3$—Ph | 4-Pyr | 1-Tmor-(CH$_2$)$_3$ |
| 2-1476 | 3-CF$_3$—Ph | 4-Pyr | 1-Piz-(CH$_2$)$_3$ |
| 2-1477 | 3-CF$_3$—Ph | 4-Pyr | 4-Me-1-Piz-(CH$_2$)$_3$ |
| 2-1478 | 3-CF$_3$—Ph | 4-Pyr | 3-Azt |
| 2-1479 | 3-CF$_3$—Ph | 4-Pyr | 1-Me-3-Azt |
| 2-1480 | 3-CF$_3$—Ph | 4-Pyr | 3-Pyrd |
| 2-1481 | 3-CF$_3$—Ph | 4-Pyr | 1-Me-3-Pyrd |
| 2-1482 | 3-CF$_3$—Ph | 4-Pyr | 4-Pip |
| 2-1483 | 3-CF$_3$—Ph | 4-Pyr | 4-(3,4-deH-Pip) |
| 2-1484 | 3-CF$_3$—Ph | 4-Pyr | 1-Me-4-Pip |
| 2-1485 | 3-CF$_3$—Ph | 4-Pyr | 1-Me-4-(3,4-deH-Pip) |
| 2-1486 | 3-CF$_3$—Ph | 4-Pyr | 1-Piz |
| 2-1487 | 3-CF$_3$—Ph | 4-Pyr | 4-Me-1-Piz |
| 2-1488 | 3-CF$_3$—Ph | 4-Pyr | 4-Pyr |
| 2-1489 | 3-CF$_3$—Ph | 4-Pyr | 3-Pyr |
| 2-1490 | 3-CF$_3$—Ph | 4-Pyr | 4-Pym |
| 2-1491 | 3-CF$_3$—Ph | 4-Pyr | 5-Pym |
| 2-1492 | 3-CF$_3$—Ph | 4-Pyr | 3-Pyrd-CH$_2$ |
| 2-1493 | 3-CF$_3$—Ph | 4-Pyr | 1-Me-3-Pyrd-CH$_2$ |
| 2-1494 | 3-CF$_3$—Ph | 4-Pyr | 4-Pip-CH$_2$ |
| 2-1495 | 3-CF$_3$—Ph | 4-Pyr | 1-Me-4-Pip-CH$_2$ |
| 2-1496 | 3-CF$_3$—Ph | 4-Pyr | 2-Piz-CH$_2$ |
| 2-1497 | 3-CF$_3$—Ph | 4-Pyr | 4-Pyr-CH$_2$ |
| 2-1498 | 3-CF$_3$—Ph | 4-Pyr | 3-Pyr-CH$_2$ |
| 2-1499 | 3-CF$_3$—Ph | 4-Pyr | 4-Pym-CH$_2$ |
| 2-1500 | 3-CF$_3$—Ph | 4-Pyr | 5-Pym-CH$_2$ |
| 2-1501 | 3-CF$_3$—Ph | 4-Pyr | 2-Pym-CH$_2$ |
| 2-1502 | 3-CHF$_2$O—Ph | 4-Pyr | H$_2$N—(CH$_2$)$_3$ |
| 2-1503 | 3-CHF$_2$O—Ph | 4-Pyr | MeNH—(CH$_2$)$_3$ |
| 2-1504 | 3-CHF$_2$O—Ph | 4-Pyr | EtNH—(CH$_2$)$_3$ |
| 2-1505 | 3-CHF$_2$O—Ph | 4-Pyr | Me$_2$N—(CH$_2$)$_3$ |
| 2-1506 | 3-CHF$_2$O—Ph | 4-Pyr | 1-Azt-(CH$_2$)$_3$ |
| 2-1507 | 3-CHF$_2$O—Ph | 4-Pyr | 1-Pyrd-(CH$_2$)$_3$ |
| 2-1508 | 3-CHF$_2$O—Ph | 4-Pyr | 1-Pip-(CH$_2$)$_3$ |
| 2-1509 | 3-CHF$_2$O—Ph | 4-Pyr | 1-Mor-(CH$_2$)$_3$ |
| 2-1510 | 3-CHF$_2$O—Ph | 4-Pyr | 1-Tmor-(CH$_2$)$_3$ |
| 2-1511 | 3-CHF$_2$O—Ph | 4-Pyr | 1-Piz-(CH$_2$)$_3$ |
| 2-1512 | 3-CHF$_2$O—Ph | 4-Pyr | 4-Me-1-Piz-(CH$_2$)$_3$ |
| 2-1513 | 3-CHF$_2$O—Ph | 4-Pyr | 3-Azt |
| 2-1514 | 3-CHF$_2$O—Ph | 4-Pyr | 1-Me-3-Azt |
| 2-1515 | 3-CHF$_2$O—Ph | 4-Pyr | 3-Pyrd |
| 2-1516 | 3-CHF$_2$O—Ph | 4-Pyr | 1-Me-3-Pyrd |
| 2-1517 | 3-CHF$_2$O—Ph | 4-Pyr | 4-Pip |
| 2-1518 | 3-CHF$_2$O—Ph | 4-Pyr | 4-(3,4-deH-Pip) |
| 2-1519 | 3-CHF$_2$O—Ph | 4-Pyr | 1-Me-4-Pip |
| 2-1520 | 3-CHF$_2$O—Ph | 4-Pyr | 1-Me-4-(3,4-deH-Pip) |
| 2-1521 | 3-CHF$_2$O—Ph | 4-Pyr | 1-Piz |
| 2-1522 | 3-CHF$_2$O—Ph | 4-Pyr | 4-Me-1-Piz |
| 2-1523 | 3-CHF$_2$O—Ph | 4-Pyr | 4-Pyr |
| 2-1524 | 3-CHF$_2$O—Ph | 4-Pyr | 3-Pyr |
| 2-1525 | 3-CHF$_2$O—Ph | 4-Pyr | 4-Pym |
| 2-1526 | 3-CHF$_2$O—Ph | 4-Pyr | 5-Pym |
| 2-1527 | 3-CHF$_2$O—Ph | 4-Pyr | 3-Pyrd-CH$_2$ |
| 2-1528 | 3-CHF$_2$O—Ph | 4-Pyr | 1-Me-3-Pyrd-CH$_2$ |
| 2-1529 | 3-CHF$_2$O—Ph | 4-Pyr | 4-Pip-CH$_2$ |
| 2-1530 | 3-CHF$_2$O—Ph | 4-Pyr | 1-Me-4-Pip-CH$_2$ |
| 2-1531 | 3-CHF$_2$O—Ph | 4-Pyr | 2-Piz-CH$_2$ |
| 2-1532 | 3-CHF$_2$O—Ph | 4-Pyr | 4-Pyr-CH$_2$ |
| 2-1533 | 3-CHF$_2$O—Ph | 4-Pyr | 3-Pyr-CH$_2$ |
| 2-1534 | 3-CHF$_2$O—Ph | 4-Pyr | 4-Pym-CH$_2$ |
| 2-1535 | 3-CHF$_2$O—Ph | 4-Pyr | 5-Pym-CH$_2$ |
| 2-1536 | 3-CHF$_2$O—Ph | 4-Pyr | 2-Pym-CH$_2$ |
| 2-1537 | 3-Cl-4-F—Ph | 2-NH$_2$-4-Pym | H$_2$—(CH$_2$)$_3$ |
| 2-1538 | 3-Cl-4-F—Ph | 2-NH$_2$-4-Pym | MeNH—(CH$_2$)$_3$ |
| 2-1539 | 3-Cl-4-F—Ph | 2-NH$_2$-4-Pym | EtNH—(CH$_2$)$_3$ |
| 2-1540 | 3-Cl-4-F—Ph | 2-NH$_2$-4-Pym | Me$_2$N—(CH$_2$)$_3$ |
| 2-1541 | 3-Cl-4-F—Ph | 2-Nh$_2$-4-Pym | 1-Azt-(CH$_2$)$_3$ |
| 2-1542 | 3-Cl-4-F—Ph | 2-NH$_2$-4-Pym | 1-Pyrd-(CH$_2$)$_3$ |
| 2-1543 | 3-Cl-4-F—Ph | 2-NH$_2$-4-Pym | 1-Pip-(CH$_2$)$_3$ |
| 2-1544 | 3-Cl-4-F—Ph | 2-NH$_2$-4-Pym | 1-Mor-(CH$_2$)$_3$ |
| 2-1545 | 3-Cl-4-F—Ph | 2-NH$_2$-4-Pym | 1-Tmor-(CH$_2$)$_3$ |
| 2-1546 | 3-Cl-4-F—Ph | 2-NH$_2$-4-Pym | 1-Piz-(CH$_2$)$_3$ |
| 2-1547 | 3-Cl-4-F—Ph | 2-NH$_2$-4-Pym | 4-Me-1-Piz-(CH$_2$)$_3$ |
| 2-1548 | 3-Cl-4-F—Ph | 2-NH$_2$-4-Pym | 3-Azt |
| 2-1549 | 3-Cl-4-F—Ph | 2-NH$_2$-4-Pym | 1-Me-3-Azt |
| 2-1550 | 3-Cl-4-F—Ph | 2-NH$_2$-4-Pym | 3-Pyrd |
| 2-1551 | 3-Cl-4-F—Ph | 2-NH$_2$-4-Pym | 1-Me-3-Pyrd |
| 2-1552 | 3-Cl-4-F—Ph | 2-NH$_2$-4-Pym | 4-Pip |
| 2-1553 | 3-Cl-4-F—Ph | 2-NH$_2$-4-Pym | 4-(3,4-deH-Pip) |
| 2-1554 | 3-Cl-4-F—Ph | 2-NH$_2$-4-Pym | 1-Me-4-Pip |
| 2-1555 | 3-Cl-4-F—Ph | 2-NH$_2$-4-Pym | 1-Me-4-(3,4-deH-Pip) |
| 2-1556 | 3-Cl-4-F—Ph | 2-NH$_2$-4-Pym | 1-Piz |
| 2-1557 | 3-Cl-4-F—Ph | 2-NH$_2$-4-Pym | 4-Me-1-Piz |
| 2-1558 | 3-Cl-4-F—Ph | 2-NH$_2$-4-Pym | 4-Pyr |
| 2-1559 | 3-Cl-4-F—Ph | 2-NH$_2$-4-Pym | 3-Pyr |
| 2-1560 | 3-Cl-4-F—Ph | 2-NH$_2$-4-Pym | 4-Pym |
| 2-1561 | 3-Cl-4-F—Ph | 2-NH$_2$-4-Pym | 5-Pym |
| 2-1562 | 3-Cl-4-F—Ph | 2-NH$_2$-4-Pym | 3-Pyrd-CH$_2$ |
| 2-1563 | 3-Cl-4-F—Ph | 2-NH$_2$-4-Pym | 1-Me-3-Pyrd-CH$_2$ |
| 2-1564 | 3-Cl-4-F—Ph | 2-NH$_2$-4-Pym | 4-Pip-CH$_2$ |
| 2-1565 | 3-Cl-4-F—Ph | 2-NH$_2$-4-Pym | 1-Me-4-Pip-CH$_2$ |
| 2-1566 | 3-Cl-4-F—Ph | 2-NH$_2$-4-Pym | 2-Piz-CH$_2$ |
| 2-1567 | 3-Cl-4-F—Ph | 2-NH$_2$-4-Pym | 4-Pyr-CH$_2$ |
| 2-1568 | 3-Cl-4-F—Ph | 2-NH$_2$-4-Pym | 3-Pyr-CH$_2$ |
| 2-1569 | 3-Cl-4-F—Ph | 2-NH$_2$-4-Pym | 4-Pym-CH$_2$ |
| 2-1570 | 3-Cl-4-F—Ph | 2-NH$_2$-4-Pym | 5-Pym-CH$_2$ |
| 2-1571 | 3-Cl-4-F—Ph | 2-NH$_2$-4-Pym | 2-Pym-CH$_2$ |
| 2-1572 | 3,4,5-triF-Ph | 2-NH$_2$-4-Pym | H$_2$—(CH$_2$)$_3$ |
| 2-1573 | 3,4,5-triF-Ph | 2-NH$_2$-4-Pym | MeNH—(CH$_2$)$_3$ |
| 2-1574 | 3,4,5-triF-Ph | 2-NH$_2$-4-Pym | EtNH—(CH$_2$)$_3$ |
| 2-1575 | 3,4,5-triF-Ph | 2-NH$_2$-4-Pym | Me$_2$N—(CH$_2$)$_3$ |
| 2-1576 | 3,4,5-triF-Ph | 2-NH$_2$-4-Pym | 1-Azt-(CH$_2$)$_3$ |
| 2-1577 | 3,4,5-triF-Ph | 2-NH$_2$-4-Pym | 1-Pyrd-(CH$_2$)$_3$ |

TABLE 2-continued

| Compound No. | R¹ | R² | R³ |
|---|---|---|---|
| 2-1578 | 3,4,5-triF-Ph | 2-NH$_2$-4-Pym | 1-Pip-(CH$_2$)$_3$ |
| 2-1579 | 3,4,5-triF-Ph | 2-NH$_2$-4-Pym | 1-Mor-(CH$_2$)$_3$ |
| 2-1580 | 3,4,5-triF-Ph | 2-NH$_2$-4-Pym | 1-Tmor-(CH$_2$)$_3$ |
| 2-1581 | 3,4,5-triF-Ph | 2-NH$_2$-4-Pym | 1-Piz-(CH$_2$)$_3$ |
| 2-1582 | 3,4,5-triF-Ph | 2-NH$_2$-4-Pym | 4-Me-1-Piz-(CH$_2$)$_3$ |
| 2-1583 | 3,4,5-triF-Ph | 2-NH$_2$-4-Pym | 3-Azt |
| 2-1584 | 3,4,5-triF-Ph | 2-NH$_2$-4-Pym | 1-Me-3-Azt |
| 2-1585 | 3,4,5-triF-Ph | 2-NH$_2$-4-Pym | 3-Pyrd |
| 2-1586 | 3,4,5-triF-Ph | 2-NH$_2$-4-Pym | 1-Me-3-Pyrd |
| 2-1587 | 3,4,5-triF-Ph | 2-NH$_2$-4-Pym | 4-Pip |
| 2-1588 | 3,4,5-triF-Ph | 2-NH$_2$-4-Pym | 4-(3,4-deH-Pip) |
| 2-1589 | 3,4,5-triF-Ph | 2-NH$_2$-4-Pym | 1-Me-4-Pip |
| 2-1590 | 3,4,5-triF-Ph | 2-NH$_2$-4-Pym | 1-Me-4-(3,4-deH-Pip) |
| 2-1591 | 3,4,5-triF-Ph | 2-NH$_2$-4-Pym | 1-Piz |
| 2-1592 | 3,4,5-triF-Ph | 2-NH$_2$-4-Pym | 4-Me-1-Piz |
| 2-1593 | 3,4,5-triF-Ph | 2-NH$_2$-4-Pym | 4-Pyr |
| 2-1594 | 3,4,5-triF-Ph | 2-NH$_2$-4-Pym | 3-Pyr |
| 2-1595 | 3,4,5-triF-Ph | 2-NH$_2$-4-Pym | 4-Pym |
| 2-1596 | 3,4,5-triF-Ph | 2-NH$_2$-4-Pym | 5-Pym |
| 2-1597 | 3,4,5-triF-Ph | 2-NH$_2$-4-Pym | 3-Pyrd-CH$_2$ |
| 2-1598 | 3,4,5-triF-Ph | 2-NH$_2$-4-Pym | 1-Me-3-Pyrd-CH$_2$ |
| 2-1599 | 3,4,5-triF-Ph | 2-NH$_2$-4-Pym | 4-Pip-CH$_2$ |
| 2-1600 | 3,4,5-triF-Ph | 2-NH$_2$-4-Pym | 1-Me-4-Pip-CH$_2$ |
| 2-1601 | 3,4,5-triF-Ph | 2-NH$_2$-4-Pym | 2-Piz-CH$_2$ |
| 2-1602 | 3,4,5-triF-Ph | 2-NH$_2$-4-Pym | 4-Pyr-CH$_2$ |
| 2-1603 | 3,4,5-triF-Ph | 2-NH$_2$-4-Pym | 3-Pyr-CH$_2$ |
| 2-1604 | 3,4,5-triF-Ph | 2-NH$_2$-4-Pym | 4-Pym-CH$_2$ |
| 2-1605 | 3,4,5-triF-Ph | 2-NH$_2$-4-Pym | 5-Pym-CH$_2$ |
| 2-1606 | 3,4,5-triF-Ph | 2-NH$_2$-4-Pym | 2-Pym-CH$_2$ |
| 2-1607 | 3-CF$_3$—Ph | 2-NH$_2$-4-Pym | H$_2$—(CH$_2$)$_3$ |
| 2-1608 | 3-CF$_3$—Ph | 2-NH$_2$-4-Pym | MeNH—(CH$_2$)$_3$ |
| 2-1609 | 3-CF$_3$—Ph | 2-NH$_2$-4-Pym | EtNH—(CH$_2$)$_3$ |
| 2-1610 | 3-CF$_3$—Ph | 2-NH$_2$-4-Pym | Me$_2$N—(CH$_2$)$_3$ |
| 2-1611 | 3-CF$_3$—Ph | 2-NH$_2$-4-Pym | 1-Azt-(CH$_2$)$_3$ |
| 2-1612 | 3-CF$_3$—Ph | 2-NH$_2$-4-Pym | 1-Pyrd-(CH$_2$)$_3$ |
| 2-1613 | 3-CF$_3$—Ph | 2-NH$_2$-4-Pym | 1-Pip-(CH$_2$)$_3$ |
| 2-1614 | 3-CF$_3$—Ph | 2-NH$_2$-4-Pym | 1-Mor-(CH$_2$)$_3$ |
| 2-1615 | 3-CF$_3$—Ph | 2-NH$_2$-4-Pym | 1-Tmor-(CH$_2$)$_3$ |
| 2-1616 | 3-CF$_3$—Ph | 2-NH$_2$-4-Pym | 1-Piz-(CH$_2$)$_3$ |
| 2-1617 | 3-CF$_3$—Ph | 2-NH$_2$-4-Pym | 4-Me-1-Piz-(CH$_2$)$_3$ |
| 2-1618 | 3-CF$_3$—Ph | 2-NH$_2$-4-Pym | 3-Azt |
| 2-1619 | 3-CF$_3$—Ph | 2-NH$_2$-4-Pym | 1-Me-3-Azt |
| 2-1620 | 3-CF$_3$—Ph | 2-NH$_2$-4-Pym | 3-Pyrd |
| 2-1621 | 3-CF$_3$—Ph | 2-NH$_2$-4-Pym | 1-Me-3-Pyrd |
| 2-1622 | 3-CF$_3$—Ph | 2-NH$_2$-4-Pym | 4-Pip |
| 2-1623 | 3-CF$_3$—Ph | 2-NH$_2$-4-Pym | 4-(3,4-deH-Pip) |
| 2-1624 | 3-CF$_3$—Ph | 2-NH$_2$-4-Pym | 1-Me-4-Pip |
| 2-1625 | 3-CF$_3$—Ph | 2-NH$_2$-4-Pym | 1-Me-4-(3,4-deH-Pip) |
| 2-1626 | 3-CF$_3$—Ph | 2-NH$_2$-4-Pym | 1-Piz |
| 2-1627 | 3-CF$_3$—Ph | 2-NH$_2$-4-Pym | 4-Me-1-Piz |
| 2-1628 | 3-CF$_3$—Ph | 2-NH$_2$-4-Pym | 4-Pyr |
| 2-1629 | 3-CF$_3$—Ph | 2-NH$_2$-4-Pym | 3-Pyr |
| 2-1630 | 3-CF$_3$—Ph | 2-NH$_2$-4-Pym | 4-Pym |
| 2-1631 | 3-CF$_3$—Ph | 2-NH$_2$-4-Pym | 5-Pym |
| 2-1632 | 3-CF$_3$—Ph | 2-NH$_2$-4-Pym | 3-Pyrd-CH$_2$ |
| 2-1633 | 3-CF$_3$—Ph | 2-NH$_2$-4-Pym | 1-Me-3-Pyrd-CH$_2$ |
| 2-1634 | 3-CF$_3$—Ph | 2-NH$_2$-4-Pym | 4-Pip-CH$_2$ |
| 2-1635 | 3-CF$_3$—Ph | 2-NH$_2$-4-Pym | 1-Me-4-Pip-CH$_2$ |
| 2-1636 | 3-CF$_3$—Ph | 2-NH$_2$-4-Pym | 2-Piz-CH$_2$ |
| 2-1637 | 3-CF$_3$—Ph | 2-NH$_2$-4-Pym | 4-Pyr-CH$_2$ |
| 2-1638 | 3-CF$_3$—Ph | 2-NH$_2$-4-Pym | 3-Pyr-CH$_2$ |
| 2-1639 | 3-CF$_3$—Ph | 2-NH$_2$-4-Pym | 4-Pym-CH$_2$ |
| 2-1640 | 3-CF$_3$—Ph | 2-NH$_2$-4-Pym | 5-Pym-CH$_2$ |
| 2-1641 | 3-CF$_3$—Ph | 2-NH$_2$-4-Pym | 2-Pym-CH$_2$ |
| 2-1642 | 3-CHF$_2$O—Ph | 2-NH$_2$-4-Pym | H$_2$—(CH$_2$)$_3$ |
| 2-1643 | 3-CHF$_2$O—Ph | 2-NH$_2$-4-Pym | MeNH—(CH$_2$)$_3$ |
| 2-1644 | 3-CHF$_2$O—Ph | 2-NH$_2$-4-Pym | EtNH—(CH$_2$)$_3$ |
| 2-1645 | 3-CHF$_2$O—Ph | 2-NH$_2$-4-Pym | Me$_2$N—(CH$_2$)$_3$ |
| 2-1646 | 3-CHF$_2$O—Ph | 2-NH$_2$-4-Pym | 1-Azt-(CH$_2$)$_3$ |
| 2-1647 | 3-CHF$_2$O—Ph | 2-NH$_2$-4-Pym | 1-Pyrd-(CH$_2$)$_3$ |
| 2-1648 | 3-CHF$_2$O—Ph | 2-NH$_2$-4-Pym | 1-Pip-(CH$_2$)$_3$ |
| 2-1649 | 3-CHF$_2$O—Ph | 2-NH$_2$-4-Pym | 1-Mor-(CH$_2$)$_3$ |
| 2-1650 | 3-CHF$_2$O—Ph | 2-NH$_2$-4-Pym | 1-Tmor-(CH$_2$)$_3$ |
| 2-1651 | 3-CHF$_2$O—Ph | 2-NH$_2$-4-Pym | 1-Piz-(CH$_2$)$_3$ |
| 2-1652 | 3-CHF$_2$O—Ph | 2-NH$_2$-4-Pym | 4-Me-1-Piz-(CH$_2$)$_3$ |
| 2-1653 | 3-CHF$_2$O—Ph | 2-NH$_2$-4-Pym | 3-Azt |
| 2-1654 | 3-CHF$_2$O—Ph | 2-NH$_2$-4-Pym | 1-Me-3-Azt |
| 2-1655 | 3-CHF$_2$O—Ph | 2-NH$_2$-4-Pym | 3-Pyrd |
| 2-1656 | 3-CHF$_2$O—Ph | 2-NH$_2$-4-Pym | 1-Me-3-Pyrd |
| 2-1657 | 3-CHF$_2$O—Ph | 2-NH$_2$-4-Pym | 4-Pip |
| 2-1658 | 3-CHF$_2$O—Ph | 2-NH$_2$-4-Pym | 4-(3,4-deH-Pip) |
| 2-1659 | 3-CHF$_2$O—Ph | 2-NH$_2$-4-Pym | 1-Me-4-Pip |
| 2-1660 | 3-CHF$_2$O—Ph | 2-NH$_2$-4-Pym | 1-Me-4-(3,4-deH-Pip) |
| 2-1661 | 3-CHF$_2$O—Ph | 2-NH$_2$-4-Pym | 1-Piz |
| 2-1662 | 3-CHF$_2$O—Ph | 2-NH$_2$-4-Pym | 4-Me—i—Piz |
| 2-1663 | 3-CHF$_2$O—Ph | 2-NH$_2$-4-Pym | 4-Pyr |
| 2-1664 | 3-CHF$_2$O—Ph | 2-NH$_2$-4-Pym | 3-Pyr |
| 2-1665 | 3-CHF$_2$O—Ph | 2-NH$_2$-4-Pym | 4-Pym |
| 2-1666 | 3-CHF$_2$O—Ph | 2-NH$_2$-4-Pym | 5-Pym |
| 2-1667 | 3-CHF$_2$O—Ph | 2-NH$_2$-4-Pym | 3-Pyrd-CH$_2$ |
| 2-1668 | 3-CHF$_2$O—Ph | 2-NH$_2$-4-Pym | 1-Me-3-Pyrd-CH$_2$ |
| 2-1669 | 3-CHF$_2$O—Ph | 2-NH$_2$-4-Pym | 4-Pip-CH$_2$ |
| 2-1670 | 3-CHF$_2$O—Ph | 2-NH$_2$-4-Pym | 1-Me-4-Pip-CH$_2$ |
| 2-1671 | 3-CHF$_2$O—Ph | 2-NH$_2$-4-Pym | 2-Piz-CH$_2$ |
| 2-1672 | 3-CHF$_2$O—Ph | 2-NH$_2$-4-Pym | 4-Pyr-CH$_2$ |
| 2-1673 | 3-CHF$_2$O—Ph | 2-NH$_2$-4-Pym | 3-Pyr-CH$_2$ |
| 2-1674 | 3-CHF$_2$O—Ph | 2-NH$_2$-4-Pym | 4-Pym-CH$_2$ |
| 2-1675 | 3-CHF$_2$O—Ph | 2-NH$_2$-4-Pym | 5-Pym-CH$_2$ |
| 2-1676 | 3-CHF$_2$O—Ph | 2-NH$_2$-4-Pym | 2-Pym-CH$_2$ |
| 2-1677 | 3-Cl-4-F—Ph | 2-MeNH-4-Pym | H$_2$—(CH$_2$)$_3$ |
| 2-1678 | 3-Cl-4-F—Ph | 2-MeNH-4-Pym | MeNH—(CH$_2$)$_3$ |
| 2-1679 | 3-Cl-4-F—Ph | 2-MeNH-4-Pym | EtNH—(CH$_2$)$_3$ |
| 2-1680 | 3-Cl-4-F—Ph | 2-MeNH-4-Pym | Me$_2$N—(CH$_2$)$_3$ |
| 2-1681 | 3-Cl-4-F—Ph | 2-MeNH-4-Pym | 1-Azt-(CH$_2$)$_3$ |
| 2-1682 | 3-Cl-4-F—Ph | 2-MeNH-4-Pym | 1-Pyrd-(CH$_2$)$_3$ |
| 2-1683 | 3-Cl-4-F—Ph | 2-MeNH-4-Pym | 1-Pip-(CH$_2$)$_3$ |
| 2-1684 | 3-Cl-4-F—Ph | 2-MeNH-4-Pym | 1-Mor-(CH$_2$)$_3$ |
| 2-1685 | 3-Cl-4-F—Ph | 2-MeNH-4-Pym | 1-Tmor-(CH$_2$)$_3$ |
| 2-1686 | 3-Cl-4-F—Ph | 2-MeNH-4-Pym | 1-Piz-(CH$_2$)$_3$ |
| 2-1687 | 3-Cl-4-F—Ph | 2-MeNH-4-Pym | 4-Me-1-Piz-(CH$_2$)$_3$ |
| 2-1688 | 3-Cl-4-F—Ph | 2-MeNH-4-Pym | 3-Azt |
| 2-1689 | 3-Cl-4-F—Ph | 2-MeNH-4-Pym | 1-Me-3-Azt |
| 2-1690 | 3-Cl-4-F—Ph | 2-MeNH-4-Pym | 3-Pyrd |
| 2-1691 | 3-Cl-4-F—Ph | 2-MeNH-4-Pym | 1-Me-3-Pyrd |
| 2-1692 | 3-Cl-4-F—Ph | 2-MeNH-4-Pym | 4-Pip |
| 2-1693 | 3-Cl-4-F—Ph | 2-MeNH-4-Pym | 4-(3,4-deH-Pip) |
| 2-1694 | 3-Cl-4-F—Ph | 2-MeNH-4-Pym | 1-Me-4-Pip |
| 2-1695 | 3-Cl-4-F—Ph | 2-MeNH-4-Pym | 1-Me-4-(3,4-deH-Pip) |
| 2-1696 | 3-Cl-4-F—Ph | 2-MeNH-4-Pym | 1-Piz |
| 2-1697 | 3-Cl-4-F—Ph | 2-MeNH-4-Pym | 4-Me-1-Piz |
| 2-1698 | 3-Cl-4-F—Ph | 2-MeNH-4-Pym | 4-Pyr |
| 2-1699 | 3-Cl-4-F—Ph | 2-MeNH-4-Pym | 3-Pyr |
| 2-1700 | 3-Cl-4-F—Ph | 2-MeNH-4-Pym | 4-Pym |
| 2-1701 | 3-Cl-4-F—Ph | 2-MeNH-4-Pym | 5-Pym |
| 2-1702 | 3-Cl-4-F—Ph | 2-MeNH-4-Pym | 3-Pyrd-CH$_2$ |
| 2-1703 | 3-Cl-4-F—Ph | 2-MeNH-4-Pym | 1-Me-3-Pyrd-CH$_2$ |
| 2-1704 | 3-Cl-4-F—Ph | 2-MeNH-4-Pym | 4-Pip-CH$_2$ |
| 2-1705 | 3-Cl-4-F—Ph | 2-MeNH—Pym | 1-MeA-Pip-CH$_2$ |
| 2-1706 | 3-Cl-4-F—Ph | 2-MeNH—Pym | 2-Piz-CH$_2$ |
| 2-1707 | 3-Cl-4-F—Ph | 2-MeNH—Pym | 4-Pyr-CH$_2$ |
| 2-1708 | 3-Cl-4-F—Ph | 2-MeNH-4-Pym | 3-Pyr-CH$_2$ |
| 2-1709 | 3-Cl-4-F—Ph | 2-MeNH-4-Pym | 4-Pym-CH$_2$ |
| 2-1710 | 3-Cl-4-F—Ph | 2-MeNH-4-Pym | 5-Pym-CH$_2$ |
| 2-1711 | 3-Cl-4-F—Ph | 2-MeNH-4-Pym | 2-Pym-CH$_2$ |
| 2-1712 | 3,4,5-triF-Ph | 2-MeNH-4-Pym | H$_2$—(CH$_2$)$_3$ |
| 2-1713 | 3,4,5-triF-Ph | 2-MeNH-4-Pym | MeNH—(CH$_2$)$_3$ |
| 2-1714 | 3,4,5-triF-Ph | 2-MeNH-4-Pym | EtNH—(CH$_2$)$_3$ |
| 2-1715 | 3,4,5-triF-Ph | 2-MeNH-4-Pym | Me$_2$N—(CH$_2$)$_3$ |
| 2-1716 | 3,4,5-triF-Ph | 2-MeNH-4-Pym | 1-Azt-(CH$_2$)$_3$ |
| 2-1717 | 3,4,5-triF-Ph | 2-MeNH-4-Pym | 1-Pyrd-(CH$_2$)$_3$ |
| 2-1718 | 3,4,5-triF-Ph | 2-MeNH-4-Pym | 1-Pip-(CH$_2$)$_3$ |
| 2-1719 | 3,4,5-triF-Ph | 2-MeNH-4-Pym | 1-Mor-(CH$_2$)$_3$ |
| 2-1720 | 3,4,5-triF-Ph | 2-MeNH-4-Pym | 1-Tmor-(CH$_2$)$_3$ |
| 2-1721 | 3,4,5-triF-Ph | 2-MeNH-4-Pym | 1-Piz-(CH$_2$)$_3$ |
| 2-1722 | 3,4,5-triF-Ph | 2-MeNH-4-Pym | 4-Me-1-Piz-(CH$_2$)$_3$ |
| 2-1723 | 3,4,5-triF-Ph | 2-MeNH-4-Pym | 3—Azi |
| 2-1724 | 3,4,5-triF-Ph | 2-MeNH-4-Pym | 1-Me-3-Azt |
| 2-1725 | 3,4,5-triF-Ph | 2-MeNH-4-Pym | 3-Pyrd |
| 2-1726 | 3,4,5-triF-Ph | 2-MeNH-4-Pym | 1-Me-3-Pyrd |
| 2-1727 | 3,4,5-triF-Ph | 2-MeNH-4-Pym | 4-Pip |

TABLE 2-continued

| Compound No. | R¹ | R² | R³ |
|---|---|---|---|
| 2-1728 | 3,4,5-triF-Ph | 2-MeNH-4-Pym | 4-(3,4-deH-Pip) |
| 2-1729 | 3,4,5-triF-Ph | 2-MeNH-4-Pym | 1-Me-4-Pip |
| 2-1730 | 3,4,5-triF-Ph | 2-MeNH-4-Pym | 1-Me-4-(3,4-deH-Pip) |
| 2-1731 | 3,4,5-triF-Ph | 2-MeNH-4-Pym | 1-Piz |
| 2-1732 | 3,4,5-triF-Ph | 2-MeNH-4-Pym | 4-Me-1-Piz |
| 2-1733 | 3,4,5-triF-Ph | 2-MeNH-4-Pym | 4-Pyr |
| 2-1734 | 3,4,5-triF-Ph | 2-MeNH-4-Pym | 3-Pyr |
| 2-1735 | 3,4,5-triF-Ph | 2-MeNH-4-Pym | 4-Pym |
| 2-1736 | 3,4,5-triF-Ph | 2-MeNH-4-Pym | 5-Pym |
| 2-1737 | 3,4,5-triF-Ph | 2-MeNH-4-Pym | 3-Pyrd-CH$_2$ |
| 2-1738 | 3,4,5-triF-Ph | 2-MeNH-4-Pym | 1-Me-3-Pyrd-CH$_2$ |
| 2-1739 | 3,4,5-triF-Ph | 2-MeNH-4-Pym | 4-Pip-CH$_2$ |
| 2-1740 | 3,4,5-triF-Ph | 2-MeNH-4-Pym | 1-Me-4-Pip-CH$_2$ |
| 2-1741 | 3,4,5-triF-Ph | 2-MeNH-4-Pym | 2-Piz-CH$_2$ |
| 2-1742 | 3,4,5-triF-Ph | 2-MeNH-4-Pym | 4-Pyr-CH$_2$ |
| 2-1743 | 3,4,5-triF-Ph | 2-MeNH-4-Pym | 3-Pyr-CH$_2$ |
| 2-1744 | 3,4,5-triF-Ph | 2-MeNH-4-Pym | 4-Pym-CH$_2$ |
| 2-1745 | 3,4,5-triF-Ph | 2-MeNH-4-Pym | 5-Pym-CH$_2$ |
| 2-1746 | 3,4,5-triF-Ph | 2-MeNH-4-Pym | 2-Pym-CH$_2$ |
| 2-1747 | 3-CF$_3$—Ph | 2-MeNH-4-Pym | H$_2$—(CH$_2$)$_3$ |
| 2-1748 | 3-CF$_3$—Ph | 2-MeNH-4-Pym | MeNH—(CH$_2$)$_3$ |
| 2-1749 | 3-CF$_3$—Ph | 2-MeNH-4-Pym | EtNH—(CH$_2$)$_3$ |
| 2-1750 | 3-CF$_3$—Ph | 2-MeNH-4-Pym | Me$_2$N—(CH$_2$)$_3$ |
| 2-1751 | 3-CF$_3$—Ph | 2-MeNH-4-Pym | 1-Azt-(CH$_2$)$_3$ |
| 2-1752 | 3-CF$_3$—Ph | 2-MeNH-4-Pym | 1-Pyrd-(CH$_2$)$_3$ |
| 2-1753 | 3-CF$_3$—Ph | 2-MeNH-4-Pym | 1-Pip-(CH$_2$)$_3$ |
| 2-1754 | 3-CF$_3$—Ph | 2-MeNH-4-Pym | 1-Mor-(CH$_2$)$_3$ |
| 2-1755 | 3-CF$_3$—Ph | 2-MeNH-4-Pym | 1-Tmor-(CH$_2$)$_3$ |
| 2-1756 | 3-CF$_3$—Ph | 2-MeNH-4-Pym | 1-Piz-(CH$_2$)$_3$ |
| 2-1757 | 3-CF$_3$—Ph | 2-MeNH-4-Pym | 4-Me-1-Piz-(CH$_2$)$_3$ |
| 2-1758 | 3-CF$_3$—Ph | 2-MeNH-4-Pym | 3-Azt |
| 2-1759 | 3-CF$_3$—Ph | 2-MeNH-4-Pym | 1-Me-3-Azt |
| 2-1760 | 3-CF$_3$—Ph | 2-MeNH-4-Pym | 3-Pyrd |
| 2-1761 | 3-CF$_3$—Ph | 2-MeNH-4-Pym | 1-Me-3-Pyrd |
| 2-1762 | 3-CF$_3$—Ph | 2-MeNH-4-Pym | 4-Pip |
| 2-1763 | 3-CF$_3$—Ph | 2-MeNH-4-Pym | 4-(3,4-deH-Pip) |
| 2-1764 | 3-CF$_3$—Ph | 2-MeNH-4-Pym | 1-Me-4-Pip |
| 2-1765 | 3-CF$_3$—Ph | 2-MeNH-4-Pym | 1-Me-4-(3,4-deH-Pip) |
| 2-1766 | 3-CF$_3$—Ph | 2-MeNH-4-Pym | 1-Piz |
| 2-1767 | 3-CF$_3$—Ph | 2-MeNH-4-Pym | 4-Me-1-Piz |
| 2-1768 | 3-CF$_3$—Ph | 2-MeNH-4-Pym | 4-Pyr |
| 2-1769 | 3-CF$_3$—Ph | 2-MeNH-4-Pym | 3-Pyr |
| 2-1770 | 3-CF$_3$—Ph | 2-MeNH-4-Pym | 4-Pym |
| 2-1771 | 3-CF$_3$—Ph | 2-MeNH-4-Pym | 5-Pym |
| 2-1772 | 3-CF$_3$—Ph | 2-MeNH-4-Pym | 3-Pyrd-CH$_2$ |
| 2-1773 | 3-CF$_3$—Ph | 2-MeNH-4-Pym | 1-Me-3-Pyrd-CH$_2$ |
| 2-1774 | 3-CF$_3$—Ph | 2-MeNH-4-Pym | 4-Pip-CH$_2$ |
| 2-1775 | 3-CF$_3$—Ph | 2-MeNH-4-Pym | 1-Me-4-Pip-CH$_2$ |
| 2-1776 | 3-CF$_3$—Ph | 2-MeNH-4-Pym | 2-Piz-CH$_2$ |
| 2-1777 | 3-CF$_3$—Ph | 2-MeNH-4-Pym | 4-Pyr-CH$_2$ |
| 2-1778 | 3-CF$_3$—Ph | 2-MeNH-4-Pym | 3-Pyr-CH$_2$ |
| 2-1779 | 3-CF$_3$—Ph | 2-MeNH-4-Pym | 4-Pym-CH$_2$ |
| 2-1780 | 3-CF$_3$—Ph | 2-MeNH-4-Pym | 5-Pym-CH$_2$ |
| 2-1781 | 3-CF$_3$—Ph | 2-MeNH-4-Pym | 2-Pym-CH$_2$ |
| 2-1782 | 3-CHF$_2$O—Ph | 2-MeNH-4-Pym | H$_2$—(CH$_2$)$_3$ |
| 2-1783 | 3-CHF$_2$O—Ph | 2-MeNH-4-Pym | MeNH—(CH$_2$)$_3$ |
| 2-1784 | 3-CHF$_2$O—Ph | 2-MeNH-4-Pym | EtNH—(CH$_2$)$_3$ |
| 2-1785 | 3-CHF$_2$O—Ph | 2-MeNH-4-Pym | Me$_2$N—(CH$_2$)$_3$ |
| 2-1786 | 3-CHF$_2$O—Ph | 2-MeNH-4-Pym | 1-Azt-(CH$_2$)$_3$ |
| 2-1787 | 3-CHF$_2$O—Ph | 2-MeNH-4-Pym | 1-Pyrd-(CH$_2$)$_3$ |
| 2-1788 | 3-CHF$_2$O—Ph | 2-MeNH-4-Pym | 1-Pip-(CH$_2$)$_3$ |
| 2-1789 | 3-CHF$_2$O—Ph | 2-MeNH-4-Pym | 1-Mor-(CH$_2$)$_3$ |
| 2-1790 | 3-CHF$_2$O—Ph | 2-MeNH-4-Pym | 1-Tmor-(CH$_2$)$_3$ |
| 2-1791 | 3-CHF$_2$O—Ph | 2-MeNH-4-Pym | 1-Piz-(CH$_2$)$_3$ |
| 2-1792 | 3-CHF$_2$O—Ph | 2-MeNH-4-Pym | 4-Me-1-Piz-(CH$_2$)$_3$ |
| 2-1793 | 3-CHF$_2$O—Ph | 2-MeNH-4-Pym | 3-Azt |
| 2-1794 | 3-CHF$_2$O—Ph | 2-MeNH-4-Pym | 1-Me-3-Azt |
| 2-1795 | 3-CHF$_2$O—Ph | 2-MeNH-4-Pym | 3-Pyrd |
| 2-1796 | 3-CHF$_2$O—Ph | 2-MeNH-4-Pym | 1-Me-3-Pyrd |
| 2-1797 | 3-CHF$_2$O—Ph | 2-MeNH-4-Pym | 4-Pip |
| 2-1798 | 3-CHF$_2$O—Ph | 2-MeNH-4-Pym | 4-(3,4-deH-Pip) |
| 2-1799 | 3-CHF$_2$O—Ph | 2-MeNH-4-Pym | 1-Me-4-Pip |
| 2-1800 | 3-CHF$_2$O—Ph | 2-MeNH-4-Pym | 1-Me-4-(3,4-deH-Pip) |
| 2-1801 | 3-CHF$_2$O—Ph | 2-MeNH-4-Pym | 1-Piz |
| 2-1802 | 3-CHF$_2$O—Ph | 2-MeNH-4-Pym | 4-Me-1-Piz |
| 2-1803 | 3-CHF$_2$O—Ph | 2-MeNH-4-Pym | 4-Pyr |
| 2-1804 | 3-CHF$_2$O—Ph | 2-MeNH-4-Pym | 3-Pyr |
| 2-1805 | 3-CHF$_2$O—Ph | 2-MeNH-4-Pym | 4-Pym |
| 2-1806 | 3-CHF$_2$O—Ph | 2-MeNH-4-Pym | 5-Pym |
| 2-1807 | 3-CHF$_2$O—Ph | 2-MeNH-4-Pym | 3-Pyrd-CH$_2$ |
| 2-1808 | 3-CHF$_2$O—Ph | 2-MeNH-4-Pym | 1-Me-3-Pyrd-CH$_2$ |
| 2-1809 | 3-CHF$_2$O—Ph | 2-MeNH-4-Pym | 4-Pip-CH$_2$ |
| 2-1810 | 3-CHF$_2$O—Ph | 2-MeNH-4-Pym | 1-Me-4-Pip-CH$_2$ |
| 2-1811 | 3-CHF$_2$O—Ph | 2-MeNH-4-Pym | 2-Piz-CH$_2$ |
| 2-1812 | 3-CHF$_2$O—Ph | 2-MeNH-4-Pym | 4-Pyr-CH$_2$ |
| 2-1813 | 3-CHF$_2$O—Ph | 2-MeNH-4-Pym | 3-Pyr-CH$_2$ |
| 2-1814 | 3-CHF$_2$O—Ph | 2-MeNH-4-Pym | 4-Pym-CH$_2$ |
| 2-1815 | 3-CHF$_2$O—Ph | 2-MeNH-4-Pym | 5-Pym-CH$_2$ |
| 2-1816 | 3-CHF$_2$O—Ph | 2-MeNH-4-Pym | 2-Pym-CH$_2$ |
| 2-1817 | Ph | 2-NH$_2$-4-Pyr | H$_2$—(CH$_2$)$_3$ |
| 2-1818 | Ph | 2-NH$_2$-4-Pyr | MeNH—(CH$_2$)$_3$ |
| 2-1819 | Ph | 2-NH$_2$-4-Pyr | EtNH—(CH$_2$)$_3$ |
| 2-1820 | Ph | 2-NH$_2$-4-Pyr | Me$_2$N—(CH$_2$)$_3$ |
| 2-1821 | Ph | 2-NH$_2$-4-Pyr | 1-Azt-(CH$_2$)$_3$ |
| 2-1822 | Ph | 2-NH$_2$-4-Pyr | 1-Pyrd-(CH$_2$)$_3$ |
| 2-1823 | Ph | 2-NH$_2$-4-Pyr | 1-Pip-(CH$_2$)$_3$ |
| 2-1824 | Ph | 2-NH$_2$-4-Pyr | 1-Mor-(CH$_2$)$_3$ |
| 2-1825 | Ph | 2-NH$_2$-4-Pyr | 1-Tmor-(CH$_2$)$_3$ |
| 2-1826 | Ph | 2-NH$_2$-4-Pyr | 1-Piz-(CH$_2$)$_3$ |
| 2-1827 | Ph | 2-NH$_2$-4-Pyr | 4-Me-1-Piz-(CH$_2$)$_3$ |
| 2-1828 | Ph | 2-NH$_2$-4-Pyr | 3-Azt |
| 2-1829 | Ph | 2-NH$_2$-4-Pyr | 1-Me-3-Azt |
| 2-1830 | Ph | 2-NH$_2$-4-Pyr | 3-Pyrd |
| 2-1831 | Ph | 2-NH$_2$-4-Pyr | 1-Me-3-Pyrd |
| 2-1832 | Ph | 2-NH$_2$-4-Pyr | 4-Pip |
| 2-1833 | Ph | 2-NH$_2$-4-Pyr | 4-(3,4-deH-Pip) |
| 2-1834 | Ph | 2-NH$_2$-4-Pyr | 1-Me-4-Pip |
| 2-1835 | Ph | 2-NH$_2$-4-Pyr | 1-Me-4-(3,4-deH-Pip) |
| 2-1836 | Ph | 2-NH$_2$-4-Pyr | 1-Piz |
| 2-1837 | Ph | 2-NH$_2$-4-Pyr | 4-Me-1-Piz |
| 2-1838 | Ph | 2-NH$_2$-4-Pyr | 4-Pyr |
| 2-1839 | Ph | 2-NH$_2$-4-Pyr | 3-Pyr |
| 2-1840 | Ph | 2-NH$_2$-4-Pyr | 4-Pym |
| 2-1841 | Ph | 2-NH$_2$-4-Pyr | 5-Pym |
| 2-1842 | Ph | 2-NH$_2$-4-Pyr | 3-Pyrd-CH$_2$ |
| 2-1843 | Ph | 2-NH$_2$-4-Pyr | 1-Me-3-Pyrd-CH$_2$ |
| 2-1844 | Ph | 2-NH$_2$-4-Pyr | 4-Pip-CH$_2$ |
| 2-1845 | Ph | 2-NH$_2$-4-Pyr | 1-Me-4-Pip-CH$_2$ |
| 2-1846 | Ph | 2-NH$_2$-4-Pyr | 2-Piz-CH$_2$ |
| 2-1847 | Ph | 2-NH$_2$-4-Pyr | 4-Pyr-CH$_2$ |
| 2-1848 | Ph | 2-NH$_2$-4-Pyr | 3-Pyr-CH$_2$ |
| 2-1849 | Ph | 2-NH$_2$-4-Pyr | 4-Pym-CH$_2$ |
| 2-1850 | Ph | 2-NH$_2$-4-Pyr | 5-Pym-CH$_2$ |
| 2-1851 | Ph | 2-NH$_2$-4-Pyr | 2-Pym-CH$_2$ |
| 2-1852 | 4-F—Ph | 2-NH$_2$-4-Pyr | H$_2$—(CH$_2$)$_3$ |
| 2-1853 | 4-F—Ph | 2-NH$_2$-4-Pyr | MeNH—(CH$_2$)$_3$ |
| 2-1854 | 4-F—Ph | 2-NH$_2$-4-Pyr | EtNH—(CH$_2$)$_3$ |
| 2-1855 | 4-F—Ph | 2-NH$_2$-4-Pyr | Me$_2$N—(CH$_2$)$_3$ |
| 2-1856 | 4-F—Ph | 2-NH$_2$-4-Pyr | 1-Azt-(CH$_2$)$_3$ |
| 2-1857 | 4-F—Ph | 2-NH$_2$-4-Pyr | 1-Pyrd-(CH$_2$)$_3$ |
| 2-1858 | 4-F—Ph | 2-NH$_2$-4-Pyr | 1-Pip-(CH$_2$)$_3$ |
| 2-1859 | 4-F—Ph | 2-NH$_2$-4-Pyr | 1-Mor-(CH$_2$)$_3$ |
| 2-1860 | 4-F—Ph | 2-NH$_2$-4-Pyr | 1-Tmor-(CH$_2$)$_3$ |
| 2-1861 | 4-F—Ph | 2-NH$_2$-4-Pyr | 1-Piz-(CH$_2$)$_3$ |
| 2-1862 | 4-F—Ph | 2-NH$_2$-4-Pyr | 4-Me-1-Piz-(CH$_2$)$_3$ |
| 2-1863 | 4-F—Ph | 2-NH$_2$-4-Pyr | 3-Azt |
| 2-1864 | 4-F—Ph | 2-NH$_2$-4-Pyr | 1-Me-3-Azt |
| 2-1865 | 4-F—Ph | 2-NH$_2$-4-Pyr | 3-Pyrd |
| 2-1866 | 4-F—Ph | 2-NH$_2$-4-Pyr | 1-Me-3-Pyrd |
| 2-1867 | 4-F—Ph | 2-NH$_2$-4-Pyr | 4-Pip |
| 2-1868 | 4-F—Ph | 2-NH$_2$-4-Pyr | 4-(3,4-deH-Pip) |
| 2-1869 | 4-F—Ph | 2-NH$_2$-4-Pyr | 1-Me-4-Pip |
| 2-1870 | 4-F—Ph | 2-NH$_2$-4-Pyr | 1-Me-4-(3,4-deH-Pip) |
| 2-1871 | 4-F—Ph | 2-NH$_2$-4-Pyr | 1-Piz |
| 2-1872 | 4-F—Ph | 2-NH$_2$-4-Pyr | 4-Me-1-Piz |
| 2-1873 | 4-F—Ph | 2-NH$_2$-4-Pyr | 4-Pyr |
| 2-1874 | 4-F—Ph | 2-NH$_2$-4-Pyr | 3-Pyr |
| 2-1875 | 4-F—Ph | 2-NH$_2$-4-Pyr | 4-Pym |
| 2-1876 | 4-F—Ph | 2-NH$_2$-4-Pyr | 5-Pym |
| 2-1877 | 4-F—Ph | 2-NH$_2$-4-Pyr | 3-Pyrd-CH$_2$ |

TABLE 2-continued

| Compound No. | R¹ | R² | R³ |
|---|---|---|---|
| 2-1878 | 4-F—Ph | 2-NH₂-4-Pyr | 1-Me-3-Pyrd-CH₂ |
| 2-1879 | 4-F—Ph | 2-NH₂-4-Pyr | 4-Pip-CH₂ |
| 2-1880 | 4-F—Ph | 2-NH₂-4-Pyr | 1-Me-4-Pip-CH₂ |
| 2-1881 | 4-F—Ph | 2-NH₂-4-Pyr | 2-Piz-CH₂ |
| 2-1882 | 4-F—Ph | 2-NH₂-4-Pyr | 4-Pyr-CH₂ |
| 2-1883 | 4-F—Ph | 2-NH₂-4-Pyr | 3-Pyr-CH₂ |
| 2-1884 | 4-F—Ph | 2-NH₂-4-Pyr | 4-Pym-CH₂ |
| 2-1885 | 4-F—Ph | 2-NH₂-4-Pyr | 5-Pym-CH₂ |
| 2-1886 | 4-F—Ph | 2-NH₂-4-Pyr | 2-Pym-CH₂ |
| 2-1887 | 3-F—Ph | 2-NH₂-4-Pyr | H₂—(CH₂)₃ |
| 2-1888 | 3-F—Ph | 2-NH₂-4-Pyr | MeNH—(CH₂)₃ |
| 2-1889 | 3-F—Ph | 2-NH₂-4-Pyr | EtNH—(CH₂)₃ |
| 2-1890 | 3-F—Ph | 2-NH₂-4-Pyr | Me₂N—(CH₂)₃ |
| 2-1891 | 3-F—Ph | 2-NH₂-4-Pyr | 1-Azt-(CH₂)₃ |
| 2-1892 | 3-F—Ph | 2-NH₂-4-Pyr | 1-Pyrd-(CH₂)₃ |
| 2-1893 | 3-F—Ph | 2-NH₂-4-Pyr | 1-Pip-(CH₂)₃ |
| 2-1894 | 3-F—Ph | 2-NH₂-4-Pyr | 1-Mor-(CH₂)₃ |
| 2-1895 | 3-F—Ph | 2-NH₂-4-Pyr | 1-Tmor-(CH₂)₃ |
| 2-1896 | 3-F—Ph | 2-NH₂-4-Pyr | 1-Piz-(CH₂)₃ |
| 2-1897 | 3-F—Ph | 2-NH₂-4-Pyr | 4-Me-1-Piz-(CH₂)₃ |
| 2-1898 | 3-F—Ph | 2-NH₂-4-Pyr | 3-Azt |
| 2-1899 | 3-F—Ph | 2-NH₂-4-Pyr | 1-Me-3-Azt |
| 2-1900 | 3-F—Ph | 2-NH₂-4-Pyr | 3-Pyrd |
| 2-1901 | 3-F—Ph | 2-NH₂-4-Pyr | 1-Me-3-Pyrd |
| 2-1902 | 3-F—Ph | 2-NH₂-4-Pyr | 4-Pip |
| 2-1903 | 3-F—Ph | 2-NH₂-4-Pyr | 4-(3,4-deH-Pip) |
| 2-1904 | 3-F—Ph | 2-NH₂-4-Pyr | 1-Me-4-Pip |
| 2-1905 | 3-F—Ph | 2-NH₂-4-Pyr | 1-Me-4-(3,4-deH-Pip) |
| 2-1906 | 3-F—Ph | 2-NH₂-4-Pyr | 1-Piz |
| 2-1907 | 3-F—Ph | 2-NH₂-4-Pyr | 4-Me-1-Piz |
| 2-1908 | 3-F—Ph | 2-NH₂-4-Pyr | 4-Pyr |
| 2-1909 | 3-F—Ph | 2-NH₂-4-Pyr | 3-Pyr |
| 2-1910 | 3-F—Ph | 2-NH₂-4-Pyr | 4-Pym |
| 2-1911 | 3-F—Ph | 2-NH₂-4-Pyr | 5-Pym |
| 2-1912 | 3-F—Ph | 2-NH₂-4-Pyr | 3-Pyrd-CH₂ |
| 2-1913 | 3-F—Ph | 2-NH₂-4-Pyr | 1-Me-3-Pyrd-CH₂ |
| 2-1914 | 3-F—Ph | 2-NH₂-4-Pyr | 4-Pip-CH₂ |
| 2-1915 | 3-F—Ph | 2-NH₂-4-Pyr | 1-Me-4-Pip-CH₂ |
| 2-1916 | 3-F—Ph | 2-NH₂-4-Pyr | 2-Piz-CH₂ |
| 2-1917 | 3-F—Ph | 2-NH₂-4-Pyr | 4-Pyr-CH₂ |
| 2-1918 | 3-F—Ph | 2-NH₂-4-Pyr | 3-Pyr-CH₂ |
| 2-1919 | 3-F—Ph | 2-NH₂-4-Pyr | 4-Pym-CH₂ |
| 2-1920 | 3-F—Ph | 2-NH₂-4-Pyr | 5-Pym-CH₂ |
| 2-1921 | 3-F—Ph | 2-NH₂-4-Pyr | 2-Pym-CH₂ |
| 2-1922 | 3,4-diF—Ph | 2-NH₂-4-Pyr | H₂—(CH₂)₃ |
| 2-1923 | 3,4-diF—Ph | 2-NH₂-4-Pyr | MeNH—(CH₂)₃ |
| 2-1924 | 3,4-diF—Ph | 2-NH₂-4-Pyr | EtNH—(CH₂)₃ |
| 2-1925 | 3,4-diF—Ph | 2-NH₂-4-Pyr | Me₂N—(CH₂)₃ |
| 2-1926 | 3,4-diF—Ph | 2-NH₂-4-Pyr | 1-Azt-(CH₂)₃ |
| 2-1927 | 3,4-diF—Ph | 2-NH₂-4-Pyr | 1-Pyrd-(CH₂)₃ |
| 2-1928 | 3,4-diF—Ph | 2-NH₂-4-Pyr | 1-Pip-(CH₂)₃ |
| 2-1929 | 3,4-diF—Ph | 2-NH₂-4-Pyr | 1-Mor-(CH₂)₃ |
| 2-1930 | 3,4-diF—Ph | 2-NH₂-4-Pyr | 1-Tmor-(CH₂)₃ |
| 2-1931 | 3,4-diF—Ph | 2-NH₂-4-Pyr | 1-Piz-(CH₂)₃ |
| 2-1932 | 3,4-diF—Ph | 2-NH₂-4-Pyr | 4-Me-1-Piz-(CH₂)₃ |
| 2-1933 | 3,4-diF—Ph | 2-NH₂-4-Pyr | 3-Azt |
| 2-1934 | 3,4-diF—Ph | 2-NH₂-4-Pyr | 1-Me-3-Azt |
| 2-1935 | 3,4-diF—Ph | 2-NH₂-4-Pyr | 3-Pyrd |
| 2-1936 | 3,4-diF—Ph | 2-NH₂-4-Pyr | 1-Me-3-Pyrd |
| 2-1937 | 3,4-diF—Ph | 2-NH₂-4-Pyr | 4-Pip |
| 2-1938 | 3,4-diF—Ph | 2-NH₂-4-Pyr | 4-(3,4-deH-Pip) |
| 2-1939 | 3,4-diF—Ph | 2-NH₂-4-Pyr | 1-Me-4-Pip |
| 2-1940 | 3,4-diF—Ph | 2-NH₂-4-Pyr | 1-Me-4-(3,4-deH-Pip) |
| 2-1941 | 3,4-diF—Ph | 2-NH₂-4-Pyr | 1-Piz |
| 2-1942 | 3,4-diF—Ph | 2-NH₂-4-Pyr | 4-Me-1-Piz |
| 2-1943 | 3,4-diF—Ph | 2-NH₂-4-Pyr | 4-Pyr |
| 2-1944 | 3,4-diF—Ph | 2-NH₂-4-Pyr | 3-Pyr |
| 2-1945 | 3,4-diF—Ph | 2-NH₂-4-Pyr | 4-Pym |
| 2-1946 | 3,4-diF—Ph | 2-NH₂-4-Pyr | 5-Pym |
| 2-1947 | 3,4-diF—Ph | 2-NH₂-4-Pyr | 3-Pyrd-CH₂ |
| 2-1948 | 3,4-diF—Ph | 2-NH₂-4-Pyr | 1-Me-3-Pyrd-CH₂ |
| 2-1949 | 3,4-diF—Ph | 2-NH₂-4-Pyr | 4-Pip-CH₂ |
| 2-1950 | 3,4-diF—Ph | 2-NH₂-4-Pyr | 1-Me-4-Pip-CH₂ |
| 2-1951 | 3,4-diF—Ph | 2-NH₂-4-Pyr | 2-Piz-CH₂ |
| 2-1952 | 3,4-diF—Ph | 2-NH₂-4-Pyr | 4-Pyr-CH₂ |
| 2-1953 | 3,4-diF—Ph | 2-NH₂-4-Pyr | 3-Pyr-CH₂ |
| 2-1954 | 3,4-diF—Ph | 2-NH₂-4-Pyr | 4-Pym-CH₂ |
| 2-1955 | 3,4-diF—Ph | 2-NH₂-4-Pyr | 5-Pym-CH₂ |
| 2-1956 | 3,4-diF—Ph | 2-NH₂-4-Pyr | 2-Pym-CH₂ |
| 2-1957 | 3-Cl—Ph | 2-NH₂-4-Pyr | H₂N—(CH₂)₃ |
| 2-1959 | 3-Cl—Ph | 2-NH₂-4-Pyr | EtNH—(CH₂)₃ |
| 2-1960 | 3-Cl—Ph | 2-NH₂-4-Pyr | Me₂N—(CH₂)₃ |
| 2-1961 | 3-Cl—Ph | 2-NH₂-4-Pyr | 1-Azt-(CH₂)₃ |
| 2-1962 | 3-Cl—Ph | 2-NH₂-4-Pyr | 1-Pyrd-(CH₂)₃ |
| 2-1963 | 3-Cl—Ph | 2-NH₂-4-Pyr | 1-Pip-(CH₂)₃ |
| 2-1964 | 3-Cl—Ph | 2-NH₂-4-Pyr | 1-Mor-(CH₂)₃ |
| 2-1965 | 3-Cl—Ph | 2-NH₂-4-Pyr | 1-Tmor-(CH₂)₃ |
| 2-1966 | 3-Cl—Ph | 2-NH₂-4-Pyr | 1-Piz-(CH₂)₃ |
| 2-1967 | 3-Cl—Ph | 2-NH₂-4-Pyr | 4-Me-1-Piz-(CH₂)₃ |
| 2-1968 | 3-Cl—Ph | 2-NH₂-4-Pyr | 3-Azt |
| 2-1969 | 3-Cl—Ph | 2-NH₂-4-Pyr | 1-Me-3-Azt |
| 2-1970 | 3-Cl—Ph | 2-NH₂-4-Pyr | 3-Pyrd |
| 2-1971 | 3-Cl—Ph | 2-NH₂-4-Pyr | 1-Me-3-Pyrd |
| 2-1972 | 3-Cl—Ph | 2-NH₂-4-Pyr | 4-Pip |
| 2-1973 | 3-Cl—Ph | 2-NH₂-4-Pyr | 4-(3,4-deH-Pip) |
| 2-1974 | 3-Cl—Ph | 2-NH₂-4-Pyr | 1-Me-4-Pip |
| 2-1975 | 3-Cl—Ph | 2-NH₂-4-Pyr | 1-Me-4-(3,4-deH-Pip) |
| 2-1976 | 3-Cl—Ph | 2-NH₂-4-Pyr | 1-Piz |
| 2-1977 | 3-Cl—Ph | 2-NH₂-4-Pyr | 4-Me-1-Piz |
| 2-1978 | 3-Cl—Ph | 2-NH₂-4-Pyr | 4-Pyr |
| 2-1979 | 3-Cl—Ph | 2-NH₂-4-Pyr | 3-Pyr |
| 2-1980 | 3-Cl—Ph | 2-NH₂-4-Pyr | 4-Pym |
| 2-1981 | 3-Cl—Ph | 2-NH₂-4-Pyr | 5-Pym |
| 2-1982 | 3-Cl—Ph | 2-NH₂-4-Pyr | 3-Pyrd-CH₂ |
| 2-1983 | 3-Cl—Ph | 2-NH₂-4-Pyr | 1-Me-3-Pyrd-CH₂ |
| 2-1984 | 3-Cl—Ph | 2-NH₂-4-Pyr | 4-Pip-CH₂ |
| 2-1985 | 3-Cl—Ph | 2-NH₂-4-Pyr | 1-Me-4-Pip-CH₂ |
| 2-1986 | 3-Cl—Ph | 2-NH₂-4-Pyr | 2-Piz-CH₂ |
| 2-1987 | 3-Cl—Ph | 2-NH₂-4-Pyr | 4-Pyr-CH₂ |
| 2-1988 | 3-Cl—Ph | 2-NH₂-4-Pyr | 3-Pyr-CH₂ |
| 2-1989 | 3-Cl—Ph | 2-NH₂-4-Pyr | 4-Pym-CH₂ |
| 2-1990 | 3-Cl—Ph | 2-NH₂-4-Pyr | 5-Pym-CH₂ |
| 2-1991 | 3-Cl—Ph | 2-NH₂-4-Pyr | 2-Pym-CH₂ |
| 2-1992 | Ph | 2-MeNH-4-Pyr | H₂—(CH₂)₃ |
| 2-1993 | Ph | 2-MeNH-4-Pyr | MeNH—(CH₂)₃ |
| 2-1994 | Ph | 2-MeNH-4-Pyr | EtNH—(CH₂)₃ |
| 2-1995 | Ph | 2-MeNH-4-Pyr | Me₂N—(CH₂)₃ |
| 2-1996 | Ph | 2-MeNH-4-Pyr | 1-Azt-(CH₂)₃ |
| 2-1997 | Ph | 2-MeNH-4-Pyr | 1-Pyrd-(CH₂)₃ |
| 2-1998 | Ph | 2-MeNH-4-Pyr | 1-Pip-(CH₂)₃ |
| 2-1999 | Ph | 2-MeNH-4-Pyr | 1-Mor-(CH₂)₃ |
| 2-2000 | Ph | 2-MeNH-4-Pyr | 1-Tmor-(CH₂)₃ |
| 2-2001 | Ph | 2-MeNH-4-Pyr | 1-Piz-(CH₂)₃ |
| 2-2002 | Ph | 2-MeNH-4-Pyr | 4-Me-1-Piz-(CH₂)₃ |
| 2-2003 | Ph | 2-MeNH-4-Pyr | 3-Azt |
| 2-2004 | Ph | 2-MeNH-4-Pyr | 1-Me-3-Azt |
| 2-2005 | Ph | 2-MeNH-4-Pyr | 3-Pyrd |
| 2-2006 | Ph | 2-MeNH-4-Pyr | 1-Me-3-Pyrd |
| 2-2007 | Ph | 2-MeNH-4-Pyr | 4-Pip |
| 2-2008 | Ph | 2-MeNH-4-Pyr | 4-(3,4-deH-Pip) |
| 2-2009 | Ph | 2-MeNH-4-Pyr | 1-Me-4-Pip |
| 2-2010 | Ph | 2-MeNH-4-Pyr | 1-Me-4-(3,4-deH-Pip) |
| 2-2011 | Ph | 2-MeNH-4-Pyr | 1-Piz |
| 2-2012 | Ph | 2-MeNH-4-Pyr | 4-Me-1-Piz |
| 2-2013 | Ph | 2-MeNH-4-Pyr | 4-Pyr |
| 2-2014 | Ph | 2-MeNH-4-Pyr | 3-Pyr |
| 2-2015 | Ph | 2-MeNH-4-Pyr | 4-Pym |
| 2-2016 | Ph | 2-MeNH-4-Pyr | 5-Pym |
| 2-2017 | Ph | 2-MeNH-4-Pyr | 3-Pyrd-CH₂ |
| 2-2018 | Ph | 2-MeNH-4-Pyr | 1-Me-3-Pyrd-CH₂ |
| 2-2019 | Ph | 2-MeNH-4-Pyr | 4-Pip-CH₂ |
| 2-2020 | Ph | 2-MeNH-4-Pyr | 1-Me-4-Pip-CH₂ |
| 2-2021 | Ph | 2-MeNH-4-Pyr | 2-Piz-CH₂ |
| 2-2022 | Ph | 2-MeNH-4-Pyr | 4-Pyr-CH₂ |
| 2-2023 | Ph | 2-MeNH-4-Pyr | 3-Pyr-CH₂ |
| 2-2024 | Ph | 2-MeNH-4-Pyr | 4-Pym-CH₂ |
| 2-2025 | Ph | 2-MeNH-4-Pyr | 5-Pym-CH₂ |
| 2-2026 | Ph | 2-MeNH-4-Pyr | 2-Pym-CH₂ |
| 2-2027 | 4-F—Ph | 2-MeNH-4-Pyr | H₂—(CH₂)₃ |

TABLE 2-continued

| Compound No. | R¹ | R² | R³ |
|---|---|---|---|
| 2-2028 | 4-F—Ph | 2-MeNH-4-Pyr | MeNH—(CH$_2$)$_3$ |
| 2-2029 | 4-F—Ph | 2-MeNH-4-Pyr | EtNH—(CH$_2$)$_3$ |
| 2-2030 | 4-F—Ph | 2-MeNH-4-Pyr | Me$_2$N—(CH$_2$)$_3$ |
| 2-2031 | 4-F—Ph | 2-MeNH-4-Pyr | 1-Azt-(CH$_2$)$_3$ |
| 2-2032 | 4-F—Ph | 2-MeNH-4-Pyr | 1-Pyrd-(CH$_2$)$_3$ |
| 2-2033 | 4-F—Ph | 2-MeNH-4-Pyr | 1-Pip-(CH$_2$)$_3$ |
| 2-2034 | 4-F—Ph | 2-MeNH-4-Pyr | 1-Mor-(CH$_2$)$_3$ |
| 2-2035 | 4-F—Ph | 2-MeNH-4-Pyr | 1-Tmor-(CH$_2$)$_3$ |
| 2-2036 | 4-F—Ph | 2-MeNH-4-Pyr | 1-Piz-(CH$_2$)$_3$ |
| 2-2037 | 4-F—Ph | 2-MeNH-4-Pyr | 4-Me-1-Piz-(CH$_2$)$_3$ |
| 2-2038 | 4-F—Ph | 2-MeNH-4-Pyr | 3-Azt |
| 2-2039 | 4-F—Ph | 2-MeNH-4-Pyr | 1-Me-3-Azt |
| 2-2040 | 4-F—Ph | 2-MeNH-4-Pyr | 3-Pyrd |
| 2-2041 | 4-F—Ph | 2-MeNH-4-Pyr | 1-Me-3-Pyrd |
| 2-2042 | 4-F—Ph | 2-MeNH-4-Pyr | 4-Pip |
| 2-2043 | 4-F—Ph | 2-MeNH-4-Pyr | 4-(3,4-deH-Pip) |
| 2-2044 | 4-F—Ph | 2-MeNH-4-Pyr | 1-Me-4-Pip |
| 2-2045 | 4-F—Ph | 2-MeNH-4-Pyr | 1-Me-4-(3,4-deH-Pip) |
| 2-2046 | 4-F—Ph | 2-MeNH-4-Pyr | 1-Piz |
| 2-2047 | 4-F—Ph | 2-MeNH-4-Pyr | 4-Me-1-Piz |
| 2-2048 | 4-F—Ph | 2-MeNH-4-Pyr | 4-Pyr |
| 2-2049 | 4-F—Ph | 2-MeNH-4-Pyr | 3-Pyr |
| 2-2050 | 4-F—Ph | 2-MeNH-4-Pyr | 4-Pym |
| 2-2051 | 4-F—Ph | 2-MeNH-4-Pyr | 5-Pym |
| 2-2052 | 4-F—Ph | 2-MeNH-4-Pyr | 3-Pyrd-CH$_2$ |
| 2-2053 | 4-F—Ph | 2-MeNH-4-Pyr | 1-Me-3-Pyrd-CH$_2$ |
| 2-2054 | 4-F—Ph | 2-MeNH-4-Pyr | 4-Pip-CH$_2$ |
| 2-2055 | 4-F—Ph | 2-MeNH-4-Pyr | 1-Me-4-Pip-CH$_2$ |
| 2-2056 | 4-F—Ph | 2-MeNH-4-Pyr | 2-Piz-CH$_2$ |
| 2-2057 | 4-F—Ph | 2-MeNH-4-Pyr | 4-Pyr-CH$_2$ |
| 2-2058 | 4-F—Ph | 2-MeNH-4-Pyr | 3-Pyr-CH$_2$ |
| 2-2059 | 4-F—Ph | 2-MeNH-4-Pyr | 4-Pym-CH$_2$ |
| 2-2060 | 4-F—Ph | 2-MeNH-4-Pyr | 5-Pym-CH$_2$ |
| 2-2061 | 4-F—Ph | 2-MeNH-4-Pyr | 2-Pym-CH$_2$ |
| 2-2062 | 3-F—Ph | 2-MeNH-4-Pyr | H$_2$—(CH$_2$)$_3$ |
| 2-2063 | 3-F—Ph | 2-MeNH-4-Pyr | MeNH—(CH$_2$)$_3$ |
| 2-2064 | 3-F—Ph | 2-MeNH-4-Pyr | EtNH—(CH$_2$)$_3$ |
| 2-2065 | 3-F—Ph | 2-MeNH-4-Pyr | Me$_2$N—(CH$_2$)$_3$ |
| 2-2066 | 3-F—Ph | 2-MeNH-4-Pyr | 1-Azt-(CH$_2$)$_3$ |
| 2-2067 | 3-F—Ph | 2-MeNH-4-Pyr | 1-Pyrd-(CH$_2$)$_3$ |
| 2-2068 | 3-F—Ph | 2-MeNH-4-Pyr | 1-Pip-(CH$_2$)$_3$ |
| 2-2069 | 3-F—Ph | 2-MeNH-4-Pyr | 1-Mor-(CH$_2$)$_3$ |
| 2-2070 | 3-F—Ph | 2-MeNH-4-Pyr | 1-Tmor-(CH$_2$)$_3$ |
| 2-2071 | 3-F—Ph | 2-MeNH-4-Pyr | 1-Piz-(CH$_2$)$_3$ |
| 2-2072 | 3-F—Ph | 2-MeNH-4-Pyr | 4-Me-1-Piz-(CH$_2$)$_3$ |
| 2-2073 | 3-F—Ph | 2-MeNH-4-Pyr | 3-Azt |
| 2-2074 | 3-F—Ph | 2-MeNH-4-Pyr | 1-Me-3-Azt |
| 2-2075 | 3-F—Ph | 2-MeNH-4-Pyr | 3-Pyrd |
| 2-2076 | 3-F—Ph | 2-MeNH-4-Pyr | 1-Me-3-Pyrd |
| 2-2077 | 3-F—Ph | 2-MeNH-4-Pyr | 4-Pip |
| 2-2078 | 3-F—Ph | 2-MeNH-4-Pyr | 4-(3,4-deH-Pip) |
| 2-2079 | 3-F—Ph | 2-MeNH-4-Pyr | 1-Me-4-Pip |
| 2-2080 | 3-F—Ph | 2-MeNH-4-Pyr | 1-Me-4-(3,4-deH-Pip) |
| 2-2081 | 3-F—Ph | 2-MeNH-4-Pyr | 1-Piz |
| 2-2082 | 3-F—Ph | 2-MeNH-4-Pyr | 4-Me-1-Piz |
| 2-2083 | 3-F—Ph | 2-MeNH-4-Pyr | 4-Pyr |
| 2-2084 | 3-F—Ph | 2-MeNH-4-Pyr | 3-Pyr |
| 2-2085 | 3-F—Ph | 2-MeNH-4-Pyr | 4-Pym |
| 2-2086 | 3-F—Ph | 2-MeNH-4-Pyr | 5-Pym |
| 2-2087 | 3-F—Ph | 2-MeNH-4-Pyr | 3-Pyrd-CH$_2$ |
| 2-2088 | 3-F—Ph | 2-MeNH-4-Pyr | 1-Me-3-Pyrd-CH$_2$ |
| 2-2089 | 3-F—Ph | 2-MeNH-4-Pyr | 4-Pip-CH$_2$ |
| 2-2090 | 3-F—Ph | 2-MeNH-4-Pyr | 1-Me-4-Pip-CH$_2$ |
| 2-2091 | 3-F—Ph | 2-MeNH-4-Pyr | 2-Piz-CH$_2$ |
| 2-2092 | 3-F—Ph | 2-MeNH-4-Pyr | 4-Pyr-CH$_2$ |
| 2-2093 | 3-F—Ph | 2-MeNH-4-Pyr | 3-Pyr-CH$_2$ |
| 2-2094 | 3-F—Ph | 2-MeNH-4-Pyr | 4-Pym-CH$_2$ |
| 2-2095 | 3-F—Ph | 2-MeNH-4-Pyr | 5-Pym-CH$_2$ |
| 2-2096 | 3-F—Ph | 2-MeNH-4-Pyr | 2-Pym-CH$_2$ |
| 2-2097 | 3,4-diF—Ph | 2-MeNH-4-Pyr | H$_2$—(CH$_2$)$_3$ |
| 2-2098 | 3,4-diF—Ph | 2-MeNH-4-Pyr | MeNH—(CH$_2$)$_3$ |
| 2-2099 | 3,4-diF—Ph | 2-MeNH-4-Pyr | EtNH—(CH$_2$)$_3$ |
| 2-2100 | 3,4-diF—Ph | 2-MeNH-4-Pyr | Me$_2$N—(CH$_2$)$_3$ |
| 2-2101 | 3,4-diF—Ph | 2-MeNH-4-Pyr | 1-Azt-(CH$_2$)$_3$ |
| 2-2102 | 3,4-diF—Ph | 2-MeNH-4-Pyr | 1-Pyrd-(CH$_2$)$_3$ |
| 2-2103 | 3,4-diF—Ph | 2-MeNH-4-Pyr | 1-Pip-(CH$_2$)$_3$ |
| 2-2104 | 3,4-diF—Ph | 2-MeNH-4-Pyr | 1-Mor-(CH$_2$)$_3$ |
| 2-2105 | 3,4-diF—Ph | 2-MeNH-4-Pyr | 1-Tmor-(CH$_2$)$_3$ |
| 2-2106 | 3,4-diF—Ph | 2-MeNH-4-Pyr | 1-Piz-(CH$_2$)$_3$ |
| 2-2107 | 3,4-diF—Ph | 2-MeNH-4-Pyr | 4-Me-1-Piz-(CH$_2$)$_3$ |
| 2-2108 | 3,4-diF—Ph | 2-MeNH-4-Pyr | 3-Azt |
| 2-2109 | 3,4-diF—Ph | 2-MeNH-4-Pyr | 1-Me-3-Azt |
| 2-2110 | 3,4-diF—Ph | 2-MeNH-4-Pyr | 3-Pyrd |
| 2-2111 | 3,4-diF—Ph | 2-MeNH-4-Pyr | 1-Me-3-Pyrd |
| 2-2112 | 3,4-diF—Ph | 2-MeNH-4-Pyr | 4-Pip |
| 2-2113 | 3,4-diF—Ph | 2-MeNH-4-Pyr | 4-(3,4-deH-Pip) |
| 2-2114 | 3,4-diF—Ph | 2-MeNH-4-Pyr | 1-Me-4-Pip |
| 2-2115 | 3,4-diF—Ph | 2-MeNH-4-Pyr | 1-Me-4-(3,4-deH-Pip) |
| 2-2116 | 3,4-diF—Ph | 2-MeNH-4-Pyr | 1-Piz |
| 2-2117 | 3,4-diF—Ph | 2-MeNH-4-Pyr | 4-Me-1-Piz |
| 2-2118 | 3,4-diF—Ph | 2-MeNH-4-Pyr | 4-Pyr |
| 2-2119 | 3,4-diF—Ph | 2-MeNH-4-Pyr | 3-Pyr |
| 2-2120 | 3,4-diF—Ph | 2-MeNH-4-Pyr | 4-Pym |
| 2-2121 | 3,4-diF—Ph | 2-MeNH-4-Pyr | 5-Pym |
| 2-2122 | 3,4-diF—Ph | 2-MeNH-4-Pyr | 3-Pyrd-CH$_2$ |
| 2-2123 | 3,4-diF—Ph | 2-MeNH-4-Pyr | 1-Me-3-Pyrd-CH$_2$ |
| 2-2124 | 3,4-diF—Ph | 2-MeNH-4-Pyr | 4-Pip-CH$_2$ |
| 2-2125 | 3,4-diF—Ph | 2-MeNH-4-Pyr | 1-Me-4-Pip-CH$_2$ |
| 2-2126 | 3,4-diF—Ph | 2-MeNH-4-Pyr | 2-Piz-CH$_2$ |
| 2-2127 | 3,4-diF—Ph | 2-MeNH-4-Pyr | 4-Pyr-CH$_2$ |
| 2-2128 | 3,4-diF—Ph | 2-MeNH-4-Pyr | 3-Pyr-CH$_2$ |
| 2-2129 | 3,4-diF—Ph | 2-MeNH-4-Pyr | 4-Pym-CH$_2$ |
| 2-2130 | 3,4-diF—Ph | 2-MeNH-4-Pyr | 5-Pym-CH$_2$ |
| 2-2131 | 3,4-diF—Ph | 2-MeNH-4-Pyr | 2-Pym-CH$_2$ |
| 2-2132 | 3-Cl—Ph | 2-MeNH-4-Pyr | H$_2$—(CH$_2$)$_3$ |
| 2-2133 | 3-Cl—Ph | 2-MeNH-4-Pyr | MeNH—(CH$_2$)$_3$ |
| 2-2134 | 3-Cl—Ph | 2-MeNH-4-Pyr | EtNH—(CH$_2$)$_3$ |
| 2-2135 | 3-Cl—Ph | 2-MeNH-4-Pyr | Me$_2$N—(CH$_2$)$_3$ |
| 2-2136 | 3-Cl—Ph | 2-MeNH-4-Pyr | 1-Azt-(CH$_2$)$_3$ |
| 2-2137 | 3-Cl—Ph | 2-MeNH-4-Pyr | 1-Pyrd-(CH$_2$)$_3$ |
| 2-2138 | 3-Cl—Ph | 2-MeNH-4-Pyr | 1-Pip-(CH$_2$)$_3$ |
| 2-2139 | 3-Cl—Ph | 2-MeNH-4-Pyr | 1-Mor-(CH$_2$)$_3$ |
| 2-2140 | 3-Cl—Ph | 2-MeNH-4-Pyr | 1-Tmor-(CH$_2$)$_3$ |
| 2-2141 | 3-Cl—Ph | 2-MeNH-4-Pyr | 1-Piz-(CH$_2$)$_3$ |
| 2-2142 | 3-Cl—Ph | 2-MeNH-4-Pyr | 4-Me-1-Piz-(CH$_2$)$_3$ |
| 2-2143 | 3-Cl—Ph | 2-MeNH-4-Pyr | 3-Azt |
| 2-2144 | 3-Cl—Ph | 2-MeNH-4-Pyr | 1-Me-3-Azt |
| 2-2145 | 3-Cl—Ph | 2-MeNH-4-Pyr | 3-Pyrd |
| 2-2146 | 3-Cl—Ph | 2-MeNH-4-Pyr | 1-Me-3-Pyrd |
| 2-2147 | 3-Cl—Ph | 2-MeNH-4-Pyr | 4-Pip |
| 2-2148 | 3-Cl—Ph | 2-MeNH-4-Pyr | 4-(3,4-deH-Pip) |
| 2-2149 | 3-Cl—Ph | 2-MeNH-4-Pyr | 1-Me-4-Pip |
| 2-2150 | 3-Cl—Ph | 2-MeNH-4-Pyr | 1-Me-4-(3,4-deH-Pip) |
| 2-2151 | 3-Cl—Ph | 2-MeNH-4-Pyr | 1-Piz |
| 2-2152 | 3-Cl—Ph | 2-MeNH-4-Pyr | 4-Me-1-Piz |
| 2-2153 | 3-Cl—Ph | 2-MeNH-4-Pyr | 4-Pyr |
| 2-2154 | 3-Cl—Ph | 2-MeNH-4-Pyr | 3-Pyr |
| 2-2155 | 3-Cl—Ph | 2-MeNH-4-Pyr | 4-Pym |
| 2-2156 | 3-Cl—Ph | 2-MeNH-4-Pyr | 5-Pym |
| 2-2157 | 3-Cl—Ph | 2-MeNH-4-Pyr | 3-Pyrd-CH$_2$ |
| 2-2158 | 3-Cl—Ph | 2-MeNH-4-Pyr | 1-Me-3-Pyrd-CH$_2$ |
| 2-2159 | 3-Cl—Ph | 2-MeNH-4-Pyr | 4-Pip-CH$_2$ |
| 2-2160 | 3-Cl—Ph | 2-MeNH-4-Pyr | 1-Me-4-Pip-CH$_2$ |
| 2-2161 | 3-Cl—Ph | 2-MeNH-4-Pyr | 2-Piz-CH$_2$ |
| 2-2162 | 3-Cl—Ph | 2-MeNH-4-Pyr | 4-Pyr-CH$_2$ |
| 2-2163 | 3-Cl—Ph | 2-MeNH-4-Pyr | 3-Pyr-CH$_2$ |
| 2-2164 | 3-Cl—Ph | 2-MeNH-4-Pyr | 4-Pym-CH$_2$ |
| 2-2165 | 3-Cl—Ph | 2-MeNH-4-Pyr | 5-Pym-CH$_2$ |
| 2-2166 | 3-Cl—Ph | 2-MeNH-4-Pyr | 2-Pym-CH$_2$ |
| 2-2167 | Ph | 4-Pym | H$_2$—(CH$_2$)$_3$ |
| 2-2168 | Ph | 4-Pym | MeNH—(CH$_2$)$_3$ |
| 2-2169 | Ph | 4-Pym | EtNH—(CH$_2$)$_3$ |
| 2-2170 | Ph | 4-Pym | Me$_2$N—(CH$_2$)$_3$ |
| 2-2171 | Ph | 4-Pym | 1-Azt-(CH$_2$)$_3$ |
| 2-2172 | Ph | 4-Pym | 1-Pyrd-(CH$_2$)$_3$ |
| 2-2173 | Ph | 4-Pym | 1-Pip-(CH$_2$)$_3$ |
| 2-2174 | Ph | 4-Pym | 1-Mor-(CH$_2$)$_3$ |
| 2-2175 | Ph | 4-Pym | 1-Tmor-(CH$_2$)$_3$ |
| 2-2176 | Ph | 4-Pym | 1-Piz-(CH$_2$)$_3$ |
| 2-2177 | Ph | 4-Pym | 4-Me-1-Piz-(CH$_2$)$_3$ |

TABLE 2-continued

| Compound No. | R¹ | R² | R³ |
|---|---|---|---|
| 2-2178 | Ph | 4-Pym | 3-Azt |
| 2-2179 | Ph | 4-Pym | 1-Me-3-Azt |
| 2-2180 | Ph | 4-Pym | 3-Pyrd |
| 2-2181 | Ph | 4-Pym | 1-Me-3-Pyrd |
| 2-2182 | Ph | 4-Pym | 4-Pip |
| 2-2183 | Ph | 4-Pym | 4-(3,4-deH-Pip) |
| 2-2184 | Ph | 4-Pym | 1-Me-4-Pip |
| 2-2185 | Ph | 4-Pym | 1-Me-4-(3,4-deH-Pip) |
| 2-2186 | Ph | 4-Pym | 1-Piz |
| 2-2187 | Ph | 4-Pym | 4-Me-1-Piz |
| 2-2188 | Ph | 4-Pym | 4-Pyr |
| 2-2189 | Ph | 4-Pym | 3-Pyr |
| 2-2190 | Ph | 4-Pym | 4-Pym |
| 2-2191 | Ph | 4-Pym | 5-Pym |
| 2-2192 | Ph | 4-Pym | 3-Pyrd-CH₂ |
| 2-2193 | Ph | 4-Pym | 1-Me-3-Pyrd-CH₂ |
| 2-2194 | Ph | 4-Pym | 4-Pip-CH₂ |
| 2-2195 | Ph | 4-Pym | 1-Me-4-Pip-CH₂ |
| 2-2196 | Ph | 4-Pym | 2-Piz-CH₂ |
| 2-2197 | Ph | 4-Pym | 4-Pyr-CH₂ |
| 2-2198 | Ph | 4-Pym | 3-Pyr-CH₂ |
| 2-2199 | Ph | 4-Pym | 4-Pym-CH₂ |
| 2-2200 | Ph | 4-Pym | 5-Pym-CH₂ |
| 2-2201 | Ph | 4-Pym | 2-Pym-CH₂ |
| 2-2202 | 4-F—Ph | 4-Pym | H₂—(CH₂)₃ |
| 2-2203 | 4-F—Ph | 4-Pym | MeNH—(CH₂)₃ |
| 2-2204 | 4-F—Ph | 4-Pym | EtNH—(CH₂)₃ |
| 2-2205 | 4-F—Ph | 4-Pym | Me₂N—(CH₂)₃ |
| 2-2206 | 4-F—Ph | 4-Pym | 1-Azt-(CH₂)₃ |
| 2-2207 | 4-F—Ph | 4-Pym | 1-Pyrd-(CH₂)₃ |
| 2-2208 | 4-F—Ph | 4-Pym | 1-Pip-(CH₂)₃ |
| 2-2209 | 4-F—Ph | 4-Pym | 1-Mor-(CH₂)₃ |
| 2-2210 | 4-F—Ph | 4-Pym | 1-Tmor-(CH₂)₃ |
| 2-2211 | 4-F—Ph | 4-Pym | 1-Piz-(CH₂)₃ |
| 2-2212 | 4-F—Ph | 4-Pym | 4-Me-1-Piz-(CH₂)₃ |
| 2-2213 | 4-F—Ph | 4-Pym | 3-Azt |
| 2-2214 | 4-F—Ph | 4-Pym | 1-Me-3-Azt |
| 2-2215 | 4-F—Ph | 4-Pym | 3-Pyrd |
| 2-2216 | 4-F—Ph | 4-Pym | 1-Me-3-Pyrd |
| 2-2217 | 4-F—Ph | 4-Pym | 4-Pip |
| 2-2218 | 4-F—Ph | 4-Pym | 4-(3,4-deH-Pip) |
| 2-2219 | 4-F—Ph | 4-Pym | 1-Me-4-Pip |
| 2-2220 | 4-F—Ph | 4-Pym | 1-Me-4-(3,4-deH-Pip) |
| 2-2221 | 4-F—Ph | 4-Pym | 1-Piz |
| 2-2222 | 4-F—Ph | 4-Pym | 4-Me-1-Piz |
| 2-2223 | 4-F—Ph | 4-Pym | 4-Pyr |
| 2-2224 | 4-F—Ph | 4-Pym | 3-Pyr |
| 2-2225 | 4-F—Ph | 4-Pym | 4-Pym |
| 2-2226 | 4-F—Ph | 4-Pym | 5-Pym |
| 2-2227 | 4-F—Ph | 4-Pym | 3-Pyrd-CH₂ |
| 2-2228 | 4-F—Ph | 4-Pym | 1-Me-3-Pyrd-CH₂ |
| 2-2229 | 4-F—Ph | 4-Pym | 4-Pip-CH₂ |
| 2-2230 | 4-F—Ph | 4-Pym | 1-Me-4-Pip-CH₂ |
| 2-2231 | 4-F—Ph | 4-Pym | 2-Piz-CH₂ |
| 2-2232 | 4-F—Ph | 4-Pym | 4-Pyr-CH₂ |
| 2-2233 | 4-F—Ph | 4-Pym | 3-Pyr-CH₂ |
| 2-2234 | 4-F—Ph | 4-Pym | 4-Pym-CH₂ |
| 2-2235 | 4-F—Ph | 4-Pym | 5-Pym-CH₂ |
| 2-2236 | 4-F—Ph | 4-Pym | 2-Pym-CH₂ |
| 2-2237 | 3-F—Ph | 4-Pym | H₂—(CH₂)₃ |
| 2-2238 | 3-F—Ph | 4-Pym | MeNH—(CH₂)₃ |
| 2-2239 | 3-F—Ph | 4-Pym | EtNH—(CH₂)₃ |
| 2-2240 | 3-F—Ph | 4-Pym | Me₂N—(CH₂)₃ |
| 2-2241 | 3-F—Ph | 4-Pym | 1-Azt-(CH₂)₃ |
| 2-2242 | 3-F—Ph | 4-Pym | 1-Pyrd-(CH₂)₃ |
| 2-2243 | 3-F—Ph | 4-Pym | 1-Pip-(CH₂)₃ |
| 2-2244 | 3-F—Ph | 4-Pym | 1-Mor-(CH₂)₃ |
| 2-2245 | 3-F—Ph | 4-Pym | 1-Tmor-(CH₂)₃ |
| 2-2246 | 3-F—Ph | 4-Pym | 1-Piz-(CH₂)₃ |
| 2-2247 | 3-F—Ph | 4-Pym | 4-Me-1-Piz-(CH₂)₃ |
| 2-2248 | 3-F—Ph | 4-Pym | 3-Azt |
| 2-2249 | 3-F—Ph | 4-Pym | 1-Me-3-Azt |
| 2-2250 | 3-F—Ph | 4-Pym | 3-Pyrd |
| 2-2251 | 3-F—Ph | 4-Pym | 1-Me-3-Pyrd |
| 2-2252 | 3-F—Ph | 4-Pym | 4-Pip |
| 2-2253 | 3-F—Ph | 4-Pym | 4-(3,4-deH-Pip) |
| 2-2254 | 3-F—Ph | 4-Pym | 1-Me-4-Pip |
| 2-2255 | 3-F—Ph | 4-Pym | 1-Me-4-(3,4-deH-Pip) |
| 2-2256 | 3-F—Ph | 4-Pym | 1-Piz |
| 2-2257 | 3-F—Ph | 4-Pym | 4-Me-1-Piz |
| 2-2258 | 3-F—Ph | 4-Pym | 4-Pyr |
| 2-2259 | 3-F—Ph | 4-Pym | 3-Pyr |
| 2-2260 | 3-F—Ph | 4-Pym | 4-Pym |
| 2-2261 | 3-F—Ph | 4-Pym | 5-Pym |
| 2-2262 | 3-F—Ph | 4-Pym | 3-Pyrd-CH₂ |
| 2-2263 | 3-F—Ph | 4-Pym | 1-Me-3-Pyrd-CH₂ |
| 2-2264 | 3-F—Ph | 4-Pym | 4-Pip-CH₂ |
| 2-2265 | 3-F—Ph | 4-Pym | 1-Me-4-Pip-CH₂ |
| 2-2266 | 3-F—Ph | 4-Pym | 2-Piz-CH₂ |
| 2-2267 | 3-F—Ph | 4-Pym | 4-Pyr-CH₂ |
| 2-2268 | 3-F—Ph | 4-Pym | 3-Pyr-CH₂ |
| 2-2269 | 3-F—Ph | 4-Pym | 4-Pym-CH₂ |
| 2-2270 | 3-F—Ph | 4-Pym | 5-Pym-CH₂ |
| 2-2271 | 3-F—Ph | 4-Pym | 2-Pym-CH₂ |
| 2-2272 | 3,4-diF—Ph | 4-Pym | H₂—(CH₂)₃ |
| 2-2273 | 3,4-diF—Ph | 4-Pym | MeNH—(CH₂)₃ |
| 2-2274 | 3,4-diF—Ph | 4-Pym | EtNH—(CH₂)₃ |
| 2-2275 | 3,4-diF—Ph | 4-Pym | Me₂N—(CH₂)₃ |
| 2-2276 | 3,4-diF—Ph | 4-Pym | 1-Azt-(CH₂)₃ |
| 2-2277 | 3,4-diF—Ph | 4-Pym | 1-Pyrd-(CH₂)₃ |
| 2-2278 | 3,4-diF—Ph | 4-Pym | 1-Pip-(CH₂)₃ |
| 2-2279 | 3,4-diF—Ph | 4-Pym | 1-Mor-(CH₂)₃ |
| 2-2280 | 3,4-diF—Ph | 4-Pym | 1-Tmor-(CH₂)₃ |
| 2-2281 | 3,4-diF—Ph | 4-Pym | 1-Piz-(CH₂)₃ |
| 2-2282 | 3,4-diF—Ph | 4-Pym | 4-Me-1-Piz-(CH₂)₃ |
| 2-2283 | 3,4-diF—Ph | 4-Pym | 3-Azt |
| 2-2284 | 3,4-diF—Ph | 4-Pym | 1-Me-3-Azt |
| 2-2285 | 3,4-diF—Ph | 4-Pym | 3-Pyrd |
| 2-2286 | 3,4-diF—Ph | 4-Pym | 1-Me-3-Pyrd |
| 2-2287 | 3,4-diF—Ph | 4-Pym | 4-Pip |
| 2-2288 | 3,4-diF—Ph | 4-Pym | 4-(3,4-deH-Pip) |
| 2-2289 | 3,4-diF—Ph | 4-Pym | 1-Me-4-Pip |
| 2-2290 | 3,4-diF—Ph | 4-Pym | 1-Me-4-(3,4-deH-Pip) |
| 2-2291 | 3,4-diF—Ph | 4-Pym | 1-Piz |
| 2-2292 | 3,4-diF—Ph | 4-Pym | 4-Me-1-Piz |
| 2-2293 | 3,4-diF—Ph | 4-Pym | 4-Pyr |
| 2-2294 | 3,4-diF—Ph | 4-Pym | 3-Pyr |
| 2-2295 | 3,4-diF—Ph | 4-Pym | 4-Pym |
| 2-2296 | 3,4-diF—Ph | 4-Pym | 5-Pym |
| 2-2297 | 3,4-diF—Ph | 4-Pym | 3-Pyrd-CH₂ |
| 2-2298 | 3,4-diF—Ph | 4-Pym | 1-Me-3-Pyrd-CH₂ |
| 2-2299 | 3,4-diF—Ph | 4-Pym | 4-Pip-CH₂ |
| 2-2300 | 3,4-diF—Ph | 4-Pym | 1-Me-4-Pip-CH₂ |
| 2-2301 | 3,4-diF—Ph | 4-Pym | 2-Piz-CH₂ |
| 2-2302 | 3,4-diF—Ph | 4-Pym | 4-Pyr-CH₂ |
| 2-2303 | 3,4-diF—Ph | 4-Pym | 3-Pyr-CH₂ |
| 2-2304 | 3,4-diF—Ph | 4-Pym | 4-Pym-CH₂ |
| 2-2305 | 3,4-diF—Ph | 4-Pym | 5-Pym-CH₂ |
| 2-2306 | 3,4-diF—Ph | 4-Pym | 2-Pym-CH₂ |
| 2-2307 | 3-Cl—Ph | 4-Pym | H₂—(CH₂)₃ |
| 2-2308 | 3-Cl—Ph | 4-Pym | MeNH—(CH₂)₃ |
| 2-2309 | 3-Cl—Ph | 4-Pym | EtNH—(CH₂)₃ |
| 2-2310 | 3-Cl—Ph | 4-Pym | Me₂N—(CH₂)₃ |
| 2-2311 | 3-Cl—Ph | 4-Pym | 1-Azt-(CH₂)₃ |
| 2-2312 | 3-Cl—Ph | 4-Pym | 1-Pyrd-(CH₂)₃ |
| 2-2313 | 3-Cl—Ph | 4-Pym | 1-Pip-(CH₂)₃ |
| 2-2314 | 3-Cl—Ph | 4-Pym | 1-Mor-(CH₂)₃ |
| 2-2315 | 3-Cl—Ph | 4-Pym | 1-Tmor-(CH₂)₃ |
| 2-2316 | 3-Cl—Ph | 4-Pym | 1-Piz-(CH₂)₃ |
| 2-2317 | 3-Cl—Ph | 4-Pym | 4-Me-1-Piz-(CH₂)₃ |
| 2-2318 | 3-Cl—Ph | 4-Pym | 3-Azt |
| 2-2319 | 3-Cl—Ph | 4-Pym | 1-Me-3-Azt |
| 2-2320 | 3-Cl—Ph | 4-Pym | 3-Pyrd |
| 2-2321 | 3-Cl—Ph | 4-Pym | 1-Me-3-Pyrd |
| 2-2322 | 3-Cl—Ph | 4-Pym | 4-Pip |
| 2-2323 | 3-Cl—Ph | 4-Pym | 4-(3,4-deH-Pip) |
| 2-2324 | 3-Cl—Ph | 4-Pym | 1-Me-4-Pip |
| 2-2325 | 3-Cl—Ph | 4-Pym | 1-Me-4-(3,4-deH-Pip) |
| 2-2326 | 3-Cl—Ph | 4-Pym | 1-Piz |
| 2-2327 | 3-Cl—Ph | 4-Pym | 4-Me-1-Piz |

TABLE 2-continued

| Compound No. | R¹ | R² | R³ |
|---|---|---|---|
| 2-2328 | 3-Cl—Ph | 4-Pym | 4-Pyr |
| 2-2329 | 3-Cl—Ph | 4-Pym | 3-Pyr |
| 2-2330 | 3-Cl—Ph | 4-Pym | 4-Pym |
| 2-2331 | 3-Cl—Ph | 4-Pym | 5-Pym |
| 2-2332 | 3-Cl—Ph | 4-Pym | 3-Pyrd-CH$_2$ |
| 2-2333 | 3-Cl—Ph | 4-Pym | 1-Me-3-Pyrd-CH$_2$ |
| 2-2334 | 3-Cl—Ph | 4-Pym | 4-Pip-CH$_2$ |
| 2-2335 | 3-Cl—Ph | 4-Pym | 1-Me-4-Pip-CH$_2$ |
| 2-2336 | 3-Cl—Ph | 4-Pym | 2-Piz-CH$_2$ |
| 2-2337 | 3-Cl—Ph | 4-Pym | 4-Pyr-CH$_2$ |
| 2-2338 | 3-Cl—Ph | 4-Pym | 3-Pyr-CH$_2$ |
| 2-2339 | 3-Cl—Ph | 4-Pym | 4-Pym-CH$_2$ |
| 2-2340 | 3-Cl—Ph | 4-Pym | 5-Pym-CH$_2$ |
| 2-2341 | 3-Cl—Ph | 4-Pym | 2-Pym-CH$_2$ |
| 2-2342 | Ph | 2-MeO-4-Pym | H$_2$N—(CH$_2$)$_3$ |
| 2-2343 | Ph | 2-MeO-4-Pym | MeNH—(CH$_2$)$_3$ |
| 2-2344 | Ph | 2-MeO-4-Pym | EtNH—(CH$_2$)$_3$ |
| 2-2345 | Ph | 2-MeO-4-Pym | Me$_2$N—(CH$_2$)$_3$ |
| 2-2346 | Ph | 2-MeO-4-Pym | 1-Azt-(CH$_2$)$_3$ |
| 2-2347 | Ph | 2-MeO-4-Pym | 1-Pyrd-(CH$_2$)$_3$ |
| 2-2348 | Ph | 2-MeO-4-Pym | 1-Pip-(CH$_2$)$_3$ |
| 2-2349 | Ph | 2-MeO-4-Pym | 1-Mor-(CH$_2$)$_3$ |
| 2-2350 | Ph | 2-MeO-4-Pym | 1-Tmor-(CH$_2$)$_3$ |
| 2-2351 | Ph | 2-MeO-4-Pym | 1-Piz-(CH$_2$)$_3$ |
| 2-2352 | Ph | 2-MeO-4-Pym | 4-Me-1-Piz-(CH$_2$)$_3$ |
| 2-2353 | Ph | 2-MeO-4-Pym | 3-Azt |
| 2-2354 | Ph | 2-MeO-4-Pym | 1-Me-3-Azt |
| 2-2355 | Ph | 2-MeO-4-Pym | 3-Pyrd |
| 2-2356 | Ph | 2-MeO-4-Pym | 1-Me-3-Pyrd |
| 2-2357 | Ph | 2-MeO-4-Pym | 4-Pip |
| 2-2358 | Ph | 2-MeO-4-Pym | 4-(3,4-deH-Pip) |
| 2-2359 | Ph | 2-MeO-4-Pym | 1-Me-4-Pip |
| 2-2360 | Ph | 2-MeO-4-Pym | 1-Me-4-(3,4-deH-Pip) |
| 2-2361 | Ph | 2-MeO-4-Pym | 1-Piz |
| 2-2362 | Ph | 2-MeO-4-Pym | 4-Me-1-Piz |
| 2-2363 | Ph | 2-MeO-4-Pym | 4-Pyr |
| 2-2364 | Ph | 2-MeO-4-Pym | 3-Pyr |
| 2-2365 | Ph | 2-MeO-4-Pym | 4-Pym |
| 2-2366 | Ph | 2-MeO-4-Pym | 5-Pym |
| 2-2367 | Ph | 2-MeO-4-Pym | 3-Pyrd-CH$_2$ |
| 2-2368 | Ph | 2-MeO-4-Pym | 1-Me-3-Pyrd-CH$_2$ |
| 2-2369 | Ph | 2[]MeO-4-Pym | 4-Pip-CH$_2$ |
| 2-2370 | Ph | 2-MeO-4-Pym | 1-Me-4-Pip-CH$_2$ |
| 2-2371 | Ph | 2-MeO-4-Pym | 2-Piz-CH$_2$ |
| 2-2372 | Ph | 2-MeO-4-Pym | 4-Pyr-CH$_2$ |
| 2-2373 | Ph | 2-MeO-4-Pym | 3-Pyr-CH$_2$ |
| 2-2374 | Ph | 2-MeO-4-Pym | 4-Pym-CH$_2$ |
| 2-2375 | Ph | 2-MeO-4-Pym | 5-Pym-CH$_2$ |
| 2-2376 | Ph | 2-MeO-4-Pym | 2-Pym-CH$_2$ |
| 2-2377 | 4-F—Ph | 2-MeO-4-Pym | H$_2$—(CH$_2$)$_3$ |
| 2-2378 | 4-F—Ph | 2-MeO-4-Pym | MeNH—(CH$_2$)$_3$ |
| 2-2379 | 4-F—Ph | 2-MeO-4-Pym | EtNH—(CH$_2$)$_3$ |
| 2-2380 | 4-F—Ph | 2-MeO-4-Pym | Me$_2$N—(CH$_2$)$_3$ |
| 2-2381 | 4-F—Ph | 2-MeO-4-Pym | 1-Azt-(CH$_2$)$_3$ |
| 2-2382 | 4-F—Ph | 2-MeO-4-Pym | 1-Pyrd-(CH$_2$)$_3$ |
| 2-2383 | 4-F—Ph | 2-MeO-4-Pym | 1-Pip-(CH$_2$)$_3$ |
| 2-2384 | 4-F—Ph | 2-MeO-4-Pym | 1-Mor-(CH$_2$)$_3$ |
| 2-2385 | 4-F—Ph | 2-MeO-4-Pym | 1-Tmor-(CH$_2$)$_3$ |
| 2-2386 | 4-F—Ph | 2-MeO-4-Pym | 1-Piz-(CH$_2$)$_3$ |
| 2-2387 | 4-F—Ph | 2-MeO-4-Pym | 4-Me-1-Piz-(CH$_2$)$_3$ |
| 2-2388 | 4-F—Ph | 2-MeO-4-Pym | 3-Azt |
| 2-2389 | 4-F—Ph | 2-MeO-4-Pym | 1-Me-3-Azt |
| 2-2390 | 4-F—Ph | 2-MeO-4-Pym | 3-Pyrd |
| 2-2391 | 4-F—Ph | 2-MeO-4-Pym | 1-Me-3-Pyrd |
| 2-2392 | 4-F—Ph | 2-MeO-4-Pym | 4-Pip |
| 2-2393 | 4-F—Ph | 2-MeO-4-Pym | 4-(3,4-deH-Pip) |
| 2-2394 | 4-F—Ph | 2-MeO-4-Pym | 1-Me-4-Pip |
| 2-2395 | 4-F—Ph | 2-MeO-4-Pym | 1-Me-4-(3,4-deH-Pip) |
| 2-2396 | 4-F—Ph | 2-MeO-4-Pym | 1-Piz |
| 2-2397 | 4-F—Ph | 2-MeO-4-Pym | 4-Me-1-Piz |
| 2-2398 | 4-F—Ph | 2-MeO-4-Pym | 4-Pyr |
| 2-2399 | 4-F—Ph | 2-MeO-4-Pym | 3-Pyr |
| 2-2400 | 4-F—Ph | 2-MeO-4-Pym | 4-Pym |
| 2-2401 | 4-F—Ph | 2-MeO-4-Pym | 5-Pym |
| 2-2402 | 4-F—Ph | 2-MeO-4-Pym | 3-Pyrd-CH$_2$ |
| 2-2403 | 4-F—Ph | 2-MeO-4-Pym | 1-Me-3-Pyrd-CH$_2$ |
| 2-2404 | 4-F—Ph | 2-MeO-4-Pym | 4-Pip-CH$_2$ |
| 2-2405 | 4-F—Ph | 2-MeO-4-Pym | 1-Me-4-Pip-CH$_2$ |
| 2-2406 | 4-F—Ph | 2-MeO-4-Pym | 2-Piz-CH$_2$ |
| 2-2407 | 4-F—Ph | 2-MeO-4-Pym | 4-Pyr-CH$_2$ |
| 2-2408 | 4-F—Ph | 2-MeO-4-Pym | 3-Pyr-CH$_2$ |
| 2-2409 | 4-F—Ph | 2-MeO-4-Pym | 4-Pym-CH$_2$ |
| 2-2410 | 4-F—Ph | 2-MeO-4-Pym | 5-Pym-CH$_2$ |
| 2-2411 | 4-F—Ph | 2-MeO-4-Pym | 2-Pym-CH$_2$ |
| 2-2412 | 3-F—Ph | 2-MeO-4-Pym | H$_2$—(CH$_2$)$_3$ |
| 2-2413 | 3-F—Ph | 2-MeO-4-Pym | MeNH—(CH$_2$)$_3$ |
| 2-2414 | 3-F—Ph | 2-MeO-4-Pym | EtNH—(CH$_2$)$_3$ |
| 2-2415 | 3-F—Ph | 2-MeO-4-Pym | Me$_2$N—(CH$_2$)$_3$ |
| 2-2416 | 3-F—Ph | 2-MeO-4-Pym | 1-Azt-(CH$_2$)$_3$ |
| 2-2417 | 3-F—Ph | 2-MeO-4-Pym | 1-Pyrd-(CH$_2$)$_3$ |
| 2-2418 | 3-F—Ph | 2-MeO-4-Pym | 1-Pip-(CH$_2$)$_3$ |
| 2-2419 | 3-F—Ph | 2-MeO-4-Pym | 1-Mor-(CH$_2$)$_3$ |
| 2-2420 | 3-F—Ph | 2-MeO-4-Pym | 1-Tmor-(CH$_2$)$_3$ |
| 2-2421 | 3-F—Ph | 2-MeO-4-Pym | 1-Piz-(CH$_2$)$_3$ |
| 2-2422 | 3-F—Ph | 2-MeO-4-Pym | 4-Me-1-Piz-(CH$_2$)$_3$ |
| 2-2423 | 3-F—Ph | 2-MeO-4-Pym | 3-Azt |
| 2-2424 | 3-F—Ph | 2-MeO-4-Pym | 1-Me-3-Azt |
| 2-2425 | 3-F—Ph | 2-MeO-4-Pym | 3-Pyrd |
| 2-2426 | 3-F—Ph | 2-MeO-4-Pym | 1-Me-3-Pyrd |
| 2-2427 | 3-F—Ph | 2-MeO-4-Pym | 4-Pip |
| 2-2428 | 3-F—Ph | 2-MeO-4-Pym | 4-(3,4-deH-Pip) |
| 2-2429 | 3-F—Ph | 2-MeO-4-Pym | 1-Me-4-Pip |
| 2-2430 | 3-F—Ph | 2-MeO-4-Pym | 1-Me-4-(3,4-deH-Pip) |
| 2-2431 | 3-F—Ph | 2-MeO-4-Pym | 1-Piz |
| 2-2432 | 3-F—Ph | 2-MeO-4-Pym | 4-Me-1-Piz |
| 2-2433 | 3-F—Ph | 2-MeO-4-Pym | 4-Pyr |
| 2-2434 | 3-F—Ph | 2-MeO-4-Pym | 3-Pyr |
| 2-2435 | 3-F—Ph | 2-MeO-4-Pym | 4-Pym |
| 2-2436 | 3-F—Ph | 2-MeO-4-Pym | 5-Pym |
| 2-2437 | 3-F—Ph | 2-MeO-4-Pym | 3-Pyrd-CH$_2$ |
| 2-2438 | 3-F—Ph | 2-MeO-4-Pym | 1-Me-3-Pyrd-CH$_2$ |
| 2-2439 | 3-F—Ph | 2-MeO-4-Pym | 4-Pip-CH$_2$ |
| 2-2440 | 3-F—Ph | 2-MeO-4-Pym | 1-Me-4-Pip-CH$_2$ |
| 2-2441 | 3-F—Ph | 2-MeO-4-Pym | 2-Piz-CH$_2$ |
| 2-2442 | 3-F—Ph | 2-MeO-4-Pym | 4-Pyr-CH$_2$ |
| 2-2443 | 3-F—Ph | 2-MeO-4-Pym | 3-Pyr-CH$_2$ |
| 2-2444 | 3-F—Ph | 2-MeO-4-Pym | 4-Pym-CH$_2$ |
| 2-2445 | 3-F—Ph | 2-MeO-4-Pym | 5-Pym-CH$_2$ |
| 2-2446 | 3-F—Ph | 2-MeO-4-Pym | 2-Pym-CH$_2$ |
| 2-2447 | 3,4-diF—Ph | 2-MeO-4-Pym | H$_2$—(CH$_2$)$_3$ |
| 2-2448 | 3,4-diF—Ph | 2-MeO-4-Pym | MeNH—(CH$_2$)$_3$ |
| 2-2449 | 3,4-diF—Ph | 2-MeO-4-Pym | EtNH—(CH$_2$)$_3$ |
| 2-2450 | 3,4-diF—Ph | 2-MeO-4-Pym | Me$_2$N—(CH$_2$)$_3$ |
| 2-2451 | 3,4-diF—Ph | 2-MeO-4-Pym | 1-Azt-(CH$_2$)$_3$ |
| 2-2452 | 3,4-diF—Ph | 2-MeO-4-Pym | 1-Pyrd-(CH$_2$)$_3$ |
| 2-2453 | 3,4-diF—Ph | 2-MeO-4-Pym | 1-Pip-(CH$_2$)$_3$ |
| 2-2454 | 3,4-diF—Ph | 2-MeO-4-Pym | 1-Mor-(CH$_2$)$_3$ |
| 2-2455 | 3,4-diF—Ph | 2-MeO-4-Pym | 1-Tmor-(CH$_2$)$_3$ |
| 2-2456 | 3,4-diF—Ph | 2-MeO-4-Pym | 1-Piz-(CH$_2$)$_3$ |
| 2-2457 | 3,4-diF—Ph | 2-MeO-4-Pym | 4-Me-1-Piz-(CH$_2$)$_3$ |
| 2-2458 | 3,4-diF—Ph | 2-MeO-4-Pym | 3-Azt |
| 2-2459 | 3,4-diF—Ph | 2-MeO-4-Pym | 1-Me-3-Azt |
| 2-2460 | 3,4-diF—Ph | 2-MeO-4-Pym | 3-Pyrd |
| 2-2461 | 3,4-diF—Ph | 2-MeO-4-Pym | 1-Me-3-Pyrd |
| 2-2462 | 3,4-diF—Ph | 2-MeO-4-Pym | 4-Pip |
| 2-2463 | 3,4-diF—Ph | 2-MeO-4-Pym | 4-(3,4-deH-Pip) |
| 2-2464 | 3,4-diF—Ph | 2-MeO-4-Pym | 1-Me-4-Pip |
| 2-2465 | 3,4-diF—Ph | 2-MeO-4-Pym | 1-Me-4-(3,4-deH-Pip) |
| 2-2466 | 3,4-diF—Ph | 2-MeO-4-Pym | 1-Piz |
| 2-2467 | 3,4-diF—Ph | 2-MeO-4-Pym | 4-Me-1-Piz |
| 2-2468 | 3,4-diF—Ph | 2-MeO-4-Pym | 4-Pyr |
| 2-2469 | 3,4-diF—Ph | 2-MeO-4-Pym | 3-Pyr |
| 2-2470 | 3,4-diF—Ph | 2-MeO-4-Pym | 4-Pym |
| 2-2471 | 3,4-diF—Ph | 2-MeO-4-Pym | 5-Pym |
| 2-2472 | 3,4-diF—Ph | 2-MeO-4-Pym | 3-Pyrd-CH$_2$ |
| 2-2473 | 3,4-diF—Ph | 2-MeO-4-Pym | 1-Me-3-Pyrd-CH$_2$ |
| 2-2474 | 3,4-diF—Ph | 2-MeO-4-Pym | 4-Pip-CH$_2$ |
| 2-2475 | 3,4-diF—Ph | 2-MeO-4-Pym | 1-Me-4-Pip-CH$_2$ |
| 2-2476 | 3,4-diF—Ph | 2-MeO-4-Pym | 2-Piz-CH$_2$ |
| 2-2477 | 3,4-diF—Ph | 2-MeO-4-Pym | 4-Pyr-CH$_2$ |

TABLE 2-continued

| Compound No. | R¹ | R² | R³ |
|---|---|---|---|
| 2-2478 | 3,4-diF—Ph | 2-MeO-4-Pym | 3-Pyr-CH₂ |
| 2-2479 | 3,4-diF—Ph | 2-MeO-4-Pym | 4-Pym-CH₂ |
| 2-2480 | 3,4-diF—Ph | 2-MeO-4-Pym | 5-Pym-CH₂ |
| 2-2481 | 3,4-diF—Ph | 2-MeO-4-Pym | 2-Pym-CH₂ |
| 2-2482 | 3-Cl—Ph | 2-MeO-4-Pym | H₂—(CH₂)₃ |
| 2-2483 | 3-Cl—Ph | 2-MeO-4-Pym | MeNH—(CH₂)₃ |
| 2-2484 | 3-Cl—Ph | 2-MeO-4-Pym | EtNH—(CH₂)₃ |
| 2-2485 | 3-Cl—Ph | 2-MeO-4-Pym | Me₂N—(CH₂)₃ |
| 2-2486 | 3-Cl—Ph | 2-MeO-4-Pym | 1-Azt-(CH₂)₃ |
| 2-2487 | 3-Cl—Ph | 2-MeO-4-Pym | 1-Pyrd-(CH₂)₃ |
| 2-2488 | 3-Cl—Ph | 2-MeO-4-Pym | 1-Pip-(CH₂)₃ |
| 2-2489 | 3-Cl—Ph | 2-MeO-4-Pym | 1-Mor-(CH₂)₃ |
| 2-2490 | 3-Cl—Ph | 2-MeO-4-Pym | 1-Tmor-(CH₂)₃ |
| 2-2491 | 3-Cl—Ph | 2-MeO-4-Pym | 1-Piz-(CH₂)₃ |
| 2-2492 | 3-Cl—Ph | 2-MeO-4-Pym | 4-Me-1-Piz-(CH₂)₃ |
| 2-2493 | 3-Cl—Ph | 2-MeO-4-Pym | 3-Azt |
| 2-2494 | 3-Cl—Ph | 2-MeO-4-Pym | 1-Me-3-Azt |
| 2-2495 | 3-Cl—Ph | 2-MeO-4-Pym | 3-Pyrd |
| 2-2496 | 3-Cl—Ph | 2-MeO-4-Pym | 1-Me-3-Pyrd |
| 2-2497 | 3-Cl—Ph | 2-MeO-4-Pym | 4-Pip |
| 2-2498 | 3-Cl—Ph | 2-MeO-4-Pym | 4-(3,4-deH-Pip) |
| 2-2499 | 3-Cl—Ph | 2-MeO-4-Pym | 1-Me-4-Pip |
| 2-2500 | 3-Cl—Ph | 2-MeO-4-Pym | 1-Me-4-(3,4-deH-Pip) |
| 2-2501 | 3-Cl—Ph | 2-MeO-4-Pym | 1-Piz |
| 2-2502 | 3-Cl—Ph | 2-MeO-4-Pym | 4-Me-1-Piz |
| 2-2503 | 3-Cl—Ph | 2-MeO-4-Pym | 4-Pyr |
| 2-2504 | 3-Cl—Ph | 2-MeO-4-Pym | 3-Pyr |
| 2-2505 | 3-Cl—Ph | 2-MeO-4-Pym | 4-Pym |
| 2-2506 | 3-Cl—Ph | 2-MeO-4-Pym | 5-Pym |
| 2-2507 | 3-Cl—Ph | 2-MeO-4-Pym | 3-Pyrd-CH₂ |
| 2-2508 | 3-Cl—Ph | 2-MeO-4-Pym | 1-Me-3-Pyrd-CH₂ |
| 2-2509 | 3-Cl—Ph | 2-MeO-4-Pym | 4-Pip-CH₂ |
| 2-2510 | 3-Cl—Ph | 2-MeO-4-Pym | 1-Me-4-Pip-CH₂ |
| 2-2511 | 3-Cl—Ph | 2-MeO-4-Pym | 2-Piz-CH₂ |
| 2-2512 | 3-Cl—Ph | 2-MeO-4-Pym | 4-Pyr-CH₂ |
| 2-2513 | 3-Cl—Ph | 2-MeO-4-Pym | 3-Pyr-CH₂ |
| 2-2514 | 3-Cl—Ph | 2-MeO-4-Pym | 4-Pym-CH₂ |
| 2-2515 | 3-Cl—Ph | 2-MeO-4-Pym | 5-Pym-CH₂ |
| 2-2516 | 3-Cl—Ph | 2-MeO-4-Pym | 2-Pym-CH₂ |
| 2-2517 | 4-F—Ph | 4-Pyr | H₂N—CH₂CH=CH |
| 2-2518 | 4-F—Ph | 4-Pyr | MeNH—CH₂CH=CH |
| 2-2519 | 4-F—Ph | 4-Pyr | Me₂N—CH₂CH=CH |
| 2-2520 | 4-F—Ph | 4-Pyr | 3-Pip-CH₂ |
| 2-2521 | 4-F—Ph | 4-Pyr | 1-Me-3-Pip-CH₂ |
| 2-2522 | 4-F—Ph | 4-Pyr | 2-Me-4-Pip |
| 2-2523 | 4-F—Ph | 4-Pyr | 2,2,6,6-tetraMe-4-Pip |
| 2-2524 | 4-F—Ph | 4-Pyr | 1-Ac-4-Pip |
| 2-2525 | 4-F—Ph | 4-Pyr | 1-Ac-4-(3,4-deH-Pip) |
| 2-2526 | 4-F—Ph | 4-Pyr | 4-OH-4-Pip |
| 2-2527 | 4-F—Ph | 4-Pyr | 4-OH-1-Me-4-Pip |
| 2-2528 | 4-F—Ph | 4-Pyr | AcNH—(CH₂)₃ |
| 2-2529 | 4-F—Ph | 4-Pyr | 4-NH₂-cHx |
| 2-2530 | 4-F—Ph | 4-Pyr | 4-Pyr-CH(OH) |
| 2-2531 | 4-F—Ph | 4-Pyr | 3-Pyr-CH(OH) |
| 2-2532 | 4-F—Ph | 4-Pyr | 2-Pyr-CH(OH) |
| 2-2533 | 4-F—Ph | 4-Pyr | CF₃CONH—(CH₂)₃ |
| 2-2534 | 4-F—Ph | 4-Pyr | BzNH—(CH₂)₃ |
| 2-2535 | 4-F—Ph | 4-Pyr | 2,4,6-triF—BzNH—CH₂ |
| 2-2536 | 4-F—Ph | 4-Pyr | MeSO₂NH—(CH₂)₃ |
| 2-2537 | 4-F—Ph | 4-Pyr | 1-NO₂(CH₂)₂-4-Pip |
| 2-2538 | 4-F—Ph | 4-Pyr | 2,3,5,6-tetraF-4-Pyr |
| 2-2539 | 4-F—Ph | 4-Pyr | 3-Qun |
| 2-2540 | 4-F—Ph | 4-Pyr | 3-(2,3-deH-Qun) |
| 2-2541 | 4-F—Ph | 4-Pyr | 3-ABO |
| 2-2542 | 4-F—Ph | 4-Pyr | 8-Me-3-ABO |
| 2-2543 | 4-F—Ph | 4-Pyr | 3-(2,3-deH-ABO) |
| 2-2544 | 4-F—Ph | 4-Pyr | 8-Me-3-(2,3-deH-ABO) |
| 2-2545 | 4-F—Ph | 4-Pyr | 3-ABN |
| 2-2546 | 4-F—Ph | 4-Pyr | 9-Me-3-ABN |
| 2-2547 | 4-F—Ph | 4-Pyr | 3-(2,3-deH-ABN) |
| 2-2548 | 4-F—Ph | 4-Pyr | 9-Me-3-(2,3-deH-ABN) |
| 2-2549 | 4-F—Ph | 2-NH₂-4-Pym | H₂—CH₂CH=CH |
| 2-2550 | 4-F—Ph | 2-NH₂-4-Pym | MeNH—CH₂CH=CH |
| 2-2551 | 4-F—Ph | 2-NH₂-4-Pym | Me₂N—CH₂CH=CH |
| 2-2552 | 4-F—Ph | 2-NH₂-4-Pym | 3-Pip-CH₂ |
| 2-2553 | 4-F—Ph | 2-NH₂-4-Pym | 1-Me-3-Pip-CH₂ |
| 2-2554 | 4-F—Ph | 2-NH₂-4-Pym | 2-Me-4-Pip |
| 2-2555 | 4-F—Ph | 2-NH₂-4-Pym | 2,2,6,6-tetraMe-4-Pip |
| 2-2556 | 4-F—Ph | 2-NH₂-4-Pym | 1-Ac-4-Pip |
| 2-2557 | 4-F—Ph | 2-NH₂-4-Pym | 1-Ac-4-(3,4-deH-Pip) |
| 2-2558 | 4-F—Ph | 2-NH₂-4-Pym | 4-OH-4-Pip |
| 2-2559 | 4-F—Ph | 2-NH₂-4-Pym | 4-OH-1-Me4-Pip |
| 2-2560 | 4-F—Ph | 2-NH₂-4-Pym | AcNH—(CH₂)₃ |
| 2-2561 | 4-F—Ph | 2-NH₂-4-Pym | 4-NH₂-cHx |
| 2-2562 | 4-F—Ph | 2-NH₂-4-Pym | 3-Qun |
| 2-2563 | 4-F—Ph | 2-NH₂-4-Pym | 3-(2,3-deH-Qun) |
| 2-2564 | 4-F—Ph | 2-NH₂-4-Pym | 3-ABO |
| 2-2565 | 4-F—Ph | 2-NH₂-4-Pym | 8-Me-3-ABO |
| 2-2566 | 4-F—Ph | 2-NH₂-4-Pym | 3-(2,3-deH-ABO) |
| 2-2567 | 4-F—Ph | 2-NH₂-4-Pym | 8-Me-3-(2,3-deH-ABO) |
| 2-2568 | 4-F—Ph | 2-NH₂-4-Pym | 3-ABN |
| 2-2569 | 4-F—Ph | 2-NH₂-4-Pym | 9-Me-3-ABN |
| 2-2570 | 4-F—Ph | 2-NH₂-4-Pym | 3-(2,3-deH-ABN) |
| 2-2571 | 4-F—Ph | 2-NH₂-4-Pym | 9-Me-3-(2,3-deH-ABN) |
| 2-2572 | 4-F—Ph | 2-MeNH-4-Pym | H₂—CH₂CH=CH |
| 2-2573 | 4-F—Ph | 2-MeNH-4-Pym | MeNH—CH₂CH=CH |
| 2-2574 | 4-F—Ph | 2-MeNH-4-Pym | Me₂N—CH₂CH=CH |
| 2-2575 | 4-F—Ph | 2-MeNH-4-Pym | 3-Pip-CH₂ |
| 2-2576 | 4-F—Ph | 2-MeNH-4-Pym | 1-Me-3-Pip-CH₂ |
| 2-2577 | 4-F—Ph | 2-MeNH-4-Pym | 2-Me-4-Pip |
| 2-2578 | 4-F—Ph | 2-MeNH-4-Pym | 2,2,6,6-tetraMe-4-Pip |
| 2-2579 | 4-F—Ph | 2-MeNH-4-Pym | 1-Ac-4-Pip |
| 2-2580 | 4-F—Ph | 2-MeNH-4-Pym | 1-Ac-4-(3,4-deH-Pip) |
| 2-2581 | 4-F—Ph | 2-MeNH-4-Pym | 4-OH-4-Pip |
| 2-2582 | 4-F—Ph | 2-MeNH-4-Pym | 4-OH-1-Me-4-Pip |
| 2-2583 | 4-F—Ph | 2-MeNH-4-Pym | AcNH—(CH₂)₃ |
| 2-2584 | 4-F—Ph | 2-MeNH-4-Pym | 4-NH₂-cHx |
| 2-2585 | 4-F—Ph | 2-MeNH-4-Pym | 3-Qun |
| 2-2586 | 4-F—Ph | 2-MeNH-4-Pym | 3-(2,3-deH-Qun) |
| 2-2587 | 4-F—Ph | 2-MeNH-4-Pym | 3-ABO |
| 2-2588 | 4-F—Ph | 2-MeNH-4-Pym | 8-Me-3-ABO |
| 2-2589 | 4-F—Ph | 2-MeNH-4-Pym | 3-(2,3-deH-ABO) |
| 2-2590 | 4-F—Ph | 2-MeNH-4-Pym | 8-Me-3-(2,3-deH-ABO) |
| 2-2591 | 4-F—Ph | 2-MeNH-4-Pym | 3-ABN |
| 2-2592 | 4-F—Ph | 2-MeNH-4-Pym | 9-Me-3-ABN |
| 2-2593 | 4-F—Ph | 2-MeNH-4-Pym | 3-(2,3-deH-ABN) |
| 2-2594 | 4-F—Ph | 2-MeNH-4-Pym | 9-Me-3-(2,3-deH-ABN) |
| 2-2595 | 4-F—Ph | 2-BnNH-4-Pyr | 4-Pip |
| 2-2596 | 4-F—Ph | 2-BnNH-4-Pyr | 4-(3,4-deH-Pip) |
| 2-2597 | 4-F—Ph | 2-BnNH-4-Pym | 4-Pip |
| 2-2598 | 4-F—Ph | 2-BnNH-4-Pym | 4-(3,4-deH-Pip) |
| 2-2599 | 4-F—Ph | 2-( -Me-BnNH)-4-Pyr | 4-Pip |
| 2-2600 | 4-F—Ph | 2-( -Me-BnNH)-4-Pyr | 4-(3,4-deH-Pip) |
| 2-2601 | 4-F—Ph | 2-( -Me-BnNH)-4-Pym | 4-Pip |
| 2-2602 | 4-F—Ph | 2-( -Me-BnNH)-4-Pym | 4-(3,4-deH-Pip) |
| 2-2603 | 3-Cl—Ph | 2-BnNH-4-Pyr | 4-Pip |
| 2-2604 | 3-Cl—Ph | 2-BnNH-4-Pyr | 4-(3,4-deH-Pip) |
| 2-2605 | 3-Cl—Ph | 2-BnNH-4-Pym | 4-Pip |
| 2-2606 | 3-Cl—Ph | 2-BnNH-4-Pym | 4-(3,4-deH-Pip) |
| 2-2607 | 3-Cl—Ph | 2-( -Me-BnNH)-4-Pyr | 4-Pip |
| 2-2608 | 3-Cl—Ph | 2-( -Me-BnNH)-4-Pyr | 4-(3,4-deH-Pip) |
| 2-2609 | 3-Cl—Ph | 2-( -Me-BnNH)-4-Pym | 4-Pip |
| 2-2610 | 3-Cl—Ph | 2-( -Me-BnNH)-4-Pym | 4-(3,4-deH-Pip) |
| 2-2611 | 3-CF₃—Ph | 2-BnNH-4-Pyr | 4-Pip |
| 2-2612 | 3-CF₃—Ph | 2-BnNH-4-Pyr | 4-(3,4-deH-Pip) |
| 2-2613 | 3-CF₃—Ph | 2-BnNH-4-Pym | 4-Pip |
| 2-2614 | 3-CF₃—Ph | 2-BnNH-4-Pym | 4-(3,4-deH-Pip) |
| 2-2615 | 3-CF₃—Ph | 2-( -Me-BnNH)-4-Pyr | 4-Pip |
| 2-2616 | 3-CF₃—Ph | 2-( -Me-BnNH)-4-Pyr | 4-(3,4-deH-Pip) |
| 2-2617 | 3-CF₃—Ph | 2-( -Me-BnNH)-4-Pym | 4-Pip |
| 2-2618 | 3-CF₃—Ph | 2-( -Me-BnNH)-4-Pym | 4-(3,4-deH-Pip) |
| 2-2619 | 4-F—Ph | 4-Pyr | 2-NH₂-4-Pym |
| 2-2620 | 4-F—Ph | 4-Pyr | 2-MeNH-4-Pym |
| 2-2621 | 4-F—Ph | 4-Pyr | 2-NH₂-4-Pyr |

TABLE 2-continued

| Compound No. | R¹ | R² | R³ |
|---|---|---|---|
| 2-2622 | 4-F—Ph | 4-Pyr | 2-MeNH-4-Pyr |
| 2-2623 | 4-F—Ph | 4-Pyr | H₂N—CH₂C(Me)₂CH₂ |
| 2-2624 | 4-F—Ph | 4-Pyr | MeNH—CH₂C(Me)₂CH₂ |
| 2-2625 | 4-F—Ph | 4-Pyr | EtNH—CH₂C(Me)₂CH₂ |
| 2-2626 | 4-F—Ph | 4-Pyr | Me₂N—CH₂C(Me)₂CH₂ |
| 2-2627 | 4-F—Ph | 4-Pyr | 3-(3,4-deH-Pip) |
| 2-2628 | 4-F—Ph | 4-Pyr | 1-Me-3-(3,4-deH-Pip) |
| 2-2629 | 4-F—Ph | 4-Pyr | 1-Et-4-(3,4-deH-Pip) |
| 2-2630 | 4-F—Ph | 4-Pyr | 1-Pr-4-(3,4-deH-Pip) |
| 2-2631 | 4-F—Ph | 4-Pyr | 1-Pr-4-Pip |
| 2-2632 | 4-F—Ph | 4-Pyr | 1-iPr-4-(3,4-deH-Pip) |
| 2-2633 | 4-F—Ph | 4-Pyr | 1-iPr-4-Pip |
| 2-2634 | 4-F—Ph | 4-Pyr | 1-Bu-4-(3,4-deH-Pip) |
| 2-2635 | 4-F—Ph | 4-Pyr | 1-tBu-4-(3,4-deH-Pip) |
| 2-2636 | 4-F—Ph | 4-Pyr | 1-Pn-4-(3,4-deH-Pip) |
| 2-2637 | 4-F—Ph | 4-Pyr | 1-Hx-4-(3,4-deH-Pip) |
| 2-2638 | 4-F—Ph | 4-Pyr | 1-Hp-4-(3,4-deH-Pip) |
| 2-2639 | 4-F—Ph | 4-Pyr | 1-Oc-4-(3,4-deH-Pip) |
| 2-2640 | 4-F—Ph | 4-Pyr | 1-Nn-4-(3,4-deH-Pip) |
| 2-2641 | 4-F—Ph | 4-Pyr | 1-cPr-4-(3,4-deH-Pip) |
| 2-2642 | 4-F—Ph | 4-Pyr | 1-cPn-4-(3,4-deH-Pip) |
| 2-2643 | 4-F—Ph | 4-Pyr | 1-cHx-4-(3,4-deH-Pip) |
| 2-2644 | 4-F—Ph | 4-Pyr | 1-Bn4-(3,4-deH-Pip) |
| 2-2645 | 4-F—Ph | 4-Pyr | 1-Phet-4-(3,4-deH-Pip) |
| 2-2646 | 4-F—Ph | 4-Pyr | 1-(3-Ph—Pr)-4-(3,4-deH-Pip) |
| 2-2647 | 4-F—Ph | 4-Pyr | 1-(4-Ph—Bu)-4-(3,4-deH-Pip) |
| 2-2648 | 4-F—Ph | 4-Pyr | 1-Allyl-4-(3,4-deH-Pip) |
| 2-2649 | 4-F—Ph | 4-Pyr | 1-Propargy1-4-(3,4-deH-Pip) |
| 2-2650 | 4-F—Ph | 4-Pyr | 2,2,6,6-tetraMe-4-(3,4-deH-Pip) |
| 2-2651 | 4-F—Ph | 4-Pyr | 1,2,2,6,6-pentaMe-4-(3,4-deH-Pip) |
| 2-2652 | 4-F—Ph | 4-Pyr | 1,2,2,6,6-pentaMe-4-Pip |
| 2-2653 | 4-F—Ph | 4-Pyr | 7-(1,2,3,5,6,8a-hexaH-Ind) |
| 2-2654 | 4-F—Ph | 4-Pyr | 7-(1,2,3,5,8,8a-hexaH-Ind) |
| 2-2655 | 4-F—Ph | 4-Pyr | 7-octaH-Ind |
| 2-2656 | 4-F—Ph | 4-Pyr | 8-(1,3,4,6,7,9a-hexaH-2H-Qui) |
| 2-2657 | 4-F—Ph | 4-Pyr | 8-(1,3,4,6,9,9a-hexaH-2H-Qui) |
| 2-2658 | 4-F—Ph | 4-Pyr | 8-octaH-Qui |
| 2-2659 | 4-F—Ph | 4-Pyr | 2,2-diMe-4-(3,4-deh-Pip) |
| 2-2660 | 4-F—Ph | 4-Pyr | 1,2,2-triMe-4-(3,4-deH-Pip) |
| 2-2661 | 4-F—Ph | 4-Pyr | 2,2-diMe-4-(4,5-deH-Pip) |
| 2-2662 | 4-F—Ph | 4-Pyr | 1,2,2-triMe-4-(4,5-deH-Pip) |
| 2-2663 | 4-F—Ph | 4-Pyr | 2,6-diMe-4-(3,4-deH-Pip) |
| 2-2664 | 4-F—Ph | 4-Pyr | 1,2,6-triMe-4-(3,4-deH-Pip) |
| 2-2665 | 4-F—Ph | 4-Pyr | 2-Me-4-(3,4-deH-Pip) |
| 2-2666 | 4-F—Ph | 4-Pyr | 1,2-diMe-4-(3,4-deH-Pip) |
| 2-2667 | 4-F—Ph | 4-Pyr | 1-Et-2-Me-4-(3,4-deH-Pip) |
| 2-2668 | 4-F—Ph | 4-Pyr | 1-Pr-2-Me-4-(3,4-deH-Pip) |
| 2-2669 | 4-F—Ph | 4-Pyr | 1-Bu-2-Me-4-(3,4-deH-Pip) |
| 2-2670 | 4-F—Ph | 4-Pyr | 1-Phet-2-Me-4-(3,4-deH-Pip) |
| 2-2671 | 4-F—Ph | 4-Pyr | 2-Et-4-(3,4-deH-Pip) |
| 2-2672 | 4-F—Ph | 4-Pyr | 1-Me-2-Et-4-(3,4-deH-Pip) |
| 2-2673 | 4-F—Ph | 4-Pyr | 1,2-diEt-4-(3,4-deH-Pip) |
| 2-2674 | 4-F—Ph | 4-Pyr | 1-Pr-2-Et-4-(3,4-deH-Pip) |
| 2-2675 | 4-F—Ph | 4-Pyr | 1-Bu-2-Et-4-(3,4-deH-Pip) |
| 2-2676 | 4-F—Ph | 4-Pyr | 1-Phet-2-Et-4-(3,4-deH-Pip) |
| 2-2677 | 4-F—Ph | 4-Pyr | 2-Pr-4-(3,4-deH-Pip) |
| 2-2678 | 4-F—Ph | 4-Pyr | 1-Me-2-Pr-4-(3,4-deH-Pip) |
| 2-2679 | 4-F—Ph | 4-Pyr | 1-Et-2-Pr-4-(3,4-deH-Pip) |
| 2-2680 | 4-F—Ph | 4-Pyr | 1,2-diPr-4-(3,4-deH-Pip) |
| 2-2681 | 4-F—Ph | 4-Pyr | 1-Bu-2-Pr-4-(3,4-deH-Pip) |
| 2-2682 | 4-F—Ph | 4-Pyr | 1-Phet-2-Pr-4-(3,4-deH-Pip) |
| 2-2683 | 4-F—Ph | 4-Pyr | 2-Bu-4-(3,4-deH-Pip) |
| 2-2684 | 4-F—Ph | 4-Pyr | 1-Me-2-Bu-4-(3,4-deH-Pip) |
| 2-2685 | 4-F—Ph | 4-Pyr | 1-Et-2-Bu-4-(3,4-deH-Pip) |
| 2-2686 | 4-F—Ph | 4-Pyr | 1-Pr-2-Bu-4-(3,4-deH-Pip) |
| 2-2687 | 4-F—Ph | 4-Pyr | 1,2-diBu-4-(3,4-deH-Pip) |
| 2-2688 | 4-F—Ph | 4-Pyr | 1-Phet-2-Bu-4-(3,4-deH-Pip) |
| 2-2689 | 4-F—Ph | 4-Pyr | 2-Allyl-4-(3,4-deH-Pip) |
| 2-2690 | 4-F—Ph | 4-Pyr | 1-Me-2-Allyl-4-(3,4-deH-Pip) |
| 2-2691 | 4-F—Ph | 4-Pyr | 1-Et-2-Allyl-4-(3,4-deH-Pip) |
| 2-2692 | 4-F—Ph | 4-Pyr | 1-Pr-2-Allyl-4-(3,4-deH-Pip) |
| 2-2693 | 4-F—Ph | 4-Pyr | 1-Bu-2-Allyl-4-(3,4-deH-Pip) |
| 2-2694 | 4-F—Ph | 4-Pyr | 1-Phet-2-Allyl-4-(3,4-deH-Pip) |
| 2-2695 | 4-F—Ph | 4-Pyr | 2-Bn-4-(3,4-deH-Pip) |
| 2-2696 | 4-F—Ph | 4-Pyr | 1-Me-2-Bn-4-(3,4-deH-Pip) |
| 2-2697 | 4-F—Ph | 4-Pyr | 1-Et-2-Bn-4-(3,4-deH-Pip) |
| 2-2698 | 4-F—Ph | 4-Pyr | 1-Pr-2-Bn-4-(3,4-deH-Pip) |
| 2-2699 | 4-F—Ph | 4-Pyr | 1-Bu-2-Bn-4-(3,4-deH-Pip) |
| 2-2700 | 4-F—Ph | 4-Pyr | 1-Phet-2-Bn-4-(3,4-deH-Pip) |
| 2-2701 | 4-F—Ph | 4-Pyr | 2-Phet-4-(3,4-deH-Pip) |
| 2-2702 | 4-F—Ph | 4-Pyr | 1-Me-2-Phet-4-(3,4-deH-Pip) |
| 2-2703 | 4-F—Ph | 4-Pyr | 1-Et-2-Phet-4-(3,4-deH-Pip) |
| 2-2704 | 4-F—Ph | 4-Pyr | 1-Pr-2-Phet-4-(3,4-deH-Pip) |
| 2-2705 | 4-F—Ph | 4-Pyr | 1-Bu-2-Phet-4-(3,4-deH-Pip) |
| 2-2706 | 4-F—Ph | 4-Pyr | 1,2-diPhet-4-(3,4-deH-Pip) |
| 2-2707 | 4-F—Ph | 4-Pyr | 2-Me-4-(4,5-deH-Pip) |
| 2-2708 | 4-F—Ph | 4-Pyr | 1,2-diMe-4-(4,5-deH-Pip) |
| 2-2709 | 4-F—Ph | 4-Pyr | 1-Et-2-Me-4-(4,5-deH-Pip) |
| 2-2710 | 4-F—Ph | 4-Pyr | 1-Pr-2-Me-4-(4,5-deH-Pip) |
| 2-2711 | 4-F—Ph | 4-Pyr | 1-Bu-2-Me-4-(4,5-deH-Pip) |
| 2-2712 | 4-F—Ph | 4-Pyr | 1-Phet-2-Me-4-(4,5-deH-Pip) |
| 2-2713 | 4-F—Ph | 4-Pyr | 2-Et-4-(4,5-deH-Pip) |
| 2-2714 | 4-F—Ph | 4-Pyr | 1-Me-2-Et-4-(4,5-deH-Pip) |
| 2-2715 | 4-F—Ph | 4-Pyr | 1,2-diFt-4-(4,5-deH-Pip) |
| 2-2716 | 4-F—Ph | 4-Pyr | 1-Pr-2-Et-4-(4,5-deH-Pip) |
| 2-2717 | 4-F—Ph | 4-Pyr | 1-Bu-2-Et-4-(4,5-deH-Pip) |
| 2-2718 | 4-F—Ph | 4-Pyr | 1-Phet-2-Et-4-(4,5-deH-Pip) |
| 2-2719 | 4-F—Ph | 4-Pyr | 2-Pr-4-(4,5-deH-Pip) |
| 2-2720 | 4-F—Ph | 4-Pyr | 1-Me-2-Pr-4-(4,5-deH-Pip) |
| 2-2721 | 4-F—Ph | 4-Pyr | 1-Et-2-Pr-4-(4,5-deH-Pip) |
| 2-2722 | 4-F—Ph | 4-Pyr | 1,2-diPr-4-(4,5-deH-Pip) |
| 2-2723 | 4-F—Ph | 4-Pyr | 1-Bu-2-Pr-4-(4,5-deH-Pip) |
| 2-2724 | 4-F—Ph | 4-Pyr | 1-Phet-2-Pr-4-(4,5-deH-Pip) |
| 2-2725 | 4-F—Ph | 4-Pyr | 2-Bu-4-(4,5-deH-Pip) |
| 2-2726 | 4-F—Ph | 4-Pyr | 1-Me-2-Bu-4-(4,5-deH-Pip) |
| 2-2727 | 4-F—Ph | 4-Pyr | 1-Et-2-Bu-4-(4,5-deH-Pip) |
| 2-2728 | 4-F—Ph | 4-Pyr | 1-Pr-2-Bu-4-(4,5-deH-Pip) |
| 2-2729 | 4-F—Ph | 4-Pyr | 1,2-diBu-4-(4,5-deH-Pip) |
| 2-2730 | 4-F—Ph | 4-Pyr | 1-Phet-2-Bu-4-(4,5-deH-Pip) |
| 2-2731 | 4-F—Ph | 4-Pyr | 2-Allyl-4-(4,5-deH-Pip) |
| 2-2732 | 4-F—Ph | 4-Pyr | 1-Me-2-Allyl-4-(4,5-deH-Pip) |
| 2-2733 | 4-F—Ph | 4-Pyr | 1-Et-2-Allyl-4-(4,5-deH-Pip) |
| 2-2734 | 4-F—Ph | 4-Pyr | 1-Pr-2-Allyl-4-(4,5-deH-Pip) |
| 2-2735 | 4-F—Ph | 4-Pyr | 1-Bu-2-Allyl-4-(4,5-deH-Pip) |

TABLE 2-continued

| Compound No. | R¹ | R² | R³ |
|---|---|---|---|
| 2-2736 | 4-F—Ph | 4-Pyr | 1-Phet-2-Allyl-4-(4,5-deH-Pip) |
| 2-2737 | 4-F—Ph | 4-Pyr | 2-Bn-4-(4,5-deH-Pip) |
| 2-2738 | 4-F—Ph | 4-Pyr | 1-Me-2-Bn-4-(4,5-deH-Pip) |
| 2-2739 | 4-F—Ph | 4-Pyr | 1-Et-2-Bn-4-(4,5-deH-Pip) |
| 2-2740 | 4-F—Ph | 4-Pyr | 1-Pr-2-Bn-4-(4,5-deH-Pip) |
| 2-2741 | 4-F—Ph | 4-Pyr | 1-Bu-2-Bn-4-(4,5-deH-Pip) |
| 2-2742 | 4-F—Ph | 4-Pyr | 1-Phet-2-Bn-4-(4,5-deH-Pip) |
| 2-2743 | 4-F—Ph | 4-Pyr | 2-Phet-4-(4,5-deH-Pip) |
| 2-2744 | 4-F—Ph | 4-Pyr | 1-Me-2-Phet-4-(4,5-deH-Pip) |
| 2-2745 | 4-F—Ph | 4-Pyr | 1-Et-2-Phet-4-(4,5-deH-Pip) |
| 2-2746 | 4-F—Ph | 4-Pyr | 1-Pr-2-Phet-4-(4,5-deH-Pip) |
| 2-2747 | 4-F—Ph | 4-Pyr | 1-Bu-2-Phet-4-(4,5-deH-Pip) |
| 2-2748 | 4-F—Ph | 4-Pyr | 1,2-diPhet-4-(4,5-deH-Pip) |
| 2-2749 | 4-F—Ph | 2-NH₂-4-Pym | H₂—CH₂C(Me)₂CH₂ |
| 2-2750 | 4-F—Ph | 2-NH₂-4-Pym | MeNH—CH₂C(Me)₂CH₂ |
| 2-2751 | 4-F—Ph | 2-NH₂-4-Pym | EtNH—CH₂C(Me)₂CH₂ |
| 2-2752 | 4-F—Ph | 2-NH₂-4-Pym | Me₂N—CH₂C(Me)₂CH₂ |
| 2-2753 | 4-F—Ph | 2-NH₂-4-Pym | 3-(3,4-deH-Pip) |
| 2-2754 | 4-F—Ph | 2-NH₂-4-Pym | 1-Me-3-(3,4-deH-Pip) |
| 2-2755 | 4-F—Ph | 2-NH₂-4-Pym | 1-Et-4-(3,4-deH-Pip) |
| 2-2756 | 4-F—Ph | 2-NH₂-4-Pym | 1-Pr-4-(3,4-deH-Pip) |
| 2-2757 | 4-F—Ph | 2-NH₂-4-Pym | 1-Pr-4-Pip |
| 2-2758 | 4-F—Ph | 2-NH₂-4-Pym | 1-iPr-4-(3,4-deH-Pip) |
| 2-2759 | 4-F—Ph | 2-NH₂-4-Pym | 1-iPr-4-Pip |
| 2-2760 | 4-F—Ph | 2-NH₂-4-Pym | 1-Bu-4-(3,4-deH-Pip) |
| 2-2761 | 4-F—Ph | 2-NH₂-4-Pym | 1-tBu-4-(3,4-deH-Pip) |
| 2-2762 | 4-F—Ph | 2-NH₂-4-Pym | 1-Pn-4-(3,4-deH-Pip) |
| 2-2763 | 4-F—Ph | 2-NH₂-4-Pym | 1-Hx-4-(3,4-deH-Pip) |
| 2-2764 | 4-F—Ph | 2-NH₂-4-Pym | 1-Hp-4-(3,4-deH-Pip) |
| 2-2765 | 4-F—Ph | 2-NH₂-4-Pym | 1-Oc-4-(3,4-deH-Pip) |
| 2-2766 | 4-F—Ph | 2-NH₂-4-Pym | 1-Nn-4-(3,4-deH-Pip) |
| 2-2767 | 4-F—Ph | 2-NH₂-4-Pym | 1-cPr-4-(3,4-deH-Pip) |
| 2-2768 | 4-F—Ph | 2-NH₂-4-Pym | 1-cPn-4-(3,4-deH-Pip) |
| 2-2769 | 4-F—Ph | 2-NH₂-4-Pym | 1-cHx-4-(3,4-deH-Pip) |
| 2-2770 | 4-F—Ph | 2-NH₂-4-Pym | 1-Bn-4-(3,4-deH-Pip) |
| 2-2771 | 4-F—Ph | 2-NH₂-4-Pym | 1-Phet-4-(3,4-deH-Pip) |
| 2-2772 | 4-F—Ph | 2-NH₂-4-Pym | 1-(3-Ph—Pr)-4-(3,4-deH-Pip) |
| 2-2773 | 4-F—Ph | 2-NH₂-4-Pym | 1-(4-Ph—Bu)-4-(3,4-deH-Pip) |
| 2-2774 | 4-F—Ph | 2-NH₂-4-Pym | 1-Allyl-4-(3,4-deH-Pip) |
| 2-2775 | 4-F—Ph | 2-NH₂-4-Pym | 1-Propargyl-4-(3,4-deH-Pip) |
| 2-2776 | 4-F—Ph | 2-NH₂-4-Pym | 2,2,6,6-tetraMe-4-(3,4-deH-Pip) |
| 2-2777 | 4-F—Ph | 2-NH₂-4-Pym | 1,2,2,6,6-pentaMe-4-(3,4-deH-Pip) |
| 2-2778 | 2-NH₂-4-Pym 4-F—Ph | 1,2,2,6,6-pentaMe-4-Pip | |
| 2-2779 | 2-NH₂-4-Pym 4-F—Ph | 7-(1,2,3,5,6,8a-hexaH-Ind) | |
| 2-2780 | 2-NH₂-4-Pym 4-F—Ph | 7-(1,2,3,5,8,8a-hexaH-Ind) | |
| 2-2781 | 4-F—Ph | 2-NH₂-4-Pym | 7-octaH-Ind |
| 2-2782 | 4-F—Ph | 2-NH₂-4-Pyni | 8-(1,3,4,6,7,9a-hexaH-2H-Qui) |
| 2-2783 | 4-F—Ph | 2-NH₂-4-Pym | 8-(1,3,4,6,9,9a-hexaH-2H-Qui) |
| 2-2784 | 4-F—Ph | 2-NH₂-4-Pym | 8-octaH-Qui |
| 2-2785 | 4-F—Ph | 2-NH₂-4-Pym | 2,2-diMe-4-(3,4-deH-Pip) |
| 2-2786 | 4-F—Ph | 2-NH₂-4-Pym | 1,2,2-triMe-4-(3,4-deH-Pip) |
| 2-2787 | 4-F—Ph | 2-NH₂-4-Pym | 2,2-diMe-4-(4,5-deH-Pip) |
| 2-2788 | 4-F—Ph | 2-NH₂-4-Pym | 1,2,2-triMe-4-(4,5-deH-Pip) |
| 2-2789 | 4-F—Ph | 2-NH₂-4-Pym | 2,6-diMe-4-(3,4-deH-Pip) |
| 2-2790 | 4-F—Ph | 2-NH₂-4-Pym | 1,2,6-triMe-4-(3,4-deH-Pip) |
| 2-2791 | 4-F—Ph | 2-NH₂-4-Pym | 2-Me-4-(3,4-deH-Pip) |
| 2-2792 | 4-F—Ph | 2-NH₂-4-Pym | 1,2-diMe-4-(3,4-deH-Pip) |
| 2-2793 | 4-F—Ph | 2-NH₂-4-Pym | 1-Et-2-Me-4-(3,4-deH-Pip) |
| 2-2794 | 4-F—Ph | 2-NH₂-4-Pym | 1-Pr-2-Me-4-(3,4-deH-Pip) |
| 2-2795 | 4-F—Ph | 2-NH₂-4-Pym | 1-Bu-2-Me-4-(3,4-deH-Pip) |
| 2-2796 | 4-F—Ph | 2-NH₂-4-Pym | 1-Phet-2-Me-4-(3,4-deH-Pip) |
| 2-2797 | 4-F—Ph | 2-NH₂-4-Pym | 2-Et-4-(3,4-deH-Pip) |
| 2-2798 | 4-F—Ph | 2-NH₂-4-Pym | 1-Me-2-Et-4-(3,4-deH-Pip) |
| 2-2799 | 4-F—Ph | 2-NH₂-4-Pym | 1,2-diEt-4-(3,4-deH-Pip) |
| 2-2800 | 4-F—Ph | 2-NH₂-4-Pym | 1-Pr-2-Et-4-(3,4-deH-Pip) |
| 2-2801 | 4-F—Ph | 2-NH₂-4-Pym | 1-Bu-2-Et-4-(3,4-deH-Pip) |
| 2-2802 | 4-F—Ph | 2-NH₂-4-Pym | 1-Phet-2-Et-4-(3,4-deH-Pip) |
| 2-2803 | 4-F—Ph | 2-NH₂-4-Pym | 2-Pr-4-(3,4-deH-Pip) |
| 2-2804 | 4-F—Ph | 2-NH₂-4-Pym | 1-Me-2-Pr-4-(3,4-deH-Pip) |
| 2-2805 | 4-F—Ph | 2-NH₂-4-Pym | 1-Et-2-Pr-4-(3,4-deH-Pip) |
| 2-2806 | 4-F—Ph | 2-NH₂-4-Pym | 1,2-diPr-4-(3,4-deH-Pip) |
| 2-2807 | 4-F—Ph | 2-NH₂-4-Pym | 1-Bu-2-Pr-4-(3,4-deH-Pip) |
| 2-2808 | 4-F—Ph | 2-NH₂-4-Pym | 1-Phet-2-Pr-4-(3,4-deH-Pip) |
| 2-2809 | 4-F—Ph | 2-NH₂-4-Pym | 2-Bu-4-(3,4-deH-Pip) |
| 2-2810 | 4-F—Ph | 2-NH₂-4-Pym | 1-Me-2-Bu-4-(3,4-deH-Pip) |
| 2-2811 | 4-F—Ph | 2-NH₂-4-Pym | 1-Et-2-Bu-4-(3,4-deH-Pip) |
| 2-2812 | 4-F—Ph | 2-NH₂-4-Pym | 1-Pr-2-Bu-4-(3,4-deH-Pip) |
| 2-2813 | 4-F—Ph | 2-NH₂-4-Pym | 1,2-diBu-4-(3,4-deH-Pip) |
| 2-2814 | 4-F—Ph | 2-NH₂-4-Pym | 1-Phet-2-Bu-4-(3,4-deH-Pip) |
| 2-2815 | 4-F—Ph | 2-NH₂-4-Pym | 2-Allyl-4-(3,4-deH-Pip) |
| 2-2816 | 4-F—Ph | 2-NH₂-4-Pym | 1-Me-2-Allyl-4-(3,4-deH-Pip) |
| 2-2817 | 4-F—Ph | 2-NH₂-4-Pym | 1-Et-2-Allyl-4-(3,4-deH-Pip) |
| 2-2818 | 4-F—Ph | 2-NH₂-4-Pym | 1-Pr-2-Allyl-4-(3,4-deH-Pip) |
| 2-2819 | 4-F—Ph | 2-NH₂-4-Pym | 1-Bu-2-Allyl-4-(3,4-deH-Pip) |
| 2-2820 | 4-F—Ph | 2-NH₂-4-Pym | 1-Phet-2-Allyl-4-(3,4-deH-Pip) |
| 2-2821 | 4-F—Ph | 2-NH₂-4-Pym | 2-Bn-4-(3,4-deH-Pip) |
| 2-2822 | 4-F—Ph | 2-NH₂-4-Pym | 1-Me-2-Bn-4-(3,4-deH-Pip) |
| 2-2823 | 4-F—Ph | 2-NH₂-4-Pym | 1-Et-2-Bn-4-(3,4-deH-Pip) |
| 2-2824 | 4-F—Ph | 2-NH₂-4-Pym | 1-Pr-2-Bn-4-(3,4-deH-Pip) |
| 2-2825 | 4-F—Ph | 2-NH₂-4-Pym | 1-Bu-2-Bn-4-(3,4-deH-Pip) |
| 2-2826 | 4-F—Ph | 2-NH₂-4-Pym | 1-Phet-2-Bn-4-(3,4-deH-Pip) |
| 2-2827 | 4-F—Ph | 2-NH₂-4-Pym | 2-Phet-4-(3,4-deH-Pip) |
| 2-2828 | 4-F—Ph | 2-NH₂-4-Pym | 1-Me-2-Phet-4-(3,4-deH-Pip) |
| 2-2829 | 4-F—Ph | 2-NH₂-4-Pym | 1-Et-2-Phet-4-(3,4-deH-Pip) |
| 2-2830 | 4-F—Ph | 2-NH₂-4-Pym | 1-Pr-2-Phet-4-(3,4-deH-Pip) |
| 2-2831 | 4-F—Ph | 2-NH₂-4-Pym | 1-Bu-2-Phet-4-(3,4-deH-Pip) |
| 2-2832 | 4-F—Ph | 2-NH₂-4-Pym | 1,2-diPhet-4-(3,4-deH-Pip) |
| 2-2833 | 4-F—Ph | 2-NH₂-4-Pym | 2-Me-4-(4,5-deH-Pip) |
| 2-2834 | 4-F—Ph | 2-NH₂-4-Pym | 1,2-diMe-4-(4,5-deH-Pip) |
| 2-2835 | 4-F—Ph | 2-NH₂-4-Pym | 1-Et-2-Me-4-(4,5-deH-Pip) |
| 2-2836 | 4-F—Ph | 2-NH₂-4-Pym | 1-Pr-2-Me-4-(4,5-deH-Pip) |
| 2-2837 | 4-F—Ph | 2-NH₂-4-Pym | 1-Bu-2-Me-4-(4,5-deH-Pip) |
| 2-2838 | 4-F—Ph | 2-NH₂-4-Pym | 1-Phet-2-Me-4-(4,5-deH-Pip) |
| 2-2839 | 4-F—Ph | 2-NH₂-4-Pym | 2-Et-4-(4,5-deH-Pip) |
| 2-2840 | 4-F—Ph | 2-NH₂-4-Pym | 1-Me-2-Et-4-(4,5-deH-Pip) |
| 2-2841 | 4-F—Ph | 2-NH₂-4-Pym | 1,2-diFt-4-(4,5-deH-Pip) |
| 2-2842 | 4-F—Ph | 2-NH₂-4-Pym | 1-Pr-2-Et-4-(4,5-deH-Pip) |
| 2-2843 | 4-F—Ph | 2-NH₂-4-Pym | 1-Bu-2-Et-4-(4,5-deH-Pip) |
| 2-2844 | 4-F—Ph | 2-NH₂-4-Pym | 1-Phet-2-Et-4-(4,5-deH-Pip) |
| 2-2845 | 4-F—Ph | 2-NH₂-4-Pym | 2-Pr-4-(4,5-deH-Pip) |
| 2-2846 | 4-F—Ph | 2-NH₂-4-Pym | 1-Me-2-Pr-4-(4,5-deH-Pip) |
| 2-2847 | 4-F—Ph | 2-NH₂-4-Pym | 1-Et-2-Pr-4-(4,5-deH-Pip) |
| 2-2848 | 4-F—Ph | 2-NH₂-4-Pym | 1,2-diPr-4-(4,5-deH-Pip) |

TABLE 2-continued

| Compound No. | R¹ | R² | R³ |
| --- | --- | --- | --- |
| 2-2849 | 4-F—Ph | 2-NH₂-4-Pym | 1-Bu-2-Pr-4-(4,5-deH-Pip) |
| 2-2850 | 4-F—Ph | 2-NH₂-4-Pym | 1-Phet-2-Pr-4-(4,5-deH-Pip) |
| 2-2851 | 4-F—Ph | 2-NH₂-4-Pym | 2-Bu-4-(4,5-deH-Pip) |
| 2-2852 | 4-F—Ph | 2-NH₂-4-Pym | 1-Me-2-Bu-4-(4,5-deH-Pip) |
| 2-2853 | 4-F—Ph | 2-NH₂-4-Pym | 1-Et-2-Bu-4-(4,5-deH-Pip) |
| 2-2854 | 4-F—Ph | 2-NH₂-4-Pym | 1-Pr-2-Bu-4-(4,5-deH-Pip) |
| 2-2855 | 4-F—Ph | 2-NH₂-4-Pym | 1,2-diBu-4-(4,5-deH-Pip) |
| 2-2856 | 4-F—Ph | 2-NH₂-4-Pym | 1-Phet-2-Bu-4-(4,5-deH-Pip) |
| 2-2857 | 4-F—Ph | 2-NH₂-4-Pym | 2-Allyl-4-(4,5-deH-Pip) |
| 2-2858 | 4-F—Ph | 2-NH₂-4-Pym | 1-Me-2-Allyl-4-(4,5-deH-Pip) |
| 2-2859 | 4-F—Ph | 2-NH₂-4-Pym | 1-Et-2-Allyl-4-(4,5-deH-Pip) |
| 2-2860 | 4-F—Ph | 2-NH₂-4-Pym | 1-Pr-2-Allyl-4-(4,5-deH-Pip) |
| 2-2861 | 4-F—Ph | 2-NH₂-4-Pym | 1-Bu-2-Allyl-4-(4,5-deH-Pip) |
| 2-2862 | 4-F—Ph | 2-NH₂-4-Pym | 1-Phet-2-Allyl-4-(4,5-deH-Pip) |
| 2-2863 | 4-F—Ph | 2-NH₂-4-Pym | 2-Bn-4-(4,5-deH-Pip) |
| 2-2864 | 4-F—Ph | 2-NH₂-4-Pym | 1-Me-2-Bn-4-(4,5-deH-Pip) |
| 2-2865 | 4-F—Ph | 2-NH₂-4-Pym | 1-Et-2-Bn-4-(4,5-deH-Pip) |
| 2-2866 | 4-F—Ph | 2-NH₂-4-Pym | 1-Pr-2-Bn-4-(4,5-deH-Pip) |
| 2-2867 | 4-F—Ph | 2-NH₂-4-Pym | 1-Bu-2-Bn-4-(4,5-deH-Pip) |
| 2-2868 | 4-F—Ph | 2-NH₂-4-Pym | 1-Phet-2-Bn-4-(4,5-deH-Pip) |
| 2-2869 | 4-F—Ph | 2-NH₂-4-Pym | 2-Phet-4-(4,5-deH-Pip) |
| 2-2870 | 4-F—Ph | 2-NH₂-4-Pym | 1-Me-2-Phet-4-(4,5-deH-Pip) |
| 2-2871 | 4-F—Ph | 2-NH₂-4-Pym | 1-Et-2-Phet-4-(4,5-deH-Pip) |
| 2-2872 | 4-F—Ph | 2-NH₂-4-Pym | 1-Pr-2-Phet-4-(4,5-deH-Pip) |
| 2-2873 | 4-F—Ph | 2-NH₂-4-Pym | 1-Bu-2-Phet-4-(4,5-deH-Pip) |
| 2-2874 | 4-F—Ph | 2-NH₂-4-Pym | 1,2-diPhet-4-(4,5-deH-Pip) |
| 2-2875 | 4-F—Ph | 2-MeNH-4-Pym | H₂—CH₂C(Me)₂CH₂ |
| 2-2876 | 4-F—Ph | 2-MeNH-4-Pym | MeNH—CH₂C(Me)₂CH₂ |
| 2-2877 | 4-F—Ph | 2-MeNH-4-Pym | EtNH—CH₂C(Me)₂CH₂ |
| 2-2878 | 4-F—Ph | 2-MeNH-4-Pym | Me₂N—CH₂C(Me)₂CH₂ |
| 2-2879 | 4-F—Ph | 2-MeNH-4-Pym | 3-(3,4-deH-Pip) |
| 2-2880 | 4-F—Ph | 2-MeNH-4-Pym | 1-Me-3-(3,4-deH-Pip) |
| 2-2881 | 4-F—Ph | 2-MeNH-4-Pym | 1-Et-4-(3,4-deH-Pip) |
| 2-2882 | 4-F—Ph | 2-MeNH-4-Pym | 1-Pr-4-(3,4-deH-Pip) |
| 2-2883 | 4-F—Ph | 2-MeNH-4-Pym | 1-Pr-4-Pip |
| 2-2884 | 4-F—Ph | 2-MeNH-4-Pym | 1-iPr-4-(3,4-deH-Pip) |
| 2-2885 | 4-F—Ph | 2-MeNH-4-Pym | 1-iPr-4-Pip |
| 2-2886 | 4-F—Ph | 2-MeNH-4-Pym | 1-Bu-4-(3,4-deH-Pip) |
| 2-2887 | 4-F—Ph | 2-MeNH-4-Pym | 1-tBu-4-(3,4-deH-Pip) |
| 2-2888 | 4-F—Ph | 2-MeNH-4-Pym | 1-Pn-4-(3,4-deH-Pip) |
| 2-2889 | 4-F—Ph | 2-MeNH-4-Pym | 1-Hx-4-(3,4-deH-Pip) |
| 2-2890 | 4-F—Ph | 2-MeNH-4-Pym | 1-Hp-4-(3,4-deH-Pip) |
| 2-2891 | 4-F—Ph | 2-MeNH-4-Pym | 1-Oc-4-(3,4-deH-Pip) |
| 2-2892 | 4-F—Ph | 2-MeNH-4-Pym | 1-Nn-4-(3,4-deH-Pip) |
| 2-2893 | 4-F—Ph | 2-MeNH-4-Pym | 1-cPr-4-(3,4-deH-Pip) |
| 2-2894 | 4-F—Ph | 2-MeNH-4-Pym | 1-cPn-4-(3,4-deH-Pip) |
| 2-2895 | 4-F—Ph | 2-MeNH-4-Pym | 1-cHx-4-(3,4-deH-Pip) |
| 2-2896 | 4-F—Ph | 2-MeNH-4-Pym | 1-Bn-4-(3,4-deH-Pip) |
| 2-2897 | 4-F—Ph | 2-MeNH-4-Pym | 1-Phet-4-(3,4-deH-Pip) |
| 2-2898 | 4-F—Ph | 2-MeNH-4-Pym | 1-(3-Ph—Pr)-4-(3,4-deH-Pip) |
| 2-2899 | 4-F—Ph | 2-MeNH-4-Pym | 1-(4-Ph—Bu)-4-(3,4-deH-Pip) |
| 2-2900 | 4-F—Ph | 2-MeNH-4-Pym | 1-Allyl-4-(3,4-deH-Pip) |
| 2-2901 | 4-F—Ph | 2-MeNH-4-Pym | 1-Propargyl-4-(3,4-deH-Pip) |
| 2-2902 | 4-F—Ph | 2-MeNH-4-Pym | 2,2,6,6-tetraMe-4-(3,4-deH-Pip) |
| 2-2903 | 4-F—Ph | 2-MeNH-4-Pym | 1,2,2,6,6-pentaMe-4-(3,4-deH-Pip) |
| 2-2904 | 4-F—Ph | 2-MeNH-4-Pym | 1,2,2,6,6-pentaMe-4-Pip |
| 2-2905 | 4-F—Ph | 2-MeNH-4-Pym | 7-(1,2,3,5,6,8a-hexaH-Ind) |
| 2-2906 | 4-F—Ph | 2-MeNH-4-Pym | 7-(1,2,3,5,8,8a-hexaH-Ind) |
| 2-2907 | 4-F—Ph | 2-MeNH-4-Pym | 7-octaH-Ind |
| 2-2908 | 4-F—Ph | 2-MeNH-4-Pym | 8-(1,3,4,6,7,9a-hexaH-2H-Qui) |
| 2-2909 | 4-F—Ph | 2-MeNH-4-Pym | 8-(1,3,4,6,9,9a-hexaH-2H-Qui) |
| 2-2910 | 4-F—Ph | 2-MeNH-4-Pym | 8-octaH-Qui |
| 2-2911 | 4-F—Ph | 2-MeNH-4-Pym | 2,2-diMe-4-(3,4-deH-Pip) |
| 2-2912 | 4-F—Ph | 2-MeNH-4-Pym | 1,2,2-triMe-4-(3,4-deH-Pip) |
| 2-2913 | 4-F—Ph | 2-MeNH-4-Pym | 2,2-diMe-4-(4,5-deH-Pip) |
| 2-2914 | 4-F—Ph | 2-MeNH-4-Pym | 1,2,2-triMe-4-(4,5-deH-Pip) |
| 2-2915 | 4-F—Ph | 2-MeNH-4-Pym | 2,6-diMe-4-(3,4-deH-Pip) |
| 2-2916 | 4-F—Ph | 2-MeNH-4-Pym | 1,2,6-triMe-4-(3,4-deH-Pip) |
| 2-2917 | 4-F—Ph | 2-MeNH-4-Pym | 2-Me-4-(3,4-deH-Pip) |
| 2-2918 | 4-F—Ph | 2-MeNH-4-Pym | 1,2-diMe-4-(3,4-deH-Pip) |
| 2-2919 | 4-F—Ph | 2-MeNH-4-Pym | 1-Et-2-Me-4-(3,4-deH-Pip) |
| 2-2920 | 4-F—Ph | 2-MeNH-4-Pym | 1-Pr-2-Me-4-(3,4-deH-Pip) |
| 2-2921 | 4-F—Ph | 2-MeNH-4-Pym | 1-Bu-2-Me-4-(3,4-deH-Pip) |
| 2-2922 | 4-F—Ph | 2-MeNH-4-Pym | 1-Phet-2-Me-4-(3,4-deH-Pip) |
| 2-2923 | 4-F—Ph | 2-MeNH-4-Pym | 2-Et-4-(3,4-deH-Pip) |
| 2-2924 | 4-F—Ph | 2-MeNH-4-Pym | 1-Me-2-Et-4-(3,4-deH-Pip) |
| 2-2925 | 4-F—Ph | 2-MeNH-4-Pym | 1,2-diEt-4-(3,4-deH-Pip) |
| 2-2926 | 4-F—Ph | 2-MeNH-4-Pym | 1-Pr-2-Et-4-(3,4-deH-Pip) |
| 2-2927 | 4-F—Ph | 2-MeNH-4-Pym | 1-Bu-2-Et-4-(3,4-deH-Pip) |
| 2-2928 | 4-F—Ph | 2-MeNH-4-Pym | 1-Phet-2-Et-4-(3,4-deH-Pip) |
| 2-2929 | 4-F—Ph | 2-MeNH-4-Pym | 2-Pr-4-(3,4-deH-Pip) |
| 2-2930 | 4-F—Ph | 2-MeNH-4-Pym | 1-Me-2-Pr-4-(3,4-deH-Pip) |
| 2-2931 | 4-F—Ph | 2-MeNH-4-Pym | 1-Et-2-Pr-4-(3,4-deH-Pip) |
| 2-2932 | 4-F—Ph | 2-MeNH-4-Pym | 1,2-diPr-4-(3,4-deH-Pip) |
| 2-2933 | 4-F—Ph | 2-MeNH-4-Pym | 1-Bu-2-Pr-4-(3,4-deH-Pip) |
| 2-2934 | 4-F—Ph | 2-MeNH-4-Pym | 1-Phet-2-Pr-4-(3,4-deH-Pip) |
| 2-2935 | 4-F—Ph | 2-MeNH-4-Pym | 2-Bu-4-(3,4-deH-Pip) |
| 2-2936 | 4-F—Ph | 2-MeNH-4-Pym | 1-Me-2-Bu-4-(3,4-deH-Pip) |
| 2-2937 | 4-F—Ph | 2-MeNH-4-Pym | 1-Et-2-Bu-4-(3,4-deH-Pip) |
| 2-2938 | 4-F—Ph | 2-MeNH-4-Pym | 1-Pr-2-Bu-4-(3,4-deH-Pip) |
| 2-2939 | 4-F—Ph | 2-MeNH-4-Pym | 1,2-diBu-4-(3,4-deH-Pip) |
| 2-2940 | 4-F—Ph | 2-MeNH-4-Pym | 1-Phet-2-Bu-4-(3,4-deH-Pip) |
| 2-2941 | 4-F—Ph | 2-MeNH-4-Pym | 2-Allyl-4-(3,4-deH-Pip) |
| 2-2942 | 4-F—Ph | 2-MeNH-4-Pym | 1-Me-2-Allyl-4-(3,4-deH-Pip) |
| 2-2943 | 4-F—Ph | 2-MeNH-4-Pym | 1-Et-2-Allyl-4-(3,4-deH-Pip) |
| 2-2944 | 4-F—Ph | 2-MeNH-4-Pym | 1-Pr-2-Allyl-4-(3,4-deH-Pip) |
| 2-2945 | 4-F—Ph | 2-MeNH-4-Pym | 1-Bu-2-Allyl-4-(3,4-deH-Pip) |
| 2-2946 | 4-F—Ph | 2-MeNH-4-Pym | 1-Phet-2-Allyl-4-(3,4-deH-Pip) |
| 2-2947 | 4-F—Ph | 2-MeNH-4-Pym | 2-Bn-4-(3,4-deH-Pip) |
| 2-2948 | 4-F—Ph | 2-MeNH-4-Pym | 1-Me-2-Bn-4-(3,4-deH-Pip) |
| 2-2949 | 4-F—Ph | 2-MeNH-4-Pym | 1-Et-2-Bn-4-(3,4-deH-Pip) |
| 2-2950 | 4-F—Ph | 2-MeNH-4-Pym | 1-Pr-2-Bn-4-(3,4-deH-Pip) |
| 2-2951 | 4-F—Ph | 2-MeNH-4-Pym | 1-Bu-2-Bn-4-(3,4-deH-Pip) |
| 2-2952 | 4-F—Ph | 2-MeNH-4-Pym | 1-Phet-2-Bn-4-(3,4-deH-Pip) |
| 2-2953 | 4-F—Ph | 2-MeNH-4-Pym | 2-Phet-4-(3,4-deH-Pip) |
| 2-2954 | 4-F—Ph | 2-MeNH-4-Pym | 1-Me-2-Phet-4-(3,4-deH-Pip) |
| 2-2955 | 4-F—Ph | 2-MeNH-4-Pym | 1-Et-2-Phet-4-(3,4-deH-Pip) |
| 2-2956 | 4-F—Ph | 2-MeNH-4-Pym | 1-Pr-2-Phet-4-(3,4-deH-Pip) |
| 2-2957 | 4-F—Ph | 2-MeNH-4-Pym | 1-Bu-2-Phet-4-(3,4-deH-Pip) |
| 2-2958 | 4-F—Ph | 2-MeNH-4-Pym | 1,2-diPhet-4-(3,4-deH-Pip) |
| 2-2959 | 4-F—Ph | 2-MeNH-4-Pym | 2-Me-4-(4,5-deH-Pip) |
| 2-2960 | 4-F—Ph | 2-MeNH-4-Pym | 1,2-diMe-4-(4,5-deH-Pip) |

TABLE 2-continued

| Compound No. | R¹ | R² | R³ |
|---|---|---|---|
| 2-2961 | 4-F—Ph | 2-MeNH-4-Pym | 1-Et-2-Me-4-(4,5-deH-Pip) |
| 2-2962 | 4-F—Ph | 2-MeNH-4-Pym | 1-Pr-2-Me-4-(4,5-deH-Pip) |
| 2-2963 | 4-F—Ph | 2-MeNH-4-Pym | 1-Bu-2-Me-4-(4,5-deH-Pip) |
| 2-2964 | 4-F—Ph | 2-MeNH-4-Pym | 1-Phet-2-Me-4-(4,5-deH-Pip) |
| 2-2965 | 4-F—Ph | 2-MeNH-4-Pym | 2-Et-4-(4,5-deH-Pip) |
| 2-2966 | 4-F—Ph | 2-MeNH-4-Pym | 1-Me-2-Et-4-(4,5-deH-Pip) |
| 2-2967 | 4-F—Ph | 2-MeNH-4-Pym | 1,2-diEt-4-(4,5-deH-Pip) |
| 2-2968 | 4-F—Ph | 2-MeNH-4-Pym | 1-Pr-2-Et-4-(4,5-deH-Pip) |
| 2-2969 | 4-F—Ph | 2-MeNH-4-Pym | 1-Bu-2-Et-4-(4,5-deH-Pip) |
| 2-2970 | 4-F—Ph | 2-MeNH-4-Pym | 1-Phet-2-Et-4-(4,5-deH-Pip) |
| 2-2971 | 4-F—Ph | 2-MeNH-4-Pym | 2-Pr-4-(4,5-deH-Pip) |
| 2-2972 | 4-F—Ph | 2-MeNH-4-Pym | 1-Me-2-Pr-4-(4,5-deH-Pip) |
| 2-2973 | 4-F—Ph | 2-MeNH-4-Pym | 1-Et-2-Pr-4-(4,5-deH-Pip) |
| 2-2974 | 4-F—Ph | 2-MeNH-4-Pym | 1,2-diPr-4-(4,5-deH-Pip) |
| 2-2975 | 4-F—Ph | 2-MeNH-4-Pym | 1-Bu-2-Pr-4-(4,5-deH-Pip) |
| 2-2976 | 4-F—Ph | 2-MeNH-4-Pym | 1-Phet-2-Pr-4-(4,5-deH-Pip) |
| 2-2977 | 4-F—Ph | 2-MeNH-4-Pym | 2-Bu-4-(4,5-deH-Pip) |
| 2-2978 | 4-F—Ph | 2-MeNH-4-Pym | 1-Me-2-Bu-4-(4,5-deH-Pip) |
| 2-2979 | 4-F—Ph | 2-MeNH-4-Pym | 1-Et-2-Bu-4-(4,5-deH-Pip) |
| 2-2980 | 4-F—Ph | 2-MeNH-4-Pym | 1-Pr-2-Bu-4-(4,5-deH-Pip) |
| 2-2981 | 4-F—Ph | 2-MeNH-4-Pym | 1,2-diBu-4-(4,5-deH-Pip) |
| 2-2982 | 4-F—Ph | 2-MeNH-4-Pym | 1-Phet-2-Bu-4-(4,5-deH-Pip) |
| 2-2983 | 4-F—Ph | 2-MeNH-4-Pym | 2-Allyl-4-(4,5-deH-Pip) |
| 2-2984 | 4-F—Ph | 2-MeNH-4-Pym | 1-Me-2-Allyl-4-(4,5-deH-Pip) |
| 2-2985 | 4-F—Ph | 2-MeNH-4-Pym | 1-Et-2-Allyl-4-(4,5-deH-Pip) |
| 2-2986 | 4-F—Ph | 2-MeNH-4-Pym | 1-Pr-2-Allyl-4-(4,5-deH-Pip) |
| 2-2987 | 4-F—Ph | 2-MeNH-4-Pym | 1-Bu-2-Allyl-4-(4,5-deH-Pip) |
| 2-2988 | 4-F—Ph | 2-MeNH-4-Pym | 1-Phet-2-Allyl-4-(4,5-deH-Pip) |
| 2-2989 | 4-F—Ph | 2-MeNH-4-Pym | 2-Bn-4-(4,5-deH-Pip) |
| 2-2990 | 4-F—Ph | 2-MeNH-4-Pym | 1-Me-2-Bn-4-(4,5-deH-Pip) |
| 2-2991 | 4-F—Ph | 2-MeNH-4-Pym | 1-Et-2-Bn-4-(4,5-deH-Pip) |
| 2-2992 | 4-F—Ph | 2-MeNH-4-Pym | 1-Pr-2-Bn-4-(4,5-deH-Pip) |
| 2-2993 | 4-F—Ph | 2-MeNH-4-Pym | 1-Bu-2-Bn-4-(4,5-deH-Pip) |
| 2-2994 | 4-F—Ph | 2-MeNH-4-Pym | 1-Phet-2-Bn-4-(4,5-deH-Pip) |
| 2-2995 | 4-F—Ph | 2-MeNH-4-Pym | 2-Phet-4-(4,5-deH-Pip) |
| 2-2996 | 4-F—Ph | 2-MeNH-4-Pym | 1-Me-2-Phet-4-(4,5-deH-Pip) |
| 2-2997 | 4-F—Ph | 2-MeNH-4-Pym | 1-Et-2-Phet-4-(4,5-deH-Pip) |
| 2-2998 | 4-F—Ph | 2-MeNH-4-Pym | 1-Pr-2-Phet-4-(4,5-deH-Pip) |
| 2-2999 | 4-F—Ph | 2-MeNH-4-Pym | 1-Bu-2-Phet-4-(4,5-deH-Pip) |
| 2-3000 | 4-F—Ph | 2-MeNH-4-Pym | 1,2-diPhet-4-(4,5-deH-Pip) |
| 2-3001 | 4-F—Ph | 2-NH₂-4-Pyr | H₂—CH₂C(Me)₂CH₂ |
| 2-3002 | 4-F—Ph | 2-NH₂-4-Pyr | MeNH—CH₂C(Me)₂CH₂ |
| 2-3003 | 4-F—Ph | 2-NH₂-4-Pyr | EtNH—CH₂C(Me)₂CH₂ |
| 2-3004 | 4-F—Ph | 2-NH₂-4-Pyr | Me₂N—CH₂C(Me)₂CH₂ |
| 2-3005 | 4-F—Ph | 2-NH₂-4-Pyr | 3-(3,4-deH-Pip) |
| 2-3006 | 4-F—Ph | 2-NH₂-4-Pyr | 1-Me-3-(3,4-deH-Pip) |
| 2-3007 | 4-F—Ph | 2-NH₂-4-Pyr | 1-Et-4-(3,4-deH-Pip) |
| 2-3008 | 4-F—Ph | 2-NH₂-4-Pyr | 1-Pr-4-(3,4-deH-Pip) |
| 2-3009 | 4-F—Ph | 2-NH₂-4-Pyr | 1-Pr-4-Pip |
| 2-3010 | 4-F—Ph | 2-NH₂-4-Pyr | 1-iPr-4-(3,4-deH-Pip) |
| 2-3011 | 4-F—Ph | 2-NH₂-4-Pyr | 1-iPr-4-Pip |
| 2-3012 | 4-F—Ph | 2-NH₂-4-Pyr | 1-Bu-4-(3,4-deH-Pip) |
| 2-3013 | 4-F—Ph | 2-NH₂-4-Pyr | 1-tBu-4-(3,4-deH-Pip) |
| 2-3014 | 4-F—Ph | 2-NH₂-4-Pyr | 1-Pn-4-(3,4-deH-Pip) |
| 2-3015 | 4-F—Ph | 2-NH₂-4-Pyr | 1-Hx-4-(3,4-deH-Pip) |
| 2-3016 | 4-F—Ph | 2-NH₂-4-Pyr | 1-Hp-4-(3,4-deH-Pip) |
| 2-3017 | 4-F—Ph | 2-NH₂-4-Pyr | 1-Oc-4-(3,4-deH-Pip) |
| 2-3018 | 4-F—Ph | 2-NH₂-4-Pyr | 1-Nn-4-(3,4-deH-Pip) |
| 2-3019 | 4-F—Ph | 2-NH₂-4-Pyr | 1-cPr-4-(3,4-deH-Pip) |
| 2-3020 | 4-F—Ph | 2-NH₂-4-Pyr | 1-cPn-4-(3,4-deH-Pip) |
| 2-3021 | 4-F—Ph | 2-NH₂-4-Pyr | 1-cHx-4-(3,4-deH-Pip) |
| 2-3022 | 4-F—Ph | 2-NH₂-4-Pyr | 1-Bn-4-(3,4-deH-Pip) |
| 2-3023 | 4-F—Ph | 2-NH₂-4-Pyr | 1-Phet-4-(3,4-deH-Pip) |
| 2-3024 | 4-F—Ph | 2-NH₂-4-Pyr | 1-(3-Ph—Pr)-4-(3,4-deH-Pip) |
| 2-3025 | 4-F—Ph | 2-NH₂-4-Pyr | 1-(4-Ph—Bu)-4-(3,4-deH-Pip) |
| 2-3026 | 4-F—Ph | 2-NH₂-4-Pyr | 1-Allyl-4-(3,4-deH-Pip) |
| 2-3027 | 4-F—Ph | 2-NH₂-4-Pyr | 1-Propargyl-4-(3,4-deH-Pip) |
| 2-3028 | 4-F—Ph | 2-NH₂-4-Pyr | 2,2,6,6—tetraMe-4-(3,4-deH-Pip) |
| 2-3029 | 4-F—Ph | 2-NH₂-4-Pyr | 1,2,2,6,6-pentaMe-4-(3,4-deH-Pip) |
| 2-3030 | 4-F—Ph | 2-NH₂-4-Pyr | 1,2,2,6,6-pentaMe-4-Pip |
| 2-3031 | 4-F—Ph | 2-NH₂-4-Pyr | 7-(1,2,3,5,6,8a-hexaH-Ind) |
| 2-3032 | 4-F—Ph | 2-NH₂-4-Pyr | 7-(1,2,3,5,8,8a-hexaH-Ind) |
| 2-3033 | 4-F—Ph | 2-NH₂-4-Pyr | 7-octaH-Ind |
| 2-3034 | 4-F—Ph | 2-NH₂-4-Pyr | 8-(1,3,4,6,7,9a-hexaH-2H-Qui) |
| 2-3035 | 4-F—Ph | 2-NH₂-4-Pyr | 8-(1,3,4,6,9,9a-hexaH-2H-Qui) |
| 2-3036 | 4-F—Ph | 2-NH₂-4-Pyr | 8-octaH-Qui |
| 2-3037 | 4-F—Ph | 2-NH₂-4-Pyr | 2,2-diMe-4-(3,4-deH-Pip) |
| 2-3038 | 4-F—Ph | 2-NH₂-4-Pyr | 1,2,2-triMe-4-(3,4-deH-Pip) |
| 2-3039 | 4-F—Ph | 2-NH₂-4-Pyr | 2,2-diMe-4-(4,5-deH-Pip) |
| 2-3040 | 4-F—Ph | 2-NH₂-4-Pyr | 1,2,2-triMe-4-(4,5-deH-Pip) |
| 2-3041 | 4-F—Ph | 2-NH₂-4-Pyr | 2,6-diMe-4-(3,4-deH-Pip) |
| 2-3042 | 4-F—Ph | 2-NH₂-4-Pyr | 1,2,6-triMe-4-(3,4-deH-Pip) |
| 2-3043 | 4-F—Ph | 2-NH₂-4-Pyr | 2-Me-4-(3,4-deH-Pip) |
| 2-3044 | 4-F—Ph | 2-NH₂-4-Pyr | 1,2-diMe-4-(3,4-deH-Pip) |
| 2-3045 | 4-F—Ph | 2-NH₂-4-Pyr | 1-Et-2-Me-4-(3,4-deH-Pip) |
| 2-3046 | 4-F—Ph | 2-NH₂-4-Pyr | 1-Pr-2-Me-4-(3,4-deH-Pip) |
| 2-3047 | 4-F—Ph | 2-NH₂-4-Pyr | 1-Bu-2-Me-4-(3,4-deH-Pip) |
| 2-3048 | 4-F—Ph | 2-NH₂-4-Pyr | 1-Phet-2-Me-4-(3,4-deH-Pip) |
| 2-3049 | 4-F—Ph | 2-NH₂-4-Pyr | 2-Et-4-(3,4-deH-Pip) |
| 2-3050 | 4-F—Ph | 2-NH₂-4-Pyr | 1-Me-2-Et-4-(3,4-deH-Pip) |
| 2-3051 | 4-F—Ph | 2-NH₂-4-Pyr | 1,2-diEt-4-(3,4-deH-Pip) |
| 2-3052 | 4-F—Ph | 2-NH₂-4-Pyr | 1-Pr-2-Et-4-(3,4-deH-Pip) |
| 2-3053 | 4-F—Ph | 2-NH₂-4-Pyr | 1-Bu-2-Et-4-(3,4-deH-Pip) |
| 2-3054 | 4-F—Ph | 2-NH₂-4-Pyr | 1-Phet-2-Et-4-(3,4-deH-Pip) |
| 2-3055 | 4-F—Ph | 2-NH₂-4-Pyr | 2-Pr-4-(3,4-deH-Pip) |
| 2-3056 | 4-F—Ph | 2-NH₂-4-Pyr | 1-Me-2-Pr-4-(3,4-deH-Pip) |
| 2-3057 | 4-F—Ph | 2-NH₂-4-Pyr | 1-Et-2-Pr-4-(3,4-deH-Pip) |
| 2-3058 | 4-F—Ph | 2-NH₂-4-Pyr | 1,2-diPr-4-(3,4-deH-Pip) |
| 2-3059 | 4-F—Ph | 2-NH₂-4-Pyr | 1-Bu-2-Pr-4-(3,4-deH-Pip) |
| 2-3060 | 4-F—Ph | 2-NH₂-4-Pyr | 1-Phet-2-Pr-4-(3,4-deH-Pip) |
| 2-3061 | 4-F—Ph | 2-NH₂-4-Pyr | 2-Bu-4-(3,4-deH-Pip) |
| 2-3062 | 4-F—Ph | 2-NH₂-4-Pyr | 1-Me-2-Bu-4-(3,4-deH-Pip) |
| 2-3063 | 4-F—Ph | 2-NH₂-4-Pyr | 1-Et-2-Bu-4-(3,4-deH-Pip) |
| 2-3064 | 4-F—Ph | 2-NH₂-4-Pyr | 1-Pr-2-Bu-4-(3,4-deH-Pip) |
| 2-3065 | 4-F—Ph | 2-NH₂-4-Pyr | 1,2-diBu-4-(3,4-deH-Pip) |
| 2-3066 | 4-F—Ph | 2-NH₂-4-Pyr | 1-Phet-2-Bu-4-(3,4-deH-Pip) |
| 2-3067 | 4-F—Ph | 2-NH₂-4-Pyr | 2-Allyl-4-(3,4-deH-Pip) |
| 2-3068 | 4-F—Ph | 2-NH₂-4-Pyr | 1-Me-2-Allyl-4-(3,4-deH-Pip) |
| 2-3069 | 4-F—Ph | 2-NH₂-4-Pyr | 1-Et-2-Allyl-4-(3,4-deH-Pip) |
| 2-3070 | 4-F—Ph | 2-NH₂-4-Pyr | 1-Pr-2-Allyl-4-(3,4-deH-Pip) |
| 2-3071 | 4-F—Ph | 2-NH₂-4-Pyr | 1-Bu-2-Allyl-4-(3,4-deH-Pip) |
| 2-3072 | 4-F—Ph | 2-NH₂-4-Pyr | 1-Phet-2-Allyl-4-(3,4-deH-Pip) |
| 2-3073 | 4-F—Ph | 2-NH₂-4-Pyr | 2-Bn-4-(3,4-deH-Pip) |
| 2-3074 | 4-F—Ph | 2-NH₂-4-Pyr | 1-Me-2-Bn-4-(3,4-deH-Pip) |

TABLE 2-continued

| Compound No. | R¹ | R² | R³ |
|---|---|---|---|
| 2-3075 | 4-F—Ph | 2-NH₂-4-Pyr | 1-Et-2-Bn-4-(3,4-deH-Pip) |
| 2-3076 | 4-F—Ph | 2-NH₂-4-Pyr | 1-Pr-2-Bn-4-(3,4-deH-Pip) |
| 2-3077 | 4-F—Ph | 2-NH₂-4-Pyr | 1-Bu-2-Bn-4-(3,4-deH-Pip) |
| 2-3078 | 4-F—Ph | 2-NH₂-4-Pyr | 1-Phet-2-Bn-4-(3,4-deH-Pip) |
| 2-3079 | 4-F—Ph | 2-NH₂-4-Pyr | 2-Phet-4-(3,4-deH-Pip) |
| 2-3080 | 4-F—Ph | 2-NH₂-4-Pyr | 1-Me-2-Phet-4-(3,4-deH-Pip) |
| 2-3081 | 4-F—Ph | 2-NH₂-4-Pyr | 1-Et-2-Phet-4-(3,4-deH-Pip) |
| 2-3082 | 4-F—Ph | 2-NH₂-4-Pyr | 1-Pr-2-Phet-4-(3,4-deH-Pip) |
| 2-3083 | 4-F—Ph | 2-NH₂-4-Pyr | 1-Bu-2-Phet-4-(3,4-deH-Pip) |
| 2-3084 | 4-F—Ph | 2-NH₂-4-Pyr | 1,2-diPhet-4-(3,4-deH-Pip) |
| 2-3085 | 4-F—Ph | 2-NH₂-4-Pyr | 2-Me-4-(4,5-deH-Pip) |
| 2-3086 | 4-F—Ph | 2-NH₂-4-Pyr | 1,2-diMe-4-(4,5-deH-Pip) |
| 2-3087 | 4-F—Ph | 2-NH₂-4-Pyr | 1-Et-2-Me-4-(4,5-deH-Pip) |
| 2-3088 | 4-F—Ph | 2-NH₂-4-Pyr | 1-Pr-2-Me-4-(4,5-deH-Pip) |
| 2-3089 | 4-F—Ph | 2-NH₂-4-Pyr | 1-Bu-2-Me-4-(4,5-deH-Pip) |
| 2-3090 | 4-F—Ph | 2-NH₂-4-Pyr | 1-Phet-2-Me-4-(4,5-deH-Pip) |
| 2-3091 | 4-F—Ph | 2-NH₂-4-Pyr | 2-Et-4-(4,5-deH-Pip) |
| 2-3092 | 4-F—Ph | 2-NH₂-4-Pyr | 1-Me-2-Et-4-(4,5-deH-Pip) |
| 2-3093 | 4-F—Ph | 2-NH₂-4-Pyr | 1,2-diEt-4-(4,5-deH-Pip) |
| 2-3094 | 4-F—Ph | 2-NH₂-4-Pyr | 1-Pr-2-Et-4-(4,5-deH-Pip) |
| 2-3095 | 4-F—Ph | 2-NH₂-4-Pyr | 1-Bu-2-Et-4-(4,5-deH-Pip) |
| 2-3096 | 4-F—Ph | 2-NH₂-4-Pyr | 1-Phet-2-Et-4-(4,5-deH-Pip) |
| 2-3097 | 4-F—Ph | 2-NH₂-4-Pyr | 2-Pr-4-(4,5-deH-Pip) |
| 2-3098 | 4-F—Ph | 2-NH₂-4-Pyr | 1-Me-2-Pr-4-(4,5-deH-Pip) |
| 2-3099 | 4-F—Ph | 2-NH₂-4-Pyr | 1-Et-2-Pr-4-(4,5-deH-Pip) |
| 2-3100 | 4-F—Ph | 2-NH₂-4-Pyr | 1,2-diPr-4-(4,5-deH-Pip) |
| 2-3101 | 4-F—Ph | 2-NH₂-4-Pyr | 1-Bu-2-Pr-4-(4,5-deH-Pip) |
| 2-3102 | 4-F—Ph | 2-NH₂-4-Pyr | 1-Phet-2-Pr-4-(4,5-deH-Pip) |
| 2-3103 | 4-F—Ph | 2-NH₂-4-Pyr | 2-Bu-4-(4,5-deH-Pip) |
| 2-3104 | 4-F—Ph | 2-NH₂-4-Pyr | 1-Me-2-Bu-4-(4,5-deH-Pip) |
| 2-3105 | 4-F—Ph | 2-NH₂-4-Pyr | 1-Et-2-Bu-4-(4,5-deH-Pip) |
| 2-3106 | 4-F—Ph | 2-NH₂-4-Pyr | 1-Pr-2-Bu-4-(4,5-deH-Pip) |
| 2-3107 | 4-F—Ph | 2-NH₂-4-Pyr | 1,2-diiBu-4-(4,5-deH-Pip) |
| 2-3108 | 4-F—Ph | 2-NH₂-4-Pyr | 1-Phet-2-Bu-4-(4,5-deH-Pip) |
| 2-3109 | 4-F—Ph | 2-NH₂-4-Pyr | 2-Allyl-4-(4,5-deH-Pip) |
| 2-3110 | 4-F—Ph | 2-NH₂-4-Pyr | 1-Me-2-Allyl-4-(4,5-deH-Pip) |
| 2-3111 | 4-F—Ph | 2-NH₂-4-Pyr | 1-Et-2-Allyl-4-(4,5-deH-Pip) |
| 2-3112 | 4-F—Ph | 2-NH₂-4-Pyr | 1-Pr-2-Allyl-4-(4,5-deH-Pip) |
| 2-3113 | 4-F—Ph | 2-NH₂-4-Pyr | 1-Bu-2-Allyl-4-(4,5-deH-Pip) |
| 2-3114 | 4-F—Ph | 2-NH₂-4-Pyr | 1-Phet-2-Allyl-4-(4,5-deH-Pip) |
| 2-3115 | 4-F—Ph | 2-NH₂-4-Pyr | 2-Bn-4-(4,5-deH-Pip) |
| 2-3116 | 4-F—Ph | 2-NH₂-4-Pyr | 1-Me-2-Bn-4-(4,5-deH-Pip) |
| 2-3117 | 4-F—Ph | 2-NH₂-4-Pyr | 1-Et-2-Bn-4-(4,5-deH-Pip) |
| 2-3118 | 4-F—Ph | 2-NH₂-4-Pyr | 1-Pr-2-Bn-4-(4,5-deH-Pip) |
| 2-3119 | 4-F—Ph | 2-NH₂-4-Pyr | 1-Bu-2-Bn-4-(4,5-deH-Pip) |
| 2-3120 | 4-F—Ph | 2-NH₂-4-Pyr | 1-Phet-2-Bn-4-(4,5-deH-Pip) |
| 2-3121 | 4-F—Ph | 2-NH₂-4-Pyr | 2-Phet-4-(4,5-deH-Pip) |
| 2-3122 | 4-F—Ph | 2-NH₂-4-Pyr | 1-Me-2-Phet-4-(4,5-deH-Pip) |
| 2-3123 | 4-F—Ph | 2-NH₂-4-Pyr | 1-Et-2-Phet-4-(4,5-deH-Pip) |
| 2-3124 | 4-F—Ph | 2-NH₂-4-Pyr | 1-Pr-2-Phet-4-(4,5-deH-Pip) |
| 2-3125 | 4-F—Ph | 2-NH₂-4-Pyr | 1-Bu-2-Phet-4-(4,5-deH-Pip) |
| 2-3126 | 4-F—Ph | 2-NH₂-4-Pyr | 1,2-diPhet-4-(4,5-deH-Pip) |
| 2-3127 | 4-F—Ph | 2-MeNH-4-Pyr | H₂—CH₂C(Me)₂CH₂ |
| 2-3128 | 4-F—Ph | 2-MeNH-4-Pyr | MeNH—CH₂C(Me)₂CH₂ |
| 2-3129 | 4-F—Ph | 2-MeNH-4-Pyr | EtNH—CH₂C(Me)₂CH₂ |
| 2-3130 | 4-F—Ph | 2-MeNH-4-Pyr | Me₂N—CH₂C(Me)₂CH₂ |
| 2-3131 | 4-F—Ph | 2-MeNH-4-Pyr | 3-(3,4-deH-Pip) |
| 2-3132 | 4-F—Ph | 2-MeNH-4-Pyr | 1-Me-3-(3,4-deH-Pip) |
| 2-3133 | 4-F—Ph | 2-MeNH-4-Pyr | 1-Et-4-(3,4-deH-Pip) |
| 2-3134 | 4-F—Ph | 2-MeNH-4-Pyr | 1-Pr-4-(3,4-deH-Pip) |
| 2-3135 | 4-F—Ph | 2-MeNH-4-Pyr | 1-Pr-4-Pip |
| 2-3136 | 4-F—Ph | 2-MeNH-4-Pyr | 1-iPr-4-(3,4-deH-Pip) |
| 2-3137 | 4-F—Ph | 2-MeNH-4-Pyr | 1-iPr-4-Pip |
| 2-3138 | 4-F—Ph | 2-MeNH-4-Pyr | 1-Bu-4-(3,4-deH-Pip) |
| 2-3139 | 4-F—Ph | 2-MeNH-4-Pyr | 1-tBu-4-(3,4-deH-Pip) |
| 2-3140 | 4-F—Ph | 2-MeNH-4-Pyr | 1-Pn-4-(3,4-deH-Pip) |
| 2-3141 | 4-F—Ph | 2-MeNH-4-Pyr | 1-Hx-4-(3,4-deH-Pip) |
| 2-3142 | 4-F—Ph | 2-MeNH-4-Pyr | 1-Hp-4-(3,4-deH-Pip) |
| 2-3143 | 4-F—Ph | 2-MeNH-4-Pyr | 1-Oc-4-(3,4-deH-Pip) |
| 2-3144 | 4-F—Ph | 2-MeNH-4-Pyr | 1-Nn-4-(3,4-deH-Pip) |
| 2-3145 | 4-F—Ph | 2-MeNH-4-Pyr | 1-cPr-4-(3,4-deH-Pip) |
| 2-3146 | 4-F—Ph | 2-MeNH-4-Pyr | 1-cPn-4-(3,4-deH-Pip) |
| 2-3147 | 4-F—Ph | 2-MeNH-4-Pyr | 1-cHx-4-(3,4-deH-Pip) |
| 2-3148 | 4-F—Ph | 2-MeNH-4-Pyr | 1-Bn-4-(3,4-deH-Pip) |
| 2-3149 | 4-F—Ph | 2-MeNH-4-Pyr | 1-Phet-4-(3,4-deH-Pip) |
| 2-3150 | 4-F—Ph | 2-MeNH-4-Pyr | 1-(3-Ph—Pr)-4-(3,4-deH-Pip) |
| 2-3151 | 4-F—Ph | 2-MeNH-4-Pyr | 1-(4-Ph—Bu)-4-(3,4-deH-Pip) |
| 2-3152 | 4-F—Ph | 2-MeNH-4-Pyr | 1-Allyl-4-(3,4-deH-Pip) |
| 2-3153 | 4-F—Ph | 2-MeNH-4-Pyr | 1-Propargyl-4-(3,4-deH-Pip) |
| 2-3154 | 4-F—Ph | 2-MeNH-4-Pyr | 2,2,6,6-tetraMe-4-(3,4-deH-Pip) |
| 2-3155 | 4-F—Ph | 2-MeNH-4-Pyr | 1,2,2,6,6-pentaMe-4-(3,4-deH-Pip) |
| 2-3156 | 4-F—Ph | 2-MeNH-4-Pyr | 1,2,2,6,6-pentaMe-4-Pip |
| 2-3157 | 4-F—Ph | 2-MeNH-4-Pyr | 7-(1,2,3,5,6,8a-hexaH-Ind) |
| 2-3158 | 4-F—Ph | 2-MeNH-4-Pyr | 7-(1,2,3,5,8,8a-hexaH-Ind) |
| 2-3159 | 4-F—Ph | 2-MeNH-4-Pyr | 7-octaH-Ind |
| 2-3160 | 4-F—Ph | 2-MeNH-4-Pyr | 8-(1,3,4,6,7,9a-hexaH-2H-Qui) |
| 2-3161 | 4-F—Ph | 2-MeNH-4-Pyr | 8-(1,3,4,6,9, 9a-hexaH-2H-Qui) |
| 2-3162 | 4-F—Ph | 2-MeNH-4-Pyr | 8-octaH-Qui |
| 2-3163 | 4-F—Ph | 2-MeNH-4-Pyr | 2,2-diMe-4-(3,4-deH-Pip) |
| 2-3164 | 4-F—Ph | 2-MeNH-4-Pyr | 1,2,2-triMe-4-(3,4-deH-Pip) |
| 2-3165 | 4-F—Ph | 2-MeNH-4-Pyr | 2,2-diMe-4-(4,5-deH-Pip) |
| 2-3166 | 4-F—Ph | 2-MeNH-4-Pyr | 1,2,2-triMe-4-(4,5-deH-Pip) |
| 2-3167 | 4-F—Ph | 2-MeNH-4-Pyr | 2,6-diMe-4-(3,4-deH-Pip) |
| 2-3168 | 4-F—Ph | 2-MeNH-4-Pyr | 1,2,6-triMe-4-(3,4-deH-Pip) |
| 2-3169 | 4-F—Ph | 2-MeNH-4-Pyr | 2-Me-4-(3,4-deH-Pip) |
| 2-3170 | 4-F—Ph | 2-MeNH-4-Pyr | 1,2-diMe-4-(3,4-deH-Pip) |
| 2-3171 | 4-F—Ph | 2-MeNH-4-Pyr | 1-Et-2-Me-4-(3,4-deH-Pip) |
| 2-3172 | 4-F—Ph | 2-MeNH-4-Pyr | 1-Pr-2-Me-4-(3,4-deH-Pip) |
| 2-3173 | 4-F—Ph | 2-MeNH-4-Pyr | 1-Bu-2-Me-4-(3,4-deH-Pip) |
| 2-3174 | 4-F—Ph | 2-MeNH-4-Pyr | 1-Phet-2-Me-4-(3,4-deH-Pip) |
| 2-3175 | 4-F—Ph | 2-MeNH-4-Pyr | 2-Et-4-(3,4-deH-Pip) |
| 2-3176 | 4-F—Ph | 2-MeNH-4-Pyr | 1-Me-2-Et-4-(3,4-deH-Pip) |
| 2-3177 | 4-F—Ph | 2-MeNH-4-Pyr | 1,2-diFt-4-(3,4-deH-Pip) |
| 2-3178 | 4-F—Ph | 2-MeNH-4-Pyr | 1-Pr-2-Et-4-(3,4-deH-Pip) |
| 2-3179 | 4-F—Ph | 2-MeNH-4-Pyr | 1-Bu-2-Et-4-(3,4-deH-Pip) |
| 2-3180 | 4-F—Ph | 2-MeNH-4-Pyr | 1-Phet-2-Et-4-(3,4-deH-Pip) |
| 2-3181 | 4-F—Ph | 2-MeNH-4-Pyr | 2-Pr-4-(3,4-deH-Pip) |
| 2-3182 | 4-F—Ph | 2-MeNH-4-Pyr | 1-Me-2-Pr-4-(3,4-deH-Pip) |
| 2-3183 | 4-F—Ph | 2-MeNH-4-Pyr | 1-Et-2-Pr-4-(3,4-deH-Pip) |
| 2-3184 | 4-F—Ph | 2-MeNH-4-Pyr | 1,2-diPr-4-(3,4-deH-Pip) |
| 2-3185 | 4-F—Ph | 2-MeNH-4-Pyr | 1-Bu-2-Pr-4-(3,4-deH-Pip) |
| 2-3186 | 4-F—Ph | 2-MeNH-4-Pyr | 1-Phet-2-Pr-4-(3,4-deH-Pip) |
| 2-3187 | 4-F—Ph | 2-MeNH-4-Pyr | 2-Bu-4-(3,4-deH-Pip) |
| 2-3188 | 4-F—Ph | 2-MeNH-4-Pyr | 1-Me-2-Bu-4-(3,4-deH-Pip) |
| 2-3189 | 4-F—Ph | 2-MeNH-4-Pyr | 1-Et-2-Bu-4-(3,4-deH-Pip) |

TABLE 2-continued

| Compound No. | R¹ | R² | R³ |
|---|---|---|---|
| 2-3190 | 4-F—Ph | 2-MeNH-4-Pyr | 1-Pr-2-Bu-4-(3,4-deH-Pip) |
| 2-3191 | 4-F—Ph | 2-MeNH-4-Pyr | 1,2-diBu-4-(3,4-deH-Pip) |
| 2-3192 | 4-F—Ph | 2-MeNH-4-Pyr | 1-Phet-2-Bu-4-(3,4-deH-Pip) |
| 2-3193 | 4-F—Ph | 2-MeNH-4-Pyr | 2-AllyL-4-(3,4-deH-Pip) |
| 2-3194 | 4-F—Ph | 2-MeNH-4-Pyr | 1-Me-2-Allyl-4-(3,4-deH-Pip) |
| 2-3195 | 4-F—Ph | 2-MeNH-4-Pyr | 1-Et-2-Allyl-4-(3,4-deH-Pip) |
| 2-3196 | 4-F—Ph | 2-MeNH-4-Pyr | 1-Pr-2-Allyl-4-(3,4-deH-Pip) |
| 2-3197 | 4-F—Ph | 2-MeNH-4-Pyr | 1-Bu-2-Allyl-4-(3,4-deH-Pip) |
| 2-3198 | 4-F—Ph | 2-MeNH-4-Pyr | 1-Phet-2-Allyl-4-(3,4-deH-Pip) |
| 2-3199 | 4-F—Ph | 2-MeNH-4-Pyr | 2-Bn-4-(3,4-deH-Pip) |
| 2-3200 | 4-F—Ph | 2-MeNH-4-Pyr | 1-Me-2-Bn-4-(3,4-deH-Pip) |
| 2-3201 | 4-F—Ph | 2-MeNH-4-Pyr | 1-Et-2-Bn-4-(3,4-deH-Pip) |
| 2-3202 | 4-F—Ph | 2-MeNH-4-Pyr | 1-Pr-2-Bn-4-(3,4-deH-Pip) |
| 2-3203 | 4-F—Ph | 2-MeNH-4-Pyr | 1-Bu-2-Bn-4-(3,4-deH-Pip) |
| 2-3204 | 4-F—Ph | 2-MeNH-4-Pyr | 1-Phet-2-Bn-4-(3,4-deH-Pip) |
| 2-3205 | 4-F—Ph | 2-MeNH-4-Pyr | 2-Phet-4-(3,4-deH-Pip) |
| 2-3206 | 4-F—Ph | 2-MeNH-4-Pyr | 1-Me-2-Phet-4-(3,4-deH-Pip) |
| 2-3207 | 4-F—Ph | 2-MeNH-4-Pyr | 1-Et-2-Phet-4-(3,4-deH-Pip) |
| 2-3208 | 4-F—Ph | 2-MeNH-4-Pyr | 1-Pr-2-Phet-4-(3,4-deH-Pip) |
| 2-3209 | 4-F—Ph | 2-MeNH-4-Pyr | 1-Bu-2-Phet-4-(3,4-deH-Pip) |
| 2-3210 | 4-F—Ph | 2-MeNH-4-Pyr | 1,2-diPhet-4-(3,4-deH-Pip) |
| 2-3211 | 4-F—Ph | 2-MeNH-4-Pyr | 2-Me-4-(4,5-deH-Pip) |
| 2-3212 | 4-F—Ph | 2-MeNH-4-Pyr | 1,2-diMe-4-(4,5-deH-Pip) |
| 2-3213 | 4-F—Ph | 2-MeNH-4-Pyr | 1-Et-2-Me-4-(4,5-deH-Pip) |
| 2-3214 | 4-F—Ph | 2-MeNH13 4-Pyr | 1-Pr-2-Me-4-(4,5-deH-Pip) |
| 2-3215 | 4-F—Ph | 2-MeNH-4-Pyr | 1-Bu-2-Me-4-(4,5-deH-Pip) |
| 2-3216 | 4-F—Ph | 2-MeNH-4-Pyr | 1-Phet-2-Me-4-(4,5-deH-Pip) |
| 2-3217 | 4-F—Ph | 2-MeNH-4-Pyr | 2-Et-4-(4,5-deH-Pip) |
| 2-3218 | 4-F—Ph | 2-MeNH-4-Pyr | 1-Me-2-Et-4-(4,5-deH-Pip) |
| 2-3219 | 4-F—Ph | 2-MeNH-4-Pyr | 1,2-diEt-4-(4,5-deH-Pip) |
| 2-3220 | 4-F—Ph | 2-MeNH-4-Pyr | 1-Pr-2-Et-4-(4,5-deH-Pip) |
| 2-3221 | 4-F—Ph | 2-MeNH-4-Pyr | 1-Bu-2-Et-4-(4,5-deH-Pip) |
| 2-3222 | 4-F—Ph | 2-MeNH-4-Pyr | 1-Phet-2-Et-4-(4,5-deH-Pip) |
| 2-3223 | 4-F—Ph | 2-MeNH-4-Pyr | 2-Pr-4-(4,5-deH-Pip) |
| 2-3224 | 4-F—Ph | 2-MeNH-4-Pyr | 1-Me-2-Pr-4-(4,5-deH-Pip) |
| 2-3225 | 4-F—Ph | 2-MeNH-4-Pyr | 1-Et-2-Pr-4-(4,5-deH-Pip) |
| 2-3226 | 4-F—Ph | 2-MeNH-4-Pyr | 1,2-diPr-4-(4,5-deH-Pip) |
| 2-3227 | 4-F—Ph | 2-MeNH-4-Pyr | 1-Bu-2-Pr-4-(4,5-deH-Pip) |
| 2-3228 | 4-F—Ph | 2-MeNH-4-Pyr | 1-Phet-2-Pr-4-(4,5-deH-Pip) |
| 2-3229 | 4-F—Ph | 2-MeNH-4-Pyr | 2-Bu-4-(4,5-deH-Pip) |
| 2-3230 | 4-F—Ph | 2-MeNH-4-Pyr | 1-Me-2-Bu-4-(4,5-deH-Pip) |
| 2-3231 | 4-F—Ph | 2-MeNH-4-Pyr | 1-Et-2-Bu-4-(4,5-deH-Pip) |
| 2-3232 | 4-F—Ph | 2-MeNH-4-Pyr | 1-Pr-2-Bu-4-(4,5-deH-Pip) |
| 2-3233 | 4-F—Ph | 2-MeNH-4-Pyr | 1,2-diBu4-(4,5-deH-Pip) |
| 2-3234 | 4-F—Ph | 2-MeNH-4-Pyr | 1-Phet-2-Bu-4-(4,5-deH-Pip) |
| 2-3235 | 4-F—Ph | 2-MeNH-4-Pyr | 2-Allyl-4-(4,5-deH-Pip) |
| 2-3236 | 4-F—Ph | 2-MeNH-4-Pyr | 1-Me-2-Allyl-4-(4,5-deH-Pip) |
| 2-3237 | 4-F—Ph | 2-MeNH-4-Pyr | 1-Et-2-Allyl-4-(4,5-deH-Pip) |
| 2-3238 | 4-F—Ph | 2-MeNH-4-Pyr | 1-Pr-2-Allyl-4-(4,5-deH-Pip) |
| 2-3239 | 4-F—Ph | 2-MeNH-4-Pyr | 1-Bu-2-Allyl-4-(4,5-deH-Pip) |
| 2-3240 | 4-F—Ph | 2-MeNH-4-Pyr | 1-Phet-2-Allyl-4-(4,5-deH-Pip) |
| 2-3241 | 4-F—Ph | 2-MeNH-4-Pyr | 2-Bn-4-(4,5-deH-Pip) |
| 2-3242 | 4-F—Ph | 2-MeNH-4-Pyr | 1-Me-2-Bn-4-(4,5-deH-Pip) |
| 2-3243 | 4-F—Ph | 2-MeNH-4-Pyr | 1-Et-2-Bn-4-(4,5-deH-Pip) |
| 2-3244 | 4-F—Ph | 2-MeNH-4-Pyr | 1-Pr-2-Bn-4-(4,5-deH-Pip) |
| 2-3245 | 4-F—Ph | 2-MeNH-4-Pyr | 1-Bu-2-Bn-4-(4,5-deH-Pip) |
| 2-3246 | 4-F—Ph | 2-MeNH-4-Pyr | 1-Phet-2-Bn-4-(4,5-deH-Pip) |
| 2-3247 | 4-F—Ph | 2-MeNH-4-Pyr | 2-Phet-4-(4,5-deH-Pip) |
| 2-3248 | 4-F—Ph | 2-MeNH-4-Pyr | 1-Me-2-Phet-4-(4,5-deH-Pip) |
| 2-3249 | 4-F—Ph | 2-MeNH-4-Pyr | 1-Et-2-Phet-4-(4,5-deH-Pip) |
| 2-3250 | 4-F—Ph | 2-MeNH-4-Pyr | 1-Pr-2-Phet-4-(4,5-deH-Pip) |
| 2-3251 | 4-F—Ph | 2-MeNH-4-Pyr | 1-Bu-2-Phet-4-(4,5-deH-Pip) |
| 2-3252 | 4-F—Ph | 2-MeNH-4-Pyr | 1,2-diphet-4-(4,5-deH-Pip) |
| 2-3253 | Ph | 4-Pyr | 7-(1,2,3,5,6,8a-hexaH-Ind) |
| 2-3254 | Ph | 4-Pyr | 7-(1,2,3,5,8,8a-hexaH-Ind) |
| 2-3255 | 3-F—Ph | 4-Pyr | 7-(1,2,3,5,6,8a-hexaH-Ind) |
| 2-3256 | 3-F—Ph | 4-Pyr | 7-(1,2,3,5,8,8a-hexaH-Ind) |
| 2-3257 | 3-Cl—Ph | 4-Pyr | 7-(1,2,3,5,6,8a-hexaH-Ind) |
| 2-3258 | 3-Cl—Ph | 4-Pyr | 7-(1,2,3,5,8,8a-hexaH-Ind) |
| 2-3259 | 3,4-diF—Ph | 4-Pyr | 7-(1,2,3,5,6,8a-hexaH-Ind) |
| 2-3260 | 3,4-diF—Ph | 4-Pyr | 7-(1,2,3,5,8,8a-hexaH-Ind) |
| 2-3261 | 3-CF₃—Ph | 4-Pyr | 7-(1,2,3,5,6,8a-hexaH-Ind) |
| 2-3262 | 3-CF₃—Ph | 4-Pyr | 7-(1,2,3,5,8,8a-hexaH-Ind) |
| 2-3263 | 4-F—Ph | 4-Pyr | 2-Pyrd-CH=CH— |
| 2-3264 | 4-F—Ph | 4-Pyr | 1-Me-2-Pyrd-CH=CH— |
| 2-3265 | 4-F—Ph | 4-Pyr | 1-Et-2-Pyrd-CH=CH— |
| 2-3266 | 4-F—Ph | 4-Pyr | 1-Pr-2-Pyrd-CH=CH— |
| 2-3267 | 4-F—Ph | 4-Pyr | 2-Pip-CH=CH— |
| 2-3268 | 4-F—Ph | 4-Pyr | 1-Me-2-Pip-CH=CH— |
| 2-3269 | 4-F—Ph | 4-Pyr | 1-Et-2-Pip-CH=CH— |
| 2-3270 | 4-F—Ph | 4-Pyr | 1-Pr-2-Pip-CH=CH— |
| 2-3271 | Ph | 4-Pyr | 2-Pyrd-CH=CH— |
| 2-3272 | Ph | 4-Pyr | 1-Me-2-Pyrd-CH=CH— |
| 2-3273 | Ph | 4-Pyr | 1-Et-2-Pyrd-CH=CH— |
| 2-3274 | Ph | 4-Pyr | 1-Pr-2-Pyrd-CH=CH— |
| 2-3275 | Ph | 4-Pyr | 2-Pip-CH=CH— |
| 2-3276 | Ph | 4-Pyr | 1-Me-2-Pip-CH=CH— |
| 2-3277 | Ph | 4-Pyr | 1-Et-2-Pip-CH=CH— |
| 2-3278 | Ph | 4-Pyr | 1-Pr-2-Pip-CH=CH— |
| 2-3279 | 3-F—Ph | 4-Pyr | 2-Pyrd-CH=CH— |
| 2-3280 | 3-F—Ph | 4-Pyr | 1-Me-2-Pyrd-CH=CH— |
| 2-3281 | 3-F—Ph | 4-Pyr | 1-Et-2-Pyrd-CH=CH— |
| 2-3282 | 3-F—Ph | 4-Pyr | 1-Pr-2-Pyrd-CH=CH— |
| 2-3283 | 3-F—Ph | 4-Pyr | 2-Pip-CH=CH— |
| 2-3284 | 3-F—Ph | 4-Pyr | 1-Me-2-Pip-CH=CH— |
| 2-3285 | 3-F—Ph | 4-Pyr | 1-Et-2-Pip-CH=CH— |
| 2-3286 | 3-F—Ph | 4-Pyr | 1-Pr-2-Pip-CH=CH— |
| 2-3287 | 3-Cl—Ph | 4-Pyr | 2-Pyrd-CH=CH— |
| 2-3288 | 3-Cl—Ph | 4-Pyr | 1-Me-2-Pyrd-CH=CH— |
| 2-3289 | 3-Cl—Ph | 4-Pyr | 1-Et-2-Pyrd-CH=CH— |
| 2-3290 | 3-Cl—Ph | 4-Pyr | 1-Pr-2-Pyrd-CH=CH— |
| 2-3291 | 3-Cl—Ph | 4-Pyr | 2-Pip-CH=CH— |
| 2-3292 | 3-Cl—Ph | 4-Pyr | 1-Me-2-Pip-CH=CH— |
| 2-3293 | 3-Cl—Ph | 4-Pyr | 1-Et-2-Pip-CH=CH— |
| 2-3294 | 3-Cl—Ph | 4-Pyr | 1-Pr-2-Pip-CH=CH— |
| 2-3295 | 3,4-diF—Ph | 4-Pyr | 2-Pyrd-CH=CH— |
| 2-3296 | 3,4-diF—Ph | 4-Pyr | 1-Me-2-Pyrd-CH=CH— |
| 2-3297 | 3,4-diF—Ph | 4-Pyr | 1-Et-2-Pyrd-CH=CH— |
| 2-3298 | 3,4-diF—Ph | 4-Pyr | 1-Pr-2-Pyrd-CH=CH— |
| 2-3299 | 3,4-diF—Ph | 4-Pyr | 2-Pip-CH=CH— |
| 2-3300 | 3,4-diF—Ph | 4-Pyr | 1-Me-2-Pip-CH=CH— |
| 2-3301 | 3,4-diF—Ph | 4-Pyr | 1-Et-2-Pip-CH=CH— |
| 2-3302 | 3,4-diF—Ph | 4-Pyr | 1-Pr-2-Pip-CH=CH— |
| 2-3303 | 3-CF₃—Ph | 4-Pyr | 2-Pyrd-CH=CH— |
| 2-3304 | 3-CF₃—Ph | 4-Pyr | 1-Me-2-Pyrd-CH=CH— |
| 2-3305 | 3-CF₃—Ph | 4-Pyr | 1-Et-2-Pyrd-CH=CH— |
| 2-3306 | 3-CF₃—Ph | 4-Pyr | 1-Pr-2-Pyrd-CH=CH— |
| 2-3307 | 3-CF₃—Ph | 4-Pyr | 2-Pip-CH=CH— |
| 2-3308 | 3-CF₃—Ph | 4-Pyr | 1-Me-2-Pip-CH=CH— |
| 2-3309 | 3-CF₃—Ph | 4-Pyr | 1-Et-2-Pip-CH=CH— |
| 2-3310 | 3-CF₃—Ph | 4-Pyr | 1-Pr-2-Pip-CH=CH— |

TABLE 2-continued

| Compound No. | R¹ | R² | R³ |
|---|---|---|---|
| 2-3311 | 4-F—Ph | 4-Pyr | 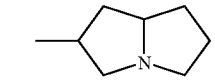 |
| 2-3312 | 4-F—Ph | 4-Pyr | 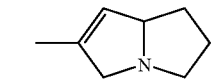 |
| 2-3313 | 4-F—Ph | 4-Pyr | 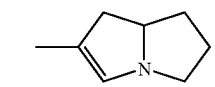 |
| 2-3314 | 4-F—Ph | 4-Pyr | 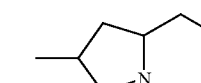 |
| 2-3315 | 4-F—Ph | 4-Pyr | 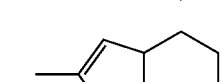 |
| 2-3316 | 4-F—Ph | 4-Pyr |  |
| 2-3317 | 4-F—Ph | 4-Pyr | 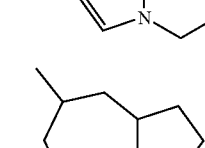 |
| 2-3318 | 4-F—Ph | 4-Pyr | 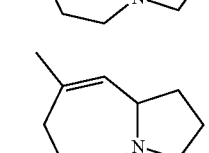 |
| 2-3319 | 4-F—Ph | 4-Pyr | 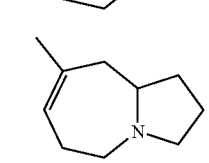 |
| 2-3320 | 4-F—Ph | 4-Pyr | 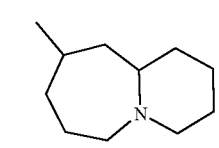 |
| 2-3321 | 4-F—Ph | 4-Pyr | 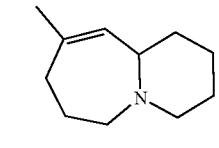 |
| 2-3322 | 4-F—Ph | 4-Pyr | 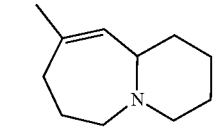 |

Of the above compounds in Tables 1 and 2, the following are preferred, that is to say Compounds Nos.: 1-1 to 1-32, 1-35, 1-38, 1-40, 1-42, 1-43, 1-45 to 1-52, 1-65 to 1-67, 1-71 to 1-76, 1-88 to 1-90, 1-94 to 1-126, 1-129, 1-132, 1-134 to 1-137, 1-139 to 1-146, 1-159 to 1-161, 1-165 to 1-170, 1-182 to 1-184, 1-188 to 1-219, 1-222, 1-225, 1-227, 1-229, 1-230, 1-232 to 1-239, 1-252 to 1-254, 1-258 to 1-263, 1-275 to 1-277, 1-281 to 1-312, 1-315, 1-318, 1-320, 1-322, 1-323, 1-325 to 1-332, 1-345 to 1-347, 1-351 to 1-356, 1-368 to 1-370, 1-374 to 1-405, 1-408, 1-411, 1-413, 1-415, 1-416, 1-418 to 1-425, 1-438 to 1-440, 1-444 to 1-449, 1-461 to 1-463, 1-467 to 1-498, 1-501, 1-504, 1-506, 1-508, 1-509, 1-511 to 1-518, 1-531 to 1-533, 1-537 to 1-542, 1-554 to 1-556, 1-560 to 1-591, 1-594, 1-597, 1-599, 1-601, 1-602, 1-604 to 1-611, 1-624 to 1-626, 1-630 to 1-635, 1-647 to 1-649, 1-653 to 1-684, 1-687, 1-690, 1-692, 1-694, 1-695, 1-697 to 1-704, 1-717 to 1-719, 1-723 to 1-728, 1-740 to 1-742, 1-746 to 1-777, 1-780, 1-783, 1-785, 1-787, 1-788, 1-790 to 1-797, 1-810 to 1-812, 1-816 to 1-821, 1-833 to 1-835, 1-839 to 1-870, 1-873, 1-876, 1-878, 1-880, 1-881, 1-883 to 1-890, 1-903 to 1-905, 1-909 to 1-914, 1-926 to 1-928, 1-932 to 1-963, 1-966, 1-969, 1-971, 1-973, 1-974, 1-976 to 1-983, 1-996 to 1-998, 1-1002 to 1-1007, 1-1019 to 1-1021, 1-1025 to 1-1056, 1-1059, 1-1062, 1-1064, 1-1066, 1-1067, 1-1069 to 1-1076, 1-1089 to 1-1091, 1-1095 to 1-1100, 1-1112 to 1-1114, 1-1118 to 1-1149, 1-1152, 1-1155, 1-1157, 1-1159, 1-1160, 1-1162 to 1-1169, 1-1182 to 1-1184, 1-1188 to 1-1193, 1-1205 to 1-1207, 1-1211 to 1-1242, 1-1245, 1-1248, 1-1250, 1-1252, 1-1253, 1-1255 to 1-1262, 1-1275 to 1-1277, 1-1281 to 1-1286, 1-1298 to 1-1300, 1-1304 to 1-1335, 1-1338, 1-1341, 1-1343, 1-1345, 1-1346, 1-1348 to 1-1355, 1-1368 to 1-1370, 1-1374 to 1-1379, 1-1391 to 1-1393, 1-1397 to 1-1405, 1-1407 to 1-1415, 1-1418, 1-1419, 1-1422 to 1-1425, 1-1427, 1-1428, 1-1432 to 1-1440, 1-1442 to 1-1450, 1-1453, 1-1454, 1-1457 to 1-1460, 1-1462, 1-1463, 1-1467 to 1-1475, 1-1477 to 1-1485, 1-1488, 1-1489, 1-1492 to 1-1495, 1-1497, 1-1498, 1-1502 to 1-1510, 1-1512 to 1-1520, 1-1523, 1-1524, 1-1527 to 1-1530, 1-1532, 1-1533, 1-1537 to 1-1545, 1-1547 to 1-1555, 1-1558, 1-1559, 1-1562 to 1-1565, 1-1567, 1-1568, 1-1572 to 1-1580, 1-1582 to 1-1590, 1-1593, 1-1594, 1-1597 to 1-1600, 1-1602, 1-1603, 1-1607 to 1-1615, 1-1617 to 1-1625, 1-1628, 1-1629, 1-1632 to 1-1635, 1-1637, 1-1638, 1-1642 to 1-1650, 1-1652 to 1-1660, 1-1663, 1-1664, 1-1667 to 1-1670, 1-1672, 1-1673, 1-1677 to 1-1685, 1-1687 to 1-1695, 1-1698, 1-1699, 1-1702 to 1-1705, 1-1707, 1-1708, 1-1712 to 1-1720, 1-1722 to 1-1730, 1-1733, 1-1734, 1-1737 to 1-1740, 1-1742, 1-1743, 1-1747 to 1-1755, 1-1757 to 1-1765, 1-1768, 1-1769, 1-1772 to 1-1775, 1-1777, 1-1778, 1-1782 to 1-1790, 1-1792 to 1-1800, 1-1803, 1-1804, 1-1807 to 1-1810, 1-1812, 1-1813, 1-1817 to 1-1825, 1-1827 to 1-1835, 1-1838, 1-1839, 1-1842 to 1-1845, 1-1847, 1-1848, 1-1852 to 1-1860, 1-1862 to 1-1870, 1-1873, 1-1874, 1-1877 to 1-1880, 1-1882, 1-1883, 1-1887 to 1-1895, 1-1897 to 1-1905, 1-1908, 1-1909, 1-1912 to 1-1915, 1-1917, 1-1918, 1-1922 to 1-1930, 1-1932 to 1-1940, 1-1943, 1-1944, 1-1947 to 1-1950, 1-1952, 1-1953, 1-1957 to 1-1965, 1-1967 to 1-1975, 1-1978, 1-1979, 1-1982 to 1-1985, 1-1987, 1-1988, 1-1992 to 1-2000, 1-2002 to 1-2010, 1-2013, 1-2014, 1-2017 to 1-2020, 1-2022, 1-2023, 1-2027 to 1-2035, 1-2037 to 1-2045, 1-2048, 1-2049, 1-2052 to 1-2055, 1-2057, 1-2058, 1-2062 to 1-2070, 1-2072 to 1-2080, 1-2083, 1-2084, 1-2087 to 1-2090, 1-2092, 1-2093, 1-2097 to 1-2105, 1-2107 to 1-2115, 1-2118, 1-2119, 1-2122 to 1-2125, 1-2127, 1-2128, 1-2132 to 1-2140, 1-2142 to 1-2150, 1-2153, 1-2154, 1-2157 to 1-2160, 1-2162, 1-2163, 1-2167 to 1-2175, 1-2177 to 1-2185, 1-2188, 1-2189, 1-2192 to 1-2195, 1-2197, 1-2198, 1-2202 to 1-2210, 1-2212 to 1-2220, 1-2223, 1-2224, 1-2227 to 1-2230, 1-2232, 1-2233, 1-2237 to 1-2245, 1-2247 to 1-2255, 1-2258, 1-2259, 1-2262 to 1-2265, 1-2267, 1-2268, 1-2272 to 1-2280, 1-2282 to 1-2290, 1-2293, 1-2294, 1-2297 to 1-2300, 1-2302, 1-2303, 1-2307 to 1-2315, 1-2317 to 1-2325, 1-2328, 1-2329, 1-2332 to 1-2335, 1-2337, 1-2338, 1-2342 to 1-2350, 1-2352 to 1-2360, 1-2363, 1-2364, 1-2367 to 1-2370, 1-2372, 1-2373, 1-2377 to 1-2385, 1-2387 to 1-2395, 1-2398, 1-2399, 1-2402 to 1-2405, 1-2407, 1-2408, 1-2412 to 1-2420, 1-2422 to 1-2430, 1-2433, 1-2434, 1-2437 to 1-2440, 1-2442, 1-2443, 1-2447 to 1-2455, 1-2457 to 1-2465, 1-2468, 1-2469, 1-2472 to 1-2475, 1-2477, 1-2478, 1-2482 to 1-2490, 1-2492 to 1-2500, 1-2503, 1-2504, 1-2507 to 1-2510, 1-2512, 1-2513, 1-2517 to 1-2529, 1-2539 to 1-2594, 1-2623 to 1-3322, 2-1 to 2-32, 2-35, 2-38, 2-40, 2-42, 2-43, 2-45 to 2-52, 2-65 to 2-67, 2-71 to 2-76, 2-88 to 2-90, 2-94 to 2-126, 2-129, 2-132, 2-134 to 2-137, 2-139 to 2-146, 2-159 to 2-161, 2-165 to 2-170, 2-182 to 2-184, 2-188 to 2-219, 2-222, 2-225, 2-227, 2-229, 2-230, 2-232 to 2-239, 2-252 to 2-254, 2-258 to 2-263, 2-275 to 2-277, 2-281 to 2-312, 2-315, 2-318, 2-320, 2-322, 2-323, 2-325 to 2-332, 2-345 to 2-347, 2-351 to 2-356, 2-368 to 2-370, 2-374 to 2-405, 2-408, 2-411, 2-413, 2-415, 2416, 2-418 to 2-425, 2-438 to 2-440, 2-444 to 2-449, 2-461 to 2-463, 2-467 to 2-498, 2-501, 2-504, 2-506, 2-508, 2-509, 2-511 to 2-518, 2-531 to 2-533, 2-537 to 2-542, 2-554 to 2-556, 2-560 to 2-591, 2-594, 2-597, 2-599, 2-601, 2-602, 2-604 to 2-611, 2-624 to 2-626, 2-630 to 2-635, 2-647 to 2-649, 2-653 to 2-684, 2-687, 2-690, 2-692, 2-694, 2-695, 2-697 to 2-704, 2-717 to 2-719, 2-723 to 2-728, 2-740 to 2-742, 2-746 to 2-777, 2-780, 2-783, 2-785, 2-787, 2-788, 2-790 to 2-797, 2-810 to 2-812, 2-816 to 2-821, 2-833 to 2-835, 2-839 to 2-870, 2-873, 2-876, 2-878, 2-880, 2-881, 2-883 to 2-890, 2-903 to 2-905, 2-909 to 2-914, 2-926 to 2-928, 2-932 to 2-963, 2-966, 2-969, 2-971, 2-973, 2-974, 2-976 to 2-983, 2-996 to 2-998, 2-1002 to 2-1007, 2-1019 to 2-1021, 2-1025 to 2-1056, 2-1059, 2-1062, 2-1064, 2-1066, 2-1067, 2-1069 to 2-1076, 2-1089 to 2-1091, 2-1095 to 2-1100, 2-1112 to 2-1114, 2-1118 to 2-1149, 2-1152, 2-1155, 2-1157, 2-1159, 2-1160, 2-1162 to 2-1169, 2-1182 to 2-1184, 2-1188 to 2-1193, 2-1205 to 2-1207, 2-1211 to 2-1242, 2-1245, 2-1248, 2-1250, 2-1252, 2-1253, 2-1255 to 2-1262, 2-1275 to 2-1277, 2-1281 to 2-1286, 2-1298 to 2-1300, 2-1304 to 2-1335, 2-1338, 2-1341, 2-1343, 2-1345, 2-1346, 2-1348 to 2-1355, 2-1368 to 2-1370, 2-1374 to 2-1379, 2-1391 to 2-1393, 2-1397 to 2-1405, 2-1407 to 2-1415, 2-1418, 2-1419, 2-1422 to 2-1425, 2-1427, 2-1428, 2-1432 to 2-1440, 2-1442 to 2-1450, 2-1453, 2-1454, 2-1457 to 2-1460, 2-1462, 2-1463, 2-1467 to 2-1475, 2-1477 to 2-1485, 2-1488, 2-1489, 2-1492 to 2-1495, 2-1497, 2-1498, 2-1502 to 2-1510, 2-1512 to 2-1520, 2-1523, 2-1524, 2-1527 to 2-1530, 2-1532, 2-1533, 2-1537 to 2-1545, 2-1547 to 2-1555, 2-1558, 2-1559, 2-1562 to 2-1565, 2-1567, 2-1568, 2-1572 to 2-1580, 2-1582 to 2-1590, 2-1593, 2-1594, 2-1597 to 2-1600, 2-1602, 2-1603, 2-1607 to 2-1615, 2-1617 to 2-1625, 2-1628, 2-1629, 2-1632 to 2-1635, 2-1637, 2-1638, 2-1642 to 2-1650, 2-1652 to 2-1660, 2-1663, 2-1664, 2-1667 to 2-1670, 2-1672, 2-1673, 2-1677 to 2-1685, 2-1687 to 2-1695, 2-1698, 2-1699, 2-1702 to 2-1705, 2-1707, 2-1708, 2-1712 to 2-1720, 2-1722 to 2-1730, 2-1733, 2-1734, 2-1737 to 2-1740, 2-1742, 2-1743, 2-1747 to 2-1755, 2-1757 to 2-1765, 2-1768, 2-1769, 2-1772 to 2-1775, 2-1777, 2-1778, 2-1782 to 2-1790, 2-1792 to 2-1800, 2-1803, 2-1804, 2-1807 to 2-1810, 2-1812, 2-1813, 2-1817 to 2-1825, 2-1827 to 2-1835, 2-1838, 2-1839, 2-1842 to 2-1845, 2-1847, 2-1848, 2-1852 to 2-1860, 2-1862 to 2-1870, 2-1873, 2-1874, 2-1877 to 2-1880, 2-1882, 2-1883, 2-1887 to 2-1895, 2-1897 to 2-1905, 2-1908, 2-1909, 2-1912 to 2-1915, 2-1917, 2-1918, 2-1922 to 2-1930, 2-1932 to 2-1940, 2-1943, 2-1944, 2-1947 to 2-1950, 2-1952, 2-1953, 2-1957 to 2-1965, 2-1967 to 2-1975, 2-1978, 2-1979, 2-1982 to 2-1985, 2-1987, 2-1988, 2-1992 to 2-2000, 2-2002 to 2-2010, 2-2013, 2-2014, 2-2017 to 2-2020, 2-2022, 2-2023, 2-2027 to 2-2035, 2-2037 to 2-2045, 2-2048, 2-2049, 2-2052 to 2-2055, 2-2057, 2-2058, 2-2062 to 2-2070, 2-2072 to 2-2080, 2-2083, 2-2084, 2-2087 to 2-2090, 2-2092, 2-2093, 2-2097 to 2-2105, 2-2107 to 2-2115, 2-2118, 2-2119, 2-2122 to 2-2125, 2-2127, 2-2128, 2-2132 to 2-2140, 2-2142 to 2-2150, 2-2153, 2-2154, 2-2157 to 2-2160, 2-2162, 2-2163, 2-2167 to 2-2175, 2-2177 to 2-2185, 2-2188, 2-2189, 2-2192 to 2-2195, 2-2197, 2-2198, 2-2202 to 2-2210, 2-2212 to 2-2220, 2-2223, 2-2224, 2-2227 to 2-2230, 2-2232, 2-2233, 2-2237 to 2-2245, 2-2247 to 2-2255, 2-2258, 2-2259, 2-2262 to 2-2265, 2-2267, 2-2268, 2-2272 to 2-2280, 2-2282 to 2-2290, 2-2293, 2-2294, 2-2297 to 2-2300, 2-2302, 2-2303, 2-2307 to 2-2315, 2-2317 to 2-2325, 2-2328, 2-2329, 2-2332 to 2-2335, 2-2337, 2-2338, 2-2342 to 2-2350, 2-2352 to 2-2360, 2-2363, 2-2364, 2-2367 to 2-2370, 2-2372, 2-2373, 2-2377 to 2-2385, 2-2387 to 2-2395, 2-2398, 2-2399, 2-2402 to 2-2405, 2-2407, 2-2408, 2-2412 to 2-2420, 2-2422 to 2-2430, 2-2433, 2-2434, 2-2437 to 2-2440, 2-2442, 2-2443, 2-2447 to 2-2455, 2-2457 to 2-2465, 2-2468, 2-2469, 2-2472 to 2-2475, 2-2477, 2-2478, 2-2482 to 2-2490, 2-2492 to 2-2500, 2-2503, 2-2504, 2-2507 to 2-2510, 2-2512, 2-2513, 2-2517 to 2-2529, 2-2539 to 2-2594 and 2-2623 to 2-3322; more preferred are Compounds Nos.: 1-2 to 1-4, 1-6 to 1-8, 1-11, 1-14 to 1-16, 1-18 to 1-20, 1-22 to 1-24, 1-26 to 1-28, 1-30 to 1-32, 1-35, 1-42, 1-43, 145 to 1-52, 1-65, 1-66, 1-71 to 1-75, 1-89, 1-94, 1-96 to 1-98, 1-100 to 1-102, 1-105, 1-108 to 1-110, 1-112 to 1-114, 1-116 to 1-118, 1-120 to 1-122, 1-124 to 1-126, 1-129, 1-136, 1-137, 1-139 to 1-146, 1-159, 1-160, 1-165 to 1-169, 1-183, 1-189 to 1-191, 1-193 to 1-195, 1-198, 1-201 to 1-203, 1-205 to 1-207, 1-209 to 1-211, 1-213 to 1-215, 1-217 to 1-219, 1-222, 1-229, 1-230, 1-232 to 1-239, 1-252, 1-253, 1-258 to 1-262, 1-276, 1-282 to 1-284, 1-286 to 1-288, 1-291, 1-294 to 1-296, 1-298 to 1-300, 1-302 to 1-304, 1-306 to 1-308, 1-310 to 1-312, 1-315, 1-322, 1-323, 1-325 to 1-332, 1-345, 1-346, 1-351 to 1-355, 1-369, 1-375 to 1-377, 1-379 to 1-381, 1-384, 1-387 to 1-389, 1-391 to 1-393, 1-395 to 1-397, 1-399 to 1-401, 1-403 to 1-405, 1-408, 1-415, 1-416, 1-418 to 1425, 1-438, 1-439, 1-444 to 1-448, 1462, 1-468 to 1470, 1472 to 1-474, 1-477, 1-480 to 1-482, 1-484 to 1-486, 1-488 to 1-490, 1-492 to 1-494, 1-496 to 1-498, 1-501, 1-508, 1-509, 1-511 to 1-518, 1-531, 1-532, 1-537 to 1-541, 1-555, 1-561 to 1-563, 1-565 to 1-567, 1-570, 1-573 to 1-575, 1-577 to 1-579, 1-581 to 1-583, 1-585 to 1-587, 1-589 to 1-591, 1-594, 1-601, 1-602, 1-604 to 1-611, 1-624, 1-625, 1-630 to 1-634, 1-648, 1-654 to 1-656, 1-658 to 1-660, 1-663, 1-666 to 1-668, 1-670 to 1-672, 1-674 to 1-676, 1-678 to 1-680, 1-682 to 1-684, 1-687, 1-694, 1-695, 1-697 to 1-704, 1-717, 1-718, 1-723 to 1-727, 1-741, 1-747 to 1-749, 1-751 to 1-753, 1-756, 1-759 to 1-761, 1-763 to 1-765, 1-767 to 1-769, 1-771 to 1-773, 1-775 to 1-777, 1-780, 1-787, 1-788, 1-790 to 1-797, 1-810, 1-811, 1-816 to 1-820, 1-834, 1-840 to 1-842, 1-844 to 1-846, 1-849, 1-852 to 1-854, 1-856 to 1-858, 1-860 to 1-862, 1-864 to 1-866, 1-868 to 1-870, 1-873, 1-880, 1-881, 1-883 to 1-890, 1-903, 1-904, 1-909 to 1-913, 1-927, 1-933 to 1-935, 1-937 to 1-939, 1-942, 1-945 to 1-947, 1-949 to 1-951, 1-953 to 1-955, 1-957 to 1-959, 1-961 to 1-963, 1-966, 1-973, 1-974, 1-976 to 1-983, 1-996, 1-997, 1-1002 to 1-1006, 1-1020, 1-1026 to 1-1028, 1-1030 to 1-1032, 1-1035, 1-1038 to 1-1040, 1-1042 to 1-1044, 1-1046 to 1-1048, 1-1050 to 1-1052, 1-1054 to 1-1056, 1-1059, 1-1066, 1-1067, 1-1069 to 1-1076, 1-1089, 1-1090, 1-1095 to 1-1099, 1-1113, 1-1119 to 1-1121, 1-1123 to 1-1125, 1-1128, 1-1131 to 1-1133, 1-1135 to 1-1137, 1-1139 to 1-1141, 1-1143 to 1-1145, 1-1147 to 1-1149, 1-1152, 1-1159, 1-1160, 1-1162 to 1-1169, 1-1182, 1-1183, 1-1188 to 1-1192, 1-1206, 1-1212 to 1-1214, 1-1216 to 1-1218, 1-1221, 1-1224 to 1-1226, 1-1228 to 1-1230, 1-1232 to 1-1234, 1-1236 to 1-1238, 1-1240 to 1-1242, 1-1245, 1-1252, 1-1253, 1-1255 to 1-1262, 1-1275, 1-1276, 1-1281 to 1-1285, 1-1299, 1-1305 to 1-1307, 1-1309 to 1-1311, 1-1314, 1-1317 to 1-1319, 1-1321 to 1-1323, 1-1325 to 1-1327, 1-1329 to 1-1331, 1-1333 to 1-1335, 1-1338, 1-1345, 1-1346, 1-1348 to 1-1355, 1-1368, 1-1369, 1-1374 to 1-1378, 1-1392, 1-1397 to 1-1405, 1-1408 to 1-1415, 1-1418, 1-1419, 1-1422 to 1-1424, 1-1428, 1-1432 to 1-1440, 1-1443 to 1-1450, 1-1453, 1-1454, 1-1457 to 1-1459, 1-1463, 1-1467 to 1-1475, 1-1478 to 1-1485, 1-1488, 1-1489, 1-1492 to 1-1494, 1-1498, 1-1502 to 1-1510, 1-1513 to 1-1520, 1-1523, 1-1524, 1-1527 to 1-1529, 1-1533, 1-1537 to 1-1545, 1-1548 to 1-1555, 1-1558, 1-1559, 1-1562 to 1-1564, 1-1568, 1-1572 to 1-1580, 1-1583 to 1-1590, 1-1593, 1-1594, 1-1597 to 1-1599, 1-1603, 1-1607 to 1-1615, 1-1618 to 1-1625, 1-1628, 1-1629, 1-1632 to 1-1634, 1-1638, 1-1642 to 1-1650, 1-1653 to 1-1660, 1-1663, 1-1664, 1-1667 to 1-1669, 1-1673, 1-1677 to 1-1685, 1-1688 to 1-1695, 1-1698, 1-1699, 1-1702 to 1-1704, 1-1708, 1-1712 to 1-1720, 1-1723 to 1-1730, 1-1733, 1-1734, 1-1737 to 1-1739, 1-1743, 1-1747 to 1-1755, 1-1758 to 1-1765, 1-1768, 1-1769, 1-1772 to 1-1774, 1-1778, 1-1782 to 1-1790, 1-1793 to 1-1800, 1-1803, 1-1804, 1-1807 to 1-1809, 1-1813, 1-1817 to 1-1825, 1-1828 to 1-1835, 1-1838, 1-1839, 1-1842 to 1-1844, 1-1848, 1-1852 to 1-1860, 1-1863 to 1-1870, 1-1873, 1-1874, 1-1877 to 1-1879, 1-1883, 1-1887 to 1-1895, 1-1898 to 1-1905, 1-1908, 1-1909, 1-1912 to 1-1914, 1-1918, 1-1922 to 1-1930, 1-1933 to 1-1940, 1-1943, 1-1944, 1-1947 to 1-1949, 1-1953, 1-1957 to 1-1965, 1-1968 to 1-1975, 1-1978, 1-1979, 1-1982 to 1-1984, 1-1988, 1-1992 to 1-2000, 1-2003 to 1-2010, 1-2013, 1-2014, 1-2017 to 1-2019, 1-2023, 1-2027 to 1-2035, 1-2038 to 1-2045, 1-2048, 1-2049, 1-2052 to 1-2054, 1-2058, 1-2062 to 1-2070, 1-2073 to 1-2080, 1-2083, 1-2084, 1-2087 to 1-2089, 1-2093, 1-2097 to 1-2105, 1-2108 to 1-2115, 1-2118, 1-2119, 1-2122 to 1-2124, 1-2128, 1-2132 to 1-2140, 1-2143 to 1-2150, 1-2153, 1-2154, 1-2157 to 1-2159, 1-2163, 1-2167 to 1-2175, 1-2178 to 1-2185, 1-2188, 1-2189, 1-2192 to 1-2194, 1-2198, 1-2202 to 1-2210, 1-2213 to 1-2220, 1-2223, 1-2224, 1-2227 to 1-2229, 1-2233, 1-2237 to 1-2245, 1-2248 to 1-2255, 1-2258, 1-2259, 1-2262 to 1-2264, 1-2268, 1-2272 to 1-2280, 1-2283 to 1-2290, 1-2293, 1-2294, 1-2297 to 1-2299, 1-2303, 1-2307 to 1-2315, 1-2318 to 1-2325, 1-2328, 1-2329, 1-2332 to 1-2334, 1-2338, 1-2342 to 1-2350, 1-2353 to 1-2360, 1-2363, 1-2364, 1-2367 to 1-2369, 1-2373, 1-2377 to 1-2385, 1-2388 to 1-2395, 1-2398, 1-2399, 1-2402 to 1-2404, 1-2408, 1-2412 to 1-2420, 1-2423 to 1-2430, 1-2433, 1-2434, 1-2437 to 1-2439, 1-2443, 1-2447 to 1-2455, 1-2458 to 1-2465, 1-2468, 1-2469, 1-2472 to 1-2474, 1-2478, 1-2482 to 1-2490, 1-2493 to 1-2500, 1-2503, 1-2504, 1-2507 to 1-2509, 1-2513, 1-2517 to 1-2526, 1-2528, 1-2529, 1-2539 to 1-2554, 1-2556 to 1-2558, 1-2560 to 1-2577, 1-2579 to 1-2581, 1-2583 to 1-2594, 1-2626, 1-2629 to 1-2643, 1-2645, 1-2648 to 1-2651, 1-2653 to 1-2748, 1-2779, 1-2780, 1-2782, 1-2783, 1-2905, 1-2906, 1-2908, 1-2909, 1-3031, 1-3032, 1-3157, 1-3158, 1-3253 to 1-3322, 2-2 to 2-4, 2-6 to 2-8, 2-11, 2-14 to 2-16, 2-18 to 2-20, 2-22 to 2-24, 2-26 to 2-28, 2-30 to 2-32, 2-35, 2-42, 2-43, 2-45 to 2-52, 2-65, 2-66, 2-71 to 2-75, 2-89, 2-94, 2-96 to 2-98, 2-100 to 2-102, 2-105, 2-108 to 2-110, 2-112 to 2-114, 2-116 to 2-118, 2-120 to 2-122, 2-124 to 2-126, 2-129, 2-136, 2-137, 2-139 to 2-146, 2-159, 2-160, 2-165 to 2-169, 2-183, 2-189 to 2-191, 2-193 to 2-195, 2-198, 2-201 to 2-203, 2-205 to 2-207, 2-209 to 2-211, 2-213 to 2-215, 2-217 to 2-219, 2-222, 2-229, 2-230, 2-232 to 2-239, 2-252, 2-253, 2-258 to 2-262, 2-276, 2-282 to 2-284, 2-286 to 2-288, 2-291, 2-294 to 2-296, 2-298 to 2-300, 2-302 to 2-304, 2-306 to 2-308, 2-310 to 2-312, 2-315, 2-322, 2-323, 2-325 to 2-332, 2-345, 2-346, 2-351 to 2-355, 2-369, 2-375 to 2-377, 2-379 to 2-381, 2-384, 2-387 to 2-389, 2-391 to 2-393, 2-395 to 2-397, 2-399 to 2-401, 2-403 to 2-405, 2-408, 2-415, 2-416, 2-418 to 2-425, 2-438, 2-439, 2-444 to 2448, 2-462, 2-468 to 2-470, 2-472 to 2-474, 2-477, 2-480 to 2-482, 2-484 to 2-486, 2-488 to 2-490, 2-492 to 2-494, 2496 to 2-498, 2-501, 2-508, 2-509, 2-511 to 2-518, 2-531, 2-532, 2-537 to 2-541, 2-555, 2-561 to 2-563, 2-565 to 2-567, 2-570, 2-573 to 2-575, 2-577 to 2-579, 2-581 to 2-583, 2-585 to 2-587, 2-589 to 2-591, 2-594, 2-601, 2-602, 2-604 to 2-611, 2-624, 2-625, 2-630 to 2-634, 2-648, 2-654 to 2-656, 2-658 to 2-660, 2-663, 2-666 to 2-668, 2-670 to 2-672, 2-674 to 2-676, 2-678 to 2-680, 2-682 to 2-684, 2-687, 2-694, 2-695, 2-697 to 2-704, 2-717, 2-718, 2-723 to 2-727, 2-741, 2-747 to 2-749, 2-751 to 2-753, 2-756, 2-759 to 2-761, 2-763 to 2-765, 2-767 to 2-769, 2-771 to 2-773, 2-775 to 2-777, 2-780, 2-787, 2-788, 2-790 to 2-797, 2-810, 2-811, 2-816 to 2-820, 2-834, 2-840 to 2-842, 2-844 to 2-846, 2-849, 2-852 to 2-854, 2-856 to 2-858, 2-860 to 2-862, 2-864 to 2-866, 2-868 to 2-870, 2-873, 2-880, 2-881, 2-883 to 2-890, 2-903, 2-904, 2-909 to 2-913, 2-927, 2-933 to 2-935, 2-937 to 2-939, 2-942, 2-945 to 2-947, 2-949 to 2-951, 2-953 to 2-955, 2-957 to 2-959, 2-961 to 2-963, 2-966, 2-973, 2-974, 2-976 to 2-983, 2-996, 2-997, 2-1002 to 2-1006, 2-1020, 2-1026 to 2-1028, 2-1030 to 2-1032, 2-1035, 2-1038 to 2-1040, 2-1042 to 2-1044, 2-1046 to 2-1048, 2-1050 to 2-1052, 2-1054 to 2-1056, 2-1059, 2-1066, 2-1067, 2-1069 to 2-1076, 2-1089, 2-1090, 2-1095 to 2-1099, 2-1113, 2-1119 to 2-1121, 2-1123 to 2-1125, 2-1128, 2-1131 to 2-1133, 2-1135 to 2-1137, 2-1139 to 2-1141, 2-1143 to 2-1145, 2-1147 to 2-1149, 2-1152, 2-1159, 2-1160, 2-1162 to 2-1169, 2-1182, 2-1183, 2-1188 to 2-1192, 2-1206, 2-1212 to 2-1214, 2-1216 to 2-1218, 2-1221, 2-1224 to 2-1226, 2-1228 to 2-1230, 2-1232 to 2-1234, 2-1236 to 2-1238, 2-1240 to 2-1242, 2-1245, 2-1252, 2-1253, 2-1255 to 2-1262, 2-1275, 2-1276, 2-1281 to 2-1285, 2-1299, 2-1305 to 2-1307, 2-1309 to 2-1311, 2-1314, 2-1317 to 2-1319, 2-1321 to 2-1323, 2-1325 to 2-1327, 2-1329 to 2-1331, 2-1333 to 2-1335, 2-1338, 2-1345, 2-1346, 2-1348 to 2-1355, 2-1368, 2-1369, 2-1374 to 2-1378, 2-1392, 2-1397 to 2-1405, 2-1408 to 2-1415, 2-1418, 2-1419, 2-1422 to 2-1424, 2-1428, 2-1432 to 2-1440, 2-1443 to 2-1450, 2-1453, 2-1454, 2-1457 to 2-1459, 2-1463, 2-1467 to 2-1475, 2-1478 to 2-1485, 2-1488, 2-1489, 2-1492 to 2-1494, 2-1498, 2-1502 to 2-1510, 2-1513 to 2-1520, 2-1523, 2-1524, 2-1527 to 2-1529, 2-1533, 2-1537 to 2-1545, 2-1548 to 2-1555, 2-1558, 2-1559, 2-1562 to 2-1564, 2-1568, 2-1572 to 2-1580, 2-1583 to 2-1590, 2-1593, 2-1594, 2-1597 to 2-1599, 2-1603, 2-1607 to 2-1615, 2-1618 to 2-1625, 2-1628, 2-1629, 2-1632 to 2-1634, 2-1638, 2-1642 to 2-1650, 2-1653 to 2-1660, 2-1663, 2-1664, 2-1667 to 2-1669, 2-1673, 2-1677 to 2-1685, 2-1688 to 2-1695, 2-1698, 2-1699, 2-1702 to 2-1704, 2-1708, 2-1712 to 2-1720, 2-1723 to 2-1730, 2-1733, 2-1734, 2-1737 to 2-1739, 2-1743, 2-1747 to 2-1755, 2-1758 to 2-1765, 2-1768, 2-1769, 2-1772 to 2-1774, 2-1778, 2-1782 to 2-1790, 2-1793 to 2-1800, 2-1803, 2-1804, 2-1807 to 2-1809, 2-1813, 2-1817 to 2-1825, 2-1828 to 2-1835, 2-1838, 2-1839, 2-1842 to 2-1844, 2-1848, 2-1852 to 2-1860, 2-1863 to 2-1870, 2-1873, 2-1874, 2-1877 to 2-1879, 2-1883, 2-1887 to 2-1895, 2-1898 to 2-1905, 2-1908, 2-1909, 2-1912 to 2-1914, 2-1918, 2-1922 to 2-1930, 2-1933 to 2-1940, 2-1943, 2-1944, 2-1947 to 2-1949, 2-1953, 2-1957 to 2-1965, 2-1968 to 2-1975, 2-1978, 2-1979, 2-1982 to 2-1984, 2-1988, 2-1992 to 2-2000, 2-2003 to 2-2010, 2-2013, 2-2014, 2-2017 to 2-2019, 2-2023, 2-2027 to 2-2035, 2-2038 to 2-2045, 2-2048, 2-2049, 2-2052 to 2-2054, 2-2058, 2-2062 to 2-2070, 2-2073 to 2-2080, 2-2083, 2-2084, 2-2087 to 2-2089, 2-2093, 2-2097 to 2-2105, 2-2108 to 2-2115, 2-2118, 2-2119, 2-2122 to 2-2124, 2-2128, 2-2132 to 2-2140, 2-2143 to 2-2150, 2-2153, 2-2154, 2-2157 to 2-2159, 2-2163, 2-2167 to 2-2175, 2-2178 to 2-2185, 2-2188, 2-2189, 2-2192 to 2-2194, 2-2198, 2-2202 to 2-2210, 2-2213 to 2-2220, 2-2223, 2-2224, 2-2227 to 2-2229, 2-2233, 2-2237 to 2-2245, 2-2248 to 2-2255, 2-2258, 2-2259, 2-2262 to 2-2264, 2-2268, 2-2272 to 2-2280, 2-2283 to 2-2290, 2-2293, 2-2294, 2-2297 to 2-2299, 2-2303, 2-2307 to 2-2315, 2-2318 to 2-2325, 2-2328, 2-2329, 2-2332 to 2-2334, 2-2338, 2-2342 to 2-2350, 2-2353 to 2-2360, 2-2363, 2-2364, 2-2367 to 2-2369, 2-2373, 2-2377 to 2-2385, 2-2388 to 2-2395, 2-2398, 2-2399, 2-2402 to 2-2404, 2-2408, 2-2412 to 2-2420, 2-2423 to 2-2430, 2-2433, 2-2434, 2-2437 to 2-2439, 2-2443, 2-2447 to 2-2455, 2-2458 to 2-2465, 2-2468, 2-2469, 2-2472 to 2-2474, 2-2478, 2-2482 to 2-2490, 2-2493 to 2-2500, 2-2503, 2-2504, 2-2507 to 2-2509, 2-2513, 2-2517 to 2-2522, 2-2524 to 2-2526, 2-2528, 2-2529, 2-2539 to 2-2554, 2-2556 to 2-2558, 2-2560 to 2-2577, 2-2579 to 2-2581, 2-2583 to 2-2594 and 2-3253 to 2-3322; still more preferred are Compounds Nos.: 1-3, 1-7, 1-11, 1-15, 1-19, 1-23, 1-27, 1-31, 1-35, 1-42, 1-45, 1-47 to 1-51, 1-65, 1-71, 1-73, 1-89, 1-94, 1-97, 1-98, 1-101, 1-105, 1-109, 1-113, 1-117, 1-121, 1-125, 1-129, 1-136, 1-139, 1-141 to 1-146, 1-159, 1-165, 1-167, 1-183, 1-190, 1-194, 1-198, 1-202, 1-206, 1-210, 1-214, 1-218, 1-222, 1-229, 1-232, 1-234 to 1-238, 1-252, 1-258, 1-260, 1-276, 1-283, 1-287, 1-291, 1-295, 1-299, 1-303, 1-307, 1-311, 1-315, 1-322, 1-325, 1-327 to 1-331, 1-345, 1-351, 1-353, 1-369, 1-376, 1-380, 1-384, 1-388, 1-392, 1-396, 1-400, 1-404, 1-408, 1-415, 1-418, 1420 to 1-424, 1-438, 1-444, 1-446, 1-462, 1-469, 1-473, 1-477, 1-481, 1-485, 1-489, 1-493, 1-497, 1-501, 1-508, 1-511, 1-513 to 1-517, 1-531, 1-537, 1-539, 1-555, 1-562, 1-566, 1-570, 1-574, 1-578, 1-582, 1-586, 1-590, 1-594, 1-601, 1-604, 1-606 to 1-610, 1-624, 1-630, 1-632, 1-648, 1-655, 1-659, 1-663, 1-667, 1-671, 1-675, 1-679, 1-683, 1-687, 1-694, 1-697, 1-699 to 1-703, 1-717, 1-723, 1-725, 1-741, 1-748, 1-752, 1-756, 1-760, 1-764, 1-768, 1-772, 1-776, 1-780, 1-787, 1-790, 1-792 to 1-796, 1-810, 1-816, 1-818, 1-834, 1-841, 1-845, 1-849, 1-853, 1-857, 1-861, 1-865, 1-869, 1-873, 1-880, 1-883, 1-885 to 1-889, 1-903, 1-909, 1-911, 1-927, 1-934, 1-938, 1-942, 1-946, 1-950, 1-954, 1-958, 1-962, 1-966, 1-973, 1-976, 1-978 to 1-982, 1-996, 1-1002, 1-1004, 1-1020, 1-1027, 1-1031, 1-1035, 1-1039, 1-1043, 1-1047, 1-1051, 1-1055, 1-1059, 1-1066, 1-1069, 1-1071 to 1-1075, 1-1089, 1-1095, 1-1097, 1-1113, 1-1120, 1-1124, 1-1128, 1-1132, 1-1136, 1-1140, 1-1144, 1-1148, 1-1152, 1-1159, 1-1162, 1-1164 to 1-1168, 1-1182, 1-1188, 1-1190, 1-1206, 1-1213, 1-1217, 1-1221, 1-1225, 1-1229, 1-1233, 1-1237, 1-1241, 1-1245, 1-1252, 1-1255, 1-1257 to 1-1261, 1-1275, 1-1281, 1-1283, 1-1299, 1-1306, 1-1310, 1-1314, 1-1318, 1-1322, 1-1326, 1-1330, 1-1334, 1-1338, 1-1345, 1-1348, 1-1350 to 1-1354, 1-1368, 1-1374, 1-1376, 1-1392, 1-1397 to 1-1405, 1-1408, 1-1410, 1-1412 to 1-1415, 1-1418, 1-1422, 1-1428, 1-1432 to 1-1440, 1-1443, 1-1445, 1-1447 to 1-1450, 1-1453, 1-1457, 1-1463, 1-1467 to 1-1475, 1-1478, 1-1480, 1-1482 to 1-1485, 1-1488, 1-1492, 1-1498, 1-1502 to 1-1510, 1-1513, 1-1515, 1-1517 to 1-1520, 1-1523, 1-1527, 1-1533, 1-1537 to 1-1545, 1-1548, 1-1550, 1-1552 to 1-1555, 1-1558, 1-1562, 1-1568, 1-1572 to 1-1580, 1-1583, 1-1585, 1-1587 to 1-1590, 1-1593, 1-1597, 1-1603, 1-1607 to 1-1615, 1-1618, 1-1620, 1-1622 to 1-1625, 1-1628, 1-1632, 1-1638, 1-1642 to 1-1650, 1-1653, 1-1655, 1-1657 to 1-1660, 1-1663, 1-1667, 1-1673, 1-1677 to 1-1685, 1-1688, 1-1690, 1-1692 to 1-1695, 1-1698, 1-1702, 1-1708, 1-1712 to 1-1720, 1-1723, 1-1725, 1-1727 to 1-1730, 1-1733, 1-1737, 1-1743, 1-1747 to 1-1755, 1-1758, 1-1760, 1-1762 to 1-1765, 1-1768, 1-1772, 1-1778, 1-1782 to 1-1790, 1-1793, 1-1795, 1-1797 to 1-1800, 1-1803, 1-1807, 1-1813, 1-1817 to 1-1825, 1-1828, 1-1830, 1-1832 to 1-1835, 1-1838, 1-1842, 1-1848, 1-1852 to 1-1860, 1-1863, 1-1865, 1-1867 to 1-1870, 1-1873, 1-1877, 1-1883, 1-1887 to 1-1895, 1-1898, 1-1900, 1-1902 to 1-1905, 1-1908, 1-1912, 1-1918, 1-1922 to 1-1930, 1-1933, 1-1935, 1-1937 to 1-1940, 1-1943, 1-1947, 1-1953, 1-1957 to 1-1965, 1-1968, 1-1970, 1-1972 to 1-1975, 1-1978, 1-1982, 1-1988, 1-1992 to 1-2000, 1-2003, 1-2005, 1-2007 to 1-2010, 1-2013, 1-2017, 1-2023, 1-2027 to 1-2035, 1-2038, 1-2040, 1-2042 to 1-2045, 1-2048, 1-2052, 1-2058, 1-2062 to 1-2070, 1-2073, 1-2075, 1-2077 to 1-2080, 1-2083, 1-2087, 1-2093, 1-2097 to 1-2105, 1-2108, 1-2110, 1-2112 to 1-2115, 1-2118, 1-2122, 1-2128, 1-2132 to 1-2140, 1-2143, 1-2145, 1-2147 to 1-2150, 1-2153, 1-2157, 1-2163, 1-2167 to 1-2175, 1-2178, 1-2180, 1-2182 to 1-2185, 1-2188, 1-2192, 1-2198, 1-2202 to 1-2210, 1-2213, 1-2215, 1-2217 to 1-2220, 1-2223, 1-2227, 1-2233, 1-2237 to 1-2245, 1-2248, 1-2250, 1-2252 to 1-2255, 1-2258, 1-2262, 1-2268, 1-2272 to 1-2280, 1-2283, 1-2285, 1-2287 to 1-2290, 1-2293, 1-2297, 1-2303, 1-2307 to 1-2315, 1-2318, 1-2320, 1-2322 to 1-2325, 1-2328, 1-2332, 1-2338, 1-2342 to 1-2350, 1-2353, 1-2355, 1-2357 to 1-2360, 1-2363, 1-2367, 1-2373, 1-2377 to 1-2385, 1-2388, 1-2390, 1-2392 to 1-2395, 1-2398, 1-2402, 1-2408, 1-2412 to 1-2420, 1-2423, 1-2425, 1-2427 to 1-2430, 1-2433, 1-2437, 1-2443, 1-2447 to 1-2455, 1-2458, 1-2460, 1-2462 to 1-2465, 1-2468, 1-2472, 1-2478, 1-2482 to 1-2490, 1-2493, 1-2495, 1-2497 to 1-2500, 1-2503, 1-2507, 1-2513, 1-2517 to 1-2520, 1-2522 to 1-2524, 1-2525, 1-2528, 1-2529, 1-2539 to 1-2541, 1-2543, 1-2545, 1-2547, 1-2549 to 1-2552, 1-2554, 1-2556, 1-2557, 1-2560 to 1-2564, 1-2566, 1-2568, 1-2570, 1-2572 to 1-2575, 1-2577, 1-2579, 1-2580, 1-2583 to 1-2587, 1-2589, 1-2591, 1-2593, 1-2629, 1-2630, 1-2632, 1-2645, 1-2650, 1-2651, 1-2653, 1-2654, 1-2656, 1-2657, 1-2665 to 1-2667, 1-2707 to 1-2709, 1-2779, 1-2780, 1-2782, 1-2783, 1-2905, 1-2906, 1-2908, 1-2909, 1-3031, 1-3032, 1-3157, 1-3158, 1-3253 to 1-3322, 2-3, 2-7, 2-11, 2-15, 2-19, 2-23, 2-27, 2-31, 2-35, 2-42, 2-45, 2-47 to 2-51, 2-65, 2-71, 2-73, 2-89, 2-94, 2-97, 2-101, 2-105, 2-109, 2-113, 2-117, 2-121, 2-125, 2-129, 2-136, 2-139, 2-141 to 2-145, 2-159, 2-165, 2-167, 2-183, 2-190, 2-194, 2-198, 2-202, 2-206, 2-210, 2-214, 2-218, 2-222, 2-229, 2-232, 2-234 to 2-238, 2-252, 2-258, 2-260, 2-276, 2-283, 2-287, 2-291, 2-295, 2-299, 2-303, 2-307, 2-311, 2-315, 2-322, 2-325, 2-327 to 2-331, 2-345, 2-351, 2-353, 2-369, 2-376, 2-380, 2-384, 2-388, 2-392, 2-396, 2-400, 2-404, 2-408, 2-415, 2-418, 2-420 to 2-424, 2-438, 2-444, 2-446, 2-462, 2-469, 2-473, 2-477, 2-481, 2-485, 2-489, 2-493, 2-497, 2-501, 2-508, 2-511, 2-513 to 2-517, 2-531, 2-537, 2-539, 2-555, 2-562, 2-566, 2-570, 2-574, 2-578, 2-582, 2-586, 2-590, 2-594, 2-601, 2-604, 2-606 to 2-610, 2-624, 2-630, 2-632, 2-648, 2-655, 2-659, 2-663, 2-667, 2-671, 2-675, 2-679, 2-683, 2-687, 2-694, 2-697, 2-699 to 2-703, 2-717, 2-723, 2-725, 2-741, 2-748, 2-752, 2-756, 2-760, 2-764, 2-768, 2-772, 2-776, 2-780, 2-787, 2-790, 2-792 to 2-796, 2-810, 2-816, 2-818, 2-834, 2-841, 2-845, 2-849, 2-853, 2-857, 2-861, 2-865, 2-869, 2-873, 2-880, 2-883, 2-885 to 2-889, 2-903, 2-909, 2-911, 2-927, 2-934, 2-938, 2-942, 2-946, 2-950, 2-954, 2-958, 2-962, 2-966, 2-973, 2-976, 2-978 to 2-982, 2-996, 2-1002, 2-1004, 2-1020, 2-1027, 2-1031, 2-1035, 2-1039, 2-1043, 2-1047, 2-1051, 2-1055, 2-1059, 2-1066, 2-1069, 2-1071 to 2-1075, 2-1089, 2-1095, 2-1097, 2-1113, 2-1120, 2-1124, 2-1128, 2-1132, 2-1136, 2-1140, 2-1144, 2-1148, 2-1152, 2-1159, 2-1162, 2-1164 to 2-1168, 2-1182, 2-1188, 2-1190, 2-1206, 2-1213, 2-1217, 2-1221, 2-1225, 2-1229, 2-1233, 2-1237, 2-1241, 2-1245, 2-1252, 2-1255, 2-1257 to 2-1261, 2-1275, 2-1281, 2-1283, 2-1299, 2-1306, 2-1310, 2-1314, 2-1318, 2-1322, 2-1326, 2-1330, 2-1334, 2-1338, 2-1345, 2-1348, 2-1350 to 2-1354, 2-1368, 2-1374, 2-1376, 2-1392, 2-1397 to 2-1405, 2-1408, 2-1410, 2-1412 to 2-1415, 2-1418, 2-1422, 2-1428, 2-1432 to 2-1440, 2-1443, 2-1445, 2-1447 to 2-1450, 2-1453, 2-1457, 2-1463, 2-1467 to 2-1475, 2-1478, 2-1480, 2-1482 to 2-1485, 2-1488, 2-1492, 2-1498, 2-1502 to 2-1510, 2-1513, 2-1515, 2-1517 to 2-1520, 2-1523, 2-1527, 2-1533, 2-1537 to 2-1545, 2-1548, 2-1550, 2-1552 to 2-1555, 2-1558, 2-1562, 2-1568, 2-1572 to 2-1580, 2-1583, 2-1585, 2-1587 to 2-1590, 2-1593, 2-1597, 2-1603, 2-1607 to 2-1615, 2-1618, 2-1620, 2-1622 to 2-1625, 2-1628, 2-1632, 2-1638, 2-1642 to 2-1650, 2-1653, 2-1655, 2-1657 to 2-1660, 2-1663, 2-1667, 2-1673, 2-1677 to 2-1685, 2-1688, 2-1690, 2-1692 to 2-1695, 2-1698, 2-1702, 2-1708, 2-1712 to 2-1720, 2-1723, 2-1725, 2-1727 to 2-1730, 2-1733, 2-1737, 2-1743, 2-1747 to 2-1755, 2-1758, 2-1760, 2-1762 to 2-1765, 2-1768, 2-1772, 2-1778, 2-1782 to 2-1790, 2-1793, 2-1795, 2-1797 to 2-1800, 2-1803, 2-1807, 2-1813, 2-1817 to 2-1825, 2-1828, 2-1830, 2-1832 to 2-1835, 2-1838, 2-1842, 2-1848, 2-1852 to 2-1860, 2-1863, 2-1865, 2-1867 to 2-1870, 2-1873, 2-1877, 2-1883, 2-1887 to 2-1895, 2-1898, 2-1900, 2-1902 to 2-1905, 2-1908, 2-1912, 2-1918, 2-1922 to 2-1930, 2-1933, 2-1935, 2-1937 to 2-1940, 2-1943, 2-1947, 2-1953, 2-1957 to 2-1965, 2-1968, 2-1970, 2-1972 to 2-1975, 2-1978, 2-1982, 2-1988, 2-1992 to 2-2000, 2-2003, 2-2005, 2-2007 to 2-2010, 2-2013, 2-2017, 2-2023, 2-2027 to 2-2035, 2-2038, 2-2040, 2-2042 to 2-2045, 2-2048, 2-2052, 2-2058, 2-2062 to 2-2070, 2-2073, 2-2075, 2-2077 to 2-2080, 2-2083, 2-2087, 2-2093, 2-2097 to 2-2105, 2-2108, 2-2110, 2-2112 to 2-2115, 2-2118, 2-2122, 2-2128, 2-2132 to 2-2140, 2-2143, 2-2145, 2-2147 to 2-2150, 2-2153, 2-2157, 2-2163, 2-2167 to 2-2175, 2-2178, 2-2180, 2-2182 to 2-2185, 2-2188, 2-2192, 2-2198, 2-2202 to 2-2210, 2-2213, 2-2215, 2-2217 to 2-2220, 2-2223, 2-2227, 2-2233, 2-2237 to 2-2245, 2-2248, 2-2250, 2-2252 to 2-2255, 2-2258, 2-2262, 2-2268, 2-2272 to 2-2280, 2-2283, 2-2285, 2-2287 to 2-2290, 2-2293, 2-2297, 2-2303, 2-2307 to 2-2315, 2-2318, 2-2320, 2-2322 to 2-2325, 2-2328, 2-2332, 2-2338, 2-2342 to 2-2350, 2-2353, 2-2355, 2-2357 to 2-2360, 2-2363, 2-2367, 2-2373, 2-2377 to 2-2385, 2-2388, 2-2390, 2-2392 to 2-2395, 2-2398, 2-2402, 2-2408, 2-2412 to 2-2420, 2-2423, 2-2425, 2-2427 to 2-2430, 2-2433, 2-2437, 2-2443, 2-2447 to 2-2455, 2-2458, 2-2460, 2-2462 to 2-2465, 2-2468, 2-2472, 2-2478, 2-2482 to 2-2490, 2-2493, 2-2495, 2-2497 to 2-2500, 2-2503, 2-2507, 2-2513, 2-2517 to 2-2520, 2-2522, 2-2524, 2-2525, 2-2528, 2-2529, 2-2539 to 2-2541, 2-2543, 2-2545, 2-2547 to 2-2549 to 2-2552, 2-2554, 2-2556, 2-2557, 2-2560 to 2-2564, 2-2566, 2-2568, 2-2570, 2-2572 to 2-2575, 2-2577, 2-2579, 2-2580, 2-2583 to 2-2587, 2-2589, 2-2591, 2-2593 and 2-3253 to 2-3322.

The most preferred compounds are:
4-(3-aminopropyl)-2-(4-fluorophenyl)-3-(pyridin-4-yl)-1H-pyrrole,
4-(3-acetylaminopropyl)-2-(4-fluorophenyl)-3-(pyridin-4-yl)-1H-pyrrole,
2-(4-fluorophenyl)-4-(3-methylaminopropyl)-3-(pyridin-4-yl)-1H-pyrrole,
[5-(4-fluorophenyl)-4-(pyridin-4-yl)-1H-pyrrol-3-yl]-(pyridin-4-yl)methanol,
4-(1-acetyl-1,2,3,6-tetrahydropyridin-4-yl)-2-(4-fluorophenyl)-3-(pyridin-4-yl)-1H-pyrrole,
2-(4-fluorophenyl)-3-(pyridin-4-yl)-4-(1,2,3,6-tetrahydropyridin-4-yl)-1H-pyrrole,
2-(4-fluorophenyl)-4-(piperidin-4-yl)-3-(pyridin-4-yl)-1H-pyrrole,
3-(4-fluorophenyl)-1-(piperidin-4-yl)-2-(pyridin-4-yl)-1H-pyrrole,
1-(1-acetylpiperidin-4-yl)-3-(4-fluorophenyl)-2-(pyridin-4-yl)-1H-pyrrole,
3-(4-fluorophenyl)-1-[1-(2-nitroethyl)piperidin-4-yl]-2-(pyridin-4-yl)-1H-pyrrole,
3-(4-fluorophenyl)-1-[3-(morpholin-1-yl)propyl]-2-(pyridin-4-yl)-1H-pyrrole,
3-(4-fluorophenyl)-1-(piperidin-3-yl)-2-(pyridin-4-yl)-1H-pyrrole,
1-(azetidin-3-yl)-3-(4-fluorophenyl)-2-(pyridin-4-yl)-1H-pyrrole,
4-(3-dimethylaminopropyl)-2-(4-fluorophenyl)-3-(pyridin-4-yl)-1H-pyrrole,
2-(4-fluorophenyl)-4-[3-(piperidin-1-yl)propyl]-3-(pyridin-4-yl)-1H-pyrrole,
2-(4-fluorophenyl)-4-[3-(1-methylpiperazin-4-yl)propyl]-3-(pyridin-4-yl)-1H-pyrrole,
2-(4-fluorophenyl)-4-(1-methyl-1,2,3,6-tetrahydropyridin-4-yl)-3-(pyridin-4-yl)-1H-pyrrole,
2-(4-fluorophenyl)-4-(1-methylpiperidin-4-yl)-3-(pyridin-4-yl)-1H-pyrrole,
3-(4-fluorophenyl)-2-(pyridin-4-yl)-1-(2,2,6,6-tetramethylpiperidin-4-yl)-1H-pyrrole,
2-(4-fluorophenyl)-3-(pyridin-4-yl)-4-(quinuclidin-2-en-3-yl)-1H-pyrrole,
2-(4-fluorophenyl)-3-(pyridin-4-yl)-4-(quinuclidin-3-yl)-1H-pyrrole,
2-(4-fluorophenyl)-4-(4-hydroxypiperidin-4-yl)-3-(pyridin-4-yl)-1H-pyrrole,
3-(4-fluorophenyl)-2-(pyridin-4-yl)-1-(quinuclidin-3-yl)-1H-pyrrole,
1-(4-aminocyclohexyl)-3-(4-fluorophenyl)-2-(pyridin-4-yl)-1H-pyrrole,
3-(4-fluorophenyl)-2-(2-methylaminopyrimidin-4-yl) 1-(piperidin-4-yl)-1H-pyrrole,
2-(4-fluorophenyl)-4-(8-methyl-8-azabicyclo[3.2.1]oct-2-en-3-yl)-3-(pyridin-4-yl)-1H-pyrrole,
2-(4-fluorophenyl)-4-(8-methyl-8-azabicyclo[3.2.1]octan-3-yl)-3-(pyridin-4-yl)-1H-pyrrole,
4-(8-azabicyclo[3.2.1]oct-2-en-3-yl)-2-(4-fluorophenyl)-3-(pyridin-4-yl)-1H-pyrrole,
2-(4-fluorophenyl)-3-(pyridin-4-yl)-4-(1,2,3,6-tetrahydro-2,2,6,6-tetramethylpyridin-4-yl)-1H-pyrrole,
2-(4-fluorophenyl)-3-(pyridin-4-yl)-4-(2,2,6,6-tetramethylpiperidin-4-yl)-1H-pyrrole,
2-(4-fluorophenyl)-4-(2-methyl-1,2,3,6-tetrahydropyridin-4-yl)-3-(pyridin-4-yl)-1H-pyrrole, 2-(4-fluorophenyl)-4-(6-methyl-1,2,3,6-tetrahydropyridin-4-yl)-3-(pyridin-4-yl)-1H-pyrrole,
4-(1-ethyl-1,2,3,6-tetrahydropyridin-4-yl)-2-(4-fluorophenyl)-3-(pyridin-4-yl)-1H-pyrrole,
4-(1-ethylpiperidin-4-yl)-2-(4-fluorophenyl)-3-(pyridin-4-yl)-1H-pyrrole,
2-(4-fluorophenyl)-4-(1-isopropyl-1,2,3,6-tetrahydropyridin-4-yl)-3-(pyridin-4-yl)-1H-pyrrole,
2-(4-fluorophenyl)-4-(1-propyl-1,2,3,6-tetrahydropyridin-4-yl)-3-(pyridin-4-yl)-1H-pyrrole,
2-(4-fluorophenyl)-4-(1-phenethyl-1,2,3,6-tetrahydropyridin-4-yl)-3-(pyridin-4-yl)-1H-pyrrole,
2-(4-fluorophenyl)-4-(1,2,3,5,8,8a-hexahydroindolizin-7-yl)-3-(pyridin-4-yl)-1H-pyrrole,
2-(4-fluorophenyl)-4-(1,2,3,5,6,8a-hexahydroindolizin-7-yl)-3-(pyridin-4-yl)-1H-pyrrole,
4-(1,6-dimethyl-1,2,3,6-tetrahydropyridin-4-yl)-2-(4-fluorophenyl)-3-(pyridin-4-yl)-1H-pyrrole,
4-(1,2-dimethyl-1,2,3,6-tetrahydropyridin-4-yl)-2-(4-fluorophenyl)-3-(pyridin-4-yl)-1H-pyrrole,
2-(4-fluorophenyl)-4-(1,2,2,6,6-pentamethyl-1,2,3,6-tetrahydropyridin-4-yl)-3-(pyridin-4-yl)-1H-pyrrole,
4-(3-dimethylamino-1-propen-1-yl)-2-(4-fluorophenyl)-3-(pyridin-4-yl)-1H-pyrrole,
4-(4-aminobutyl)-2-(4-fluorophenyl)-3-(pyridin-4-yl)-1H-pyrrole,
4-(1-ethyl-6-methyl-1,2,3,6-tetrahydropyridin-4-yl)-2-(4-fluorophenyl)-3-(pyridin-4-yl)-1H-pyrrole,
4-(1-ethyl-2-methyl-1,2,3,6-tetrahydropyridin-4-yl)-2-(4-fluorophenyl)-3-(pyridin-4-yl)-1H-pyrrole,
1-(3-dimethylaminopropyl)-3-(4-fluorophenyl)-2-(pyridin-4-yl)-1H-pyrrole,
2-(4-fluorophenyl)-4-(1,2,3,5,6,7,8,8a-octahydroindolizin-7-yl)-3-(pyridin-4-yl)-1H-pyrrole,
4-(6-allyl-1-methyl-1,2,3,6-tetrahydropyridin-4-yl)-2-(4-fluorophenyl)-3-(pyridin-4-yl)-1H-pyrrole,
4-(2-allyl-1-methyl-1,2,3,6-tetrahydropyridin-4-yl)-2-(4-fluorophenyl)-3-(pyridin-4-yl)-1H-pyrrole,
4-(6-benzyl-1-methyl-1,2,3,6-tetrahydropyridin-4-yl)-2-(4-fluorophenyl)-3-(pyridin-4-yl)-1H-pyrrole,
4-(2-benzyl-1-methyl-1,2,3,6-tetrahydropyridin-4-yl)-2-(4-fluorophenyl)-3-(pyridin-4-yl)-1H-pyrrole,
2-(4-fluorophenyl)-4-(6-methyl-1-propyl-1,2,3,6-tetrahydropyridin-4-yl)-3-(pyridin-4-yl)-1H-pyrrole,
2-(4-fluorophenyl)-4-(2-methyl-1-propyl-1,2,3,6-tetrahydropyridin-4-yl)-3-(pyridin-4-yl)-1H-pyrrole,
2-(4-fluorophenyl)-4-(1,3,4,6,7,9a-hexahydro-2H-quinolizin-8-yl)-3-(pyridin-4-yl)-1H-pyrrole,
2-(4-fluorophenyl)-4-(1,3,4,6,9,9a-hexahydro-2H-quinolizin-8-yl)-3-(pyridin-4-yl)-1H-pyrrole,
2-(4-fluorophenyl)-4-(1,2,3,5,8,8a-hexahydroindolizin-7-yl)-3-(2-methylaminopyrimidin-4-yl)-1H-pyrrole,
2-(4-fluorophenyl)-4-(1,2,3,5,6,8a-hexahydroindolizin-7-yl)-3-(2-methylaminopyrimidin-4-yl)-1H-pyrrole,
2-(3,4-difluorophenyl)-4-(1,2,3,5,8,8a-hexahydroindolizin-7-yl)-3-(pyridin-4-yl)-1H-pyrrole,
2-(3,4-difluorophenyl)-4-(1,2,3,5,6,8a-hexahydroindolizin-7-yl)-3-(pyridin-4-yl)-1H-pyrrole,
4-(1,2,3,5,8,8a-hexahydroindolizin-7-yl)-3-(pyridin-4-yl)-2-(3-trifluoromethylphenyl)-1H-pyrrole,
4-(1,2,3,5,6,8a-hexahydroindolizin-7-yl)-3-(pyridin-4-yl)-2-(3-trifluoromethylphenyl)-1H-pyrrole,
2-(3-fluorophenyl)-4-(1,2,3,5,8,8a-hexahydroindolizin-7-yl)-3-(pyridin-4-yl)-1H-pyrrole,
2-(3-fluorophenyl)-4-(1,2,3,5,6,8a-hexahydroindolizin-7-yl)-3-(pyridin-4-yl)-1H-pyrrole,
2-(3-chlorophenyl)-4-(1,2,3,5,8,8a-hexahydroindolizin-7-yl)-3-(pyridin-4-yl)-1H-pyrrole,
2-(3-chlorophenyl)-4-(1,2,3,5,6,8a-hexahydroindolizin-7-yl)-3-(pyridin-4-yl)-1H-pyrrole,
4-(1,2,3,5,8,8a-hexahydroindolizin-7-yl)-2-phenyl-3-(pyridin-4-yl)-1H-pyrrole, and
4-(1,2,3,5,6,8a-hexahydroindolizin-7-yl)-2-phenyl-3(pyridin-4-yl) 1H-pyrrole;

and pharmacologically acceptable salts, esters or other derivatives thereof.

It should be noted that the specific combination of substituents $R^1$, $R^2$ and $R^3$ shown in the above Tables 1 and 2 can also be applied to the substituents $R^1$, $R^2$ and $R^3$ in formulae (I-2), (I-4) and (I-5) above.

The compounds of formula (I) and pharmacologically acceptable salts, esters and other derivatives thereof of the present invention can be prepared according to a variety of processes well known in the art for the preparation of compounds of this type, for example as described in the following Methods A to M below.

Method A

Method A is a method to prepare compounds of formula (I-1) of the present invention.

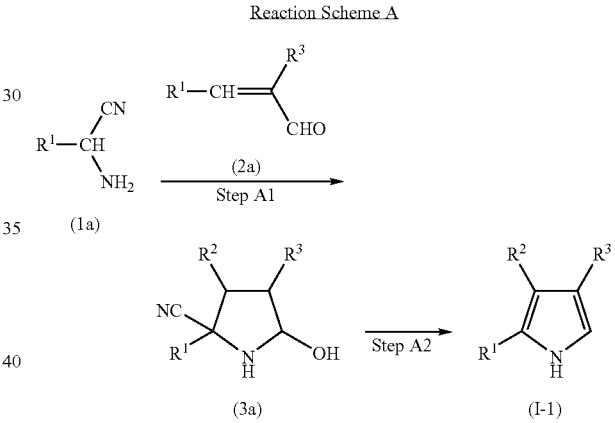

Reaction Scheme A

In the above formulae, $R^1$, $R^2$ and $R^3$ are as defined above.

Step A1

In this Step, a pyrrolidine compound of formula (3a) is prepared by reacting an aminonitrile compound of formula (1a) with an α,β-unsaturated aldehyde compound of formula (2a). This reaction is well known in the field of synthetic organic chemistry and can be carried out using well known techniques, for example according to the method described in EP 0733823, the contents of which are incorporated herein by reference thereto.

In more detail, this Step is carried out in the presence of a base. There is no particular restriction on the nature of the bases used, and any base commonly used in reactions of this type may equally be used here. Examples of such bases include: alkali metal hydroxides, such as lithium hydroxide, sodium hydroxide and potassium hydroxide; alkali metal hydrides, such as lithium hydride, sodium hydride and potassium hydride; alkali metal amides, such as lithium amide, sodium amide, potassium amide and lithium bis(trimethylsilyl)amide; and alkali metal alkoxides, such as lithium ethoxide, sodium methoxide, sodium ethoxide and potassium t-butoxide. Of these, we prefer the lithium amides.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane and heptane; aromatic hydrocarbons, such as benzene, toluene and xylene; ethers, such as diethyl ether, diisopropyl ether, tetrahydrofuran and dioxane; and alcohols, such as methanol ethanol, propanol, isopropanol and butanol. Of these, we prefer the ethers.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from –78° C. to 100° C., more preferably from –78° C. to room temperature. The time required for the reaction may also vary widely, depending on many factors, notably the reaction temperature and the nature of the reagents and solvent employed. However, provided that the reaction is effected under the preferred conditions outlined above, a period of from 10 minutes to 30 hours, more preferably from 1 hour to 20 hours, will usually suffice.

Step A2

In this Step, the desired pyrrole derivative of formula (I-1) of the present invention is prepared by the elimination of hydrogen cyanide and water from the compound of formula (3a) prepared in Step A1 above. These reactions are well known in the field of synthetic organic chemitry and can be carried out using well known techniques, for example according to the methods described in detail in EP 0799823.

In more detail, this may be achieved by heating the residue obtained by distilling off the solvent from the product of Step A1, or by heating the material obtained by extracting that residue, washing it with water and distilling off the solvent, preferably at a temperature not lower than 100° C., in the presence or absence of a solvent after completion of the reaction of Step A1. The reaction proceeds sufficiently in the absence of a solvent, but, when a solvent is used, the solvent is preferably inert and has a higher boiling point. Examples of suitable solvents include: toluene, xylene, dimethylformamide, dimethylacetamide, dimethyl sulfoxide, diglyme and diphenyl ether.

Method B, Method C, Method D and Method E

Method B, Method C, Method D and Method E are used to prepare compounds of formulae (I-2), (I-3), (I-4) and (I-5) respectively using the processes outlined in Reaction Schemes B to E below.

Reaction Scheme B

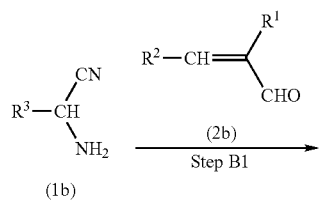

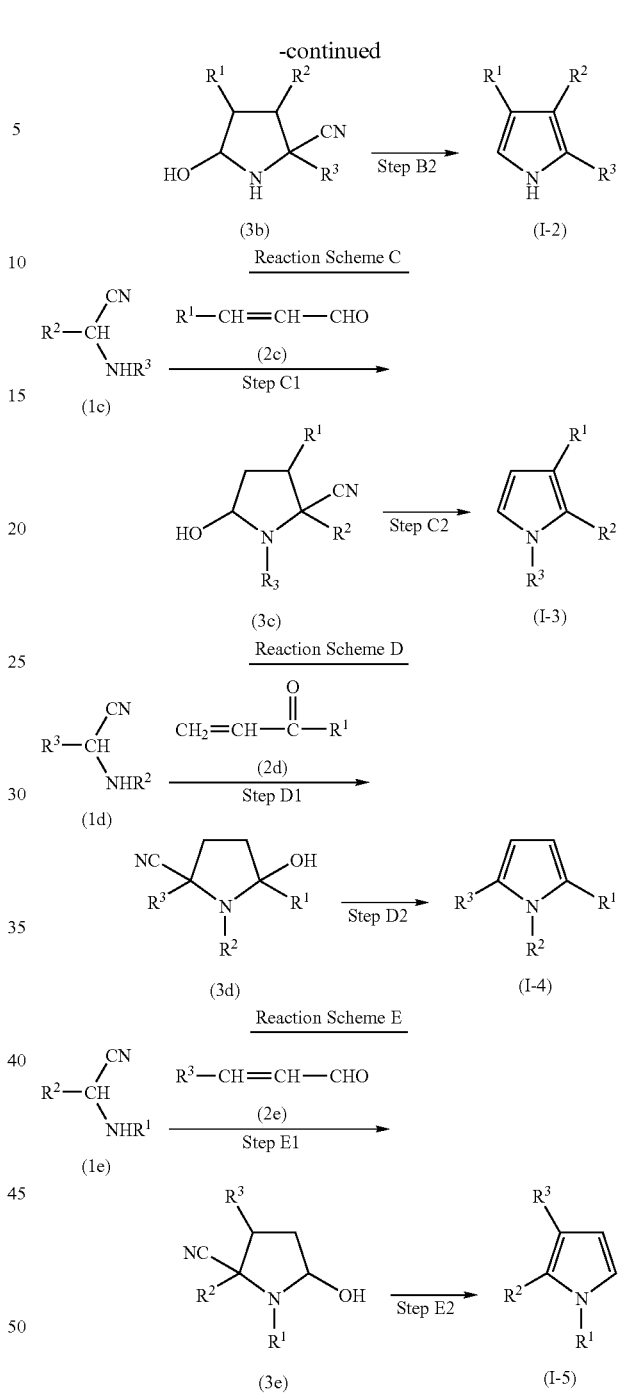

In the above formulae, $R^1$, $R^2$ and $R^3$ are as defined above.

In the above Reaction Schemes Step B1, Step C1, Step D1 and Step E1 are carried out in a similar manner to Step A1 above, and Step B2, Step C2, Step D2 and Step E2 are carried out similarly to Step A2 above.

Method F

In this method, compounds of formula (I-1) of the present invention wherein $R^3$ is an aminomethyl, aminoethyl, aminopropyl or aminopropenyl group [(I-1a), (I-1b), (I-1c) and (I-1d) respectively] are prepared as shown in Reaction Scheme F.

Reaction Scheme F

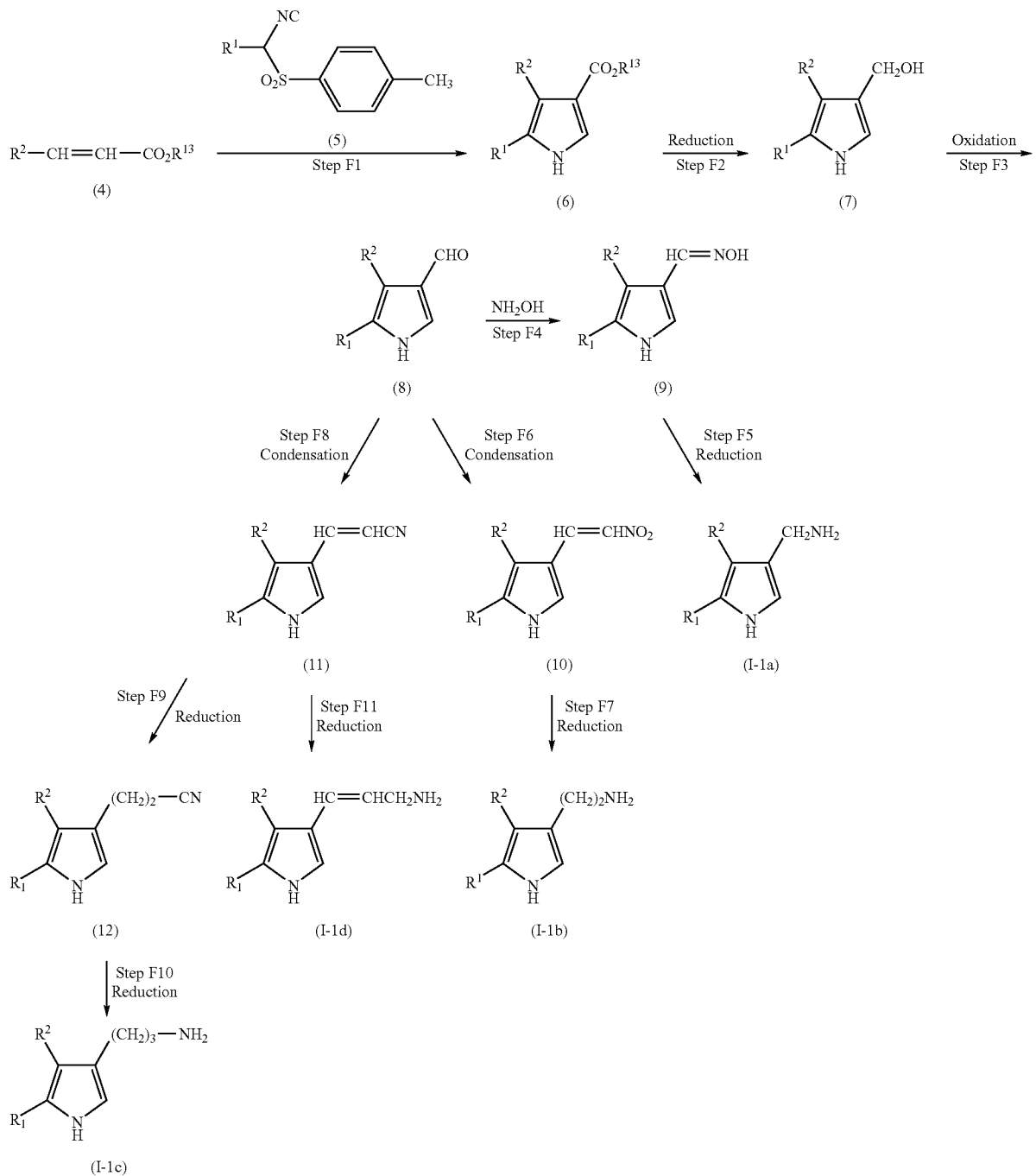

In the above formulae, $R^1$ and $R^2$ are as defined above and $R^{13}$ is selected from the group consisting of hydrogen atoms, lower alkyl groups as defined and exemplified above and aralkyl groups as defined and exemplified above.

Step F1

In this Step, a pyrrole carboxylic acid derivative of formula (6) is prepared by reacting an α,β-unsaturated compound of formula (4) with an isonitrile compound of formula (5). Reactions of this type are well known in the field of synthetic organic chemistry and can be carried out using well known techniques, for example according to the methods described in detail in R. Di Santo et al., Synthetic Communications, 25(6), pp. 795–802 (1995), the contents of which are incorporated herein by reference thereto.

Step F2

In this Step, a hydroxymethyl compound of formula (7) is prepared by reducing the pyrrole carboxylic acid derivative of formula (6) prepared in Step F1 above. Reduction reactions of this type are well known in the field of synthetic organic chemistry and can be carried out using well known techniques, for example according to the method described in detail in R. F. Nystrom et al., J. Am. Chem. Soc., 71, 3245 (1945), the contents of which are incorporated herein by reference thereto, using a reducing agent such as lithium aluminum hydride, lithium borohydride or diisobutyl aluminum hydride.

Step F3

In this Step, an aldehyde compound of formula (8) is prepared by oxidizing the hydroxymethyl compound of formula (7) prepared in Step F2 above. Oxidation reactions of this type are well known in the field of synthetic organic chemistry and can be carried out using well known techniques, for example according to the method described in detail in S. Bartel & F. Bohlmann, Tetrahedron Lett., 685 (1985), the contents of which are incorporated herein by reference thereto, using an oxidizing agent such as chromic acid, manganese dioxide or dimethylsulfoxide.

Step F4

In this Step, an oxime compound of formula (9) is prepared by reacting the aldehyde compound of formula (8) prepared in Step F3 above with hydroxyamine. Dehydration condensation reactions of this type are well known in the field of synthetic organic chemistry and can be carried out using well known techniques.

Step F5

In this Step, the desired compound of formula (I-1a) of the present invention is prepared by reducing the oxime compound of formula (9) prepared in Step F4 above. Reduction reactions of this type are well known in the field of synthetic organic chemistry and can be carried out using well known techniques, for example by catalytic reduction or reduction with diborane, examples of which are disclosed in detail in P. N. Rylander & D. R. Steele, Engelhald Ind. Tech. Bull., 3, 19 (1962), and J. A. Secrist, III & M. W. Logue, J. Org. Chem., 37, 335 (1972), the contents of which are incorporated herein by reference thereto.

Step F6

In this Step, a nitroolefin compound of formula (10) is prepared by a dehydration condensation (aldol condensation) of the aldehyde compound of formula (8) prepared in Step F3 above and nitromethane. Dehydration condensation reactions of this type are well known in the field of synthetic organic chemistry and can be carried out using well known techniques, for example according to the method described in detail in D. E. Worall, Org. Synth., I, 413 (1941), the contents of which are incorporated herein by reference thereto.

Step F7

In this Step, the desired compound of formula (I-1b) of the present invention is prepared by reducing the nitroolefin compound of formula (10) prepared in Step F6 above. Reduction reactions of this type are well known in the field of synthetic organic chemistry and can be carried out using well known techniques, for example according to the method described in detail in S. I. Murahashi et al., Bull. Chem. Soc. Jpn., 63, 1252 (1990), the contents of which are incorporated herein by reference thereto.

Step F8

In this Step, a cyanoolefin compound of formula (11) is prepared from the aldehyde compound of formula (8) prepared in Step F3 above. This transformation can be performed, for example, via an aldol condensation reaction similar to that employed in Step F6 above, a Wittig reaction [for example according to the method described in detail in The Organic Chemistry of Phosphorous, Elsevier (1967), the contents of which are incorporated herein by reference thereto], or a Wittig-Homer reaction [for example according to the method described in detail in L. Homer et al., Chem. Ber., 95, 581 (1962), the contents of which are incorporated herein by reference thereto].

Step F9

In this Step, a cyanoethyl compound of formula (12) is prepared by reduction of the double bond of the cyanoolefin compound of formula (11) prepared in step F8 above. Reduction reactions of this type are well known in the field of synthetic organic chemistry and can be carried out using well known techniques, for example according to the method described in detail in S. M. Kerwin et al., J. Org. Chem., 52, 1686 (1987) and T. Hudlicky et al., J. org. Chem., 52, 4641 (1987), the contents of which are incorporated herein by reference thereto.

Step F10

In this Step, the desired compound of formula (I-1c) of the present invention is prepared by reducing the cyano group of the cyanoethyl compound of formula (12) prepared in Step F9 above. Reduction reactions of this type are well known in the field of synthetic organic chemistry and can be carried out using well known techniques, for example according to the methods described in detail in N. M. Yoon & H. C. Brown, J. Am. Chem. Soc., 90, 2927 (1968) and J. Meinweld et al., J. Org. Chem., 29, 2914 (1964), the contents of which are incorporated herein by reference thereto, using lithium aluminum hydride or diisobutyl aluminum hydride.

Step F11

In this Step, the desired compound of formula (I-1d) of the present invention is prepared by reducing the cyano group of the cyanoolefin compound of formula (11) prepared in Step F8 above. This reduction is carried out in a similar manner to that described in Step F10 above.

Derivatives of the compounds of formula (I-1 a), (I-1b), (I-1c) and (I-1d) prepared above in which a nitrogen atom of an amino group present therein is substituted can be synthesized by alkylating, acylating and/or sulfonylating said amino group according to techniques well known in the field of synthetic organic chemistry.

Method G

In this method, compounds of formula (I-1) of the present invention wherein $R^3$ is a heterocyclyl group which may optionally be substituted with at least one group selected from Substituent group α and Substituent group δ and which is substituted with at least one group selected from Substituent group β and Substituent group γ, as defined above, a heterocyclyl group having at least one nitrogen atom which may be optionally substituted with at least one group selected from Substituent group α and Substituent group δ, as defined above, or a group of the general formula —CH(OH)—(CH$^2$)$_k$—R$^4$ (wherein R is as defined above, and the moiety —CH(OH)—(CH$_2$)$_k$— is a lower alkylene group as defined above for the group of formula X which is substituted with a hydroxy group, and k is 0 or an integer of from 1 to 5) can be prepared, as shown in Reaction Scheme G below.

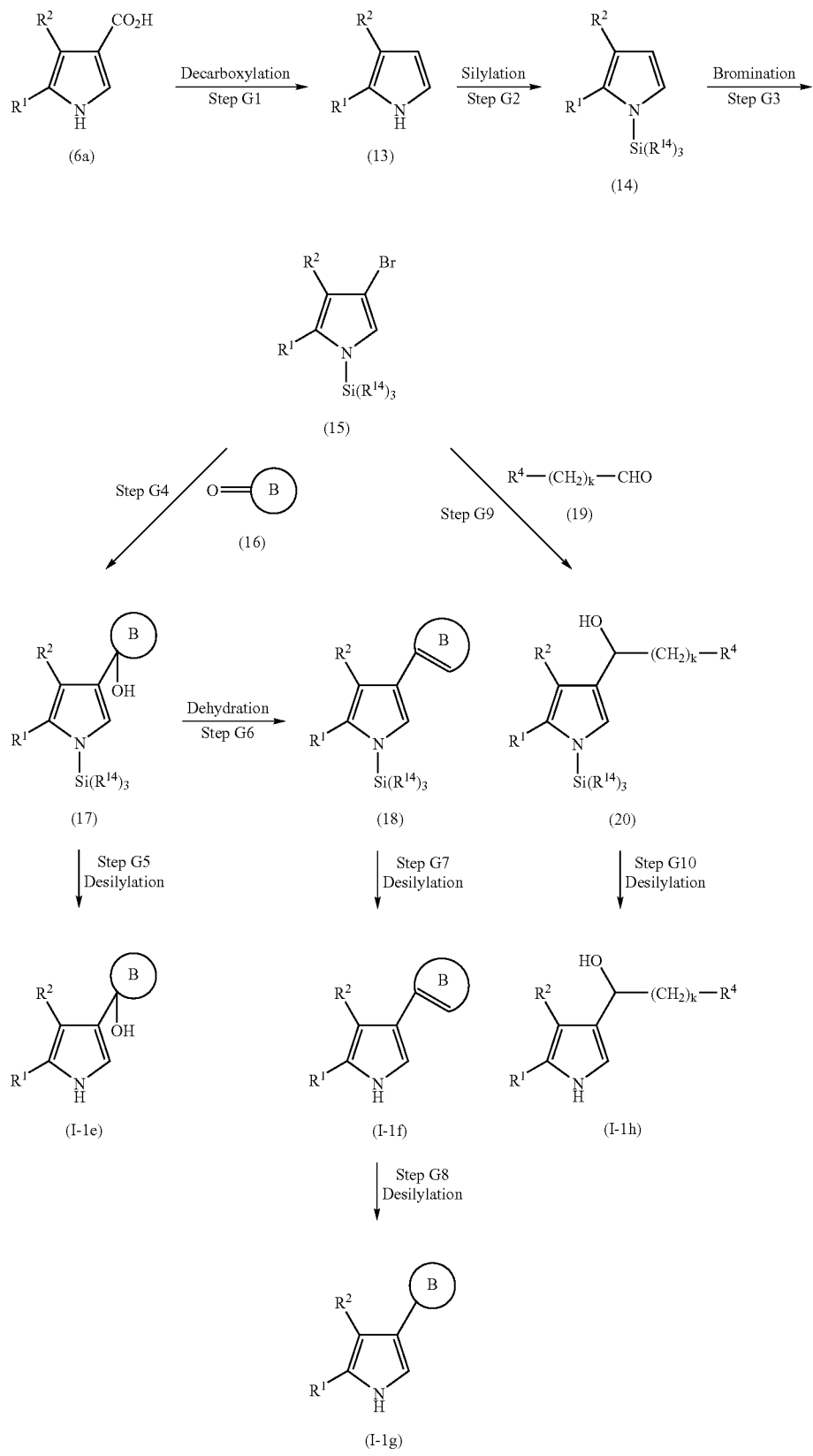

In the above formulae,

R¹, R², R⁴ and k are as defined above, the substituents $R^{14}$ may be the same or different from one another and each is selected from the group consisting of hydrogen atoms, lower alkyl groups as defined and exemplified above and aralkyl groups as defined and exemplified above, and cyclic group B is a heterocycl group corresponding to the heterocyclyl group which may be optionally substituted with at least one group selected from Substituent group a and Substituent group δ and which is substituted with at least one group selected from Substituent group β and Substituent group γ or the heterocyclyl group having at least one nitrogen atom, which may be optionally substituted with at least one group selected from Substituent group α and Substituent group δ as defined above in the definition of R⁴.

Step G1

In this Step, a di-substituted pyrrole compound of formula (13) is prepared by decarboxylating a carboxylic acid compound of formula (6a). Decarboxylation of the compound of formula (6a) can be performed by heating under acidic, alkaline or neutral conditions according to techniques conventionally used in synthetic organic chemistry, for example according to the methods described in detail in N. Yoshida et al., Yakugaku Zasshi, 93(5), 584–598 (1973), the contents of which are incorporated herein by reference thereto.

Steps G2 to G5

In Step G2, a silyl compound of formula (14) is prepared by silylating the nitrogen atom at the 1-position of the di-substituted pyrrole compound of formula (13) prepared in Step G1 above.

In Step G3, a bromopyrrole compound of formula (15) is prepared by brominating the silyl compound of formula (14) prepared in Step G2 above with a brominating agent (for example, N-bromosuccinimide, etc.).

In Step G4, a hydroxyheterocyclyl compound of formula (17) is prepared by lithiating the compound of formula (15) prepared in Step G3 above and then reacting it with a heterocyclyl ketone of formula (16).

In Step G5, the desired compound of formula (I-1e) is prepared by deprotecting (desilylating) the compound of formula (17) prepared in Step G4 above with a desilylating agent [e.g. tetrabutylammonium fluoride (TBAF)].

Each of the reactions in Steps G2 to G5 is well known in the field of synthetic organic chemistry and can be carried out using well known techniques. For example, the reactions in Steps G2 to G5 can be carried out according to the method described in detail in Brian L. Bray et al., J. Org. Chem., 55, 6317–6318 (1990), the contents of which are incorporated herein by reference thereto.

Step G6

In this Step, an unsaturated heterocyclyl compound of formula (18) is prepared by subjecting the hydroxyheterocyclyl compound of formula (17) prepared in Step G4 above to a dehydration reaction. Dehydration reactions of this type are well known in the field of synthetic organic chemistry and can be carried out using well known techniques. For example, the dehydration reaction can typically be carried out in the presence of an acid catalyst such as sulfuric acid, a solid catalyst such as alumina or a halogenating agent such as thionyl chloride [e.g. in accordance with the methods described in detail in G. H. Coleman & H. F. Johnstone, Org. Synth., I, 183 (1941), R. L. Sawyer & D. W. Andrus, Org. Synth., III, 276 (1955) and J. S. Lomas et al., Tetrahedron Lett., 599 (1971), the contents of which are incorporated herein by reference thereto]. Alternatively, the dehydration reaction of this step can be accomplished by a reaction using a trialkylsilane, such as triethylsilane, tripropylsilane or tributylsilane, and trifluoroacetic acid, for example in accordance with the method described by Francis A. Carey & Henry S. Tremper, J. Am. Chem. Soc., 91, 2967–2972 (1969), the contents of which are incorporated herein by reference thereto.

Step G7

In this Step, the desired compound of formula (I-1f) of the present invention is prepared by removing the protecting group (the silyl group) from the unsaturated heterocyclyl compound of formula (18) prepared in Step G6 above in a similar manner to that performed in Step G5 above.

Step G8

In this Step, the desired compound of formula (I-1g) of the present invention is prepared by reducing the double bond in the cyclic group B of the compound of formula (I-1f) prepared in Step G7 above. This is carried out in a similar manner to the procedure described in Step F9 above.

Step G9

In this Step, a hydroxy compound of formula (20) is prepared by reaction between the bromopyrrole compound of formula (15) prepared in Step G3 above and an aldehyde compound of formula (19). This is carried out in a procedure similar to that described in Step G4 above.

Step G10

In this Step, the desired compound of formula (I-1h) of the present invention is prepared by removing the protecting group (silyl group) from the hydroxy compound of formula (20) prepared in Step G9 above. This is carried out in a similar manner to that described in Step G5 above.

Where k in the compound of formula (I-1h) above is an integer of from 1 to 5, the hydroxyalkane moiety can be converted into the corresponding alkenylene moiety by subjecting such a compound to a dehydration reaction in a similar manner to that described in Step G6 above.

Method H

Generally, the compounds of formula (I) of the present invention can be prepared by introducing the R³ group into a pyrrole compound already substituted on the pyrrole ring with the R¹ group and R² group. Compounds of formula (I-1) can be prepared, for example, according to the Method H, as shown in Reaction Scheme H below.

Reaction Scheme H

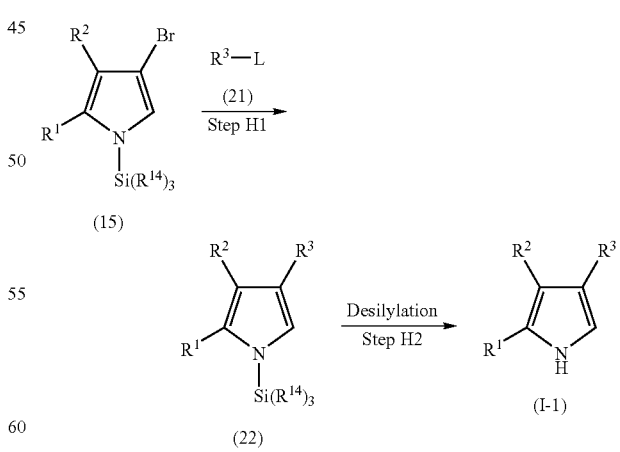

In the above formulae, R¹, R², R³ and $R^{14}$ are as defined above, and L represents a leaving group.

The leaving group L is a group which is capable of leaving as a nucleophilic residue. Examples include halogen atoms such as fluorine, chlorine, bromine and iodine, trihalogenomethyloxy groups such as trichloromethoxy, lower alkanesulfonyloxy groups such as methanesulfonyloxy and ethanesulfonyloxy groups, lower halogeno alkane sulfonyloxy groups such as trifluoromethanesulfonyloxy and pentafluoroethanesulfonyloxy groups, and arylsulfonyloxy groups such as benzenesulfonyloxy, p-toluenesulfonyloxy and p-nitrobenzenesulfonyloxy groups. Of these, halogen atoms are preferred, and bromine atoms are particularly preferred.

Step H1

In this Step, a compound of formula (22) is prepared by lithiating the bromopyrrole compound of formula (15) prepared in Step G3 above using a procedure similar to that described in Step G4 above and then reacting the lithiated intermediate with a compound of formula (21). Substitution reactions of a lithiated pyrrole intermediate of this type are well known in the field of synthetic organic chemistry and can be carried out using well known techniques, for example according to the methods described in detail in WO 99/01449, the contents of which are incorporated herein by reference thereto.

Step H2

In this Step, the desired compound of formula (I-1) is prepared by removing the protecting group (silyl group) from the compound of formula (22) prepared in Step H1 above according to a procedure similar to that used in Step G5 above.

Method I

In this method, compounds of formula (I) of the present invention wherein substituent $R^3$ is a group of formula —X—$R^4_a$, wherein $R^4_a$ is a heterocyclyl group which may be optionally substituted with at least one group selected from Substituent group α and Substituent group δ and which is substituted with at least one group selected from Substituent group β and Substituent group γ, as defined above, a heterocyclyl group having at least one nitrogen atom, which may be optionally substituted with at least one group selected from Substituent group α and Substituent group δ, as defined above, or a group of formula —$NR^aR^b$, wherein $R^a$ and $R^b$ are as defined above, in which said group is bonded to the group X through the nitrogen atom in said group $R^4_a$, can be prepared as shown in Reaction Scheme I below.

Reaction Scheme I

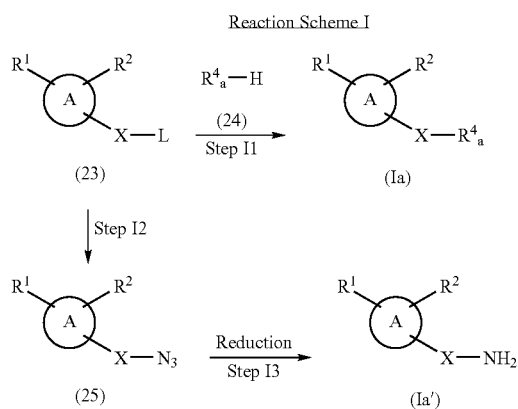

In the above formulae, A, $R^1$, $R^2$, $R^4_a$, L and X are as defined above.

Step I1

In this Step, the desired compound of formula (Ia) of the present invention is prepared by reacting a compound of formula (23) with an amine compound of formula (24) so as to replace the group L with the group $R^4_a$. Nucleophilic substitution reactions of this type are well known in the field of synthetic organic chemistry and can be carried out using well known techniques. This reaction is usually carried out in a solvent in the presence or absence of a base.

There is no particular restriction on the solvent used, provided that it has no adverse effect on the reaction or the reagents involved and that it can dissolve the reagents, at least to some extent. Examples of suitable solvents which can be used include: alcohols such as methanol, ethanol, propanol and isopropanol; ethers such as diethyl ether, diisopropyl ether, tetrahydrofuran and dioxane; aprotic polar solvents such as dimethylformamide, dimethylacetamide and dimethyl sulfoxide; nitrites such as acetonitrile; esters such as methyl acetate and ethyl acetate; aromatic hydrocarbons such as benzene, toluene and xylene; and aliphatic hydrocarbons such as pentane, hexane and heptane.

Examples of the base which can be used include: alkali metal alkoxides such as sodium methoxide, sodium ethoxide and potassium t-butoxide; alkali metal hydrides such as sodium hydride and lithium hydride; alkali metal hydroxides such as sodium hydroxide and potassium hydroxide; alkali metal carbonates such as sodium carbonate and potassium carbonate; and amines such as triethylamine, tributylamine, pyridine, picoline and 1,8-diazabicyclo[5.4.0]-7-undecene.

A compound of formula (Ia') of the present invention, which is a compound of formula (Ia) wherein $R^4_a$ is an amino group (—NH$_2$), can also be prepared via an azide compound (25) according to Steps I2 and I13 below.

Step I2

In this Step, an azide compound of formula (25) is prepared by reacting a compound of formula (23) with sodium azide in the presence of a solvent.

There is no particular restriction on the solvent used, provided that it has no adverse effect on the reaction or the reagents involved and that it can dissolve the reagents, at least to some extent. Examples of suitable solvents which can be used include: halogenated hydrocarbons such as dichloromethane, chloroform, carbon tetrachloride and dichloroethane; ethers such as diethyl ether, diisopropyl ether, tetrahydrofuran and dioxane; aprotic polar solvents such as dimethylformamide, dimethylacetamide and dimethylsulfoxide; nitriles such as acetonitrile; esters such as methyl acetate and ethyl acetate; aromatic hydrocarbons such as benzene, toluene and xylene; aliphatic hydrocarbons such as pentane, hexane and heptane; and mixtures thereof.

Step I3

In this Step, the desired compound of formula (Ia') of the present invention is prepared by reducing the azide compound of formula (25) prepared in Step I2 above. Reduction reactions of this type are well known in the field of synthetic organic chemistry and can be carried out using well known techniques, for example according to the catalytic reduction method described in detail in E. J. Corey et al., Synthesis, 590 (1975), the contents of which are incorporated herein by reference thereto.

Method J

In this method, compounds of formula (Ib) of the present invention wherein $R^2$ is a heteroaryl group having at least one nitrogen atom and is substituted with a group of formula —$NR^cR^d$, wherein $R^c$ and $R^d$ are as defined above can be prepared, as shown in Reaction Scheme J below.

Reaction Scheme J

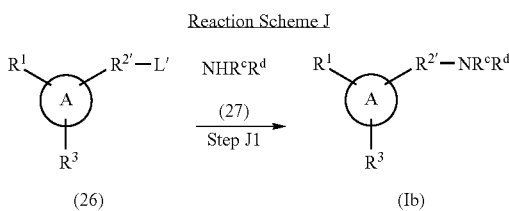

In the above formulae, the cyclic group A, $R^1$, $R^3$, $R^c$ and $R^d$ are as defined above, $R^{2'}$ is a heteroaryl group having at least one nitrogen atom as defined above in the definition of substituent $R^2$ and L' is a leaving group. Thus, the group —$R^{2'}$-L' is, for example, 2-methanesulfonylpyrimidin-4-yl, 2-methanesulfonylpyridin-4-yl, etc.

The leaving group L' is a similar group to the leaving groups defined and exemplified above in the definition of L or it is a lower alkylsulfonyl group as defined and exemplified above, such as a methanesulfonyl, ethanesulfonyl, propanesulfonyl or butanesulfonyl group. The group L' is preferably a lower alkylsulfonyl group, and more preferably a methanesulfonyl group.

Step J1

In this Step, the desired compound of formula (Ib) of the present invention is prepared by reacting a compound of formula (26) with an amine compound of formula (27) to replace the leaving group with a group of formula —$NR^cR^d$. This step is carried out using a procedure similar to that used in Step I1 above.

Method K

In this method, compounds of formula (I) of the present invention wherein $R^3$ is a group containing a pyridine ring can be prepared by subjecting a compound of formula (I) in which $R^3$ is a tetrahydropyridine group to a dehydrogenation reaction to convert the tetrahydropyridine group to a pyridine group, this dehydrogenation being as shown in Reaction Scheme K below.

Reaction Scheme K

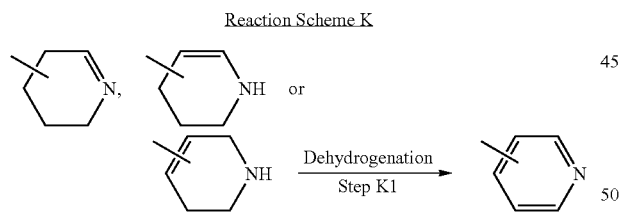

Dehydrogenation reactions of the type depicted in Step K1 above are well known in the field of synthetic organic chemistry and can be carried out using well known techniques, for example according to the method described in detail in G. Wieslaw et al., J. Med. Chem., 28, 311–317 (1985), the contents of which are incorporated herein by reference thereto, using a palladium-carbon catalyst.

The compounds which can be used as starting materials in Method A to Method J above, that is the compounds of formulae (1a), (1b), (1c), (1d), (1e), (2a), (2b), (2c), (2d), (2e), (4), (5), (6a), (16), (19), (21), (24) and (27), are either known compounds themselves or are compounds which are easily obtainable by treating known compounds according to known methods (for example, according to the methods described in WO 97/5877, the contents of which are incorporated herein by reference thereto). The starting materials of formulae (23) and (26) in Methods I and J respectively can be easily synthesized from known compounds by carrying out similar reactions to those described in Method A to Method E above.

Method L

In this method, a 4-oxopiperidine compound of formula (35), which is a starting material falling within the scope of the compounds of formula (16) above, is prepared as shown in the following Reaction Scheme L.

Reaction Scheme L

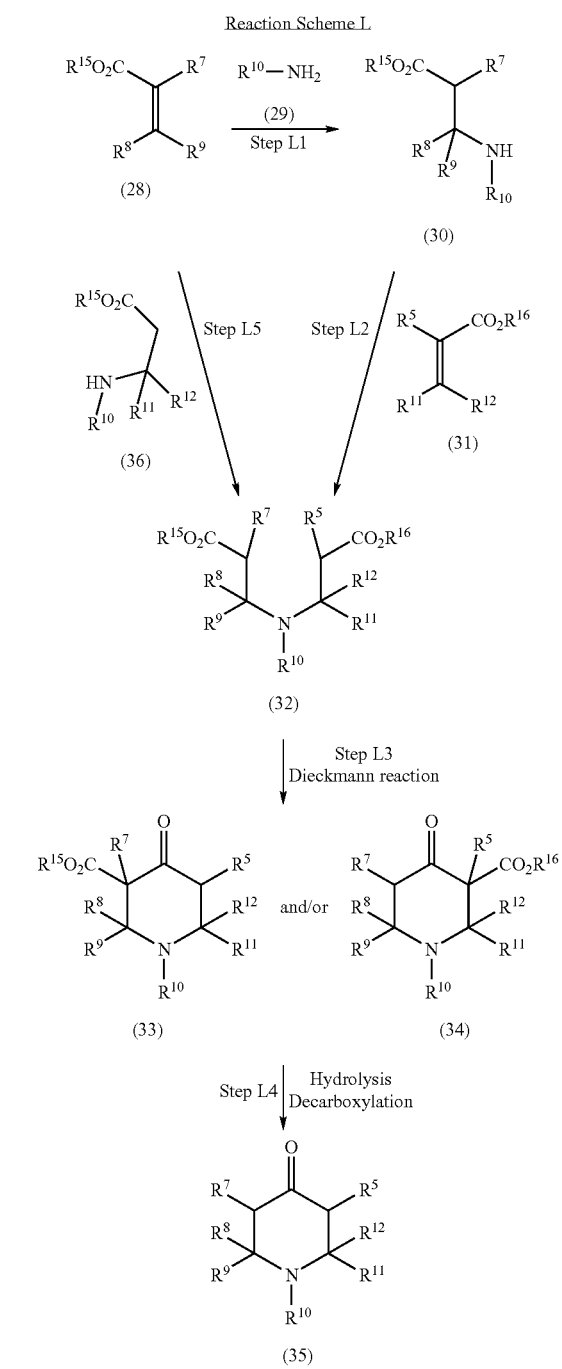

In the above formulae $R^5$, $R^7$, $R^8$, $R^9$, $R^{10}$, $R^{11}$ and $R^{12}$ are as defined above, and $R^{15}$ and $R^{16}$ are the same or different and each is a lower alkyl group as defined above or an aralkyl group as defined above.

Steps L1 to L5

In step L1, an amino ester compound of formula (30) is prepared by an addition reaction between an unsaturated ester compound of formula (28) and an amine compound of formula (29).

In Step L2, a diester compound of formula (32) is obtained by a further addition reaction between an unsaturated ester compound of formula (31) and the amino ester compound of formula (30) prepared in Step L1 above.

In Step L3, the compound of formula (32) prepared in Step L2 above is subjected to Dieckmann reaction to give a keto ester compound of formula (33) and/or formula (34).

In Step L4, the compound of formula (33) and/or the compound of formula (34) prepared in Step L3 above is subjected to consecutive hydrolysis and decarboxylation reactions to prepare the desired 4-oxopiperidine compound of formula (35).

Step L5 is an alternative process for the preparation of the diester compound of formula (32) and it involves reaction of the unsaturated ester compound of formula (28) with an amino ester compound of formula (36). This is carried out in a similar manner to that described in Step L2 above. Step L5 is preferably employed where the compound of formula (32) to be prepared is one wherein $R^{10}$ and $R^{11}$ together form an alkylene group having from 1 to 6 carbon atoms which is unsubstituted or is substituted with at least one substituent selected from the group consisting of Substituent group α defined above, Substituent group β defined above, Substituent group γ defined above and Substituent group δ defined above.

Each of the reactions in Steps L1 to L5 is well known in the field of synthetic organic chemistry and can be carried out using well known techniques. For example, the reactions in Steps L1 to L5 can be carried out according to the method described in detail in U. M. Teotino, J. Org. Chem., 27, 1406 (1962), the contents of which are incorporated herein by reference thereto.

Method M

In this method, a compound of formula (35a), which is a 4-oxopiperidine compound of formula (35) above wherein $R^{10}$ and $R^{11}$ together form an alkylene group having from 1 to 6 carbon atoms which is unsubstituted or is substituted with at least one substituent selected from the group consisting of Substituent group α defined above, Substituent group β defined above, Substituent group γ defined above and Substituent group δ defined above and each of $R^5$, $R^7$ to $R^9$ and $R^{12}$ is a hydrogen atom can be prepared as shown in Reaction Scheme M below.

Reaction Scheme M

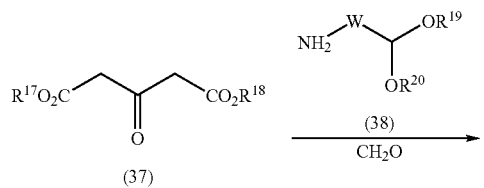

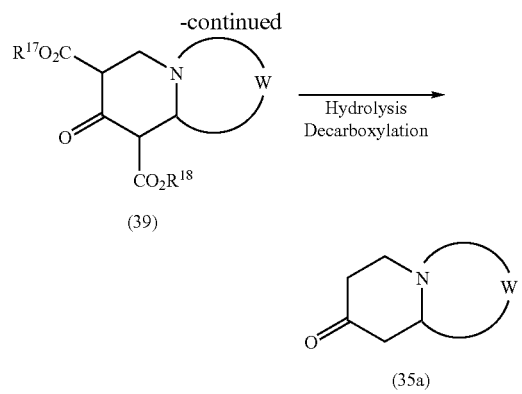

In the above formulae, $R^{17}$ and $R^{18}$ may be the same or different and each represents a lower alkyl group as defined and exemplified above or an aralkyl group as defined and exemplified above, $R^{19}$ and $R^{20}$ may be the same or different and each represents a lower alkyl group as defined and exemplified above or $R^{19}$ and $R^{20}$ together represent a lower alkylene group as defined and exemplified above, and W represents an alkylene group having from 1 to 6 carbon atoms which is unsubstituted or is substituted with at least one substituent selected from the group consisting of Substituent group α defined above, Substituent group β defined above, Substituent group γ defined above and Substituent group δ defined above.

The two steps of Method M can be carried out according to the methods described in detail in O. Pollet et al., Heterocycles, 43, 1391 (1996) and Anet et al., Austral. J. Scient. Res., <A3>, 635–640 (1950), the contents of which are incorporated herein by reference thereto.

After completion of each of the reactions described in the steps of Method A to Method M above, the desired compound may be isolated from the reaction mixture in a conventional manner. For example, it can be obtained by neutralizing the reaction mixture as needed, removing insoluble matters by filtration, if any are present, adding organic solvents which are not miscible with each other, such as water and ethyl acetate, washing with water or the like, separating the organic layer containing the desired compound, drying it over anhydrous magnesium sulfate or the like and then distilling off the solvent.

If necessary, the desired compound thus obtained can be isolated and purified by using a conventional method such as recrystallization or reprecipitation or by a chromatographic method. Examples of chromatography include adsorption column chromatography using a carrier such as silica gel, alumina or magnesium-silica gel type Florisil, chromatography using a synthetic adsorbent, for example, partition column chromatography using a carrier such as Sephadex LH-20 (product of Pharmacia), Amberlite XAD-11 (product of Rohm & Haas) or Diaion HP-20 (product of Mitsubishi Chemical), ion exchange chromatography and normal-phase reverse-phase column chromatography (high-performance liquid chromatography) using a silica gel or alkylated silica gel. If necessary, two or more of these techniques can be used in combination to isolate and purify the desired compound.

The heteroaryl-substituted pyrrole derivatives of the present invention exhibit excellent inhibitory activity against the production of inflammatory cytokines. Consequently, they are effective as a medicament, particularly as an agent for the prophylaxis or treatment of diseases mediated by inflammatory cytokines. Examples of such a medicament include analgesics, anti-inflammatory drugs and virucides, and agents for the prophylaxis and treatment of chronic rheumatoid arthritis, osteoarthritis, allergic diseases, asthma, septicaemia, psoriasis, osteoporosis, autoimmune diseases (e.g. systemic lupus erythematosus, ulcerative colitis and Crohn's disease), diabetes, nephritis, hepatitis, arteriosclerosis, cancer, ischemic heart disease and Alzheimer's disease. Of these, the compounds of the present invention are particularly useful as analgesics and anti-inflammatory drugs and as agents for the prophylaxis and treatment of chronic rheumatism, osteoarthritis, allergosis, sepsis, psoriasis, osteoporosis, ulcerative colitis, diabetes, hepatitis and arteriosclerosis.

The compounds of formula (I) and pharmacologically acceptable salts, esters and other derivatives thereof according to the present invention can be administered by a number of different routes. Examples of these administration routes include oral administration in the form of tablets, capsules, granules, powders or syrups and parenteral administration in the form of injections or suppositories. Such formulations can be prepared in a known manner by using carriers which may be and/or incorporate additives such as excipients, lubricants, binders, disintegrators, stabilizers, corrigents and diluents.

Examples of suitable excipients include: organic excipients, examples of which include sugar derivatives such as lactose, sucrose, dextrose, mannitol and sorbitol, starch derivatives such as corn starch, potato starch, α-starch, dextrin and carboxymethyl starch, cellulose derivatives such as crystalline cellulose, low-substituted hydroxypropylcellulose, hydroxypropylmethylcellulose, carboxymethylcellulose, calcium carboxymethylcellulose and sodium internally-crosslinked carboxymethylcellulose, gum arabic, dextran and pullulan; and inorganic excipients, examples of which include silicate derivatives such as soft silicic acid anhydride, synthetic aluminum silicate and magnesium aluminometasilicate, phosphates such as calcium phosphate, carbonates such as calcium carbonate, and sulfates such as calcium sulfate.

Examples of suitable lubricants include, stearic acid; metal salts of stearic acid such as calcium stearate and magnesium stearate; talc; colloidal silica; waxes such as bee gum and spermaceti; boric acid; adipic acid; sulfates such as sodium sulfate; glycol; fumaric acid; sodium benzoate; DL-leucine; sodium salts of an aliphatic acid; lauryl sulfates such as sodium lauryl sulfate and magnesium lauryl sulfate; silicic acid derivatives such as silicic anhydride and silicic acid hydrate; and starch derivatives exemplified above as examples of suitable excipients.

Examples of suitable binders include polyvinylpyrrolidone, Macrogol and compounds similar to those exemplified above as suitable excipients.

Examples of suitable disintegrators include compounds similar to those exemplified above as suitable excipients and chemically modified starch or cellulose derivatives such as sodium cross carmellose, sodium carboxymethyl starch and crosslinked polyvinylpyrrolidone.

Examples of suitable stabilizers include: paraoxybenzoate esters such as methylparaben and propylparaben; alcohols such as chlorobutanol, benzyl alcohol and phenylethyl alcohol; benzalkonium chloride; phenol derivatives such as phenol and cresol; thimerosal; dehydroacetic acid; and sorbic acid. Examples of suitable corrigents include sweeteners, acidifiers and flavors commonly employed for this purpose.

The dose of the compound of formula (I) or a pharmacologically acceptable salt, ester or other derivative thereof according to the present invention will vary depending on a variety of factors including the condition to be treated, the age of the patient and the administration route. When administered orally, it is administered to an adult in an amount of 0.1 mg (preferably 0.5 mg) a day as a lower limit and 2000 mg preferably 500 mg) a day as an upper limit. It can be administered in from one to several portions depending on the condition of the patient. When administered intravenously, it is administered to an adult in an amount of 0.01 mg (preferably 0.05 mg) a day as a lower limit and 200 mg (preferably 50 mg) a day as an upper limit. It can be administered in from one to several portions depending on the condition of the patient.

The requirement that the substituents $R^{1'}$ and $R^{3'}$ must be bonded to the two atoms of the pyrrole ring which are adjacent to the atom of the pyrrole ring to which the substituent $R^{2'}$ is bonded in the compounds of the above formula (I)' means that the compounds of formula (I)' are selected from compounds of the following formulae (I-1)' to (I-5)':

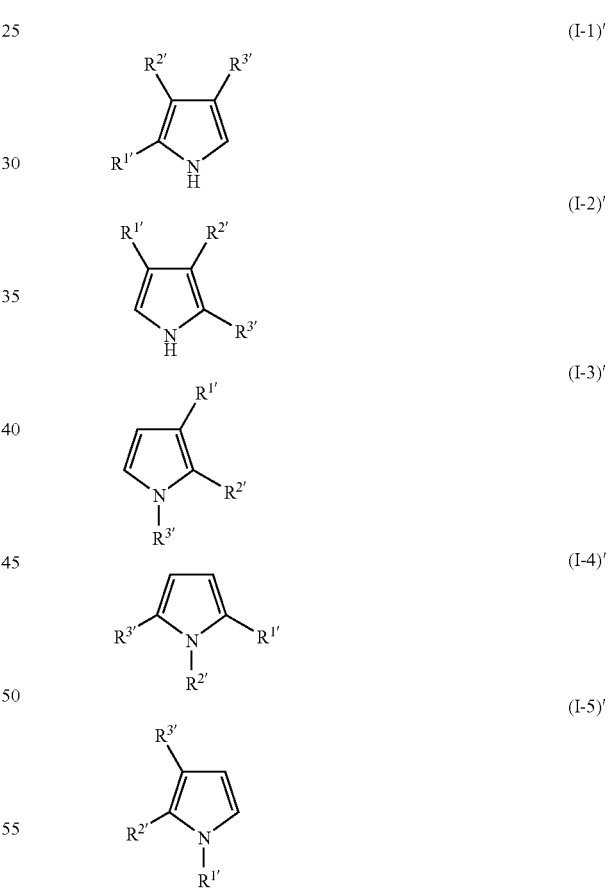

wherein $R^{1'}$, $R^{2'}$, and $R^{3'}$ are as defined above.

In the general formula (I)' above, the group $R^{4'}$ in the groups of general formulae (IIa)', (IIb)' and (IIc)' is defined as representing "from 1 to 3 substituents which are independently selected from the group consisting of Substituent group α' defined below, Substituent group β' defined below and Substituent group γ' defined below, or where B' is a heterocyclic ring which is fused with an aryl group, a heteroaryl group, a cycloalkyl group or a heterocyclyl group, $R^{4'}$ may be a hydrogen atom." This means that the following options are covered: (i) compounds of formula (I)' in which there are 1, 2 or 3 substituents selected from Substituent group α', Substituent group β' and Substituent group γ' anywhere on the bicyclic ring systems of formulae (IIa)', (IIb)' and (IIc)'; and (ii) compounds of formula (I)' in which the heterocyclic group B' is fused with an aryl group, a heteroaryl group, a cycloalkyl group or a heterocyclyl group and there are 0 ($R^{4'}$ represents hydrogen), 1, 2 or 3 substituents selected from Substituent group α', Substituent group β' and Substituent group γ' anywhere on the ring systems of formulae (IIa)', (IIb)' and (IIc)'.

Where $R^{1'}$ represents an aryl group which may optionally be substituted with at least one substituent selected from the group consisting of Substituent group α' defined above and Substituent group β' defined above, or where Substituent γ' represents an aryl group which is optionally substituted with at least one substituent selected from the group consisting of Substituent group α' defined above and Substituent group β' defined above, said aryl groups are aromatic hydrocarbon groups having from 6 to 14 carbon atoms in one or more rings, preferably from 6 to 10 carbon atoms, and examples include phenyl, naphthyl, phenanthryl and anthracenyl groups. Of these, we prefer phenyl and naphthyl groups, most preferably phenyl groups.

The aryl groups defined and exemplified above may be fused with a cycloalkyl group having from 3 to 10 carbon atoms. Examples of such a fused ring group include 5-indanyl groups.

Where $R^{1'}$ or Substituent γ' represents an aryl group which is substituted with at least one substituent selected from the group consisting of Substituent group α defined above and Substituent group β' defined above, it is preferably an aryl group substituted with 1 to 4 substituents selected from the group consisting of Substituent group α and Substituent group β', and more preferably it is an aryl group substituted with 1 to 3 substituents selected from Substituent group α and Substituent group β'. Examples of such substituted aryl groups include 4-fluorophenyl, 3-fluorophenyl, 4-chlorophenyl, 3-chlorophenyl, 3,4-difluorophenyl, 3,4-dichlorophenyl, 3,4,5-trifluorophenyl, 3-chloro-4-fluorophenyl, 3-difluoromethoxyphenyl, 3-trifluoromethoxyphenyl and 3-trifluoromethylphenyl.

Where $R^{1'}$ represents a heteroaryl group which may optionally be substituted with at least one substituent selected from the group consisting of Substituent group α' defined above and Substituent group β' defined above, said heteroaryl groups are 5- to 7-membered aromatic heterocyclic groups containing from 1 to 3 heteroatoms selected from the group consisting of sulfur atoms, oxygen atoms and nitrogen atoms. Examples of such heteroaryl groups include furyl, thienyl, pyrrolyl, pyrazolyl, imidazolyl, oxazolyl, isoxazolyl, thiazolyl, isothiazolyl, triazolyl, tetrazolyl, thiadiazolyl, pyridyl, pyridazinyl, pyrimidinyl and pyrazinyl groups. We prefer 5- or 6-membered aromatic heterocyclic groups containing one or two heteroatoms selected from the group consisting of sulfur atoms, oxygen atoms and nitrogen atoms, examples of which include furyl, thienyl, pyrrolyl, pyrazolyl, imidazolyl, oxazolyl, isoxazolyl, thiazolyl, isothiazolyl, pyridyl, pyridazinyl, pyrimidinyl and pyrazinyl groups. Of these, furyl, thienyl, pyridyl and pyrimidinyl groups are particularly preferred.

The heteroaryl groups defined and exemplified above may be fused with another cyclic group selected from the group consisting of aryl groups defined above and cycloalkyl groups having from 3 to 10 carbon atoms Examples of such a fused heteroaryl group include indolyl, benzofuranyl, benzothienyl, quinolyl, isoquinolyl, quinazolyl, tetrahydroquinolyl and tetrahydroisoquinolyl groups.

Where $R^{1'}$ represents a heteroaryl group which is substituted with at least one substituent selected from the group consisting of Substituent group α' and Substituent group β', said heteroaryl group is preferably a heteroaryl group substituted with from 1 to 3 substituents selected from the group consisting of Substituent group α' and Substituent group β', and more preferably it is a heteroaryl group substituted with one or two substituents selected from the group consisting of Substituent group α and Substituent group β'. Examples of such substituted heteroaryl groups include 5-fluoro-2-furyl, 4-chloro-2-thienyl, 5-difluoromethoxy-3-furyl, 5-trifluoromethyl-3-thienyl and 5-fluoro-2-oxazolyl groups.

Where $R^{2'}$ represents a heteroaryl group having at least one ring nitrogen atom, said heteroaryl group optionally being substituted with at least one substituent selected from the group consisting of Substituent group α defined above and Substituent group β' defined above, said heteroaryl groups are 5- to 7-membered aromatic heterocyclic groups containing at least one nitrogen atom and optionally containing one or two further heteroatoms selected from the group consisting of sulfur atoms, oxygen atoms and nitrogen atoms. Examples of such groups include pyrrolyl, pyrazolyl, imidazolyl, oxazolyl, isoxazolyl, thiazolyl, isothiazolyl, triazolyl, tetrazolyl, thiadiazolyl, pyridyl, pyridazinyl, pyrimidinyl and pyrazinyl groups. Of these, we prefer 5- or 6-membered aromatic heterocyclic groups containing one nitrogen atom and optionally containing one further heteroatom selected from the group consisting of sulfur atoms, oxygen atoms and nitrogen atoms, examples of which include pyrrolyl, pyrazolyl, imidazolyl, oxazolyl, isoxazolyl, thiazolyl, isothiazolyl, pyridyl, pyridazinyl, pyrimidinyl and pyrazinyl groups. 5- or 6-membered aromatic heterocyclic groups containing one or two nitrogen atoms, such as imidazolyl, pyridyl, pyridazinyl, pyrimidinyl and pyrazinyl groups are more preferred and pyridyl and pyrimidinyl groups are particularly preferred.

Where $R^{2'}$ represents a heteroaryl group having at least one ring nitrogen atom. 4-pyridyl and 4-pyrimidinyl groups are most preferred.

Where $R^{2'}$ represents a heteroaryl group having at least one ring nitrogen atom, said heteroaryl group optionally being substituted with at least one substituent selected from the group consisting of Substituent group α' and Substituent group β', said heteroaryl group is preferably a group substituted with 1 to 3 substituents selected from the group consisting of Substituent group α' and Substituent group β', more preferably it is a heteroaryl group substituted with one or two substituents selected from the group consisting of Substituent group α' and Substituent group β', still more preferably it is a heteroaryl group substituted with one substituent selected from the group consisting of Substituent group α' and Substituent group β', and particularly preferably it is a 4-pyridyl or 4-pyrimidinyl group which is substituted at the 2-position of said group with one substituent selected from Substituent group α and Substituent group β'. Most preferably, said heteroaryl group is a 4-pyridyl or 4-pyrimidinyl group which is substituted at the 2-position with a substituent of formula —$NR^{a'}R^{b'}$ (wherein $R^{a'}$ and $R^{b'}$ are same or different, and each independently represents a hydrogen atom, a lower alkyl group, a lower alkenyl group, a lower alkynyl group, an aralkyl group or a lower alkylsulfonyl group, or $R^{a'}$ and $R^{b'}$, taken together with the nitrogen atom to which they are attached, form a heterocyclyl group) or a lower alkyl group substituted with a substituent of formula —NR$^{a'}$R$^{b'}$ (wherein R$^{a'}$ and R$^{b'}$ have the same meaning as above). Preferred examples of such a group include 2-amino-4-pyridyl, 2-amino-4-pyrimidinyl, 2-methylamino-4-pyridyl, 2-methylamino-4-pyrimidinyl, 2-methoxy-4-pyridyl. 2-methoxy-4-pyrimidinyl, 2-benzylamino-4-pyridyl, 2-benzylamino 4-pyrimidinyl, 2-(α'-methylbenzylamino)-4-pyridyl and 2-α-methylbenzylamino)-4-pyrimidinyl.

The ring B' is defined as a "4- to 7-membered heterocyclic ring which has at least one ring nitrogen atom", by which we mean a 4- to 7-membered heterocyclic ring which consists of group D', group E', and 2 to 5 atoms or groups selected from carbon atoms, nitrogen atoms, oxygen atoms, sulfur atoms, >SO and >SO$_2$, said heterocyclic ring containing at least one ring nitrogen atom. It will be appreciated that, where said ring B' contains only one ring nitrogen atom, then this nitrogen atom is either group D' or group E'. The 4- to 7-membered heterocyclic ring of ring B' may be a saturated heterocyclic ring or an unsaturated heterocyclic ring. Preferably, the ring B' is a 5- or 6-membered heterocyclic ring which contains one nitrogen atom and which may optionally contain one further ring heteroatom or ring group selected from nitrogen atoms, oxygen atoms, sulfur atoms, >SO and >SO$_2$; more preferably it is pyrrolidine, pyrroline, imidazolidine, imidazoline, pyrazolidine, pyrazoline, oxazolidine, thiazolidine, piperidine, tetrahydropyridine, dihydropyridine, piperazine, morpholine or thiomorpholine; still more preferably it is pyrrolidine, pyrroline or imidazoline; and most preferably it is pyrrolidine or pyrroline.

The heterocyclic ring B' defined and exemplified above may optionally be fused with an aryl group, a heteroaryl group, a cycloalkyl group or a heterocyclyl group, said aryl, heteroaryl and heterocyclyl groups optionally being substituted with at least one substituent selected from Substituent group α' defined above and Substituent group β' defined above. Said aryl groups are as defined and exemplified above for substituent R$^{1'}$ and Substituent group γ'. Said heteroaryl groups are as defined and exemplified above for substituent R$^{1'}$. Said cycloalkyl groups are cycloalkyl groups having from 3 to 7 carbon atoms, such as cyclopropyl, cyclobutyl, cyclopentyl, cyclohexyl and cycloheptyl groups, of which we prefer cycloalkyl groups having from 3 to 6 carbon atoms. Said heterocyclyl groups are 4- to 7-membered heterocyclyl groups which have from 1 to 3 ring sulfur atoms, oxygen atoms and/or nitrogen atoms, and preferably 4- to 7-membered heterocyclyl groups which have 1 or 2 heteroatoms selected from the group consisting of sulfur atoms, oxygen atoms and nitrogen atoms. Of these, 5- or 6-membered heterocyclyl groups which contain one ring nitrogen atom and which may optionally contain one further oxygen atom, sulfur atom or nitrogen atom are preferred, and examples of such groups include azetidinyl, pyrrolidinyl, pyrrolinyl, imidazolidinyl, imidazolinyl, pyrazolidinyl, pyrazolinyl, oxazolidinyl, thiazolidinyl, piperidyl, tetrahydropyridyl, dihydropyridyl, piperazinyl, morpholinyl, thiomorpholinyl and homopiperidyl.

Examples of such a fused ring system for ring B' include tetrahydroquinoline, octahydroquinoline, decahydroquinoline, tetrahydroisoquinoline, octahydroisoquinoline, decahydroisoquinoline, indoline, octahydroindole, isoindoline and octahydroisoindole.

The lower alkyl groups in the definitions of R$^{a'}$, R$^{b'}$ and Substituent group β', and the lower alkyl moiety of the lower alkyl groups which may optionally be substituted with at least one substituent selected from Substituent group α' in the definition of Substituent group β' are straight or branched alkyl groups having from 1 to 6 carbon atoms. Examples of said lower alkyl groups include methyl, ethyl, propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl groups. Alkyl groups having from 1 to 4 carbon atoms are preferred, methyl, ethyl, propyl, isopropyl and butyl groups are more preferred, and methyl, ethyl and propyl groups are most preferred.

The lower alkenyl groups in the definitions of R$^{a'}$, R$^{b'}$ and Substituent group β', and the lower alkenyl moiety of the lower alkenyl groups which may optionally be substituted with at least one substituent selected from Substituent group α' in the definition of Substituent group β' are straight or branched alkenyl groups having from 2 to 6 carbon atoms. Examples of said lower alkenyl groups include vinyl, 2-propenyl, 1-methyl-2-propenyl, 2-methyl-2-propenyl, 2-ethyl-2-propenyl, 2-butenyl, 1-methyl-2-butenyl, 2-methyl-2-butenyl, 1-ethyl-2-butenyl, 3-butenyl, 1-methyl-3-butenyl, 2-methyl-3-butenyl, 1-ethyl-3-butenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methylpentenyl, 2-methyl-4-pentenyl, 2-hexenyl, 3-hexenyl, 4-hexenyl and 5-hexenyl groups. Alkenyl groups having from 2 to 4 carbon atoms are preferred, and alkenyl groups having 2 or 3 carbon atoms are most preferred.

The lower alkynyl groups in the definitions of R$^{a'}$, R$^{b'}$ and Substituent group β', and the lower alkynyl moiety of the lower alkynyl groups which may optionally be substituted with at least one substituent selected from Substituent group α' in the definition of Substituent group β' are straight or branched alkynyl groups having from 2 to 6 carbon atoms. Examples of said lower alkynyl groups include ethynyl, 2-propynyl, 1-methyl-2-propynyl, 2-butynyl, 1-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 3-pentynyl, 1-methyl-3-pentynyl, 2-methyl-,-pentynyl, 4-pentynyl, 1-methyl-4-pentynyl, 2-methyl 4-pentynyl, 2-hexynyl, 3-hexynyl, 4-hexynyl and 5-hexynyl groups. Alkynyl groups having from 2 to 4 carbon atoms are preferred, and alkynyl groups having 2 or 3 carbon atoms are most preferred.

The aralkyl group in the definitions of R$^{a'}$, R$^{b'}$ and Substituent group β' is a lower alkyl group as defined above which is substituted with at least one aryl group as defined above which may optionally be substituted with from 1 to 3 substituents selected from Substituent group α' defined above and Substituent group β' defined above. Examples of such a group include benzyl, indenylmethyl, phenanthrylmethyl, anthrylmethyl, α-naphthylmethyl, β-naphthylmethyl, diphenylmethyl, triphenylmethyl, α-naphthyldiphenylmethyl, β-anthrylmethyl, piperonyl, 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 1-phenylpentyl, 2-phenylpentyl, 3-phenylpentyl, 4-phenylpentyl, 5-phenylpentyl, 1-naphthylpentyl, 2-naphthylpentyl, 3-naphthylpentyl, 4-naphthylpentyl, 5-naphthylpenthyl, 1-phenylhexyl, 2-phenylhexyl, 3-phenylhexyl, 4-phenylhexyl, 5-phenylhexyl, 6-phenylhexyl, 1-naphthylhexyl, 2-naphthylhexyl, 3-naphthylhexyl, 4-naphthylhexyl, 5-naphthylhexyl and 6-naphthylhexyl. Of these, benzyl, phenanthrylmethyl, anthrylmethyl, α-naphthylmethyl, β-naphthylmethyl, diphenylmethyl, triphenylmethyl, 9-anthrylmethyl, piperonyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl are preferred.

As noted above, the aryl moiety of the aralkyl groups may optionally be substituted with from 1 to 3 substituents selected from Substituent group α' and Substituent group β' defined above. Examples of such a substituted aralkyl group include aralkyl groups substituted with halogen atoms such as 2-fluorobenzyl, 3-fluorobenzyl, 4-fluorobenzyl, 2-chlorobenzyl, 3-chlorobenzyl, 4-chlorobenzyl, 2-bromobenzyl, 3-bromobenzyl, 4-bromobenzyl, 3,5-difluorobenzyl, 2,5-difluorophenethyl, 2,6-difluorobenzyl, 2,4-difluorophenethyl, 3,5-dibromobenzyl, 2,5-dibromophenethyl, 2,6-dichlorobenzyl, 2,4-dichlorophenethyl, 2,3,6-trifluorobenzyl, 2,3,4-trifluorophenethyl, 3,4,5-trifluorobenzyl, 2,5,6-trifluorophenethyl, 2,4,6-trifluorobenzyl, 2,3,6-tribromophenetyl, 2,3,4-tribromobenzyl, 3,4,5-tribromophenethyl, 2,5,6-trichlorobenzyl, 2,4,6-trichlorophenethyl, 1-fluoro-2-naphthylmethyl, 2-fluoro-1-naphthylethyl, 3-fluoro-1-naphthylmethyl, 1-chloro-2-naphthylethyl, 2-chloro-1-naphthylmethyl, 3-bromo-1-naphthylethyl, 3,8-difluoro-1-naphthylmethyl, 2,3-difluoro-1-naphthylethyl, 4,8-difluoro-1-naphthylmethyl, 5,6-difluoro-1-naphthylethyl, 3,8-dichloro-1-naphthylmethyl, 2,3-dichloro-1-naphthylethyl, 4,8-dibromo-1-naphthylmethyl, 5,6-dibromo-1-naphthylethyl, 2,3,6-trifluoro-1-naphthylmethyl, 2,3,4-trifluoro-1-naphthylethyl, 3,4,5-trifluoro-1-naphthylmethyl, 4,5,6-trifluoro-1-naphthylethyl, 2,4,8-trifluoro-1-naphthylmethyl, bis(2-fluorophenyl)methyl, 3-fluorophenylphenylmethyl, bis(4-fluorophenyl)methyl, 4-fluorophenylphenylmethyl, bis(2-chlorophenyl)methyl, bis(3-chlorophenyl)methyl, bis(4-chlorophenyl)methyl, 4-chlorophenylphenylmethyl, 2-bromophenylphenylmethyl, 3-bromophenylphenylmethyl, bis(4-bromophenyl)methyl, bis(3,5-difluorophenyl)methyl, bis(2,5-difluorophenyl)methyl, bis(2.6-difluorophenyl)methyl, 2,4-difluorophenylphenylmethyl, bis(3,5-dibromophenyl)methyl, 2,5-dibromophenylphenylmethyl, 2,6-dichlorophenylphenylmethyl, bis(2,4-dichlorophenyl)methyl and bis(2,3,6-trifluorophenyl)methyl; aralkyl groups substituted with halogeno lower alkyl groups such as 2-trifluoromethylbenzyl, 3-trifluoromethylphenethyl, 4-trifluoromethylbenzyl, 2-trichloromethylphenethyl, 3-dichloromethylbenzyl, 4-trichloromethylphenethyl, 2-tribromomethylbenzyl, 3-dibromomethylphenethyl, 4-dibromomethylbenzyl, 3,5-bistrifluoromethylphenethyl, 2,5-bistrifluoromethylbenzyl, 2,6-bistrifluoromethylphenethyl, 2,4-bistrifluoromethylbenzyl, 3,5-bistribromomethylphenethyl, 2,5-bisdibromomethylbenzyl, 2,6-bisdichloromethylmethylphenethyl, 2,4-bisdichloromethylbenzyl, 2,3,6-tristrifluoromethylphenethyl, 2,3,4-tristrifluoromethylbenzyl, 3,4,5-tristrifluoromethylphenethyl, 2,5,6-tristrifluoromethylbenzyl, 2,4,6-tristrifluoromethylphenethyl, 2,3,6-tristribromomethylbenzyl, 2,3,4-trisdibromomethylphenethyl, 3,4,5-tristribromomethylbenzyl, 2,5,6-trisdichloromethylmethylphenethyl, 2,4,6-trisdichloromethylbenzyl, 1-tifluoromethyl-2-naphthylethyl, 2-trifluoromethyl-1-naphthylmethyl, 3-trifluoromethyl-1-naphthylethyl, 1-trichloromethyl-2-naphthylmethyl, 2-dichloromethyl-1-naphthylethyl, 3-tribromomethyl-1-naphthylmethyl, 3,8-bistrifluoromethyl-1-naphthylethyl, 3,8-bistrifluoromethyl-1-naphthylmethyl, 2,3-bistrifluoromethyl-1-naphthylmethyl, 4,8-bistrifluoromethyl-1-naphthylethyl, 5,6-bistrifluoromethyl-1-naphthylmethyl, 3,8-bistrichloromethyl-1-naphthylethyl, 2,3-bisdichloromethyl-1-naphthylmethyl, 4,8-bisdibromomethyl-1-naphthylethyl, 5,6-bistribromomethyl-1-naphthylmethyl, 2,3,6-tristrifluoromethyl-1-naphthylethyl, 2,3,4-tristrifluoromethyl-1-naphthylmethyl, 3,4,5-tristrifluoromethyl-1-naphthylethyl, 4,5,6-tristrifluoromethyl-1-naphthylmethyl, 2,4,8-tristrifluoromethyl-1-naphthylmethyl, bis(4-trifluoromethylphenyl)methyl, 4-trifluoromethylphenylphenylmethyl, bis(2-trichloromethylphenyl)methyl, bis(3-trichloromethylphenyl)methyl, bis(4-trichloromethylphenyl)methyl, 2-tribromomethylphenylmethyl, 3-tribromomethylphenylphenylmethyl, bis(4-tribromomethylphenyl)methyl, bis(3,5-bistrifluoromethylphenyl)methyl, bis(2,5-bistrifluoromethylphenyl)methyl, bis(2,6-bistrifluoromethylphenyl)methyl, 2,4-bistrifluoromethylphenylphenylmethyl, bis(3,5-bistribromomethylphenyl)methyl, 2,5-bistribromomethylphenylphenylmethyl, 2,6-bistrichloromethylphenylphenylmethyl, bis(2,4-bistrichloromethylphenyl)methyl and bis(2,3,6-tristrifluoromethylphenyl)methyl, aralkyl groups substituted with lower alkyl groups such as 2-methylbenzyl, 3-methylbenzyl, 4-methylbenzyl, 2-methylphenethyl, 4-methylphenethyl, 2-ethylbenzyl, 3-propylphenethyl, 4-ethylbenzyl, 2-butylphenethyl, 3-pentylbenzyl, 4-pentylphenethyl, 3,5-dimethylbenzyl, 2,5-dimethylphenethyl, 2,6-dimethylbenzyl, 2,4-dimethylphenethyl, 3,5-dibutylbenzyl, 2,5-dipentylphenethyl, 2,6-dipropylbenzyl, 2,4-dipropylphenethyl, 2,3,6-trimethylbenzyl, 2,3,4-trimethylphenethyl, 3,4,5-trimethylbenzyl, 2,4,6-trimethylbenzyl, 2,5,6-trimethylphenethyl, 2,3,6-tributylphenethyl, 2,3,4-tripentylbenzyl, 3,4,5-tributylphenethyl, 2,5,6-tripropylbenzyl, 2,4,6-tripropylphenethyl, 1-methyl-2-naphthylmethyl, 2-methyl-1-naphthylethyl, 3-methyl-1-naphthylmethyl, 1-ethyl-2-naphthylethyl, 2-propyl-1-naphthylmethyl, 3-butyl-1-naphthylethyl, 3,8-dimethyl-1-naphthylmethyl, 2,3-dimethyl-1-naphthylethyl, 4,8-dimethyl-1-naphthylmethyl, 5,6-dimethyl-1-naphthylethyl, 3,8-diethyl-1-naphthylmethyl, 2,3-dipropyl-1-naphthylmethyl, 4,8-dipentyl-1-naphthylethyl, 5,6-dibutyl-1-naphthylmethyl, 2,3,6-trimethyl-1-naphthylmethyl, 2,3,4-trimethyl-1-naphthylethyl, 3,4,5-trimethyl-1-naphthylmethyl, 4,5,6-trimethyl-1-naphthylmethyl, 2,4,8-trimethyl-1-naphthylmethyl, bis(2-methylphenyl)methyl, 3-methylphenylphenylmethyl, bis(4-methylphenyl)methyl, 4-methylphenylphenylmethyl, bis(2-ethylphenyl)methyl, bis(3-ethylphenyl)methyl, bis(4-ethylphenyl)methyl, 2-propylphenylphenylmethyl, 3-methyl, bis(2,5-dimethylphenyl)methyl, bis(2,6-dimethylphenyl)methyl, 2,4-dimethylphenylphenylmethyl, bis(3,5-dipropylphenyl)methyl, 2,5-dipropylphenylphenylmethyl, 2,6-diethylphenylphenylmethyl, bis(2,4-diethylphenyl)methyl and bis(2,3,6-trimethylphenyl)methyl; aralkyl groups substituted with lower alkoxy groups such as 2-methoxybenzyl, 3-methoxybenzyl, 4-methoxybenzyl, 3-methoxyphenethyl, 2-ethoxyphenethyl, 3-propoxybenzyl, 4-ethoxyphenethyl, 2-butoxybenzyl, 3-pentoxyphenethyl, 4-pentoxybenzyl, 3,5-dimethoxyphenethyl, 2,5-dimethoxybenzyl, 2,6-dimethoxyphenethyl, 2,4-dimethoxybenzyl, 3,5-dibutoxyphenethyl, 2,5-dipentoxybenzyl, 2,6-dipropoxyphenethyl, 2,4-dipropoxybenzyl, 2,3,6-trimethoxyphenethyl, 2,3,4-trimethoxybenzyl, 3,4,5-trimethoxyphenethyl, 2,5,6-trimethoxybenzyl, 2,4,6-trimethoxyphenethyl, 2,3,6-tributoxybenzyl, 2,3,4-tripentoxyphenethyl, 3,4,5-tributoxybenzyl, 2,5,6-tripropoxyphenethyl, 2,4,6-tripropoxybenzyl, 1-methoxy-2-naphthylmethyl, 2-methoxy-1-naphthylethyl, 3-methoxy-1-naphthylethyl, 1-ethoxy-2-naphthylmethyl, 2-propoxy-1-naphthylmethyl, 3-butoxy-1-naphthylethyl, 3,8-dimethoxy- 1-naphthylmethyl, 2,3-dimethoxy-1-naphthylmethyl, 4,8-dimethoxy-1-naphthylethyl, 5,6-dimethoxy-1-naphthylmethyl, 3,8-diethoxy-1-naphthylmethyl, 2,3-dipropoxy-1-naphthylethyl, 4,8-dipentoxy-1-naphthylmethyl, 5,6-dibutoxy-1-naphthylmethyl, 2,3,6-trimethoxy-1-naphthylethyl, 2,3,4-trimethoxy-1-naphthylmethyl, 3,4,5-trimethoxy-1-naphthylmethyl, 4,5,6-trimethoxy-1-naphthylethyl, 2,4,8-trimethoxy-1-naphthylmethyl, bis(2-methoxyphenyl)methyl, 3-methoxyphenylphenylmethyl, bis(4-methoxyphenyl)methyl, 4-methoxyphenylphenylmethyl, bis(2-ethoxyphenyl)methyl, bis(3-ethoxyphenyl)methyl, bis(4-ethoxyphenyl)methyl, 2-propoxyphenylphenylmethyl, 3-propoxyphenylphenylmethyl, bis(4-propoxyphenyl)methyl, bis(3,5-dimethoxyphenyl)methyl, bis(2,5-dimethoxyphenyl)methyl, bis(2,6-dimethoxyphenyl)methyl, 2,4-dimethoxyphenylphenylmethyl, bis(3,5-dipropoxyphenyl)methyl, 2,5-dipropoxyphenylphenylmethyl, 2,6-diethoxyphenylphenylmethyl, bis(2,4-diethoxyphenyl)methyl and bis(2,3,6-trimethoxyphenyl)methyl; aralkyl groups substituted with amino groups such as 2-aminophenethyl, 3-aminobenzyl, 4-aminophenethyl, 3,5-diaminobenzyl, 2,5-diaminophenethyl, 2,6-diaminobenzyl, 2,4-diaminophenethyl, 2,3,6-triaminobenzyl, 2,3,4-triaminophenethyl, 3,4,5-triaminobenzyl, 2,5,6-triaminophenethyl, 2,4,6-triaminobenzyl, 1-amino-2-naphthylmethyl, 2-amino-1-naphthylethyl, 3-amino-1-naphthylmethyl, 3,8-diamino-1-naphthylmethyl, 2,3-diamino-1-naphthylethyl, 4,8-diamino-1-naphthylmethyl, 5,6-diamino-1-naphthylmethyl, 2,3,6-triamino-1-naphthylethyl, 2,3,4-triamino-1-naphthylmethyl, 3,4,5-triamino-1-naphthylmethyl, 4,5,6-triamino-1-naphthylethyl, 2,4,8-triamino-1-naphthylmethyl, bis(2-aminophenyl)methyl, 3-aminophenylphenylmethyl, bis(4 aminophenyl)methyl, 4-aminophenylphenylmethyl, bis(3,5-diaminophenyl)methyl, bis(2,5-diaminophenyl)methyl, bis(2,6-diaminophenyl)methyl, 2,4-diaminophenylphenylmethyl and bis(2,3,6-triaminophenyl)methyl; aralkyl groups substituted with nitro groups such as 2-nitrophenethyl, 3-nitrobenzyl, 4-nitrobenzyl, 4-nitrophenethyl, 3,5-dinitrobenzyl, 2,5-dinitrophenethyl, 2,6-dinitrobenzyl, 2,4-dinitrophenethyl, 2,3,6-trinitrobenzyl, 2,3,4-trinitrophenethyl, 3,4,5-trinitrobenzyl, 2,5,6-trinitrophenethyl, 2,4,6-trinitrobenzyl, 1-nitro-2-naphthylmethyl, 2-nitro-1-naphthylethyl, 3-nitro-1-naphthylmethyl, 3,8-dinitro-1-naphthylmethyl, 2,3-dinitro-1-naphthylethyl, 4,8-dinitro-1-naphthylmethyl, 5,6-dinitro-1-naphthylmethyl, 2,3,6-trinitro-1-naphthylethyl, 2,3,4-trinitro-1-naphthylmethyl, 3,4,5-trinitro-1-naphthylmethyl, 4,5,6-trinitro-1-naphthylethyl, 2,4,8-trinitro-1-naphthylmethyl, bis(2-nitrophenyl)methyl, 3-nitrophenylphenylmethyl, bis(4-nitrophenyl)methyl, 4-nitrophenylphenylmethyl, bis(3,5-dinitrophenyl)methyl, bis(2,5-dinitrophenyl)methyl, bis(2,6-dinitrophenyl)methyl, 2,4-dinitrophenylphenylmethyl and bis(2,3,6-trinitrophenyl)methyl; and aralkyl groups substituted with cyano groups such as 2-cyanophenethyl, 3-cyanobenzyl, 4-cyanobenzyl, 4-cyanobenzyldiphenylmethyl, 4-cyanophenethyl, 3,5-dicyanobenzyl, 2,5-dicyanophenethyl, 2,6-dicyanobenzyl, 2,4-dicyanophenethyl, 2,3,6-tricyanobenzyl, 2,3,4-tricyanophenethyl, 3,4,5-tricyanobenzyl, 2,5,6-tricyanophenethyl, 2,4,6-tricyanobenzyl, 1-cyano-2-naphthylmethyl, 3-cyano-1-naphthylmethyl, 3,8-dicyano-1-naphthylmethyl, 2,3-dicyano-1-naphthylethyl, 4,8-dicyano-1-naphthylmethyl, 5,6-dicyano-1-naphthylmethyl, 2,3,6-tricyano-1-naphthylethyl, 2,3,4-tricyano-1-naphthylmethyl, 3,4,5-tricyano-1-naphthylmethyl, 4,5,6-tricyano-1-naphthylethyl, 2,4,8-tricyano-1-naphthylmethyl, bis(2-cyanophenyl)methyl, 3-cyanophenylphenylmethyl, bis(4-cyanophenyl)methyl, 4-cyanophenylphenylmethyl, bis(3,5-dicyanophenyl)methyl, bis(2,5-dicyanophenyl)methyl, bis(2,6-dicyanophenyl)methyl, 2,4-dicyanophenylphenylmethyl and bis(2,3,6-tricyanophenyl)methyl.

Of the above, unsubstituted aralkyl groups and aralkyl groups substituted with at least one substituent selected from the group consisting of halogen atoms, lower alkyl groups and lower alkoxy groups are preferred, unsubstituted aralkyl groups and aralkyl groups substituted with at least one substituent selected from the group consisting of halogen atoms and lower alkyl groups are more preferred, and unsubstituted aralkyl groups are most preferred.

Where $R^{a'}$, $R^{b'}$ or Substituent γ' represent a lower alkylsulfonyl group, this is a group in which a lower alkyl group, defined and exemplified above, is bonded to a sulfonyl group (—$SO_2$—). The lower alkylsulfonyl group is preferably a straight or branched alkylsulfonyl group having from 1 to 4 carbon atoms, more preferably a methylsulfonyl, ethylsulfonyl, propylsulfonyl, isopropylsulfonyl or butylsulfonyl group, and most preferably a methylsulfonyl, ethylsulfonyl or propylsulfonyl group.

Where $R^{a'}$ and $R^{b'}$ together with the nitrogen atom to which they are attached represent a heterocyclyl group, said heterocyclyl group is a 4- to 7-membered heterocyclyl group which contains one nitrogen atom and which optionally contains one further heteroatom selected from the group consisting of oxygen atoms, sulfur atoms and nitrogen atoms. Examples of such heterocyclyl groups include 1-azetidinyl, 1-pyrrolidinyl, 1-pyrrolinyl, 1-imidazolidinyl, 1-imidazolinyl, 1-pyrazolidinyl, 1-pyrazolinyl, 3-oxazoldinyl, 3-thiazolidinyl, 1-piperidyl, tetrahydropyridin-1-yl, dihydropyridin-1-yl, 1-piperazinyl, 4-morpholinyl, 4-thiomorpholinyl, 1-homopiperidyl, 8-azabicyclo[3.2.1]octan-8-yl, 8-azabicyclo-[3.2.1]octen-8-yl, 9-azabicyclo[3.3.1]nonan-9-yl and 9-azabicyclo[3.3.1]nonen-9-yl.

Where substituents $R^{a'}$ and $R^{b'}$ together with the nitrogen atom to which they are bonded form a heterocyclyl group as defined and exemplified above, said heterocyclyl groups may be fused with another cyclic group selected from the group consisting of aryl groups defined above and heteroaryl groups defined above. Examples of such fused heterocyclyl groups include tetrahydroquinolin-1-yl and tetrahydroisoquinolin-2-yl.

The halogen atoms in the definition of Substituent group α' include fluorine, chlorine, bromine and iodine atoms, of which fluorine and chlorine atoms are preferred.

Where the substituent in the definition of Substituent group α' is a lower alkoxy group, this is a group in which an oxygen atom is bonded to a lower alkyl group as defined and exemplified above. The alkoxy groups are preferably straight or branched alkoxy groups having 1 to 4 carbon atoms, more preferably, methoxy, ethoxy, propoxy, isopropoxy or butoxy groups, and particularly preferably methoxy, ethoxy or propoxy groups.

Where the substituent in the definition of Substituent group α' is a halogeno lower alkoxy group this is a group in which a lower alkoxy group as defined above is substituted with at least one halogen atom as exemplified above. The halogeno lower alkoxy groups preferably have from 1 to 4 carbon atoms, and are more preferably selected from the group consisting of difluoromethoxy, trifluoromethoxy and 2,2,2-trifluoroethoxy groups. Difluoromethoxy groups are most preferred.

Where the substituent in the definition of Substituent group α' is a lower alkylthio group this is a group in which a sulfur atom is bonded to a lower alkyl group as defined and exemplified above. The lower alkylthio groups are preferably straight or branched alkylthio groups having 1 to 4 carbon atoms, more preferably methylthio, ethylthio, propylthio, isopropylthio or butylthio groups, and particularly preferably methylthio, ethylthio or propylthio groups.

Where the substituent in the definition of Substituent group α' is a halogeno lower alkylthio group this is a group in which a lower alkylthio group as defined above is substituted with at least one halogen atom as exemplified above. The halogeno lower alkylthio groups preferably have from 1 to 4 carbon atoms, and are more preferably selected from the group consisting of difluoromethylthio, trifluoromethylthio and 2,2,2-trifluoroethylthio groups.

Where the substituent in the definition of Substituent group β' represents a cycloalkyl group, said cycloalkyl group is a cycloalkyl group having from 3 to 7 carbon atoms, such as cyclopropyl, cyclobutyl, cyclopentyl, cyclohexyl and cycloheptyl groups, of which we prefer cycloalkyl groups having from 3 to 6 carbon atoms, especially cyclopentyl and cyclohexyl groups.

Where the substituent in the definition of Substituent group γ' represents a lower alkoxyimino group this is a group wherein the hydrogen atom of a hydroxyimino group is replaced by a lower alkyl group as defined and exemplified above. It is preferably an alkoxyimino group having from 1 to 4 carbon atoms, and more preferably a methoxyimino, ethoxyimino or propoxyimino group.

Where the substituent in the definition of Substituent group γ' represents a lower alkylene group it is a straight or branched chain alkylene group having from 2 to 6 carbon atoms, examples of which include ethylene, trimethylene, propylene, tetramethylene, 1-methyltrimethylene, 2-methyltrimethylene, 1,1-dimethylethylene, pentamethylene, 1,1-dimethyltrimethylene, 2,2-dimethyltrimethylene, 1,2-dimethyltrimethylene and hexamethylene groups. It is preferably a straight or branched chain alkylene group having from 2 to 4 carbon atoms, and more preferably it is an ethylene, trimethylene, propylene or tetramethylene group. It will be appreciated that the lower alkylene group together with the atom of the group of formula (IIa)', (IIb)' or (IIc)' to which it is attached form a spiro group.

Where the substituent in the definition of Substituent group γ' represents a lower alkylenedioxy group this is a group wherein the alkylene moiety, which is a straight or branched chain alkylene group having from 1 to 6 carbon atoms, such as a methylene, ethylene, trimethylene, propylene, tetramethylene, 1-methyltrimethylene, 2-methyltrimethylene, 1,1-dimethylethylene, pentamethylene, 1,1-dimethyltrimethylene, 2,2-dimethyltrimethylene, 1,2-dimethyltrimethylene and hexamethylene, is subsitituted with 2 oxy groups. Preferably, the alkylenedioxy group is a straight or branched chain alkylenedioxy group having from 1 to 4 carbon atoms, and more preferably it is a methylenedioxy, ethylenedioxy, trimethylenedioxy, propylenedioxy or tetramethylenedioxy group. It will be appreciated that the lower alkylenedioxy group together with the atom of the group of formula (IIa)', (IIb)' or (IIc)' to which the 2 oxy groups are attached form a spiro group.

Where the substituent in the definition of Substituent group γ' represents a lower alkylsulfinyl group, this is a group in which a lower alkyl group, defined and exemplified above, is bonded to a sulfinyl group (—SO—). The lower alkylsulfinyl group is preferably a straight or branched alkylsulfinyl group having from 1 to 4 carbon atoms, more preferably a methylsulfinyl, ethylsulfinyl, propylsulfinyl, isopropylsulfinyl or butylsulfinyl group, and most preferably a methylsulfinyl, ethylsulfinyl or propylsulfinyl group.

Where the substituent in the definition of Substituent group γ' represents a lower alkylidenyl group, this is a straight or branched alkylidenyl group having from 1 to 6 carbon atoms, examples of which include methylidenyl, ethylidenyl, propylidenyl, 1-methylethylidenyl, butylidenyl and 1-methylpropylidenyl groups. The lower alkylidenyl group is preferably a straight or branched alkylidenyl group having from 1 to 4 carbon atoms, and most preferably it is a methylidenyl, ethylidenyl or propylidenyl group.

Where the substituent in the definition of Substituent group γ' represents an aralkylidenyl group, this is a straight or branched alkylidenyl group as defined and exemplified above which is substituted with 1 or more aryl groups as defined and exemplified above. Examples of these lower aralkylidenyl groups include benzylidenyl, phenylethylidenyl, phenylpropylidenyl and naphthylmethylidenyl groups. The aralkylidenyl group is preferably a straight or branched alkylidenyl group having from 1 to 4 carbon atoms which is substituted with a phenyl group or a naphthyl group, and most preferably it is a benzylidenyl or phenylethylidenyl group.

Where Substituent γ represents an aryloxy group which is optionally substituted with at least one substituent selected from the group consisting of Substituent group α' defined above and Substituent group β' defined above, said aryloxy groups are oxygen atoms which are attached to an aryl group as defined and exemplified above, and examples include phenoxy, naphthyloxy, phenanthryloxy and anthracenyloxy groups. Of these, we prefer phenoxy and naphthyloxy groups, most preferably phenoxy groups.

A preferred group of substituents of Substituent group α' is Substituent group $\alpha^{1'}$ which consists of halogen atoms, lower alkoxy groups as defined above, halogeno lower alkoxy groups as defined above and groups of formula —$NR^{a'}R^{b'}$ (wherein one of $R^{a'}$ and $R^{b'}$ represents a hydrogen atom or a lower alkyl group as defined above, and the other represents a hydrogen atom, a lower alkyl group as defined above or an aralkyl group as defined above).

A preferred group of substituents of Substituent group β' is Substituent group $\beta^{1'}$ which consists of lower alkyl groups as defined above, halogeno lower alkyl groups as defined above, hydroxyl lower alkyl groups, nitro lower alkyl groups, amino lower alkyl groups, lower alkylamino lower alkyl groups, di(lower alkyl)amino lower alkyl groups and aralkylamino lower alkyl groups.

Where the substituent in the definition of Substituent group $\beta^{1'}$ represents a halogeno lower alkyl group, this is a group in which a lower alkyl group as defined and exemplified above is substituted with at least one halogen atom as exemplified above. It is preferably a straight or branched halogenoalkyl group having from 1 to 4 carbon atoms; more preferably it is a trifluoromethyl, trichloromethyl, difluoromethyl, dichloromethyl, dibromomethyl, fluoromethyl. 2,2,2-trichloroethyl, 2,2,2-trifluoroethyl, 2-bromoethyl, 2-chloroethyl, 2-fluoroethyl or 2,2-dibromoethyl group; still more preferably it is a trifluoromethyl, trichloromethyl, difluoromethyl or fluoromethyl group; and most preferably it is a trifluoromethyl group.

Where the substituent in the definition of Substituent group $\beta^{1'}$ represents a hydroxy lower alkyl group, this is a group in which a lower alkyl group as defined and exemplified above is substituted with at least one hydroxy group. It is preferably a hydroxyalkyl group having from 1 to 4 carbon atoms, and most preferably it is a hydroxymethyl, 2-hydroxyethyl or 3-hydroxypropyl group.

Where the substituent in the definition of Substituent group $\beta^{1'}$ represents a nitro lower alkyl group, this is a group in which a lower alkyl group as defined and exemplified above is substituted with at least one nitro group. It is preferably a nitroalkyl group having from 1 to 4 carbon atoms, and most preferably it is a nitromethyl, 2-nitroethyl or 3-nitropropyl group.

Where the substituent in the definition of Substituent group $\beta^{1'}$ represents an amino lower alkyl group, a lower alkylamino lower alkyl group, a di(lower alkyl)amino lower alkyl group or an aralkylamino lower alkyl group, this is a group in which a lower alkyl group as defined and exemplified above is substituted with a group of formula —$NR^{a'}R^{b'}$ (wherein one of $R^{a'}$ and $R^{b'}$ represents a hydrogen atom or a lower alkyl group as defined above, and the other represents a hydrogen atom, a lower alkyl group as defined above or an aralkyl group as defined above). Of these, substituents in which the alkyl moiety which is substituted with the group —$NR^{a'}R^{b'}$ has from 1 to 4 carbon atoms are preferred. Aminomethyl, 2-aminoethyl, 3-aminopropyl, methylaminomethyl, 2-(methylamino)ethyl, 3-(methylamino)propyl, ethylaminomethyl, 2-(ethylamino)ethyl, 3-(ethylamino)propyl, dimethylaminomethyl, 2-(dimethylamino)ethyl, 3-(dimethylamino)propyl, diethylaminomethyl, 2-(diethylamino)ethyl, 3-(diethylamino)propyl, benzylaminomethyl, 2-(benzylamino)ethyl and 3-(benzylamino)propyl groups are more preferred.

The present invention encompasses esters and other derivatives of the compounds of formula (I)'. These esters and other derivatives are compounds of formula (I)' in which a functional group (for example, a hydroxyl group, an amino group, an imino group or a sulfonamide group) of said compound of formula (I)' is modified by the addition of a protecting group using conventional techniques well-known in the art (see, for example, "Protective Groups in Organic Synthesis, Second Edition, Theodora W. Greene and Peter G. M. Wuts, 1991, John Wiley & Sons, Inc.).

There is no particular restriction on the nature of this protecting group, provided that, where the ester or other derivative is intended for therapeutic purposes, it must be pharmacologically acceptable, i.e. the protecting group must be capable of being removed by a metabolic process (e.g. hydrolysis) on administration of said compound to the body of a live mammal to give a compound of formula (I)' or a salt thereof. In other words, the pharmacologically acceptable esters or other derivatives are pro-drugs of the compounds of formula (I)' of the present invention. Where, however, the ester or other derivative of the compound of formula (I)' of the present invention is intended for non-therapeutic purposes (e.g. as an intermediate in the preparation of other compounds), then the requirement that said ester or other derivative is pharmacologically acceptable does not apply.

Whether an ester or other derivative of a compound of formula (I)' of the present invention is pharmacologically acceptable can be easily determined. The compound under investigation is intravenously administered to an experimental animal such as a rat or mouse and the body fluids of the animal are thereafter studied. If a compound of formula (I)' or a pharmacologically acceptable salt thereof can be detected in the body fluids, the compound under investigation is judged to be a pharmacologically acceptable ester or other derivative.

The compounds of formula (I)' of the present invention can be converted to an ester, examples of which include a compound of formula (I)' in which a hydroxyl group present therein is esterified. The ester residue may be a general protecting group where the esterified compound is to be used as an intermediate or a protecting group which is capable of being removed by a metabolic process (e.g. hydrolysis) in vivo where the esterified compound is one which is pharmacologically acceptable.

The general protecting group referred to above is a protecting group which is removable by a chemical process such as hydrolysis, hydrogenolysis, electrolysis or photolysis. Preferred examples of such a general protecting group used to synthesise a compound of formula (I)' in which a hydroxyl residue therein is modified include the following:

(i) aliphatic acyl groups, examples of which include
  alkylcarbonyl groups having from 1 to 25 carbon atoms, examples of which include formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl and heneicosanoyl groups,
  halogenated alkylcarbonyl groups having from 1 to 25 carbons in which the alkyl moiety thereof is substituted by at least one halogen atom, examples of which include chloroacetyl, dichloroacetyl, trichloroacetyl and trifluoroacetyl groups,
  lower alkoxyalkylcarbonyl groups which comprise an alkylcarbonyl group having from 1 to 25 carbon atoms in which the alkyl moiety thereof is substituted with at least one lower alkoxy group as defined above, examples of said lower alkoxyalkylcarbonyl groups including methoxyacetyl groups, and
  unsaturated alkylcarbonyl groups having from 1 to 25 carbon atoms, examples of which include acryloyl, propioloyl, methacryloyl, crotonoyl, isocrotonoyl and (E)-2-methyl-2-butenoyl groups;
  of these, alkylcarbonyl groups having from 1 to 6 carbon atoms are preferred;

(ii) aromatic acyl groups, examples of which include
  arylcarbonyl groups which comprise a carbonyl group which is substituted with an aryl group as defined above, examples of which include benzoyl, α-naphthoyl and β-naphthoyl groups,
  halogenated arylcarbonyl groups which comprise an arylcarbonyl group as defined above which is substituted with at least one halogen atom, examples of which include 2-bromobenzoyl, 4-chlorobenzoyl and 2,4,6-trifluorobenzoyl groups,
  lower alkylated arylcarbonyl groups which comprise an arylcarbonyl group as defined above which is substituted with at least one lower alkyl group as defined above, examples of which include 2,4,6-trimethyl-benzoyl and 4-toluoyl groups,
  lower alkoxylated arylcarbonyl groups which comprise an arylcarbonyl group as defined above which is substituted with at least one lower alkoxy group as defined above, examples of which include 4-anisoyl groups,
  nitrated arylcarbonyl groups which comprise an arylcarbonyl group as defined above which is substituted with at least one nitro group, examples of which include 4-nitrobenzoyl and 2-nitrobenzoyl groups,
  lower alkoxycarbonylated arylcarbonyl groups which comprise an arylcarbonyl group as defined above which is substituted with a carbonyl group which is itself substituted with a lower alkoxy group as defined above, examples of which include 2-(methoxycarbonyl)benzoyl groups, and arylated arylcarbonyl groups which comprise an arylcarbonyl group as defined above which is substituted with at least one aryl group as defined above, examples of which include 4-phenylbenzoyl groups;

(iii) alkoxycarbonyl groups, examples of which include lower alkoxycarbonyl groups which comprise a carbonyl group substituted with a lower alkoxy group as defined above, examples of which include methoxycarbonyl, ethoxycarbonyl, propoxycarbonyl, butoxycarbonyl, s-butoxycarbonyl, t-butoxycarbonyl and isobutoxycarbonyl groups, and lower alkoxycarbonyl groups as defined above which are substituted with at least one substituent selected from the group consisting of halogen atoms and tri(lower alkyl)silyl groups (wherein said lower alkyl groups are as defined above), examples of which include 2,2,2-trichloroethoxycarbonyl and 2-trimethylsilylethoxycarbonyl groups;

(iv) tetrahydropyranyl or tetrahydrothiopyranyl groups which may optionally be substituted with at least one substituent selected from lower alkyl groups as defined above, halogen atoms and lower alkoxy groups as defined above, examples of which include tetrahydropyran-2-yl, 3-bromotetrahydropyran-2-yl, 4-methoxytetrahydropyran-4-yl, tetrahydrothiopyran-2-yl and 4-methoxytetrahydrothiopyran-4-yl groups;

(v) tetrahydrofuranyl or tetrahydrothiofuranyl groups which may optionally be substituted with at least one substituent selected from lower alkyl groups as defined above, halogen atoms and lower alkoxy groups as defined above, examples of which include tetrahydrofuran-2-yl and tetrahydrothiofuran-2-yl groups;

(vi) silyl groups, examples of which include tri(lower alkyl)silyl groups (wherein said lower alkyl groups are as defined above), examples of which include trimethylsilyl, triethylsilyl, isopropyldimethylsilyl, t-butyldimethylsilyl, methyldiisopropylsilyl, methyl-di-t-butylsilyl and triisopropylsilyl groups, and tri(lower alkyl)silyl groups in which at least one of said lower alkyl groups is replaced with 1 or 2 aryl groups as defined above, examples of which include diphenylmethylsilyl, diphenylbutylsilyl, diphenylisopropylsilyl and phenyldiisopropylsilyl groups;

(vii) alkoxymethyl groups, examples of which include lower alkoxymethyl groups which comprise a methyl group which is substituted with a lower alkoxy group as defined above, examples of which include methoxymethyl, 1,1-dimethyl-1-methoxymethyl, ethoxymethyl, propoxymethyl, isopropoxymethyl, butoxymethyl and t-butoxymethyl groups, lower alkoxylated lower alkoxymethyl groups which comprise a lower alkoxymethyl group as defined above in which the alkoxy moiety thereof is substituted with a lower alkoxy group as defined above, examples of which include 2-methoxyethoxymethyl groups, and lower halogeno alkoxymethyl groups which comprise a lower alkoxymethyl group as defined above in which the alkoxy moiety thereof is substituted with at least one halogen atom, examples of which include 2,2,2-trichloroethoxymethyl and bis(2-chloroethoxy)methyl groups;

(viii) substituted ethyl groups, examples of which include lower alkoxylated ethyl groups which comprise an ethyl group which is substituted with a lower alkoxy group as defined above, examples of which include 1-ethoxyethyl and 1-(isopropoxy)ethyl groups, and halogenated ethyl groups such as 2,2,2-trichloroethyl groups;

(ix) aralkyl groups as define above, examples of which include lower alkyl groups as defined above which are substituted with from 1 to 3 aryl groups as defined above, examples of which include benzyl, α-naphthylmethyl, β-naphthylmethyl, diphenylmethyl, triphenylmethyl, α-naphthyldiphenylmethyl and 9-anthrylmethyl groups, and lower alkyl groups as defined above which are substituted with from 1 to 3 aryl groups as defined above in which said aryl moiety is substituted with at least one substituent selected from the group consisting of lower alkyl groups as defined above, lower alkoxy groups as defined above, nitro groups, halogen atoms and cyano groups, examples of which include 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, chlorobenzyl, 4-bromobenzyl and 4-cyanobenzyl groups;

(x) "alkenyloxycarbonyl groups" which comprise a carbonyl group which is substituted with an alkenyloxy group having from 2 to 6 carbon atoms, examples of which include vinyloxycarbonyl and allyloxycarbonyl groups; and (xi) aralkyloxycarbonyl groups which comprise a carbonyl group which is substituted with an aralkyloxy group (which is an oxygen atom substituted with an aralkyl group as defined above), in which the aryl moiety thereof may optionally be substituted with one or two substituents selected from lower alkoxy groups as defined above and nitro groups, examples of which include benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups.

The protecting group which is capable of being removed by a metabolic process (e.g. hydrolysis) in vivo is one, which on administration to the body of a live mammal is removable by a metabolic process (e.g. hydrolysis) to give a compound of formula (I)or a salt thereof. Preferred examples of such a protecting group include the following:

(i) 1-(acyloxy)lower alkyl groups, examples of which include 1-(aliphatic acyloxy)lower alkyl groups which comprise a lower alkyl group as defined above which is substituted with an alkylcarbonyloxy group having from 1 to 6 carbon atoms, examples of which include formyloxymethyl, acetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl and 1-pivaloyloxyhexyl groups, 1-(cycloalkylcarbonyloxy)lower alkyl groups which comprise a lower alkyl group as defined above which is substituted with a cycloalkylcarbonyloxy group in which a carbonyloxy group is substituted with a cycloalkyl group as defined above, examples of which include cyclopentylcarbonyloxymethyl, cyclohexylcarbonyloxymethyl, 1-cyclopentylcarbonyloxyethyl, 1-cyclohexylcarbonyloxyethyl, 1-cyclopentylcarbonyloxypropyl, 1-cyclohexylcarbonyloxypropyl, 1-cyclopentylcarbonyloxybutyl and 1-cyclohexylcarbonyloxybutyl groups, and 1-(aromatic acyloxy)lower alkyl groups which comprise a lower alkyl group as defined above which is substituted with an arylcarbonyloxy group which comprises an oxygen atom which is substituted with an arylcarbonyl group, examples of which include benzoyloxymethyl groups;

(ii) substituted carbonyloxyalkyl groups, examples of which include (lower alkoxycarbonyloxy)alkyl groups which comprise a lower alkyl group as defined above or a cycloalkyl group as defined above which is substituted with a lower alkoxycarbonyloxy group which comprises a carbonyloxy group substituted with a lower alkoxy group as defined above or a cycloalkoxy group, examples of which include methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, pentyloxycarbonyloxymethyl, hexyloxycarbonyloxymethyl, cyclohexyloxycarbonyloxymethyl, cyclohexyloxycarbonyloxy(cyclohexyl)methyl, 1-(methoxycarbonyloxy)ethyl, 1-(ethoxycarbonyloxy)ethyl, 1-(propoxycarbonyloxy)ethyl, 1-(isopropoxycarbonyloxy)ethyl, 1-(butoxycarbonyloxy)ethyl, 1-(isobutoxycarbonyloxy)ethyl, 1-(t-butoxycarbonyloxy)ethyl, 1-(pentyloxycarbonyloxy)ethyl, 1-(hexyloxycarbonyloxy)ethyl, 1-(cyclopentyloxycarbonyloxy)ethyl, 1-(cyclopentyloxycarbonyloxy)propyl, 1-(cyclohexyloxycarbonyloxy)propyl, 1-(cyclopentyloxycarbonyloxy)butyl, 1-(cyclohexyloxycarbonyloxy)butyl, 1-(cyclohexyloxycarbonyloxy)ethyl, 1-(ethoxycarbonyloxy)propyl, 1-(methoxycarbonyloxy)propyl, 1-(ethoxycarbonyloxy)propyl, 1-(propoxycarbonyloxy)propyl, 1-(isopropoxycarbonyloxy)propyl, 1-(butoxycarbonyloxy)propyl, 1-(isobutoxycarbonyloxy)propyl, 1-(pentyloxycarbonyloxy)propyl, 1-(hexyloxycarbonyloxy)propyl, 1-(methoxycarbonyloxy)butyl, 1-(ethoxycarbonyloxy)butyl, 1-(propoxycarbonyloxy)butyl, 1-(isopropoxycarbonyloxy)butyl, 1-(butoxycarbonyloxy)butyl, 1-(isobutoxycarbonyloxy)butyl, 1-(methoxycarbonyloxy)pentyl, 1-(ethoxycarbonyloxy)pentyl, 1-(methoxycarbonyloxy)hexyl and 1-(ethoxycarbonyloxy)hexyl groups, and oxodioxolenylmethyl groups, which comprise a methyl group which is substituted with an oxodioxolenyl group which itself may optionally be substituted with a group selected from the group consisting of lower alkyl groups as defined above and aryl groups as defined above which may optionally be substituted with at least one lower alkyl group as defined above, lower alkoxy group as defined above or halogen atom, examples of which include (5-phenyl-2-oxo-1,3-dioxolen-4-yl)methyl, [5-(4-methylphenyl)-2-oxo-1,3-dioxolen]methyl, [5-(4-methoxyphenyl)-2-oxo-1,3-dioxolen-4-yl]methyl, [5-(4-fluorophenyl)-2-oxo-1,3-dioxolen]methyl, [5-(4-chlorophenyl)-2-oxo-1,3-dioxolen-4-yl]methyl, (2-oxo-1,3-dioxolen-4-yl)methyl, (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl and (5-butyl-2-oxo-1,3-dioxolen-4-yl)methyl groups;

(iii) phthalidyl groups which comprise a phthalidyl group which may optionally be substituted with a substituent selected from the group consisting of lower alkyl groups as defined above and lower alkoxy groups as defined above, examples of which include phthalidyl, dimethylphthalidyl and dimethoxyphthalidyl groups;

(iv) aliphatic acyl groups as defined and exemplified above in relation to the general protecting group for a hydroxyl group;

(v) aromatic acyl groups as defined and exemplified above in relation to the general protecting group for a hydroxyl group;

(vi) half-ester salt residues of succinic acid;

(vii) phosphate ester salt residues;

(viii) ester-forming residues of an amino acid;

(ix) carbamoyl groups which may optionally be substituted with 1 or 2 lower alkyl groups as defined above; and (x) 1-(acyloxy)alkoxycarbonyl groups which comprise a lower alkoxycarbonyl group as defined above in which the lower alkoxy moiety is substituted with an aliphatic acyloxy group as defined above or an aromatic acyloxy group as defined above, examples of which include pivaloyloxymethyloxycarbonyl groups.

Of the above protecting groups which are capable of being removed by a metabolic process (e.g. hydrolysis) in vivo which are used to synthesise a compound of formula (I)' in which a hydroxyl residue therein is modified, the substituted carbonyloxyalkyl groups are preferred.

In the case where the compound of formula (I)' of the present invention has an amino group, an imino group and/or a sulfonamide group, the compound can be converted to a derivative other than the esters described above and the pharmacologically acceptable salts described below. The "other derivatives" of the compounds of formula (I)' include such derivatives. Example of such derivatives include an amide derivative in which an aliphatic acyl group defined and exemplified above or an aromatic acyl group defined and exemplified above is bonded to a nitrogen atom of an amino group, imino group and/or sulfonamide group present in said compound of formula (I)'. Where said derivative is a pharmacologically acceptable derivative of a compound of formula (I)' it must be capable of being removed by a metabolic process (e.g. hydrolysis) on administration of said compound to the body of a live mammal to give a compound of formula (I)' or a salt thereof.

Where the compound of formula (I)' of the present invention or a pharmacologically acceptable ester or other derivative thereof has a basic group, such as an amino group, the compound can be converted to a salt by reacting it with an acid, and in the case where the compound of formula (I)' of the present invention or a pharmacologically acceptable ester or other derivative thereof has an acidic group, such as a sulfonamide group, the compound can be converted to a salt by reacting it with a base. The compounds of the present invention encompass such salts. Where said salts are to be used for a therapeutic use, they must be pharmacologically acceptable.

Preferred examples of the salts formed with a basic group present in the compound of formula (I)' of the present invention include inorganic acid salts such as hydrohalogenated acid salts (e.g. hydrochlorides, hydrobromides and hydroiodides), nitrates, perchlorates, sulfates and phosphates; organic acid salts such as lower alkanesulfonates in which the lower alkyl moiety thereof is as defined above (e.g. methanesulfonates, trifluoromethanesulfonates and ethanesulfonates), arylsulfonates in which the aryl moiety thereof is as defined above (e.g. benzenesulfonate or p-toluenesulfonate), acetates, malates, fumarates, succinates, citrates, ascorbates, tartrates, oxalates and maleates; and amino acid salts such as glycine salts, lysine salts, arginine salts, ornithine salts, glutamates and aspartates.

Preferred examples of the salts formed with an acidic group present in the compound of formula (I)' of the present invention include metal salts such as alkali metal salts (e.g. sodium salts, potassium salts and lithium salts), alkali earth metal salts (e.g. calcium salts and magnesium salts), aluminum salts and iron salts; amine salts such as inorganic amine salts (e.g. ammonium salts) and organic amine salts (e.g. t-octylamine salts, dibenzylamine salts, morpholine salts, glucosamine salts, phenylglycinealkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzylphenethylamine salts, piperazine salts, tetramethylammonium salts and tris(hydroxymethyl)aminomethane salts; and amino acid salts such as glycine salts, lysine salts, arginine salts, ornithine salts, glutamates and aspartates.

The compound of formula (I)' of the present invention can sometimes take up water upon exposure to the atmosphere or when recrystallized to absorb water or to form a hydrate and such hydrates are also included within the scope of the present invention. Additionally, certain other solvents may be taken up by the compounds of the present invention to produce solvates, which also form a part of the present, invention.

The compounds of formula (I)' of the present invention can sometimes exist in the form of geometrical isomers (cis and trans isomers, or E and Z isomers) and, where said compounds contain one or more asymmetric centres, optical isomers. For the compounds of the present invention, each of said isomers and mixture of said isomers are depicted by a single formula, i.e. the formula (I)'. Accordingly, the present invention covers both the individual isomers and mixtures thereof in any proportion, including racemic mixtures.

Preferred classes of compounds of the present invention are those compounds of formula (I)' and pharmacologically acceptable salts, esters and other derivatives thereof wherein:

(A) $R^{1'}$ is an aryl group which may optionally be substituted with at least one substituent selected from Substituent group α' defined above and Substituent group β' defined above;

(B) $R^{1'}$ is a phenyl or naphthyl group, said groups optionally being substituted with at least one substituent selected from Substituent group α' defined above and Substituent group β' defined above;

(C) $R^{1'}$ is a phenyl group which may optionally be substituted with at least one substituent selected from Substituent group $α^{1'}$ defined above and Substituent group $β^{1'}$ defined above;

(D) $R^{1'}$ is a phenyl group which may optionally be substituted with at least one substituent selected from the group consisting of halogen atoms, halogeno lower alkyl groups defined above and halogeno lower alkoxy groups defined above;

(E) $R^{1'}$ is a substituent selected from the group consisting of phenyl, 4-fluorophenyl, 3-fluorophenyl, 3-chlorophenyl, 3,4-difluorophenyl, 3,4,5-trifluorophenyl, 3-chloro-4-fluorophenyl, 3-difluoromethoxyphenyl and 3-trifluoromethylphenyl groups;

(F) $R^{2'}$ is a 5- or 6-membered aromatic heterocyclic group which has one or two nitrogen atoms, said group optionally being substituted with at least one substituent selected from Substituent group α' defined above and Substituent group β' defined above;

(G) $R^{2'}$ is a pyridyl or pyrimidinyl group, said groups optionally being substituted with at least one substituent selected from the group consisting of Substituent group α' defined above and Substituent group β' defined above;

(H) $R^{2'}$ is a 4-pyridyl or 4-pyrimidinyl group, said groups optionally being substituted with at least one substituent selected from the group consisting of Substituent group α' defined above and Substituent group β' defined above;

(I) $R^{2'}$ is a 4-pyridyl or 4-pyrimidinyl group, said groups optionally being substituted at the 2-position thereof with a substituent selected from the group consisting of Substituent group α' defined above and Substituent group β' defined above;

(J) $R^{2'}$ is a 4-pyridyl or 4-pyrimidinyl group, said groups optionally being substituted at the 2-position thereof with a substituent selected from the group consisting of methoxy, amino, methylamino, benzylamino, and α-methylbenzylamino groups;

(K) B' is a 5- or 6-membered heterocyclic ring which has one ring nitrogen atom and optionally has one further ring heteroatom or ring group selected from a nitrogen atom, oxygen atom, sulfur atom, >SO and >$SO_2$ (said ring may be saturated or unsaturated and may optionally be fused with an aryl group defined above, a heteroaryl group defined above, a cycloalkyl group defined above or a heterocyclyl group defined above);

(L) B' is a 5- or 6-membered heterocyclic ring which consists of the group D', the group E and three or four carbon atoms (said ring may be saturated or unsaturated and may optionally be fused with an aryl group defined above, a heteroaryl group defined above, a cycloalkyl group defined above or a heterocyclyl group defined above);

(M) B' is a pyrrolidinyl ring or a pyrrolinyl ring;

(N) $R^{3'}$ is a group of general formula (IIa)' or general formula (IIb)';

(O) $R^{3'}$ is a group of general formula (IIa)';

(P) m' is 1;

(O) $R^{4'}$ is 1 or 2 substituents which are independently selected from the group consisting of Substituent group α defined above, Substituent group β' defined above and Substituent group $γ^{1'}$, wherein Substituent group $γ^{1'}$ consists of oxo groups, hydroxyimino groups, lower alkoxyimino groups defined above, lower alkylene groups defined above, lower alkylenedioxy groups defined above, lower alkylsulfinyl groups defined above, lower alkylsulfonyl groups defined above and aryl groups defined above which may optionally be substituted with at least one substituent selected from Substituent group α' defined above and Substituent group β' defined above;

(R) $R^{4'}$ is a substituent selected from the group consisting of hydroxy groups, halogen atoms, lower alkoxy groups defined above, lower alkylthio groups defined above, halogeno lower alkoxy groups defined above, lower alkyl groups defined above, halogeno lower alkyl groups defined above, oxo groups, aryl groups defined above optionally substituted with at least one substituent selected from Substituent group α' defined above and Substituent group β' defined above, lower alkylenedioxy groups defined above, lower alkylene groups defined above and lower alkylsulfonyl groups defined above;

(S) $R^{4'}$ is a substituent selected from the group consisting of hydroxy groups, fluorine atoms, chlorine atoms, methoxy groups, ethoxy groups, propoxy groups, methyl groups, ethyl groups, propyl groups and phenyl groups which may optionally be substituted with at least one substituent selected from Substituent group α' defined above and Substituent group β' defined above;
(T) R⁴' is a substituent selected from the group consisting of methoxy groups, methyl groups, ethyl groups, propyl groups and phenyl groups;
(U) R⁴' is a substituent selected from the group consisting of aryloxy groups defined above which may optionally be substituted with at least one substituent selected from Substituent group α' defined above and Substituent group β' defined above, alkylidene groups defined above and aralkylidene groups defined above;
(V) R⁴' is a substituent selected from the group consisting of phenoxy, methylidene, ethylidene, propylidene and benzylidene groups;
(W) D' is a group of formula >C(R⁵')— (wherein R⁵' is selected from the group consisting of hydrogen atoms, Substituent group α' defined above and Substituent group β' defined above) and E' is a nitrogen atom;
(X) the compounds of formula (I)' are represented by the general formula (I-1)' or (I-3)' shown below:

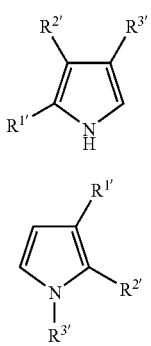

(Y) the compounds of formula (I)' are represented by the general formula (I-1)' below:

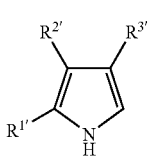

Compounds of formula (I)' which comprise any combination of the factors selected freely from the eight groups consisting of (A) to (E) above; (F) to (J) above; (K) to (M) above; (N) and (O) above; (P) above; (Q) to (V) above; (W) above; and (X) and (Y) above are preferred.

More preferred compounds of the present invention are compounds of formula (I)' and pharmacologically acceptable salts, esters and other derivatives thereof, wherein:
(i) R¹' is as defined in (A) above, R²' is as defined in (F) above and R³' is as defined in (N) above wherein m' is as defined in (P) above, D' and E' are as defined in (W) above and R⁴' is as defined in (O) above;
(ii) R¹' is as defined in (B) above, R²' is as defined in (G) above and R³' is as defined in (N) above wherein m' is as defined in (P) above, D' and E' are as defined in (W) above and R⁴' is as defined in (R) above;
(iii) R¹' is as defined in (C) above, R²' is as defined in (H) above and R³' is as defined in (N) above wherein m' is as defined in (P) above, D' and E' are as defined in (W) above and R⁴' is as defined in (R) above;
(iv) R¹' is as defined in (D) above, R²' is as defined in (D) above and R³' is as defined in (O) above wherein m' is as defined in (P) above, D' and E' are as defined in (W) above and R⁴' is as defined in (S) above;
(v) R¹' is as defined in (E) above, R²' is as defined in (J) above and R³' is as defined in (O) above wherein m' is as defined in (P) above, D' and E' are as defined in (W) above and R⁴' is as defined in (T) above;
(vi) R¹' is as defined in (A) above, R²' is as defined in (F) above and R³' is as defined in (N) above wherein m' is as defined in (P) above, D' and E' are as defined in (W) above and R⁴' is as defined in (U) above;
(vii) R¹' is as defined in (B) above, R²' is as defined in (G) above and R³' is as defined in (N) above wherein m' is as defined in (P) above, D' and E' are as defined in (W) above and R⁴' is as defined in (U) above;
(viii) R¹' is as defined in (C) above, R²' is as defined in (H) above and R³' is as defined in (N) above wherein m' is as defined in (P) above, D' and E' are as defined in (W) above and R⁴' is as defined in (U) above;
(ix) R¹' is as defined in (D) above, R²' is as defined in (I) above and R³' is as defined in (O) above wherein m' is as defined in (P) above, D' and E' are as defined in (W) above and R⁴' is as defined in (V) above;
(x) R¹' is as defined in (E) above, R²' is as defined in (J) above and R³' is as defined in (O) above wherein m' is as defined in (P) above, D' and E' are as defined in (W) above and R⁴' is as defined in (V) above;
(xi) any of the above compounds (i) to (x) wherein the compound of formula (I)' is a compound of formula (I-1)' or (I-3)' as defined in (X) above; and
(xii) any of the above compounds (i) to (x) wherein the compound of formula (I)' is a compound of formula (I-1)' as defined in (Y) above.

Of the above, preferred compounds of the present invention are compounds of formula (I)' selected from the following group of compounds, and pharmacologically acceptable salts, esters and other derivatives thereof:
2-(3-fluorophenyl)-4-[2-methyl-1,2,3,5,6,8a-hexahydroindolizin-7-yl]-3-(pyridin-4-yl)-1H-pyrrole,
2-(3-fluorophenyl)-4-[2-phenyl-1,2,3,5,6,8a-hexahydroindolizin-7-yl]-3-(pyridin-4-yl)-1H-pyrrole,
2-(3-fluorophenyl)-4-[2-hydroxy-1,2,3,5,6,8a-hexahydroindolizin-7-yl]-3-(pyridin-4-yl)-1H-pyrrole,
2-(3-fluorophenyl)-4-[2-methoxy-1,2,3,5,6,8a-hexahydroindolizin-7-yl]-3-(pyridin-4-yl)-1H-pyrrole,
4-[2-fluoro-1,2,3,5,6,8a-hexahydroindolizin-7-yl]-2-(3-fluorophenyl)-3-(pyridin-4-yl)-1H-pyrrole,
2-(4-fluorophenyl)-4-[2-methyl-1,2,3,5,6,8a-hexahydroindolizin-7-yl]-3-(pyridin-4-yl)-1H-pyrrole,
2-(4-fluorophenyl)-4-[2-phenyl-1,2,3,5,6,8a-hexahydroindolizin-7-yl]-3-(pyridin-4-yl)-1H-pyrrole,
2-(4-fluorophenyl)-4-[2-hydroxy-1,2,3,5,6,8a-hexahydroindolizin-7-yl]-3-(pyridin-4-yl)-1H-pyrrole,
2-(4-fluorophenyl)-4-[2-methoxy-1,2,3,5,6,8a-hexahydroindolizin-7-yl]-3-(pyridin-4-yl)-1H-pyrrole,
4-[2,2-ethylenedioxy-1,2,3,5,6,8a-hexahydroindolizin-7-yl]-2-(4-fluorophenyl)-3-(pyridin-4-yl)-1H-pyrrole,
2-(4-fluorophenyl)-4-[2-oxo-1,2,3,5,6,8a-hexahydroindolizin-7-yl]-3-(pyridin-4-yl)-1H-pyrrole,
4-[2-fluoro-1,2,3,5,6,8a-hexahydroindolizin-7-yl]-2-(4-fluorophenyl)-3-(pyridin-4-yl)-1H-pyrrole, 4-[2-chloro-1,2,3,5,6,8a-hexahydroindolizin-7-yl]-2-(4-fluorophenyl)-3-(pyridin-4-yl)-1H-pyrrole,
4-[2,2-difluoro-1,2,3,5,6,8a-hexahydroindolizin-7-yl]-2-(4-fluorophenyl)-3-(pyridin-4-yl)-1H-pyrrole,
2-(3-chlorophenyl)-4-[2-methyl-1,2,3,5,6,8a-hexahydroindolizin-7-yl]-3-(pyridin-4-yl)-1H-pyrrole,
2-(3-chlorophenyl)-4-[2-phenyl-1,2,3,5,6,8a-hexahydroindolizin-7-yl]-3-(pyridin-4-yl)-1H-pyrrole,
2-(3-chlorophenyl)-4-[2-hydroxy-1,2,3,5,6,8a-hexahydroindolizin-7-yl]-3-(pyridin-4-yl)-1H-pyrrole,
2-(3-chlorophenyl)-4-[2-methoxy-1,2,3,5,6,8a-hexahydroindolizin-7-yl]-3-(pyridin-4-yl)-1H-pyrrole,
2-(3-chlorophenyl)-4-[2-fluoro-1,2,3,5,6,8a-hexahydroindolizin-7-yl]-3-(pyridin-4-yl)-1H-pyrrole,
4-[2-chloro-1,2,3,5,6,8a-hexahydroindolizin-7-yl]-2-(3-chlorophenyl)-3-(pyridin-4-yl)-1H-pyrrole,
4-[2-methyl-1,2,3,5,6,8a-hexahydroindolizin-7-yl]-3-(pyridin-4-yl)-2-(3-trifluoromethylphenyl)-1H-pyrrole,
4-[2-phenyl-1,2,3,5,6,8a-hexahydroindolizin-7-yl]-3-(pyridin-4-yl)-2-(3-trifluoromethylphenyl)-1H-pyrrole,
4-[2-hydroxy-1,2,3,5,6,8a-hexahydroindolizin-7-yl]-3-(pyridin-4-yl)-2-(3-trifluoromethylphenyl)-1H-pyrrole,
4-[2-methoxy-1,2,3,5,6,8a-hexahydroindolizin-7-yl]-3-(pyridin-4-yl)-2-(3-trifluoromethylphenyl)-1H-pyrrole,
4-[2-fluoro-1,2,3,5,6,8a-hexahydroindolizin-7-yl]-3-(pyridin-4-yl)-2-(3-trifluoromethylphenyl)-1H-pyrrole,
4-[2-chloro-1,2,3,5,6,8a-hexahydroindolizin-7-yl]-3-(pyridin-4-yl)-2-(3-trifluoromethylphenyl)-1H-pyrrole,
4-[2,8-dimethyl-1,2,3,5,6,8a-hexahydroindolizin-7-yl]-2-(4-fluorophenyl)-3-(pyridin-4-yl)-1H-pyrrole,
2-(4-fluorophenyl)-4-[2-hydroxy-8-methyl-1,2,3,5,6,8a-hexahydroindolizin-7-yl]-3-(pyridin-4-yl)-1H-pyrrole,
2-(4-fluorophenyl)-4-[2-methoxy-8-methyl-1,2,3,5,6,8a-hexahydroindolizin-7-yl]-3-(pyridin-4-yl)1H-pyrrole,
4-[2-fluoro-8-methyl-1,2,3,5,6,8a-hexahydroindolizin-7-yl]-2-(4-fluorophenyl)-3-(pyridin-4-yl) 1H-pyrrole,
4-[2-chloro-8-methyl-1,2,3,5,6,8a-hexahydroindolizin-7-yl]-2-(4-fluorophenyl)-3-(pyridin-4-yl)-1H-pyrrole,
2-(4-fluorophenyl)-4-[2-methyl-1,2,3,5,6,8a-tetrahydroindolizin-7-yl]-3-(pyridin-4-yl)-1H-pyrrole,
2-(4-fluorophenyl)-4-[2-hydroxy-1,2,3,5,8,8a-hexahydroindolizin-7-yl]-3-(pyridin-4-yl)-1H-pyrrole,
2-(4-fluorophenyl)-4-[2-methoxy-1,2,3,5,8,8a-hexahydroindolizin-7-yl]-3-(pyridin-4-yl)-1H-pyrrole,
4-[2-chloro-1,2,3,5,8,8a-hexahydroindolizin-7-yl]-2-(4-fluorophenyl)-3-(pyridin-4-yl)-1H-pyrrole,
4-[2,2-difluoro-1,2,3,5,8,8a-hexahydroindolizin-7-yl]-2-(4-fluorophenyl)-3-(pyridin-4-yl)-1H-pyrrole,
4-[cyclopropanespiro-6'-(1',2',3',5',6',8a'-hexahydroindolizin)-7'-yl]-2-(4-fluorophenyl)-3-(pyridin-4-yl)-1H-pyrrole,
2-(4-fluorophenyl)-4-[2-methylidene-1,2,3,5,6,8a-hexahydroindolizin-7-yl]-3-(pyridin-4-yl)-1H-pyrrole,
4-[2,2-dimethyl-1,2,3,5,6,8a-hexahydroindolizin-7-yl]-2-(4-fluorophenyl)-3-(pyridin-4-yl)-1H-pyrrole,
2-(4-fluorophenyl)-4-[2-methylthio-1,2,3,5,6,8a-hexahydroindolizin-7-yl]-3-(pyridin-4-yl)-1H-pyrrole,
4-[2-ethyl-1,2,3,5,6,8a-hexahydroindolizin-7-yl]-2-(4-fluorophenyl)-3-(pyridin-4-yl)-1H-pyrrole,
4-[2-ethyl-1,2,3,5,6,8a-hexahydroindolizin-7-yl]-2-(3-fluorophenyl)-3-(pyridin 4-yl)-1H-pyrrole,
2-(3-chlorophenyl)-4-[2-ethyl-1,2,3,5,6,8a-hexahydroindolizin-7-yl]-3-(pyridin-4-yl)-1H-pyrrole,
4-[2-ethyl-1,2,3,5,6,8a-hexahydroindolizin-7-yl]-3-(pyridin-4-yl)-2-(3-trifluoromethylphenyl)-1H-pyrrole,
2-(4-chlorophenyl)-4-[2-ethyl-1,2,3,5,6,8a-hexahydroindolizin-7-yl]-3-(pyridin-4-yl)-1H-pyrrole,
4-[2-butylthio-1,2,3,5,6,8a-hexahydroindolizin-7-yl]-2-(4-fluorophenyl)-3-(pyridin-4-yl)-1H-pyrrole,
4-[2-ethylthio-1,2,3,5,6,8a-hexahydroindolizin-7-yl]-2-(4-fluorophenyl)-3-(pyridin-4-yl)-1H-pyrrole,
4-[2-ethylidene-1,2,3,5,6,8a-hexahydroindolizin-7-yl]-2-(4-fluorophenyl)-3-(pyridin-4-yl)-1H-pyrrole,
2-(4-fluorophenyl)-4-[2-propyl-1,2,3,5,6,8a-hexahydroindolizin-7-yl]-3-(pyridin-4-yl)-1H-pyrrole,
2-(3-fluorophenyl)-4-[2-propyl-1,2,3,5,6,8a-hexahydroindolizin-7-yl]-3-(pyridin-4-yl)-1H-pyrrole,
2-(3-chlorophenyl)-4-[2-propyl-1,2,3,5,6,8a-hexahydroindolizin-7-yl]-3-(pyridin-4-yl)-1H-pyrrole,
4-[2-propyl-1,2,3,5,6,8a-hexahydroindolizin-7-yl]-3-(pyridin-4-yl)-2-(3-trifluoromethylphenyl)-1H-pyrrole,
2-(4-chlorophenyl)-4-[2-propyl-1,2,3,5,6,8a-hexahydroindolizin-7-yl]-3-(pyridin-4-yl)-1H-pyrrole,
4-[2-ethoxy-1,2,3,5,6,8a-hexahydroindolizin-7-yl]-2-(4-fluorophenyl)-3-(pyridin-4-yl)-1H-pyrrole,
4-[cyclopentanespiro-2'-(1',2',3',5',6',8a'-hexahydroindolizin)-7'-yl]-2-(4-fluorophenyl)-3-(pyridin-4-yl)-1H-pyrrole,
4-[2-benzylidene-1,2,3,5,6,8a-hexahydroindolizin-7-yl]-2-(4-fluorophenyl)-3-(pyridin-4-yl)-1H-pyrrole,
2-(4-fluorophenyl)-4-[2-propylidene-1,2,3,5,6,8a-hexahydroindolizin-7-yl]-3-(pyridin-4-yl)-1H-pyrrole,
4-[5,5-dimethyl-1,2,3,5,6,8a-hexahydroindolizin-7-yl]-2-(4-fluorophenyl)-3-(pyridin-4-yl)-1H-pyrrole,
4-[2-ethyl-3,5,6,8a-tetrahydroindolizin-7-yl]-2-(4-fluorophenyl)-3-(pyridin-4-yl)-1H-pyrrole,
2-(4-fluorophenyl)-4-[2-propyl-3,5,6,8a-tetrahydroindolizin-7-yl]-3-(pyridin-4-yl)-1H-pyrrole,
2-(4-fluorophenyl)-4-[2-phenyl-3,5,6,8a-tetrahydroindolizin-7-yl]-3-(pyridin-4-yl)-1H-pyrrole,
2-(4-chlorophenyl)-4-[2-methoxy-1,2,3,5,6,8a-hexahydroindolizin-7-yl]-3-(pyridin-4-yl)-1H-pyrrole,
2-(4-chlorophenyl)-4-[2-methyl-1,2,3,5,6,8a-hexahydroindolizin-7-yl]-3-(pyridin-4-yl)-1H-pyrrole, and
2-(4-chlorophenyl)-4-[2-phenyl-1,2,3,5,6,8a-hexahydroindolizin-7-yl]-3-(pyridin-4-yl)-1H-pyrrole.

Of the above, more preferred compounds of the present invention are compounds of formula (I)' selected from the following group of compounds, and pharmacologically acceptable salts, esters and other derivatives thereof:
2-(3-fluorophenyl)-4-[2-methyl-1,2,3,5,6,8a-hexahydroindolizin-7-yl]-3-(pyridin-4-yl)-1H-pyrrole,
2-(3-fluorophenyl)-4-[2-phenyl-1,2,3,5,6,8a-hexahydroindolizin-7-yl]-3-(pyridin-4-yl)-1H-pyrrole,
2-(3-fluorophenyl)-4-[2-methoxy-1,2,3,5,6,8a-hexahydroindolizin-7-yl]-3-(pyridin-4-yl)-1H-pyrrole,
2-(4-fluorophenyl)-4-[2-methyl-1,2,3,5,6,8a-hexahydroindolizin-7-yl]-3-(pyridin-4-yl)-1H-pyrrole,
2-(4-fluorophenyl)-4-[2-phenyl-1,2,3,5,6,8a-hexahydroindolizin-7-yl]-3-(pyridin-4-yl)-1H-pyrrole,
2-(4-fluorophenyl)-4-[2-methoxy-1,2,3,5,6,8a-hexahydroindolizin-7-yl]-3-(pyridin-4-yl)-1H-pyrrole,
2-(3-chlorophenyl)-4-[2-methyl-1,2,3,5,6,8a-hexahydroindolizin-7-yl]-3-(pyridin-4-yl)-1H-pyrrole,
2-(3-chlorophenyl)-4-[2-phenyl-1,2,3,5,6,8a-hexahydroindolizin-7-yl]-3-(pyridin-4-yl)-1H-pyrrole,
2-(3-chlorophenyl)-4-[2-methoxy-1,2,3,5,6,8a-hexahydroindolizin-7-yl]-3-(pyridin-4-yl)-1H-pyrrole,
4-[2-methyl-1,2,3,5,6,8a-hexahydroindolizin-7-yl]-3-(pyridin-4-yl)-2-(3-trifluoromethylphenyl)-1H-pyrrole.
4-[2-phenyl-1,2,3,5,6,8a-hexahydroindolizin-7-yl]-3-(pyridin-4-yl)-2-(3-trifluoromethylphenyl)-1H-pyrrole,
4-[2-methoxy-1,2,3,5,6,8a-hexahydroindolizin-7-yl]-3-(pyridin-4-yl)-2-(3-trifluoromethylphenyl)-1H-pyrrole, 2-(4-fluorophenyl)-4-[2-methyl-3,5,6,8a-tetahydroin-dolizin-7-yl]-3-(pyridin-4-yl)-1H-pyrrole,
2-(4-fluorophenyl)-4-[2-methylidene-1,2,3,5,6,8a-hexahy-droindolizin-7-yl]-3-(pyridin-4-yl)-1H-pyrrole,
4-[2-ethyl-1,2,3,5,6,8a-hexahydroindolizin-7-yl]-2-(4-fluo-rophenyl)-3-(pyridin-4-yl)-1H-pyrrole,
4-[2-ethyl-1,2,3,5,6,8a-hexahydroindolizin-7-yl]-2-(3-fluo-rophenyl)-3-(pyridin-4-yl)-1H-pyrrole,
2-(3-chlorophenyl)-4-[2-ethyl-1,2,3,5,6,8a-hexahydroin-dolizin-7-yl]-3-(pyridin-4-yl)-1H-pyrrole,
4-[2-ethyl-1,2,3,5,6,8a-hexahydroindolizin-7-yl]-3-(pyri-din-4-yl)-2-(3-trifluoromethylphenyl)-1H-pyrrole,
2-(4-fluorophenyl)-4-[2-propyl-1,2,3,5,6,8a-hexahydroin-dolizin-7-yl]-3-(pyridin-4-yl)-1H-pyrrole,
2-(3-fluorophenyl)-4-[2-propyl-1,2,3,5,6,8a-hexahydroin-dolizin-7-yl]-3-(pyridin-4-yl)-1H-pyrrole,
2-(3-chlorophenyl)-4-[2-propyl-1,2,3,5,6,8a-hexahydroin-dolizin-7-yl]-3-(pyridin-4-yl)-1H-pyrrole,
4-[2-propyl-1,2,3,5,6,8a-hexahydroindolizin-7-yl]-3-(pyri-din-4-yl)-2-(3-trifluoromethylphenyl)-1H-pyrrole,
4-[2-ethyl-3,5,6,8a-tetrahydroindolizin-7-yl]-2-(4-fluo-rophenyl)-3-(pyridin-4-yl)-1H-pyrrole,
2-(4-fluorophenyl)-4-[2-propyl-3,5,6,8a-tetrahydroin-dolizin-7-yl]-3-(pyridin-4-yl)-1H-pyrrole, and
2-(4-fluorophenyl)-4-[2-phenyl-3,5,6,8a-tetrahydroin-dolizin-7-yl]-3-(pyridin-4-yl)-1H-pyrrole.

Of the above, the most preferred compounds of the present invention are compounds of formula (I)' selected from the following group of compounds, and pharmacologically acceptable salts, esters and other derivatives thereof:

2-(4-fluorophenyl)-4-[(2R,8aS)-2-phenyl-1,2,3,5,6,8a-hexahydroindolizin-7-yl]-3-(pyridin-4-yl)-1H-pyrrole,
2-(4-fluorophenyl)-4[(8aS)-2-methyl-1,2,3,5,6,8a-hexahy-droindolizin-7-yl]-3-(pyridin-4-yl)-1H-pyrrole,
2-(4-fluorophenyl)-4-[(8aS)-2-methylidene-1,2,3,5,6,8a-hexahydroindolizin-7-yl]-3-(pyridin-4-yl)-1H-pyrrole,
2-(4-fluorophenyl)-4-[(8aS)-2-methyl-3,5,6,8a-tetrahy-droindolizin-7-yl]-3-(pyridin-4-yl)-1H-pyrrole,
4-[(2S,8aS)-2-ethyl-1,2,3,5,6,8a-hexahydroindolizin-7-yl]-2-(4-fluorophenyl)-3-(pyridin-4-yl)-1H-pyrrole, and
2-(4-fluorophenyl)-4-[(2S,8aS)-2-propyl-1,2,3,5,6,8a-hexahydroindolizin-7-yl]-3-(pyridin-4-yl)-1H-pyrrole.

Specific examples of compounds of formula (I)' of the present invention include the following compounds in Tables 1' to 6' below.

TABLE 1'

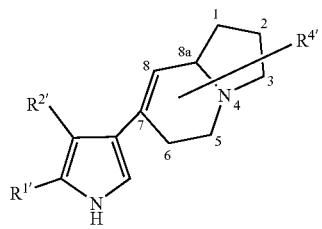

| Compound No. | $R^{1'}$ | $R^{2'}$ | $R^{4'}$ |
|---|---|---|---|
| 1-1' | Ph | 4-Pyr | 1-Me |
| 1-2' | Ph | 4-Pyr | 1-Et |
| 1-3' | Ph | 4-Pyr | 1-Pr |
| 1-4' | Ph | 4-Pyr | 1,1-diMe |
| 1-5' | Ph | 4-Pyr | 2-Me |
| 1-6' | Ph | 4-Pyr | 2-Et |
| 1-7' | Ph | 4-Pyr | 2-Pr |
| 1-8' | Ph | 4-Pyr | 2-Bu |
| 1-9' | Ph | 4-Pyr | 2-Allyl |
| 1-10' | Ph | 4-Pyr | 2-Ph |
| 1-11' | Ph | 4-Pyr | 2-Bn |
| 1-12' | Ph | 4-Pyr | 2-Phet |
| 1-13' | Ph | 4-Pyr | 2,2-diMe |
| 1-14' | Ph | 4-Pyr | 2-OH |
| 1-15' | Ph | 4-Pyr | 2-MeO |
| 1.16' | Ph | 4-Pyr | 2-EtO |
| 1-17' | Ph | 4-Pyr | 2-PrO |
| 1-18' | Ph | 4-Pyr | 2,2-di(MeO) |
| 1-19' | Ph | 4-Pyr | 2,2-di(EtO) |
| 1-20' | Ph | 4-Pyr | 2,2-OCH$_2$CH$_2$O— |
| 1-21' | Ph | 4-Pyr | 2-Oxo |
| 1-22' | Ph | 4-Pyr | 2-F |
| 1-23' | Ph | 4-Pyr | 2-Cl |
| 1-24' | Ph | 4-Pyr | 2-Br |
| 1-25' | Ph | 4-Pyr | 2-I |
| 1-26' | Ph | 4-Pyr | 2,2-diF |
| 1-27' | Ph | 4-Pyr | 2,2-diCl |
| 1-28' | Ph | 4-Pyr | 2,2-diBr |
| 1-29' | Ph | 4-Pyr | 3-Me |
| 1-30' | Ph | 4-Pyr | 3-Et |
| 1-31' | Ph | 4-Pyr | 3-Pr |
| 1-32' | Ph | 4-Pyr | 3,3-diMe |
| 1-33' | Ph | 4-Pyr | 5-Me |

TABLE 1'-continued

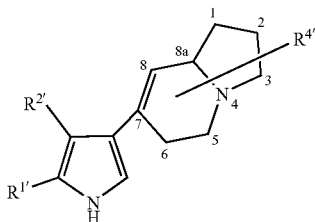

| Compound No. | R¹' | R²' | R⁴' |
|---|---|---|---|
| 1-34' | Ph | 4-Pyr | 5-Et |
| 1-35' | Ph | 4-Pyr | 5-Pr |
| 1-36' | Ph | 4-Pyr | 5,5-diMe |
| 1-37' | Ph | 4-Pyr | 6-Me |
| 1-38' | Ph | 4-Pyr | 6-Et |
| 1-39' | Ph | 4-Pyr | 6-Pr |
| 1-40' | Ph | 4-Pyr | 6,6-diMe |
| 1-41' | Ph | 4-Pyr | 6-Oxo |
| 1-42' | Ph | 4-Pyr | 8-Me |
| 1-43' | Ph | 4-Pyr | 8-Et |
| 1-44' | Ph | 4-Pyr | 8-Pr |
| 1-45' | Ph | 4-Pyr | 8-Ph |
| 1-46' | Ph | 4-Pyr | 8a-Me |
| 1-47' | Ph | 4-Pyr | 8a-Et |
| 1-48' | Ph | 4-Pyr | 8a-Pr |
| 1-49' | Ph | 2-NH$_2$-4-Pym | 1-Me |
| 1-50' | Ph | 2-NH$_2$-4-Pym | 1-Et |
| 1-51' | Ph | 2-NH$_2$-4-Pym | 1-Pr |
| 1-52' | Ph | 2-NH$_2$-4-Pym | 1,1-diMe |
| 1-53' | Ph | 2-NH$_2$-4-Pym | 2-Me |
| 1-54' | Ph | 2-NH$_2$-4-Pym | 2-Et |
| 1-55' | Ph | 2-NH$_2$-4-Pym | 2-Pr |
| 1-56' | Ph | 2-NH$_2$-4-Pym | 2-Bu |
| 1-57' | Ph | 2-NH$_2$-4-Pym | 2-Allyl |
| 1-58' | Ph | 2-NH$_2$-4-Pym | 2-Ph |
| 1-59' | Ph | 2-NH$_2$-4-Pym | 2-Bn |
| 1-60' | Ph | 2-NH$_2$-4-Pym | 2-Phet |
| 1-61' | Ph | 2-NH$_2$-4-Pym | 2,2-diMe |
| 1-62' | Ph | 2-NH$_2$-4-Pym | 2-OH |
| 1-63' | Ph | 2-NH$_2$-4-Pym | 2-MeO |
| 1-64' | Ph | 2-NH$_2$-4-Pym | 2-EtO |
| 1-65' | Ph | 2-NH$_2$-4-Pym | 2-PrO |
| 1-66' | Ph | 2-NH$_2$-4-Pym | 2,2-di(MeO) |
| 1-67' | Ph | 2-NH$_2$-4-Pym | 2,2-di(EtO) |
| 1-68' | Ph | 2-NH$_2$-4-Pym | 2,2-OCH$_2$CH$_2$O— |
| 1-69' | Ph | 2-NH$_2$-4-Pym | 2-Oxo |
| 1-70' | Ph | 2-NH$_2$-4-Pym | 2-F |
| 1-71' | Ph | 2-NH$_2$-4-Pym | 2-Cl |
| 1-72' | Ph | 2-NH$_2$-4-Pym | 2-Br |
| 1-73' | Ph | 2-NH$_2$-4-Pym | 2-I |
| 1-74' | Ph | 2-NH$_2$-4-Pym | 2,2-diF |
| 1-75' | Ph | 2-NH$_2$-4-Pym | 2,2-diCl |
| 1-76' | Ph | 2-NH$_2$-4-Pym | 2,2-diBr |
| 1-77' | Ph | 2-NH$_2$-4-Pym | 3-Me |
| 1-78' | Ph | 2-NH$_2$-4-Pym | 3-Et |
| 1-79' | Ph | 2-NH$_2$-4-Pym | 3-Pr |
| 1-80' | Ph | 2-NH$_2$-4-Pym | 3,3-diMe |
| 1-81' | Ph | 2-NH$_2$-4-Pym | 5-Me |
| 1-82' | Ph | 2-NH$_2$-4-Pym | 5-Et |
| 1-83' | Ph | 2-NH$_2$-4-Pym | 5-Pr |
| 1-84' | Ph | 2-NH$_2$-4-Pym | 5,5-diMe |
| 1-85' | Ph | 2-NH$_2$-4-Pym | 6-Me |
| 1-86' | Ph | 2-NH$_2$-4-Pym | 6-Et |
| 1-87' | Ph | 2-NH$_2$-4-Pym | 6-Pr |
| 1-88' | Ph | 2-NH$_2$-4-Pym | 6,6-diMe |
| 1-89' | Ph | 2-NH$_2$-4-Pym | 6-Oxo |
| 1-90' | Ph | 2-NH$_2$-4-Pym | 8-Me |
| 1-91' | Ph | 2-NH$_2$-4-Pym | 8-Et |
| 1-92' | Ph | 2-NH$_2$-4-Pym | 8-Pr |
| 1-93' | Ph | 2-NH$_2$-4-Pym | 8-Ph |
| 1-94' | Ph | 2-NH$_2$-4-Pym | 8a-Me |
| 1-95' | Ph | 2-NH$_2$-4-Pym | 8a-Et |
| 1-96' | Ph | 2-NH$_2$-4-Pym | 8a-Pr |
| 1-97' | Ph | 2-MeNH$_2$-4-Pym | 1-Me |

TABLE 1'-continued

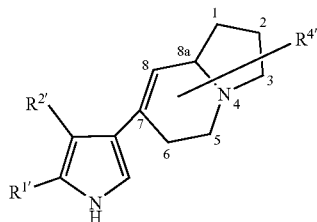

| Compound No. | R¹' | R²' | R⁴' |
|---|---|---|---|
| 1-98' | Ph | 2-MeNH$_2$-4-Pym | 1-Et |
| 1-99' | Ph | 2-MeNH$_2$-4-Pym | 1-Pr |
| 1-100' | Ph | 2-MeNH$_2$-4-Pym | 1,1-diMe |
| 1-101' | Ph | 2-MeNH$_2$-4-Pym | 2-Me |
| 1-102' | Ph | 2-MeNH$_2$-4-Pym | 2-Et |
| 1-103' | Ph | 2-MeNH$_2$-4-Pym | 2-Pr |
| 1-104' | Ph | 2-MeNH$_2$-4-Pym | 2-Bu |
| 1-105' | Ph | 2-MeNH$_2$-4-Pym | 2-Allyl |
| 1-106' | Ph | 2-MeNH$_2$-4-Pym | 2-Ph |
| 1-107' | Ph | 2-MeNH$_2$-4-Pym | 2-Bn |
| 1-lO8' | Ph | 2-MeNH$_2$-4-Pym | 2-Phet |
| 1-109' | Ph | 2-MeNH$_2$-4-Pym | 2,2-diMe |
| 1-110' | Ph | 2-MeNH$_2$-4-Pym | 2-OH |
| 1-111' | Ph | 2-MeNH$_2$-4-Pym | 2-MeO |
| 1-112' | Ph | 2-MeNH$_2$-4-Pym | 2-EtO |
| 1-113' | Ph | 2-MeNH$_2$-4-Pym | 2-PrO |
| 1-114' | Ph | 2-MeNH$_2$-4-Pym | 2,2-di(MeO) |
| 1-115' | Ph | 2-MeNH$_2$-4-Pym | 2,2-di(EtO) |
| 1-116' | Ph | 2-MeNH$_2$-4-Pym | 2,2-OCH$_2$CH$_2$O— |
| 1-117' | Ph | 2-MeNH$_2$-4-Pym | 2-Oxo |
| 1-118' | Ph | 2-MeNH$_2$-4-Pym | 2-F |
| 1-119' | Ph | 2-MeNH$_2$-4-Pym | 2-Cl |
| 1-120' | Ph | 2-MeNH$_2$-4-Pym | 2-Br |
| 1-121' | Ph | 2-MeNH$_2$-4-Pym | 2-I |
| 1-122' | Ph | 2-MeNH$_2$-4-Pym | 2,2-diF |
| 1-123' | Ph | 2-MeNH$_2$4-Pym | 2,2-diCl |
| 1-124' | Ph | 2-MeNH$_2$-4-Pym | 2,2-diBr |
| 1-125' | Ph | 2-MeNH$_2$-4-Pym | 3-Me |
| 1-126' | Ph | 2-MeNH$_2$-4-Pym | 3-Et |
| 1-127' | Ph | 2-MeNH$_2$-4-Pym | 3-Pr |
| 1-128' | Ph | 2-MeNH$_2$-4-Pym | 3,3-diMe |
| 1-129' | Ph | 2-MeNH$_2$-4-Pym | 5-Me |
| 1-130' | Ph | 2-MeNH$_2$-4-Pym | 5-Et |
| 1-131' | Ph | 2-MeNH$_2$-4-Pym | 5-Pr |
| 1-132' | Ph | 2-MeNH$_2$-4-Pym | 5,5-diMe |
| 1-133' | Ph | 2-MeNH$_2$-4-Pym | 6-Me |
| 1-134' | Ph | 2-MeNH$_2$-4-Pym | 6-Et |
| 1-135' | Ph | 2-MeNH$_2$-4-Pym | 6-Pr |
| 1-136' | Ph | 2-MeNH$_2$4-Pym | 6,6-diMe |
| 1-137' | Ph | 2-MeNH$_2$-4-Pym | 6-Oxo |
| 1-138' | Ph | 2-MeNH$_2$-4-Pym | 8-Me |
| 1-139' | Ph | 2-MeNH$_2$-4-Pym | 8-Et |
| 1-140' | Ph | 2-MeNH$_2$-4-Pym | 8-Pr |
| 1-141' | Ph | 2-MeNH$_2$-4-Pym | 8-Ph |
| 1-142' | Ph | 2-MeNH$_2$-4-Pym | 8a-Me |
| 1-143' | Ph | 2-MeNH$_2$-4-Pym | 8a-Et |
| 1-144' | Ph | 2-MeNH$_2$-4-Pym | 8a-Pr |
| 1-145' | 3-F-Ph | 4-Pyr | 1-Me |
| 1-146' | 3-F-Ph | 4-Pyr | 1-Et |
| 1-147' | 3-F-Ph | 4-Pyr | 1-Pr |
| 1-148' | 3-F-Ph | 4-Pyr | 1,1-diMe |
| 1-149' | 3-F-Ph | 4-Pyr | 2-Me |
| 1-150' | 3-F-Ph | 4-Pyr | 2-Et |
| 1-151' | 3-F-Ph | 4-Pyr | 2-Pr |
| 1-152' | 3-F-Ph | 4-Pyr | 2-Bu |
| 1-153' | 3-F-Ph | 4-Pyr | 2-Allyl |
| 1-154' | 3-F-Ph | 4-Pyr | 2-Ph |
| 1-155' | 3-F-Ph | 4-Pyr | 2-Bn |
| 1-156' | 3-F-Ph | 4-Pyr | 2-Phet |
| 1-157' | 3-F-Ph | 4-Pyr | 2,2-diMe |
| 1-158' | 3-F-Ph | 4-Pyr | 2-OH |
| 1-159' | 3-F-Ph | 4-Pyr | 2-MeO |
| 1-160' | 3-F-Ph | 4-Pyr | 2-EtO |
| 1-161' | 3-F-Ph | 4-Pyr | 2-PrO |

TABLE 1'-continued

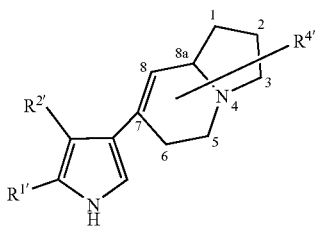

| Compound No. | R1' | R2' | R4' |
|---|---|---|---|
| 1-162' | 3-F-Ph | 4-Pyr | 2,2-di(MeO) |
| 1-163' | 3-F-Ph | 4-Pyr | 2,2-di(EtO) |
| 1-164' | 3-F-Ph | 4-Pyr | 2,2-OCH$_2$CH$_2$O— |
| 1-165' | 3-F-Ph | 4-Pyr | 2-Oxo |
| 1-166' | 3-F-Ph | 4-Pyr | 2-F |
| 1-167' | 3-F-Ph | 4-Pyr | 2-Cl |
| 1-168' | 3-F-Ph | 4-Pyr | 2-Br |
| 1-169' | 3-F-Ph | 4-Pyr | 2-I |
| 1-170' | 3-F-Ph | 4-Pyr | 2,2-diF |
| 1-171' | 3-F-Ph | 4-Pyr | 2,2-diCl |
| 1-172' | 3-F-Ph | 4-Pyr | 2,2-diBr |
| 1-173' | 3-F-Ph | 4-Pyr | 3-Me |
| 1-174' | 3-F-Ph | 4-Pyr | 3-Et |
| 1-175' | 3-F-Ph | 4-Pyr | 3-Pr |
| 1-176' | 3-F-Ph | 4-Pyr | 3,3-diMe |
| 1-177' | 3-F-Ph | 4-Pyr | 5-Me |
| 1-178' | 3-F-Ph | 4-Pyr | 5-Et |
| 1-179' | 3-F-Ph | 4-Pyr | 5-Pr |
| 1-180' | 3-F-Ph | 4-Pyr | 5,5-diMe |
| 1-181' | 3-F-Ph | 4-Pyr | 6-Me |
| 1-182' | 3-F-Ph | 4-Pyr | 6-Et |
| 1-183' | 3-F-Ph | 4-Pyr | 6-Pr |
| 1-184' | 3-F-Ph | 4-Pyr | 6,6-diMe |
| 1-185' | 3-F-Ph | 4-Pyr | 6-Oxo |
| 1-186' | 3-F-Ph | 4-Pyr | 8-Me |
| 1-187' | 3-F-Ph | 4-Pyr | 8-Et |
| 1-188' | 3-F-Ph | 4-Pyr | 8-Pr |
| 1-189' | 3-F-Ph | 4-Pyr | 8-Ph |
| 1-190' | 3-F-Ph | 4-Pyr | 8a-Me |
| 1-191' | 3-F-Ph | 4-Pyr | 8a-Et |
| 1-192' | 3-F-Ph | 4-Pyr | 8a-Pr |
| 1-193' | 3-F-Ph | 2-NH$_2$-4-Pym | 1-Me |
| 1-194' | 3-F-Ph | 2-NH$_2$-4-Pym | 1-Et |
| 1-195' | 3-F-Ph | 2-NH$_2$-4-Pym | 1-Pr |
| 1-196' | 3-F-Ph | 2-NH$_2$-4-Pym | 1,1-diMe |
| 1-197' | 3-F-Ph | 2-NH$_2$-4-Pym | 2-Me |
| 1-198' | 3-F-Ph | 2-NH$_2$-4-Pym | 2-Et |
| 1-199' | 3-F-Ph | 2-NH$_2$-4-Pym | 2-Pr |
| 1-200' | 3-F-Ph | 2-NH$_2$-4-Pym | 2-Bu |
| 1-201' | 3-F-Ph | 2-NH$_2$-4-Pym | 2-Allyl |
| 1-202' | 3-F-Ph | 2-NH$_2$-4-Pym | 2-Ph |
| 1-203' | 3-F-Ph | 2-NH$_2$-4-Pym | 2-Bn |
| 1-204' | 3-F-Ph | 2-NH$_2$-4-Pym | 2-Phet |
| 1-205' | 3-F-Ph | 2-NH$_2$-4-Pym | 2,2-diMe |
| 1-206' | 3-F-Ph | 2-NH$_2$-4-Pym | 2-OH |
| 1-207' | 3-F-Ph | 2-NH$_2$-4-Pym | 2-MeO |
| 1-208' | 3-F-Ph | 2-NH$_2$-4-Pym | 2-EtO |
| 1-209' | 3-F-Ph | 2-NH$_2$-4-Pym | 2-PrO |
| 1-210' | 3-F-Ph | 2-NH$_2$-4-Pym | 2,2-di(MeO) |
| 1-211' | 3-F-Ph | 2-NH$_2$-4-Pym | 2,2-di(EtO) |
| 1-212' | 3-F-Ph | 2-NH$_2$-4-Pym | 2,2-OCH$_2$CH$_2$O— |
| 1-213' | 3-F-Ph | 2-NH$_2$-4-Pym | 2-Oxo |
| 1-214' | 3-F-Ph | 2-NH$_2$-4-Pym | 2-F |
| 1-215' | 3-F-Ph | 2-NH$_2$-4-Pym | 2-Cl |
| 1-216' | 3-F-Ph | 2-NH$_2$-4-Pym | 2-Br |
| 1-217' | 3-F-Ph | 2-NH$_2$-4-Pym | 2-I |
| 1-218' | 3-F-Ph | 2-NH$_2$-4-Pym | 2,2-diF |
| 1-219' | 3-F-Ph | 2-NH$_2$-4-Pym | 2,2-diCl |
| 1-220' | 3-F-Ph | 2-NH$_2$-4-Pym | 2,2-diBr |
| 1-221' | 3-F-Ph | 2-NH$_2$-4-Pym | 3-Me |
| 1-222' | 3-F-Ph | 2-NH$_2$-4-Pym | 3-Et |
| 1-223' | 3-F-Ph | 2-NH$_2$-4-Pym | 3-Pr |
| 1-224' | 3-F-Ph | 2-NH$_2$-4-Pym | 3,3-diMe |
| 1-225' | 3-F-Ph | 2-NH$_2$-4-Pym | 5-Me |

TABLE 1'-continued

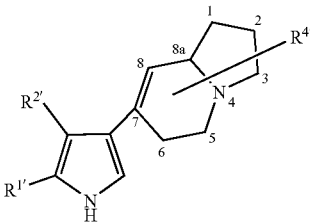

| Compound No. | R[1'] | R[2'] | R[4'] |
|---|---|---|---|
| 1-226' | 3-F-Ph | 2-NH$_2$-4-Pym | 5-Et |
| 1-227' | 3-F-Ph | 2-NH$_2$-4-Pym | 5-Pr |
| 1-228' | 3-F-Ph | 2-NH$_2$-4-Pym | 5,5-diMe |
| 1-229' | 3-F-Ph | 2-NH$_2$-4-Pym | 6-Me |
| 1-230' | 3-F-Ph | 2-NH$_2$-4-Pym | 6-Et |
| 1-231' | 3-F-Ph | 2-NH$_2$-4-Pym | 6-Pr |
| 1-232' | 3-F-Ph | 2-NH$_2$-4-Pym | 6,6-diMe |
| 1-233' | 3-F-Ph | 2-NH$_2$-4-Pym | 6-Oxo |
| 1-234' | 3-F-Ph | 2-NH$_2$-4-Pym | 8-Me |
| 1-235' | 3-F-Ph | 2-NH$_2$-4-Pym | 8-Et |
| 1-236' | 3-F-Ph | 2-NH$_2$-4-Pym | 8-Pr |
| 1-237' | 3-F-Ph | 2-NH$_2$-4-Pym | 8-Ph |
| 1-238' | 3-F-Ph | 2-NH$_2$-4-Pym | 8a-Me |
| 1-239' | 3-F-Ph | 2-NH$_2$-4-Pym | 8a-Et |
| 1-240' | 3-F-Ph | 2-NH$_2$-4-Pym | 8a-Pr |
| 1-241' | 3-F-Ph | 2-MeNH$_2$-4-Pym | 1-Me |
| 1-242' | 3-F-Ph | 2-MeNH$_2$-4-Pym | 1-Et |
| 1-243' | 3-F-Ph | 2-MeNH$_2$-4-Pym | 1-Pr |
| 1-244' | 3-F-Ph | 2-MeNH$_2$-4-Pym | 1,1-diMe |
| 1-245' | 3-F-Ph | 2-MeNH$_2$-4-Pym | 2-Me |
| 1-246' | 3-F-Ph | 2-MeNH$_2$-4-Pym | 2-Et |
| 1-247' | 3-F-Ph | 2-MeNH$_2$-4-Pym | 2-Pr |
| 1-248' | 3-F-Ph | 2-MeNH$_2$-4-Pym | 2-Bu |
| 1-249' | 3-F-Ph | 2-MeNH$_2$-4-Pym | 2-Allyl |
| 1-250' | 3-F-Ph | 2-MeNH$_2$-4-Pym | 2-Ph |
| 1-251' | 3-F-Ph | 2-MeNH$_2$4-Pym | 2-Bn |
| 1-252' | 3-F-Ph | 2-MeNH$_2$-4-Pym | 2-Phet |
| 1-253' | 3-F-Ph | 2-MeNH$_2$-4-Pym | 2,2-diMe |
| 1-254' | 3-F-Ph | 2-MeNH$_2$-4-Pym | 2-OH |
| 1-255' | 3-F-Ph | 2-MeNH$_2$-4-Pym | 2-MeO |
| 1-256' | 3-F-Ph | 2-MeNH$_2$-4-Pym | 2-EtO |
| 1-257' | 3-F-Ph | 2-MeNH$_2$-4-Pym | 2-PrO |
| 1-258' | 3-F-Ph | 2-MeNH$_2$-4-Pym | 2,2-di(MeO) |
| 1-259' | 3-F-Ph | 2-MeNH$_2$-4-Pym | 2,2-di(EtO) |
| 1-260' | 3-F-Ph | 2-MeNH$_2$-4-Pym | 2,2-OCH$_2$CH$_2$O— |
| 1-261' | 3-F-Ph | 2-MeNH$_2$-4-Pym | 2-Oxo |
| 1-262' | 3-F-Ph | 2-MeNH$_2$-4-Pym | 2-F |
| 1-263' | 3-F-Ph | 2-MeNH$_2$-4-Pym | 2-Cl |
| 1-264' | 3-F-Ph | 2-MeNH$_2$-4-Pym | 2-Br |
| 1-265' | 3-F-Ph | 2-MeNH$_2$-4-Pym | 2-I |
| 1-266' | 3-F-Ph | 2-MeNH$_2$-4-Pym | 2,2-diF |
| 1-267' | 3-F-Ph | 2-MeNH$_2$-4-Pym | 2,2-diCl |
| 1-268' | 3-F-Ph | 2-MeNH$_2$-4-Pym | 2,2-diBr |
| 1-269' | 3-F-Ph | 2-MeNH$_2$-4-Pym | 3-Me |
| 1-270' | 3-F-Ph | 2-MeNH$_2$-4-Pym | 3-Et |
| 1-271' | 3-F-Ph | 2-MeNH$_2$-4-Pym | 3-Pr |
| 1-272' | 3-F-Ph | 2-MeNH$_2$-4-Pym | 3,3-diMe |
| 1-273' | 3-F-Ph | 2-MeNH$_2$-4-Pym | 5-Me |
| 1-274' | 3-F-Ph | 2-MeNH$_2$-4-Pym | 5-Et |
| 1-275' | 3-F-Ph | 2-MeNH$_2$-4-Pym | 5-Pr |
| 1-276' | 3-F-Ph | 2-MeNH$_2$-4-Pym | 5,5-diMe |
| 1-277' | 3-F-Ph | 2-MeNH$_2$-4-Pym | 6-Me |
| 1-278' | 3-F-Ph | 2-MeNH$_2$-4-Pym | 6-Et |
| 1-279' | 3-F-Ph | 2-MeNH$_2$-4-Pym | 6-Pr |
| 1-280' | 3-F-Ph | 2-MeNH$_2$-4-Pym | 6-6-diMe |
| 1-281' | 3-F-Ph | 2-MeNH$_2$-4-Pym | 6-Oxo |
| 1-282' | 3-F-Ph | 2-MeNH$_2$-4-Pym | 8-Me |
| 1-283' | 3-F-Ph | 2-MeNH$_2$-4-Pym | 8-Et |
| 1-284' | 3-F-Ph | 2-MeNH$_2$-4-Pym | 8-Pr |
| 1-285' | 3-F-Ph | 2-MeNH$_2$-4-Pym | 8-Ph |
| 1-286' | 3-F-Ph | 2-MeNH$_2$-4-Pym | 8a-Me |
| 1-287' | 3-F-Ph | 2-MeNH$_2$-4-Pym | 8a-Et |
| 1-288' | 3-F-Ph | 2-MeNH$_2$-4-Pym | 8a-Pr |
| 1-289' | 4-F-Ph | 4-Pyr | 1-Me |

TABLE 1'-continued

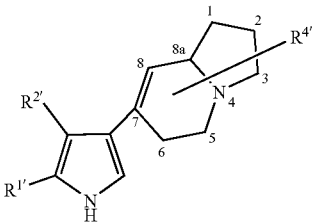

| Compound No. | R$^{1'}$ | R$^{2'}$ | R$^{4'}$ |
|---|---|---|---|
| 1-290' | 4-F-Ph | 4-Pyr | 1-Et |
| 1-291' | 4-F-Ph | 4-Pyr | 1-Pr |
| 1-292' | 4-F-Ph | 4-Pyr | 1,1-diMe |
| 1-293' | 4-F-Ph | 4-Pyr | 2-Me |
| 1-294' | 4-F-Ph | 4-Pyr | 2-Et |
| 1-295' | 4-F-Ph | 4-Pyr | 2-Pr |
| 1-296' | 4-F-Ph | 4-Pyr | 2-Bu |
| 1-297' | 4-F-Ph | 4-Pyr | 2-Allyl |
| 1-298' | 4-F-Ph | 4-Pyr | 2-Ph |
| 1-299' | 4-F-Ph | 4-Pyr | 2-Bn |
| 1-300' | 4-F-Ph | 4-Pyr | 2-Phet |
| 1-301' | 4-F-Ph | 4-Pyr | 2,2-diMe |
| 1-302' | 4-F-Ph | 4-Pyr | 2-OH |
| 1-303' | 4-F-Ph | 4-Pyr | 2-MeO |
| 1-304' | 4-F-Ph | 4-Pyr | 2-EtO |
| 1-305' | 4-F-Ph | 4-Pyr | 2-PrO |
| 1-306' | 4-F-Ph | 4-Pyr | 2,2-di(MeO) |
| 1-307' | 4-F-Ph | 4-Pyr | 2,2-di(EtO) |
| 1-308' | 4-F-Ph | 4-Pyr | 2,2-OCH$_2$CH$_2$O— |
| 1-309' | 4-F-Ph | 4-Pyr | 2-Oxo |
| 1-310' | 4-F-Ph | 4-Pyr | 2-F |
| 1-311' | 4-F-Ph | 4-Pyr | 2-Cl |
| 1-312' | 4-F-Ph | 4-Pyr | 2-Br |
| 1-313' | 4-F-Ph | 4-Pyr | 2-I |
| 1-314' | 4-F-Ph | 4-Pyr | 2,2-diF |
| 1-315' | 4-F-Ph | 4-Pyr | 2,2-diCl |
| 1-316' | 4-F-Ph | 4-Pyr | 2,2-diBr |
| 1-317' | 4-F-Ph | 4-Pyr | 3-Me |
| 1-318' | 4-F-Ph | 4-Pyr | 3-Et |
| 1-319' | 4-F-Ph | 4-Pyr | 3-Pr |
| 1-320' | 4-F-Ph | 4-Pyr | 3,3-diMe |
| 1-321' | 4-F-Ph | 4-Pyr | 5-Me |
| 1-322' | 4-F-Ph | 4-Pyr | 5-Et |
| 1-323' | 4-F-Ph | 4-Pyr | 5-Pr |
| 1-324' | 4-F-Ph | 4-Pyr | 5,5-diMe |
| 1-325' | 4-F-Ph | 4-Pyr | 6-Me |
| 1-326' | 4-F-Ph | 4-Pyr | 6-Et |
| 1-327' | 4-F-Ph | 4-Pyr | 6-Pr |
| 1-328' | 4-F-Ph | 4-Pyr | 6,6-diMe |
| 1-329' | 4-F-Ph | 4-Pyr | 6-Oxo |
| 1-330' | 4-F-Ph | 4-Pyr | 8-Me |
| 1-331' | 4-F-Ph | 4-Pyr | 8-Et |
| 1-332' | 4-F-Ph | 4-Pyr | 8-Pr |
| 1-333' | 4-F-Ph | 4-Pyr | 8-Ph |
| 1-334' | 4-F-Ph | 4-Pyr | 8a-Me |
| 1-335' | 4-F-Ph | 4-Pyr | 8a-Et |
| 1-336' | 4-F-Ph | 4-Pyr | 8a-Pr |
| 1-337' | 4-F-Ph | 2-NH$_2$-4-Pym | 1-Me |
| 1-338' | 4-F-Ph | 2-NH$_2$-4-Pym | 1-Et |
| 1-339' | 4-F-Ph | 2-NH$_2$-4-Pym | 1-Pr |
| 1-340' | 4-F-Ph | 2-NH$_2$-4-Pym | 1,1-diMe |
| 1-341' | 4-F-Ph | 2-NH$_2$-4-Pym | 2-Me |
| 1-342' | 4-F-Ph | 2-NH$_2$-4-Pym | 2-Et |
| 1-343' | 4-F-Ph | 2-NH$_2$-4-Pym | 2-Pr |
| 1-344' | 4-F-Ph | 2-NH$_2$-4-Pym | 2-Bu |
| 1-345' | 4-F-Ph | 2-NH$_2$-4-Pym | 2-Allyl |
| 1-346' | 4-F-Ph | 2-NH$_2$-4-Pym | 2-Ph |
| 1-347' | 4-F-Ph | 2-NH$_2$-4-Pym | 2-Bn |
| 1-348' | 4-F-Ph | 2-NH$_2$-4-Pym | 2-Phet |
| 1-349' | 4-F-Ph | 2-NH$_2$-4-Pym | 2,2-diMe |
| 1-350' | 4-F-Ph | 2-NH$_2$-4-Pym | 2-OH |
| 1-351' | 4-F-Ph | 2-NH$_2$-4-Pym | 2-MeO |
| 1-352' | 4-F-Ph | 2-NH$_2$-4-Pym | 2-EtO |
| 1-353' | 4-F-Ph | 2-NH$_2$-4-Pym | 2-PrO |

TABLE 1'-continued

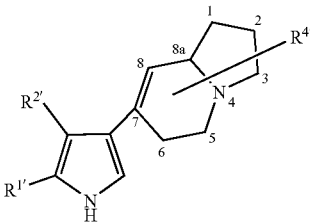

| Compound No. | R$^{1'}$ | R$^{2'}$ | R$^{4'}$ |
|---|---|---|---|
| 1-354' | 4-F-Ph | 2-NH$_2$-4-Pym | 2,2-di(MeO) |
| 1-355' | 4-F-Ph | 2-NH$_2$-4-Pym | 2,2-di(EtO) |
| 1-356' | 4-F-Ph | 2-NH$_2$-4-Pym | 2,2-OCH$_2$CH$_2$O— |
| 1-357' | 4-F-Ph | 2-NH$_2$-4-Pym | 2-Oxo |
| 1-358' | 4-F-Ph | 2-NH$_2$-4-Pym | 2-F |
| 1-359' | 4-F-Ph | 2-NH$_2$-4-Pym | 2-Cl |
| 1-360' | 4-F-Ph | 2-NH$_2$-4-Pym | 2-Br |
| 1-361' | 4-F-Ph | 2-NH$_2$-4-Pym | 2-I |
| 1-362' | 4-F-Ph | 2-NH$_2$-4-Pym | 2,2-diF |
| 1-363' | 4-F-Ph | 2-NH$_2$-4-Pym | 2,2-diCl |
| 1-364' | 4-F-Ph | 2-NH$_2$-4-Pym | 2,2-diBr |
| 1-365' | 4-F-Ph | 2-NH$_2$-4-Pym | 3-Me |
| 1-366' | 4-F-Ph | 2-NH$_2$-4-Pym | 3-Et |
| 1-367' | 4-F-Ph | 2-NH$_2$-4-Pym | 3-Pr |
| 1-368' | 4-F-Ph | 2-NH$_2$-4-Pym | 3,3-diMe |
| 1-369' | 4-F-Ph | 2-NH$_2$-4-Pym | 5-Me |
| 1-370' | 4-F-Ph | 2-NH$_2$-4-Pym | 5-Et |
| 1-371' | 4-F-Ph | 2-NH$_2$-4-Pym | 5-Pr |
| 1-372' | 4-F-Ph | 2-NH$_2$-4-Pym | 5,5-diMe |
| 1-373' | 4-F-Ph | 2-NH$_2$-4-Pym | 6-Me |
| 1-374' | 4-F-Ph | 2-NH$_2$-4-Pym | 6-Et |
| 1-375' | 4-F-Ph | 2-NH$_2$-4-Pym | 6-Pr |
| 1-376' | 4-F-Ph | 2-NH$_2$-4-Pym | 6,6-diMe |
| 1-377' | 4-F-Ph | 2-NH$_2$-4-Pym | 6-Oxo |
| 1-378' | 4-F-Ph | 2-NH$_2$-4-Pym | 8-Me |
| 1-379' | 4-F-Ph | 2-NH$_2$-4-Pym | 8-Et |
| 1-380' | 4-F-Ph | 2-NH$_2$-4-Pym | 8-Pr |
| 1-381' | 4-F-Ph | 2-NH$_2$-4-Pym | 8-Ph |
| 1-382' | 4-F-Ph | 2-NH$_2$-4-Pym | 8a-Me |
| 1-383' | 4-F-Ph | 2-NH$_2$-4-Pym | 8a-Et |
| 1-384' | 4-F-Ph | 2-NH$_2$-4-Pym | 8a-Pr |
| 1-385' | 4-F-Ph | 2-MeNH$_2$-4-Pym | 1-Me |
| 1-386' | 4-F-Ph | 2-MeNH$_2$-4-Pym | 1-Et |
| 1-387' | 4-F-Ph | 2-MeNH$_2$-4-Pym | 1-Pr |
| 1-388' | 4-F-Ph | 2-MeNH$_2$-4-Pym | 1,1-diMe |
| 1-389' | 4-F-Ph | 2-MeNH$_2$-4-Pym | 2-Me |
| 1-390' | 4-F-Ph | 2-MeNH$_2$-4-Pym | 2-Et |
| 1-391' | 4-F-Ph | 2-MeNH$_2$-4-Pym | 2-Pr |
| 1-392' | 4-F-Ph | 2-MeNH$_2$-4-Pym | 2-Bu |
| 1-393' | 4-F-Ph | 2-MeNH$_2$-4-Pym | 2-Allyl |
| 1-394' | 4-F-Ph | 2-MeNH$_2$-4-Pym | 2-Ph |
| 1-395' | 4-F-Ph | 2-MeNH$_2$-4-Pym | 2-Bn |
| 1-396' | 4-F-Ph | 2-MeNH$_2$-4-Pym | 2-Phet |
| 1-397' | 4-F-Ph | 2-MeNH$_2$-4-Pym | 2,2-diMe |
| 1-398' | 4-F-Ph | 2-MeNH$_2$-4-Pym | 2-OH |
| 1-399' | 4-F-Ph | 2-MeNH$_2$-4-Pym | 2-MeO |
| 1-400' | 4-F-Ph | 2-MeNH$_2$-4-Pym | 2-EtO |
| 1-401' | 4-F-Ph | 2-MeNH$_2$-4-Pym | 2-PrO |
| 1-402' | 4-F-Ph | 2-MeNH$_2$-4-Pym | 2,2-di(MeO) |
| 1-403' | 4-F-Ph | 2-MeNH$_2$-4-Pym | 2,2-di(EtO) |
| 1-404' | 4-F-Ph | 2-MeNH$_2$-4-Pym | 2,2-OCH$_2$CH$_2$O— |
| 1-405' | 4-F-Ph | 2-MeNH$_2$-4-Pym | 2-Oxo |
| 1-406' | 4-F-Ph | 2-MeNH$_2$-4-Pym | 2-F |
| 1-407' | 4-F-Ph | 2-MeNH$_2$-4-Pym | 2-Cl |
| 1-408' | 4-F-Ph | 2-MeNH$_2$-4-Pym | 2-Br |
| 1-409' | 4-F-Ph | 2-MeNH$_2$-4-Pym | 2-I |
| 1-410' | 4-F-Ph | 2-MeNH$_2$-4-Pym | 2,2-diF |
| 1-411' | 4-F-Ph | 2-MeNH$_2$-4-Pym | 2,2-diCl |
| 1-412' | 4-F-Ph | 2-MeNH$_2$-4-Pym | 2,2-diBr |
| 1-413' | 4-F-Ph | 2-MeNH$_2$-4-Pym | 3-Me |
| 1-414' | 4-F-Ph | 2-MeNH$_2$-4-Pym | 3-Et |
| 1-415' | 4-F-Ph | 2-MeNH$_2$-4-Pym | 3-Pr |
| 1-416' | 4-F-Ph | 2-MeNH$_2$-4-Pym | 3,3-diMe |
| 1-417' | 4-F-Ph | 2-MeNH$_2$-4-Pym | 5-Me |

TABLE 1'-continued

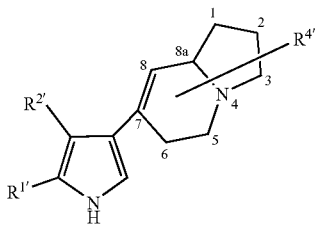

| Compound No. | R$^{1'}$ | R$^{2'}$ | R$^{4'}$ |
|---|---|---|---|
| 1-418' | 4-F-Ph | 2-MeNH$_2$-4-Pym | 5-Et |
| 1-419' | 4-F-Ph | 2-MeNH$_2$-4-Pym | 5-Pr |
| 1-420' | 4-F-Ph | 2-MeNH$_2$-4-Pym | 5,5-diMe |
| 1-421' | 4-F-Ph | 2-MeNH$_2$-4-Pym | 6-Me |
| 1-422' | 4-F-Ph | 2-MeNH$_2$-4-Pym | 6-Et |
| 1-423' | 4-F-Ph | 2-MeNH$_2$-4-Pym | 6-Pr |
| 1-424' | 4-F-Ph | 2-MeNH$_2$-4-Pym | 6,6-diMe |
| 1-425' | 4-F-Ph | 2-MeNH$_2$-4-Pym | 6-Oxo |
| 1-426' | 4-F-Ph | 2-MeNH$_2$-4-Pym | 8-Me |
| 1-427' | 4-F-Ph | 2-MeNH$_2$-4-Pym | 8-Et |
| 1-428' | 4-F-Ph | 2-MeNH$_2$-4-Pym | 8-Pr |
| 1-429' | 4-F-Ph | 2-MeNH$_2$-4-Pym | 8-Ph |
| 1-430' | 4-F-Ph | 2-MeNH$_2$-4-Pym | 8a-Me |
| 1-431' | 4-F-Ph | 2-MeNH$_2$-4-Pym | 8a-Et |
| 1-432' | 4-F-Ph | 2-MeNH$_2$-4-Pym | 8a-Pr |
| 1-433' | 3-Cl-Ph | 4-Pyr | 1-Me |
| 1-134' | 3-Cl-Ph | 4-Pyr | 1-Et |
| 1-435' | 3-Cl-Ph | 4-Pyr | 1-Pr |
| 1-436' | 3-Cl-Ph | 4-Pyr | 1,1-diMe |
| 1-437' | 3-Cl-Ph | 4-Pyr | 2-Me |
| 1-438' | 3-Cl-Ph | 4-Pyr | 2-Et |
| 1-439' | 3-Cl-Ph | 4-Pyr | 2-Pr |
| 1-440' | 3-Cl-Ph | 4-Pyr | 2-Bu |
| 1-441' | 3-Cl-Ph | 4-Pyr | 2-Allyl |
| 1-442' | 3-Cl-Ph | 4-Pyr | 2-Ph |
| 1-443' | 3-Cl-Ph | 4-Pyr | 2-Bn |
| 1-444' | 3-Cl-Ph | 4-Pyr | 2-Phet |
| 1-445' | 3-Cl-Ph | 4-Pyr | 2,2-diMe |
| 1-446' | 3-Cl-Ph | 4-Pyr | 2-OH |
| 1-447' | 3-Cl-Ph | 4-Pyr | 2-MeO |
| 1-448' | 3-Cl-Ph | 4-Pyr | 2-EtO |
| 1-449' | 3-Cl-Ph | 4-Pyr | 2-PrO |
| 1-450' | 3-Cl-Ph | 4-Pyr | 2,2-di(MeO) |
| 1-451' | 3-Cl-Ph | 4-Pyr | 2,2-di(EtO) |
| 1-452' | 3-Cl-Ph | 4-Pyr | 2,2-OCH$_2$CH$_2$O— |
| 1-453' | 3-Cl-Ph | 4-Pyr | 2-Oxo |
| 1-454' | 3-Cl-Ph | 4-Pyr | 2-F |
| 1-455' | 3-Cl-Ph | 4-Pyr | 2-Cl |
| 1-456' | 3-Cl-Ph | 4-Pyr | 2-Br |
| l-45T' | 3-Cl-Ph | 4-Pyr | 2-I |
| 1-458' | 3-Cl-Ph | 4-Pyr | 2,2-diF |
| 1-459' | 3-Cl-Ph | 4-Pyr | 2,2-diCl |
| 1-460' | 3-Cl-Ph | 4-Pyr | 2,2-diBr |
| 1-461' | 3-Cl-Ph | 4-Pyr | 3-Me |
| 1-462' | 3-Cl-Ph | 4-Pyr | 3-Et |
| 1-463' | 3-Cl-Ph | 4-Pyr | 3-Pr |
| 1-464' | 3-Cl-Ph | 4-Pyr | 3,3-diMe |
| 1-465' | 3-Cl-Ph | 4-Pyr | 5-Me |
| 1-466' | 3-Cl-Ph | 4-Pyr | 5-Et |
| 1-467' | 3-Cl-Ph | 4-Pyr | 5-Pr |
| 1-468' | 3-Cl-Ph | 4-Pyr | 5,5-diMe |
| 1-469' | 3-Cl-Ph | 4-Pyr | 6-Me |
| 1-470' | 3-Cl-Ph | 4-Pyr | 6-Et |
| 1-471' | 3-Cl-Ph | 4-Pyr | 6-Pr |
| 1-472' | 3-Cl-Ph | 4-Pyr | 6,6-diMe |
| 1-473' | 3-Cl-Ph | 4-Pyr | 6-Oxo |
| 1-474' | 3-Cl-Ph | 4-Pyr | 8-Me |
| 1-475' | 3-Cl-Ph | 4-Pyr | 8-Et |
| 1-476' | 3-Cl-Ph | 4-Pyr | 8-Pr |
| 1-477' | 3-Cl-Ph | 4-Pyr | 8-Ph |
| 1-478' | 3-Cl-Ph | 4-Pyr | 8a-Me |
| 1-479' | 3-Cl-Ph | 4-Pyr | 8a-Et |
| 1-480' | 3-Cl-Ph | 4-Pyr | 8a-Pr |
| 1-481' | 3-Cl-Ph | 2-NH$_2$-4-Pym | 1-Me |

TABLE 1'-continued

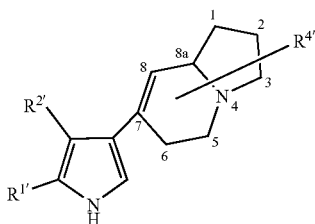

| Compound No. | R[1'] | R[2'] | R[4'] |
|---|---|---|---|
| 1-482' | 3-Cl-Ph | 2-NH$_2$4-Pym | 1-Et |
| 1-483' | 3-Cl-Ph | 2-NH$_2$-4-Pym | 1-Pr |
| 1-484' | 3-Cl-Ph | 2-NH$_2$-4-Pym | 1-diMe |
| 1-485' | 3-Cl-Ph | 2-NH$_2$-4-Pym | 2-Me |
| 1-486' | 3-Cl-Ph | 2-NH$_2$-4-Pym | 2-Et |
| 1-487' | 3-Cl-Ph | 2-NH$_2$-4-Pym | 2-Pr |
| 1-488' | 3-Cl-Ph | 2-NH$_2$-4-Pym | 2-Bu |
| 1-489' | 3-Cl-Ph | 2-NH$_2$-4-Pym | 2-Allyl |
| 1-490' | 3-Cl-Ph | 2-NH$_2$-4-Pym | 2-Ph |
| 1-491' | 3-Cl-Ph | 2-NH$_2$-4-Pym | 2-Bn |
| 1-492' | 3-Cl-Ph | 2-NH$_2$-4-Pym | 2-Phet |
| 1-493' | 3-Cl-Ph | 2-NH$_2$-4-Pym | 2,2-diMe |
| 1-494' | 3-Cl-Ph | 2-NH$_2$-4-Pym | 2-OH |
| 1-495' | 3-Cl-Ph | 2-NH$_2$-4-Pym | 2-MeO |
| 1-496' | 3-Cl-Ph | 2-NH$_2$-4-Pym | 2-EtO |
| 1-497' | 3-Cl-Ph | 2-NH$_2$-4-Pym | 2-PrO |
| 1-498' | 3-Cl-Ph | 2-NH$_2$-4-Pym | 2,2-di(MeO) |
| 1-499' | 3-Cl-Ph | 2-NH$_2$-4-Pym | 2,2-di(EtO) |
| 1-500' | 3-Cl-Ph | 2-NH$_2$-4-Pym | 2,2-OCH$_2$CH$_2$O— |
| 1-501' | 3-Cl-Ph | 2-NH$_2$-4-Pym | 2-Oxo |
| 1-502' | 3-Cl-Ph | 2-NH$_2$-4-Pym | 2-F |
| 1-503' | 3-Cl-Ph | 2-NH$_2$-4-Pym | 2-Cl |
| 1-504' | 3-Cl-Ph | 2-NH$_2$-4-Pym | 2-Br |
| 1-505' | 3-Cl-Ph | 2-NH$_2$-4-Pym | 2-I |
| 1-506' | 3-Cl-Ph | 2-NH$_2$-4-Pym | 2,2-diF |
| 1-507' | 3-Cl-Ph | 2-NH$_2$-4-Pym | 2,2-diCl |
| 1-508' | 3-Cl-Ph | 2-NH$_2$-4-Pym | 2,2-diBr |
| 1-509' | 3-Cl-Ph | 2-NH$_2$-4-Pym | 3-Me |
| 1-510' | 3-Cl-Ph | 2-NH$_2$-4-Pym | 3-Et |
| 1-511' | 3-Cl-Ph | 2-NH$_2$-4-Pym | 3-Pr |
| 1-512' | 3-Cl-Ph | 2-NH$_2$-4-Pym | 3,3-diMe |
| 1-513' | 3-Cl-Ph | 2-NH$_2$-4-Pym | 5-Me |
| 1-514' | 3-Cl-Ph | 2-NH$_2$-4-Pym | 5-Et |
| 1-515' | 3-Cl-Ph | 2-NH$_2$-4-Pym | 5-Pr |
| 1-516' | 3-Cl-Ph | 2-NH$_2$-4-Pym | 5,5-diMe |
| 1-517' | 3-Cl-Ph | 2-NH$_2$-4-Pym | 6-Me |
| 1-518' | 3-Cl-Ph | 2-NH$_2$-4-Pym | 6-Et |
| 1-519' | 3-Cl-Ph | 2-NH$_2$-4-Pym | 6-Pr |
| 1-520' | 3-Cl-Ph | 2-NH$_2$-4-Pym | 6,6-diMe |
| 1-521' | 3-Cl-Ph | 2-NH$_2$-4-Pym | 6-Oxo |
| 1-522' | 3-Cl-Ph | 2-NH$_2$-4-Pym | 8-Me |
| 1-523' | 3-Cl-Ph | 2-NH$_2$-4-Pym | 8-Et |
| 1-524' | 3-Cl-Ph | 2-NH$_2$-4-Pym | 8-Pr |
| 1-525' | 3-Cl-Ph | 2-NH$_2$-4-Pym | 8-Ph |
| 1-526' | 3-Cl-Ph | 2-NH$_2$-4-Pym | 8a-Me |
| 1-527' | 3-Cl-Ph | 2-NH$_2$-4-Pym | 8a-Et |
| 1-528' | 3-Cl-Ph | 2-NH$_2$-4-Pym | 8a-Pr |
| 1-529' | 3-Cl-Ph | 2-MeNH$_2$-4-Pym | 1-Me |
| 1-530' | 3-Cl-Ph | 2-MeNH$_2$-4-Pym | 1-Et |
| 1-531' | 3-Cl-Ph | 2-MeNH$_2$-4-Pym | 1-Pr |
| 1-532' | 3-Cl-Ph | 2-MeNH$_2$-4-Pym | 1,1-diMe |
| 1-533' | 3-Cl-Ph | 2-MeNH$_2$-4-Pym | 2-Me |
| 1-534' | 3-Cl-Ph | 2-MeNH$_2$-4-Pym | 2-Et |
| 1-535' | 3-Cl-Ph | 2-MeNH$_2$-4-Pym | 2-Pr |
| 1-536' | 3-Cl-Ph | 2-MeNH$_2$-4-Pym | 2-Bu |
| 1-537' | 3-Cl-Ph | 2-MeNH$_2$-4-Pym | 2-Allyl |
| 1-538' | 3-Cl-Ph | 2-MeNH$_2$-4-Pym | 2-Ph |
| 1-539' | 3-Cl-Ph | 2-MeNH$_2$-4-Pym | 2-Bn |
| 1-540' | 3-Cl-Ph | 2-MeNH$_2$-4-Pym | 2-Phet |
| 1-541' | 3-Cl-Ph | 2-MeNH$_2$-4-Pym | 2,2-diMe |
| 1-542' | 3-Cl-Ph | 2-MeNH$_2$-4-Pym | 2-OH |
| 1-543' | 3-Cl-Ph | 2-MeNH$_2$-4-Pym | 2-MeO |
| 1-544' | 3-Cl-Ph | 2-MeNH$_2$-4-Pym | 2-EtO |
| 1-545' | 3-Cl-Ph | 2-MeNH$_2$-4-Pym | 2-PrO |

TABLE 1'-continued

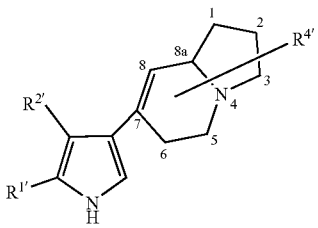

| Compound No. | R1' | R2' | R4' |
|---|---|---|---|
| 1-546' | 3-Cl-Ph | 2-MeNH$_2$-4-Pym | 2,2-di(MeO) |
| 1-547' | 3-Cl-Ph | 2-MeNH$_2$-4-Pym | 2,2-di(EtO) |
| 1-548' | 3-Cl-Ph | 2-MeNH$_2$-4-Pym | 2,2-OCH$_2$CH$_2$O— |
| 1-549' | 3-Cl-Ph | 2-MeNH$_2$-4-Pym | 2-Oxo |
| 1-550' | 3-Cl-Ph | 2-MeNH$_2$-4-Pym | 2-F |
| 1-551' | 3-Cl-Ph | 2-MeNH$_2$-4-Pym | 2-Cl |
| 1-552' | 3-Cl-Ph | 2-MeNH$_2$-4-Pym | 2-Br |
| 1-553' | 3-Cl-Ph | 2-MeNH$_2$-4-Pym | 2-I |
| 1-554' | 3-Cl-Ph | 2-MeNH$_2$-4-Pym | 2,2-diF |
| 1-555' | 3-Cl-Ph | 2-MeNH$_2$-4-Pym | 2,2-diCl |
| 1-556' | 3-Cl-Ph | 2-MeNH$_2$-4-Pym | 2,2-diBr |
| 1-557' | 3-Cl-Ph | 2-MeNH$_2$-4-Pym | 3-Me |
| 1-558' | 3-Cl-Ph | 2-MeNH$_2$-4-Pym | 3-Et |
| 1-559' | 3-Cl-Ph | 2-MeNH$_2$-4-Pym | 3-Pr |
| 1-560' | 3-Cl-Ph | 2-MeNH$_2$-4-Pym | 3,3-diMe |
| 1-561' | 3-Cl-Ph | 2-MeNH$_2$-4-Pym | 5-Me |
| 1-562' | 3-Cl-Ph | 2-MeNH$_2$-4-Pym | 5-Et |
| 1-563' | 3-Cl-Ph | 2-MeNH$_2$-4-Pym | 5-Pr |
| 1-564' | 3-Cl-Ph | 2-MeNH$_2$-4-Pym | 5,5-diMe |
| 1-565' | 3-Cl-Ph | 2-MeNH$_2$-4-Pym | 6-Me |
| 1-566' | 3-Cl-Ph | 2-MeNH$_2$-4-Pym | 6-Et |
| 1-567' | 3-Cl-Ph | 2-MeNH$_2$-4-Pym | 6-Pr |
| 1-568' | 3-Cl-Ph | 2-MeNH$_2$-4-Pym | 6,6-diMe |
| 1-569' | 3-Cl-Ph | 2-MeNH$_2$-4-Pym | 6-Oxo |
| 1-570' | 3-Cl-Ph | 2-MeNH$_2$-4-Pym | 8-Me |
| 1-571' | 3-Cl-Ph | 2-MeNH$_2$-4-Pym | 8-Et |
| 1-572' | 3-Cl-Ph | 2-MeNH$_2$-4-Pym | 8-Pr |
| 1-573' | 3-Cl-Ph | 2-MeNH$_2$-4-Pym | 8-Ph |
| 1-574' | 3-Cl-Ph | 2-MeNH$_2$-4-Pym | 8a-Me |
| 1-575' | 3-Cl-Ph | 2-MeNH$_2$-4-Pym | 8a-Et |
| 1-576' | 3-Cl-Ph | 2-MeNH$_2$-4-Pym | 8a-Pr |
| 1-577' | 3-CF$_3$-Ph | 4-Pyr | 1-Me |
| 1-578' | 3-CF$_3$-Ph | 4-Pyr | 1-Et |
| 1-579' | 3-CF$_3$-Ph | 4-Pyr | 1-Pr |
| 1-580' | 3-CF$_3$-Ph | 4-Pyr | 1,1-diMe |
| 1-581' | 3-CF$_3$-Ph | 4-Pyr | 2-Me |
| 1-582' | 3-CF$_3$-Ph | 4-Pyr | 2-Et |
| 1-583' | 3-CF$_3$-Ph | 4-Pyr | 2-Pr |
| 1-584' | 3-CF$_3$-Ph | 4-Pyr | 2-Bu |
| 1-585' | 3-CF$_3$-Ph | 4-Pyr | 2-Allyl |
| 1-586' | 3-CF$_3$-Ph | 4-Pyr | 2-Ph |
| 1-587' | 3-CF$_3$-Ph | 4-Pyr | 2-Bn |
| 1-588' | 3-CF$_3$-Ph | 4-Pyr | 2-Phex |
| 1-589' | 3-CF$_3$-Ph | 4-Pyr | 2,2-diMe |
| 1-590' | 3-CF$_3$-Ph | 4-Pyr | 2-OH |
| 1-591' | 3-CF$_3$-Ph | 4-Pyr | 2-MeO |
| 1-592' | 3-CF$_3$-Ph | 4-Pyr | 2-EtO |
| 1-593' | 3-CF$_3$-Ph | 4-Pyr | 2-PrO |
| 1-594' | 3-CF$_3$-Ph | 4-Pyr | 2,2-di(MeO) |
| 1-595' | 3-CF$_3$-Ph | 4-Pyr | 2,2-di(EtO) |
| 1-596' | 3-CF$_3$-Ph | 4-Pyr | 2,2-OCH$_2$CH$_2$O— |
| 1-597' | 3-CF$_3$-Ph | 4-Pyr | 2-Oxo |
| 1-598' | 3-CF$_3$-Ph | 4-Pyr | 2-F |
| 1-599' | 3-CF$_3$-Ph | 4-Pyr | 2-Cl |
| 1-600' | 3-CF$_3$-Ph | 4-Pyr | 2-Br |
| 1-601' | 3-CF$_3$-Ph | 4-Pyr | 2-I |
| 1-602' | 3-CF$_3$-Ph | 4-Pyr | 2,2-diF |
| 1-603' | 3-CF$_3$-Ph | 4-Pyr | 2,2-diCl |
| 1-604' | 3-CF$_3$-Ph | 4-Pyr | 2,2-diBr |
| 1-605' | 3-CF$_3$-Ph | 4-Pyr | 3-Me |
| 1-606' | 3-CF$_3$-Ph | 4-Pyr | 3-Et |
| 1-607' | 3-CF$_3$-Ph | 4-Pyr | 3-Pr |
| 1-608' | 3-CF$_3$-Ph | 4-Pyr | 3,3-diMe |
| 1-609' | 3-CF$_3$-Ph | 4-Pyr | 5-Me |

TABLE 1'-continued

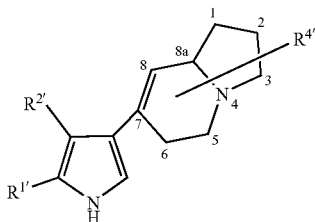

| Compound No. | R¹' | R²' | R⁴' |
|---|---|---|---|
| 1-610' | 3-CF₃-Ph | 4-Pyr | 5-Et |
| 1-611' | 3-CF₃-Ph | 4-Pyr | 5-Pr |
| 1-612' | 3-CF₃-Ph | 4-Pyr | 5,5-diMe |
| 1-613' | 3-CF₃-Ph | 4-Pyr | 6-Me |
| 1-614' | 3-CF₃-Ph | 4-Pyr | 6-Et |
| 1-615' | 3-CF₃-Ph | 4-Pyr | 6-Pr |
| 1-616' | 3-CF₃-Ph | 4-Pyr | 6,6-diMe |
| 1-617' | 3-CF₃-Ph | 4-Pyr | 6-Oxo |
| 1-618' | 3-CF₃-Ph | 4-Pyr | 8-Me |
| 1-619' | 3-CF₃-Ph | 4-Pyr | 8-Et |
| 1-620' | 3-CF₃-Ph | 4-Pyr | 8-Pr |
| 1-621' | 3-CF₃-Ph | 4-Pyr | 8-Ph |
| 1-622' | 3-CF₃-Ph | 4-Pyr | 8a-Me |
| 1-623' | 3-CF₃-Ph | 4-Pyr | 8a-Et |
| 1-624' | 3-CF₃-Ph | 4-Pyr | 8a-Pr |
| 1-625' | 3-CF₃-Ph | 2-NH₂-4-Pym | 1-Me |
| 1-626' | 3-CF₃-Ph | 2-NH₂-4-Pym | 1-Et |
| 1-627' | 3-CF₃-Ph | 2-NH₂-4-Pym | 1-Pr |
| 1-628' | 3-CF₃-Ph | 2-NH₂-4-Pym | 1,1-diMe |
| 1-629' | 3-CF₃-Ph | 2-NH₂-4-Pym | 2-Me |
| 1-630' | 3-CF₃-Ph | 2-NH₂-4-Pym | 2-Et |
| 1-631' | 3-CF₃-Ph | 2-NH₂-4-Pym | 2-Pr |
| 1-632' | 3-CF₃-Ph | 2-NH₂-4-Pym | 2-Bu |
| 1-633' | 3-CF₃-Ph | 2-NH₂-4-Pym | 2-Allyl |
| 1-634' | 3-CF₃-Ph | 2-NH₂-4-Pym | 2-Ph |
| 1-635' | 3-CF₃-Ph | 2-NH₂-4-Pym | 2-Bn |
| 1-636' | 3-CF₃-Ph | 2-NH₂-4-Pym | 2-Phet |
| 1-637' | 3-CF₃-Ph | 2-NH₂-4-Pym | 2,2-diMe |
| 1-638' | 3-CF₃-Ph | 2-NH₂-4-Pym | 2-OH |
| 1-639' | 3-CF₃-Ph | 2-NH₂-4-Pym | 2-MeO |
| 1-640' | 3-CF₃-Ph | 2-NH₂-4-Pym | 2-EtO |
| 1-641' | 3-CF₃-Ph | 2-NH₂-4-Pym | 2-PrO |
| 1-642' | 3-CF₃-Ph | 2-NH₂-4-Pym | 2,2-di(MeO) |
| 1-643' | 3-CF₃-Ph | 2-NH₂-4-Pym | 2,2-di(EtO) |
| 1-644' | 3-CF₃-Ph | 2-NH₂-4-Pym | 2,2-OCH₂CH₂O— |
| 1-645' | 3-CF₃-Ph | 2-NH₂-4-Pym | 2-Oxo |
| 1-646' | 3-CF₃-Ph | 2-NH₂-4-Pym | 2-F |
| 1-647' | 3-CF₃-Ph | 2-NH₂-4-Pym | 2-Cl |
| 1-648' | 3-CF₃-Ph | 2-NH₂-4-Pym | 2-Br |
| 1-649' | 3-CF₃-Ph | 2-NH₂-4-Pym | 2-I |
| 1-650' | 3-CF₃-Ph | 2-NH₂-4-Pym | 2,2-diF |
| 1-651' | 3-CF₃-Ph | 2-NH₂-4-Pym | 2,2-diCl |
| 1-652' | 3-CF₃-Ph | 2-NH₂-4-Pym | 2,2-diBr |
| 1-653' | 3-CF₃-Ph | 2-NH₂-4-Pym | 3-Me |
| 1-654' | 3-CF₃-Ph | 2-NH₂-4-Pym | 3-Et |
| 1-655' | 3-CF₃-Ph | 2-NH₂-4-Pym | 3-Pr |
| 1-656' | 3-CF₃-Ph | 2-NH₂-4-Pym | 3,3-diMe |
| 1-657' | 3-CF₃-Ph | 2-NH₂-4-Pym | 5-Me |
| 1-658' | 3-CF₃-Ph | 2-NH₂-4-Pym | 5-Et |
| 1-659' | 3-CF₃-Ph | 2-NH₂-4-Pym | 5-Pr |
| 1-660' | 3-CF₃-Ph | 2-NH₂-4-Pym | 5,5-diMe |
| 1-661' | 3-CF₃-Ph | 2-NH₂-4-Pym | 6-Me |
| 1-662' | 3-CF₃-Ph | 2-NH₂-4-Pym | 6-Et |
| 1-663' | 3-CF₃-Ph | 2-NH₂-4-Pym | 6-Pr |
| 1-664' | 3-CF₃-Ph | 2-NH₂-4-Pym | 6,6-diMe |
| 1-665' | 3-CF₃-Ph | 2-NH₂-4-Pym | 6-Oxo |
| 1-666' | 3-CF₃-Ph | 2-NH₂-4-Pym | 8-Me |
| 1-667' | 3-CF₃-Ph | 2-NH₂-4-Pym | 8-Ph |
| 1-668' | 3-CF₃-Ph | 2-NH₂-4-Pym | 8-Pr |
| 1-669' | 3-CF₃-Ph | 2-NH₂-4-Pym | 8-Ph |
| 1-670' | 3-CF₃-Ph | 2-NH₂-4-Pym | 8a-Me |
| 1-671' | 3-CF₃-Ph | 2-NH₂-4-Pym | 8a-Et |
| 1-672' | 3-CF₃-Ph | 2-NH₂-4-Pym | 8a-Pr |
| 1-673' | 3-CF₃-Ph | 2-MeNH₂-4-Pym | 1-Me |

TABLE 1'-continued

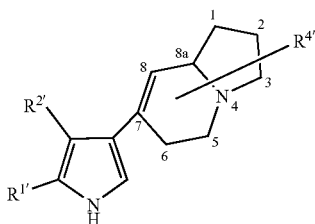

| Compound No. | R1' | R2' | R4' |
|---|---|---|---|
| 1-674' | 3-CF3-Ph | 2-MeNH2-4-Pym | 1-Et |
| 1-675' | 3-CF3-Ph | 2-MeNH2-4-Pym | 1-Pr |
| 1-676' | 3-CF3-Ph | 2-MeNH2-4-Pym | 1,1-diMe |
| 1-677' | 3-CF3-Ph | 2-MeNH2-4-Pym | 2-Me |
| 1-678' | 3-CF3-Ph | 2-MeNH2-4-Pym | 2-Et |
| 1-679' | 3-CF3-Ph | 2-MeNH2-4-Pym | 2-Pr |
| 1-680' | 3-CF3-Ph | 2-MeNH2-4-Pym | 2-Bu |
| 1-681' | 3-CF3-Ph | 2-MeNH2-4-Pym | 2-Allyl |
| 1-682' | 3-CF3-Ph | 2-MeNH2-4-Pym | 2-Ph |
| 1-683' | 3-CF3-Ph | 2-MeNH2-4-Pym | 2-Bn |
| 1-684' | 3-CF3-Ph | 2-MeNH2-4-Pym | 2-Phet |
| 1-685' | 3-CF3-Ph | 2-MeNH2-4-Pym | 2,2-diMe |
| 1-686' | 3-CF3-Ph | 2-MeNH2-4-Pym | 2-OH |
| 1-687' | 3-CF3-Ph | 2-MeNH2-4-Pym | 2-MeO |
| 1-688' | 3-CF3-Ph | 2-MeNH2-4-Pym | 2-EtO |
| 1-689' | 3-CF3-Ph | 2-MeNH2-4-Pym | 2-PrO |
| 1-690' | 3-CF3-Ph | 2-MeNH2-4-Pym | 2,2-di(MeO) |
| 1-691' | 3-CF3-Ph | 2-MeNH2-4-Pym | 2,2-di(EtO) |
| 1-692' | 3-CF3-Ph | 2-MeNH2-4-Pym | 2,2-OCH2CH2O— |
| 1-693' | 3-CF3-Ph | 2-MeNH2-4-Pym | 2-Oxo |
| 1-694' | 3-CF3-Ph | 2-MeNH2-4-Pym | 2-F |
| 1-695' | 3-CF3-Ph | 2-MeNH2-4-Pym | 2-Cl |
| 1-696' | 3-CF3-Ph | 2-MeNH2-4-Pym | 2-Br |
| 1-697' | 3-CF3-Ph | 2-MeNH2-4-Pym | 2-I |
| 1-698' | 3-CF3-Ph | 2-MeNH2-4-Pym | 2,2-diF |
| 1-699' | 3-CF3-Ph | 2-MeNH2-4-Pym | 2,2-diCl |
| 1-700' | 3-CF3-Ph | 2-MeNH2-4-Pym | 2,2-diBr |
| 1-701' | 3-CF3-Ph | 2-MeNH2-4-Pym | 3-Me |
| 1-702' | 3-CF3-Ph | 2-MeNH2-4-Pym | 3-Et |
| 1-703' | 3-CF3-Ph | 2-MeNH2-4-Pym | 3-Pr |
| 1-704' | 3-CF3-Ph | 2-MeNH2-4-Pym | 3,3-diMe |
| 1-705' | 3-CF3-Ph | 2-MeNH2-4-Pym | 5-Me |
| 1-706' | 3-CF3-Ph | 2-MeNH2-4-Pym | 5-Et |
| 1-707' | 3-CF3-Ph | 2-MeNH2-4-Pym | 5-Pr |
| 1-708' | 3-CF3-Ph | 2-MeNH2-4-Pym | 5,5-diMe |
| 1-709' | 3-CF3-Ph | 2-MeNH2-4-Pym | 6-Me |
| 1-710' | 3-CF3-Ph | 2-MeNH2-4-Pym | 6-Et |
| 1-711' | 3-CF3-Ph | 2-MeNH2-4-Pym | 6-Pr |
| 1-712' | 3-CF3-Ph | 2-MeNH2-4-Pym | 6,6-diMe |
| 1-713' | 3-CF3-Ph | 2-MeNH2-4-Pym | 6-Oxo |
| 1-714' | 3-CF3-Ph | 2-MeNH2-4-Pym | 8-Me |
| 1-715' | 3-CF3-Ph | 2-MeNH2-4-Pym | 8-Et |
| 1-716' | 3-CF3-Ph | 2-MeNH2-4-Pym | 8-Pr |
| 1-717' | 3-CF3-Ph | 2-MeNH2-4-Pym | 8-Ph |
| 1-718' | 3-CF3-Ph | 2-MeNH2-4-Pym | 8a-Me |
| 1-719' | 3-CF3-Ph | 2-MeNH2-4-Pym | 8a-Et |
| 1-720' | 3-CF3-Ph | 2-MeNH2-4-Pym | 8a-Pr |
| 1-721' | 3,4-diF-Ph | 4-Pyr | 1-Me |
| 1-722' | 3,4-diF-Ph | 4-Pyr | 1-Et |
| 1-723' | 3,4-diF-Ph | 4-Pyr | 1-Pr |
| 1-724' | 3,4-diF-Ph | 4-Pyr | 1,1-diMe |
| 1-725' | 3,4-diF-Ph | 4-Pyr | 2-Me |
| 1-726' | 3,4-diF-Ph | 4-Pyr | 2-Et |
| 1-727' | 3,4-diF-Ph | 4-Pyr | 2-Pr |
| 1-728' | 3,4-diF-Ph | 4-Pyr | 2-Bu |
| 1-729' | 3,4-diF-Ph | 4-Pyr | 2-Allyl |
| 1-730' | 3,4-diF-Ph | 4-Pyr | 2-Ph |
| 1-731' | 3,4-diF-Ph | 4-Pyr | 2-Bn |
| 1-732' | 3,4-diF-Ph | 4-Pyr | 2-Phet |
| 1-733' | 3,4-diF-Ph | 4-Pyr | 2,2-diMe |
| 1-734' | 3,4-diF-Ph | 4-Pyr | 2-OH |
| 1-735' | 3,4-diF-Ph | 4-Pyr | 2-MeO |
| 1-736' | 3,4-diF-Ph | 4-Pyr | 2-EtO |
| 1-737' | 3,4-diF-Ph | 4-Pyr | 2-PrO |

TABLE 1'-continued

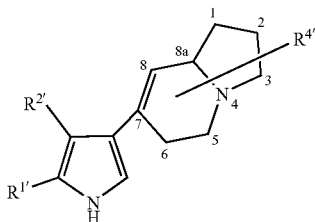

| Compound No. | $R^{1'}$ | $R^{2'}$ | $R^{4'}$ |
|---|---|---|---|
| 1-738' | 3,4-diF-Ph | 4-Pyr | 2,2-di(MeO) |
| 1-739' | 3,4-diF-Ph | 4-Pyr | 2,2-di(EtO) |
| 1-740' | 3,4-diF-Ph | 4-Pyr | 2,2-OCH$_2$CH$_2$O— |
| 1-741' | 3,4-diF-Ph | 4-Pyr | 2-Oxo |
| 1-742' | 3,4-diF-Ph | 4-Pyr | 2-F |
| 1-743' | 3,4-diF-Ph | 4-Pyr | 2-Cl |
| 1-744' | 3,4-diF-Ph | 4-Pyr | 2-Br |
| 1-745' | 3,4-diF-Ph | 4-Pyr | 2-I |
| 1-746' | 3,4-diF-Ph | 4-Pyr | 2,2-diF |
| 1-747' | 3,4-diF-Ph | 4-Pyr | 2,2-diCl |
| 1-748' | 3,4-diF-Ph | 4-Pyr | 2,2-diBr |
| 1-749' | 3,4-diF-Ph | 4-Pyr | 3-Me |
| 1-750' | 3,4-diF-Ph | 4-Pyr | 3-Et |
| 1-751' | 3,4-diF-Ph | 4-Pyr | 3-Pr |
| 1-752' | 3,4-diF-Ph | 4-Pyr | 3,3-diMe |
| 1-753' | 3,4-diF-Ph | 4-Pyr | 5-Me |
| 1-754' | 3,4-diF-Ph | 4-Pyr | 5-Et |
| 1-755' | 3,4-diF-Ph | 4-Pyr | 5-Pr |
| 1-756' | 3,4-diF-Ph | 4-Pyr | 5,5-diMe |
| 1-757' | 3,4-diF-Ph | 4-Pyr | 6-Me |
| 1-758' | 3,4-diF-Ph | 4-Pyr | 6-Et |
| 1-759' | 3,4-diF-Ph | 4-Pyr | 6-Pr |
| 1-760' | 3,4-diF-Ph | 4-Pyr | 6,6-diMe |
| 1-761' | 3,4-diF-Ph | 4-Pyr | 6-Oxo |
| 1-762' | 3,4-diF-Ph | 4-Pyr | 8-Me |
| 1-763' | 3,4-diF-Ph | 4-Pyr | 8-Et |
| 1-764' | 3,4-diF-Ph | 4-Pyr | 8-Pr |
| 1-765' | 3,4-diF-Ph | 4-Pyr | 8-Ph |
| 1-766' | 3,4-diF-Ph | 4-Pyr | 8a-Me |
| 1-767' | 3,4-diF-Ph | 4-Pyr | 8a-Et |
| 1-768' | 3,4-diF-Ph | 4-Pyr | 8a-Pr |
| 1-769' | 3,4-diF-Ph | 2-NH$_2$-4-Pym | 1-Me |
| 1-770' | 3,4-diF-Ph | 2-NH$_2$-4-Pym | 1-Et |
| 1-771' | 3,4-diF-Ph | 2-NH$_2$-4-Pym | 1-Pr |
| 1-772' | 3,4-diF-Ph | 2-NH$_2$-4-Pym | 1,1-diMe |
| 1-773' | 3,4-diF-Ph | 2-NH$_2$-4-Pym | 2-Me |
| 1-774' | 3,4-diF-Ph | 2-NH$_2$-4-Pym | 2-Et |
| 1-775' | 3,4-diF-Ph | 2-NH$_2$-4-Pym | 2-Pr |
| 1-776' | 3,4-diF-Ph | 2-NH$_2$-4-Pym | 2-Bu |
| 1-777' | 3,4-diF-Ph | 2-NH$_2$-4-Pym | 2-Allyl |
| 1-778' | 3,4-diF-Ph | 2-NH$_2$-4-Pym | 2-Ph |
| 1-779' | 3,4-diF-Ph | 2-NH$_2$-4-Pym | 2-Bn |
| 1-780' | 3,4-diF-Ph | 2-NH$_2$-4-Pym | 2-Phet |
| 1-781' | 3,4-diF-Ph | 2-NH$_2$-4-Pym | 2,2-diMe |
| 1-782' | 3,4-diF-Ph | 2-NH$_2$-4-Pym | 2-OH |
| 1-783' | 3,4-diF-Ph | 2-NH$_2$-4-Pym | 2-MeO |
| 1-784' | 3,4-diF-Ph | 2-NH$_2$-4-Pym | 2-EtO |
| 1-785' | 3,4-diF-Ph | 2-NH$_2$-4-Pym | 2-PrO |
| 1-786' | 3,4-diF-Ph | 2-NH$_2$-4-Pym | 2,2-di(MeO) |
| 1-787' | 3,4-diF-Ph | 2-NH$_2$-4-Pym | 2,2-di(EtO) |
| 1-788' | 3,4-diF-Ph | 2-NH$_2$-4-Pym | 2,2-OCH$_2$—CH$_2$O— |
| 1-789' | 3,4-diF-Ph | 2-NH$_2$-4-Pym | 2-Oxo |
| 1-790' | 3,4-diF-Ph | 2-NH$_2$-4-Pym | 2-F |
| 1-791' | 3,4-diF-Ph | 2-NH$_2$-4-Pym | 2-Cl |
| 1-792' | 3,4-diF-Ph | 2-NH$_2$-4-Pym | 2-Br |
| 1-793' | 3,4-diF-Ph | 2-NH$_2$-4-Pym | 2-I |
| 1-794' | 3,4-diF-Ph | 2-NH$_2$-4-Pym | 2,2-diF |
| 1-795' | 3,4-diF-Ph | 2-NH$_2$-4-Pym | 2,2-diCl |
| 1-796' | 3,4-diF-Ph | 2-NH$_2$-4-Pym | 2,2-diBr |
| 1-797' | 3,4-diF-Ph | 2-NH$_2$-4-Pym | 3-Me |
| 1-798' | 3,4-diF-Ph | 2-NH$_2$-4-Pym | 3-Et |
| 1-799' | 3,4-diF-Ph | 2-NH$_2$-4-Pym | 3-Pr |
| 1-800' | 3,4-diF-Ph | 2-NH$_2$-4-Pym | 3,3-diMe |
| 1-801' | 3,4-diF-Ph | 2-NH$_2$-4-Pym | 5-Me |

TABLE 1'-continued

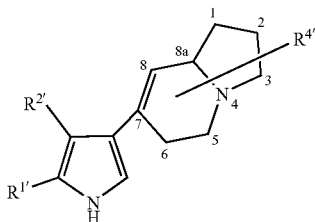

| Compound No. | R¹' | R²' | R⁴' |
|---|---|---|---|
| 1-802' | 3,4-diF-Ph | 2-NH₂-4-Pym | 5-Et |
| 1-803' | 3,4-diF-Ph | 2-NH₂-4-Pym | 5-Pr |
| 1-804' | 3,4-diF-Ph | 2-NH₂-4-Pym | 5,5-diMe |
| 1-805' | 3,4-diF-Ph | 2-NH₂-4-Pym | 6-Me |
| 1-806' | 3,4-diF-Ph | 2-NH₂-4-Pym | 6-Et |
| 1-807' | 3,4-diF-Ph | 2-NH₂-4-Pym | 6-Pr |
| 1-808' | 3,4-diF-Ph | 2-NH₂-4-Pym | 6,6-diMe |
| 1-809' | 3,4-diF-Ph | 2-NH₂-4-Pym | 6-Oxo |
| 1-810' | 3,4-diF-Ph | 2-NH₂-4-Pym | 8-Me |
| 1-811' | 3,4-diF-Ph | 2-NH₂-4-Pym | 8-Et |
| 1-812' | 3,4-diF-Ph | 2-NH₂-4-Pym | 8-Pr |
| 1-813' | 3,4-diF-Ph | 2-NH₂-4-Pym | 8-Ph |
| 1-814' | 3,4-diF-Ph | 2-NH₂-4-Pym | 8a-Me |
| 1-815' | 3,4-diF-Ph | 2-NH₂-4-Pym | 8a-Et |
| 1-816' | 3,4-diF-Ph | 2-NH₂-4-Pym | 8a-Pr |
| 1-817' | 3,4-diF-Ph | 2-MeNH₂-4-Pym | 1-Me |
| 1-818' | 3,4-diF-Ph | 2-MeNH₂-4-Pym | 1-Et |
| 1-819' | 3,4-diF-Ph | 2-MeNH₂-4-Pym | 1-Pr |
| 1-820' | 3,4-diF-Ph | 2-MeNH₂-4-Pym | 1,1-diMe |
| 1-821' | 3,4-diF-Ph | 2-MeNH₂-4-Pym | 2-Me |
| 1-822' | 3,4-diF-Ph | 2-MeNH₂-4-Pym | 2-Et |
| 1-823' | 3,4-diF-Ph | 2-MeNH₂-4-Pym | 2-Pr |
| 1-824' | 3,4-diF-Ph | 2-MeNH₂-4-Pym | 2-Bu |
| 1-825' | 3,4-diF-Ph | 2-MeNH₂-4-Pym | 2-Allyl |
| 1-826' | 3,4-diF-Ph | 2-MeNH₂-4-Pym | 2-Ph |
| 1-827' | 3,4-diF-Ph | 2-MeNH₂-4-Pym | 2-Bn |
| 1-828' | 3,4-diF-Ph | 2-MeNH₂-4-Pym | 2-Phet |
| 1-829' | 3,4-diF-Ph | 2-MeNH₂-4-Pym | 2,2-diMe |
| 1-830' | 3,4-diF-Ph | 2-MeNH₂-4-Pym | 2-OH |
| 1-831' | 3,4-diF-Ph | 2-MeNH₂-4-Pym | 2-MeO |
| 1-832' | 3,4-diF-Ph | 2-MeNH₂-4-Pym | 2-EtO |
| 1-833' | 3,4-diF-Ph | 2-MeNH₂-4-Pym | 2-PrO |
| 1-834' | 3,4-diF-Ph | 2-MeNH₂-4-Pym | 2,2-di(MeO) |
| 1-835' | 3,4-diF-Ph | 2-MeNH₂-4-Pym | 2,2-di(EtO) |
| 1-836' | 3,4-diF-Ph | 2-MeNH₂-4-Pym | 2,2-OCH₂CH₂O— |
| 1-837' | 3,4-diF-Ph | 2-MeNH₂-4-Pym | 2-Oxo |
| 1-838' | 3,4-diF-Ph | 2-MeNH₂-4-Pym | 2-F |
| 1-839' | 3,4-diF-Ph | 2-MeNH₂-4-Pym | 2-Cl |
| 1-840' | 3,4-diF-Ph | 2-MeNH₂-4-Pym | 2-Br |
| 1-841' | 3,4-diF-Ph | 2-MeNH₂-4-Pym | 2-I |
| 1-842' | 3,4-diF-Ph | 2-MeNH₂-4-Pym | 2,2-diF |
| 1-843' | 3,4-diF-Ph | 2-MeNH₂-4-Pym | 2,2-diCl |
| 1-844' | 3,4-diF-Ph | 2-MeNH₂-4-Pym | 2,2-diBr |
| 1-845' | 3,4-diF-Ph | 2-MeNH₂-4-Pym | 3-Me |
| 1-846' | 3,4-diF-Ph | 2-MeNH₂-4-Pym | 3-Et |
| 1-847' | 3,4-diF-Ph | 2-MeNH₂-4-Pym | 3-Pr |
| 1-848' | 3,4-diF-Ph | 2-MeNH₂-4-Pym | 3,3-diMe |
| 1-849' | 3,4-diF-Ph | 2-MeNH₂-4-Pym | 5-Me |
| 1-850' | 3,4-diF-Ph | 2-MeNH₂-4-Pym | 5-Et |
| 1-851' | 3,4-diF-Ph | 2-MeNH₂-4-Pym | 5-Pr |
| 1-852' | 3,4-diF-Ph | 2-MeNH₂-4-Pym | 5,5-diMe |
| 1-853' | 3,4-diF-Ph | 2-MeNH₂1-4-Pym | 6-Me |
| 1-854' | 3,4-diF-Ph | 2-MeNH₂-4-Pym | 6-Et |
| 1-855' | 3,4-diF-Ph | 2-MeNH₂-4-Pym | 6-Pr |
| 1-856' | 3,4-diF-Ph | 2-MeNH₂-4-Pym | 6,6-diMe |
| 1-857' | 3,4-diF-Ph | 2-MeNH₂-4-Pym | 6-Oxo |
| 1-857' | 3,4-diF-Ph | 2-MeNH₂-4-Pym | 6-Oxo |
| 1-858' | 3,4-diF-Ph | 2-MeNH₂-4-Pym | 8-Me |
| 1-859' | 3,4-diF-Ph | 2-MeNH₂-4-Pym | 8-Et |
| 1-860' | 3,4-diF-Ph | 2-MeNH₂-4-Pym | 8-Pr |
| 1-861' | 3,4-diF-Ph | 2-MeNH₂-4-Pym | 8-Ph |
| 1-862' | 3,4-diF-Ph | 2-MeNH₂-4-Pym | 8a-Me |
| 1-863' | 3,4-diF-Ph | 2-MeNH₂-4-Pym | 8a-Et |
| 1-864' | 3,4-diF-Ph | 2-MeNH₂-4-Pym | 8a-Pr |

TABLE 1'-continued

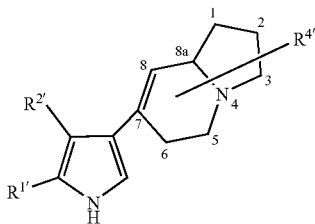

| Compound No. | R¹' | R²' | R⁴' |
|---|---|---|---|
| 1-865' | 4-F-Ph | 2-MeO-4-Pyr | 2-OH |
| 1-866' | 4-F-Ph | 2-MeO-4-Pyr | 2-MeO |
| 1-867' | 4-F-Ph | 2-MeO-4-Pyr | 2-Ph |
| 1-868' | 4-F-Ph | 2-MeO-4-Pyr | 8-Me |
| 1-869' | 4-F-Ph | 2-MeO-4-Pyr | 2-F |
| 1-870' | 4-F-Ph | 2-MeO-4-Pyr | 2-Cl |
| 1-871' | 4-F-Ph | 2-MeO-4-Pyr | 2-Br |
| 1-872' | 4-F-Ph | 2-MeO-4-Pyr | 2,2-diF |
| 1-873' | 4-F-Ph | 2-MeO-4-Pyr | 2,2-diCl |
| 1-874' | 4-F-Ph | 2-NH$_2$-4-Pyr | 2-OH |
| 1-875' | 4-F-Ph | 2-NH$_2$-4-Pyr | 2-MeO |
| 1-876' | 4-F-Ph | 2-NH$_2$-4-Pyr | 2-Ph |
| 1-877' | 4-F-Ph | 2-NH$_2$-4-Pyr | 8-Me |
| 1-878' | 4-F-Ph | 2-NH$_2$-4-Pyr | 2-F |
| 1-879' | 4-F-Ph | 2-NH$_2$-4-Pyr | 2-Cl |
| 1-880' | 4-F-Ph | 2-NH$_2$-4-Pyr | 2-Br |
| 1-881' | 4-F-Ph | 2-NH$_2$-4-Pyr | 2,2-diF |
| 1-882' | 4-F-Ph | 2-NH$_2$-4-Pyr | 2,2-diCl |
| 1-883' | 4-F-Ph | 2-MeNH$_2$-4-Pyr | 2-OH |
| 1-884' | 4-F-Ph | 2-MeNH$_2$-4-Pyr | 2-MeO |
| 1-885' | 4-F-Ph | 2-MeNH$_2$-4-Pyr | 2-Ph |
| 1-886' | 4-F-Ph | 2-MeNH$_2$-4-Pyr | 8-Me |
| 1-887' | 4-F-Ph | 2-MeNH$_2$-4-Pyr | 2-F |
| 1-888' | 4-F-Ph | 2-MeNH$_2$-4-Pyr | 2-Cl |
| 1-889' | 4-F-Ph | 2-MeNH$_2$-4-Pyr | 2-Br |
| 1-890' | 4-F-Ph | 2-MeNH$_2$-4-Pyr | 2,2-diF |
| 1-891' | 4-F-Ph | 2-MeNH$_2$-4-Pyr | 2,2-diCl |
| 1-892' | 4-F-Ph | 2-(α-Me-BnNH$_2$)-4-Pyr | 2-OH |
| 1-893' | 4-F-Ph | 2-(α-Me-BnNH$_2$)-4-Pyr | 2-MeO |
| 1-894' | 4-F-Ph | 2-(α-Me-BnNH$_2$)-4-Pyr | 2-Ph |
| 1-895' | 4-F-Ph | 2-(α-Me-BnNH$_2$)-4-Pyr | 8-Me |
| 1-896' | 4-F-Ph | 2-(α-Me-BnNH$_2$)-4-Pyr | 2-F |
| 1-897' | 4-F-Ph | 2-(α-Me-BnNH$_2$)-4-Pyr | 2-Cl |
| 1-898' | 4-F-Ph | 2-(α-Me-BnNH$_2$)-4-Pyr | 2-Br |
| 1-899' | 4-F-Ph | 2-(α-Me-BnNH$_2$)-4-Pyr | 2,2-diF |
| 1-900' | 4-F-Ph | 2-(α-Me-BnNH$_2$)-4-Pyr | 2,2-diCl |
| 1-901' | 4-F-Ph | 2-BnNH$_2$-4-Pyr | 2-OH |
| 1-902' | 4-F-Ph | 2-BriNH$_2$-4-Pyr | 2-MeO |
| 1-903' | 4-F-Ph | 2-BnNH$_2$-4-Pyr | 2-Ph |
| 1-904' | 4-F-Ph | 2-BnNH$_2$-4-Pyr | 8-Me |
| 1-905' | 4-F-Ph | 2-BnNH$_2$-4-Pyr | 2-F |
| 1-906' | 4-F-Ph | 2-BnNH$_2$-4-Pyr | 2-Cl |
| 1-907' | 4-F-Ph | 2-BnNH$_2$-4-Pyr | 2-Br |
| 1-908' | 4-F-Ph | 2-BnNH$_2$-4-Pyr | 2,2-diF |
| 1-909' | 4-F-Ph | 2-BnNH$_2$-4-Pyr | 2,2-diCl |
| 1-910' | 4-F-Ph | 4-Pym | 2-OH |
| 1-911' | 4-F-Ph | 4-Pym | 2-MeO |
| 1-912' | 4-F-Ph | 4-Pym | 2-Ph |
| 1-913' | 4-F-Ph | 4-Pym | 8-Me |
| 1-914' | 4-F-Ph | 4-Pym | 2-F |
| 1-915' | 4-F-Ph | 4-Pym | 2-Cl |
| 1-916' | 4-F-Ph | 4-Pym | 2-Br |
| 1-917' | 4-F-Ph | 4-Pym | 2,2-diF |
| 1-918' | 4-F-Ph | 4-Pym | 2,2-diCl |
| 1-919' | 4-F-Ph | 2-MeO-4-Pym | 2-OH |
| 1-920' | 4-F-Ph | 2-MeO-4-Pym | 2-MeO |
| 1-921' | 4-F-Ph | 2-MeO-4-Pym | 2-Ph |
| 1-922' | 4-F-Ph | 2-MeO-4-Pym | 8-Me |
| 1-923' | 4-F-Ph | 2-MeO-4-Pym | 2-F |
| 1-924' | 4-F-Ph | 2-MeO-4-Pym | 2-Cl |
| 1-925' | 4-F-Ph | 2-MeO-4-Pym | 2-Br |
| 1-926' | 4-F-Ph | 2-MeO-4-Pym | 2,2-diF |
| 1-927' | 4-F-Ph | 2-MeO-4-Pym | 2,2-diCl |
| 1-928' | 4-F-Ph | 2-(α-Me-BnNH$_2$)-4-Pym | 2-OH |

TABLE 1'-continued

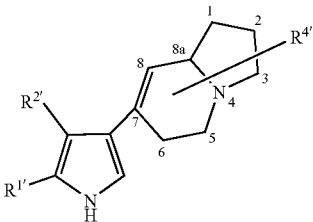

| Compound No. | $R^{1'}$ | $R^{2'}$ | $R^{4'}$ |
| --- | --- | --- | --- |
| 1-929' | 4-F-Ph | 2-(α-Me-BnNH$_2$)-4-Pym | 2-MeO |
| 1-930' | 4-F-Ph | 2-(α-Me-BnNH$_2$)-4-Pym | 2-Ph |
| 1-931' | 4-F-Ph | 2-(α-Me-BnNH$_2$)-4-Pym | 8-Me |
| 1-932' | 4-F-Ph | 2-(α-Me-BnNH$_2$)-4-Pym | 2-F |
| 1-933' | 4-F-Ph | 2-(α-Me-BnNH$_2$)-4-Pym | 2-Cl |
| 1-934' | 4-F-Ph | 2-(α-Me-BnNH$_2$)-4-Pym | 2-Br |
| 1-935' | 4-F-Ph | 2-(α-Me-BnNH$_2$)-4-Pym | 2,2-diF |
| 1-936' | 4-F-Ph | 2-(α-Me-BnNH$_2$)-4-Pym | 2,2-diCl |
| 1-937' | 4-F-Ph | 2-BnNH$_2$-4-Pym | 2-OH |
| 1-938' | 4-F-Ph | 2-BnNH$_2$-4-Pym | 2-MeO |
| 1-939' | 4-F-Ph | 2-BnNH$_2$-4-Pym | 2-Ph |
| 1-940' | 4-F-Ph | 2-BnNH$_2$-4-Pym | 8-Me |
| 1-941' | 4-F-Ph | 2-BnNH$_2$-4-Pym | 2-F |
| 1-942' | 4-F-Ph | 2-BnNH$_2$-4-Pym | 2-Cl |
| 1-943' | 4-F-Ph | 2-BnNH$_2$-4-Pym | 2-Br |
| 1-944' | 4-F-Ph | 2-BnNH$_2$-4-Pym | 2,2-diF |
| 1-945' | 4-F-Ph | 2-BnNH$_2$-4-Pym | 2,2-diCl |
| 1-946' | Ph | 4-Pyr | 6,6-(CH$_2$)$_2$— |
| 1-947' | Ph | 2-NH$_2$-4-Pym | 6,6-(CH$_2$)$_2$— |
| 1-948' | Ph | 2-MeNH$_2$-4-Pym | 6,6-(CH$_2$)$_2$— |
| 1-949' | 3-F-Ph | 4-Pyr | 6,6-(CH$_2$)$_2$— |
| 1-950' | 3-F-Ph | 2-NH$_2$-4-Pym | 6,6-(CH$_2$)$_2$— |
| 1-951' | 3-F-Ph | 2-MeNH$_2$-4-Pym | 6,6-(CH$_2$)$_2$— |
| 1-952' | 4-F-Ph | 4-Pyr | 6,6-(CH$_2$)$_2$— |
| 1-953' | 4-F-Ph | 2-NH$_2$-4-Pym | 6,6-(CH$_2$)$_2$— |
| 1-954' | 4-F-Ph | 2-MeNH$_2$-4-Pym | 6,6-(CH$_2$)$_2$— |
| 1-955' | 3-Cl-Ph | 4-Pyr | 6,6-(CH$_2$)$_2$— |
| 1-956' | 3-Cl-Ph | 2-NH$_2$-4-Pym | 6,6-(CH$_2$)$_2$— |
| 1-957' | 3-Cl-Ph | 2-MeNH$_2$-4-Pym | 6,6-(CH$_2$)$_2$— |
| 1-958' | 3-CF$_3$-Ph | 4-Pyr | 6,6-(CH$_2$)$_2$— |
| 1-959' | 3-CF$_3$-Ph | 2-NH$_2$-4-Pym | 6,6-(CH$_2$)$_2$— |
| 1-960' | 3-CF$_3$-Ph | 2-MeNH$_2$-4-Pym | 6,6-(CH$_2$)$_2$— |
| 1-961' | 3,4-diF-Ph | 4-Pyr | 6,6-(CH$_2$)$_2$— |
| 1-962' | 3,4-diF-Ph | 2-NH$_2$-4-Pym | 6,6-(CH$_2$)$_2$— |
| 1-963' | 3,4-diF-Ph | 2-MeNH$_2$-4-Pym | 6,6-(CH$_2$)$_2$— |
| 1-964' | Ph | 4-Pyr | 6,6-diF |
| 1-965' | Ph | 2-NH$_2$-4-Pym | 6,6-diF |
| 1-966' | Ph | 2-MeNH$_2$-4-Pym | 6,6-diF |
| 1-967' | 3-F-Ph | 4-Pyr | 6,6-diF |
| 1-968' | 3-F-Ph | 2-NH$_2$-4-Pym | 6,6-diF |
| 1-969' | 3-F-Ph | 2-MeNH$_2$-4-Pym | 6,6-diF |
| 1-970' | 4-F-Ph | 4-Pyr | 6,6-diF |
| 1-971' | 4-F-Ph | 2-NH$_2$-4-Pym | 6,6-diF |
| 1-972' | 4-F-Ph | 2-MeNH$_2$-4-Pym | 6,6-diF |
| 1-973' | 3-Cl-Ph | 4-Pyr | 6,6-diF |
| 1-974' | 3-Cl-Ph | 2-NH$_2$-4-Pym | 6,6-diF |
| 1-975' | 3-Cl-Ph | 2-MeNH$_2$-4-Pym | 6,6-diF |
| 1-976' | 3-CF$_3$-Ph | 4-Pyr | 6,6-diF |
| 1-977' | 3-CF$_3$-Ph | 2-NH$_2$-4-Pym | 6,6-diF |
| 1-978' | 3-CF$_3$-Ph | 2-MeNH$_2$-4-Pym | 6,6-diF |
| 1-979' | 3,4-diF-Ph | 4-Pyr | 6,6-diF |
| 1-980' | 3,4-diF-Ph | 2-NH$_2$-4-Pym | 6,6-diF |
| 1-981' | 3,4-diF-Ph | 2-MeNH$_2$-4-Pym | 6,6-diF |
| 1-982' | 4-F-Ph | 4-Pyr | 2->CH$_2$ |
| 1-983' | 4-F-Ph | 4-Pyr | 2->CHMe |
| 1-984' | 4-F-Ph | 4-Pyr | 2->CHEt |
| 1-985' | 4-F-Ph | 4-Pyr | 2->CHPr |
| 1-986' | 4-F-Ph | 4-Pyr | 2->C(Me)$_2$ |
| 1-987' | 4-F-Ph | 4-Pyr | 2->CHPh |
| 1-988' | 4-F-Ph | 4-Pyr | 2,2-diFh |
| 1-989' | 4-F-Ph | 4-Pyr | 2,2-O(CH$_2$)$_3$O— |
| 1-990' | 4-F-Ph | 4-Pyr | 2,2-OCH$_2$C(Me)$_2$CH$_2$O— |
| 1-991' | 4-F-Ph | 4-Pyr | 2,2-(CH$_2$)$_2$— |
| 1-992' | 4-F-Ph | 4-Pyr | 2,2-(CH$_2$)$_3$— |

TABLE 1'-continued

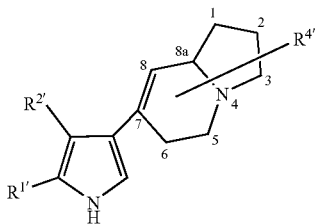

| Compound No. | R[1'] | R[2'] | R[4'] |
|---|---|---|---|
| 1-993' | 4-F-Ph | 4-Pyr | 2,2-(CH$_2$)$_4$— |
| 1-994' | 4-F-Ph | 4-Pyr | 2,2-(CH$_2$)$_5$— |
| 1-995' | 4-F-Ph | 4-Pyr | 2-MeS |
| 1-996' | 4-F-Ph | 4-Pyr | 2-EtS |
| 1-997' | 4-F-Ph | 4-Pyr | 2-PrS |
| 1-998' | 4-F-Ph | 4-Pyr | 2-BuS |
| 1-999' | 4-F-Ph | 4-Pyr | 2-MeSO$_2$ |
| 1-1000' | 4-F-Ph | 4-Pyr | 2-PhO |
| 1-1001' | 4-Cl-Ph | 4-Pyr | 1-Me |
| 1-1002' | 4-Cl-Ph | 4-Pyr | 1-Et |
| 1-1003' | 4-Cl-Ph | 4-Pyr | 1-Pr |
| 1-1004' | 4-Cl-Ph | 4-Pyr | 1,1-diMe |
| 1-1005' | 4-Cl-Ph | 4-Pyr | 2-Me |
| 1-1006' | 4-Cl-Ph | 4-Pyr | 2-Et |
| 1-1007' | 4-Cl-Ph | 4-Pyr | 2-Pr |
| 1-1008' | 4-Cl-Ph | 4-Pyr | 2-Bu |
| 1-1009' | 4-Cl-Ph | 4-Pyr | 2-Allyl |
| 1-1010' | 4-Cl-Ph | 4-Pyr | 2-Ph |
| 1-1011' | 4-Cl-Ph | 4-Pyr | 2-Bn |
| 1-1012' | 4-Cl-Ph | 4-Pyr | 2-Phet |
| 1-1013' | 4-Cl-Ph | 4-Pyr | 2,2-diMe |
| 1-1014' | 4-Cl-Ph | 4-Pyr | 2-OH |
| 1-1015' | 4-Cl-Ph | 4-Pyr | 2-MeO |
| 1-1016' | 4-Cl-Ph | 4-Pyr | 2-EtO |
| 1-1017' | 4-Cl-Ph | 4-Pyr | 2-PrO |
| 1-1018' | 4-Cl-Ph | 4-Pyr | 2,2-di(MeO) |
| 1-1019' | 4-Cl-Ph | 4-Pyr | 2,2-di(EtO) |
| 1-1020' | 4-Cl-Ph | 4-Pyr | 2,2-OCH$_2$CH$_2$O— |
| 1-1021' | 4-Cl-Ph | 4-Pyr | 2-Oxo |
| 1-1022' | 4-Cl-Ph | 4-Pyr | 2-F |
| 1-1023' | 4-Cl-Ph | 4-Pyr | 2-Cl |
| 1-1024' | 4-Cl-Ph | 4-Pyr | 2-Br |
| 1-1025' | 4-Cl-Ph | 4-Pyr | 2-I |
| 1-1026' | 4-Cl-Ph | 4-Pyr | 2,2-diF |
| 1-1027' | 4-Cl-Ph | 4-Pyr | 2,2-diCl |
| 1-1028' | 4-Cl-Ph | 4-Pyr | 2,2-diBr |
| 1-1029' | 4-Cl-Ph | 4-Pyr | 3-Me |
| 1-1030' | 4-Cl-Ph | 4-Pyr | 3-Et |
| 1-1031' | 4-Cl-Ph | 4-Pyr | 3-Pr |
| 1-1032' | 4-Cl-Ph | 4-Pyr | 3,3-diMe |
| 1-1033' | 4-Cl-Ph | 4-Pyr | 5-Me |
| 1-1034' | 4-Cl-Ph | 4-Pyr | 5-Et |
| 1-1035' | 4-Cl-Ph | 4-Pyr | 5-Pr |
| 1-1036' | 4-Cl-Ph | 4-Pyr | 5,5-diMe |
| 1-1037' | 4-Cl-Ph | 4-Pyr | 6-Me |
| 1-1038' | 4-Cl-Ph | 4-Pyr | 6-Et |
| 1-1039' | 4-Cl-Ph | 4-Pyr | 6-Pr |
| 1-1040' | 4-Cl-Ph | 4-Pyr | 6,6-diMe |
| 1-1041' | 4-Cl-Ph | 4-Pyr | 6-Oxo |
| 1-1042' | 4-Cl-Ph | 4-Pyr | 8-Me |
| 1-1043' | 4-Cl-Ph | 4-Pyr | 8-Et |
| 1-1044' | 4-Cl-Ph | 4-Pyr | 8-Pr |
| 1-1045' | 4-Cl-Ph | 4-Pyr | 8-Ph |
| 1-1046' | 4-Cl-Ph | 4-Pyr | 8a-Me |
| 1-1047' | 4-Cl-Ph | 4-Pyr | 8a-Et |
| 1-1048' | 4-Cl-Ph | 4-Pyr | 8a-Pr |
| 1-1049' | 4-Cl-Ph | 4-Pyr | 6,6-(CH$_2$)$_2$— |
| 1-1050' | 4-Cl-Ph | 4-Pyr | 6,6-diF |
| 1-1051' | 4-Cl-Ph | 4-Pyr | 2->CH$_2$ |
| 1-1052' | 4-Cl-Ph | 4-Pyr | 2->CHMe |
| 1-1053' | 4-Cl-Ph | 4-Pyr | 2->CHEt |
| 1-1054' | 4-Cl-Ph | 4-Pyr | 2->CHPr |
| 1-1055' | 4-Cl-Ph | 4-Pyr | 2->C(Me)$_2$ |
| 1-1056' | 4-Cl-Ph | 4-Pyr | 2->CHPh |

TABLE 1'-continued

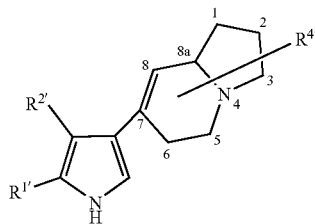

| Compound No. | R¹' | R²' | R⁴' |
|---|---|---|---|
| 1-1057' | 4-Cl-Ph | 4-Pyr | 2,2-diFh |
| 1-1058' | 4-Cl-Ph | 4-Pyr | 2,2-O(CH₂)₃O— |
| 1-1059' | 4-Cl-Ph | 4-Pyr | 2,2-OCH₂C(Me)₂CH₂O— |
| 1-1060' | 4-Cl-Ph | 4-Pyr | 2,2-(CH₂)₂— |
| 1-1061' | 4-Cl-Ph | 4-Pyr | 2,2-(CH₂)₃— |
| 1-1062' | 4-Cl-Ph | 4-Pyr | 2,2-(CH₂)₄— |
| 1-1063' | 4-Cl-Ph | 4-Pyr | 2,2-(CH₂)₅— |
| 1-1064' | 4-Cl-Ph | 4-Pyr | 2-MeS |
| 1-1065' | 4-Cl-Ph | 4-Pyr | 2-EtS |
| 1-1066' | 4-Cl-Ph | 4-Pyr | 2-PrS |
| 1-1067' | 4-Cl-Ph | 4-Pyr | 2-BuS |
| 1-1068' | 4-Cl-Ph | 4-Pyr | 2-MeSO₂ |
| 1-1069' | 4-Cl-Ph | 4-Pyr | 2-PhO |
| 1-1070' | 4-F-Ph | 4-Pyr | 2-(4-MeO-Ph) |
| 1-1071' | 4-F-Ph | 4-Pyr | 2-(4-Me-Ph) |
| 1-1072' | 4-F-Ph | 4-Pyr | 2-(4-F-Ph) |
| 1-1073' | 4-F-Ph | 4-Pyr | 2-(4-CF₃-Ph) |
| 1-1074' | 4-F-Ph | 4-Pyr | 2-(4-Cl-Ph) |
| 1-1075' | 4-F-Ph | 4-Pyr | 2-(2,4-diF-Ph) |
| 1-1076' | 3-CF₃-Ph | 4-Pyr | 2-(4-MeO-Ph) |
| 1-1077' | 3-CF₃-Ph | 4-Pyr | 2-(4-Me-Ph) |
| 1-1078' | 3-CF₃-Ph | 4-Pyr | 2-(4-F-Ph) |
| 1-1079' | 3-CF₃-Ph | 4-Pyr | 2-(4-CF₃-Ph) |
| 1-1080' | 3-CF₃-Ph | 4-Pyr | 2-(4-Cl-Ph) |
| 1-1081' | 3-CF₃-Ph | 4-Pyr | 2-(2,4-diF-Ph) |

TABLE 2'

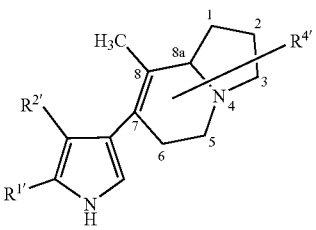

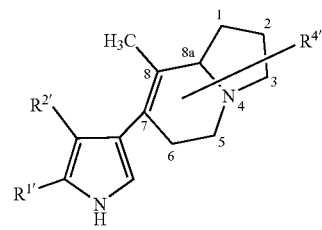

| Compound No. | R¹' | R²' | R⁴' |
|---|---|---|---|
| 2-1' | Ph | 4-Pyr | 1-Me |
| 2-2' | Ph | 4-Pyr | 1-Et |
| 2-3' | Ph | 4-Pyr | 1-Pr |
| 2-4' | Ph | 4-Pyr | 1,1-diMe |
| 2-5' | Ph | 4-Pyr | 2-Me |
| 2-6' | Ph | 4-Pyr | 2-Et |
| 2-7' | Ph | 4-Pyr | 2-Pr |
| 2-8' | Ph | 4-Pyr | 2-Bu |
| 2-9' | Ph | 4-Pyr | 2-Allyl |
| 2-10' | Ph | 4-Pyr | 2-Ph |
| 2-11' | Ph | 4-Pyr | 2-Bn |
| 2-12' | Ph | 4-Pyr | 2-Phet |
| 2-13' | Ph | 4-Pyr | 2,2-diMe |
| 2-14' | Ph | 4-Pyr | 2-OH |
| 2-15' | Ph | 4-Pyr | 2-MeO |
| 2-16' | Ph | 4-Pyr | 2-EtO |
| 2-17' | Ph | 4-Pyr | 2-PrO |
| 2-18' | Ph | 4-Pyr | 2,2-di(MeO) |
| 2-19' | Ph | 4-Pyr | 2,2-di(EtO) |
| 2-20' | Ph | 4-Pyr | 2,2-OCH₂CH₂O— |
| 2-21' | Ph | 4-Pyr | 2-Oxo |
| 2-22' | Ph | 4-Pyr | 2-F |
| 2-23' | Ph | 4-Pyr | 2-Cl |
| 2-24' | Ph | 4-Pyr | 2-Br |
| 2-25' | Ph | 4-Pyr | 2-I |
| 2-26' | Ph | 4-Pyr | 2,2-diF |
| 2-27' | Ph | 4-Pyr | 2,2-diCi |
| 2-28' | Ph | 4-Pyr | 2,2-diBr |
| 2-29' | Ph | 4-Pyr | 3-Me |
| 2-30' | Ph | 4-Pyr | 3-Et |
| 2-31' | Ph | 4-Pyr | 3-Pr |
| 2-32' | Ph | 4-Pyr | 3,3-diMe |
| 2-33' | Ph | 4-Pyr | 5-Me |
| 2-34' | Ph | 4-Pyr | 5-Et |
| 2-35' | Ph | 4-Pyr | 5-Pr |
| 2-36' | Ph | 4-Pyr | 5,5-diMe |

TABLE 2'-continued

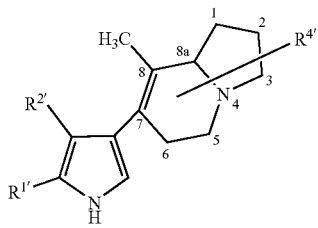

| Compound No. | R[1'] | R[2'] | R[4'] |
|---|---|---|---|
| 2-37' | Ph | 4-Pyr | 6-Me |
| 2-38' | Ph | 4-Pyr | 6-Et |
| 2-39' | Ph | 4-Pyr | 6-Pr |
| 2-40' | Ph | 4-Pyr | 6,6-diMe |
| 2-41' | Ph | 4-Pyr | 6-Oxo |
| 2-42' | Ph | 4-Pyr | 8a-Me |
| 2-43' | Ph | 4-Pyr | 8a-Et |
| 2-44' | Ph | 4-Pyr | 8a-Pr |
| 2-45' | 3-F-Ph | 4-Pyr | 1-Me |
| 2-46' | 3-F-Ph | 4-Pyr | 1-Et |
| 2-47' | 3-F-Ph | 4-Pyr | 1-Pr |
| 2-48' | 3-F-Ph | 4-Pyr | 1,1-diMe |
| 2-49' | 3-F-Ph | 4-Pyr | 2-Me |
| 2-50' | 3-F-Ph | 4-Pyr | 2-Et |
| 2-51' | 3-F-Ph | 4-Pyr | 2-Pr |
| 2-52' | 3-F-Ph | 4-Pyr | 2-Bu |
| 2-53' | 3-F-Ph | 4-Pyr | 2-Allyl |
| 2-54' | 3-F-Ph | 4-Pyr | 2-Ph |
| 2-55' | 3-F-Ph | 4-Pyr | 2-Bn |
| 2-56' | 3-F-Ph | 4-Pyr | 2-Phet |
| 2-57' | 3-F-Ph | 4-Pyr | 2,2-diMe |
| 2-58' | 3-F-Ph | 4-Pyr | 2-OH |
| 2-59' | 3-F-Ph | 4-Pyr | 2-MeO |
| 2-60' | 3-F-Ph | 4-Pyr | 2-EtO |
| 2-61' | 3-F-Ph | 4-Pyr | 2-PrO |
| 2-62' | 3-F-Ph | 4-Pyr | 2,2-di(MeO) |
| 2-63' | 3-F-Ph | 4-Pyr | 2,2-di(EtO) |
| 2-64' | 3-F-Ph | 4-Pyr | 2,2-OCH$_2$CH$_2$O— |
| 2-65' | 3-F-Ph | 4-Pyr | 2-Oxo |
| 2-66' | 3-F-Ph | 4-Pyr | 2-F |
| 2-67' | 3-F-Ph | 4-Pyr | 2-Cl |
| 2-68' | 3-F-Ph | 4-Pyr | 2-Br |
| 2-69' | 3-F-Ph | 4-Pyr | 2-I |
| 2-70' | 3-F-Ph | 4-Pyr | 2,2-diF |
| 2-71' | 3-F-Ph | 4-Pyr | 2,2-diCl |
| 2-72' | 3-F-Ph | 4-Pyr | 2,2-diBr |
| 2-73' | 3-F-Ph | 4-Pyr | 3-Me |
| 2-74' | 3-F-Ph | 4-Pyr | 3-Et |
| 2-75' | 3-F-Ph | 4-Pyr | 3-Pr |
| 2-76' | 3-F-Ph | 4-Pyr | 3,3-diMe |
| 2-77' | 3-F-Ph | 4-Pyr | 5-Me |
| 2-78' | 3-F-Ph | 4-Pyr | 5-Et |
| 2-79' | 3-F-Ph | 4-Pyr | 5-Pr |
| 2-80' | 3-F-Ph | 4-Pyr | 5,5-diMe |
| 2-81' | 3-F-Ph | 4-Pyr | 6-Me |
| 2-82' | 3-F-Ph | 4-Pyr | 6-Et |
| 2-83' | 3-F-Ph | 4-Pyr | 6-Pr |
| 2-84' | 3-F-Ph | 4-Pyr | 6,6-diMe |
| 2-85' | 3-F-Ph | 4-Pyr | 6-Oxo |
| 2-86' | 3-F-Ph | 4-Pyr | 8a-Me |
| 2-87' | 3-F-Ph | 4-Pyr | 8a-Et |
| 2-88' | 3-F-Ph | 4-Pyr | 8a-Pr |
| 2-89' | 4-F-Ph | 4-Pyr | 1-Me |
| 2-90' | 4-F-Ph | 4-Pyr | 1-Et |
| 2-91' | 4-F-Ph | 4-Pyr | 1-Pr |
| 2-92' | 4-F-Ph | 4-Pyr | 1,1-diMe |
| 2-93' | 4-F-Ph | 4-Pyr | 2-Me |
| 2-94' | 4-F-Ph | 4-Pyr | 2-Et |
| 2-95' | 4-F-Ph | 4-Pyr | 2-Pr |
| 2-96' | 4-F-Ph | 4-Pyr | 2-Bu |
| 2-97' | 4-F-Ph | 4-Pyr | 2-Allyl |
| 2-98' | 4-F-Ph | 4-Pyr | 2-Ph |
| 2-99' | 4-F-Ph | 4-Pyr | 2-Bn |
| 2-100' | 4-F-Ph | 4-Pyr | 2-Phet |

TABLE 2'-continued

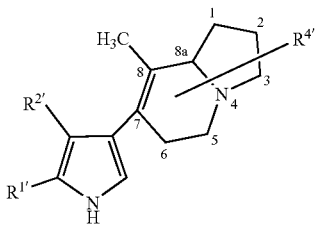

| Compound No. | R[1'] | R[2'] | R[4'] |
|---|---|---|---|
| 2-101' | 4-F-Ph | 4-Pyr | 2,2-diMe |
| 2-102' | 4-F-Ph | 4-Pyr | 2-OH |
| 2-103' | 4-F-Ph | 4-Pyr | 2-MeO |
| 2-104' | 4-F-Ph | 4-Pyr | 2-EtO |
| 2-105' | 4-F-Ph | 4-Pyr | 2-PrO |
| 2-106' | 4-F-Ph | 4-Pyr | 2,2-di(MeO) |
| 2-107' | 4-F-Ph | 4-Pyr | 2,2-di(EtO) |
| 2-108' | 4-F-Ph | 4-Pyr | 2,2-OCH$_2$CH$_2$O— |
| 2-109' | 4-F-Ph | 4-Pyr | 2-Oxo |
| 2-110' | 4-F-Ph | 4-Pyr | 2-F |
| 2-111' | 4-F-Ph | 4-Pyr | 2-Cl |
| 2-112' | 4-F-Ph | 4-Pyr | 2-Br |
| 2-113' | 4-F-Ph | 4-Pyr | 2-I |
| 2-114' | 4-F-Ph | 4-Pyr | 2,2-diF |
| 2-115' | 4-F-Ph | 4-Pyr | 2,2-diCl |
| 2-116' | 4-F-Ph | 4-Pyr | 2,2-diBr |
| 2-117' | 4-F-Ph | 4-Pyr | 3-Me |
| 2-118' | 4-F-Ph | 4-Pyr | 3-Et |
| 2-119' | 4-F-Ph | 4-Pyr | 3-Pr |
| 2-120' | 4-F-Ph | 4-Pyr | 3,3-diMe |
| 2-121' | 4-F-Ph | 4-Pyr | 5-Me |
| 2-122' | 4-F-Ph | 4-Pyr | 5-Et |
| 2-123' | 4-F-Ph | 4-Pyr | 5-Pr |
| 2-124' | 4-F-Ph | 4-Pyr | 5,5-diMe |
| 2-125' | 4-F-Ph | 4-Pyr | 6-Me |
| 2-126' | 4-F-Ph | 4-Pyr | 6-Et |
| 2-127' | 4-F-Ph | 4-Pyr | 6-Pr |
| 2-128' | 4-F-Ph | 4-Pyr | 6,6-diMe |
| 2-129' | 4-F-Ph | 4-Pyr | 6-Oxo |
| 2-130' | 4-F-Ph | 4-Pyr | 8a-Me |
| 2-131' | 4-F-Ph | 4-Pyr | 8a-Et |
| 2-132' | 4-F-Ph | 4-Pyr | 8a-Pr |
| 2-133' | 3-Cl-Ph | 4-Pyr | 1-Me |
| 2-134' | 3-Cl-Ph | 4-Pyr | 1-Et |
| 2-135' | 3-Cl-Ph | 4-Pyr | 1-Pr |
| 2-136' | 3-Cl-Ph | 4-Pyr | 1,1-diMe |
| 2-137' | 3-Cl-Ph | 4-Pyr | 2-Me |
| 2-138' | 3-Cl-Ph | 4-Pyr | 2-Et |
| 2-139' | 3-Cl-Ph | 4-Pyr | 2-Pr |
| 2-140' | 3-Cl-Ph | 4-Pyr | 2-Bu |
| 2-141' | 3-Cl-Ph | 4-Pyr | 2-Allyl |
| 2-142' | 3-Cl-Ph | 4-Pyr | 2-Ph |
| 2-143' | 3-Cl-Ph | 4-Pyr | 2-Bn |
| 2-144' | 3-Cl-Ph | 4-Pyr | 2-Phet |
| 2-145' | 3-Cl-Ph | 4-Pyr | 2,2-diMe |
| 2-146' | 3-Cl-Ph | 4-Pyr | 2-OH |
| 2-147' | 3-Cl-Ph | 4-Pyr | 2-MeO |
| 2-148' | 3-Cl-Ph | 4-Pyr | 2-EtO |
| 2-149' | 3-Cl-Ph | 4-Pyr | 2-PrO |
| 2-150' | 3-Cl-Ph | 4-Pyr | 2,2-di(MeO) |
| 2-151' | 3-Cl-Ph | 4-Pyr | 2,2-di(EtO) |
| 2-152' | 3-Cl-Ph | 4-Pyr | 2,2-OCH$_2$CH$_2$O— |
| 2-153' | 3-Cl-Ph | 4-Pyr | 2-Oxo |
| 2-154' | 3-Cl-Ph | 4-Pyr | 2-F |
| 2-155' | 3-Cl-Ph | 4-Pyr | 2-Cl |
| 2-156' | 3-Cl-Ph | 4-Pyr | 2-Br |
| 2-157' | 3-Cl-Ph | 4-Pyr | 2-I |
| 2-158' | 3-Cl-Ph | 4-Pyr | 2,2-diF |
| 2-159' | 3-Cl-Ph | 4-Pyr | 2,2-diCl |
| 2-160' | 3-Cl-Ph | 4-Pyr | 2,2-diBr |
| 2-161' | 3-Cl-Ph | 4-Pyr | 3-Me |
| 2-162' | 3-Cl-Ph | 4-Pyr | 3-Et |
| 2-163' | 3-Cl-Ph | 4-Pyr | 3-Pr |
| 2-164' | 3-Cl-Ph | 4-Pyr | 3,3-diMe |

TABLE 2'-continued

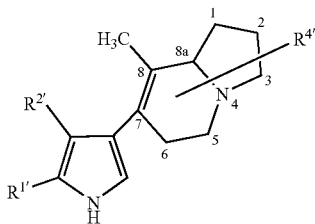

| Compound No. | $R^{1'}$ | $R^{2'}$ | $R^{4'}$ |
|---|---|---|---|
| 2-165' | 3-Cl-Ph | 4-Pyr | 5-Me |
| 2-166' | 3-Cl-Ph | 4-Pyr | 5-Et |
| 2-167' | 3-Cl-Ph | 4-Pyr | 5-Pr |
| 2-168' | 3-Cl-Ph | 4-Pyr | 5,5-diMe |
| 2-169' | 3-Cl-Ph | 4-Pyr | 6-Me |
| 2-170' | 3-Cl-Ph | 4-Pyr | 6-Et |
| 2-171' | 3-Cl-Ph | 4-Pyr | 6-Pr |
| 2-172' | 3-Cl-Ph | 4-Pyr | 6,6-diMe |
| 2-173' | 3-Cl-Ph | 4-Pyr | 6-Oxo |
| 2-174' | 3-Cl-Ph | 4-Pyr | 8a-Me |
| 2-175' | 3-Cl-Ph | 4-Pyr | 8a-Et |
| 2-176' | 3-Cl-Ph | 4-Pyr | 8a-Pr |
| 2-177' | 3-CF$_3$-Ph | 4-Pyr | 1-Me |
| 2-178' | 3-CF$_3$-Ph | 4-Pyr | 1-Et |
| 2-179' | 3-CF$_3$-Ph | 4-Pyr | 1-Pr |
| 2-180' | 3-CF$_3$-Ph | 4-Pyr | 1,1-diMe |
| 2-181' | 3-CF$_3$-Ph | 4-Pyr | 2-Me |
| 2-182' | 3-CF$_3$-Ph | 4-Pyr | 2-Et |
| 2-183' | 3-CF$_3$-Ph | 4-Pyr | 2-Pr |
| 2-184' | 3-CF$_3$-Ph | 4-Pyr | 2-Bu |
| 2-185' | 3-CF$_3$-Ph | 4-Pyr | 2-Allyl |
| 2-186' | 3-CF$_3$-Ph | 4-Pyr | 2-Ph |
| 2-187' | 3-CF$_3$-Ph | 4-Pyr | 2-Bn |
| 2-188' | 3-CF$_3$-Ph | 4-Pyr | 2-Phet |
| 2-189' | 3-CF$_3$-Ph | 4-Pyr | 2,2-diMe |
| 2-190' | 3-CF$_3$-Ph | 4-Pyr | 2-OH |
| 2-191' | 3-CF$_3$-Ph | 4-Pyr | 2-MeO |
| 2-192' | 3-CF$_3$-Ph | 4-Pyr | 2-EtO |
| 2-193' | 3-CF$_3$-Ph | 4-Pyr | 2-PrO |
| 2-194' | 3-CF$_3$-Ph | 4-Pyr | 2,2-di(MeO) |
| 2-195' | 3-CF$_3$-Ph | 4-Pyr | 2,2-di(EtO) |
| 2-196' | 3-CF$_3$-Ph | 4-Pyr | 2,2-OCH$_2$CH$_2$O— |
| 2-197' | 3-CF$_3$-Ph | 4-Pyr | 2-Oxo |
| 2-198' | 3-CF$_3$-Ph | 4-Pyr | 2-F |
| 2-199' | 3-CF$_3$-Ph | 4-Pyr | 2-Cl |
| 2-200' | 3-CF$_3$-Ph | 4-Pyr | 2-Br |
| 2-201' | 3-CF$_3$-Ph | 4-Pyr | 2-I |
| 2-202' | 3-CF$_3$-Ph | 4-Pyr | 2,2-diF |
| 2-203' | 3-CF$_3$-Ph | 4-Pyr | 2,2-diCl |
| 2-204' | 3-CF$_3$-Ph | 4-Pyr | 2,2-diBr |
| 2-205' | 3-CF$_3$-Ph | 4-Pyr | 3-Me |
| 2-206' | 3-CF$_3$-Ph | 4-Pyr | 3-Et |
| 2-207' | 3-CF$_3$-Ph | 4-Pyr | 3-Pr |
| 2-208' | 3-CF$_3$-Ph | 4-Pyr | 3,3-diMe |
| 2-209' | 3-CF$_3$-Ph | 4-Pyr | 5-Me |
| 2-210' | 3-CF$_3$-Ph | 4-Pyr | 5-Et |
| 2-211' | 3-CF$_3$-Ph | 4-Pyr | 5-Pr |
| 2-212' | 3-CF$_3$-Ph | 4-Pyr | 5,5-diMe |
| 2-213' | 3-CF$_3$-Ph | 4-Pyr | 6-Me |
| 2-214' | 3-CF$_3$-Ph | 4-Pyr | 6-Et |
| 2-215' | 3-CF$_3$-Ph | 4-Pyr | 6-Pr |
| 2-216' | 3-CF$_3$-Ph | 4-Pyr | 6,6-diMe |
| 2-217' | 3-CF$_3$-Ph | 4-Pyr | 6-Oxo |
| 2-218' | 3-CF$_3$-Ph | 4-Pyr | 8a-Me |
| 2-219' | 3-CF$_3$-Ph | 4-Pyr | 8a-Et |
| 2-220' | 3-CF$_3$-Ph | 4-Pyr | 8a-Pr |
| 2-221' | 3,4-diF-Ph | 4-Pyr | 1-Me |
| 2-222' | 3,4-diF-Ph | 4-Pyr | 1-Et |
| 2-223' | 3,4-diF-Ph | 4-Pyr | 1-Pr |
| 2-224' | 3,4-diF-Ph | 4-Pyr | 1,1-diMe |
| 2-225' | 3,4-diF-Ph | 4-Pyr | 2-Me |
| 2-226' | 3,4-diF-Ph | 4-Pyr | 2-Et |
| 2-227' | 3,4-diF-Ph | 4-Pyr | 2-Pr |
| 2-228' | 3,4-diF-Ph | 4-Pyr | 2-Bu |

TABLE 2'-continued

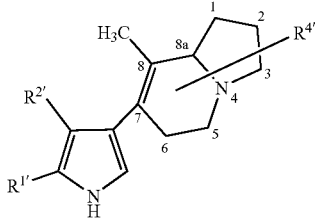

| Compound No. | $R^{1'}$ | $R^{2'}$ | $R^{4'}$ |
|---|---|---|---|
| 2-229' | 3,4-diF-Ph | 4-Pyr | 2-Allyl |
| 2-230' | 3,4-diF-Ph | 4-Pyr | 2-Ph |
| 2-231' | 3,4-diF-Ph | 4-Pyr | 2-Bn |
| 2-232' | 3,4-diF-Ph | 4-Pyr | 2-Phet |
| 2-233' | 3,4-diF-Ph | 4-Pyr | 2,2-diMe |
| 2-234' | 3,4-diF-Ph | 4-Pyr | 2-OH |
| 2-235' | 3,4-diF-Ph | 4-Pyr | 2-MeO |
| 2-236' | 3,4-diF-Ph | 4-Pyr | 2-EtO |
| 2-237' | 3,4-diF-Ph | 4-Pyr | 2-PrO |
| 2-238' | 3,4-diF-Ph | 4-Pyr | 2,2-di(MeO) |
| 2-239' | 3,4-diF-Ph | 4-Pyr | 2,2-di(EtO) |
| 2-240' | 3,4-diF-Ph | 4-Pyr | 2,2-OCH$_2$CH$_2$O— |
| 2-241' | 3,4-diF-Ph | 4-Pyr | 2-Oxo |
| 2-242' | 3,4-diF-Ph | 4-Pyr | 2-F |
| 2-243' | 3,4-diF-Ph | 4-Pyr | 2-Cl |
| 2-244' | 3,4-diF-Ph | 4-Pyr | 2-Br |
| 2-245' | 3,4-diF-Ph | 4-Pyr | 2-I |
| 2-246' | 3,4-diF-Ph | 4-Pyr | 2,2-diF |
| 2-247' | 3,4-diF-Ph | 4-Pyr | 2,2-diCl |
| 2-248' | 3,4-diF-Ph | 4-Pyr | 2,2-diBr |
| 2-249' | 3,4-diF-Ph | 4-Pyr | 3-Me |
| 2-250' | 3,4-diF-Ph | 4-Pyr | 3-Et |
| 2-251' | 3,4-diF-Ph | 4-Pyr | 3-Pr |
| 2-252' | 3,4-diF-Ph | 4-Pyr | 3,3-diMe |
| 2-253' | 3,4-diF-Ph | 4-Pyr | 5-Me |
| 2-254' | 3,4-diF-Ph | 4-Pr | 5-Et |
| 2-255' | 3,4-diF-Ph | 4-Pyr | 5-Pr |
| 2-256' | 3,4-diF-Ph | 4-Pyr | 5,5-diMe |
| 2-257' | 3,4-diF-Ph | 4-Pyr | 6-Me |
| 2-258' | 3,4-diF-Ph | 4-Pyr | 6-Et |
| 2-259' | 3,4-diF-Ph | 4-Pyr | 6-Pr |
| 2-260' | 3,4-diF-Ph | 4-Pyr | 6,6-diMe |
| 2-261' | 3,4-diF-Ph | 4-Pyr | 6-Oxo |
| 2-262' | 3,4-diF-Ph | 4-Pyr | 8a-Me |
| 2-263' | 3,4-diF-Ph | 4-Pyr | 8a-Et |
| 2-264' | 3,4-diF-Ph | 4-Pyr | 8a-Pr |
| 2-265' | Ph | 4-Pyr | 6,6-(CH$_2$)$_2$— |
| 2-266' | 3-F-Ph | 4-Pyr | 6,6-(CH$_2$)$_2$— |
| 2-267' | 4-F-Ph | 4-Pyr | 6,6-(CH$_2$)$_2$— |
| 2-268' | 3-Cl-Ph | 4-Pyr | 6,6-(CH$_2$)$_2$— |
| 2-269' | 3-CF$_3$-Ph | 4-Pyr | 6,6-(CH$_2$)$_2$— |
| 2-270' | 3,4-diF-Ph | 4-Pyr | 6,6-(CH$_2$)$_2$— |
| 2-271' | Ph | 4-Pyr | 6,6-diF |
| 2-272' | 3-F-Ph | 4-Pyr | 6,6-diF |
| 2-273' | 4-F-Ph | 4-Pyr | 6,6-diF |
| 2-274' | 3-Cl-Ph | 4-Pyr | 6,6-diF |
| 2-275' | 3-CF$_3$-Ph | 4-Pyr | 6,6-diF |
| 2-276' | 3,4-diF-Ph | 4-Pyr | 6,6-diF |

TABLE 3'

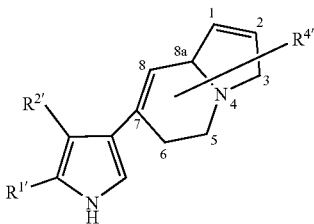

| Compound No. | R¹' | R²' | R⁴' |
|---|---|---|---|
| 3-1' | 4-F-Ph | 4-Pyr | 2-Me |
| 3-2' | 4-F-Ph | 4-Pyr | 2-Et |
| 3-3' | 4-F-Ph | 4-Pyr | 2-Pr |
| 3-4' | 4-F-Ph | 4-Pyr | 2-Bu |
| 3-5' | 4-F-Ph | 4-Pyr | 2-Allyl |
| 3-6' | 4-F-Ph | 4-Pyr | 2-Ph |
| 3-7' | 4-F-Ph | 4-Pyr | 2-Bn |
| 3-8' | 4-F-Ph | 4-Pyr | 2-Phet |
| 3-9' | 4-F-Ph | 4-Pyr | 3-Me |
| 3-10' | 4-F-Ph | 4-Pyr | 3-Et |
| 3-11' | 4-F-Ph | 4-Pyr | 3-Pr |
| 3-12' | 4-F-Ph | 4-Pyr | 3,3-diMe |
| 3-13' | 4-F-Ph | 4-Pyr | 5-Me |
| 3-14' | 4-F-Ph | 4-Pyr | 5-Et |
| 3-15' | 4-F-Ph | 4-Pyr | 5-Pr |
| 3-16' | 4-F-Ph | 4-Pyr | 5,5-diMe |
| 3-17' | 4-F-Ph | 4-Pyr | 6-Me |
| 3-18' | 4-F-Ph | 4-Pyr | 6-Et |
| 3-19' | 4-F-Ph | 4-Pyr | 6-Pr |
| 3-20' | 4-F-Ph | 4-Pyr | 6,6-diMe |
| 3-21' | 4-F-Ph | 4-Pyr | 6,6-(CH₂)₂— |
| 3-22' | 4-F-Ph | 4-Pyr | 6-Oxo |
| 3-23' | 4-F-Ph | 4-Pyr | 8-Me |
| 3-24' | 4-F-Ph | 4-Pyr | 8-Et |
| 3-25' | 4-F-Ph | 4-Pyr | 8-Pr |
| 3-26' | 4-F-Ph | 4-Pyr | 8-Ph |
| 3-27' | 4-F-Ph | 4-Pyr | 8a-Me |
| 3-28' | 4-F-Ph | 4-Pyr | 8a-Et |
| 3-29' | 4-F-Ph | 4-Pyr | 8a-Pr |

TABLE 4'

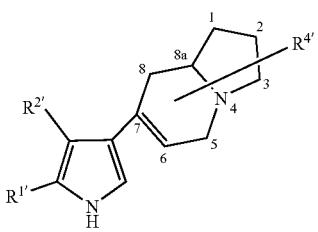

| Compound No. | R¹' | R²' | R⁴' |
|---|---|---|---|
| 4-1' | 4-F-Ph | 4-Pyr | 1-Me |
| 4-2' | 4-F-Ph | 4-Pyr | 1-Et |
| 4-3' | 4-F-Ph | 4-Pyr | 1-Pr |
| 4-4' | 4-F-Ph | 4-Pyr | 1,1-diMe |
| 4-5' | 4-F-Ph | 4-Pyr | 2-Me |
| 4-6' | 4-F-Ph | 4-Pyr | 2-Et |
| 4-7' | 4-F-Ph | 4-Pyr | 2-Pr |
| 4-8' | 4-F-Ph | 4-Pyr | 2-Bu |
| 4-9' | 4-F-Ph | 4-Pyr | 2-Allyl |
| 4-10' | 4-F-Ph | 4-Pyr | 2-Ph |
| 4-11' | 4-F-Ph | 4-Pyr | 2-Bn |
| 4-12' | 4-F-Ph | 4-Pyr | 2-Phet |
| 4-13' | 4-F-Ph | 4-Pyr | 2,2-diMe |
| 4-14' | 4-F-Ph | 4-Pyr | 2-OH |
| 4-15' | 4-F-Ph | 4-Pyr | 2-MeO |
| 4-16' | 4-F-Ph | 4-Pyr | 2-EtO |

TABLE 4'-continued

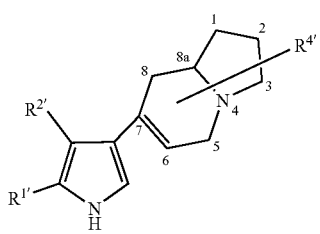

| Compound No. | R¹' | R²' | R⁴' |
|---|---|---|---|
| 4-17' | 4-F-Ph | 4-Pyr | 2-PrO |
| 4-18' | 4-F-Ph | 4-Pyr | 2,2-di(MeO) |
| 4-19' | 4-F-Ph | 4-Pyr | 2,2-di(EtO) |
| 4-20' | 4-F-Ph | 4-Pyr | 2,2-OCH₂CH₂O— |
| 4-21' | 4-F-Ph | 4-Pyr | 2-Oxo |
| 4-22' | 4-F-Ph | 4-Pyr | 2-F |
| 4-23' | 4-F-Ph | 4-Pyr | 2-Cl |
| 4-24' | 4-F-Ph | 4-Pyr | 2-Br |
| 4-25' | 4-F-Ph | 4-Pyr | 2-I |
| 4-26' | 4-F-Ph | 4-Pyr | 2,2-diF |
| 4-27' | 4-F-Ph | 4-Pyr | 2,2-diCl |
| 4-28' | 4-F-Ph | 4-Pyr | 2,2-diBr |
| 4-29' | 4-F-Ph | 4-Pyr | 3-Me |
| 4-30' | 4-F-Ph | 4-Pyr | 3-Et |
| 4-31' | 4-F-Ph | 4-Pyr | 3-Pr |
| 4-32' | 4-F-Ph | 4-Pyr | 3,3-diMe |
| 4-33' | 4-F-Ph | 4-Pyr | 5-Me |
| 4-34' | 4-F-Ph | 4-Pyr | 5-Et |
| 4-35' | 4-F-Ph | 4-Pyr | 5-Pr |
| 4-36' | 4-F-Ph | 4-Pyr | 5,5-diMe |
| 4-37' | 4-F-Ph | 4-Pyr | 6-Me |
| 4-38' | 4-F-Ph | 4-Pyr | 6-Et |
| 4-39' | 4-F-Ph | 4-Pyr | 6-Pr |
| 4-40' | 4-F-Ph | 4-Pyr | 6-Ph |
| 4-41' | 4-F-Ph | 4-Pyr | 8-Me |
| 4-42' | 4-F-Ph | 4-Pyr | 8-Et |
| 4-43' | 4-F-Ph | 4-Pyr | 8-Pr |
| 4-44' | 4-F-Ph | 4-Pyr | 8,8-diMe |
| 4-45' | 4-F-Ph | 4-Pyr | 8,8-(CH₂)₂— |
| 4-46' | 4-F-Ph | 4-Pyr | 8-Oxo |
| 4-47' | 4-F-Ph | 4-Pyr | 8a-Me |
| 4-48' | 4-F-Ph | 4-Pyr | 8a-Et |
| 4-49' | 4-F-Ph | 4-Pyr | 8a-Pr |
| 4-50' | 4-F-Ph | 4-Pyr | 2->CH₂ |
| 4-51' | 4-F-Ph | 4-Pyr | 2->CHMe |
| 4-52' | 4-F-Ph | 4-Pyr | 2->CHEt |
| 4-53' | 4-F-Ph | 4-Pyr | 2->CHPr |
| 4-54' | 4-F-Ph | 4-Pyr | 2->C(Me)₂ |
| 4-55' | 4-F-Ph | 4-Pyr | 2->CHPh |
| 4-56' | 4-F-Ph | 4-Pyr | 2,2-diPh |
| 4-57' | 4-F-Ph | 4-Pyr | 2,2-O(CH₂)₃O— |
| 4-58' | 4-F-Ph | 4-Pyr | 2,2-OCH₂C(Me)₂CH₂O— |
| 4-59' | 4-F-Ph | 4-Pyr | 2,2-(CH₂)₂ |
| 4-60' | 4-F-Ph | 4-Pyr | 2,2-(CH₂)₃— |
| 4-61' | 4-F-Ph | 4-Pyr | 2,2-(CH₂)₄— |
| 4-62' | 4-F-Ph | 4-Pyr | 2,2-(CH₂)₅— |
| 4-63' | 4-F-Ph | 4-Pyr | 2-MeS |
| 4-64' | 4-F-Ph | 4-Pyr | 2-EtS |
| 4-65' | 4-F-Ph | 4-Pyr | 2-PrS |
| 4-66' | 4-F-Ph | 4-Pyr | 2-BuS |
| 4-67' | 4-F-Ph | 4-Pyr | 2-MeSO₂ |
| 4-68' | 4-F-Ph | 4-Pyr | 2-PhO |

TABLE 5'

(I-1)'

[Structure: pyrrole with R1' at 2-position, R2' at 3-position, R3' at 4-position, NH]

| Compound No. | R1' | R2' | R3' |
|---|---|---|---|
| 5-1' | 4-F-Ph | 4-Pyr | [structure] |
| 5-2' | 4-F-Ph | 4-Pyr | [structure] |
| 5-3' | 4-F-Ph | 4-Pyr | [structure] |
| 5-4' | 4-F-Ph | 4-Pyr | [structure] |
| 5-5' | 4-F-Ph | 4-Pyr | [structure] |
| 5-6' | 4-F-Ph | 4-Pyr | [structure] |
| 5-7' | 4-F-Ph | 4-Pyr | [structure] |
| 5-8' | 4-F-Ph | 4-Pyr | [structure] |

TABLE 6

[Structure: fused bicyclic system with numbered positions 1, 2, 3, 4, 5, 6, 8, 8a and R4' substituent, connected to pyrrole with R1', R2', NH]

| Compound No. | R1' | R2' | R4' |
|---|---|---|---|
| 6-1' | 4-F-Ph | 4-Pyr | 2-Me |
| 6-2' | 4-F-Ph | 4-Pyr | 2-Et |
| 6-3' | 4-F-Ph | 4-Pyr | 2-Pr |
| 6-4' | 4-F-Ph | 4-Pyr | 2-Bu |
| 6-5' | 4-F-Ph | 4-Pyr | 2-Allyl |
| 6-6' | 4-F-Ph | 4-Pyr | 2-Ph |
| 6-7' | 4-F-Ph | 4-Pyr | 2-Bn |
| 6-8' | 4-F-Ph | 4-Pyr | 2-Phet |
| 6-9' | 4-F-Ph | 4-Pyr | 3-Me |
| 6-10' | 4-F-Ph | 4-Pyr | 3-Et |
| 6-11' | 4-F-Ph | 4-Pyr | 3-Pr |
| 6-12' | 4-F-Ph | 4-Pyr | 3,3-diMe |
| 6-13' | 4-F-Ph | 4-Pyr | 5-Me |
| 6-14' | 4-F-Ph | 4-Pyr | 5-Et |
| 6-15' | 4-F-Ph | 4-Pyr | 5-Pr |
| 6-16' | 4-F-Ph | 4-Pyr | 5,5-diMe |
| 6-17' | 4-F-Ph | 4-Pyr | 6-Me |
| 6-18' | 4-F-Ph | 4-Pyr | 6-Et |
| 6-19' | 4-F-Ph | 4-Pyr | 6-Pr |
| 6-20' | 4-F-Ph | 4-Pyr | 6,6-diMe |
| 6-21' | 4-F-Ph | 4-Pyr | 6,6-$(CH_2)_2$— |
| 6-22' | 4-F-Ph | 4-Pyr | 6-Oxo |
| 6-23' | 4-F-Ph | 4-Pyr | 8-Me |
| 6-24' | 4-F-Ph | 4-Pyr | 8-Et |
| 6-25' | 4-F-Ph | 4-Pyr | 8-Pr |
| 6-26' | 4-F-Ph | 4-Pyr | 8-Ph |
| 6-27' | 4-F-Ph | 4-Pyr | 8a-Me |
| 6-28' | 4-F-Ph | 4-Pyr | 8a-Et |
| 6-29' | 4-F-Ph | 4-Pyr | 8a-Pr |

In the above tables, the following abbreviations are used:
Bn represents benzyl,
Bu represents butyl,
Et represents ethyl,
Me represents methyl,
Ph represents phenyl,
Phet represents phenethyl,
Pr represents propyl,
Pym represents pyrimidinyl
Pyr represents pyridyl,
>$CH_2$ represents methylidenyl,
>CHMe represents ethylidenyl,
>CHEt represents propylidenyl,
>$C(Me)_2$ represents isopropylidenyl,
>CHPr represents butylidenyl, and
>CHPh represents benzylidenyl.

In the above Tables 1' to 6', examples of preferred compounds include the compounds of Compound Nos. 1-5' to 1-7', 1-10', 1-14' to 1-23', 1-26', 1-27', 1-37' to 1-40', 1-42' to 1-44', 1-149' to 1-151', 1-154', 1-158' to 1-167', 1-170', 1-171', 1-181' to 1-184', 1-186' to 1-188', 1-197' to 1-199', 1-202', 1-206' to 1-215', 1-218', 1-219', 1-229' to 1-232', 1-234' to 1-236', 1-245' to 1-247', 1-250', 1-254' to 1-263', 1-266', 1-267', 1-277' to 1-280', 1-282' to 1-284', 1-293' to 1-296', 1-298', 1-301' to 1-311', 1-314', 1-315', 1-324' to 1-328', 1-330' to 1-332', 1-341' to 1-343', 1-346', 1-350' to 1-359', 1-362', 1-363', 1-373' to 1-376', 1-378' to 1-380', 1-389' to 1-391', 1-394', 1-398' to 1-407', 1-410', 1-411', 1-421' to 1-424', 1-426' to 1-428', 1-433' to 1-439', 1-442', 1-446' to 1-455', 1-458', 1-459', 1-469' to 1-472', 1-474' to 1-476', 1-485' to 1-487', 1-490', 1-494' to 1-503', 1-506', 1-507', 1-517' to 1-520', 1-522' to 1-524', 1-533' to 1-535', 1-538', 1-542' to 1-551', 1-554', 1-555', 1-565' to 1-568', 1-570' to 1-572', 1-581' to 1-583', 1-586', 1-590' to 1-599', 1-602', 1-603', 1-613' to 1-616', 1-618' to 1-620', 1-629' to 1-631', 1-634', 1-638' to 1-647', 1-650', 1-651', 1-661' to 1-664', 1-666' to 1-668', 1-677' to 1-679', 1-682', 1-686' to 1-695', 1-698', 1-699', 1-709' to 1-712', 1-714' to 1-716', 1-725' to 1-727', 1-730', 1-734' to 1-743', 1-746', 1-747', 1-757' to 1-760', 1-762' to 1-764', 1-946' to 1-987', 1-989' to 1-998', 1-1005' to 1-1008', 1-1010', 1-1014' to 1-1023', 1-1026', 1-1027', 1-1037' to 1-1040', 1-1042' to 1-1044', 1-1049' to 1-1056', 1-1058' to 1-1067', 1-1070' to 1-1081', 2-5' to 2-7', 2-10', 2-14' to 2-23', 2-26', 2-27', 2-37' to 2-40', 2-49' to 2-51', 2-54', 2-58' to 2-67', 2-70', 2-71', 2-81' to 2-84', 2-93' to 2-95', 2-98', 2-102' to 2-111', 2-114', 2-115', 2-125' to 2-128', 2-137' to 2-139', 2-142', 2-146' to 2-155', 2-158', 2-159', 2-169' to 2-172', 2-181' to 2-183', 2-186', 2-190' to 2-199', 2-202', 2-203', 2-213' to 2-216', 2-225' to 2-227', 2-230', 2-234' to 2-243', 2-246', 2-247', 2-257' to 2-260', 2-265' to 2-276', 3-1' to 3-4', 3-6', 3-17' to 3-21', 3-23' to 3-25', 4-5' to 4-7', 4-10', 4-14' to 4-23', 4-26', 4-27', 4-50' to 4-55', 4-57' to 4-66', 5-1', 5-3', 5-5' to 5-8', 6-1' to 6-3' and 6-6'.

Examples of more preferred compounds include the compounds of Compound Nos. 1-5', 1-6', 1-10', 1-14' to 1-16', 1-18' to 1-23', 1-26', 1-27', 1-37', 1-38', 1-40', 1-42', 1-43', 1-149' to 1-151', 1-154', 1-158' to 1-160', 1-162' to 1-167', 1-170', 1-171', 1-181', 1-182', 1-184', 1-186', 1-187', 1-197', 1-198', 1-202', 1-206' to 1-208', 1-210' to 1-215', 1-218', 1-219', 1-229', 1-230', 1-232', 1-234', 1-235', 1-245', 1-246', 1-250', 1-254' to 1-256', 1-258' to 1-263', 1-266', 1-267', 1-277', 1-278', 1-280', 1-282', 1-283', 1-293' to 1-295', 1-298', 1-301' to 1-304', 1-306' to 1-311', 1-314', 1-315', 1-324' to 1-326', 1-328', 1-330', 1-331', 1-341', 1-342', 1-346', 1-350' to 1-352', 1-354' to 1-359', 1-362', 1-363', 1-373', 1-374', 1-376', 1-378', 1-379', 1-389', 1-390', 1-394', 1-398' to 1-400', 1-402' to 1-407', 1-410', 1-411', 1-421', 1-422', 1-424', 1-426', 1-427', 1-437' to 1-439', 1-442', 1-446' to 1-448', 1-450' to 1-455', 1-458', 1-459', 1-469', 1-470', 1-472', 1-474', 1-475', 1-485'1-486', 1-490', 1-494' to 1-496', 1-498' to 1-503', 1-506', 1-507', 1-517', 1-518', 1-520', 1-522', 1-523', 1-533', 1-534', 1-538', 1-542' to 1-544', 1-546' to 1-551', 1-554', 1-555', 1-565', 1-566', 1-568', 1-570', 1-571', 1-581' to 1-583', 1-586', 1-590' to 1-592', 1-594' to 1-599', 1-602', 1-603', 1-613', 1-614', 1-616', 1-618', 1-619', 1-629', 1-630', 1-634', 1-638' to 1-640', 1-642' to 1-647', 1-650', 1-651', 1-661', 1-662', 1-664', 1-666', 1-667', 1-677', 1-678', 1-682', 1-686' to 1-688', 1-690' to 1-695', 1-698', 1-699', 1-709', 1-710', 1-712', 1-714', 1-715', 1-725', 1-726', 1-730', 1-734' to 1-736', 1-738' to 1-743', 1-746', 1-747', 1-757', 1-758', 1-760', 1-762', 1-763', 1-946' to 1-987', 1-989' to 1-998', 1-1005' to 1-1008', 1-1010', 1-1014' to 1-1023', 1-1051' to 1-1056', 1-1058' to 1-1067', 1-1070' to 1-1075', 2-93', 2-94', 2-98', 2-102' to 2-104', 2-106' to 2-111', 2-114', 2-115', 2-125', 2-126', 2-128', 2-137', 2-138', 2-142', 2-146', 2-147', 2-150' to 2-155', 2-158', 2-159', 2-169', 2-170', 2-172', 2-181', 2-182', 2-186', 2-190' to 2-192', 2-194' to 2-199', 2-202', 2-203', 2-213', 2-214', 2-216', 2-265' to 2-276', 3-1' to 3-4', 3-6', 3-17', 3-18', 3-20', 3-23', 3-24', 4-5', 4-10', 4-14' to 4-16', 4-20' to 4-23', 4-26', 4-27', 5-1', 5-3', and 5-5' to 5-8'.

Examples of still preferred compounds include the compounds of Compound Nos. 1-5', 1-10', 1-14', 1-15', 1-20' to 1-23', 1-26', 1-37', 1-40', 1-42', 1-149' to 1-151', 1-154', 1-158', 1-159', 1-164' to 1-167', 1-170', 1-181', 1-184', 1-186', 1-197', 1-202', 1-206', 1-207', 1-212' to 1-215', 1-218', 1-229', 1-232', 1-234', 1-245', 1-250', 1-254', 1-255', 1-260' to 1-263', 1-266', 1-277', 1-280', 1-282', 1-293' to 1-295', 1-298', 1-301' to 1-304', 1-308' to 1-311', 1-314', 1-324', 1-325', 1-328', 1-330', 1-341', 1-346' to 1-350', 1-351', 1-356' to 1-359', 1-362', 1-373', 1-376', 1-378', 1-389', 1-394', 1-398', 1-399', 1-404' to 1-407', 1-410', 1-421', 1-424', 1-426', 1-437' to 1-439', 1-442', 1-446', 1-447', 1-452' to 1-455', 1-458', 1-469', 1-472', 1-474', 1-485', 1-490', 1-494', 1-495', 1-500' to 1-503', 1-506', 1-517', 1-520', 1-522', 1-533', 1-538', 1-542', 1-543', 1-548' to 1-551', 1-554', 1-565', 1-568', 1-570', 1-581' to 1-583', 1-586', 1-590', 1-591', 1-596' to 1-599', 1-602', 1-613', 1-616', 1-618', 1-629', 1-634', 1-638', 1-639', 1-644' to 1-647', 1-650', 1-661', 1-664', 1-666', 1-677', 1-682', 1-686', 1-687', 1-692' to 1-695', 1-698', 1-709', 1-712', 1-714', 1-725', 1-730', 1-734', 1-735', 1-740' to 1-743', 1-746', 1-757', 1-760', 1-946', 1-949', 1-952' to 1-961', 1-964', 1-967', 1-970' to 1-979', 1-982' to 1-987', 1-991' to 1-996', 1-998', 1-1005' to 1-1008', 1-1010', 1-1014' to 1-1016', 1-1051' to 1-1056', 1-1070' to 1-1075', 2-93', 2-98', 2-102', 2-103', 2-108' to 2-111', 2-114', 2-125', 2-128', 2-137', 2-142', 2-146', 2-147', 2-152' to 2-155', 2-158', 2-169', 2-172', 2-181', 2-186', 2-190', 2-191', 2-196' to 2-199', 2-202', 2-213', 2-216', 3-1' to 3-4', 3-6', 3-17', 3-20', 3-23', 4-14', 4-15', 4-22', 4-23', and 4-26'.

Examples of particularly preferred compounds include the following compounds:

2-(3-fluorophenyl)-4-[2-methyl-1,2,3,5,6,8a-hexahydroindolizin-7-yl]-3-(pyridin-4-yl)-1H-pyrrole, 2-(3-fluorophenyl)-4-[2-phenyl-1,2,3,5,6,8a-hexahydroindolizin-7-yl]-3-(pyridin-4-yl)-1H-pyrrole, 2-(3-fluorophenyl)-4-[2-hydroxy-1,2,3,5,6,8a-hexahydroindolizin-7-yl]-3-(pyridin-4-yl)-1H-pyrrole, 2-(3-fluorophenyl)-4-[2-methoxy-1,2,3,5,6,8a-hexahydroindolizin-7-yl]-3-(pyridin-4-yl)-1H-pyrrole, 4-[2-fluoro-1,2,3,5,6,8a-hexahydroindolizin-7-yl]-2-(3-fluorophenyl)-3-(pyridin-4-yl)-1H-pyrrole, 2-(4-fluorophenyl)4-[2-methyl-1,2,3,5,6,8a-hexahydroindolizin-7-yl]-3-(pyridin-4-yl)-1H-pyrrole, 2-(4-fluorophenyl)-4-[2-phenyl-1,2,3,5,6,8a-hexahydroindolizin-7-yl]-3-(pyridin-4-yl)-1H-pyrrole, 2-(4-fluorophenyl)-4-[2-hydroxy-1,2,3,5,6,8a-hexahydroindolizin-7-yl]-3-(pyridin-4-yl)-1H-pyrrole, 2-(4-fluorophenyl)-4-[2-methoxy-1,2,3,5,6,8a-hexahydroindolizin-7-yl]-3-(pyridin-4-yl)-1H-pyrrole, 4-[2,2-ethylenedioxy-1,2,3,5,6,8a-hexahydroindolizin-7-yl]-2-(4-fluorophenyl)-3-(pyridin-4-yl)-1H-pyrrole, 2-(4-fluorophenyl)-4-[2-oxo-1,2,3,5,6,8a-hexahydroindolizin-7-yl]-3-(pyridin-4-yl)-1H-pyrrole, 4-[2-fluoro-1,2,3,5,6,8a-hexahydroindolizin-7-yl]-2-(4-fluorophenyl)-3-(pyridin-4-yl)-1H-pyrrole, 4-[2-chloro-1,2,3,5,6,8a-hexahydroindolizin-7-yl]-2-(4-fluorophenyl)-3-(pyridin-4-yl)-1H-pyrrole,
4-[2,2-difluoro-1,2,3,5,6,8a-hexahydroindolizin-7-yl]-2-(4-fluorophenyl)-3-(pyridin-4-yl)-1H-pyrrole,
2-(3-chlorophenyl)-4-[2-methyl-1,2,3,5,6,8a-hexahydroindolizin-7-yl]-3-(pyridin-4-yl)-1H-pyrrole,
2-(3-chlorophenyl)-4-[2-phenyl-1,2,3,5,6,8a-hexahydroindolizin-7-yl]-3-(pyridin-4-yl)-1H-pyrrole,
2-(3-chlorophenyl)-4-[2-hydroxy-1,2,3,5,6,8a-hexahydroindolizin-7-yl]-3-(pyridin-4-yl)-1H-pyrrole,
2-(3-chlorophenyl)-4-[2-methoxy-1,2,3,5,6,8a-hexahydroindolizin-7-yl]-3-(pyridin-4-yl)-1H-pyrrole,
2-(3-chlorophenyl)-4-[2-fluoro-1,2,3,5,6,8a-hexahydroindolizin-7-yl]-3-(pyridin-4-yl)-1H-pyrrole,
4-[2-chloro-1,2,3,5,6,8a-hexahydroindolizin-7-yl]-2-(3-chlorophenyl)-3-(pyridin-4-yl)-1H-pyrrole,
4-[2-methyl-1,2,3,5,6,8a-hexahydroindolizin-7-yl]-3-(pyridin-4-yl)-2-(3-trifluoromethylphenyl)-1H-pyrrole,
4-[2-phenyl-1,2,3,5,6,8a-hexahydroindolizin-7-yl]-3-(pyridin-4-yl)-2-(3-trifluoromethylphenyl)-1H-pyrrole,
4-[2-hydroxy-1,2,3,5,6,8a-hexahydroindolizin-7-yl]-3-(pyridin-4-yl)-2-(3-trifluoromethylphenyl)-1H-pyrrole,
4-[2-methoxy-1,2,3,5,6,8a-hexahydroindolizin-7-yl]-3-(pyridin-4-yl)-2-(3-trifluoromethylphenyl)-1H-pyrrole,
4-[2-fluoro-1,2,3,5,6,8a-hexahydroindolizin-7-yl]-3-(pyridin-4-yl)-2-(3-trifluoromethylphenyl)-1H-pyrrole,
4-[2-chloro-1,2,3,5,6,8a-hexahydroindolizin-7-yl]-3-(pyridin-4-yl)-2-(3-trifluoromethylphenyl)-1H-pyrrole,
4-[2,8-dimethyl-1,2,3,5,6,8a-hexahydroindolizin-7-yl]-2-(4-fluorophenyl)-3-(pyridin-4-yl)-1H-pyrrole,
2-(4-fluorophenyl)-4-[2-hydroxy-8-methyl-1,2,3,5,6,8a-hexahydroindolizin-7-yl]-3-(pyridin-4-yl)-1H-pyrrole,
2-(4-fluorophenyl)-4-[2-methoxy-8-methyl-1,2,3,5,6,8a-hexahydroindolizin-7-yl]-3-(pyridin-4-yl)-1H-pyrrole,
4-[2-fluoro-8-methyl-1,2,3,5,6,8a-hexahydroindolizin-7-yl]-2-(4-fluorophenyl)-3-(pyridin-4-yl)-1H-pyrrole,
4-[2-chloro-8-methyl-1,2,3,5,6,8a-hexahydroindolizin-7-yl]-2-(4-fluorophenyl)-3-(pyridin-4-yl)-1H-pyrrole,
2-(4-fluorophenyl)-4-[2-methyl-3,5,6,8-etrahydroindolizin-7-yl]-3-(pyridin-4-yl)-1H-pyrrole,
2-(4-fluorophenyl)-4-[2-hydroxy-1,2,3,5,8,8a-hexahydroindolizin-7-yl]-3-(pyridin-4-yl)-1H-pyrrole,
2-(4-fluorophenyl)-4-[2-methoxy-1,2,3,5,8,8a-hexahydroindolizin-7-yl]-3-(pyridin-4-yl)-1H-pyrrole,
4-[2-chloro-1,2,3,5,8,8a-hexahydroindolizin-7-yl]-2-(4-fluorophenyl)-3-(pyridin-4-yl)-1H-pyrrole,
4-[2,2-difluoro-1,2,3,5,8,8a-hexahydroindolizin-7-yl]-2-(4-fluorophenyl)-3-(pyridin-4-yl)-1H-pyrrole,
4-[cyclopropanespiro-6'-(1',2',3',5',6',8a'-hexahydroindolizin)-7'-yl]-2-(4-fluorophenyl)-3-(pyridin-4-yl)-1H-pyrrole,
2-(4-fluorophenyl)-4-[2-methylidene-1,2,3,5,6,8a-hexahydroindolizin-7-yl]-3-(pyridin-4-y)-1H-pyrrole,
4-[2,2-dimethyl-1,2,3,5,6,8a-hexahydroindolizin-7-yl]-2-(4-fluorophenyl)-3-(pyridin-4-yl)-1H-pyrrole,
2-(4-fluorophenyl)-4-[2-methylthio-1,2,3,5,6,8a-hexahydroindolizin-7-yl]-3-(pyridin-4-yl)-1H-pyrrole,
4-[2-ethyl-1,2,3,5,6,8a-hexahydroindolizin-7-yl]-2-(4-fluorophenyl)-3-(pyridin-4-yl)-1H-pyrrole,
4-[2-ethyl-1,2,3,5,6,8a-hexahydroindolizin-7-yl]-2-(3-fluorophenyl)-3-(pyridin-4-yl)-1H-pyrrole,
2-(3-chlorophenyl)-4-[2-ethyl-1,2,3,5,6,8a-hexahydroindolizin-7-yl]-3-(pyridin-4-yl)-1H-pyrrole,
4-[2-ethyl-1,2,3,5,6,8a-hexahydroindolizin-7-yl]-3-(pyridin-4-yl)-2-(3-trifluoromethylphenyl)-1H-pyrrole,
2-(4-chlorophenyl)-4-[2-ethyl-1,2,3,5,6,8a-hexahydroindolizin-7-yl]-3-(pyridin-4-yl)-1H-pyrrole,
4-[2-butylthio-1,2,3,5,6,8a-hexahydroindolizin-7-yl]-2-(4-fluorophenyl)-3-(pyridin-4-yl)-1H-pyrrole,
4-[2-ethylthio-1,2,3,5,6,8a-hexahydroindolizin-7-yl]-2-(4-fluorophenyl)-3-(pyridin-4-yl)-1H-pyrrole,
4-[2-ethylidene-1,2,3,5,6,8a-hexahydroindolizin-7-yl]-2-(4-fluorophenyl)-3-(pyridin-4-yl)-1H-pyrrole,
2-(4-fluorophenyl)-4-[2-propyl-1,2,3,5,6,8a-hexahydroindolizin-7-yl]-3-(pyridin-4-yl)-1H-pyrrole,
2-(3-fluorophenyl)-4-[2-propyl-1,2,3,5,6,8a-hexahydroindolizin-7-yl]-3-(pyridin-4-yl)-1H-pyrrole,
2-(3-chlorophenyl)-4-[2-propyl-1,2,3,5,6,8a-hexahydroindolizin-7-yl]-3-(pyridin-4-yl)-1H-pyrrole,
4-[2-propyl-1,2,3,5,6,8a-hexahydroindolizin-7-yl]-3-(pyridin-4-yl)-2-(3-trifluoromethylphenyl)-1H-pyrrole,
2-(4-chlorophenyl)-4-[2-propyl-1,2,3,5,6,8a-hexahydroindolizin-7-yl]-3-(pyridin-4-yl)-1H-pyrrole,
4-[2-ethoxy-1,2,3,5,6,8a-hexahydroindolizin-7-yl]-2-(4-fluorophenyl)-3-(pyridin-4-yl)-1H-pyrrole,
4-[cyclopentanespiro-2'-(1',2',3',5',6',8a'-hexahydroindolizin)-7'-yl]-2-(4-fluorophenyl)-3-(pyridin-4-yl)-1H-pyrrole,
4-[2-benzylidene-1,2,3,5,6,8a-hexahydroindol-7-yl]-2-(4-fluorophenyl)-3-(pyridin-4-yl)-1H-pyrrole,
2-(4-fluorophenyl)-4-[2-propylidene-1,2,3,5,6,8a-hexahydroindolizin-7-yl]-3-(pyridin-4-yl)-1H-pyrrole,
4-[5,5-dimethyl-1,2,3,5,6,8a-hexahydroindolizin-7-yl]-2-(4-fluorophenyl)-3-(pyridin-4-yl)-1H-pyrrole,
4-[2-ethyl-3,5,6,8a-tetrahydroindolizin-7-yl]-2-(4-fluorophenyl)-3-(pyridin-4-yl)-1H-pyrrole,
2-(4-fluorophenyl)-4-[2-propyl-3,5,6,8a-tetrahydroindolizin-7-yl]-3-(pyridin-4-yl)-1H-pyrrole,
2-(4-fluorophenyl)-4-[2-phenyl-3,5,6,8a-tetrahydroindolizin-7-yl]-3-(pyridin-4-yl)-1H-pyrrole,
2-(4-chlorophenyl)-4-[2-methoxy-1,2,3,5,6,8a-hexahydroindolizin-7-yl]-3-(pyridin-4-yl)-1H-pyrrole,
2-(4-chlorophenyl)-4-[2-methyl-1,2,3,5,6,8a-hexahydroindolizin-7-yl]-3-(pyridin-4-yl)-1H-pyrrole, and
2-(4-chlorophenyl)-4-[2-phenyl-1,2,3,5,6,8a-hexahydroindolizin-7-yl]-3-(pyridin-4-yl)-1H-pyrrole.

Examples of especially preferred compounds include the following compounds:
2-(3-fluorophenyl)-4-[2-methyl-1,2,3,5,6,8a-hexahydroindolizin-7-yl]-3-(pyridin-4-yl)-1H-pyrrole,
2-(3-fluorophenyl)-4-[2-phenyl-1,2,3,5,6,8a-hexahydroindolizin-7-yl]-3-(pyridin-4-yl)-1H-pyrrole,
2-(3-fluorophenyl)-4-[2-methoxy-1,2,3,5,6,8a-hexahydroindolizin-7-yl]-3-(pyridin-4-yl)-1H-pyrrole,
2-(4-fluorophenyl)-4-[2-methyl-1,2,3,5,6,8a-hexahydroindolizin-7-yl]-3-(pyridin-4-yl)-1H-pyrrole,
2-(4-fluorophenyl)-4-[2-phenyl-1,2,3,5,6,8a-hexahydroindolizin-7-yl]-3-(pyridin-4-yl)-1H-pyrrole,
2-(4-fluorophenyl)-4-[2-methoxy-1,2,3,5,6,8a-hexahydroindolizin-7-yl]-3-(pyridin-4-yl)-1H-pyrrole,
2-(3-chlorophenyl)-4-[2-methyl-1,2,3,5,6,8a-hexahydroindolizin-7-yl]-3-(pyridin-4-yl)-1H-pyrrole,
2-(3-chlorophenyl)-4-[2-phenyl-1,2,3,5,6,8a-hexahydroindolizin-7-yl]-3-(pyridin-4-yl)-1H-pyrrole,
2-(3-chlorophenyl)-4-[2-methoxy-1,2,3,5,6,8a-hexahydroindolizin-7-yl]-3-(pyridin-4-yl)-1H-pyrrole,
4-[2-methyl-1,2,3,5,6,8a-hexahydroindolizin-7-yl]-3-(pyridin-4-yl)-2-(3-trifluoromethylphenyl)-1H-pyrrole,
4-[2-phenyl-1,2,3,5,6,8a-hexahydroindolizin-7-yl]-3-(pyridin-4-yl)-2-(3-trifluoromethylphenyl)-1H-pyrrole,
4-[2-methoxy-1,2,3,5,6,8a-hexahydroindolizin-7-yl]-3-(pyridin-4-yl)-2-(3-trifluoromethylphenyl)-1H-pyrrole,
2-(4-fluorophenyl)-4-[2-methyl-3,5,6,8a-tetrahydroindolizin-7-yl]-3-(pyridin-4-yl)-1H-pyrrole, 2-(4-fluorophenyl)-4-[2-methylidene-1,2,3,5,6,8a-hexahydroindolizin-7-yl]-3-(pyridin-4-yl)-1H-pyrrole,
4-[2-ethyl-1,2,3,5,6,8a-hexahydroindolizin-7-yl]-2-(4-fluorophenyl)-3-(pyridin-4-yl)-1H-pyrrole,
4-[2-ethyl-1,2,3,5,6,8a-hexahydroindolizin-7-yl]-2-(3-fluorophenyl)-3-(pyridin-4-yl)-1H-pyrrole,
2-(3-chlorophenyl)-4-[2-ethyl-1,2,3,5,6,8a-hexahydroindolizin-7-yl]-3-(pyridin-4-yl)-1H-pyrrole,
4-[2-ethyl-1,2,3,5,6,8a-hexahydroindolizin-7-yl]-3-(pyridin-4-yl)-2-(3-trifluoromethylphenyl)-1H-pyrrole,
2-(4-fluorophenyl)-4-[2-propyl-1,2,3,5,6,8a-hexahydroindolizin-7-yl]-3-(pyridin-4-yl)-1H-pyrrole,
2-(3-fluorophenyl)-4-[2-propyl-1,2,3,5,6,8a-hexahydroindolizin-7-yl]-3-(pyridin-4-yl)-1H-pyrrole,
2-(3-chlorophenyl)-4-[2-propyl-1,2,3,5,6,8a-hexahydroindolizin-7-yl]-3-(pyridin-4-yl)-1H-pyrrole,
4-[2-propyl-1,2,3,5,6,8a-hexahydroindolizin-7-yl]-3-(pyridin-4-yl)-2-(3-triuoromethylphenyl)-1H-pyrrole,
4-[2-ethyl-3,5,6,8a-tetrahydroindolizin-7-yl]-2-(4-fluorophenyl)-3-(pyridin-4-yl)-1H-pyrrole,
2-(4-fluorophenyl)-4-[2-propyl-3,5,6,8a-tetrahydroindolizin-7-yl]-3-(pyridin-4-yl)-1H-pyrrole, and
2-(4-fluorophenyl)-4-[2-phenyl-3,5,6,8a-tetrahydroindolizin-7-yl]-3-(pyridin-4-yl)-1H-pyrrole.

Examples of the most preferred compounds include the following compounds:
2-(4-fluorophenyl)-4-[(2R,8aS)-2-phenyl-1,2,3,5,6,8a-hexahydroindolizin-7-yl]-3-(pyridin-4-yl)-1H-pyrrole,
2-(4-fluorophenyl)-4-[(8aS)-2-methyl-1,2,3,5,6,8a-hexahydroindolizin-7-yl]-3-(pyridin-4-yl)-1H-pyrrole,
2-(4-fluorophenyl)-4-[(8aS)-2-methylidene-1,2,3,5,6,8a-hexahydroindolizin-7-yl]-3-(pyridin-4-yl)-1H-pyrrole,
2-(4-fluorophenyl)-4-[(8aS)-2-methyl-3,5,6,8a-tetrahydroindolizin-7-yl]-3-(pyridin-4-yl)-1H-pyrrole,
4-[(2S,8aS)-2-ethyl-1,2,3,5,6,8a-hexahydroindolizin-7-yl]-2-(4-fluorophenyl)-3-(pyridin-4-yl)-1H-pyrrole, and
2-(4-fluorophenyl)-4-[(2S,8aS)-2-propyl-1,2,3,5,6,8a-hexahydroindolizin-7-yl]-3-(pyridin-4-yl)-1H-pyrrole.

The compounds of Tables 1' to 6' are of general formula (I-1)'. The combinations of substituents (R$^{1'}$, R$^{2'}$ and R$^{3'}$) which are thus exemplified for (I-1)' can also be applied to the general formulae (I-2)', (I-3)', (I-4)' and (I-5)', and compounds represented by the general formulae (I-2)', (I-3)', (I-4)' and (I-5)' which correspond to the compounds mentioned above as preferred compounds are also preferred.

Compounds of formula (I)' of the present invention can be prepared by methods mentioned below.

Method A

Method A is a method for preparing a compound of formula (I)' which is represented by the general formula (I-1)'

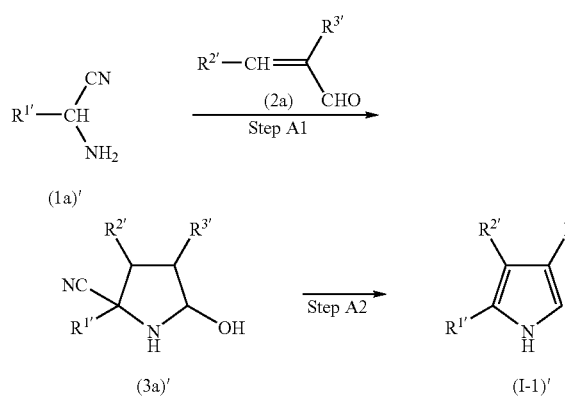

In the above formulae, R$^{1'}$, R$^{2'}$ and R$^{3'}$ are as defined above.

Step A1

In this Step, a pyrrolidine compound of formula (3a)' is prepared by reacting an aminonitrile compound of formula (1a)' with an α,β-unsaturated aldehyde compound of formula (2a)'. This reaction is well known in the field of synthetic organic chemistry and can be carried out using well known techniques, for example according to the method described in EP 0799823, the contents of which are incorporated herein by reference thereto.

In more detail, this Step is carried out in the presence of a base. There is no particular restriction on the nature of the bases used, and any base commonly used in reactions of this type may equally be used here. Examples of such bases include: alkali metal hydroxides, such as lithium hydroxide, sodium hydroxide and potassium hydroxide; alkali metal hydrides, such as lithium hydride, sodium hydride and potassium hydride; alkali metal amides, such as lithium amide, sodium amide, potassium amide and lithium bis(trimethylsilyl)amide; and alkali metal alkoxides, such as lithium ethoxide, sodium methoxide, sodium ethoxide and potassium t-butoxide. Of these, we prefer the lithium amides.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane and heptane; aromatic hydrocarbons, such as benzene, toluene and xylene; ethers, such as diethyl ether, diisopropyl ether, tetrahydrofuran and dioxane; and alcohols, such as methanol, ethanol, propanol, isopropanol and butanol. Of these, we prefer the ethers.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −78° C. to 100° C., more preferably from −78° C. to room temperature. The time required for the reaction may also vary widely, depending on many factors, notably the reaction temperature and the nature of the reagents and solvent employed. However, provided that the reaction is effected under the preferred conditions outlined above, a period of from 10 minutes to 30 hours, more preferably from 1 hour to 20 hours, will usually suffice.

Step A2

In this Step, the desired pyrrole derivative of formula (I-1)' of the present invention is prepared by the elimination of hydrogen cyanide and water from the compound of formula (3a)' prepared in Step A1 above. These reactions are well known in the field of synthetic organic chemitry and can be carried out using well known techniques, for example according to the methods described in detail in EP 0799823.

In more detail, this may be achieved by heating the residue obtained by distilling off the solvent from the product of Step A1, or by heating the material obtained by extracting that residue, washing it with water and distilling off the solvent, preferably at a temperature not lower than 100° C., in the presence or absence of a solvent after completion of the reaction of Step A1. The reaction proceeds sufficiently in the absence of a solvent, but, when a solvent is used, the solvent is preferably inert and has a higher boiling point. Examples of suitable solvents include: toluene, xylene, dimethylformamide, dimethylacetamide, dimethyl sulfoxide, diglyme and diphenyl ether.

Method B, Method C, Method D and Method E

Method B, Method C, Method D and Method E are used to prepare compounds of formulae (I-2)', (I-3)', (I-4)' and (I-5)' respectively using the processes outlined in Reaction Schemes B to E below.

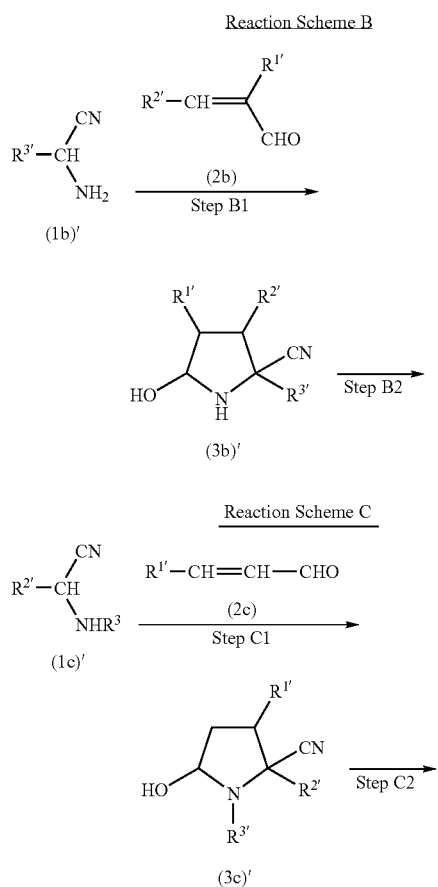

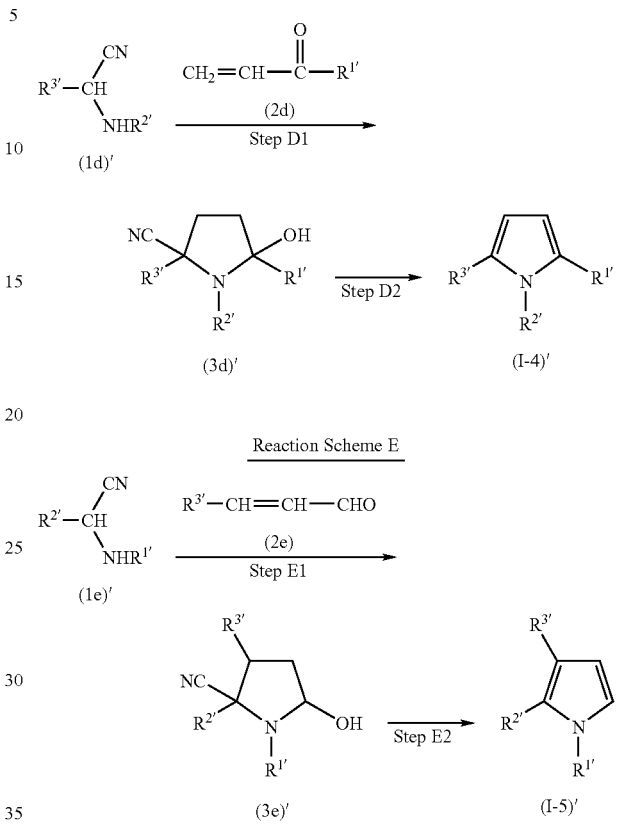

In the above formulae, $R^{1\prime}$, $R^{2\prime}$ and $R^{3\prime}$ are as defined above.

In the above Reaction Schemes Step B1, Step C1, Step D1 and Step E1 are carried out in a similar manner to Step A1 above, and Step B2, Step C2, Step D2 and Step E2 are carried out similarly to Step A2 above.

Method F

In this method, compounds of formula (I-1)' of the present invention [(I-1a)', (I-1b)' and (I-1c)'] are prepared as shown in Reaction Scheme F.

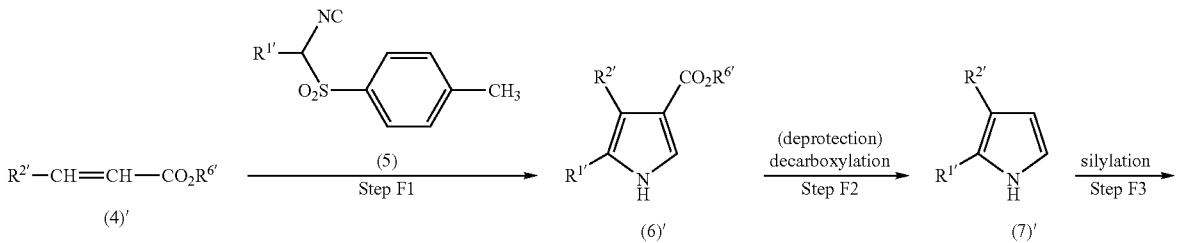

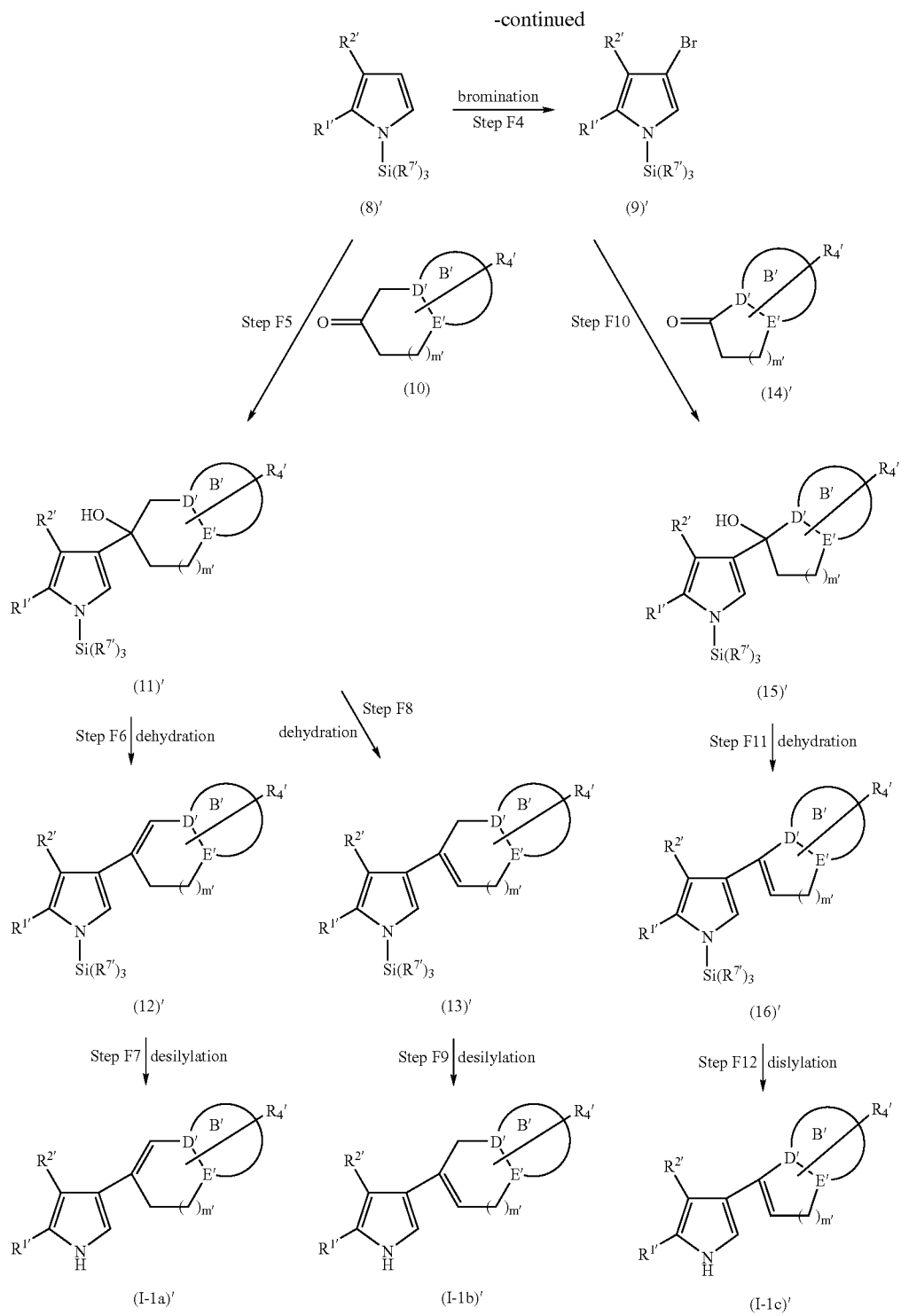

In the above formulae, B', D', E', R$^{1\prime}$, R$^{2\prime}$, R$^{4\prime}$ and m have the same meanings as defined above, R$^{6\prime}$ represents a hydrogen atom, a lower alkyl group as defined above or an aralkyl group as defined above, and each R$^{7\prime}$ is the same or different, and each represents a hydrogen atom, a lower alkyl group as defined above, an aryl group as defined above or an aralkyl group as defined above.

Step F1

In this Step, a pyrrole carboxylic acid derivative of formula (6)' is prepared by reacting an α,β-unsaturated compound of formula (4)' with an isonitrile compound of formula (5)'. Reactions of this type are well known in the field of synthetic organic chemistry and can be carried out using well known techniques, for example according to the methods described in detail in R. Di Santo et al., Synthetic Communications, 25(6), pp. 795–802 (1995), the contents of which are incorporated herein by reference thereto.

Step F2

In this Step, a disubstituted pyrrole compound (7)' is produced by first, where $R^{6'}$ represents a lower alkyl group or an aralkyl group from the pyrrole-carboxylic acid ester (6)', removing said protecting group $R^{6'}$ to give the pyrrole-carboxylic acid compound (6)' (wherein $R^{6'}$ represents a hydrogen atom) and then performing a decarboxylation reaction on said compound. Decarboxylation reactions of this type are well known in the field of synthetic organic chemistry and can be carried out using well known techniques, for example according to the methods described in detail in N. Yoshida et al.: Yakugaku Zasshi, 93(5), 584–598 (1973) (the contents of which are incorporated herein by reference thereto) which employ heating under acidic, basic or neutral conditions; for example, it can be carried out using a solvent and an acid or base under conditions described below. When $R^{6'}$ is a lower alkyl group or an aralkyl group, the deprotection reaction can be carried out using well known techniques according to the methods described in detail in T. W. Greene et al.: Protective Groups in Organic Synthesis, John Willey & Sons, Inc.

The decarboxylation reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include water and mixtures of water and an organic solvent, examples of which include aliphatic hydrocarbons such as pentane, hexane and heptane; aromatic hydrocarbons such as benzene, toluene and xylene; halogenated hydrocarbons such as dichloromethane, chloroform, carbon tetrachloride and dichloroethane; ethers such as diethyl ether, diisopropyl ether, tetrahydrofuran and dioxane; alcohols such as methanol, ethanol, propanol, isopropanol, butanol, s-butanol, isobutanol and t-butanol; aprotic polar solvents such as N,N-dimethylformamide, N,N-dimethylacetamide and dimethyl sulfoxide; nitriles such as acetonitrile; and esters such as methyl acetate and ethyl acetate, of which water, alcohols or a mixture thereof is preferred.

The acid to be used in the decarboxylation reaction is not particularly limited provided that it is one that is conventionally used as an acid in hydrolysis reactions, and examples thereof include mineral acids such as hydrochloric acid, sulfuric acid and phosphoric acid; carboxylic acids such as formic acid, acetic acid, propionic acid and trfluoroacetic acid; and sulfonic acids such as methanesulfonic acid and ethanesulfonic acid, of which hydrochloric acid, sulfuric acid or acetic acid is preferred.

The base to be used in the decarboxylation reaction is not particularly limited provided that it is one that is conventionally used as a base in hydrolysis reactions, and examples thereof include alkali metal hydrides such as sodium hydride and lithium hydride; alkali metal hydroxides such as sodium hydroxide and potassium hydroxide; alkali metal carbonates such as sodium carbonate and potassium carbonate; and amines such as triethylamine, tributylamine, pyridine, picoline and 1,8-diazabicyclo[5.4.0]undec-7-ene, of which sodium hydroxide or potassium hydroxide is preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. and 150° C., and preferably between 0° C. and 100° C. The time required for the reaction may also vary widely, depending on many factors, notably the reaction temperature and the nature of the reagents and solvent employed. However, provided that the reaction is effected under the preferred conditions outlined above, a period of from 10 minutes to 48 hours, and preferably from 30 minutes to 12 hours is usually sufficient.

Steps F3 to F5

In Step F3, a silylated compound (8)' is produced by silylating a nitrogen atom at the 1-position of the disubstituted pyrrole compound (7)' obtained according to the method of Step F2.

In Step F4, the silylated compound (8)' obtained according to the method of Step F3 is converted into a brominated pyrrole compound (9)' using a brominating agent (e.g. N-bromosuccinimide); and, in Step F5, the isolated compound (9)' thus obtained is first lithiated and then reacted with a heterocyclyl ketone (10)' to afford a hydroxyheterocyclyl compound (11)'.

The reactions of Steps F3, F4 and F5 can be carried out according to conventional techniques known in the field of synthetic organic chemistry, such as the methods described in detail in Brian L. Bray et al., J. Org. Chem., 55, 6317–6318 (1990), the contents of which are incorporated herein by reference thereto.

Step F6

In this Step, an unsaturated heterocyclyl compound (12)' is prepared by subjecting the hydroxyheterocyclyl compound (11)' obtained in Step F5 to a dehydration reaction. The dehydration reaction is well known in the field of synthetic organic chemistry and can be carried out using well known techniques. For example, it can be carried out in the presence of an acid catalyst such as sulfuric acid, a solid catalyst such as alumina or a halogenation agent such as thionyl chloride [these reactions are described in detail, for example, in G. H. Coleman & H. F. Johnstone, Org. Synth., I, 183 (1941); R L. Sawyer & D. W. Andrus, Org. Synth., III, 276 (1955); and J. S. Lamos et al., Tetrahedron Lett., 599 (1971), the contents of which are incorporated herein by reference thereto]. Alternatively, the dehydration reaction in this step can be performed by reaction of the hydroxyheterocyclyl compound (11)' with a trialkylsilane, such as triethylsilane, tripropylsilane or tributylsilane, and trifluoroacetic acid [see, for example, Francis A. Carey & Henry S. Tremper, J. Am. Chem. Soc., 91, 2967–2972 (1969), the contents of which are incorporated herein by reference thereto].

Step F7

In this Step, the desired compound of formula (I-1a)' of the present invention is prepared by removing the protecting group (the silyl group) from the pyrrole nitrogen of the unsaturated heterocyclyl compound (12)' prepared in Step F6. Desilylation reactions of this type are well known in the field of synthetic organic chemistry and can be carried out using well known techniques, for example using a desilylating reagent such as tetrabutylammonium fluoride (TBAF) according to the procedure described in detail in Brian L. Bray et al., J. Org. Chem., 55, 6317–6318 (1990), the contents of which are incorporated herein by reference thereto.

Step F8

In this Step, an unsaturated heterocyclyl compound (13)' is prepared by subjecting the hydroxyheterocyclyl compound (11)' obtained in Step F5 to a dehydration reaction. This dehydration reaction is carried out in a manner similar to that described for Step F6 above.

Step F9

In this Step, the desired compound of formula (I-1b)' of the present invention is prepared by removing the protecting group (the silyl group) from the pyrrole nitrogen of the unsaturated heterocyclyl compound (13)' prepared in Step F8. This Step can be performed in a manner similar to that described for Step F7 above.

Step F10

In this Step, a hydroxyheterocyclyl compound (15)' is prepared by first lithiating the compound (9)' prepared in Step F4 and then reacting it with a heterocyclyl ketone (14)'. This Step can be carried out in a manner similar to that described for Step F5 above.

Step F11

In this Step, an unsaturated heterocyclyl compound (16)' is prepared by subjecting the hydroxyheterocyclyl compound (15)' obtained in Step F10 to a dehydration reaction. This dehydration reaction is carried out in a manner similar to that described for Step F6 above.

Step F12

In this Step, the desired compound of formula (I-1c)' of the present invention is prepared by removing the protecting group (the silyl group) from the pyrrole nitrogen of the unsaturated heterocyclyl compound (16)' prepared in Step F11. This Step can be performed in a manner similar to that described for Step F7 above.

Method G

Generally, the compounds of formula (I)' of the present invention can be prepared by introducing the $R^{3'}$ group into a pyrrole compound already substituted on the pyrrole ring with the $R^{1'}$ group and $R^2$ group. Compounds of formula (I-1)' can be prepared, for example, according to the Method G, as shown in Reaction Scheme G below.

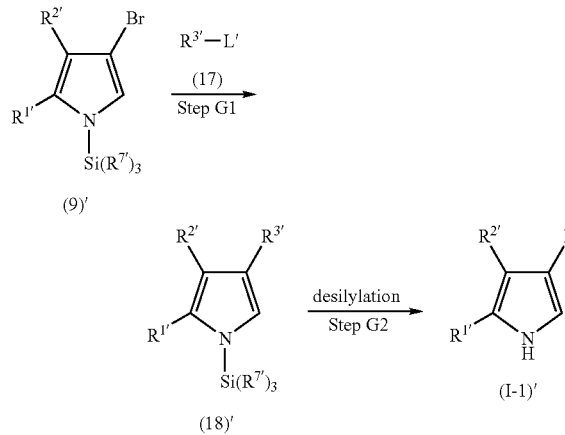

In the above formulae, $R^{1'}$, $R^{2'}$, $R^{3'}$ and $R^{7'}$ are as defined above, and L' represents a leaving group.

The leaving group L' is a group which is capable of leaving as a nucleophilic residue. Examples include halogen atoms such as fluorine, chlorine, bromine and iodine, trihalogenomethyloxy groups such as trichloromethoxy, lower alkanesulfonyloxy groups such as methanesulfonyloxy and ethanesulfonyloxy groups, lower halogeno alkane sulfonyloxy groups such as trifluoromethanesulfonyloxy and pentafluoroethanesulfonyloxy groups, and arylsulfonyloxy groups such as benzenesulfonyloxy, p-toluenesulfonyloxy and p-nitrobenzenesulfonyloxy groups. Of these, halogen atoms are preferred, and bromine atoms are particularly preferred.

Step G1

In this Step, a compound of formula (18)' is prepared by first lithiating a bromopyrrole compound of formula (9)' (prepared as described in Step F4 above) and then reacting the lithiated intermediate with a compound of formula (17)' in a manner similar to Step F5 above. Substitution reactions of a lithiated pyrrole intermediate of this type are well known in the field of synthetic organic chemistry and can be carried out using well known techniques, for example according to the methods described in detail in WO 99/01449, the contents of which are incorporated herein by reference thereto.

Step G2

In this Step, a compound of formula (I-1)' of the present invention is prepared by removing the protecting group (silyl group) of the compound of formula (18)' obtained in Step G1 above according to a procedure similar that described in Step F7 above.

Method H

In this method, compounds of formula (Ia)' of the present invention wherein $R^2$ is a heteroaryl group which has at least one ring nitrogen atom and which is substituted with a group of formula $NR^{a'}R^{b'}$ can be prepared, as shown in Reaction Scheme H below.

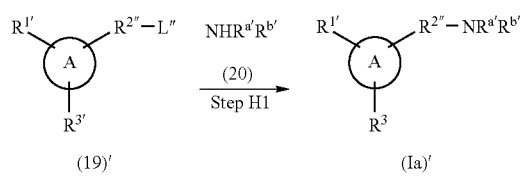

In the above formulae, the cyclic group A', $R^{1'}$, $R^{3'}$, $R^{a'}$ and $R^{b'}$ are defined above, $R^{2''}$ is a heteroaryl group which has at least one ring nitrogen atom and L" represents a leaving group, such that the group —$R^{2''}$-L" represents a heteroaryl group which has at least one ring nitrogen atom (as defined and exemplified above for the substituent $R^{2''}$) which is substituted with a leaving group (e.g. 2-methanesulfonylpyrimidin-4-yl, 2-methanesulfonylpyridin-4-yl or the like).

The leaving group L" is a similar group to the leaving groups defined and exemplified above in the definition of L' or it is a lower alkylsulfonyl group as defined and exemplified above, such as a methanesulfonyl, ethanesulfonyl, propanesulfonyl or butanesulfonyl group, or an arylsulfonyl group, such as a benzenesulfonyl, p-toluenesulfonyl or p-nitrobenzenesulfonyl group. The group L" is preferably a lower alkylsulfonyl group, and more preferably a methanesulfonyl group.

Step H1

In this Step, the desired compound of formula (Ia)' of the present invention is prepared by reacting a compound of formula (19)' with an amine compound of formula (20)' to replace the leaving group with a group of formula —NR$^a$R$^{b'}$. This reaction is usually carried out in a solvent in the presence or absence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols such as methanol, ethanol, propanol and isopropanol; ethers such as diethyl ether, diisopropyl ether, tetrahydrofuran and dioxane; aprotic polar solvents such as dimethylformamide, dimethylacetamide and dimethylsulfoxide; nitriles such as acetonitrile; esters such as methyl acetate and ethyl acetate; aromatic hydrocarbons such as benzene, toluene and xylene; and aliphatic hydrocarbons such as pentane, hexane and heptane, of which alcohols are preferred and methanol and ethanol are more preferred.

The base to be used in this step is not particularly limited, as long as it is effective in such reactions, and examples include: alkali metal alkoxides such as sodium methoxide, sodium ethoxide and potassium t-butoxide; alkali metal hydrides such as sodium hydride and lithium hydride; alkali metal hydroxides such as sodium hydroxide and potassium hydroxide; alkali metal carbonates such as sodium carbonate and potassium carbonate; and amines such as triethylamine, tributylamine, pyridine, picoline and 1,8-diazabicyclo[5.4.0] undec-7-ene, of which amines are preferred, and triethylamine, pyridine and 1,8-diazabicyclo[5.4.0)]undec-7-ene are more preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. and 150° C., and preferably between 0° C. and 100° C. The time required for the reaction may also vary widely, depending on many factors, notably the reaction temperature and the nature of the reagents and solvent employed. However, provided that the reaction is effected under the preferred conditions outlined above, a period of from 10 minutes to 48 hours, and preferably from 30 minutes to 12 hours is usually sufficient.

Nearly all of the starting materials used in Methods A to H above, namely compounds (1a)', (1b)', (1c)', (1d)', (1e)', (2a)', (2b)', (2c)', (2d)', (2e)', (4)', (5)', (10)', (14)', (17)' and (20)', are either known compounds or they are compounds which can be prepared easily from known compounds by known methods (for example, the methods described in WO 97/5877), while the compound (19)' can be synthesized from known compounds by performing reactions in a manner similar to that described in each of Methods A to E above.

Alternatively, starting compounds of general formula (10)' defined above can also be prepared by Methods I to M described below.

Method I

This is a method for the preparation of compounds of formula (26)' and (27)' below which are compounds of formula (10)' wherein D represents a group of formula >CR$^{4a'}$— wherein R$^{4a'}$ is as defined below and E represents a nitrogen atom, the method being carried out as shown in Reaction Scheme I below.

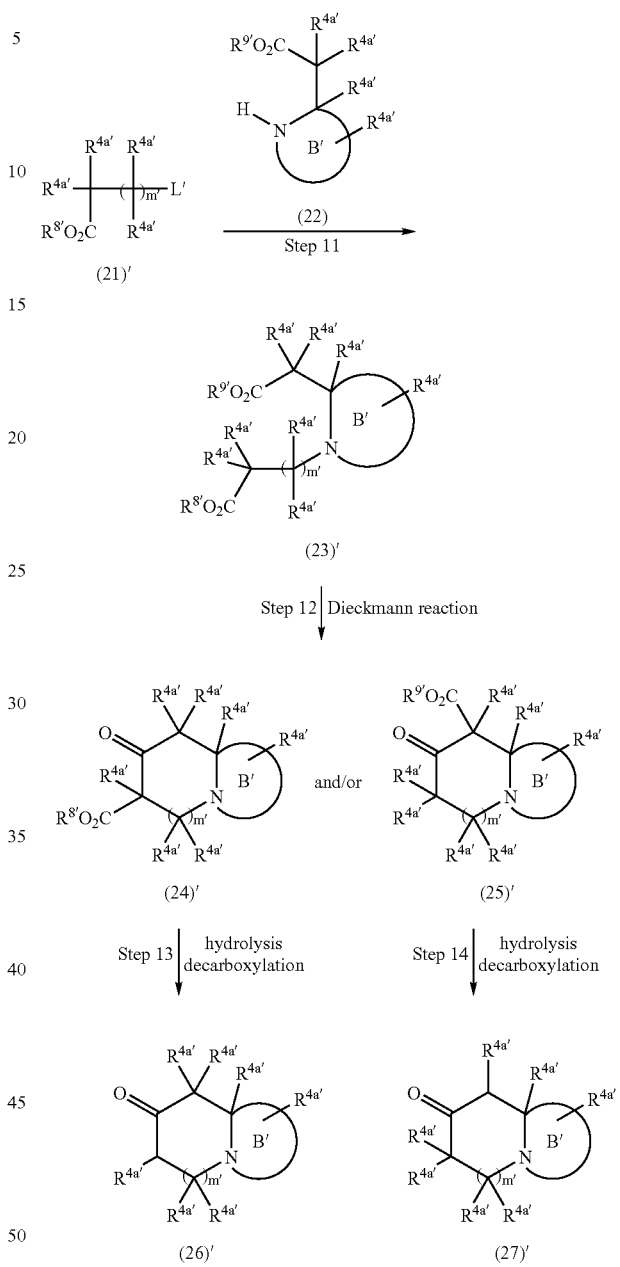

In the above formulae, B', L' and m' are as defined above, each of the groups R$^{4a'}$ is the same or different and represents a hydrogen atom or a group of formula R$^{4'}$ as defined above (provided that at least one of the R$^{4a'}$ groups is the same group as that defined for R$^{4}$)', and R$^{8'}$ and R$^{9'}$ are the same or different, and each represent a lower alkyl group as defined above or an aralkyl group as defined above.

Step I1

In this Step, a cyclic amine diester compound of formula (23)' is prepared by the condensation of a cyclic amino acid ester compound of formula (22)' with a carboxylic acid ester compound of formula (21)' which has a leaving group (L)'.

This reaction is usually carried out in a solvent in the presence or absence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols such as methanol, ethanol, propanol and isopropanol; ethers such as diethyl ether, diisopropyl ether, tetrahydrofuran and dioxane; aprotic polar solvents such as dimethylformamide, dimethylacetamide and dimethyl sulfoxide; nitriles such as acetonitrile; esters such as methyl acetate and ethyl acetate; aromatic hydrocarbons such as benzene, toluene and xylene; and aliphatic hydrocarbons such as pentane, hexane and heptane, of which alcohols, ethers, aprotic polar solvents and esters are preferred.

The base to be used in this step is not particularly limited, as long as it is effective in such reactions, and examples include: alkali metal alkoxides such as sodium methoxide, sodium ethoxide and potassium t-butoxide; alkali metal hydrides such as sodium hydride and lithium hydride; alkali metal hydroxides such as sodium hydroxide and potassium hydroxide; alkali metal carbonates such as sodium carbonate and potassium carbonate; and amines such as triethylamine, tributylamine, pyridine, picoline and 1,8-diazabicyclo[5.4.0]undec-7-ene, of which sodium carbonate, potassium carbonate, triethylamine, pyridine and 1,8-diazabicyclo[5.4.0]undec-7-ene are preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. and 150° C., and preferably between 0° C. and 100° C. The time required for the reaction may also vary widely, depending on many factors, notably the reaction temperature and the nature of the reagents and solvent employed. However, provided that the reaction is effected under the preferred conditions outlined above, a period of from 10 minutes to 48 hours, and preferably from 30 minutes to 12 hours is usually sufficient.

Steps I2 to I4

In Step I2, the cyclic amine diester compound of formula (23)' prepared in Step I1 above is converted into a keto ester compound of formula (24)' and/or a keto ester compound of formula (25)' using a Dieckmann reaction. In Steps I3 and I4, the product of formula (24)' and/or the product of formula (25)' thus obtained is/are then hydrolyzed and decarboxylated successively to prepare the desired cyclic aminoketone compound of formula (26)' and/or the desired cyclic aminoketone compound of formula (27)'.

The reactions in Steps I2 to I4 can be carried out according to the procedures described in J. R. Harrison et al., J. Chem. Soc., Perkin Trans. 1, 1999, 3623–3631, the contents of which are incorporated herein by reference thereto. For example, Steps I3 and I4 can be carried out as follows.

The reactions of Steps I3 and I4 are usually carried out in a single step in the presence or absence of a solvent in the presence or absence of an acid or base.

The reactions are normally and preferably effected in the presence of a solvent. There is no particular restriction on the nature of the solvent to be employed, provided that it has no adverse effect on the reactions or on the reagents involved and that it can dissolve the reagents, at least to some extent. Examples of suitable solvents include: water, or a mixture of water and an organic solvent, (examples of which include: aliphatic hydrocarbons such as pentane, hexane and heptane; aromatic hydrocarbons such as benzene, toluene and xylene; halogenated hydrocarbons such as dichloromethane, chloroform, carbon tetrachloride and dichloroethane; ethers such as diethyl ether, diisopropyl ether, tetrahydrofuran and dioxane; alcohols such as methanol, ethanol, propanol, isopropanol, butanol, s-butanol, isobutanol and t-butanol; aprotic polar solvents such as N,N-dimethylformamide, N,N-dimethylacetamide and dimethyl sulfoxide; nitriles such as acetonitrile; and esters such as methyl acetate and ethyl acetate), of which water, a mixture of water and an alcohol and a mixture of water and an ether are preferred.

The acid to be used in the reactions is not particularly limited provided that it is one that is usually used as an acid in hydrolysis reactions, and examples thereof include: mineral acids such as hydrochloric acid, sulfuric acid and phosphoric acid; carboxylic acids such as formic acid, acetic acid, propionic acid or trifluoroacetic acid; and sulfonic acids such as methanesulfonic acid or ethanesulfonic acid. The two-step reaction is accelerated by the addition of an acid, of which mineral acids and carboxylic acids are preferred, and hydrochloric acid, sulfuric acid, formic acid and acetic acid are more preferred.

The base to be used in the reactions is not particularly limited provided that it is one that is usually used as a base in hydrolysis reactions, and examples thereof include: alkali metal hydrides such as sodium hydride and lithium hydride; alkali metal hydroxides such as sodium hydroxide and potassium hydroxide; alkali metal carbonates such as sodium carbonate and potassium carbonate; and amines such as triethylamine, tributylamine, pyridine, picoline and 1,8-diazabicyclo[5.4.0]undec-7-ene, of which alkali metal hydroxides are preferred, and sodium hydroxide and potassium hydroxide are more preferred.

The reactions can take place over a wide range of temperatures, and the precise reaction temperature is not critical to the invention. The preferred reaction temperature will depend upon such factors as the nature of the solvent, and the starting material or reagent used. However, in general, we find it convenient to carry out the reactions at a temperature of from −20° C. and 150° C., and preferably between 0° C. and 100° C. The time required for the reactions may also vary widely, depending on many factors, notably the reaction temperature and the nature of the reagents and solvent employed. However, provided that the two-step reaction is effected under the preferred conditions outlined above, a period of from 10 minutes to 48 hours, and preferably from 30 minutes to 12 hours is usually sufficient.

Method J

This is a method for the preparation of a compound of formula (32)' below which is a compound of formula (10)' wherein E' represents a nitrogen atom, D' represents a group of formula >CH—, $R^{4a'}$ is as defined above and W is as defined below, the method being carried out as shown in Reaction Scheme J below.

Reaction Scheme J

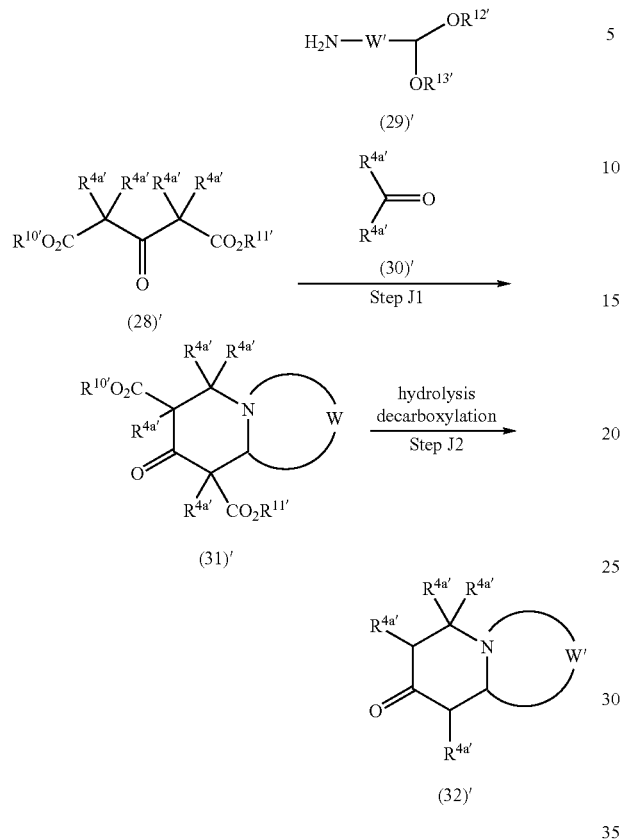

Reaction Scheme K

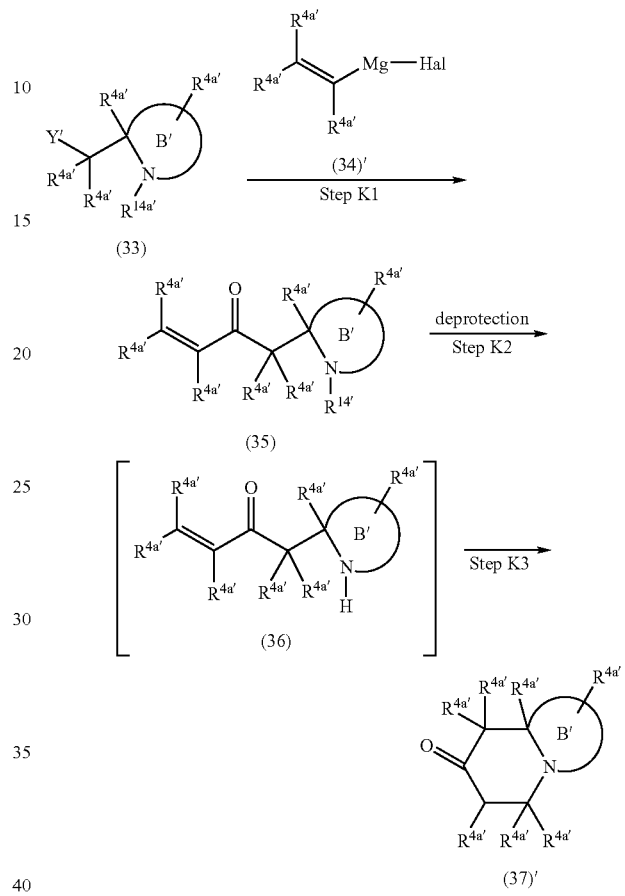

In the above formulae, $R^{4a'}$ is as defined above, $R^{10'}$ and $R^{11'}$ are the same or different, and each represents a lower alkyl group as defined above or an aralkyl group as defined above, $R^{12'}$ and $R^{13'}$ are the same or different, and each represents a lower alkyl group as defined above or $R^{12'}$ and $R^{13'}$ together form a lower alkylene group as defined above, W' represents a lower alkylene group as defined above which is substituted with from one to three $R^{4'}$ groups as defined above, said alkylene group optionally being interrupted by one or two atoms or groups selected from the group consisting of nitrogen atoms, oxygen atoms, sulfur atoms, >SO groups and >SO$_2$ groups, and the cyclic group containing W shown in general formulae (31)' and (32)' is a group which corresponds to the cyclic group B' as defined above which is unsubstitited or is substituted with from one to three $R^{4'}$ groups.

Step J1 and Step J2 are both reactions which are well known in the field of organic chemistry and can be performed using any combination of such known methods; for example, they can be conducted in a manner similar to the reactions described in detail in O. Pollet et al., Heterocycles, 43, 1391 (1996) or Anet et al., Austral. J. Scient. Res., <A>3, 635–640 (1950), the contents of which are incorporated herein by reference thereto.

Method K

This is a method for the preparation of a compound of formula (37)' below which is a compound of formula (10)' wherein D' represents a group of formula >CR$^{4a'}$— wherein $R^{4a'}$ is as defined above and E' represents a nitrogen atom, the method being carried out as shown in Reaction Scheme K below.

In the above formulae, B' and $R^{4a'}$ are as defined above, $R^{14'}$ represents an amino protecting group, Hal represents a halogen atom (preferably, it is a chlorine atom, bromine atom or iodine atom), and Y' represents a halogenocarbonyl group (for example, —CO—Cl, —CO—Br or —CO—I), a N-(lower alkoxy)-N-lower alkyl)carbamoyl group, wherein said lower alkoxy and lower alkyl moieties are as defined above (examples of such groups include N-methoxy-N-methylcarbamoyl, N-ethoxy-N-methylcarbamoyl an d N-ethyl-N-methoxycarbamoyl groups) or a cyano group.

The amino protecting group in the definition of $R^{14'}$ can be any protecting group for an amino group which is commonly used in organic synthesis, examples of which are found in T. W. Greene et al.: Protective Groups in Organic Synthesis, John Willey & Sons, Inc. Specific examples of suitable amino protecting groups include aliphatic acyl groups as defined and exemplified above, aromatic acyl groups as defined and exemplified above, silyl groups as defined and exemplified above, aralkyl groups as defined and exemplified above, alkoxycarbonyl groups as defined and exemplified above, alkenyloxycarbonyl groups as defined and exemplified above and aralkyloxycarbonyl groups as defined and exemplified above, of which alkoxycarbonyl groups are preferred, and t-butoxycarbonyl groups are more preferred.

Step K1

In this Step, an α,β-unsaturated ketone derivative of formula (35)' is prepared by reacting a cyclic amino acid derivative of formula (33)' with a Grignard reagent of an olefin compound of formula (34)'. Reactions of this type are well known for the preparation of ketones from carboxylic acid derivatives and Grignard reagents, and any such reaction known in the field of organic synthesis can be employed; for example, it can be carried out using the procedures described in detail in H. R. Snyder et al., Org. Synth., III, 798 (1955); J. Cason et al., J. Org. Chem., 26, 1768 (1961); G. H. Posner et al., J. Am. Chem. Soc., 94, 5106 (1972); and G. H. Posner, Org. React., 19, 1 (1972), the contents of which are incorporated herein by reference thereto.

Steps K2 and K3

In Step K2, the nitrogen protecting group $(R^{14})'$ in the α,β-unsaturated ketone derivative of formula (35)' prepared in Step K1 above is removed to afford a deprotected intermediate of formula (36)' which is then cyclized in Step K3 to give the desired cyclic aminoketone compound of formula (37)'. In Step K2, the deprotection reaction employed can be any which is conventionally used in organic synthesis (examples of which are described in T. W. Greene et al., Protective Groups in Organic Synthesis, John Willey & Sons, Inc.). Preferably, the deprotection reaction is conducted under neutral or acidic conditions. After the deprotection reaction, the resulting product of formula (36)', which is not isolated, cyclizes immediately to give the desired aminoketone compound of formula (37)'. The deprotection reaction is more preferably conducted under acidic conditions, and the aminoketone compound of formula (37)' is prepared without further reaction by neutralizing the reaction mixture.

Method L

This is a method for the preparation of a compound of formula (40)' below which is a compound of formula (10)' wherein D' represents a group of formula $>CR^{4a'}$ — wherein $R^{4a'}$ is as defined above and E' represents a nitrogen atom, the method being carried out as shown in Reaction Scheme L below.

Reaction Scheme L

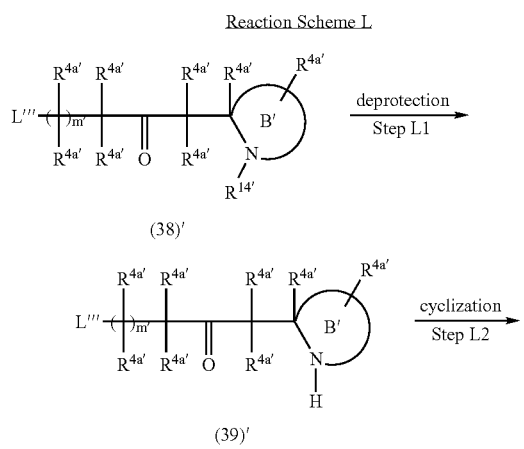

(38)'

(39)'

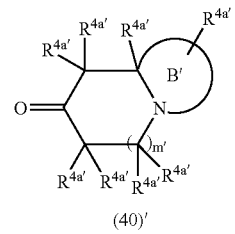

(40)'

In the above formulae, B', $R^{4a'}$, $R^{14'}$ and m are as defined above, and L''' represents a leaving group as defined for the leaving group L above, a lower alkylsulfonyl group as defined above, an arylsulfonyl group as defined above or a halogeno lower alkylsulfonyl group wherein the halogeno lower alkyl moiety is as defined above (examples of said group including trifluoromethanesulfonyl and pentafluoroethanesulfonyl groups).

Steps L1 and L2

Steps L1 and L2 involve first removing the amino protecting group $(R^{14})'$ from the ketone compound (38)' having the leaving group L''' to afford a deprotected intermediate of formula (39)', and then cyclizing said intermediate to produce the desired aminoketone compound of formula (40)'. These steps can be carried out in a manner similar to the reactions described in Steps K2 and K3 above.

The starting compound of formula (38)' used as the starting material in this method is either a known compound or it can be prepared from a known compound using known methods [for example, the methods described in S. W. Goldstein et al., J. Org. Chem., 57, 1179–1190 (1992); and B. Achille et al., J. Comb. Chem., 2, 337–340 (2000), the contents of which are incorporated herein by reference thereto].

Method M

This is a method for the preparation of a compound of formula (47)' below which is a compound of formula (10)' wherein D' represents a group of formula $>CR^{4a'}$ — wherein $R^{4'}$ is as defined above and E' represents a nitrogen atom, the method being carried out as shown in Reaction Scheme M below.

Reaction Scheme M

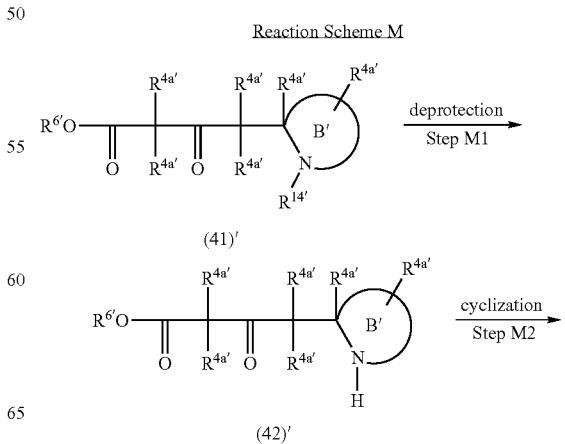

(41)'

(42)'

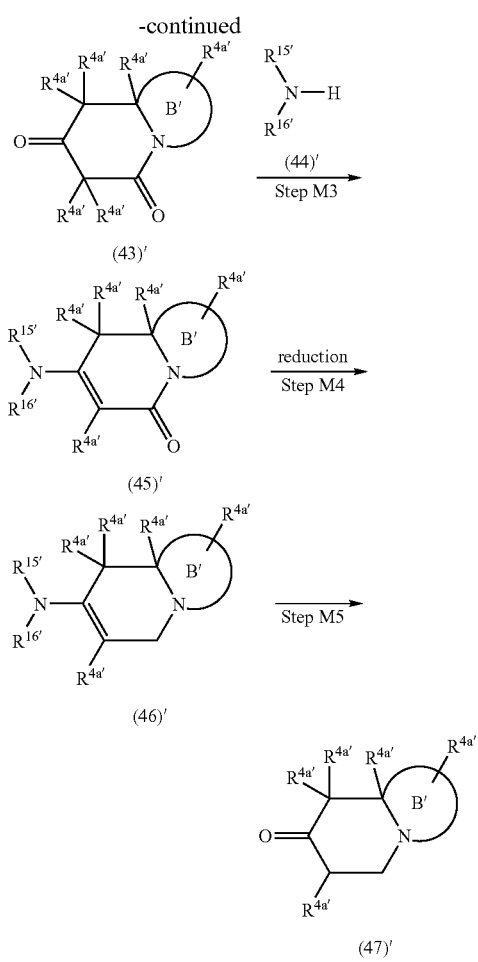

In the above formulae, $R^{4a'}$, $R^{6'}$, $R^{14'}$ and B' are as defined above, and $R^{15'}$ and $R^{16'}$ are the same or different, and each represents a hydrogen atom, a lower alkyl group as defined above or an aralkyl group as defined above, or $R^{15'}$ and $R^{16'}$, together with the nitrogen atom to which they are attached, form a 5- or 6-membered heterocyclic ring which includes one ring nitrogen atom and which may optionally include one further heteroatom selected from oxygen, sulfur and nitrogen atoms (examples of such groups include pyrrolidinyl, piperidyl, piperazinyl, morpholinyl and thiomorpholinyl groups).

Steps M1 and M2

In these Steps, a ketolactam compound of formula (43)' is prepared by first removing the amino protecting group $(R^{14})'$ from an α-ketoacid compound of formula (41)' to afford a deprotected intermediate of formula (42)', and then cyclizing said intermediate. These steps are conducted in a manner similar to that described in Steps K2 and K3 above.

Step M3

In this Step, a cyclic enaminolactam compound of formula (45)' is prepared by reacting the ketolactam compound of formula (43)' prepared in Step M2 above with a secondary amine compound of formula (44)'. Any of the techniques conventionally used in the field of organic synthetic chemistry for the preparation of enamine derivatives can be employed. For example, the step can be carried out according to the procedure described in G. Stork et al., J. Am, Chem. Soc., 85, 207 (1963) (the contents of which are incorporated herein by reference thereto) or as described below.

The reaction is usually carried out in a solvent in the presence or absence of an acid.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons such as pentane, hexane and heptane; aromatic hydrocarbons such as benzene, toluene and xylene; halogenated hydrocarbons such as dichloromethane, chloroform, carbon tetrachloride and dichloroethane; ethers such as diethyl ether, diisopropyl ether, tetrahydrofuran and dioxane; alcohols such as methanol, ethanol, propanol, isopropanol, butanol, s-butanol, isobutanol and t-butanol; aprotic polar solvents such as N,N-dimethylformamide, N,N-dimethylacetamide and dimethyl sulfoxide; nitriles such as acetonitrile; and esters such as methyl acetate and ethyl acetate, of which ethers are preferred.

The acid to be used in the reaction is not particularly limited provided that it is one that is usually used in such reactions, and examples thereof include: inorganic acids such as hydrogen chloride, hydrogen bromide, sulfuric acid, perchloric acid and phosphoric acid; and organic acids such as acetic acid, formic acid, oxalic acid, methanesulfonic acid, p-toluenesulfonic acid, trifluoroacetic acid and trifluoromethanesulfonic acid. Of these, sulfuric acid, hydrochloric acid and p-toluensulfonic acid are preferred.

The reaction of this step can be carried out efficiently by removing water produced during the reaction by using molecular sieves or a water separator (for example, a Dean Stark Water Separator which can be obtained from Aldrich).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. and 150° C., and preferably between 0° C. and 100° C. The time required for the reaction may also vary widely, depending on many factors, notably the reaction temperature and the nature of the reagents and solvent employed. However, provided that the reaction is effected under the preferred conditions outlined above, a period of from 10 minutes to 48 hours, and preferably from 30 minutes to 12 hours is usually sufficient.

Step M4

In this Step, a cyclic enamine compound of formula (46)' is produced by reducing the cyclic enaminolactam compound of formula (45)' prepared in Step M3 above. Any of the techniques conventionally used in the field of organic synthetic chemistry for performing reduction reactions can be employed. For example, the reduction can be carried out according to the procedures described in S. Cortes et al., J. Org. Chem., 48, 2246 (1983); Y. Tsuda et al., Synthesis, 652 (1977); H. C. Brown et al., J. Am. Chem. Soc., 86, 3566 (1964) and R. J. Sundberg et al., J. Org. Chem., 46, 3730 (1981) (the contents of which are incopated herein by reference thereto); or, alternatively, can be performed as described below.

This reaction is usually carried out in a solvent in the presence of a reducing reagent.

Examples of the reducing reagent to be employed include hydride reagents such as alkali metal borohydrides e.g. sodium borohydride and lithium borohydride, and aluminum hydrides e.g. lithium aluminum hydride and lithium triethoxyaluminohydride; a combination of a Lewis acid such as aluminum chloride, tin tetrachloride or titanium tetrachloride and a hydride reagent as defined above; and boron compounds such as diborane, of which lithium aluminum hydride is preferred.

In the reduction reaction, non-polar solvents can be used, preferred examples of which include: aliphatic hydrocarbons such as pentane, hexane and heptane; aromatic hydrocarbons such as benzene, toluene and xylene; halogenated hydrocarbons such as dichloromethane, chloroform, carbon tetrachloride and dichloroethane; and ethers such as diethyl ether, diisopropyl ether, tetrahydrofuran and dioxane, of which ethers are preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. and 150° C., and preferably between 0° C. and 100° C. The time required for the reaction may also vary widely, depending on many factors, notably the reaction temperature and the nature of the reagents and solvent employed. However, provided that the reaction is effected under the preferred conditions outlined above, a period of from 10 minutes to 48 hours, and preferably from 30 minutes to 12 hours is usually sufficient.

Step M5

In this Step, the desired cyclic aminoketone compound of formula (47)' is obtained by hydrolizing the cyclic enamine compound of formula (46)' prepared in Step M4 above. This reaction is performed by bringing the cyclic enamine compound of formula (46)' into contact with water in the presence or absence of a solvent with or without the addition of an acid or base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include water, or a mixture of water and an organic solvent (examples of which include: aliphatic hydrocarbons such as pentane, hexane and heptane; aromatic hydrocarbons such as benzene, toluene and xylene; halogenated hydrocarbons such as dichloromethane, chloroform, carbon tetrachloride and dichloroethane; ethers such as diethyl ether, diisopropyl ether, tetrahydrofuran and dioxane; alcohols such as methanol, ethanol, propanol, isopropanol, butanol, s-butanol, isobutanol and t-butanol; aprotic polar solvents such as N,N-dimethylformamide, N,N-dimethylacetamide and dimethyl sulfoxide; nitriles such as acetonitrile; and esters such as methyl acetate and ethyl acetate), of which water, a mixture of water and an alcohol and a mixture of water and an ether are preferred.

The acid to be used is not particularly limited provided that it is one that is usually used as an acid in hydrolysis reactions, and examples thereof include mineral acids such as hydrochloric acid, sulfuric acid and phosphoric acid; carboxylic acids such as formic acid, acetic acid, propionic acid and trifluoroacetic acid; and sulfonic acids such as methanesulfonic acid and ethanesulfonic acid, of which hydrochloric acid, sulfuric acid and acetic acid are preferred. The hydrolysis reaction is accelerated by the addition of an acid.

The base to be used is not particularly limited provided that it is one that is usually used as a base in hydrolysis reactions, and examples thereof include alkali metal hydrides such as sodium hydride and lithium hydride; alkali metal hydroxides such as sodium hydroxide and potassium hydroxide; alkali metal carbonates such as sodium carbonate and potassium carbonate; and amines such as triethylamine, tributylamine, pyridine, picoline and 1,8-diazabicyclo[5.4.0]undec-7-ene, of which sodium hydroxide and potassium hydroxide are preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. and 150° C. and preferably between 0° C. and 100° C. The time required for the reaction may also vary widely, depending on many factors, notably the reaction temperature and the nature of the reagents and solvent employed. However, provided that the reaction is effected under the preferred conditions outlined above, a period of from 10 minutes to 48 hours, and preferably from 30 minutes to 12 hours is usually sufficient.

Method N

The compound of formula (45)', which is an intermediate in the preparation of the cyclic aminoketone compound of formula (47)' in Method M above, can also be produced by Method N according to Reaction Scheme N below.

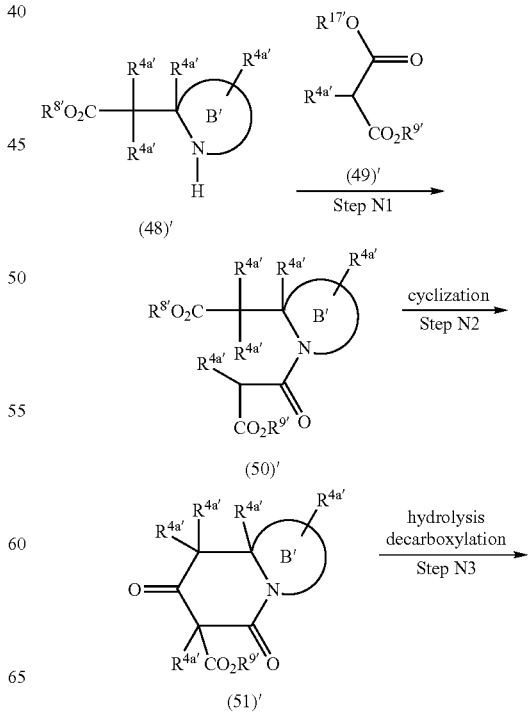

Reaction Scheme N

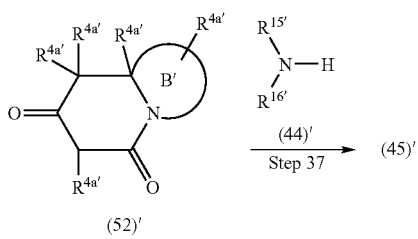

In the above formulae, B', $R^{4a'}$, $R^{8'}$, $R^{9'}$, $R^{15'}$ sand $R^{16'}$ are as defined above, and $R^{17'}$ represents a hydrogen atom or a carboxyl protecting group.

The carboxyl protecting group in the definition of $R^{17'}$ can be any such protecting group conventionally used in the organic chemistry; preferably, it is a lower alkyl group as defined above or an aralkyl group as defined above.

Step N1

In this Step, an aminodiester compound of formula (50)' is produced by the reaction of a cyclic amino acid ester compound of formula (48)' with a malonic acid derivative of formula (49)' or a reactive derivative thereof. Any of the techniques conventionally used in the field of organic synthetic chemistry for amidation reactions can be employed, and this step can, for example, be carried out in the manner described in processes (a), (b) and (c) described below.

(a) When $R^{17'}$ is a hydrogen atom, the reaction is conducted in a solvent in the presence of a condensing agent and in the presence or absence of a base.

There is no particular restriction on the nature of the solvent to be employed, provided that it has no adverse effect on the reaction or on the reagents involved and that it can dissolve the reagents, at least to some extent. Examples of the solvent to be employed include: aliphatic hydrocarbons such as pentane, hexane and heptane; aromatic hydrocarbons such as benzene, toluene and xylene; halogenated hydrocarbons such as dichloromethane, chloroform, carbon tetrachloride and dichloroethane; ethers such as diethyl ether, diisopropyl ether, tetrahydrofuran and dioxane; alcohols such as methanol, ethanol, propanol, isopropanol, butanol, s-butanol, isobutanol and t-butanol; aprotic polar solvents such as N,N-dimethylformamide, N,N-dimethylacetamide and dimethyl sulfoxide; nitriles such as acetonitrile; esters such as methyl acetate and ethyl acetate; water; or a mixture of these solvents described above, of which halogenated hydrocarbons, ethers and esters are preferred and dichloromethane, tetrahydrofuran and ethyl acetate are more preferred.

Any suitable condensing agent that is conventionally employed in such reactions can be employed, and examples include dicyclohexylcarbodiimide, 1-ethyl-3-(3-dimethylaminopropyl)carbodiimide, N,N'-carbonyldiimidazole and the like.

The base to be used is not particularly limited provided that it is one that is usually used as a base in such reactions, and examples thereof include alkali metal alkoxides such as sodium methoxide, sodium ethoxide and potassium t-butoxide; alkali metal hydrides such as sodium hydride and lithium hydride; alkali metal hydroxides such as sodium hydroxide and potassium hydroxide; alkali metal carbonates such as sodium carbonate and potassium carbonate; and amines such as triethylamine, tributylamine, pyridine, picoline and 1,8-diazabicyclo[5.4.0]undec-7-ene, of which amines are preferred, and triethylamine, pyridine and 1,8-diazabicyclo-[5.4.0]undec-7-ene are more preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. and 150° C., and preferably between 0° C. and 100° C. The time required for the reaction may also vary widely, depending on many factors, notably the reaction temperature and the nature of the reagents and solvent employed. However, provided that the reaction is effected under the preferred conditions outlined above, a period of from 10 minutes to 48 hours, and preferably from 30 minutes to 12 hours is usually sufficient.

Alternatively, where $R^{17'}$ is a hydrogen atom, the reaction of Step N1 can also be carried out by converting the compound of formula (49)' into a reactive derivative thereof followed by the procedure described in process (c) below.

(b) When $R^{17'}$ is a carboxyl protecting group (preferably a lower alkyl group as defined above or an aralkyl group as defined above), the reaction is performed by heating in the presence or absence of a solvent.

When the reaction is conducted in a solvent, the same solvent as that described in process (a) can be used. The temperature for the reaction is between 30° C. and 100° C., preferably between the range of ±5° C. of the boiling point of the solvent that is employed. Most preferable the reaction is carried out by heating the reaction mixture under reflux.

When a solvent is not used in this reaction, the desired compound is prepared by heating a mixture of the compounds of formulae (48)' and (49)'. The reaction can take place over a wide range of temperatures, and the precise reaction temperature is not critical to the invention. The preferred reaction temperature will depend upon such factors as the nature of the starting materials used. However, in general, we find it convenient to carry out the reaction at a temperature of from 30° C. and 150° C., and preferably between 50° C. and 120° C. The time required for the reaction may also vary widely, depending on many factors, notably the reaction temperature and the nature of the reagents and solvent employed. However, provided that the reaction is effected under the preferred conditions outlined above, a period of from 10 minutes to 48 hours, and preferably from 30 minutes to 12 hours is usually sufficient.

(c) When a reactive derivative of a compound of formula (49)' is used, the reactive derivative can be an acid halide, a mixed acid anhydride, an activated ester, an active amide or the like, and the reaction is conducted in a solvent in the presence of a condensing agent and in the presence or absence of a base.

The acid halide of the compound of formula (49)' is prepared by the reaction of a compound of formula (49)' wherein $R^{17'}$ is a hydrogen atom with a halogenation reagent (for example, thionyl chloride, oxalyl chloride or the like); the mixed acid anhydride is prepared by the reaction of a compound of formula (49)' wherein $R^{17'}$ is a hydrogen atom with an acid halide (for example, methyl chlorocarbonate, ethyl chlorocarbonate or the like); the activated ester is prepared by the reaction of a compound of formula (49)' wherein $R^{17'}$ is a hydrogen atom with a compound containing a hydroxyl group (for example, N-hydroxysuccinimide, N-hydroxyphthalimide or the like) in the presence of a condensing agent such as those described in process (a)

above; and the active amide (for example, a Weinreb amide) is prepared by the reaction of a compound of formula (49)' wherein $R^{17'}$ is a hydrogen atom with an N-(lower alkoxy)-N-(lower alkyl)hydroxylamine (for example, N-methoxy-N-methylhydroxylamine or the like) in the presence of a condensing agent such as those described in process (a) above. Each of these reactions described can be conducted under reaction conditions usually used in organic synthetic chemistry for such reactions.

With regard to the solvent, condensing agent and base, the solvents, condensing agents and bases described in process (a) above can be used.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. and 150° C., and preferably between 0° C. and 100° C. The time required for the reaction may also vary widely, depending on many factors, notably the reaction temperature and the nature of the reagents and solvent employed. However, provided that the reaction is effected under the preferred conditions outlined above, a period of from 10 minutes to 48 hours, and preferably from 30 minutes to 12 hours is usually sufficient.

Steps N2 and N3

In Steps N2 and N3, a ketolactam compound of formula (52)' is prepared by first executing a Dieckman reaction on the amido diester compound of formula (50)' produced in Step N1 above to afford a ketolactam ester compound (51)', followed by the performance of hydrolysis and decarboxylation reactions on the product thus obtained. These steps can be conducted in a manner similar to that described in Steps I2 and I3 above.

Step N4

In this step, the target cyclic enaminolactam compound of formula (45)' is prepared by the reaction of the ketolactam compound of formula (52)' obtained in Step N3 above with a secondary amine compound of formula (44)', and the reaction is carried out in a manner similar to that described in Step M3 above.

Method O

The compound of formula (51)', which is an intermediate in Method N described above, can also be synthesized by Method O according to Reaction Scheme O below.

Reaction Scheme O

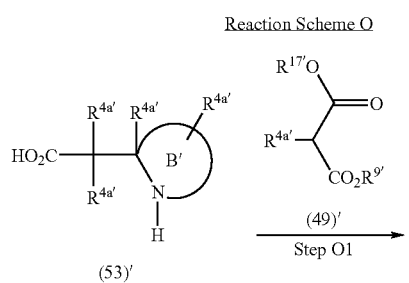

(53)'

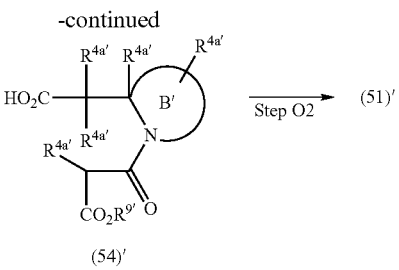

(54)'

In the above formulae, B', $R^{4a'}$, $R^{9'}$ and $R^{17'}$ are as defined above.

Step O1

In this Step, an amido monoester compound of formula (54)' is prepared by the reaction of a cyclic amino acid compound of formula (53)' with a malonic acid derivative of formula (49)' or a reactive derivative thereof. This step is carried out in a manner similar to that described in processes (a), (b) and (c) of Step N1 above.

Step O2

In this Step, the target ketolactam ester compound of formula (51)' is prepared by the intramolecular condensation of a carboxyl group and an active methylene group of the amido monoester compound of formula (54)' prepared in Step O1 above. In this step, the compound of formula (54)' is either used in underivatised form or after first being converted into a reactive derivative thereof.

(a) When the compound of formula (54)' is used in underivatised form, the reaction is conducted in a solvent in the presence of a condensing agent and with or without a base.

There is no particular restriction on the nature of the solvent to be employed, provided that it has no adverse effect on the reaction or on the reagents involved and that it can dissolve the reagents, at least to some extent. Examples of the solvent to be employed include: halogenated hydrocarbons such as dichloromethane, chloroform, carbon tetrachloride and dichloroethane; ethers such as diethyl ether, diisopropyl ether, tetrahydrofuran and dioxane; alcohols such as methanol, ethanol, propanol, isopropanol, butanol, s-butanol, isobutanol and t-butanol; aprotic polar solvents such as N,N-dimethylformamide, N,N-dimethylacetamide and dimethyl sulfoxide; nitriles such as acetonitrile; and esters such as methyl acetate and ethyl acetate; water; or a mixture of these solvents described above, of which halogentated hydrocarbons, ethers and esters are preferred, and dichloromethane, tetrahydrofuran and ethyl acetate are more preferred.

Any suitable condensing agent that is conventionally employed in such reactions can be employed, and examples include dicyclohexylcarbodiimide, 1-ethyl-3-(3-dimethylaminopropyl)carbodiimide, N,N'-carbonyldiimidazole or the like.

The base to be used is not particularly limited provided that it is one that is usually used as a base in such reactions, and examples thereof include alkali metal alkoxides such as sodium methoxide, sodium ethoxide and potassium t-butoxide; alkali metal hydrides such as sodium hydride and lithium hydride; alkali metal hydroxides such as sodium hydroxide and potassium hydroxide; alkali metal carbonates such as sodium carbonate and potassium carbonate; and amines such as triethylamine, tributylamine, pyridine, picoline and 1,8-diazabicyclo[5.4.0]undec-7-ene, of which amines are preferred, and triethylamine, pyridine and 1,8-diazabicyclo-[5.4.0]undec-7-ene are more preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. and 150° C., and preferably between 0° C. and 100° C. The time required for the reaction may also vary widely, depending on many factors, notably the reaction temperature and the nature of the reagents and solvent employed. However, provided that the reaction is effected under the preferred conditions outlined above, a period of from 10 minutes to 48 hours, and preferably from 30 minutes to 12 hours is usually sufficient.

(b) When the compound (54)' is used after first being converted into a reactive derivative, examples of the reactive derivative include acid halides, mixed acid anhydrides, activated esters, active amides and the like.

The acid halides are prepared by the reaction of the compound of formula (54)' with a halogenation reagent (for example, thionyl chloride, oxalyl chloride or the like); the mixed acid anhydride is prepared by the reaction of the compound of formula (54)' with an acid halide (for example, methyl chlorocarbonate, ethyl chlorocarbonate or the like); the activated ester is prepared by the reaction of the compound of formula (54)' with a compound containing a hydroxyl group (for example, N-hydroxysuccinimide, N-hydroxyphthalimide or the like) in the presence of a condensing agent such as those described in process (a) above; and the active amide (for example, Weinreb amide) is prepared by the reaction of the compound of formula (54)' with a N-(lower alkoxy)-N-(lower alkyl)hydroxylamine (for example, N-methoxy-N-methylhydroxylamine or the like) in the presence of a condensing agent such as those described in process (a) above. Each of these reactions described above can be conducted employing reaction conditions conventionally employed in organic synthetic chemistry for such reactions.

The cyclisation of said reactive derivative is usually carried out in a solvent in the presence or absence of a base.

With regard to the solvent, condensing agent and base, the solvents, condensing agents and bases described in process (a) above can be used.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. and 150° C., and preferably between 0° C. and 100° C. The time required for the reaction may also vary widely, depending on many factors, notably the reaction temperature and the nature of the reagents and solvent employed. However, provided that the reaction is effected under the preferred conditions outlined above, a period of from 10 minutes to 48 hours, and preferably from 30 minutes to 12 hours is usually sufficient.

The substituent $R^{3'}$, which is one of the components of the compound of general formula (I)', can be substituted with various substituents ($R^{4'}$). The substituents $R^{4'}$ can be converted into other substituents falling within the scope of the definition of $R^{4'}$ in each of the steps described above. The substituent $R^{4'}$ can, for example, be converted as illustrated below employing conventional organic synthetic methods.

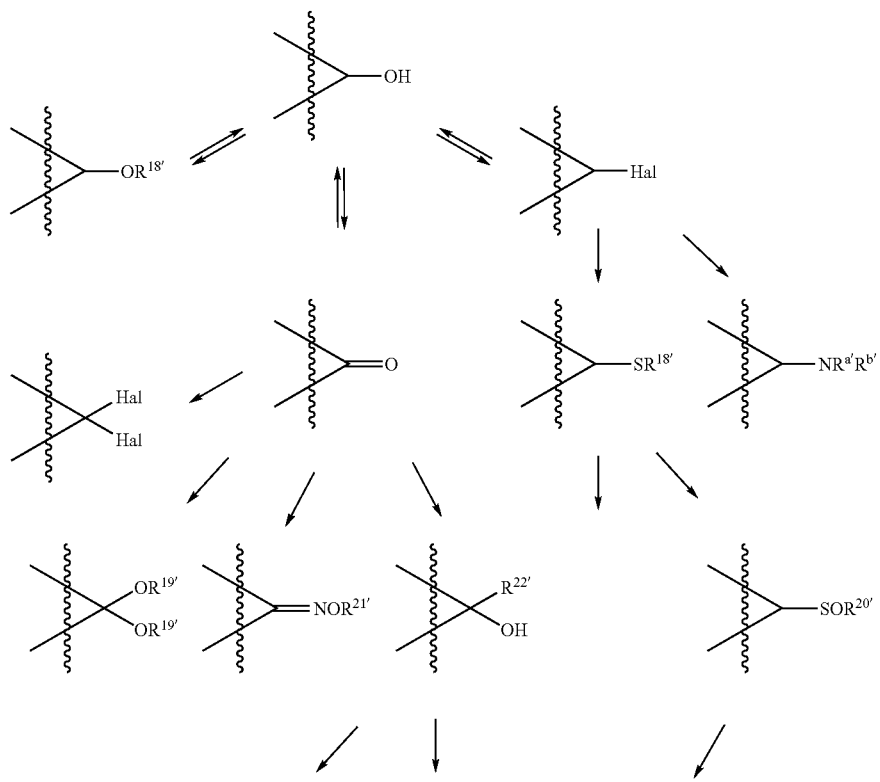

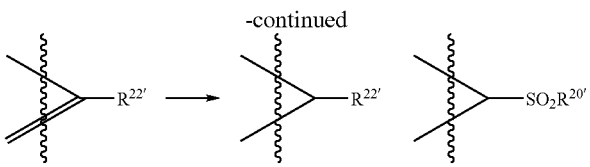

In the above formulae, $R^{a'}$, $R^{b'}$ and Hal have the same meanings as defined above, $R^{18'}$ represents a lower alkyl group as defined above, a halogenated lower alkyl group as defined above or an aryl group which may optionally be substituted with at least one substituent selected from Substituent group α' and Substituent group β' as defined above, the groups $R^{19'}$ are the same or different, and each represents a lower alkyl group as defined above or a halogenated lower alkyl group as defined above, or the two groups $R^{19'}$ can together form a lower alkylene group as defined above, $R^{20'}$ represents a lower alkyl group as defined above, $R^{21'}$ represents a hydrogen atom or a lower alkyl group as defined above, and $R^{12'}$ represents a lower alkyl group which may optionally be substituted with at least one substituent selected from Substituent group α', a lower alkenyl group which may optionally be substituted with at least one substituent selected from Substituent group α', a lower alkynyl group which may optionally be substituted with at least one substituent selected from Substituent group α', an aralkyl group or a cycloalkyl group as defined above in the definition of Substituent group β', or an aryl group which may optionally be substituted with at least one substituent selected from Substituent group α' and Substituent group β' as defined above.

Furthermore, when $R^{4'}$ is a halogen atom, a hydroxyl group, a cyano group or a lower alkylsulfonyl group. $R^{4'}$ can be converted into a hydrogen atom by the formation of a double bond, followed by the reduction of said double bond using conventional methods as illustrated below.

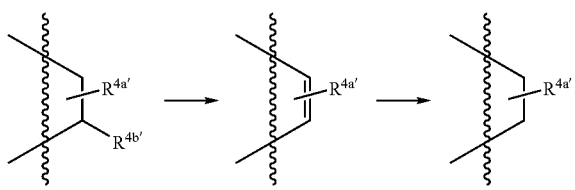

In the above formulae, $R^{4a'}$ has the same meaning as defined above, and $R^{4b'}$ represents a halogen atom, hydroxyl group, cyano group or lower alkylsulfonyl group.

Where $R^{4'}$ represents a lower alkylidenyl group or an aralkylidenyl group, such a compound can be prepared from the corresponding oxo derivative as shown below. Subsequently, the alkylidenyl or aralkylidenyl compound can be converted to the corresponding alkyl or aralkyl derivative by reduction of the double bond.

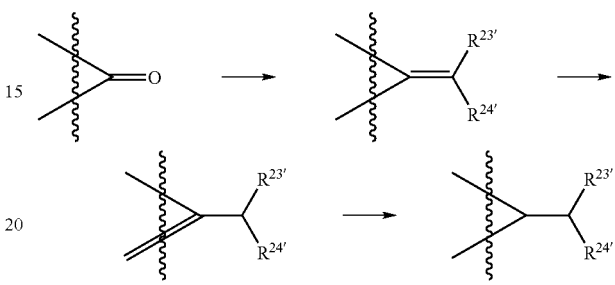

In the above formulae, $R^{23'}$ and $R^{24'}$ are the same or different, and each represents a hydrogen atom, a lower alkyl group as defined above, an aryl group as defined above or an aralkyl group as defined above.

After completion of each of the reactions described in the steps of Method A to Method O above, the desired compound may be isolated from the reaction mixture in a conventional manner. For example, it can be obtained by neutralizing the reaction mixture as needed, removing insoluble matters by filtration, if any are present, adding organic solvents which are not miscible with each other, such as water and ethyl acetate, washing with water or the like, separating the organic layer containing the desired compound, drying it over anhydrous magnesium sulfate or the like and then distilling off the solvent.

If necessary, the desired compound thus obtained can be isolated and purified by using a conventional method such as recrystallization or reprecipitation or by a chromatographic method. Examples of chromatography include adsorption column chromatography using a carrier such as silica gel, alumina or magnesium-silica gel type Florisil, chromatography using a synthetic adsorbent, for example, partition column chromatography using a carrier such as Sephadex LH-20 (product of Pharmacia), Amberlite XAD-11 (product of Rohm & Haas) or Diaion HP-20 (product of Mitsubishi Chemical), ion exchange chromatography and normal-phasereverse-phase column chromatography (high-performance liquid chromatography) using a silica gel or alkylated silica gel. If necessary, two or more of these techniques can be used in combination to isolate and purify the desired compound.

The pyrrole derivatives of the present invention exhibit excellent inhibitory activity against the production of inflammatory cytokines. Consequently, they are effective as a medicament, particularly as an agent for the prophylaxis or treatment of diseases mediated by inflammatory cytokines. Examples of such a medicament include analgesics, anti-inflammatory drugs and virucides, and agents for the prophylaxis or treatment of chronic rheumatoid arthritis, osteoarthritis, allergic diseases, asthma, septicaemia, psoriasis, osteoporosis, autoimmune diseases (e.g. systemic lupus erythematosus, ulcerative colitis and Crohn's disease), diabetes, nephritis, hepatitis, cancer, ischemic heart disease, Alzheimer's disease and arteriosclerosis. Of these, the compounds of the present invention are particularly useful as analgesics and anti-inflammatory drugs and as agents for the prophylaxis or treatment of chronic rheumatism, osteoarthritis, allergic diseases, septicaemia, psoriasis, osteoporosis, ulcerative colitis, diabetes, hepatitis and arteriosclerosis.

The compounds of formula (I)' and pharmacologically acceptable salts, esters and other derivatives thereof according to the present invention can be administered by a number of different routes. Examples of these administration routes include oral administration in the form of tablets, capsules, granules, powders or syrups and parenteral administration in the form of injections or suppositories. Such formulations can be prepared in a known manner by using carriers or additives such as excipients, lubricants, binders, disintegrators, stabilizers, corrigents and diluents.

Examples of suitable excipients include: organic excipients, examples of which include sugar derivatives such as lactose, sucrose, dextrose, mannitol and sorbitol, starch derivatives such as corn starch, potato starch, α-starch, dextrin and carboxymethyl starch, cellulose derivatives such as crystalline cellulose, low-substituted hydroxypropylcellulose, hydroxypropylmethylcellulose, carboxymethylcellulose, calcium carboxymethylcellulose and sodium internally-crosslinked carboxymethylcellulose, gum arabic, dextran and pullulan; and inorganic excipients, examples of which include silicate derivatives such as soft silicic acid anhydride, synthetic aluminum silicate and magnesium aluminometasilicate, phosphates such as calcium phosphate, carbonates such as calcium carbonate, and sulfates such as calcium sulfate.

Examples of suitable lubricants include: stearic acid; metal salts of stearic acid such as calcium stearate and magnesium stearate; talc; colloidal silica; waxes such as bee gum and spermaceti; boric acid; adipic acid; sulfates such as sodium sulfate; glycol; fumaric acid; sodium benzoate; DL-leucine; sodium salts of an aliphatic acid; lauryl sulfates such as sodium lauryl sulfate and magnesium lauryl sulfate; silicic acid derivatives such as silicic anhydride and silicic acid hydrate; and starch derivatives exemplified above as examples of suitable excipients.

Examples of suitable binders include polyvinylpyrrolidone, Macrogol™ and compounds similar to those exemplified above as suitable excipients.

Examples of suitable disintegrators include compounds similar to those exemplified above as suitable excipients and chemically modified starch or cellulose derivatives such as sodium cross carmellose, sodium carboxymethyl starch and crosslinked polyvinylpyrrolidone.

Examples of suitable stabilizers include: paraoxybenzoate esters such as methylparaben and propylparaben; alcohols such as chlorobutanol, benzyl alcohol and phenylethyl alcohol; benzalkonium chloride; phenol derivatives such as phenol and cresol; thimerosal; dehydroacetic acid; and sorbic acid. Examples of suitable corrigents include sweeteners, acidifiers and flavors commonly employed for this purpose.

The dose of the compound of formula (I)' or a pharmacologically acceptable salt, ester or other derivative thereof according to the present invention will vary depending on a variety of factors including the condition to be treated, the age of the patient and the administration route. When administered orally, it is administered to a human adult in an amount of 0.1 mg (preferably 0.5 mg) a day as a lower limit and 2000 mg (preferably 500 mg) a day as an upper limit. It can be administered in from one to several portions depending on the condition of the patient. When administered intravenously, it is administered to a human adult in an amount of 0.01 mg (preferably 0.05 mg) a day as a lower limit and 200 mg (preferably 50 mg) a day as an upper limit. It can be administered in from one to several portions depending on the condition of the patent.

The following examples, preparative examples, formulation examples and test examples are intended to further illustrate the present invention and are not intended to limit the scope of this invention in any way.

EXAMPLE 1

4-(3-Aminopropyl)-2-(4-fluorophenyl)-3-(pyridin-4-yl)-1H-pyrrole (Compound No. 1-97)

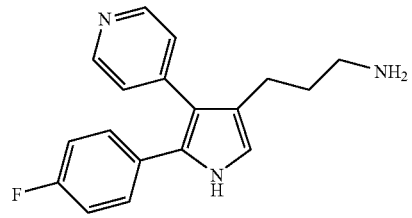

1(i) 4-Ethoxycarbonyl-2-(4-fluorophenyl)-3-(pyridin-4-yl)-1H-pyrrole 36 ml (54.7 mmol) of a 1.53 N solution of butyllithium in hexane were added to 240 ml of tetrahydrofuran. A solution of 15.90 g (54.7 mmol) of α-(p-toluenesulfonyl)-4-fluorobenzylisonitrile in 120 ml of tetrahydrofuran was then added to the resulting solution at −45° C., followed by stirring of the resulting mixture for 10 minutes at the same temperature. At the end of this time, 25.00 g (273 mmol) of 95% lithium bromide were added, the resulting mixture was stirred for 30 minutes and then a solution of 8.73 g (49.2 mmol) of ethyl 3-(4-pyridyl)acrylate in 120 ml of tetrahydrofuran was added. The resulting mixture was stirred at the same temperature for 1 hour and then the cooling bath was removed and the mixture was stirred at room temperature for a further 1 hour. At the end of this time, 500 ml of water were added and the resulting mixture was extracted with ethyl acetate. The organic extract was washed with water and then dried over anhydrous sodium sulfate, after which it was concentrated by evaporation under reduced pressure to afford a solid. The solid was washed with diethyl ether to give 13.61 g (yield 89%) of the title compound as a pale yellow powder.

$^1$H-Nuclear magnetic resonance spectrum (500 MHz, CDCl$_3$) δ ppm: 8.84 (1H, broad singlet); 8.51 (2H, doublet, J=7 Hz); 7.58 (1H, doublet, J=3 Hz); 7.21 (2H, doublet, J=6 Hz); 7.11 (2H, doublet of doublets, J=9 Hz, 5 Hz); 6.97 (2H, triplet, J=9 Hz); 4.18 (2H, quartet, J=7 Hz); 1.20 (3H, triplet, J=7 Hz).

1 (ii) 2-(4-Fluorophenyl)-4-hydroxymethyl-3-(pyridin-4-yl)-1H-pyrrole 121.4 ml (121.4 mmol) of a 1M solution of diisobutylaluminium hydride in toluene were slowly added dropwise to a solution of 12.56 g (40.47 mmol) of 4-ethoxycarbonyl-2-(4-fluorophenyl)-3-(pyridin-4-yl)-1H-pyrrole [which was obtained in step (i) above] in 630 ml of tetrahydrofuran with ice-cooling. After completing the addition, the cooling bath was removed and the mixture was stirred at room temperature for 5 hours. At the end of this time, a saturated aqueous solution of ammonium chloride was added to the reaction mixture and the resulting mixture was extracted with ethyl acetate. The organic extract was washed with water, dried over anhydrous magnesium sulfate and then concentrated by evaporation under reduced pressure to give 10.80 g (yield 99%) of the title compound as a pale orange powder.

$^1$H-Nuclear magnetic resonance spectrum (500 MHz, CDCl$_3$) δ ppm: 10.52 (1H, broad singlet); 8.46 (2H, doublet, J=6 Hz); 7.31 (2H, doublet, J=6 Hz); 7.26 (2H, doublet of doublets, J=9 Hz, 5 Hz); 6.98 (2H, triplet, J=9 Hz); 6.95 (1H, doublet, J=3 Hz); 4.50 (2H, singlet); 3.49 (1H, broad singlet).

1(iii) 2-(4-Fluorophenyl)-4-formyl-3-(pyridin-4-yl)-1H-pyrrole 118.00 g (440 mmol) of manganese dioxide were added to a solution of 10.73 g (40 mmol) of 2-(4-fluorophenyl)-4-hydroxymethyl-3-(pyridin-4-yl)-1H-pyrrole [prepared as described in step (ii) above] in 120 ml of dimethyl sulfoxide, after which the resulting mixture was stirred at 50° C. overnight. At the end of this time, the reaction mixture was filtered, water was added to the filtrate, and this was then extracted with ethyl acetate. The organic extract was washed with water, dried over anhydrous magnesium sulfate and then concentrated by evaporation under reduced pressure to afford a solid which was washed with diethyl ether to give 7.35 g (yield 69%) of the title compound as a brown powder.

$^1$H-Nuclear magnetic resonance spectrum (500 MHz, CDCl$_3$—CD$_3$OD) δ ppm: 9.76 (1H, singlet); 8.48 (2H, doublet, J=6 Hz); 7.59 (1H, singlet); 7.26 (2H, doublet, J=6 Hz); 7.19 (2H, doublet of doublets, J=9 Hz, 6 Hz); 7.01 (2H, triplet, J=9 Hz).

1(iv) 3-[2-(4-Fluorophenyl)-3-(pyridin-4-yl)-1H-pyrrol-4-yl]acrylonitrile 2.92 ml (18.02 mmol) of diethylphosphonoacetonitrile were added to 16 ml of tetrahydrofuran and the resulting solution was added to a suspension of 786 mg (18.02 mmol) of 55% sodium hydride in 60 ml of tetrahydrofuran with ice-cooling, and the resulting mixture was then stirred at room temperature for 1.5 hours. At the end of this time, a suspension of 4.00 g (15.02 mmol) of 2-(4-fluorophenyl)-4-formyl-3-(pyridin-4-yl)-1H-pyrrole [prepared as described in step (iii) above] in 30 ml of tetrahydrofuran was added to this mixture and the resulting mixture was stirred at room temperature for 1 hour. At the end of this time, water was added to the reaction mixture and the resulting mixture was extracted with ethyl acetate. The organic extract was washed with water, dried over anhydrous magnesium sulfate and then concentrated by evaporation under reduced pressure to afford a solid which was washed with diethyl ether to give 2.94 g (yield 68%) of the title compound as a pale brown powder.

$^1$H-Nuclear magnetic resonance spectrum (500 MHz, CDCl$_3$-DMSO-d$_6$) δ ppm: 11.30 (1H, broad singlet); 8.57 (2H, doublet, J=6 Hz); 7.24 (1H, doublet, J=4 Hz); 7.21 (1H, doublet, J=17 Hz); 7.19 (2H, doublet of doublets, J=9 Hz, 5 Hz); 7.13 (2H, doublet, J=6 Hz); 6.97 (2H, doublet, J=9 Hz); 5.39 (1H, doublet, J=17 Hz).

1(v) 4-(2-Cyanoethyl)-2-(4-fluorophenyl)-3-(pyridin-4-yl)-1H-pyrrole 2.94 g (10.16 mmol) of 3-[2-(4-fluorophenyl)-3-(pyridin-4-yl)-1H-pyrrol-4-yl]acrylonitrile [prepared as described in step (iv) above] were dissolved in a mixture of 20 ml of tetrahydrofuran and 20 ml of methanol, after which 2.94 g of 10% palladium on carbon were added to the solution. The mixture was stirred under a hydrogen atmosphere at room temperature for 8 hours. At the end of this time, the reaction mixture was filtered and the filtrate was concentrated under reduced pressure. The resulting residue was washed with a mixture of 30 ml of diethyl ether and 30 ml of ethanol to give 1.80 g (yield 61%) of the title compound as a pale orange powder.

$^1$H-Nuclear magnetic resonance spectrum (500 MHz, CDCl$_3$) δ ppm: 8.55 (2H, doublet, J=6 Hz); 8.27 (1H, broad singlet); 7.13 (2H, doublet of doublets, J=9 Hz, 5 Hz); 7.12 (2H, doublet, J=6 Hz); 6.98 (2H, triplet, J=9 Hz); 6.89 (1H, doublet, J=3 Hz); 2.88 (2H, triplet, J=7 Hz); 2.43 (2H, triplet, J=7 Hz).

1(vi) 4-(3-Aminopropyl)-2-(4-fluorophenyl)-3-(pyridin-4-yl)-1H-pyrrole 1.80 g (6.18 mmol) of 4-(2-cyanoethyl)-2-(4-fluorophenyl)-3-(pyridin-4-yl)-1H-pyrrole [prepared as described in step (v) above] were added to 100 ml of tetrahydrofuran and the resulting solution was slowly added dropwise with stirring at room temperature to a suspension of 469 mg (12.36 mmol) of lithium aluminum hydride in 150 ml of tetrahydrofuran. This mixture was stirred at 60° C. for 30 minutes. At the end of this time, the reaction mixture was cooled to room temperature, 25 ml of water and 0.5 ml of a 15% aqueous solution of sodium hydroxide were slowly added to the reaction mixture and the resulting mixture was then filtered. The filtrate was concentrated under reduced pressure, after which the residue was dehydrated by azeotropic distillation under reduced pressure using toluene. This azeotropic distillation was carried out three times to give 1.71 g (yield 94%) of the title compound as a white powder.

Melting point: 198–199° C. $^1$H-Nuclear magnetic resonance spectrum (500 MHz, DMSO-d$_6$) δ ppm: 11.16 (1H, broad singlet); 8.46 (2H, doublet, J=6 Hz); 7.18 (2H, doublet of doublets, J=9 Hz, 6 Hz); 7.13 (2H, doublet, J=6 Hz); 7.11 (2H, triplet, J=9 Hz); 6.74 (1H, doublet, J=3 Hz); 2.49 (2H, triplet, J=7 Hz); 2.41 (2H, triplet, J=8 Hz); 1.48 (2H, quintet, J=8 Hz).

EXAMPLE 2

2-(4-Fluorophenyl)-3-(pyridin-4-yl)-4-(3-trifluoroacetylaminopropyl)-1H-pyrrole (Compound No. 1-2533)

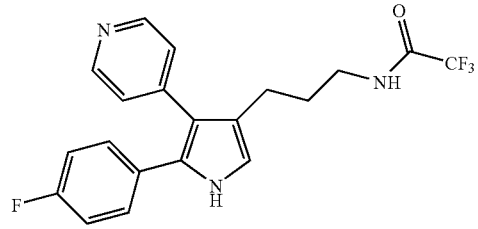

3.3 ml (23.2 mmol) of trifluoroacetic anhydride were added to a solution of 685 mg (2.32 mmol) of 4-(3-aminopropyl)-2-(4-fluorophenyl)-3-(pyridin-4-yl)-1H-pyrrole (which was prepared as described in Example 1 above) in 70 ml of tetrahydrofuran. The resulting mixture was stirred at room temperature for 30 minutes. At the end of this time, 200 ml of a saturated aqueous solution of sodium hydrogencarbonate were added to the reaction mixture, and then this was extracted with ethyl acetate. The organic extract was washed with water and concentrated by evaporation under reduced pressure. The resulting residue was purified by chromatography on a silica gel column using a 1:1 by volume mixture of hexane and ethyl acetate as the eluant to give 280 mg (yield 31%) of the title compound as a white powder.

Melting point: 229–230° C. $^1$H-Nuclear magnetic resonance spectrum (500 MHz, CDCl$_3$) δ ppm: 10.09 (1H, broad singlet); 8.49 (2H, doublet, J=6 Hz); 7.93 (1H, broad singlet); 7.18 (2H, doublet of doublets, J=9 Hz, 5 Hz); 7.13 (2H, doublet, J=6 Hz); 6.94 (2H, triplet, J=9 Hz); 6.74 (1H, doublet, J=3 Hz); 3.29 (2H, doublet of doublets, J=13 Hz, 7 Hz); 2.56 (2H, triplet, J=8 Hz); 1.74 (2H, quintet, J=8 Hz).

EXAMPLE 3

4-(3-Acetylaminopropyl)-2-(4-fluorophenyl)-3-(pyridin-4-yl)-1H-pyrrole (Compound No. 1-2528)

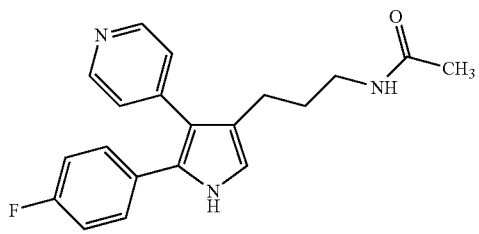

In a similar manner to that described in Example 2 above, a reaction was carried out using acetic anhydride instead of trifluoroacetic anhydride to give the title compound (yield 99%) as a pale yellow powder.

Melting point: 218–220° C. $^1$H-Nuclear magnetic resonance spectrum (400 MHz, DMSO-d$_6$) δ ppm: 11.19 (1H, broad singlet); 8.46 (2H, doublet, J=6 Hz); 7.77 (1H, broad triplet, J=5 Hz); 7.18 (2H, doublet of doublets, J=9 Hz, 5 Hz); 7.15–7.08 (4H, multiplet); 6.77 (1H, d, 2 Hz); 2.99 (2H, doublet of doublets, J=13 Hz, 7 Hz); 2.39 (2H, triplet, J=8 Hz); 1.75 (3H, singlet); 1.53 (2H, quintet, J=7 Hz).

EXAMPLE 4

2-(4-Fluorophenyl)-4-(3-methylaminopropyl)-3-(pyridin-4-yl)-1H-pyrrole (Compound No. 1-101)

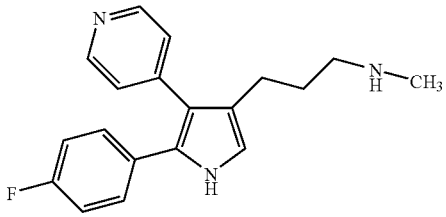

4(i) 4-[3-(t-Butoxycarbonylamino)propyl]-2-(4-fluorophenyl)-3-(pyridin-4-yl)-1H-pyrrole In a similar manner to that described in Example 2 above, a reaction was carried out using di-t-butyl dicarbonate instead of trifluoroacetic anhydride and using methanol instead of tetrahydrofuran to give the title compound (yield 68%) as a white powder.

$^1$H-Nuclear magnetic resonance spectrum (400 MHz, CDCl$_3$) δ ppm: 8.51 (2H, doublet, J=6 Hz); 8.26 (1H, broad singlet); 7.15–7.12 (4H, multiplet); 6.96 (2H, triplet, J=9 Hz); 6.75 (1H, doublet, J=3 Hz); 4.45 (1H, broad singlet); 3.12–3.09 (2H, multiplet); 2.54 (2H, triplet, J=8 Hz); 1.67–1.63 (2H, multiplet); 1.43 (9H, singlet).

4(ii) 2-(4-Fluorophenyl)-4-(3-methylaminopropyl)-3-(pyridin-4-yl)-1H-pyrrole 400 mg (1.01 mmol) of 4-[3-(t-butoxycarbonylamino)propyl]-2-(4-fluorophenyl)-3-(pyridin-4-yl)-1H-pyrrole [prepared as described in step 4(i) above] were added to a suspension of 154 mg of lithium aluminum hydride in 8 ml of tetrahydrofuran. The resulting mixture was heated under reflux for 2 hours. At the end of this time, the reaction mixture was worked up and then purified in the same manner as that described in Example 1(vi) above to give 300 mg (yield 96%) of the title compound as a white powder.

Melting point: 193–198° C. $^1$H-Nuclear magnetic resonance spectrum (400 MHz, CDCl$_3$) δ ppm: 8.51 (2H, doublet, J=6 Hz); 8.34 (1H, broad singlet); 7.17–7.12 (4H, multiplet); 6.96 (2H, triplet, J=9 Hz); 6.74 (1H, doublet, J=3 Hz); 2.57 (2H, triplet, J=7 Hz); 2.54 (2H, triplet, J=7 Hz); 2.38 (3H, singlet); 1.69 (2H, quintet, J=7 Hz).

EXAMPLE 5

4-Aminomethyl-2-(4-fluorophenyl)-3-(pyridin-4-yl)-1H-pyrrole dihydrochloride (Dihydrochloride of Compound No. 1-95)

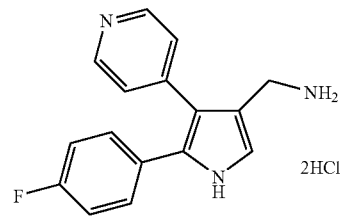

5(i) 5-(4-Fluorophenyl)-4-(pyridin-4-yl)-1H-pyrrole-3-carboxaldehyde O-methyloxime 0.83 g (9.58 mmol) of O-methylhydroxylamine hydrochloride and 1.56 ml (11.2 mmol) of triethylamine were added to a solution of 0.85 mg (3.2 mmol) of 2-(4-fluorophenyl)-4-formyl-3-(pyridin-4-yl)-1H-pyrrole [prepared as described in Example 1(iii) above] in 17 ml of methanol. The resulting mixture was heated under reflux for 30 minutes, after which water was added to the reaction mixture which was then extracted with ethyl acetate. The organic extract was washed with water and concentrated by evaporation under reduced pressure. The resulting residue was purified by chromatography on a silica gel column using ethyl acetate as the eluant to afford 728 mg (yield 77%) of the title compound as a pale yellow powder.

Melting point: 242–248° C. $^1$H-Nuclear magnetic resonance spectrum (500 MHz, DMSO-d$_6$) δ ppm: 11.88 (1H, broad singlet); 8.54 (0.2H, doublet, J=6 Hz); 8.49 (1.8H, doublet, J=6 Hz); 7.88 (0.9H, singlet); 7.76 (0.1H, singlet); 7.34 (0.9H, singlet); 7.25–7.12 (6H, multiplet); 6.98 (0.1H, singlet); 3.92 (0.4H, singlet); 3.71 (2.6H, singlet).

5(ii) 4-Aminomethyl-2-(4-fluorophenyl)-3-(pyridin-4-yl)-1H-pyrrole dihydrochloride 10 ml of 10% hydrochloric acid and 0.50 g of 10% palladium on carbon were added to a solution of 497 mg (1.68 mmol) of 5-(4-fluorophenyl)-4-(pyridin-4-yl)-1H-pyrrole-3-carboxaldehyde O-methyloxime [which was prepared as described in step 5(i) above] in 10 ml of methanol. The mixture was stirred under a hydrogen atmosphere at room temperature for 2 hours. At the end of this time, the reaction mixture was filtered and the filtrate thus obtained was concentrated by evaporation under reduced pressure. The residue was washed with diisopropylether and then with diethylether to give 391 mg (yield 68%) of the title compound as a yellowish orange powder.

Melting point: 235–240° C. (decomposition) ¹H-Nuclear magnetic resonance spectrum (500 MHz, CD₃OD) δ ppm: 11.85 (1H, broad singlet); 8.65 (2H, doublet, J=7 Hz); 7.81 (2H, doublet, J=7 Hz); 7.32 (2H, doublet of doublets, J=9 Hz, 5 Hz); 7.24 (1H, doublet, J=3 Hz); 7.14 (2H, triplet, J=9 Hz); 4.22 (2H, singlet).

EXAMPLE 6

2-(4-Fluorophenyl)-3-(pyridin-4-yl)-4-(2,4,6-trifluorobenzoylaminomethyl)-1H-pyrrole (Compound No. 1-2535)

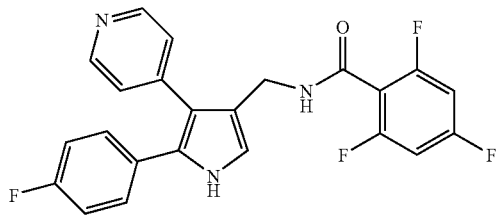

265 µl (1.905 mmol) of triethylamine and 96 mg (0.493 mmol) of 2,4,6-trifluorobenzoyl chloride were added to a suspension of 162 mg (0.476 mmol) of 4-aminomethyl-2-(4-fluorophenyl)-3-(pyridin-4-yl)-1H-pyrrole dihydrochloride [prepared as described in Example 5 above] in 3.3 ml of tetrahydrofuran. The resulting mixture was stirred at room temperature for 4 hours. At the end of this time, water was added to the reaction mixture and then this was extracted with ethyl acetate. The organic extract was washed with water, dried over anhydrous sodium sulfate and then concentrated by evaporation under reduced pressure. The residue thus obtained was washed with diethylether to give 78 mg (yield 38%) of the title compound as a pale yellow powder.

Melting point: 243–245° C. (decomposition) ¹H-Nuclear magnetic resonance spectrum (500 MHz, DMSO-d₆) δ ppm: 11.41 (1H, broad singlet); 8.99 (1H, broad triplet, J=5 Hz); 8.46 (2H, doublet, J=6 Hz); 7.29–7.19 (4H, multiplet); 7.19–7.13 (4H, multiplet); 6.94 (1H, doublet, J=3 Hz); 4.27 (2H, doublet, J=5 Hz).

EXAMPLE 7

2-(4-Fluorophenyl)-3-(pyridin-4-yl)-4-(2,3,5,6-tetrafluoropyridin-4-yl)-1H-pyrrole (Compound No. 1-2538)

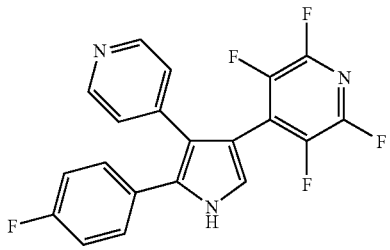

7(i) 2-(4-Fluorophenyl)-3-(pyridin-4-yl)-1H-pyrrole 15.00 g (48.3 mmol) of 4-ethoxycarbonyl-2-(4-fluorophenyl)-3-(pyridin-4-yl)-1H-pyrrole [prepared as described in Example 1(i) above] were dissolved in a mixture of 90 ml of acetic acid, 30 ml of sulfuric acid and 60 ml of water and the resulting solution was stirred at 100° C. for 16 hours. At the end of this time, the reaction mixture was cooled to room temperature and then made alkaline with a 10% aqueous solution of sodium hydroxide. The resulting mixture was extracted with ethyl acetate and the organic extract was washed with water, dried over anhydrous sodium sulfate and then concentrated by evaporation under reduced pressure to give 11.40 g (yield 99%) of the title compound as a pale red powder.

¹H-Nuclear magnetic resonance spectrum (500 MHz, CDCl₃) δ ppm: 9.78 (1H, broad singlet); 8.42 (2H, doublet, J=7 Hz); 7.37 (2H, doublet of doublets, J=9 Hz, 5 Hz); 7.22 (2H, doublet, J=6 Hz); 7.06 (2H, triplet, J=9 Hz); 6.90 (1H, triplet, J=3 Hz); 6.47 (1H, triplet, J=3 Hz).

7(ii) 2-(4-Fluorophenyl)-3-(pyridin-4-yl)-1-triisopropylsilyl-1H-pyrrole 31 ml (47.4 mmol) of a 1.57 N solution of butyllithium in hexane were added to a solution of 11.30 g (47.4 mmol) of 2-(4-fluorophenyl)-3-(pyridin-4-yl)-1H-pyrrole [prepared as described in step 7(i) above] in 300 ml of tetrahydrofuran at –78° C. and the mixture was stirred for 10 minutes. At the end of this time, 13.4 ml (49.8 mmol) of triisopropylsilyl triflate were added to the reaction mixture at the same temperature. After removal of the cooling bath, the mixture was stirred at room temperature for 30 minutes. 200 ml of water and 300 ml of a saturated aqueous solution of sodium hydrogencarbonate were then added to the reaction mixture before extracting with ethyl acetate. The organic extract was washed with water, dried over anhydrous sodium sulfate and then concentrated by evaporation under reduced pressure to give 18.70 g (quantitative yield) of the title compound as a reddish purple oil.

¹H-Nuclear magnetic resonance spectrum (500 MHz, DMSO-d₆) δ ppm: 8.25 (2H, doublet, J=6 Hz); 7.39 (2H, doublet of doublets, J=9 Hz, 6 Hz); 7.28 (2H, triplet, J=9 Hz); 7.00 (1H, doublet, J=3 Hz); 6.91(2H, doublet, J=7 Hz); 6.71 (1H, doublet, J=3 Hz); 1.15–1.05 (3H, multiplet); 0.98 (18H, doublet, J=8 Hz).

7(iii) 4-Bromo-2-(4-fluorophenyl)-3-(pyridin-4-yl)-1-triisopropylsilyl-1H-pyrrole A suspension of 8.61 g (47.4 mmol) of N-bromosuccinimide in 100 ml of tetrahydrofuran was added to a solution of 18.70 g (47.4 mmol) of 2-(4-fluorophenyl)-3-(pyridin-4-yl)-1-triisopropylsilyl-1H-pyrrole [prepared as described in step 7(ii) above] in 300 ml of tetrahydrofuran at –78° C., after which the resulting mixture was stirred at the same temperature for 6 hours. After removal of the cooling bath, the mixture was then stirred at room temperature for a further 1 hour. At the end of this time, 400 ml of hexane was added to the reaction mixture and the insoluble material was removed by filtration. The resulting filtrate was concentrated by evaporation under reduced pressure and the residue thus obtained was purified by chromatography on a silica gel column using a 2:1 by volume mixture of hexane and ethyl acetate as the eluant to give 9.57 g (yield 43%) of the title compound as pale yellow prismatic crystals.

¹H-Nuclear magnetic resonance spectrum (500 MHz, DMSO-d₆) δ ppm: 8.36 (2H, doublet, J=6 Hz); 7.34 (2H, doublet of doublets, J=9 Hz, 6 Hz); 7.18 (2H, triplet, J=9 Hz); 7.12 (1H, singlet); 7.04 (2H, doublet, J=6 Hz); 1.16–1.08 (3H, multiplet); 0.99 (18H, doublet, J=8 Hz).

7(iv) 2-(4-Fluorophenyl)-3-(pyridin-4-yl)-4-(2,3,5,6-tetrafluoropyridin-4-yl)-1H-pyrrole 1.8 ml (2.75 mmol) of 1.54 N solution of t-butyllithium in pentane were added to a solution of 650 mg (1.37 mmol) of 4-bromo-2-(4-fluorophenyl)-3-(pyridin-4-yl)-1-triisopropylsilyl-1H-pyrrole [prepared as described in step 7(iii) above] in 15 ml of tetrahydrofuran at −78° C. and the mixture was stirred for 10 minutes. At the end of this time, 165 μl (1.51 mmol) of pentafluoropyridine were added to the reaction mixture. The cooling bath was then removed and the mixture was stirred for 30 minutes. At the end of this time, 70 ml of water and 50 ml of a saturated aqueous solution of sodium hydrogencarbonate were added to the reaction mixture, and then this was extracted with ethyl acetate. The organic extract was washed with water and then concentrated by evaporation under reduced pressure. The residue thus obtained was purified by chromatography on a silica gel column using a 4:1 by volume mixture of hexane and ethyl acetate as the eluant to give 346 mg (yield 65%) of the title compound as a pale yellow powder.

Melting point: >300° $^1$H-Nuclear magnetic resonance spectrum (500 MHz, CD$_3$OD) δ ppm: 8.34 (2H, doublet, J=8 Hz); 7.32 (1H, singlet); 7.30 (2H, doublet of doublets, J=11 Hz, 7 Hz); 7.09 (2H, triplet, J=11 Hz); 7.06(2H, doublet, J=8 Hz).

EXAMPLE 8

(±)-[5-(4-Fluorophenyl)-4-(pyridin-4-yl)-1H-pyrrol-3-yl]-(pyridin-4-yl)methanol (Compound No. 1-2530)

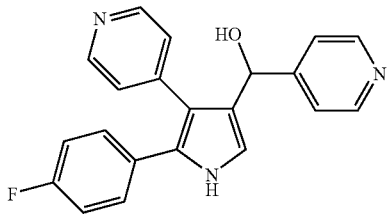

8(i) (±)-[5-(4-Fluorophenyl)-4-(pyridin-4-yl)-1-triisopropylsilyl-1H-pyrrol-3-yl]-(pyridin-4-yl)methanol In a similar manner to that described in Example 7(iv) above, a reaction was carried out using 4-formylpyridine instead of pentafluoropyridine to give the title compound (yield 56%) as a pale yellow oil.

$^1$H-Nuclear magnetic resonance spectrum (500 MHz, CD$_3$OD) δ ppm: 8.39 (2H, doublet, J=7 Hz); 8.21 (2H, doublet, J=6 Hz); 7.38 (2H, doublet, J=7 Hz); 7.29 (2H, doublet of doublets, J=9 Hz, 6 Hz); 7.17 (2H, doublet. J=6 Hz); 7.03 (2H, triplet, J=9 Hz); 6.67 (1H, singlet); 5.82 (1H, singlet); 1.14–1.05 (3H, multiplet); 1.01 (9H, doublet, J=7 Hz); 1.00 (9H, doublet, J=7 Hz).

8(ii) (±)-[5-(4-Fluorophenyl)-4-(pyridin-4-yl)-1H-pyrrol-3-yl]-(pyridin-4-yl)methano 0.59 ml (0.59 mmol) of a 1 M solution of tetrabutylammonium fluoride in tetrahydrofuran were added to a solution of 148 mg (0.295 mmol) of [5-(4-fluorophenyl)-4-(pyridin-4-yl)-1-triisopropylsilyl-1H-pyrrol-3-yl]-(pyridin-4-yl) methanol [prepared as described in step 8(i) above] in 3 ml of tetrahydrofuran. The resulting mixture was stirred at room temperature for 10 minutes, after which water was added to the reaction mixture and the resulting mixture was acidified with 1 N hydrochloric acid and then extracted with ethyl acetate. The water layer was made alkaline with potassium carbonate and then extracted with ethyl acetate. The organic extract was washed with water, dried over anhydrous sodium sulfate and then concentrated by evaporation under reduced pressure. The residual oil thus obtained was solidified by the addition of isopropanol to give 83 mg (yield 82%) of the title compound as a white powder.

Melting point: 202–205° C. $^1$H-Nuclear magnetic resonance spectrum (500 MHz, DMSO-d$_6$) δ ppm: 11.39 (1H, broad singlet); 8.43 (2H, doublet, J=6 Hz); 8.41 (2H, doublet, J=6 Hz); 7.26–7.21 (4H, multiplet); 7.18(2H, doublet of doublets, J=9 Hz, 6 Hz); 7.13 (2H, triplet, J=9 Hz); 6.55 (1H, doublet, J=3 Hz); 5.77 (1H, doublet, J=5 Hz); 5.54 (1H, doublet, J=4 Hz).

EXAMPLE 9

4-(1-Acetyl-1,2,3,6-tetrahydropyridin-4-yl)-2-(4-fluorophenyl)-3-(pyridin-4-yl)-1H-pyrrole (Compound No. 1-2525)

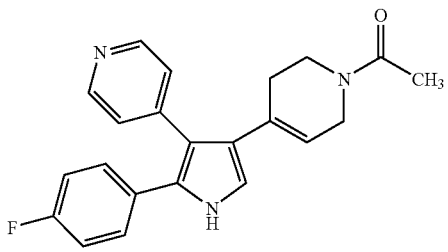

9(i) 4-(1-Benzyl-4-hydroxypiperidin-4-yl)-2-(4-fluorophenyl)-3-(pyridin-4-yl)-1-triisopropylsilyl-1H-pyrrole In a similar manner to that described in Example 7(iv) above, a reaction was carried out using 1-benzylpiperidine-4-one instead of pentafluoropyridine to afford the title compound (yield 61%) as white needle-like crystals.

$^1$H-Nuclear magnetic resonance spectrum (500 MHz, CD$_3$OD) δ ppm: 8.21 (2H, doublet, J=6 Hz); 7.35–7.15 (9H, multiplet); 6.93 (2H, triplet, J=9 Hz); 6.90 (1H, singlet); 3.49 (2H, singlet); 2.58–2.41 (4H, broad multiplet); 2.00–1.91 (2H, broad multiplet); 1.83–1.74 (2H, broad multiplet); 1.20–1.10 (3H, multiplet); 1.06 (18H, doublet, J=7 Hz).

9(ii) 2-(4-Fluorophenyl)-4-(4-hydroxypiperidin-4-yl)-3-(pyridin-4-yl)-1-triisopropylsilyl-1H-pyrrole 0.58 g of 10% palladium on carbon were added to a solution of 0.58 g (1.00 mmol) of 4-(1-benzyl-4-hydroxypiperidin-4-yl)-2-(4-fluorophenyl)-3-(pyridin-4-yl)-1-triisopropylsilyl-1H-pyrrole [prepared as described in step 9(i) above] in 15 ml of methanol. The resulting mixture was stirred under a hydrogen atmosphere at room temperature for 5 hours. At the end of this time, the reaction mixture was filtered and the filtrate was concentrated by evaporation under reduced pressure to give 483 mg (yield 98%) of the title compound as a white amorphous solid.

$^1$H-Nuclear magnetic resonance spectrum (500 Mz, CD$_3$OD) δ ppm: 8.22 (2H, doublet, J=7 Hz); 7.27 (2H, doublet, J=6 Hz); 7.21 (2H, doublet of doublets, J=9 Hz, 6 Hz); 6.94 (2H, triplet, J=9 Hz); 6.92 (1H, singlet); 2.98–2.90 (2H, multiplet); 2.76–2.68 (2H, multiplet); 1.93–1.84 (2H, multiplet); 1.77–1.69 (2H, multiplet); 1.20–1.11 (3H, multiplet); 1.07 (18H, doublet, J=7 Hz).

9(iii) 4-(1-Acetyl-1,2,3,6-tetrahydropyridin-4-yl)-2-(4-fluorophenyl)-3-(pyridin-4-yl)-1H-pyrrole 1.4 ml (8.70 mmol) of triethylsilane and 2.25 ml (29.0 mmol) of trifluoroacetic acid were added to a solution of 3.58 g (7.25 mmol) of 2-(4-fluorophenyl)-4-(4-hydroxypiperidin-4-yl)-3-(pyridin-4-yl)-1-triisopropylsilyl-1H-pyrrole [prepared as described in step 9(ii) above] in 40 ml of dichloromethane, after which the resulting mixture was stirred at room temperature for 5 hours. At the end of this time, a saturated aqueous solution of sodium hydrogencarbonate was added to the reaction mixture and then this was extracted with ethyl acetate. The organic extract was washed with water, dried over anhydrous sodium sulfate and then concentrated by evaporation under reduced pressure to afford 3.90 g of dehydrated product as a yellow amorphous solid.

All of the 3.90 g of dehydrated product thus obtained was dissolved in 80 ml of tetrahydrofuran, and then 0.76 ml (8.0 mmol) of acetic anhydride and 2.25 ml (16.0 mmol) of triethylamine were added to the solution. The resulting mixture was stirred at room temperature for 20 minutes, after which 16 ml (16.0 mmol) of a 1 M solution of tetrabutylammonium fluoride in tetrahydrofuran were added before stirring for a further 10 minutes. 150 ml of a saturated aqueous solution of sodium hydrogencarbonate were added to the reaction mixture and then this was extracted with ethyl acetate. After washing the organic extract with water, 1 N hydrochloric acid was added thereto. The water layer was washed with ethyl acetate, made alkaline with potassium carbonate and finally extracted with ethyl acetate. The organic extract thus obtained was washed with water, dried over anhydrous sodium sulfate and then concentrated by evaporation under reduced pressure to give 1.78 g (yield 68%) of the title compound as a pale brown powder.

Melting point: 262–264° C. (decomposition) $^1$H-Nuclear magnetic resonance spectrum (500 MHz, DMSO-$d_6$) δ ppm: 11.43 (1H, broad singlet); 8.48–8.44 (2H, multiplet); 7.20–7.09 (6H, multiplet); 6.96 (0.5H, doublet, J=3 Hz); 6.94 (0.5H, doublet, J=3 Hz); 5.32–5.29 (0.5H, broad multiplet); 5.29–5.25 (0.5H, broad multiplet); 3.92–3.88 (1H, multiplet); 3.87–3.84 (1H, multiplet); 3.50 (1H, triplet, J=6 Hz); 3.46 (1H, triplet, J=6 Hz); 2.22–2.17 (1H, broad multiplet); 2.16–2.11 (1H, broad multiplet); 2.00(1.5H, singlet); 1.96 (1.5H, singlet).

EXAMPLE 10

2-(4-Fluorophenyl)-3-(pyridin-4-yl)-4-(1,2,3,6-tetrahydropyridin-4-yl)-1H-pyrrole dihydrochloride (dihydrochloride of Compound No. 1-143)

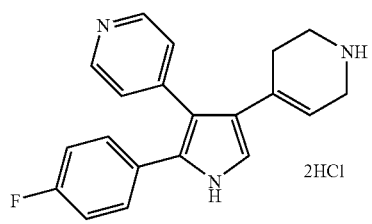

249 mg (0.689 mmol) of 4-(1-acetyl-1,2,3,6-tetrahydropyridin-4-yl)-2-(4-fluorophenyl)-3-(pyridin-4-yl)-1H-pyrrole [prepared as described in Example 9 above] were dissolved in a mixture of 2.5 ml of methanol and 2.5 ml of water, after which 2.43 ml (9.646 mmol) of a 4 N solution of hydrogen chloride in dioxane were added to the solution. The resulting mixture was heated under reflux for 11 hours, after which the reaction mixture was concentrated by evaporation under reduced pressure and the residual solid was washed with hot isopropanol to give 216 mg (yield 80%) of the title compound as a pale yellow powder.

Melting point: 290–295° C. (decomposition) $^1$H-Nuclear magnetic resonance spectrum (500 MHz, CD$_3$OD) δ ppm: 11.63 (1H, broad singlet); 8.54 (2H, doublet, J=7 Hz); 7.74 (2H, doublet, J=7 Hz); 7.29 (2H, doublet of doublets, J=9 Hz, 5 Hz); 7.14 (2H, triplet, J=9 Hz); 7.06 (1H, doublet, J=2 Hz); 5.51–5.47 (1H, broad multiplet); 3.72 (2H, doublet, J=3 Hz); 3.42 (2H, triplet, J=6 Hz); 2.66–2.55 (2H, broad multiplet).

EXAMPLE 11

2-(4-Fluorophenyl)-4-(piperidin-4-yl)-3-(pyridin-4-yl)-1H-pyrrole (Compound No. 1-142)

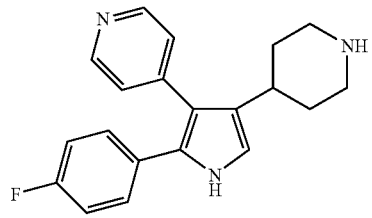

120 mg of 10% palladium on carbon were added to a solution of 120 mg (0.306 mmol) of 2-(4-fluorophenyl)-3-(pyridin-4-yl)-4-(1,2,3,6-tetrahydropyridin-4-yl)-1H-pyrrole dihydrochloride [prepared as described in Example 10 above] in 10 ml of methanol. The resulting mixture was stirred under a hydrogen atmosphere at room temperature for 1 hour, after which the reaction mixture was filtered. The filtrate thus obtained was concentrated by evaporation under reduced pressure. Water was added to the resulting residue and then this mixture was made alkaline with a 1 N aqueous solution of sodium hydroxide. The resulting precipitate was collected by filtration to give 84 mg (yield 85%) of the title compound as a pale red powder.

Melting point: 265–267° C. (decomposition) $^1$H-Nuclear magnetic resonance spectrum (500 MHz, DMSO-$d_6$) δ ppm: 11.17 (1H, broad singlet); 8.48 (2H, doublet, J=6 Hz); 7.20–7.04 (6H, multiplet); 6.73 (1H, doublet, J=3 Hz); 2.88 (2H, doublet, J=12 Hz); 2.46 (1H, triplet of triplets, J=12 Hz, 4 Hz); 2.38 (2H, triplet, J=12 Hz); 1.58 (2H, doublet, J=13 Hz); 1.35 (2H, double doublet of triplets, J=13 Hz, 12 Hz, 4 Hz).

EXAMPLE 12

1-(1-Benzylpiperidin-4-yl)-3-(4-fluorophenyl)-2-(pyridin-4-yl)-1H-pyrrole (Compound No. 2-147)

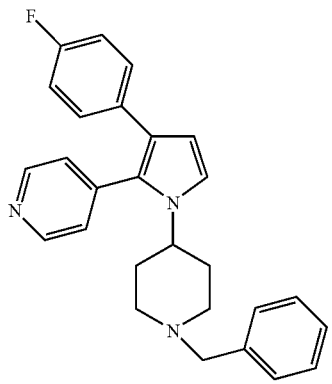

12(i) 1-Benzyl-4-(pyridin-4-yl)methyleneaminopiperidine 8.57 ml (42.01 mmol) of 4-amino-1-benzylpiperidine were added to a solution of 3.95 ml (42.01 mmol) of 4-formylpyridine in 5 ml of ethanol, and the resulting mixture was then heated under reflux for 1 hour. At the end of this time, the solvent was distilled off from the reaction mixture by evaporation under reduced pressure to afford 11.78 g (quantitative yield) of the title compound as a pale brown powder.

$^1$H-Nuclear magnetic resonance spectrum (400 MHz, CDCl$_3$) δ ppm: 8.68 (2H, doublet, J=6 Hz); 8.30 (1H, singlet); 7.60 (2H, doublet, J=6 Hz); 7.38–7.22 (5H, multiplet); 3.56 (2H, singlet); 3.37–3.27 (1H, multiplet); 3.00–2.90 (2H, multiplet); 2.23–2.10 (2H, multiplet); 1.96–1.83 (2H, multiplet); 1.79–1.60 (2H, multiplet).

12(ii) (±)-α-(1-Benzylpiperidin-4-yl)amino-α-(pyridin-4-yl)acetonitrile

A mixture of 11.73 g (42.00 mmol) of 1-benzyl-4-(pyridin-4-yl)-methyleneaminopiperidine [prepared as described in step 12(i) above] and 9.22 ml (65.67 mmol) of 95% trimethylsilyl cyanide was stirred at 100° C. for 3 hours and then it was cooled to room temperature. 100 ml of methanol were added to the reaction mixture and the resulting mixture was then stirred for 30 minutes. At the end of this time, the solvent was distilled off from the reaction mixture by evaporation under reduced pressure to afford 12.87 g (quantitative yield) of the title compound as a brown oil.

$^1$H-Nuclear magnetic resonance spectrum (400 MHz, CDCl$_3$) δ ppm: 8.67 (2H, doublet, J=6 Hz); 7.50 (2H, doublet, J=6 Hz); 7.37–7.22 (5H, multiplet); 4.85 (1H, singlet); 3.53 (2H, singlet); 2.98–2.77 (4H, multiplet); 2.33–1.44 (5H, multiplet).

12(iii) 1-(1-Benzylpiperidin-4-yl)-3-(4-fluorophenyl)-2-(pyridin-4-yl)-1H-pyrrole 14.25 g (46.51 mmol) of α-(1-benzylpiperidin-4-yl) amino-α-(pyridin-4-yl)acetonitrile [prepared as described in step 12(ii) above] and 6.98 g (46.51 mmol) of 3-(4-fluorophenyl)acrolein were dissolved in 145 ml of N,N-dimethylacetamide, 1.29 g (9.30 mmol) of potassium carbonate were added to the solution, and then this was stirred at room temperature for 5 hours. At the end of this time, water was added to the reaction mixture and then this was extracted with ethyl acetate. The organic extract was washed with water and then concentrated by evaporation under reduced pressure. 150 ml of ethylene glycol were added to the residue thus obtained and the resulting mixture was stirred at 180° C. for 1 hour. After cooling to room temperature, a saturated aqueous solution of sodium hydrogencarbonate was added to the reaction mixture which was then extracted with ethyl acetate. The organic extract was washed with water and then concentrated by evaporation under reduced pressure. The residue thus obtained was purified by chromatography on a silica gel column using a 1:3 by volume mixture of hexane and ethyl acetate as the eluant to give 10.31 g (yield 49%) of the title compound as a pale brown powder.

Melting point: 132–139° C. $^1$H-Nuclear magnetic resonance spectrum (400 MHz, CDCl$_3$) δ ppm: 8.61 (2H, doublet, J=6 Hz); 7.37–7.23 (5H, multiplet); 7.13 (2H, doublet, J=6 Hz); 7.03 (2H, doublet of doublets, J=9 Hz, 5 Hz); 6.96 (1H, doublet, J=3 Hz); 6.87 (2H, triplet, J=9 Hz); 6.38 (1H, doublet, J=3 Hz); 3.87–3.80 (1H, multiplet); 3.50 (2H, singlet); 2.97 (2H, doublet, J=12 Hz); 2.12–1.56 (6H, multiplet).

EXAMPLE 13

3-(4-Fluorophenyl)-1-(piperidin-4-yl)-2-(pyridin-4-yl)-1H-pyrrole (Compound No. 2-142)

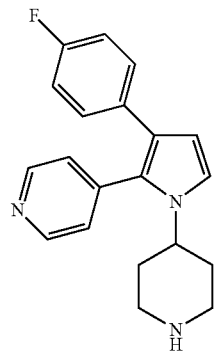

In a similar manner to that described in Example 9(ii) above, 1-(1-benzylpiperidin-4-yl)-3-(4-fluorophenyl)-2-(pyridin-4-yl)-1H-pyrrole (prepared as described in Example 12 above) was debenzylated to give the title compound (yield 30%) as a white powder.

Melting point: 191–192° C. $^1$H-Nuclear magnetic resonance spectrum (400 MHz, CDCl$_3$) δ ppm: 8.62 (2H, doublet, J=6 Hz); 7.15 (2H, doublet, J=6 Hz); 7.04 (2H, doublet of doublets, J=9 Hz, 5 Hz); 6.97 (1H, doublet, J=3 Hz); 6.88 (2H, triplet, J=9 Hz); 6.39 (1H, doublet, J=3 Hz); 3.97–3.86 (1H, multiplet); 3.17 (2H, doublet, J=12 Hz); 2.58 (2H, doublet of triplets, J=12 Hz, 3 Hz); 1.98–1.82 (4H, multiplet).

EXAMPLE 14

3-(4-Fluorophenyl)-1-(1-methylpiperidin-4-yl)-2-(pyridin-4-yl)-1H-pyrrole (Compound No. 2-144)

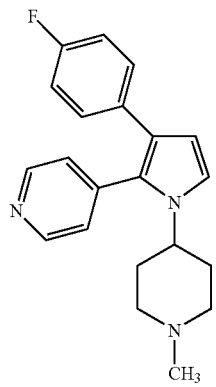

In a similar manner to the procedures described in Examples 4(i) and 4(ii) above, 3-(4-fluorophenyl)-1-(piperidin-4-yl)-2-(pyridin-4-yl)-1H-pyrrole (prepared as described in Example 13 above) was subjected consecutively to N-t-butoxycarbonylation and reduction to give the title compound (total yield for the two steps: 55%) as a white powder.

Melting point: 187–189° C. $^1$H-Nuclear magnetic resonance spectrum (400 MHz, CDCl$_3$) δ ppm: 8.62 (2H, doublet, J=6 Hz); 7.14 (2H, doublet, J=6 Hz); 7.04 (2H, doublet of doublets, J=9 Hz, 5 Hz); 6.96 (1H, doublet, J=3 Hz); 6.87 (2H, triplet, J=9 Hz); 6.39 (1H, doublet, J=3 Hz); 3.87–3.77 (1H, multiplet); 2.93 (2H, doublet, J=12 Hz); 2.29 (3H, singlet); 2.13–1.85 (6H, multiplet).

EXAMPLE 15

1-(1-Acetylpiperidin-4-yl)-3-(4-fluorophenyl)-2-(pyridin-4-yl)-1H-pyrrole (Compound No. 2-2524)

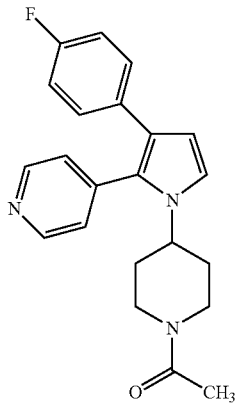

In a similar manner to that described in Example 3 above, a reaction was carried out using 3-(4-fluorophenyl)-1-(piperidin-4-yl)-2-(pyridin-4-yl)-1H-pyrrole (prepared as described in Example 13 above) to give the title compound (yield 98%) as a white powder.

Melting point: 223–224° C. $^1$H-Nuclear magnetic resonance spectrum (400 MHz, CDCl$_3$) δ ppm: 8.64 (2H, doublet, J=6 Hz); 7.15 (2H, doublet, J=6 Hz); 7.04 (2H, doublet of doublets, J=9 Hz, 5 Hz); 6.88 (2H, triplet, J=9 Hz); 6.87 (1H, doublet, J=3 Hz); 6.41 (1H, doublet, J=3 Hz); 4.84–4.74 (1H, multiplet); 4.05 (1H, doublet of triplets, J=12 Hz, 4 Hz); 3.95–3.83 (1H, multiplet); 3.08–2.97 (1H, multiplet); 2.58–2.48 (1H, multiplet); 2.13 (3H, singlet); 2.04–1.78 (4H, multiplet).

EXAMPLE 16

3-(4-Fluorophenyl)-1-[1-(2-nitroethyl)piperidin-4-yl]-2-(pyridin-4-yl)-1H-pyrrole (Compound No. 2-2537)

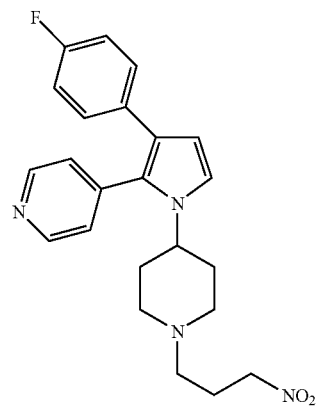

186 mg (1.40 mmol) of 2-nitroethyl acetate were added to a solution of 300 mg (0.93 mmol) of 3-(4-fluorophenyl)-1-(piperidin-4-yl)-2-(pyridin-4-yl)-1H-pyrrole (prepared as described in Example 13 above) in 6 ml of ethanol. The resulting mixture was stirred at room temperature for 30 minutes, after which the solvent was distilled off under reduced pressure. A saturated aqueous solution of sodium hydrogencarbonate was added to the residue and then this was extracted with ethyl acetate. The organic extract was washed with water, dried over anhydrous magnesium sulfate and then concentrated by evaporation under reduced pressure. The residual solid was washed with diethylether to give 280 mg (yield 76%) of the title compound as a white powder.

Melting point: 172–173° C. $^1$H-Nuclear magnetic resonance spectrum (400 MHz, CDCl$_3$) δ ppm: 8.61 (2H, doublet, J=6 Hz); 7.13 (2H, doublet, J=6 Hz); 7.04 (2H, doublet of doublets, J=9 Hz, 5 Hz); 6.93 (1H, doublet, J=3 Hz); 6.87 (2H, triplet, J=9 Hz); 6.39 (1H, doublet, J=3 Hz); 4.47 (2H, triplet, J=6 Hz); 3.82 (1H, doublet of triplets, J=12 Hz, 4 Hz); 3.03–2.92 (4H, multiplet); 2.16–1.85 (6H, multiplet).

EXAMPLE 17

3-(4-Fluorophenyl)-1-[3-(morpholin-1-yl)propyl]-2-(pyridin-4-yl)-1H-pyrrole (Compound No. 2-125)

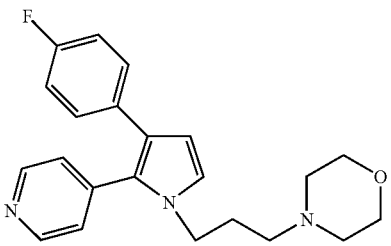

In a similar manner to the procedures described in Examples 12(i), 12(ii) and 12(iii) above, reactions were carried out using 1-(3-aminopropyl)morpholine instead of 4-amino-1-benzylpiperidine to give the title compound (total yield 13%) as pale brown needle-like crystals.

Melting point: 111–112° C. $^1$H-Nuclear magnetic resonance spectrum (500 MHz, CDCl$_3$) δ ppm: 8.59 (2H, doublet, J=6 Hz); 7.18 (2H, doublet, J=6 Hz); 7.06 (2H, doublet of doublets, J=9 Hz, 5 Hz); 6.89 (2H, triplet, J=9 Hz); 6.84 (1H, doublet, J=3 Hz); 6.34 (1H, doublet, J=3 Hz); 3.96 (2H, triplet, J=7 Hz); 3.64 (2H, triplet, J=5 Hz); 2.33–2.22 (4H, multiplet); 2.20 (2H, triplet, J=7 Hz); 1.72 (2H, quintet, J=7 Hz).

EXAMPLE 18

(±)-3-(4-Fluorophenyl)-2-(pyridin-4-yl)-1-(pyrrolidin-3-yl)-1H-pyrrole (Compound No. 2-139)

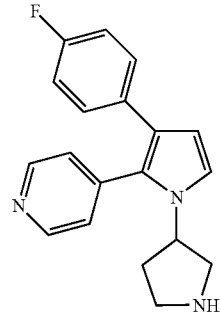

18(i) (±)-1-[1-(t-Butoxycarbonyl)pyrrolidin-3-yl]-3-(4-fluorophenyl)-2-(pyridin-4-yl)-1H-pyrrole In a similar manner to the procedures described in Examples 12(i), 12(ii) and 12(iii) above, reactions were carried out using (±)-3-amino-1-(t-butoxycarbonyl)pyrrolidine as a starting material instead of 4-amino-1-benzylpiperidine to give the title compound (total yield 31%) as a brown amorphous solid. $^1$H-Nuclear magnetic resonance spectrum (400 MHz, CDCl$_3$) δ ppm: 8.63 (2H, doublet, J=6 Hz); 7.17 (2H, doublet, J=6 Hz); 7.03 (2H, doublet of doublets, J=9 Hz, 5 Hz); 6.93–6.84 (3H, multiplet); 6.41 (1H, doublet, J=3 Hz); 4.70–4.55 (1H, multiplet); 3.80–3.36 (4H, multiplet); 2.30–2.12 (2H, multiplet); 1.47 (9H, singlet).

18(ii) (±)-3-(4-Fluorophenyl)-2-(pyridin-4-yl)-1-(pyrrolidin-3-yl)-1H-pyrrole 6.01 ml (24.05 mmol) of a 4N solution of hydrogen chloride in dioxane were added to a solution of 1.96 g (4.81 mmol) of (±)-1-[1-(t-butoxycarbonyl)pyrrolidin-3-yl]-3-(4-fluorophenyl)-2-(pyridin-4-yl)-1H-pyrrole [prepared as described in step 18(i) above] in 10 ml of ethanol. The resulting mixture was stirred at 50° C. for 30 minutes, after which the solvent was distilled off under reduced pressure. A saturated aqueous solution of sodium hydrogencarbonate was added to the residue thus obtained, and then this was extracted with ethyl acetate. The organic extract was washed with water, dried over anhydrous magnesium sulfate and then concentrated by evaporation under reduced pressure to give 1.29 g (yield 87%) of the title compound as a pale yellow powder.

Melting point: 145–147° C. $^1$H-Nuclear magnetic resonance spectrum (500 MHz, CDCl$_3$) δ ppm: 8.61 (2H, doublet, J=6 Hz); 7.16 (2H, doublet, J=6 Hz); 7.05 (2H, doublet of doublets, J=9 Hz, 5 Hz); 7.00 (1H, doublet, J=3 Hz); 6.88 (2H, triplet, J=9 Hz); 6.39 (1H, doublet, J=3 Hz); 4.61–4.53 (1H, multiplet); 3.30–3.17 (2H, multiplet); 3.10–2.97 (2H, multiplet); 2.28–2.18 (2H, multiplet); 2.11–2.01 (2H, multiplet).

EXAMPLE 19

(±)-3-(4-Fluorophenyl)-1-(piperidin-3-yl)-2-(pyridin-4-yl)-1H-pyrrole (Compound No. 2-141)

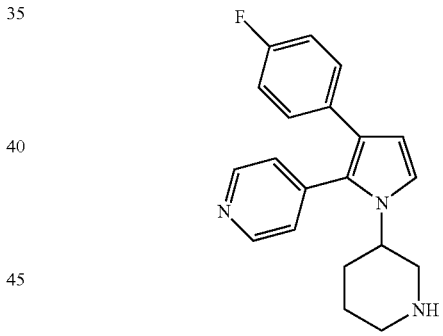

In a similar manner to the procedures described in Examples 18(i) and 18(ii) above, reactions were carried out using (±)-3-amino-1-(t-butoxycarbonyl)piperidine as a starting material instead of (±)-3-amino-1-(t-butoxycarbonyl)pyrrolidine to give the title compound (total yield 21%) as a white powder.

Melting point 189–191° C. $^1$H-Nuclear magnetic resonance spectrum (400 MHz, CDCl$_3$) δ ppm: 8.61 (2H, doublet, J=6 Hz); 7.15 (2H, doublet, J=6 Hz); 7.04 (2H, doublet of doublets, J=9 Hz, 5 Hz); 6.93 (1H, doublet, J=3 Hz); 6.87 (2H, triplet, J=9 Hz); 6.38 (1H, doublet, J=3 Hz); 3.93 (1H, triplet of triplets, J=11 Hz, 4 Hz); 3.20–3.12 (1H, multiplet); 3.05–2.96 (1H, multiplet); 2.83 (1H, triplet, J=11 Hz); 2.58 (1H, doublet of triplets, J=12 Hz, 3 Hz); 2.17–2.08 (1H, multiplet); 1.90–1.76 (2H, multiplet); 1.58–1.43 (1H, multiplet).

EXAMPLE 20

3-(4-Fluorophenyl)-1-(piperidin-4-yl)methyl-2-(pyridin-4-yl)-1H-pyrrole (Compound No. 2-169)

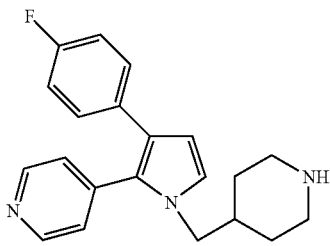

In a similar manner to the procedures described in Examples 18(i) and 18(ii) above, reactions were carried out using 4-aminomethyl-1-(t-butoxycarbonyl)piperidine as a starting material instead of 3-amino-1-(t-butoxycarbonyl)pyrrolidine to give the title compound (total yield 4%) as a white powder.

Melting point 174–176° C. $^1$H-Nuclear magnetic resonance spectrum (400 MHz, CDCl$_3$) δ ppm: 8.59 (2H, doublet, J=6 Hz); 7.15 (2H, doublet, J=6 Hz); 7.06 (2H, doublet of doublets, J=9 Hz, 5 Hz); 6.88 (2H, triplet, J=9 Hz); 6.79 (1H, doublet, J=3 Hz); 6.34 (1H, doublet, J=3 Hz); 3.75 (2H, doublet, J=7 Hz); 3.05–2.95 (2H, multiplet); 2.45 (2H, doublet of triplets, J=12 Hz, 2 Hz); 1.62–1.52 (1H, multiplet); 1.46–1.38 (2H, multiplet); 1.05–0.93 (2H, multiplet).

EXAMPLE 21

1-(Azetidin-3-yl)-3-(4-fluorophenyl)-2-(pyridin-4-yl)-1H-pyrrole dihydrochloride (Dihydrochloride of Compound No. 2-136)

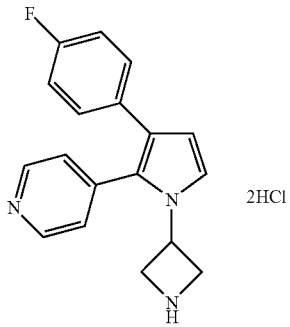

21(i) 1-(1-Diphenylmethylazetidin-3-yl)-3-(4-fluorophenyl)-2-(pyridin-4-yl)-1H-pyrrole In a similar manner to the procedures in Examples 12(i), 12(ii) and 12(iii) above, reactions were carried out using 3-amino-1-diphenylmethylazetidine as a starting material instead of 4-amino-1-benzylpiperidine to afford the title compound (total yield 20%) as a pale brown powder.

$^1$H-Nuclear magnetic resonance spectrum (400 MHz, CDCl$_3$) δ ppm: 8.56 (2H, doublet, J=6 Hz); 7.43–7.18 (11H, multiplet); 7.07–7.02 (4H, multiplet); 6.88 (2H, triplet, J=9 Hz); 6.43 (1H, doublet, J=3 Hz); 4.74–4.66 (1H, multiplet); 4.41 (1H, singlet); 3.58–3.52 (2H, multiplet); 3.34–3.28 (2H, multiplet).

21 (ii) 1-(Azetidin-3-yl)-3-(4-fluorophenyl)-2-(pyridin-4-yl)-1H-pyrrole dihydrochloride 0.45 ml of concentrated hydrochloric acid and 0.12 g of 20% palladium hydroxide on carbon were added to a solution of 1.20 g (2.61 mmol) of 1-(1-diphenylmethylazetidin-3-yl)-3-(4-fluorophenyl)-2-(pyridin-4-yl)-1H-pyrrole [prepared as described in step 21(i) above] in 12 ml of ethanol. The resulting mixture was stirred under a hydrogen atomosphere at 50° C. for 20 hours. After cooling to room temperature, the reaction mixture was then filtered and the filtrate was concentrated by evaporaration under reduced pressure. The residual solid was washed with diethylether to give 0.91 g (yield 95%) of the title compound as a pale yellow amorphous solid.

$^1$H-Nuclear magnetic resonance spectrum (400 MHz, DMSO-d$_6$) δ ppm: 9.84–9.64 (1H, broad singlet); 9.58–9.37 (1H, broad singlet); 9.80 (2H, doublet, J=6 Hz); 7.94 (1H, doublet, J=3 Hz); 7.64 (2H, doublet, J=6 Hz); 7.25 (2H, triplet, J=9 Hz); 7.20–7.07 (4H, multiplet); 7.62 (1H, doublet, J=3 Hz); 5.19–5.08 (1H, multiplet); 4.43–4.23 (4H, multiplet).

EXAMPLE 22

1-(3-Aminopropyl)-3-(4-fluorophenyl)-2-(pyridin-4-yl)-1H-pyrrole (Compound No. 2-97)

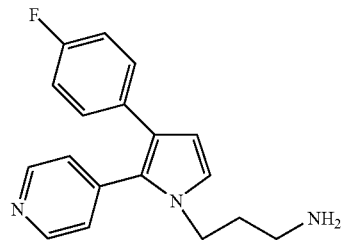

22(i) 1-(3-Benzyloxypropyl)-3-(4-fluorophenyl)-2-(pyridin-4-yl)-1H-pyrrole

In a similar manner to the procedures described in Examples 12(i), 12(ii) and 12(iii), reactions were carried out using 3-benzyloxypropylamine as a starting material instead of 4-amino-1-benzylpiperidine to give the title compound (total yield 34%) as a brown oil.

$^1$H-Nuclear magnetic resonance spectrum (400 MHz, CDCl$_3$) δ ppm: 8.55 (2H, doublet, J=6 Hz); 7.38–7.23 (5H, multiplet); 7.16 (2H, doublet, J=6 Hz); 7.07 (2H, doublet of doublets, J=9 Hz, 5 Hz); 6.89 (2H, triplet, J=9 Hz); 6.81 (1H, doublet, J=3 Hz); 6.34 (1H, doublet, J=3 Hz); 4.41 (2H, singlet); 4.03 (2H, triplet, J=7 Hz); 3.36 (2H, triplet, J=7 Hz); 1.86 (2H, quintet, J=7 Hz).

22(ii) 3-(4-Fluorophenyl)-1-(3-hydroxypropyl)-2-(pyridin-4-yl)-1H-pyrrole

In a similar manner to that described in Example 9(ii) above, 1-(3-benzyloxypropyl)-3-(4-fluorophenyl)-2-(pyridin-4-yl)-1H-pyrrole [prepared as described in step 22(i) above] was debenzylated to afford the title compound (yield 55%) as a white powder.

$^1$H-Nuclear magnetic resonance spectrum (400 MHz, CDCl$_3$) δ ppm: 8.59 (2H, doublet, J=6 Hz); 7.19 (2H, doublet, J=6 Hz); 7.05 (2H, doublet of doublets, J=9 Hz, 5 Hz); 6.89 (2H, triplet, J=9 Hz); 6.87 (1H, doublet, J=3 Hz); 6.36 (1H, doublet, J=3 Hz); 4.05 (2H, triplet, J=7 Hz); 3.55 (2H, triplet, J=7 Hz); 1.80 (2H, quintet, J=7 Hz).

22(iii) 3-(4-Fluorophenyl)-2-(pyridin-4-yl)-1-[3-(p-toluenesulfonyloxy)propyl]-1H-pyrrole 1.99 g (6.09 mmol) of p-toluenesulfonic anhydride and 0.85 ml (6.09 mmol) of triethylamine were added to a solution of 1.64 g (5.53 mmol) of 3-(4-fluorophenyl)-1-(3-hydroxypropyl)-2-(pyridin-4-yl)-1H-pyrrole [prepared as described in step 22(ii) above] in 16 ml of dichloromethane. The resulting mixture was stirred at room temperature for 2 hours, after which the solvent was distilled off by evaporation under reduced pressure. The resulting residue was purified by chromatography on a silica gel column using a 1:1 by volume mixture of hexane and ethyl acetate as the eluant to afford 1.33 g (yield 53%) of the title compound as a yellow powder.

$^1$H-Nuclear magnetic resonance spectrum (400 MHz, CDCl$_3$) δ ppm: 8.57 (2H, doublet, J=6 Hz); 7.74 (2H, doublet, J=8 Hz); 7.35 (2H, doublet, J=8 Hz); 7.10 (2H, doublet, J=6 Hz); 7.03 (2H, doublet of doublets, J=9 Hz, 5 Hz); 6.88 (2H, triplet, J=9 Hz); 6.71 (1H, doublet, J=3 Hz); 6.29 (1H, doublet, J=3 Hz); 3.98 (2H, triplet, J=7 Hz); 3.89 (2H, triplet, J=7 Hz); 2.46 (3H, singlet); 1.84 (2H, quintet, J=7 Hz).

22(iv) 1-(3-Azidopropyl)-3-(4-fluorophenyl)-2-(pyridin-4-yl)-1H-pyrrole 0.38 g (5.90 mmol) of sodium azide were added to a solution of 1.33 g (2.95 mmol) of 3-(4-fluorophenyl)-2-(pyridin-4-yl)-1-[3-(p-toluenesulfonyloxy)propyl]-1H-pyrrole [prepared as described in step 22(iii) above] in 13 ml of dimethylsulfoxide. The resulting mixture was stirred at 70° C. for 1 hour. At the end of this time water was added to the reaction mixture and then this was extracted with dichloromethane. The organic extract was washed with water and then concentrated under reduced pressure. The residue thus obtained was purified by chromatography on a silica gel column using a 1:1 by volume mixture of hexane and ethylacetate as the eluant to afford 100 mg (yield 11%) of the title compound as a pale brown powder.

$^1$H-Nuclear magnetic resonance spectrum (400 MHz, CDCl$_3$) δ ppm: 8.16 (2H, doublet, J=6 Hz); 7.17 (2H, doublet, J=6 Hz); 7.07 (2H, doublet of doublets, J=9 Hz, 5 Hz); 6.89 (2H, triplet, J=9 Hz); 6.83 (1H, doublet, J=3 Hz); 6.37 (1H, doublet, J=3 Hz); 4.00 (2H, triplet, J=7 Hz); 3.18 (2H, triplet, J=7 Hz); 1.78 (2H, quintet, J=7 Hz).

22(v) 1-(3-Aminopropyl)-3-(4-fluorophenyl)-2-(pyridin-4-yl)-1H-pyrrole 20 mg of 10% palladium on carbon were added to a solution of 100 mg (0.31 mmol) of 1-(3-azidopropyl)-3-(4-fluoropenyl)-2-(pyridin-4-yl)-1H-pyrrole [prepared as described in Step 22(iv) above] in 2 ml of ethanol. The resulting mixture was stirred under a hydrogen atmosphere at room temperature for 1 hour, after which the reaction mixture was filtered and the filtrate was concentrated by evaporation under reduced pressure. The residual solid was washed with diethylether to give 43 mg (yield 47%) of the title compound as a pale yellow powder.

Melting point: 219–222° C. $^1$H-Nuclear magnetic resonance spectrum (400 MHz, CDCl$_3$) δ ppm: 8.61 (2H, doublet, J=6 Hz); 7.74–7.40 (2H, broad singlet); 7.27 (2H, doublet, J=6 Hz); 7.12–7.00 (5H, multiplet); 6.38 (1H, doublet, J=3 Hz); 3.97 (2H, triplet, J=7 Hz); 2.60 (2H, triplet, J=7 Hz); 1.73 (2H, quintet, J=7 Hz).

EXAMPLE 23

2-(4-Fluorophenyl)-3-(pyridin-4-yl)-4-[3-(thiomorpholin-1-yl)propyl]-1H-pyrrole (Compound No. 1-129)

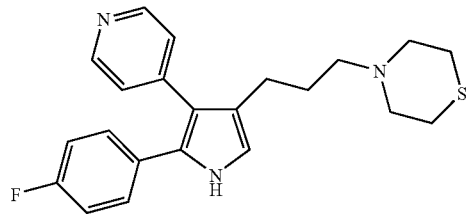

23(i) Ethyl 3-[2-(4-fluorophenyl)-3-(pyridin-4-yl)-1H-pyrrol-4-yl]acrylate

In a similar manner to that described in Example 1(iv) above, a reaction was carried out using ethyl diethylphosphonoacetate instead of diethylphosphonoacetonitrile to afford the title compound (yield 60%) as a brown powder.

$^1$H-Nuclear magnetic resonance spectrum (400 MHz, CDCl$_3$) δ ppm: 8.64 (1H, broad singlet); 8.56 (2H, doublet, J=6 Hz); 7.54 (1H, doublet, J=16 Hz); 7.16 (2H, doublet, J=6 Hz); 7.16–7.13 (3H, multiplet); 6.99 (2H, triplet, J=9 Hz); 6.07 (1H, doublet, J=16 Hz); 4.20 (2H, quartet, J=7 Hz); 1.28 (3H, triplet, J=7 Hz).

23(ii) 4-(2-Ethoxycarbonylethyl)-2-(4-fluorophenyl)-3-(pyridin-4-yl)-1H-pyrrole

In a similar manner to that described in Example 1(v) above, ethyl 3-[2-(4-fluorophenyl)-3-(pyridin-4-yl)-1H-pyrrol-4-yl]acrylate [prepared as described in step 23(i) above] was reduced to afford the title compound (yield 73%) as a pale brown powder.

$^1$H-Nuclear magnetic resonance spectrum (400 MHz, CDCl$_3$) δ ppm: 8.51 (2H, doublet, J=4 Hz); 8.33 (1H, broad singlet); 7.15 (2H, doublet, J=4 Hz); 7.16–7.12 (2H, multiplet); 6.96 (2H, triplet, J=9 Hz); 6.74 (1H, doublet, J=3 Hz); 4.11 (2H, quartet, J=7 Hz); 2.85 (2H, triplet, J=8 Hz); 2.50 (2H, triplet, J=8 Hz); 1.23 (3H, triplet, J=7 Hz).

23(iii) 2-(4-Fluorophenyl)-4-(3-hydroxypropyl)-3-(pyridin-4-yl)-1H-pyrrole

In a similar manner to that described in Example 1(vi) above, 4-(2-ethoxycarbonylethyl)-2-(4-fluorophenyl)-3-(pyridin-4-yl)-1H-pyrrole [prepared as described in step 23(ii) above] was reduced using lithium aluminum hydride to afford the title compound (yield 91%) as a pale brown powder.

$^1$H-Nuclear magnetic resonance spectrum (400 MHz, CDCl$_3$) δ ppm: 8.51 (2H, doublet, J=5 Hz); 8.23 (1H, broad singlet); 7.17–7.12 (4H, multiplet); 7.00 (2H, triplet, J=9 Hz); 6.75 (1H, doublet, J=3 Hz); 3.65 (2H, triplet, J=6 Hz); 2.61 (2H, triplet, J=8 Hz); 1.79–1.72 (2H, multiplet); 1.61 (1H, broad singlet).

23(iv) 2-(4-Fluorophenyl)-3-(pyridin-4-yl)-4-[3-(p-toluenesulfonyloxy)propyl]-1H-pyrrole In a similar manner to that described in Example 22(iii) above, p-toluensulfonylation was carried out using 2-(4-fluorophenyl)-4-(3-hydroxypropyl)-3-(pyridin-4-yl)-1H-pyrrole [prepared as described in step 23(iii) above] to afford the title compound (yield 71%) as a pale yellow powder.

¹H-Nuclear magnetic resonance spectrum (400 MHz, CDCl₃) δ ppm: 8.49 (2H, doublet, J=6 Hz); 8.20 (1H, broad singlet); 7.59 (2H, doublet, J=8 Hz); 7.33 (2H, doublet, J=8 Hz); 7.12 (2H, doublet of doublets, J=9 Hz, 5 Hz); 7.08 (2H, doublet, J=6 Hz); 6.96 (2H, triplet, J=9 Hz); 6.69 (1H, doublet, J=3 Hz); 4.00 (2H, triplet, J=6 Hz); 2.56 (2H, triplet, J=8 Hz); 2.44 (3H, singlet); 1.81–1.74 (2H, multiplet).

23(v) 2-(4-Fluorophenyl)-3-(pyridin-4-yl)-4-[3-(thiomorpholin 1-yl)propyl]-1H-pyrrole 163 mg (1.18 mmol) of potassium carbonate and 122 µl (1.29 mmol) of thiomorpholine were added to a solution of 450 mg (1.07 mmol) of 2-(4-fluorophenyl)-3-(pyridin-4-yl)-4-[3-(p-toluenesulfonyloxy)propyl]-1H-pyrrole [prepared as described in step 23(iv) above] in 50 ml of acetonitrile. The resulting mixture was heated under reflux overnight. After cooling the reaction mixture to room temperature, water was added and then this was extracted with ethyl acetate. The organic extract was washed with water and then concentrated by evaporation under reduced pressure. The residue thus obtained was purified by chromatography on a silica gel column using a 95:5 by volume mixture of ethyl acetate and methanol as the eluant to give 340 mg (yield 83%) of the title compound as a pale yellow powder.

Melting point: 205–207° C. ¹H-Nuclear magnetic resonance spectrum (400 MHz, CDCl₃) δ ppm: 8.51 (2H, doublet, J=6 Hz); 8.20 (1H, broad singlet); 7.14 (2H, doublet of doublets, J=9 Hz, 5 Hz); 7.13 (2H, doublet, J=6 Hz); 6.96 (2H, triplet, J=9 Hz); 6.72 (1H, doublet, J=3 Hz); 2.65 (8H, singlet); 2.50 (2H, triplet, J=8 Hz); 2.35 (2H, triplet, J=8 Hz); 1.66 (2H, quintet, J=8 Hz).

EXAMPLE 24

4-[3-(1-Benzylpiperazin-4-yl)propyl]-2-(4-fluorophenyl)-3-(pyridin-yl-1)-1H-pyrrole (Compound No. 1-135)

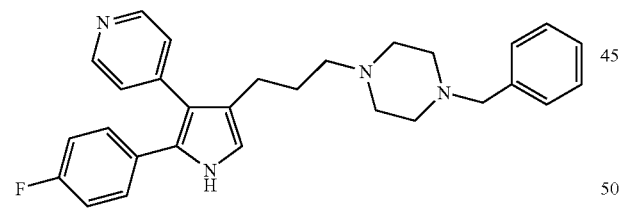

In a similar manner to that described in Example 23(v) above, a reaction was carried out using 1-benzylpiperazine instead of thiomorpholine to give the title compound (yield 52%) as a white powder.

Melting point: 153–154° C. ¹H-Nuclear magnetic resonance spectrum (400 MHz, CDCl₃) δ ppm: 8.50 (2H, doublet, J=5 Hz); 8.28 (1H, broad singlet); 7.31 (4H, doublet, J=4 Hz); 7.28–7.22 (1H, multiplet); 7.13 (2H, doublet of doublets, J=9 Hz, 5 Hz); 7.13 (2H, doublet, J=5 Hz); 6.96 (2H, triplet, J=9 Hz); 6.72 (1H, doublet, J=2 Hz); 3.50 (2H, singlet); 2.50 (2H, triplet, J=8 Hz); 2.44 (8H, broad singlet); 2.34 (2H, triplet, J=8 Hz); 1.69 (2H, quintet, J=8 Hz).

EXAMPLE 25

2-(4-Fluorophenyl)-4-[3-(piperazin-1-yl)propyl]-3-(pyridin-4-yl)-1H-pyrrole (Compound No. 1-133)

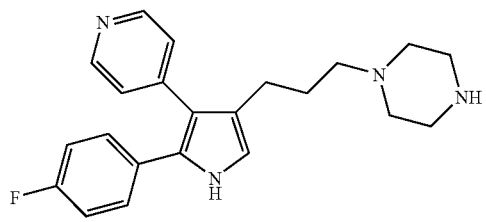

In a similar manner to that described in Example 9(ii) above, 4-[3-(1-benzylpiperazin-4-yl)propyl]-2-(4-fluorophenyl)-3-(pyridin-4-yl)-1H-pyrrole (prepared as described in Example 24 above) was debenzylated to give the title compound (yield 98%) as a white powder.

Melting point: 162–164° C. ¹H-Nuclear magnetic resonance spectrum (400 MHz, CDCl₃) δ ppm: 8.51 (2H, doublet, J=6 Hz); 8.20 (1H, broad singlet); 7.14 (2H, doublet of doublets, J=9 Hz, 5 Hz); 7.14 (2H, doublet, J=6 Hz); 6.96 (2H, triplet, J=9 Hz); 6.73 (1H, doublet, J=2 Hz); 2.87 (4H, triplet, J=5 Hz); 2.51 (2H, triplet, J=8 Hz); 2.36 (4H, broad singlet); 2.32 (2H, triplet, J=8 Hz); 1.70 (2H, quintet, J=8 Hz).

EXAMPLE 26

4-(3-Dimethylaminopropyl)-2-(4-fluorophenyl)-3-(pyridin-4-yl)-1H-pyrrole (Compound No. 1-109)

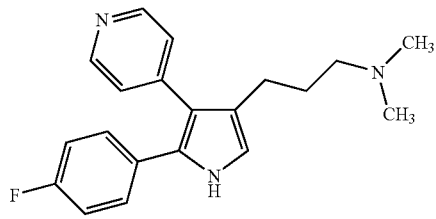

In a similar manner to that described in Example 23(v) above, a reaction was carried out using dimethylamine instead of thiomorpholine to give the title compound (yield 66%) as a white powder.

Melting point: 177–179° C. ¹H-Nuclear magnetic resonance spectrum (500 MHz, CDCl₃) δ ppm: 8.51 (2H, doublet, J=5 Hz); 8.24 (1H, broad singlet); 7.15–7.13 (2H, multiplet); 7.14 (2H, doublet, J=5 Hz); 6.96 (2H, triplet, J=9 Hz); 6.74 (1H, doublet, J=2 Hz); 2.52 (2H, triplet, J=8 Hz); 2.28 (2H, triplet, J=8 Hz); 2.19 (6H, singlet); 1.74–1.59 (2H, multiplet).

EXAMPLE 27

2-(4-Fluorophenyl)-4-[3-(molpholin-1-yl)propyl]-3-(pyridin-4-yl)-1H-pyrrole (Compound No. 1-125)

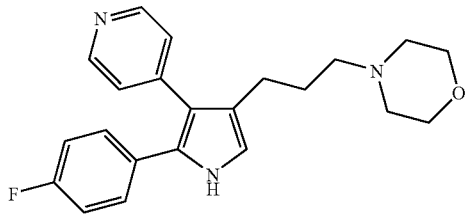

In a similar manner to that described in Example 23(v) above, a reaction was carried out using morpholine instead of thiomorpholine to give the title compound (yield 45%) as a pale yellow powder.

Melting point: 182–183° C. $^1$H-Nuclear magnetic resonance spectrum (400 MHz, CDCl$_3$) δ ppm: 8.62 (1H, broad singlet); 8.50 (2H, doublet, J=5 Hz); 7.17–7.12 (2H, multiplet); 7.14 (2H, doublet, J=5 Hz); 6.96 (2H, triplet, J=9 Hz); 6.73 (1H, doublet, J=3 Hz); 3.70–3.68 (4H, multiplet); 2.53 (2H, triplet, J=8 Hz); 2.41–2.34 (4H, multiplet); 2.33 (2H, triplet, J=8 Hz); 1.68 (2H, quintet, J=8 Hz).

EXAMPLE 28

2-(4-Fluorophenyl)-4-[3-(piperidin-1-yl)propyl]-3-(pyridin-4-yl)-1H-pyrrole (Compound No. 1-121)

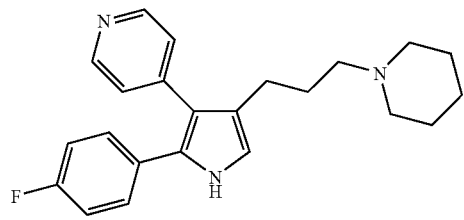

In a similar manner to that described in Example 23(v) above, a reaction was carried out using piperidine instead of thiomorpholine to give the title compound (yield 63%) as a pale yellow powder.

Melting point: 195–197° C. $^1$H-Nuclear magnetic resonance spectrum (500 MHz, CDCl$_3$) δ ppm: 8.50 (2H, doublet, J=6 Hz); 8.19 (1H, broad singlet); 7.14 (2H, doublet of doublets, J=9 Hz, 6 Hz); 6.96 (2H, triplet, J=9 Hz); 6.74 (1H, doublet, J=2 Hz); 2.50 (2H, triplet, J=8 Hz); 2.40–2.30 (4H, multiplet); 1.75–1.55 (8H, multiplet); 1.43–1.42 (2H, multiplet).

EXAMPLE 29

2-(4-Fluorophenyl)-4-[3-(1-methylpiperazin-4-yl)propyl]-3-(pyridin-4-yl)-1H-pyrrole (Compound No. 1-134)

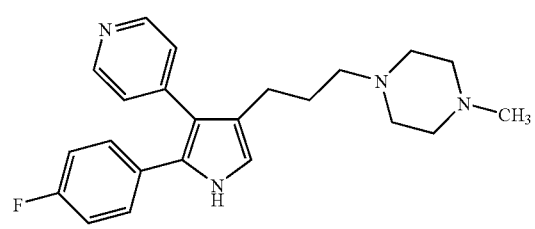

In a similar manner to that described in Example 23(v) above, a reaction was carried out using 1-methylpiperazine instead of thiomorpholine to give the title compound (yield 64%) as a pale yellow powder.

Melting point: 190–192° C. $^1$H-Nuclear magnetic resonance spectrum (400 MHz, CDCl$_3$) δ ppm: 8.65 (1H, broad singlet); 8.49 (2H, doublet, J=6 Hz); 7.16–7.12 (2H, multiplet); 7.14 (2H, doublet, J=6 Hz); 6.95 (2H, triplet, J=9 Hz); 6.73 (1H, doublet, J=3 Hz); 2.52 (2H, triplet, J=8 Hz); 2.53–2.36 (8H, multiplet); 2.36 (2H, triplet, J=8 Hz); 2.28 (3H, singlet); 1.70 (2H, quintet, J=8 Hz).

EXAMPLE 30

1-(3-Dimethylaminopropyl)-3-(4-fluorophenyl)-2-(pyridin-4-yl)-1H-pyrrole (Compound No. 2-109)

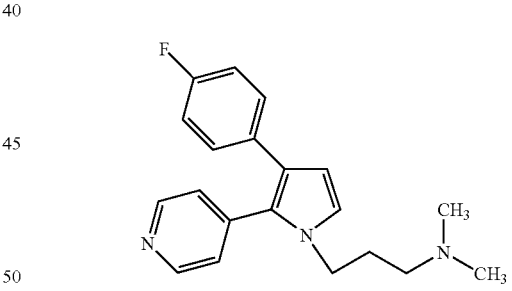

In a similar manner to the procedures described in Examples 12(i), 12(ii) and 12(iii) above, reactions were carried out using 3-dimethylaminopropylamine as a starting material instead of 4-amino-1-benzylpiperidine to give the title compound (total yield 9%) as a white powder.

Melting point: 93–95° C. $^1$H-Nuclear magnetic resonance spectrum (400 MHz, CDCl$_3$) δ ppm: 8.59 (2H, doublet, J=6 Hz); 7.18 (2H, doublet, J=6 Hz); 7.07 (2H, doublet of doublets, J=9 Hz, 6 Hz); 6.89 (2H, triplet, J=9 Hz); 6.84 (1H, doublet, J=3 Hz); 6.35 (1H, doublet, J=3 Hz); 3.93 (2H, triplet, J=7 Hz); 2.14 (2H, triplet, J=7 Hz); 2.11 (6H, singlet); 1.71 (2H, quintet, J=7 Hz).

EXAMPLE 31

2-(4-Fluorophenyl)-3,4-bis(pyridin-4-yl)-1H-pyrrole (Compound No. 1-159)

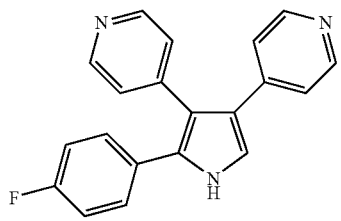

450 mg (1.15 mmol) of 2-(4-fluorophenyl)-3-(pyridin-4-yl)-4-(1,2,3,6-tetrahydropyridin-4-yl)-1H-pyrrole dihydrochloride [prepared as described in Example 10 above] were suspended in a mixture of 25 ml of xylene and 2 ml of methanol and 450 mg of 10% palladium on carbon and 320 mg (2.30 mmol) of sodium carbonate were added to the suspension. The resulting mixture was heated under reflux for 4 hours. At the end of this time, the reaction mixture was filtered and the resulting filtrate was concentrated by evaporation under reduced pressure. The residue thus obtained was purified by chromatography on a silica gel column using a 10:1:1 by volume mixture of ethyl acetate, methanol and isopropylamine as the eluant to give 192 mg (yield 53%) of the title compound as a pale yellow powder.

Melting point: 325–330° C. (decomposition) $^1$H-Nuclear magnetic resonance spectrum (500 MHz, DMSO-$d_6$) δ ppm: 11.87 (1H, broad singlet); 8.47 (2H, doublet, J=6 Hz); 8.35 (2H, doublet, J=6 Hz); 7.39 (1H, doublet, J=3 Hz); 7.21 (2H, doublet of doublets, J=9 Hz, 5 Hz); 7.16 (2H, triplet, J=9 Hz); 7.08 (2H, doublet, J=6 Hz); 7.03 (2H, doublet, J=6 Hz).

EXAMPLE 32

2-(4-Fluorophenyl)-4-(1-methyl-1,2,3,6-tetrahydropyridin-4-yl)-3-(pyridin-4-yl)-1H-pyrrole (Compound No. 1-145)

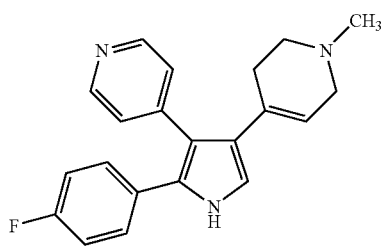

32(i) 2-(4-Fluorophenyl)-4-(4-hydroxy-1-methylpiperidin-4-yl)-3-(pyridin-4-yl)-1-triisopropylsilyl-1H-pyrrole In a similar manner to that described in Example 7(iv) above, a reaction was carried out using 1-methylpiperidine-4-one instead of pentafluoropyridine to afford the title compound (yield 47%) as a pale brown powder.

$^1$H-Nuclear magnetic resonance spectrum (500 MHz, CD$_3$OD) δ ppm: 8.22 (2H, doublet, J=6 Hz); 7.27 (2H, doublet, J=6 Hz); 7.21 (2H, doublet of doublets, J=9 Hz, 5 Hz); 6.94 (2H, triplet, J=9 Hz); 6.92 (1H, singlet); 2.56–2.42 (4H, broad multiplet); 2.22 (3H, singlet); 2.00–1.91 (2H, broad multiplet); 1.84–1.78 (2H, broad multiplet); 1.20–1.11 (3H, multiplet); 1.06 (18H, doublet, J=7 Hz).

32(ii) 2-(4-Fluorophenyl)-4-(1-methyl-1,2,3,6-tetrahydropyridin-4-yl)-3-(pyridin-4-yl)-1H-pyrrole In a similar manner to that described in Example 9(iii) above, using 2-(4-fluorophenyl)- 4-(4-hydroxy-1-methylpiperidin-4-yl)-3-(pyridin-4-yl)-1-triisopropylsilyl- 1H-pyrrole [prepared as described in step 32(i) above], dehydration with triethylsilane/trifluoroacetic acid and desilylation with tetrabutylammonium fluoride were carried out to give the title compound (yield 91%) as a pale yellow powder.

Melting point: 230–232° C. (decomposition) $^1$H-Nuclear magnetic resonance spectrum (500 MHz, DMSO-$d_6$) δ ppm: 11.36 (1H, broad singlet); 8.45 (2H, doublet, J=6 Hz); 7.19–7.14 (6H, multiplet); 6.90 (1H, doublet, J=3 Hz); 5.24–5.21 (1H, broad multiplet); 2.78–2.75 (2H, broad multiplet); 2.40 (2H, triplet, J=5 Hz); 2.18 (3H, singlet); 2.20–2.13 (2H, broad multiplet).

EXAMPLE 33

2-(4-Fluorophenyl)-4-(1-methylpiperidin-4-yl)-3-(pyridin-4-yl)-1H-pyrrole (Compound No. 1-144)

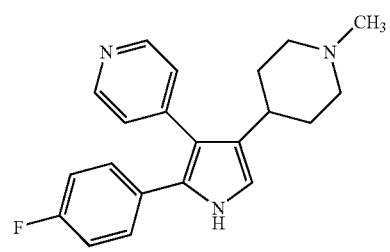

In a similar manner to that described in Example 11 above, 2-(4-fluorophenyl)-4-(1-methyl-1,2,3,6-tetrahydropyridin-4-yl)-3-(pyridin-4-yl)-1H-pyrrole [prepared as described in Example 32 above] was reduced to give the title compound (yield 85%) as a white powder.

Melting point: 284–285° C. (decomposition) $^1$H-Nuclear magnetic resonance spectrum (500 MHz, DMSO-$d_6$) δ ppm: 11.20 (1H, broad singlet); 8.48 (2H, doublet, J=6 Hz); 7.19–7.16 (4H, multiplet); 7.10 (2H, triplet, J=9 Hz); 6.76 (1H, doublet, J=2 Hz); 2.73 (2H, doublet, J=12 Hz); 2.35 (1H, triplet of triplets, J=2 Hz, 4 Hz); 2.12 (3H, singlet); 1.77 (2H, triplet, J=12 Hz); 1.61 (2H, doublet, J=12 Hz); 1.51 (2H, double doublet of triplets, J=13 Hz, 12 Hz, 4 Hz).

EXAMPLE 34

3-(4-Fluorophenyl)-2-(pyridin-4-yl)-1-(2,2,6,6-tetramethylpiperidin-4-yl)-1H-pyrrole (Compound No. 2-2523)

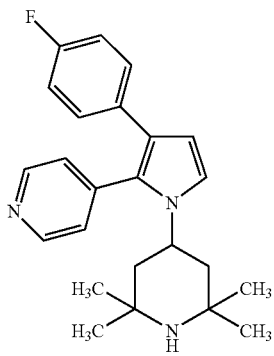

In a similar manner to the procedures described in Examples 12(i), 12(ii) and 12(iii) above, reactions were carried out using 4-amino-2,2,6,6-tetramethylpiperidine as a starting material instead of 4-amino-1-benzylpiperidine to give the title compound (total yield 12%) as a white powder.

Melting point: 118–119° C. $^1$H-Nuclear magnetic resonance spectrum (500 MHz, CDCl$_3$) δ ppm: 8.62 (2H, doublet, J=6 Hz); 7.18 (2H, doublet, J=6 Hz); 7.07 (2H, doublet of doublets, J=9 Hz, 6 Hz); 6.89 (1H, doublet, J=3 Hz); 6.88 (2H, triplet, J=9 Hz); 6.39 (1H, doublet, J=3 Hz); 4.43–4.38 (1H, multiplet); 1.86 (2H, doublet of doublets, J=13 Hz, 3 Hz); 1.55–1.38 (3H, multiplet); 1.15 (6H, singlet); 1.05 (6H, singlet).

EXAMPLE 35

2-(4-Fluorophenyl)-3-(pyridin-4-yl)-4-(quinuclidin-2-en-3-yl-1H-pyrrole (Compound No. 1-2540)

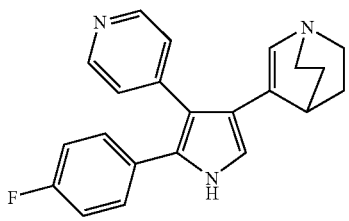

35(i) (±)-2-(4-Fluorophenyl)-4-(3-hydroxyquinuclidin-3-yl)-3-(pyridin-4-yl)-1-triisopropylsilyl-1H-pyrrole In a similar manner to that described in Example 7(iv) above, a reaction was carried out using quinuclidine-3-one instead of pentafluoropyridine to afford the title compound (yield 37%) as a pale brown powder.

$^1$H-Nuclear magnetic resonance spectrum (500 MHz, DMSO-d$_6$) δ ppm: 8.25 (2H, doublet, J=6 Hz); 7.25 (2H, doublet, J=6 Hz); 7.26–7.16 (2H, broad multiplet); 7.08 (2H, triplet, J=9 Hz); 6.80 (1H, singlet); 4.82 (1H, singlet); 2.81 (1H, doublet, J=14 Hz); 2.72–2.64 (1H, broad multiplet); 2.59 (1H, doublet, J=15 Hz); 2.60–2.50 (2H, broad multiplet); 2.46–2.37 (1H, broad multiplet); 2.03–1.91 (2H, broad multiplet); 1.49–1.37 (2H, broad multiplet); 1.26–1.17 (1H, broad multiplet); 1.15–1.05 (3H, multiplet); 1.03–0.95 (18H, multiplet).

35(ii) 2-(4-Fluorophenyl)-3-(pyridin-4-yl)-4-(quinuclidin-2-en-3-yl)-1H-pyrrole 24 ml of formic acid were added to 1.20 g (2.31 mmol) of (±)-2-(4-fluorophenyl)-4-(3-hydroxyquinuclidin-3-yl)-3-(pyridin-4-yl)-1-triisopropylsilyl-1H-pyrrole [prepared as described in step 35(i) above]. The resulting mixture was stirred at 90° C. for 3 hours. After cooling to room temperature, water was added to the reaction mixture. The pH of the mixture was adjusted to greater than 10 through the addition of a 10% aqueous solution of sodium hydroxide and then the resulting mixture was extracted with ethyl acetate. The organic extract was washed with water, dried over anhydrous sodium sulfate and then concentrated by evaporation under reduced pressure. The residual solid was washed with a 1:1 by volume mixture of ethyl acetate and diethyl ether to give 568 mg (yield 71%) of the title compound as a pale brown powder.

Melting point: 246–248 (decomposition) $^1$H-Nuclear magnetic resonance spectrum (500 MHz, DMSO-d$_6$) δ ppm: 11.48 (1H, broad singlet); 8.47 (2H, doublet, J=6 Hz); 7.19–7.14 (4H, multiplet); 7.11 (2H, triplet, J=9 Hz); 7.00 (1H, doublet, J=2 Hz); 5.86 (1H, singlet); 2.77 (2H, double doublet of doublets, J=13 Hz, 9 Hz, 5 Hz); 2.61–2.56 (1H, broad multiplet); 2.40–2.31 (2H, multiplet); 1.58–1.49 (2H, broad multiplet); 1.43–1.34 (2H, broad multiplet).

EXAMPLE 36

(±)-2-(4-Fluorophenyl)-3-(pyridin-4-yl)-4-(quinuclidin-3-yl)-1H-pyrrole (Compound No. 1-2539)

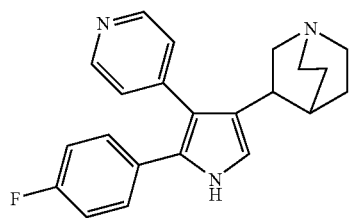

In a similar manner to that described in Example 11 above, 2-(4-fluorophenyl)-3-(pyridin-4-yl)-4-(quinuclidin-2-en-3-yl)-1H-pyrrole (prepared as described in Example 35 above) was reduced to give the title compound (yield 82%) as a white powder Melting point: 239–241° C. (decomposition) $^1$H-Nuclear magnetic resonance spectrum (500 MHz, DMSO-d$_6$) δ ppm: 11.25 (1H, broad singlet); 8.47 (2H, doublet, J=6 Hz); 7.18–7.07 (6H, multiplet); 6.93 (1H, doublet, J=2 Hz); 2.98–2.90 (1H, multiplet); 2.89–2.76 (2H, broad multiplet); 2.74–2.58 (4H, broad multiplet); 1.73–1.64 (1H, broad multiplet); 1.54–1.46 (2H, broad multiplet); 1.42–1.33 (1H, broad multiplet); 1.26–1.17 (1H, broad multiplet).

EXAMPLE 37

2-(4-Fluorophenyl)-4-(4-hydroxypiperidin-4-yl)-3-(pyridin-4-yl)-1H-pyrrole (Compound No. 1-2526)

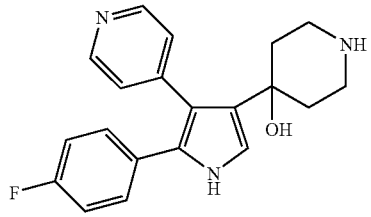

2.73 ml (2.73 mmol) of a 1M solution of tetrabutylammonium fluoride in tetrahydrofuran were added to a solution of 675 mg (1.37 mmol) of 2-(4-fluorophenyl)-4-(4-hydroxypiperidin-4-yl)-3-(pyridin-4-yl)-1-triisopropylsilyl-1H-pyrrole [prepared as described in Example 9(iii) above] in 14 ml of tetrahydrofuran and the resulting mixture was stirred at room temperature for 30 minutes. At the end of this time, the solvent was distilled off under reduced pressure. Water was added to the resulting residue and the precipitate thus obtained was collected by filtration and then washed with ethyl acetate to give 363 mg (yield 79%) of the title compound as a white powder.

Melting point: 197–199° C. $^1$H-Nuclear magnetic resonance spectrum (500 MHz, DMSO-$d_6$) δ ppm: 11.16 (1H, broad singlet); 8.42 (2H, doublet, J=6 Hz); 7.32 (2H, doublet, J=6 Hz); 7.04–7.01 (4H, multiplet); 6.79 (1H, doublet, J=2 Hz); 4.45 (1H, singlet); 2.78–2.70 (2H, multiplet); 2.55–2.45 (2H, these overlaped with protons derived from remaining DMSO-$d_6$); 1.63–1.48 (4H, multiplet).

EXAMPLE 38

2-(4-Fluorophenyl)-4-(3-methanesulfonylaminopropyl)-3-(pyridin-4-yl)-1H-pyrrole (Compound No. 1-2536)

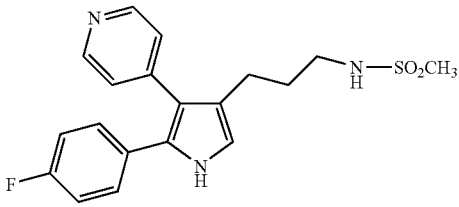

188 mg (1.08 mmol) of methanesulfonic anhydride were added to a solution of 290 mg (0.982 mmol) of 4-(3-aminopropyl)-2-(4-fluorophenyl)-3-(pyridin-4-yl)-1H-pyrrole (prepared as described in Example 1 above) in 5 ml of pyridine and the resulting mixture was allowed to stand overnight. At the end of this time, water was added to the reaction mixture, giving a precipitate which was collected by filtration and washed with ethyl acetate to give 208 mg (yield 57%) of the title compound as a pale brown powder.

Melting point: 210–214° C. $^1$H-Nuclear magnetic resonance spectrum (400 MHz, CDCl$_3$) δ ppm: 8.52 (2H, doublet, J=6 Hz); 8.23 (1H, broad singlet); 7.15–7.12 (4H, multiplet); 6.97 (2H, triplet, J=9 Hz); 6.76 (1H, doublet, J=2 Hz); 4.15 (1H, broad singlet); 3.13–3.09 (2H, multiplet); 2.89 (3H, singlet); 2.61 (2H, triplet, J=7 Hz); 1.72 (2H, quintet, J=7 Hz).

EXAMPLE 39

(±)-3-(4-Fluorophenyl)-2-(pyridin-4-yl)-1-(quinuclidin-3-yl)-1H-pyrrole (Compound No. 2-2539)

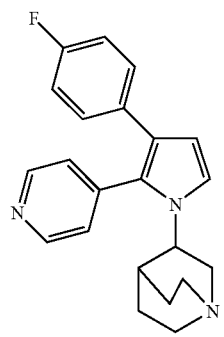

In a similar manner to the procedures described in Examples 12(i), 12(ii) and 12(iii) above, reactions were carried out using (±)-3-aminoquinuclidine as a starting material instead of 4-amino-1-benzylpiperidine to give the title compound (total yield 25%) as a pale brown powder.

Melting point: 229–230° C. $^1$H-Nuclear magnetic resonance spectrum (400 MHz, CDCl$_3$) δ ppm: 8.61 (2H, doublet, J=6 Hz); 7.16 (2H, doublet, J=6 Hz); 7.13 (1H, doublet, J=3 Hz); 7.04 (2H, doublet of doublets, J=9 Hz, 5 Hz); 6.87 (2H, triplet, J=9 Hz); 6.42 (1H, doublet, J=3 Hz); 4.24–4.15 (1H, multiplet); 3.33–3.23 (1H, multiplet); 3.22–3.05 (2H, multiplet); 2.98–2.79 (2H, multiplet); 2.78–2.67 (1H, multiplet); 1.95–1.81 (2H, multiplet); 1.71–1.58 (1H, multiplet); 1.56–1.37 (2H, multiplet).

EXAMPLE 40

(±)-3-(4-Fluorophenyl)-1-(piperidin-3-yl)methyl-2-(pyridin-4-yl)-1H-pyrrole (Compound No. 2-2520)

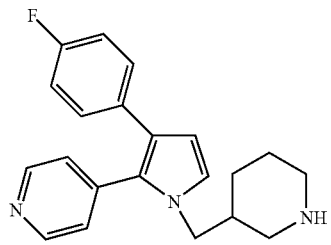

In a similar manner to the procedures described in Examples 18(i) and 18(ii) above, reactions were carried out using (±)-3-aminomethyl-(1-t-butoxycarbonyl)piperidine as a starting material instead of (±)-3-amino-1-(t-butoxycarbonyl)pyrrolidine to give the title compound (total yield 7%) as a white powder.

Melting point 134–135° C. $^1$H-Nuclear magnetic resonance spectrum (400 MHz, CDCl$_3$) δ ppm: 8.59 (2H, doublet, J=6 Hz); 7.16 (2H, doublet, J=6 Hz); 7.06 (2H, doublet of doublets, J=9 Hz, 5 Hz); 6.88 (2H, triplet, J=9

Hz); 6.79 (1H, doublet, J=3 Hz); 6.34 (1H, doublet, J=3 Hz); 3.74 (2H, doublet, J=8 Hz); 2.94–2.87 (1H, multiplet); 2.83–2.73 (1H, multiplet); 2.46 (1H, doublet of doublets, J=12 Hz, 3 Hz); 2.13 (1H, doublet of doublets, J=12 Hz, 10 Hz); 1.75–1.51 (3H, multiplet); 1.40–1.28 (1H, multiplet); 0.98–0.85 (1H, multiplet).

EXAMPLE 41 cis-1-(4-Aminocyclohexyl)-3-(4-fluorophenyl)-2-(pyridin-4-yl)-1H-pyrrole (Compound No. 2-2529)

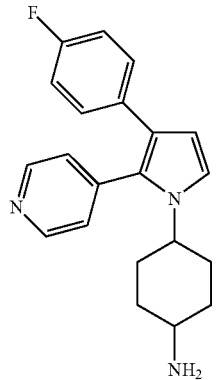

In a similar manner to the procedures described in Examples 18(i) and 18(ii) above, reactions were carried out using cis-4-(t-butoxycarbonylamino)-cyclohexylamine as a starting material instead of (±)-3-amino-1-(t-butoxycarbonyl)-pyrrolidine to give the title compound (total yield 10%) as a pale brown powder.

Melting point 163–164° C. $^1$H-Nuclear magnetic resonance spectrum (400 MHz, CDCl$_3$) δ ppm: 8.61 (2H, doublet, J=6 Hz); 7.14 (2H, doublet, J=6 Hz); 7.05 (2H, doublet of doublets, J=9 Hz, 5 Hz); 7.03 (1H, doublet, J=3 Hz); 6.87 (2H, triplet, J=9 Hz); 6.83 (1H, doublet, J=3 Hz); 3.82 (1H, triplet of triplets, J=12 Hz, 4 Hz); 3.29–3.22 (1H, multiplet); 2.22–2.07 (2H, multiplet); 1.82–1.41 (6H, multiplet).

EXAMPLE 42

3-(4-Fluorophenyl)-2-(2-methylaminopyrimidin-4-yl)-1-(piperidin-4-yl)-1H-pyrrole
(Compound No. 2-1072)

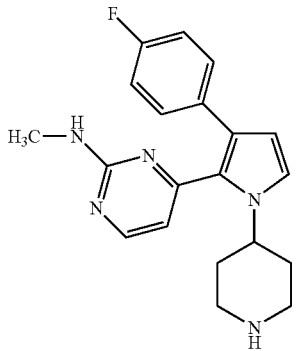

42(i) 1-(1-Benzylpiperidin-4-yl)-3-(4-fluorophenyl)-2-(2-methylthiopyrimidin-4-yl)-1H-pyrrole In a similar manner to the procedures described in Examples 12(i), 12(ii) and 12(iii) above, reactions were carried out using 4-formyl-2-methylthiopyrimidine as a starting material instead of 4-formylpyridine to give the title compound (total yield 34%) as a brown oil.

$^1$H-Nuclear magnetic resonance spectrum (400 MHz, CDCl$_3$) δ ppm: 8.21 (1H, doublet, J=5 Hz); 7.39–7.24 (5H, multiplet); 7.16 (2H, doublet of doublets, J=9 Hz, 5 Hz); 7.06 (1H, doublet, J=3 Hz); 6.96 (2H, triplet, J=9 Hz); 6.57 (1H, doublet, J=5 Hz); 6.27 (1H, doublet, J=3 Hz); 4.83–4.73 (1H, multiplet); 3.54 (2H, singlet); 3.02 (2H, doublet, J=9 Hz); 2.75 (2H, triplet, J=6 Hz); 2.46 (2H, triplet, J=6 Hz); 2.13–1.96 (2H, multiplet).

42(ii) 1-(1-benzylpiperidin-4-yl)-3-(4-fluorophenyl)-2-(2-methanesulfonylpyrimidin-4-yl)-1H-pyrrole 3.51 g (15.26 mmol) of 69–75 wt. % of m-chloroperbenzoic acid were added in small portions to a solution of 3.50 g (7.63 mmol) of 1-(1-benzylpiperidin-4-yl)-3-(4-fluorophenyl)-2-(2-methylthiopyrimidin-4-yl)-1H-pyrrole [prepared as described in step 42(i) above] in 35 ml of ethyl acetate with ice-cooling. The resulting mixture was stirred at room temperature 2 days, after which a 10% aqueous solution of sodium thiosulfate was added to the reaction mixture followed by extraction with ethyl acetate. The organic extract was washed with water and then concentrated by evaporation under reduced pressure. The residue thus obtained was purified by chromatography on a silica gel column using a 9:1 by volume mixture of dichloromethane and methanol as the eluant to give 2.48 g (yield 66%) of the title compound as a pale brown amorphous solid.

$^1$H-Nuclear magnetic resonance spectrum (400 MHz, CDCl$_3$) δ ppm: 8.35 (1H, doublet, J=5 Hz); 7.63–7.56 (2H, multiplet); 7.47–7.38 (3H, multiplet); 7.29–7.24 (1H, multiplet); 7.22 (2H, doublet of doublets, J=9 Hz, 5 Hz); 7.05 (2H, triplet, J=9 Hz); 6.90 (2H, doublet, J=5 Hz); 6.29 (1H, doublet, J=3 Hz); 5.43–5.33 (1H, multiplet); 4.46 (2H, singlet); 3.56–3.27 (4H, multiplet); 3.03–2.86 (2H, multiplet); 2.93 (3H, singlet); 2.26–2.14 (1H, multiplet); 2.10–2.01 (1H, multiplet).

42(iii) 1-(1-Benzylpiperidin-4-yl)-3-(4-fluorophenyl)-2-(2-methylaminopyrimidin-4-yl)-1H-pyrrole A mixture of 1.19 g (2.43 mmol) of 1-(1-benzylpiperidin-4-yl)-3-(4-fluorophenyl)-2-(2-methanesulfonylpyrimidin-4-yl)-1H-pyrrole [prepared as described in Step 42(ii) above] and 13 ml of a 2M solution of methylamine in tetrahydrofuran was stirred at 100° C. for 30 minutes in a sealed tube. At the end of this time, the solvent was distilled off under reduced pressure. The resulting residue was purified by chromatography on a silica gel column using a 1:2 by volume mixture of hexane and ethyl acetate as the eluant to give 260 mg (yield 24%) of the title compound as a yellow amorphous solid.

$^1$H-Nuclear magnetic resonance spectrum (500 MHz, CDCl$_3$) δ ppm: 8.03 (1H, doublet, J=5 Hz); 7.42–7.23 (5H, multiplet); 7.18 (2H, doublet of doublets, J=9 Hz, 5 Hz); 7.00 (1H, doublet, J=3 Hz); 6.94 (2H, triplet, J=9 Hz); 6.26 (1H, doublet, J=3 Hz); 6.23 (1H, doublet, J=5 Hz); 5.14–5.04 (1H, multiplet); 4.82–4.68 (1H, multiplet); 3.53 (2H, singlet); 3.10–2.95 (5H, multiplet); 2.12–1.96 (6H, multiplet).

42(iv) 3-(4-Fluorophenyl)-2-(2-methylaminopyrimidin-4-yl)-1-(piperidin-4-yl)-1H-pyrrole In a similar manner to that described in Example 9(ii) above, 1-(1-benzylpiperidin-4-yl)-3-(4-fluorophenyl)-2-(2-methylaminopyrimidin-4-yl)-1H-pyrrole [prepared as described in step 42(iii) above] was debenzylated to give the title compound (yield 39%) as a pale yellow powder.

Melting point: 189–191° C. $^1$H-Nuclear magnetic resonance spectrum (500 Mz, CDCl$_3$) δ ppm: 8.05 (1H, doublet, J=5 Hz); 7.19 (2H, doublet of doublets, J=9 Hz, 5 Hz); 7.00 (1H, doublet, J=3 Hz); 6.95 (2H, triplet, J=9 Hz); 6.28 (1H, doublet, J=3 Hz); 6.24 (1H, doublet, J=5 Hz); 5.14–5.04 (1H, multiplet); 4.96–4.81 (1H, multiplet); 3.24 (1H, doublet, J=12 Hz); 3.04 (3H, doublet, J=5 Hz); 2.70 (2H, doublet of quartets, J=12 Hz, 2 Hz); 2.14 (2H, doublet, J=12 Hz); 1.91 (2H, doublet of quartets, J=12 Hz, 4 Hz).

EXAMPLE 43

(±)-2-(4-Fluorophenyl)-4-(8-methyl-8-azabicyclo [3.2.1]oct-2-en-3-yl)-3-(pyridin-4-yl)-1H-pyrrole (Compound No. 1-2544)

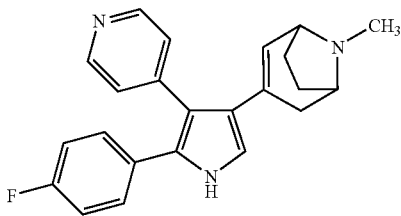

43(i) 2-(4-Fluorophenyl)-4-(3-hydroxy-8-methyl-8-azabicyclo[3.2.1]octan-3-yl)-3-(pyridin-4-yl)-1-triisopropylsilyl-1H-pyrrole In a similar manner to that described in Example 7(iv) above, a reaction was carried out using 8-methyl-8-azabicyclo[3.2.1]octane-3-one instead of pentafluoropyridine to give a mixture of isomers of the title compound (yield 49%) as a pale brown powder.

From the mixture thus obtained, isomer A (Rf value=0.45, pale brown powder) and isomer B (Rf value=0.40, pale brown powder) were separated by chromatography on an alumina column using a 10:1 by volume mixture of ethyl acetate and methanol as the eluant (the ratio of isomer A:isomer B was 85:90 by weight).

isomer A $^1$H-Nuclear magnetic resonance spectrum (500 MHz, CD$_3$OD) δ ppm: 8.21 (2H, doublet, J=6 Hz); 7.26 (2H, doublet, J=6 Hz); 7.17 (2H, doublet of doublets, J=9 Hz, 5 Hz); 6.92 (2H, triplet, J=9 Hz); 6.84 (1H, singlet); 3.14–3.06 (1H, broad multiplet); 2.28–2.15 (4H, multiplet); 2.20 (3H, singlet); 1.95–1.84 (4H, broad multiplet); 1.19–1.09 (3H, multiplet); 1.05 (18H, doublet, J=7 Hz).

isomer B $^1$H-Nuclear magnetic resonance spectrum (500 MHz, CD$_3$OD) δ ppm: 8.22 (2H, doublet, J=6 Hz); 7.27 (2H, doublet, J=6 Hz); 7.18 (2H, doublet of doublets, J=9 Hz, 5 Hz); 6.93 (2H, triplet, J=9 Hz); 6.85 (1H, singlet); 3.38 (1H, broad singlet); 2.41 (3H, singlet); 2.38–2.27 (4H, multiplet); 2.06–1.95 (4H, broad multiplet); 1.20–1.10 (3H, multiplet); 1.06 (18H, doublet, J=7 Hz).

43(ii) (±)-2-(4-Fluorophenyl)-4-(8-methyl-8-azabicyclo[3.2.1]oct-2-en-3-yl)-3-(pyridin-4-yl)-1H-pyrrole In a similar manner to that described in Example 9(iii) above, 2-(4-fluorophenyl)-4-(3-hydroxy-8-methyl-8-azabicyclo[3.2.1]octan-3-yl)-3-(pyridin-4-yl)-1-triisopropylsilyl-1H-pyrrole (a mixture of isomers A and B, prepared as described in step 43(i) above] was subjected to dehydration using triethylsilane and trifluoroacetic acid followed by desilylation (deprotection) with tetrabutylammonium fluoride to give the title compound (yield 83%) as a white powder.

Melting point: 243–245° C. $^1$H-Nuclear magnetic resonance spectrum (500 MHz, CD$_3$OD) δ ppm: 8.39 (2H, doublet, J=7 Hz); 7.25 (2H, doublet, J=6 Hz); 7.16 (2H, doublet of doublets, J=9 Hz, 5 Hz); 6.99 (2H, triplet, J=9 Hz); 6.83 (1H, singlet); 5.45 (1H, broad doublet, J=6 Hz); 3.28–3.24 (1H, broad multiplet); 3.22 (1H, triplet, J=6 Hz); 2.68 (1H, broad doublet, J=16 Hz); 2.37 (3H, singlet); 2.20–2.11 (1H, broad multiplet); 2.09–1.99 (1H, multiplet); 1.90–1.80 (2H, broad multiplet); 1.69–1.61 (1H, multiplet).

EXAMPLE 44

2-(4-Fluorophenyl)-4-(8-methyl-8-azabicyclo[3.2.1] octan-3-yl)-3-(pyridin-4-yl)-1H-pyrrole (Compound No. 1-2542)

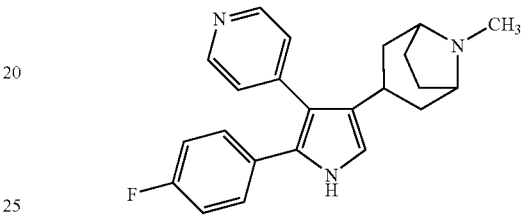

In a similar manner to that described in Example 11 above, (±)-2-(4-fluorophenyl)-4-(8-methyl-8-azabicyclo [3.2.1]oct-2-en-3-yl)-3-(pyridin-4-yl)-1H-pyrrole [prepared as described in Example 43 above] was reduced to give the title compound (yield 57%) as a white powder.

Melting point: 233–234° C. (decomposition) $^1$H-Nuclear magnetic resonance spectrum (500 MHz, DMSO-d$_6$) δ ppm: 11.13 (1H, broad singlet); 8.49 (2H, doublet, J=6 Hz); 7.14–7.05 (6H, multiplet); 6.76 (1H, doublet, J=3 Hz); 3.03–2.85 (3H, broad multiplet); 2.16–2.07 (2H, multiplet); 2.04 (3H, singlet); 1.98–1.90 (2H, multiplet); 1.45–1.36 (2H, multiplet); 1.24–1.14 (2H, multiplet).

EXAMPLE 45

(±)-4-(8-Azabicyclo[3.2.1]oct-2-en-3-yl)-2-(4-fluorophenyl)-3-(pyridin-4-yl)-1H-pyrrole (Compound No. 1-2543)

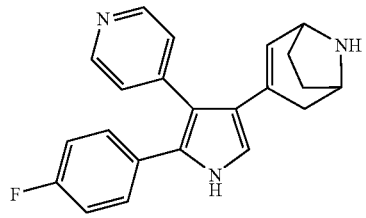

In a similar manner to the procedures described in Examples 9(i), 9(ii) and 9(iii) above, coupling, debenzylation, dehydration and desilylation reactions were carried out using 8-benzyl-8-azabicyclo[3.2.1]octane-3-one as a starting material instead of 1-benzylpiperidine-4-one to give the title compound (yield 35%) as a pale yellow powder.

Melting point: 212–213° C. $^1$H-Nuclear magnetic resonance spectrum (500 MHz, DMSO-d$_6$) δ ppm: 11.32 (1H, broad singlet); 8.45 (2H, doublet, J=6 Hz); 7.17–7.07 (6H, multiplet); 6.81 (1H, doublet, J=3 Hz); 5.45 (1H, doublet, J=6 Hz); 3.53–3.46 (1H, multiplet); 3.38–3.32 (1H, multiplet); 2.55–2.48 (1H, broad multiplet); 1.86–1.69 (3H, multiplet); 1.66–1.55 (1H, multiplet); 1.52–1.44 (1H, multiplet).

EXAMPLE 46

4-(8-Azabicyclo[3.2.1]octan-3-yl)-2-(4-fluorophenyl)-3-(pyridin-4-yl)-1H-pyrrole (Compound No. 1-2541)

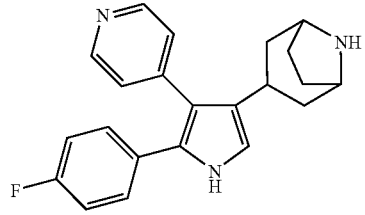

In a similar manner to that described in Example 11 above, (±)-4-(8-azabicyclo[3.2.1]oct-2-en-3-yl)-2-(4-fluorophenyl)-3-(pyridin-4-yl)-1H-pyrrole [prepared as described in Example 45 above] was reduced to give the title compound (yield 74%) as a white powder.

Melting point: 235–237° C. (decomposition) $^1$H-Nuclear magnetic resonance spectrum (500 MHz, DMSO-$d_6$) δ ppm: 11.14 (1H, broad singlet); 8.48 (2H, doublet, J=6 Hz); 7.15–7.05 (6H, multiplet); 6.73 (1H, doublet, J=2 Hz); 3.18–3.15 (2H, multiplet); 2.86–2.78 (1H, multiplet); 2.05–1.96 (2H, multiplet); 1.63–1.56 (2H, multiplet); 1.50–1.43 (2H, multiplet); 1.17–1.08 (2H, multiplet).

EXAMPLE 47

2-(4-Fluorophenyl)-3-(pyridin-4-yl)-4-(1,2,3,6-tetrahydro-2,2,6,6-tetramethylpyridin-4-yl)-1H-pyrrole (Compound No. 1-2650)

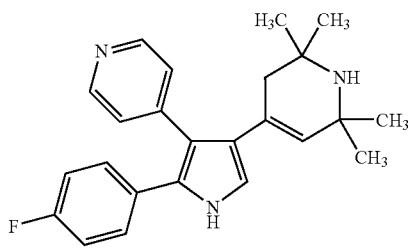

In a similar manner to the procedures described in Examples 9(i) and 9(iii) above, coupling, dehydration and desilylation reactions were carried out using 2,2,6,6-tetramethylpiperidine-4-one as a starting material instead of 1-benzylpiperidine-4-one to give the title compound (yield 50%) as a white powder.

Melting point: 258–259° C. $^1$H-Nuclear magnetic resonance spectrum (500 MHz, DMSO-$d_6$) δ ppm: 11.37 (1H, broad singlet); 8.42 (2H, doublet, J=6 Hz); 7.19–7.09 (6H, multiplet); 6.86 (1H, doublet, J=2 Hz); 5.04–5.02 (1H, broad multiplet); 1.93 (2H, singlet); 1.25–1.15 (1H, broad singlet); 04 (6H, singlet); 0.94 (6H, singlet).

EXAMPLE 48

2-(4-Fluorophenyl)-3-(pyridin-4-yl)-4-(2.2.6.6-tetramethylpiperidin-4-yl)-1H-pyrrole (Compound No. 1-2523)

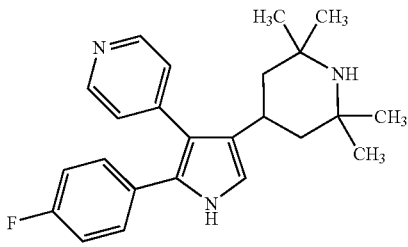

In a similar manner to that described in Example 11 above, 2-(4-fluorophenyl)-3-(pyridin-4-yl)-4-(1,2,3,6-tetrahydro-2,2,6,6-tetramethylpyridin-4-yl)-1H-pyrrole [prepared as described in Example 47 above] was reduced to give the title compound (yield 77%) as a white powder.

Melting point: 242–243° C. $^1$H-Nuclear magnetic resonance spectrum (500 MHz, DMSO-$d_6$) δ ppm: 11.18 (1H, broad singlet); 8.47 (2H, doublet, J=6 Hz); 7.21–7.15 (4H, multiplet); 7.11 (2H, triplet, J=9 Hz); 6.70 (1H, doublet, J=2 Hz); 2.95 (1H, triplet of triplets, J=13 Hz, 3 Hz); 1.50 (2H, doublet of doublets, J=13 Hz, 3 Hz); 1.09 (2H, triplet, J=13 Hz); 1.01 (6H, singlet); 0.96 (6H, singlet).

EXAMPLE 49

(±)-2-(4-Fluorophenyl)-4-(2-methyl-1,2,3,6-tetrahydropyridin-4-yl)-3-(pyridin-4-yl)-1H-pyrrole (Compound No. 1-2707)

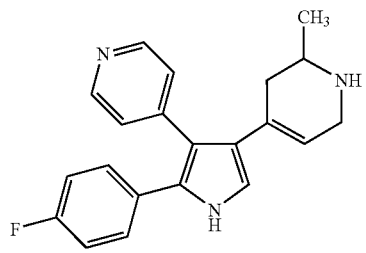

In a similar manner to the procedures described in Examples 9(i), 9(ii) and 9(iii) above, coupling, debenzylation, dehydration and desilylation reactions were carried out using (±)-1-benzyl-2-methylpiperidine-4-one as a starting material instead of 1-benzylpiperidine-4-one to afford a mixture of the title compound and the (6-methyl-1,2,3,6-tetrahydropyridin-4-yl) isomer thereof (which is the title compound of Example 50). The mixture was separated by chromatography on a silica gel column using a 25:1 by volume mixture of ethyl acetate and isopropylamine as the eluant to give the title compound (yield 3%, Rf value=0.50) as a white powder.

Melting point: 178–180° C. (decomposition) $^1$H-Nuclear magnetic resonance spectrum (500 MHz, CD$_3$OD) δ ppm: 8.36 (2H, doublet, J=6 Hz); 7.24 (2H, doublet, J=6 Hz); 7.17 (2H, doublet of doublets, J=9 Hz, 6 Hz); 7.00 (2H, triplet, J=9 Hz); 6.85 (1H, singlet); 5.40–5.35 (1H, broad multiplet); 3.46–3.38 (1H, multiplet); 3.36–3.28 (1H, multiplet);

2.96–2.88 (1H, multiplet); 2.23–2.15 (1H, multiplet); 2.06–1.97 (1H, multiplet); 1.14 (3H, doublet, J=6 Hz).

EXAMPLE 50

(±)-2-(4-Fluorophenyl)-4-(6-methyl-1,2,3,6-tetrahydropyridin-4-yl)-3-(pyridin-4-yl)-1H-pyrrole (Compound No. 1-2665)

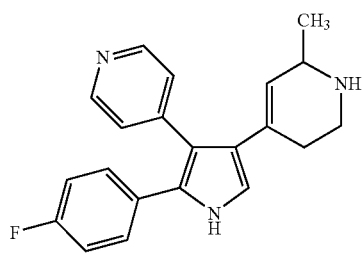

The title compound (yield 5%, Rf value=0.45) was obtained as a white powder during the chromatography performed in Example 49 above.

Melting point: 201–204° C. (decomposition) $^1$H-Nuclear magnetic resonance spectrum (500 MHz, CD$_3$OD) δ ppm: 8.36 (2H, doublet, J=6 Hz); 7.24 (2H, doublet, J=6 Hz); 7.18 (2H, doublet of doublets, J=9 Hz, 6 Hz); 7.00 (2H, triplet, J=9 Hz); 6.86 (1H, singlet); 5.24–5.20 (1H, multiplet); 3.48–3.40 (1H, multiplet); 3.16–3.09 (1H, multiplet); 2.90–2.82 (1H, multiplet); 2.37–2.27 (1H, multiplet); 2.18–2.10 (1H, multiplet); 1.05 (3H, doublet, J=7 Hz).

EXAMPLE 51

(±)-2-(4-Fluorophenyl)-4-(2-methylpiperidin-4-yl)-3-(pyridin-4-yl)-1H-pyrrole (Compound No. 1-2522)

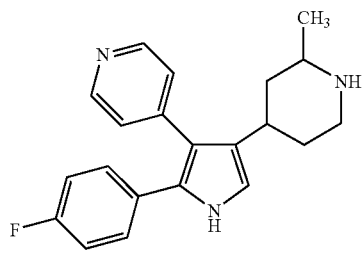

In a similar manner to the procedure in Example 11 above, (±)-2-(4-fluorophenyl)-4-(6-methyl-1,2,3,6-tetrahydropyridin-4-yl)-3-(pyridin-4-yl)-1H-pyrrole [prepared as described in Example 50 above] was reduced to give the title compound (yield 83%) as a pale yellow powder.

Melting point: 198–205° C. $^1$H-Nuclear magnetic resonance spectrum (500 MHz, CDCl$_3$) δ ppm: 8.53 (2H, doublet, J=4 Hz); 8.33 (0.5H, broad singlet); 8.31 (0.5H, broad singlet); 7.14 (2H, doublet, J=4 Hz); 7.11 (2H, doublet of doublets, J=9 Hz, 5 Hz); 6.95 (2H, triplet, J=9 Hz); 6.79 (0.5H, doublet, J=3 Hz); 6.74 (0.5H, doublet, J=3 Hz); 3.25–2.63 (4H, multiplet); 1.74–1.43 (5H, multiplet); 1.11 (1.5H, doublet, J=7 Hz); 1.07 (1.5H, doublet, J=7 Hz).

EXAMPLE 52

4-(1-Ethyl-1,2,3,6-tetrahydropyridin-4-yl)-2-(4-fluorophenyl)-3-(pyridin-4-yl)-1H-pyrrole (Compound No. 1-2629)

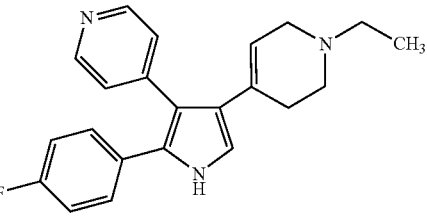

In a similar manner to the procedures described in Examples 9(i) and 9(iii) above, coupling, dehydration and desilylation reactions were carried out using 1-ethylpiperidine-4-one as a starting material instead of 1-benzylpiperidine-4-one to give the title compound (yield 55%) as a pale yellow powder.

Melting point: 234–236° C. (decomposition) $^1$H-Nuclear magnetic resonance spectrum (500 MHz, DMSO-d$_6$) δ ppm: 11.36 (1H, broad singlet); 8.45 (2H, doublet, J=6 Hz); 7.18–7.08 (6H, multiplet); 6.90 (1H, doublet, J=3 Hz); 5.26–5.22 (1H, broad multiplet); 2.84–2.79 (2H, broad multiplet); 2.45 (2H, triplet, J=6 Hz); 2.34 (2H, quartet, J=8 Hz); 2.18–2.12 (2H, broad multiplet); 0.99 (3H, triplet, J=8 Hz).

EXAMPLE 53

4-(1-Ethylpiperidin-4-yl)-2-(4-fluorophenyl)-3-(pyridin-4-yl)-1H-pyrrole (Compound No. 1-146)

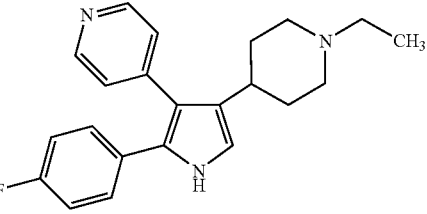

In a similar manner to the procedure described in Example 11 above, 4-(1-ethyl-1,2,3,6-tetrahydropyridin-4-yl)-2-(4-fluorophenyl)-3-(pyridin-4-yl)-1H-pyrrole [prepared as described in Example 52 above] was reduced to give the title compound (yield 95%) as a white powder.

Melting point: 262–263° C. (decomposition) $^1$H-Nuclear magnetic resonance spectrum (500 MHz, DMSO-d$_6$) δ ppm: 11.19 (1H, broad singlet); 8.48 (2H, doublet, J=6 Hz); 7.18–7.07 (6H, multiplet); 6.76 (1H, doublet, J=2 Hz); 2.87–2.79 (2H, broad multiplet); 2.37 (1H, triplet of triplets, J=12 Hz, 4 Hz); 2.26 (2H, quartet, J=7 Hz); 1.80–1.71 (2H, broad multiplet); 1.66–1.59 (2H, broad multiplet); 1.55–1.43 (2H, multiplet); 0.96 (3H, triplet, J=7 Hz).

EXAMPLE 54

2-(4-Fluorophenyl)-4-(1-isopropyl-1,2,3,6-tetrahydropyridin-4-yl)-3-(pyridin-4-yl)-1H-pyrrole (Compound No. 1-2632)

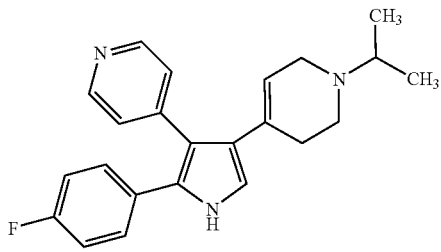

In a similar manner to the procedures described in Examples 9(i) and 9(iii) above, coupling, dehydration and desilylation reactions were carried out using 1-isopropylpiperidine-4-one as a starting material instead of 1-benzylpiperidine-4-one to give the title compound (yield 42%) as a pale yellow powder.

Melting point: 237–240° C. (decomposition) $^1$H-Nuclear magnetic resonance spectrum (500 MHz, DMSO-$d_6$) δ ppm: 11.35 (1H, broad singlet); 8.45 (2H, doublet, J=6 Hz); 7.18–7.08 (6H, multiplet); 6.88 (1H, doublet, J=3 Hz); 5.28–5.24 (1H, broad multiplet); 2.94–2.89 (2H, broad multiplet); 2.64 (1H, septet, J=6 Hz); 2.49 (2H, triplet, J=6 Hz); 2.15–2.09 (2H, broad multiplet); 0.96 (6H, doublet, J=6 Hz).

EXAMPLE 55

2-(4-Fluorophenyl)-4-(1-isopropylpiperidin-4-yl)-3-(pyridin-4-yl)-1H-pyrrole (Compound No. 1-2633)

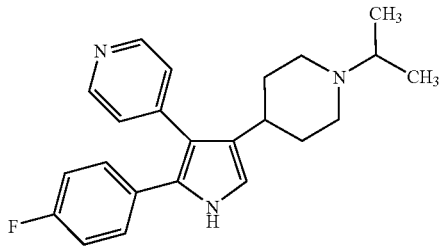

In a similar manner to that described in Example 11 above, 2-(4-fluorophenyl)-4-(1-isopropyl-1,2,3,6-tetrahydropyridin-4-yl)-3-(pyridin-4-yl)-1H-pyrrole (prepared as described in Example 54 above) was reduced to give the title compound (yield 80%) as white needle-like crystals.

Melting point: 264–266° C. (decomposition) $^1$H-Nuclear magnetic resonance spectrum (500 MHz, DMSO-$d_6$) δ ppm: 11.18 (1H, broad singlet); 8.48 (2H, doublet, J=6 Hz); 7.17–7.06 (6H, multiplet); 6.76 (1H, singlet); 2.77–2.70 (2H, broad multiplet); 2.63 (1H, septet, J=6 Hz); 2.35 (1H, triplet of triplets, J=12 Hz, 4 Hz); 2.06–1.97 (2H, multiplet); 1.67–1.60 (2H, broad multiplet); 1.52–1.40 (2H, multiplet); 0.92 (6H, doublet, J=6 Hz).

EXAMPLE 56

2-(4-Fluorophenyl)-4-(1-propyl-1,2,3,6-tetrahydropyridin-4-yl)-3-(pyridin-4-yl)-1H-pyrrole (Compound No. 1-2630)

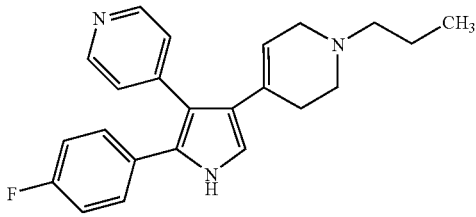

In a similar manner to the procedures described in Examples 9(i) and 9(iii) above, coupling, dehydration and desilylation reactions were carried out using 1-propylpiperidine-4-one as a starting material instead of 1-benzylpiperidine-4-one to give the title compound (yield 46%) as a white powder.

Melting point: 236–238° C. (decomposition) $^1$H-Nuclear magnetic resonance spectrum (500 MHz, DMSO-$d_6$) δ ppm: 11.36 (1H, broad singlet); 8.45 (2H, doublet, J=6 Hz); 7.18–7.08 (6H, multiplet); 6.90 (1H, doublet, J=3 Hz); 5.26–5.23 (1H, multiplet); 2.84–2.79 (2H, multiplet); 2.44 (2H, triplet, J=5 Hz); 2.25 (2H, triplet, J=8 Hz); 2.17–2.11 (2H, broad multiplet); 1.43 (2H, triplet of quartets, J=8 Hz, 8 Hz); 0.84 (3H, triplet, J=8 Hz).

EXAMPLE 57

4-(1-Benzyl-1,2,3,6-tetrahydropyridin-4-yl)-2-(4-fluorophenyl)-3-(pyridin-4-yl)-1H-pyrrole (Compound No. 1-2644)

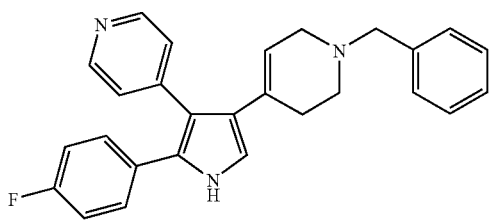

In a similar manner to that described in Example 9(iii) above, dehydration and desilylation reactions were carried out using 4-(1-benzyl-4-hydroxypiperidin-4-yl)-2-(4-fluorophenyl)-3-(pyridin-4-yl)-1-triisopropylsilyl-1H-pyrrole [prepared as described in Example 9(i) above] to give the title compound (yield 88%) as a pale yellow powder.

Melting point: 217–219° C. (decomposition) $^1$H-Nuclear magnetic resonance spectrum (500 MHz, DMSO-$d_6$) δ ppm: 11.37 (1H, broad singlet); 8.45 (2H, doublet, J=6 Hz); 7.34–7.21 (5H, multiplet); 7.18–7.08 (6H, multiplet); 6.90 (1H, doublet, J=3 Hz); 5.23–5.21 (1H, broad multiplet); 3.50 (2H, singlet); 2.86–2.81 (2H, broad multiplet) 2.48 (2H, triplet, J=6 Hz); 2.18–2.12 (2H, broad multiplet).

EXAMPLE 58

2-(4-Fluorophenyl)-4-(1-phenethyl-1,2,3,6-tetrahydropyridin-4-yl)-3-(pyridin-4-yl)-1H-pyrrole (Compound No. 1-2645)

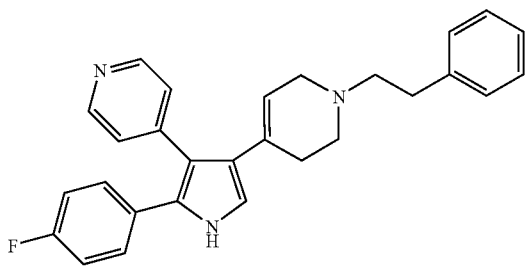

In a similar manner to the procedures described in Examples 9(i) and 9(iii) above, coupling, dehydration and desilylation reactions were carried out using 1-phenethylpiperidine-4-one as a starting material instead of 1-benzylpiperidine-4-one to give the title compound (yield 46%) as a pale brown powder.

Melting point: 219–221° C. (decomposition) $^1$H-Nuclear magnetic resonance spectrum (500 MHz, DMSO-$d_6$) δ ppm: 11.37 (1H, broad singlet); 8.45 (2H, doublet, J=6 Hz); 7.29–7.09 (1H, multiplet); 6.90 (1H, doublet, J=3 Hz); 5.28–5.24 (1H, broad multiplet); 2.95–2.89 (2H, broad multiplet); 2.76–2.69 (2H, multiplet); 2.57–2.51 (4H, multiplet); 2.19–2.12 (2H, broad multiplet).

EXAMPLE 59

(±)-2-(4-Fluorophenyl)-4-(1,2,3,5,8,8a-hexahydroindolizin-7-yl)-3-(pyridin-4-yl)-1H-pyrrole (Compound No. 1-26541)

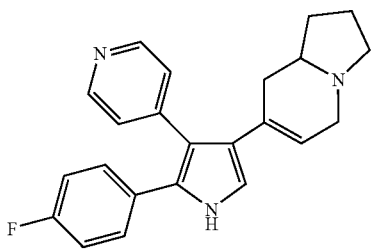

In a similar manner to the procedures described in Examples 9(i) and 9(iii) above, coupling, dehydration and desilylation reactions were carried out using (±)-1,2,3,5,6,7,8,8a-octahydroindolizine-7-one as a starting material instead of 1-benzylpiperidine-4-one to give a mixture of the title compound and the (1,2,3,5,6,8a-hexahydroindolizin-7-yl) isomer thereof (which is the compound of Example 60 below). The mixture was separated by chromatography on a silica gel column using a 10:1:1 by volume mixture of ethyl acetate, methanol and isopropylamine as the eluant to give the title compound (yield 24%, Rf value=0.50) as a white powder.

Melting point: 220–222° C. (decomposition) $^1$H-Nuclear magnetic resonance spectrum (500 MHz, CD$_3$OD) δ ppm: 8.36 (2H, doublet, J=6 Hz); 7.24 (2H, doublet, J=6 Hz); 7.17 (2H, doublet of doublets, J=9 Hz, 6 Hz); 7.00 (2H, triplet, J=9 Hz); 6.85 (1H, singlet); 5.41–5.37 (1H, multiplet); 3.47–3.40 (1H, multiplet); 3.18–3.12 (1H, multiplet); 2.84–2.77 (1H, multiplet); 2.40–2.26 (2H, multiplet); 2.23–2.11 (2H, multiplet); 2.05–1.97 (1H, multiplet); 1.90–1.75 (2H, multiplet); 1.46–1.36 (1H, multiplet).

EXAMPLE 60

(±)-2-(4-Fluorophenyl)-4-(1,2,3,5,6,8a-hexahydroindolizin-7-yl)-3-(pyridin-4-yl)-1H-pyrrole (Compound No. 1-2653)

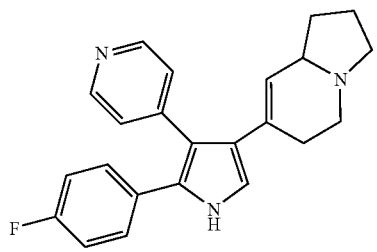

The title compound (yield 27%, Rf value=0.40) was obtained as a pale yellow powder during the chromatography performed in Example 59 above.

Melting point: 188–190° C. (decomposition) $^1$H-Nuclear magnetic resonance spectrum (500 MHz, CD$_3$OD) δ ppm: 8.37 (2H, doublet, J=6 Hz); 7.23 (2H, doublet, J=6 Hz); 7.18 (2H, doublet of doublets, J=9 Hz, 5 Hz); 7.00 (2H, triplet, J=9 Hz); 6.86 (1H, singlet); 5.34–5.30 (1H, broad multiplet); 3.38–3.30 (1H, multiplet); 2.99–2.86 (2H, multiplet); 2.82–2.73 (2H, multiplet); 2.40–2.31 (1H, multiplet); 2.25–2.16 (1H, multiplet); 1.97–1.86 (2H, multiplet); 1.84–1.73 (1H, multiplet); 1.48–1.38 (1H, multiplet).

EXAMPLE 61

(±)-4-(1,6-Dimethyl-1,2,3,6-tetrahydropyridin-4-yl)-2-(4-fluorophenyl)-3-(pyridin-4-yl)-1H-pyrrole (Compound No. 1-2666)

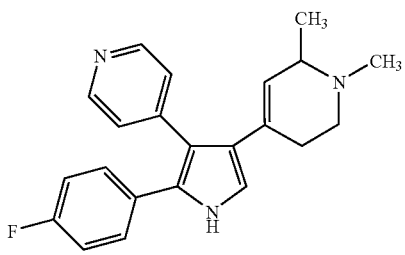

In a similar manner to the procedures described in Examples 9(i) and 9(iii) above, coupling, dehydration and desilylation reactions were carried out using (±)-1,2-dimethylpiperidine-4-one as a starting material instead of 1-benzylpiperidine-4-one to give a mixture of the title compound and the (1,2-dimethyl-1,2,3,6-tetrahydropyridin-4-yl) isomer thereof (which is the compound of Example 62 below). The mixture was separated by chromatography on a silica gel column using a 99:1 by volume mixture of ethyl acetate and isopropylamine as the eluant to give the title compound (yield 10%, Rf value=0.40) as a pale yellow powder.

Melting point: 208–209° C. (decomposition) ¹H-Nuclear magnetic resonance spectrum (500 MHz, CDCl₃) δ ppm: 8.47 (2H, doublet, J=6 Hz); 8.29–8.10 (1H, broad singlet); 7.17 (2H, doublet, J=6 Hz); 7.13 (2H, doublet of doublets, J=9 Hz, 5 Hz); 6.97 (2H, triplet, J=9 Hz); 6.83 (1H, doublet, J=3 Hz); 5.19 (1H, singlet); 2.90–2.83 (1H, multiplet); 2.55–2.32 (2H, multiplet); 2.37 (3H, singlet); 2.17–2.07 (2H, multiplet); 1.05 (3H, doublet, J=7 Hz).

EXAMPLE 62

(±)-4-(1,2-Dimethyl-1,2,3,6-tetrahydropyridin-4-yl)-2-(4-fluorophenyl)-3-(pyridin-4-yl)-1H-pyrrole (Compound No. 1-2708)

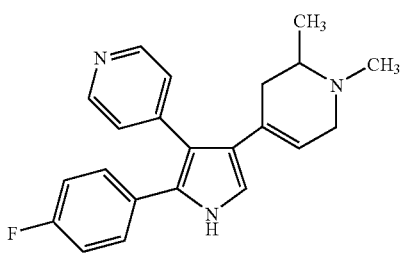

The title compound (yield 14%, Rf value=0.30) was obtained as a pale yellow powder during the chromatography performed in Example 61 above.

Melting point: 198–201° C. ¹H-Nuclear magnetic resonance spectrum (400 MHz, CDCl₃) δ ppm: 8.47 (2H, doublet, J=6 Hz); 8.33 (1H, broad singlet); 7.17 (2H, doublet, J=6 Hz); 7.12 (2H, doublet of doublets, J=9 Hz, 5 Hz); 6.97 (2H, triplet, J=9 Hz); 6.82 (1H, doublet, J=3 Hz); 5.40 (1H, singlet); 3.22–3.18 (1H, multiplet); 2.95–2.91 (1H, multiplet); 2.57–2.46 (1H, multiplet); 2.34 (3H, singlet); 2.27–2.23 (1H, multiplet); 2.11–2.09 (1H, multiplet); 1.08 (3H, doublet, J=6 Hz).

EXAMPLE 63

2-(4-Fluorophenyl)-4-(1,2,2,6,6-pentamethyl-1,2,3,6-tetrahydropyridin-4-yl)-3-(pyridin-4-yl)-1H-pyrrole (Compound No. 1-2651)

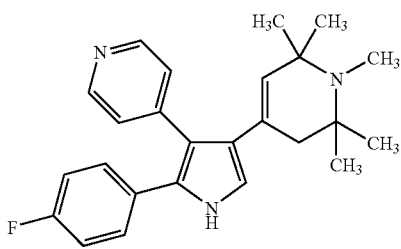

In a similar manner to the procedures described in Example 9(i) and 9(iii) above, coupling, dehydration and desilylation reactions were carried out using 1,2,2,6,6-pentamethylpiperidine-4-one as a starting material instead of 1-benzylpiperidine-4-one to give the title compound (yield 69%) as a white powder.

Melting point: 264–268° C. (decomposition) ¹H-Nuclear magnetic resonance spectrum (500 MHz, DMSO-d₆) δ ppm: 11.38 (1H, broad singlet); 8.43 (2H, doublet, J=6 Hz); 7.20–7.09 (6H, multiplet); 6.88 (1H, doublet, J=3 Hz); 4.88 (1H, singlet); 2.18 (3H, singlet); 2.07 (2H, singlet); 1.01 (6H, singlet); 0.90 (6H, singlet).

EXAMPLE 64

2-(4-Fluorophenyl)-4-(1,2,2,6,6-pentamethylpiperidin-4-yl)-3-(pyridin-4-yl)-1H-pyrrole (Compound No. 1-2652)

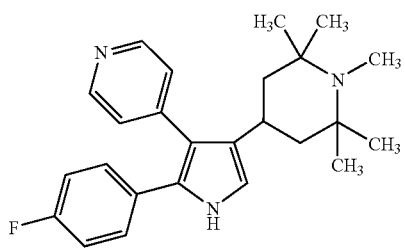

In a similar manner to that described in Example 11 above, 2-(4-fluorophenyl)-4-(1,2,2,6,6-pentamethyl-1,2,3,6-tetrahydropyridin-4-yl)-3-(pyridin-4-yl)-1H-pyrrole (prepared as described in Example 63 above) was reduced to give the title compound (yield 82%) as a white powder.

Melting point: 248–250° C. (decomposition) ¹H-Nuclear magnetic resonance spectrum (500 MHz, DMSO-d₆) δ ppm: 11.19 (1H, broad singlet); 8.47 (2H, doublet, J=6 Hz); 7.21–7.15 (4H, multiplet); 7.11 (2H, triplet, J=9 Hz); 6.73 (1H, doublet, J=2 Hz); 2.91–2.82 (1H, multiplet); 2.14 (3H, singlet); 1.54–1.47 (2H, multiplet); 1.36 (2H, triplet, J=13 Hz); 1.01 (6H, singlet); 0.86 (6H, singlet).

EXAMPLE 65

2-(4-Fluorophenyl)-3-(pyridin-4-yl)-4-(1,2,3,6-tetrahydropyridin-5-yl)-1H-pyrrole (Compound No. 1-2627)

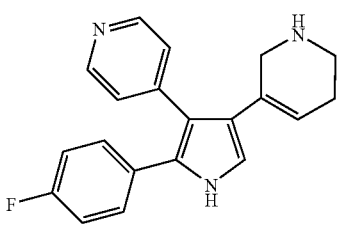

In a similar manner to the procedures described in Example 9(i), 9(ii) and 9(iii) above, coupling, debenzylation, dehydration and desilylation reactions were carried out using 1-benzylpiperidine-3-one as a starting material instead of 1-benzylpiperidine-4-one to give the title compound (yield 12%) as a pale brown powder.

Melting point: 230–233° C. (decomposition) ¹H-Nuclear magnetic resonance spectrum (500 MHz, CD₃OD) δ ppm: 8.36 (2H, doublet, J=6 Hz); 7.24 (2H, doublet, J=6 Hz); 7.18 (2H, doublet of doublets, J=9 Hz, 6 Hz); 7.01 (2H, triplet, J=9 Hz); 6.82 (1H, singlet); 5.55–5.50 (1H, broad multiplet); 3.36–3.30 (2H, multiplet); 2.90 (2H, triplet, J=6 Hz); 2.16–2.09 (2H, broad multiplet).

EXAMPLE 66

4-(3-Dimethylamino-1-propen-1-yl)-2-(4-fluorophenyl)-3-(pyridin-4-yl)-1H-pyrrole (Compound No. 1-2519)

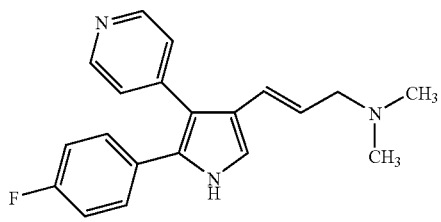

66(i) 2-(4-Fluorophenyl)-4-(3-hydroxy-1-propen-1-yl)-3-(pyridin-4-yl)-1H-pyrrole 27.6 ml (27.6 mmol) of a 1M solution of diisobutylaluminum hydride in dichloromethane were added dropwise to a solution of 3.88 g (12.5 mmol) of ethyl 3-[2-(4-fluorophenyl)-3-(pyridin-4-yl)-1H-pyrrol-4-yl]acrylate in 120 ml of dichloromethane at −78° C. with stirring. The resulting mixture was stirred at the same temperature for 3 hours. At the end of this time, the reaction mixture was added to a saturated aqueous solution of sodium hydrogencarbonate and the resulting mixture was filtered. The filtrate was extracted with dichloromethane and the organic extract was washed with water, dried over anhydrous sodium sulfate and then concentrated by evaporation under reduced pressure. The residue thus obtained was purified by chromatography on a silica gel column using a 9:1 by volume mixture of hexane and ethyl acetate as the eluant to afford 3.42 g (yield 93%) of the title compound as a pale brown powder.

$^1$H-Nuclear magnetic resonance spectrum (400 MHz, CD$_3$OD) δ ppm: 8.41 (2H, doublet, J=6 Hz); 7.23 (2H, doublet, J=6 Hz); 7.20 (2H, doublet of doublets, J=9 Hz, 5 Hz); 7.08 (1H, singlet); 7.01 (2H, triplet, J=9 Hz); 6.39 (1H, doublet, J=16 Hz); 5.98 (1H, doublet of triplets, J=16 Hz, 6 Hz); 4.09 (2H, doublet of doublets, J=6 Hz, 1 Hz).

66(ii) 3-[2-(4-Fluorophenyl)-3-(pyridin-4-yl)-1H-pyrrol-4-yl]acrylaldehyde 16.32 g of activated manganese oxide were added to a solution of 1.63 g (5.54 mmol) of 2-(4-fluorophenyl)-4-(3-hydroxy-1-propen-1-yl)-3-(pyridin-4-yl)-1H-pyrrole [prepared as described in step 66(i) above] in 80 ml of dimethylsulfoxide. The resulting mixture was stirred at room temperature for 24 hours. At the end of this time, ethyl acetate was added to the reaction mixture and then this was filtered. Water was added to the resulting filtrate and then this was extracted with ethyl acetate. The organic extract was washed with water, dried over anhydrous magnesium sulfate and then concentrated by evaporation under reduced pressure. The residue thus obtained was washed with dichloromethane to afford 1.36 g (yield 84%) of the title compound as a pale brown powder.

$^1$H-Nuclear magnetic resonance spectrum (400 MHz, CD$_3$OD-CDCl$_3$) δ ppm: 9.42 (1H, doublet, J=8 Hz); 8.51 (2H, doublet, J=6 Hz); 7.49 (1H, singlet); 7.45 (1H, doublet, J=16 Hz); 7.27 (2H, doublet, J=6 Hz); 7.22 (2H, doublet of doublets, J=9 Hz, 5 Hz); 7.01 (2H, triplet, J=9 Hz); 6.39 (11H, doublet of doublets, J=16 Hz, 8 Hz).

66(iii) 4-(3-Dimethylamino-1-propen-1-yl)-2-(4-fluorophenyl)-3-(pyridin-4-yl)-1H-pyrrole 700 mg (2.38 mmol) of 3-[2-(4-fluorophenyl)-3-(pyridin-4-yl)-1H-pyrrol-4-yl]acrylaldehyde [prepared as described in step 66 (i) above] and 1.95 g (23.8 mmol) of dimethylamine hydrochloride were dissolved in 110 ml of a 1:1 by volume mixture of methanol and tetrahydrofuran, after which 226 mg (3.59 mmol) of sodium cyanotrihydridoborate were added to the solution. The resulting mixture was stirred at room temperature for 19 hours. At the end of this time, the reaction mixture was added to a saturated aqueous solution of sodium hydrogencarbonate and then this was extracted with ethyl acetate. The organic extract was washed with water, dried over anhydrous magnesium sulfate and then concentrated by evaporation under reduced pressure. The residue thus obtained was purified by chromatography on a silica gel column using a 20:1:1 by volume mixture of ethyl acetate, methanol and isopropylamine as the eluant to give 429 mg (yield 56%) of the title compound as a white powder.

Melting point: 196–198° C. (decomposition) $^1$H-Nuclear magnetic resonance spectrum (400 MHz, CD$_3$OD-CDCl$_3$) δ ppm: 8.42 (2H, doublet, J=6 Hz); 7.23 (2H, doublet, J=6 Hz); 7.20 (2H, doublet of doublets, J=9 Hz, 5 Hz); 7.09 (1H, singlet); 6.98 (2H, triplet, J=9 Hz); 6.35 (1H, doublet, J=16 Hz); 5.88 (1H, doublet of triplets, J=16 Hz, 7 Hz); 3.04 (2H, doublet, J=7 Hz); 2.27 (6H, singlet).

EXAMPLE 67

4-(4-Aminobutyl)-2-(4-fluorophenyl)-3-(pyridin-4-yl)-1H-pyrrole (Compound No. 1-98)

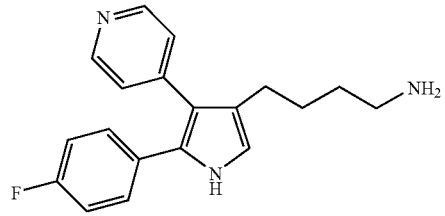

67(i) 4-(3-Cyanopropyl)-2-(4-fluorophenyl)-3-(pyridin-4-yl)-1H-pyrrole 568 mg (8.72 mmol) of potassium cyanide were added to a solution of 3.04 g (7.26 mmol) of 2-(4-fluorophenyl)-3-(pyridin-4-yl)-4-[3-(p-toluenesulfonyloxy)propyl)]1H-pyrrole [prepared as described in Example 23(iv) above] in 60 ml of N,N-dimethylformamide and the resulting mixture was stirred at 100° C. for 2 hours. After cooling to room temperature, a saturated aqueous solution of sodium hydrogencarbonate was added to the reaction mixture and then this was extracted with ethyl acetate. The organic extract was washed with water, dried over anhydrous magnesium sulfate and then concentrated by evaporation under reduced pressure. The residue thus obtained was purified by chromatography on a silica gel column using a 2:1 by volume mixture of hexane and ethyl acetate as the eluant to give 0.94 g (yield 42%) of the title compound as a pale yellow powder.

$^1$H-Nuclear magnetic resonance spectrum (500 MHz, CDCl$_3$) δ ppm: 8.53 (2H, doublet, J=6 Hz); 8.25 (1H, broad singlet); 7.13 (2H, doublet of doublets, J=9 Hz, 5 Hz); 7.12 (2H, doublet, J=6 Hz); 6.97 (2H, triplet, J=9 Hz); 6.75 (1H, doublet, J=3 Hz); 2.70 (2H, triplet, J=7 Hz); 2.28 (2H, triplet, J=7 Hz); 1.76 (2H, quintet, J=7 Hz).

67(ii) 4-(4-Aminobutyl)-2-(4-fluorophenyl)-3-(pyridin-4-yl)-1H-pyrrole

A solution of 0.94 g (3.08 mmol) of 4-(3-cyanopropyl)-2-(4-fluorophenyl)-3-(pyridin-4-yl)-1H-pyrrole [prepared as described in step 67(i) above] in 50 ml of tetrahydrofuran was added dropwise to a suspension of 468 mg (12.32 mmol) of lithium aluminum hydride in 100 ml of tetrahydrofuran at room temperature with stirring. The resulting mixture was stirred at 60° C. for 3 hours. After cooling to room temperature, 0.47 ml of a 15% aqueous solution of sodium hydroxide and 20 ml of water were successively added gradually to the reaction mixture. The resulting mixture was filtered and the filtrate thus obtained was concentrated by evaporation under reduced pressure. The resulting residue was purified by chromatography on a silica gel column using a 25:1 by volume mixture of ethyl acetate and isopropylamine as the eluant to give 410 mg (yield 43%) of the title compound as a pale red powder.

Melting point: 185–187° C. $^1$H-Nuclear magnetic resonance spectrum (400 MHz, CDCl$_3$) δ ppm: 10.02 (1H, broad singlet); 8.49 (2H, doublet, J=4 Hz); 7.19 (2H, doublet of doublets, J=9 Hz, 5 Hz); 7.14 (2H, doublet, J=4 Hz); 6.94 (2H, triplet, J=9 Hz); 6.72 (1H, doublet, J=2 Hz); 2.65 (2H, triplet, J=7 Hz); 2.51 (2H, doublet, J=7 Hz); 2.46–2.08 (2H, multiplet); 1.52–1.46 (4H, multiplet).

EXAMPLE 68

1-(2-Dimethylaminoethyl)-3-(4-fluorophenyl)-2-(pyridin-4-yl)-1H-pyrrole (Compound No. 2-108)

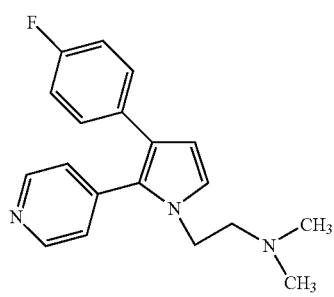

In a similar manner to the procedures described in Examples 12(i), 12(ii) and 12(iii) above, reactions were carried out using 2-dimethylaminoethylamine as a starting material instead of 4-amino-1-benzylpiperidine to give the title compound (yield 8%) as a pale brown powder.

Melting point: 70–73° C. $^1$H-Nuclear magnetic resonance spectrum (400 MHz, CDCl$_3$) δ ppm: 8.60 (2H, doublet, J=6 Hz); 7.19 (2H, doublet, J=6 Hz); 7.07 (2H, doublet of doublets, J=9 Hz, 5 Hz); 6.89 (2H, triplet, J=9 Hz); 6.88 (1H, doublet, J=3 Hz); 6.36 (1H, doublet, J=3 Hz); 3.96 (2H, triplet, J=7 Hz); 2.48 (2H, triplet, J=7 Hz); 2.15 (6H, singlet).

EXAMPLE 69

1-(2,2-Dimethyl-3-dimethylaminopropyl)-3-(4-fluorophenyl)-2-(pyridin-4-yl)-1H-pyrrole (Compound No. 2-2626)

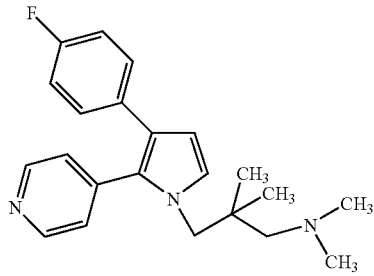

In a similar manner to the procedures described in Examples 12(i), 12(ii) and 12(iii) above, reactions were carried out using 2,2-dimethyl-3-dimethylaminopropylamine as a starting material instead of 4-amino-1-benzylpiperidine to give the title compound (yield 21%) as a white powder.

Melting point: 101–103° C. $^1$H-Nuclear magnetic resonance spectrum (400 MHz, CDCl$_3$) δ ppm: 8.58 (2H, doublet, J=6 Hz); 7.14 (2H, doublet, J=6 Hz); 7.04 (2H, doublet of doublets, J=9 Hz, 5 Hz); 6.88 (2H, triplet, J=9 Hz); 6.84 (1H, doublet, J=3 Hz); 6.32 (1H, doublet, J=3 Hz); 3.90 (2H, singlet); 2.22 (6H, singlet); 2.00 (2H, singlet); 0.64 (6H, singlet).

EXAMPLE 70

1-(8-Azabicyclo[3.2.1]octan-3-yl)-3-(4-fluorophenyl)-2-(pyridin-4-yl)-1H-pyrrole (Compound No. 2-2541)

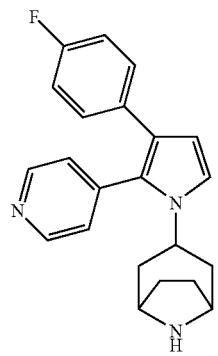

In a similar manner to the procedures described in Examples 12(i), 12(ii) and 12(iii) above, reactions were carried out using 3-amino-8-benzyl-8-azabicyclo[3.2.1]octane as a starting material instead of 4-amino-1-benzylpiperidine to afford the N-benzyl derivative of the title compound. The N-benzyl derivative was then debenzylated in a similar manner to that described in Example 9(ii) above to give the title compound (yield 90%) as a white powder.

Melting point: 204–205° C. $^1$H-Nuclear magnetic resonance spectrum (500 MHz, CDCl$_3$) δ ppm: 8.60 (2H, doublet, J=6 Hz); 7.14 (2H, doublet, J=6 Hz); 7.02 (2H, doublet of doublets, J=9 Hz, 5 Hz); 6.88 (1H, doublet, J=3 Hz); 6.86 (2H, triplet, J=9 Hz); 6.38 (1H, doublet, J=3 Hz); 4.36–4.25 (1H, multiplet); 3.67–3.53 (2H, multiplet); 2.51–2.39 (2H, multiplet); 1.90–1.67 (4H, multiplet); 1.57–1.47 (2H, multiplet).

EXAMPLE 71

(±)-3-(4-Fluorophenyl)-1-(2-methylpiperidin-4-yl)-2-(pyridin-4-yl)-1H-pyrrole (Compound No. 2-2522)

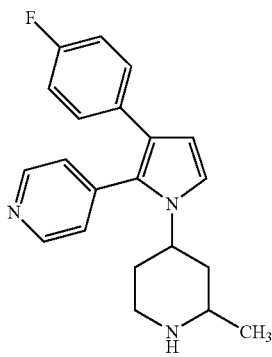

In a similar manner to the procedures described in Examples 12(i), 12(ii) and 12(iii) above, reactions were carried out using (±)-4-amino-1-benzyl-2-methylpiperidine as a starting material instead of 4-amino-1-benzylpiperidine to afford the N-benzyl derivative of the title compound. The N-benzyl derivative was then debenzylated in a similar manner to that described in Example 9(ii) above to give the title compound (yield 24%) as a white powder.

Melting point: 173–175° C. $^1$H-Nuclear magnetic resonance spectrum (500 MHz, CDCl$_3$) δ ppm: 8.61 (2H, doublet, J=5 Hz); 7.15 (1H, doublet, J=5 Hz); 7.14 (1H, doublet, J=5 Hz); 7.07–7.03 (2H, multiplet); 7.00 (0.5H, doublet, J=3 Hz); 6.95 (0.5H, doublet, J=3 Hz); 6.88 (2H, triplet, J=9 Hz); 6.38 (1H, doublet, J=3 Hz); 4.30–4.26 (0.5H, multiplet); 4.00–3.91 (0.5H, multiplet); 3.47–3.39 (0.5H, multiplet); 3.17–3.15 (0.5H, multiplet); 2.98–2.88 (1H, multiplet); 2.66–2.61 (1H, multiplet); 2.06–1.76 (4H, multiplet); 1.11 (1.5H, doublet, J=7 Hz); 1.08 (1.5H, doublet, J=7 Hz).

EXAMPLE 72

3-(4-Fluorophenyl)-2-(2-methylaminopyridin-4-yl)-1-(piperidin-4-yl)-1H-pyrrole (Compound No. 2-2042)

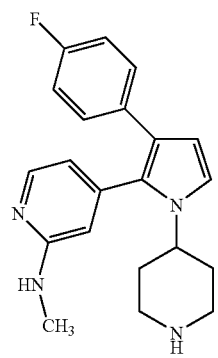

72(i) 1-(1-Benzylpiperidin-4-yl)-3-(4-fluorophenyl)-2-(2-fluoropyridin-4-yl)-1H-pyrrole In a similar manner to the procedures described in Examples 12(i), 12(ii) and 12(iii) above, reactions were carried out using 2-fluoropyridin-4-carboxyaldehyde as a starting material instead of pyridine-4-carboxyaldehyde to give the title compound (yield 49%) as a pale brown powder.

$^1$H-Nuclear magnetic resonance spectrum (400 MHz, CDCl$_3$) δ ppm: 8.20 (1H, doublet, J=5 Hz); 7.37–7.24 (5H, multiplet); 7.04 (2H, doublet of doublets, J=9 Hz, 5 Hz); 7.02–6.96 (2H, multiplet); 6.90 (2H, triplet, J=9 Hz); 6.75 (1H, singlet); 6.37 (1H, doublet, J=3 Hz); 3.89–3.78 (1H, multiplet); 3.52 (2H, singlet); 3.01–2.96 (2H, multiplet); 2.12–1.96 (4H, multiplet); 1.94–1.86 (2H, multiplet).

72(ii) 1-(1-Benzylpiperidin-4-yl)-3-(4-fluorophenyl)-2-(2-methylaminopyridin-4-yl)-1H-pyrrole A mixture of a solution of 1.50 g (3.49 mmol) of 1-(1-benzylpiperidin-4-yl)-3-(4-fluorophenyl)-2-(2-fluoropyridin-4-yl)-1H-pyrrole [prepared as described in step 72(i) above] in 30 ml of tetrahydrofuran and 50 ml (100 mmol) of a 2M solution of methylamine in tetrahydrofuran was stirred at 150° C. in an autoclave for 28 hours. At the end of this time, the solvent was distilled off from the reaction mixture under reduced pressure. Ethyl acetate and water were added to the residue, and the organic layer was separated, dried over anhydrous magnesium sulfate and then concentrated by evaporation under reduced pressure. The residue thus obtained was purified by chromatography on a silica gel column using a 20:1 by volume mixture of dichloromethane and methanol as the eluant to give 1.83 g (yield 60%) of the title compound as a pale brown amorphous solid.

$^1$H-Nuclear magnetic resonance spectrum (400 MHz, CDCl$_3$) δ ppm: 8.10 (1H, doublet, J=5 Hz); 7.35–7.23 (5H, multiplet); 7.12 (2H, doublet of doublets, J=9 Hz, 5 Hz); 6.92 (1H, doublet, J=3 Hz); 6.88 (2H, triplet, J=9 Hz); 6.48 (1H, doublet, J=5 Hz); 6.37 (1H, doublet, J=3 Hz); 6.20 (1H, singlet); 4.66–4.57 (1H, multiplet); 3.93–3.84 (1H, multiplet); 3.51 (2H, singlet); 2.99–2.91 (2H, multiplet); 2.84 (3H, doublet, J=5 Hz); 2.06–1.85 (6H, multiplet).

72(iii) 3-(4-Fluorophenyl)-2-(2-methylaminopyridin-4-yl)-1-(piperidin-4-yl)-1H-pyrrole In a similar manner to that described in Example 9(ii) above, 1-(1-benzylpiperidin-4-yl)-3-(4-fluorophenyl)-2-(2-methyl-aminopyridin-4-yl)-1H-pyrrole [prepared as described in step 72(ii) above] was debenzylated to give the title compound (yield 52%) as a white powder.

Melting point: 165–167° C. $^1$H-Nuclear magnetic resonance spectrum (400 MHz, CDCl$_3$) δ ppm: 8.12 (1H, doublet, J=5 Hz); 7.13 (2H, doublet of doublets, J=9 Hz, 5 Hz); 6.93 (1H, doublet, J=3 Hz); 6.88 (2H, triplet, J=9 Hz); 6.49 (1H, doublet of doublets, J=5 Hz, 1 Hz); 6.38 (1H, doublet, J=3 Hz); 6.21 (1H, doublet, J=1 Hz); 4.65–4.55 (1H, multiplet); 4.02–3.97 (1H, multiplet); 3.16 (2H, broad doublet, J=12 Hz); 2.85 (3H, doublet, J=5 Hz); 2.60 (2H, doublet of triplets, J=12 Hz, 3 Hz); 1.99–1.81 (4H, multiplet).

EXAMPLE 73

2-(4-Fluorophenyl)-3-[2-(1(S)-phenylethylamino)pyridin-4-yl]-4-(1,2,3,6-tetrahydropyridin-4-yl)-1H-pyrrole (Compound No. 1-2600)

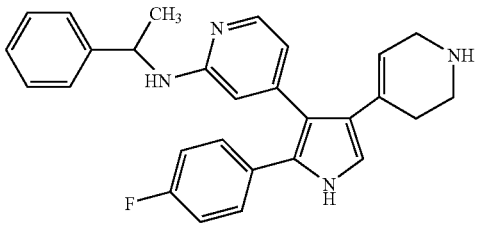

73(i) 4-Bromo-2-(4-fluorophenyl)-3-(2-fluoropyridin-4-yl)-1-triisopropylsilyl-1H-pyrrole In a similar manner to the procedures described in Examples 1(i), 7(i), 7(ii) and 7(iii) above, a pyrrole ring-forming reaction, a decarboxylation reaction, a silylation reaction and a bromination reaction were carried out using ethyl 3-(2-fluoropyridin-4-yl)acrylate as a starting material instead of ethyl 3-(4-pyridyl)acrylate to give the title compound (yield 48%) as a pale yellow powder.

$^1$H-Nuclear magnetic resonance spectrum (400 MHz, DMSO-d$_6$) δ ppm: 8.05 (1H, doublet, J=5 Hz); 7.38 (2H, doublet of doublets, J=9 Hz, 5 Hz); 7.20 (2H, triplet, J=9 Hz); 7.15 (1H, singlet); 7.01–6.97 (1H, multiplet); 6.78 (1H, singlet); 1.20–1.07 (3H, multiplet); 0.99 (18H, doublet, J=7 Hz).

73(ii) 4-(1-Allyloxycarbonyl-1,2,3,6-tetrahydropyridin-4-yl)-2-(4-fluorophenyl)-3-(2-fluoropyridin-4-yl)-1H-pyrrole In a similar manner to the procedures described in Examples 9(i) and 9(iii) above, coupling, dehydration and desilylation reactions were carried out using 4-bromo-2-(4-fluorophenyl)-3-(2-fluoropyridin-4-yl)-1-triisopropylsilyl-1H-pyrrole [prepared as described in step 73(i) above] instead of 4-bromo-2-(4-fluorophenyl)-3-(pyridin-4-yl)-1-triisopropylsilyl-1H-pyrrole and using 1-allyloxycarbonylpiperidine-4-one instead of 1-benzylpiperidine-4-one to give the title compound (yield 6%) as a white powder.

$^1$H-Nuclear magnetic resonance spectrum (500 MHz, CDCl$_3$) δ ppm: 8.42–8.31 (1H, broad singlet); 8.09 (1H, doublet, J=5 Hz); 7.15 (2H, doublet of doublets, J=9 Hz, 5 Hz); 7.04–6.97 (3H, multiplet); 6.82 (1H, singlet); 6.77 (1H, singlet); 6.00–5.89 (1H, multiplet); 5.63–5.39 (1H, multiplet); 5.31 (1H, doublet, J=16 Hz); 5.21 (1H, doublet, J=11 Hz); 4.62 (2H, doublet, J=5 Hz); 4.04–3.96 (2H, broad singlet); 3.63–3.52 (2H, broad singlet); 2.29–2.12 (2H, multiplet).

73(iii) 4-(1-Allyloxycarbonyl-1,2,3,6-tetrahydropyridin-4-yl)-2-(4-fluorophenyl)-3-[2-(1(S)-phenylethylamino)pyridin-4-yl]-1H-pyrrole A mixture of 360 mg (0.85 mmol) of 4-(1-allyloxycarbonyl-1,2,3,6-tetrahydropyridin-4-yl)-2-(4-fluorophenyl)-3-(2-fluoropyridin-4-yl)-1H-pyrrole [prepared as described in step 73 (ii) above], 3.6 ml (28.3 mmol) of 1(S)-phenylethylamine and 0.36 ml of concentrated hydrochloric acid was stirred at 150° C. for 10 hours. At the end of this time, a saturated aqueous solution of sodium hydrogencarbonate was added to the reaction mixture and then this was extracted with ethyl acetate. The organic extract was washed with water, dried over anhydrous magnesium sulfate and then concentrated by evaporation under reduced pressure. The residue thus obtained was purified by chromatography on a silica gel column using a 1:1 by volume mixture of hexane and ethyl acetate as the eluant to give 229 mg (yield 49%) of the title compound as a brown amorphous solid.

$^1$H-Nuclear magnetic resonance spectrum (500 MHz, CDCl$_3$) δ ppm: 8.20–8.12 (1H, broad singlet); 7.96 (1H, doublet, J=5 Hz); 7.25 (4H, singlet); 7.22–7.16 (1H, multiplet); 7.04 (2H, doublet of doublets, J=9 Hz, 5 Hz); 6.89 (2H, triplet, J=9 Hz); 6.74 (1H, singlet); 6.44 (1H, doublet, J=4 Hz); 6.10 (1H, singlet); 6.00–5.89 (1H, multiplet); 5.54–5.33 (1H, multiplet); 5.32 (1H, doublet, J=16 Hz); 5.22 (1H, doublet, J=11 Hz); 5.05 (1H, broad doublet, J=6 Hz); 4.62 (2H, doublet, J=5 Hz); 4.54–4.46 (1H, multiplet); 3.93–3.83 (2H, multiplet); 3.50–3.38 (2H, multiplet); 2.20–2.05 (2H, multiplet); 1.48 (3H, doublet, J=7 Hz).

73(iv) 2-(4-Fluorophenyl)-3-[2-(1(S)-phenylethylamino)pyridin-4-yl]-4-(1,2,3,6-tetrahydropyridin-4-yl)-1H-pyrrole A mixture of 229 mg (0.44 mmol) of 4-(1-allyloxycarbonyl-1,2,3,6-tetrahydropyridin-4-yl)-2-(4-fluorophenyl)-3-[2-(1(S)-phenylethylamino)pyridin-4-yl]-1H-pyrrole [prepared as described in step 73(iii) above] in 2.5 ml of a 10:1 by volume mixture of dioxane and water, 55 µl (0.66 mmol) of pyrrolidine and 5 mg (0.0044 mmol) of tetrakis(triphenylphosphine)palladium (0) was stirred at 0° C. for 10 minutes. At the end of this time, water was added to the reaction mixture and then this was extracted with ethyl acetate. The organic extract was washed with water and then concentrated by evaporation under reduced pressure. The residue thus obtained was purified by chromatography on a silica gel column using a 10:1:1 by volume mixture of ethyl acetate, methanol and isopropylamine as the eluant to give 41 mg (yield 21%) of the title compound as a pale brown amorphous solid.

$^1$H-Nuclear magnetic resonance spectrum (500 MHz, CDCl$_3$) δ ppm: 8.19–8.01 (1H, broad singlet); 7.96 (1H, doublet, J=5 Hz); 7.26 (4H, singlet); 7.24–7.18 (1H, multiplet); 7.06 (2H, doublet of doublets, J=9 Hz, 5 Hz); 6.89 (2H, triplet, J=9 Hz); 6.74 (1H, singlet); 6.47 (1H, doublet, J=4 Hz); 6.15 (1H, singlet); 5.47 (1H, doublet, J=3 Hz); 5.05 (1H, broad doublet, J=6 Hz); 4.60–4.52 (1H, multiplet); 3.31–3.26 (2H, multiplet); 2.94–2.84 (2H, multiplet); 2.13–2.07 (2H, multiplet); 1.48 (3H, doublet, J=7 Hz).

EXAMPLE 74

4-(1-t-Butyl-1,2,3,6-tetrahydropyridin-4-yl)-2-(4-fluorophenyl)-3-(pyridin-4-yl)-1H-pyrrole (Compound No. 1-2635)

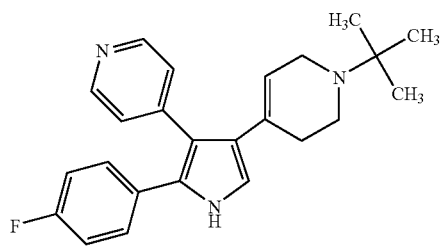

In a similar manner to the procedures described in Examples 9(i), 9(ii) and 9(iii) above, coupling, dehydration and desilylation reactions were carried out using 1-t-butylpiperidine-4-one as a starting material instead of 1-benzylpiperidine-4-one to give the title compound (yield 20%) as a pale yellow powder.

Melting point: 242–244° C. $^1$H-Nuclear magnetic resonance spectrum (400 MHz, CDCl$_3$-DMSO-d$_6$) δ ppm: 9.72

(1H, broad singlet); 8.46 (2H, doublet, J=6 Hz); 7.19 (2H, doublet, J=6 Hz); 7.16 (2H, doublet of doublets, J=9 Hz, 5 Hz); 6.94 (2H, triplet, J=9 Hz); 6.81 (1H, doublet, J=3 Hz); 5.46 (1H, singlet); 3.19–3.11 (2H, multiplet); 2.66–2.58 (2H, multiplet); 2.26–2.18 (2H, multiplet); 1.10 (9H, singlet).

EXAMPLE 75

2-(4-Fluorophenyl)-4-(1-octyl-1,2,3,6-tetrahydropyridin-4-yl)-3-(pyridin-4-yl)-1H-pyrrole (Compound No. 1-2639)

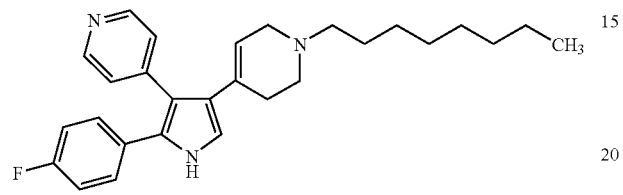

In a similar manner to the procedures described in Examples 9(i) and 9(iii) above, coupling, dehydration and desilylation reactions were carried out using 1-octylpiperidine-4-one as a starting material instead of 1-benzylpiperidine-4-one to give the title compound (yield 26%) as a white powder.

Melting point: 173–175° C. $^1$H-Nuclear magnetic resonance spectrum (400 MHz, CDCl$_3$) δ ppm: 8.47 (2H, doublet, J=6 Hz); 8.29 (1H, broad singlet); 7.17 (2H, doublet, J=6 Hz); 7.12 (2H, doublet of doublets, J=9 Hz, 5 Hz); 6.96 (2H, triplet, J=9 Hz); 6.82 (1H, doublet, J=3 Hz); 5.45 (1H, singlet); 2.99 (2H, broad doublet, J=3 Hz); 2.56 (2H, triplet, J=6 Hz); 2.39 (2H, triplet, J=8 Hz); 2.28–2.23 (2H, multiplet); 1.55–1.48 (2H, multiplet); 1.31–1.22 (10H, multiplet); 0.88 (3H, triplet, J=7 Hz).

EXAMPLE 76

(±)-4-(1-Ethyl-6-methyl-1,2,3,6-tetrahydropyridin-4-yl)-2-(4-fluorophenyl)-3-(pyridin-4-yl)-1H-pyrrole (Compound No. 1-2667)

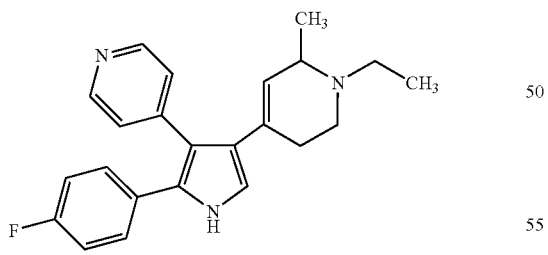

In a similar manner to the procedures described in Examples 9(i) and 9(iii) above, coupling, dehydration and desilylation reactions were carried out using (±)-1-ethyl-2-methylpiperidine-4-one as a starting material instead of 1-benzylpiperidine-4-one to afford a mixture of the title compound and the (1-ethyl-2-methyl-1,2,3,6-tetrahydropyridin-4-yl) isomer thereof (which is the compound of Example 77 below). The mixture was separated by chromatography on a silica gel column using a 50:1 by volume mixture of ethyl acetate and isopropylamine as the eluant to give the title compound (yield 33%, Rf value=0.20) as a pale yellow powder.

Melting point: 210–212° C. (decomposition) $^1$H-Nuclear magnetic resonance spectrum (400 MHz, CDCl$_3$) δ ppm: 8.47 (2H, doublet, J=6 Hz); 8.31 (1H, broad singlet); 7.17 (2H, doublet, J=6 Hz); 7.13 (2H, doublet of doublets, J=9 Hz, 5 Hz); 6.97 (2H, triplet, J=9 Hz); 6.82 (1H, singlet); 5.27 (1H, singlet); 3.09–3.00 (1H, multiplet); 2.97–2.88 (1H, multiplet); 2.84–2.73 (1H, multiplet); 2.48–2.24 (3H, multiplet); 2.22–2.11 (1H, multiplet); 1.09 (3H, triplet, J=7 Hz); 1.04 (3H, doublet, J=7 Hz).

EXAMPLE 77

(±)-4-(1-Ethyl-2-methyl-1,2,3,6-tetrahydropyridin-4-yl)-2-(4-fluorophenyl)-3-(pyridin-4-yl)-1H-pyrrole (Compound No. 1-2709)

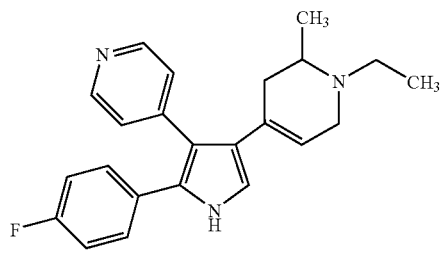

The title compound (yield 46%, Rf value=0.15) was obtained as an orange powder during the chromatography performed in Example 76.

Melting point: 218–220° C. (decomposition) $^1$H-Nuclear magnetic resonance spectrum (400 MHz, CDCl$_3$) δ ppm: 8.47 (2H, doublet, J=6 Hz); 8.32 (1H, broad singlet); 7.17 (2H, doublet, J=6 Hz); 7.12 (2H, doublet of doublets, J=9 Hz, 5 Hz); 6.96 (2H, triplet, J=9 Hz); 6.82 (1H, singlet); 5.44 (1H, singlet); 3.16–2.99 (2H, multiplet); 2.90–2.79 (1H, multiplet); 2.76–2.64 (1H, multiplet); 2.51–2.32 (2H, multiplet); 2.03–1.98 (1H, multiplet); 1.08 (3H, triplet, J=7 Hz); 1.01 (3H, doublet, J=6 Hz).

EXAMPLE 78

(±)-2-(4-Fluorophenyl)-4-(1,2,3,5,6,7,8,8a-octahydroindolizin-7-yl)-3-(pyridin-4-yl)-1H-pyrrole (Compound No. 1-2655)

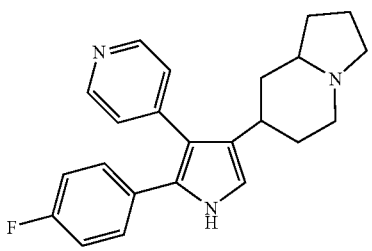

In a similar manner to that described in Example 11 above, (±)-2-(4-fluorophenyl)-4-(1,2,3,5,8,8a-hexahydroindolizin-7-yl)-3-(pyridin-4-yl)-1H-pyrrole (prepared as described in Example 59 above) was reduced to give the title compound (yield 52%) as a white powder.

Melting point: 263–265° C. ¹H-Nuclear magnetic resonance spectrum (500 MHz, DMSO-d₆) δ ppm: 11.20 (1H, broad singlet); 8.48 (2H, doublet, J=6 Hz); 7.18–7.12 (4H, multiplet); 7.09 (2H, triplet, J=9 Hz); 6.76 (1H, doublet, J=2 Hz); 2.98–2.92 (1H, multiplet); 2.92–2.86 (1H, broad triplet, J=8 Hz); 2.46 (1H, triplet of triplets, J=13 Hz, 3 Hz); 1.98–1.45 (9H, multiplet); 1.30–1.14 (2H, multiplet).

EXAMPLE 79

(±)-4-(6-Allyl-1-methyl-1,2,3,6-tetrahydropyridin-4-yl)-2-(4-fluorophenyl)-3-(pyridin-4-yl)-1H-pyrrole
(Compound No. 1-2690)

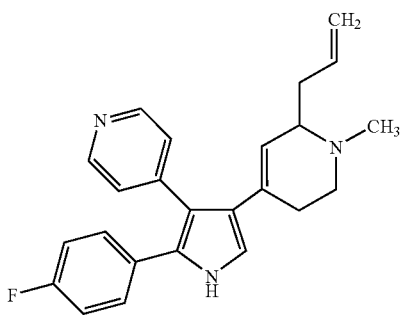

In a similar manner to the procedures described in Examples 9(i) and 9(iii) above, coupling, dehydration and desilylation reactions were carried out using (±)-2-allyl-1-methylpiperidine-4-one as a starting material instead of 1-benzylpiperidine-4-one to afford a mixture of the title compound and the (2-allyl-1-methyl-1,2,3,6-tetrahydropyridin-4-yl) isomer thereof (which is the compound of Example 80 below). The mixture was separated by chromatography on a silica gel column using a 100:1 by volume mixture of ethyl acetate and isopropylamine as the eluant to give the title compound (yield 20%, Rf value=0.40) as a pale yellow powder.

Melting point: 218–220° C. ¹H-Nuclear magnetic resonance spectrum (500 MHz, CDCl₃) δ ppm: 8.48 (2H, doublet, J=6 Hz); 8.39 (1H, broad singlet); 7.17 (2H, doublet, J=6 Hz); 7.11 (2H, doublet of doublets, J=9 Hz, 5 Hz); 6.96 (2H, triplet, J=9 Hz); 6.83 (1H, doublet, J=3 Hz); 5.66–5.58 (1H, multiplet); 5.34 (1H, singlet); 4.96 (1H, doublet, J=10 Hz); 4.90 (1H, doublet, J=17 Hz); 2.89–2.87 (1H, multiplet); 2.71–2.67 (1H, multiplet); 2.46–2.43 (2H, multiplet); 2.37 (3H, singlet); 2.35–2.32 (1H, multiplet); 2.12–2.07 (2H, multiplet).

EXAMPLE 80

(±)-4-(2-Allyl-1-methyl-1,2,3,6-tetrahydropyridin-4-yl)-2-(4-fluorophenyl)-3-(pyridin-4-yl)-1H-pyrrole
(Compound No. 1-2732)

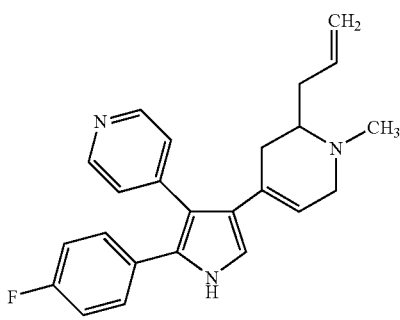

The title compound (yield 18%, Rf value=0.35) was obtained as a pale yellow powder during the chromatography performed in Example 79 above.

Melting point: 178–180° C. ¹H-Nuclear magnetic resonance spectrum (500 MHz, CDCl₃) δ ppm: 8.47 (2H, doublet, J=6 Hz); 8.38 (1H, broad singlet); 7.17 (2H, doublet, J=6 Hz); 7.12 (2H, doublet of doublets, J=9 Hz, 5 Hz); 6.96 (2H, triplet, J=9 Hz); 6.82 (1H, doublet, J=3 Hz); 5.77–5.69 (1H, multiplet); 5.39 (1H, singlet); 5.03 (1H, doublet, J=4 Hz); 5.00 (1H, singlet); 3.19–3.15 (1H, multiplet); 2.99–2.95 (1H, multiplet); 2.57–2.41 (1H, multiplet); 2.36 (3H, singlet); 2.36–2.31 (1H, multiplet); 2.24–2.09 (3H, multiplet).

EXAMPLE 81

(±)-4-(6-Benzyl-1-methyl-1,2,3,6-tetrahydropyridin-4-yl)-2-(4-fluorophenyl)-3-(pyridin-4-yl)-1H-pyrrole
(Compound No. 1-2696)

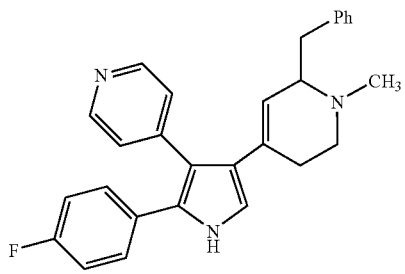

In a similar manner to the procedures described in Examples 9(i) and 9(iii) above, coupling, dehydration and desilylation reactions were carried out using (±)-2-benzyl-1-methylpiperidine-4-one as a starting material instead of 1-benzylpiperidine-4-one to afford a mixture of the title compound and the (2-benzyl-1-methyl-1,2,3,6-tetrahydropyridin-4-yl) isomer thereof (which is the compound of Example 82 below). The mixture was separated by chromatography on a silica gel column using a 100:1 by volume mixture of ethyl acetate and isopropylamine as the eluant to give the title compound (yield 11%, Rf value=0.38) as a pale yellow powder.

Melting point: 198–200° C. ¹H-Nuclear magnetic resonance spectrum (500 MHz, CDCl₃) δ ppm: 8.45 (2H, doublet, J=6 Hz); 8.28 (1H, broad singlet); 7.20–7.12 (3H, multiplet); 7.09 (2H, doublet, J=6 Hz); 7.10–7.07 (2H, multiplet); 6.97–6.91 (4H, multiplet); 6.76 (1H, doublet, J=3 Hz); 5.24 (1H, singlet); 3.13–3.10 (1H, multiplet); 2.94–2.89 (2H, multiplet); 2.51 (3H, singlet); 2.49–2.35 (3H, multiplet); 2.11–2.05 (1H, multiplet).

EXAMPLE 82

(±)-4-(2-benzyl-1-methyl-1,2,3,6-tetrahydropyridin-4-yl)-2-(4-fluorophenyl)-3-(pyridin-4-yl)-1H-pyrrole
(Compound No. 1-2738)

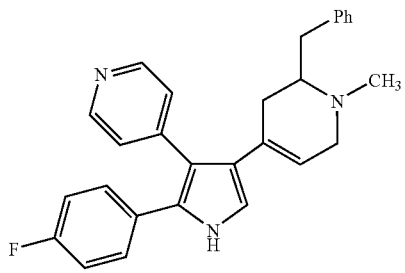

The title compound (yield 4%, Rf value=0.33) was obtained as a pale yellow powder during the chromatography performed in Example 81 above.

Melting point: 198–199° C. $^1$H-Nuclear magnetic resonance spectrum (500 MHz, CDCl$_3$) δ ppm: 8.55 (1H, broad singlet); 8.43 (2H, doublet, J=6 Hz); 7.23 (2H, triplet, J=7 Hz); 7.16 (2H, triplet, J=7 Hz); 7.12 (2H, doublet, J=6 Hz); 7.10–7.05 (4H, multiplet); 6.94 (2H, triplet, J=9 Hz); 6.72 (1H, doublet, J=3 Hz); 5.40 (1H, singlet); 3.20–3.17 (1H, multiplet); 3.08–3.04 (2H, multiplet); 2.81–2.78 (1H, multiplet); 2.46 (3H, singlet); 2.43–2.38 (1H, multiplet); 2.10–2.00 (2H, multiplet).

EXAMPLE 83

(−)-2-(4-Fluorophenyl)-4-(1,2,3,5,6,8a-hexahydroindolizin-7-yl)-3-(pyridin-4-yl)-1H-pyrrole (Compound No. 1-2653)

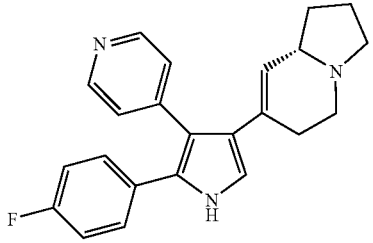

(±)-2-(4-Fluorophenyl)-4-(1,2,3,5,6,8a-hexahydroindolizin-7-yl)-3-(pyridin-4-yl)-1H-pyrrole (prepared as described in Example 60 above) was subjected to High Performance Liquid Chromatography using a chiral column and employing the conditions described below to give the title compound (retention time: 4.51 minutes, yield 94%) as a pale yellow powder.

Melting point: 204–205° C. (Decomposition) [α]$^{27}_D$−50.67° (c=0.975, methanol) <HPLC>Column: CHIRAL-PAK AD (product of Daicel Chemical Industries, Ltd.) Eluant: n-hexane: ethanol=80:20 Flow rate: 1.0 ml/minute Temperature: 40° C. Detection: 254 nm (UV).

EXAMPLE 84

(+)-2-(4-Fluorophenyl)-4-(1,2,3,5,6,8a-hexahydroindolizin-7-yl)-3-(pyridin-4-yl)-1H-pyrrole (Compound No. 1-2653)

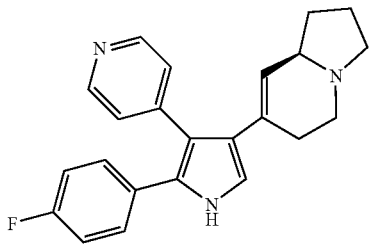

The title compound (retention time: 6.23 minutes, yield 95%) was obtained as a pale yellow powder during the High Performance Liquid Chromatography performed in Example 83 above.

Melting Point: 207–210° C. (Decomposition) [α]$^{24}_D$+46.59° (c=0.920, methanol)

EXAMPLE 85

(±)-2-(4-Fluorophenyl)-4-(6-methyl-1-propyl-1,2,3,6-tetrahydropyridin-4-yl)-3-(pyridin-4-yl)-1H-pyrrole (Compound No. 1-2668)

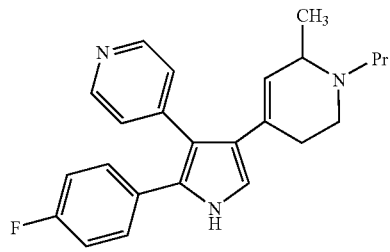

In a similar manner to the procedures described in Examples 9(i) and 9(iii) above, coupling, dehydration and desilylation reactions were carried out using (±)-2-methyl-1-propylpiperidine-4-one as a starting material instead of 1-benzylpiperidine-4-one to afford a mixture of the title compound and the (2-methyl-1-propyl-1,2,3,6-tetrahydropyridin-4-yl) isomer thereof (which is the compound of Example 86 below). The mixture was separated by chromatography on a silica gel column using a 100:1 by volume mixture of ethyl acetate and isopropylamine as the eluant to give the title compound (yield 6%, Rf value=0.35) as a white powder.

Melting point: 214–215° C. (decomposition) $^1$H-Nuclear magnetic resonance spectrum (400 MHz, CDCl$_3$) δ ppm: 8.47 (2H, doublet, J=6 Hz); 8.22 (1H, broad singlet); 7.17 (2H, doublet, J=6 Hz); 7.13 (2H, doublet of doublets, J=9 Hz, 5 Hz); 6.97 (2H, triplet, J=9 Hz); 6.83 (1H, singlet); 5.27 (1H, singlet); 3.07–2.98 (1H, multiplet); 2.97–2.89 (1H, multiplet); 2.68–2.56 (1H, multiplet); 2.47–2.39 (1H, multiplet); 2.37–2.23 (2H, multiplet); 2.20–2.10 (1H, multiplet); 1.62–1.43 (2H, multiplet); 1.04 (3H, doublet, J=7 Hz); 0.90 (3H, triplet, J=7 Hz).

EXAMPLE 86

(±)-2-(4-Fluorophenyl)-4-(2-methyl-1-propyl-1,2,3,6-tetrahydropyridin-4-yl)-3-(pyridin-4-yl)-1H-pyrrole (Compound No. 1-2710)

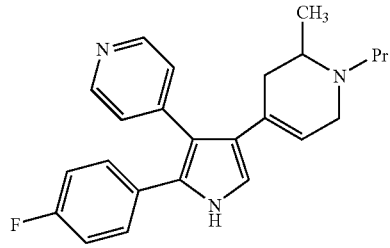

The title compound (yield 8%, Rf value=0.32) was obtained as a white powder during the chromatography performed in Example 85 above.

Melting point: 210–218° C. (decomposition) $^1$H-Nuclear magnetic resonance spectrum (400 MHz, CDCl$_3$) δ ppm: 8.47 (2H, doublet, J=6 Hz); 8.23 (1H, broad singlet); 7.17 (2H, doublet, J=6 Hz); 7.12 (2H, doublet of doublets, J=9 Hz, 5 Hz); 6.96 (2H, triplet, J=9 Hz); 6.82 (1H, singlet); 5.43

(1H, singlet); 3.16–3.01 (2H, multiplet); 2.89–2.82 (1H, multiplet); 2.58–2.50 (1H, multiplet); 2.42–2.30 (2H, multiplet); 2.00–1.92 (1H, multiplet); 1.57–1.45 (2H, multiplet); 1.01 (3H, doublet, J=6 Hz); 0.90 (3H, triplet, J=7 Hz).

EXAMPLE 87

(±)-2-(4-Fluorophenyl)-4-(1,3,4,6,7,9a-hexahydro-2H-quinolizin-8-yl)-3-(pyridin-4-yl)-1H-pyrrole (Compound No. 1-2656)

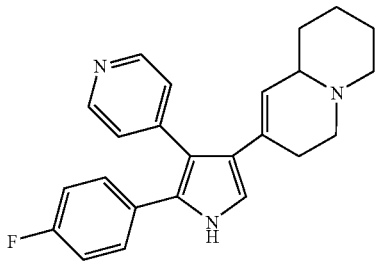

In a similar manner to the procedures described in Examples 9(i) and 9(iii) above, coupling, dehydration and desilylation reactions were carried out using (±)-octahydro-2H-quinolizine-2-one as a starting material instead of 1-benzylpiperidine-4-one to afford a mixture of the title compound and the (1,3,4,6,9,9a-hexahydro-2H-quinolizin-8-yl) isomer thereof (which is the compound of Example 88 below). The mixture was separated by chromatography on a silica gel column using a 100:1 by volume mixture of ethyl acetate and isopropylamine as the eluant to give the title compound (yield 6%, Rf value=0.35) as a pale yellow powder.

Melting point: 223–224° C. $^1$H-Nuclear magnetic resonance spectrum (500 MHz, CDCl$_3$) δ ppm: 8.47 (2H, doublet, J=6 Hz); 8.30 (1H, broad singlet); 7.17 (2H, doublet, J=6 Hz); 7.12 (2H, doublet of doublets, J=9 Hz, 5 Hz); 6.96 (2H, triplet, J=39 Hz); 6.83 (1H, doublet, J=3 Hz); 5.13 (1H, singlet); 2.88–2.81 (2H, multiplet); 2.67–2.56 (1H, multiplet); 2.45–2.43 (1H, multiplet); 2.40–2.35 (1H, multiplet); 2.17–2.07 (2H, multiplet); 1.76–1.73 (1H, multiplet); 1.69–1.64 (2H, multiplet); 1.44–1.41 (1H, multiplet); 1.34–1.18 (2H, multiplet).

EXAMPLE 88

(±)-2-(4-Fluorophenyl)-4-(1,3,4,6,9,9a-hexahydro-2H-quinolizin-8-yl)-3-(pyridin-4-yl)-1H-pyrrole (Compound No. 1-2657)

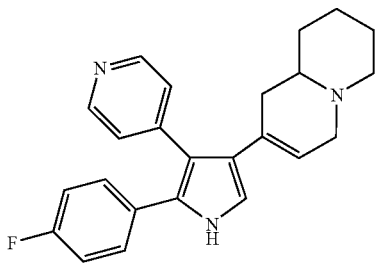

The title compound (yield 19%, Rf value=0.30) was obtained as a pale yellow powder during the chromatography performed in Example 87 above.

Melting point: 228–234° C. (decomposition) $^1$H-Nuclear magnetic resonance spectrum (500 MHz, CDCl$_3$) δ ppm: 8.47 (2H, doublet, J=6 Hz); 8.28 (1H, broad singlet); 7.17 (2H, doublet, J=6 Hz); 7.12 (2H, doublet of doublets, J=9 Hz, 5 Hz); 6.96 (2H, triplet, J=9 Hz); 6.81 (1H, doublet, J=3 Hz); 5.42 (1H, singlet); 3.30–3.25 (1H, multiplet); 2.98–2.95 (1H, multiplet); 2.77–2.73 (1H, multiplet); 2.14–1.99 (5H, multiplet); 1.74–1.65 (3H, multiplet); 1.31–1.21 (2H, multiplet).

EXAMPLE 89

(±)-2-(4-Fluorophenyl)-4-(1,2,3,5,8,8a-hexahydroindolizin-7-yl)-3-(2-methylaminolpyrimidin-4-yl)-1H-pyrrole (Compound No. 1-2906)

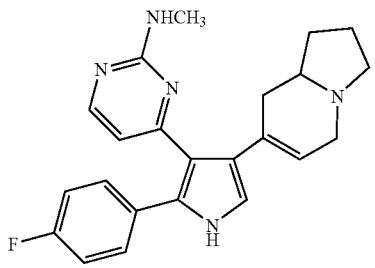

In a similar manner to the procedures described in Examples 9(i) and 9(iii) above, coupling, dehydration and desilylation reactions were carried out using 4-bromo-2-(4-fluorophenyl)-3-(2-methylaminopyrimidin-4-yl)-1-triisopropylsilyl-1H-pyrrole (prepared as described in Preparative Example 1 below) instead of 4-bromo-2-(4-fluorophenyl)-3-(pyridin-4-yl)-1-triisopropylsilyl-1H-pyrrole, and (±)-1,2,3,5,6,7,8,8a-octahydroindolizine-7-one, instead of 1-benzylpiperidine-4-one, as starting materials to afford a mixture of the title compound and the (1,2,3,5,6,8a-hexahydroindolizin-7-yl) isomer thereof (which is the compound of Example 90 below). The mixture was separated by chromatography on a silica gel column using a 200:20:1 by volume mixture of ethyl acetate, methanol and isopropylamine as the eluant to give the title compound (yield 15%, Rf value=0.55) as a pale brown amorphous solid.

$^1$H-Nuclear magnetic resonance spectrum (400 MHz, CD$_3$OD) δ ppm: 8.08 (1H, doublet, J=5 Hz); 7.30 (2H, doublet of doublets, J=9 Hz, 5 Hz); 7.02 (2H, triplet, J=9 Hz); 6.82 (1H, singlet); 6.49 (1H, doublet, J=5 Hz); 5.57–5.51 (1H, multiplet); 3.53–3.45 (1H, multiplet); 3.21–3.11 (1H, multiplet); 2.90–2.81 (1H, multiplet); 2.80 (3H, singlet); 2.47–2.28 (2H, multiplet); 2.26–2.13 (2H, multiplet); 2.07–1.96 (1H, multiplet); 1.91–1.73 (2H, multiplet); 1.49–1.37 (1H, multiplet).

EXAMPLE 90

(±)-2-(4-Fluorophenyl)-4-(1,2,3,5,6,8a-hexahydroindolizin-7-yl)-3-(2-methylaminopyrimidin-4-yl)-1H-pyrrole (Compound No. 1-2905)

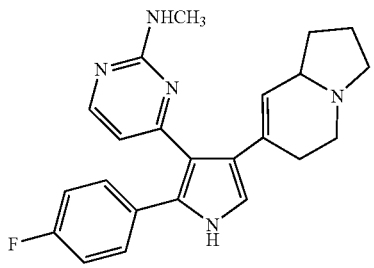

The title compound (yield 12%, Rf value=0.50) was obtained as a pale brown amorphous solid during the chromatography performed in Example 89 above.

¹H-Nuclear magnetic resonance spectrum (400 MHz, CD$_3$OD) δ ppm: 8.09 (1H, doublet, J=5 Hz); 7.30 (2H, doublet of doublets, J=9 Hz, 5 Hz); 7.02 (2H, triplet, J=9 Hz); 6.83 (1H, singlet); 6.46 (1H, doublet, J=5 Hz); 5.48–5.42 (1H, multiplet); 3.47–3.38 (1H, multiplet); 3.03–2.75 (4H, multiplet); 2.81 (3H, singlet); 2.46–2.36 (1H, multiplet); 2.29–2.20 (1H, multiplet); 2.03–1.87 (2H, multiplet); 1.83–1.75 (1H, multiplet); 1.54–1.43 (1H, multiplet).

EXAMPLE 91

(±)-2-(3,4-Difluorophenyl)-4-(1,2,3,5,8,8a-hexahydroindolizin-7-yl)-3-(pyridin-4-yl)-1H-pyrrole
(Compound No. 1-3260)

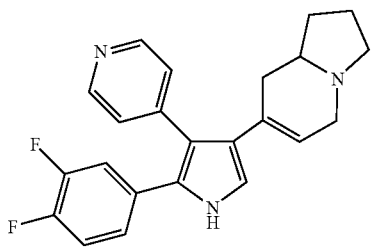

In a similar manner to the procedures described in Examples 9(i) and 9(iii) above, coupling, dehydration and desilylation reactions were carried out using 4-bromo-2-(3,4-difluorophenyl)-3-(pyridin-4-yl)-1-triisopropylsilyl-1H-pyrrole (prepared as described in Preparative Example 5 below), instead of 4-bromo-2-(4-fluorophenyl)-3-(pyridin-4-yl)-1-triisopropylsilyl-1H-pyrrole, and (±)-1,2,3,5,6,7,8,8a-octahydroindolizine-7-one, instead of 1-benzylpiperidine-4-one, as starting materials to afford a mixture of the title compound and the (1,2,3,5,6,8a-hexahydroindolizin-7-yl) isomer thereof (which is the compound of Example 92 below). The mixture was separated by chromatography on a silica gel column using a 100:10:1 by volume mixture of ethyl acetate, methanol and isopropylamine as the eluant to give the title compound (yield 29%, Rf value=0.66) as a pale pink powder.

Melting point: 215–217° C. (decomposition) ¹H-Nuclear magnetic resonance spectrum (400 MHz, DMSO-d$_6$) δ ppm: 11.48 (1H, broad singlet); 8.48 (2H, doublet, J=6 Hz); 7.37–7.28 (1H, multiplet); 7.21–7.10 (1H, multiplet); 7.14 (2H, doublet, J=6 Hz); 6.96 (1H, doublet, J=3 Hz); 6.93–6.86 (1H, multiplet); 5.27–5.20 (1H, multiplet); 3.33–3.23 (1H, multiplet); 3.05–2.97 (1H, multiplet); 2.65–2.56 (1H, multiplet); 2.30–2.22 (1H, multiplet); 2.12–1.93 (3H, multiplet); 1.91–1.81 (1H, multiplet); 1.75–1.57 (2H, multiplet); 1.33–1.20 (1H, multiplet).

EXAMPLE 92

(±)-2-(3,4-Difluorophenyl)-4-(1,2,3,5,6,8a-hexahydroindolizin-7-yl)-3-(pyridin-4-yl)-1H-pyrrole
(Compound No. 1-3259)

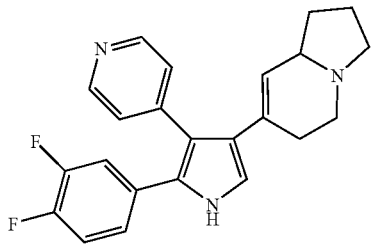

The title compound (yield 23%, Rf value=0.31) was obtained as a pale pink powder during the chromatography performed in Example 91 above.

Melting point: 187–190° C. (decomposition) ¹H-Nuclear magnetic resonance spectrum (400 MHz, DMSO-d$_6$) δ ppm: 11.48 (1H, broad singlet); 8.47 (2H, doublet, J=6 Hz); 7.39–7.29 (1H, multiplet); 7.21–7.10 (1H, multiplet); 7.14 (2H, doublet, J=6 Hz); 6.96 (1H, doublet, J=3 Hz); 6.94–6.87 (1H, multiplet); 5.18–5.13 (1H, multiplet); 3.10–3.02 (1H, multiplet); 2.89–2.82 (1H, multiplet); 2.79–2.71 (1H, multiplet); 2.63–2.45 (2H, multiplet); 2.30–2.20 (1H, multiplet); 2.06–1.97 (1H, multiplet); 1.78–1.53 (3H, multiplet); 1.22–1.10 (1H, multiplet).

EXAMPLE 93

(±)-4-(1,2,3,5,8,8a-Hexahydroindolizin-7-yl)-3-(pyridin-4-yl)-2-(3-trifluoromethylphenyl)-1H-pyrrole
(Compound No. 1-3262)

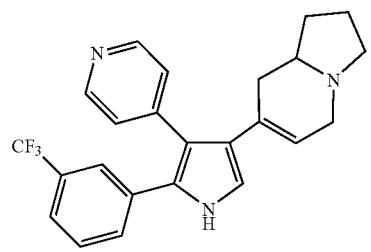

In a similar manner to the procedures described in Examples 9(i) and 9(iii) above, coupling, dehydration and desilylation reactions were carried out using 4-bromo-3-(pyridin-4-yl)-2-(3-trifluoromethylphenyl)-1-triisopropylsilyl-1H-pyrrole (prepared as described in Preparative Example 6 below), instead of 4-bromo-2-(4-fluorophenyl)-3-(pyridin-4-yl)-1-triisopropylsilyl-1H-pyrrole, and (±)-1,2,3,5,6,7,8,8a-octahydroindolizine-7-one, instead of 1-benzylpiperidine-4-one, as starting materials to afford a mixture of the title compound and the (1,2,3,5,6,8a-hexahydroindolizin-7-yl) isomer thereof (which is the compound of Example 94 below). The mixture was separated by chromatography on a silica gel column using a 100:10:1 by volume mixture of ethyl acetate, methanol and isopropylamine as the eluant to give the title compound (yield 26%, Rf value=0.65) as a pale brown powder.

Melting point: 220–223° C. (decomposition) ¹H-Nuclear magnetic resonance spectrum (400 MHz, DMSO-d$_6$) δ ppm:

11.62 (1H, broad singlet); 8.49 (2H, doublet, J=6 Hz); 7.54–7.35 (4H, multiplet); 7.16 (2H, doublet, J=6 Hz); 7.02 (1H, doublet, J=3 Hz); 5.29–5.21 (1H, multiplet); 3.35–3.24 (1H, multiplet); 3.06–2.98 (1H, multiplet); 2.65–2.56 (1H, multiplet); 2.34–2.24 (1H, multiplet); 2.13–1.94 (3H, multiplet); 1.92–1.82 (1H, multiplet); 1.75–1.58 (2H, multiplet); 1.34–1.21 (1H, multiplet).

EXAMPLE 94

(±)-4-(1,2,3,5,6,8a-Hexahydroindolizin-7-yl)-3-(pyridin-4-yl)-2-(3-trifluoromethylphenyl)-1H-pyrrole (Compound No. 1-3261)

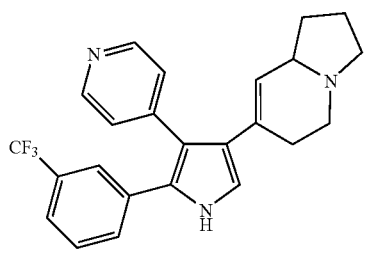

The title compound (yield 17%, Rf value=0.31) was obtained as a pale brown powder during the chromatography performed in Example 93 above.

Melting point: 189–191° C. (decomposition) $^1$H-Nuclear magnetic resonance spectrum (400 MHz, DMSO-$d_6$) δ ppm: 11.63 (1H, broad singlet); 8.48 (2H, doublet, J=6 Hz); 7.55–7.37 (4H, multiplet); 7.15 (2H, doublet, J=6 Hz); 7.02 (1H, doublet, J=3 Hz); 5.19–5.14 (1H, multiplet); 3.12–3.03 (1H, multiplet); 2.91–2.82 (1H, multiplet); 2.80–2.71 (1H, multiplet); 2.64–2.45 (2H, multiplet); 2.33–2.21 (1H, multiplet); 2.09–1.98 (1H, multiplet); 1.78–1.53 (3H, multiplet); 1.21–1.10 (1H, multiplet).

EXAMPLE 95

(±)-2-(3-Fluorophenyl)-4-(1,2,3,5,8,8a-hexahydroindolizin-7-yl)-3-(pyridin-4-yl)-1H-pyrrole (Compound No. 1-3256)

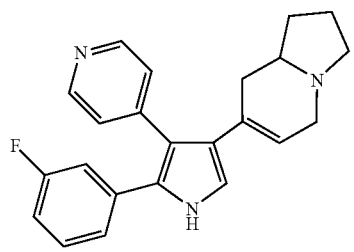

In a similar manner to the procedures described in Examples 9(i) and 9(iii) above, coupling, dehydration and desilylation reactions were carried out using 4-bromo-2-(3-fluorophenyl)-3-(pyridin-4-yl)-1-triisopropylsilyl-1H-pyrrole (prepared as described in Preparative Example 4 below), instead of 4-bromo-2-(4-fluorophenyl)-3-(pyridin-4-yl)-1-triisopropylsilyl-1H-pyrrole, and (±)-1,2,3,5,6,7,8,8a-octahydroindolizine-7-one, instead of 1-benzylpiperidine-4-one, as starting materials to afford a mixture of the title compound and the (1,2,3,5,6,8a-hexahydroindolizin-7-yl) isomer thereof (which is the compound of Example 96 below). The mixture was separated by chromatography on a silica gel column using a 30:1 by volume mixture of ethyl acetate and isopropylamine as the eluant to give the title compound (yield 17%, Rf value=0.25) as a pale pink powder.

Melting point: 199–203° C. (decomposition) $^1$H-Nuclear magnetic resonance spectrum (400 MHz, CDCl$_3$) δ ppm: 8.49 (2H, doublet, J=6 Hz); 8.30 (1H, broad singlet); 7.23–7.18 (3H, multiplet); 6.96–6.82 (4H, multiplet); 5.50–5.47 (1H, multiplet); 3.53–2.96 (1H, multiplet); 3.20 (1H, triplet, J=9 Hz); 2.79 (1H, doublet, J=17 Hz); 2.32–2.08 (4H, multiplet); 2.00–1.67 (3H, multiplet); 1.48–1.33 (1H, multiplet).

EXAMPLE 96

(±)-2-(3-Fluorophenyl)-4-(1,2,3,5,6,8a-hexahydroindolizin-7-yl-3-(pyridin-4-yl)-1H-pyrrole (Compound No. 1-3255)

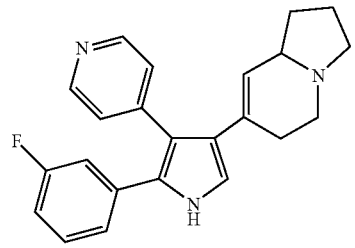

The title compound (yield 12%, Rf value=0.10) was obtained as a pale brown powder during the chromatography performed in Example 95 above.

Melting point: 178–181° C. (decomposition) $^1$H-Nuclear magnetic resonance spectrum (400 MHz, CDCl$_3$) δ ppm: 8.50 (2H, doublet, J=6 Hz); 8.34 (1H, broad singlet); 7.26–7.18 (3H, multiplet); 6.95–6.84 (4H, multiplet); 5.42 (1H, singlet); 3.23–3.17 (1H, multiplet); 3.02–2.82 (2H, multiplet); 2.78–2.61 (2H, multiplet); 2.42–2.30 (1H, multiplet); 2.16–2.04 (1H, multiplet); 1.95–1.68 (3H, multiplet); 1.44–1.32 (1H, multiplet).

EXAMPLE 97

(±)-2-(3-Chlorophenyl)-4-(1,2,3,5,8,8a-hexahydroindolizin-7-yl)-3-(pyridin-4-yl)-1H-pyrrole (Compound No. 1-3258)

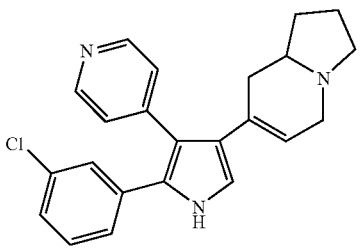

In a similar manner to the procedures described in Examples 9(i) and 9(iii) above, coupling, dehydration and desilylation reactions were carried out using 4-bromo-2-(3-chlorophenyl)-3-(pyridin-4-yl)-1-triisopropylsilyl-1H-pyrrole (prepared as described in Preparative Example 3 below), instead of 4-bromo-2-(4-fluorophenyl)-3-(pyridin-4-yl)-1-triisopropylsilyl-1H-pyrrole, and (±)-1,2,3,5,6,7,8,8a-octahydroindolizine-7-one, instead of 1-benzylpiperidine-4-one, as starting materials to afford a mixture of the title compound and the (1,2,3,5,6,8a-hexahydroindolizin-7-yl) isomer thereof (which is the compound of Example 98 below). The mixture was separated by chromatography on a silica gel column using a 30:1 by volume mixture of ethyl acetate and isopropylamine as the eluant to give the title compound (yield 18%, Rf value=0.25) as a pale pink powder.

Melting point: 197–201° C. (decomposition) $^1$H-Nuclear magnetic resonance spectrum (400 MHz, CDCl$_3$) δ ppm: 8.49 (2H, doublet, J=6 Hz); 8.32 (1H, broad singlet); 7.25–7.13 (5H, multiplet); 6.96 (1H, doublet, J=7 Hz); 6.85 (1H, doublet, J=3 Hz); 5.50–5.47 (1H, multiplet); 3.54–3.45 (1H, multiplet); 3.20 (1H, triplet, J=9 Hz); 2.79 (1H, doublet, J=16 Hz); 2.31–2.07 (4H, multiplet); 2.00–1.67 (3H, multiplet); 1.48–1.33 (1H, multiplet).

EXAMPLE 98

(±)-2-(3-Chlorophenyl)-4-(1,2,3,5,6,8a-hexahydroindolizin-7-yl)-3-(pyridin-4-yl)-1H-pyrrole (Compound No. 1-3257)

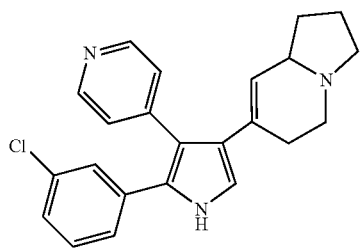

The title compound (yield 16%, Rf value=0.10) was obtained as a pale brown powder during the chromatography performed in Example 97 above.

Melting point: 193–195° C. (decomposition) $^1$H-Nuclear magnetic resonance spectrum (400 MHz, CDCl$_3$) δ ppm: 8.50 (2H, doublet, J=6 Hz); 8.42 (1H, broad singlet); 7.25–7.13 (5H, multiplet); 6.96 (1H, doublet, J=7 Hz); 6.85 (1H, doublet, J=3 Hz); 5.42 (1H, singlet); 3.26–3.17 (1H, multiplet); 3.02–2.82 (2H, multiplet); 2.78–2.60 (2H, multiplet); 2.42–2.30 (1H, multiplet); 2.16–2.03 (1H, multiplet); 1.95–1.65 (3H, multiplet); 1.45–1.32 (1H, multiplet).

EXAMPLE 99

(±)-4-(1,2,3,5,8,8a-Hexahydroindolizin-7-yl)-2-phenyl-3-(pyridin-4-yl)-1H-pyrrole (Compound No. 1-3254)

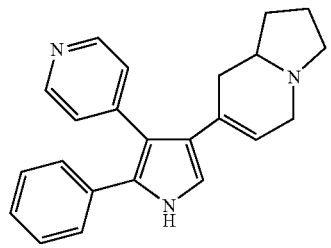

In a similar manner to the procedures described in Examples 9(i) and 9(iii) above, coupling, dehydration and desilylation reactions were carried out using 4-bromo-2-phenyl-3-(pyridin-4-yl)-1-triisopropylsilyl-1H-pyrrole (prepared as described in Preparative Example 2 below), instead of 4-bromo-2-(4-fluorophenyl)-3-(pyridin-4-yl)-1-triisopropylsilyl-1H-pyrrole, and (±)-1,2,3,5,6,7,8,8a-octahydroindolizine-7-one, instead of 1-benzylpiperidine-4-one, as starting materials to afford a mixture of the title compound and the (1,2,3,5,6,8a-hexahydroindolizin-7-yl) isomer thereof (which is the compound of Example 100 below). The mixture was separated by chromatography on a silica gel column using a 30:1 by volume mixture of ethyl acetate and isopropylamine as the eluant to give the title compound (yield 14%, Rf value=0.24) as a pale brown powder.

Melting point: 201–204° C. (decomposition) $^1$H-Nuclear magnetic resonance spectrum (400 MHz, CDCl$_3$) δ ppm: 8.46 (2H, doublet, J=6 Hz); 8.28 (1H, broad singlet); 7.30–7.13 (7H, multiplet); 6.84 (1H, doublet, J=3 Hz); 5.50–5.47 (1H, multiplet); 3.54–3.45 (1H, multiplet); 3.50 (1H, triplet, J=9 Hz); 2.79 (1H, doublet, J=17 Hz); 2.32–2.07 (4H, multiplet); 2.00–1.67 (3H, multiplet); 1.48–1.33 (1H, multiplet).

EXAMPLE 100

(±)-4-(1,2,3,5,6,8a-Hexahydroindolizin-7-yl)-2-phenyl-3-(pyrizin-4-yl)-1H-pyrrole (Compound No. 1-3253)

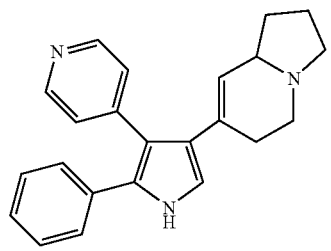

The title compound (yield 10%, Rf value=0.11) was obtained as a pale brown powder during the chromatography performed in Example 99 above.

Melting point: 180–183° C. (decomposition) $^1$H-Nuclear magnetic resonance spectrum (400 MHz, CDCl$_3$) δ ppm: 8.47 (2H, doublet, J=6 Hz); 8.34 (1H, broad singlet);

7.30–7.13 (7H, multiplet); 6.84 (1H, doublet, J=3 Hz); 5.44 (1H, singlet); 3.27–3.18 (1H, multiplet); 3.02–2.82 (2H, multiplet); 2.78–2.60 (2H, multiplet); 2.43–2.30 (1H, multiplet); 2.17–2.06 (1H, multiplet); 1.95–1.65 (3H, multiplet); 1.45–1.32 (1H, multiplet).

PREPARATIVE EXAMPLES

Preparative Example 1

4-Bromo-2-(4-fluorophenyl)-3-(2-methylaminopyrimidin-4-yl)-1-triisopropylsilyl-1H-pyrrole 1(i)  2-(4-Fluorophenyl)-3-(2-methylthiopyrimidin-4-yl)-1H-pyrrole In a similar manner to the procedures described in Example 1 (i) above (pyrrole ring forming reaction) and Example 7(i) above (decarboxylation), reactions were carried out using ethyl 3-(2-methylthiopyrimidin-4-yl)acrylate instead of ethyl 3-(4-pyridyl)acrylate as a starting material to afford the title compound (yield 37%) as a white powder.

$^1$H-Nuclear magnetic resonance spectrum (400 MHz, CDCl$_3$) δ ppm: 8.41 (1H, broad singlet); 8.24 (1H, doublet, J=5 Hz); 7.42 (1H, doublet of doublets, J=9 Hz, 5 Hz); 7.10 (2H, triplet, J=9 Hz); 6.88 (1H, triplet, J=3 Hz); 6.84 (1H, doublet, J=5 Hz); 6.81 (1H, triplet, J=3 Hz); 2.33 (3H, singlet).

1(ii)  2-(4-Fluorophenyl)-3-(2-methanesulfonylpyrimidin-4-yl)-1H-pyrrole

In a similar manner to that described in Example 42(ii) above, 2-(4-fluorophenyl)-3-(2-methylthiopyrimidin-4-yl)-1H-pyrrole [which was prepared as described in step 1(i) above] was oxidized to afford the title compound (yield 81%) as a pale yellow powder.

$^1$H-Nuclear magnetic resonance spectrum (400 MHz, CDCl$_3$—CD$_3$OD) δ ppm: 8.58 (1H, doublet, J=6 Hz); 7.50 (2H, doublet of doublets, J=9 Hz, 6 Hz); 7.47 (1H, doublet, J=6 Hz); 7.16 (2H, triplet, J=9 Hz); 6.90 (1H, doublet, J=3 Hz); 6.84 (1H, doublet, J=3 Hz); 3.05 (3H, singlet).

1(iii)  2-(4-Fluorophenyl)-3-(2-methylaminopyrimidin-4-yl)-1H-pyrrole

In a similar manner to that described in Example 42(iii) above, 2-(4-fluorophenyl)-3-(2-methanesulfonylpyrimidin-4-yl)-1H-pyrrole [prepared as described in step 1(ii) above] was reacted with methylamine to afford the title compound (quantitative yield) as a pale brown amorphous solid.

$^1$H-Nuclear magnetic resonance spectrum (400 MHz, CDCl$_3$) δ ppm: 8.37 (1H, broad singlet); 8.08 (1H, doublet, J=5 Hz); 7.44 (2H, doublet of doublets, J=9 Hz, 6 Hz); 7.08 (2H, triplet, J=9 Hz); 6.85 (1H, triplet, J=3 Hz); 6.75 (1H, triplet, J=3 Hz); 6.47 (1H, doublet, J=5 Hz); 4.90 (1H, broad quartet, J=5 Hz); 2.87 (3H, doublet, J=5 Hz).

1(iv)  2-(4-Fluorophenyl)-3-(2-methylaminopyrimidin-4-yl)-1-triisopropylsilyl-1H-pyrrole In a similar manner to that described in Example 7(ii) above, 2-(4-fluorophenyl)-3-(2-methylaminopyrimidin-4-yl)-1H-pyrrole [prepared as described in step 1(iii) above] was reacted with triisopropylsilyl triflate, to afford the title compound (yield 82%) as a white powder.

$^1$H-Nuclear magnetic resonance spectrum (400 MHz, CDCl$_3$) δ ppm: 7.92 (1H, doublet, J=5 Hz); 7.36 (2H, doublet of doublets, J=9 Hz, 6 Hz); 7.06 (2H, triplet, J=9 Hz); 6.90 (1H, doublet, J=3 Hz); 6.89 (1H, doublet, J=3 Hz); 5.93 (1H, doublet, J=5 Hz); 4.80 (1H, broad quartet, J=5 Hz); 2.83 (3H, doublet, J=5 Hz); 1.15–0.92 (21H, multiplet).

1(v)  3-[2-(N-t-Butoxycarbonyl-N-methylamino)pyrimidin-4-yl-2-(4-fluorophenyl)-1-triisopropylsilyl]-1H-pyrrole In a similar manner to that described in Example 4(i) above, 2-(4-fluorophenyl)-3-(2-methylaminopyrimidin-4-yl)-1-triisopropylsilyl-1H-pyrrole [prepared as described in step 1(iv)] was reacted with di-t-butyl dicarbonate to afford the title compound (yield 90%) as colorless oil.

$^1$H-Nuclear magnetic resonance spectrum (400 MHz, CDCl$_3$) δ ppm: 8.24 (1H, doublet, J=5 Hz); 7.36 (2H, doublet of doublets, J=9 Hz, 5 Hz); 7.09 (2H, triplet, J=9 Hz); 6.95 (1H, doublet, J=3 Hz); 6.90 (1H, doublet, J=3 Hz); 6.28 (1H, doublet, J=5 Hz); 3.20 (3H, singlet); 1.51 (9H, singlet); 1.15–0.94 (21H, multiplet).

1(vi)  4-Bromo-3-[2-(N-t-butoxycarbonyl-N-methylamino)pyrimidin-4-yl]-2-(4-fluorophenyl)-1-triisopropylsilyl-1H-pyrrole In a similar manner to that described in Example 7(iii) above, 3-[2-(N-t-butoxycarbonyl-N-methylamino)pyrimidin-4-yl]-2-(4-fluorophenyl)-1-triisopropylsilyl-1H-pyrrole [prepared as described in step 1(v) above] was brominated to afford the title compound (yield 79%) as a pale brown amorphous solid.

$^1$H-Nuclear magnetic resonance spectrum (400 MHz, CDCl$_3$) δ ppm: 8.42 (1H, doublet, J=5 Hz); 7.28 (2H, doublet of doublets, J=9 Hz, 5 Hz); 7.00 (2H, triplet, J=9 Hz); 6.93 (1H, singlet); 6.78 (1H, doublet, J=5 Hz); 3.13 (3H, singlet); 1.49 (9H, singlet); 1.15–0.93 (21H, multiplet).

1(vii)  4-Bromo-2-(4-fluorophenyl)-3-(2-methylaminopyrimidin-4-yl)-1H-pyrrole 472 mg (0.782 mmol) of 4-bromo-3-[2-(N-t-butoxycarbonyl-N-methylamino)pyrimidin-4-yl]-2-(4-fluorophenyl)-1-triisopropylsilyl-1H-pyrrole [prepared as described in step (vi) above] were dissolved in 10 of ml tetrahydrofuran, 0.98 ml (3.91 mmol) of a 4N solution of hydrogen chloride in dioxane were added to the solution, and the resulting mixture was stirred for 3 hours at 50° C. At the end of this time, water was added to the reaction mixture and then it was neutralized with a saturated aqueous solution of sodium hydrogencarbonate. This was extracted with ethyl acetate, and the organic extract was concentrated under reduced pressure. The resulting residue was purified by chromatography on a silica gel column using a 7:3 by volume mixture of hexane and ethyl acetate as the eluant to afford 202 mg (yield 74%) of the title compound as a pale brown amorphous solid.

$^1$H-Nuclear magnetic resonance spectrum (400 MHz, CDCl$_3$) δ ppm: 8.66 (1H, broad singlet); 8.21 (1H, doublet, J=5 Hz); 7.26 (2H, doublet of doublets, J=9 Hz, 5 Hz); 7.01 (2H, triplet, J=9 Hz); 6.88 (1H, doublet, J=3 Hz); 6.61 (1H, doublet, J=5 Hz); 4.96 (1H, broad quartet, J=5 Hz); 2.86 (3H, doublet, J=5 Hz).

1(viii)  4-Bromo-2-(4-fluorophenyl)-3-(2-methylaminopyrimidin-4-yl)-1-triisopropylsilyl-1H-pyrrole In a similar manner to the procedures described in Example 7(ii) above, 4-bromo-2-(4-fluorophenyl)-3-(2-methylaminopyrimidin-4-yl)-1H-pyrrole [prepared as described in step 1(vii) above] was reacted with triisopropylsilyl triflate to afford the title compound (yield 67%) as a pale brown amorphous solid.

$^1$H-Nuclear magnetic resonance spectrum (400 MHz, CDCl$_3$) δ ppm: 8.04 (1H, doublet, J=5 Hz); 7.30 (2H, doublet of doublets, J=9 Hz, 6 Hz); 6.98 (2H, triplet, J=9 Hz); 6.91 (1H, singlet); 6.32 (1H, broad singlet); 4.85 (1H, broad quartet, J=4 Hz); 2.82 (3H, doublet, J=4 Hz); 1.15–0.92 (21H, multiplet).

Preparative Example 2

4-Bromo-2-phenyl-3-(pyridin-4-yl)-1-triisopropylsilyl-1H-pyrrole

In a similar manner to the procedures described in Example 1(i) above (pyrrole ring forming reaction), Example 7(i) above (decarboxylation), Example 7(ii) above (reaction with triisopropylslyl triflate) and Example 7(iii) above (bromination), reactions were carried out using α-(p-toluenesulfonyl)benzylisonitrile, instead of α-(p-toluenesulfonyl)-4-fluorobenzylisonitrile, as a starting material to afford the title compound as a pale purple powder.

$^1$H-Nuclear magnetic resonance spectrum (400 MHz, $CDCl_3$) δ ppm: 8.35 (2H, doublet, J=6 Hz); 7.36–7.30 (1H, multiplet); 7.28–7.21 (4H, multiplet); 7.03 (2H, doublet, J=6 Hz); 6.94 (1H, singlet); 1.15–1.02 (21H, multiplet).

Preparative Example 3

4-Bromo-2-(3-chlorophenyl)-3-(pyridin-4-yl)-1-triisopropylsilyl-1H-pyrrole

In a similar manner to the procedures described in Example 1(i) above (pyrrole ring forming reaction), Example 7(i) above (decarboxylation), Example 7(ii) above (reaction with triisopropysilyl triflate) and Example 7(iii) above(bromination), reactions were carried out using α-(p-toluenesulfonyl)-3-chlorobenzylisonitrile, instead of α-(p-toluenesulfonyl)-4-fluorobenzylisonitrile, as a starting material to afford the title compound as a pale purple powder.

$^1$H-Nuclear magnetic resonance spectrum (400 MHz, $CDCl_3$) δ ppm: 8.40 (2H, doublet, J=6 Hz); 7.33–7.29 (2H, multiplet); 7.18 (1H, triplet, J=8 Hz); 7.09 (1H, doublet, J=8 Hz); 7.03 (2H, doublet, J=6 Hz); 6.95 (1H, singlet); 1.12–0.99 (21H, multiplet).

Preparative Example 4

4-Bromo-2-(3-fluorophenyl)-3-(pyridin-4-yl)-1-triisopropylsilyl-1H-pyrrole

In a similar manner to the procedures described in Example 1(i) above (pyrrole ring forming reaction), Example 7(i) above (decarboxylation), Example 7(ii) above (reaction with triisopropylsilyl triflate) and Example 7(iii) above (bromination), reactions were carried out using α-(p-toluenesulfonyl)-3-fluorobenzylisonitnile, instead of α-(p-toluenesulfonyl)-4-fluorobenzylisonitrile, as a starting material to afford the title compound as a pale purple powder.

$^1$H-Nuclear magnetic resonance spectrum (400 MHz, $CDCl_3$) δ ppm: 8.39 (2H, doublet, J=6 Hz); 7.22 (1H, doublet of doublets, J=8 Hz, 6 Hz); 7.07–7.01 (4H, multiplet); 6.98–6.94 (2H, multiplet); 1.14–0.98 (21H, multiplet).

Preparative Example 5

4-Bromo-2-(3,4-difluorophenyl)-3-(pyridin-4-yl)-1-triisopropylsilyl-1H-pyrrole In a similar manner to the procedures described in Example 1(i) above (pyrrole ring forming reaction), Example 7(i) above (decarboxylation), Example 7(ii) above (reaction with triisopropylsilyl triflate) and Example 7(iii) above (bromination), reactions were carried out using α-(p-toluenesulfonyl)-3,4-difluorobenzylisonitrile, instead of α-(p-toluenesulfonyl)-4-fluorobenzylisonitrile, as a starting material to afford the title compound as a pale purple powder.

$^1$H-Nuclear magnetic resonance spectrum (400 MHz, $CDCl_3$) δ ppm: 8.42 (2H, doublet, J=6 Hz); 7.12–6.93 (3H, multiplet); 7.02 (2H, doublet, J=6 Hz); 6.94 (1H, singlet); 1.18–0.94 (21H, multiplet).

Preparative Example 6

4-Bromo-2-(3-trifluoromethylphenyl)-3-(pyridin-4-yl)-1-triisopropylsilyl-1H-pyrrole In a similar manner to the procedures described in Example 1(i) above (pyrrole ring forming reaction), Example 7(i) above (decarboxylation), Example 7(ii) above (reaction with triisopropysilyl triflate) and Example 7(iii) above (bromination), reactions were carried out using α-(p-toluenesulfonyl)-3-trifluoromethyl-benzylisonitrile, instead of α-(p-toluenesulfonyl)-4-fluorobenzylisonitrile, as a starting material to afford the title compound as a pale purple powder.

$^1$H-Nuclear magnetic resonance spectrum (400 MHz, $CDCl_3$) δ ppm: 8.39 (2H, doublet, J=6 Hz); 7.64–7.57 (2H, multiplet); 7.40–7.33 (2H, multiplet); 7.00 (2H, doublet, J=6 Hz); 6.98 (1H, singlet); 1.15–0.94 (21H, multiplet).

FORMULATION EXAMPLES

A pharmaceutical preparation containing a compound of the present invention having the above formula (I), or a pharmacologically acceptable salt, ester or other derivative thereof as its active ingredient can be produced according to, for example, the following methods.

Formulation Example 1

Powder 5 g of the compound of Example 2, 895 g of lactose and 100 g of corn starch were mixed in a blender to provide the desired powder.

Formulation Example 2

Granules 5 g of the compound of Example 5, 865 g of lactose and 100 g of low-substituted hydroxypropyl cellulose were mixed, 300 g of a 10% aqueous hydroxypropyl cellulose solution were added to the resulting mixture, and this was then kneaded. The product thus obtained was then granulated using an extrusion granulating machine and dried to provide the desired granules.

Preparation Example 3

Capsules 5 g of the compound of Example 6, 115 g of lactose, 58 g of corn starch and 2 g of magnesium stearate were mixed using a V-shaped mixer, no. 3 capsules were chosen and then each of said no. 3 capsules was filled with 180 mg of the resulting mixture to provide the desired capsules.

Preparation Example 4

Tablets 5 g of the compound of Example 83, 90 g of lactose, 34 g of corn starch, 20 g of crystalline cellulose and 1 g of magnesium stearate were mixed in a blender, and the resulting mixture was then formed into tablets with a tablet machine to provide the desired tablets.

TEST EXAMPLEs

The biological activity of the compounds of the present invention is illustrated by the following Test Examples.

Test Example 1

Inhibition of the Production of the Cytokines IL-1β and TNFα in Vitro in Human Whole Blood This test was performed according to the method of Hartman, et al. [D. A. Hartman, S. J. Ochalski and R. P. Carlson; The effects of anti-inflammatory and antiallergic drugs on cytokine release after stimulation of human whole blood by lipopolysaccharide and zymosan A: Inflamm. Res., 44, 269 (1995)].

Peripheral blood samples were collected in the presence of heparin from healthy adult volunteers. 1000 μl of whole blood were added to an Eppendorf tube to which 2 μl of a dimethyl sulfoxide solution of the test compound had been added in advance, after which 10 μl of lipopolysaccharide (*E. coli* 026: B6 origin, Difco) were added as a stimulant (final concentration of said lipopolysaccharide: 10 μg/ml). This was mixed well and then incubated for 6 hours at 37° C. in the presence of 5% $CO_2$. At the end of the incubation, the mixture was cooled to 4° C. to stop the reaction, followed immediately by centrifuging for 5 minutes at 14,000 rpm to separate and collect the supernatant plasma. The IL-1β and TNFα produced and released into the plasma were measured using a commercially available enzyme immunoassay (ELISA) kit [Cayman (IL-1β) and Genzyme (TNFα)]. The procedure was also repeated in the absence of test compound. The inhibitory effect [$IC_{50}$ (μM)] on the production of IL-1β and TNFα was determined from the amounts of the cytokines produced in the presence and absence of the test compound.

The results for the inhibition of the production in vitro of TNFα are shown in Table 3 below for the most preferred compounds of the present invention which are the subject of the original species claims. In this Table, Compounds A and B are as follows:

TABLE 3

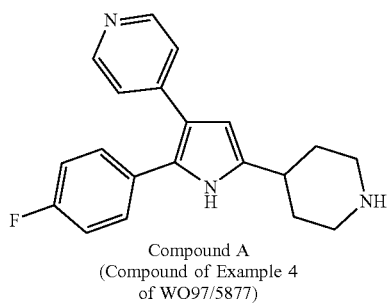

Compound A
(Compound of Example 4
of WO97/5877)

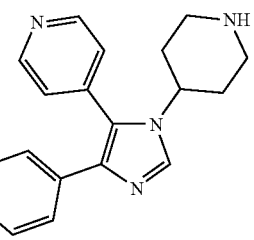

Compound B
(Compound of Example 23
of WO96/21452)

| Example No. | Inhibitory Effect on TNFα Production [$IC_{50}$ (μM)] |
|---|---|
| Compound A | 1.90 |
| Compound B | 1.73 |
| 45 | 0.14 |
| 58 | 0.089 |
| 60 | 0.047 |
| 83 | 0.026 |
| 85 | 0.44 |
| 86 | 0.29 |
| 87 | 0.31 |
| 92 | 0.045 |
| 94 | 0.031 |

Table 3 above demonstrates excellent inhibitory activity against the production of TNFα in vitro for said most preferred compounds of the present invention.

The compounds of the present invention were also found to show excellent inhibitory activity against the production of IL-β in vitro.

Test Example 2

Inhibition of the Production of TNFα In Vivo

This test was performed according to the method of Ochalski, et al. [S. J. Ochalski, D. A. Hartman, M. T. Belfast, T. L. Walter, K. B. Glaser and R. P. Carlson; Inhibition of endotoxin-induced hypothermia and serum TNF-α levels in CD-1 mice by various pharmacological agents: Agents Actions 39, C52–C54 (1993)].

The production of TNFα was induced in mice by the intravenous injection of lipopolysaccharide (*E. coli* O26: B6 origin, Difco) which was prepared to a concentration of 0.045 mg/ml using physiological saline. The saline preparation of lipopolysaccharide was administered at the rate of 10 ml/1 kg of body weight into the caudal vein of Balb/c mice (males, age 5–7 weeks, body weight: approx. 22 g, Japan Charles River) which had been fasted overnight starting on the day before the experiment. One hour after administration, the mice were laparotomized under ether anaesthesia and blood was collected from the abdominal vena cava. Blood collection was performed using a 1 ml volume disposable syringe equipped with a 23G needle which had been moistened with heparin on the inside wall. Following blood collection, the blood was immediately transferred to a 1.5 ml volume Eppendorf tube and centrifuged at 4° C. and 14,000 rpm to separate the plasma. This plasma was then stored at −20° C. until measurement of TNFα. The measurement of the amount of TNFα was performed with a commercially available enzyme immunoassay (ELISA) kit (Mouse TNFα ELISA KIT, Genzyme).

To determine the inhibitory activity of the test compounds, each test compound was suspended in a 0.5% tragacanth solution and then administered orally to the Balb/c mice at the rate of 10 ml/1 kg of body weight 30 minutes before injection of lipopolysaccharide. The level of TNFα production was then determined as described above. In the control group, 0.5% tragacanth solution was administered at the rate of 10 ml/1 kg of body weight to the test mice instead of the solutions of the test compounds. A minimum of 3 dose levels of the test compound was administered to groups of 5 test mice for each test compound. The inhibitory rate relative to the control group was calculated for each dose level. From the inhibitory rates and the dosages, $ID_{50}$ values were calculated by the least squares method.

The compounds of the present invention were found to show excellent inhibitory activity against the production of TNFα in vivo.

Test Example 3

Inhibition of the Production of IL-1β In Vivo

This test was performed according to the method of Griffiths, et al. [Richard J. Griffiths, Ethan J. Stam, James T. Downs and Ivan G. Otterness; ATP Induces the Release of IL-1 from LPS-Primed Cells In Vivo: J. Immunol., 154, 2821–2828 (1995)].

The production of IL-1 was induced in mice by the intraperitoneal injection of lipopolysaccharide followed by the intraperitoneal injection of adenosine triphosphate (ATP). This was achieved by first administering a solution of lipopolysaccharide (*E. coli* O26: B6 origin, Difco), which had been prepared to a concentration of 0.0045 mg/ml using physiological saline, at the rate of 10 ml of said saline solution/1 kg of body weight into the peritoneal cavity of Balb/c mice (males, age 5–7 weeks, body weight: approx. 22 g, Japan Charles River) which had been fasted overnight starting on the day before the experiment. Two hours later, 0.5 ml of ATP, which had been prepared to a concentration of 6.03 mg/ml using physiological saline, were administered into the peritoneal cavity. 0.5 hours after the administration of ATP, the mice were sacrificed by suffocation using dry ice followed immediately by intraperitoneal injection of 3 ml of washing phosphate buffer solution [containing heparin (10 U/ml), p-toluenesulfonyl fluoride (0.25 mM), leupepsin (1 μg/ml), pepstatin (1 μg/ml) and EDTA (1 mM)] to wash the peritoneal cavity. A 1 ml volume disposable syringe equipped with a 21 G needle was then used to recover the washing liquid. After the recovery, the washing liquid from the peritoneal cavity was immediately transferred to a 1.5 ml volume Eppendorf tube and centrifuged at 4° C. and 7,500 rpm to separate the supernatant. This supernatant was then stored at −20° C. until measurement of IL-1β.

The measurement of the amount of IL-1β was performed with an enzyme immunoassay (ELISA) kit (Mouse IL-1β ELISA KIT, Genzyme).

To determine the inhibitory activity of the test compounds, each test compound was suspended in a 0.5% tragacanth solution and then administered orally to the Balb/c mice at the rate of 10 ml/1 kg of body weight 30 minutes before injection of lipopolysaccharide. The level of TNFα production was then determined as described above. In the control group, 0.5% tragacanth solution was administered to the test mice at the rate of 10 ml/1 kg of body weight instead of the solutions of the test compounds. A minimum of 3 dose levels of the test compound was administered to groups of 5 test mice for each test compound. The mean inhibitory rate relative to the control group was calculated for each dose level.

In this test, the compounds of the present invention demonstrated an excellent inhibitory effect against the production of IL-1β in vivo.

Test Example 4

Activity in Preventing the Development of Adjuvant-Induced Arthritis In Vivo

The test was performed according to the method described by Winder et al. (Arthritis Rheum., 12, 472–482, 1969).

Heat-killed dried *Mycobacterium butyricum* (Difco Laboratories, Lot 679123) was ground on an agate mortar, and was then suspended in dry-sterilised liquid paraffin (first grade, Wako Pure Chemical Industries, Ltd.) to make a 2 ml suspension. The resulting suspension was then sonicated and used as an adjuvant. Arthritis was induced by the intradermal injection of the adjuvant (100 μg of heat killed dried bacterium/0.05 ml of paraffin/paw) into the heel of the right hind paw of a Lewis rat (male, age 8 weeks, Japan Charles River). The test compounds, which had been suspended in 0.5% sodium carboxymethyl cellulose solution (CMC, Daiichi Pure Chemicals, Co., Ltd.), were administered orally once a day from the day of injection of the adjuvant (day 0) to day 20.

The volumes of the injected (right) and non-injected (left) hind paws were measured on days 3, 5, 7, 10, 13, 15, 18 and 21 using a Plethysmometer™ (Ugo Basile), the hind paws being soaked from the toe to the hairline in the bath of the Plethysmometer™. The volumes of the swollen feet (adjuvant-injected right hind foot volume—non-injected left hind foot volume) were calculated. The percent inhibition of swelling of the injected foot of the treated animals as compared to that of the control animals on day 21 was calculated as follows.

Inhibition (%)={1−(swollen foot volume of compound-treated animals)/(swollen foot volume of control animals)}×100

A linear regression curve was obtained from the percent inhibition and the logarithmic value of the dosage by the least squares method. $ID_{50}$ values were calculated using this curve.

In this test, the compounds of the present invention showed excellent activity in preventing the development of adjuvant-induced arthritis.

Test Example 5

Activity in Preventing the Development of Arthritis Induced by Anti-Collagen Antibody In Vivo In this test, an anti-collagen antibody-induced mouse arthritis model was employed.

0.5 ml (2 mg of antibody) of an anti-collagen antibody solution (4 mg/ml, Arthritogenic mAb Cocktail: product of Immuno-Biological Laboratories Co., Ltd) were injected into the caudal vein of Balb/c mice (males, age 5–6 weeks old, Japan Charles River). Three days after injection, 0.1 ml [0.05 mg of lipopolysaccharide] of a lipopolysaccharide solution (0.5 mg/ml, Arthritogenic mAb Cocktail: product of Immuno-Biological Laboratories Co., Ltd) were administered to the mice by intraperitoneal injection.

The test compounds, which had been suspended in 0.5% tragacanth were administered orally to the test animals at the rate of 10 ml/1 kg of body weight once per day for 7 days from the day when the anti-collagen antibody was administered. To the mice of the control group, 0.5% tragacanth solution was administered at the rate of 10 ml/kg of body weight once per day for 7 days from the day when the anti-collagen antibody was administered, instead of solutions of the test compounds.

After the administration of the test compounds (or 0.5% tragacanth solution), the degree of edema in the 4 paws of each test mouse was scored according to the following basis:

0: normal (edema is not observed);
1: edema is observed in one of the five toes;
2: edema is observed in two or more of the five toes;
3: the whole of the paw is swollen.

The degree of arthritis in the test mouse was evaluated by the total of the edema scores in the 4 paws. The rate of suppression was calculated from the degrees of arthritis of the control animals and of the animals treated with the test compounds. From the rates of suppression and the dosages, $ID_{50}$ values were calculated by the least squares method.

In this test, the compounds of the present invention showed excellent activity in preventing the development of arthritis induced by anti-collagen antibody.

Test Example 6

Activity in Treating Arthritis Induced by Anti-Collagen Antibody In Vivo

In this test, an anti-collagen antibody-induced mouse arthritis model was employed.

0.5 ml (2 mg of antibody) of an anti-collagen antibody solution (4 mg/ml, Arthritogenic mAb Cocktail: product of Immuno-Biological Laboratories Co., Ltd) were injected into the caudal vein of Balb/c mice (males, age 5–6 weeks old, Japan Charles River). Three days after injection, 0.1 ml [0.05 mg of lipopolysaccharide] of a lipopolysaccharide solution (0.5 mg/ml, Arthritogenic mAb Cocktail: product of Immuno-Biological Laboratories Co., Ltd) were administered to the mice by intraperitoneal injection.

7 days after the administration of the anti-collagen antibody solution, the degree of edema in the 4 paws of each test mouse was scored according to the basis as shown in Test Example 5 above.

Those mice in which edema in both the hind paws had been scored as "3" were selected. Test compounds, which had been suspended in 0.5% tragacanth solution, were administered orally to the selected mice at the rate of 10 ml/kg of body weight once per day for 3 days. To the mice of the control group, 0.5% tragacanth solution was administered at the rate of 10 ml/kg of body weight once per day for 3 days instead of solutions of the test compounds.

After the administration of the test compounds (or 0.5% tragacanth solution), the degree of arthritis in each test mouse was evaluated in the same manner as described in Test Example 5. The rates of treatment of arthritis induced by anti-collagen antibody were calculated from the degrees of arthritis of the control animals and of the compound-treated animals.

From the rates of treatment and the dosages, $ID_{50}$ values were calculated by the least squares method.

In this test, the compounds of the present invention showed excellent activity in treating arthritis induced by anti-collagen antibody.

As illustrated above, the compounds of the present invention exhibit excellent activity in inhibiting the production of inflammatory cytokines, particularly in inhibiting the production of IL-1β and TNFα. Furthermore, the compounds of the present invention have satisfactory oral absorptivity and a low level of toxicity. Consequently, the compounds of the present invention are useful as pharmaceuticals, suitable for the prohylaxis and treatment of both humans and animals. They can, for example, be used as an analgesic, an anti-inflammatory agent and an antiviral agent as well as an agent for use in the prophylaxis and treatment of chronic rheumatoid arthritis, degenerative arthritis, allergic diseases, asthma, septicaemia, psoriasis, osteoporosis, autoimmune diseases (e.g., systemic lupus erythematosus, ulcerative colitis and Crohn's disease), diabetes, glomerular nephritis, hepatitis and arteriosclerosis. Of these applications, the compounds of the present invention are particularly useful as an analgesic and an anti-inflammatory agent and as an agent for the prophlaxis and treatment of chronic rheumatoid arthritis, degenerative arthritis, allergic diseases, septicaemia, psoriasis, osteoporosis, ulcerative colitis, diabetes, hepatitis and arteriosclerosis.

Example 1'

2-(4-fluorophenyl)-4-[(2R,8aS)-2-methoxy-1,2,3,5,8, 8a-hexahydroindolizin-7-yl]-3-(pyridin-4-yl)-1H-pyrrole (Compound No. 4-15')

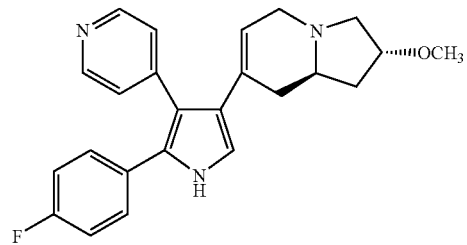

1(i)' 4-Ethoxycarbonyl-2-(4-fluorophenyl)-3-(pyridin-4-yl)-1H-pyrrole 36 ml (54.7 mmol) of a 1.53N solution of butyllithium in hexane were added to 240 ml of tetrahydrofuran. A solution of 15.90 g (54.7 mmol) of α-(p-toluene-sulfonyl)-4-fluorobenzyl isocyanide in 120 ml of tetrahydrofuran was then added to the resulting solution at—45° C., followed by stirring of the resulting mixture for 10 minutes at the same temperature. At the end of this time, 25.00 g (273 mmol) of 95% lithium bromide were added, the resulting mixture was stirred for 30 minutes and then a solution of 8.73 g (49.2 mmol) of ethyl 3-(4-pyridyl)acrylate in 120 ml of tetrahydrofuran was added. The resulting mixture was stirred at the same temperature for 1 hour and then the cooling bath was removed and the mixture was stirred at room temperature for a further 1 hour. At the end of this time, 500 ml of water were added and the resulting mixture was extracted with ethyl acetate. The organic extract was washed with water and then dried over anhydrous sodium sulfate, after which it was concentrated by evaporation under reduced pressure to afford a solid. The solid was washed with diethyl ether to give 13.61 g (yield: 89%) of the title compound as a pale yellow powder.

$^1$H-NMR spectrum (500 MHz, $CDCl_3$) δ ppm: 8.84 (1H, broad singlet); 8.51 (2H, doublet, J=7 Hz); 7.58 (1H, doublet. J=3 Hz); 7.21 (2H, doublet, J=6 Hz); 7.11 (2H, doublet of doublets, J=9 Hz, 5 Hz); 6.97 (2H, triplet, J=9 Hz); 4.18 (2H, quartet, J=7 Hz); 1.20 (3H, triplet, J=7 Hz).

1(ii)' 2-(4-Fluorophenyl)-3-(pyridin-4-yl)-1H-pyrrole 15.00 g (48.3 mmol) of 4-ethoxycarbonyl-2-(4-fluorophenyl)-3-(pyridin-4-yl)-1H-pyrrole [obtained as described in Example 1(i)' above] were dissolved in a mixture of 90 ml of acetic acid, 30 ml of sulfuric acid and 60 ml of water, and the resulting solution was stirred at 100° C. for 16 hours. After being cooled to room temperature, the reaction mixture was made basic by the addition of a 10% aqueous solution of sodium hydroxide before extracting with ethyl acetate. The organic extract thus obtained was washed with water, dried over anhydrous sodium sulfate and then concentrated by evaporation under reduced pressure to give 11.40 g (yield: 99%) of the title compound as a pale red powder.

$^1$H-NMR spectrum (500 MHz, CDCl$_3$) δ ppm: 9.78 (1H, broad singlet); 8.42 (2H, doublet, J=7 Hz); 7.37 (2H, doublet of doublets, J=9 Hz. 5 Hz); 7.22 (2H, doublet, J=6 Hz); 7.06 (2H, triplet, J=9 Hz): 6.90 (1H, triplet, J=3 Hz); 6.47 (1H, triplet, J=3 Hz).

1(iii)' 2-(4-Fluorophenyl)-3-(pyridin-4-yl)-1-triisopropylsilyl-1H-pyrrole 11.30 g (47.4 mmol) of 2-(4-fluorophenyl)-3-(pyridin-4-yl)-1H-pyrrole [obtained as described in Example (ii)' above] were dissolved in 300 ml of tetrahydrofuran. 31 ml (47.4 mmol) of a 1.57N solution of butyllithium in hexane were then added to the resulting solution at −78° C. After stirring the reaction mixture for 10 minutes, 13.4 ml (49.8 mmol) of triisopropylsilyl triflate were added at the same temperature. The resulting mixture was stirred at room temperature for 30 minutes. At the end of this time 200 ml of water and 300 ml of a saturated aqueous solution of sodium hydrogencarbonate were added, and the mixture was extracted with ethyl acetate. The organic extract was washed with water, dried over anhydrous sodium sulfate and then concentrated by evaporation under reduced pressure to afford 18.70 g (quantitative yield) of the title compound as a reddish purple oil.

$^1$H-NMR spectrum (500 MHz. DMSO-d$_6$) δ ppm: 8.25 (2H, doublet, J=6 Hz); 7.39 (2H, doublet of doublets, J=9 Hz. 6 Hz); 7.28 (2H, triplet, J=9 Hz); 7.00 (1H, doublet, J=3 Hz): 6.91(2H, doublet, J=7 Hz); 6.71 (1H, doublet, J=3 Hz); 1.15–1.05 (3H, multiplet); 0.98 (18H, doublet, J=8 Hz).

1(iv)' 4-Bromo-2-(4-fluorophenyl)-3-(pyridin-4-yl)-1-triisopropylsilyl-1H-pyrrole 18.70 g (47.4 mmol) of 2-(4-fluorophenyl)-3-(pyridin-4-yl)-1-triisopropylsilyl-1H-pyrrole [obtained as described in Example 1(iii)' above] were dissolved in 300 ml of tetrahydrofuran. A suspension of 8.61 g (47.4 mmol) of N-bromosuccinimide in 100 ml of tetrahydrofuran was then gradually added to the resulting mixture at −78° C. The resulting reaction mixture was then stirred at −78° C. for 6 hours followed by a further 1 hour of stirring at room temperature, after which time 400 ml of hexane were added and any insoluble materials were filtered off. The filtrate was concentrated by evaporation under reduced pressure. The resulting residue was purified by chromatography on a silica gel column using a 2:1 by volume mixture of hexane and ethyl acetate as the eluant to afford 9.57 g (yield: 43%) of the title compound as pale yellow prisms.

$^1$H-NMR spectrum (500 MHz, DMSO-d$_6$) δ ppm: 8.36 (2H, doublet, J=6 Hz); 7.34 (2H, doublet of doublets, J=9 Hz, 6 Hz); 7.18 (2H, triplet, J=9 Hz); 7.12 (1H, singlet); 7.04 (2H, doublet, J=6 Hz); 1.16–1.08 (3H, multiplet); 0.99 (18H, doublet, J=8 Hz).

1(v)' 2-(4-Fluorophenyl)-4-[(2R,8aS)-2-methoxy-1,2,3,5,8,8a-hexahydroindolizin-7-yl]-3-(pyridin-4-yl)-1H-pyrrole 3.00 g (6.34 mmol) of 4-bromo-2-(4-fluorophenyl)-3-(pyridin-4-yl)-1-triisopropylsilyl-1H-pyrrole [obtained as described in Example 1(iv)' above] were dissolved in 60 ml of tetrahydrofuran. 4.36 ml (6.97 mmol) of a 1.6M solution of butyllithium in hexane were then added to the resulting solution at −78° C. After stirring the reaction mixture at −78° C. for 10 minutes, 1.29 g (7.60 mmol) of (2R,8aS)-2-methoxy-1,2,3,5,6,7,8,8a-octahydroindolizin-7-one (prepared as described in Preparative Example 1' below) were added at the same temperature. The resulting mixture was stirred at −780° C. for 2 hours and then at room temperature for 1 hour. At the end of this time a saturated aqueous solution of sodium hydrogencarbonate was added, and the reaction mixture was then extracted with ethyl acetate. The organic extract was washed with water, dried over anhydrous sodium sulfate and then concentrated by evaporation under reduced pressure.

The resulting residue was dissolved in 40 ml of dichloroethane, 1.95 ml (25.3 mmol) of trifluoroacetic acid were added to the solution thus obtained and the reaction mixture was then heated under reflux for 1 hour. After being cooled to room temperature, the reaction mixture was concentrated by evaporation under reduced pressure. The residue thus obtained was dissolved in 30 ml of tetrahydrofuran. 25.3 ml (25.3 mmol) of a 1M solution of tetrabutylammonium fluoride in tetrahydrofuran were added to the resulting solution and the mixture was then stirred for 10 minutes at room temperature. Water was added at the end of this time, and the resulting mixture was acidified with 1N hydrochloric acid and then extracted with ethyl acetate. The aqueous layer was made basic by the addition of sodium carbonate and then extracted with ethyl acetate. The organic extract was washed with water, dried over anhydrous sodium sulfate and then concentrated by evaporation under reduced pressure. The resulting residue was purified by chromatography on a silica gel column using a 100:10:1 by volume mixture of ethyl acetate, methanol and isopropylamine respectively as the eluant to afford 545 mg (yield: 22%) of the title compound (Rf value=0.45) as a pale brown powder.

Melting point: 203–205° C. (decomposition) $^1$H-NMR spectrum (400 MHz. DMSO-d$_6$) δ ppm: 11.38 (1H, broad singlet); 8.44 (2H, doublet, J=6 Hz); 7.20–7.06 (6H, multiplet); 6.90 (1H, doublet, J=3 Hz); 5.27–5.22 (1H, multiplet); 3.92–3.85 (1H, multiplet); 3.40 (1H, doublet of doublets, J=9 Hz, 7 Hz); 3.29–3.19 (1H, multiplet); 3.16 (3H, singlet); 2.71–2.62 (1H, multiplet); 2.37–2.20 (2H, multiplet); 2.04–1.90 (2H, multiplet); 1.88–1.80 (1H, multiplet); 1.51–1.41 (1H, multiplet).

Example 2'

2-(4-Fluorophenyl)-4-[(2R,8aS)-2-methoxy-1,2,3,5,6,8a-hexahydroindolizin-7-yl]-3-(pyridin-4-yl)-1H-pyrrole (Compound No. 1-303')

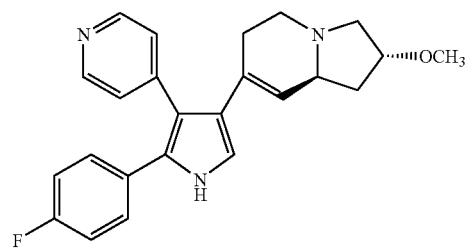

The silica gel column chromatography performed in Example 1(v)' above also provided 300 mg (yield: 12%) of the title compound (Rf value=0.40) as a pale brown powder.

Melting point: 198–200° C. (decomposition) $^1$H-NMR spectrum (400 MHz. DMSO-d$_6$) δ ppm: 11.39 (1H, broad singlet); 8.44 (2H, doublet, J=6 Hz); 7.21–7.05 (6H, multiplet); 6.92 (1H, doublet, J=3 Hz); 5.16–5.11 (1H, multiplet); 3.92–3.84 (1H, multiplet); 3.39–3.25 (1H, multiplet); 3.23–3.11 (1H, multiplet); 3.15 (3H, singlet); 3.05 (1H, doublet of doublets, J=10 Hz, 6 Hz); 2.86–2.77 (1H, multiplet); 2.64–2.54 (1H, multiplet); 2.30–2.19 (1H, multiplet); 2.10–2.00 (1H, multiplet); 1.76–1.67 (1H, multiplet); 1.48–1.38 (1H, multiplet).

Example 3'

2-(4-Fluorophenyl)-4-[(2R,8aS)-2-hydroxy-1,2,3,5,8,8a-hexahydroindolizin-7-yl]-3-(pyridin-4-yl)-1H-pyrrole (Compound No. 4-14')

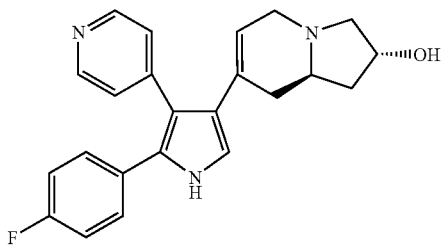

In a similar manner to the procedure described in Example 1(v)' above, a reaction and silica gel column chromatography (using a 100:10:2.5 by volume mixture of ethyl acetate methanol and isopropylamine respectively as the eluant) were conducted, using (2R8aS)-2-(t-butyldimethylsilyloxy)-1,2,3,5,6,7,8,8a-octahydroindolizin-7-one (prepared as described in Preparative Example 2' below) in place of (2R,8aS)-2-methoxy-1,2,3,5,6,7,8,8a-octahydroindolizin-7-one, to give 587 mg (yield: 25%) of the title compound (Rf value=0.25) as a pale brown powder.

Melting point: 208–210° C. (decomposition) $^1$H-NMR spectrum (400 MHz, DMSO-d$_6$) δ ppm: 11.37 (1H, broad singlet); 8.44 (2H, doublet, J=6 Hz); 7.20–7.06 (6H, multiplet); 6.90 (1H, doublet, J=3 Hz); 5.26–5.22 (1H, multiplet); 4.72 (1H, doublet, J=4 Hz); 4.25–4.16 (1H, multiplet); 3.38–3.27 (1H, multiplet); 3.25–3.17 (1H, multiplet); 2.72–2.63 (1H, multiplet); 2.45–2.35 (1H, multiplet); 2.26–2.18 (1H, multiplet); 1.98–1.87 (2H, multiplet); 1.71–1.64 (1H, multiplet): 1.57–1.46 (1H, multiplet).

Example 4'

2-(4-Fluorophenyl)-4-[(2R,8aS)-2-hydroxy-1,2,3,5,6,8a-hexahydroindolizin-7-yl]-3-(pyridin-4-yl)-1H-pyrrole (Compound No. 1-302')

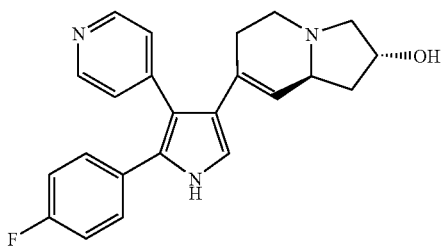

The silica gel column chromatography performed in Example 3' above also provided 213 mg (yield: 9%) of the title compound (Rf value=0.20) as a pale brown powder.

Melting point: 209–211°° C. (decomposition) $^1$H-NMR spectrum (400 MHz, DMSO-d$_6$) δ ppm: 11.38 (1H, broad singlet); 8.44 (2H, doublet, J=5 Hz); 7.20–7.05 (6H, multiplet); 6.90 (1H, doublet, J=3 Hz); 5.16–5.12 (1H, multiplet); 4.63 (1H, doublet, J=5 Hz); 4.25–4.16 (1H, multiplet); 3.30–3.20 (1H, multiplet); 3.00 (1H, doublet of doublets, J=10 Hz, 6 Hz); 2.84–2.74 (1H, multiplet); 2.63–2.53 (1H, multiplet); 2.40 (1H, doublet of doublets, J=10 Hz, 4 Hz); 2.27–2.16 (1H, multiplet); 2.08–1.98 (1H, multiplet); 1.62–1.52 (1H, multiplet); 1.52–1.42 (1H, multiplet).

Example 5'

4-[(2S,8aS)-2-Chloro-1,2,3,5,8,8a-hexahydroindolizin-7-yl]-2-(4-fluorophenyl)-3-(pyridin-4-yl)-1H-pyrrole (Compound No. 4-23')

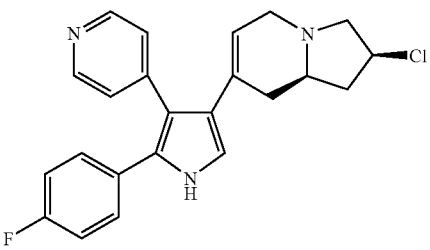

In a similar manner to the procedure described in Example 1(v)' above, a reaction and silica gel column chromatography (using a 40:1:1 by volume mixture of ethyl acetate, methanol and isopropylamine respectively as the eluent) were conducted, using (2S,8aS)-2-chloro-1,2,3,5,6,7,8,8a-octahydroindolizin-7-one (prepared as described in Preparative Example 3' below) in place of (2R,8aS)-2-methoxy-1,2,3,5,6,7,8,8a-octahydroindolizin-7-one, to give 520 mg (yield: 21%) of the title compound (Rf value=0.45) as a pale brown powder.

Melting point: 195–197° C. (decomposition) $^1$H-NMR spectrum (400 MHz, CDCl$_3$) δ ppm: 8.46 (2H, doublet, J=6 Hz); 8.38 (1H, broad singlet); 7.16 (2H, doublet, J=6 Hz); 7.13 (2H, doublet of doublets, J=9 Hz, 5 Hz); 6.97 (2H, triplet, J=9 Hz); 6.83 (1H, doublet, J=3 Hz); 5.54–5.53 (1H, multiplet); 4.42–4.36 (1H, multiplet); 3.54 (1H, doublet of doublets, J=16 Hz, 5 Hz); 3.39 (1H, doublet, J=11 Hz); 2.79 (1H, doublet, J=16 Hz); 2.68–2.60 (2H, multiplet); 2.30–2.16 (3H, multiplet); 1.85–1.76 (1H, multiplet).

Example 6'

4-[(2S,8aS)-2-Chloro-1,2,3,5,6,8a-hexahydroindolizin-7-yl]-2-(4-fluorophenyl)-3-(pyridin-4-yl)-1H-pyrrole (Compound No. 1-311')

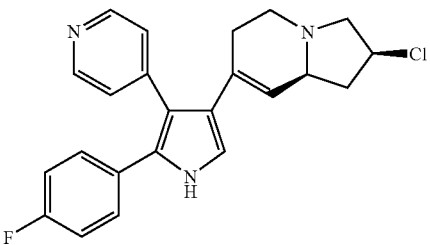

The silica gel column chromatography performed in Example 5' above also provided 400 mg (yield: 16%) of the title compound (Rf value=0.35) as a pale brown powder.

Melting point: 177–180° C. (decomposition) ¹H-NMR spectrum (400 MHz, CDCl₃) δ ppm: 8.49 (2H, doublet, J=5 Hz); 8.37 (1H, broad singlet); 7.17 (2H, doublet, J=5 Hz); 7.13 (2H, doublet of doublets, J=8 Hz, 5 Hz); 6.98 (2H, triplet, J=8 Hz); 6.84 (1H, doublet, J=3 Hz); 5.40 (1H, singlet); 4.38–4.32 (1H, multiplet); 3.53–3.45 (1H, multiplet); 3.23 (1H, doublet of doublets, J=11 Hz, 7 Hz); 3.13–3.06 (2H, multiplet); 2.90–2.82 (1H, multiplet); 2.59 (1H, doublet of triplets, J=14 Hz, 8 Hz); 2.43–2.31 (1H, multiplet); 2.13–2.02 (1H, multiplet); 1.79–1.69 (1H, multiplet).

Example 7'

4-[(8aS)-2,2-Difluoro-1,2,3,5,8,8a-hexahydroindolizin-7-yl]-2-(4-fluorophenyl)-3-(pyridin-4-yl)-1H-pyrrole (Compound No. 4-26')

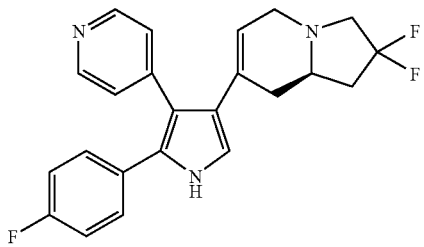

In a similar manner to the procedure described in Example 1(v)' above, a reaction and silica gel column chromatography (using a 49:1 by volume mixture of dichloromethane and methanol as the eluant) were conducted, using (8aS)-2,2-difluoro-1,2,3,5,6,7,8,8a-octahydroindolizin-7-one (prepared as described in Preparative Example 4' below) in place of (2R,8aS)-2-methoxy-1,2,3,5,6,7,8,8a-octahydroindolizin-7-one, to give 358 mg (yield: 28%) of the title compound (Rf value=0.35) as a pale brown powder.

Melting point: 201–203° C. (decomposition) ¹H-NMR spectrum (400 MHz, DMSO-d₆) δ ppm: 11.42 (1H, broad singlet); 8.45 (2H, doublet, J=6 Hz); 7.21–7.02 (6H, multiplet); 6.93 (1H, doublet, J=3 Hz); 5.27–5.22 (1H, multiplet); 3.48–3.37 (1H, multiplet); 3.33–3.22 (1H, multiplet); 2.77–2.68 (1H, multiplet); 2.59–2.36 (3H, multiplet). 2.34–2.26 (3H, multiplet); 2.16–2.06 (1H, multiplet); 1.96–1.78 (1H, multiplet).

Example 8'

4-[(8aS)-2,2-Difluoro-1,2,3,5,6,8a-hexahydroindolizin-7-yl-]-2-(4-fluorophenyl)-3-(pyridin-4-yl)-1H-pyrrole (Compound No. 1-314')

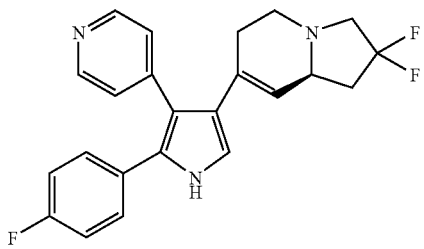

The silica gel column chromatography performed in Example 7' above also provided 290 mg (yield: 23%) of the title compound (Rf value=0.30) as a pale brown powder.

Melting point: 202–204° C. (decomposition) ¹H-NMR spectrum (400 MHz, DMSO-d₆) δ ppm: 11.44 (1H, broad singlet); 8.43 (2H, doublet, J=6 Hz); 7.21–7.07 (6H, multiplet); 6.96 (1H, doublet, J=3 Hz); 5.15–5.11 (H, multiplet); 3.46–3.39 (1H, multiplet); 3.26–3.15 (1H, multiplet); 2.98–2.85 (2H, multiplet); 2.71–2.62 (1H, multiplet); 2.39–2.25 (2H, multiplet); 2.12–2.04 (1H, multiplet); 1.83–1.67 (1H, multiplet).

Example 9'

(±)-2-(4-Fluorophenyl)-3-(pyridin-4-yl)-4-(6,9,9a,10-tetrahydropyrido[1,2-a]indol-8-yl)-1H-pyrrole (Compound No. 5-8)

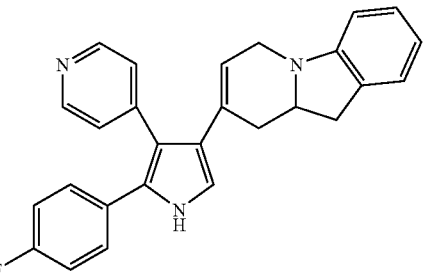

In a similar manner to the procedure described in Example 1(v)' above, a reaction and silica gel column chromatography (using a 1:1 by volume mixture of ethyl acetate and hexane as the eluant) were conducted, using (±)6,7,8,9,9a,10-hexahydropyrido[1,2-a]indol-8-one (prepared as described in Preparative Example 5' below) in place of (2R,8aS)-2-methoxy-1,2,3,5,6,7,8,8a-octahydroindolizin-7-one, to give 70 mg (yield: 5%) of the title compound (Rf value=0.40) as a pale yellow powder.

Melting point: 214–216° C. (decomposition) ¹H-NMR spectrum (400 MHz, CDCl₃) δ ppm: 8.48 (2H, doublet, J=6 Hz); 8.29 (1H, broad singlet); 7.18 (2H, doublet, J=6 Hz); 7.14 (2H, doublet of doublets, J=9 Hz, 5 Hz); 7.11–7.06 (2H, multiplet); 6.98 (2H, triplet, J=9 Hz); 6.87 (1H, doublet, J=3 Hz); 6.69 (1H, triplet, J=8 Hz); 6.46 (1H, doublet, J=8 Hz); 5.62–5.60 (1H, multiplet); 4.00–3.90 (1H, multiplet); 3.47–3.34 (2H, multiplet); 3.03 (1H, doublet of doublets, J=15 Hz, 8 Hz); 2.61 (1H, doublet of doublets, J=15 Hz, 12 Hz); 2.51–2.13 (2H, multiplet).

Example 10'

(±)-2-(4-Fluorophenyl)-3-(Pyridin-4-yl)-4-(6,7,9a,10-tetrahydropyrido[1,2-a]indol-8-yl)-1H-pyrrole (Compound No. 5-1')

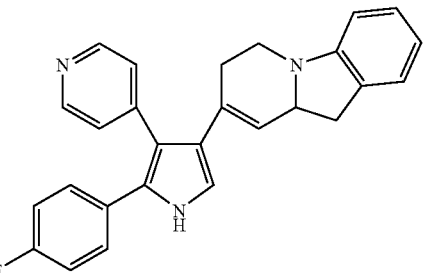

The silica gel column chromatography performed in Example 9' above also provided 230 mg (yield: 15%) of the title compound (Rf value=0.20) as a pale yellow powder.

Melting point: 205–207° C. (decomposition) ¹H-NMR spectrum (400 MHz, CDCl₃) δ ppm: 8.32 (2H, doublet, J=6 Hz); 8.27 (1H, broad singlet); 7.15–7.05 (4H, multiplet); 6.95 (2H, triplet, J=9 Hz); 6.88 (2H, doublet, J=6 Hz); 6.77–6.72 (2H, multiplet); 6.60 (1H, doublet, J=8 Hz); 5.26 (1H, singlet); 4.35–4.26 (1H, multiplet); 3.77 (1H, doublet of doublets, J=14 Hz, 6 Hz); 3.35–3.27 (1H, multiplet); 3.13 (1H, doublet of doublets, J=15 Hz, 10 Hz); 2.55 (1H, doublet, J=15 Hz); 2.50–2.39 (1H, multiplet); 1.91–1.82 (1H, multiplet).

Example 11'

2-(4-Fluorophenyl)-4-[(2R,8aS)-2-phenyl-1,2,3,5,8,8a-hexahydroindolizin-7-yl]-3-(pyridin-4-yl)-1H-pyrrole (Compound No. 4-10')

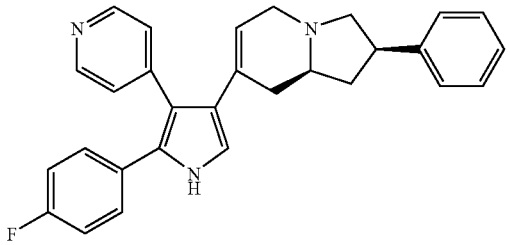

In a similar manner to the procedure described in Example 1(v)' above, a reaction and silica gel column chromatography (using a 100:10:1 by volume mixture of ethyl acetate, methanol and isopropylamine respectively as the eluant) were conducted, using (2R,8aS)-2-phenyl-1,2,3,5,6,7,8,8a-octahydroindolizin-7-one (prepared as described in Preparative Example 6' below) in place of (2R,8aS)-2-methoxy-1,2,3,5,6,7,8,8a-octahydroindolizin-7-one, to give 399 mg (yield: 19%) of the title compound (Rf value=0.45) as a pale brown powder.

Melting point: 191–193° C. (decomposition) ¹H-NMR spectrum (400 MHz. DMSO-d₆) δ ppm: 11.39 (1H, broad singlet); 8.46 (2H, doublet, J=5 Hz); 7.38–7.06 (1H, multiplet); 6.94 (1H, doublet, J=2 Hz); 5.36–5.29 (1H, multiplet); 3.42–3.27 (2H, multiplet); 3.07–2.98 (1H, multiplet); 2.75–2.63 (1H, multiplet); 2.62–2.50 (1H, multiplet); 2.46–2.22 (3H, multiplet); 2.16–2.05 (1H, multiplet); 1.40–1.29 (1H, multiplet).

Example 12'

2-(4-Fluorophenyl)-4-[(2R,8aS)-2-phenyl-1,2,3,5,6,8a-hexahydroindolizin-7-yl]-3-(pyridin-4-yl)-1H-pyrrole (Compound No. 1-298')

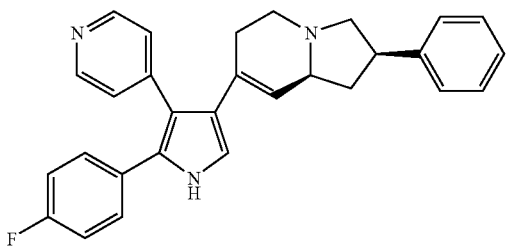

The silica gel column chromatography performed in Example 11' above also provided 369 mg (yield: 17%) of the title compound (Rf value=0.30) as a white powder.

Melting point: 208–210° C. (decomposition) ¹H-NMR spectrum (400 MHz, DMSO-d₆) δ ppm: 11.40 (1H, broad singlet); 8.35 (2H, doublet, J=6 Hz); 7.38–7.07 (11H, multiplet); 6.95 (1H, doublet, J=3 Hz); 5.25–5.20 (1H, multiplet); 3.49–3.40 (1H, multiplet); 3.33–3.21 (1H, multiplet); 3.04–2.90 (2H, multiplet); 2.83–2.69 (2H, multiplet); 2.39–2.26 (2H, multiplet); 2.04–1.95 (1H, multiplet); 1.32–1.22 (1H, multiplet).

Example 13'

4-[(8aS)-2,2-Ethylenedioxy-1,2,3,5,8,8a-hexahydroindolizin-7-yl]-2-(4-fluorophenyl)-3-(pyridin-4-yl)-1H-pyrrole (Compound No. 4-20')

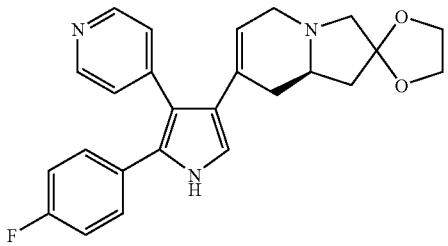

In a similar manner to the procedure described in Example 1(v)' above, a reaction and silica gel column chromatography (using a 100:10:0.5 by volume mixture of ethyl acetate, methanol and isopropylamine as the eluant), were conducted, using (8aS)-2,2-ethylenedioxy-1,2,3,5,6,7,8,8actahydroindolizin-7-one (prepared as described in Preparative Example 7' below) in place of (2R,8aS)-2-methoxy-1,2,3,5,6,7,8,8a-octahydroindolizin-7-one, to give 694 mg (yield: 30%) of the title compound (Rf value=0.55) as a white powder.

Melting point: 230–232° C. (decomposition) ¹H-NMR spectrum (400 MHz, DMSO-d₆) δ ppm: 11.39 (1H, broad singlet); 8.44 (2H, doublet, J=6 Hz); 7.21–7.06 (6H, multiplet); 6.91 (1H, doublet, J=2 Hz); 5.27–5.21 (1H, multiplet); 3.91–3.71 (4H, multiplet); 3.27–3.18 (1H, multiplet); 3.12 (1H, doublet, J=10 Hz); 2.68–2.58 (1H, multiplet); 2.37–2.16 (3H, multiplet); 2.11–1.97 (2H, multiplet); 1.55 (1H, doublet of doublets, J=13 Hz, 10 Hz).

Example 14'

4-[(8aS)-2,2-Ethylenedioxy-1,2,3,5,6,8a-hexahydroindolizin-7-yl]-2-(4-fluorophenyl)-3-(pyridin-4-yl)-1H-pyrrole (Compound No. 1-308')

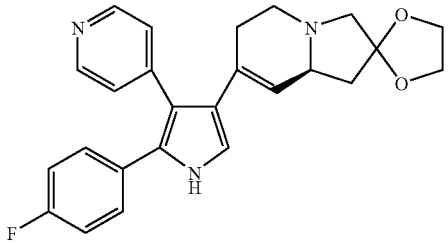

The silica gel column chromatography performed in Example 13' above also yielded 409 mg (yield: 8%) of the title compound (Rf value=0.40) as a pale brown powder.

Melting point: 196–198° C. (decomposition) $^1$H-NMR spectrum (400 MHz, DMSO-$d_6$) δ ppm: 11.40 (1H, broad singlet); 8.43 (2H, doublet, J=6 Hz); 7.21–7.05 (6H, multiplet); 6.93 (1H, doublet, J=3 Hz); 5.19–5.14 (1H, multiplet); 3.89–3.72 (4H, multiplet); 3.23–3.14 (1H, multiplet); 2.96–2.85 (2H, multiplet); 2.62–2.48 (2H, multiplet); 2.34–2.21 (1H, multiplet); 2.12–2.01 (1H, multiplet); 1.93 (1H, doublet of doublets, J=13 Hz, 7 Hz); 1.51 (1H, doublet of doublets, J=13 Hz, 9 Hz).

Example 15'

2-(4-Fluorophenyl)-4-[(8aS)-2-methyl-1,2,3,5,8,8a-hexahydroindolizin-7-yl]-3-(pyridin-4-yl)-1H-pyrrole (Compound No. 4-5)

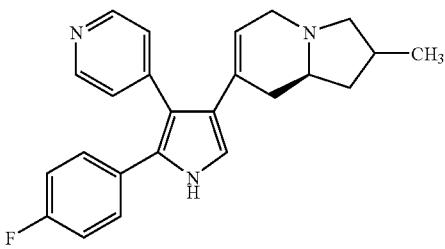

In a similar manner to the procedure described in Example 1(v)' above, a reaction and silica gel column chromatography (using a 10:1:1 by volume mixture of ethyl acetate, methanol and isopropylamine respectively as the eluant) were conducted, using (8aS)-2-methyl-1,2,3,5,6,7,8,8a-octahydroindolizin-7-one (prepared as described in Preparative Example 8' below) in place of (2R,8aS)-2-methoxy-1,2,3,5,6,7,8,8a-octahydroindolizin-7-one, to give 253 mg (yield: 9%) of the title compound (Rf value=0.65) as a pale brown powder.

Melting point: 190–193° C. (decomposition) $^1$H-NMR spectrum (400 MHz, CDCl$_3$) δ ppm: 8.46 (2H, doublet, J=6 Hz); 8.32 (1H, broad singlet); 7.17 (2H, doublet, J=6 Hz); 7.13 (2H, doublet of doublets, J=9 Hz, 5 Hz); 6.97 (2H, triplet, J=9 Hz); 6.82 (1H, doublet, J=3 Hz); 5.53–5.51 (1H, multiplet); 3.49–3.43 (1H, multiplet); 2.83 (1H, doublet of doublets, J=9 Hz, 3 Hz); 2.82–2.73 (1H, multiplet); 2.41 (1H, triplet, J=9 Hz); 2.30–2.05 (5H, multiplet); 1.09 (3H, doublet, J=7 Hz); 1.06–0.98 (1H, multiplet).

Example 16'

2-(4-Fluorophenyl)-4-[(8aS)-2-methyl-1,2,3,5,6,8a-hexahydroindolizin-7-yl]-3-(pyridin-4-yl)1H-pyrrole (Compound No. 1-293')

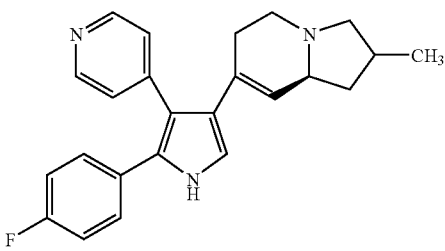

The silica gel column chromatography performed in Example 15' above also provided 280 mg (yield: 10%) of the title compound (Rf value=0.40) as a pale brown powder.

Melting point: 181–185° C. (decomposition) $^1$H-NMR spectrum (400 MHz, CDCl$_3$) δ ppm: 8.47 (2H, doublet, J=6 Hz); 8.30 (1H, broad singlet); 7.16 (2H, doublet, J=6 Hz); 7.13 (2H, doublet of doublets, J=9 Hz, 5 Hz); 6.97 (2H, triplet, J=9 Hz); 6.82 (1H, doublet, J=3 Hz); 5.41 (0.2H, singlet); 5.39 (0.8H, singlet); 3.53–3.43 (0.8H, multiplet); 3.41–3.22 (0.2H, multiplet); 3.11–3.05 (0.2H, multiplet); 3.04–2.90 (1H, multiplet); 2.89–2.77 (1.6H, multiplet); 2.73–2.64 (0.2H, multiplet); 2.48 (0.8H, triplet, J=9 Hz); 2.41–2.07 (3.2H, multiplet); 2.04–1.93 (1H, multiplet); 1.06 (2.4H, doublet, J=7 Hz); 1.02 (0.6H, doublet, J=7 Hz); 0.99–0.93 (1H, multiplet).

Example 17'

2-(4-Fluorophenyl)-4-[(8aS)-8-methyl-1,2,3,5,8,8a-hexahydroindolizin-7-yl]-3-(pyridin-4-yl)-1H-pyrrole (Compound No. 4-41')

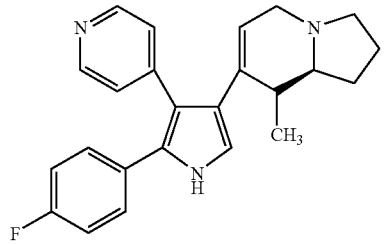

In a similar manner to the procedure described in Example 1(v)' above, a reaction and silica gel column chromatography (using a 10:0.5:0.5 by volume mixture of ethyl acetate, methanol and isopropylamine respectively as the eluant) were conducted, using (8aS)-8-methyl-1,2,3,5,6,7,8,8a-octahydroindolizin-7-one (prepared as described in Preparative Example 9' below) in place of (2R,8aS)-2-methoxy-1,2,3,5,6,7,8,8a-octahydroindolizin-7-one, to give 57 mg (yield: 5%) of the title compound (Rf value=0.45) as an orange powder.

Melting point: 205–207° C. (decomposition) $^1$H-NMR spectrum (500 MHz, CDCl$_3$) δ ppm: 8.46 (2H, doublet, J=8 Hz); 8.29–8.18 (1H, broad singlet); 7.18–7.13 (4H, multiplet); 6.97 (2H, triplet, J=9 Hz); 6.73 (1H, doublet, J=3 Hz); 5.62–5.55 (1H, multiplet); 3.58–3.50 (1H, multiplet); 3.24–3.17 (1H, multiplet); 2.77–2.68 (1H, multiplet); 2.23–2.08 (2H, multiplet); 2.04–1.95 (1H, multiplet); 1.90–1.78 (2H, multiplet); 1.77–1.68 (1H, multiplet); 1.43–1.33 (1H, multiplet); 0.76 (3H, doublet, J=7 Hz).

Example 18'

2-(4-Fluorophenyl)-4-[(8aS)-8-methyl-1,2,3,5,6,8a-hexahydroindolizin-7-yl]-3-(pyridin-4-yl)-1H-pyrrole (Compound No. 1-330')

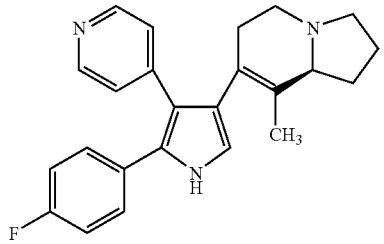

The silica gel column chromatography performed in Example 17' above also provided 708 mg (yield: 17%) of the title compound (Rf value=0.30) as a pale pink powder.

Melting point: 233–234° C. ¹H-NMR spectrum (500 MHz, CDCl₃) δ ppm: 8.43 (2H, doublet, J=8 Hz); 8.36–8.25 (1H, broad singlet); 7.22 (2H, doublet of doublets, J=9 Hz, 5 Hz); 7.08 (2H, doublet, J=8 Hz); 7.00 (2H, triplet, J=9 Hz); 6.70 (1H, doublet, J=3 Hz); 3.07–3.01 (1H, multiplet); 2.97–2.92 (1H, multiplet); 2.91–2.84 (1H, multiplet); 2.70–2.62 (1H, multiplet); 2.57–2.49 (1H, multiplet); 2.34–2.24 (1H, multiplet); 2.12–2.03 (1H, multiplet); 2.02–1.94 (1H, multiplet); 1.92–1.84 (1H, multiplet); 1.81–1.70 (1H, multiplet); 1.55–1.45 (1H, multiplet); 1.46 (3H, singlet).

Example 19'

4-[Cyclopropanespiro-6'-[(8a'S)-1',2',3',5',6',8a'-hexahydroindolizin]-7'-yl]-2-(4-fluorophenyl)-3-(pyridin-4-yl)-1H-pyrrole (Compound No. 1-952')

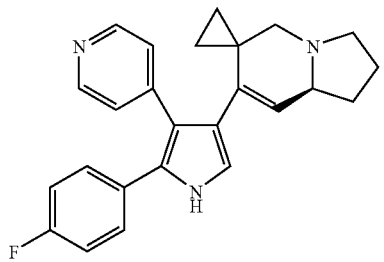

In a similar manner to the procedure described in Example 1(v)' above, a reaction and silica gel column chromatography (using a 100:10:1 by volume mixture of ethyl acetate, methanol and isopropylamine respectively as the eluant) were conducted, using cyclopropanespiro-6'-[(8a'S)-1',2',3',5',6',7',8',8a'-octahydroindolizin]-7'-one (prepared as described in Preparative Example 16' below) in place of (2R,8aS2-methoxy-1,2,3,5,6,7,8,8a-octahydroindolizin-7-one, to give 170 mg (yield: 11%) of the title compound (Rf value=0.24) as a pale brown powder.

Melting point: 189–191° C. (decomposition) ¹H-NMR spectrum (400 MHz, DMSO-d₆) δ ppm: 11.35 (1H, broad singlet); 8.39 (2H, doublet, J=6 Hz); 7.23 (2H, doublet of doublets, J=9 Hz, 6 Hz); 7.14 (2H, triplet, J=9 Hz); 7.09 (2H, doublet, J=6 Hz); 6.69 (1H, doublet, J=2 Hz); 5.33–5.30 (1H, multiplet); 3.50–3.42 (1H, multiplet); 2.98–2.85 (2H, multiplet); 2.65–2.57 (1H, multiplet); 2.39 (1H, doublet, J=13 Hz); 1.91–1.80 (1H, multiplet); 1.76–1.53 (2H, multiplet); 1.31–1.20 (1H, multiplet); 0.56–0.42 (3H, multiplet); 0.22–0.15 (1H, multiplet).

Example 20'

2-(4-Fluorophenyl)-4-8 (2S,8aS)-2-methoxy-1,2,3,5,8,8a-hexahydroindolizin-7-yl]-3-(pyridin-4-yl)-1H-pyrrole (Compound No. 4-15')

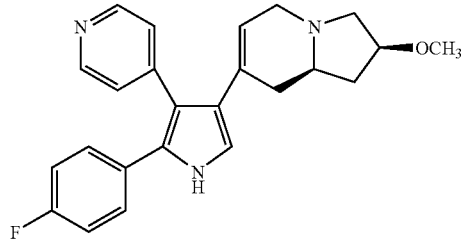

In a similar manner to the procedure described in Example 1(v)' above, a reaction and silica gel column chromatography (using a 100:10:1 by volume mixture of ethyl acetate, methanol and isopropylamine respectively as the eluant) were conducted, using (2S,8aS)-2-methoxy-1,2,3,5,6,7,8,8a-octahydroindolizin-7-one (prepared as described in Preparative Example 10' below) in place of (2R,8aS)-2-methoxy-1,2,3,5,6,7,8,8a-octahydroindolizin-7-one, to give 228 mg (yield: 6%) of the title compound (Rf value=0.50) as a white powder.

Melting point: 212–213° C. (decomposition) ¹H-NMR spectrum (500 MHz, CDCl₃) δ ppm: 8.46 (2H, doublet, J=6 Hz). 8.38–8.27 (1H, broad singlet); 7.16 (2H, doublet, J=6 Hz); 7.12 (2H, doublet of doublets, J=9 Hz, 5 Hz); 6.97 (2H, triplet, J=9 Hz); 6.81 (1H, doublet, J=3 Hz); 5.52–5.47 (1H, multiplet); 3.91–3.84 (1H, multiplet); 3.54–3.47 (1H, multiplet); 3.30–3.24 (1H, multiplet); 3.27 (3H, singlet); 2.78–2.69 (1H, multiplet); 2.35 (1H, quintet, J=7 Hz); 2.27–2.10 (4H, multiplet); 1.48–1.39 (1H, multiplet).

Example 21'

2-(4-Fluorophenyl)-4-[(2S,8aS)-2-methoxy-1,2,3,5,6,8a-hexahydroindolizin-7-yl]-3-(pyridin-4-yl)-1H-pyrrole (Compound No. 1-303')

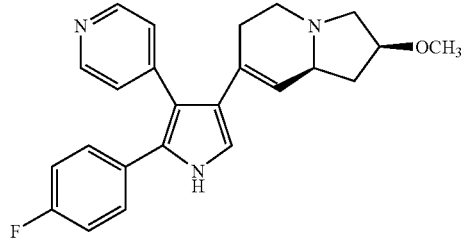

The silica gel column chromatography performed in Example 20' above also provided 184 mg (yield: 5%) of the title compound (Rf value=0.30) as a pale brown powder.

Melting point: 219–220° C. (decomposition) ¹H-NMR spectrum (500 MHz, CDCl₃) δ ppm: 8.47 (2H, doublet J=6

Hz); 8.41–8.30 (1H, broad singlet); 7.17 (2H, doublet, J=6 Hz); 7.12 (2H, doublet of doublets, J=9 Hz, 5 Hz); 6.97 (2H, triplet, J=9 Hz); 6.82 (1H, doublet, J=3 Hz); 5.45–5.41 (1H, multiplet); 4.01–3.93 (1H, multiplet); 3.30 (3H, singlet); 3.28–3.17 (1H, broad singlet); 3.10–3.03 (1H, multiplet); 2.95 (1H, doublet of doublets, J=10 Hz, 4 Hz); 2.87–2.78 (1H, multiplet); 2.75–2.65 (1H, multiplet); 2.45–2.35 (1H, multiplet); 2.30–2.21 (1H, multiplet); 2.17–2.07 (1H, multiplet); 1.51–1.41 (1H, multiplet).

Example 22'

2-(4-Fluorophenyl)-4-[(8aS)-2-methylidene-1,2,3,5,8,8a-hexahydroindolizin-7-yl]-3-(pyridin-4-yl)-1H-pyrrole (Compound No. 4-50')

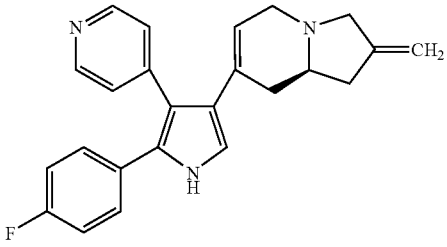

In a similar manner to the procedure described in Example 1(v)' above, a reaction and silica gel column chromatography (using a 10:1:1 by volume mixture of ethyl acetate, methanol and isopropylamine respectively as the eluant) were conducted, using (8aS)-2-methylidene-1,2,3,5,6,7,8,8a-octahydroindolizin-7-one (prepared as described in Preparative Example 11' below) in place of (2R,8aS)-2-methoxy-1,2,3,5,6,7,8,8a-octahydroindolizin-7-one, to give 184 mg (yield: 10%) of the title compound (Rf value=0.50) as a pale pink powder.

Melting point: 212–214° C. (decomposition) ¹H-NMR spectrum (400 MHz, CDCl₃) δ ppm: 8.47 (2H, doublet, J=6 Hz); 8.29 (1H, broad singlet); 7.17 (2H, doublet, J=6 Hz); 7.13 (2H, doublet of doublets, J=9 Hz, 5 Hz); 6.97 (2H, triplet, J=9 Hz); 6.83 (1H, doublet, J=3 Hz); 5.52–5.48 (1H, multiplet); 4.92 (1H, broad singlet); 4.89 (1H, broad singlet); 3.79 (1H, doublet, J=13 Hz); 3.54–3.43 (1H, multiplet); 2.92–2.80 (2H, multiplet); 2.59 (1H, doublet of doublets. J=16 Hz, 6 Hz); 2.50–2.38 (1H, multiplet); 2.33–2.25 (1H, multiplet); 2.24–2.10 (2H, multiplet).

Example 23'

2-(4-Fluorophenyl)-4-[(8aS)-2-methylidene-1,2,3,5,6,8a-hexahydroindolizin-7-yl]-3-(pyridin-4-yl)-1H-pyrrole (Compound No. 1-982')

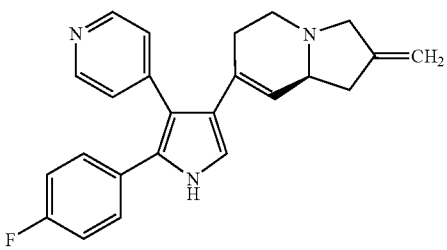

The silica gel column chromatography performed in Example 22' above also provided 195 mg (yield: 11%) of the title compound (Rf value=0.30) as a white powder.

Melting point: 217–218° C. (decomposition) ¹H-NMR spectrum (400 MHz, CDCl₃) δ ppm: 8.46 (2H, doublet, J=6 Hz); 8.29 (1H, broad singlet); 7.20–7.09 (4H, multiplet); 6.97 (2H, triplet, J=9 Hz); 6.83 (1H, doublet, J=3 Hz); 5.42 (1H, doublet, J=2 Hz); 4.953 (1H, broad singlet); 4.949 (1H, broad singlet); 3.50–3.32 (3H, multiplet); 2.99–2.93 (1H, multiplet); 2.80–2.72 (1H, multiplet); 2.56 (1H, doublet of doublets, J=16 Hz, 7 Hz); 2.42–2.31 (1H, multiplet); 2.22–2.10 (2H, multiplet).

Example 24'

(±)-4-(2,2-Diphenyl-1,2,3,5,8,8a-hexahydroindolizin-7-yl)-2-(4-fluorophenyl)-3-(pyridin-4-yl)-1H-pyrrole (Compound No. 4-56')

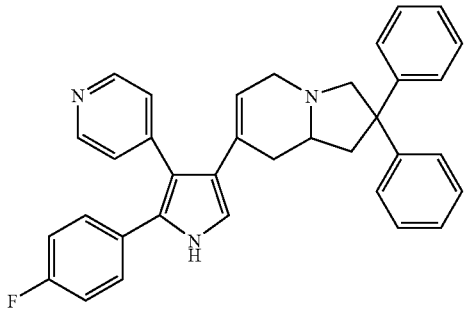

In a similar manner to the procedure described in Example 1(v)' above, a reaction and silica gel column chromatography (using a 39:1 by volume mixture of methylene chloride and methanol as the eluant) were conducted, using (±)-2,2-diphenyl-1,2,3,5,6,7,8,8a-octahydroindolizin-7-one [prepared as described in J. Med. Chem., 31, 9, 1708–1712 (1988)] in place of (2R,8aS)-2-methoxy-1,2,3,5,6,7,8,8a-octahydroindolizin-7-one, to give 363 mg (yield: 11%) of the title compound (Rf value=0.50) as a pale brown powder.

Melting point: 224–227° C. (decomposition) ¹H-NMR spectrum (400 MHz, DMSO-d₆) δ ppm: 11.39 (1H, broad singlet); 8.44 (2H, doublet, J=5 Hz); 7.33–7.07 (16H, multiplet); 6.93 (1H, doublet, J=3 Hz); 5.34–5.29 (1H, multiplet); 3.85 (1H, doublet, J=9 Hz); 3.42–3.32 (1H, multiplet); 2.86 (1H, doublet of doublets, J=13 Hz, 7 Hz); 2.75–2.65 (2H, multiplet); 2.49–2.39 (1H, multiplet); 2.33–2.24 (1H, multiplet); 2.16–2.03 (2H, multiplet).

Example 25'

(±)-4-(2,2-Diphenyl-1,2,3,5,6,8a-hexahydroindolizin-7-yl)-2-(4-fluorophenyl)-3-(pyridin-4-yl)-1H-pyrrole (Compound No. 1-988)

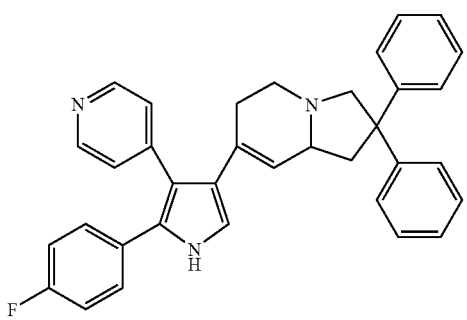

The silica gel column chromatography performed in Example 24' above also provided 0.50 g (yield: 15%) of the title compound (Rf value=0.30) as a pale brown powder.

Melting point: 241–244° C. (decomposition) $^1$H-NMR spectrum (400 MHz, DMSO-$d_6$) δ ppm: 11.38 (1H, broad singlet); 8.21 (2H, doublet, J=6 Hz); 7.36–7.28 (4H, multiplet); 7.25–7.08 (1H, multiplet); 7.02 (2H, doublet, J=6 Hz); 6.91 (1H, doublet, J=3 Hz); 5.24–5.21 (1H, multiplet); 3.62–3.55 (1H, multiplet); 3.53–3.47 (1H, multiplet); 3.17 (1H, doublet, J=6 Hz); 2.94–2.75 (3H, multiplet); 2.35–2.24 (1H, multiplet); 1.97–1.87 (1H, multiplet); 1.75 (1H, doublet of doublets, 13 Hz, 8 Hz).

Example 26'

4-[(8aS)-2,2-Dimethyl-1,2,3,5,8,8a-hexahydroindolizin-7-yl]-2-(4-fluorophenyl)-3-(pyridin-4-yl)-1H-pyrrole (Compound No. 4-13')

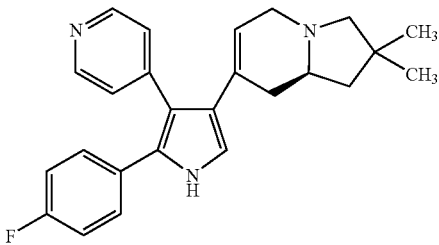

In a similar manner to the procedure described in Example 1(v)' above, a reaction and silica gel column chromatography (using a 100:10:1 by volume mixture of ethyl acetate, methanol and isopropylamine respectively as the eluant) were conducted, using (8aS)-2,2-dimethyl-1,2,3,5,6,7,8,8a-octahydroindolizin-7-one (prepared as described in Preparative Example 17' below) in place of (2R,8aS)-2-methoxy-1,2,3,5,6,7,8,8a-octahydroindolizin-7-one, to give 0.85 g (yield: 32%) of the title compound (Rf value=0.50) as a pale brown powder.

Melting point: 193–196° C. (decomposition) $^1$H-NMR spectrum (400 MHz, DMSO-$d_6$) δ ppm: 11.37 (1H, broad singlet); 8.44 (2H, doublet, J=6 Hz); 7.19–7.07 (6H, multiplet); 6.90 (1H, doublet, J=3 Hz); 5.27–5.22 (1H, multiplet); 3.27–3.18 (1H, multiplet); 2.78 (1H, doublet, J=9 Hz); 2.64–2.54 (1H, multiplet); 2.33–2.15 (2H, multiplet); 2.06–1.94 (1H, multiplet); 1.93–1.85 (1H, multiplet); 1.67 (1H, doublet of doublets, J=12 Hz, 7 Hz); 1.21–1.12 (1H, multiplet); 1.07 (3H, singlet); 1.02 (3H, singlet).

Example 27'

4-[(8aS)-2,2-Dimethyl-1,2,3,5,6,8a-hexahydroindolizin-1-yl-2-(4-fluorophenyl)-3-(pyridin-4-yl-1H-pyrrole (Compound No. 1-301')

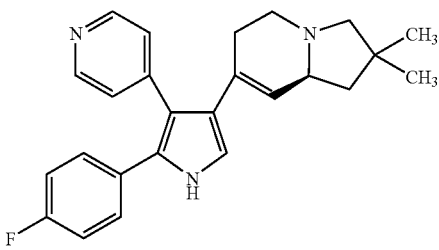

The silica gel column chromatography performed in Example 26' above also provided 0.47 g (yield: 18%) of the title compound (Rf value=0.25) as a pale brown powder.

Melting point: 190–193° C. (decomposition) $^1$H-NMR spectrum (400 MHz, DMSO-$d_6$) δ ppm: 11.38 (1H, broad singlet); 8.43 (2H, doublet, J=6 Hz); 7.20–7.08 (6H, multiplet); 6.91 (1H, doublet, J=3 Hz); 5.15–5.11 (1H, multiplet); 3.28–3.19 (1H, multiplet); 2.95–2.86 (1H, multiplet); 2.66–2.55 (2H, multiplet); 2.36–2.21 (2H, multiplet); 2.00–1.92 (1H, multiplet); 1.56 (1H, doublet of doublets, J=12 Hz, 7 Hz); 1.10–0.98 (1H, multiplet); 1.05 (3H, singlet); 1.02 (3H, singlet).

Example 28'

2-(4-Fluorophenyl)-4-[(2S,8aS)-2-methylthio-1,2,3,5,8,8a-hexahydroindolizin-7-yl]-3-(pyridin-4-yl)-1H-pyrrole (Compound No. 4-63')

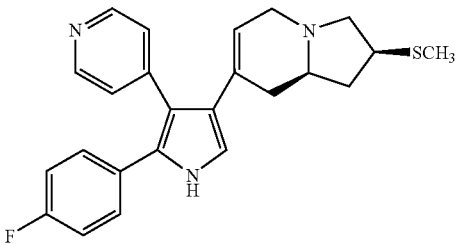

In a similar manner to the procedure described in Example 1(v)' above, a reaction and silica gel column chromatography (using a 100:1:1 by volume mixture of ethyl acetate, methanol and isopropylamine respectively as the eluant) were conducted, using (2S,8aS)-2-methylthio-1,2,3,5,6,7,8,8a-octahydroindolizin-7-one (prepared as described in Preparative Example 12' below) in place of (2R,8aS)-2-methoxy-1,2,3,5,6,7,8,8a-octahydroindolizin-7-one, to give 1.51 g (yield: 17%) of the title compound (Rf value=0.25) as a pale brown powder.

Melting point: 212–213° C. (decomposition) $^1$H-NMR spectrum (400 MHz, CD$_3$OD) δ ppm: 8.35 (2H, doublet of doublets, J=5 Hz, 1 Hz); 7.24 (2H, doublet of doublets, J=5 Hz, 1 Hz); 7.20–7.15 (2H, multiplet); 7.03–6.98 (2H, multiplet); 6.85 (1H, singlet); 5.38 (1H, triplet, J=2 Hz); 3.43–3.37 (1H, multiplet); 3.31–3.24 (1H, multiplet); 3.15 (1H, doublet of doublets, J=10 Hz, 3 Hz); 2.82–2.77 (1H, multiplet); 2.63 (1H, doublet of doublets, J=10 Hz, 9 Hz); 2.49–2.30 (3H, multiplet); 2.27–2.13 (1H, multiplet); 2.10 (3H, singlet); 1.37–1.29 (1H, multiplet).

Example 29'

2-(4-Fluorophenyl)-4-[(2S,8aS)-2-methylthio-1,2,3,5,6,8a-hexahydroindolizin-7-yl]-3-(pyridin-4-yl)-1H-pyrrole (Compound No. 1-995')

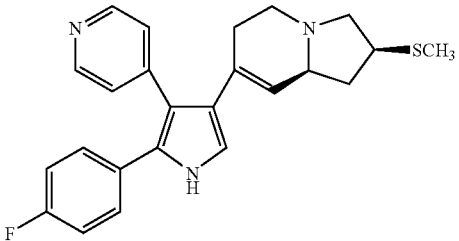

The silica gel column chromatography performed in Example 28' above also provided 1.03 g (yield: 12%) of the title compound (Rf value=0.10) as a pale brown powder.

Melting point: 198–200° C. (decomposition) $^1$H-NMR spectrum (400 MHz, CD$_3$OD) δ ppm: 8.38 (2H, doublet of doublets, J=4 Hz, 1 Hz); 7.24 (2H, doublet of doublets, J=4 Hz, 1 Hz); 7.20–7.15 (2H, multiplet); 7.03–6.97 (2H, multiplet); 6.86 (1H, singlet); 5.28 (1H, doublet, J=2 Hz); 3.53–3.48 (1H, multiplet); 3.25 (1H, quintet, J=8 Hz); 3.14 (1H, doublet of doublets, J=10 Hz, 8 Hz); 3.08–3.03 (1H, multiplet); 2.87–2.78 (2H, multiplet); 2.40 (1H, doublet of double doublets, J=13 Hz, 8 Hz, 3 Hz); 2.36–2.30 (1H, multiplet); 2.17–2.16 (1H, multiplet); 2.14 (3H, singlet); 1.36 (1H, doublet of double doublets, J=13 Hz, 8 Hz, 3 Hz).

Example 30'

2-(4-Fluorophenyl)-4-[(8aS)-2-methyl-3,5,8,8a-tetrahydroindolizin-7-yl]-3-(pyridin-4-yl)-1H-pyrrole (Compound No. 6-1')

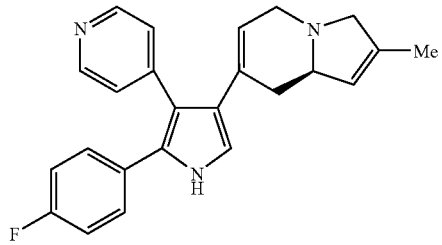

In a similar manner to the procedure described in Example 1(v)' above a reaction and silica gel column chromatography (using a 10:1:1 by volume mixture of ethyl acetate, methanol and isopropylamine respectively as the eluant) were conducted, using (8aS)-2-methyl-3,5,6,7,8,8a-hexahydroindolizin-7-one (prepared as described in Preparative Example 19' below) in place of (2R,8aS)-2-methoxy-1,2,3,5,6,7,8,8a-octahydroindolizin-7-one, to give 130 mg (yield: 3%) of the title compound (Rf value=0.50) as a pale brown powder.

Melting point: 183–185° C. (decomposition) $^1$H-NMR spectrum (400 MHz, CDCl$_3$) δ ppm: 8.48 (2H, doublet, J=6 Hz); 8.37 (1H, broad singlet); 7.20–7.09 (4H, multiplet); 6.97 (2H, triplet, J=9 Hz); 6.83 (1H, doublet, J=3 Hz); 5.58–5.50 (1H, multiplet); 5.38–5.32 (1H, multiplet); 3.71–3.32 (4H, multiplet); 3.30–3.20 (1H, multiplet); 2.50–2.28 (2H, multiplet); 1.79 (3H, multiplet).

Example 31'

2-(4-Fluorophenyl)-4-[(8aS)-2-methyl-3,5,6,8a-tetrahydroindolizin-7-yl]-3-(pyridin-4-yl)-1H-pyrrole (Compound No. 3-1)

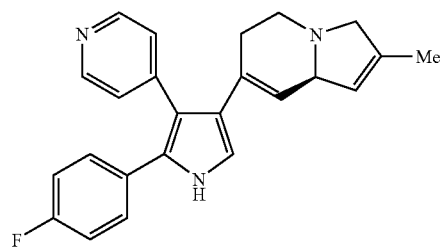

The silica gel column chromatography performed in Example 30' above also provided 190 mg (yield: 5%) of the title compound (Rf value=0.30) as a pale brown powder.

Melting point: 181–183° C. (decomposition) $^1$H-NMR spectrum (400 MHz, CDCl$_3$) δ ppm: 8.45 (2H, doublet, J=6 Hz); 8.37 (1H, broad singlet); 7.20–7.09 (4H, multiplet); 6.97 (2H, triplet, J=9 Hz); 6.81 (1H, doublet, J=3 Hz); 5.44 (1H, broad singlet); 5.24 (1H, broad singlet); 4.42–4.38 (1H, multiplet); 3.60–3.44 (2H, multiplet); 3.04–2.92 (2H, multiplet); 2.40–2.28 (1H, multiplet); 1.97–1.85 (1H, multiplet); 1.75 (3H, singlet).

Example 32'

4-[(2S,8aS)-2-Ethyl-1,2,3,5,6,8a-hexahydroindolizin-7-yl]-2-(4-fluorophenyl)-3-(pyridin-4-yl)-1H-pyrrole (Compound No. 1-294')

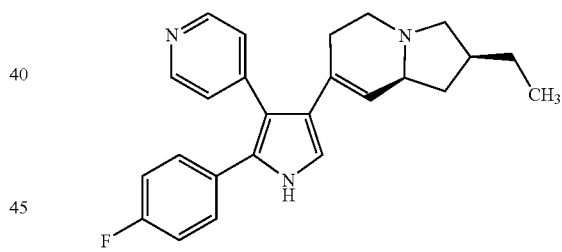

In a similar manner to the procedure described in Example 1(v)' above, a reaction and silica gel column chromatography (using a 100:10:5 by volume mixture of ethyl acetate, methanol and isopropylamine respectively as the eluant) were conducted, using (2S,8aS)-2-ethyl-1,2,3,5,6,7,8,8a-octahydroindolizin-7-one (prepared as described in Preparative Example 27' below) in place of (2R,8aS)-2-methoxy-1,2,3,5,6,7,8,8a-octahydroindolizin-7-one, to give 1.12 g (yield: 21%) of the title compound (Rf value=0.50) as a pale brown powder.

Melting point: 203–205° C. (decomposition) $^1$H-NMR spectrum (400 MHz, CDCl$_3$) δ ppm: 11.39–11.38 (1H, broad singlet); 8.43 (2H, doublet, J=6 Hz); 7.19–7.16 (2H, multiplet); 7.15–7.10 (4H, multiplet); 6.91 (1H, doublet, J=3 Hz); 5.13–5.12 (1H, broad singlet); 3.32–3.26 (2H, multiplet); 2.94–2.90 (1H, multiplet); 2.70–2.64 (2H, multiplet); 2.50–2.41 (1H, multiplet); 2.31–2.25 (1H, multiplet); 2.02–1.88 (3H, multiplet); 1.38–1.28 (2H, multiplet); 0.85 (3H, triplet, J=7 Hz)

Example 33'

4-[(2S,8aS)-2-Butylthio-1,2,3,5,8,8a-hexahydroindolizin-7-yl)-2-(4-fluorophenyl)-3-(pyridin-4-yl)-1H-pyrrole (Compound No. 4-66')

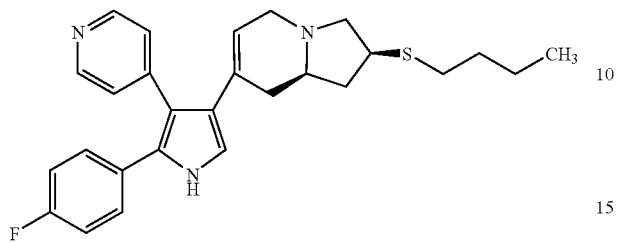

In a similar manner to the procedure described in Example 1(v)' above, a reaction and silica gel column chromatography (using a 100:1:1 by volume mixture of ethyl acetate, methanol and isopropylamine respectively as the eluant) were conducted, using (2S,8aS)-2-butylthio-1,2,3,5,6,7,8,8a-octahydroindolizin-7-one (prepared as described in Preparative Example 14' below) in place of (2R,8aS)-2-methoxy-1,2,3,5,6,7,8,8a-octahydroindolizin-7-one, to give 426 mg (yield: 8%) of the title compound (Rf value=0.25) as a pale pink powder.

Melting point: 189–190° C. (decomposition) $^1$H-NMR spectrum (400 MHz, CD$_3$OD) δ ppm: 8.35 (2H, doublet of doublets, J=5 Hz, 2 Hz); 7.24 (2H, doublet of doublets, J=5 Hz, 2 Hz); 7.15 (2H, doublet of doublets, J=5 Hz, 3 Hz); 7.03–6.97 (2H, multiplet); 6.85 (1H, singlet); 5.37 (1H, triplet, J=2 Hz); 3.42–3.33 (2H, multiplet); 3.13 (1H, doublet of doublets, J=10 Hz, 3 Hz); 2.83–2.77 (1H, multiplet); 2.66 (1H, triplet, J=10 Hz); 2.56 (2H, triplet, J=7 Hz); 2.53–2.30 (3H, multiplet); 2.21–2.13 (1H, multiplet); 1.57 (2H, quintet, J=8 Hz); 1.42 (2H, sextet, J=7 Hz); 1.36–1.29 (1H, multiplet); 0.92 (3H, triplet, J=7 Hz).

Example 34'

4-[(2S,8aS)-2-Butylthio-1,2,3,5,6,8a-hexahydroindolizin-7-yl)-2-(4-fluorophenyl)-3-(pyridin-4yl)-1H-pyrrole (Compound No. 1-998')

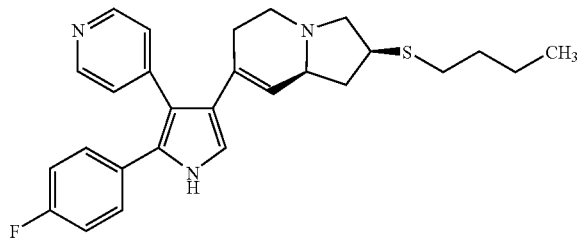

The silica gel column chromatography performed in Example 33' above also provided 612 mg (yield: 13%) of the title compound (Rf value=0.10) as a pale brown powder.

Melting point: 199–200° C. (decomposition) $^1$H-NMR spectrum (400 MHz, CD$_3$OD) δ ppm: 8.37 (2H, doublet of doublets, J=5 Hz, 2 Hz); 7.23 (2H, doublet of doublets, J=5 Hz, 2 Hz); 7.17 (2H, doublet of doublets, J=6 Hz, 3 Hz); 7.03–6.97 (2H, multiplet); 6.86 (1H, singlet); 5.26 (1H, doublet, J=1 Hz); 3.53–3.49 (1H, multiplet); 3.14 (1H, doublet of doublets, J=10 Hz, 8 Hz); 3.08–3.03 (1H, multiplet); 2.88–2.76 (2H, multiplet); 2.59 (2H, triplet, J=7 Hz); 2.44–2.29 (2H, multiplet); 2.16–2.11 (1H, multiplet); 1.59 (2H, triplet of triplets, J=16 Hz, 7 Hz); 1.44 (2H, sextet, J=7 Hz); 1.35 (2H, triplet of triplets, J=13 Hz, 8 Hz); 1.24 (3H, triplet, J=7 Hz).

Example 35'

4-[(2S,8aS)-2-Ethylthio-1,2,3,5,8,8a-hexahydroindolizin-7-yl]-2-(4-fluorophenyl)-3-(pyridin-4-yl)-1H-pyrrole (Compound No. 4-64')

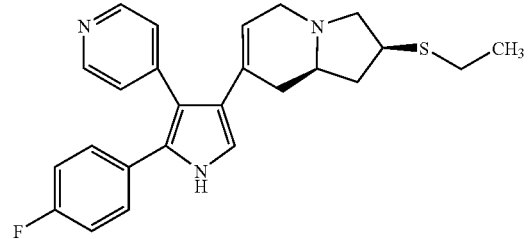

In a similar manner to the procedure described in Example 1(v)' above, a reaction and silica gel column chromatography (using a 100:1:1 by volume mixture of ethyl acetate, methanol and isopropylamine respectively as the eluant) were conducted, using (2S,8aS)-2-ethylthio-1,3,5,6,7,8,8a-octahydroindolizin-7-one (prepared as described in Preparative Example 13' below) in place of (2R,8aS)-2-methoxy-1,2,3,5,6,7,8,8a-octahydroindolizin-7-one, to give 672 mg (yield: 24%) of the title compound (Rf value=0.25) as a pale brown powder.

Melting point: 205–207° C. (decomposition) $^1$H-NMR spectrum (400 MHz, CD$_3$OD) δ ppm: 8.35 (2H, doublet of doublets, J=4 Hz, 1 Hz); 7.23 (2H, doublet of doublets, J=4 Hz, 1 Hz); 7.19–7.15 (2H, multiplet); 7.03–6.97 (2H, multiplet); 6.85 (1H, singlet); 5.38 (1H, triplet, J=2 Hz); 3.42–3.33 (2H, multiplet); 3.13 (1H, doublet of doublets, J=10 Hz, 3 Hz); 2.83–2.77 (1H, multiplet); 2.66 (1H, doublet of doublets, J=10 Hz, 8 Hz); 2.57 (2H, quartet, J=7 Hz); 2.50–2.33 (2H, multiplet); 2.31–2.30 (1H, multiplet); 2.21–2.13 (1H, multiplet); 1.38–1.30 (1H, multiplet); 1.25 (3H, triplet, J=7 Hz).

Example 36'

4-[(2S,8aS)-2-Ethylthio-1,2,3,5,6,8a-hexahydroindolizin-7-yl]-2-(4-fluorophenyl)-3-(pyridin-4-yl)-1H-pyrrole (Compound No. 1-996')

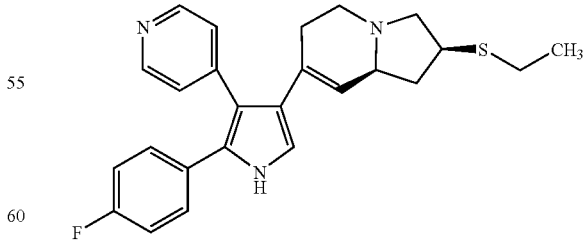

The silica gel column chromatography performed in Example 35' above also provided 563 mg (yield: 20%) of the title compound (Rf value=0.10) as a pale pink powder.

Melting point: 193–196° C. (decomposition) $^1$H-NMR spectrum (400 MHz, CD$_3$OD) δ ppm: 8.37 (2H, doublet of doublets, J=4 Hz, 2 Hz); 7.23 (2H, doublet of doublets, J=4 Hz, 2 Hz); 7.21–7.15 (2H, multiplet); 7.02–6.98 (2H, multiplet); 6.86 (1H, singlet); 5.27 (1H, broad singlet); 3.54–3.49 (1H, multiplet); 3.32 (1H, quintet J=8 Hz); 3.14 (1H, doublet of doublets, J=10 Hz, 8 Hz); 3.08–3.02 (1H, doublet of triplets, J=12 Hz, 5 Hz); 2.85 (1H, triplet of doublets, J=12 Hz, 5 Hz); 2.78 (1H, doublet of triplets, J=10 Hz, 8 Hz); 2.60 (2H, quartet, J=8 Hz); 2.41 (1H, doublet of triplets, J=12 Hz, 9 Hz); 2.36–2.29 (1H, multiplet); 2.17–2.11 (1H, multiplet); 1.35 (1H, doublet of triplets, J=13 Hz, 8 Hz); 1.27 (3H, triplet, J=8 Hz).

Example 37'

4-[(8aS)-2-Ethylidene-1,2,3,5,6,8a-hexahydroindolizin-7-yl]-2-(4-fluorophenyl)-3-(pyridin-4-yl)-1H-pyrrole (Compound No. 1-983')

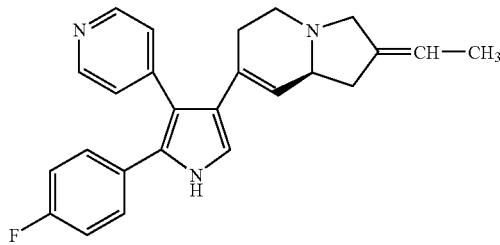

In a similar manner to the procedure described in Example 1(v)' above, a reaction and silica gel column chromatography (using a 100:5:3 by volume mixture of ethyl acetate, methanol and isopropylamine respectively as the eluant) were conducted, using (8aS)-2-ethylidene-1,2,3,5,6,7,8,8a-octahydroindolizin-7-one (prepared as described in Preparative Example 24' below) in place of (2R,8aS)-2-methoxy-1,2,3,5,6,7,8,8a-octahydroindolizin-7-one, to give 474 mg (yield: 4%) of the title compound (Rf value=0.50) as a white powder.

Melting point: 244–246° C. (decomposition) $^1$H-NMR spectrum (400 MHz, CDCl$_3$) δ ppm: 8.42 (2H, doublet. J=6 Hz); 7.18–7.12 (4H, multiplet); 7.10–7.07 (2H, multiplet); 6.93 (1H, doublet, J=3 Hz); 5.31–5.29 (1H, broad singlet); 5.18–5.16 (1H, broad singlet); 3.30–3.29 (1H, multiplet); 3.24–3.23 (1H, multiplet); 3.19–3.10 (1H, multiplet); 2.84–2.80 (1H, multiplet); 2.64–2.55 (1H, multiplet); 2.35–2.26 (2H, multiplet); 2.10–2.07 (1H, multiplet); 1.82–1.78 (1H, multiplet); 1.53 (3H, doublet, J=6 Hz).

Example 38'

2-(4-Fluorophenyl)-4-[(8aS)-2,2-propylenedioxy-1,2,3,5,8,8a-hexahydroindolizin-7-yl]-3-(pyridin-4-yl)-1H-pyrrole (Compound No. 4-57')

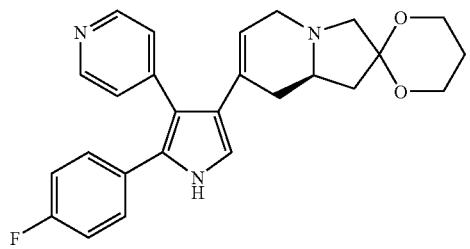

In a similar manner to the procedure described in Example 1(v)' above, a reaction and silica gel column chromatography (using a 100:10:0.25 by volume mixture of ethyl acetate, methanol and isopropylamine respectively as the eluant) were conducted, using (8aS)-2,2-propylenedioxy-1,2,3,5,6,7,8,8a-octahydroindolizin-7-one (prepared as described in Preparative Example 21' below) in place of (2R,8aS)-2-methoxy-1,2,3,5,6,7,8,8a-octahydroindolizin-7-one, to give 2.11 g (yield: 29%) of the title compound (Rf value=0.48) as a pale brown powder.

Melting point: 164–166° C. (decomposition) $^1$H-NMR spectrum (400 MHz, DMSO-d$_6$) δ ppm: 11.39 (1H, broad singlet); 8.45 (2H, doublet, J=6 Hz); 7.20–7.08 (6H, multiplet); 6.91 (1H, doublet, J=3 Hz); 5.27–5.22 (1H, multiplet); 3.86–3.69 (4H, multiplet); 3.39 (1H, doublet, J=10 Hz); 3.27–3.19 (1H, multiplet); 2.66–2.57 (1H, multiplet); 2.35–2.19 (3H, multiplet); 2.15 (1H, doublet, J=10 Hz); 2.06–1.96 (1H, multiplet); 1.62–1.54 (2H, multiplet); 1.50–1.42 (1H, multiplet).

Example 39'

2-(4-Fluorophenyl)-4-[(8aS)-2,2-propylenedioxy-1,2,3,5,6,8a-hexahydroindolizin-7-yl]-3-(pyridin-4-yl)-1H-pyrrole (Compound No. 1-989')

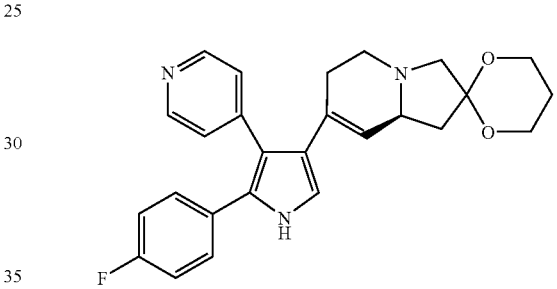

The silica gel column chromatography performed in Example 38' above also provided 1.38 g (yield: 19%) of the title compound (Rf value=0.22) as a pale brown powder.

Melting point: 214–216° C. (decomposition) $^1$H-NMR spectrum (400 MHz DMSO-d$_6$) δ ppm: 11.40 (1H, broad singlet); 8.43 (2H, doublet, J=6 Hz); 7.22–7.07 (6H, multiplet); 6.93 (1H, doublet, J=3 Hz); 5.20–5.16 (1H, multiplet); 3.85–3.70 (4H, multiplet); 3.14–3.04 (1H, multiplet); 3.07 (1H, doublet, J=10 Hz); 2.93–2.85 (1H, multiplet); 2.62 (1H, doublet, J=10 Hz); 2.54–2.44 (1H, multiplet); 2.33–2.21 (1H, multiplet); 2.16–2.04 (2H, multiplet); 1.68–1.44 (2H, multiplet); 1.47 (1H, doublet of doublets, J=13 Hz, 9 Hz).

Example 40'

4-[(8aS)-2,2-(2',2'-Dimethylpropylenedioxy)-1,2,3,5,8,8a-hexahydroindolizin-7-yl]-2-(4-fluorophenyl)-3-(pyridin-4-yl)-1H-pyrrole (Compound No. 4-58')

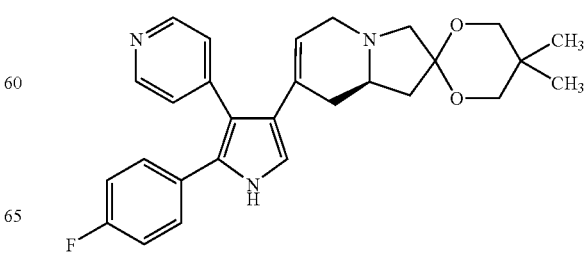

In a similar manner to the procedure described in Example 1(v)' above, a reaction and silica gel column chromatography (using a 100:10:0.25 by volume mixture of ethyl acetate, methanol and isopropylamine respectively as the eluant) were conducted, using (8aS)-2,2-(2',2'-dimethyl-propylenedioxy)-1,2,3,5,6,7,8,8a-octahydroindolizin-7-one (prepared as described in Preparative Example 22' below) in place of (2R,8aS)-2-methoxy-1,2,3,5,6,7,8,8a-octahydroindolizin-7-one, to give 1.85 g (yield: 26%) of the title compound (Rf value=0.58) as a pale brown powder.

Melting point: 235–237° C. (decomposition) $^1$H-NMR spectrum (400 MHz. DMSO-$d_6$) δ ppm: 11.39 (1H, broad singlet); 8.45 (2H, doublet, J=6 Hz); 7.20–7.08 (6H, multiplet); 6.91 (1H, doublet, J=3 Hz); 5.27–5.22 (1H, multiplet); 3.47–3.30 (5H, multiplet); 3.26–3.18 (1H, multiplet); 2.66–2.58 (1H, multiplet); 2.36–2.19 (3H, multiplet); 2.16 (1H, doublet, J=10 Hz); 2.07–1.96 (1H, multiplet); 1.47 (1H, doublet of doublets, J=12 Hz, 10 Hz); 0.88 (6H, singlet).

Example 41'

4-[(8aS)-2,2-(2',2'-Dimethylpropylenedioxy)-1,2,3,5,6,8a-hexahydroindolizin-7-yl]-2-(4-fluorophenyl)-3-(pyridin-4-yl)-1H-pyrrole (Compound No. 1-990')

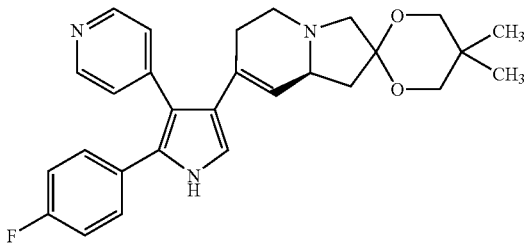

The silica gel column chromatography performed in Example 40' above also provided 1.37 g (yield: 19%) of the title compound (Rf value=0.20) as a white powder.

Melting point: 235–237° C. (decomposition) $^1$H-NMR spectrum (400 MHz, DMSO-$d_6$) δ ppm: 11.40 (1H, broad singlet); 8.43 (2H, doublet, J=6 Hz); 7.19–7.08 (6H, multiplet); 6.93 (1H, doublet, J=3 Hz); 5.19–5.15 (1H, multiplet); 3.47–3.29 (4H, multiplet); 3.14–3.05 (2H, multiplet); 2.93–2.85 (1H, multiplet); 2.63 (1H, doublet, J=10 Hz); 2.54–2.45 (1H, multiplet); 2.33–2.22 (1H, multiplet); 2.14–2.04 (2H, multiplet); 1.46 (1H, doublet of doublets, J=13 Hz, 9 Hz); 0.91 (3H, singlet); 0.85 (3H, singlet).

Example 42'

2-(4-Fluorophenyl)-4-[(2S,8aS)-2-propyl-1,2,3,5,8,8a-hexahydroindolizin-7-yl]-3-(pyridin-4-yl)-1H-pyrrole (Compound No. 4-7')

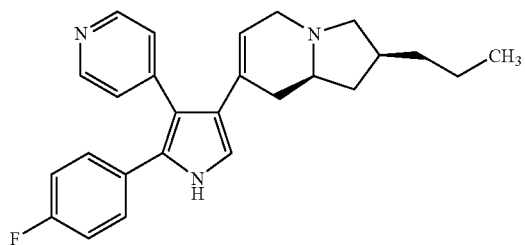

In a similar manner to the procedure described in Example 1(v)' above, a reaction and silica gel column chromatography (using a 100:5:1 by volume mixture of ethyl acetate, methanol and isopropylamine respectively as the eluant) were conducted, using (2S,8aS)-2-propyl-1,2,3,5,6,7,8,8a-octahydroindolizin-7-one (prepared as described in Preparative Example 28' below) in place of (2R,8aS)-2-methoxy-1,2,3,5,6,7,8,8a-octahydroindolizin-7-one, to give 684 mg (yield: 5%) of the title compound (Rf value=0.60) as a pale yellow powder.

Melting point: 205–206° C. (decomposition) $^1$H-NMR spectrum (400 MHz, CDCl$_3$) δ ppm: 11.36–11.35 (1H, broad singlet); 8.44 (2H, doublet, J=6 Hz); 7.17–7.14 (4H, multiplet); 7.13–7.09 (2H, multiplet); 6.90 (1H, doublet, J=3 Hz); 5.25–5.24 (1H, broad singlet); 3.36–3.30 (1H, multiplet); 3.27–3.22 (1H, multiplet); 2.74–2.72 (1H, multiplet); 2.61–2.51 (1H, multiplet); 2.23–2.10 (3H, multiplet); 2.07–1.97 (3H, multiplet); 1.38–1.20 (4H, multiplet); 0.86 (3H, triplet, J=7 Hz).

Example 43'

2-(4-Fluorophenyl)-4-[(2S,8aS)-2-propyl-1,2,3,5,6,8a-hexahydroindolizin-7-yl]-3-(pyridin-4-yl)-1H-pyrrole (Compound No. 1-295')

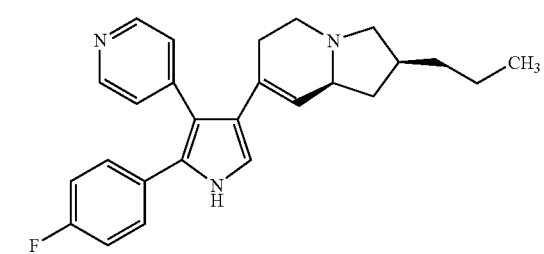

The silica gel column chromatography performed in Example 42' above also provided 359 mg (yield: 3%) of the title compound (Rf value=0.50) as a pale yellow powder.

Melting point: 202–203° C. (decomposition) $^1$H-NMR spectrum (400 MHz, CDCl$_3$) δ ppm: 11.38–11.37 (1H, broad singlet); 8.42 (2H, doublet, J=6 Hz); 7.18–7.13 (4H, multiplet); 7.12–7.09 (2H, multiplet); 6.91 (1H, doublet, J=3 Hz); 5.12–5.11 (1H, broad singlet); 3.31–3.23 (1H, multiplet); 2.92–2.88 (1H, multiplet); 2.67–2.61 (2H, multiplet); 2.51–2.49 (1H, multiplet); 2.42–2.38 (1H, multiplet); 2.30–2.25 (1H, multiplet); 2.02–1.89 (3H, multiplet); 1.36–1.22 (4H, multiplet); 0.88 (3H, doublet, J=7 Hz).

Example 44'

4-[(2R,8aS)-2-Ethoxy-1,2,3,5,8,8a-hexahydroindolizin-7-yl]-2-(4-fluorophenyl)-3-(pyridin-4-yl)-1H-pyrrole (Compound No. 4-16')

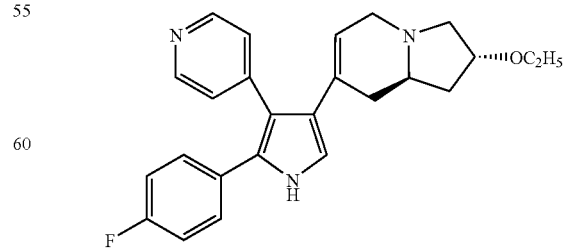

In a similar manner to the procedure described in Example 1(v)' above, a reaction and silica gel column chromatography (using a 10:1:1 by volume mixture of ethyl acetate, methanol and isopropylamine respectively as the eluant) were conducted, using (2R,8aS)-2-ethoxy-1,2,3,5,6, 7,8,8a-octahydroindolizin-7-one (prepared as described in Preparative Example 20' below) in place of (2R,8aS)-2-methoxy-1,2,3,5,6,7,8,8a-octahydroindolizin-7-one, to give 285 mg (yield: 9%) of the title compound (Rf value=0.65) as a pale brown powder.

Melting point: 194–196° C. (decomposition) $^1$H-NMR spectrum (400 MHz, CDCl$_3$) δ ppm: 8.46 (2H, doublet, J=6 Hz); 8.23 (1H, broad singlet); 7.16 (2H, doublet, J=6 Hz); 7.12 (2H, doublet of doublets, J=9 Hz, 5 Hz); 6.97 (2H, triplet, J=9 Hz); 6.82 (1H, doublet, J=3 Hz); 5.51–5.47 (1H, multiplet); 4.14–4.08 (1H, multiplet); 3.62–3.53 (1H, multiplet); 3.50–3.36 (3H, multiplet); 2.93–2.82 (1H, multiplet); 2.59–2.46 (1H, multiplet); 2.32–2.15 (2H, multiplet); 2.14–2.01 (1H, multiplet); 2.00–1.92 (1H, multiplet); 1.70–1.60 (1H, multiplet); 1.19 (3H, triplet, J=7 Hz).

Example 45'

4-[(2R,8aS)-2-Ethoxy-1,2,3,5,6,8a-hexahydroindolizin-7-yl]-2-(4-fluorophenyl)-3-(pyridin-4-yl)-1H-pyrrole (Compound No. 1-304')

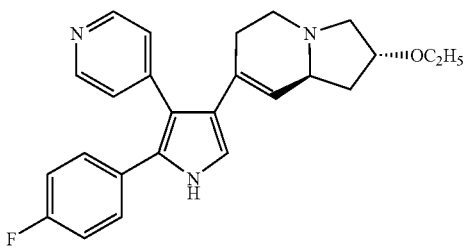

The silica gel column chromatography performed in Example 44' above also provided 231 mg (yield: 7%) of the title compound (Rf value=0.60) as a pale brown powder.

Melting point: 192–195° C. (decomposition) $^1$H-NMR spectrum (400 MHz, CDCl$_3$) δ ppm: 8.47 (2H, doublet, J=6 Hz); 8.25 (1H, broad singlet); 7.20–7.09 (4H, multiplet); 6.97 (2H, triplet, J=9 Hz); 6.82 (1H, doublet, J=3 Hz); 5.40 (1H, doublet, J=2 Hz); 4.10–4.02 (1H, multiplet); 3.50–3.34 (3H, multiplet); 3.16 (1H, doublet of doublets, J=11 Hz, 6 Hz); 2.99–2.90 (1H, multiplet); 2.80–2.65 (2H, multiplet); 2.46–2.30 (1H, multiplet); 2.18–2.04 (1H, multiplet); 1.96–1.88 (1H, multiplet); 1.69–1.60 (1H, multiplet); 1.19 (3H, triplet, J=7 Hz).

Example 46'

(±)-4-[Cyclopentanespiro-2'-(1',2',3',5',8',8a'-hexahydroindolizin)-7'-yl]-2-(4-fluorophenyl)-3-(pyridin-4-yl)-1H-pyrrole (Compound No. 4-61')

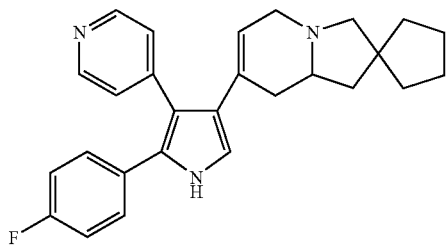

In a similar manner to the procedure described in Example 1(v)' above, a reaction and silica gel column chromatography (using a 100:10:0.25 by volume mixture of ethyl acetate, methanol and isopropylamine respectively as the eluant) were conducted, using (±)-cyclopentanespiro-2'-(1',2',3',5',6',7',8',8a'-octahydroindolizin)-7'-one (prepared as described in Preparative Example 18' below) in place of (2R,8aS)-2-methoxy-1,2,3,5,6,7,8,8a-octahydroindolizin-7-one, to give 2.05 g (yield: 29%) of the title compound (Rf value=0.53) as a pale brown powder.

Melting point: 206–208° C. (decomposition) $^1$H-NMR spectrum (400 MHz, DMSO-d$_6$) δ ppm: 11.37 (1H, broad singlet); 8.45 (2H, doublet, J=5 Hz); 7.20–7.07 (6H, multiplet); 6.90 (1H, doublet, J=3 Hz); 5.27–5.22 (1H, multiplet); 3.28–3.20 (1H, multiplet); 2.90 (1H, doublet, J=9 Hz); 2.64–2.55 (1H, multiplet); 2.29–2.17 (2H, multiplet); 2.05–1.94 (2H, multiplet); 1.80 (1H, doublet of doublets, J=12 Hz, 6 Hz); 1.64–1.42 (8H, multiplet); 1.26 (1H, doublet of doublets, J=12 Hz, 10 Hz).

Example 47'

(±)-4-[Cyclopentanespiro-2'-(1',2',3',5',6',8a'-hexahydroindolizin)-7'-yl]-2-(4-fluorophenyl)-3-(pyridin-4-yl)-1H-pyrrole (Compound No. 1-993')

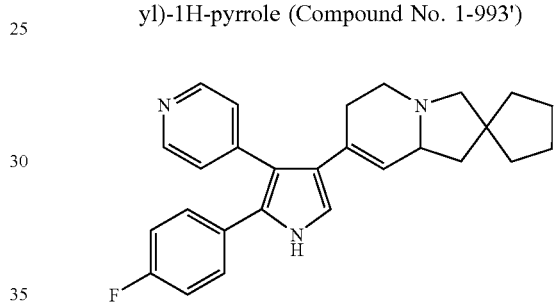

The silica gel column chromatography performed in Example 46' above also provided 1.31 g (yield: 19%) of the title compound (Rf value=0.19) as a pale brown powder.

Melting point: 202–204° C. (decomposition) $^1$H-NMR spectrum (400 MHz, DMSO-d$_6$) δ ppm: 11.38 (1H, broad singlet); 8.43 (2H, doublet, J=6 Hz); 7.20–7.08 (6H, multiplet); 6.91 (1H, doublet, J=3 Hz); 5.17–5.13 (1H, multiplet); 3.25–3.18 (1H, multiplet); 2.92–2.85 (1H, multiplet); 2.70 (1H, doublet, J=9 Hz); 2.65–2.56 (1H, multiplet); 2.37 (1H, doublet, J=9 Hz); 2.34–2.23 (1H, multiplet); 2.01–1.92 (1H, multiplet); 1.69 (1H, doublet of doublets, J=12 Hz, 7 Hz); 1.61–1.39 (8H, multiplet); 1.15 (1H, doublet of doublets, J=12 Hz, 8 Hz).

Example 48

4-[(2S,8aS)-2-Benzyl-1,2,3,5,6,8a-hexahydroindolizin-7-yl]-2-(4-fluorophenyl)-3-(pyridin-4-yl)-1H-pyrrole (Compound No. 1-299')

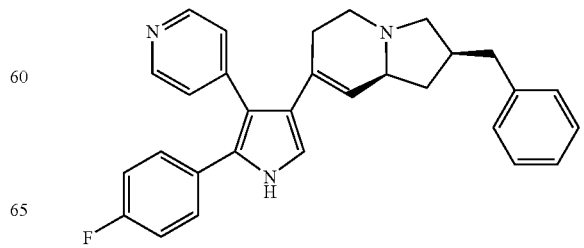

In a similar manner to the procedure described in Example 1(v)' above, a reaction and silica gel column chromatography (using a 100:10:2 by volume mixture of ethyl acetate, methanol and isopropylamine respectively as the eluant) were conducted, using (2S,8aS)-2-benzyl-1,2,3,5,6,7,8,8a-octahydroindolizin-7-one (prepared as described in Preparative Example 29' below) in place of (2R,8aS)-2-methoxy-1,2,3,5,6,7,8,8a-octahydroindolizin-7-one, to give 252 mg (yield: 11%) of the title compound (Rf value=0.50) as a pale brown powder.

Melting point: 207–209° C. (decomposition) ¹H-NMR spectrum (400 MHz, CDCl₃) δ ppm: 11.39–11.38 (1H, broad singlet); 8.46 (2H, doublet, J=6 Hz); 7.28 (2H, triplet, J=8 Hz); 7.20–7.11 (9H, multiplet); 6.92 (1H, doublet, J=3 Hz); 5.14–5.13 (1H, broad singlet); 3.39–3.21 (2H, multiplet); 2.91–2.83 (1H, multiplet); 2.65–2.49 (5H, multiplet); 2.32–2.29 (2H, multiplet); 1.99–1.87 (2H, multiplet).

Example 49'

4-[(8aS)-2-Benzylidene-1,2,3,5,6,8a-hexahydroindolizin-7-yl]-2-(4-fluorophenyl)-3-(pyridin-4-yl)-1H-pyrrole (Compound No. 1-987')

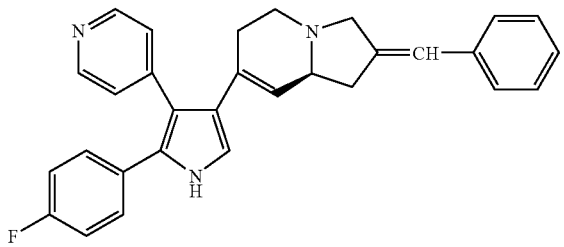

In a similar manner to the procedure described in Example 1(v)' above, a reaction and silica gel column chromatography (using a 100:10:2 by volume mixture of ethyl acetate, methanol and isopropylamine respectively as the eluant) were conducted, using (8aS)-2-benzylidene-1,2,3,5,6,7,8,8a-octahydroindolizin-7-one (prepared as described in Preparative Example 26' below) in place of (2R,8aS)-2-methoxy-1,2,3,5,6,7,8,8a-octahydroindolizin-7-one, to give 17 mg (yield: 3%) of the title compound (Rf value=0.50) as a pale brown powder.

Melting point: 243–245° C. (decomposition) ¹H-NMR spectrum (400 MHz, CDCl₃) δ ppm: 8.41 (2H, doublet, J=6 Hz); 8.31–8.29 (1H, broad singlet); 7.38–7.27 (4H, multiplet); 7.21 (1H, triplet, J=7 Hz); 7.15–7.10 (4H, multiplet); 6.97 (2H, triplet, J=9 Hz); 6.84 (1H, doublet, J=3 Hz); 6.40 (1H, singlet); 5.50–5.49 (1H, broad singlet); 3.65–3.58 (3H, multiplet); 2.96–2.93 (1H, multiplet); 2.85–2.78 (2H, multiplet); 2.47–2.42 (1H, multiplet); 2.36–2.21 (2H, multiplet).

Example 50'

2-(4-Fluorophenyl)-4-[(2S,8aS)-2-phenoxy-1,2,3,5,8,8a-hexahydroindolizin-7-yl]-3-(pyridin-4-yl)-1H-pyrrole (Compound No. 4-68')

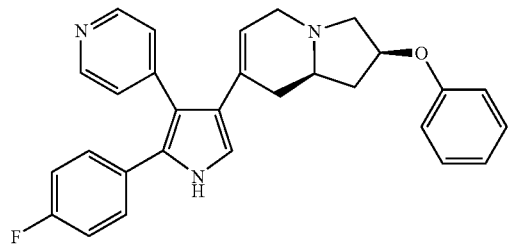

In a similar manner to the procedure described in Example 1(v)' above, a reaction and silica gel column chromatography (using a 19:1 by volume mixture of ethyl acetate and methanol as the eluant) were conducted, using (2S,8aS)-2-phenoxy-1,2,3,5,6,7,8,8a-octahydroindolizin-7-one (prepared as described in Preparative Example 23' below) in place of (2R,8aS)-2-methoxy-1,2,3,5,6,7,8,8a-octahydroindolizin-7-one, to give 2.00 g (yield: 33%) of the title compound (Rf value=0.63) as a white powder.

Melting point: 212–214° C. (decomposition) ¹H-NMR spectrum (400 MHz, DMSO-d₆) δ ppm: 11.40 (1H, broad singlet); 8.45 (2H, doublet, J=6 Hz); 7.27 (2H, triplet, J=8 Hz); 7.21–7.08 (6H, multiplet); 6.96–6.82 (4H, multiplet); 5.28–5.24 (1H, multiplet); 4.88–4.80 (1H, multiplet); 3.34–3.27 (1H, multiplet); 3.19–3.11 (1H, multiplet); 2.70–2.50 (2H, multiplet); 2.46–2.05 (4H, multiplet); 1.47–1.37 (1H, multiplet).

Example 51'

2-(4-fluorophenyl)-4-[(2S,8aS)-2-phenoxy-1,2,3,5,6,8a-hexahydroindolizin-7-yl]-3-(pyridin-4-yl)-1H-Pyrrole (Compound No. 1-1000')

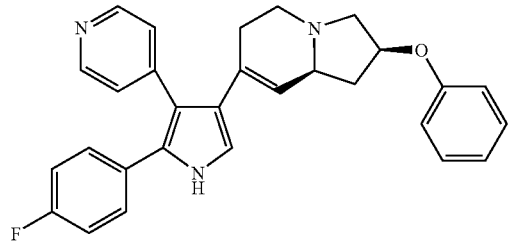

The silica gel column chromatography performed in Example 50' above also provided 0.90 g (yield: 15%) of the title compound (Rf value=0.10) as a pale brown powder.

Melting point: 199–201° C. (decomposition) ¹H-NMR spectrum (400 MHz, DMSO-d₆) δ ppm: 11.41 (1H, broad singlet); 8.33 (2H, doublet, J=6 Hz); 7.29 (2H, triplet, J=8 Hz); 7.21–7.08 (6H, multiplet); 6.97–6.86 (4H, multiplet); 5.28–5.24 (1H, multiplet); 4.88–4.82 (1H, multiplet); 3.21–3.14 (1H, multiplet); 3.04–2.91 (3H, multiplet); 2.67–2.57 (1H, multiplet); 2.44–2.35 (1H, multiplet); 2.33–2.23 (1H, multiplet); 2.11–2.02 (1H, multiplet); 1.44–1.36 (1H, multiplet).

Example 52'

2-(4-Fluorophenyl)-4-[(2S,8aS)-2-methylsulfonyl-1,2,3,5,8,8a-hexahydroindolizin-7-yl]-3-(pyridin-4-yl)-1H-pyrrole (Compound No. 4-67')

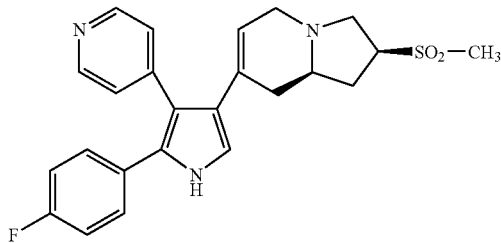

In a similar manner to the procedure described in Example 1(v)' above, a reaction and silica gel column chromatography (using a 100:1:1 by volume mixture of ethyl acetate, methanol and isopropylamine respectively as the eluant) were conducted, using (2S,8aS)-2-methylsulfonyl-1,2,3,5,6,7,8,8a-octahydroindolizin-7-one (prepared as described in Preparative Example 15' below) in place of (2R,8aS)-2-methoxy-1,2,3,5,6,7,8,8a-octahydroindolizin-7-one, to give 30 mg (yield: 2%) of the title compound (Rf value=0.2) as a brown powder.

Melting point: >250° C. (decomposition) $^1$H-NMR spectrum (400 MHz, CD$_3$OD) δ ppm: 8.40–8.36 (2H, multiplet); 7.25 (2H, doublet, J=5 Hz); 7.22–7.15 (2H, multiplet); 7.05–6.98 (2H, multiplet); 6.87 (1H, singlet); 5.39 (1H, triplet, J=2 Hz); 3.81–3.74 (1H, multiplet); 3.59 (1H, doublet of doublets, J=11 Hz, 3 Hz); 3.49–3.44 (1H, multiplet); 2.93 (3H, singlet); 2.90–2.83 (1H, multiplet); 2.67 (1H, triplet, J=11 Hz); 2.57–2.27 (3H, multiplet); 2.27–2.20 (1H, multiplet); 1.88–1.80 (1H, multiplet).

Example 53'

2-(4-Fluorophenyl)-4-[(2S,8aS)-2-methylsulfonyl-1,2,3,5,6,8a-hexahydroindolizin-7-yl]-3-(pyridin-4-yl)-1H-pyrrole (Compound No. 1-999')

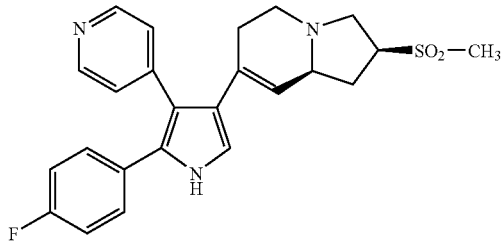

The silica gel column chromatography performed in Example 52' above also provided 46 mg (yield: 2%) of the title compound (Rf value=0.05) as a brown powder.

Melting point: 147–150° C. (decomposition) $^1$H-NMR spectrum (400 MHz, CD$_3$OD) δ ppm: 8.39–8.35 (2H, multiplet); 7.24 (2H, doublet, J=5 Hz); 7.19–7.16 (2H, multiplet); 7.03–6.87 (2H, multiplet); 6.86 (1H, singlet); 5.38 (1H, triplet, J=2 Hz); 3.69–3.65 (1H, multiplet); 3.62–3.56 (1H, multiplet); 3.44–3.38 (1H, multiplet); 2.92 (3H, singlet); 2.82–2.78 (1H, multiplet); 2.63–2.53 (1H, multiplet); 2.50–2.39 (1H, multiplet); 2.36–2.15 (3H, multiplet); 1.92–1.76 (1H, multiplet).

Example 54'

2-(4-Fluorophenyl)-4-[(8aS)-2-propylidene-1,2,3,5,6,8a-hexahydroindolizin-7-yl]-3-(pyridin-4-yl)-1H-pyrrole (Compound No. 1-984')

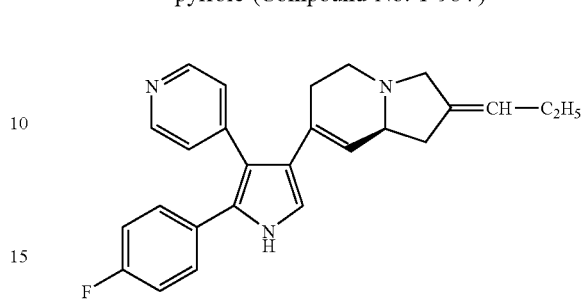

In a similar manner to the procedure described in Example 1(v)' above, a reaction and silica gel column chromatography (using a 100:5:1 by volume mixture of ethyl acetate, methanol and isopropylamine respectively as the eluant) were conducted, using (8aS)-2-propylidene-1,2,3,5,6,7,8,8a-octahydroindolizin-7-one (prepared as described in Preparative Example 25' below) in place of (2R,8aS)-2-methoxy-1,2,3,5,6,7,8,8a-octahydroindolizin-7-one, to give the title compound as two gemoetric isomers, the E-form and Z-form:

Isomer A

Rf value=0.50, 0.56 g (yield: 4%) of an orange powder

Melting point: 185–187° C. (decomposition) $^1$H-NMR spectmen (400 MHz, CDCl$_3$) δ ppm: 11.41–11.40 (1H, broad singlet); 8.41 (2H, doublet, J=6 Hz); 7.18–7.11 (4H, multiplet); 7.10–7.07 (2H, multiplet); 6.93 (1H, doublet, J=3 Hz); 5.23–5.18 (1H, multiplet); 5.14–5.13 (1H, broad singlet); 3.41–3.36 (1H, multiplet); 3.22–3.13 (2H, multiplet); 2.93–2.89 (1H, multiplet); 2.68–2.66 (1H, multiplet); 2.40–2.29 (2H, multiplet); 2.10–2.06 (1H, multiplet); 1.97–1.87 (2H, multiplet); 1.57–1.55 (1H, multiplet); 0.94 (3H, doublet, J=7 Hz).

Isomer B

Rf value=0.45, 1.58 g of a white powder (yield: 11%)

Melting point: 249–251° C. (decomposition) $^1$H-NMR spectrum (400 MHz, CDCl$_3$) δ ppm: 11.47–11.46 (1H, broad singlet); 8.42 (2H, doublet, J=6 Hz); 7.19–7.14 (4H, multiplet); 7.13–7.07 (2H, multiplet); 6.92 (1H, doublet, J=3 Hz); 5.27–5.23 (1H, multiplet); 5.18–5.17 (1H, broad singlet); 4.14 (1H, quartet, J=5 Hz); 3.24–3.21 (1H, multiplet); 3.13–3.10 (1H, multiplet); 2.85–2.80 (1H, multiplet); 2.63–2.58 (1H, multiplet); 2.37–2.31 (2H, multiplet); 2.11–2.07 (1H, multiplet); 1.95–1.90 (2H, multiplet); 1.88–1.78 (1H, multiplet); 0.92 (3H, doublet, J=8 Hz).

Preparative Examples

Preparative Example 1'

(2R8aS)-2-Methoxy-1,2,3,5,6,7,8,8a-octahydroindolizin-7-one

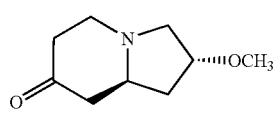

1(i)' (2S,4R)-1-Benzyloxycarbonyl-2-cyanomethyl-4-methoxypyrrolidine 17.9 ml (17.9 mmol) of a 1M solution of borane-tetrahydrofuran complex in tetrahydrofuran were added at 0° C. with stirring to a solution of 2.00 g (7.16 mmol) of (2S,4R)-1-benzyloxycarbonyl-4-methoxyproline in 20 ml of tetrahydrofuran. The resulting mixture was stirred at 0° C. for 1 hour and then at room temperature for 3 hours, at the end of which time the reaction mixture was cooled to 0° C. again. Methanol was then added carefully to the cooled mixture, and the mixture was then concentrated by evaporation under reduced pressure. A saturated aqueous solution of sodium hydrogencarbonate was added to the residue thus obtained, and the mixture was extracted with ethyl acetate. The organic extract was washed with water, dried over anhydrous magnesium sulfate and then concentrated by evaporation under reduced pressure to afford 1.82 g of the reduced product, an alcohol derivative, as a brown oil.

1.13 ml (8.14 mmol) of triethylamine were added to a solution of the oil obtained above in 25 ml of dichloromethane, and then 0.58 ml (7.46 mmol) of methanesulfonyl chloride were added to the ice-cooled mixture with stirring. After stirring at the same temperature for 30 minutes, a saturated aqueous solution of sodium hydrogencarbonate was added, and the mixture was extracted with dichloromethane. The organic extract was washed with water, dried over anhydrous magnesium sulfate and then concentrated by evaporation under reduced pressure to afford 2.19 g of the mesylated derivative as a brown oil.

0.31 g (6.32 mmol) of sodium cyanide were added to a solution of the mesylated derivative obtained above in 22 ml of dimethyl sulfoxide, and the resulting mixture was stirred at 100° C. for 30 minutes. At the end of this time, a saturated aqueous solution of sodium hydrogencarbonate was added to the reaction mixture, and the mixture was extracted with ethyl acetate. The organic extract was washed with water, dried over anhydrous sodium sulfate and then concentrated under reduced pressure to afford 1.70 g (yield: 88%) of the title compound as a pale brown oil.

$^1$H-NMR spectrum (400 MHz, CDCl$_3$) δ ppm: 7.43–7.28 (5H, multiplet); 5.26–5.08 (2H, multiplet); 4.20–4.10 (1H, multiplet; 4.03–3.93 (1H, multiplet); 3.90 (0.4H, doublet, J=12 Hz); 3.74 (0.6H, doublet, J=12 Hz); 3.56–3.44 (1H, multiplet); 3.31 (1.2H, singlet); 3.30 (1.8H, singlet); 3.16 (0.6H, doublet of doublets, J=17 Hz, 6 Hz); 2.80 (0.4H, doublet of doublets, J=17 Hz. 6 Hz); 2.76–2.58 (1H, multiplet); 2.39–2.30 (1H, multiplet); 2.08–1.97 (1H, multiplet).

1(ii)' (2S,4R)-1-Benzyloxycarbonyl-2-(3-ethoxycarbonyl-2-oxopropyl)-4-methoxypyrrolidine 0.5 ml (4.51 mmol) of ethyl bromoacetate were added at 90° C. to a suspension of 57.19 g (875 mmol) of zinc powder in 600 ml of tetrahydrofuran and the resulting reaction mixture was heated under reflux for 1 hour. A solution of 30.00 g (109 mmol) of (2S,4R)-1-benzyloxycarbonyl-2-cyanomethyl-4-methoxypyrrolidine [prepared as described in Preparative Example 1(i)' above] in 30 ml of tetrahydrofuran and 84.9 ml (766 mmol) of ethyl bromoacetate were added successively to this reaction mixture, and the resulting mixture was then heated under reflux for a further 1.5 hours. After being cooled to room temperature, the reaction mixture was filtrated and the filtrate was concentrated by evaporation under reduced pressure. The residue thus obtained was dissolved in ethyl acetate and washed with a saturated aqueous solution of sodium hydrogencarbonate. The organic extract was washed with water, dried over anhydrous magnesium sulfate and then concentrated by evaporation under reduced pressure. The residue thus obtained was dissolved in a mixture of 200 ml of dioxane and 100 ml of a 1N aqueous solution of hydrochloric acid and then allowed to stand at room temperature for 3 hours. At the end of this time, water was added to the reaction mixture which was then extracted with ethyl acetate. The organic extract was washed with water and then concentrated by evaporation under reduced pressure. The resulting residue was purified by chromatography on a silica gel column using a 2:3 by volume mixture of ethyl acetate and hexane as the eluant to afford 28.23 g (yield: 71%) of the title compound as a pale yellow oil.

$^1$H-NMR spectrum (400 MHz, CDCl$_3$) δ ppm: 7.43–7.27 (5H, multiplet); 5.24–5.06 (2H, multiplet); 4.33–4.10 (3H, multiplet); 3.93–3.86 (1H, multiplet); 3.78 (0.4H, doublet, J=12 Hz); 3.65 (0.6H, doublet, J=12 Hz); 3.52–3.24 (3.6H, multiplet); 3.29 (3H, singlet); 3.14–3.05 (0.4H, multiplet); 2.80–2.62 (1H, multiplet); 2.42–2.32 (1H, multiplet); 1.84–1.73 (1H, multiplet); 1.34–1.21 (3H, multiplet).

1(iii)' (2R,8aS)-2-Methoxy-1,2,3,5,6,7,8,8a-octahydroindolizin-7-one 3.79 ml (45.4 mmol) of pyrrolidine, 1.50 g of molecular sieves (MS4A) and 3.75 g of 20% palladium hydroxide on carbon were added to a solution of 15.00 g (41.3 mmol) of (2S,4R)-1-benzyloxycarbonyl-2-(3-ethoxycarbonyl-2-oxopropyl)-4-methoxypyrrolidine [prepared as described in Preparative Example 1(ii)' above] in 150 ml of ethyl acetate and the mixture was then stirred for 2 hours at room temperature under a hydrogen atmosphere. At the end of this time, the reaction mixture was filtered and the filtrate was concentrated by evaporation under reduced pressure. The resulting residue was dissolved in 150 ml of tetrahydrofuran, and the solution thus obtained was added dropwise with stirring to an ice-cooled suspension of 4.70 g (124 mmol) of lithium aluminum hydride in 100 m] of tetrahydrofuran, and the reaction mixture was then stirred for a further 18 hours at room temperature. At the end of this time, 19 ml of a 4% aqueous solution of sodium hydroxide were added carefully to the reaction mixture at 0° C., and after the addition of 250 ml of ethanol, the resulting mixture was filtered. The filtrate thus obtained was concentrated by evaporation under reduced pressure and the residue was purified by chromatography on an alumina column using ethyl acetate as the eluant to afford 4.13 g (yield: 59%) of the title compound as a pale brown powder.

$^1$H-NMR spectrum (400 MHz, CDCl$_3$) δ ppm: 4.12–4.04 (1H, multiplet); 3.54 (1H, doublet of doublets, J=10 Hz, 7 Hz); 3.34–3.24 (1H, multiplet); 3.29 (3H, singlet); 2.63–2.30 (5H, multiplet); 2.29–2.19 (2H, multiplet); 2.00 (1H, doublet of double doublets, J=13 Hz, 6 Hz, 1 Hz); 1.79–1.67 (1H, multiplet).

Preparative Example 2'

(2R,8aS)-2-(t-Butyldimethylsilyloxy)-1,2,3,5,6,7,8,8a-octahydroindolizin-7-one

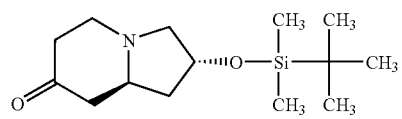

2(i)' (2R8aS)-2-Hydroxy-1,2,3,5,6,7,8,8a-octahydroindolizin-7-one 2.63 g (15.5 mmol) of (2R,8aS)-2-methoxy-1,2,3,5,6,7,8,8a-octahydroindolizin-7-one [prepared as described in the Preparative Example 1' above] were dissolved in 26 ml of a 47% aqueous solution of hydrobromic acid and the resulting mixture was stirred for 8 hours at 100° C. After being cooled to 0° C., the reaction mixture was neutralized by the addition of sodium carbonate and then concentrated by evaporation under reduced pressure. Ethanol was added to the residue thus obtained and all insoluble materials were filtered off. The filtrate thus obtained was concentrated by evaporation under reduced pressure, and the resulting residue was purified by chromatography on an alumina column using a 39:1 by volume mixture of ethyl acetate and methanol as the eluant to afford 1.30 g (yield: 52%) of the title compound as a pale yellow oil.

$^1$H NMR spectrum (400 MHz, CDCl$_3$) δ ppm: 4.63–4.56 (1H, multiplet); 3.58 (1H, doublet of doublets, J=10 Hz, 7 Hz); 3.31–3.24 (1H, multiplet); 2.72–2.44 (4H, multiplet); 2.39–2.32 (1H, multiplet); 2.29–2.20 (2H, multiplet); 1.97–1.70 (3H, multiplet).

2(ii)' (2R8aS)-2-(t-Butyldimethylsilyloxy)-1,2,3,5,6,7,8,8a-octahydroindolizin-7-one 1.70 g (24.9 mmol) of imidazole and 1.88 g (12.5 mmol) of t-butyldimethylsilyl chloride were added to a solution of 1.30 g (8.1 mmol) of (2R,8aS)-2-hydroxy-1,2,3,5,6,7,8,8a-octahydroindolizin-7-one [obtained as described in Preparative Example 2(i)' above] in 30 ml of dichloromethane and the resulting mixture was stirred for 20 hours at room temperature. At the end of this time, water was added and the reaction mixture was extracted with dichloromethane. The organic extract was washed with water and concentrated by evaporation under reduced pressure, and the resulting residue was then purified by chromatography on an alumina column using a 9:1 by volume mixture of hexane and ethyl acetate as the elaunt to afford 1.98 g (yield: 88%) of the title compound as a colorless oil.

$^1$H-NMR spectrum (400 MHz, CDCl$_3$) δ ppm: 4.56–4.48 (1H, multiplet); 3.50–3.42 (1H, multiplet); 3.30–3.273 (1H, multiplet); 2.69–2.32 (5H, multiplet); 2.30–2.17 (2H, multiplet); 1.90–1.78 (2H, multiplet); 0.88 (9H, singlet); 0.06 (3H, singlet); 0.05 (3H, singlet).

Preparative Example 3'

(2S,8aS)-2-Chloro-1,2,3,5,6,7,8,8a-octahydroindolizin-7-one

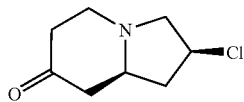

3.93 g (15.0 mmol) of triphenylphosphine were added to a solution of 1.55 g (10.0 mmol) of (2R,8aS2-hydroxy-1,2,3,5,6,7,8,8a-octahydroindolizin-7-one [obtained as described in Preparative Example 2(i)' above] in 45 ml of carbon tetrachloride and the resulting mixture was heated under reflux for 5 hours. After removal of the solvent by evaporation under reduced pressure, the residue was purified by chromatography on an alumina column using a 1:1 by volume mixture of ethyl acetate and hexane as the eluant to afford 1.52 g (yield: 88%) of the title compound as a pale yellow oil.

$^1$H-NMR spectrum (400 MHz, CDCl$_3$) δ ppm: 4.47–4.40 (1H, multiplet); 3.39–3.31 (2H, multiplet); 2.78–2.63 (3H, multiplet); 2.57–2.42 (2H, multiplet); 2.42–2.26 (3H, multiplet); 1.94 (1H, doublet of double doublets, J=14 Hz, 10 Hz, 5 Hz).

Preparative Example 4'

(8aS)-2.2-Difluoro-1,2,3,5,6,7,8,8a-octahydroindolizin-7-one

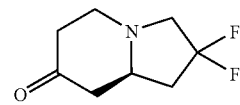

In a similar manner to the procedures described in Preparative Examples 1(i)', (ii) and (iii) above, reactions were carried out successively, using (2S)-1-benzyloxycarbonyl-4,4-difluoroproline as a starting material instead of (2S,4R)-1-benzyloxycarbonyl-4-methoxyproline, to give the title compound as a pale yellow oil (total yield for the 3 steps: 14%).

$^1$H-NMR spectrum (400 MHz, CDCl$_3$) δ ppm: 3.55–3.45 (1H, multiplet); 3.33–3.24 (1H, multiplet); 2.72–2.33 (8H, multiplet); 2.17–2.00 (1H, multiplet).

Preparative Example 5'

(±)-6,7,8,9,9a,10-Hexahydropyrido[1,2-a]indol-8-one

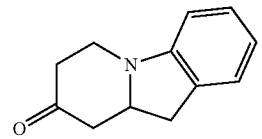

5(i) 1-Benzyloxycarbonylindoline-2-methanol 4.6 g (212 mmol) of lithium borohydride were added in three portions to a solution of 33.0 g (106 mmol) of methyl 1-benzyloxycarbonylindoline-2-carboxylate in 450 ml of tetrahydrofuran, and the resulting mixture was stirred for 5 hours at room temperature. At the end of this time, ice was added and the mixture was stirred for a further 1 hour before extracting with ethyl acetate. The organic extract was washed with water, dried over anhydrous magnesium sulfate and then concentrated by evaporation under reduced pressure. The resulting residue was purified by chromatography on a silica gel column using a 2:5 by volume mixture of ethyl acetate and hexane as the eluant to afford 25.0 g (yield: 83%) of the title compound as a colorless oil.

$^1$H-NMR spectrum (400 MHz, CDCl$_3$) δ ppm: 7.47–7.28 (6H, multiplet); 7.19–7.10 (2H, multiplet); 6.97 (1H, triplet, J=7 Hz); 5.30 (2H, singlet); 4.72–.53 (2H, multiplet); 3.82–3.63 (2H, multiplet); 3.33 (1H, doublet of doublets, J=16 Hz, 10 Hz); 3.00–2.77 (1H, multiplet).

5(ii)' 1-Benzyloxycarbonyl-2-cyanomethylindoline

In a similar manner to the procedures described in Preparative Example 1(i)' above, methanesulfonylation and cyanogenation were carried out, using 1-benzyloxycarbonylindoline-2-methanol [obtained as described in Preparative Example 5(i) above], to give the title compound as an orange oil (yield: 65%).

$^1$H-NMR spectrum (400 MHz, CDCl$_3$) δ ppm: 7.48–7.32 (6H, multiplet); 7.23–7.16 (2H, multiplet); 7.02 (1H, triplet, J=7 Hz); 5.31 (2H, singlet); 4.81–4.68 (1H, multiplet); 3.50 (1H, doublet of doublets, J=16 Hz, 10 Hz); 3.01 (1H, doublet, J=16 Hz); 2.99–2.50 (2H, multiplet).

5(iii)' 1-Benzyloxycarbonyl-2-(3-ethoxycarbonyl-2-oxopropyl)indoline

In a similar manner to that described in Preparative Example 1(ii)' above, a reaction was carried out, using 1-benzyloxycarbonyl-2-cyanomethylindoline [obtained as described in Preparative Example 5(ii)' above] instead of (2S,4R)-1-benzyloxycarbonyl-2-cyanomethyl]-4-methoxypyrrolidine, to give the title compound as a yellow oil (yield: 47%).

$^1$H-NMR spectrum (400 MHz, CDCl$_3$) δ ppm: 7.45–7.32 (6H, multiplet); 7.22–7.13 (2H, multiplet); 6.97 (1H, triplet, J=37 Hz); 5.28 (2H, singlet); 4.92–4.84 (1H, multiplet); 4.22–4.12 (2H, multiplet); 3.46 (1H, doublet of doublets, J=16 Hz, 9 Hz); 3.43–3.31 (2H, multiplet); 2.84 (1H, doublet of doublets, J=6 Hz, 4 Hz); 2.80 (1H, doublet of doublets, J=6 Hz, 4 Hz), 2.74 (1H, doublet of doublets, J=16 Hz, 2 Hz); 1.29 (3H, triplet, J=7 Hz).

5(iv)' 2-(3-Ethoxycarbonyl-2-oxopropyl)indoline

In a similar manner to that described in Preparative Example 1(iii)' above, a debenzylation reaction using hydrogen gas and palladium hydroxide on carbon was performed, using 1-benzyloxycarbonyl-2-(3-ethoxycarbonyl-2-oxopropyl)indoline [obtained as described in Preparative Example 5(iii)' above] instead of (2S, 4R)-1-benzyloxycarbonyl-2-(3-ethoxycarbonyl-2-oxopropyl)-4-methoxypyrrolidine, to give the title compound as an orange oil (yield: quantitative).

$^1$H-NMR spectrum (400 MHz, CDCl$_3$) δ ppm: 7.08 (1H, doublet, J=7 Hz); 6.99 (1H, triplet, J=7 Hz); 6.68 (1H, triplet, J=7 Hz); 6.57 (1H, doublet, J=7 Hz); 4.28–4.16 (1H, multiplet); 4.12–4.01 (2H, multiplet); 3.39–3.18 (4H, multiplet); 3.03–2.81 (1H, multiplet); 2.81–2.71 (1H, multiplet); 1.32–1.21 (3H, multiplet).

5(v) (±)-6,7,8,9,9a, 10-Hexahydropyrido[1,2-a]indol-8-one 14.1 ml (56.6 mmol) of a 4N solution of hydrogen chloride in dioxane were added to a solution of 7.0 g (28.3 mmol) of 2-(3-ethoxycarbonyl-2-oxopropyl)indoline [obtained as described in Preparative Example 5(iv)' above] in 140 ml dichloromethane and the resulting mixture was stirred for 2 hours at room temperature. At the end of this time, the reaction mixture was concentrated by evaporation under reduced pressure. 2.6 ml (31.1 mmol) of pyrrolidine were added to a solution of the residue in 140 ml of ethanol, and the mixture was then stirred for 5 hours at room temperature before concentrating by evaporation under reduced pressure. 3.18 g (84.9 mmol) of lithium aluminum hydride were then added to a solution of the resulting residue in 100 ml of tetrahydrofuran with ice-cooling and the resulting mixture was stirred for 18 hours at room temperature.

At the end of this time, 13 ml of a 4% aqueous solution of sodium hydroxide were added carefully at 0° C. to the reaction mixture, and after the addition of 150 ml of ethanol, the resulting mixture was filtered. The filtrate thus obtained was concentrated by evaporation under reduced pressure and the residue was purified by chromatography on an alumina column using a 1:5 by volume mixture of ethyl acetate and hexane as the eluant to afford 720 mg (yield: 14%) of the title compound as a pale yellow oil.

$^1$H-NMR spectrum (400 MHz, CDCl$_3$) δ ppm: 7.20–7.10 (2H, multiplet); 6.61–6.52 (2H, multiplet); 3.20–3.09 (2H, multiplet); 2.74–2.33 (7H, multiplet).

Preparative Example 6'

(2R,8aS)-2-Phenyl-1,2,3,5,6,7,8,8a-octahydroindolizin-7-one

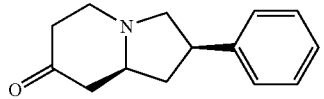

6(i)' (S)-1-Benzyloxycarbonyl-2-hydroxymethyl-4-phenyl-3-pyrroline

Methyl (S)-1-benzyloxycarbonyl-4-phenyl-3-pyrroline-2-carboxylate was reduced with using lithium borohydride, in a similar manner to that described in Preparative Example 5(i)' above, to afford the title compound as a pale yellow powder (yield: 78%).

$^1$H-NMR spectrum (400 MHz, CDCl$_3$) δ ppm: 7.47–7.27 (10H, multiplet); 6.11–6.07 (0.2H, multiplet); 6.03–5.99 (0.8H, multiplet); 5.23 (2H, doublet of doublets, J=16 Hz, 12 Hz); 5.00–4.94 (0.8H, multiplet); 4.85–4.80 (0.2H, multiplet); 4.77–4.70 (0.2H, multiplet); 4.65 (0.8H, triplet of doublets, J=15 Hz, 2 Hz); 4.56 (1H, doublet of double doublets, J=15 Hz, 5 Hz, 2 Hz); 4.26 (1H, broad singlet); 3.94–3.83 (1H, multiplet); 3.80–3.74 (0.2H, multiplet); 3.72 (0.8H, doublet of doublets, J=12 Hz, 7 Hz).

6(ii) (S)-1-Benzyloxycarbonyl-2-cyanomethyl-4-phenyl-3-pyrroline

In a similar manner to the procedures described in Preparative Example 1(i)' above, methanesulfonylation and cyanogenation were performed, using (S)-1-benzyloxycarbonyl-2-hydroxymethyl-4-phenyl-3-pyrroline [obtained as described in Preparative Example 6(i)' above], to give the title compound as a pale yellow powder (yield: 80%).

$^1$H-NMR spectrum (400 MHz, CDCl$_3$) δ ppm: 7.47–7.29 (10H, multiplet); 6.17–6.11 (1H, multiplet); 5.25 (1H, doublet, J=12 Hz) 5.18 (1H, doublet, J=12 Hz); 5.01–4.90 (1H, multiplet); 4.77–4.60 (2H, multiplet); 3.10 (0.7H, doublet of doublets, J=17 Hz, 6 Hz); 2.90 (0.7H, doublet of doublets, J=17 Hz, 3 Hz); 2.86–2.73 (0.6H, multiplet).

6(iii)' (2S 4R)-1-Benzyloxycarbonyl-2-cyanomethyl-4-phenylpyrrolidine 2.32 g of 20% palladium hydroxide on carbon were added to a solution of 11.60 g (36.4 mmol) of (S)-1-benzyloxycarbonyl-2-cyanomethyl-4-phenyl-3-pyrroline [obtained as described in Preparative Example 6(ii)' above] in 150 ml of ethyl acetate, and the resulting mixture was stirred for 7 hours at room temperature under a hydrogen atmosphere. At the end of this time, the reaction mixture was filtered and the filtrate was concentrated by evaporation under reduced pressure. The resulting residue was purified by chromatography on a silica gel column using a 4:1 by volume mixture of hexane and ethyl acetate as the eluant to afford 8.18 g (yield: 70%) of the title compound as a pale brown oil.

$^1$H-NMR spectrum (400 MHz, CDCl$_3$) δ ppm: 7.44–7.17 (10H, multiplet); 5.26–5.09 (2H, multiplet); 4.32–4.06 (2H, multiplet); 3.50–3.41 (1H, multiplet); 3.37–3.26 (1H, multiplet); 3.21 (0.7H, doublet of doublets, J=17 Hz, 6 Hz); 2.93 (0.3 Hz, doublet of doublets, J=17 Hz, 6 Hz); 2.88–2.59 (2H, multiplet); 2.19–2.07 (1H, multiplet).

6(iv)' (2S,4R)-1-Benzyloxycarbonyl-2-(3-ethoxycarbonyl-2oxopropyl)-4-phenylpyrrolidine In a similar manner to that described in Preparative Example 1(ii)' above, a reaction was performed, using (2S,4R)-1-benzyloxycarbonyl-2-cyanomethyl-4-phenylpyr rolidine [obtained as described in Preparative Example 6(iii)' above] instead of (2S,4R)-1-benzyloxycarbonyl-2-cyanomethyl-4-methoxypyrrolidine, to give the title compound as a pale yellow oil (yield: 72%).

¹H-NMR spectrum (400 MHz, CDCl₃) δ ppm: 7.43–7.17 (10H, multiplet); 5.23–5.07 (2H, multiplet); 4.314.10 (4H, multiplet); 3.55–3.20 (5H, multiplet); 2.87–2.67 (2H, multiplet); 1.85–1.74 (1H, multiplet); 1.32–1.21 (3H, multiplet).

6(v)' (2R,8aS)-2-Phenyl-1,2,3,5,6,7,8,8a-octahydroindolizin-7-one

In a similar manner to that described in Preparative Example 1(iii)' above, a reaction was conducted, using (2S,4R)-1-benzyloxycarbonyl-2-(3-ethoxycarbonyl-2-oxopropyl)-4-phenylpyrrolidine [obtained as described in Preparative Example 6(iv)' above] instead of (2S,4R)-1-benzyloxycarbonyl-2-(3-ethoxycarbonyl-2-oxopropyl)-4-methoxypyrrolidine, to give the title compound as a pale yellow oil (yield: 27%).

¹H-NMR spectrum (400 MHz, CDCl₃) δ ppm: 7.42–7.14 (5H, multiplet); 3.42–3.28 (2H, multiplet); 3.18 (1H, doublet of doublets, J=9 Hz, 3 Hz); 2.77–2.63 (2H, multiplet); 2.58–2.30 (6H, multiplet); 1.70–1.58 (1H, multiplet).

Preparative Example 7'

(8aS)-2,2-Ethylenedioxy-1,2,3,5,6,7,8,8a-octahydroindolizin-7-one

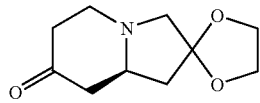

7(i)' (S)-1-Benzyloxycarbonyl-4,4-ethylenedioxy-2-hydroxymethylpyrrolidine (S)-1-Benzyloxycarbonyl-4,4-ethylenedioxyproline methyl ester was reduced using lithium borohydride, in a similar manner to that described in Preparative Example 5(i)' above, to afford the title compound as a colorless oil (yield: 85%).

¹H-NMR spectrum (400 MHz, CDCl₃) δ ppm: 7.42–7.29 (5H, multiplet); 5.14 (2H, singlet); 4.22–4.08 (1H, multiplet); 4.02–3.88 (4H, multiplet); 3.82–3.62 (2H, multiplet): 3.59 (1H, doublet, J=12 Hz); 3.47 (1H, doublet, J=12 Hz); 2.27–2.18 (1H, multiplet); 1.90–1.82 (1H, multiplet).

7(ii)' (S)-1-Benzyloxycarbonyl-2-cyanomethyl-4,4-ethylenedioxypyrrolidine

In a similar manner to the procedures described in Preparative Example 1(i)' above, methanesulfonylation and cyanogenation were performed, using (S)-1-benzyloxycarbonyl-4,4-ethylenedioxy-2-hydroxymethylpyrrolidine [obtained as described in Preparative Example 7(i)' above], to give the title compound as a colorless oil (yield: 88%).

¹H-NMR spectrum (400 MHz, CDCl₃) δ ppm: 7.43–7.28 (5H, multiplet); 5.22–5.08 (2H, multiplet); 4.30–4.21 (1H, multiplet); 4.06–3.88 (4H, multiplet); 3.62–3.44 (2H, multiplet); 3.00–2.72 (2H, multiplet); 2.41–2.29 (1H, multiplet); 2.17–2.10 (1H, multiplet).

7(iii)' (8aS)-2,2-Ethylenedioxy-1,2,3,5,6,7,8,8a-octahydroindolizin-7-one

In a similar manner to the procedures described in Preparative Examples 1(ii)' and 1(iii)' above, reactions were carried out successively, using (S)-1-benzyloxycarbonyl-2-cyanomethyl-4,4-ethylenedioxypyrrolidine [obtained as described in Preparative Example 7(ii)' above] as the starting material instead of (2S,4R) 1-benzyloxycarbonyl-2-cyanomethyl-4-methoxypyrrolidine, to give the title compound as a white powder (total yield for the two steps: 17%).

¹H-NMR spectrum (400 MHz, CDCl₃) δ ppm: 4.06–3.84 (4H, multiplet); 3.32–3.24 (1H, multiplet); 3.22 (1H, doublet, J=10 Hz); 2.73–2.61 (1H, multiplet); 2.58–2.32 (6H, multiplet); 2.23 (1H, doublet of doublets, J=13 Hz, 6 Hz); 1.89 (1H, doublet of doublets, J=13 Hz, 10 Hz).

Preparative Example 8'

(8aS)-2-Methyl-1,2,3,5,6,7,8,8a-octahydroindolizin-7-one

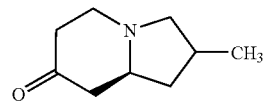

8(i)' (S)-1-Benzyloxycarbonyl-4-methylideneproline Methyl Ester 4.80 g (13.4 mmol) of methyltriphenylphosphonium bromide were added to a suspension of 1.41 g (12.6 mmol) of potassium t-butoxide in 100 ml of diethyl ether, and the resulting mixture was stirred for 15 minutes at 5° C. At the end of this time, a solution of 2.50 g (9.0 mmol) of (S)-1-benzyloxycarbonyl-4-oxoproline methyl ester in 30 ml of diethyl ether was added to the mixture thus obtained, and the mixture was stirred for an additional 3 hours at 35° C. At the end of this time, 50 ml of a saturated aqueous solution of ammonium chloride were added to the reaction mixture with ice-cooling, and the resulting mixture was partitioned. The organic extract thus obtained was washed with water, dried over anhydrous magnesium sulfate and then concentrated by evaporation under reduced pressure. The residue was purified by chromatography on a silica gel column using a 1:3 by volume mixture of ethyl acetate and hexane as the eluant to afford 1.80 g (yield: 72%) of the title compound as a pale yellow oil.

¹H-NMR spectrum (400 MHz, CDCl₃) δ ppm: 7.40–7.23 (5H, multiplet); 5.21–4.95 (4H, multiplet); 4.60–4.50 (1H, multiplet); 4.20–4.09 (2H, multiplet); 3.74 (1.5H, singlet); 3.60 (1.5H, singlet); 3.07–2.91 (1H, multiplet); 2.65 (1H, doublet, J=16 Hz).

8(ii)' (2S)-4-Methylproline Methyl Ester 180 mg of 10% palladium on carbon were added to a solution of 1.80 g (6.5 mmol) of (S)-1-benzyloxycarbonyl-4-methylideneproline methyl ester [obtained as described in Preparative Example 8(i)' above] in 50 ml of methanol, and the resulting mixture was stirred for 2 hours at room temperature under a hydrogen atmosphere. At the end of this time, the reaction mixture was filtered and the filtrate was concentrated by evaporation under reduced pressure to afford 0.93 g (quantitative yield) of the title compound as a pale yellow oil.

¹H-NMR spectrum (400 MHz, CDCl₃) δ ppm: 3.82 (1H, triplet, J=8 Hz); 3.74 (3H, singlet); 3.08 (1H, doublet of doublets, J=10 Hz, 7 Hz); 2.60 (1H, doublet of doublets, J=10 Hz, 8 Hz); 2.33 (1H, doublet of triplets, J=12 Hz, 8 Hz); 2.28–2.15 (1H, multiplet); 1.44–1.37 (1H, multiplet); 1.27 (1H, doublet of doublets, J=14 Hz, 7 Hz); 1.02 (3H, doublet, J=7 Hz).-

8(iii)' (2S)-1-Benzyloxycarbonyl-2-hydroxymethyl-4-methylpyrrolidine 20 ml of an aqueous solution containing 1.89 g (22.5 mmol) of sodium hydrogencarbonate and 1.54 ml (10.8 mmol) of benzyl chloroformate were added to a solution of 0.93 g (6.5 mmol) of (2S)-4-methylproline methyl ester [obtained as described in Preparative Example 8(ii)' above] in 20 ml of toluene, and the resulting mixture was stirred at room temperature over night. At the end of this time, the reaction mixture was extracted with ethyl acetate. The organic extract was washed with water and concentrated under reduced pressure to afford 1.78 g (yield: 99%) of (2S)-1-benzyloxycarbonyl-4-methylproline methyl ester as a pale yellow oil. Subsequently, all of the compound thus obtained was reduced using lithium borohydride, in a similar manner to that described in Preparative Example 5(i)' above, to afford 1.07 g (yield: 66%) of the title compound as a pale yellow oil.

$^1$H-NMR spectrum (400 MHz, CDCl$_3$) δ ppm: 7.42–7.29 (5H, multiplet); 5.14 (2H, broad singlet); 5.07–4.90 (1H, multiplet); 4.08–3.87 (1H, multiplet); 3.86–3.40 (4H, multiplet); 2.90–2.65 (1H, multiplet); 2.40–2.05 (2H, multiplet); 1.02 (3H, doublet, J=6 Hz).

8(iv)' (2S)-1-Benzyloxycarbonyl-2-cyanomethyl-4-methylpyrrolidine

In a similar manner to the procedures described in Preparative Example 1(i)' above, methanesulfonylation and cyanogenation were conducted, using (2S)-1-benzyloxycarbonyl-2-hydroxymethyl-4-methylpyrrolidine [obtained as described in Preparative Example 8(iii)' above], to give the title compound as a colorless oil (yield: 70%).

$^1$H-NMR spectrum (400 MHz, CDCl$_3$) δ ppm: 7.50–7.30 (5H, multiplet); 5.25–5.05 (2H, multiplet); 4.20–3.78 (1.8H, multiplet); 3.70–3.62 (0.2H, multiplet); 3.15–2.88 (1.4H, multiplet); 2.84–2.67 (1.2H, multiplet); 2.62–2.50 (0.4H, multiplet); 2.45–2.30 (0.8H, multiplet); 2.23–2.00 (1H, multiplet); 1.89–1.77 (0.2H, multiplet); 1.60–1.49 (1H, multiplet); 1.10–1.03 (3H, multiplet).

8(v)' (2S)-1-Benzyloxycarbonyl-2-(3-ethoxycarbonyl-2-oxopropyl)-4-methylpyrrolidine In a similar manner to that described in Preparative Example 1(ii)' above, a reaction was performed, using (2S)-1-benzyloxycarbonyl-2-cyanomethyl-4-methylpyrrolidine [obtained as described in Preparative Example 8(iv)' above] instead of (2S,4R) 1-benzyloxycarbonyl-2-cyanomethyl-4-methoxypyrrolidine, to give the title compound as a pale yellow oil (yield: 66%).

$^1$H-NMR spectrum (400 MHz, CDCl$_3$) δ ppm: 7.43–7.28 (5H, multiplet); 5.20–4.99 (2H, multiplet); 4.27–4.03 (3H, multiplet); 3.56–3.40 (1.6H, multiplet); 3.37–3.25 (0.4H, multiplet); 3.00–2.89 (0.2H, multiplet); 2.89–2.75 (0.8H, multiplet); 2.75–2.56 (1H, multiplet); 2.50–2.22 (1H, multiplet); 2.20–2.05 (1H, multiplet); 1.32–1.15 (4H, multiplet); 1.08 (0.6H, doublet, J=6 Hz); 1.02 (2.4H, doublet, J=6 Hz).

8(vi)' (8aS)-2-Methyl-1,2,3,5,6,7,8,8a-octahydroindolizin-7-one

In a similar manner to that described in Preparative Example 1(iii)' above, a reaction was performed, using (2S)-1-benzyloxycarbonyl-2-(3-ethoxycarbonyl-2-oxopropyl)-4-methylpyrrolidine [obtained as described in Preparative Example 8(v)' above] instead of (2S,4R)-1-benzyloxycarbonyl-2-(3-ethoxycarbonyl-2-oxopropyl)-4-methoxypyrrolidine, to give the title compound as a colorless oil (yield: 34%).

$^1$H-NMR spectrum (400 MHz, CDCl$_3$) δ ppm: 3.34–3.22 (1.2H, multiplet); 2.77 (0.8H, doublet of doublets, J=9 Hz, 3 Hz); 2.68–2.55 (1H, multiplet); 2.51–2.43 (2H, multiplet); 2.39–2.24 (5H, multiplet); 2.20–2.10 (1H, multiplet); 1.87–1.75 (0.8H, multiplet); 1.57–1.51 (0.2H, multiplet); 1.14 (2.4H, doublet, J=7 Hz); 1.04 (0.6H, doublet, J=7 Hz).

Preparative Example 9'

(8aS)-8-Methyl-1,2,3,5,6,7,8,8a-octahydroindolizin-7-one

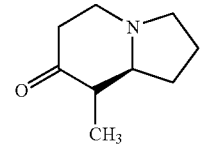

9(i)' (2S)-1-Methylmalonyl-2-(1-carboxyethyl)pyrrolidine 2.01 ml (18.7 mmol) of methyl malonyl chloride were added dropwise to a stirred, ice-cooled mixture of a solution of 2.43 g (17.0 mmol) of (2S)-2-(1-carboxyethyl)pyrrolidine [prepared as described in Tetrahedron Lett., 40, 2891–2894 (1999)] in 60 ml of dichloromethane and 2.61 ml (18.7 mmol) of triethylamine. After stirring the resulting mixture at the same temperature for 15 minutes and then at room temperature for 30 minutes, a saturated aqueous solution of sodium hydrogencarbonate was added. Subsequently, the resulting mixture was adjusted to pH 2 with concentrated hydrochloric acid and then extracted with a 4:1 by volume mixture of dichloromethane and isopropanol. The organic extract was washed with water, dried over anhydrous magnesium sulfate and then concentrated by evaporation under reduced pressure to afford 4.47 g (yield: quantitative) of the title compound as a pale brown oil.

$^1$H-NMR spectrum (500 MHz CDCl$_3$) δ ppm: 4.55–4.47 (0.4H, multiplet); 4.34–4.25 (0.6H, multiplet); 3.76 (2.4H, singlet); 3.59–3.42 (4H, multiplet); 3.25–3.16 (0.6H, multiplet); 2.14–1.80 (5H, multiplet); 1.18 (1.8H, doublet, J=7 Hz); 1.08 (1.2H, doublet, J=7 Hz).

9(ii)' (8aS)-6-Methoxycarbonyl-8-methyl-1,2,3,5,6,7,8,8a-octahydroindolizine-5,7-dione 4.13 g (25.5 mmol) of carbonyldiimidazole were added to a solution of 4.47 g (17.0 mmol) of (2S)-1-methylmalonyl-2-(1-carboxyethyl)pyrrolidine [obtained as described in Preparative Example 9(i)' above] in 120 ml of tetrahydrofuran at room temperature, and the resulting mixture was stirred for 30 minutes at room temperature. At the end of this time, 3.81 ml (25.5 mmol) of 1.8-diazabicyclo[5.4.0]undec-7-ene were added and the resulting mixture was stirred for an additional 1 hour. The reaction mixture was then concentrated by evaporation under reduced pressure, and the residue was partitioned between dichloromethane and a 1N aqueous solution of hydrochloric acid. The separated organic extract was washed with water, dried over anhydrous magnesium sulfate and then concentrated by evaporation under reduced pressure to afford 4.16 g (yield: quantitative) of the title compound as a brown oil.

$^1$H-NMR spectrum (500 MHz, CDCl$_3$) δ ppm: 3.90 (3H, singlet); 3.89–3.82 (1H, multiplet); 3.73–3.64 (1H, multiplet); 3.53–3.32 (2H, multiplet); 2.67–2.52 (2H, multiplet); 2.33–2.25 (0.5H, multiplet); 2.07–1.96 (1.5H, multiplet); 1.87–1.74 (1H, multiplet); 1.68–1.55 (1H, multiplet); 1.43 (1.5H, doublet, J=7 Hz); 1.12 (1.5H, doublet, J=7 Hz).

9(iii)' (8aS)-8-Methyl-1,2,3,5,6,7,8,8a-octahydroindolizine-5,7-dione 4.16 g (17.0 mmol) of (8aS)-6-methoxycarbonyl-8-methyl-1,2,3,5,6,7,8,8a-octahydroindolizine-5,7-dione [obtained as described in Preparative Example 9(ii)' above] were dissolved in 40 ml of a 10% aqueous solution of acetic acid and the resulting solution was stirred at 110° C. for 30 minutes. After being cooled to room temperature, the reaction mixture was made basic using a saturated aqueous solution of sodium hydrogencarbonate and then extracted with a 4:1 by volume mixture of dichloromethane and isopropanol. The organic extract was washed with water, dried over anhydrous magnesium sulfate and then concentrated by evaporation under reduced pressure to afford 2.62 g (yield: 92%) of the title compound as a brown oil.

$^1$H-NMR spectrum (500 MHz, CDCl$_3$) δ ppm: 4.03–3.97 (0.3H, multiplet); 3.74–3.41 (2.7H, multiplet); 3.27 (1.4H, singlet); 3.26 (0.6H, singlet); 2.73–2.67 (0.3H, multiplet); 2.38–2.32 (0.7H, multiplet); 2.30–2.23 (0.7H, multiplet); 2.14–2.01 (1.3H, multiplet); 1.96–1.86 (1H, multiplet); 1.73–1.63 (1H, multiplet); 1.77 (2.1H, doublet, J=7 Hz); 1.08 (0.9H, doublet, J=7 Hz).

9(iv)' (8aS)-8-Methyl-7-(1-pyrrolidinyl)-1,2,3,5,8,8a-hexahydroindolizin-5-one 2.62 ml (31.4 mmol) of pyrrolidine were added to a solution of 2.62 g (15.7 mmol) of (8aS)-8-methyl-1,2,3,5,6,7,8,8a-octahydroindolizine-5,7-dione [obtained as described in Preparative Example 9(iii)' above] in 30 ml of ethanol and the resulting mixture was stirred for 30 minutes at 80° C. After the reaction was completed, the solvent and excess pyrrolidine were removed from the reaction mixture by evaporation under reduced pressure to afford 3.67 g (yield: quantitative) of the title compound as a brown oil.

$^1$H-NMR spectrum (500 MHz, CDCl$_3$) δ ppm: 4.52 (1H, singlet); 3.80–3.65 (2H, multiplet); 3.44–3.34 (1H, multiplet); 3.33–3.17 (4H, multiplet); 2.61–2.43 (1H, multiplet); 2.02–1.89 (6H, multiplet); 1.88–1.72 (4H, multiplet); 1.01 (3H, doublet, J=7 Hz).

9(v)' (8aS)-8-Methyl-1,2,3,5,6,7,8,8a-octahydroindolizin-7-one 1.79 g (47.1 mmol) of lithium aluminum hydride were added in several portions to a stirred, ice-cooled solution of 3.67 g (15.7 mmol) of (8aS)-8-methyl-7-(1-pyrrolidinyl)-1,2,3,5,8,8a-hexahydroindolizin-5-one [obtained as described in Preparative Example 9(iv)' above] in 50 ml of tetrahydrofuran and the resulting mixture was stirred at room temperature overnight. At the end of this time, 7.22 ml of a 1N aqueous solution of sodium hydroxide were added followed by the addition of ethanol, and any insoluble material was then filtered off. The filtrate thus obtained was concentrated by evaporation under reduced pressure, and the resulting residue was purified by chromatography on an alumina column using ethyl acetate as the eluant to afford 1.69 g (yield: 70%) of the title compound as a pale yellow oil.

$^1$H-NMR spectrum (500 MHz, CDCl$_3$) δ ppm: 3.36–3.29 (1H, multiplet); 3.18–3.13 (1H, multiplet); 2.72–2.63 (1H, multiplet); 2.40–2.30 (3H, multiplet); 2.26–2.17 (1H, multiplet); 2.05–1.91 (3H, multiplet); 1.87–1.78 (1H, multiplet); 1.64–1.55 (2H, multiplet); 1.01 (3H, doublet, J=7 Hz).

Preparative Example 10'

(2S,8aS)-2-Methoxy-1,2,3,5,6,7,8,8a-octahydroindolizin-7-one

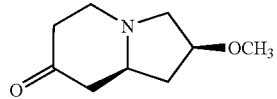

10(i)' (2S,4S)-4-Methoxy-1-methylmalonylhomoproline 7.52 ml (54 mmol) of triethylamine were added dropwise with ice-cooling and stirring to a suspension of 4.40 g (22.5 mmol) of (2S,4S)-4-methoxyhomoproline hydrochloride in 100 ml of methylene chloride, followed by the further dropwise addition with ice-cooling of 2.66 ml (24.8 mmol) of methyl malonyl chloride, and the resulting mixture was then stirred for 15 minutes at the same temperature. After the reaction mixture was stirred for a further 2 hours at room temperature, a saturated aqueous solution of sodium hydrogencarbonate was added, the pH value of the separated aqueous layer was adjusted to 2 by the addition of concentrated hydrochloric acid, and then the mixture was extracted with a 4:1 by volume mixture of methylene chloride and isopropanol. The organic extract was washed with water, dried over anhydrous magnesium sulfate and then concentrated by evaporation under reduced pressure to afford 5.83 g (yield: quantitative) of the title compound as a brown oil.

$^1$H-NMR spectrum (500 MHz, CDCl$_3$) δ ppm: 4.51–4.44 (0.8H, multiplet); 4.36–4.30 (0.2H, multiplet); 4.05–3.97 (1H, multiplet); 3.78–3.73 (2.6H, multiplet); 3.67–3.52 (2.4H, multiplet); 3.48–3.38 (2H, multiplet); 3.35–3.30 (3H, multiplet); 3.14–3.08 (0.8H, multiplet); 3.03 (0.2H, doublet of doublets, J=16 Hz, 9 Hz); 2.83–2.77 (0.2H, multiplet); 2.69 (0.8H, doublet of doublets, J=16 Hz, 9 Hz); 2.21–2.12 (3H, multiplet).

10(ii)' (2S,8aS)-2-Methoxy-6-methoxycarbonyl-1,2,3,5,6,7,8,8a-octahydroindolizine-5,7-dione 4.02 g (24.8 mmol) of carbonyldiimidazole were added to a suspension of 5.83 g (22.5 mmol) of (2S,4S)-4-methoxy-1-methylmalonylhomoproline [obtained as described in Preparative Example 10(i)' above] in 90 ml of tetrahydrofuran and the resulting mixture was then stirred for 30 minutes at room temperature. At the end of this time, 3.71 ml (24.8 mmol) of 1,8-diazabicyclo[5.4.0]undec-7-ene were added and the resulting reaction mixture was stirred for 1 hour at room temperature. The reaction mixture was then concentrated by evaporation under reduced pressure and the resulting residue was partitioned between methylene chloride and a 1N aqueous hydrochloric acid solution. The organic extract thus obtained was washed with water, dried over anhydrous magnesium sulfate and then concentrated by evaporation under reduced pressure to afford 5.21 g (yield: quantitative) of the title compound as a brown oil.

$^1$H-NMR spectrum (500 MHz, CDCl$_3$) δ ppm: 4.02–3.96 (1H, multiplet); 3.90 (3H, singlet); 3.87–3.79 (1H, multiplet); 3.78–3.72 (1H, multiplet); 3.55 (1H, doublet of doublets, J=13 Hz, 6 Hz); 3.39–3.29 (4H, multiplet); 2.74 (1H, doublet of doublets, J=17 Hz, 13 Hz); 2.59 (1H, doublet of doublets, J=13 Hz, 4 Hz); 2.49–2.42 (1H, multiplet); 1.84–1.77 (1H, multiplet).-

10(iii)(2S,8aS)-2-Methoxy-1,2,3,5,6,7,8,8a-octahydroindolizine-5,7-dione 5.21 g (22.5 mmol) of (2S,8aS)-2-methoxy-6-methoxycarbonyl-1,2,3,5,6,7,8,8a-octahydroindolizine-5,7-dione [obtained as described in Preparative Example 10(ii)' above] were dissolved in 50 ml of a 10% aqueous solution of acetic acid and the resulting mixture was stirred for 1 hour at 110° C; After it was cooled to room temperature, the reaction mixture was made alkaline by the addition of a saturated aqueous solution of sodium hydrogencarbonate, and it was then extracted with a 4:1 by volume mixture of methylene chloride and isopropanol. The organic extract was washed with water, dried over anhydrous magnesium sulfate and then concentrated by evaporation under reduced pressure to afford 3.38 g (yield: 82%) of the title compound as a pale brown oil.

¹H-NMR spectrum (500 MHz, CDCl₃) δ ppm: 4.06–3.90 (3H, multiplet); 3.52 (1H, doublet of doublets, J=12 Hz, 5 Hz); 3.37–3.28 (5H, multiplet); 2.73 (1H, doublet of doublets, J=17 Hz, 3 Hz); 2.55–2.43 (2H, multiplet); 1.95–1.87 (1H, multiplet).

10(iv)' (2S,8aS)-2-Methoxy-7-(1-pyrrolidinyl)-1,2,3,5,8,8a-hexahydroindolizin-5-one 3.07 ml (36.8 mmol) of pyrrolidine were added to a solution of 3.38 g (18.4 mmol) of (2S,8aS)-2-methoxy-1,2,3,5,6,7,8,8a-octahydroindolizine-5,7-dione [obtained as described in Preparative Example 10(iii)' above] in 34 ml of ethanol, and the resulting mixture was left to stand for 30 minutes at room temperature. At the end of this time, the solvent and any excess pyrrolidine were distilled off under reduced pressure to afford 4.26 g (yield: 98%) of the title compound as a brown oil.

¹H-NMR spectrum (500 MHz, CDCl₃) δ ppm: 4.60 (1H, singlet); 4.05–3.96 (1H, multiplet); 3.77–3.65 (2H, multiplet); 3.57 (1H, doublet of doublets, J=12 Hz, 5 Hz); 3.34 (3H, singlet); 3.33–3.16 (4H, multiplet); 2.87 (1H, doublet of doublets, J=16 Hz, 5 Hz); 2.50–2.37 (2H, multiplet); 2.02–1.83 (4H, multiplet); 1.80–1.70 (1H, multiplet).

10(v)' (2S,8aS)-2-Methoxy-1,2,3,5,6,7,8,8a-octahydroindolizin-7-one 2.10 g (55 mmol) of lithium aluminum hydride were added, with stirring and ice-cooling, to a solution of 4.26 g (18.1 mmol) of (2S,8aS)-2-methoxy-7-(1-pyrrolidinyl)-1,2,3,5,8,8a-hexahydroindolizin-5-one [obtained as described in Preparative Example 10(iv)' above] in 50 ml of tetrahydrofuran, and the resulting mixture was then stirred for a further 3 hours at room temperature. At the end of this time, 8.40 ml of a 1N aqueous solution of sodium hydroxide were carefully added to the reaction mixture, followed by the addition of ethanol, and then any insoluble materials were removed by filtration. The filtrate thus obtained was concentrated by evaporation under reduced pressure and the resulting residue was purified by chromatography on an alumina column using ethyl acetate as the eluant afford to 1.60 g (yield: 51%) of the title compound as a pale brown oil.

¹H-NMR spectrum (500 MHz, CDCl₃) δ ppm: 3.96–3.90 (1H, multiplet); 3.35–3.21 (2H, multiplet); 3.32 (3H, singlet); 2.75–2.65 (1H, multiplet); 2.55–2.17 (5H, multiplet); 1.63–1.53 (2H, multiplet); 1.32–1.20 (1H, multiplet).

Preparative Example 11'

(8aS)-2-Methylidene-1,2,3,5,6,7,8,8a-octahydroindolizin-7-one

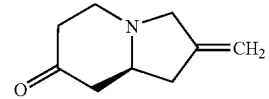

11(i)' (S)-1-Benzyloxycarbonyl-2-cyanomethyl-4-methylidenepyrrolidine

In a similar manner to the procedures described in Preparative Examples 5(i)' and 5(ii) above, reduction, methanesulfonylation and cyanogenation were conducted, using (S)-1-benzyloxycarbonyl-4-methylideneproline methyl ester [obtained as described in Preparative Example 8(i)' above], instead of methyl 1-benzyloxycarbonylindoline-2-carboxylate, to give the title compound as a colorless oil (yield: 61%).

¹H-NMR spectrum (400 MHz, CDCl₃) δ ppm: 7.42–7.30 (5H, multiplet); 5.20–5.02 (4H, multiplet); 4.36–4.27 (1H, multiplet); 4.22–3.93 (2H, multiplet); 2.92 (1H, doublet of doublets, J=16 Hz, 9 Hz); 2.80–2.38 (3H, multiplet).

11(ii)' (S)-1-(t-Butoxycarbonyl)-4-methylidenehomoproline ethyl ester 7.00 g (27.3 mmol) of (S)-1-benzyloxycarbonyl-2-cyanomethyl-4-methylidenepyrrolidine [obtained as described in Preparative Example 11(i)' above] were dissolved in 100 ml of ethanol, and the resulting solution was stirred for 1 hour at room temperature while bubbling hydrogen chloride gas through it, before raising the temperature to 80° C. and continuing to bubble hydrogen chloride gas through with stirring for a further 2 hours. The ethanol was then distilled off and the resulting residue was dissolved in 100 ml of water. The aqueous layer was washed with ethyl acetate and 50 ml of dioxane were then added to the aqueous layer. The aqueous dioxane solution thus obtained was neutralized by the addition of triethylamine. A further 3.80 ml (27.3 mmol) of triethylamine were then added, followed by the addition of 8.95 g (41.0 mmol) of di-t-butyl dicarbonate. The resulting mixture was stirred for 2 hours at room temperature, at the end of which time the reaction mixture was extracted with ethyl acetate. The organic extract was washed with water, dried over anhydrous magnesium sulfate and then concentrated by evaporation under reduced pressure. The resulting residue was purified by chromatography on a silica gel column using a 1:3 by volume mixture of ethyl acetate and hexane as the eluant to afford 3.40 g (yield: 46%) of the title compound as a colorless oil.

¹H-NMR spectrum (400 MHz, CDCl₃) δ ppm: 5.01 (2H, broad singlet); 4.43–4.21 (1H, multiplet), 4.12 (2H, doublet of doublets, J=14 Hz, 7 Hz); 4.08–3.90 (1H, multiplet); 3.84 (1H, doublet of doublets, J=15 Hz, 2 Hz); 2.88–2.55 (2H, multiplet); 2.41–2.29 (2H, multiplet); 1.49 (9H, singlet); 1.30–1.18 (3H, multiplet).

11(iii)' (S)-4-Methylidenehomoproline Trifluoroacetate 18.9 ml (18.9 mmol) of a 1N aqueous solution of sodium hydroxide were added to a solution of 3.40 g (12.6 mmol) of (S)-1-(t-butoxycarbonyl)-4-methylidenehomoproline ethyl ester [obtained as described in Preparative Example 11(ii)' above] in 35 ml of ethanol, and the resulting mixture was stirred for 2 hours at room temperature. At the end of this time, the reaction mixture was concentrated by evaporation under reduced pressure and then partitioned between ethyl acetate and water. The organic extract was washed with water, dried over anhydrous magnesium sulfate and then concentrated by evaporation under reduced pressure. The resulting residue was dissolved in 30 ml of methylene chloride and 9.7 ml (126 mmol) of trifluoroacetic acid were added to the solution thus obtained, which was then stirred for 2 hours at room temperature. At the end of this time, the reaction mixture was concentrated by evaporation under reduced pressure to afford 3.08 g (yield: 96%) of the title compound as a white powder.

$^1$H-NMR spectrum (400 MHz, CDCl$_3$) δ ppm: 5.22–5.12 (2H, multiplet); 4.03–3.88 (2H, multiplet); 3.80–3.30 (3H, multiplet); 2.91–2.79 (2H, multiplet).

11(iv)' (8aS)-2-Methylidene-1,2,3,5,6,7,8,8a-octahydroindolizin-7-one

In a similar manner to the procedures described in Preparative Examples 10(i)', 10(ii), 10(iii), 10(iv) and 10(v) above, reactions were conducted in turn, using (S)-4-methylidenehomoproline trifluoroacetate [obtained as described in Preparative Example 11(iii)' above] in place of (2S,4S)-4-methoxyhomoproline hydrochloride, to give the title compound as a yellow oil (yield: 39%).

$^1$H-NMR spectrum (400 MHz, CDCl$_3$) δ ppm: 4.97 (1H, broad singlet); 4.94 (1H, broad singlet); 3.72 (1H, doublet, J=13 Hz); 3.34–3.25 (1H, multiplet); 3.00–2.91 (1H, multiplet); 2.70–2.20 (8H, multiplet).

Preparative Example 12'

(2S,8aS)-2-Methylthio-1,2,3,5,6,7,8,8a-octahydroindolizin-7-one

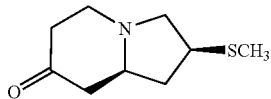

12(i)' (2S,4R)-1-Benzyloxycarbonyl-2-hydroxymethyl-4-(p-toluenesulfonyloxy)pyrrolidine a) 37.5 ml (270 mmol) of triethylamine, 49.04 g (257 mmol) of p-toluenesulfonyl chloride and 2.99 g (24.5 mmol) of 4-dimethylaminopyridine were added in turn to a solution of 77.70 g (245 mmol) of (2S,4R)-1-benzyloxycarbonyl-4-hydroxyproline methyl ester in 600 ml of methylene chloride, and the resulting mixture was then stirred at room temperature overnight. At the end of this time, the reaction mixture was concentrated by evaporation under reduced pressure and the residue was partitioned between ethyl acetate and water. The organic extract was washed with water, dried over anhydrous magnesium sulfate and then concentrated by evaporation under reduced pressure. The resulting residue was purified by chromatography on a silica gel column using a 1:1 by volume mixture of hexane and ethyl acetate as the eluant to afford 106.18 g (quantitative yield) of (2S,4R)-1-benzyloxycarbonyl-4-(p-toluenesulfonyloxy)proline methyl ester as a yellow oil.

b) In a similar manner to the procedures described in Preparative Example 5(i)' above, 106.18 g (245 mmol) of (2S,4R)-1-benzyloxycarbonyl-4-(p-toluenesulfonyloxy)proline methyl ester[prepared as described in step (a) above] were reduced to give the title compound 104.98 g as a yellow oil (yield: quantitative).

12(ii)' (2S,4S)-1-Benzyloxycarbonyl-2-(t-butyldimethylsilyloxy)methyl-4-acetylthiopyrrolidine a) 37.4 ml (269 mmol) of triethylamine, 38.76 g (257 mmol) of t-butyldimethylsilyl chloride and 2.99 g (24.5 mmol) of 4-dimethylaminopyridine were added, in turn, to a solution of 104.98 g (245 mmol) of (2S,4R)-1-benzyloxycarbonyl-2-hydroxymethyl-4-(p-toluenesulfonyloxy)pyrrolidine [obtained as described in Preparative Example 12(i)' above] in 610 ml of methylene chloride, and the resulting mixture was then stirred at room temperature overnight. At the end of this time, the reaction mixture was concentrated by evaporation under reduced pressure, and the resulting residue was partitioned between ethyl acetate and water. The organic extract was washed with water, dried over anhydrous magnesium sulfate and then concentrated by evaporation under reduced pressure. The resulting residue was purified by chromatography on a silica gel column using a 1:1 by volume mixture of hexane and ethyl acetate as the eluant to afford 119.34 g (yield: 94%) of (2S,4R)-1-benzyloxycarbonyl-2-(t-butyldimethylsilyloxy)methyl-4-(p-toluenesulfonyloxy)pyrrolidine as a yellow oil.

b) 29.34 g (257 mmol) of sodium thioacetate were added to a solution of 127.17 g (245 mmol) of (2S,4R)-1-benzyloxycarbonyl-2-(t-butyldimethylsilyloxy)methyl-4-(p-toluenesulfonyloxy)pyrrolidine [obtained as described in step (a) above] in 245 ml of dimethylformamide, and the resulting mixture was stirred for 1.5 hours at 60° C. After it was cooled to room temperature, water was added and it was extracted with ethyl acetate. The organic extract was washed with water, dried over anhydrous magnesium sulfate and then concentrated by evaporation under reduced pressure. The resulting residue was purified by chromatography on a silica gel using an 8:1 by volume mixture of hexane and ethyl acetate as the eluant to afford 91.67 g (yield: 88%) of the title compound as an orange oil.

12(iii)' (2S,4S)-1-Benzyloxycarbonyl-2-(t-butyldimethylsilyloxy)methyl-4-methylthiopyrrolidine 6.22 ml (99.9 mmol) of methyl iodide were added at room temperature to a solution of 35.26 g (83.2 mmol) of (2S,4S)-1-benzyloxycarbonyl-2-(t-butyldimethylsilyloxy)-methyl-4-acetylthiopyrrolidine [obtained as described in Preparative Example 12(ii)' above] in 166 ml methanol, 149 ml (41.6 mmol) of a 28% solution of sodium methoxide in methanol were further added at 0° C., and then the resulting mixture was stirred for 1 hour at the same temperature. At the end of this time, the reaction mixture was concentrated by evaporation under reduced pressure, and the residue was partitioned between ethyl acetate and water. The organic extract was washed with water, dried over anhydrous magnesium sulfate and then concentrated by evaporation under reduced pressure. The residue was purified by chromatography on a silica gel column using a 9:1 by volume mixture of hexane and ethyl acetate as the eluant to afford 30.74 g (yield: 93%) of the title compound as a yellow oil.

12(iv)' (2S,4S)-1-Benzyloxycarbonyl-2-hydroxymethyl-4-methylthiopyrrolidine 85.5 ml (85.5 mmol) of a 1M solution of tetrabutylammonium fluoride in tetrahydrofuran were added to a solution of 30.74 g (77.7 mmol) of (2S,4S)-1-benzyloxycarbonyl-2-(t-butyldimethylsilyloxy)methyl-4-methylthiopyrrolidine [obtained as described in Preparative Example in 12(iii)' above] in 155 ml of tetrahydrofuran, and the resulting mixture was stirred at room temperature overnight. At the end of this time, the reaction mixture was concentrated by evaporation under reduced pressure and the resulting residue was partitioned between ethyl acetate and water. The organic extract was washed with water, dried over anhydrous magnesium sulfate and then concentrated by evaporation under reduced pressure. The resulting residue was purified by chromatography on a silica gel column using a 1:1 by volume mixture of hexane and ethyl acetate as the eluant to afford 21.87 g (yield: quantitative) of the title compound as a yellow oil.

12(v)' (2S,4S)-1-Benzyloxycarbonyl-2-cyanomethyl-4-methylthiopyrrolidine

In a similar manner to the procedures described in Preparative Example 1 (i)' above, methanesulfonylation and cyanogenation were conducted, using (2S,4S)-1-benzyloxycarbonyl-2-hydroxymethyl-4-methylthiopyrrolidine [obtained as described in Preparative Example 12(iv)' above], to give the title compound (yield: 52%) as a yellow oil.

12(vi)' (2S,4S)-4-Methylthiohomoproline Hydrochloride 37 ml of a 35% aqueous hydrochloric acid solution were added to 7.43 g (25.6 mmol) of (2S,4S)-1-benzyloxycarbonyl-2-cyanomethyl-4-methylthiopyrrolidine [obtained as described in Preparative Example 12(v)' above], and the resulting solution was stirred at 80° C. overnight. At the end of this time, the reaction mixture was concentrated by evaporation under reduced pressure and the resulting residue was washed with ethyl acetate followed by the addition of ethanol. The insoluble materials were removed by filtration and the filtrate was concentrated by evaporation under reduced pressure to afford 5.39 g (yield: quantitative) of the title compound as a brown oil.

12(vii)' (2S,8aS)-2-Methylthio-1,2,3,5,6,7,8,8a-octahydroindolizin-7-one

In a similar manner to the procedures described in Preparative Examples 10(i)', 10(ii)', 10(iii)', 10(iv)' and 10(v)' above, reactions were conducted in turn, using (2S,4S)-4-methylthiohomoproline hydrochloride [obtained as described in Preparative Example 12(vi)' above] in place of (2S,4S)-4-methoxyhomoproline hydrochloride, to give (yield: 37%) of the title compound as yellow oil.

$^1$H-NMR spectrum (400 MHz, CDCl$_3$) δ ppm: 3.32–3.23 (2H, multiplet); 3.17 (1H, doublet of doublets, J=10 Hz, 2 Hz); 2.72–2.59 (2H, multiplet); 2.51–2.40 (2H, multiplet); 2.37–2.31 (4H, multiplet); 2.15 (3H, singlet); 1.52–1.45 (1H, multiplet).

Preparative Example 13'

(2S,8aS)-2-Ethylthio-1,2,3,5,6,7,8,8a-octahydroindolizin-7-one

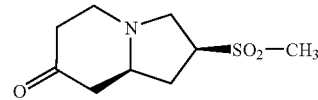

In a similar manner to the procedures described in Preparative Examples 12(iii)', 12(iv)', 12(v)', 12(vi)' and 12(vii)' above, reactions were conducted in turn, using ethyl iodide in place of methyl iodide, to give the title compound as a yellow oil (yield: 8%).

$^1$H-NMR spectrum (400 MHz, CDCl$_3$) δ ppm: 3.36–3.28 (2H, multiplet); 3.16 (1H, doublet of doublets, J=10 Hz, 2 Hz); 2.74–2.57 (4H, multiplet); 2.52–2.41 (2H, multiplet); 2.38–2.27 (4H, multiplet); 1.53–1.46 (1H, multiplet); 1.28 (3H, triplet, J=7 Hz).

Preparative Example 14'

(2S,8aS)-2-Butylthio-1,2,3,5,6,7,8,8a-octahydroindolizin-7-one

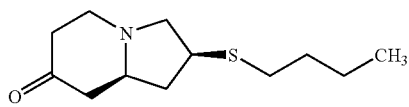

In a similar manner to the procedures described in Preparative Examples 12(iii)', 12(iv)', 12(v)', 12(vi)' and 12(vii)' above, reactions were conducted in turn, using butyl bromide in place of methyl iodide, to give the title compound as a brown oil (yield: 13%).

Preparative Example 15'

(2S,8aS)-2-Methylsulfonyl-1,2,3,5,6,7,8,8a-octahydroindolizin-7-one

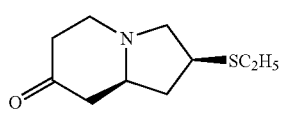

4.6 ml (9.23 mmol) of a 2N aqueous sulfuric acid solution and 3 ml of an aqueous solution of sodium tungstate dihydrate (101 mg, 0.31 mmol) were added to a solution of 1.14 g (6.15 mmol) of (2S,8aS)-2-methylthio-1,2,3,5,6,7,8,8a-octahydroindolizin-7-one [obtained as described in Preparative Example 12' above] in 15 ml of methanol, and 1.35 ml (12.3 mmol) of a 30% aqueous solution of hydrogen peroxide were then added dropwise at 55° C. to the resulting mixture. The mixture was then stirred for 1 hour at the same temperature, at the end of which time 30 ml of a saturated aqueous solution of sodium hydrogencarbonate were added to it before extracting with methylene chloride. The organic extract was washed with water, dried over anhydrous magnesium sulfate and then concentrated by evaporation under reduced pressure. The resulting residue was purified by chromatography on an alumina column using ethyl acetate as the eluant to afford 945 mg (yield: 71%) of the title compound as a yellow oil.

$^1$H-NMR spectrum (400 MHz, CDCl$_3$) δ ppm: 3.62–3.55 (2H, multiplet); 3.63–3.32 (1H, multiplet); 2.93 (3H, singlet); 2.69–2.56 (3H, multiplet); 2.52–2.43 (2H, multiplet); 2.41–2.33 (3H, multiplet); 2.02–1.94 (1H, multiplet).

Preparative Example 16'

Cyclopropanespiro-6'-[(8a'S)-1',2',3',5',6',7',8',8a'-octahydroindolizin]-7'-one

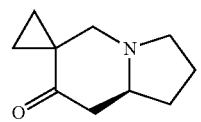

16(i)' 1-Ethoxycarbonyl-1-[(S)-2-ethoxycarbonylmethylpyrrolidin-1-yl]methylcycloprolane 4.25 g of 10% palladium on carbon were added to a solution of 12.74 g (43.7 mmol) of (S)-1-benzyloxycarbonylhomoproline ethyl ester in 200 ml of ethanol, and the resulting mixture was stirred at room temperature for 2 hours under a hydrogen atmosphere. At the end of this time, the reaction mixture was filtered and the filtrate was concentrated by evaporation under reduced pressure. The resulting residue was dissolved in 150 ml of ethanol and 6.84 g (48.1 mmol) of 1-ethoxycarbonyl-1-formylcyclopropane were added to the solution thus obtained with ice-cooling. After the resulting mixture was stirred for 1 hour at 0° C., 1.92 g (30.6 mmol) of sodium cyanotrihydroborate were added and the mixture was then stirred for 2 hours at room temperature. At the end of this time, 300 ml of water were added to the reaction mixture, and it was then extracted with ethyl acetate. The organic extract was washed with water, dried over anhydrous magnesium sulfate and then concentrated by evaporation under reduced pressure. The resulting residue was purified by chromatography on a silica gel column using a 7:3 by volume mixture of hexane and ethyl acetate as the eluant to afford 3.07 g (yield: 25%) of the title compound as a pale brown oil.

$^1$H-NMR spectrum (400 MHz, CDCl$_3$) δ ppm: 4.21–4.07 (4H, multiplet); 3.24 (1H, doublet, J=13 Hz); 3.22–3.12 (1H, multiplet); 2.82–2.68 (2H, multiplet); 2.28–2.13 (3H, multiplet); 2.03–1.90 (1H, multiplet); 1.82–1.64 (2H, multiplet); 1.56–1.45 (1H, multiplet); 1.36–1.21 (7H, multiplet); 1.12–1.03 (1H, multiplet); 0.84–0.70 (2H, multiplet).

16(ii)' Cyclopropanespiro-6'-[(8a'S)-8'-ethoxycarbonyl-1',2', 3',5',6',7', 8',8a'-octahydroindolizin]-7'-one 518 mg (11.9 mmol) of 55% sodium hydride were suspended in 20 ml of toluene, 3 drops of methanol were added using a Pasteur pipette and the resulting mixture was heated to 130° C. 3.06 g (10.8 mmol) of 1-ethoxycarbonyl-1-[(S)-2-ethoxycarbonylmethylpyrrolidin-1-yl]methylcyclopropane [obtained as described in Preparative Example 16(i)' above] were then added and the resulting mixture was heated for 10 minutes under reflux. After the reaction mixture was cooled to 0° C., it was partitioned between a saturated aqueous solution of sodium chloride and ethyl acetate. The organic extract was washed with water dried over anhydrous magnesium sulfate and then concentrated by evaporation under reduced pressure. The resulting residue was purified by chromatography on a silica gel column using a 9:1 by volume mixture of ethyl acetate and methanol as the eluant to afford 2.02 g (yield: 79%) of the title compound as a colorless oil.

$^1$H-NMR spectrum (400 MHz, CDCl$_3$) δ ppm: 4.3–14.15 (2H, multiplet); 3.32 (1H, doublet, J=11 Hz); 3.15 (1H, triplet of doublets, J=9 Hz, 3 Hz); 2.92–2.82 (2H, multiplet); 2.67 (1H, doublet, J=11 Hz); 2.29 (1H, quartet, J=9 Hz); 2.12–1.80 (3H, multiplet); 1.71–1.55 (2H, multiplet); 1.29 (3H, triplet, J=7 Hz); 1.09–1.02 (1H, multiplet); 0.99–0.92 (1H, multiplet); 0.69–0.62 (1H, multiplet).

16(iii)' Cyclopropanespiro-6'-[(8a'S)-1',2',3',5',6',7',8',8a'-octahydroindolizin]-7'-one 1 ml of a 1N aqueous solution of sodium hydroxide was added to a solution of 50 mg (0.21 mmol) of cyclopropanespiro-6'-[(8a'S)-8'-ethoxycarbonyl-1',2',3',5',6',7',8',8a'-octahydroindolizin]-7'-one [obtained as described in Preparative Example 16(ii)' above] in 1 ml of ethanol, and the mixture thus obtained was heated for 1 hour under reflux. At the end of this time, the reaction mixture was concentrated by evaporation under reduced pressure, and the resulting residue was purified by chromatography on an alumina column using ethyl acetate as the eluant to afford 10 mg (yield: 29%) of the title compound as a colorless oil.

$^1$H-NMR spectrum (400 MHz, CDCl$_3$) δ ppm: 3.17 (1H, triplet of doublets, J=9 Hz, 3 Hz); 2.76 (1H, doublet, J=12 Hz); 2.69 (1H, doublet, J=12 Hz); 2.67 (1H, doublet of doublets, J=16 Hz, 3 Hz); 2.56–2.44 (1H, multiplet); 2.34 (1H, doublet of doublets, J=16 Hz, 12 Hz); 2.30–2.18 (1H, multiplet); 2.12–1.93 (2H, multiplet); 1.90–1.78 (1H, multiplet); 1.64–1.50 (2H, multiplet); 1.08–1.00 (1H, multiplet); 0.96–0.88 (1H, multiplet); 0.67–0.58 (1H, multiplet).

Preparative Example 17'

(8aS)-2,2-Dimethyl-1,2,3,5,6,7,8,8a-octahydroindolizin-7-one

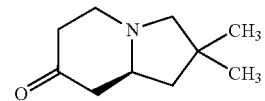

17(i)' (S)-1-Benzyloxycarbonyl-4,4-dimethyl-2-hydroxymethylpyrrolidine

A solution of 32.35 g (226 mmol) of (S)4,4-dimethyl-2-hydroxymethyl-5-oxopyrrolidine in 300 ml of tetrahydrofuran was added dropwise over a period of 20 minutes with ice-cooling and stirring to keep the temperature between 8 and 17° C., to a suspension of 25.72 g (678 mmol) of lithium aluminum hydride in 500 ml of tetrahydrofuran. The resulting mixture was then heated under reflux for 7 hours, at the end of which time it was cooled to 0° C. and 103 ml of a 4% aqueous solution of sodium hydroxide were added carefully thereto. Any insoluble material was removed by filtration and the filtrate was concentrated by evaporation under reduced pressure. The residue thus obtained was dissolved in 500 ml of methylene chloride and then 40.94 ml (294 mmol) of triethylamine were added, followed by the further addition of 38.71 ml (271 mmol) of benzyloxycarbonyl chloride with ice-cooling and stirring. The resulting mixture was stirred for 1 hour at the same temperature and then stirred for a further 1 hour at room temperature. At the end of this time, a saturated aqueous solution of sodium hydrogencarbonate was added to the reaction mixture, and it was then extracted with methylene chloride. The organic extract was washed with water, dried over anhydrous magnesium sulfate and then concentrated by evaporation under reduced pressure. The resulting residue was purified by chromatography on a silica gel column using a 1:1 by volume mixture of hexane and ethyl acetate as the eluant to afford 43.97 g (yield: 74%) of the title compound as a colorless oil.

$^1$H-NMR spectrum (400 MHz, CDCl$_3$) δ ppm: 7.42–7.29 (5H, multiplet); 5.20–5.10 (2H, multiplet); 4.89 (1H, doublet of doublets, J=9 Hz, 3 Hz); 4.14–4.05 (1H, multiplet); 3.73–3.59 (2H, multiplet); 3.41 (1H, doublet, J=11 Hz); 3.06 (1H, doublet, J=11 Hz); 1.80 (1H, doublet of double doublets, J=13 Hz, 7 Hz, 1 Hz); 1.33 (1H, doublet of doublets, J=12 Hz, 10 Hz); 1.08 (3H, singlet); 1.02 (3H, singlet).

17(ii)' (8aS)-2,2-Dimethyl-1,2,3,5,6,7,8,8a-octahydroindolizin-7-one

In a similar manner to the procedures described in Preparative Examples 12(v)', 12(vi)' and 12(vii)' above, reactions were conducted in turn, using (S)-1-benzyloxycarbonyl-4,4-dimethyl-2-hydroxymethylpyrrolidine [obtained as described in Preparative Example 17(i)' above] instead of (2S,4S)-1-benzyloxycarbonyl-2-hydroxymethyl-4-methylthiopyrrolidine, to give the title compound as a brown oil (yield: 36%).

$^1$H-NMR spectrum (400 MHz, CDCl$_3$) δ ppm: 3.26–3.19 (1H, multiplet); 2.89 (1H, doublet, J=9 Hz); 2.68–2.57 (1H, multiplet); 2.49–2.25 (5H, multiplet); 2.07 (1H, doublet, J=9 Hz); 1.73 (1H, doublet of doublets, J=12 Hz, 6 Hz); 1.40 (1H, doublet of doublets, J=12 Hz, 10 Hz); 1.20 (3H, singlet); 1.07 (3H, singlet).

Preparative Example 18'

Cyclopentanespiro-2'-(1',2',3',5',6',7',8',8a'-octahydroindolizin)-7'-one

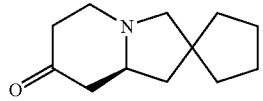

18(i)' 1-Cyano-1-formylmethylcyclopentane Diethyl acetal 100 ml (157 mmol) of a 1.57M solution of n-butyllithium in hexane were added dropwise with ice-cooling to a solution of 22.00 ml (157 mmol) of diisopropylamine in 500 ml of tetrahydrofuran, and the resulting mixture was then stirred for 30 minutes at the same temperature. At the end of this time, 14.89 ml (143 mmol) of cyclopentanecarbonitrile were added dropwise to the reaction mixture on a dry ice-acetone bath. The resulting mixture was stirred for 15 minutes at −78° C., at the end of which time a solution of 27.31 ml (157 mmol) of hexamethylphosphoramide in 50 ml of tetrahydrofuran were added dropwise. After stirring the resulting mixture for 30 minutes at −78° C., 23.62 ml (157 mmol) of bromoacetaldehyde diethyl acetal were added dropwise and the resulting mixture was then stirred for 2 hours at −78° C. and for a further 20 hours at room temperature. At the end of this time, ice-water was added to the reaction mixture, which was then extracted with ethyl acetate. The organic extract was washed with water, dried over anhydrous magnesium sulfate and then concentrated by evaporation under reduced pressure. The resulting residue was purified by chromatography on a silica gel column using a 19:1 by volume mixture of hexane and ethyl acetate as the eluant to afford 23.92 g (yield: 79%) of the title compound as a colorless oil.

$^1$H-NMR spectrum (400 MHz CDCl$_3$) δ ppm: 4.75 (1H, triplet, J=5 Hz); 3.76–3.66 (2H, multiplet); 3.61–3.52 (2H, multiplet); 2.22–2.13 (2H, multiplet); 1.93 (2H, doublet, J=5 Hz); 1.91–1.63 (6H, multiplet); 1.23 (6H, triplet, J=7 Hz).

18(ii)' 1-Aminomethyl-1-formylmethylcyclopentane diethyl acetal 8.66 ml (162 mmol) of concentrated sulfuric acid were added dropwise over a period of 10 minutes with ice-cooling and stirring to a suspension of 12.33 g (325 mmol) of lithium aluminum hydride in 460 ml of tetrahydrofuran. The resulting mixture was stirred for 1 hour at 0° C., at the end of which time 22.88 g (108 mmol) of 1-cyano-1-formylmethylcyclopentane diethylacetal [obtained as described in Preparative Example 18(i)' above] were added to the reaction mixture in small portions before stirring the reaction mixture for 2 hours at room temperature. At the end of this time, the reaction mixture was cooled to 0° C. again and 49.3 ml of a 4% aqueous solution of sodium hydroxide were added carefully. The insoluble materials were removed from the mixture by filtration and the filtrate was concentrated by evaporation under reduced pressure to afford 18.69 g (yield: 80%) of the title compound as a pale yellow oil.

$^1$H-NMR spectrum (400 MHz. CDCl$_3$) δ ppm: 4.51 (1H, triplet J=5 Hz); 3.70–3.60 (2H, multiplet); 3.54–3.41 (2H, multiplet); 2.50 (2H, singlet); 1.70 (2H, doublet, J=5 Hz); 1.69–1.34 (10H, multiplet); 1.21 (6H, triplet, J=7 Hz).

18(iii)' Cyclopentanespiro-2'-(1',2',3',5',6',7',8',8a'-octahydroindolizin)-7'-one 8.67 ml (104 mmol) of methylvinylketone were added with ice-cooling and stirring to a solution of 18.68 g (86.7 mmol) of 1-aminomethyl-1-formylmethylcyclopentane diethyl acetal [obtained as described in Preparative Example 18(ii)' above] in 400 ml of diethyl ether, and then the resulting mixture was stirred for 24 hours at room temperature. At the end of this time, the reaction mixture was extracted with 200 ml of a 3N aqueous hydrochloric acid solution and the aqueous layer was stirred for 3 hours at 100° C. The reaction mixture was then cooled to room temperature, made alkaline by the addition of sodium hydrogencarbonate and then extracted with ethyl acetate. The organic extract was washed with water, dried over anhydrous magnesium sulfate and then concentrated by evaporation under reduced pressure. The resulting residue was purified by chromatography on an alumina column using a 9:1 by volume mixture of hexane and ethyl acetate as the eluant to afford 5.75 g (yield: 34%) of the title compound as a colorless oil.

$^1$H-NMR spectrum (400 MHz, CDCl$_3$) δ ppm: 3.27–3.21 (1H, multiplet); 3.03 (1H, doublet, J=9 Hz); 2.69–2.59 (1H, multiplet); 2.47 (1H, doublet of triplets, J=13 Hz, 2 Hz); 2.42–2.26 (4H, multiplet); 2.19 (1H, doublet, J=9 Hz); 1.86 (1H, doublet of doublets, J=12 Hz, 5 Hz); 1.80–1.46 (9H, multiplet).

Preparative Example 19'

(8aS)-2-Methyl-3,5,6,7,8,8a-hexahydroindolizin-7-one

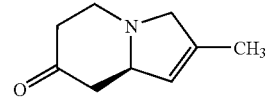

19(i)' (S)-2-Carboxymethyl-4-methyl-3-pyrroline hydrochloride 150 ml of concentrated hydrochloric acid were added to 24.00 g (93.6 mmol) of (S)-1-benzyloxycarbonyl-2-cyanomethyl-4-methylidenepyrrolidine [obtained as described in Preparative Example 11(i)' above], and the solution was stirred at 80° C. overnight. At the end of this time, the reaction solution was concentrated by evaporation under reduced pressure and ethyl acetate was added to the residue thus obtained. The aqueous layer was then concentrated by evaporation under reduced pressure to afford 16.60 g (yield: quantitative) of the title compound as a white powder.

$^1$H-NMR spectrum (400 MHz, DMSO-d$_6$) δ ppm: 5.47–5.40 (1H, multiplet); 4.60–4.47 (1H, multiplet); 4.15–3.75 (2H, multiplet); 3.60–3.35 (2H, multiplet); 1.74 (3H, multiplet).

19(ii)' (8aS)-2-Methyl-3,5,6,7,8,8a-hexahydroindolizin-7-one

In a similar manner to the procedures described in Preparative Examples 10(i)', 10(ii)', 10(iii)', 10(iv)' and 10(v)' above, reactions were conducted in turn, using (S)-2-carboxymethyl-4-methyl-3-pyrroline hydrochloride [obtained as described in Prepararive Example 19(i)' above] in place of (2S,4S)-4-methoxyhomoproline hydrochloride, to give the title compound as an orange oil (yield: 10%).

¹H-NMR spectrum (400 MHz, CDCl₃) δ ppm: 5.4–45.38 (1H, multiplet); 3.75–3.67 (1H, multiplet); 3.58 (1H, doublet of doublets. J=13 Hz, 3 Hz); 3.48–3.39 (1H, multiplet); 3.30–3.21 (1H, multiplet); 3.01–2.92 (1H, multiplet); 2.63–2.49 (2H, multiplet); 2.45–2.35 (2H, multiplet); 1.79 (3H, singlet).

Preparative Example 20'

(2R,8aS)-2-Ethoxy-1,2,3,5,6,7,8,8a-octahydroindolizin-7one

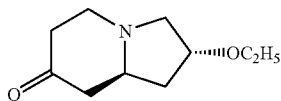

In a similar manner to the procedures described in Preparative Examples 1(i)' 1(ii)' and 1(iii)' above, reactions were conducted in turn, using (2S,4R)-1-benzyloxycarbonyl-4-ethoxyproline instead of (2S,4R)-1-benzyloxycarbonyl-4-methoxyproline, to give the title compound as an orange oil (yield: 5%).

¹H-NMR spectrum (400 MHz, CDCl₃) δ ppm: 4.21–4.13 (1H, multiplet); 3.60–3.38 (3H, multiplet); 3.28 (1H, doublet of doublets, J=11 Hz, 7 Hz); 2.66–2.20 (7H, multiplet); 1.99 (1H, doublet of doublets, J=13 Hz, 6 Hz); 1.82–1.70 (1H, multiplet); 1.20 (3H, triplet, J=7 Hz).

Preparative Example 21'

(8aS)-2,2-Propylenedioxy-1,2,3,5,6,7,8,8a-octahydroindolizin-7-one

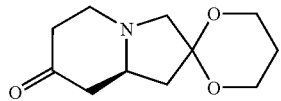

In a similar manner to the procedures described iii Preparative Examples 7(i)', 7(ii)' and 7(iii)' above, reactions were conducted in turn, using (S)-1-benzyloxycarbonyl-4,4-propylenedioxyproline methyl ester in place of (S)-1-benzyloxycarbonyl-4,4-ethylenedioxyproline methyl ester to give the title compound as a pale yellow powder (yield: 16%)

¹H-NMR spectrum (400 MHz, CDCl₃) δ ppm: 4.00–3.82 (4H, multiplet); 3.51 (1H, doublet, J=10 Hz); 3.33–3.25 (1H, multiplet); 2.74–2.62 (1H, multiplet); 2.57–2.48 (2H, multiplet); 2.43–2.31 (5H, multiplet); 1.86–1.62 (2H, multiplet); 1.82 (1H, doublet of doublets, J=13 Hz, 10 Hz).

Preparative Example 22'

(8aS)-2,2-(2',2'-Dimethylpropylenedioxy)-1,2,3,5,6,7,8,8a-octahydroindolizin-7-one

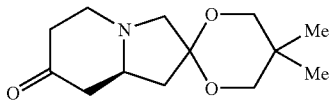

In a similar manner to the procedures described in Preparative Examples 7(i)', 7(ii)' and 7(iii)' above, reactions were conducted in turn, using (S)-1-benzyloxycarbonyl-4,4-(2',2'-dimethylpropylenedioxy)proline methyl ester in place of (S)-1-benzyloxycarbonyl-4,4-ethylenedioxyproline methyl ester, to give the title compound as a pale yellow powder (yield: 19%).

¹H-NMR spectrum (400 MHz, CDCl₃) δ ppm: 3.57–3.41 (5H, multiplet); 3.31–3.24 (1H, multiplet); 2.73–2.62 (1H, multiplet); 2.57–2.46 (2H, multiplet); 2.42–2.31 (5H, multiplet); 1.82 (1H, doublet of doublets, J=13 Hz, 10 Hz); 1.00 (3H, singlet); 0.96 (3H, singlet).

Preparative Example 23'

(2S,8aS)-2-Phenoxy-1,2,3,5,6,7,8,8a-octahydroindolizin-7-one

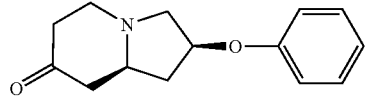

23(i)' (2S,4S)-]-Benzyloxycarbonyl-4-phenoxyhomoproline benzyl ester 6.53 ml (74.3 mmol) of phenol and 19.48 g (74.3 mmol) of triphenylphosphine were added to a solution of 18.29 g (49.5 mmol) of (2S,4R)-1-benzyloxycarbonyl-4-hydroxyhomoproline benzyl ester in 300 ml of tetrahydrofuran, and the resulting mixture was cooled to 0° C. 11.69 ml (74.3 mmol) of diethylazodicarboxylate (DEAD) were added dropwise to the mixture at the same temperaure, and then the resulting mixture was stirred at room temperature overnight. At the end of this time, the reaction mixture was concentrated by evaporation under reduced pressure, diethyl ether was added to the residue, and then the insoluble materials were removed by filtration. The resulting filtrate was washed with a saturated aqueous solution of sodium hydrogencarbonate and with water in turn, dried over anhydrous magnesium sulfate and then concentrated by evaporation under reduced pressure. The resulting residue was purified by chromatography on a silica gel column using a 3:1 by volume mixture of hexane and ethyl acetate as the elaunt to afford 11.14 g (yield: 51%) of the title compound as a colorless oil.

¹H-NMR spectrum (400 MHz. CDCl₃) δ ppm: 7.40–7.21 (12H, multiplet); 6.97 (1H, triplet, J=7 Hz); 6.84 (2H, doublet, J=8 Hz); 5.21–4.99 (4H, multiplet); 4.93–4.83 (1H, multiplet); 4.48–4.38 (1H, multiplet); 3.84–3.68 (2H, multiplet); 3.24–3.15 (0.6H, multiplet); 3.04–2.95 (0.4H, multiplet); 2.92–2.76 (1H, multiplet); 2.39–2.30 (1H, multiplet); 2.26–2.17 (1H, multiplet).

23(ii)' (2S,4S)-4-Phenoxyhomoproline Hydrochloride 2.22 g of 20% palladium hydroxide on carbon were added to a solution of 11.09 g (24.9 mmol) of (2S,4S)-1-benzyloxycarbonyl-4-phenoxyhomoproline benzyl ester [obtained as described in Preparative Example 23(i)' above] in 220 ml of tetrahydrofuran, and then the mixture was stirred for 6 hours at room temperature under a hydrogen atmosphere. At the end of this time, 6.85 ml (27.4 mmol) of a 4N solution of hydrogen chloride in dioxane were added to the reaction mixture, and the mixture was filtered. The filtrate thus obtained was concentrated by evaporation under reduced pressure to afford 6.39 g (yield: quantitative) of the title compound as a pale brown powder.

¹H-NMR spectrum (400 MHz, DMSO-d₆) δ ppm: 12.70 (1H, broad singlet); 7.33 (2H, doublet of doublets, J=8 Hz, 7 Hz); 6.99 (1H, triplet, J=7 Hz); 6.96 (2H, doublet, J=8 Hz); 5.16–5.09 (1H, multiplet); 3.98–3.87 (1H, multiplet); 3.50 (1H, doublet of doublets, J=13 Hz, 5 Hz); 3.42–3.28 (2H, multiplet); 2.89 (1H, doublet of doublets, J=18 Hz, 8 Hz); 2.80 (1H, doublet of doublets, J=18 Hz, 6 Hz); 2.64–2.54 (1H, multiplet); 1.91–1.81 (1H, multiplet).

23(iii) (2S,8aS)-2-Phenoxy-1,2,3,5,6,7,8,8a-octahydroindolizin-7-one

In a similar manner to the procedures described in Preparative Examples 10(i)', 10(ii)', 10(iii)', 10(iv)' and 10(v)' above, reactions were conducted in turn, using (2S,4S)-4-phenoxyhomoproline hydrochloride [obtained as described in Preparative Example 23(ii)' above] in place of (2S,4S)-4-methoxyhomoproline hydrochloride, to give the title compound as a pale brown powder (yield: 25%).

¹H-NMR spectrum (400 MHz, CDCl₃) δ ppm: 7.28 (2H, doublet of doublets, J=8 Hz, 7 Hz); 6.95 (1H, triplet, J=7 Hz); 6.87 (2H, doublet, J=8 Hz); 4.90–4.82 (1H, multiplet); 3.40 (1H, doublet, J=11 Hz); 3.39–3.32 (1H, multiplet); 2.80–2.68 (1H, multiplet); 2.67–2.27 (7H, multiplet); 1.86–1.74 (1H, multiplet).

Preparative Example 24'

(8a-2-Ethylidene-1,2,3,5,6,7,8,8a-octahydroindolizin-7-one

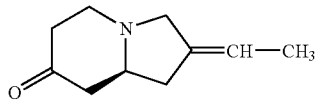

In a similar manner to the procedures described in Preparative Example 8(i)' above, reactions were conducted in turn using ethyltriphenylphosphoniun bromide in place of methyltriphenylphosphonium bromide, and then the resulting (S)-1-benzyloxycarbonyl-4-ethylideneproline methyl ester was subjected to reactions in turn in a similar manner to the procedures described in Preparative Examples 11(i)', 11(ii)', 11(iii)' and 11(iv)' above to give the title compound as a brown oil (yield: 9%).

¹H-NMR spectrum (400 MHz, CDCl₃) δ ppm: 5.45–5.30 (1H, multiplet); 3.78 (0.5H, doublet, J=3 Hz); 3.64 (0.5H, doublet, J=3 Hz); 3.37–3.28 (1H, multiplet); 2.94–2.85 (1H, multiplet); 2.69–2.09 (8H, multiplet); 1.68–1.61 (3H, multiplet).

Preparative Example 25'

(8aS)-2-Propylidene-1,2,3,5,6,7,8,8a-octahydroindolizin-7-one

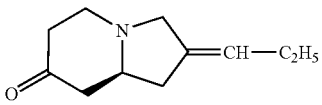

In a similar manner to the procedures described in Preparative Example 8(i) above, reactions were conducted in turn, using propyltriphenylphosphonium bromide in place of methyltriphenylphosphonium bromide, and then the resulting (S)-1-benzyloxycarbonyl-4-propylideneproline methyl ester was subjected to reactions in turn in a similar manner to the procedures described in Preparative Examples 11(i)', 11(ii)', 11(iii)' and 11(iv)' above to give the title compound as a brown oil (yield: 10%).

¹H-NMR spectrum (400 MHz, CDCl₃) δ ppm: 5.37–5.25 (1H, multiplet); 3.78 (0.5H, doublet, J=3 Hz); 3.62 (0.5H, doublet, J=3 Hz); 3.36–3.28 (1H, multiplet); 2.94–2.85 (1H, multiplet); 2.69–2.10 (8H, multiplet); 2.04–1.91 (2H, multiplet); 1.01–0.92 (3H, multiplet).

Preparative Example 26'

(8aS)-2-Benzylidene-1,2,3,5,6,7,8,8a-octahydroindolizin-7-one

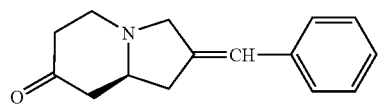

In a similar manner to the procedures described in Preparative Example 8(i)' above, reactions were conducted in turn, using benzyltriphenylphosphonium bromide in place of methyltriphenylphosphonium bromide, and then the resulting (S)-1-benzyloxycarbonyl-4-benzylideneproline methyl ester was subjected to reactions in turn in a similar manner to the procedures described in Preparative Examples 11(i)', 11(ii)', 11(iii)' and 11(iv)' above to give the title compound as a brown oil (yield: 0.4%).

¹H-NMR spectrum (400 MHz, CDCl₃) δ ppm: 7.41–7.26 (4H, multiplet); 7.21–7.15 (1H, multiplet); 6.39–6.32 (1H, multiplet); 4.70–4.02 (1H, multiplet); 3.89–3.72 (1H, multiplet); 3.40–3.35 (1H, multiplet); 3.26–3.10 (1H, multiplet); 2.98–2.78 (1H, multiplet); 2.75–2.38 (5H, multiplet); 2.11–1.84 (1H, multiplet).

Preparative Example 27'

(2S,8aS)-2-Ethyl-1,2,3,5,6,7,8,8a-octahydroindolizin-7-one

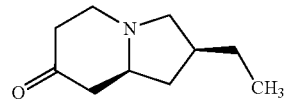

In a similar manner to the procedures described in. Preparative Examples 8(ii)', 8(iii)', 8(iv)', 8(v)' and 8(vi)' above, reactions were conducted in turn, using (S)-1-benzyloxycarbonyl-4-ethylideneproline methyl ester [prepared as described in Preparative Example 24' above] instead of (S)-1-benzyloxycarbonyl-4-methylideneproline methyl ester, to give the title compound as a brown oil (yield: 10%).

¹H-NMR spectrum (400 MHz, CDCl₃) δ ppm: 3.28–3.23 (1H, multiplet); 2.87 (1H, doublet, J=9 Hz); 2.67–2.58 (1H, multiplet); 2.56–2.40 (2H, multiplet); 2.32–2.26 (4H, multiplet); 2.13–2.05 (2H, multiplet); 1.54–1.45 (2H, multiplet); 1.18 (1H, doublet, J=6 Hz); 0.90 (3H, triplet, J=7 Hz).

Preparative Example 28'

(2S,8aS)-2-Propyl-1,2,3,5,6,7,8,8a-octahydroindolizin-7-one

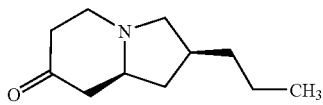

In a similar manner to the procedures described in Preparative Examples 8(ii)', 8(iii)', 8(iv)', 8(v)' and 8(vi)' above, reactions were conducted in turn, using (S)-1-benzyloxycarbonyl-4-propylideneproline methyl ester [prepared as described in Preparative Example 25' above] instead of (S)-1-benzyloxycarbonyl-4methylideneproline methyl ester, to give the title compound as a brown oil (yield: 24%).

$^1$H-NMR spectrum (400 MHz, CDCl$_3$) δ ppm: 3.29–3.21 (1H, multiplet); 2.87–2.73 (1H, multiplet); 2.67–2.57 (1H, multiplet); 2.53–2.41 (1H, multiplet); 2.40–2.24 (3H, multiplet); 2.22–2.09 (2H, multiplet); 1.99–1.85 (1H, multiplet); 1.83–1.56 (1H, multiplet); 1.53–1.39 (2H, multiplet); 1.37–1.22 (2H, multiplet); 1.21–1.14 (1H, multiplet); 0.93–0.86 (3H, multiplet).

Preparative Example 29'

(2S,8aS)-2-Benzyl-1,2,3,5,6,7,8,8a-octahydroindolizin-7-one

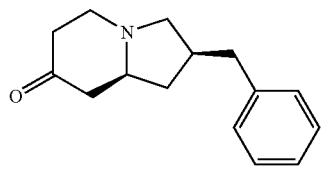

In a similar manner to the procedures described in Preparative Examples 8(ii)', 8(iii)', 8(iv)', 8(v)' and 8(vi)' above, reactions were conducted in turn, using (S)-1-benzyloxycarbonyl-4-benzylideneproline methyl ester [prepared as described in Preparative Example 26' above] instead of (S)-1-benzyloxycarbonyl-4-methylideneproline methyl ester, to give the title compound as a brown oil (yield: 4%).

$^1$H-NMR spectrum (400 MHz, CDCl$_3$) δ ppm: 7.38–7.28 (2H, multiplet); 7.27–7.11 (3H, multiplet); 3.36–3.23 (1H, multiplet); 3.04–2.88 (1H, multiplet), 2.86–2.21 (8H, multiplet); 2.11–2.05 (1H, multiplet); 2.02–1.72 (2H, multiplet); 1.34–1.25 (2H, multiplet).

Formulation Examples

The formulations containing a compound represented by the general formula (I)' defined above, or a pharmaceutically acceptable salt, ester or other derivative thereof of the present invention can be prepared by methods such as the followings.

Formulation Example 1'

Powder 5 g of the compound of Example 2, 895 g of lactose and 100 g of corn starch are mixed in a blender to provide the desired powder.

Formulation Example 2'

Granules 5 g of the compound of Example 4, 865 g of lactose and 100 g of low-substituted hydroxypropylcellulose are mixed, 300 g of a 10% aqueous hydroxypropyl cellulose solution are added to the resulting mixture, and this is then kneaded. The product thus obtained is then granulated using an extrusion granulating machine and dried to provide the desired granules.

Formulation Example 3'

Capsules 5 g of the compound of Example 6, 115 g of lactose, 58 g of corn starch and 2 g of magnesium stearate are mixed using a V-shaped mixer, No. 3 capsules are chosen and then each of said No. 3 capsules is filled with 180 mg of the resulting mixture to provide the desired capsules.

Formulation Example 4'

Tablets 5 g of the compound of Example 8, 90 g of lactose, 34 g of corn starch, 20 g of crystalline cellulose and 1 g of magnesium stearate are mixed in a blender, and the resulting mixture is then formed into tablets with a tablet machine to provide the desired tablets.

Test Examples

Test Example 1'

Inhibition of the Production of the Cytokines IL-1β and TNFα In Vitro in Human Whole Blood This test was performed according to the method of Hartman, et al. [D. A. Hartman, S. J. Ochalski and R. P. Carlson; The effects of anti-inflammatory and antiallergic drugs on cytokine release after stimulation of human whole blood by lipopolysaccharide and zymosan A: Inflamm. Res., 44, 269 (1995)].

Peripheral blood samples were collected in the presence of heparin from healthy adult volunteers. 1000 µl of whole blood were added to an Eppendorf tube to which 2 µl of a dimethyl sulfoxide solution of the test compound had been added in advance, after which 10 µl of lipopolysaccharide (E. coli O26: B6 origin, Difco) were added as a stimulant (final concentration of said lipopolysaccharide: 10 µg/ml). This was mixed well and then incubated for 6 hours at 37° C. in the presence of 5% CO$_2$. At the end of the incubation, the mixture was cooled to 4° C. to stop the reaction, followed immediately by centrifuging for 5 minutes at 14,000 rpm to separate and collect the supernatant plasma The IL-1β and TNFα produced and released into the plasma were measured using a commercially available enzyme immunoassay (ELISA) kits [Cayman (IL-1β) and Genzyme (TNFα)]. The procedure was also repeated in the absence of test compound. The inhibitory effect [IC$_{50}$ (µM)] on the production of IL-1β and TNFα was determined by the method of least squares from the amounts of the cytokines produced in the presence and absence of the test compound. The results for the inhibitory effect on TNFα production are as shown in Table 7' below.

TABLE 7'

Inhibitory Effect on TNFα Production (in vitro)

| Test compound | IC$_{50}$ [μM] |
|---|---|
| Compound of Example 2' | 0.062 |
| Compound of Example 4' | 0.054 |
| Compound of Example 6' | 0.027 |
| Compound of Example 12' | 0.0025 |
| Compound of Example 14' | 0.0040 |
| Compound of Example 16' | 0.0022 |
| Compound of Example 19' | 0.044 |
| Compound of Example 21' | 0.046 |
| Compound of Example 23' | 0.0037 |
| Compound of Example 27' | 0.0038 |
| Compound of Example 29' | 0.0036 |
| Compound of Example 31' | 0.0024 |
| Compound of Example 32' | 0.0045 |
| Compound of Example 34' | 0.046 |
| Compound of Example 36' | 0.018 |
| Compound of Example 37' | 0.010 |
| Compound of Example 43' | 0.006 |
| Compound of Example 47' | 0.010 |
| Compound A | 1.90 |
| Compound B | 1.73 |

In Table 7 above. Compounds A and B are the following prior art compounds:

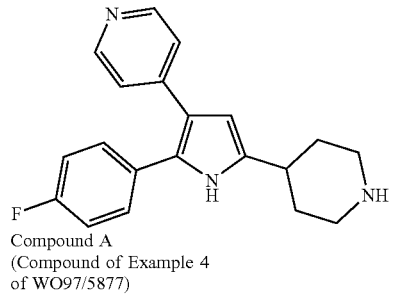

Compound A
(Compound of Example 4 of WO97/5877)

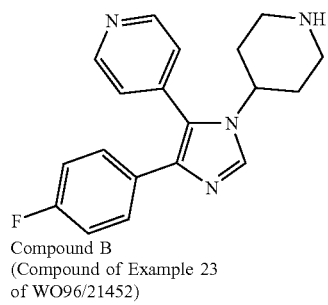

Compound B
(Compound of Example 23 of WO96/21452)

The results for the inhibitory effect on IL-1β production are as shown in Table 8' below.

TABLE 8

Inhibitory Effect on IL-1β Production (in vitro)

| Test compound | IC$_{50}$ [μM] |
|---|---|
| Compound of Example 2' | 0.031 |
| Compound of Example 4' | 0.041 |
| Compound of Example 12' | 0.0026 |
| Compound of Example 14' | 0.0092 |
| Compound of Example 16' | 0.0017 |
| Compound of Example 19' | 0.0083 |
| Compound of Example 21' | 0.018 |
| Compound of Example 23' | 0.0038 |
| Compound of Example 27' | 0.0014 |
| Compound of Example 29' | 0.0010 |
| Compound of Example 31' | 0.0046 |

TABLE 8-continued

Inhibitory Effect on IL-1β Production (in vitro)

| Test compound | IC$_{50}$ [μM] |
|---|---|
| Compound of Example 32' | 0.0027 |
| Compound of Example 34' | 0.049 |
| Compound of Example 36' | 0.026 |
| Compound of Example 37' | 0.058 |
| Compound of Example 43' | 0.008 |
| Compound of Example 47' | 0.033 |

As shown in Tables 7' and 8' above, in this test, the above-tested compounds of the present invention showed excellent inhibitory activity against the production of TNFα and IL-1β In vitro.

Test Example 2'

Inhibition of the Production of TNFα in Vivo

This test was performed according to the method of Ochalski, et al. [S. J. Ochalski, D. A. Hartman, M. T. Belfast, T. L. Walter, K. B. Glaser and R. P. Carlson; Inhibition of endotoxin-induced hypothermia and serum TNF-α levels in CD-1 mice by various pharmacological agents: Agents Actions 39, C52–C54 (1993)].

The production of TNFα was induced in mice by the intravenous injection of lipopolysaccharide (*E. coli* O26: B6 origin, Difco) which was prepared to a concentration of 0.045 mg/ml using physiological saline. The saline preparation of lipopolysaccharide was administered at the rate of 10 ml/1 kg of body weight into the caudal vein of Balb/c mice (males, age 5–7 weeks, body weight: approx. 22 g, Japan Charles River) which had been fasted overnight starting on the day before the experiment. One hour after administration, the mice were laparotomized under ether anaesthesia and blood was collected from the abdominal vena cava. Blood collection was performed using a 1 ml volume disposable syringe equipped with a 23 G needle which had been moistened with heparin on the inside wall. Following blood collection, the blood was immediately transferred to a 1.5 ml volume Eppendorf tube and centrifuged at 4° C. and 14,000 rpm to separate the plasma. This plasma was then stored at −20° C. until measurement of TNFα. The measurement of the amount of TNFα was performed with a commercially available enzyme immunoassay (ELISA) kit (Mouse TNFα ELISA KIT, Genzyme).

To determine the inhibitory activity of the test compounds, each test compound was suspended in a 0.5% tragacanth solution and then administered orally to the Balb/c mice at the rate of 10 ml/1 kg of body weight 30 minutes before injection of lipopolysaccharide. The level of TNFα production was then determined as described above. In the control group, 0.5% tragacanth solution was administered at the rate of 10 ml/1 kg of body weight to the test mice instead of the solutions of the test compounds. A minimum of 3 dose levels of the test compound was administered to groups of 5 test mice for each test compound. The inhibitory rate relative to the control group was calculated for each dose level. From the inhibitory rates and the dosages, ID$_{50}$ values were calculated by the least squares method, the results being shown in Table 9' below.

TABLE 9

Inhibitory Effect on TNFα Production (in vivo)

| Test compound | IC$_{50}$ [mg/kg] |
| --- | --- |
| Compound of Example 16' | 0.71 |
| Compound of Example 31' | 0.36 |
| Compound of Example 32' | 0.61 |
| Compound of Example 43' | 0.40 |

As can be seen from Table 9' above, the above-tested compounds of the present invention were found to show excellent inhibitory activity against the production of TNFα in vivo.

Test Example 3'

Inhibition of the Production of IL-1β In Vivo

This test was performed according to the method of Griffiths, et al. [Richard J. Griffiths, Ethan J. Stam, James T. Downs and Ivan G. Otterness; ATP Induces the Release of IL-1 from LPS-Primed Cells In Vivo: J. Immunol., 154, 2821–2828 (1995)].

The production of IL-1β was induced in mice by the intraperitoneal injection of lipopolysaccharide followed by the intraperitoneal injection of adenosine triphosphate (ATP). This was achieved by first administering a solution of lipopolysaccharide (E. coli O26: B6 origin, Difco), which had been prepared to a concentration of 0.0045 mg/ml using physiological saline, at the rate of 10 ml of said saline solution/1 kg of body weight into the peritoneal cavity of Balb/c mice (males, age 5–7 weeks, body weight: approx. 22 g, Japan Charles River) which had been fasted overnight starting on the day before the experiment. Two hours later, 0.5 ml of ATP, which had been prepared to a concentration of 6.03 mg/ml using physiological saline, were administered into the peritoneal cavity. 0.5 hours after the administration of ATP, the mice were sacrificed by suffocation using dry ice followed immediately by intraperitoneal injection of 3 ml of washing phosphate buffer solution [containing heparin (10 U/ml), p-toluenesulfonyl fluoride (0.25 mM), leupepsin (1 μg/ml), pepstatin (1 μg/ml) and EDTA (1 mM)] to wash the peritoneal cavity. A 1 ml volume disposable syringe equipped with a 21 G needle was then used to recover the washing liquid. After the recovery, the washing liquid from the peritoneal cavity was immediately transferred to a 1.5 ml volume Eppendorf tube and centrifuged at 4° C. and 7,500 rpm to separate the supernatant. This supernatant was then stored at −20° C. until measurement of IL-1β.

The measurement of the amount of IL-1β was performed with an enzyme immunoassay (ELISA) kit (Mouse IL-1β ELISA KIT, Genzyme).

To determine the inhibitory activity of the test compounds, each test compound was suspended in a 0.5% tragacanth solution and then administered orally to the Balb/c mice at the rate of 10 ml/1 kg of body weight 30 minutes before injection of lipopolysaccharide. The level of TNFα production was then determined as described above. In the control group, 0.5% tragacanth solution was administered to the test mice at the rate of 10 ml/1 kg of body weight instead of the solutions of the test compounds. A minimum of 3 dose levels of the test compound was administered to groups of 5 test mice for each test compound. The mean inhibitory rate relative to the control group was calculated for each dose level.

In this test, the compounds of the present invention that were tested demonstrated an excellent inhibitory effect against the production of IL-1β in vivo.

Test Example 4'

Activity in Preventing the Development of Adjuvant-Induced Arthritis In Vivo

The test was performed according to the method described by Winder et al. (Arthritis Rheum., 12, 472–482, 1969).

Heat-killed dried Mycobacterium butyricum (Difco Laboratories, Lot 679123) was ground on an agate mortar and was then suspended in dry-sterilised liquid paraffin (first grade, Wako Pure Chemical Industries, Ltd.) to make a 2 mg/ml suspension. The resulting suspension was then sonicated and used as an adjuvant. Arthritis was induced by the intradermal injection of the adjuvant (100 μg of heat killed dried bacterium/0.05 ml of paraffin/paw) into the heel of the right hind paw of a Lewis rat (male, age 9 weeks, 190 g, Japan Charles River). The test compounds, which had been suspended in a 0.5% aqueous sodium carboxymethyl cellulose solution (CMC, Daiichi Pure Chemicals, Co., Ltd.), were administered orally at the rate of 5 ml/kg once a day from the day of injection of the adjuvant (day 0) to day 20.

The volumes of the right hind paw (adjuvant-injected paw) and left hind paw (non-injected paw) were measured on days 3, 5, 7, 10, 13, 15, 18 and 21 using a Plethysmometer™ (Ugo Basile), the hind paws being soaked from the toe to the hairline in the bath of the Plethysmometer™. The volumes of the swollen feet (adjuvant-injected right hind foot volume—non-injected left hind foot volume) were calculated. The percent inhibition of swelling of the injected foot of the treated animals as compared to that of the control animals on day 21 was calculated as follows.

Inhibition (%)={1−(swollen foot volume of compound-treated animals)/(swollen foot volume of control animals)}×100

A linear regression curve was obtained from the percent inhibition and the logarithmic value of the dosage by the least squares method. ID$_{50}$ values were calculated using this curve, the results being shown in Table 10' below.

TABLE 10

Activity in Preventing the Development of Adjuvant-Induced Arthritis in vivo

| Test compound | IC$_{50}$ [mg/kg] |
| --- | --- |
| Compound of Example 12' | 2.1 |
| Compound of Example 16' | 1.2 |

As can be seen from Table 10' above, in this test, the above-tested compounds of the present invention showed excellent activity in preventing the development of adjuvant-induced arthritis.

Test Example 5'

Activity in Preventing the Development of Arthritis Induced by Anti-Collagen Antibody In Vivo In this test, an anti-collagen antibody-induced mouse arthritis model was employed.

0.5 ml (2 mg of antibody) of an anti-collagen antibody solution (4 mg/ml, Arthritogenic mAb Cocktail: product of Immuno-Biological Laboratories Co., Ltd) were injected into the caudal vein of Balb/c mice (males, age 5–6 weeks old, Japan Charles River). Three days after injection, 0.1 ml [0.05 mg of lipopolysaccharide] of a lipopolysaccharide solution (0.5 mg/ml, Arthritogenic mAb Cocktail: product of Immuno-Biological Laboratories Co., Ltd) were administered to the mice by intraperitoneal injection.

The test compounds, which had been suspended in 0.5% tragacanth were administered orally to the test animals at the rate of 10 ml/1 kg of body weight once per day for 7 days from the day when the anti-collagen antibody was administered. To the mice of the control group, 0.5% tragacanth solution was administered at the rate of 10 ml/kg of body weight once per day for 7 days from the day when the anti-collagen antibody was administered, instead of solutions of the test compounds.

After the administration of the test compounds (or 0.5% tragacanth solution), the degree of edema in the 4 paws of each test mouse was scored according to the following basis:

0: normal (edema is not observed);
1: edema is observed in one of the five toes;
2: edema is observed in two or more of the five toes;
3: the whole of the paw is swollen.

The degree of arthritis in the test mouse was evaluated by the total of the edema scores in the 4 paws. The rate of suppression was calculated from the degrees of arthritis of the control animals and of the animals treated with the test compounds. From the rates of suppression and the dosages, $ID_{50}$ values were calculated by the least squares method.

In this test, the compounds of the present invention that were tested showed excellent activity in preventing the development of arthritis induced by anti-collagen antibody.

Test Example 6'

Activity in Treating Arthritis Induced by Anti-Collagen Antibody In Vivo

In this test, an anti-collagen antibody-induced mouse arthritis model was employed.

0.5 ml (2 mg of antibody) of an anti-collagen antibody solution (4 mg/ml, Arthritogenic mAb Cocktail: product of Immuno-Biological Laboratories Co., Ltd) were injected into the caudal vein of Balb/c mice (males, age 5–6 weeks old, Japan Charles River). Three days after injection, 0.1 ml [0.05 mg of lipopolysaccharide] of a lipopolysaccharide solution (0.5 mg/ml, Arthritogenic mAb Cocktail: product of Immuno-Biological Laboratories Co., Ltd) were administered to the mice by intraperitoneal injection.

7 days after the administration of the anti-collagen antibody solution, the degree of edema in the 4 paws of each test mouse was scored according to the basis as shown in Test Example 5'above.

Those mice in which edema in both the hind paws had been scored as "3" were selected. Test compounds, which had been suspended in 0.5% tragacanth solution, were administered orally to the selected mice at the rate of 10 ml/kg of body weight once per day for 3 days. To the mice of the control group, 0.5% tragacanth solution was administered at the rate of 10 ml/kg of body weight once per day for 3 days instead of solutions of the test compounds.

After the administration of the test compounds (or 0.5% tragacanth solution), the degree of arthritis in each test mouse was evaluated in the same manner as described in Test Example 5'. The rates of treatment of arthritis induced by anti-collagen antibody were calculated from the degrees of arthritis of the control animals and of the compound-treated animals.

From the rates of treatment and the dosages, $ID_{50}$ values were calculated by the least squares method.

In this test, the compounds of the present invention that were tested showed excellent activity in treating arthritis induced by anti-collagen antibody.

As illustrated above, the compounds of the present invention exhibit excellent activity in inhibiting the production of inflammatory cytokines, particularly in inhibiting the production of IL-1β and TNFα. Furthermore, the compounds of the present invention have satisfactory oral absorptivity and a low level of toxicity. Consequently, the compounds of the present invention are useful as pharmaceuticals, suitable for the prophylaxis and treatment of both humans and animals. They can, for example, be used as an analgesic, an anti-inflammatory agent (to relieve or treat inflammation) and an antiviral agent (such as for AIDS, herpes or viral myocarditis) as well as an agent for use in the prophylaxis and treatment of chronic rheumatoid arthritis, degenerative arthritis, allergic diseases (such as asthma, chronic obstructive pulmonary diseases (COPD), atopic dermatitis and contact dermatitis), septicaemia, psoriasis, osteoporosis, autoimmune diseases (e.g., systemic lupus erythematosus, ulcerative colitis, Crohn's disease and the like), diabetes, glomerular nephritis, hepatitis, cancer (such as colorectal cancer, brain cancer, bone cancer, epitherial cell-derived neoplasia (epithelial carcinoma), such as basal cell carcinoma, adenocarcinoma, gastrointestinal cancer, such as lip cancer, mouth cancer, esophageal cancer, small bowel cancer and stomach cancer, colon cancer, liver cancer, bladder cancer, pancreas cancer, ovarian cancer, cervical cancer, lung cancer, breast cancer and skin cancer, such as squamus cell and basal cell cancers, prostate cancer, and renal cell carcinoma), ischemic heart disease, Alzheimer's disease and arteriosclerosis. Of these applications, the compounds of the present invention are particularly useful as an analgesic and an anti-inflammatory agent and as an agent for the prophylaxis and treatment of chronic rheumatoid arthritis, degenerative arthritis, allergic diseases, septicaemia, psoriasis, osteoporosis, ulcerative colitis, diabetes, hepatitis and arteriosclerosis.

What is claimed is:

1. A compound of formula (I)', or a pharmacologically acceptable salt, ester or amide thereof:

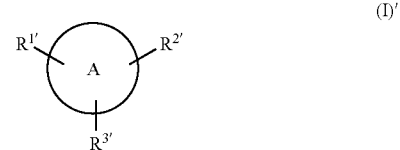

(I)' wherein:
  A' represents a pyrrole ring;
  $R^{1'}$ is an aryl group selected from the group consisting of phenyl and naphthyl, which are unsubstituted or substituted with at least one substituent selected from the group consisting of Substituent group α' defined below and Substituent group β' defined below;
  $R^{2'}$ is a pyridyl group which is unsubstituted or substituted with at least one substituent selected from the group consisting of Substituent group α' defined below and Substituent group β' defined below; and R³' represents a group of formula (IIa)', (IIb)' or (IIc)' shown below:

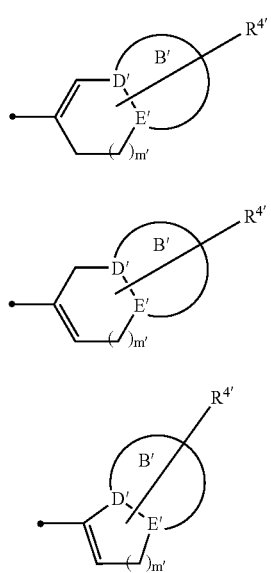

wherein m' represents 1,

E' represents a nitrogen atom and D' represents a group of formula >C(R⁵')—, wherein R⁵' is selected from the group consisting of hydrogen atoms, Substituent group α' defined below and Substituent group β' defined below, B' represents a 5-membered heterocyclic ring which has one ring nitrogen atom, said heterocyclic ring being saturated or unsaturated, and is unfused or fused with a group selected from the group consisting of aryl groups defined below, heteroaryl groups defined below, cycloalkyl groups defined below and heterocyclyl groups defined below, and R⁴' represents from 1 to 3 substituents which are independently selected from the group consisting of Substituent group α' defined below, Substituent group β' defined below and Substituent group γ' defined below, or when B' is a heterocyclic ring which is fused to an aryl group, a heteroaryl group, a cycloalkyl group or a heterocyclyl group, R⁴' may be a hydrogen atom;

provided that said substituents R¹' and R³' are bonded to the two atoms of said pyrrole ring which are adjacent to the atom of the pyrrole ring to which said substituent R²' is bonded;

Substituent group α' is selected from the group consisting of hydroxyl groups, nitro groups, cyano groups, halogen atoms, lower alkoxy groups defined below, halogeno lower alkoxy groups defined below, lower alkylthio groups defined below, halogeno lower alkylthio groups defined below and groups of formula —NRᵃ'Rᵇ', wherein Rᵃ' and Rᵇ' are the same or different from each other and each is independently selected from the group consisting of hydrogen atoms, lower alkyl groups defined below, lower alkenyl groups defined below, lower alkynyl groups defined below, aralkyl groups defined below and lower alkylsulfonyl groups defined below, or Rᵃ' and Rᵇ', taken together with the nitrogen atom to which they are attached, form a heterocyclyl group;

Substituent group β' is selected from the group consisting of lower alkyl groups defined below which are unsubstituted or substituted with at least one substituent selected from the group consisting of Substituent group α defined above, lower alkenyl groups defined below which are unsubstituted or substituted with at least one substituent selected from the group consisting of Substituent group α' defined above, lower alkynyl groups defined below which are unsubstituted or substituted with at least one substituent selected from the group consisting of Substituent group α' defined above, aralkyl groups defined below and cycloalkyl groups defined below;

Substituents group γ' is selected from the group consisting of oxo groups, hydroxyimino groups, lower alkoxyimino groups defined below, lower alkylene groups defined below, lower alkylenedioxy groups defined below, lower alkylsulfinyl groups defined below, lower alkylsulfonyl groups defined below, aryl groups defined below which are unsubstituted or substituted with at least one substituent selected from the group consisting of Substituent group α' defined above and Substituent group β' defined above, aryloxy groups defined below which are unsubstituted or substituted with at least one substituent selected from the group consisting of Substituent group α' defined above, Substituent group β' defined above, lower alkylidenyl groups and aralkylidenyl groups;

said aryl groups in the definitions of ring B' and Substituent group γ' above are aromatic hydrocarbon groups having from 6 to 14 carbon atoms in one or more rings, said aryl groups being unfused or fused with a cycloalkyl group having from 3 to 10 carbon atoms;

said heteroaryl groups in the definition of ring B' above are 5- to 7-membered aromatic heterocyclic groups containing from 1 to 3 heteroatoms selected from the group consisting of sulfur atoms, oxygen atoms and nitrogen atoms, said heteroaryl groups being unfused or fused with another cyclic group selected from the group consisting of aryl groups defined above and cycloalkyl groups having from 3 to 10 carbon atoms;

said lower alkyl groups in the definitions of Rᵃ', Rᵇ' and Substituent group β' above, and the lower alkyl moiety of said lower alkyl groups which are unsubstituted or substituted with at least one substituent selected from Substituent group α' in the definition of Substituent group β' above are straight or branched alkyl groups having from 1 to 6 carbon atoms;

said lower alkenyl groups in the definitions of Rᵃ', Rᵇ' and Substituent group β' above, and the lower alkenyl moiety of said lower alkenyl groups which are unsubstituted or substituted with at least one substituent selected from Substituent group α' in the definition of Substituent group β' above are straight or branched alkenyl groups having from 2 to 6 carbon atoms;

said lower alkynyl groups in the definitions of Rᵃ', Rᵇ' and Substituent group β' above, and the lower alkynyl moiety of said lower alkynyl groups which are unsubstituted or substituted with at least one substituent selected from Substituent group α' in the definition of Substituent group β' above are straight or branched alkynyl groups having from 2 to 6 carbon atoms;

said aralkyl groups in the definitions of Rᵃ', Rᵇ' and Substituent group β' above are lower alkyl groups as defined above which are substituted with at least one aryl group as defined above which are unsubstituted or substituted with from 1 to 3 substituents selected from the group consisting of Substituent group α' defined above and Substituent group β' defined above;

said lower alkylsulfonyl groups in the definitions of $R^{a'}$, $R^{b'}$ and Substituent γ' above are lower alkyl groups as defined above which are bonded to a sulfonyl group;

where ring B' is fused with a heterocyclyl group, said heterocyclyl groups are 4- to 7-membered heterocyclyl groups which contain from 1 to 3 ring heteroatoms selected from the group consisting of oxygen atoms, sulfur atoms and nitrogen atoms;

where $R^{a'}$ and $R^{b'}$ together with the nitrogen atom to which they are attached represent a heterocyclyl group, said heterocyclyl groups are 4- to 7-membered heterocyclyl groups which contain one nitrogen atom and which do not contain any further heteroatoms or contain one further heteroatom selected from the group consisting of oxygen atoms, sulfur atoms and nitrogen atoms, said heterocyclyl groups being unfused or fused with another cyclic group selected from the group consisting of aryl groups defined above and heteroaryl groups defined above;

said lower alkoxy groups in the definition of Substituent group α' above are groups in which an oxygen atom is bonded to a lower alkyl group as defined above;

said halogeno lower alkoxy groups in the definition of Substituent group α' above are groups in which a lower alkoxy group as defined above is substituted with at least one halogen atom;

said lower alkylthio groups in the definition of Substituent group α' above are groups in which a sulfur atom is bonded to a lower alkyl group as defined above;

said halogeno lower alkylthio groups in the definition of Substituent group α' above are groups in which a lower alkylthio group as defined above is substituted with at least one halogen atom;

said cycloalkyl groups in the definitions of Substituent group β' and ring B' are cycloalkyl groups having from 3 to 7 carbon atoms;

said lower alkoxyimino groups in the definition of Substituent group γ' above are groups wherein the hydrogen atom of a hydroxyimino group is replaced by a lower alkyl group as defined above;

said lower alkylene groups in the definition of Substituent group γ' above are alkylene groups having from 2 to 6 carbon atoms;

said lower alkylenedioxy groups in the definition of Substituent group γ' above are groups wherein an alkylene moiety, which is a straight or branched chain alkylene group having from 1 to 6 carbon atoms, is subsitituted with 2 oxy groups;

said lower alkylsulfinyl groups in the definition of Substituent group γ' above are groups in which a lower alkyl group as defined above is bonded to a sulfinyl group;

said lower alkylidenyl groups in the definition of Substituent group γ' above are straight or branched alkylidenyl groups having from 1 to 6 carbon atoms;

said aralkylidenyl groups in the definition of Substituent group γ' above are lower alkylidenyl groups as defined above which are substituted with 1 or more aryl groups as defined above;

said unsubstituted or substituted aryloxy groups in the definition of Substituent group γ' above are groups in which an oxygen atom is attached to an aryl group as defined above.

2. A compound according to claim 1 or a pharmacologically acceptable salt, ester or amide thereof, wherein $R^{1'}$ is a phenyl group which optionally is substituted with at least one substituent selected from the group consisting of Substituent group $α^{1'}$ defined below and Substituent group $β^{1'}$ defined below;

said Substituent group $α^{1'}$ is selected from the group consisting of halogen atoms, lower alkoxy groups, halogeno lower alkoxy groups and groups of formula —$NR^{a'}R^{b'}$, wherein one of $R^{a'}$ and $R^{b'}$ represents a hydrogen atom or a lower alkyl group, and the other represents a hydrogen atom, a lower alkyl group or an aralkyl group;

said Substituent group $β^{1'}$ is selected from the group consisting of lower alkyl groups, halogeno lower alkyl groups, hydroxyl lower alkyl groups, nitro lower alkyl groups, amino lower alkyl groups, lower alkylamino lower alkyl groups, di(lower alkyl)amino lower alkyl groups and aralkylamino lower alkyl groups.

3. A compound according to claim 1 or a pharmacologically acceptable salt, ester or amide thereof, wherein $R^{1'}$ is a phenyl group which optionally is substituted with at least one substituent selected from the group consisting of halogen atoms, halogeno lower alkyl groups and halogeno lower alkoxy groups.

4. A compound according to claim 1 or a pharmacologically acceptable salt, ester or amide thereof, wherein $R^{1'}$ is selected from the group consisting of phenyl, 4-fluorophenyl, 3-fluorophenyl, 3-chlorophenyl, 3,4-difluorophenyl, 3,4,5-trifluorophenyl, 3-chloro-4-fluorophenyl, 3-difluoromethoxyphenyl and 3-trifluoromethylphenyl groups.

5. A compound according to claim 1 or a pharmacologically acceptable salt, ester or amide thereof, wherein $R^{2'}$ is a 4-pyridyl which is unsubstituted or substituted with at least one substituent selected from the group consisting of said Substituent group α' and said Substituent group β'.

6. A compound according to claim 1 or a pharmacologically acceptable salt, ester or amide thereof, wherein $R^{2'}$ is a 4-pyridyl which is unsubstituted or substituted at the 2-position thereof with a substituent selected from the group consisting of said Substituent group α' and said Substituent group β'.

7. A compound according to claim 1 or a pharmacologically acceptable salt, ester or amide thereof, wherein $R^{2'}$ is a 4-pyridyl which is unsubstituted or substituted at the 2-position thereof with a substituent selected from the group consisting of methoxy, amino, methylamino, benzylamino, and α-methylbenzylamino groups.

8. A compound according to claim 1 or a pharmacologically acceptable salt, ester or amide thereof, wherein B' has one further ring heteroatom or ring group selected from the group consisting of a nitrogen atom, oxygen atom, sulfur atom, >SO and >$SO_2$, said ring is saturated or unsaturated and optionally is fused with an aryl group, a heteroaryl group, a cycloalkyl group or a heterocyclyl group.

9. A compound according to claim 1 or a pharmacologically acceptable salt, ester or amide thereof, wherein B' is saturated or unsaturated and is fused with an aryl group, a heteroaryl group, a cycloalkyl group or a heterocyclyl group.

10. A compound according to claim 1 or a pharmacologically acceptable salt, ester or amide thereof, wherein B' is a pyrrolidinyl ring or a pyrrolinyl ring.

11. A compound according to claim 1 or a pharmacologically acceptable salt, ester or amide thereof, wherein $R^{3'}$ is a group of formula (IIa)' or formula (IIb)'.

12. A compound according to claim 1 or a pharmacologically acceptable salt, ester or amide thereof, wherein $R^{3'}$ is a group of formula (IIa)'.

13. A compound according to claim 1 or a pharmacologically acceptable salt, ester or amide thereof, wherein $R^{4'}$ is 1 or 2 substituents which are selected independently from the group consisting of said Substituent group α, said Substituent group β' and Substituent group $γ^{1'}$, wherein said Substituent group $γ^{1'}$ is selected from the group consisting of oxo groups, hydroxyimino groups, lower alkoxyimino groups, lower alkylene groups, lower alkylenedioxy groups, lower alkylsulfinyl groups, lower alkylsulfonyl groups and aryl groups which optionally are substituted with at least one substituent selected from the group consisting of said Substituent group α' and said Substituent group β'.

14. A compound according to claim 1 or a pharmacologically acceptable salt, ester or amide thereof, wherein $R^{4'}$ is a substituent selected from the group consisting of hydroxy groups, halogen atoms, lower alkoxy groups, lower alkylthio groups, halogeno lower alkoxy groups, lower alkyl groups, halogeno lower alkyl groups, oxo groups, aryl groups optionally substituted with at least one substituent selected from the group consisting of said Substituent group α', said Substituent group β', lower alkylenedioxy groups, lower alkylene groups and lower alkylsulfonyl groups.

15. A compound according to claim 1 or a pharmacologically acceptable salt, ester or amide thereof, wherein $R^{4'}$ is a substituent selected from the group consisting of hydroxy groups, fluorine atoms, chlorine atoms, methoxy groups, ethoxy groups, propoxy groups, methyl groups, ethyl groups, propyl groups and phenyl groups which is optionally substituted with at least one substituent selected from the group consisting of said Substituent group α' and said Substituent group β' as defined in claim 1.

16. A compound according to claim 1 or a pharmacologically acceptable salt, ester or amide thereof, wherein $R^{4'}$ is a substituent selected from the group consisting of methoxy groups, methyl groups, ethyl groups, propyl groups and phenyl groups.

17. A compound according to claim 1 or a pharmacologically acceptable salt, ester or amide thereof, wherein $R^{4'}$ is a substituent selected from the group consisting of aryloxy groups which optionally are substituted with at least one substituent selected from the group consisting of said Substituent group α', said Substituent group β', alkylidene groups and aralkylidene groups.

18. A compound according to claim 1 or a pharmacologically acceptable salt, ester or amide thereof, wherein $R^{4'}$ is a substituent selected from the group consisting of phenoxy, methylidene, ethylidene, propylidene and benzylidene groups.

19. A compound according to claim 1 or a pharmacologically acceptable salt, ester or amide thereof, wherein said compound of formula (I)' is represented by the formula (I-1)' or (I-3)' shown below:

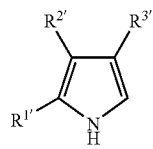
(I-1)'

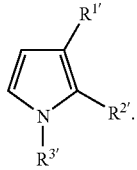
(I-3)'

20. A compound according to claim 1 or a pharmacologically acceptable salt, ester or amide thereof, wherein the compound of formula (I)' is represented by the formula (I-1)' below:

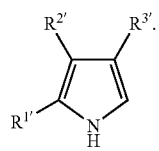
(I-1)'

21. A compound according to claim 1 or a pharmacologically acceptable salt, ester or amide thereof, wherein:

$R^{3'}$ is a group of formula (IIa)' or formula (IIb)'; and $R^{4'}$ is 1 or 2 substituents which are selected independently from the group consisting of said Substituent group α', said Substituent group β' and Substituent group $γ^{1'}$, wherein said Substituent group $γ^{1'}$ is selected from the group consisting of oxo groups, hydroxyimino groups, lower alkoxyimino groups, lower alkylene groups, lower alkylenedioxy groups, lower alkylsulfinyl groups, lower alkylsulfonyl groups and aryl groups which are unsubstituted or substituted with at least one substituent selected from the group consisting of said Substituent group α' and said Substituent group β'.

22. A compound according to claim 1 or a pharmacologically acceptable salt, ester or amide thereof, wherein:

$R^{3'}$ is a group of formula (IIa)' or formula (IIb)'; and $R^{4'}$ is a substituent selected from the group consisting of hydroxy groups, halogen atoms, lower alkoxy groups, lower alkylthio groups, halogeno lower alkoxy groups, lower alkyl groups, halogeno lower alkyl groups, oxo groups, aryl groups which are unsubstituted or substituted with at least one substituent selected from the group consisting of said Substituent group α', said Substituent group β', lower alkylenedioxy groups, lower alkylene groups and lower alkylsulfonyl groups.

23. A compound according to claim 1 or a pharmacologically acceptable salt, ester or amide thereof, wherein:

$R^{1'}$ is a phenyl group which is unsubstituted or substituted with at least one substituent selected from the group consisting of Substituent group $α^{1'}$ defined below and Substituent group $β^{1'}$ defined below;

said Substituent group $α^{1'}$ is selected from the group consisting of halogen atoms, lower alkoxy groups, halogeno lower alkoxy groups and groups of formula —NR$^{a'}$R$^{b'}$, wherein one of R$^{a'}$ and R$^{b'}$ represents a hydrogen atom or a lower alkyl group, and the other represents a hydrogen atom, a lower alkyl group or an aralkyl group;

said Substituent group β$^{1'}$ is selected from the group consisting of lower alkyl groups, halogeno lower alkyl groups, hydroxyl lower alkyl groups, nitro lower alkyl groups, amino lower alkyl groups, lower alkylamino lower alkyl groups, di(lower alkyl)amino lower alkyl groups and aralkylamino lower alkyl groups;

R$^{2'}$ is a 4-pyridyl which is unsubstituted or substituted with at least one substituent selected from the group consisting of said Substituent group α' and said Substituent group β';

R$^{3'}$ is a group of formula (IIa)' or formula (IIb)'; and

R$^{4'}$ is a substituent selected from the group consisting of hydroxy groups, halogen atoms, lower alkoxy groups, lower alkylthio groups, halogeno lower alkoxy groups, lower alkyl groups, halogeno lower alkyl groups, oxo groups, aryl groups which are unsubstituted or substituted with at least one substituent selected from the group consisting of said Substituent group α', said Substituent group β', lower alkylenedioxy groups, lower alkylene groups and lower alkylsulfonyl groups.

24. A compound according to claim 1 or a pharmacologically acceptable salt, ester or amide thereof, wherein:

R$^{1'}$ is a phenyl group which is unsubstituted or substituted with at least one substituent selected from the group consisting of halogen atoms, halogeno lower alkyl groups and halogeno lower alkoxy groups;

R$^{2'}$ is a 4-pyridyl which is unsubstituted or substituted at the 2-position thereof with a substituent selected from the group consisting of said Substituent group α' and said Substituent group β';

R$^{3'}$ is a group of formula (IIa)'; and

R$^{4'}$ is a substituent selected from the group consisting of hydroxy groups, fluorine atoms, chlorine atoms, methoxy groups, ethoxy groups, propoxy groups, methyl groups, ethyl groups, propyl groups and phenyl groups which are unsubstituted or substituted with at least one substituent selected from the group consisting of said Substituent group α' and said Substituent group β'.

25. A compound according to claim 1 or a pharmacologically acceptable salt, ester or amide thereof, wherein:

R$^{1'}$ is a substituent selected from the group consisting of phenyl, 4-fluorophenyl, 3-fluorophenyl, 3-chlorophenyl, 3,4-difluorophenyl, 3,4,5-trifluorophenyl, 3-chloro-4-fluorophenyl, 3-difluoromethoxyphenyl and 3-trifluoromethylphenyl groups;

R$^{2'}$ is a 4-pyridyl which is unsubstituted or substituted at the 2-position thereof with a substituent selected from the group consisting of methoxy, amino, methylamino, benzylamino, and α-methylbenzylamino groups;

R$^{3'}$ is a group of formula (IIa)'; and

R$^{4'}$ is a substituent selected from the group consisting of methoxy groups, methyl groups, ethyl groups, propyl groups and phenyl groups.

26. A compound according to claim 1 or a pharmacologically acceptable salt, ester or amide thereof, wherein:

R$^{3'}$ is a group of formula (IIa)' or formula (IIb)'; and

R$^{4'}$ is a substituent selected from the group consisting of aryloxy groups which are unsubstituted or substituted with at least one substituent selected from the group consisting of said Substituent group α', said Substituent group β', alkylidene groups and aralkylidene groups.

27. A compound according to claim 1 or a pharmacologically acceptable salt, ester or amide thereof, wherein:

R$^{1'}$ is a phenyl group which is unsubstituted or substituted with at least one substituent selected from the group consisting of Substituent group α$^{1'}$ defined below and Substituent group β$^{1'}$ defined below, said Substituent group α$^{1'}$ is selected from the group consisting of halogen atoms, lower alkoxy groups, halogeno lower alkoxy groups and groups of formula —NR$^{a'}$R$^{b'}$, wherein one of R$^{a'}$ and R$^{b'}$ represents a hydrogen atom or a lower alkyl group, and the other represents a hydrogen atom, a lower alkyl group or an aralkyl group, and said Substituent group β$^{1'}$ is selected from the group consisting of lower alkyl groups, halogeno lower alkyl groups, hydroxyl lower alkyl groups, nitro lower alkyl groups, amino lower alkyl groups, lower alkylamino lower alkyl groups, di(lower alkyl)amino lower alkyl groups and aralkylamino lower alkyl groups;

R$^{2'}$ is a 4-pyridyl which is unsubstituted or substituted with at least one substituent selected from the group consisting of said Substituent group α' and said Substituent group β';

R$^{3'}$ is a group of formula (IIa)' or formula (IIb)'; and

R$^{4'}$ is a substituent selected from the group consisting of aryloxy groups which are unsubstituted or substituted with at least one substituent selected from the group consisting of said Substituent group α' and said Substituent group β', alkylidene groups and aralkylidene groups.

28. A compound according to claim 1 or a pharmacologically acceptable salt, ester or amide thereof, wherein:

R$^{1'}$ is a phenyl group which is unsubstituted or substituted with at least one substituent selected from the group consisting of halogen atoms, halogeno lower alkyl groups and halogeno lower alkoxy groups;

R$^{2'}$ is a 4-pyridyl which is unsubstituted or substituted at the 2-position thereof with a substituent selected from the group consisting of said Substituent group α' and said Substituent group β';

R$^{3'}$ is a group of formula (IIa)', and

R$^{4'}$ is a substituent selected from the group consisting of phenoxy, methylidene, ethylidene, propylidene and benzylidene groups.

29. A compound according to claim 1 or a pharmacologically acceptable salt, ester or amide thereof, wherein:

R$^{1'}$ is a substituent selected from the group consisting of phenyl, 4-fluorophenyl, 3-fluorophenyl, 3-chlorophenyl, 3,4-difluorophenyl, 3,4,5-trifluorophenyl, 3-chloro-4-fluorophenyl, 3-difluoromethoxyphenyl and 3-trifluoromethylphenyl groups;

R$^{2'}$ is a 4-pyridyl which is unsubstituted or substituted at the 2-position thereof with a substituent selected from the group consisting of methoxy, amino, methylamino, benzylamino, and α-methylbenzylamino groups;

R$^{3'}$ is a group of formula (IIa)', and

R$^{4'}$ is a substituent selected from the group consisting of phenoxy, methylidene, ethylidene, propylidene and benzylidene groups.

30. A compound according to any one of claim 21, 22, 23, 24, 25, 26, 27, 28 or 29 or a pharmacologically acceptable salt, ester or amide thereof, wherein the compound of formula (I)' is a compound of formula (I-1)' or (I-3)' shown below:

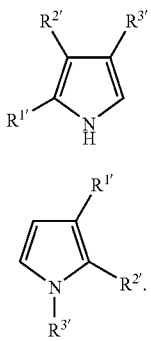

31. A compound according to any one of claim 21, 22, 23, 24, 25, 26, 27, 28 or 29 or a pharmacologically acceptable salt, ester or amide thereof, wherein the compound of formula (I)' is a compound of formula (I-1)' shown below:

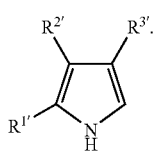

32. A compound according to claim 1 or a pharmacologically acceptable salt, ester or amide thereof, wherein the compound is selected from the group consisting of
2-(3-fluorophenyl)-4-[2-methyl-1,2,3,5,6,8a-hexahydroindolizin-7-yl]-3-(pyridin-4-yl)-1H-pyrrole,
2-(3-fluorophenyl)-4-[2-phenyl-1,2,3,5,6,8a-hexahydroindolizin-7-yl]-3-(pyridin-4-yl)-1H-pyrrole,
2-(3-fluorophenyl)-4-[2-methoxy-1,2,3,5,6,8a-hexahydroindolizin-7-yl]-3-(pyridin-4-yl)-1H-pyrrole,
2-(4-fluorophenyl)-4-[2-methyl-1,2,3,5,6,8a-hexahydroindolizin-7-yl]-3-(pyridin-4-yl)-1H-pyrrole,
2-(4-fluorophenyl)-4-[2-phenyl-1,2,3,5,6,8a-hexahydroindolizin-7-yl]-3-(pyridin-4-yl)-1H-pyrrole,
2-(4-fluorophenyl)-4-[2-methoxy-1,2,3,5,6,8a-hexahydroindolizin-7-yl]-3-(pyridin-4-yl)-1H-pyrrole,
2-(3-chlorophenyl)-4-[2-methyl-1,2,3,5,6,8a-hexahydroindolizin-7-yl]-3-(pyridin-4-yl)-1H-pyrrole,
2-(3-chlorophenyl)-4-[2-phenyl-1,2,3,5,6,8a-hexahydroindolizin-7-yl]-3-(pyridin-4-yl)-1H-pyrrole,
2-(3-chlorophenyl)-4-[2-methoxy-1,2,3,5,6,8a-hexahydroindolizin-7-yl]-3-(pyridin-4-yl)-1H-pyrrole,
4-[2-methyl-1,2,3,5,6,8a-hexahydroindolizin-7-yl]-3-(pyridin-4-yl)-2-(3-trifluoromethylphenyl)-1H-pyrrole,
4-[2-phenyl-1,2,3,5,6,8a-hexahydroindolizin-7-yl]-3-(pyridin-4-yl)-2-(3-trifluoromethylphenyl)-1H-pyrrole,
4-[2-methoxy-1,2,3,5,6,8a-hexahydroindolizin-7-yl]-3-(pyridin-4-yl)-2-(3-trifluoromethylphenyl)-1H-pyrrole,
2-(4-fluorophenyl)-4-[2-methyl-3,5,6,8a-tetrahydroindolizin-7-yl]-3-(pyridin-4-yl)-1H-pyrrole,
2-(4-fluorophenyl)-4-[2-methylidene-1,2,3,5,6,8a-hexahydroindolizin-7-yl]-3-(pyridin-4-yl)-1H-pyrrole,
4-[2-ethyl-1,2,3,5,6,8a-hexahydroindolizin-7-yl]-2-(4-fluorophenyl)-3-(pyridin-4-yl)-1H-pyrrole,
4-[2-ethyl-1,2,3,5,6,8a-hexahydroindolizin-7-yl]-2-(3-fluorophenyl)-3-(pyridin-4-yl)-1H-pyrrole,
2-(3-chlorophenyl)-4-[2-ethyl-1,2,3,5,6,8a-hexahydroindolizin-7-yl]-3-(pyridin-4-yl)-1H-pyrrole,
4-[2-ethyl-1,2,3,5,6,8a-hexahydroindolizin-7-yl]-3-(pyridin-4-yl)-2-(3-trifluoromethylphenyl)-1H-pyrrole,
2-(4-fluorophenyl)-4-[2-propyl-1,2,3,5,6,8a-hexahydroindolizin-7-yl]-3-(pyridin-4yl)-1H-pyrrole,
2-(3-fluorophenyl)-4-[2-propyl-1,2,3,5,6,8a-hexahydroindolizin-7-yl]-3-(pyridin-4-yl)-1H-pyrrole,
2-(3-chlorophenyl)-4-[2-propyl-1,2,3,5,6,8a-hexahydroindolizin-7-yl]-3-(pyridin-4-yl)-1H-pyrrole,
4-[2-propyl-1,2,3,5,6,8a-hexahydroindolizin-7-yl]-3-(pyridin-4-yl)-2-(3-trifluoromethylphenyl)-1H-pyrrole,
4-[2-ethyl-3,5,6,8a-tetrahydroindolizin-7-yl]-2-(4-fluorophenyl)-3-(pyridin-4-yl)-1H-pyrrole,
2-(4-fluorophenyl)-4-[2-propyl-3,5,6,8a-tetrahydroindolizin-7-yl]-3-(pyridin-4-yl)-1H-pyrrole, and
2-(4-fluorophenyl)-4-[2-phenyl-3,5,6,8a-tetrahydroindolizin-7-yl]-3-(pyridin-4-yl)-1H-pyrrole.

33. A compound according to claim 1, wherein the compound is 2-(4-fluorophenyl)-4-[(2R,8aS)-2-phenyl-1,2,3,5,6,8a-hexahydroindolizin-7-yl]-3-(pyridin-4-yl)-1H-pyrrole or a pharmacologically acceptable salt, ester or amide thereof.

34. A compound according to claim 1, wherein the compound is 2-(4-fluorophenyl)-4-[(8aS)-2-methyl-1,2,3,5,6,8a-hexahydroindolizin-7-yl]-3-(pyridin-4-yl)-1H-pyrrole or a pharmacologically acceptable salt, ester or amide thereof.

35. A compound according to claim 1, wherein the compound is 2-(4-fluorophenyl)-4-[(8aS)-2-methylidene-1,2,3,5,6,8a-hexahydroindolizin-7-yl]-3-(pyridin-4-yl)-1H-pyrrole or a pharmacologically acceptable salt, ester or amide thereof.

36. A compound according to claim 1, wherein the compound is 2-(4-fluorophenyl)-4-[(8aS)-2-methylidene-3,5,6,8a-hexahydroindolizin-7-yl]-3-(pyridin-4-yl)-1H-pyrrole or a pharmacologically acceptable salt, ester or amide thereof.

37. A compound according to claim 1, wherein the compound is 4-[(2S,8aS)-2-ethyl-1,2,3,5,6,8a-hexahydroindolizin-7-yl]-2-(4-flurophenyl)-3-(pyridin-4-yl)-1H-pyrrole or a pharmacologically acceptable salt, ester or amide thereof.

38. A compound according to claim 1, wherein the compound is 2-(4-fluorophenyl)-4-[(2S,8aS)-2-propyl-1,2,3,5,6,8hexahydroindolizin-7yl]-3-(pyridin-4-yl)-1H-pyrrole or a pharmacologically acceptable salt, ester or amide thereof.

39. A compound according to claim 1, wherein the compound is 2-(4-fluorophenyl)-4-[(2R,8aS)-2-methoxy-1,2,3,5,6,8a-hexahydroindolizin-7-yl]-3-(pyridin-4-yl)-1H pyrrole or a pharmaceutically acceptable salt, ester or amide thereof.

40. A pharmaceutical composition comprising a pharmaceutically effective amount of a pharmacologically active compound together with a carrier therefor, wherein said pharmacologically active compound is a compound of formula (I)' or a pharmacologically acceptable salt, ester or amide thereof:

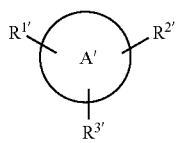

(I)' wherein:

A' represents a pyrrole ring;

$R^{1'}$ is an aryl group selected from the group consisting of phenyl and naphthyl, which are unsubstituted or substituted with at least one substituent selected from the group consisting of Substituent group α' defined below and Substituent group β' defined below; and $R^{2'}$ is a pyridyl group which is unsubstituted or substituted with at least one substituent selected from the group consisting of Substituent group α' defined below and Substituent group β' defined below; and $R^{3'}$ represents a group of formula (IIa)', (IIb)' or (IIc)' shown below:

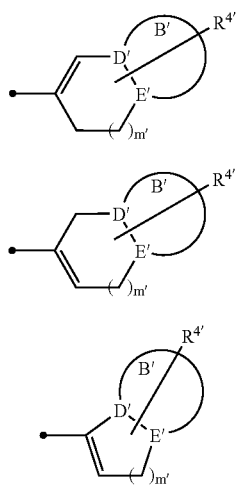

wherein m' represents 1,

E' represents a nitrogen atom and D' represents a group of formula >C($R^{5'}$)—, wherein $R^{5'}$ is selected from the group consisting of hydrogen atoms, Substituent group α' defined below and Substituent group β' defined below, B' represents a 5-membered heterocyclic ring which has one ring nitrogen atom, said heterocyclic ring being saturated or unsaturated, and is unfused or fused with a group selected from the group consisting of aryl groups defined below, heteroaryl groups defined below, cycloalkyl groups defined below and heterocyclyl groups defined below, and $R^{4'}$ represents from 1 to 3 substituents which are independently selected from the group consisting of Substituent group α' defined below, Substituent group β' defined below and Substituent group γ' defined below, or when B' is a heterocyclic ring which is fused to an aryl group, a heteroaryl group, a cycloalkyl group or a heterocyclyl group, $R^{4'}$ may be a hydrogen atom;

provided that said substituents $R^{1'}$ and $R^{3'}$ are bonded to the two atoms of said pyrrole ring which are adjacent to the atom of the pyrrole ring to which said substituent $R^{2'}$ is bonded;

Substituent group α' is selected from the group consisting of hydroxyl groups, nitro groups, cyano groups, halogen atoms, lower alkoxy groups defined below, halogeno lower alkoxy groups defined below, lower alkylthio groups defined below, halogeno lower alkylthio groups defined below and groups of formula —$NR^{a'}R^{b'}$, wherein $R^{a'}$ and $R^{b'}$ are the same or different from each other and each is independently selected from the group consisting of hydrogen atoms, lower alkyl groups defined below, lower alkenyl groups defined below, lower alkynyl groups defined below, aralkyl groups defined below and lower alkylsulfonyl groups defined below, or $R^{a'}$ and $R^{b'}$, taken together with the nitrogen atom to which they are attached, form a heterocyclyl group;

Substituent group β' is selected from the group consisting of lower alkyl groups defined below which are unsubstituted or substituted with at least one substituent selected from the group consisting of Substituent group α' defined above, lower alkenyl groups defined below which are unsubstituted or substituted with at least one substituent selected from the group consisting of Substituent group α' defined above, lower alkynyl groups defined below which are unsubstituted or substituted with at least one substituent selected from the group consisting of Substituent group α' defined above, aralkyl groups defined below and cycloalkyl groups defined below;

Substituents group γ' is selected from the group consisting of oxo groups, hydroxyimino groups, lower alkoxyimino groups defined below, lower alkylene groups defined below, lower alkylenedioxy groups defined below, lower alkylsulfinyl groups defined below, lower alkylsulfonyl groups defined below, aryl groups defined below which are unsubstituted or substituted with at least one substituent selected from the group consisting of Substituent group α' defined above and Substituent group β' defined above, aryloxy groups defined below which are unsubstituted or substituted with at least one substituent selected from the group consisting of Substituent group α' defined above, Substituent group β' defined above, lower alkylidenyl groups and aralkylidenyl groups;

said aryl groups in the definitions of ring B' and Substituent group γ' above are aromatic hydrocarbon groups having from 6 to 14 carbon atoms in one or more rings, said aryl groups being unfused or fused with a cycloalkyl group having from 3 to 10 carbon atoms;

said heteroaryl groups in the definition of ring B' above are 5- to 7-membered aromatic heterocyclic groups containing from 1 to 3 heteroatoms selected from the group consisting of sulfur atoms, oxygen atoms and nitrogen atoms, said heteroaryl groups being unfused or fused with another cyclic group selected from the group consisting of aryl groups defined above and cycloalkyl groups having from 3 to 10 carbon atoms;

said lower alkyl groups in the definitions of $R^{a'}$, $R^{b'}$ and Substituent group β' above, and the lower alkyl moiety of said lower alkyl groups which are unsubstituted or substituted with at least one substituent selected from Substituent group α' in the definition of Substituent group β' above are straight or branched alkyl groups having from 1 to 6 carbon atoms;

said lower alkenyl groups in the definitions of $R^{a'}$, $R^{b'}$ and Substituent group β' above, and the lower alkenyl moiety of said lower alkenyl groups which are unsubstituted or substituted with at least one substituent selected from Substituent group α' in the definition of Substituent group β' above are straight or branched alkenyl groups having from 2 to 6 carbon atoms;

said lower alkynyl groups in the definitions of $R^{a'}$, $R^{b'}$ and Substituent group β' above, and the lower alkynyl moiety of said lower alkynyl groups which are unsubstituted or substituted with at least one substituent selected from Substituent group α' in the definition of Substituent group β' above are straight or branched alkynyl groups having from 2 to 6 carbon atoms;

said aralkyl groups in the definitions of $R^{a'}$, $R^{b'}$ and Substituent group β' above are lower alkyl groups as defined above which are substituted with at least one aryl group as defined above which are unsubstituted or substituted with from 1 to 3 substituents selected from the group consisting of Substituent group α' defined above and Substituent group β' defined above;

said lower alkylsulfonyl groups in the definitions of $R^{a'}$, $R^{b'}$ and Substituent γ' above are lower alkyl groups as defined above which are bonded to a sulfonyl group;

where ring B' is fused with a heterocyclyl group, said heterocyclyl groups are 4 to 7-membered heterocyclyl groups which contain from 1 to 3 ring heteroatoms selected from the group consisting of oxygen atoms, sulfur atoms and nitrogen atoms;

where $R^{a'}$ and $R^{b'}$ together with the nitrogen atom to which they are attached represent a heterocyclyl group, said heterocyclyl groups are 4 to 7-membered heterocyclyl groups which contain one nitrogen atom and which do not contain any further heteroatoms or contain one further heteroatom selected from the group consisting of oxygen atoms, sulfur atoms and nitrogen atoms, said heterocyclyl groups being unfused or fused with another cyclic group selected from the group consisting of aryl groups defined above and heteroaryl groups defined above;

said lower alkoxy groups in the definition of Substituent group α' above are groups in which an oxygen atom is bonded to a lower alkyl group as defined above;

said halogeno lower alkoxy groups in the definition of Substituent group α' above are groups in which a lower alkoxy group as defined above is substituted with at least one halogen atom;

said lower alkylthio groups in the definition of Substituent group α' above are groups in which a sulfur atom is bonded to a lower alkyl group as defined above;

said halogeno lower alkylthio groups in the definition of Substituent group α' above are groups in which a lower alkylthio group as defined above is substituted with at least one halogen atom;

said cycloalkyl groups in the definitions of Substituent group β' and ring B' above are cycloalkyl groups having from 3 to 7 carbon atoms;

said lower alkoxyimino groups in the definition of Substituent group γ' above are groups wherein the hydrogen atom of a hydroxyimino group is replaced by a lower alkyl group as defined above;

said lower alkylene groups in the definition of Substituent group γ' above are alkylene groups having from 2 to 6 carbon atoms;

said lower alkylenedioxy groups in the definition of Substituent group γ' above are groups wherein an alkylene moiety, which is a straight or branched chain alkylene group having from 1 to 6 carbon atoms, is subsititutied with 2 oxy groups;

said lower alkylsulfinyl groups in the definition of Substituent group γ' above are groups in which a lower alkyl group as defined above is bonded to a sulfinyl group;

said lower alkylidenyl groups in the definition of Substituent group γ' above are straight or branched alkylidenyl groups having from 1 to 6 carbon atoms; said aralkylidenyl groups in the definition of Substituent group γ' above are lower alkylidenyl groups as defined above which are substituted with 1 or more aryl groups as defined above;

said unsubstituted or substituted aryloxy groups in the definition of Substituent group γ' above are groups in which an oxygen atom is attached to an aryl group as defined above.

41. A pharmaceutical composition according to claim 40, wherein $R^{1'}$ is a phenyl group which optionally is substituted with at least one substituent selected from the group consisting of Substituent group $\alpha^{1'}$ defined below and Substituent group $\beta^{1'}$ defined below;

said Substituent group $\alpha^{1'}$ is selected from the group consisting of halogen atoms, lower alkoxy groups, halogeno lower alkoxy groups and groups of formula —$NR^{a'}R^{b'}$, wherein one of $R^{a'}$ and $R^{b'}$ represents a hydrogen atom or a lower alkyl group, and the other represents a hydrogen atom, a lower alkyl group or an aralkyl group;

said Substituent group $\beta^{1'}$ is selected from the group consisting of lower alkyl groups, halogeno lower alkyl groups, hydroxyl lower alkyl groups, nitro lower alkyl groups, amino lower alkyl groups, lower alkylamino lower alkyl groups, di(lower alkyl)amino lower alkyl groups and aralkylamino lower alkyl groups.

42. A pharmaceutical composition according to claim 40, wherein $R^{1'}$ is a phenyl group which optionally is substituted with at least one substituent selected from the group consisting of halogen atoms, halogeno lower alkyl and halogeno lower alkoxy groups.

43. A pharmaceutical composition according to claim 40, wherein $R^{1'}$ is a substituent selected from the group consisting of phenyl, 4-fluorophenyl, 3-fluorophenyl, 3-chlorophenyl, 3,4difluorophenyl, 3,4,5trifluorophenyl, 3-chloro-4-fluorophenyl, 3-difluoromethoxyphenyl and 3-trifluoromethylphenyl groups.

44. A pharmaceutical composition according to claim 40, wherein $R^{2'}$ is a 4-pyridyl group which is unsubstituted or substituted with at least one substituent selected from the group consisting of said Substituent group α' and said Substituent group β'.

45. A pharmaceutical composition according to claim 40, wherein $R^{2'}$ is a 4-pyridyl group which is unsubstituted or substituted at the 2-position thereof with a substituent selected from the group consisting of said Substituent group α' and said Substituent group β'.

46. A pharmaceutical composition according to claim 40, wherein $R^{2'}$ is a 4-pyridyl group which is unsubstituted or substituted at the 2-position thereof with a substituent selected from the group consisting of methoxy, amino, methylamino, benzylamino, and α-methylbenzylamino groups.

47. A pharmaceutical composition according to claim 40, wherein B' has one further ring heteroatom or ring group selected from the group consisting of a nitrogen atom, oxygen atom, sulfur atom, >SO and >SO₂, said ring is saturated or unsaturated and optionally is fused with an aryl group, a heteroaryl group, a cycloalkyl group or a heterocyclyl group.

48. A pharmaceutical composition according to claim 40, wherein B' is saturated or unsaturated and is fused with an aryl group, a heteroaryl group, a cycloalkyl group or a heterocyclyl group.

49. A pharmaceutical composition according to claim 40, wherein B' is a pyrrolidinyl ring or a pyrrolinyl ring.

50. A pharmaceutical composition according to claim 40, wherein $R^{3'}$ is a group of formula (IIa)' or formula (IIb)'.

51. A pharmaceutical composition according to claim 40, wherein $R^{3'}$ is a group of formula (IIa)'.

52. A pharmaceutical composition according to claim 40, wherein $R^{4'}$ is 1 or 2 substituents which are independently selected from the group consisting of said Substituent group α', said Substituent group β' and Substituent group $γ^{1'}$, wherein said Substituent group $γ^{1'}$ is selected from the group consisting of oxo groups, hydroxyimino groups, lower alkoxyimino groups, lower alkylene groups, lower alkylenedioxy groups, lower alkylsulfinyl groups, lower alkylsulfonyl groups and aryl groups which optionally are substituted with at least one substituent selected from the group consisting of Substituent group α' and Substituent group β'.

53. A pharmaceutical composition according to claim 40, wherein $R^{4'}$ is a substituent selected from the group consisting of hydroxy groups, halogen atoms, lower alkoxy groups, lower alkylthio groups, halogeno lower alkoxy groups, lower alkyl groups, halogeno lower alkyl groups, oxo groups, aryl groups optionally substituted with at least one substituent selected from the group consisting of said Substituent group α' and said Substituent group β', lower alkylenedioxy groups, lower alkylene groups and lower alkylsulfonyl groups.

54. A pharmaceutical composition according to claim 40, wherein $R^{4'}$ is a substituent selected from the group consisting of hydroxy groups, fluorine atoms, chlorine atoms, methoxy groups, ethoxy groups, propoxy groups, methyl groups, ethyl groups, propyl groups and phenyl groups which optionally is substituted with at least one substituent selected from the group consisting of said Substituent group α' and said Substituent group β'.

55. A pharmaceutical composition according to claim 40, wherein $R^{4'}$ is a substituent selected from the group consisting of methoxy groups, methyl groups, ethyl groups, propyl groups and phenyl groups.

56. A pharmaceutical composition according to claim 40, wherein $R^{4'}$ is a substituent selected from the group consisting of aryloxy groups which optionally are substituted with at least one substituent selected from the group consisting of said Substituent group α' and said Substituent group β', alkylidene groups and aralkylidene groups.

57. A pharmaceutical composition according to claim 40, wherein $R^{4'}$ is a substituent selected from the group consisting of phenoxy, methylidene, ethylidene, propylidene and benzylidene groups.

58. A pharmaceutical composition according to claim 40, wherein said compound of formula (I)' is represented by the formula (I-1)' or (T-3)' shown below:

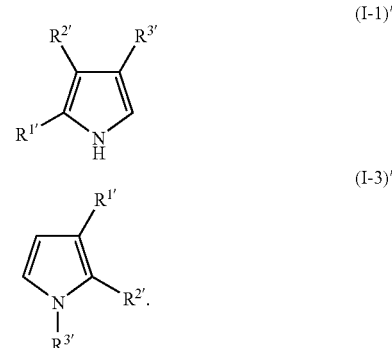

59. A pharmaceutical composition according to claim 40, wherein the compound of formula (I)' is represented by the formula (I-1)' below:

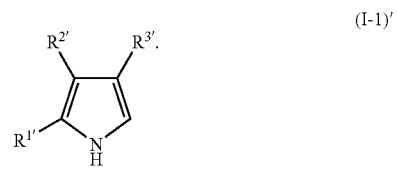

60. A pharmaceutical composition according to claim 40, wherein:
  $R^{3'}$ is a group of formula (IIa)' or formula (IIb)'; and
  $R^{4'}$ is 1 or 2 substituents which are independently selected from the group consisting of said Substituent group α', said Substituent group β' and Substituent group $γ^{1'}$, wherein said Substituent group $γ^{1'}$ is selected from the group consisting of oxo groups, hydroxyimino groups, lower alkoxyimino groups, lower alkylene groups, lower alkylenedioxy groups, lower alkylsulfinyl groups, lower alkylsulfonyl groups and aryl groups which are unsubstituted or substituted with at least one substituent selected from the group consisting of said Substituent group α' and said Substituent group β'.

61. A pharmaceutical composition according to claim 40, wherein:
  $R^{3'}$ is a group of formula (IIa)' or formula (IIb)'; and
  $R^{4'}$ is a substituent selected from the group consisting of hydroxy groups, halogen atoms, lower alkoxy groups, lower alkylthio groups, halogeno lower alkoxy groups, lower alkyl groups, halogeno lower alkyl groups, oxo groups, aryl groups which are unsubstituted or substituted with at least one substituent selected from the group consisting of said Substituent group α', said Substituent group β', lower alkylenedioxy groups, lower alkylene groups and lower alkylsulfonyl groups.

62. A pharmaceutical composition according to claim 40, wherein:
  $R^{1'}$ is a phenyl group which is unsubstituted or substituted with at least one substituent selected from the group consisting of Substituent group $α^{1'}$ defined below and Substituent group $β^{1'}$ defined below;
  $R^{3'}$ is a group of formula (IIa)' or formula (IIb)';
  said Substituent group $α^{1'}$ is selected from the group consisting of halogen atoms, lower alkoxy groups, halogeno lower alkoxy groups and groups of formula —$NR^{a'}R^{b'}$, wherein one of $R^{a'}$ and $R^{b'}$ represents a hydrogen atom or a lower alkyl group, and the other represents a hydrogen atom, a lower alkyl group or an aralkyl group;

said Substituent group $\beta^{1'}$ is selected from the group consisting of lower alkyl groups, halogeno lower alkyl groups, hydroxyl lower alkyl groups, nitro lower alkyl groups, amino lower alkyl groups, lower alkylamino lower alkyl groups, di(lower alkyl)amino lower alkyl groups and aralkylamino lower alkyl groups;

$R^{2'}$ is a 4-pyridyl group which is unsubstituted or substituted with at least one substituent selected from the group consisting of said Substituent group $\alpha'$ and said Substituent group $\beta'$; and $R^{4'}$ is a substituent selected from the group consisting of hydroxy groups, halogen atoms, lower alkoxy groups, lower alkylthio groups, halogeno lower alkoxy groups, lower alkyl groups, halogeno lower alkyl groups, oxo groups, aryl groups which are unsubstituted or substituted with at least one substituent selected from the group consisting of said Substituent group $\alpha'$, said Substituent group $\beta'$, lower alkylenedioxy groups, lower alkylene groups and lower alkylsulfonyl groups.

63. A pharmaceutical composition according to claim 40, wherein:

$R^{1'}$ is a phenyl group which is unsubstituted or substituted with at least one substituent selected from the group consisting of halogen atoms, halogeno lower alkyl groups and halogeno lower alkoxy groups;

$R^{2'}$ is a 4pyridyl group which is unsubstituted or substituted at the 2-position thereof with a substituent selected from the group consisting of said Substituent group $\alpha'$ and said Substituent group $\beta'$; and $R^{3'}$ is a group of formula (IIa)';

$R^{4'}$ is a substituent selected from the group consisting of hydroxy groups, fluorine atoms, chlorine atoms, methoxy groups, ethoxy groups, propoxy groups, methyl groups, ethyl groups, propyl groups and phenyl groups which are unsubstituted or substituted with at least one substituent selected from the group consisting of said Substituent group $\alpha'$ and said Substituent group $\beta'$.

64. A pharmaceutical composition according to claim 40, wherein:

$R^{1'}$ is a substituent selected from the group consisting of phenyl, 4-fluorophenyl, 3-fluorophenyl, 3-chlorophenyl, 3,4-difluorophenyl, 3,4,5-trifluorophenyl, 3-chloro-4-fluorophenyl, 3-difluoromethoxyphenyl and 3-trifluoromethylphenyl groups;

$R^{2'}$ is a 4-pyridyl group which is unsubstituted or substituted at the 2-position thereof with a substituent selected from the group consisting of methoxy, amino, methylamino, benzylamino, and α-methylbenzylamino groups; and $R^{3'}$ is a group of formula (IIa)';

$R^{4'}$ is a substituent selected from the group consisting of methoxy groups, methyl groups, ethyl groups, propyl groups and phenyl groups.

65. A pharmaceutical composition according to claim 40, wherein:

$R^{3'}$ is a group of formula (IIa)' or formula (IIb)'; and $R^{4'}$ is a substituent selected from the group consisting of aryloxy groups which are unsubstituted or substituted with at least one substituent selected from the group consisting of said Substituent group $\alpha'$, said Substituent group $\beta'$, alkylidene groups and aralkylidene groups.

66. A pharmaceutical composition according to claim 40, wherein:

$R^{1'}$ is a phenyl group which is unsubstituted or substituted with at least one substituent selected from the group consisting of Substituent group $\alpha^{1'}$ defined below and Substituent group $\beta^{1'}$ defined below, said Substituent group $\alpha^{1'}$ is selected from the group consisting of halogen atoms, lower alkoxy groups, halogeno lower alkoxy groups and groups of formula —NR$^{a'}$R$^{b'}$, wherein one of R$^{a'}$ and R$^{b'}$ represents a hydrogen atom or a lower alkyl group, and the other represents a hydrogen atom, a lower alkyl group or an aralkyl group, and said Substituent group $\beta^{1'}$ is selected from the group consisting of lower alkyl groups, halogeno lower alkyl groups, hydroxyl lower alkyl groups, nitro lower alkyl groups, amino lower alkyl groups, lower alkylamino lower alkyl groups, di(lower alkyl)amino lower alkyl groups and aralkylamino lower alkyl groups;

$R^{2'}$ is a 4pyridyl group which is unsubstituted or substituted with at least one substituent selected from the group consisting of said Substituent group $\alpha'$ and said Substituent group $\beta'$;

$R^{3'}$ is a group of formula (IIa)' or formula (IIb)'; and $R^{4'}$ is a substituent selected from the group consisting of aryloxy groups which are unsubstituted or substituted with at least one substituent selected from the group consisting of said Substituent group $\alpha'$, said Substituent group $\beta'$, alkylidene groups and aralkylidene groups.

67. A pharmaceutical composition according to claim 40, wherein:

$R^{1'}$ is a phenyl group which is unsubstituted or substituted with at least one substituent selected from the group consisting of halogen atoms, halogeno lower alkyl groups and halogeno lower alkoxy groups;

$R^{2'}$ is a 4-pyridyl group which is unsubstituted or substituted at the 2-position thereof with a substituent selected from the group consisting of said Substituent group $\alpha'$ and said Substituent group $\beta'$;

$R^{3'}$ is a group of formula (IIa)'; and $R^{4'}$ is a substituent selected from the group consisting of phenoxy, methylidene, ethylidene, propylidene and benzylidene groups.

68. A pharmaceutical composition according to claim 40, wherein:

$R^{1'}$ is a substituent selected from the group consisting of phenyl, 4-fluorophenyl, 3-fluorophenyl, 3-chlorophenyl, 3,4-difluorophenyl, 3,4,5-trifluorophenyl, 3-chloro-4-fluorophenyl, 3-difluoromethoxyphenyl and 3-trifluoromethylphenyl groups;

$R^{2'}$ is a 4pyridyl group which is unsubstituted or substituted at the 2-position thereof with a substituent selected from the group consisting of methoxy, amino, methylamino, benzylamino, and α-methylbenzylamino groups;

$R^{3'}$ is a group of formula (IIa)'; and $R^{4'}$ is a substituent selected from the group consisting of phenoxy, methylidene, ethylidene, propylidene and benzylidene groups.

69. A pharmaceutical composition according to any one of claim 60, 61, 62, 63, 64, 65, 66, 67 or 68, wherein the compound of formula (I)' is a compound of formula (I-1)' or (I-3)' shown below:

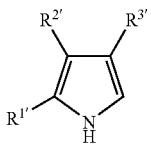
(I-1)'

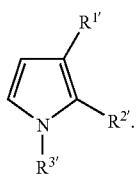
(I-3)'

70. A pharmaceutical composition according to any one of claim 60, 61, 62, 63, 64, 65, 66, 67 or 68, wherein the compound of formula (I)' is a compound of formula (I-1)':

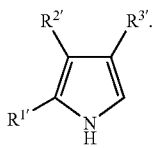
(I-1)'

71. A pharmaceutical composition according to claim 40, wherein the compound of formula (I)' is selected from the group consisting of
2-(3-fluorophenyl)-4-[2-methyl-1,2,3,5,6,8a-hexahydroindolizin-7yl]-3- (pyridin-4-yl)-1H-pyrrole,
2-(3-fluorophenyl)-4-[2-phenyl-1,2,3,5,6,8a-hexahydroindolizin-7yl]-3- (pyridin-4-yl)-1H-pyrrole,
2-(3-fluorophenyl)-4-[2-methoxy-1,2,3,5,6,8a-hexahydroindolizin-7-yl]-3-(pyridin-4-yl)-1H-pyrrole,
2-(4-fluorophenyl)-4-[2-methyl-1,2,3,5,6,8a-hexahydroindolizin-7-yl]-3-(pyridin-4-yl)-1H-pyrrole,
2-(4-fluorophenyl)-4-[2-phenyl-1,2,3,5,6,8a-hexahydroindolizin-7-yl]-3-(pyridin-4-yl)-1H-pyrrole,
2-(4-fluorophenyl)-4-[2-methoxy-1,2,3,5,6,8a-hexahydroindolizin7yl]-3-(pyridin-4-yl)-1H-pyrrole,
2-(3-chlorophenyl)-4-[2methyl-1,2,3,5,6,8a-hexahydroindolizin7yl]-3-(pyridin-4-yl)-1H-pyrrole,
2-(3-chlorophenyl)-4-[2-phenyl-1,2,3,5,6,8a-hexahydroindolizin7yl]-3-(pyridin-4-yl)-1H-pyrrole,
2-(3-chlorophenyl)-4-[2methoxy-1,2,3,5,6,8a-hexahydroindolizin7yl]-3-(pyridin-4-yl)-1H-pyrrole,
4-[2-methyl-1,2,3,5,6,8a-hexahydroindolizin-7-yl]-3-(pyridin-4-yl)-2-(3-trifluoromethylphenyl)-1H-pyrrole,
4-[2-phenyl-1,2,3,5,6,8a-hexahydroindolizin-7-yl]-3-(pyridin-4-yl)-2-(3-trifluoromethylphenyl)-1H-pyrrole,
4-[2-methoxy-1,2,3,5,6,8a-hexahydroindolizin-7-yl]-3-(pyridin-4-yl)-2-(3-trifluoromethylphenyl)-1H-pyrrole,
2-(4-fluorophenyl)-4-[2-methyl-3,5,6,8a-tetrahydroindolizin-7-yl]-3-(pyridin-4-yl)-1H-pyrrole,
2-(4-fluorophenyl)-4-[2-methylidene-1,2,3,5,6,8a-hexahydroindolizin-7-yl]-3-(pyridin-4-yl)-1H-pyrrole,
4-[2ethyl-1,2,3,5,6,8a-hexahydroindolizin-7-yl]-2-(4-fluorophenyl)-3-(pyridin-4-yl)-1H-pyrrole,
4-[2-ethyl-1,2,3,5,6,8a-hexahydroindolizin-7-yl]-2-(3-fluorophenyl)-3-(pyridin-4-yl)-1H-pyrrole,
2-(3-chlorophenyl)-4-[2-ethyl-1,2,3,5,6,8a-hexahydroindolizin-7-yl]-3-(pyridin-4yl)-1H-pyrrole,
4-[2ethyl-1,2,3,5,6,8a-hexahydroindolizin-7-yl]-3-(pyridin-4-yl)-2-(3-trifluoromethylphenyl)-1H-pyrrole,
2-(4-fluorophenyl)-4-[2-propyl-1,2,3,5,6,8a-hexahydroindolizin-7-yl]-3-(pyridin-4-yl)-1H-pyrrole,
2-(3-fluorophenyl)-4-[2-propyl-1,2,3,5,6,8a-hexahydroindolizin-7yl]-3-(pyridin-4-yl)-1H-pyrrole,
2-(3-chlorophenyl)-4-[2-propyl-1,2,3,5,6,8a-hexahydroindolizin-7yl]-3-(pyridin-4-yl)-1H-pyrrole,
4-[2-propyl-1,2,3,5,6,8a-hexahydroindolizin-7yl]-3-(pyridin-4-yl)-2-(3-trifluoromethylphenyl)-1H-pyrrole,
4-[2-ethyl-3,5,6,8a-tetrahydroindolizin-7-yl]-2-(4 -fluorophenyl)-3-(pyridin-4-yl)-1H-pyrrole,
2-(4-fluorophenyl)-4-[2-propyl-3,5,6,8a-tetrahydroindolizin-7-yl]-3-(pyridin-4-yl)-1H-pyrrole, and
2-(4-fluorophenyl)4-[2-phenyl-3,5,6,8a-tetrahydroindolizin-7-yl]-3-(pyridin-4-yl)-1H-pyrrole, or a pharmacologically acceptable salt, ester or amide thereof.

72. A composition according to claim 40, wherein said compound of formula (I)' is selected from 2-(4-fluorophenyl)-4-[(2R,8aS)-2-phenyl-1,2,3,5,6,8a-hexahydro-indolizin-7-yl]-3-(pyridin-4-yl)-1H-pyrrole or a pharmacologically acceptable salt, ester or amide thereof.

73. A composition according to claim 40, wherein said compound of formula (I)' is selected from 2-(4-fluorophenyl)-4-[(8aS)-2-methyl-1,2,3,5,6,8a-hexahydroindolizin-7yl]-3-(pyridin-4-yl)-1H-pyrrole or a pharmacologically acceptable salt, ester or amide thereof.

74. A composition according to claim 40, wherein said compound of formula (I)' is selected from 2-(4fluorophenyl)-4-[(8aS)-2-methylidene-1,2,3,5,6,8a-hexahydroindolizin-7-yl]-3-(pyridin-4-yl)-1H- or a pharmacologically acceptable salt, ester or amide thereof.

75. A composition according to claim 40, wherein said compound of formula (I)' is selected from 2-(4-fluorophenyl)-4-[(8aS)-2-methyl-3,5,6,8a-tetrahydroindolizin-7-yl]-3-(pyridin-4-yl)-1H-pyrrole or a pharmacologically acceptable salt, ester or amide thereof.

76. A composition according to claim 40, wherein said compound of formula (I)' is selected from 4-[(2S,8aS)-2-ethyl-1,2,3,5,6,8a-hexahydroindolizin-7-yl]-2-(4-fluorophenyl)-3-(pyridin-4-yl)-1H-pyrrole or a pharmacologically acceptable salt, ester or amide thereof.

77. A composition according to claim 40, wherein said compound of formula (I)' is selected from 2-(4-fluorophenyl)-4-[(2S,8aS)-2-propyl-1,2,3,5,6,8a-hexahydroindolizin-7-yl]-3-(pyridin-4-yl)-1H-pyrrole or a pharmacologically acceptable salt, ester or amide thereof.

78. A composition according to claim 40, wherein said compound of formula (I)' is selected from 2-(4-fluorophenyl)-4-[(2R,8aS)-2-methoxy-1,2,3,5,6,8a-hexahydroindolizin-7yl]-3-(pyridin-4-yl)-1-H-pyrrole or a pharmacologically acceptable salt, ester or amide thereof.

79. A method for the treatment of rheumatoid arthritis which comprises administering to a mammal a pharmaceutically effective amount of a compound of formula (I)' or a pharmacologically acceptable salt, ester or amide thereof:

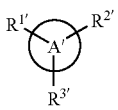
(I)' wherein:

A' represents a pyrrole ring;

R$^{1'}$ is an aryl group selected from the group consisting of phenyl and naphthyl, which are unsubstituted or substituted with at least one substituent selected from the group consisting of Substituent group α' defined below and Substituent group β' defined below;

R$^{2'}$ is a pyridyl group which is unsubstituted or substituted with at least one substituent selected from Substituent group α' defined below and Substituent group β' defined below; and R$^{3'}$ represents a group of formula (IIa)', (IIb)' or (IIc)' shown below:

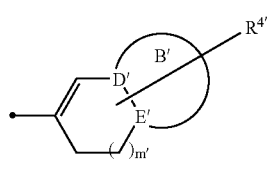
(IIa)'

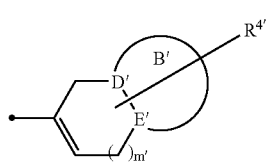
(IIb)'

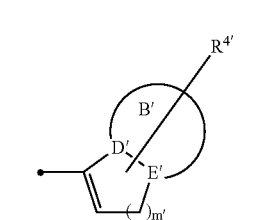
(IIc)' wherein m' represents 1,

E' represents a nitrogen atom and D represents a group of formula >C(R$^{5'}$), wherein R$^{5'}$ is selected from the group consisting of hydrogen atoms, Substituent group α' defined below and Substituent group β' defined below, B' represents a 5-membered heterocyclic ring which has one ring nitrogen atom, said heterocyclic ring being saturated or unsaturated, and is unfused or fused with a group selected from the group consisting of aryl groups defined below, heteroaryl groups defined below, cycloalkyl groups defined below and heterocyclyl groups defined below, and R$^{4'}$ represents from 1 to 3 substituents which are independently selected from the group consisting of Substituent group α' defined below, Substituent group β' defined below and Substituent group γ' defined below, or when B' is a heterocyclic ring which is fused to an aryl group, a heteroaryl group, a cyclolkyl group or a heterocyclyl group, R$^{4'}$ may be a hydrogen atom;

provided that said substituents R$^{1'}$ and R$^{3'}$ are bonded to the two atoms of said pyrrole ring which are adjacent to the atom of the pyrrole ring to which said substituent R$^{2'}$ is bonded;

Substituent group α' is selected from the group consisting of hydroxyl groups, nitro groups, cyano groups, halogen atoms, lower alkoxy groups defined below, halogeno lower alkoxy groups defined below, lower alkylthio groups defined below, halogeno lower alkylthio groups defined below and groups of formula —NR$^{a'}$R$^{b'}$, wherein R$^{a'}$ and R$^{b'}$ are the same or different from each other and each is independently selected from the group consisting of hydrogen atoms, lower alkyl groups defined below, lower alkenyl groups defined below, lower alkynyl groups defined below, aralkyl groups defined below and lower alkylsulfonyl groups defined below, or R$^{a'}$ and R$^{b'}$, taken together with the nitrogen atom to which they are attached, form a heterocyclyl group;

Substituent group β' is selected from the group consisting of lower alkyl groups defined below which are unsubstituted or substituted with at least one substituent selected from the group consisting of Substituent group α' defined above, lower alkenyl groups defined below which are unsubstituted or substituted with at least one substituent selected from the group consisting of Substituent group α' defined above, lower alkynyl groups defined below which are unsubstituted or substituted with at least one substituent selected from the group consisting of Substituent group α' defined above, aralkyl groups defined below and cycloalkyl groups defined below;

Substituents group γ' is selected from the group consisting of oxo groups, hydroxyimino groups, lower alkoxyimino groups defined below, lower alkylene groups defined below, lower alkylenedioxy groups defined below, lower alkylsulfinyl groups defined below, lower alkylsulfonyl groups defined below, aryl groups defined below which are unsubstituted or substituted with at least one substituent selected from the group consisting of Substituent group α' defined above, Substituent group β' defined above, aryloxy groups defined below which are unsubstituted or substituted with at least one substituent selected from the group consisting of Substituent group α' defined above, Substituent group β' defined above, lower alkylidenyl groups and aralkylidenyl groups;

said aryl groups in the definitions of ring B' and Substituent group γ' above are aromatic hydrocarbon groups having from 6 to 14 carbon atoms in one or more rings, said aryl groups being unfused or fused with a cycloalkyl group having from 3 to 10 carbon atoms;

said heteroaryl groups in the definition of ring B' above are 5- to 7-membered aromatic heterocyclic groups containing from 1 to 3 heteroatoms selected from the group consisting of sulfur atoms, oxygen atoms and nitrogen atoms, said heteroaryl groups being unfused or fused with another cyclic group selected from the group consisting of aryl groups defined above and cycloalkyl groups having from 3 to 10 carbon atoms;

said lower alkyl groups in the definitions of R$^{a'}$, R$^{b'}$ and Substituent group β' above, and the lower alkyl moiety of said lower alkyl groups which are unsubstituted or substituted with at least one selected from Substituent group α' in the definition of Substituent group β' above are straight or branched alkyl groups having from 1 to 6 carbon atoms;

said lower alkenyl groups in the definitions of $R^{a'}$, $R^{b'}$ and Substituent group β' above, and the lower alkenyl moiety of said lower alkenyl groups which are unsubstituted or substituted with at least one substituent selected from Substituent group α' in the definition of Substituent group β' above are straight or branched alkenyl groups having from 2 to 6 carbon atoms;

said lower alkynyl groups in the definitions of $R^{a'}$, $R^{b'}$ and Substituent group β' above, and the lower alkynyl moiety of said lower alkynyl groups which are unsubstituted or substituted with at least one substituent selected from Substituent group α' in the definition of Substituent group β' above are straight or branched alkynyl groups having from 2 to 6 carbon atoms;

said aralkyl groups in the definitions of $R^{a'}$, $R^{b'}$ and Substituent group β' above are lower alkyl groups as defined above which are substituted with at least one aryl group as defined above which are unsubstituted or substituted with from 1 to 3 substituents selected from the group consisting of Substituent group α' defined above and Substituent group β' defined above;

said lower alkylsulfonyl groups in the definitions of $R^{a'}$, $R^{b'}$ and Substituent γ' above are lower alkyl groups as defined above which are bonded to a sulfonyl group;

where ring B' is fused with a heterocyclyl group, said heterocyclyl groups are 4- to 7-membered heterocyclyl groups which contain from 1 to 3 ring heteroatoms selected from the group consisting of oxygen atoms, sulfur atoms and nitrogen atoms;

where $R^{a'}$ and $R^{b'}$ together with the nitrogen atom to which they are attached represent a heterocyclyl group, said heterocyclyl groups are 4- to 7-membered heterocyclyl groups which contain one nitrogen atom and which do not contain any further heteroatoms or contain one further heteroatom selected from the group consisting of oxygen atoms, sulfur atoms and nitrogen atoms, said heterocyclyl groups being unfused or fused with another cyclic group selected from the group consisting of aryl groups defined above and heteroaryl groups defined above;

said lower alkoxy groups in the definition of Substituent group α' above are groups in which an oxygen atom is bonded to a lower alkyl group as defined above;

said halogeno lower alkoxy groups in the definition of Substituent group α' above are groups in which a lower alkoxy group as defined above is substituted with at least one halogen atom;

said lower alkylthio groups in the definition of Substituent group α' above are groups in which a sulfur atom is bonded to a lower alkyl group as defined above;

said halogeno lower alkylthio groups in the definition of Substituent group α' above are groups in which a lower alkylthio group as defined above is substituted with at least one halogen atom;

said cycloalkyl groups in the definitions of Substituent group β' and ring B' above are cycloalkyl groups having from 3 to 7 carbon atoms;

said lower alkoxyimino groups in the definition of Substituent group γ' above are groups wherein the hydrogen atom of a hydroxyimino group is replaced by a lower alkyl group as defined above;

said lower alkylene groups in the definition of Substituent group γ' above are alkylene groups having from 2 to 6 carbon atoms;

said lower alkylenedioxy groups in the definition of Substituent group γ' above are groups wherein an alkylene moiety, which is a straight or branched chain alkylene group having from 1 to 6 carbon atoms, is subsitituted with 2 oxy groups;

said lower alkylsulfinyl groups in the definition of Substituent group γ' above are groups in which a lower alkyl group as defined above is bonded to a sulfinyl group;

said lower alkylidenyl groups in the definition of Substituent group γ' above are straight or branched alkylidenyl groups having from 1 to 6 carbon atoms;

said aralkylidenyl groups in the definition of Substituent group γ' above are lower alkylidenyl groups as defined above γ' which are substituted with 1 or more aryl groups as defined above;

said unsubstituted or substituted aryloxy groups in the definition of Substituent group γ' above are groups in which an oxygen atom is attached to an aryl group as defined above.

80. A method according to claim 79, wherein the mammal is a human.

81. A method according to claim 80, wherein $R^{1'}$ is a phenyl group which optionally is substituted with at least one substituent selected from the group consisting of Substituent group $α^{1'}$ defined below and Substituent group $β^{1'}$ defined below;

said Substituent group $α^{1'}$ is selected from the group consisting of halogen atoms, lower alkoxy groups, halogeno lower alkoxy groups and groups of formula —$NR^{a'}R^{b'}$, wherein one of $R^{a'}$ and $R^{b'}$ represents a hydrogen atom or a lower alkyl group, and the other represents a hydrogen atom, a lower alkyl group or an aralkyl group;

said Substituent group $β^{1'}$ is selected from the group consisting of lower alkyl groups, halogeno lower alkyl groups, hydroxyl lower alkyl groups, nitro lower alkyl groups, amino lower alkyl groups, lower alkylamino lower alkyl groups, di(lower alkyl)amino lower alkyl groups and aralkylamino lower alkyl groups.

82. A method according to claim 80, wherein $R^{1'}$ is a phenyl group which optionally is substituted with at least one substituent selected from the group consisting of halogen atoms, halogeno lower alkyl groups and halogeno lower alkoxy groups.

83. A method according to claim 80, wherein $R^{1'}$ is a substituent selected from the group consisting of phenyl, 4-fluorophenyl, 3-fluorophenyl, 3-chlorophenyl, 3,4-difluorophenyl, 3,4,5-trifluorophenyl, 3-chloro4-fluorophenyl, 3-difluoromethoxyphenyl and 3-trifluoromethylphenyl groups.

84. A method according to claim 80, wherein $R^{2'}$ is a 4-pyridyl group which is unsubstituted or substituted with at least one substituent selected from the group consisting of said Substituent group α' and said Substituent group β'.

85. A method according to claim 80, wherein $R^{2'}$ is a 4-pyridyl group which is unsubstituted or substituted at the 2-position thereof with a substituent selected from the group consisting of said Substituent group α' and said Substituent group β'.

86. A method according to claim 80, wherein $R^{2'}$ is a 4-pyridyl group which is unsubstituted or substituted at the 2-position thereof with a substituent selected from the group consisting of methoxy, amino, methylamino, benzylamino, and α-methylbenzylamino groups.

87. A method according to claim 80, wherein B' has one further ring heteroatom or ring group selected from the group consisting of a nitrogen atom, oxygen atom, sulfur atom, >SO and >SO$_2$, said ring may be saturated or unsaturated and optionally is fused with an aryl group, a heteroaryl group, a cycloalkyl group or a heterocyclyl group.

88. A method according to claim 80, wherein B' is saturated or unsaturated and is fused with an aryl group, a heteroaryl group, a cycloalkyl group or a heterocyclyl group.

89. A method according to claim 80, wherein B' is a pyrrolidinyl ring or a pyrrolinyl ring.

90. A method according to claim 80, wherein R$^{3'}$ is a group of formula (IIa)' or 1 formula (IIb)'.

91. A method according to claim 80, wherein R$^{3'}$ is a group of formula (IIa)'.

92. A method according to claim 80, wherein R$^{4'}$ is 1 or 2 substituents which are independently selected from the group consisting of said Substituent group α', Substituent group β' and Substituent group γ$^{1'}$, wherein said Substituent group γ$^{1'}$ is selected from the group consisting of oxo groups, hydroxyimino groups, lower alkoxyimino groups, lower alkylene groups, lower alkylenedioxy groups, lower alkylsulfinyl groups, lower alkylsulfonyl groups and aryl groups which optionally are substituted with at least one substituent selected from the group consisting of said Substituent group α' and said Substituent group β'.

93. A method according to claim 80, wherein R$^{4'}$ is a substituent selected from the group consisting of hydroxy groups, halogen atoms, lower alkoxy groups, lower alkylthio groups, halogeno lower alkoxy groups, lower alkyl groups, halogeno lower alkyl groups, oxo groups, aryl groups optionally substituted with at least one substituent selected from the group consisting of said Substituent group α', said Substituent group β', lower alkylenedioxy groups, lower alkylene groups and lower alkylsulfonyl groups.

94. A method according to claim 80, wherein R$^{4'}$ is a substituent selected from the group consisting of hydroxy groups, fluorine atoms, chlorine atoms, methoxy groups, ethoxy groups, propoxy groups, methyl groups, ethyl groups, propyl groups and phenyl groups which optionally are substituted with at least one substituent selected from the group consisting of said Substituent group α' and said Substituent group β'.

95. A method according to claim 80, wherein R$^{4'}$ is a substituent selected from the group consisting of methoxy groups, methyl groups, ethyl groups, propyl groups and phenyl groups.

96. A method according to claim 80, wherein R$^{4'}$ is a substituent selected from the group consisting of aryloxy groups which optionally are substituted with at least one substituent selected from the group consisting of said Substituent group α', said Substituent group β', alkylidene groups and aralkylidene groups.

97. A method according to claim 80, wherein R$^{4'}$ is a substituent selected from the group consisting of phenoxy, methylidene, ethylidene, propylidene and benzylidene groups.

98. A method according to claim 80, wherein said compound of formula (I)' is represented by the formula (I-1)' or (I-3)' shown below:

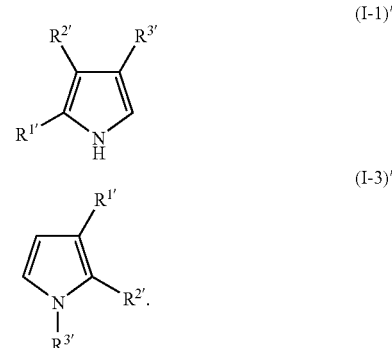

99. A method according to claim 80, wherein the compound of formula (I)' is represented by the formula (I-1)' below:

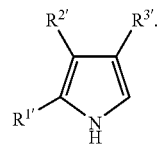

100. A method according to claim 80, wherein:
R$^{3'}$ is a group of formula (IIa)' or formula (IIb)'; and
R$^{4'}$ is 1 or 2 substituents which are independently selected from the group consisting of said Substituent group α', said Substituent group β' and Substituent group γ$^{1'}$, wherein said Substituent group γ$^{1'}$ is selected from the group consisting of oxo groups, hydroxyimino groups, lower alkoxyimino groups, lower alkylene groups, lower alkylenedioxy groups, lower alkylsulfinyl groups, lower alkylsulfonyl groups and aryl groups which are unsubstituted or substituted with at least one substituent selected from Substituent group α' and said Substituent group β'.

101. A method according to claim 80,
wherein:
R$^{3'}$ is a group of formula (IIa)' or formula (IIb)'; and
R$^{4'}$ is a substituent selected from the group consisting of hydroxy groups, halogen atoms, lower alkoxy groups, lower alkylthio groups, halogeno lower alkoxy groups, lower alkyl groups, halogeno lower alkyl groups, oxo groups, aryl groups which are unsubstituted or substituted with at least one substituent selected from the group consisting of said Substituent group α', said Substituent group β', lower alkylenedioxy groups, lower alkylene groups and lower alkylsulfonyl groups.

102. A method according to claim 80, wherein:
R$^{1'}$ is a phenyl group which is unsubstituted or substituted with at least one substituent selected from the group consisting of Substituent group α$^{1'}$ defined below and Substituent group β$^{1'}$ defined below;
said Substituent group α$^{1'}$ is selected from the group consisting of halogen atoms, lower alkoxy groups, halogeno lower alkoxy groups and groups of formula —NR$^{a'}$R$^{b'}$, wherein one of R$^{a'}$ and R$^{b'}$ represents a hydrogen atom or a lower alkyl group, and the other represents a hydrogen atom, a lower alkyl group or an aralkyl group;

said Substituent group β¹' is selected from the group consisting of lower alkyl groups, halogeno lower alkyl groups, hydroxyl lower alkyl groups, nitro lower alkyl groups, amino lower alkyl groups, lower alkylamino lower alkyl groups, di(lower alkyl)amino lower alkyl groups and aralkylamino lower alkyl groups;

$R^{2'}$ is a 4-pyridyl group which is unsubstituted or substituted with at least one substituent selected from the group consisting of said Substituent group α' and said Substituent group β';

$R^{3'}$ is a group of formula (IIa)' on formula (IIb)'; and $R^{4'}$ is a substituent selected from the group consisting of hydroxy groups, halogen atoms, lower alkoxy groups, lower alkylthio groups, halogeno lower alkoxy groups, lower alkyl groups, halogeno lower alkyl groups, oxo groups, aryl groups which are unsubstituted or substituted with at least one substituent selected from the group consisting of said Substituent group α', said Substituent group β', lower alkylenedioxy groups, lower alkylene groups and lower alkylsulfonyl groups.

103. A method according to claim 80, wherein:

$R^{1'}$ is a phenyl group which is unsubstituted or substituted with at least one substituent selected from the group consisting of halogen atoms, halogeno lower alkyl groups and halogeno lower alkoxy groups;

$R^{2'}$ is a 4-pyridyl group which is unsubstituted or substituted at the 2-position thereof with a substituent selected from the group consisting of said Substituent group α' and said Substituent group β';

$R^{3'}$ is a group of formula (IIa)'; and $R^{4'}$ is a substituent selected from the group consisting of hydroxy groups, fluorine atoms, chlorine atoms, methoxy groups, ethoxy groups, propoxy groups, methyl groups, ethyl groups, propyl groups and phenyl groups which are unsubstituted or substituted with at least one substituent selected from the group consisting of said Substituent group α' and said Substituent group β'.

104. A method according to claim 80, wherein:

$R^{1'}$ is a substituent selected from the group consisting of phenyl, 4-fluorophenyl, 3-fluorophenyl, 3-chlorophenyl, 3,4-difluorophenyl, 3,4,5-trifluorophenyl, 3-chloro-4-fluorophenyl, 3-difluoromethoxyphenyl and 3-trifluoromethylphenyl groups;

$R^{2'}$ is a 4-pyridyl group which is unsubstituted or substituted at the 2-position thereof with a substituent selected from the group consisting of methoxy, amino, methylamino, benzylamino and α-methylbenzylamino groups;

$R^{3'}$ is a group of formula (IIa)'; and $R^{4'}$ is a substituent selected from the group consisting of methoxy groups, methyl groups, ethyl groups, propyl groups and phenyl groups.

105. A method according to claim 80, wherein:

$R^{3'}$ is a group of formula (IIa)' or formula (IIb)'; and $R^{4'}$ is a substituent selected from the group consisting of aryloxy groups which are unsubstituted or substituted with at least one substituent selected from the group consisting of said Substituent group α¹', said Substituent group β¹' alkylidene groups and aralkylidene groups.

106. A method according to claim 80, wherein:

$R^{1'}$ is a phenyl group which is unsubstituted or substituted with at least one substituent selected from Substituent group α¹' defined below and Substituent group defined below, said Substituent group α¹' is selected from the group consisting of halogen atoms, lower alkoxy groups, halogeno lower alkoxy groups and groups of formula —NR$^{a'}$R$^{b'}$, wherein one of R$^{a'}$ and R$^{b'}$ represents a hydrogen atom or a lower alkyl group, and the other represents a hydrogen atom, a lower alkyl group or an aralkyl group, said Substituent group β¹' is selected from the group consisting of lower alkyl groups, halogeno lower alkyl groups, hydroxyl lower alkyl groups, nitro lower alkyl groups, amino lower alkyl groups, lower alkylamino lower alkyl groups, di(lower alkyl)amino lower alkyl groups and aralkylamino lower alkyl groups;

$R^{2'}$ is a 4-pyridyl group which is unsubstituted or substituted with at least one substituent selected from the group consisting of said Substituent group α' and said Substituent group β';

$R^{3'}$ is a group of formula (IIa)' or formula (IIb)'; and $R^{4'}$ is a substituent selected from the group consisting of aryloxy groups which are unsubstituted or substituted with at least one substituent selected from the group consisting of said Substituent group α' and said Substituent group β', alkylidene groups and aralkylidene groups.

107. A method according to claim 80, wherein:

$R^{1'}$ is a phenyl group which is unsubstituted or substituted with at least one substituent selected from the group consisting of halogen atoms, halogeno lower alkyl groups and halogeno lower alkoxy groups;

$R^{2'}$ is a 4-pyridyl group which is unsubstituted or substituted at the 2-position thereof with a substituent selected from the group consisting of said Substituent group α' and said Substituent group β'; and $R^{3'}$ is a group of formula (IIa)'; and $R^{4'}$ is a substituent selected from the group consisting of phenoxy, methylidene, ethylidene, propylidene and benzylidene groups.

108. A method according to claim 80, wherein:

$R^{1'}$ is a substituent selected from the group consisting of phenyl, 4-fluorophenyl, 3-fluorophenyl, 3-chlorophenyl, 3,4-difluorophenyl, 3,4,5-trifluorophenyl, 3-chloro-4-fluorophenyl, 3-difluoromethoxyphenyl and 3-trifluoromethylphenyl groups;

$R^{2'}$ is a 4-pyridyl group which is unsubstituted or substituted at the 2-position thereof with a substituent selected from the group consisting of methoxy, amino, methylamino, benzylamino, and α-methylbenzylamino groups;

$R^{3'}$ is a group of formula (IIa)'; and $R^{4'}$ is a substituent selected from the group consisting of phenoxy, methylidene, ethylidene, propylidene and benzylidene groups.

109. A method according to claim 80, wherein the compound of formula (I)' is selected from the group consisting of 2-(3-fluorophenyl)-4-[2-methyl-1,2,3,5,6,8a-hexahydroindolizin-7-yl]-3-(pyridin-4-yl)-1H-pyrrole, 2-(3-fluorophenyl)-4-[2-phenyl-1,2,3,5,6,8a-hexahydroindolizin-7-yl]-3-(pyridin-4-yl)-1H-pyrrole, 2-(3-fluorophenyl)-4-[2-methoxy-1,2,3,5,6,8a-hexahydroindolizin-7-yl]-3-(pyridin-4-yl)-1H-pyrrole, 2-(4-fluorophenyl)-4-[2-methyl-1,2,3,5,6,8a-hexahydroindolizin-7-yl]-3-(pyridin-4-yl)-1H-pyrrole, 2-(4-fluorophenyl)-4-[2-phenyl-1,2,3,5,6,8a-hexahydroindolizin-7-yl]-3-(pyridin-4-yl)-1H-pyrrole, 2-(4-fluorophenyl)-4-[2-methoxy-1,2,3,5,6,8a-hexahydroindolizin-7-yl]-3-(pyridin-4-yl)-1H-pyrrole, 2-(3-chlorophenyl)-4-[2-methyl-1,2,3,5,6,8a-hexahydroindolizin-7-yl]-3-(pyridin-4-yl)-1H-pyrrole, 2-(3-chlorophenyl)-4-[2-phenyl-1,2,3,5,6,8a-hexahydroindolizin-7-yl]-3-(pyridin-4-yl)-1H-pyrrole,
2-(3-chlorophenyl)-4-[2-methoxy-1,2,3,5,6,8a-hexahydroindolizin-7-yl]-3-(pyridin-4-yl)-1H-pyrrole,
4-[2-methyl-1,2,3,5,6,8a-hexahydroindolizin-7-yl]-3-(pyridin-4-yl)-2-(3-trifluoromethylphenyl)-1H-pyrrole,
4-[2-phenyl-1,2,3,5,6,8a-hexahydroindolizin-7-yl]-3-(pyridin-4-yl)-2-(3-trifluoromethylphenyl)-1H-pyrrole,
4-[2-methoxy-1,2,3,5,6,8a-hexahydroindolizin-7-yl]-3-(pyridin-4-yl)-2-(3-trifluoromethylphenyl)-1H-pyrrole,
2-(4-fluorophenyl)-4-[2-methyl-3,5,6,8a-tetrahydroindolizin-7-yl]-3-(pyridin-4-yl)-1H-pyrrole,
2-(4-fluorophenyl)-4-[2-methylidene-1,2,3,5,6,8a-hexahydroindolizin-7-yl]-3-(pyridin-4-yl)-1H-pyrrole,
4-[2-ethyl-1,2,3,5,6,8a-hexahydroindolizin-7-yl]-2-(4-fluorophenyl)-3-(pyridin-4-yl)-1H-pyrrole,
4-[2-ethyl-1,2,3,5,6,8a-hexahydroindolizin-7-yl]-2-(3-fluorophenyl)-3-(pyridin-4-yl)-1H-pyrrole,
2-(3-chlorophenyl)-4-[2-ethyl-1,2,3,5,6,8a-hexahydroindolizin-7-yl]-3-(pyridin-4-yl)-1H-pyrrole,
4-[2-ethyl-1,2,3,5,6,8a-hexahydroindolizin-7-yl]-3-(pyridin-4-yl)-2-(3-trifluoromethylphenyl)-1H-pyrrole,
2-(4-fluorophenyl)-4-[2-propyl-1,2,3,5,6,8a-hexahydroindolizin-7-yl]-3-(pyridin-4-yl)-1H-pyrrole,
2-(3-fluorophenyl)-4-[2-propyl-1,2,3,5,6,8a-hexahydroindolizin-7-yl]-3-(pyridin-4-yl)-1H-pyrrole,
2-(3-chlorophenyl)-4-[2-propyl-1,2,3,5,6,8a-hexahydroindolizin-7-yl]-3-(pyridin-4-yl)-1H-pyrrole,
4-[2-propyl-1,2,3,5,6,8a-hexahydroindolizin-7-yl]-3-(pyridin-4-yl)-2-(3-trifluoromethylphenyl)-1H-pyrrole,
4-[2-ethyl-3,5,6,8a-tetrahydroindolizin-7-yl]-2-(4-fluorophenyl)-3-(pyridin-4-yl)-1H-pyrrole,
2-(4-fluorophenyl)-4-[2-propyl-3,5,6,8a-tetrahydroindolizin-7-yl]-3-(pyridin-4-yl)-1H-pyrrole, and
2-(4-fluorophenyl)-4-[2-phenyl-3,5,6,8a-tetrahydroindolizin-7-yl]-3-(pyridin-4-yl)-1H-pyrrole, or a pharmaceutically acceptable salt, ester or amide thereof.

110. A method according to claim 80, wherein said compound of formula (I)' is selected from 2-(4-fluorophenyl)-4-[(2R,8aS)-2-phenyl-1,2,3,5,6,8a-hexahydroindolizin-7-yl]-3-(pyridin-4-yl)-1H-pyrrole or a pharmacologically acceptable salt, ester or amide thereof.

111. A method according to claim 80, wherein said compound of formula (I)' is selected from 2-(4-fluorophenyl)-4-[(8aS)-2-methyl-1,2,3,5,6,8a-hexahydroindolizin-7-yl]-3-(pyridin-4-yl)-1H-pyrrole or a pharmacologically acceptable salt, ester or amide thereof.

112. A method according to claim 80, wherein said compound of formula (I)' is selected from 2-(4-fluorophenyl)-4-[(8aS)-2-methylidene-1,2,3,5,6,8a-hexahydroindolizin-7-yl]-3-(pyridin-4-yl)-1H-pyrrole or a pharmacologically acceptable salt, ester or amide thereof.

113. A method according to claim 80, wherein said compound of formula (I)' is selected from 2-(4-fluorophenyl)-4-[(8aS)-2-methyl-3,5,6,8a-tetrahydroindolizin-7-yl]-3-(pyridin-4-yl)-1H-pyrrole or a pharmacologically acceptable salt, ester or amide thereof.

114. A method according to claim 80, wherein said compound of formula (I)' is selected from 4-[(2S,8aS)-2-ethyl-1,2,3,5,6,8a-hexahydroindolizin-7-yl)-2-(4-fluorophenyl)-3-(pyridin-4-yl)-1H-pyrrole or a pharmacologically acceptable salt, ester or amide thereof.

115. A method according to claim 80, wherein said compound of formula (I)' is selected from 2-(4-fluorophenyl)-4-[(2S,8aS)-2-propyl-1,2,3,5,6,8a-hexahydroindolizin-7-yl]-3-(pyridin-4-yl)-1H-pyrrole or a pharmacologically acceptable salt, ester or amide thereof.

116. A method according to claim 80, wherein the compound is 2-(4-fluorophenyl)-4-[(2R,8aS)-2-methoxy-1,2,3,5,6,8a-hexahydroindolizin-7-yl]-3-(pyridin-4-yl)-1H-pyrrole or a pharmacologically acceptable salt, ester or amide thereof.

117. A method according to any one of claims 95 to 103, wherein the compound of formula (I)' is a compound of formula (I-1)' or (I-3)' shown below:

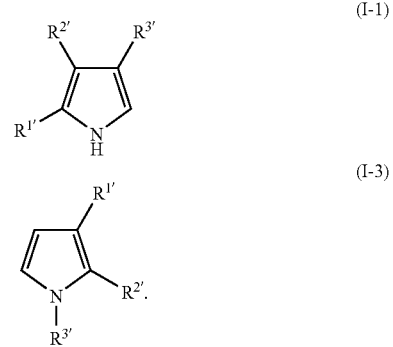

118. A method according to any one of claims 100 to 108, wherein the compound of formula (I)' is a compound of formula (I-1)' shown below:

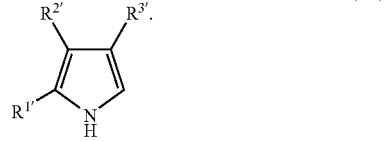

* * * * *

UNITED STATES PATENT AND TRADEMARK OFFICE
CERTIFICATE OF CORRECTION

| | | |
|---|---|---|
| PATENT NO. | : 7,122,666 B2 | |
| APPLICATION NO. | : 10/354648 | |
| DATED | : October 17, 2006 | |
| INVENTOR(S) | : Kimura et al. | |

It is certified that error appears in the above-identified patent and that said Letters Patent is hereby corrected as shown below:

Title page, left column, under "Related U.S. Application Data", (60): line 4, after "Mar. 14, 2002, now abandoned," insert --which is a division of application No. 09/619,898, filed on Jul. 19, 2000, now abandoned,--; on line 5, delete "10/051,630" and insert --10/054,630--; and on lines 6-8, delete "which is a division of application No. 09/619,898, filed on Jul. 19, 2000, now abandoned."

Signed and Sealed this

First Day of July, 2008

JON W. DUDAS
*Director of the United States Patent and Trademark Office*